US009540377B2

(12) United States Patent
Cammarano et al.

(10) Patent No.: US 9,540,377 B2
(45) Date of Patent: Jan. 10, 2017

(54) 2,6,7,8 SUBSTITUTED PURINES AS HDM2 INHIBITORS

(71) Applicant: Merck Sharp & Dohme Corp., Rahway, NJ (US)

(72) Inventors: Carolyn Michele Cammarano, West Caldwell, NJ (US); Matthew P. Christopher, Brookline, MA (US); Christopher Dinsmore, Newton, MA (US); Ronald J. Doll, Convent Station, NJ (US); Francesc Xavier Fradera Llinas, Brookline, MA (US); Chaomin Li, Boston, MA (US); Michelle Machacek, Brookline, MA (US); Michelle Martinez, Watertown, MA (US); Latha G. Nair, Edison, NJ (US); Weidong Pan, Somerset, NJ (US); Michael Hale Reutershan, Brighton, MA (US); Manami Shizuka, Lexington, MA (US); Dietrich P. Steinhuebel, Boston, MA (US); Binyuan Sun, Boston, MA (US); Christopher Francis Thompson, Arlington, MA (US); B. Wesley Trotter, Medfield, MA (US); Yaolin Wang, Short Hills, NJ (US); Liping Yang, Arlington, MA (US); Stephane L. Bogen, Somerset, NJ (US); Matthew E. Voss, Ville De West (SG); Jagannath Panda, Singapore Science Park II (SG); Anthappan Tony Kurissery, Singapore Science Park II (SG)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/762,827

(22) PCT Filed: Jan. 29, 2014

(86) PCT No.: PCT/US2014/013566
§ 371 (c)(1),
(2) Date: Jul. 23, 2015

(87) PCT Pub. No.: WO2014/120748
PCT Pub. Date: Aug. 7, 2014

(65) Prior Publication Data
US 2015/0353553 A1 Dec. 10, 2015

Related U.S. Application Data

(60) Provisional application No. 61/758,396, filed on Jan. 30, 2013.

(51) Int. Cl.
*A61K 31/52* (2006.01)
*C07D 473/16* (2006.01)
*C07D 473/00* (2006.01)
*C07D 473/34* (2006.01)
*C07D 473/30* (2006.01)

(52) U.S. Cl.
CPC ........... *C07D 473/00* (2013.01); *C07D 473/16* (2013.01); *C07D 473/30* (2013.01); *C07D 473/34* (2013.01)

(58) Field of Classification Search
CPC .............................. A61K 31/52; C07D 473/16
See application file for complete search history.

(56) References Cited

U.S. PATENT DOCUMENTS

| | | | |
|---|---|---|---|
| 3,016,378 A | 1/1962 | Roch | |
| 7,410,990 B2 | 8/2008 | Sun et al. | |
| 8,008,307 B2 * | 8/2011 | Claiborne | C07D 213/69 514/256 |
| 8,481,550 B2 * | 7/2013 | Claiborne | C07D 213/69 514/256 |
| 8,901,136 B2 * | 12/2014 | Critchley | C07D 213/69 514/263.2 |
| 2004/0259867 A1 | 12/2004 | Fotouhi | |
| 2010/0120722 A1 | 5/2010 | Ono et al. | |
| 2010/0160288 A1 | 6/2010 | Astles et al. | |
| 2011/0086840 A1 | 4/2011 | Pei et al. | |
| 2011/0251172 A1 | 10/2011 | Rivkin et al. | |

FOREIGN PATENT DOCUMENTS

| | | |
|---|---|---|
| DE | 1115260 B | 10/1961 |
| EP | 1458380 B1 | 3/2008 |
| EP | 1753727 B1 | 11/2008 |
| GB | 864145 A | 3/1961 |
| WO | 2014100065 A1 | 6/2014 |
| WO | 2014100071 A2 | 6/2014 |
| WO | 2014123882 A1 | 8/2014 |

OTHER PUBLICATIONS

Forrest, H. S. , et al, 199. Uric acid riboside. Part I. Isolation and reinvestigation of the structure, Journal of the Chemical Society, 1961, pp. 963-968.

* cited by examiner

*Primary Examiner* — Golam M M Shameem
(74) *Attorney, Agent, or Firm* — Yong Zhao; John C. Todaro

(57) ABSTRACT

The present invention provides 2,6,7,8 Substituted Purines as described herein or a pharmaceutically acceptable salt thereof. The representative compounds are useful as inhibitors of the HDM2 protein. Also disclosed are pharmaceutical compositions comprising the above compounds and potential methods of treating cancer using the same.

15 Claims, No Drawings

2,6,7,8 SUBSTITUTED PURINES AS HDM2 INHIBITORS

CROSS REFERENCE TO RELATED APPLICATIONS

This application is a U.S. National Phase application under 35 U.S.C. §371 of PCT Application No. PCT/US2014/013566 filed Jan. 29, 2014, which claims priority from U.S. Provisional Application Ser. No. 61/758,396, filed Jan. 30, 2013.

FIELD OF THE INVENTION

The present invention relates to novel compounds useful as Human Double Minute 2 ("HDM2") protein inhibitors, regulators or modulators, pharmaceutical compositions containing the compounds and potential methods of treatment using the compounds and compositions to potentially treat diseases such as, for example, cancer, diseases involving abnormal cell proliferation, and diseases caused by inadequate p53 levels.

BACKGROUND OF THE INVENTION

The tumor suppressor protein p53 plays a central role in maintaining the integrity of the genome in a cell by regulating the expression of a diverse array of genes responsible for DNA repair, cell cycle and growth arrest, and apoptosis [May et al., Oncogene 18 (53) (1999) p. 7621-7636; Oren, Cell Death Differ. 10 (4) (2003) p. 431-442, Hall and Peters, Adv. Cancer Res., 68: (1996) p. 67-108; Hainaut et al., Nucleic Acid Res., 25: (1997) p. 151-157; Sherr, Cancer Res., 60: (2000) p. 3689-95]. In response to oncogenic stress signals, the cell triggers the p53 transcription factor to activate genes implicated in the regulation cell cycle, which thereby initiates either apoptosis or cell cycle arrest. Apoptosis facilitates the elimination of damaged cells from the organism, while cell cycle arrest enables damaged cells to repair genetic damage [reviewed in Ko et al., Genes & Devel. 10: (1996) p. 1054-1072; Levine, Cell 88: (1997) p. 323-331]. The loss of the safeguard functions of p53 predisposes damaged cells to progress to a cancerous state. Inactivating p53 in mice consistently leads to an unusually high rate of tumors [Donehower et al., Nature, 356: (1992) p. 215-221].

The p53 transcription factor promotes the expression of a number of cell cycle regulatory genes, including its own negative regulator, the gene encoding the Mouse Double Minute 2 (MDM2) protein [Chene, Nature Reviews Cancer 3: (2003) p. 102-109; Momand, Gene 242 (1-2): (2000) p. 15-29; Zheleva et al. Mini. Rev. Med. Chem. 3 (3): (2003) p. 257-270]. The MDM2 protein (designated HDM2 in humans) acts to down-regulate p53 activity in an auto-regulatory manner [Wu et al, Genes Dev., 7: (1993) p. 1126-1132; Bairak et al., EMBO J, 12: (1993) p. 461-468]. In the absence of oncogenic stress signals, i.e., under normal cellular conditions, the MDM2 protein serves to maintain p53 activity at low levels [Wu et al, Genes Dev., 7: (1993) p. 1126-1132; Barak et al., EMBO J, 12: (1993) p. 461-468]. However, in response to cellular DNA damage or under cellular stress, p53 activity increases helping to prevent the propagation of permanently damaged clones of cells by induction of cell cycle and growth arrest or apoptosis.

The regulation of p53 function relies on an appropriate balance between the two components of this p53-MDM2 auto-regulatory system. Indeed, this balance appears to be essential for cell survival. There are at least three ways that MDM2 acts to down-regulate p53 activity. First, MDM2 can bind to the N-terminal transcriptional activation domain of p53 to block expression of p53-responsive genes [Kussie et al., Science, 274: (1996) p. 948-953; Oliner et al., Nature, 362: (1993) p. 857-860; Momand et al, Cell, 69: (1992) p. 1237-1245]. Second, MDM2 shuttles p53 from the nucleus to the cytoplasm to facilitate the proteolytic degradation of p53 [Roth et al, EMBO J, 17: (1998) p. 554-564; Freedman et al., Mol Cell Biol, 18: (1998) p. 7288-7293; Tao and Levine, Proc. Natl. Acad. Sci. 96: (1999) p. 3077-3080]. Finally, MDM2 possesses an intrinsic E3 ligase activity for conjugating ubiquitin to p53 for degradation within the ubiquitin-dependent 26S proteosome pathway [Honda et al., FEBS Lett, 420: (1997) p. 25-27; Yasuda, Oncogene 19: (2000) p. 1473-1476]. Thus, MDM2 impedes the ability of the p53 transcription factor to promote the expression of its target genes by binding p53 in the nucleus. Attenuating the p53-MDM2 auto-regulatory system can have a critical effect on cell homeostasis. Consistently, a correlation between the overexpression of MDM2 and tumor formation has been reported [Chene, Nature 3: (2003) p. 102-109]. Functional inactivation of wild type p53 is found in many types of human tumors. Restoring the function of p53 in tumor cells by anti-MDM2 therapy would result in slowing the tumor proliferation and instead stimulate apoptosis. Not surprisingly then, there is currently a substantial effort being made to identify new anticancer agents that hinder the ability of HDM2 to interact with p53 [Chene, Nature 3: (2003) p. 102-109]. Antibodies, peptides, and antisense oligonucleotides have been demonstrated to destroy the p53-MDM2 interaction, which would release p53 from the negative control of MDM2, leading to activation of the p53 pathway allowing the normal signals of growth arrest and/or apoptosis to function, which offers a potential therapeutic approach to treating cancer and other diseases characterized by abnormal cell proliferation. [See, e.g., Blaydes et al., Oncogene 14: (1997) p. 1859-1868; Bottger et al., Oncogene 13 (10): (1996) p. 2141-2147].

Small molecules, said to antagonize the p53-MDM2 interaction, have been described. WO 00/15657 (Zeneca Limited) describes piperizine-4-phenyl derivatives as inhibitors of the interaction between MDM2 and p53. Grasberger et al. (J. Med. Chem., 48 (2005) p. 909-912) (Johnson & Johnson Pharmaceutical Research & Development L.L.C.) describes discovery and co-crystal structure of benzodiazepinedione as HDM2 antagonists that activate p53 in cells. Galatin et al. (J. Med. Chem. 47 (2004) p. 4163-4165) describes a nonpeptidic sulfonamide inhibitor of the p53-MDM2 interaction and activator of p53 dependent transcription in MDM2-overexpressing cells.

U.S. Pub. No. 2004/0259867 A1 and 2004/0259884 A1 describes Cis-imidazoles (Hoffmann La Roche Inc.) and WO2005/110996A1 and WO 03/051359 describes Cis-Imidazolines (Hoffmann La Roche Inc.) as compounds that inhibit the interaction of MDM2 with p53-like peptides resulting in antiproliferation. WO 2004/080460 A1 describes substituted piperidine compounds as MDM2-p53 inhibitors for treating cancer (Hoffmann La Roche Inc.). EP 0947494 A1 describes phenoxy acetic acid derivatives and phenoxy methyltetrazole that act as antagonists of MDM2 and interfere with the protein-protein interaction between MDM2 and p53, which results in anti-tumor properties (Hoffmann La Roche Inc.). Duncan et al., J. Am. Chem. Soc. 123 (4): (2001) p. 554-560 describes a p-53-MDM2 antagonist, chlorofusin, from a *Fusarium* Sp. Stoll et al., Biochemistry 40 (2) (2001) p. 336-344 describes chalcone derivatives that antagonize interactions between the human oncoprotein MDM2 and p53.

There is a need for effective inhibitors of the HDM2 or MDM2 protein in order to treat or prevent cancer, other disease states associated with cell proliferation, diseases associated with HDM2, or diseases caused by inadequate p53 activity. The present application discloses compounds that have potency in inhibiting or antagonizing the HDM2-p53 and MDM2-p53 interaction and/or activating p53 proteins in cells.

In its many embodiments, the present invention provides novel compounds having HDM2 or MDM2 antagonist activity, methods of preparing such compounds, pharmaceutical compositions comprising one or more of such compounds, methods of preparing pharmaceutical formulations comprising one or more of such compounds, potential methods of treatment or prevention of one or more diseases associated with HDM2, MDM2, p53, or p53 peptides by administering such compounds or pharmaceutical compositions.

SUMMARY OF THE INVENTION

In its many embodiments, the present invention provides a novel class of 2,6,7,8 Substituted Purine compounds, pharmaceutical compositions comprising one or more said compounds, and potential methods for using said compounds for treating or preventing a disease associated with the HDM2 protein.

Accordingly, in one aspect the present invention provides a compound of Formula I:

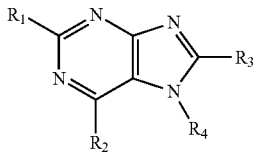

I

DETAILED DESCRIPTION OF THE INVENTION

In one embodiment, the present invention provides compounds illustrated as Formula I, as described above, or pharmaceutically acceptable salts thereof. Accordingly, in one aspect the present invention provides a compound of Formula I:

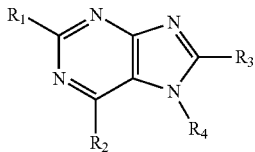

I

Wherein
$R^1$ is selected from the group consisting of $C_1$-$C_6$alkyl, —$(CR^a{}_2)_n$COOR$^{11}$, —$(CR^a{}_2)_n$NR$^5$SO$_2$R$^6$, —$(CR^a{}_2)_n$SO$_2$NR$^5$R$^6$, —$(CR^a{}_2)_n$C(O)NR$^c$SO$_2$N(R$^c$)$_2$, —$(CR^a{}_2)_n$C(O)R$^5$, —$(CR^a{}_2)_n$CONR$^5$R$^6$, —$(CR^a{}_2)_n$CONR$^5$SO$_2$R$^6$, —$(CR^a{}_2)_n$CONR$^5$OR$^6$, —$(CR^a{}_2)_n$OR$^5$, —$(CR^a{}_2)_n$S(O)R$^c$, —$(CR^a{}_2)_n$S(O)$_2$R$^c$, and nitrogen containing 5 or 6-membered heteroaryl, heterocyclic and heterocyclenyl ring, wherein the alkyl and 5 or 6-membered ring can be optionally substituted with OR$^c$, SR$^c$, NH$_2$, nitro, CN, amide, COOR$^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^2$ is selected from the group consisting of aryl, heteroaryl, $C_3$-$C_8$cycloalkyl, —W—(CR$^a$R$^9$)$_r$R$^7$, and heterocyclic, wherein W is NR$^c$ or O, wherein the aryl, heteroaryl, cycloalkyl or heterocyclic is optionally substituted with R$^{12}$ selected from the group consisting of halo, CN, haloC$_1$-C$_6$alkyl, $C_1$-$C_6$alkyl, —$(CR^a{}_2)_z$OR$^8$, —$(CR^a{}_2)_z$NHR$^8$, —$(CR^a{}_2)_z$C(O)NR$^c$R$^c$, —$(CR^a{}_2)_z$COOR$^{10}$, —$(CR^a{}_2)_z$S(O)$_2$R$^c$, —$(CR^a{}_2)_z$aryl, —$(CR^a{}_2)_z$heteroaryl, —$(CR^a{}_2)_z$heterocyclic, —$(CR^a{}_2)_z$C$_3$-C$_8$cycloalkyl, —$(CR^a{}_2)_z$cyclenyl, and —$(CR^a{}_2)_z$heterocyclenyl, wherein the alkyl, aryl, heteroaryl, heterocyclic, cycloalkyl, cyclenyl and heterocyclenyl of $R^{12}$ can be optionally substituted with OH, NH$_2$, nitro, CN, CON(R$^c$)$_2$, —$(CR^a{}_2)_z$COOR$^{10}$, $C_1$-$C_6$alkoxy, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_2$-$C_6$)alkylamino;

$R^3$ is selected from the group consisting of —$(CR^a{}_2)_q$NR$^c$R$^8$, —$(CR^a{}_2)_q$OR$^8$, —$(CR^a{}_2)_q$SR$^8$, —$(CR^a{}_2)_q$C(O)R$^8$, —$(CR^a{}_2)_q$S(O)R$^8$, —$(CR^a{}_2)_q$S(O)$_2$R$^8$, —$(CR^a{}_2)_q$CONR$^c$R$^8$, —$(CR^a{}_2)_q$NR$^c$C(O)R$^8$, -T-$C_1$-$C_6$alkyl, $C_2$-$C_6$alkenyl, -T-aryl, -T-heteroaryl, -T-heterocyclic, -T-$C_3$-$C_8$cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, SR$^c$, OR$^c$, haloC$_1$-C$_6$alkyl, haloC$_1$-C$_6$alkoxy, —$(CR^a{}_2)_z$CN, $C_1$-$C_6$alkyl, $C_2$-$C_6$alkenyl, $C_2$-$C_6$alkynyl, —$(CR^a{}_2)_z$C(O)OR$^{10}$, $(CR^a{}_2)_z$C(O)R$^8$, —$(CR^a{}_2)_z$OR$^8$, —$(CR^a{}_2)_z$NR$^c$R$^8$, —$(CR^a{}_2)_z$S(O)$_2$R$^8$, —$(CR^a{}_2)_z$C(O)NR$^c$R$^8$, —$(CR^a{}_2)_z$aryl, —$(CR^a{}_2)_z$heteroaryl, —$(CR^a{}_2)_z$ $C_3$-$C_8$cycloalkyl, —$(CR^a{}_2)_z$heterocyclic, —$(CR^a{}_2)_z$heterocyclenyl, —$(CR^a{}_2)_z$cyclenyl, —$(CR^a{}_2)_z$SO$_2$NR$^c$R$^8$, or —$(CR^a{}_2)_z$O(CR$^a{}_2)_z$D(CR$^a{}_2)_v$Q, said alkyl, alkenyl, alkynyl, aryl, heteroaryl, cycloalkyl, heterocyclic, heterocyclenyl and cyclenyl can further be optionally substituted with SH, OH, NH$_2$, nitro, CN, CON (R$^c$)$_2$, COOR$^{10}$, $C_1$-$C_6$alkoxy, $C_1$-$C_6$alkyl, $C_2$-$C_6$alkenyl, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^4$ is selected from the group consisting of $C_1$-$C_6$alkyl, —$(CR^a{}_2)_m$aryl, —$(CR^a{}_2)_m$heteroaryl, —$(CR^a{}_2)_m$heterocyclic, —$(CR^a{}_2)_m$C$_3$-C$_8$cycloalkyl, —$(CR^a{}_2)_m$cyclenyl, and —$(CR^a{}_2)_m$heterocyclenyl, wherein the alkyl, aryl, heteroaryl, heterocyclic, cycloalkyl, cyclenyl, and heterocyclenyl can be optionally substituted with OH, SH, NH$_2$, nitro, CN, CON(R$^c$)$_2$, COOR$^{10}$, $C_1$-$C_6$alkoxy, $C_1$-$C_6$alkyl, $C_3$-$C_6$cycloalkyl, haloC$_2$-C$_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^5$ is independently selected from the group consisting of H, $C_1$-$C_6$alkyl, —$C_0$-$C_6$alkyl-$C_3$-$C_8$cycloalkyl, —$C_0$-$C_6$alkylheteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, and heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkyloxy, $C_2$-$C_6$alkenyl, $C_2$-$C_6$alkynyl, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, —$C_0$-$C_6$alkylheterocyclic, —$C_0$-$C_6$alkylheterocyclenyl, —$C_0$-$C_6$alkylcyclenyl, —$(CR^a_2)_n NR^5 R^6$, —$(CR^a_2)_z NR^5 SO_2 R^6$, —$(CR^a_2)_z SO_2 NR^5 R^6$, —$(CR^a_2)_z C(O)R^5$, —$(CR^a_2)_z C(O)OR^{10}$, —$(CR^a_2)_z CONR^5 R^6$, —$(CR^a_2)_z CONR^5 OR^6$, —$(CR^a_2)_z NR^5 C(O)OR^6$, —$(CR^a_2)_z NR^5 C(O)R^6$, —$(CR^a_2)_z OR^5$, —$(CR^a_2)_z S(O)R^c$, and —$(CR^a_2)_z S(O)_2 R$;

$R^8$ is independently selected from the group consisting of H, —$(CR^a_2)_s$-heteroaryl, —$(CR^a_2)_s$-aryl, —$(CR^a_2)_s$-heterocyclic, —$(CR^a_2)_s$-heterocyclenyl, —$(CR^a_2)_s$-cyclenyl, —$(CR^a_2)_s C_3$-$C_8$cycloalkyl, and $C_1$-$C_6$alkyl, wherein the heteroaryl, aryl, heterocyclic, heterocyclenyl, cyclenyl, cycloalkyl, and alkyl can be optionally substituted with OH, —$N(R^c)_2$, $NH_2$, nitro, CN, $CON(R^c)_2$, $COOR^{10}$, $C_1$-$C_6$alkoxy, $C_1$-$C_6$alkyl, $C_2$-$C_6$alkenyl, $C_3$-$C_6$cycloalkyl, $C_1$-$C_6$haloalkyl, $C_1$-$C_6$haloalkyloxy, $C_1$-$C_6$hydroxyalkyl, $C_1$-$C_6$alkyl-C(O)O—, $C_1$-$C_6$alkyl-C(=C(O))—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino, di($C_1$-$C_6$)alkylamino, heteroaryl, aryl, heterocyclic, heterocyclenyl, or cyclenyl;

$R^9$ is independently selected from the group consisting of H, $C_1$-$C_6$alkyl, $C_1$-$C_6$haloalkyl, $C_3$-$C_8$cycloalkyl, aryl, heteroaryl, and heterocyclic, wherein the alkyl, cycloalkyl, aryl, heteroaryl, and heterocyclic can be optionally substituted with —$C_0$-$C_6$alkylOR$^c$, $C_0$-$C_6$alkylN($R^c$)$_2$, $COOR^{10}$, nitro, CN, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(O)O—, $C_1$-$C_6$alkyl-C(=O)—, $C_2$-$C_6$alkynyl, halo group, hydroxyalkoxy, —$SO_2 NR^c R^c$, $NR^c SO_2 R^c$, $C_1$-$C_6$alkylsulfonyl, heterocylic, or C(O)NHR$^c$;

$R^{10}$ is independently selected from the group consisting of $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic, wherein the heteroaryl, aryl, heterocyclic, cycloalkyl and alkyl can be optionally substituted with $C_1$-$C_6$alkyl, OH, halo, or halo$C_1$-$C_6$alkyl;

$R^{11}$ is independently selected from the group consisting of H, $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic wherein the heteroaryl, aryl, heterocyclic, cycloalkyl and alkyl can be optionally substituted with $C_1$-$C_6$alkyl, OH, halo, or halo$C_1$-$C_6$alkyl;

$R^a$ is independently H, OR$^c$, NH$_2$, halo, $C_1$-$C_3$alkyl, or $C_2$-$C_4$alkenyl, said alkyl or alkenyl is optionally substituted with OH, $C_1$-$C_4$alkoxy, NH$_2$, halo, halo$C_1$-$C_4$alkyl, $C_3$-$C_6$cycloalkyl, or $C_2$-$C_4$alkenyl;

$R^c$ is independently H or $C_1$-$C_3$alkyl optionally substituted with $C_2$-$C_3$alkenyl, $C_3$-$C_6$cycloalkyl, $C_1$-$C_3$alkoxy, OH, halo, NH$_2$, $C_1$-$C_3$alkylamino, or $C_1$-$C_3$dialkylamino;

T is independently $C_2$-$C_3$alkenyl, —$(CR^a_2)_q$—, —C(=CH$_2$)—, —$(CR^a_2)_q$—C(=CH$_2$)—, —C(=CH$_2$)—$(CR^a_2)_q$—, —C(=NH)—, —$(CR^a_2)_q$—C(=NH)—, or —C(=NH)—$(CR^a_2)_q$—;

D is a bond, —C(O)NR$^c$—, —NR$^c$C(O)—, or —NR$^c$—;
Q is H, COOR$^{10}$, OH, heteroaryl or heterocyclic;
n is independently 0, 1, 2 or 3;
m is independently 0, 1 or 2;
q is independently 0, 1, 2, or 3;
s is independently 0, 1 or 2;
t is independently 0, 1, or 2;
v is independently 1, 2, 3 or 4;
z is independently 0, 1, 2 or 3;
or a pharmaceutically acceptable salt thereof.

In one aspect of the invention,
$R^1$ is selected from the group consisting of $C_1$-$C_6$alkyl, —$(CR^a_2)_n COOR^{11}$, —$(CR^a_2)_n NR^5 SO_2 R^6$, —$(CR^a_2)_n SO_2 NR^5 R^6$, —$(CR^a_2)_n C(O)NR^c SO_2 N(R^c)_2$, —$(CR^a_2)_n C(O)R^5$, —$(CR^a_2)_n CONR^5 R^6$, —$(CR^a_2)_n CONR^c SO_2 R^6$, —$(CR^a_2)_n CONR^5 OR^6$, —$(CR^a_2)_n OR^5$, —$(CR^a_2)_n S(O)R^c$, —$(CR^a_2)_n S(O)_2 R^c$, and nitrogen containing 5 or 6-membered heteroaryl, heterocyclic and heterocyclenyl ring, wherein the alkyl and 5 or 6-membered ring can be optionally substituted with OR$^c$, SR$^c$, NH$_2$, nitro, CN, amide, COOR$^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, —W—$(CR^a R^9)_t R^7$, and heterocyclic, wherein W is NR$^c$ or O, wherein the aryl, heteroaryl, or heterocyclic is optionally substituted with $R^{12}$ selected from the group consisting of halo, CN, halo$C_1$-$C_6$alkyl, $C_1$-$C_6$alkyl, —$(CR^a_2)_z OR^c$, —$(CR^a_2)_z NR^8$, —$(CR^a_2)_z C(O)NR^c R^c$, —$(CR^a_2)_z COOR^{10}$, —$(CR^a_2)_z$aryl, —$(CR^a_2)_z$heteroaryl, —$(CR^a_2)_z$heterocyclic, —$(CR^a_2)_z C_3$-$C_8$cycloalkyl, —$(CR^a_2)_z$cyclenyl, and —$(CR^a_2)_z$heterocyclenyl, wherein the alkyl, aryl, heteroaryl, heterocyclic, cycloalkyl, cyclenyl and heterocyclenyl of $R^{12}$ can be optionally substituted with OH, NH$_2$, nitro, CN, CON($R^c$)$_2$, —$(CR^a_2)_z COOR^{10}$, $C_1$-$C_6$alkoxy, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^3$ is selected from the group consisting of —$(CR^a_2)_q NR^c R^8$, —$(CR^a_2)_q OR^8$, —$(CR^a_2)_q SR^8$, —$(CR^a_2)_q C(O)R^8$, —$(CR^a_2)_q S(O)R^8$, —$(CR^a_2)_q S(O)_2 R^8$, —$(CR^a_2)_q CONR^c R^8$, —$(CR^a_2)_q NR^c C(O)R^8$, -T-$C_1$-$C_6$alkyl, $C_2$-$C_6$alkenyl, -T-aryl, -T-heteroaryl, -T-heterocyclic, -T-$C_3$-$C_8$cycloalkyl, -T-cyclenyl, and -T-heterocyclenyl,
wherein the alkyl, alkenyl, aryl, heteroaryl, heterocyclic, cycloalkyl, cyclenyl and heterocyclenyl can be optionally substituted with halo, OR$^c$, SH, halo$C_1$-$C_6$alkyl, halo$C_1$-$C_6$alkoxy, —$(CR^a_2)_z CN$, $C_1$-$C_6$alkyl, $C_2$-$C_6$alkenyl, $C_2$-$C_6$alkynyl, —$(CR^a_2)_z C(O)OR^1$, —$(CR^a_2)_z C(O)R^8$, —$(CR^a_2)_z OR^8$, —$(CR^a_2)_z NR^c R^8$, —$(CR^a_2)_z S(O)_2 R^8$, —$(CR^a_2)_z C(O)NR^c R^8$, —$(CR^a_2)_z$aryl, —$(CR^a_2)_z$heteroaryl, —$(CR^a_2)_z C_3$-$C_8$cycloalkyl, —$(CR^a_2)_z$heterocyclic, —$(CR^a_2)_z$heterocyclenyl, —$(CR^a_2)_z$cyclenyl, —$(CR^a_2)_z SO_2 NR^c R^8$, or —$(CR^a_2)_z O(CR^a_2)_z D(CR^a_2)_v Q$, said alkyl, alkenyl, alkynyl, aryl, heteroaryl, cycloalkyl, heterocyclic, heterocyclenyl and cyclenyl can further be optionally substituted with OH, SH, $NH_2$, nitro, CN, CON$(R^c)_2$, $COOR^{10}$, $C_1$-$C_6$alkoxy, $C_1$-$C_6$alkyl, $C_2$-$C_6$alkenyl, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(O)—, $C_2$-$C_6$alkynyl, halo group, hydroxyalkoxy, —$SO_2NR^cR^c$, $NR^cSO_2R^c$, $C_1$-$C_6$alkylsulfonyl, $C_1$-$C_6$alkylamino or di($C_1$-$C_6$)alkylamino;

$R^4$ is selected from the group consisting of $C_1$-$C_6$alkyl, —$(CR^a{}_2)_m$aryl, —$(CR^a{}_2)_m$heteroaryl, —$(CR^a{}_2)_m$heterocyclic, —$(CR^a{}_2)_m C_3$-$C_8$cycloalkyl, —$(CR^a{}_2)_m$cyclenyl, and —$(CR^a{}_2)_m$heterocyclenyl, wherein the alkyl, aryl, heteroaryl, heterocyclic, cycloalkyl, cyclenyl, and heterocyclenyl can be optionally substituted with OH, SH, $NH_2$, nitro, CN, CON$(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, $NR^cSO_2R^c$, $C_1$-$C_6$alkylsulfonyl, $C_1$-$C_6$alkylamino or di($C_1$-$C_6$)alkylamino;

$R^5$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, and heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkyloxy, $C_2$-$C_6$alkenyl, $C_2$-$C_6$alkynyl, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, —$C_0$-$C_6$alkylheterocyclic, —$C_0$-$C_6$alkylheterocyclenyl, —$C_0$-$C_6$alkylcyclenyl, —$(CR^a{}_2)_z NR^5R^6$, —$(CR^a{}_2)_z NR^5SO_2R^6$, —$(CR^a{}_2)_z SO_2NR^5R^6$, —$(CR^a{}_2)_z C(O)R^5$, —$(CR^a{}_2)_z C(O)OR^{10}$, —$(CR^a{}_2)_z CONR^5R^6$, —$(CR^a{}_2)_z CONR^5OR^6$, —$(CR^a{}_2)_z NR^5C(O)OR^6$, —$(CR^a{}_2)_z NR^5C(O)R^6$, —$(CR^a{}_2)_z OR^5$, —$(CR^a{}_2)_z S(O)R^c$, and —$(CR^a{}_2)_z S(O)_2R$;

$R^8$ is independently selected from the group consisting of H, —$(CR^a{}_2)_s$-heteroaryl, —$(CR^a{}_2)_s$-aryl, —$(CR^a{}_2)_s$-heterocyclic, —$(CR^a{}_2)_s$-heterocyclenyl, —$(CR^a{}_2)_s$-cyclenyl, —$(CR^a{}_2)_s C_3$-$C_8$cycloalkyl, and $C_1$-$C_6$alkyl, wherein the heteroaryl, aryl, heterocyclic, heterocyclenyl, cyclenyl, cycloalkyl, and alkyl can be optionally substituted with OH, —$N(R^c)_2$, $NH_2$, nitro, CN, CON$(R^c)_2$, $COOR^{10}$, $C_1$-$C_6$alkoxy, $C_1$-$C_6$alkyl, $C_2$-$C_6$alkenyl, $C_3$-$C_6$cycloalkyl, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, $NR^cSO_2R^c$, $C_1$-$C_6$alkylsulfonyl, $C_1$-$C_6$alkylamino, di($C_1$-$C_6$)alkylamino, heteroaryl, aryl, heterocyclic, heterocyclenyl, or cyclenyl;

$R^9$ is selected from the group consisting of H, $C_1$-$C_6$alkyl, $C_1$-$C_6$haloalkyl, $C_3$-$C_8$cycloalkyl, aryl, heteroaryl, and heterocyclic, wherein the alkyl, cycloalkyl, aryl, heteroaryl, and heterocyclic can be optionally substituted with —$C_0$-$C_6$alkyl$OR^c$, $C_0$-$C_6$alkyl$N(R^c)_2$, $COOR^{10}$, nitro, CN, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(O)O—, $C_1$-$C_6$alkyl-C(=O)—, $C_2$-$C_6$alkynyl, halo group, hydroxyalkoxy, —$SO_2NR^cR^c$, $NR^cSO_2R^c$, $C_1$-$C_6$alkylsulfonyl, heterocylic, or C(O)$NHR^c$;

$R^{10}$ is independently selected from the group consisting of $C_1$-$C_6$alkyl, —$(CR^c{}_2)_z C_3$-$C_8$cycloalkyl, —$(CR^c{}_2)_z$-heteroaryl, —$(CR^c{}_2)_z$-aryl, and —$(CR^c{}_2)_z$-heterocyclic, wherein the heteroaryl, aryl, heterocyclic, cycloalkyl and alkyl can be optionally substituted with $C_1$-$C_6$alkyl, OH, halo, or halo$C_1$-$C_6$alkyl;

$R^{11}$ is independently selected from the group consisting of H, $C_1$-$C_6$alkyl, —$(CR^c{}_2)_z C_3$-$C_8$cycloalkyl, —$(CR^c{}_2)_z$-heteroaryl, —$(CR^c{}_2)_z$aryl, and —$(CR^c{}_2)_z$heterocyclic wherein the heteroaryl, aryl, heterocyclic, cycloalkyl and alkyl can be optionally substituted with $C_1$-$C_6$alkyl, OH, halo, or halo$C_1$-$C_6$alkyl;

$R^a$ is independently H, $OR^c$, $NH_2$, halo, $C_1$-$C_3$alkyl, or $C_2$-$C_4$alkenyl, said alkyl or alkenyl is optionally substituted with OH, $C_1$-$C_4$alkoxy, $NH_2$, halo, halo$C_1$-$C_4$alkyl, $C_3$-$C_6$cycloalkyl, or $C_2$-$C_4$alkenyl;

$R^c$ is independently H or $C_1$-$C_3$alkyl optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, or $C_1$-$C_3$dialkylamino;

T is independently $C_2$-$C_3$alkenyl, —$(CR^a{}_2)_q$—, —$C(=CH_2)$—, —$(CR^a{}_2)_q$—$C(=CH_2)$—, —$C(=CH_2)$—$(CR^a{}_2)_q$—, —$C(=NH)$—, —$(CR^a{}_2)_q$—$C(=NH)$—, or —$C(=NH)$—$(CR^a{}_2)_q$—;

D is a bond, —C(O)$NR^c$—, —$NR^c$C(O)—, or —$NR^c$—;

Q is H, $COOR^{10}$, OH, heteroaryl or heterocyclic;

n is independently 0, 1, 2 or 3;

m is independently 0, 1 or 2;

q is independently 0, 1, 2, or 3;

s is independently 0, 1 or 2;

t is independently 0, 1, or 2;

v is independently 1, 2, 3 or 4;

z is independently 0, 1, 2 or 3;

or a pharmaceutically acceptable salt thereof.

In one embodiment, $R^{1'}$ is independently $C_1$-$C_6$alkyl optionally substituted with OH, halo, or halo$C_1$-$C_6$alkyl.

In another embodiment of the invention, $R^1$ is selected from the group consisting of $C_1$-$C_6$alkyl, $COOR^{11}$, —$NR^cSO_2R^c$, —$SO_2NR^cR^c$, —C(O)$NR^cSO_2N(R^c)_2$, —C(O)$R^c$, —$CONR^cR^c$, —$CONR^cOR^c$, —$CONR^cSO_2R^c$, —$OR^c$, —S(O)$R^c$, —S(O)$_2R^c$, and nitrogen containing 5-membered heteroaryl, heterocyclic and heterocyclenyl ring, wherein the alkyl and 5-membered ring can be optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, $NR^cSO_2R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, W—$(CR^aR^9)R^7$, and heterocyclic, wherein W is $NR^c$ or O, wherein the aryl, heteroaryl, and heterocyclic is optionally substituted with $R^{12}$ selected from the group consisting of halo, CN, halo$C_1$-$C_6$alkyl, $C_1$-$C_6$alkyl, —$(CR^a{}_2)OR^c$, and —$(CR^a{}_2)C(O)NR^cR^c$, wherein the alkyl of $R^{12}$ can be optionally substituted with OH, CN, halo, halo$C_1$-$C_6$alkyl, or CON$(R^c)_2$;

$R^3$ is selected from the group consisting of —$NR^cR^8$, —$OR^8$, —$SR^8$, —$C(O)R^8$, —$S(O)R^8$, —$S(O)_2R^8$, —$CONR^cR^8$, —$NR^cC(O)R^8$, -T-$C_1$-$C_6$alkyl, $C_2$-$C_6$alkenyl, -T-aryl, -T-heteroaryl, -T-heterocyclic, -T-cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, $OR^c$, SH, halo$C_1$-$C_6$alkyl, halo$C_1$-$C_6$alkoxy, —$(CR^a_2)_zCN$, $C_1$-$C_6$alkyl, $C_2$-$C_6$alkenyl, $C_2$-$C_6$alkynyl, —$(CR^a_2)_zC(O)OR^{10}$, —$(CR^a_2)_zC(O)R^8$, —$(CR^a_2)_zOR^8$, —$(CR^a_2)_zNR^cR^8$, —$(CR^a_2)_zS(O)_2R^8$, —$(CR^a_2)_zC(O)NR^cR^8$, —$(CR^a_2)_z$aryl, —$(CR^a_2)_z$heteroaryl, —$(CR^a_2)_zC_3$-$C_8$cycloalkyl, —$(CR^a_2)_z$heterocyclic, —$(CR^a_2)_zSO_2NR^cR^8$, or —$(CR^a_2)_zO(CR^a_2)_zD(CR^a_2)_vQ$, said alkyl, alkenyl, alkynyl, aryl, heteroaryl, cycloalkyl, and heterocyclic can further be substituted with OH, SH, halo, or $C_2$-$C_6$alkenyl;

$R^4$ is selected from the group consisting of —$(CR^a_2)$aryl, —$(CR^a_2)$heteroaryl, —$(CR^a_2)$heterocyclic, —$(CR^a_2)C_3$-$C_8$cycloalkyl, —$(CR^a_2)$cyclenyl, and —$(CR^a_2)$heterocyclenyl, wherein the aryl, heteroaryl, heterocyclic, cycloalkyl, cyclenyl, and heterocyclenyl can be optionally substituted with OH, SH, $NH_2$, nitro, CN, $CON(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(O)—, $C_2$-$C_6$alkynyl, halo group, hydroxyalkoxy, —$SO_2NR^cR^c$, $NR^cSO_2R^c$, $C_1$-$C_6$alkylsulfonyl, $C_1$-$C_6$alkylamino or di($C_1$-$C_6$)alkylamino;

$R^7$ is selected from the group consisting of $C_1$-$C_6$alkyl, $C_3$-$C_8$cycloalkyl, heteroaryl, aryl, and heterocyclic, wherein the alkyl, cycloalkyl, heteroaryl, aryl or heterocyclic can be optionally substituted with halo, nitro, CN, $C_1$-$C_6$haloalkyl, $C_1$-$C_6$haloalkyloxy, $C_1$-$C_6$alkyl, or —$(CR^a_2)_zOR^c$;

$R^8$ is independently selected from the group consisting of —$(CR^a_2)$-heteroaryl, —$(CR^a_2)$-aryl, —$(CR^a_2)$-heterocyclic, —$(CR^a_2)$-heterocyclenyl, —$(CR^a_2)$cyclenyl, —$(CR^a_2)$cycloalkyl, and $C_1$-$C_6$alkyl, wherein the heteroaryl, aryl, heterocyclic, heterocyclenyl, cyclenyl, cycloalkyl, and alkyl can be optionally substituted with OH, $N(R^c)_2$, $C_1$-$C_6$alkoxy, $C_1$-$C_6$alkyl, $C_3$-$C_6$cycloalkyl, $C_1$-$C_6$haloalkyl, $C_1$-$C_6$haloalkyloxy, $C_1$-$C_6$hydroxyalkyl, or halo group;

$R^9$ is H, $C_1$-$C_3$alkyl, $C_1$-$C_3$haloalkyl, $C_3$-$C_4$cycloalkyl, wherein the alkyl or cycloalkyl can be optionally substituted with $OR^c$, $N(R^c)_2$, heterocyclic, $C(O)NHCH_2CH_2OH$, $C(O)NH_2$, or $C(O)NHC_1$-$C_3$alkyl;

$R^{10}$ is independently $C_1$-$C_6$alkyl optionally substituted with OH, halo, or halo$C_1$-$C_6$alkyl;

$R^{11}$ is independently selected from the group consisting of H and $C_1$-$C_6$alkyl, wherein alkyl can be optionally substituted with OH or halo;

$R^a$ is independently H, $OR^c$, $NH_2$, halo, $C_1$-$C_3$alkyl, or $C_2$-$C_4$alkenyl, said alkyl or alkenyl is optionally substituted with OH, $C_1$-$C_4$alkoxy, $NH_2$, F, $CF_3$, $C_3$-$C_6$cycloalkyl, or $C_2$-$C_4$alkenyl;

$R^c$ is independently H or $C_1$-$C_3$alkyl optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, or $C_1$-$C_3$dialkylamino;

T is independently $C_2$-$C_3$alkenyl, —$(CR^a_2)_q$—, or —$C(=CH_2)$—;

D is a bond, —$C(O)NR^c$—, —$NR^cC(O)$—, or —$NR^c$—;

Q is H, $COOR^{10}$, OH, heteroaryl or heterocyclic;

q is independently 0 or 1;

v is independently 1 or 2; and z is independently 0, 1 or 2.

and all other substituents are defined in the proceeding paragraphs.

In one embodiment, $R^8$ is —$(CR^a_2)_s$-heteroaryl, and the heteroaryl is pyrimidinyl, pyrazolyl, pyrazinyl, thiazolyl, or oxadiazolyl.

In another embodiment of the invention, $R^1$ is selected from the group consisting of $COOR^{11}$, —$NR^cSO_2R^c$, —$SO_2NR^cR^c$, —$C(O)NR^cSO_2N(R^c)_2$, $C(O)NR^cSO_2R^c$, —$C(O)R^c$, —$CONR^cR^c$, —$CONR^cOR^c$, —$OR^c$, —$S(O)R^c$, —$S(O)_2R^c$, and nitrogen containing 5-membered heterocyclic, heteroaryl and heterocyclenyl ring, wherein the 5-membered ring can be optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, and —$NR^c$—$(CR^aR^9)R^7$, wherein the aryl, or heteroaryl is optionally substituted with $R^{12}$ selected from the group consisting of halo, CN, halo$C_1$-$C_6$alkyl, $C_1$-$C_6$alkyl, —$(CR^a_2)OR^c$, wherein the alkyl of $R^{12}$ can be optionally substituted with OH, CN, halo, halo$C_1$-$C_6$alkyl, or $CON(R^c)_2$;

$R^3$ is selected from the group consisting of —$NR^cR^8$, -T-heteroaryl, and -T-heterocyclic, wherein the heteroaryl, and heterocyclic can be optionally substituted with halo, $OR^c$, SH, halo$C_1$-$C_6$alkyl, halo$C_1$-$C_6$alkoxy, —$(CR^a_2)_zCN$, $C_1$-$C_6$alkyl, $C_2$-$C_6$alkenyl, $C_2$-$C_6$alkynyl, —$(CR^a_2)_zC(O)OR^{10}$, —$(CR^a_2)_zC(O)R^8$, —$(CR^a_2)_zOR^8$, —$(CR^a_2)_zNR^cR^8$, —$(CR^a_2)_zS(O)_2R^8$, —$(CR^a_2)_zC(O)NR^cR^8$, —$(CR^a_2)_z$aryl, —$(CR^a_2)_z$heteroaryl, —$(CR^a_2)_zC_3$-$C_8$cycloalkyl, —$(CR^a_2)_z$heterocyclic, —$(CR^a_2)_zSO_2NR^cR^8$, or —$(CR^a_2)_zO(CR^a_2)_zD(CR^a_2)_vQ$;

said alkyl, alkenyl, alkynyl, aryl, heteroaryl, cycloalkyl, and heterocyclic can further be optionally substituted with OH, SH, halo, or $C_2$-$C_6$alkenyl;

$R^4$ is selected from the group consisting of —$(CR^a_2)$aryl, —$(CR^a_2)C_3$-$C_6$cycloalkyl, and —$(CR^a_2)C_3$-$C_6$cyclenyl, wherein the aryl, cycloalkyl, and cyclenyl can be optionally substituted with OH, SH, $NH_2$, nitro, CN, $CON(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(O)O—, $C_1$-$C_6$alkyl-C(=O)—, $C_2$-$C_6$alkynyl, halo group, hydroxyalkoxy, —$SO_2NR^cR^c$, $NR^cSO_2R^c$, $C_1$-$C_6$alkylsulfonyl, $C_1$-$C_6$alkylamino or di($C_1$-$C_6$)alkylamino;

$R^7$ is $C_3$-$C_6$cycloalkyl optionally substituted with halo, nitro, CN, $C_1$-$C_6$haloalkyl, $C_1$-$C_6$haloalkyloxy, $C_1$-$C_6$alkyl, or —$(CR^a_2)_zOR^c$;

$R^9$ is $C_1$-$C_3$alkyl;

and all other substituents are as defined above.

In one aspect of the invention for the foregoing embodiments, $R^1$ is COOH or a nitrogen containing 5-membered heteroaryl, heterocyclic or heterocyclenyl ring selected from the group consisting of tetrazolyl, oxadiazolyl, oxadiazolone, dihydro-oxadiazolyl, triazolyl, dihydro-triazolyl, dihydro-triazolone, pyrrolidinyl, and imidazolyl, wherein the nitrogen containing 5-membered ring can be optionally substituted with halo, $C_1$-$C_6$alkyl, halo$C_1$-$C_6$alkyl, $NH_2$, $OR^c$, $SR^c$, COOH, or —$NR^cSO_2R^c$.

In one embodiment, $R^1$ is COOH

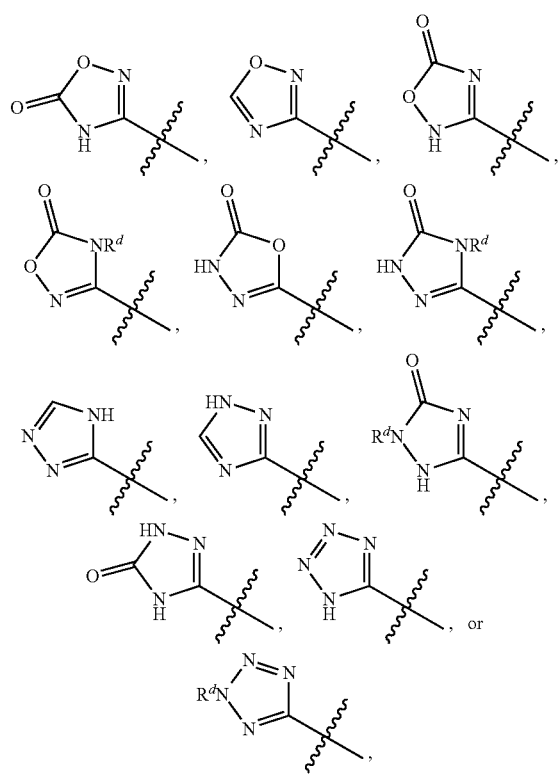

wherein $R^d$ is $CH_3$ or H.

In one embodiment, $R^1$ is

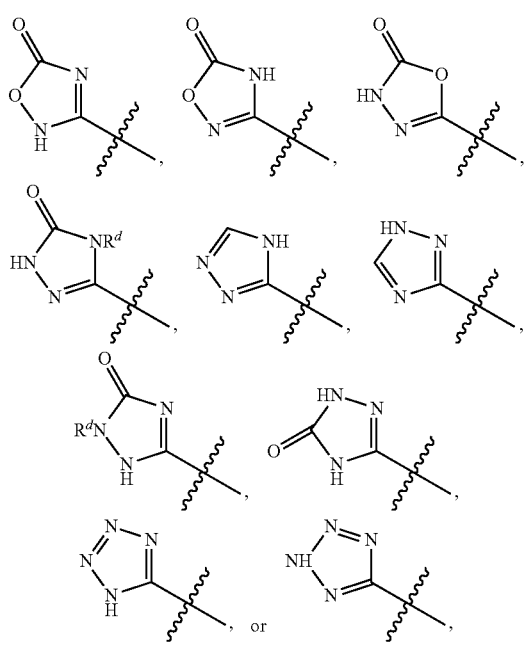

wherein $R^d$ is $CH_3$ or H.

In another embodiment, $R^1$ is COOH,

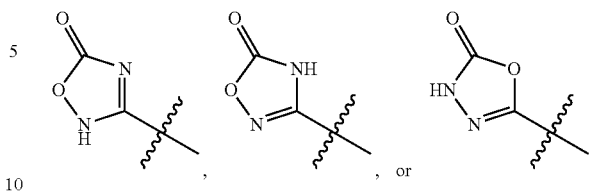

In another embodiment, $R^1$ is COOH,

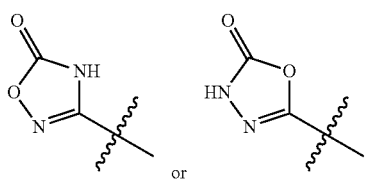

In a further embodiment, $R^1$ is

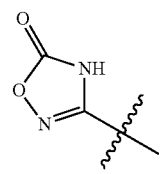

In yet a further embodiment, $R^1$ is

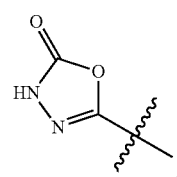

In another aspect of the invention for the foregoing embodiments, $R^7$ is cyclopropyl, cyclobutyl, cyclopentyl, or cyclohexyl. In another embodiment, $R^7$ is cyclobutyl.

In another aspect of the invention for the foregoing embodiments, $R^2$ is

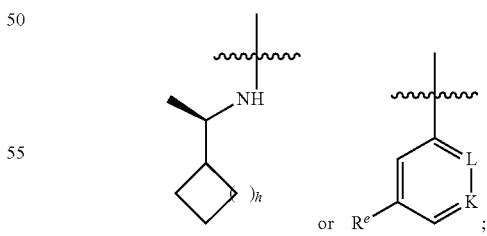

$R^e$ is H, —$(CR^a{}_2)_zC(O)OR^{10}$, halo, halo$C_1$-$C_3$alkyl or $C_1$-$C_3$alkyl;

K and L are independently $CR^{14}$ or N;

$R^{14}$ is independently H, halo, CN, halo$C_1$-$C_6$alkyl, $C_1$-$C_6$alkyl, —$(CR^a{}_2)_zC(O)NR^cR^c$, —$(CR^a{}_2)_zOR^c$, —$(CR^a{}_2)_z$aryl, —$(CR^a{}_2)_z$heteroaryl, —$(CR^a{}_2)_z$heterocyclic, —$(CR^a{}_2)_zC_3$-$C_8$cycloalkyl, —$(CR^a{}_2)_z$cyclenyl, —$(CR^a{}_2)_z$heterocyclenyl, wherein the alkyl, aryl, heteroaryl, heterocyclic, cycloalkyl, cyclenyl or heterocyclenyl can be optionally substituted with OH, CN, halo, haloC$_1$-C$_3$alkyl, or CON(R$^c$)$_2$; and h is 0 or 1.

In another embodiment, R$^2$ is

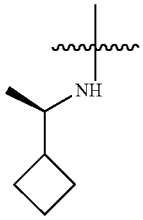

In a further embodiment, R$^2$ is

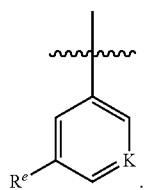

In yet a further embodiment, R$^2$ is

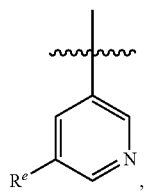

and R$^e$ is halo.

In a further aspect of the invention for the foregoing embodiments, R$^3$ is -T-heterocyclic or -T-heteroaryl, wherein the heterocyclic or heteroaryl can be optionally substituted with halo, SH, OR$^c$, haloC$_1$-C$_6$alkyl, haloC$_1$-C$_6$alkoxy, CN, C$_1$-C$_6$alkyl, C$_2$-C$_6$alkenyl, C$_2$-C$_6$alkynyl, —(CR$^a$$_2$)$_z$C(O)OR$^{10}$, —(CR$^a$$_2$)$_z$C(O)R$^8$, —(CR$^a$$_2$)$_z$OR$^8$, —(CR$^a$$_2$)$_z$NR$^c$R$^8$, —(CR$^a$$_2$)$_z$S(O)$_2$R$^8$, —(CR$^a$$_2$)$_z$C(O)NR$^c$R$^8$, —(CR$^a$$_2$)$_z$aryl, —(CR$^a$$_2$)$_z$heteroaryl, —(CR$^a$$_2$)$_z$C$_3$-C$_8$cycloalkyl, —(CR$^a$$_2$)$_z$heterocyclic, —(CR$^a$$_2$)$_z$SO$_2$NR$^c$R$^8$, or —(CR$^a$$_2$)$_z$O(CR$^a$$_2$)$_z$D(CR$^a$$_2$)$_v$Q;

said alkyl, alkenyl, alkynyl, aryl, heteroaryl, cycloalkyl, and heterocyclic can further be substituted with OH, SH, halo, or C$_2$-C$_6$alkenyl.

In one embodiment, the heteroaryl or heterocyclic group of R$^3$ is pyridyl, morpholinyl, thiomorpholinyl, phenyl, piperidinyl, benzothiophenyl, thiazolyl, pyrimidinyl, oxazolyl, imidazolyl, pyrazolyl, pyrrolidinyl, piperizinyl, tetrahydrofuranyl, benzofuranyl, quinoxalinyl, pyrazolyl, naphthalenyl, dihydro-indenyl, quinolinyl, isoindolyl, isoquinolinyl, isoxazolyl, furanyl, oxadiazolyl, octahydroquinolinyl, octahydroisoquinolinyl, azetidinyl, oxazepanyl, oxazolidinyl, dihydroisoquinolinyl, or dihydroquinolinyl.

In yet another aspect of the invention for the foregoing embodiments, R$^3$ is

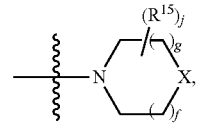

X is NR$^{19}$, CR$^{16}$$_2$, S, S(O)$_2$ or O;
R$^{15}$ is independently selected from the group consisting of phenyl, 5 or 6-membered heterocyclic or heteroaryl, haloC$_1$-C$_6$alkyl, haloC$_2$-C$_6$alkenyl, halo, C(O)R$^c$, S(O)$_2$R$^c$, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, C$_3$-C$_6$cycloalkyl, amino, CN, OH, and SH; two adjacent R$^{15}$ form a fused C$_3$-C$_7$cycloalkyl or heterocyclic ring; two non-adjacent R$^{15}$ form a C$_1$-C$_3$alkylene; or two R$^{15}$ attached to the same carbon form a C$_3$-C$_7$cycloalkyl or heterocyclic ring, wherein the phenyl, heteroaryl, cycloalkyl or heterocyclic can be optionally substituted with R$^{13}$ selected from the group consisting of haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, or SH;
R$^{16}$ is independently selected from the group consisting of H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, and SH;
R$^{19}$ is independently selected from the group consisting of H, haloC$_1$-C$_6$alkyl, haloC$_2$-C$_6$alkenyl, C$_1$-C$_6$alkoxyC$_1$-C$_6$alkyl, C$_1$-C$_6$alkyl, C$_2$-C$_6$alkenyl;
f is 0, 1 or 2;
g is 0, 1 or 2;
j is independently 0, 1, 2, 3, 4, 5, 6, 7, or 8.

In one embodiment, R$^{15}$ is independently selected from the group consisting of phenyl, 5 or 6-membered heterocyclic or heteroaryl, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, C$_3$-C$_6$cycloalkyl, amino, C(O)R$^c$, S(O)$_2$R$^c$, CN, OH, and SH; two adjacent R$^{15}$ form a fused C$_3$-C$_7$cycloalkyl or heterocyclic ring; or two R$^{15}$ attached to the same carbon form a C$_3$-C$_7$cycloalkyl or heterocyclic ring, wherein the phenyl, heteroaryl, cycloalkyl or heterocyclic can be optionally substituted with R$^{13}$ selected from the group consisting of haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, or SH;
R$^{16}$ is independently selected from the group consisting of H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, and SH.

In another embodiment, R$^{15}$ is independently halo, C$_1$-C$_3$alkyl, C$_1$-C$_3$haloalkyl, C$_1$-C$_3$alkoxy, C$_1$-C$_3$alkoxyC$_1$-C$_3$alkyl, or NH$_2$.

In one embodiment, j is independently 0, 1 or 2.
In one embodiment, f is 0 or 1.
In one embodiment, R$^3$ is

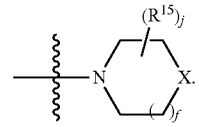

In a yet another aspect of the invention for the foregoing embodiments, R$^3$ is

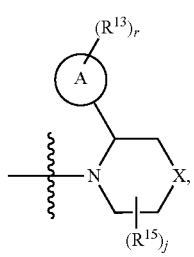

X is $CR^{16}_2$, S, or O;
$R^{13}$, $R^{15}$ and $R^{16}$ are independently H, halo$C_1$-$C_6$alkyl, halo$C_2$-$C_6$alkenyl, halo, halo$C_1$-$C_6$alkoxy, $C_1$-$C_6$alkoxy, $C_1$-$C_6$alkoxy$C_1$-$C_6$alkyl, $C_1$-$C_6$alkyl, $C_3$-$C_6$cyloalkyl, $C_2$-$C_6$alkenyl, amino, CN, OH, or SH;
A is phenyl, or 5-6 membered heteroaryl;
r is independently 0, 1, 2, 3, 4, or 5; and
j is independently 0, 1, 2, or 3.
In one embodiment, $R^{13}$, $R^{15}$ and $R^{16}$ are independently halo, $C_1$-$C_6$alkyl, $C_1$-$C_6$haloalkyl, $C_1$-$C_6$alkoxy or $NH_2$.
In one embodiment, r is independently 0 or 1; j is independently 0 or 1.
In another embodiment, X is O.
In a further embodiment, A is phenyl, pyridyl or oxadiazolyl.
In another embodiment, $R^3$ is

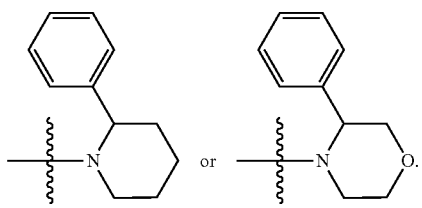 [SMILES: *N1CCCCC1c1ccccc1 ; *N1CCOCC1c1ccccc1]

In a further embodiment, $R^3$ is

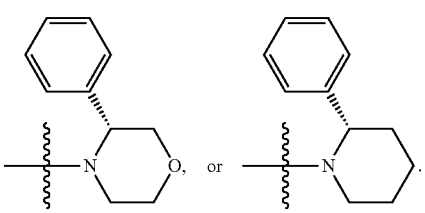 [SMILES: *N1CCOC[C@H]1c1ccccc1 ; *N1CCCC[C@H]1c1ccccc1]

In another aspect of the invention for the foregoing embodiments, $R^3$ is

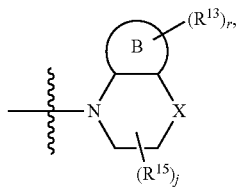

Ring B is a fused $C_3$-$C_7$cycloalkyl;
X is $CR^{16}_2$, S, or O;
$R^{13}$, $R^{15}$ and $R^{16}$ are independently H, halo$C_1$-$C_6$alkyl, halo$C_2$-$C_6$alkenyl, halo, halo$C_1$-$C_6$alkoxy, $C_1$-$C_6$alkoxy, $C_1$-$C_6$alkoxy$C_1$-$C_6$alkyl, $C_1$-$C_6$alkyl, $C_3$-$C_6$cycloalkyl, $C_2$-$C_6$alkenyl, amino, CN, OH, or SH;
r is independently 0, 1, 2, 3, 4, 5, 6, 7 or 8; and
j is independently 0, 1, 2, 3, or 4.
In one embodiment, $R^{13}$, $R^{15}$ and $R^{16}$ are independently H, halo, $C_1$-$C_6$alkyl, $C_1$-$C_6$haloalkyl, $C_1$-$C_6$alkoxy or $NH_2$.
In one embodiment, r is independently 0 or 1; j is independently 0 or 1.
In another embodiment, X is O.
In a further aspect of the invention for the foregoing embodiments, $R^3$ is

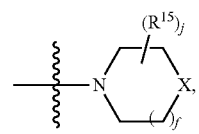

$R^{15}$ is independently halo$C_1$-$C_6$alkyl, halo$C_2$-$C_6$alkenyl, halo, halo$C_1$-$C_6$alkoxy, $C_1$-$C_6$alkoxy, $C_1$-$C_6$alkoxy$C_1$-$C_6$alkyl, $C_1$-$C_6$alkyl, $C_2$-$C_6$alkenyl, $C_3$-$C_6$cycloalkyl, amino, CN, OH, or SH; f is 0, 1 or 2; j is independently 0, 1, 2, 3, 4, 5, or 6.
In one embodiment, $R^{15}$ is independently halo, $C_1$-$C_3$alkyl, $C_1$-$C_3$haloalkyl, $C_1$-$C_3$alkoxy, $C_1$-$C_3$alkoxy$C_1$-$C_3$alkyl, or $NH_2$.
In one embodiment, j is independently 0, 1 or 2.
In one embodiment, f is 0 or 1.
In a further aspect of the invention for the foregoing embodiments, $R^3$ is

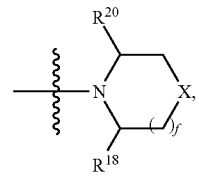

X is $CH_2$ or O;
$R^{18}$ and $R^{20}$ are independently H, halo$C_1$-$C_6$alkyl, halo$C_2$-$C_6$alkenyl, halo, halo$C_1$-$C_6$alkoxy, $C_1$-$C_6$alkoxy, $C_1$-$C_6$alkoxy$C_1$-$C_6$alkyl, $C_1$-$C_6$alkyl, $C_3$-$C_6$cycloalkyl, $C_2$-$C_6$alkenyl, $C_3$-$C_6$alkyl, amino, CN, OH, or SH; and
f is 0, 1 or 2;
In yet a further aspect of the invention for the foregoing embodiments, $R^3$ is

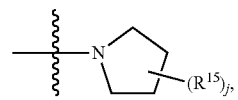

$R^{15}$ is independently halo$C_1$-$C_6$alkyl, halo$C_2$-$C_6$alkenyl, halo, halo$C_1$-$C_6$alkoxy, $C_1$-$C_6$alkoxy, $C_1$-$C_6$alkoxy$C_1$-$C_6$alkyl, $C_1$-$C_6$alkyl, $C_3$-$C_6$cycloalkyl, $C_2$-$C_6$alkenyl, amino, CN, OH, or SH;
j is independently 0, 1, 2, 3, or 4.
In one embodiment, $R^{15}$ is independently halo, $C_1$-$C_3$alkyl, $C_1$-$C_3$haloalkyl, $C_1$-$C_3$alkoxy, $C_1$-$C_3$alkoxy$C_1$-$C_3$alkyl, or $NH_2$.
In one embodiment, j is independently 0 or 1.
In yet a further aspect of the invention for the foregoing embodiments, $R^4$ is —$CH_2$-E or —$CH_2(CH_3)$-E, wherein E is phenyl, cyclopentyl, cyclopentenyl, cyclohexyl or cyclohexenyl optionally substituted with haloC$_1$-C$_3$alkyl, haloC$_2$-C$_3$alkenyl, halo, C$_3$-C$_4$cycloalkyl, haloC$_1$-C$_3$alkoxy, C$_1$-C$_3$alkoxy, C$_2$-C$_3$alkenoxy, C$_1$-C$_3$alkyl, C$_2$-C$_3$alkenyl, amino, CN, OH, or SH.

In one embodiment, R$^4$ is —CH$_2$-E or —CH$_2$(CH$_3$)-E, wherein E is phenyl or cyclohexyl, optionally substituted with CF$_3$, CHF$_2$, halo, cyclopropyl, OCF$_3$, OCH$_3$, methyl, amino, CN, OH, or SH.

In another embodiment, R$^4$ is CH$_2$-cyclohexyl,

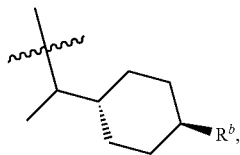

benzyl,

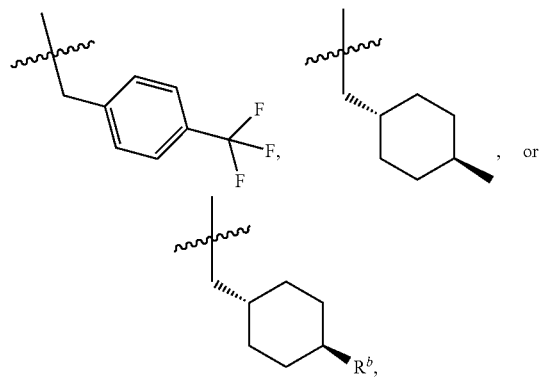

and R$^b$ is H, haloC$_1$-C$_3$alkyl, haloC$_2$-C$_3$alkenyl, halo, haloC$_1$-C$_3$alkoxy, C$_1$-C$_3$alkoxy, C$_1$-C$_3$alkyl, C$_2$-C$_3$alkenyl, amino, CN, OH, or SH.

In another embodiment, R$^4$ is

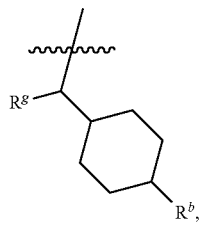

R$^g$ and R$^b$ are independently H or methyl.

Specific examples of the compounds of the invention include, but are not limited to:

(R)-6-((1-cyclobutylethyl)amino)-8-(5-(dimethylamino)-2-(trifluoromethoxy)phenyl)-7-(4-(trifluoromethyl)benzyl)-7H-purine-2-carboxylic acid;

(R)-8-(2-chloro-5-ethylphenyl)-6-((1-cyclobutylethyl)amino)-7-(4-(trifluoromethyl)benzyl)-7H-purine-2-carboxylic acid;

(R)-6-((1-cyclobutylethyl)amino)-7-(3-fluoro-4-(trifluoromethyl)benzyl)-8-(5-isopropyl-2-(trifluoromethoxy)phenyl)-7H-purine-2-carboxylic acid;

(R)-6-((1-cyclobutylethyl)amino)-8-(2-isopropylpyridin-4-yl)-7-(4-(trifluoromethyl)benzyl)-7H-purine-2-carboxylic acid;

(R)-6-((1-cyclobutylethyl)amino)-8-(6-methyl-4-(prop-1-en-2-yl)pyridin-2-yl)-7-(4-(trifluoromethyl)benzyl)-7H-purine-2-carboxylic acid;

7-(4-chloro-3-fluorobenzyl)-6-{[(1R)-1-cyclobutylethyl]amino}-8-[4-(propan-2-yl)pyridin-2-yl]-7H-purine-2-carboxylic acid;

6-{[(1R)-1-cyclobutylethyl]amino}-8-[4-(propan-2-yl)pyridin-2-yl]-7-{[5-(trifluoromethyl)thiophen-2-yl]methyl}-7H-purine-2-carboxylic acid;

6-(((R)-1-cyclobutylethyl)amino)-8-(4-(hydroxy(phenyl)methyl)pyridin-2-yl)-7-(4-(trifluoromethyl)benzyl)-7H-purine-2-carboxylic acid;

(R)-8-(4-benzylpyridin-2-yl)-6-((1-cyclobutylethyl)amino)-7-(4-(trifluoromethyl)benzyl)-7H-purine-2-carboxylic acid;

(R)-6-((1-cyclobutylethyl)amino)-8-(5-fluoro-4-isopropylpyridin-2-yl)-7-(4-(trifluoromethyl)benzyl)-7H-purine-2-carboxylic acid;

(R)-6-((1-cyclobutylethyl)amino)-8-(2-hydroxy-5-isopropylphenyl)-7-(4-(trifluoromethyl)benzyl)-7H-purine-2-carboxylic acid;

(R)-6-((1-cyclobutylethyl)amino)-8-(2-ethoxy-5-isopropylphenyl)-7-(4-(trifluoromethyl)benzyl)-7H-purine-2-carboxylic acid;

(R)-6-((1-cyclobutylethyl)(methyl)amino)-7-(3-fluoro-4-(trifluoromethyl)benzyl)-8-(4-isopropylpyridin-2-yl)-7H-purine-2-carboxylic acid;

8-(4-(sec-butyl)pyridin-2-yl)-6-(((R)-1-cyclobutylethyl)amino)-7-(4-(trifluoromethyl)benzyl)-7H-purine-2-carboxylic acid;

6-{[(1R)-1-cyclobutylethyl]amino}-8-pyridin-2-yl-7-[4-(trifluoromethyl)benzyl]-7H-purine-2-carboxylic acid;

6-{[(1R)-1-cyclobutylethyl]amino}-8-(4-methylpyridin-2-yl)-7-[4-(trifluoromethyl)benzyl]-7H-purine-2-carboxylic acid;

6-{[(1R)-1-cyclobutylethyl]amino}-8-(3-methylpyridin-2-yl)-7-[4-(trifluoromethyl)benzyl]-7H-purine-2-carboxylic acid;

6-{[(1R)-1-cyclobutylethyl]amino}-8-(6-methylpyridin-2-yl)-7-[4-(trifluoromethyl)benzyl]-7H-purine-2-carboxylic acid;

6-{[(1R)-1-cyclobutylethyl]amino}-8-(5-methoxypyridin-2-yl)-7-[4-(trifluoromethyl)benzyl]-7H-purine-2-carboxylic acid;

6-{[(1R)-1-cyclobutylethyl]amino}-8-(3,6-dimethylpyridin-2-yl)-7-[4-(trifluoromethyl)benzyl]-7H-purine-2-carboxylic acid;

6-{[(1R)-1-cyclobutylethyl]amino}-8-[4-(1-methylethyl)pyridin-2-yl]-7-[4-(trifluoromethyl)benzyl]-7H-purine-2-carboxylic acid;

6-{[(1R)-1-cyclobutylethyl]amino}-8-(3-methoxy-6-methylpyridin-2-yl)-7-[4-(trifluoromethyl)benzyl]-7H-purine-2-carboxylic acid;

6-{[(1R)-1-cyclobutylethyl]amino}-8-[4-(methylsulfonyl)phenyl]-7-[4-(trifluoromethyl)benzyl]-7H-purine-2-carboxylic acid;

6-{[(1R)-1-cyclopropylethyl]amino}-8-(7-methylquinolin-6-yl)-7-[4-(trifluoromethyl)benzyl]-7H-purine-2-carboxylic acid;

6-{[(1R)-1-cyclobutylethyl]amino}-8-(4-phenylpyridin-2-yl)-7-[4-(trifluoromethyl)benzyl]-7H-purine-2-carboxylic acid;

6-{[(1R)-1-cyclobutylethyl]amino}-8-[4-(1-hydroxy-1-methylethyl)pyridin-2-yl]-7-[4-(trifluoromethyl)benzyl]-7H-purine-2-carboxylic acid;

6-{[(1R)-1-cyclobutylethyl]amino}-8-[4-(1-hydroxyethyl)pyridin-2-yl]-7-[4-(trifluoromethyl)benzyl]-7H-purine-2-carboxylic acid;

6-{[(1R)-1-cyclobutylethyl]amino}-8-(5-ethyl-2-hydroxyphenyl)-7-[4-(trifluoromethyl)benzyl]-7H-purine-2-carboxylic acid;

6-{[(1R)-1-cyclobutylethyl]amino}-8-[2-(methoxymethoxy)-5-(1-methylethyl)phenyl]-7-[4-(trifluoromethyl)benzyl]-7H-purine-2-carboxylic acid;

6-{[(1R)-1-cyclobutylethyl]amino}-8-(5-ethyl-2-methoxyphenyl)-7-[4-(trifluoromethyl)benzyl]-7H-purine-2-carboxylic acid;

6-{[(1R)-1-cyclobutylethyl]amino}-8-(2-ethoxy-5-ethylphenyl)-7-[4-(trifluoromethyl)benzyl]-7H-purine-2-carboxylic acid;

6-{[(1R)-1-cyclobutylethyl]amino}-8-[2-ethoxy-5-(trifluoromethyl)phenyl]-7-[4-(trifluoromethyl)benzyl]-7H-purine-2-carboxylic acid;

6-{[(1R)-1-cyclobutylethyl]amino}-8-[2-methoxy-5-(trifluoromethyl)phenyl]-7-[4-(trifluoromethyl)benzyl]-7H-purine-2-carboxylic acid;

6-{[(1R)-1-cyclobutylethyl]amino}-8-[5-ethyl-2-(methoxymethoxy)phenyl]-7-[4-(trifluoromethyl)benzyl]-7H-purine-2-carboxylic acid;

8-(3-carbamoylphenyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[2-fluoro-5-(trifluoromethyl)phenyl]-7-[4-(trifluoromethyl)benzyl]-7H-purine-2-carboxylic acid;

6-{[(1R)-1-cyclobutylethyl]amino}-8-[5-(dimethylamino)-2-methylphenyl]-7-[4-(trifluoromethyl)benzyl]-7H-purine-2-carboxylic acid;

6-{[(1R)-1-cyclobutylethyl]amino}-8-(5-ethyl-2-fluorophenyl)-7-[4-(trifluoromethyl)benzyl]-7H-purine-2-carboxylic acid;

6-{[(1R)-1-cyclobutylethyl]amino}-8-[2-methoxy-5-(1-methylethyl)phenyl]-7-[4-(trifluoromethyl)benzyl]-7H-purine-2-carboxylic acid;

6-{[(1R)-1-cyclobutylethyl]amino}-8-[5-(dimethylamino)-2-hydroxyphenyl]-7-[4-(trifluoromethyl)benzyl]-7H-purine-2-carboxylic acid;

6-{[(1R)-1-cyclobutylethyl]amino}-8-(4-ethoxypyridin-2-yl)-7-[4-(trifluoromethyl)benzyl]-7H-purine-2-carboxylic acid;

8-(4-chloropyridin-2-yl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[4-(cyclobutyloxy)pyridin-2-yl]-7-[4-(trifluoromethyl)benzyl]-7H-purine-2-carboxylic acid;

6-{[(1R)-1-cyclobutylethyl]amino}-8-[4-(difluoromethyl)pyridin-2-yl]-7-[4-(trifluoromethyl)benzyl]-7H-purine-2-carboxylic acid;

6-{[(1R)-1-cyclobutylethyl]amino}-8-[4-(dimethylamino)pyridin-2-yl]-7-[4-(trifluoromethyl)benzyl]-7H-purine-2-carboxylic acid;

6-{[(1R)-1-cyclobutylethyl]amino}-8-[4-(3-methyl-1H-pyrazol-1-yl)pyridin-2-yl]-7-[4-(trifluoromethyl)benzyl]-7H-purine-2-carboxylic acid;

6-{[(1R)-1-cyclobutylethyl]amino}-7-[3-fluoro-4-(trifluoromethyl)benzyl]-8-[4-(1-methylethyl)pyridin-2-yl]-7H-purine-2-carboxylic acid;

6-{[(1S)-1-cyclobutylethyl]amino}-8-[4-(1-methylethyl)pyridin-2-yl]-7-[4-(trifluoromethyl)benzyl]-7H-purine-2-carboxylic acid;

6-{[(1R)-1-cyclobutylethyl]amino}-8-(4-cyclopropylpyridin-2-yl)-7-[4-(trifluoromethyl)benzyl]-7H-purine-2-carboxylic acid;

6-{[(1R)-1-cyclobutylethyl]amino}-8-[5-(1-methylethyl)-2-(trifluoromethoxy)phenyl]-7-[4-(trifluoromethyl)benzyl]-7H-purine-2-carboxylic acid;

8-(4-tert-butylpyridin-2-yl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(4-cyclobutylpyridin-2-yl)-7-[4-(trifluoromethyl)benzyl]-7H-purine-2-carboxylic acid;

6-{[(1R)-1-cyclobutylethyl]amino}-8-(4-cyclopentylpyridin-2-yl)-7-[4-(trifluoromethyl)benzyl]-7H-purine-2-carboxylic acid;

6-{[(1R)-1-cyclobutylethyl]amino}-8-(4-cyclohexylpyridin-2-yl)-7-[4-(trifluoromethyl)benzyl]-7H-purine-2-carboxylic acid;

6-{[(1R)-1-cyclobutylethyl]amino}-8-(4-thiophen-2-ylpyridin-2-yl)-7-[4-(trifluoromethyl)benzyl]-7H-purine-2-carboxylic acid;

6-{[(1R)-1-cyclobutylethyl]amino}-8-[4-(cyclohexyloxy)pyridin-2-yl]-7-[4-(trifluoromethyl)benzyl]-7H-purine-2-carboxylic acid;

6-{[(1R)-1-cyclobutylethyl]amino}-8-[4-(1-methylethoxyl)pyridin-2-yl]-7-[4-(trifluoromethyl)benzyl]-7H-purine-2-carboxylic acid;

6-{[(1R)-1-cyclobutylethyl]amino}-7-[4-(trifluoromethyl)benzyl]-8-[4-(trifluoromethyl)pyridin-2-yl]-7H-purine-2-carboxylic acid;

6-{[(1R)-1-cyclobutylethyl]amino}-8-(2,3-dihydro-1H-isoindol-4-yl)-7-[4-(trifluoromethyl)benzyl]-7H-purine-2-carboxylic acid;

6-{[(1R)-1-cyclobutylethyl]amino}-8-isoquinolin-3-yl-7-[4-(trifluoromethyl)benzyl]-7H-purine-2-carboxylic acid;

6-{[(1R)-1-cyclobutylethyl]amino}-8-(6-phenylpyridin-2-yl)-7-[4-(trifluoromethyl)benzyl]-7H-purine-2-carboxylic acid;

8-[4,6-bis(difluoromethyl)pyridin-2-yl]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[5-(1,3-dioxolan-2-yl)pyridin-2-yl]-7-[4-(trifluoromethyl)benzyl]-7H-purine-2-carboxylic acid;

6-{[(1R)-1-cyclobutylethyl]amino}-8-[5-(difluoromethoxy)pyridin-2-yl]-7-[4-(trifluoromethyl)benzyl]-7H-purine-2-carboxylic acid;

6-{[(1R)-1-cyclobutylethyl]amino}-8-(4-methoxypyridin-2-yl)-7-[4-(trifluoromethyl)benzyl]-7H-purine-2-carboxylic acid;

6-{[(1R)-1-cyclobutylethyl]amino}-8-(4-propylpyridin-2-yl)-7-[4-(trifluoromethyl)benzyl]-7H-purine-2-carboxylic acid;

6-{[(1R)-1-cyclobutylethyl]amino}-8-(4-ethylpyridin-2-yl)-7-[4-(trifluoromethyl)benzyl]-7H-purine-2-carboxylic acid;

6-{[(1R)-1-cyclobutylethyl]amino}-8-[6-(1-methylethyl)pyridin-2-yl]-7-[4-(trifluoromethyl)benzyl]-7H-purine-2-carboxylic acid;

6-{[(1R)-1-cyclobutylethyl]amino}-7-[3-fluoro-4-(trifluoromethoxy)benzyl]-8-[4-(1-methylethyl)pyridin-2-yl]-7H-purine-2-carboxylic acid;

6-{[(1R)-1-cyclobutylethyl]amino}-8-[4-(1-methylethyl)pyridin-2-yl]-7-[4-(trifluoromethoxy)benzyl]-7H-purine-2-carboxylic acid;

6-{[(1R)-1-cyclobutylethyl]amino}-8-isoquinolin-1-yl-7-[4-(trifluoromethyl)benzyl]-7H-purine-2-carboxylic acid;

6-{[(1R)-1-cyclobutylethyl]amino}-8-(4-methoxy-3-methylpyridin-2-yl)-7-[4-(trifluoromethyl)benzyl]-7H-purine-2-carboxylic acid;

6-{[(1R)-1-cyclobutylethyl]amino}-8-(3-phenylpyridin-2-yl)-7-[4-(trifluoromethyl)benzyl]-7H-purine-2-carboxylic acid;

8-(4-tert-butylpyridin-2-yl)-6-{[(1R)-1-cyclobutylethyl]amino}-7-[3-fluoro-4-(trifluoromethyl)benzyl]-7H-purine-2-carboxylic acid;

6-{[(1R)-1-cyclobutylethyl]amino}-8-(4-cyclopropylpyridin-2-yl)-7-[3-fluoro-4-(trifluoromethyl)benzyl]-7H-purine-2-carboxylic acid;

6-{[(1R)-1-cyclobutylethyl]amino}-8-(4-cyclobutylpyridin-2-yl)-7-[3-fluoro-4-(trifluoromethyl)benzyl]-7H-purine-2-carboxylic acid;

6-{[(1R)-1-cyclobutylethyl]amino}-8-(4-ethylpyridin-2-yl)-7-[3-fluoro-4-(trifluoromethyl)benzyl]-7H-purine-2-carboxylic acid;

6-{[(1R)-1-cyclobutylethyl]amino}-7-[3-fluoro-4-(trifluoromethyl)benzyl]-8-(4-propylpyridin-2-yl)-7H-purine-2-carboxylic acid;

6-{[(1R)-1-cyclobutylethyl]amino}-8-[5-(1-methylethyl)pyridin-3-yl]-7-[4-(trifluoromethyl)benzyl]-7H-purine-2-carboxylic acid;

6-{[(1R)-1-cyclobutylethyl]amino}-8-(3-fluoro-4-methylpyridin-2-yl)-7-[4-(trifluoromethyl)benzyl]-7H-purine-2-carboxylic acid;

6-{[(1R)-1-cyclobutylethyl]amino}-7-[3-fluoro-4-(trifluoromethoxy)benzyl]-8-[5-(1-methylethyl)-2-(trifluoromethoxy)phenyl]-7H-purine-2-carboxylic acid;

6-{[(1R)-1-cyclobutylethyl]amino}-8-[5-methyl-2-(trifluoromethoxy)phenyl]-7-[4-(trifluoromethyl)benzyl]-7H-purine-2-carboxylic acid;

6-{[(1R)-1-cyclobutylethyl]amino}-8-[4-(2-methylpropyl)pyridin-2-yl]-7-[4-(trifluoromethyl)benzyl]-7H-purine-2-carboxylic acid;

6-{[(1R)-1-cyclobutylethyl]amino}-8-[5-methyl-4-(1-methylethyl)pyridin-2-yl]-7-[4-(trifluoromethyl)benzyl]-7H-purine-2-carboxylic acid;

6-{[(1R)-1-cyclobutylethyl]amino}-8-[3-methyl-4-(1-methylethyl)pyridin-2-yl]-7-[4-(trifluoromethyl)benzyl]-7H-purine-2-carboxylic acid;

6-{[(1R)-1-cyclobutylethyl]amino}-8-[4-(3,3-dimethylbutyl)pyridin-2-yl]-7-[4-(trifluoromethyl)benzyl]-7H-purine-2-carboxylic acid;

6-{[(1R)-1-cyclobutylethyl]amino}-8-[4-(2-cyclopropylethyl)pyridin-2-yl]-7-[4-(trifluoromethyl)benzyl]-7H-purine-2-carboxylic acid;

6-{[(1R)-1-cyclobutylethyl]amino}-7-[3-fluoro-4-(trifluoromethoxy)benzyl]-8-[5-methyl-4-(1-methylethyl)pyridin-2-yl]-7H-purine-2-carboxylic acid;

6-{[(1R)-1-cyclobutylethyl]amino}-7-[3-fluoro-4-(trifluoromethoxy)benzyl]-8-[3-methyl-4-(1-methylethyl)pyridin-2-yl]-7H-purine-2-carboxylic acid;

6-{[(1R)-1-cyclobutylethyl]amino}-7-[3-fluoro-4-(trifluoromethyl)benzyl]-8-[5-methyl-4-(1-methylethyl)pyridin-2-yl]-7H-purine-2-carboxylic acid;

6-{[(1R)-1-cyclobutylethyl]amino}-8-[6-methyl-4-(1-methylethyl)pyridin-2-yl]-7-[4-(trifluoromethyl)benzyl]-7H-purine-2-carboxylic acid;

6-{[(1R)-1-cyclobutylethyl]amino}-8-(1,3-dimethyl-1H-pyrazol-5-yl)-7-[4-(trifluoromethyl)benzyl]-7H-purine-2-carboxylic acid;

6-{[(1R)-1-cyclobutylethyl]amino}-8-(1,5-dimethyl-1H-pyrazol-4-yl)-7-[4-(trifluoromethyl)benzyl]-7H-purine-2-carboxylic acid;

6-{[(1R)-1-cyclopropylethyl]amino}-8-phenyl-7-[4-(trifluoromethyl)benzyl]-7H-purine-2-carboxylic acid;

6-{[(1R)-1-cyclopropylethyl]amino}-8-(4-morpholin-4-ylphenyl)-7-[4-(trifluoromethyl)benzyl]-7H-purine-2-carboxylic acid;

6-{[(1R)-1-cyclopropylethyl]amino}-8-[3-(1-methylethoxyl)phenyl]-7-[4-(trifluoromethyl)benzyl]-7H-purine-2-carboxylic acid;

6-{[(1R)-1-cyclobutylethyl]amino}-8-(2,5-dimethylphenyl)-7-[4-(trifluoromethyl)benzyl]-7H-purine-2-carboxylic acid;

6-{[(1R)-1-cyclobutylethyl]amino}-8-[4-(difluoromethoxy)phenyl]-7-[4-(trifluoromethyl)benzyl]-7H-purine-2-carboxylic acid;

6-{[(1R)-1-cyclobutylethyl]amino}-8-[4-(1-hydroxyethyl)phenyl]-7-[4-(trifluoromethyl)benzyl]-7H-purine-2-carboxylic acid;

6-{[(1R)-1-cyclobutylethyl]amino}-8-(3-fluoro-4-methylphenyl)-7-[4-(trifluoromethyl)benzyl]-7H-purine-2-carboxylic acid;

6-{[(1R)-1-cyclobutylethyl]amino}-8-(5-fluoro-2-methylphenyl)-7-[4-(trifluoromethyl)benzyl]-7H-purine-2-carboxylic acid;

6-{[(1R)-1-cyclobutylethyl]amino}-8-(3-fluoro-4-methoxyphenyl)-7-[4-(trifluoromethyl)benzyl]-7H-purine-2-carboxylic acid;

6-{[(1R)-1-cyclobutylethyl]amino}-8-(4-methoxy-3-methylphenyl)-7-[4-(trifluoromethyl)benzyl]-7H-purine-2-carboxylic acid;

6-{[(1R)-1-cyclobutylethyl]amino}-8-quinoxalin-6-yl-7-[4-(trifluoromethyl)benzyl]-7H-purine-2-carboxylic acid;

6-{[(1R)-1-cyclobutylethyl]amino}-8-[3-(1H-pyrrol-1-yl)phenyl]-7-[4-(trifluoromethyl)benzyl]-7H-purine-2-carboxylic acid;

6-{[(1R)-1-cyclobutylethyl]amino}-8-(1-methyl-1H-indol-5-yl)-7-[4-(trifluoromethyl)benzyl]-7H-purine-2-carboxylic acid;

8-biphenyl-4-yl-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(4-cyclohexylphenyl)-7-[4-(trifluoromethyl)benzyl]-7H-purine-2-carboxylic acid;

6-{[(1R)-1-cyclobutylethyl]amino}-8-(2-methylquinolin-6-yl)-7-[4-(trifluoromethyl)benzyl]-7H-purine-2-carboxylic acid;

6-{[(1R)-1-cyclobutylethyl]amino}-8-(2-fluorobiphenyl-4-yl)-7-[4-(trifluoromethyl)benzyl]-7H-purine-2-carboxylic acid;

6-{[(1R)-1-cyclobutylethyl]amino}-8-[4-(dimethylamino)phenyl]-7-[4-(trifluoromethyl)benzyl]-7H-purine-2-carboxylic acid;

8-(4-tert-butylphenyl)-6-{[(1R)-1-cyclobutylethyl]amino}-7-[4-(trifluoromethyl)benzyl]-7H-purine-2-carboxylic acid;

8-[4-chloro-3-(trifluoromethyl)phenyl]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[4-(cyclopropylcarbonyl)phenyl]-7-[4-(trifluoromethyl)benzyl]-7H-purine-2-carboxylic acid;

8-(1-benzofuran-5-yl)-6-{[(1R)-1-cyclobutylethyl]amino}-7-[4-(trifluoromethyl)benzyl]-7H-purine-2-carboxylic acid;

6-{[(1R)-1-cyclopropylethyl]amino}-8-(2-methylpyridin-4-yl)-7-[4-(trifluoromethyl)benzyl]-7H-purine-2-carboxylic acid;

6-{[(1R)-1-cyclobutylethyl]amino}-8-(2-methoxy-5-methylphenyl)-7-[4-(trifluoromethyl)benzyl]-7H-purine-2-carboxylic acid;

8-(2-chloro-5-methylphenyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(2,3-dihydro-1-benzofuran-5-yl)-7-[4-(trifluoromethyl)benzyl]-7H-purine-2-carboxylic acid;

6-{[(1R)-1-cyclobutylethyl]amino}-7-[4-(trifluoromethyl)benzyl]-8-[6-(trifluoromethyl)pyridin-2-yl]-7H-purine-2-carboxylic acid;

6-{[(1R)-1-cyclobutylethyl]amino}-8-(3-methoxy-5-methylphenyl)-7-[4-(trifluoromethyl)benzyl]-7H-purine-2-carboxylic acid;

8-(4-chloro-3-methoxyphenyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(4-methyl-3,4-dihydro-2H-1,4-benzoxazin-7-yl)-7-[4-(trifluoromethyl)benzyl]-7H-purine-2-carboxylic acid;

6-{[(1R)-1-cyclobutylethyl]amino}-8-(2,3-dimethylphenyl)-7-[4-(trifluoromethyl)benzyl]-7H-purine-2-carboxylic acid;

6-{[(1R)-1-cyclobutylethyl]amino}-8-[3-(1-methylethoxyl)phenyl]-7-[4-(trifluoromethyl)benzyl]-7H-purine-2-carboxylic acid;

6-{[(1R)-1-cyclobutylethyl]amino}-8-(3,5-di-tert-butylphenyl)-7-[4-(trifluoromethyl)benzyl]-7H-purine-2-carboxylic acid;

6-{[(1R)-1-cyclobutylethyl]amino}-8-[2-methyl-4-(trifluoromethoxy)phenyl]-7-[4-(trifluoromethyl)benzyl]-7H-purine-2-carboxylic acid;

6-{[(1R)-1-cyclobutylethyl]amino}-8-[3-(phenylamino)phenyl]-7-[4-(trifluoromethyl)benzyl]-7H-purine-2-carboxylic acid;

6-{[(1R)-1-cyclobutylethyl]amino}-8-(3,5-dimethylphenyl)-7-[4-(trifluoromethyl)benzyl]-7H-purine-2-carboxylic acid;

8-(5-chloro-2-methylphenyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(6-methoxynaphthalen-2-yl)-7-[4-(trifluoromethyl)benzyl]-7H-purine-2-carboxylic acid;

6-{[(1R)-1-cyclobutylethyl]amino}-8-(4-methoxy-3,5-dimethylphenyl)-7-[4-(trifluoromethyl)benzyl]-7H-purine-2-carboxylic acid;

6-{[(1R)-1-cyclobutylethyl]amino}-7-[4-(trifluoromethyl)benzyl]-8-[3-(trifluoromethyl)pyridin-2-yl]-7H-purine-2-carboxylic acid;

6-{[(1R)-1-cyclobutylethyl]amino}-8-(2-fluoro-4-methoxyphenyl)-7-[4-(trifluoromethyl)benzyl]-7H-purine-2-carboxylic acid;

6-{[(1R)-1-cyclobutylethyl]amino}-8-(4-fluoro-3-methylphenyl)-7-[4-(trifluoromethyl)benzyl]-7H-purine-2-carboxylic acid;

6-{[(1R)-1-cyclobutylethyl]amino}-8-(2-ethoxy-5-methylphenyl)-7-[4-(trifluoromethyl)benzyl]-7H-purine-2-carboxylic acid;

(R)-6-((1-cyclobutylethyl)amino)-8-(3-methoxyphenyl)-7-(4-(trifluoromethyl)benzyl)-7H-purine-2-carboxylic acid;

(R)-6-((1-cyclobutylethyl)amino)-8-(4-cyclopropyl-2-methylphenyl)-7-(4-(trifluoromethyl)benzyl)-7H-purine-2-carboxylic acid;

(R)-8-benzyl-6-((1-cyclobutylethyl)amino)-7-(4-(trifluoromethyl)benzyl)-7H-purine-2-carboxylic acid;

(R)-6-((1-cyclobutylethyl)amino)-8-cyclohexyl-7-(4-(trifluoromethyl)benzyl)-7H-purine-2-carboxylic acid;

7-(4-chlorobenzyl)-8-(3-chlorophenyl)-6-{[(1R)-1-cyclopropylethyl]amino}-7H-purine-2-carboxylic acid;

7-(4-chlorobenzyl)-6-{[(1R)-1-cyclopropylethyl]amino}-8-(3-methylphenyl)-7H-purine-2-carboxylic acid;

8-(1-benzothiophen-5-yl)-7-(4-chlorobenzyl)-6-{[(1R)-1-cyclopropylethyl]amino}-7H-purine-2-carboxylic acid;

6-{[(1R)-1-cyclopropylethyl]amino}-8-(3-methylphenyl)-7-[4-(trifluoromethyl)benzyl]-7H-purine-2-carboxylic acid;

7-(4-chlorobenzyl)-8-(4-chlorophenyl)-6-{[(1R)-1-cyclopropylethyl]amino}-7H-purine-2-carboxylic acid;

8-(1-benzothiophen-5-yl)-7-(4-chlorobenzyl)-6-{[(1R)-1-cyclobutylethyl]amino}-7H-purine-2-carboxylic acid;

6-{[(1R)-1-cyclopropylethyl]amino}-8-(3-methylphenyl)-7-[4-(trifluoromethyl)benzyl]-7H-purine-2-carboxylic acid;

7-(4-chlorobenzyl)-6-{[(1R)-1-cyclopropylethyl]amino}-8-(2,5-dimethylphenyl)-7H-purine-2-carboxylic acid;

7-(4-chlorobenzyl)-6-{[(1R)-1-cyclopropylethyl]amino}-8-(4-fluoro-3-methylphenyl)-7H-purine-2-carboxylic acid;

6-{[(1R)-1-cyclopropylethyl]amino}-8-(3-methoxyphenyl)-7-[4-(trifluoromethyl)benzyl]-7H-purine-2-carboxylic acid;

6-{[(1R)-1-cyclopropylethyl]amino}-8-(3-ethoxyphenyl)-7-[4-(trifluoromethyl)benzyl]-7H-purine-2-carboxylic acid;

6-{[(1R)-1-cyclopropylethyl]amino}-8-(3-ethylphenyl)-7-[4-(trifluoromethyl)benzyl]-7H-purine-2-carboxylic acid;

6-{[(1R)-1-cyclobutylethyl]amino}-8-(3-ethoxyphenyl)-7-[4-(trifluoromethyl)benzyl]-7H-purine-2-carboxylic acid;

6-{[(1R)-1-cyclopropylethyl]amino}-8-[3-(1-methylethyl)phenyl]-7-[4-(trifluoromethyl)benzyl]-7H-purine-2-carboxylic acid;

8-(3-tert-butylphenyl)-6-{[(1R)-1-cyclopropylethyl]amino}-7-[4-(trifluoromethyl)benzyl]-7H-purine-2-carboxylic acid;

6-{[(1R)-1-cyclopropylethyl]amino}-7-[4-(trifluoromethyl)benzyl]-8-[4-(trifluoromethyl)phenyl]-7H-purine-2-carboxylic acid;

6-{[(1R)-1-cyclopropylethyl]amino}-8-(4-methoxyphenyl)-7-[4-(trifluoromethyl)benzyl]-7H-purine-2-carboxylic acid;

8-(3-chlorophenyl)-6-{[(1R)-1-cyclopropylethyl]amino}-7-[4-(trifluoromethyl)benzyl]-7H-purine-2-carboxylic acid;

6-{[(1R)-1-cyclobutylethyl]amino}-8-(3-ethylphenyl)-7-[4-(trifluoromethyl)benzyl]-7H-purine-2-carboxylic acid;

6-{[(1R)-1-cyclobutylethyl]amino}-8-[3-(1-methylethyl)phenyl]-7-[4-(trifluoromethyl)benzyl]-7H-purine-2-carboxylic acid;

8-(3-tert-butylphenyl)-6-{[(1R)-1-cyclobutylethyl]amino}-7-[4-(trifluoromethyl)benzyl]-7H-purine-2-carboxylic acid;

6-{[(1R)-1-cyclopropylethyl]amino}-8-[3-(trifluoromethoxy)phenyl]-7-[4-(trifluoromethyl)benzyl]-7H-purine-2-carboxylic acid;

6-{[(1R)-1-cyclopropylethyl]amino}-8-[4-(trifluoromethoxy)phenyl]-7-[4-(trifluoromethyl)benzyl]-7H-purine-2-carboxylic acid;

6-{[(1R)-1-cyclopropylethyl]amino}-8-(3,5-dimethoxyphenyl)-7-[4-(trifluoromethyl)benzyl]-7H-purine-2-carboxylic acid;
6-{[(1R)-1-cyclopropylethyl]amino}-8-[3-(dimethylamino)phenyl]-7-[4-(trifluoromethyl)benzyl]-7H-purine-2-carboxylic acid;
6-{[(1R)-1-cyclopropylethyl]amino}-8-(2-methylphenyl)-7-[4-(trifluoromethyl)benzyl]-7H-purine-2-carboxylic acid;
6-{[(1R)-1-cyclopropylethyl]amino}-8-(3,4-dichlorophenyl)-7-[4-(trifluoromethyl)benzyl]-7H-purine-2-carboxylic acid;
8-(4-tert-butylphenyl)-6-{[(1R)-1-cyclopropylethyl]amino}-7-[4-(trifluoromethyl)benzyl]-7H-purine-2-carboxylic acid;
6-{[(1R)-1-cyclopropylethyl]amino}-8-(4-methylphenyl)-7-[4-(trifluoromethyl)benzyl]-7H-purine-2-carboxylic acid;
6-{[(1R)-1-cyclopropylethyl]amino}-8-[2-(trifluoromethoxy)phenyl]-7-[4-(trifluoromethyl)benzyl]-7H-purine-2-carboxylic acid;
6-{[(1R)-1-cyclopropylethyl]amino}-8-(1-methyl-1H-pyrazol-4-yl)-7-[4-(trifluoromethyl)benzyl]-7H-purine-2-carboxylic acid;
6-{[(1R)-1-cyclopropylethyl]amino}-8-(6-methylpyridin-3-yl)-7-[4-(trifluoromethyl)benzyl]-7H-purine-2-carboxylic acid;
6-{[(1R)-1-cyclobutylethyl]amino}-8-[3-(dimethylamino)phenyl]-7-[4-(trifluoromethyl)benzyl]-7H-purine-2-carboxylic acid;
6-{[(1R)-1-cyclobutylethyl]amino}-7-[4-(trifluoromethyl)benzyl]-8-[3-(trifluoromethyl)phenyl]-7H-purine-2-carboxylic acid;
6-{[(1R)-1-cyclobutylethyl]amino}-8-[3-(trifluoromethoxy)phenyl]-7-[4-(trifluoromethyl)benzyl]-7H-purine-2-carboxylic acid;
8-(3-chlorophenyl)-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-[4-(methylsulfamoyl)phenyl]-7-[4-(trifluoromethyl)benzyl]-7H-purine-2-carboxylic acid;
7-(4-chlorobenzyl)-8-cyclopropyl-6-{[(1R)-1-cyclopropylethyl]amino}-7H-purine-2-carboxylic acid;
8-benzyl-7-(4-chlorobenzyl)-6-{[(1R)-1-cyclopropylethyl]amino}-7H-purine-2-carboxylic acid;
6-{[(1R)-1-cyclopropylethyl]amino}-8-pyridin-3-yl-7-[4-(trifluoromethyl)benzyl]-7H-purine-2-carboxylic acid;
8-(3-cyanophenyl)-6-{[(1R)-1-cyclobutylethyl]amino}-7-[4-(trifluoromethyl)benzyl]-7H-purine-2-carboxylic acid;
8-(5-chloro-6-methoxypyridin-3-yl)-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-(2-fluorophenyl)-7-[4-(trifluoromethyl)benzyl]-7H-purine-2-carboxylic acid;
6-{[(1R)-1-cyclopropylethyl]amino}-8-(6-methoxypyridin-3-yl)-7-[4-(trifluoromethyl)benzyl]-7H-purine-2-carboxylic acid;
6-{[(1R)-1-cyclopropylethyl]amino}-8-(5-fluoro-6-methoxypyridin-3-yl)-7-[4-(trifluoromethyl)benzyl]-7H-purine-2-carboxylic acid;
6-{[(1R)-1-cyclopropylethyl]amino}-8-(3,5-dimethylphenyl)-7-[4-(trifluoromethyl)benzyl]-7H-purine-2-carboxylic acid;
6-{[(1R)-1-cyclopropylethyl]amino}-8-(5-fluoro-6-hydroxypyridin-3-yl)-7-[4-(trifluoromethyl)benzyl]-7H-purine-2-carboxylic acid;
6-{[(1R)-1-cyclopropylethyl]amino}-8-(2,4-dimethylphenyl)-7-[4-(trifluoromethyl)benzyl]-7H-purine-2-carboxylic acid;
8-(4-chloro-3-fluorophenyl)-6-{[(1R)-1-cyclopropylethyl]amino}-7-[4-(trifluoromethyl)benzyl]-7H-purine-2-carboxylic acid;
6-{[(1R)-1-cyclopropylethyl]amino}-8-[2-methyl-4-(trifluoromethoxy)phenyl]-7-[4-(trifluoromethyl)benzyl]-7H-purine-2-carboxylic acid;
8-(2-chlorophenyl)-6-{[(1R)-1-cyclopropylethyl]amino}-7-[4-(trifluoromethyl)benzyl]-7H-purine-2-carboxylic acid;
6-{[(1R)-1-cyclopropylethyl]amino}-8-(3-fluorophenyl)-7-[4-(trifluoromethyl)benzyl]-7H-purine-2-carboxylic acid;
8-(4-cyanophenyl)-6-{[(1R)-1-cyclopropylethyl]amino}-7-[4-(trifluoromethyl)benzyl]-7H-purine-2-carboxylic acid;
6-{[(1R)-1-cyclopropylethyl]amino}-8-(2,4-dichlorophenyl)-7-[4-(trifluoromethyl)benzyl]-7H-purine-2-carboxylic acid;
6-{[(1R)-1-cyclopropylethyl]amino}-8-(2,3-dimethylphenyl)-7-[4-(trifluoromethyl)benzyl]-7H-purine-2-carboxylic acid;
6-{[(1R)-1-cyclopropylethyl]amino}-8-naphthalen-2-yl-7-[4-(trifluoromethyl)benzyl]-7H-purine-2-carboxylic acid;
8-(3-chloro-4-fluorophenyl)-6-{[(1R)-1-cyclobutylethyl]amino}-7-[4-(trifluoromethyl)benzyl]-7H-purine-2-carboxylic acid;
6-{[(1R)-1-cyclopropylethyl]amino}-8-(2,6-dimethylphenyl)-7-[4-(trifluoromethyl)benzyl]-7H-purine-2-carboxylic acid;
6-{[(1R)-1-cyclobutylethyl]amino}-8-(2,5-dichlorophenyl)-7-[4-(trifluoromethyl)benzyl]-7H-purine-2-carboxylic acid;
8-(3-cyano-5-methoxyphenyl)-6-{[(1R)-1-cyclobutylethyl]amino}-7-[4-(trifluoromethyl)benzyl]-7H-purine-2-carboxylic acid;
6-{[(1R)-1-cyclopropylethyl]amino}-8-(2-fluoro-3-methylphenyl)-7-[4-(trifluoromethyl)benzyl]-7H-purine-2-carboxylic acid;
8-(3-chloro-4-methoxyphenyl)-6-{[(1R)-1-cyclopropylethyl]amino}-7-[4-(trifluoromethyl)benzyl]-7H-purine-2-carboxylic acid;
6-{[(1R)-1-cyclobutylethyl]amino}-8-[3-(difluoromethoxy)phenyl]-7-[4-(trifluoromethyl)benzyl]-7H-purine-2-carboxylic acid;
6-{[(1R)-1-cyclobutylethyl]amino}-8-(2,4-difluorophenyl)-7-[4-(trifluoromethyl)benzyl]-7H-purine-2-carboxylic acid;
6-{[(1R)-1-cyclopropylethyl]amino}-8-quinolin-6-yl-7-[4-(trifluoromethyl)benzyl]-7H-purine-2-carboxylic acid;
6-{[(1R)-1-cyclopropylethyl]amino}-8-[2-(dimethylamino)pyrimidin-5-yl]-7-[4-(trifluoromethyl)benzyl]-7H-purine-2-carboxylic acid;
6-{[(1R)-1-cyclopropylethyl]amino}-8-(2-methoxypyridin-4-yl)-7-[4-(trifluoromethyl)benzyl]-7H-purine-2-carboxylic acid;
6-{[(1R)-1-cyclopropylethyl]amino}-8-(6-ethoxypyridin-3-yl)-7-[4-(trifluoromethyl)benzyl]-7H-purine-2-carboxylic acid;
6-{[(1R)-1-cyclopropylethyl]amino}-8-(2,3-difluorophenyl)-7-[4-(trifluoromethyl)benzyl]-7H-purine-2-carboxylic acid;
6-{[(1R)-1-cyclopropylethyl]amino}-8-(2,3-dihydro-1H-inden-5-yl)-7-[4-(trifluoromethyl)benzyl]-7H-purine-2-carboxylic acid;
8-(4-bromo-2-fluorophenyl)-6-{[(1R)-1-cyclopropylethyl]amino}-7-[4-(trifluoromethyl)benzyl]-7H-purine-2-carboxylic acid;

6-{[(1R)-1-cyclobutylethyl]amino}-8-(3,4-dichlorophenyl)-7-[4-(trifluoromethyl)benzyl]-7H-purine-2-carboxylic acid;

6-{[(1R)-1-cyclobutylethyl]amino}-8-pyridin-4-yl-7-[4-(trifluoromethyl)benzyl]-7H-purine-2-carboxylic acid;

8-(2-carbamoylphenyl)-6-{[(1R)-1-cyclopropylethyl]amino}-7-[4-(trifluoromethyl)benzyl]-7H-purine-2-carboxylic acid;

6-{[(1R)-1-cyclobutylethyl]amino}-7-[4-(trifluoromethyl)benzyl]-8-[2-(trifluoromethyl)phenyl]-7H-purine-2-carboxylic acid;

6-{[(1R)-1-cyclobutylethyl]amino}-8-(2-ethyl-5-methoxyphenyl)-7-[4-(trifluoromethyl)benzyl]-7H-purine-2-carboxylic acid;

6-{[(1R)-1-cyclobutylethyl]amino}-8-(2-ethylphenyl)-7-[4-(trifluoromethyl)benzyl]-7H-purine-2-carboxylic acid;

6-{[(1R)-1-cyclobutylethyl]amino}-8-(2-ethyl-5-methylphenyl)-7-[4-(trifluoromethyl)benzyl]-7H-purine-2-carboxylic acid;

6-{[(1R)-1-cyclobutylethyl]amino}-8-(1-methyl-1H-pyrazol-4-yl)-7-[4-(trifluoromethyl)benzyl]-7H-purine-2-carboxylic acid;

6-{[(1R)-1-cyclobutylethyl]amino}-8-(3,5-dimethylisoxazol-4-yl)-7-[4-(trifluoromethyl)benzyl]-7H-purine-2-carboxylic acid;

(R)-6-((1-cyclobutylethyl)amino)-8-(1-methyl-1H-imidazol-2-yl)-7-(4-(trifluoromethyl)benzyl)-7H-purine-2-carboxylic acid;

(R)-6-((1-cyclobutylethyl)amino)-8-(4-isopropylpyrimidin-2-yl)-7-(4-(trifluoromethyl)benzyl)-7H-purine-2-carboxylic acid;

(R)-6-((1-cyclobutylethyl)amino)-8-(5-isopropylthiazol-2-yl)-7-(4-(trifluoromethyl)benzyl)-7H-purine-2-carboxylic acid;

6-{[(1R)-1-cyclobutylethyl]amino}-8-pyrimidin-2-yl-7-[4-(trifluoromethyl)benzyl]-7H-purine-2-carboxylic acid;

6-{[(1R)-1-cyclobutylethyl]amino}-8-(1,3-oxazol-2-yl)-7-[4-(trifluoromethyl)benzyl]-7H-purine-2-carboxylic acid;

6-{[(1R)-1-cyclobutylethyl]amino}-8-[4-(1-methylethyl)-1,3-thiazol-2-yl]-7-[4-(trifluoromethyl)benzyl]-7H-purine-2-carboxylic acid;

6-{[(1R)-1-cyclobutylethyl]amino}-8-(5-methyl-1,3-thiazol-2-yl)-7-[4-(trifluoromethyl)benzyl]-7H-purine-2-carboxylic acid;

7-(4-chlorobenzyl)-6-{[(1R)-1-cyclopropylethyl]amino}-8-(1,3-thiazol-2-yl)-7H-purine-2-carboxylic acid;

6-{[(1R)-1-cyclobutylethyl]amino}-8-(1,3-thiazol-2-yl)-7-[4-(trifluoromethyl)benzyl]-7H-purine-2-carboxylic acid;

(R)-7-(4-chlorobenzyl)-6-((1-cyclobutylethyl)amino)-8-(2-ethoxy-5-methylphenyl)-7H-purine-2-carboxylic acid;

(R)-7-(4-chlorobenzyl)-6-((1-cyclobutylethyl)amino)-8-(2,5-dimethylphenyl)-7H-purine-2-carboxylic acid;

(R)-8-(2-(but-3-en-1-yloxy)-5-methylphenyl)-7-(4-chlorobenzyl)-6-((1-cyclopropylethyl)amino)-7H-purine-2-carboxylic acid;

(R)-7-(4-chlorobenzyl)-6-((1-cyclobutylethyl)amino)-8-(2-(3-methoxypropoxy)-5-methylphenyl)-7H-purine-2-carboxylic acid;

(R)-7-(4-chlorobenzyl)-6-((1-cyclopropylethyl)amino)-8-(2-(3-methoxypropoxy)-5-methylphenyl)-7H-purine-2-carboxylic acid;

(R)-7-(4-chlorobenzyl)-6-((1-cyclobutylethyl)amino)-8-(2-(3-hydroxypropoxy)-5-methylphenyl)-7H-purine-2-carboxylic acid;

(R)-7-(4-chlorobenzyl)-6-((1-cyclopropylethyl)amino)-8-(2-ethoxy-5-methylphenyl)-7H-purine-2-carboxylic acid;

(R)-7-(4-chlorobenzyl)-6-((1-cyclobutylethyl)amino)-8-(2-(2-methoxyethoxy)-5-methylphenyl)-7H-purine-2-carboxylic acid;

(R)-7-(4-chlorobenzyl)-6-((1-cyclopropylethyl)amino)-8-(2-(2-methoxyethoxy)-5-methylphenyl)-7H-purine-2-carboxylic acid;

(R)-7-(4-chlorobenzyl)-6-((1-cyclopropylethyl)amino)-8-(2-(2-hydroxyethoxy)-5-methylphenyl)-7H-purine-2-carboxylic acid;

(R)-8-(2-(2-carboxyethoxy)-5-methylphenyl)-7-(4-chlorobenzyl)-6-((1-cyclopropylethyl)amino)-7H-purine-2-carboxylic acid;

(R)-7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylic acid;

(R)-7-(4-chlorobenzyl)-6-((1-cyclopropylethyl)amino)-8-(5-methyl-2-(3-(methylamino)-3-oxopropoxy)phenyl)-7H-purine-2-carboxylic acid;

(R)-7-(4-chlorobenzyl)-6-((1-cyclopropylethyl)amino)-8-(5-methyl-2-(3-morpholinopropoxy)phenyl)-7H-purine-2-carboxylic acid;

(R)-8-(2-(3-(bis(2-methoxyethyl)amino)propoxy)-5-methylphenyl)-7-(4-chlorobenzyl)-6-((1-cyclopropylethyl)amino)-7H-purine-2-carboxylic acid;

(R)-7-(4-cyanobenzyl)-6-((1-cyclopropylethyl)amino)-8-(2-(3-hydroxypropoxy)-5-methylphenyl)-7H-purine-2-carboxylic acid;

(R)-7-(4-chlorobenzyl)-6-(1-cyclopropylethylamino)-8-(5-methyl-2-(3-(4-methylpiperazin-1-yl)propoxy)phenyl)-7H-purine-2-carboxylic acid;

(R)-7-(4-chlorobenzyl)-6-((1-cyclopropylethyl)amino)-8-(2-hydroxy-5-methylphenyl)-7H-purine-2-carboxylic acid;

7-(4-chlorobenzyl)-6-(((R)-1-cyclopropylethyl)amino)-8-(2-(2,3-dihydroxypropoxy)-5-methylphenyl)-7H-purine-2-carboxylic acid;

(R)-7-(4-chlorobenzyl)-6-((1-cyclopropylethyl)amino)-8-(2-(3-hydroxypropoxy)-5-methylphenyl)-7H-purine-2-carboxylic acid;

7-[1-(4-chlorophenyl)ethyl]-6-{[(1R)-1-cyclopropylethyl]amino}-8-(3-methylphenyl)-7H-purine-2-carboxylic acid;

7-[1-(4-chlorophenyl)ethyl]-6-[(cyclopropylmethyl)amino]-8-(3-methylphenyl)-7H-purine-2-carboxylic acid;

7-[1-(4-chlorophenyl)ethyl]-6-{[(1S)-1-cyclopropylethyl]amino}-8-(3-methylphenyl)-7H-purine-2-carboxylic acid;

6-{[(1R)-1-cyclopropylethyl]amino}-7-[4-fluoro-3-(trifluoromethyl)benzyl]-8-(3-methylphenyl)-7H-purine-2-carboxylic acid;

6-{[(1R)-1-cyclopropylethyl]amino}-7-(2-ethoxy-5-(trifluoromethyl)benzyl)-8-(3-methylphenyl)-7H-purine-2-carboxylic acid;

6-{[(1R)-1-cyclobutylethyl]amino}-7-2(ethoxybenzyl)-8-(3-methylphenyl)-7H-purine-2-carboxylic acid;

6-{[(1R)-1-cyclopropylethyl]amino}-7-[4-(1-methylethyl)benzyl]-8-(3-methylphenyl)-7H-purine-2-carboxylic acid;

6-{[(1R)-1-cyclopropylethyl]amino}-8-(3-methylphenyl)-7-[4-(trifluoromethoxy)benzyl]-7H-purine-2-carboxylic acid;

6-{[(1R)-1-cyclopropylethyl]amino}-7-[3-fluoro-4-(trifluoromethyl)benzyl]-8-(3-methylphenyl)-7H-purine-2-carboxylic acid;

6-{[(1R)-1-cyclobutylethyl]amino}-7-(4-cyclopropylbenzyl)-8-(3-methylphenyl)-7H-purine-2-carboxylic acid;

6-{[(1R)-1-cyclobutylethyl]amino}-7-(2,4-dichlorobenzyl)-8-(3-methylphenyl)-7H-purine-2-carboxylic acid;
7-[2-chloro-4-(trifluoromethyl)benzyl]-6-{[(1R)-1-cyclobutylethyl]amino}-8-(3-methylphenyl)-7H-purine-2-carboxylic acid;
6-{[(1R)-1-cyclobutylethyl]amino}-7-[4-(difluoromethoxy)benzyl]-8-(3-methylphenyl)-7H-purine-2-carboxylic acid;
6-{[(1R)-1-cyclobutylethyl]amino}-7-[3-fluoro-4-(trifluoromethoxy)benzyl]-8-(3-methylphenyl)-7H-purine-2-carboxylic acid;
7-[3-chloro-4-(trifluoromethyl)benzyl]-6-{[(1R)-1-cyclopropylethyl]amino}-8-(3-methylphenyl)-7H-purine-2-carboxylic acid;
6-{[(1R)-1-cyclopropylethyl]amino}-8-(3-methylphenyl)-7-[2-(trifluoromethyl)benzyl]-7H-purine-2-carboxylic acid;
6-{[(1R)-1-cyclobutylethyl]amino}-7-[2-fluoro-4-(trifluoromethyl)benzyl]-8-(3-methylphenyl)-7H-purine-2-carboxylic acid;
6-{[(1R)-1-cyclobutylethyl]amino}-7-[2-ethoxy-4-(trifluoromethyl)benzyl]-8-(3-methylphenyl)-7H-purine-2-carboxylic acid;
6-{[(1R)-1-cyclobutylethyl]amino}-7-(4-methoxybenzyl)-8-(3-methylphenyl)-7H-purine-2-carboxylic acid;
6-{[(1R)-1-cyclopropylethyl]amino}-7-(4-ethylbenzyl)-8-(3-methylphenyl)-7H-purine-2-carboxylic acid;
6-{[(1R)-1-cyclopropylethyl]amino}-7-(4-methylbenzyl)-8-(3-methylphenyl)-7H-purine-2-carboxylic acid;
7-[1-(4-chlorophenyl)ethyl]-6-{[(1R)-1-cyclopropylethyl]amino}-8-(3-methylphenyl)-7H-purine-2-carboxylic acid;
7-[1-(4-chlorophenyl)ethyl]-6-[(cyclopropylmethyl)amino]-8-(3-methylphenyl)-7H-purine-2-carboxylic acid;
7-[1-(4-chlorophenyl)ethyl]-6-{[(1S)-1-cyclopropylethyl]amino}-8-(3-methylphenyl)-7H-purine-2-carboxylic acid;
6-{[(1R)-1-cyclopropylethyl]amino}-7-[4-fluoro-3-(trifluoromethyl)benzyl]-8-(3-methylphenyl)-7H-purine-2-carboxylic acid;
6-{[(1R)-1-cyclopropylethyl]amino}-7-(2-ethoxy-5-(trifluoromethyl)benzyl)-8-(3-methylphenyl)-7H-purine-2-carboxylic acid;
6-{[(1R)-1-cyclobutylethyl]amino}-7-(2-ethoxybenzyl)-8-(3-methylphenyl)-7H-purine-2-carboxylic acid;
6-{[(1R)-1-cyclopropylethyl]amino}-7-[4-(1-methylethyl)benzyl]-8-(3-methylphenyl)-7H-purine-2-carboxylic acid;
6-{[(1R)-1-cyclopropylethyl]amino}-8-(3-methylphenyl)-7-[4-(trifluoromethoxy)benzyl]-7H-purine-2-carboxylic acid;
6-{[(1R)-1-cyclopropylethyl]amino}-7-[3-fluoro-4-(trifluoromethyl)benzyl]-8-(3-methylphenyl)-7H-purine-2-carboxylic acid;
6-{[(1R)-1-cyclobutylethyl]amino}-7-(4-cyclopropylbenzyl)-8-(3-methylphenyl)-7H-purine-2-carboxylic acid;
6-{[(1R)-1-cyclobutylethyl]amino}-7-(2,4-dichlorobenzyl)-8-(3-methylphenyl)-7H-purine-2-carboxylic acid;
7-[2-chloro-4-(trifluoromethyl)benzyl]-6-{[(1R)-1-cyclobutylethyl]amino}-8-(3-methylphenyl)-7H-purine-2-carboxylic acid;
6-{[(1R)-1-cyclobutylethyl]amino}-7-[4-(difluoromethoxy)benzyl]-8-(3-methylphenyl)-7H-purine-2-carboxylic acid;
6-{[(1R)-1-cyclobut ylethyl]amino}-7-[3-fluoro-4-(trifluoromethoxy)benzyl]-8-(3-methylphenyl)-7H-purine-2-carboxylic acid;
7-[3-chloro-4-(trifluoromethyl)benzyl]-6-{[(1R)-1-cyclopropylethyl]amino}-8-(3-methylphenyl)-7H-purine-2-carboxylic acid;
6-{[(1R)-1-cyclopropylethyl]amino}-8-(3-methylphenyl)-7-[2-(trifluoromethyl)benzyl]-7H-purine-2-carboxylic acid;
6-{[(1R)-1-cyclobutylethyl]amino}-7-[2-fluoro-4-(trifluoromethyl)benzyl]-8-(3-methylphenyl)-7H-purine-2-carboxylic acid;
6-{[(1R)-1-cyclobutylethyl]amino}-7-[2-ethoxy-4-(trifluoromethyl)benzyl]-8-(3-methylphenyl)-7H-purine-2-carboxylic acid;
6-{[(1R)-1-cyclobutylethyl]amino}-7-(4-methoxybenzyl)-8-(3-methylphenyl)-7H-purine-2-carboxylic acid;
6-{[(1R)-1-cyclopropylethyl]amino}-7-(4-ethylbenzyl)-8-(3-methylphenyl)-7H-purine-2-carboxylic acid;
6-{[(1R)-1-cyclopropylethyl]amino}-7-(4-methylbenzyl)-8-(3-methylphenyl)-7H-purine-2-carboxylic acid;
6-(3-ethylpyrrolidin-1-yl)-8-(3-methylphenyl)-7-[4-(trifluoromethyl)benzyl]-7H-purine-2-carboxylic acid;
7-(4-chlorobenzyl)-6-{[(1R)-1-cyclobutylethyl]amino}-8-(3-methylphenyl)-7H-purine-2-carboxylic acid;
7-(4-chlorobenzyl)-6-{[(1R)-1-cyclopentylethyl]amino}-8-(3-methylphenyl)-7H-purine-2-carboxylic acid;
7-(4-chlorobenzyl)-6-{[(1R)-1-cyclohexylethyl]amino}-8-(3-methylphenyl)-7H-purine-2-carboxylic acid;
7-(4-bromobenzyl)-6-{[(1R)-1-cyclopropylethyl]amino}-8-(3-methylphenyl)-7H-purine-2-carboxylic acid;
7-(4-chlorobenzyl)-6-[(1-cyclopropyl-1-methylethyl)amino]-8-(3-methylphenyl)-7H-purine-2-carboxylic acid;
7-(4-bromobenzyl)-6-{[(1R)-1-cyclobutylethyl]amino}-8-(3-methylphenyl)-7H-purine-2-carboxylic acid;
6-[(2-methylcyclohexyl)amino]-8-(3-methylphenyl)-7-[4-(trifluoromethyl)benzyl]-7H-purine-2-carboxylic acid;
7-(4-bromobenzyl)-6-[(2-methylcyclohexyl)amino]-8-(3-methylphenyl)-7H-purine-2-carboxylic acid;
7-(4-bromobenzyl)-6-[(2-methylcyclohexyl)amino]-8-(3-methylphenyl)-7H-purine-2-carboxylic acid;
7-(4-chlorobenzyl)-6-[(1-cyclopropylethyl)(methyl)amino]-8-(3-methylphenyl)-7H-purine-2-carboxylic acid;
7-(4-chlorobenzyl)-8-(3-chlorophenyl)-6-[(cyclopropylmethyl)amino]-7H-purine-2-carboxylic acid;
8-(1-benzothiophen-5-yl)-6-{[(1R)-1-cyclopropylethyl]amino}-7-[4-(trifluoromethyl)benzyl]-7H-purine-2-carboxylic acid;
8-(1-benzothiophen-5-yl)-6-{[(1R)-1-cyclobutylethyl]amino}-7-[4-(trifluoromethyl)benzyl]-7H-purine-2-carboxylic acid;
7-(3-chloro-4-fluorobenzyl)-6-{[(1R)-1-cyclopropylethyl]amino}-8-(3-methylphenyl)-7H-purine-2-carboxylic acid;
6-{[(1R)-1-cyclopropylethyl]amino}-7-(3,4-dichlorobenzyl)-8-(3-methylphenyl)-7H-purine-2-carboxylic acid;
7-(4-chloro-3-fluorobenzyl)-6-{[(1R)-1-cyclopropylethyl]amino}-8-(3-methylphenyl)-7H-purine-2-carboxylic acid;
3-cyclopropyl-3-({8-(3-methylphenyl)-7-[4-(trifluoromethyl)benzyl]-7H-purin-6-yl}amino)propanoic acid;
6-[(4-methylcyclohexyl)amino]-8-(3-methylphenyl)-7-[4-(trifluoromethyl)benzyl]-7H-purine-2-carboxylic acid;
6-[(3-methylcyclohexyl)amino]-8-(3-methylphenyl)-7-[4-(trifluoromethyl)benzyl]-7H-purine-2-carboxylic acid;
6-[(2-methylcyclopentyl)amino]-8-(3-methylphenyl)-7-[4-(trifluoromethyl)benzyl]-7H-purine-2-carboxylic acid;
6-(cyclopentylamino)-8-(3-methylphenyl)-7-[4-(trifluoromethyl)benzyl]-7H-purine-2-carboxylic acid;

8-(3-methylphenyl)-6-pyrrolidin-1-yl-7-[4-(trifluoromethyl)benzyl]-7H-purine-2-carboxylic acid;
6-[(dicyclopropylmethyl)amino]-8-(3-methylphenyl)-7-[4-(trifluoromethyl)benzyl]-7H-purine-2-carboxylic acid;
8-(3-methylphenyl)-6-[(2-phenylethyl)amino]-7-[4-(trifluoromethyl)benzyl]-7H-purine-2-carboxylic acid;
6-{[(1S)-1-(3-chlorophenyl)ethyl]amino}-8-(3-methylphenyl)-7-[4-(trifluoromethyl)benzyl]-7H-purine-2-carboxylic acid;
6-{[(1R)-1-(3-chlorophenyl)ethyl]amino}-8-(3-methylphenyl)-7-[4-(trifluoromethyl)benzyl]-7H-purine-2-carboxylic acid;
6-(cyclohexylamino)-8-(3-methylphenyl)-7-[4-(trifluoromethyl)benzyl]-7H-purine-2-carboxylic acid;
6-(benzylamino)-8-(3-methylphenyl)-7-[4-(trifluoromethyl)benzyl]-7H-purine-2-carboxylic acid;
8-(3-methylphenyl)-6-{[(1R)-1-phenylethyl]amino}-7-[4-(trifluoromethyl)benzyl]-7H-purine-2-carboxylic acid;
8-(3-methylphenyl)-6-{[(1S)-1-phenylethyl]amino}-7-[4-(trifluoromethyl)benzyl]-7H-purine-2-carboxylic acid;
6-[(1-cyclopentylethyl)amino]-8-(3-methylphenyl)-7-[4-(trifluoromethyl)benzyl]-7H-purine-2-carboxylic acid;
6-[(2,4-dimethylcyclohexyl)amino]-8-(3-methylphenyl)-7-[4-(trifluoromethyl)benzyl]-7H-purine-2-carboxylic acid;
6-[(2,4-dimethylcyclohexyl)amino]-8-(3-methylphenyl)-7-[4-(trifluoromethyl)benzyl]-7H-purine-2-carboxylic acid;
6-[(4-{[(tert-butoxycarbonyl)amino]methyl}cyclohexyl)amino]-8-(3-methylphenyl)-7-[4-(trifluoromethyl)benzyl]-7H-purine-2-carboxylic acid;
6-[(cyclopropylmethyl)amino]-8-(3-methylphenyl)-7-[4-(trifluoromethyl)benzyl]-7H-purine-2-carboxylic acid;
6-{[1-(2-methylcyclopropyl)ethyl]amino}-8-(3-methylphenyl)-7-[4-(trifluoromethyl)benzyl]-7H-purine-2-carboxylic acid;
6-{[1-(2-methylcyclopropyl)ethyl]amino}-8-(3-methylphenyl)-7-[4-(trifluoromethyl)benzyl]-7H-purine-2-carboxylic acid;
6-[(2-hydroxy-1,2-dimethylpropyl)amino]-8-(3-methylphenyl)-7-[4-(trifluoromethyl)benzyl]-7H-purine-2-carboxylic acid;
6-{[4-(hydroxymethyl)cyclohexyl]amino}-8-(3-methylphenyl)-7-[4-(trifluoromethyl)benzyl]-7H-purine-2-carboxylic acid;
8-(3-methylphenyl)-7-[4-(trifluoromethyl)benzyl]-6-{[(1S)-1,2,2-trimethylpropyl]amino}-7H-purine-2-carboxylic acid;
6-{[(1R)-1-cyclohexylethyl]amino}-8-(3-methylphenyl)-7-[4-(trifluoromethyl)benzyl]-7H-purine-2-carboxylic acid;
8-(3-methylphenyl)-6-(tetrahydro-2H-pyran-4-ylamino)-7-[4-(trifluoromethyl)benzyl]-7H-purine-2-carboxylic acid;
6-{[(1R)-1-(4-chlorophenyl)ethyl]amino}-8-(3-methylphenyl)-7-[4-(trifluoromethyl)benzyl]-7H-purine-2-carboxylic acid;
6-{[(1S)-1-cyclohexylethyl]amino}-8-(3-methylphenyl)-7-[4-(trifluoromethyl)benzyl]-7H-purine-2-carboxylic acid;
6-{[(1S)-1-(4-chlorophenyl)ethyl]amino}-8-(3-methylphenyl)-7-[4-(trifluoromethyl)benzyl]-7H-purine-2-carboxylic acid;
8-(3-methylphenyl)-7-[4-(trifluoromethyl)benzyl]-6-{[(1R)-1,2,2-trimethylpropyl]amino}-7H-purine-2-carboxylic acid;
6-{[(1R)-1,2-dimethylpropyl]amino}-8-(3-methylphenyl)-7-[4-(trifluoromethyl)benzyl]-7H-purine-2-carboxylic acid;
6-{[(1S)-1,2-dimethylpropyl]amino}-8-(3-methylphenyl)-7-[4-(trifluoromethyl)benzyl]-7H-purine-2-carboxylic acid;
6-[(cyclohexylmethyl)amino]-8-(3-methylphenyl)-7-[4-(trifluoromethyl)benzyl]-7H-purine-2-carboxylic acid;
6-(diethylamino)-8-(3-methylphenyl)-7-[4-(trifluoromethyl)benzyl]-7H-purine-2-carboxylic acid;
6-{[(1R)-1-cyclopropyl-2,2,2-trifluoroethyl]amino}-8-(3-methylphenyl)-7-[4-(trifluoromethyl)benzyl]-7H-purine-2-carboxylic acid;
6-{[(1S)-1-cyclopropyl-2,2,2-trifluoroethyl]amino}-8-(3-methylphenyl)-7-[4-(trifluoromethyl)benzyl]-7H-purine-2-carboxylic acid;
6-{[(1S)-1-cyclobutylpropyl]amino}-8-[4-(1-methylethyl)pyridin-2-yl]-7-[4-(trifluoromethyl)benzyl]-7H-purine-2-carboxylic acid;
6-{[(1R)-1-cyclobutylpropyl]amino}-8-[4-(1-methylethyl)pyridin-2-yl]-7-[4-(trifluoromethyl)benzyl]-7H-purine-2-carboxylic acid;
6-{[(1R)-1-(2,2-dimethylcyclopropyl)ethyl]amino}-8-(2-methoxy-5-methylphenyl)-7-[4-(trifluoromethyl)benzyl]-7H-purine-2-carboxylic acid;
6-{[(R)-cyclobutyl(phenyl)methyl]amino}-8-[4-(1-methylethyl)pyridin-2-yl]-7-[4-(trifluoromethyl)benzyl]-7H-purine-2-carboxylic acid;
6-{[(S)-cyclobutyl(phenyl)methyl]amino}-8-[4-(1-methylethyl)pyridin-2-yl]-7-[4-(trifluoromethyl)benzyl]-7H-purine-2-carboxylic acid;
6-[ethyl(methyl)amino]-8-(3-methylphenyl)-7-[4-(trifluoromethyl)benzyl]-7H-purine-2-carboxylic acid;
8-(3-methylphenyl)-6-{[(1R)-1-methylpropyl]amino}-7-[4-(trifluoromethyl)benzyl]-7H-purine-2-carboxylic acid;
8-(3-methylphenyl)-6-{[(1S)-1-methylpropyl]amino}-7-[4-(trifluoromethyl)benzyl]-7H-purine-2-carboxylic acid;
6-[(1,3-dimethylbutyl)amino]-8-(3-methylphenyl)-7-[4-(trifluoromethyl)benzyl]-7H-purine-2-carboxylic acid;
6-[(2-methylbutyl)amino]-8-(3-methylphenyl)-7-[4-(trifluoromethyl)benzyl]-7H-purine-2-carboxylic acid;
8-(3-methylphenyl)-6-[(1-propylbutyl)amino]-7-[4-(trifluoromethyl)benzyl]-7H-purine-2-carboxylic acid;
6-[cyclopentyl(methyl)amino]-8-(3-methylphenyl)-7-[4-(trifluoromethyl)benzyl]-7H-purine-2-carboxylic acid;
6-(1,3-dihydro-2H-isoindol-2-yl)-8-(3-methylphenyl)-7-[4-(trifluoromethyl)benzyl]-7H-purine-2-carboxylic acid;
6-[benzyl(methyl)amino]-8-(3-methylphenyl)-7-[4-(trifluoromethyl)benzyl]-7H-purine-2-carboxylic acid;
6-[butyl(propyl)amino]-8-(3-methylphenyl)-7-[4-(trifluoromethyl)benzyl]-7H-purine-2-carboxylic acid;
6-[butyl(ethyl)amino]-8-(3-methylphenyl)-7-[4-(trifluoromethyl)benzyl]-7H-purine-2-carboxylic acid;
6-[ethyl(propyl)amino]-8-(3-methylphenyl)-7-[4-(trifluoromethyl)benzyl]-7H-purine-2-carboxylic acid;
6-[methyl(2-methylpropyl)amino]-8-(3-methylphenyl)-7-[4-(trifluoromethyl)benzyl]-7H-purine-2-carboxylic acid;
6-[methyl(2-methylpropyl)amino]-8-(3-methylphenyl)-7-[4-(trifluoromethyl)benzyl]-7H-purine-2-carboxylic acid;
6-[(1,2-dimethylpropyl)amino]-8-(3-methylphenyl)-7-[4-(trifluoromethyl)benzyl]-7H-purine-2-carboxylic acid;
8-(3-methylphenyl)-7-[4-(trifluoromethyl)benzyl]-6-[(1,2,2-trimethylpropyl)amino]-7H-purine-2-carboxylic acid;
6-[(cyclobutylmethyl)amino]-8-(3-methylphenyl)-7-[4-(trifluoromethyl)benzyl]-7H-purine-2-carboxylic acid;
8-(3-methylphenyl)-6-[2-(2-methylpropyl)pyrrolidin-1-yl]-7-[4-(trifluoromethyl)benzyl]-7H-purine-2-carboxylic acid;
6-[methyl(3-methylbutyl)amino]-8-(3-methylphenyl)-7-[4-(trifluoromethyl)benzyl]-7H-purine-2-carboxylic acid;

6-(2-ethylpyrrolidin-1-yl)-8-(3-methylphenyl)-7-[4-(trifluoromethyl)benzyl]-7H-purine-2-carboxylic acid;

6-[methyl(1-methylbutyl)amino]-8-(3-methylphenyl)-7-[4-(trifluoromethyl)benzyl]-7H-purine-2-carboxylic acid;

6-(2-cyclohexylpyrrolidin-1-yl)-8-(3-methylphenyl)-7-[4-(trifluoromethyl)benzyl]-7H-purine-2-carboxylic acid;

6-[(1,2-dimethylpropyl)(methyl)amino]-8-(3-methylphenyl)-7-[4-(trifluoromethyl)benzyl]-7H-purine-2-carboxylic acid;

6-[(2,2-dimethylpropyl)(methyl)amino]-8-(3-methylphenyl)-7-[4-(trifluoromethyl)benzyl]-7H-purine-2-carboxylic acid;

6-[butyl(methyl)amino]-8-(3-methylphenyl)-7-[4-(trifluoromethyl)benzyl]-7H-purine-2-carboxylic acid;

6-[(dicyclopropylmethyl)(methyl)amino]-8-(3-methylphenyl)-7-[4-(trifluoromethyl)benzyl]-7H-purine-2-carboxylic acid;

6-[2-(1-methylethyl)pyrrolidin-1-yl]-8-(3-methylphenyl)-7-[4-(trifluoromethyl)benzyl]-7H-purine-2-carboxylic acid;

8-(3-methylphenyl)-6-(2-propylpyrrolidin-1-yl)-7-[4-(trifluoromethyl)benzyl]-7H-purine-2-carboxylic acid;

6-(2-tert-butylpyrrolidin-1-yl)-8-(3-methylphenyl)-7-[4-(trifluoromethyl)benzyl]-7H-purine-2-carboxylic acid;

6-[(1-cyclopropylethyl)(methyl)amino]-8-(3-methylphenyl)-7-[4-(trifluoromethyl)benzyl]-7H-purine-2-carboxylic acid;

6-[methyl(2-methylbutyl)amino]-8-(3-methylphenyl)-7-[4-(trifluoromethyl)benzyl]-7H-purine-2-carboxylic acid;

6-{[(2,2-dimethylcyclopropyl)methyl](methyl)amino}-8-(3-methylphenyl)-7-[4-(trifluoromethyl)benzyl]-7H-purine-2-carboxylic acid;

6-[methyl(pentyl)amino]-8-(3-methylphenyl)-7-[4-(trifluoromethyl)benzyl]-7H-purine-2-carboxylic acid;

6-(2-cyclobutylpyrrolidin-1-yl)-8-(3-methylphenyl)-7-[4-(trifluoromethyl)benzyl]-7H-purine-2-carboxylic acid;

6-(2-cyclobutylazetidin-1-yl)-8-(3-methylphenyl)-7-[4-(trifluoromethyl)benzyl]-7H-purine-2-carboxylic acid;

8-(3-methylphenyl)-6-[(3-methylphenyl)amino]-7-[4-(trifluoromethyl)benzyl]-7H-purine-2-carboxylic acid;

6-(2-cyclobutylpiperidin-1-yl)-8-(3-methylphenyl)-7-[4-(trifluoromethyl)benzyl]-7H-purine-2-carboxylic acid;

(R)-Methyl-7-(4-chlorobenzyl)-6-{[(1R)-1-cyclobutyl-4-hydroxybutyl]amino}-8-(3-methylphenyl)-7H-purine-2-carboxylic acid;

6-{[(1R)-1-cyclobutyl-4-hydroxybutyl]amino}-8-(3-methylphenyl)-7-[4-(trifluoromethyl)benzyl]-7H-purine-2-carboxylic acid;

(4R)-4-cyclobutyl-4-({8-(3-methylphenyl)-7-[4-(trifluoromethyl)benzyl]-7H-purin-6-yl}amino)butan-1-ol;

6-{[(1R)-1-cyclobutylbutyl]amino}-8-(3-methylphenyl)-7-[4-(trifluoromethyl)benzyl]-7H-purine-2-carboxylic acid;

6-({(1R)-1-cyclobutyl-4-[(2-hydroxyethyl)amino]-4-oxobutyl}amino)-8-(3-methylphenyl)-7-[4-(trifluoromethyl)benzyl]-7H-purine-2-carboxylic acid;

6-[(2R)-2-cyclobutylpyrrolidin-1-yl]-8-(3-methylphenyl)-7-[4-(trifluoromethyl)benzyl]-7H-purine-2-carboxylic acid;

6-[(2R)-2-cyclobutylpyrrolidin-1-yl]-8-(3-methylphenyl)-7-[4-(trifluoromethyl)benzyl]-7H-purine;

6-{[(1R)-1-cyclobutyl-4-(4-methylpiperazin-1-yl)butyl]amino}-8-(3-methylphenyl)-7-[4-(trifluoromethyl)benzyl]-7H-purine-2-carboxylic acid;

6-{[(1R)-1-cyclobutyl-4-(dimethylamino)butyl]amino}-8-(3-methylphenyl)-7-[4-(trifluoromethyl)benzyl]-7H-purine-2-carboxylic acid;

6-{[(1R)-4-amino-1-cyclobutyl-4-oxobutyl]amino}-8-(3-methylphenyl)-7-[4-(trifluoromethyl)benzyl]-7H-purine-2-carboxylic acid;

6-{[(1R)-1-cyclobutyl-4-(methylamino)-4-oxobutyl]amino}-8-(3-methylphenyl)-7-[4-(trifluoromethyl)benzyl]-7H-purine-2-carboxylic acid;

6-{[(1R)-1-cyclobutyl-3,4-dihydroxybutyl]amino}-8-(3-methylphenyl)-7-[4-(trifluoromethyl)benzyl]-7H-purine-2-carboxylic acid;

6-{[(S)-cyclobutyl(phenyl)methyl]amino}-8-[4-(1-methylethyl)pyridin-2-yl]-7-[4-(trifluoromethyl)benzyl]-7H-purine-2-carboxylic acid;

6-{[(1R)-1-(3,3-difluorocyclobutyl)ethyl]amino}-8-(2-methoxy-5-methylphenyl)-7-[4-(trifluoromethyl)benzyl]-7H-purine-2-carboxylic acid;

8-(2-methoxy-5-methylphenyl)-6-{[1-(3-methylcyclobutyl)ethyl]amino}-7-[4-(trifluoromethyl)benzyl]-7H-purine-2-carboxylic acid;

6-{[(1R)-1-(2,2-difluorocyclopropyl)ethyl]amino}-8-(2-methoxy-5-methylphenyl)-7-[4-(trifluoromethyl)benzyl]-7H-purine-2-carboxylic acid;

7-[2-amino-4-(trifluoromethyl)benzyl]-6-{[(1R)-1-cyclobutylethyl]amino}-8-[4-(1-methylethyl)pyridin-2-yl]-7H-purine-2-carboxylic acid;

6-{[(1R)-1-cyclobutylethyl]amino}-8-{[(1S)-1-(4-fluorophenyl)ethyl]amino}-7-[4-(trifluoromethyl)benzyl]-7H-purine-2-carboxylic acid;

6-{[(1R)-1-cyclobutylethyl]amino}-8-[methyl(phenyl)amino]-7-[4-(trifluoromethyl)benzyl]-7H-purine-2-carboxylic acid;

8-(2-benzylpiperidin-1-yl)-6-{[(1R)-1-cyclobutylethyl]amino}-7-[4-(trifluoromethyl)benzyl]-7H-purine-2-carboxylic acid;

3-{7-(4-chloro-3-fluorobenzyl)-6-{[(1R)-1-cyclobutylethyl]amino}-8-[(3R)-3-phenylmorpholin-4-yl]-7H-purin-2-yl}-1,2,4-oxadiazol-5(4H)-one;

6-{[(1R)-1-cyclopropylethyl]amino}-8-(4-methylpiperazin-1-yl)-7-[4-(trifluoromethyl)benzyl]-7H-purine-2-carboxylic acid;

6-{[(1R)-1-cyclobutylethyl]amino}-8-{[(1R)-2-hydroxy-1-phenylethyl]amino}-7-[4-(trifluoromethyl)benzyl]-7H-purine-2-carboxylic acid;

6-{[(1R)-1-cyclobutylethyl]amino}-8-{[(1R)-2-hydroxy-1-methylethyl]amino}-7-[4-(trifluoromethyl)benzyl]-7H-purine-2-carboxylic acid;

6-{[(1R)-1-cyclobutylethyl]amino}-8-{[(1S)-2-hydroxy-1-phenylethyl]amino}-7-[4-(trifluoromethyl)benzyl]-7H-purine-2-carboxylic acid;

7-(4-chlorobenzyl)-6-{[(1R)-1-cyclopropylethyl]amino}-8-morpholin-4-yl-7H-purine-2-carboxylic acid;

6-{[(1R)-1-cyclobutylethyl]amino}-8-{[(1S)-2-hydroxy-1-methylethyl]amino}-7-[4-(trifluoromethyl)benzyl]-7H-purine-2-carboxylic acid;

6-{[(1R)-1-cyclobutylethyl]amino}-8-piperidin-1-yl-7-[4-(trifluoromethyl)benzyl]-7H-purine-2-carboxylic acid;

6-{[(1R)-1-cyclobutylethyl]amino}-8-(cyclohexylamino)-7-[4-(trifluoromethyl)benzyl]-7H-purine-2-carboxylic acid;

8-(benzylamino)-6-{[(1R)-1-cyclobutylethyl]amino}-7-[4-(trifluoromethyl)benzyl]-7H-purine-2-carboxylic acid;

8-[benzyl(methyl)amino]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[cyclohexyl(methyl)amino]-7-[4-(trifluoromethyl)benzyl]-7H-purine-2-carboxylic acid;

6-{[(1R)-1-cyclobutylethyl]amino}-8-{[(1S)-1-phenylethyl]amino}-7-[4-(trifluoromethyl)benzyl]-7H-purine-2-carboxylic acid;

6-{[(1R)-1-cyclobutylethyl]amino}-8-{[(1R)-1-phenyl-ethyl]amino}-7-[4-(trifluoromethyl)benzyl]-7H-purine-2-carboxylic acid;

6-{[(1R)-1-cyclobutylethyl]amino}-8-(2,2-dimethylmorpholin-4-yl)-7-[4-(trifluoromethyl)benzyl]-7H-purine-2-carboxylic acid;

6-{[(1R)-1-cyclobutylethyl]amino}-8-(2,2,6,6-tetramethylmorpholin-4-yl)-7-[4-(trifluoromethyl)benzyl]-7H-purine-2-carboxylic acid;

6-{[(1R)-1-cyclobutylethyl]amino}-8-(2-methylmorpholin-4-yl)-7-[4-(trifluoromethyl)benzyl]-7H-purine-2-carboxylic acid;

6-{[(1R)-1-cyclobutylethyl]amino}-8-(phenylamino)-7-[4-(trifluoromethyl)benzyl]-7H-purine-2-carboxylic acid;

6-{[(1R)-1-cyclobutylethyl]amino}-8-(2-phenylmorpholin-4-yl)-7-[4-(trifluoromethyl)benzyl]-7H-purine-2-carboxylic acid;

6-{[(1R)-1-cyclobutylethyl]amino}-7-[4-(trifluoromethyl)benzyl]-8-[2-(trifluoromethyl)morpholin-4-yl]-7H-purine-2-carboxylic acid;

6-{[(1R)-1-cyclobutylethyl]amino}-8-[2-(methoxymethyl)morpholin-4-yl]-7-[4-(trifluoromethyl)benzyl]-7H-purine-2-carboxylic acid;

6-{[(1R)-1-cyclobutylethyl]amino}-8-(6-oxa-9-azaspiro[4.5]dec-9-yl)-7-[4-(trifluoromethyl)benzyl]-7H-purine-2-carboxylic acid;

6-{[(1R)-1-cyclobutylethyl]amino}-8-(2-prop-2-yn-1-ylmorpholin-4-yl)-7-[4-(trifluoromethyl)benzyl]-7H-purine-2-carboxylic acid;

6-{[(1R)-1-cyclobutylethyl]amino}-8-[(1R,4R)-2-oxa-5-azabicyclo[2.2.1]hept-5-yl]-7-[4-(trifluoromethyl)benzyl]-7H-purine-2-carboxylic acid;

7-(4-chlorobenzyl)-6-{[(1R)-1-cyclopropylethyl]amino}-8-[(3S)-3-methylmorpholin-4-yl]-7H-purine-2-carboxylic acid;

(2R)-2-[(6-{[(1R)-1-cyclobutylethyl]amino}-7-[4-(trifluoromethyl)benzyl]-7H-purin-8-yl)amino]-2-phenylethanol;

6-{[(1R)-1-cyclobutylethyl]amino}-8-[(1-pyridin-3-yl-ethyl)amino]-7-[4-(trifluoromethyl)benzyl]-7H-purine-2-carboxylic acid;

6-{[(1R)-1-cyclobutylethyl]amino}-8-[(1-pyridin-2-yl-ethyl)amino]-7-[4-(trifluoromethyl)benzyl]-7H-purine-2-carboxylic acid;

6-{[(1R)-1-cyclobutylethyl]amino}-8-[(3S)-3-methylmorpholin-4-yl]-7-[4-(trifluoromethyl)benzyl]-7H-purine-2-carboxylic acid;

6-{[(1R)-1-cyclobutylethyl]amino}-8-[(3R)-3-methylmorpholin-4-yl]-7-[4-(trifluoromethyl)benzyl]-7H-purine-2-carboxylic acid;

6-{[(1R)-1-cyclobutylethyl]amino}-8-{[(1S)-1-phenylpropyl]amino}-7-[4-(trifluoromethyl)benzyl]-7H-purine-2-carboxylic acid;

6-{[(1R)-1-cyclobutylethyl]amino}-8-{methyl[(1S)-1-phenylethyl]amino}-7-[4-(trifluoromethyl)benzyl]-7H-purine-2-carboxylic acid;

6-{[(1R)-1-cyclobutylethyl]amino}-8-[(phenylcarbonyl)amino]-7-[4-(trifluoromethyl)benzyl]-7H-purine-2-carboxylic acid;

6-{[(1R)-1-cyclobutylethyl]amino}-8-{[(1S)-1-(3-fluorophenyl)ethyl]amino}-7-[4-(trifluoromethyl)benzyl]-7H-purine-2-carboxylic acid;

6-{[(1R)-1-cyclobutylethyl]amino}-8-(3-methylpiperidin-1-yl)-7-[4-(trifluoromethyl)benzyl]-7H-purine-2-carboxylic acid;

6-{[(1R)-1-cyclobutylethyl]amino}-8-(3-phenylpiperidin-1-yl)-7-[4-(trifluoromethyl)benzyl]-7H-purine-2-carboxylic acid;

6-{[(1R)-1-cyclobutylethyl]amino}-8-[(3-methylbutanoyl)amino]-7-[4-(trifluoromethyl)benzyl]-7H-purine-2-carboxylic acid;

6-{[(1R)-1-cyclobutylethyl]amino}-8-[(cyclohexylcarbonyl)amino]-7-[4-(trifluoromethyl)benzyl]-7H-purine-2-carboxylic acid;

6-{[(1R)-1-cyclobutylethyl]amino}-8-(2-phenylpiperidin-1-yl)-7-[4-(trifluoromethyl)benzyl]-7H-purine-2-carboxylic acid;

6-{[(1R)-1-cyclobutylethyl]amino}-8-(3,3-dimethylpiperidin-1-yl)-7-[4-(trifluoromethyl)benzyl]-7H-purine-2-carboxylic acid;

6-{[(1R)-1-cyclobutylethyl]amino}-8-[3-(1-methylethyl)piperidin-1-yl]-7-[4-(trifluoromethyl)benzyl]-7H-purine-2-carboxylic acid;

6-{[(1R)-1-cyclobutylethyl]amino}-7-[3-fluoro-4-(trifluoromethyl)benzyl]-8-(2-phenylpiperidin-1-yl)-7H-purine-2-carboxylic acid;

6-{[(1R)-1-cyclobutylethyl]amino}-7-[3-fluoro-4-(trifluoromethyl)benzyl]-8-(2-phenylpiperidin-1-yl)-7H-purine-2-carboxylic acid;

6-{[(1R)-1-cyclobutylethyl]amino}-8-{[(1S)-1-phenyl-ethyl](propyl)amino}-7-[4-(trifluoromethyl)benzyl]-7H-purine-2-carboxylic acid;

6-{[(1R)-1-cyclobutylethyl]amino}-8-[(3R)-3-phenylmorpholin-4-yl]-7-[4-(trifluoromethyl)benzyl]-7H-purine-2-carboxylic acid;

6-{[(1R)-1-cyclobutylethyl]amino}-8-[(3S)-3-phenylmorpholin-4-yl]-7-[4-(trifluoromethyl)benzyl]-7H-purine-2-carboxylic acid;

6-{[(1R)-1-cyclobutylethyl]amino}-8-(2-phenylpyrrolidin-1-yl)-7-[4-(trifluoromethyl)benzyl]-7H-purine-2-carboxylic acid;

6-{[(1R)-1-cyclobutyletylethyl]amino}-8-(2-pyridin-2-ylpiperidin-1-yl)-7-[4-(trifluoromethyl)benzyl]-7H-purine-2-carboxylic acid;

6-{[(1R)-1-cyclobutylethyl]amino}-8-(2-phenylazetidin-1-yl)-7-[4-(trifluoromethyl)benzyl]-7H-purine-2-carboxylic acid;

3-[6-{[(1R)-1-cyclobutylethyl]amino}-7-[3-fluoro-4-(trifluoromethyl)benzyl]-8-(3-phenylmorpholin-4-yl)-7H-purin-2-yl]-1,2,4-oxadiazol-5(4H)-one;

3-[6-{[(1R)-1-cyclobutylethyl]amino}-7-[3-fluoro-4-(trifluoromethyl)benzyl]-8-(3-phenylmorpholin-4-yl)-7H-purin-2-yl]-1,2,4-oxadiazol-5(4H)-one;

3-(6-{[(1R)-1-cyclobutylethyl]amino}-8-[(3R)-3-phenylmorpholin-4-yl]-7-[4-(trifluoromethyl)benzyl]-7H-purin-2-yl]-1,2,4-oxadiazol-5(4H)-one;

6-{[(1R)-1-cyclobutylethyl]amino}-8-{methyl[(1S)-1-phenylpropyl]amino}-7-[4-(trifluoromethyl)benzyl]-7H-purine-2-carboxylic acid;

6-{[(1R)-1-cyclobutylethyl]amino}-8-(3,5-dimethyl-1H-pyrazol-1-yl)-7-[4-(trifluoromethyl)benzyl]-7H-purine-2-carboxylic acid;

6-{[(1R)-1-cyclobutylethyl]amino}-8-[2-(3-fluorophenyl)pyrrolidin-1-yl]-7-[4-(trifluoromethyl)benzyl]-7H-purine-2-carboxylic acid;

6-{[(1R)-1-cyclobutylethyl]amino}-8-(5-methyl-3-phenyl-1H-pyrazol-1-yl)-7-[4-(trifluoromethyl)benzyl]-7H-purine-2-carboxylic acid;

6-{[(1R)-1-cyclobutylethyl]amino}-8-[(2R)-2-phenylpiperidin-1-yl]-7-[4-(trifluoromethyl)benzyl]-7H-purine-2-carboxylic acid;

6-{[(1R)-1-cyclobutylethyl]amino}-8-[(2S)-2-phenylpiperidin-1-yl]-7-[4-(trifluoromethyl)benzyl]-7H-purine-2-carboxylic acid;

6-{[(1R)-1-cyclobutylethyl]amino}-8-(2-phenylpyrrolidin-1-yl)-7-[4-(trifluoromethyl)benzyl]-7H-purine-2-carboxylic acid;

6-{[(1R)-1-cyclobutylethyl]amino}-8-[3-(2-methylpropyl)morpholin-4-yl]-7-[4-(trifluoromethyl)benzyl]-7H-purine-2-carboxylic acid;

3-(6-{[(1R)-1-cyclobutylethyl]amino}-8-(2-phenylpiperidin-1-yl)-7-[4-(trifluoromethyl)benzyl]-7H-purin-2-yl)-1,2,4-oxadiazol-5(4H)-one;

6-{[(1R)-1-cyclobutylethyl]amino}-7-[4-(trifluoromethyl)benzyl]-8-{2-[3-(trifluoromethyl)benzyl]piperidin-1-yl}-7H-purine-2-carboxylic acid;

6-{[(1R)-1-cyclobutylethyl]amino}-8-[2-(4-fluorobenzyl)piperidin-1-yl]-7-[4-(trifluoromethyl)benzyl]-7H-purine-2-carboxylic acid;

6-{[(1R)-1-cyclobutylethyl]amino}-8-[2-(4-methoxyphenyl)piperidin-1-yl]-7-[4-(trifluoromethyl)benzyl]-7H-purine-2-carboxylic acid;

3-(6-{[(1R)-1-cyclobutylethyl]amino}-7-[3-fluoro-4-(trifluoromethyl)benzyl]-8-[methyl(1-phenylpropyl)amino]-7H-purin-2-yl)-1,2,4-oxadiazol-5(4H)-one;

3-(6-{[(1R)-1-cyclobutylethyl]amino}-7-[3-fluoro-4-(trifluoromethyl)benzyl]-8-[methyl(1-pyridin-2-ylethyl)amino]-7H-purin-2-yl)-1,2,4-oxadiazol-5(4H)-one;

3-(6-{[(1R)-1-cyclobutylethyl]amino}-8-{[1-(3-fluorophenyl)ethyl](methyl)amino}-7-[3-fluoro-4-(trifluoromethyl)benzyl]-7H-purin-2-yl)-1,2,4-oxadiazol-5(4H)-one;

6-{[(1R)-1-cyclobutylethyl]amino}-8-(2,3-dihydro-1'H-spiro[indene-1,2'-pyrrolidin]-1'-yl)-7-[4-(trifluoromethyl)benzyl]-7H-purine-2-carboxylic acid;

3-(6-{[(1R)-1-cyclobutylethyl]amino}-8-[(1-pyridin-2-ylethyl)amino]-7-[4-(trifluoromethyl)benzyl]-7H-purin-2-yl)-1,2,4-oxadiazol-5(4H)-one;

6-{[(1R)-1-cyclobutylethyl]amino}-8-(3-oxa-8-azabicyclo[3.2.1]oct-8-yl)-7-[4-(trifluoromethyl)benzyl]-7H-purine-2-carboxylic acid;

6-{[(1R)-1-cyclobutylethyl]amino}-8-(8-oxa-3-azabicyclo[3.2.1]oct-3-yl)-7-[4-(trifluoromethyl)benzyl]-7H-purine-2-carboxylic acid;

8-(8-azabicyclo[3.2.1]oct-8-yl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[(3-exo)-3-phenyl-8-azabicyclo[3.2.1]oct-8-yl]-7-[4-(trifluoromethyl)benzyl]-7H-purine-2-carboxylic acid;

8-[(3-exo)-3-(4-chloro-3-fluorophenoxy)-8-azabicyclo[3.2.1]oct-8-yl]-6-{[(1R)-1-cyclobutylethyl]amino}-7-[4-(trifluoromethyl)benzyl]-7H-purine-2-carboxylic acid;

3-(6-{[(1R)-1-cyclobutylethyl]amino}-8-[methyl(2-methylpropyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[cyclopentyl(methyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-(2,2-dimethylpyrrolidin-1-yl)-7-[4-(trifluoromethyl)benzyl]-7H-purin-2-yl)-1,2,4-oxadiazol-5(4H)-one;

3-(6-{[(1R)-1-cyclobutylethyl]amino}-8-[(2,2-dimethylpropyl)(methyl)amino]-7-[4-(trifluoromethyl)benzyl]-7H-purin-2-yl)-1,2,4-oxadiazol-5(4H)-one;

3-{8-(4-azaspiro[2.5]oct-4-yl)-6-{[(1R)-1-cyclobutylethyl]amino}-7-[4-(trifluoromethyl)benzyl]-7H-purin-2-yl}-1,2,4-oxadiazol-5(4H)-one;

3-(6-{[(1R)-1-cyclobutylethyl]amino}-8-[2-(1-methylethyl)pyrrolidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[cyclohexyl(methyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-(3,3-dimethylmorpholin-4-yl)-7-[4-(trifluoromethyl)benzyl]-7H-purin-2-yl)-1,2,4-oxadiazol-5(4H)-one;

3-(6-{[(1R)-1-cyclobutylethyl]amino}-8-{[1-(methoxymethyl)cyclopropyl](methyl)amino}-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(fluoromethyl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(2-methylpropyl)pyrrolidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[3-(2-methylpropyl)pyrrolidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[methyl(tetrahydro-2H-pyran-4-ylmethyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[methyl(2-phenylethyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[(cyclohexylmethyl)(ethyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[cyclohexyl(propyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[ethyl(2-pyrrolidin-1-ylethyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-{[(1,3-dimethylpyrrolidin-3-yl)methyl](methyl)amino}-7-[4-(trifluoromethyl)benzyl]-7H-purin-2-yl)-1,2,4-oxadiazol-5(4H)-one;

3-(6-{[(1R)-1-cyclobutylethyl]amino}-8-{methyl[(1-methylpiperidin-3-yl)methyl]amino}-7-[4-(trifluoromethyl)benzyl]-7H-purin-2-yl)-1,2,4-oxadiazol-5(4H)-one;

3-(6-{[(1R)-1-cyclobutylethyl]amino}-8-[methyl(3-pyrrolidin-1-ylpropyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[3-(2-methylpropyl)morpholin-4-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2,3-dihydro-1H-inden-1-yl(methyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-(2-cyclohexylpyrrolidin-1-yl)-7-[4-(trifluoromethyl)benzyl]-7H-purin-2-yl)-1,2,4-oxadiazol-5(4H)-one;

3-(6-{[(1R)-1-cyclobutylethyl]amino}-8-[methyl(2-methyl-3-pyrrolidin-1-ylpropyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(pyridin-3-ylmethyl)pyrrolidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(1-methyl-1H-imidazol-2-yl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(3-methyl-1,2,4-oxadiazol-5-yl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-(methyl {[1-(2-methylpropyl)pyrrolidin-3-yl]methyl}amino)-7-[4-(trifluoromethyl)benzyl]-7H-purin-2-yl)-1,2,4-oxadiazol-5(4H)-one;

3-{8-(2-benzylpiperidin-1-yl)-6-{[(1R)-1-cyclobutylethyl]amino}-7-[4-(trifluoromethyl)benzyl]-7H-purin-2-yl}-1,2,4-oxadiazol-5(4H)-one;

3-(6-{[(1R)-1-cyclobutylethyl]amino}-8-(2-methylpiperidin-1-yl)-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(methoxymethyl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(4-fluorophenyl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(3-fluorophenyl)piperidin-1-yl]-7-[4-(trifluoromethyl)benzyl]-7H-purin-2-yl)-1,2,4-oxadiazol-5(4H)-one;

6-{[(1R)-1-cyclobutylethyl]amino}-8-(2-pyridin-3-ylpiperidin-1-yl)-7-[4-(trifluoromethyl)benzyl]-7H-purine-2-carboxylic acid;

6-{[(1R)-1-cyclobutyletylethyl]amino}-8-(2-pyridin-4-ylpiperidin-1-yl)-7-[4-(trifluoromethyl)benzyl]-7H-purine-2-carboxylic acid;

6-{[(1R)-1-cyclobutylethyl]amino}-8-[2-(3-fluorophenyl)piperidin-1-yl]-7-[4-(trifluoromethyl)benzyl]-7H-purine-2-carboxylic acid;

6-{[(1R)-1-cyclobutylethyl]amino}-8-[2-(4-fluorophenyl)piperidin-1-yl]-7-[4-(trifluoromethyl)benzyl]-7H-purine-2-carboxylic acid;

6-{[(1R)-1-cyclobutylethyl]amino}-8-morpholin-4-yl-7-[4-(trifluoromethyl)benzyl]-7H-purine-2-carboxylic acid;

6-{[(1R)-1-cyclobutylethyl]amino}-8-[2-(1-methylethyl)piperidin-1-yl]-7-[4-(trifluoromethyl)benzyl]-7H-purine-2-carboxylic acid;

6-{[(1R)-1-cyclobutylethyl]amino}-8-[2-(2-methylpropyl)piperidin-1-yl]-7-[4-(trifluoromethyl)benzyl]-7H-purine-2-carboxylic acid;

6-{[(1R)-1-cyclobutylethyl]amino}-8-(3,4-dihydroisoquinolin-2(1H)-yl)-7-[4-(trifluoromethyl)benzyl]-7H-purine-2-carboxylic acid;

6-{[(1R)-1-cyclobutylethyl]amino}-8-(2-cyclohexylpiperidin-1-yl)-7-[4-(trifluoromethyl)benzyl]-7H-purine-2-carboxylic acid;

6-{[(1R)-1-cyclobutylethyl]amino}-8-[(1-methyl-1-phenylethyl)amino]-7-[4-(trifluoromethyl)benzyl]-7H-purine-2-carboxylic acid;

6-{[(1R)-1-cyclobutylethyl]amino}-8-(3,4-dihydroquinolin-1(2H)-yl)-7-[4-(trifluoromethyl)benzyl]-7H-purine-2-carboxylic acid;

3-(6-{[(1R)-1-cyclobutylethyl]amino}-8-[(3R)-3-methylmorpholin-4-yl]-7-[4-(trifluoromethyl)benzyl]-7H-purin-2-yl)-1,2,4-oxadiazol-5(4H)-one;

6-{[(1R)-1-cyclobutylethyl]amino}-8-(phenoxymethyl)-7-[4-(trifluoromethyl)benzyl]-7H-purine-2-carboxylic acid;

8-[(benzyloxy)methyl]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[methyl(3-methylbutanoyl)amino]-7-[4-(trifluoromethyl)benzyl]-7H-purine-2-carboxylic acid;

6-{[(1R)-1-cyclobutylethyl]amino}-8-[(cyclohexylcarbonyl)(methyl)amino]-7-[4-(trifluoromethyl)benzyl]-7H-purine-2-carboxylic acid;

6-{[(1R)-1-cyclobutylethyl]amino}-8-[1-(2-methylpropoxy)ethyl]-7-[4-(trifluoromethyl)benzyl]-7H-purine-2-carboxylic acid;

8-[1-(benzyloxy)ethyl]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(1-hydroxyethyl)-7-[4-(trifluoromethyl)benzyl]-7H-purine-2-carboxylic acid;

6-{[(1R)-1-cyclobutylethyl]amino}-8-(1-phenoxyethyl)-7-[4-(trifluoromethyl)benzyl]-7H-purine-2-carboxylic acid;

6-{[(1R)-1-cyclobutylethyl]amino}-8-{1-[methyl(2-methylpropyl)amino]ethyl}-7-[4-(trifluoromethyl)benzyl]-7H-purine-2-carboxylic acid;

6-{[(1R)-1-cyclobutylethyl]amino}-8-{1-[methyl(phenyl)amino]ethyl}-7-[4-(trifluoromethyl)benzyl]-7H-purine-2-carboxylic acid;

6-{[(1R)-1-cyclobutylethyl]amino}-8-{1-[cyclohexyl(methyl)amino]ethyl}-7-[4-(trifluoromethyl)benzyl]-7H-purine-2-carboxylic acid;

8-{1-[benzyl(methyl)amino]ethyl}-6-{[(1R)-1-cyclobutylethyl]amino}-7-[4-(trifluoromethyl)benzyl]-7H-purine-2-carboxylic acid;

8-{[benzyl(methyl)amino]methyl}-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-{[cyclohexyl(methyl)amino]methyl}-7-[4-(trifluoromethyl)benzyl]-7H-purine-2-carboxylic acid;

6-{[(1R)-1-cyclobutylethyl]amino}-8-{[(1R)-2-hydroxy-1-phenylethyl]carbamoyl}-7-[4-(trifluoromethyl)benzyl]-7H-purine-2-carboxylic acid;

6-{[(1R)-1-cyclobutylethyl]amino}-8-[(2-methylpropyl)carbamoyl]-7-[4-(trifluoromethyl)benzyl]-7H-purine-2-carboxylic acid;

6-{[(1R)-1-cyclobutylethyl]amino}-8-[(cyclopropylmethyl)carbamoyl]-7-[4-(trifluoromethyl)benzyl]-7H-purine-2-carboxylic acid;

8-(benzylcarbamoyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(cyclohexylcarbamoyl)-7-[4-(trifluoromethyl)benzyl]-7H-purine-2-carboxylic acid;

6-{[(1R)-1-cyclobutylethyl]amino}-8-(phenylcarbamoyl)-7-[4-(trifluoromethyl)benzyl]-7H-purine-2-carboxylic acid;

6-{[(1R)-1-cyclobutylethyl]amino}-8-[(3,3-dimethylpiperidin-1-yl)carbonyl]-7-[4-(trifluoromethyl)benzyl]-7H-purine-2-carboxylic acid;

6-{[(1R)-1-cyclobutylethyl]amino}-8-[(4R)-4-phenyl-4,5-dihydro-1,3-oxazol-2-yl]-7-[4-(trifluoromethyl)benzyl]-7H-purine-2-carboxylic acid;

6-{[(1R)-1-cyclobutylethyl]amino}-8-(1-methylpiperidin-2-yl)-7-[4-(trifluoromethyl)benzyl]-7H-purine-2-carboxylic acid;

6-{[(1R)-1-cyclobutylethyl]amino}-8-piperidin-2-yl-7-[4-(trifluoromethyl)benzyl]-7H-purine-2-carboxylic acid;

6-{[(1R)-1-cyclobutylethyl]amino}-8-(1-ethylpiperidin-2-yl)-7-[4-(trifluoromethyl)benzyl]-7H-purine-2-carboxylic acid;

6-{[(1R)-1-cyclobutylethyl]amino}-8-{[(1S)-1-(3-fluorophenyl)ethyl](propyl)amino}-7-[4-(trifluoromethyl)benzyl]-7H-purine-2-carboxylic acid;

6-{[(1R)-1-cyclobutylethyl]amino}-8-{[(1S)-1-(3-fluorophenyl)ethyl](prop-2-en-1-yl)amino}-7-[4-(trifluoromethyl)benzyl]-7H-purine-2-carboxylic acid;

6-{[(1R)-1-cyclobutylethyl](prop-2-en-1-yl)amino}-8-{[(1S)-1-(3-fluorophenyl)ethyl]amino}-7-[4-(trifluoromethyl)benzyl]-7H-purine-2-carboxylic acid;

6-{[(1R)-1-cyclobutylethyl]amino}-8-{(cyclopropylmethyl)[(1S)-1-phenylethyl]amino}-7-[4-(trifluoromethyl)benzyl]-7H-purine-2-carboxylic acid;

6-{[(1R)-1-cyclobutylethyl]amino}-8-[prop-2-en-1-yl(1-pyridin-2-ylethyl)amino]-7-[4-(trifluoromethyl)benzyl]-7H-purine-2-carboxylic acid;

6-{[(1R)-1-cyclobutylethyl](prop-2-en-1-yl)amino}-8-[(1-pyridin-2-ylethyl)amino]-7-[4-(trifluoromethyl)benzyl]-7H-purine-2-carboxylic acid;

6-{[(1R)-1-cyclobutylethyl]amino}-8-[propyl(1-pyridin-2-ylethyl)amino]-7-[4-(trifluoromethyl)benzyl]-7H-purine-2-carboxylic acid;

6-{[(1R)-1-cyclobutylethyl]amino}-8-(1,4-dimethylpiperidin-2-yl)-7-[(trans-4-methylcyclohexyl)methyl]-7H-purine-2-carboxylic acid;

6-{[(1R)-1-cyclobutylethyl]amino}-8-(1-ethyl-4-methylpiperidin-2-yl)-7-[(trans-4-methylcyclohexyl)methyl]-7H-purine-2-carboxylic acid;

6-{[(1R)-1-cyclobutylethyl]amino}-8-(2,3-dimethylpiperidin-1-yl)-7-[(trans-4-methylcyclohexyl)methyl]-7H-purine-2-carboxylic acid;

6-{[(1R)-1-cyclobutylethyl]amino}-7-[(trans-4-methylcyclohexyl)methyl]-8-[2-(2-methylpropyl)piperidin-1-yl]-7H-purine-2-carboxylic acid;

3-(6-{[(1R)-1-cyclobutylethyl]amino}-7-[(trans-4-methylcyclohexyl)methyl]-8-[2-(2-methylpropyl)piperidin-1-yl]-7H-purin-2-yl)-1,2,4-oxadiazol-5(4H)-one;

6-{[(1R)-1-cyclobutylethyl]amino}-8-(2-cyclohexylpiperidin-1-yl)-7-[(trans-4-methylcyclohexyl)methyl]-7H-purine-2-carboxylic acid;

3-(6-{[(1R)-1-cyclobutylethyl]amino}-8-(2-cyclohexylpiperidin-1-yl)-7-[(trans-4-methylcyclohexyl)methyl]-7H-purin-2-yl)-1,2,4-oxadiazol-5(4H)-one;

6-{[(1R)-1-cyclobutylethyl]amino}-7-[(trans-4-methylcyclohexyl)methyl]-8-(3-methyl-2-phenylpiperidin-1-yl)-7H-purine-2-carboxylic acid;

3-[6-{[(1R)-1-cyclobutylethyl]amino}-7-[(trans-4-methylcyclohexyl)methyl]-8-(3-methyl-2-phenylpiperidin-1-yl)-7H-purin-2-yl]-1,2,4-oxadiazol-5(4H)-one;

3-(6-{[(1R)-1-cyclobutylethyl]amino}-8-[(2S)-2-(fluoromethyl)pyrrolidin-1-yl]-7-[(trans-4-methylcyclohexyl)methyl]-7H-purin-2-yl)-1,2,4-oxadiazol-5(4H)-one;

3-{6-[(2R)-2-cyclobutylazetidin-1-yl]-7-[(trans-4-methylcyclohexyl)methyl]-8-[(3R)-3-phenylmorpholin-4-yl]-7H-purin-2-yl}-1,2,4-oxadiazol-5(4H)-one;

6-{[(1R)-1-cyclobutylethyl]amino}-7-[(trans-4-methylcyclohexyl)methyl]-8-[(3R)-3-phenylmorpholin-4-yl]-7H-purine-2-carboxylic acid;

3-(6-{[(1R)-1-cyclobutylethyl]amino}-7-[(trans-4-methylcyclohexyl)methyl]-8-[(3R)-3-phenylmorpholin-4-yl]-7H-purin-2-yl)-1,2,4-oxadiazol-5(4H)-one;

6-{[(1R)-1-cyclobutylethyl]amino}-7-[(trans-4-methylcyclohexyl)methyl]-8-[(2R)-2-phenylpiperidin-1-yl]-7H-purine-2-carboxylic acid;

3-(6-{[(1R)-1-cyclobutylethyl]amino}-7-[(trans-4-methylcyclohexyl)methyl]-8-[(2R)-2-phenylpiperidin-1-yl]-7H-purin-2-yl)-1,2,4-oxadiazol-5(4H)-one;

6-{[(1R)-1-cyclobutylethyl]amino}-7-[(trans-4-methylcyclohexyl)methyl]-8-[(2S)-2-phenylpiperidin-1-yl]-7H-purine-2-carboxylic acid;

3-(6-{[(1R)-1-cyclobutylethyl]amino}-7-[(trans-4-methylcyclohexyl)methyl]-8-[(2S)-2-phenylpiperidin-1-yl]-7H-purin-2-yl)-1,2,4-oxadiazol-5(4H)-one;

6-{[(1R)-1-cyclobutylethyl]amino}-8-[2-(3-fluorophenyl)piperidin-1-yl]-7-[(trans-4-methylcyclohexyl)methyl]-7H-purine-2-carboxylic acid;

6-{[(1R)-1-cyclobutylethyl]amino}-8-(3,4-dihydroisoquinolin-2(1H)-yl)-7-[(trans-4-methylcyclohexyl)methyl]-7H-purine-2-carboxylic acid;

6-{[(1R)-1-cyclobutylethyl]amino}-8-[2-(4-fluorophenyl)piperidin-1-yl]-7-[(trans-4-methylcyclohexyl)methyl]-7H-purine-2-carboxylic acid;

6-{[(1R)-1-cyclobutylethyl]amino}-7-[(trans-4-methylcyclohexyl)methyl]-8-(2-pyridin-3-ylpiperidin-1-yl)-7H-purine-2-carboxylic acid;

6-{[(1R)-1-cyclobutylethyl]amino}-7-[(trans-4-methylcyclohexyl)methyl]-8-(octahydroquinolin-1(2H)-yl)-7H-purine-2-carboxylic acid;

6-{[(1R)-1-cyclobutylethyl]amino}-7-[(trans-4-methylcyclohexyl)methyl]-8-(2-pyridin-2-ylpiperidin-1-yl)-7H-purine-2-carboxylic acid;

6-{[(1R)-1-cyclobutylethyl]amino}-7-[(trans-4-methylcyclohexyl)methyl]-8-(octahydroisoquinolin-2(1H)-yl)-7H-purine-2-carboxylic acid;

6-{[(1R)-1-cyclobutylethyl]amino}-7-[(trans-4-methylcyclohexyl)methyl]-8-(octahydroquinolin-1(2H)-yl)-7H-purine-2-carboxylic acid;

3-(6-{[(1R)-1-cyclobutylethyl]amino}-7-[(trans-4-methylcyclohexyl)methyl]-8-[methyl(1-pyridin-2-ylethyl)amino]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[methyl(1-pyridin-2-ylethyl)amino]-7H-purin-2-yl)-1,2,4-oxadiazol-5(4H)-one;

8-(8-azabicyclo[3.2.1]oct-8-yl)-6-{[(1R)-1-cyclobutylethyl]amino}-7-[(trans-4-methylcyclohexyl)methyl]-7H-purine-2-carboxylic acid;

3-{8-(8-azabicyclo[3.2.1]oct-8-yl)-6-{[(1R)-1-cyclobutylethyl]amino}-7-[(trans-4-methylcyclohexyl)methyl]-7H-purin-2-yl}-1,2,4-oxadiazol-5(4H)-one;

6-{[(1R)-1-cyclobutylethyl]amino}-8-[2-(3-fluorophenyl)pyrrolidin-1-yl]-7-[(trans-4-methylcyclohexyl)methyl]-7H-purine-2-carboxylic acid;

6-{[(1R)-1-cyclobutylethyl]amino}-7-[(trans-4-methylcyclohexyl)methyl]-8-(2-methylpiperidin-1-yl)-7H-purine-2-carboxylic acid;

6-{[(1R)-1-cyclobutylethyl]amino}-7-[(trans-4-methylcyclohexyl)methyl]-8-[methyl(2-methylpropyl)amino]-7H-purine-2-carboxylic acid;

6-{[(1R)-1-cyclobutylethyl]amino}-8-[2-(3-methoxyphenyl)piperidin-1-yl]-7-[(trans-4-methylcyclohexyl)methyl]-7H-purine-2-carboxylic acid;

3-(6-{[(1R)-1-cyclobutylethyl]amino}-8-[2-(ethoxymethyl)pyrrolidin-1-yl]-7-[(trans-4-methylcyclohexyl)methyl]-7H-purin-2-yl)-1,2,4-oxadiazol-5(2H)-one;

3-(6-{[(1R)-1-cyclobutylethyl]amino}-8-(2-ethylpyrrolidin-1-yl)-7-[(trans-4-methylcyclohexyl)methyl]-7H-purin-2-yl)-1,2,4-oxadiazol-5(2H)-one;

3-[6-{[(1R)-1-cyclobutylethyl]amino}-7-[(trans-4-methylcyclohexyl)methyl]-8-(2-methylpyrrolidin-1-yl)-7H-purin-2-yl]-1,2,4-oxadiazol-5(2H)-one;

3-[6-{[(1R)-1-cyclobutylethyl]amino}-7-[(trans-4-methylcyclohexyl)methyl]-8-(2-propylpyrrolidin-1-yl)-7H-purin-2-yl]-1,2,4-oxadiazol-5(2H)-one;

3-{8-(2-tert-butylpyrrolidin-1-yl)-6-{[(1R)-1-cyclobutylethyl]amino}-7-[(trans-4-methylcyclohexyl)methyl]-7H-purin-2-yl}-1,2,4-oxadiazol-5(2H)-one;

3-(6-{[(1R)-1-cyclobutylethyl]amino}-8-[2-(2,2-dimethylpropyl)pyrrolidin-1-yl]-7-[(trans-4-methylcyclohexyl)methyl]-7H-purin-2-yl)-1,2,4-oxadiazol-5(2H)-one;

3-(6-{[(1R)-1-cyclobutylethyl]amino}-8-(2-cyclobutylpyrrolidin-1-yl)-7-[(trans-4-methylcyclohexyl)methyl]-7H-purin-2-yl)-1,2,4-oxadiazol-5(2H)-one;

3-(6-{[(1R)-1-cyclobutylethyl]amino}-8-[2-(methoxymethyl)piperidin-1-yl]-7-[(trans-4-methylcyclohexyl)methyl]-7H-purin-2-yl)-1,2,4-oxadiazol-5(2H)-one;

3-(6-{[(1R)-1-cyclobutylethyl]amino}-8-[2-(fluoromethyl)piperidin-1-yl]-7-[(trans-4-methylcyclohexyl)methyl]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[3-(2-methylpropyl)morpholin-4-yl]-7H-purin-2-yl)-1,2,4-oxadiazol-5(2H)-one;

3-(6-{[(1R)-1-cyclobutylethyl]amino}-8-[(cyclopropylmethyl)(methyl)amino]-7-[(trans-4-methylcyclohexyl)methyl]-7H-purin-2-yl)-1,2,4-oxadiazol-5(2H)-one;

3-(6-{[(1R)-1-cyclobutylethyl]amino}-8-[(2,2-dimethylpropyl)(methyl)amino]-7-[(trans-4-methylcyclohexyl)methyl]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[methyl(propyl)amino]-7H-purin-2-yl)-1,2,4-oxadiazol-5(2H)-one;

3-{8-(2-benzylpiperidin-1-yl)-6-{[(1R)-1-cyclobutylethyl]amino}-7-[(trans-4-methylcyclohexyl)methyl]-7H-purin-2-yl}-1,2,4-oxadiazol-5(2H)-one;

3-(6-{[(1R)-1-cyclobutylethyl]amino}-7-[(trans-4-methylcyclohexyl)methyl]-8-[2-(1-methylethyl)pyrrolidin-1-yl]-7H-purin-2-yl)-1,2,4-oxadiazol-5(2H)-one;

3-[6-{[(1R)-1-cyclobutylethyl]amino}-7-[(trans-4-methylcyclohexyl)methyl]-8-(2-methylpiperidin-1-yl)-7H-purin-2-yl]-1,2,4-oxadiazol-5(4H)-one;

3-(6-{[(1R)-1-cyclobutylethyl]amino}-7-[(trans-4-methylcyclohexyl)methyl]-8-[methyl(2-methylpropyl)amino]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(2-pyridin-3-ylpiperidin-1-yl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(2-pyridin-3-ylpiperidin-1-yl)-7H-purin-2-yl]-1,2,4-oxadiazol-5(4H)-one;

7-[(trans-4-methylcyclohexyl)methyl]-8-[(3R)-3-phenylmorpholin-4-yl]-6-{[(1R)-2,2,2-trifluoro-1-methylethyl]amino}-7H-purine-2-carboxylic acid;

6-{[(1R)-1-cyclobutylethyl]amino}-8-(2-ethylpiperidin-1-yl)-7-[(trans-4-methylcyclohexyl)methyl]-7H-purine-2-carboxylic acid;

3-(7-[(trans-4-methylcyclohexyl)methyl]-8-[(3R)-3-phenylmorpholin-4-yl]-6-{[(1R)-2,2,2-trifluoro-1-methylethyl]amino}-7H-purin-2-yl)-1,2,4-oxadiazol-5(4H)-one;

6-{[(1R)-1-cyclobutylethyl]amino}-7-[(trans-4-methylcyclohexyl)methyl]-8-[2-(1-methylethyl)piperidin-1-yl]-7H-purine-2-carboxylic acid;

5-(6-{[(1R)-1-cyclobutylethyl]amino}-7-[(trans-4-methylcyclohexyl)methyl]-8-[(3R)-3-phenylmorpholin-4-yl]-7H-purin-2-yl)-1,3,4-oxadiazol-2(3H)-one;

6-{[(1R)-1-cyclobutylethyl]amino}-8-[2-(4-fluorobenzyl)piperidin-1-yl]-7-[(trans-4-methylcyclohexyl)methyl]-7H-purine-2-carboxylic acid;

3-(6-{[(1R)-1-cyclobutylethyl]amino}-8-(1H-imidazol-1-yl)-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(2R)-2-methylpiperidin-1-yl]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[(2S)-2-methylpiperidin-1-yl]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[(4aR,8aS)-octahydroquinolin-1(2H)-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(4aS,8aR)-octahydroquinolin-1(2H)-yl]-7H-purin-2-yl)-1,2,4-oxadiazol-5(4H)-one;

3-{6-(2-cyclobutylpyrrolidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-(6-{[(1R)-1-cyclobutylethyl]amino}-7-[(trans-4-methylcyclohexyl)methyl]-8-{methyl[(4-methyl-1,2,5-oxadiazol-3-yl)methyl]amino}-7H-purin-2-yl)-1,2,4-oxadiazol-5(4H)-one;

3-(6-{[(1R)-1-cyclobutylethyl]amino}-8-[(isoxazol-3-ylmethyl)(methyl)amino]-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(3R)-3-methylmorpholin-4-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(3S)-3-methylmorpholin-4-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(3S)-3-phenylmorpholin-4-yl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(4-methyl-2-phenylpiperidin-1-yl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(4-methyl-2-phenylpiperidin-1-yl)-7H-purin-2-yl]-1,2,4-oxadiazol-5(4H)-one;

3-(6-{[(1R)-1-cyclobutylethyl]amino}-7-[(trans-4-methylcyclohexyl)methyl]-8-[methyl(pyrimidin-4-ylmethyl)amino]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-{methyl[(1-methyl-1H-pyrazol-4-yl)methyl]amino}-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[methyl(pyrazin-2-ylmethyl)amino]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[methyl(1,3-thiazol-5-ylmethyl)amino]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[methyl(1,3-thiazol-4-ylmethyl)amino]-7H-purin-2-yl)-1,2,4-oxadiazol-5(2H)-one;

3-(6-{[(1R)-1-cyclobutylethyl]amino}-8-{[(5-cyclopropyl-1,2,4-oxadiazol-3-yl)methyl](methyl)amino}-7-[(trans-4-methylcyclohexyl)methyl]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-{methyl[(4-methyl-1,3-thiazol-2-yl)methyl]amino}-7H-purin-2-yl)-1,2,4-oxadiazol-5(2H)-one;

3-(6-{[(1R)-1-cyclobutylethyl]amino}-7-[(trans-4-methylcyclohexyl)methyl]-8-{methyl[(3-methylisoxazol-5-yl)methyl]amino}-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[2-(5-methylfuran-2-yl)piperidin-1-yl]-7H-purin-2-yl)-1,2,4-oxadiazol-5(4H)-one;

3-(6-{[(1R)-1-cyclobutylethyl]amino}-8-(1,1-dioxidothiomorpholin-4-yl)-7-[(trans-4-methylcyclohexyl)methyl]-7H-purin-2-yl)-1,2,4-oxadiazol-5(2H)-one;

3-(6-{[(1R)-1-cyclobutylethyl]amino}-8-(4,4-difluoropiperidin-1-yl)-7-[(trans-4-methylcyclohexyl)methyl]-7H-purin-2-yl)-1,2,4-oxadiazol-5(2H)-one;
3-{6-(2-cyclobutylpiperidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one;
3-{6-(2-cyclobutylpiperidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one;
3-(6-{[(1R)-1-cyclobutylethyl]amino}-7-[(trans-4-methylcyclohexyl)methyl]-8-[(2R)-2-(2-methylpropyl)piperidin-1-yl]-7H-purin-2-yl)-1,2,4-oxadiazol-5(4H)-one;
3-(6-{[(1R)-1-cyclobutylethyl]amino}-7-[(trans-4-methylcyclohexyl)methyl]-8-[(2S)-2-(2-methylpropyl)piperidin-1-yl]-7H-purin-2-yl)-1,2,4-oxadiazol-5(4H)-one;
3-(6-{[(1R)-1-cyclobutylethyl]amino}-7-[(trans-4-methylcyclohexyl)methyl]-8-[(1-pyrimidin-5-ylethyl)amino]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-{[1-(2-methyl-1,3-thiazol-4-yl)ethyl]amino}-7H-purin-2-yl)-1,2,4-oxadiazol-5(2H)-one;
3-(6-{[(1R)-1-cyclobutylethyl]amino}-8-[(1-isoxazol-5-ylethyl)amino]-7-[(trans-4-methylcyclohexyl)methyl]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-{[1-(1,3-thiazol-4-yl)ethyl]amino}-7H-purin-2-yl)-1,2,4-oxadiazol-5(2H)-one;
3-(6-{[(1R)-1-cyclobutylethyl]amino}-7-[(trans-4-methylcyclohexyl)methyl]-8-[(1-pyrimidin-4-ylethyl)amino]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-{[1-(3-methyl-1,2,4-oxadiazol-5-yl)ethyl]amino}-7H-purin-2-yl)-1,2,4-oxadiazol-5(2H)-one;
3-(6-{[(1R)-1-cyclobutylethyl]amino}-7-[(trans-4-methylcyclohexyl)methyl]-8-[(1-pyrazin-2-ylethyl)amino]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-[(1-pyrimidin-5-ylethyl)amino]-7H-purin-2-yl)-1,2,4-oxadiazol-5(2H)-one;
3-[6-{[(1R)-1-cyclobutylethyl]amino}-7-[(trans-4-methylcyclohexyl)methyl]-8-(3-oxa-8-azabicyclo[3.2.1]oct-8-yl)-7H-purin-2-yl]-1,2,4-oxadiazol-5(4H)-one;
3-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,2,4-oxadiazol-5(4H)-one;
5-(6-{[(1R)-1-cyclobutylethyl]amino}-7-[(trans-4-methylcyclohexyl)methyl]-8-[(3R)-3-methylmorpholin-4-yl]-7H-purin-2-yl)-1,3,4-oxadiazol-2(3H)-one;
3-(6-{[(1R)-1-cyclobutylethyl]amino}-8-(3,3-dimethylmorpholin-4-yl)-7-[(trans-4-methylcyclohexyl)methyl]-7H-purin-2-yl)-1,2,4-oxadiazol-5(4H)-one;
3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;
3-{8-[(3R)-3-benzylmorpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;
3-(6-{[(1R)-1-cyclobutylethyl]amino}-8-(3-methoxy-3-methylazetidin-1-yl)-7-[(trans-4-methylcyclohexyl)methyl]-7H-purin-2-yl)-1,2,4-oxadiazol-5(2H)-one;
3-(6-{[(1R)-1-cyclobutylethyl]amino}-8-(3-hydroxy-3-methylazetidin-1-yl)-7-[(trans-4-methylcyclohexyl)methyl]-7H-purin-2-yl)-1,2,4-oxadiazol-5(2H)-one;
3-(6-{[(1R)-1-cyclobutylethyl]amino}-8-(6,6-difluoro-1,4-oxazepan-4-yl)-7-[(trans-4-methylcyclohexyl)methyl]-7H-purin-2-yl)-1,2,4-oxadiazol-5(2H)-one;
3-[6-{[(1R)-1-cyclobutylethyl]amino}-7-[(trans-4-methylcyclohexyl)methyl]-8-(1,4-oxazepan-4-yl)-7H-purin-2-yl]-1,2,4-oxadiazol-5(2H)-one;
3-(6-{[(1R)-1-cyclobutylethyl]amino}-8-{[(1S)-1-(3-fluorophenyl)ethyl]amino}-7-[(trans-4-methylcyclohexyl)methyl]-7H-purin-2-yl)-1,2,4-oxadiazol-5(2H)-one;
3-(6-{[(1R)-1-cyclobutylethyl]amino}-8-[2-(1-methoxy-1-methylethyl)pyrrolidin-1-yl]-7-[(trans-4-methylcyclohexyl)methyl]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-[2-(4-methyl-1,2,5-oxadiazol-3-yl)pyrrolidin-1-yl]-7H-purin-2-yl)-1,2,4-oxadiazol-5(2H)-one;
3-(6-{[(1R)-1-cyclobutylethyl]amino}-8-{[(1,3-dimethyl-1H-pyrazol-4-yl)methyl]amino}-7-[(trans-4-methylcyclohexyl)methyl]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-[(2S)-2-(1-methyl-1H-tetrazol-5-yl)pyrrolidin-1-yl]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-{[(4-methyl-1,2,5-oxadiazol-3-yl)methyl]amino}-7H-purin-2-yl)-1,2,4-oxadiazol-5(2H)-one;
3-(6-{[(1R)-1-cyclobutylethyl]amino}-7-[(trans-4-methylcyclohexyl)methyl]-8-{[(3-phenyl-1H-pyrazol-4-yl)methyl]amino}-7H-purin-2-yl)-1,2,4-oxadiazol-5(2H)-one;
3-(6-{[(1R)-1-cyclobutylethyl]amino}-8-(3-hydroxy-3-methylpyrrolidin-1-yl)-7-[(trans-4-methylcyclohexyl)methyl]-7H-purin-2-yl)-1,2,4-oxadiazol-5(2H)-one;
3-(6-{[(1R)-1-cyclobutylethyl]amino}-8-(3-methoxypyrrolidin-1-yl)-7-[(trans-4-methylcyclohexyl)methyl]-7H-purin-2-yl)-1,2,4-oxadiazol-5(2H)-one;
3-(6-{[(1R)-1-cyclobutylethyl]amino}-8-[ethyl(methyl)amino]-7-[(trans-4-methylcyclohexyl)methyl]-7H-purin-2-yl)-1,2,4-oxadiazol-5(2H)-one;
3-(6-{[(1R)-1-cyclobutylethyl]amino}-8-[(2-methoxyethyl)(methyl)amino]-7-[(trans-4-methylcyclohexyl)methyl]-7H-purin-2-yl)-1,2,4-oxadiazol-5(2H)-one;
3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;
3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;
3-{8-[3-(4-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;
(5R)-4-[6-{[(1R)-1-cyclobutylethyl]amino}-7-[(trans-4-methylcyclohexyl)methyl]-2-(5-oxo-4,5-dihydro-1,2,4-oxadiazol-3-yl)-7H-purin-8-yl]-1,5-dimethylpiperazin-2-one;
3-(6-{[(1R)-1-cyclobutylethyl]amino}-8-[(2-hydroxy-1-phenylethyl)amino]-7-[(trans-4-methylcyclohexyl)methyl]-7H-purin-2-yl)-1,2,4-oxadiazol-5(4H)-one;
3-[6-{[(1R)-1-cyclobutylethyl]amino}-7-[(trans-4-methylcyclohexyl)methyl]-8-(3-methylthiomorpholin-4-yl)-7H-purin-2-yl]-1,2,4-oxadiazol-5(2H)-one;
3-[6-{[(1R)-1-cyclobutylethyl]amino}-7-[(trans-4-methylcyclohexyl)methyl]-8-(3-methyl-1,1-dioxidothiomorpholin-4-yl)-7H-purin-2-yl]-1,2,4-oxadiazol-5(2H)-one;
5-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,3,4-oxadiazol-2(3H)-one;

3-[6-{[(1R)-1-cyclobutylethyl]amino}-7-[(trans-4-methyl-cyclohexyl)methyl]-8-(2-oxa-5-azabicyclo[4.1.0]hept-5-yl)-7H-purin-2-yl]-1,2,4-oxadiazol-5(4H)-one;

3-(6-{[(1R)-1-cyclobutylethyl]amino}-7-[(trans-4-methyl-cyclohexyl)methyl]-8-[(2S)-2-(trifluoromethyl)pyrroli-din-1-yl]-7H-purin-2-yl)-1,2,4-oxadiazol-5(4H)-one;

3-(6-{[(1R)-1-cyclobutylethyl]amino}-8-[(3R,5R)-3,5-dim-ethylmorpholin-4-yl]-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methyl-cyclohexyl)methyl]-8-(2-phenylpyrrolidin-1-yl)-7H-pu-rin-2-yl]-1,2,4-oxadiazol-5(4H)-one;

3-(6-{[(1R)-1-cyclobutylethyl]amino}-8-(hexahydrocyclo-penta[b][1,4]oxazin-4(4aH)-yl)-7-[(trans-4-methylcyclo-hexyl)methyl]-7H-purin-2-yl)-1,2,4-oxadiazol-5(2H)-one;

3-(6-{[(1R)-1-cyclobutylethyl]amino}-8-{[(1R,2S)-2-hy-droxycyclohexyl](methyl)amino}-7-[(trans-4-methylcy-clohexyl)methyl]-7H-purin-2-yl)-1,2,4-oxadiazol-5(4H)-one;

3-(6-{[(1R)-1-cyclobutylethyl]amino}-8-{[(1R,2S)-2-hy-droxycyclohexyl](methyl)amino}-7-[(trans-4-methylcy-clohexyl)methyl]-7H-purin-2-yl)-1,2,4-oxadiazol-5(4H)-one;

3-[6-{[(1R)-1-cyclobutylethyl]amino}-7-[(trans-4-methyl-cyclohexyl)methyl]-8-(2-phenylpyrrolidin-1-yl)-7H-pu-rin-2-yl]-1,2,4-oxadiazol-5(4H)-one;

5-(6-{[(1R)-1-cyclobutylethyl]amino}-7-[(trans-4-methyl-cyclohexyl)methyl]-8-[(2S)-2-(trifluoromethyl)pyrroli-din-1-yl]-7H-purin-2-yl)-1,3,4-oxadiazol-2(3H)-one;

N-[(1R)-1-cyclobutylethyl]-8-[4-(propan-2-yl)pyridin-2-yl]-2-(1H-tetrazol-5-yl)-7-[4-(trifluoromethyl)benzyl]-7H-purin-6-amine;

(6-{[(1R)-1-cyclobutylethyl]amino}-8-[4-(propan-2-yl)pyridin-2-yl]-7-[4-(trifluoromethyl)benzyl]-7H-purin-2-yl)methanol;

N-[(1R)-1-cyclobutylethyl]-8-[4-(propan-2-yl)pyridin-2-yl]-2-(1H-1,2,3-triazol-5-yl)-7-[4-(trifluoromethyl)ben-zyl]-7H-purin-6-amine;

2-(aminomethyl)-N-[(1R)-1-cyclobutylethyl]-7-[(trans-4-methylcyclohexyl)methyl]-8-[4-(propan-2-yl)pyridin-2-yl]-7H-purin-6-amine;

1-(6-{[(1R)-1-cyclobutylethyl]amino}-7-[(trans-4-methyl-cyclohexyl)methyl]-8-[4-(propan-2-yl)pyridin-2-yl]-7H-purin-2-yl)ethanone;

1-(6-{[(1R)-1-cyclobutylethyl]amino}-7-[(trans-4-methyl-cyclohexyl)methyl]-8-[4-(propan-2-yl)pyridin-2-yl]-7H-purin-2-yl)ethanol;

2-(6-{[(1R)-1-cyclobutylethyl]amino}-7-[(trans-4-methyl-cyclohexyl)methyl]-8-[4-(propan-2-yl)pyridin-2-yl]-7H-purin-2-yl)propan-2-ol;

N-[(1R)-1-cyclobutylethyl]-7-[(trans-4-methylcyclohexyl)methyl]-8-[4-(propan-2-yl)pyridin-2-yl]-2-(1H-tetrazol-5-yl)-7H-purin-6-amine;

N-[(6-{[(1R)-1-cyclobutylethyl]amino}-7-[(trans-4-methyl-cyclohexyl)methyl]-8-[4-(propan-2-yl)pyridin-2-yl]-7H-purin-2-yl)methyl]methanesulfonamide;

N-[(6-{[(1R)-1-cyclobutylethyl]amino}-7-[(trans-4-methyl-cyclohexyl)methyl]-8-[4-(propan-2-yl)pyridin-2-yl]-7H-purin-2-yl)methyl]-2,2,2-trifluoroacetamide;

N-[(1R)-1-cyclobutylethyl]-7-[(trans-4-methylcyclohexyl)methyl]-2-(2-methyl-2H-tetrazol-5-yl)-8-[(3R)-3-phenyl-morpholin-4-yl]-7H-purin-6-amine;

N-[(1R)-1-cyclobutylethyl]-7-[(trans-4-methylcyclohexyl)methyl]-2-(1-methyl-1H-tetrazol-5-yl)-8-[(3R)-3-phenyl-morpholin-4-yl]-7H-purin-6-amine;

methyl 6-{[(1R)-1-cyclobutylethyl]amino}-7-[(trans-4-methylcyclohexyl)methyl]-8-[(3R)-3-phenylmorpholin-4-yl]-7H-purine-2-carboxylate;

2-(6-{[(1R)-1-cyclobutylethyl]amino}-7-[(trans-4-methyl-cyclohexyl)methyl]-8-[(3R)-3-phenylmorpholin-4-yl]-7H-purin-2-yl)propan-2-ol;

5-(6-{[(1R)-1-cyclobutylethyl]amino}-7-[(trans-4-methyl-cyclohexyl)methyl]-8-[(3R)-3-phenylmorpholin-4-yl]-7H-purin-2-yl)-4-methyl-2,4-dihydro-3H-1,2,4-triazol-3-one;

N-[(1R)-1-cyclobutylethyl]-7-[(trans-4-methylcyclohexyl)methyl]-8-[(3R)-3-phenylmorpholin-4-yl]-2-(4H-1,2,4-triazol-3-yl)-7H-purin-6-amine;

6-{[(1R)-1-cyclobutylethyl]amino}-N-ethyl-7-[(trans-4-methylcyclohexyl)methyl]-8-[(3R)-3-phenylmorpholin-4-yl]-7H-purine-2-carboxamide;

6-{[(1R)-1-cyclobutylethyl]amino}-7-[(trans-4-methylcy-clohexyl)methyl]-N-ethylsulfonyl-8-[(3R)-3-phenylmor-pholin-4-yl]-7H-purine-2-carboxamide;

5-(6-{[(1R)-1-cyclobutylethyl]amino}-7-[(trans-4-methyl-cyclohexyl)methyl]-8-[(3R)-3-phenylmorpholin-4-yl]-7H-purin-2-yl)-2-methyl-1,2-dihydro-3H-1,2,4-triazol-3-one;

1-(6-(((R)-1-cyclobutylethyl)amino)-7-((trans-4-methylcy-clohexyl)methyl)-8-((R)-3-phenylmorpholino)-7H-purin-2-yl)ethane-1,2-diol;

1-(6-{[(1R)-1-cyclobutylethyl]amino}-7-[(trans-4-methyl-cyclohexyl)methyl]-8-[(3R)-3-phenylmorpholin-4-yl]-7H-purin-2-yl)ethanone;

(6-{[(1R)-1-cyclobutylethyl]amino}-7-[(trans-4-methylcy-clohexyl)methyl]-8-[(3R)-3-phenylmorpholin-4-yl]-7H-purin-2-yl)methanol;

1-(6-{[(1R)-1-cyclobutylethyl]amino}-7-[(trans-4-methyl-cyclohexyl)methyl]-8-[(3R)-3-phenylmorpholin-4-yl]-7H-purin-2-yl)ethanone;

6-{[(1R)-1-cyclobutylethyl]amino}-N-(dimethylsulfa-moyl)-7-[(trans-4-methylcyclohexyl)methyl]-8-[(3R)-3-phenylmorpholin-4-yl]-7H-purine-2-carboxamide;

6-{[(1R)-1-cyclopropylethyl]amino}-8-(3-methylphenyl)-N-(methylsulfonyl)-7-[4-(trifluoromethyl)benzyl]-7H-purine-2-carboxamide;

N-[(1R)-1-cyclopropylethyl]-8-(3-methylphenyl)-2-(1H-tetrazol-5-yl)-7-[4-(trifluoromethyl)benzyl]-7H-purin-6-amine;

6-{[(1R)-1-cyclopropylethyl]amino}-8-(3-methylphenyl)-7-[4-(trifluoromethyl)benzyl]-7H-purine-2-carboxamide;

N-[(1R)-1-cyclopropylethyl]-8-(3-methylphenyl)-2-(1H-1,2,4-triazol-3-yl)-7-[4-(trifluoromethyl)benzyl]-7H-purin-6-amine;

6-{[(1R)-1-cyclobutylethyl]amino}-8-(3-methylphenyl)-7-[4-(trifluoromethyl)benzyl]-7H-purine-2-carboxamide;

6-{[(1R)-1-cyclobutylethyl]amino}-N-methyl-8-(3-methyl-phenyl)-7-[4-(trifluoromethyl)benzyl]-7H-purine-2-car-boxamide;

6-{[(1R)-1-cyclobutylethyl]amino}-8-(2,5-dimethylphe-nyl)-7-[4-(trifluoromethyl)benzyl]-7H-purine-2-carbox-amide;

6-{[(1R)-1-cyclobutylethyl]amino}-N-methoxy-8-[4-(1-methylethyl)pyridin-2-yl]-7-[4-(trifluoromethyl)benzyl]-7H-purine-2-carboxamide;

(6-{[(1R)-1-cyclobutylethyl]amino}-8-[(3R)-3-phenylmor-pholin-4-yl]-7-[4-(trifluoromethyl)benzyl]-7H-purin-2-yl)methanol;

(6-{[(1R)-1-cyclobutylethyl]amino}-7-[(trans-4-methylcy-clohexyl)methyl]-8-[4-(1-methylethyl)pyridin-2-yl]-7H-purin-2-yl)methanol;

2-((6-(((R)-1-cyclobutylethyl)amino)-7-((trans-4-methylcyclohexyl)methyl)-8-((R)-3-phenylmorpholino)-7H-purin-2-yl)amino)ethanol;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-L-proline;

$N^6$-[(1R)-1-cyclobutylethyl]-$N^2$-methyl-7-[(trans-4-methylcyclohexyl)methyl]-8-[(3R)-3-phenylmorpholin-4-yl]-7H-purine-2,6-diamine;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-D-proline;

N-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methylalanine;

N-(6-{[(1R)-1-cyclobutylethyl]amino}-7-[(trans-4-methylcyclohexyl)methyl]-8-[(3R)-3-phenylmorpholin-4-yl]-7H-purin-2-yl)glycine;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methyl-D-proline;

N-(6-{[(1R)-1-cyclobutylethyl]amino}-7-[(trans-4-methylcyclohexyl)methyl]-8-[(3R)-3-phenylmorpholin-4-yl]-7H-purin-2-yl)-N-methylglycine;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)pyrrolidine-3-carboxylic acid;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-3-(methylsulfanyl)pyrrolidine-3-carboxylic acid;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-4,4-dimethylpyrrolidine-3-carboxylic acid;

N—((R)-1-cyclobutylethyl)-7-((trans-4-methylcyclohexyl)methyl)-2-(methylsulfonyl)-8-((R)-3-phenylmorpholino)-7H-purin-6-amine;

N—((R)-1-cyclobutylethyl)-7-((trans-4-methylcyclohexyl)methyl)-2-(methylsulfinyl)-8-((R)-3-phenylmorpholino)-7H-purin-6-amine;

N-[(1R)-1-cyclobutylethyl]-7-[(trans-4-methylcyclohexyl)methyl]-8-[4-(1-methylethyl)pyridin-2-yl]-2-(methylsulfonyl)-7H-purin-6-amine;

N-[(1R)-1-cyclobutylethyl]-2-(ethylsulfonyl)-7-[(trans-4-methylcyclohexyl)methyl]-8-[(3R)-3-phenylmorpholin-4-yl]-7H-purin-6-amine;

N-[(1R)-1-cyclobutylethyl]-7-[(trans-4-methylcyclohexyl)methyl]-2-[(1-methylethyl)sulfonyl]-8-[(3R)-3-phenylmorpholin-4-yl]-7H-purin-6-amine;

N-[(1R)-1-cyclobutylethyl]-2-(ethylsulfinyl)-7-[(trans-4-methylcyclohexyl)methyl]-8-[(3R)-3-phenylmorpholin-4-yl]-7H-purin-6-amine;

N-[(1R)-1-cyclobutylethyl]-7-[(trans-4-methylcyclohexyl)methyl]-2-[(1-methylethyl)sulfinyl]-8-[(3R)-3-phenylmorpholin-4-yl]-7H-purin-6-amine;

N-[(1R)-1-cyclobutylethyl]-7-[(trans-4-methylcyclohexyl)methyl]-2-(methylsulfonyl)-8-(2-phenylpiperidin-1-yl)-7H-purin-6-amine;

N-[(1R)-1-cyclobutylethyl]-7-[(trans-4-methylcyclohexyl)methyl]-2-(methylsulfinyl)-8-(2-phenylpiperidin-1-yl)-7H-purin-6-amine;

N-[(1R)-1-cyclobutylethyl]-7-[(trans-4-methylcyclohexyl)methyl]-8-[(3R)-3-phenylmorpholin-4-yl]-2-[(2,2,2-trifluoroethyl)sulfonyl]-7H-purin-6-amine;

(6-{[(1R)-1-cyclobutylethyl]amino}-7-[(trans-4-methylcyclohexyl)methyl]-8-[(3R)-3-phenylmorpholin-4-yl]-7H-purin-2-yl)(2,2,2-trifluoroethyl)sulfoniumolate;

2-[(6-{[(1R)-1-cyclobutylethyl]amino}-7-[(trans-4-methylcyclohexyl)methyl]-8-[(3R)-3-phenylmorpholin-4-yl]-7H-purin-2-yl)sulfonyl]ethanol;

6-(((R)-1-cyclobutylethyl)amino)-8-(4-isopropylpyridin-2-yl)-7-((trans-4-methylcyclohexyl)methyl)-7H-purine-2-carboxylic acid;

6-(((R)-1-cyclobutylethyl)(methyl)amino)-8-(4-isopropylpyridin-2-yl)-7-((trans-4-methylcyclohexyl)methyl)-7H-purine-2-carboxylic acid;

6-(((R)-1-cyclobutylethyl)amino)-8-(4-isopropyl-6-oxo-1,6-dihydropyridin-2-yl)-7-((trans-4-methylcyclohexyl)methyl)-7H-purine-2-carboxylic acid;

6-(((R)-1-cyclobutylethyl)amino)-8-(6-ethoxy-4-isopropylpyridin-2-yl)-7-((trans-4-methyl cyclohexyl)methyl)-7H-purine-2-carboxylic acid;

3-(6-(((R)-1-cyclobutylethyl)amino)-8-(6-fluoro-4-isopropylpyridin-2-yl)-7-((trans-4-methylcyclohexyl)methyl)-7H-purin-2-yl)-1,2,4-oxadiazol-5(2H)-one;

6-(((R)-1-Cyclobutylethyl)amino)-8-(3-fluoro-4-isopropylpyridin-2-yl)-7-((trans-4-methylcyclohexyl)methyl)-7H-purine-2-carboxylic acid;

3-(6-((R)-1-cyclobutylethylamino)-8-(3-fluoro-4-isopropylpyridin-2-yl)-7-((trans-4-methylcyclohexyl)methyl)-7H-purin-2-yl)-1,2,4-oxadiazol-5(4H)-one;

6-(((R)-1-cyclobutylethyl)amino)-8-(5-fluoro-4-isopropylpyridin-2-yl)-7-((trans-4-methylcyclohexyl)methyl)-7H-purine-2-carboxylic acid;

3-(6-(((R)-1-cyclobutylethyl)amino)-8-(5-fluoro-4-(2-hydroxypropan-2-yl)pyridin-2-yl)-7-((trans-4-methylcyclohexyl)methyl)-7H-purin-2-yl)-1,2,4-oxadiazol-5(4H)-one;

3-(6-(((R)-1-cyclobutylethyl)amino)-8-(5-fluoro-4-isopropylpyridin-2-yl)-7-((trans-4-methylcyclohexyl)methyl)-7H-purin-2-yl)-1,2,4-oxadiazol-5(4H)-one;

6-(((R)-1-cyclobutylethyl)amino)-7-((trans-4-methylcyclohexyl)methyl)-8-(thiazol-2-yl)-7H-purine-2-carboxylic acid;

3-(6-(((R)-1-cyclobutylethyl)amino)-7-((trans-4-methylcyclohexyl)methyl)-8-(thiazol-2-yl)-7H-purin-2-yl)-1,2,4-oxadiazol-5(4H)-one;

6-{[(1R)-1-cyclobutylethyl]amino}-8-(2-methoxy-5-methylphenyl)-7-[(trans-4-methylcyclohexyl)methyl]-7H-purine-2-carboxylic acid;

6-{[(1R)-1-cyclobutylethyl]amino}-7-[(trans-4-methylcyclohexyl)methyl]-8-(3-methylphenyl)-7H-purine-2-carboxylic acid;

6-{[(1R)-1-cyclobutylethyl]amino}-7-[(trans-4-methylcyclohexyl)methyl]-8-[4-(1-methylethyl)pyridin-2-yl]-7H-purine-2-carboxylic acid;

8-(4-tert-butylpyridin-2-yl)-6-{[(1R)-1-cyclobutylethyl]amino}-7-[(trans-4-methylcyclohexyl)methyl]-7H-purine-2-carboxylic acid;

6-{[(1R)-1-cyclobutylethyl]amino}-8-(4-cyclopropylpyridin-2-yl)-7-[(trans-4-methylcyclohexyl)methyl]-7H-purine-2-carboxylic acid;

6-{[(1R)-1-cyclobutylethyl]amino}-8-(4-cyclobutylpyridin-2-yl)-7-[(trans-4-methylcyclohexyl)methyl]-7H-purine-2-carboxylic acid;

6-{[(1R)-1-cyclobutylethyl]amino}-8-(4-ethylpyridin-2-yl)-7-[(trans-4-methylcyclohexyl)methyl]-7H-purine-2-carboxylic acid;

8-(4-tert-butylpyridin-2-yl)-6-{[(1R)-1-cyclobutylethyl](methyl)amino}-7-[(trans-4-methylcyclohexyl)methyl]-7H-purine-2-carboxylic acid;

6-{[(1R)-1-cyclobutylethyl]amino}-8-(4,5-dimethylpyridin-2-yl)-7-[(trans-4-methylcyclohexyl)methyl]-7H-purine-2-carboxylic acid;

7-[(trans-4-methylcyclohexyl)methyl]-8-[4-(1-methylethyl)pyridin-2-yl]-6-{[(1R)-2,2,2-trifluoro-1-methylethyl]amino}-7H-purine-2-carboxylic acid;

3-(6-{[(1R)-1-cyclobutylethyl]amino}-8-[4-(1-hydroxy-1-methylethyl)pyridin-2-yl]-7-[(trans-4-methylcyclohexyl)methyl]-7H-purin-2-yl)-1,2,4-oxadiazol-5(4H)-one;

3-(6-{[(1R)-1-cyclobutylethyl](ethyl)amino}-7-[(trans-4-methylcyclohexyl)methyl]-8-[4-(1-methylethyl)pyridin-2-yl]-7H-purin-2-yl)-1,2,4-oxadiazol-5(4H)-one;

6-[6-{[(1R)-1-cyclobutylethyl]amino}-7-[(trans-4-methylcyclohexyl)methyl]-2-(5-oxo-2,5-dihydro-1,2,4-oxadiazol-3-yl)-7H-purin-8-yl]-4-(1-methylethyl)pyridin-2(1H)-one;

3-(6-(3-chlorophenyl)-7-(((trans)-4-methylcyclohexyl)methyl)-8-morpholino-7H-purin-2-yl)-1,2,4-oxadiazol-5(4H)-one;

3-(6-(3-chlorophenyl)-7-(((trans)-4-methylcyclohexyl)methyl)-8-((S)-3-methylmorpholino)-7H-purin-2-yl)-1,2,4-oxadiazol-5(4H)-one;

5-(7-(((trans)-4-methylcyclohexyl)methyl)-8-morpholino-6-(m-tolyl)-7H-purin-2-yl)-1,3,4-oxadiazol-2(3H)-one;

3-(6-(3-chlorophenyl)-8-(((R)-1-hydroxypropan-2-yl)amino)-7-(((trans)-4-methylcyclohexyl)methyl)-7H-purin-2-yl)-1,2,4-oxadiazol-5(4H)-one;

3-(6-(3-chlorophenyl)-8-(((S)-1-hydroxy-2-phenylpropan-2-yl)amino)-7-(((trans)-4-methylcyclohexyl)methyl)-7H-purin-2-yl)-1,2,4-oxadiazol-5(4H)-one;

3-(6-(3-chlorophenyl)-7-(((trans)-4-methylcyclohexyl)methyl)-8-((R)-3-methylmorpholino)-7H-purin-2-yl)-1,2,4-oxadiazol-5(4H)-one;

5-(6-(3-chlorophenyl)-7-(((trans)-4-methylcyclohexyl)methyl)-8-((R)-3-methylmorpholino)-7H-purin-2-yl)-1,3,4-oxadiazol-2(3H)-one;

3-(6-(3-chlorophenyl)-8-(((1R,2S)-2-hydroxy-1-phenylpropyl)amino)-7-(((trans)-4-methylcyclohexyl)methyl)-7H-purin-2-yl)-1,2,4-oxadiazol-5(4H)-one;

3-(6-(3-chlorophenyl)-8-((4R,5S)-5-methyl-2-oxo-4-phenyloxazolidin-3-yl)-7-(((trans)-4-methylcyclohexyl)methyl)-7H-purin-2-yl)-1,2,4-oxadiazol-5(4H)-one;

3-(6-(5-chloropyridin-3-yl)-7-(((trans)-4-methylcyclohexyl)methyl)-8-((R)-3-methylmorpholino)-7H-purin-2-yl)-1,2,4-oxadiazol-5(4H)-one;

5-(6-(5-chloropyridin-3-yl)-7-(((trans)-4-methylcyclohexyl)methyl)-8-((R)-3-methylmorpholino)-7H-purin-2-yl)-1,3,4-oxadiazol-2(3H)-one;

3-(7-(((trans)-4-methylcyclohexyl)methyl)-6-phenyl-8-((R)-3-phenylmorpholino)-7H-purin-2-yl)-1,2,4-oxadiazol-5(4H)-one;

6-(4-fluorophenyl)-7-[(trans-4-methylcyclohexyl)methyl]-8-[4-(1-methylethyl)pyridin-2-yl]-7H-purine-2-carboxylic acid;

7-[(trans-4-methylcyclohexyl)methyl]-8-[4-(1-methylethyl)pyridin-2-yl]-6-(3-methylphenyl)-7H-purine-2-carboxylic acid;

3-{7-[(trans-4-methylcyclohexyl)methyl]-8-[4-(1-methylethyl)pyridin-2-yl]-6-(3-methylphenyl)-7H-purin-2-yl}-1,2,4-oxadiazol-5(4H)-one;

3-{6-(3-chlorophenyl)-7-[(trans-4-methylcyclohexyl)methyl]-8-[4-(1-methylethyl)pyridin-2-yl]-7H-purin-2-yl}-1,2,4-oxadiazol-5(4H)-one;

3-{7-[(trans-4-methylcyclohexyl)methyl]-6-(3-methylphenyl)-8-[(3R)-3-phenylmorpholin-4-yl]-7H-purin-2-yl}-1,2,4-oxadiazol-5(4H)-one;

3-{6-(3-chlorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3,5-dichlorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3-chloro-5-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(3-chlorophenyl)-7-[(trans-4-methylcyclohexyl)methyl]-8-[(3R)-3-phenylmorpholin-4-yl]-7H-purin-2-yl}-1,3,4-oxadiazol-2(3H)-one;

6-(3-chlorophenyl)-7-[(trans-4-methylcyclohexyl)methyl]-8-[(3R)-3-phenylmorpholin-4-yl]-7H-purine-2-carboxylic acid;

3-{6-(3-chloro-2-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3-chloro-4-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloro-2-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloropyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{7-[(trans-4-methylcyclohexyl)methyl]-6-(3-methylphenyl)-8-morpholin-4-yl-7H-purin-2-yl}-1,2,4-oxadiazol-5(4H)-one;

3-{7-[(trans-4-methylcyclohexyl)methyl]-8-[(3R)-3-methylmorpholin-4-yl]-6-(3-methylphenyl)-7H-purin-2-yl}-1,2,4-oxadiazol-5(4H)-one;

3-{6-(3-chlorophenyl)-8-(3,3-dimethylmorpholin-4-yl)-7-[(trans-4-methylcyclohexyl)methyl]-7H-purin-2-yl}-1,2,4-oxadiazol-5(4H)-one;

3-{6-(3-ethylphenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-[3-(difluoromethyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one;

5-{7-[(trans-4-methylcyclohexyl)methyl]-8-[(3R)-3-methylmorpholin-4-yl]-6-(3-methylphenyl)-7H-purin-2-yl}-1,3,4-oxadiazol-2(3H)-one;

5-{6-(3-chlorophenyl)-7-[(trans-4-methylcyclohexyl)methyl]-8-morpholin-4-yl-7H-purin-2-yl}-1,3,4-oxadiazol-2(3H)-one;

3-{7-[(trans-4-methylcyclohexyl)methyl]-8-[(3S)-3-methylmorpholin-4-yl]-6-(3-methylphenyl)-7H-purin-2-yl}-1,2,4-oxadiazol-5(4H)-one;

5-{6-(5-chloropyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(3-chlorophenyl)-8-[4-(1-hydroxy-1-methylethyl)pyridin-2-yl]-7-[(trans-4-methylcyclohexyl)methyl]-7H-purin-2-yl}-1,2,4-oxadiazol-5(4H)-one;

5-{7-[(trans-4-methylcyclohexyl)methyl]-8-[(3S)-3-methylmorpholin-4-yl]-6-(3-methylphenyl)-7H-purin-2-yl}-1,3,4-oxadiazol-2(3H)-one;

3-{6-(3-chlorophenyl)-8-{[(1R)-2-hydroxy-1-phenylethyl]amino}-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[(3S)-3-(2-methylpropyl)morpholin-4-yl]-7H-purin-2-yl}-1,2,4-oxadiazol-5(4H)-one;

3-{6-(3-chlorophenyl)-7-[(trans-4-methylcyclohexyl) methyl]-8-[(3R)-3-(2-methylpropyl)morpholin-4-yl]-7H-purin-2-yl}-1,2,4-oxadiazol-5(4H)-one;

3-{6-(3-chlorophenyl)-8-[(2-hydroxy-1,1-dimethylethyl) amino]-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl) methyl]-8-[(3R)-3-(1-methylethyl)morpholin-4-yl]-7H-purin-2-yl}-1,2,4-oxadiazol-5(4H)-one;

3-{6-(5-chloropyridin-3-yl)-7-[(trans-4-methylcyclohexyl) methyl]-8-[(3S)-3-methylmorpholin-4-yl]-7H-purin-2-yl}-1,2,4-oxadiazol-5(2H)-one;

3-{6-[3-chloro-5-(hydroxymethyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3-chlorophenyl)-8-[(3R)-3-(hydroxymethyl)morpholin-4-yl]-7-[(trans-4-methylcyclohexyl)methyl]-7H-purin-2-yl}-1,2,4-oxadiazol-5(4H)-one;

5-{6-(3-chlorophenyl)-8-{[(1R)-2-hydroxy-1-methylethyl] amino}-7-[(trans-4-methylcyclohexyl)methyl]-7H-purin-2-yl}-1,3,4-oxadiazol-2(3H)-one;

3-{6-(3-chlorophenyl)-8-[(3R)-3-ethylmorpholin-4-yl]-7-[(trans-4-methylcyclohexyl)methyl]-7H-purin-2-yl}-1,2,4-oxadiazol-5(4H)-one;

methyl (3S)-4-[6-(3-chlorophenyl)-7-[(trans-4-methylcyclohexyl)methyl]-2-(5-oxo-4,5-dihydro-1,2,4-oxadiazol-3-yl)-7H-purin-8-yl]morpholine-3-carboxylate;

3-{6-(3-chlorophenyl)-8-{[(1S)-1-(3-fluorophenyl)ethyl] amino}-7-[(trans-4-methylcyclohexyl)methyl]-7H-purin-2-yl}-1,2,4-oxadiazol-5(4H)-one;

3-[6-(3-chlorophenyl)-7-[(trans-4-methylcyclohexyl) methyl]-8-{[(1S)-1-phenylpropyl]amino}-7H-purin-2-yl]-1,2,4-oxadiazol-5(4H)-one;

3-[6-(5-chloropyridin-3-yl)-7-[(trans-4-methylcyclohexyl) methyl]-8-(octahydro-4H-1,4-benzoxazin-4-yl)-7H-purin-2-yl]-1,2,4-oxadiazol-5(4H)-one;

3-{6-(3-chlorophenyl)-8-(2,4-dimethylpiperazin-1-yl)-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl) methyl]-8-[(2R)-2-methylpiperazin-1-yl]-7H-purin-2-yl}-1,2,4-oxadiazol-5(4H)-one;

5-{6-(3-chlorophenyl)-8-{[(1S)-1-(3-fluorophenyl)ethyl] amino}-7-[(trans-4-methylcyclohexyl)methyl]-7H-purin-2-yl}-1,3,4-oxadiazol-2(3H)-one;

3-{8-[benzyl(methyl)amino]-6-(3-chlorophenyl)-7-[(trans-4-methylcyclohexyl)methyl]-7H-purin-2-yl}-1,2-oxadiazol-5(4H)-one;

5-{6-(3-chlorophenyl)-8-{[(1R,2S)-2-hydroxy-1-phenylpropyl]amino}-7-[(trans-4-methylcyclohexyl)methyl]-7H-purin-2-yl}-1,3,4-oxadiazol-2(3H)-one;

5-{6-(3-chlorophenyl)-8-[(3R)-3-ethylmorpholin-4-yl]-7-[(trans-4-methylcyclohexyl)methyl]-7H-purin-2-yl}-1,3,4-oxadiazol-2(3H)-one;

3-{6-(3-chlorophenyl)-8-[(3R)-3-(methoxymethyl)morpholin-4-yl]-7-[(trans-4-methylcyclohexyl)methyl]-7H-purin-2-yl}-1,2,4-oxadiazol-5(4H)-one;

3-{6-(3-chlorophenyl)-8-[(3R,5R)-3,5-dimethylmorpholin-4-yl]-7-[(trans-4-methylcyclohexyl)methyl]-7H-purin-2-yl}-1,2,4-oxadiazol-5(4H)-one;

5-[6-(3-chlorophenyl)-7-[(trans-4-methylcyclohexyl) methyl]-8-{[(1S)-1-phenylpropyl]amino}-7H-purin-2-yl]-1,3,4-oxadiazol-2(3H)-one;

5-{8-[benzyl(methyl)amino]-6-(3-chlorophenyl)-7-[(trans-4-methylcyclohexyl)methyl]-7H-purin-2-yl}-1,3,4-oxadiazol-2(3H)-one;

3-{6-(3-chlorophenyl)-8-[(3S)-3-(1-methoxy-1-methylethyl)morpholin-4-yl]-7-[(trans-4-methylcyclohexyl) methyl]-7H-purin-2-yl}-1,2,4-oxadiazol-5(4H)-one;

3-{6-(3-chlorophenyl)-8-{[(1S)-1-(3-fluorophenyl)propyl] amino}-7-[(trans-4-methylcyclohexyl)methyl]-7H-purin-2-yl}-1,2,4-oxadiazol-5(4H)-one;

3-{6-(3-chlorophenyl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one;

3-{6-(3-chlorophenyl)-8-[(3R,5S)-3,5-dimethylmorpholin-4-yl]-7-[(trans-4-methylcyclohexyl)methyl]-7H-purin-2-yl}-1,2,4-oxadiazol-5(4H)-one;

(5R)-4-[6-(3-chlorophenyl)-7-[(trans-4-methylcyclohexyl) methyl]-2-(5-oxo-4,5-dihydro-1,2,4-oxadiazol-3-yl)-7H-purin-8-yl]-1,5-dimethylpiperazin-2-one;

3-{6-(3-chlorophenyl)-7-[(trans-4-methylcyclohexyl) methyl]-8-[(2S)-2-(trifluoromethyl)pyrrolidin-1-yl]-7H-purin-2-yl}-1,2,4-oxadiazol-5(4H)-one;

5-{6-(3-chlorophenyl)-8-[2-(1-methoxy-1-methylethyl)pyrrolidin-1-yl]-7-[(trans-4-methylcyclohexyl)methyl]-7H-purin-2-yl}-1,3,4-oxadiazol-2(3H)-one;

3-{6-(5-chloropyridin-3-yl)-8-[2-(1-methoxy-1-methylethyl)pyrrolidin-1-yl]-7-[(trans-4-methylcyclohexyl) methyl]-7H-purin-2-yl}-1,2,4-oxadiazol-5(4H)-one;

3-{6-(5-chloropyridin-3-yl)-7-[(trans-4-methylcyclohexyl) methyl]-8-[(2S)-2-(trifluoromethyl)pyrrolidin-1-yl]-7H-purin-2-yl}-1,2,4-oxadiazol-5(4H)-one;

6-ethoxy-8-(3-methylphenyl)-7-[4-(trifluoromethyl)benzyl]-7H-purine-2-carboxylic acid;

6-(cyclopropylmethoxy)-8-(3-methylphenyl)-7-[4-(trifluoromethyl)benzyl]-7H-purine-2-carboxylic acid;

6-(cyclobutylmethoxy)-8-(3-methylphenyl)-7-[4-(trifluoromethyl)benzyl]-7H-purine-2-carboxylic acid;

6-(1-cyclobutylethoxy)-8-(3-methylphenyl)-7-[4-(trifluoromethyl)benzyl]-7H-purine-2-carboxylic acid;

6-(1-cyclobutylethoxy)-7-[3-fluoro-4-(trifluoromethyl)benzyl]-8-[4-(1-methylethyl)pyridin-2-yl]-7H-purine-2-carboxylic acid;

6-(1-cyclobutylethoxy)-7-[(trans-4-methylcyclohexyl) methyl]-8-[4-(1-methylethyl)pyridin-2-yl]-7H-purine-2-carboxylic acid;

3-(8-((R)-4-acetyl-2-methylpiperazin-1-yl)-6-(((R)-1-cyclobutylethyl)amino)-7-((trans-4-methylcyclohexyl) methyl)-7H-purin-2-yl)-1,2,4-oxadiazol-5(4H)-one;

3-{8-[(2R)-4-acetyl-2-phenylpiperazin-1-yl]-6-{[(1R)-1-cyclobutylethyl]amino}-7-[(trans-4-methylcyclohexyl) methyl]-7H-purin-2-yl}-1,2,4-oxadiazol-5(4H)-one;

8-[(2R)-4-acetyl-2-phenylpiperazin-1-yl]-6-{[(1R)-1-cyclobutylethyl]amino}-7-[(trans-4-methylcyclohexyl) methyl]-7H-purine-2-carboxamide;

6-{[(1R)-1-cyclobutylethyl]amino}-7-[(trans-4-methylcyclohexyl)methyl]-8-[(2R)-4-(methylsulfonyl)-2-phenylpiperazin-1-yl]-7H-purine-2-carboxamide;

3-(6-{[(1R)-1-cyclobutylethyl]amino}-7-[(trans-4-methylcyclohexyl)methyl]-8-[(2R)-4-(methylsulfonyl)-2-phenylpiperazin-1-yl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(2R)-2-methyl-4-(methylsulfonyl) piperazin-1-yl]-7H-purin-2-yl)-1,2,4-oxadiazol-5(4H)-one;

3-(6-{[(1R)-1-cyclobutylethyl]amino}-8-[(2R)-4-(2,2-dimethylpropanoyl)-2-methylpiperazin-1-yl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[(2R)-4-(cyclopropylcarbonyl)-2-methylpiperazin-1-yl]-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-{(2R)-2-methyl-4-[(1-methylethyl)sulfonyl]piperazin-1-yl}-7H-purin-2-yl)-1,2,4-oxadiazol-5(4H)-one;

3-(6-{[(1R)-1-cyclobutylethyl]amino}-8-[(2R)-4-(hydroxyacetyl)-2-methylpiperazin-1-yl]-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(2R)-2-methylpiperazin-1-yl]-7H-purin-2-yl)-1,2,4-oxadiazol-5(4H)-one;

tert-butyl (2S,5R)-4-[6-{[(1R)-1-cyclobutylethyl]amino}-7-[(trans-4-methylcyclohexyl)methyl]-2-(5-oxo-4,5-dihydro-1,2,4-oxadiazol-3-yl)-7H-purin-8-yl]-2,5-dimethylpiperazine-1-carboxylate;

3-(6-{[(1R)-1-cyclobutylethyl]amino}-8-[(2R,5S)-2,5-dimethylpiperazin-1-yl]-7-[(trans-4-methylcyclohexyl)methyl]-7H-purin-2-yl)-1,2,4-oxadiazol-5(4H)-one;

3-{8-[(2R,5S)-4-acetyl-2,5-dimethylpiperazin-1-yl]-6-{[(1R)-1-cyclobutylethyl]amino}-7-[(trans-4-methylcyclohexyl)methyl]-7H-purin-2-yl}-1,2,4-oxadiazol-5(4H)-one;

3-(6-{[(1R)-1-cyclobutylethyl]amino}-8-[(2R,5S)-4-(cyclopropylcarbonyl)-2,5-dimethylpiperazin-1-yl]-7-[(trans-4-methylcyclohexyl)methyl]-7H-purin-2-yl)-1,2,4-oxadiazol-5(4H)-one;

6-(((R)-1-cyclobutylethyl)amino)-8-(4-isopropylpyridin-2-yl)-7-((trans-4-(trifluoromethyl)cyclohexyl)methyl)-7H-purine-2-carboxylic acid;

6-(((R)-1-cyclobutylethyl)amino)-7-((trans-4-ethylcyclohexyl)methyl)-8-(4-isopropylpyridin-2-yl)-7H-purine-2-carboxylic acid;

(R)-6-((1-cyclobutylethyl)amino)-7-((4,4-difluorocyclohexyl)methyl)-8-(4-isopropylpyridin-2-yl)-7H-purine-2-carboxylic acid;

3-(6-(((R)-1-cyclobutylethyl)amino)-7-((3-ethylcyclopentyl)methyl)-8-(4-isopropylpyridin-2-yl)-7H-purin-2-yl)-1,2,4-oxadiazol-5(4H)-one;

6-(((R)-1-cyclobutylethyl)amino)-8-(4-isopropylpyridin-2-yl)-7-((4-methylcyclohex-3-en-1-yl)methyl)-7H-purine-2-carboxylic acid;

6-(((R)-1-cyclobutylethyl)amino)-7-((4-ethylcyclohex-3-en-1-yl)methyl)-8-(4-isopropylpyridin-2-yl)-7H-purine-2-carboxylic acid;

3-(6-(((R)-1-cyclobutylethyl)amino)-7-((4-ethylcyclohex-3-en-1-yl)methyl)-8-(4-isopropylpyridin-2-yl)-7H-purin-2-yl)-1,2,4-oxadiazol-5(4H)-one;

(R)-6-((1-cyclobutylethyl)amino)-7-((4,4-dimethylcyclohexyl)methyl)-8-(4-isopropylpyridin-2-yl)-7H-purine-2-carboxylic acid;

(R)-3-(6-((1-cyclobutylethyl)amino)-7-((4,4-dimethylcyclohexyl)methyl)-8-(4-isopropylpyridin-2-yl)-7H-purin-2-yl)-1,2,4-oxadiazol-5(4H)-one;

6-(((R)-1-cyclobutylethyl)amino)-7-((trans-4-(fluoromethyl)cyclohexyl)methyl)-8-(4-isopropylpyridin-2-yl)-7H-purine-2-carboxylic acid;

3-(6-(((R)-1-cyclobutylethyl)amino)-7-((trans-3,3-difluoro-4-methylcyclohexyl)methyl)-8-(4-isopropylpyridin-2-yl)-7H-purin-2-yl)-1,2,4-oxadiazol-5(4H)-one;

3-(6-{[(1R)-1-cyclobutylethyl]amino}-7-[1-(trans-4-methylcyclohexyl)ethyl]-8-[(3R)-3-methylmorpholin-4-yl]-7H-purin-2-yl)-1,2,4-oxadiazol-5(4H)-one;

5-(6-(5-chloropyridin-3-yl)-7-(1-((trans)-4-methylcyclohexyl)ethyl)-8-((R)-3-phenylmorpholino)-7H-purin-2-yl)-1,3,4-oxadiazol-2(3H)-one;

6-{[(1R)-1-cyclobutylethyl]amino}-7-[(trans-4-ethylcyclohexyl)methyl]-8-(3-methylphenyl)-7H-purine-2-carboxylic acid;

6-{[(1R)-1-cyclobutylethyl]amino}-7-[(trans-4-ethylcyclohexyl)methyl]-8-(2-methoxy-5-methylphenyl)-7H-purine-2-carboxylic acid;

6-{[(1R)-1-cyclobutylethyl]amino}-7-[(trans-4-ethylcyclohexyl)methyl]-8-[4-(1-methylethyl)pyridin-2-yl]-7H-purine-2-carboxylic acid;

6-{[(1R)-1-cyclobutylethyl]amino}-7-[(trans-4-ethylcyclohexyl)methyl]-8-piperidin-1-yl-7H-purine-2-carboxylic acid;

6-{[(1R)-1-cyclobutylethyl]amino}-7-[(trans-4-ethylcyclohexyl)methyl]-8-morpholin-4-yl-7H-purine-2-carboxylic acid;

3-(6-{[(1R)-1-cyclobutylethyl]amino}-7-[(trans-4-ethylcyclohexyl)methyl]-8-[4-(1-methylethyl)pyridin-2-yl]-7H-purin-2-yl)-1,2,4-oxadiazol-5(4H)-one;

6-{[(1R)-1-cyclobutylethyl]amino}-7-[(trans-4-ethylcyclohexyl)methyl]-8-[(3R)-3-phenylmorpholin-4-yl]-7H-purine-2-carboxylic acid;

3-(6-{[(1R)-1-cyclobutylethyl]amino}-7-[(trans-4-ethylcyclohexyl)methyl]-8-[(3R)-3-phenylmorpholin-4-yl]-7H-purin-2-yl)-1,2,4-oxadiazol-5(4H)-one;

6-{[(1R)-1-cyclobutylethyl]amino}-7-[(4-ethylcyclohex-1-en-1-yl)methyl]-8-[4-(1-methylethyl)pyridin-2-yl]-7H-purine-2-carboxylic acid;

6-{[(1R)-1-cyclobutylethyl]amino}-7-[(4-ethylcyclohex-3-en-1-yl)methyl]-8-[4-(1-methylethyl)pyridin-2-yl]-7H-purine-2-carboxylic acid;

3-(6-{[(1R)-1-cyclobutylethyl]amino}-7-[(4-ethylcyclohex-3-en-1-yl)methyl]-8-[4-(1-methylethyl)pyridin-2-yl]-7H-purin-2-yl)-1,2,4-oxadiazol-5(4H)-one;

6-{[(1R)-1-cyclopropylethyl]amino}-8-(3-methylphenyl)-7-{[4-(trifluoromethyl)cyclohexyl]methyl}-7H-purine-2-carboxylic acid;

6-{[(1R)-1-cyclopropylethyl]amino}-8-(3-methylphenyl)-7-{[4-(trifluoromethyl)cyclohexyl]methyl}-7H-purine-2-carboxylic acid;

6-{[(1R)-1-cyclobutylethyl]amino}-8-(3-methylphenyl)-7-{[cis-4-(trifluoromethyl)cyclohexyl]methyl}-7H-purine-2-carboxylic acid;

3-(6-{[(1R)-1-cyclobutylethyl]amino}-8-[4-(1-methylethyl)pyridin-2-yl]-7-{[trans-4-(trifluoromethyl)cyclohexyl]methyl}-7H-purin-2-yl)-1,2,4-oxadiazol-5(4H)-one;

3-(6-{[(1R)-1-cyclobutylethyl]amino}-7-{[trans-3,3-difluoro-4-methylcyclohexyl]methyl}-8-[(3R)-3-methylmorpholin-4-yl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(phenylsulfanyl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(phenylsulfinyl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(phenylsulfonyl)-7H-purin-2-yl]-1,2,4-oxadiazol-5(4H)-one;

6-{[(1R)-1-cyclobutylethyl]amino}-7-[(trans-4-methylcyclohexyl)methyl]-8-(1-phenylcyclobutyl)-7H-purine-2-carboxylic acid;

6-{[(1R)-1-cyclobutylethyl]amino}-7-[(trans-4-methylcyclohexyl)methyl]-8-(1-methyl-1-phenylethyl)-7H-purine-2-carboxylic acid;

6-{[(1R)-1-cyclobutylethyl]amino}-8-(1-phenylcyclopropyl)-7-[4-(trifluoromethyl)benzyl]-7H-purine-2-carboxylic acid;

6-{[(1R)-1-cyclobutylethyl]amino}-7-[(trans-4-methylcyclohexyl)methyl]-8-(1-phenylcyclopropyl)-7H-purine-2-carboxylic acid;

3-[6-{[(1R)-1-cyclobutylethyl]amino}-7-[(trans-4-methylcyclohexyl)methyl]-8-(1-phenylcyclopropyl)-7H-purin-2-yl]-1,2,4-oxadiazol-5(4H)-one;

6-{[(1R)-1-cyclobutylethyl]amino}-8-(2,2-dimethylpropyl)-7-[(trans-4-methylcyclohexyl)methyl]-7H-purine-2-carboxylic acid;

3-(6-{[(1R)-1-cyclobutylethyl]amino}-8-(2,2-dimethylpropyl)-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(1-phenylcyclobutyl)-7H-purin-2-yl]-1,2,4-oxadiazol-5(4H)-one;

5-[6-{[(1R)-1-cyclobutylethyl]amino}-7-[(trans-4-methylcyclohexyl)methyl]-8-(1-phenylcyclobutyl)-7H-purin-2-yl]-4-methyl-2,4-dihydro-3H-1,2,4-triazol-3-one;

5-[6-{[(1R)-1-cyclobutylethyl]amino}-7-[(trans-4-methylcyclohexyl)methyl]-8-(1-phenylcyclobutyl)-7H-purin-2-yl]-1,3,4-oxadiazol-2(3H)-one;

6-{[(1R)-1-cyclobutylethyl]amino}-8-(2-phenylcyclohexyl)-7-[4-(trifluoromethyl)benzyl]-7H-purine-2-carboxylic acid;

6-{[(1R)-1-cyclobutylethyl]amino}-8-(2-phenylcyclohex-1-en-1-yl)-7-[4-(trifluoromethyl)benzyl]-7H-purine-2-carboxylic acid;

6-{[(1R)-1-cyclobutylethyl]amino}-8-(2-phenylcyclopent-1-en-1-yl)-7-[4-(trifluoromethyl)benzyl]-7H-purine-2-carboxylic acid;

6-{[(1R)-1-cyclobutylethyl]amino}-8-(2-phenylcyclopentyl)-7-[4-(trifluoromethyl)benzyl]-7H-purine-2-carboxylic acid;

6-{[(1R)-1-cyclobutylethyl]amino}-8-(2-phenylcyclopentyl)-7-[4-(trifluoromethyl)benzyl]-7H-purine-2-carboxylic acid;

6-{[(1R)-1-cyclobutylethyl]amino}-8-(4-phenyltetrahydrofuran-3-yl)-7-[4-(trifluoromethyl)benzyl]-7H-purine-2-carboxylic acid;

6-{[(1R)-1-cyclobutylethyl]amino}-8-(4-phenyltetrahydrofuran-3-yl)-7-[4-(trifluoromethyl)benzyl]-7H-purine-2-carboxylic acid;

6-{[(1R)-1-cyclobutylethyl]amino}-8-methyl-7-[(trans-4-methylcyclohexyl)methyl]-7H-purine-2-carboxylic acid;

3-(6-{[(1R)-1-cyclobutylethyl]amino}-8-methyl-7-[(trans-4-methylcyclohexyl)methyl]-7H-purin-2-yl)-1,2,4-oxadiazol-5(4H)-one;

6-{[(1R)-1-cyclobutylethyl]amino}-8-(3-oxo-2-phenylcyclohexyl)-7-[4-(trifluoromethyl)benzyl]-7H-purine-2-carboxylic acid;

6-{[(1R)-1-cyclobutylethyl]amino}-8-(2-phenylcyclohexyl)-7-[4-(trifluoromethyl)benzyl]-7H-purine-2-carboxylic acid;

3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(1-phenylethyl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(2-phenylcyclohex-1-en-1-yl)-7H-purin-2-yl]-1,2,4-oxadiazol-5(4H)-one;

6-{[(1R)-1-cyclobutylethyl]amino}-7-[(trans-4-methylcyclohexyl)methyl]-8-(2-phenylcyclohexyl)-7H-purine-2-carboxylic acid;

6-{[(1R)-1-cyclobutylethyl]amino}-7-[(trans-4-methylcyclohexyl)methyl]-8-(2-phenylcyclohex-1-en-1-yl)-7H-purine-2-carboxylic acid;

3-(6-{[(1R)-1-cyclobutylethyl]amino}-8-(1-cyclohexylethenyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(E)-2-phenylethenyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[1-(tetrahydro-2H-pyran-4-yl)ethyl]-7H-purin-2-yl)-1,2,4-oxadiazol-5(4H)-one;

3-(6-{[(1R)-1-cyclobutylethyl]amino}-8-(1-cyclohexylethyl)-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(2-phenylethyl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(2-phenylcyclohexyl)-7H-purin-2-yl]-1,2,4-oxadiazol-5(4H)-one;

3-(6-{[(1R)-1-cyclobutylethyl]amino}-8-cyclopropyl-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(3-phenyltetrahydro-2H-pyran-4-yl)-7H-purin-2-yl]-1,2,4-oxadiazol-5(4H)-one;

3-(6-{[(1R)-1-cyclobutylethyl]amino}-8-[1-(4-fluorophenyl)ethenyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[1-(4-fluorophenyl)ethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-cyclopent-1-en-1-yl-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-cyclopentyl-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(2,2-dimethylpropanoyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-hydroxy-1,2,2-trimethylpropyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[1-(2-fluorophenyl)cyclopropyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-fluoro-1-pyridin-2-ylethyl)-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(1-pyridin-2-ylcyclopropyl)-7H-purin-2-yl]-1,2,4-oxadiazol-5(4H)-one;

3-(6-{[(1R)-1-cyclobutylethyl]amino}-8-(2,2-dimethyl-1-methylidenepropyl)-7-[(trans-4-methylcyclohexyl)methyl]-7H-purin-2-yl)-1,2,4-oxadiazol-5(4H)-one;
3-[6-{[(1R)-1-cyclobutylethyl]amino}-7-[(trans-4-methylcyclohexyl)methyl]-8-(2,2,2-trifluoro-1-hydroxy-1-methylethyl)-7H-purin-2-yl]-1,2,4-oxadiazol-5(4H)-one;
3-(6-{[(1R)-1-cyclobutylethyl]amino}-8-(1-hydroxyethyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(2-hydroxy-2-methylpropyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(1,2-dihydroxyethyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[methoxy(phenyl)methyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-7-[(trans-4-methylcyclohexyl)methyl]-8-(phenylcarbonyl)-7H-purin-2-yl)-1,2,4-oxadiazol-5(4H)-one;
5-[6-{[(1R)-1-cyclobutylethyl]amino}-7-[(trans-4-methylcyclohexyl)methyl]-8-(phenylcarbonyl)-7H-purin-2-yl]-1,3,4-oxadiazol-2(3H)-one;
3-(6-{[(1R)-1-cyclobutylethyl]amino}-8-(1-hydroxy-1-phenylethyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-7-[(trans-4-methylcyclohexyl)methyl]-8-[(1R or S)-2,2,2-trifluoro-1-hydroxy-1-phenylethyl]-7H-purin-2-yl)-1,2,4-oxadiazol-5(4H)-one;
3-(6-(((R)-1-cyclobutylethyl)amino)-7-(((trans)-4-methylcyclohexyl)methyl)-8-(1-(thiazol-4-yl)ethyl)-7H-purin-2-yl)-1,2,4-oxadiazol-5(4H)-one;
3-(6-{[(1R)-1-cyclobutylethyl]amino}-8-[hydroxy(phenyl)methyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-(4-fluorophenyl)cyclopropyl]-7-[(trans-4-methylcyclohexyl)methyl]-7H-purin-2-yl)-1,2,4-oxadiazol-5(4H)-one;
3-[6-{[(1R)-1-cyclobutylethyl]amino}-7-[(trans-4-methylcyclohexyl)methyl]-8-(tetrahydro-2H-pyran-4-ylcarbonyl)-7H-purin-2-yl]-1,2,4-oxadiazol-5(4H)-one;
3-(8-acetyl-6-{[(1R)-1-cyclobutylethyl]amino}-7-[(trans-4-methylcyclohexyl)methyl]-7H-purin-2-yl)-1,2,4-oxadiazol-5(2H)-one;
3-(6-{[(1R)-1-cyclobutylethyl]amino}-8-(2,2-dimethyl-1-methylidenepropyl)-7-[(trans-4-methylcyclohexyl)methyl]-7H-purin-2-yl)-4-methyl-1,2,4-oxadiazol-5(4H)-one;
3-(6-{[(1R)-1-cyclobutylethyl]amino}-8-[hydroxy(tetrahydro-2H-pyran-4-yl)methyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-(3-fluorophenyl)-1-hydroxyethyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(1-hydroxy-1-pyridin-4-ylethyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-hydroxy-1-(tetrahydro-2H-pyran-4-yl)ethyl]-7-[(trans-4-methylcyclohexyl)methyl]-7H-purin-2-yl)-1,2,4-oxadiazol-5(4H)-one;
3-[6-{[(1R)-1-cyclobutylethyl]amino}-7-[(trans-4-methylcyclohexyl)methyl]-8-(1-pyridin-3-ylcyclopropyl)-7H-purin-2-yl]-1,2,4-oxadiazol-5(2H)-one;
3-(6-{[(1R)-1-cyclobutylethyl]amino}-8-(1-hydroxy-1-pyridin-3-ylethyl)-7-[(trans-4-methylcyclohexyl)methyl]-7H-purin-2-yl)-1,2,4-oxadiazol-5(2H)-one;
3-(6-{[(1R)-1-cyclobutylethyl]amino}-8-[cyclopentyl(hydroxy)methyl]-7-[(trans-4-methylcyclohexyl)methyl]-7H-purin-2-yl)-1,2,4-oxadiazol-5(2H)-one;
3-(6-{[(1R)-1-cyclobutylethyl]amino}-7-[(trans-4-methylcyclohexyl)methyl]-8-[1-(tetrahydro-2H-pyran-4-yl)ethenyl]-7H-purin-2-yl)-1,2,4-oxadiazol-5(4H)-one;
3-(6-{[(1R)-1-cyclobutylethyl]amino}-8-(1-hydroxycyclohexyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(1-hydroxy-1-methylethyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(1-hydroxy-2-methylpropyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(2-hydroxycyclohexyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[cyclopentyl(hydroxy)methyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(1-hydroxy-2-methylpropyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-(3-fluorophenyl)cyclopropyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-hydroxy-1-(1,3-thiazol-4-yl)ethyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(1-hydroxy-1-pyridin-3-ylethyl)-7-[(trans-4-methylcyclohexyl)methyl]-7H-purin-2-yl)-1,2,4-oxadiazol-5(2H)-one;
3-(6-{[(1R)-1-cyclobutylethyl]amino}-8-[1-hydroxy-1-(1,3-thiazol-4-yl)ethyl]-7-[(trans-4-methylcyclohexyl)methyl]-7H-purin-2-yl)-1,2,4-oxadiazol-5(4H)-one;
3-[6-{[(1R)-1-cyclobutylethyl]amino}-7-[(trans-4-methylcyclohexyl)methyl]-8-(1-pyridin-4-ylcyclopropyl)-7H-purin-2-yl]-1,2,4-oxadiazol-5(4H)-one;
3-(6-{[(1R)-1-cyclobutylethyl]amino}-7-[(trans-4-methylcyclohexyl)methyl]-8-[1-(1,3-thiazol-4-yl)cyclopropyl]-7H-purin-2-yl)-1,2,4-oxadiazol-5(4H)-one;
3-(6-{[(1R)-1-cyclobutylethyl]amino}-8-[1-hydroxy-1-(1-methyl-1H-pyrazol-3-yl)ethyl]-7-[(trans-4-methylcyclohexyl)methyl]-7H-purin-2-yl)-1,2,4-oxadiazol-5(2H)-one;
3-(6-{[(1R)-1-cyclobutylethyl]amino}-8-[1-hydroxy-1-(1,3-thiazol-2-yl)ethyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[cyclobutyl(hydroxy)methyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-hydroxy-1-(1,3-thiazol-2-yl)ethyl]-7-[(trans-4-methylcyclohexyl)methyl]-7H-purin-2-yl)-1,2,4-oxadiazol-5(4H)-one;
3-(6-{[(1R)-1-cyclobutylethyl]amino}-7-[(trans-4-methylcyclohexyl)methyl]-8-[1-(1,3-thiazol-2-yl)cyclopropyl]-7H-purin-2-yl)-1,2,4-oxadiazol-5(4H)-one;
3-(6-{[(1R)-1-cyclobutylethyl]amino}-8-(1,2-dihydroxy-1-phenylethyl)-7-[(trans-4-methylcyclohexyl)methyl]-7H-purin-2-yl)-1,2,4-oxadiazol-5(4H)-one;
3-(6-{[(1R)-1-cyclobutylethyl]amino}-8-[1-fluoro-1-(2-fluorophenyl)ethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[1-(1-methyl-1H-pyrazol-4-yl)cyclopropyl]-7H-purin-2-yl)-1,2,4-oxadiazol-5(2H)-one;

3-(6-{[(1R)-1-cyclobutylethyl]amino}-8-(4-hydroxytetrahydro-2H-pyran-4-yl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[1-fluoro-1-(2-fluorophenyl)ethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[fluoro(phenyl)methyl]-7-[(trans-4-methylcyclohexyl)methyl]-7H-purin-2-yl)-1,2,4-oxadiazol-5(4H)-one; and 3-(6-{[(1R)-1-cyclobutylethyl]amino}-8-(1-hydroxycyclobutyl)-7-[(trans-4-methylcyclohexyl)methyl]-7H-purin-2-yl)-1,2,4-oxadiazol-5(2H)-one;

or a stereoisomer thereof;
or a pharmaceutically acceptable salt thereof;
or a pharmaceutically acceptable salt of the stereoisomer thereof.

Additional examples include but are not limited to:

5-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(3R)-3-pyridin-2-ylmorpholin-4-yl]-7H-purin-2-yl)-1,2,4-oxadiazol-5(4H)-one;

3-(6-{[(1R)-1-cyclobutylethyl]amino}-8-(hexahydro-2H-pyrano[4,3-b]pyridin-1(5H)-yl)-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(3R)-3-pyridin-4-ylmorpholin-4-yl]-7H-purin-2-yl)-1,2,4-oxadiazol-5(4H)-one;

3-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[3-(methoxymethyl)morpholin-4-yl]-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[2-(trifluoromethyl)-3-azabicyclo[3.1.0]hex-3-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-{2-[(methylsulfonyl)methyl]pyrrolidin-1-yl}-7H-purin-2-yl)-1,2,4-oxadiazol-5(4H)-one;

3-(6-{[(1R)-1-cyclobutylethyl]amino}-7-[(trans-4-methylcyclohexyl)methyl]-8-{2-[(methylsulfinyl)methyl]pyrrolidin-1-yl}-7H-purin-2-yl)-1,2,4-oxadiazol-5(4H)-one;

5-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,2,4-oxadiazol-5(4H)-one;

5-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(2S,3R)-2-methyl-3-phenylmorpholin-4-yl]-7H-purin-2-yl)-1,2,4-oxadiazol-5(4H)-one;

5-(6-{[(1R)-1-cyclobutylethyl]amino}-7-[(trans-4-methylcyclohexyl)methyl]-8-[(2S,3R)-2-methyl-3-phenylmorpholin-4-yl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(2R,3R)-2-methyl-3-phenylmorpholin-4-yl]-7H-purin-2-yl)-1,2,4-oxadiazol-5(4H)-one;

5-(6-{[(1R)-1-cyclobutylethyl]amino}-7-[(trans-4-methylcyclohexyl)methyl]-8-[(2R,3R)-2-methyl-3-phenylmorpholin-4-yl]-7H-purin-2-yl)-1,3,4-oxadiazol-2(3H)-one;

5-(6-{[(1R)-1-cyclobutylethyl]amino}-8-[(trans)-2,3-dimethylmorpholin-4-yl]-7-[(trans-4-methylcyclohexyl)methyl]-7H-purin-2-yl)-1,3,4-oxadiazol-2(3H)-one;

5-{6-(3-chlorophenyl)-7-[(trans-4-methylcyclohexyl)methyl]-8-[(3R)-3-(1-methylethyl)morpholin-4-yl]-7H-purin-2-yl}-1,3,4-oxadiazol-2(3H)-one;

5-{6-(3-chlorophenyl)-8-{[(1S)-1-(3-fluorophenyl)propyl]amino}-7-[(trans-4-methylcyclohexyl)methyl]-7H-purin-2-yl}-1,3,4-oxadiazol-2(3H)-one;

3-[6-(3-chlorophenyl)-7-[(trans-4-methylcyclohexyl)methyl]-8-(octahydro-4H-1,4-benzoxazin-4-yl)-7H-purin-2-yl]-1,2,4-oxadiazol-5(4H)-one;

3-[6-(3-chlorophenyl)-7-[(trans-4-methylcyclohexyl)methyl]-8-(7-oxa-4-azaspiro[2.5]oct-4-yl)-7H-purin-2-yl]-1,2,4-oxadiazol-5(4H)-one;

3-[6-(3-chlorophenyl)-7-[(trans-4-methylcyclohexyl)methyl]-8-(8-oxa-5-azaspiro[3.5]non-5-yl)-7H-purin-2-yl]-1,2,4-oxadiazol-5(4H)-one;

3-{6-(3-chlorophenyl)-8-[(4aS,7aS)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

3-{6-(3-chlorophenyl)-8-[(4aR,7aR)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

5-{6-(3-chlorophenyl)-8-[(4aS,7aS)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

5-{6-(3-chlorophenyl)-8-[(4aR,7aR)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

3-{6-(3-chlorophenyl)-8-{[(1R)-2-methoxy-1-phenylethyl]amino}-7-[(trans-4-methylcyclohexyl)methyl]-7H-purin-2-yl}-1,2,4-oxadiazol-5(4H)-one;

3-{6-(5-chloropyridin-3-yl)-8-[(4aS,7aS)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

3-{6-(5-chloropyridin-3-yl)-8-[(4aR,7aR)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

5-[6-(3-chlorophenyl)-7-[(trans-4-methylcyclohexyl)methyl]-8-(7-oxa-4-azaspiro[2.5]oct-4-yl)-7H-purin-2-yl]-1,3,4-oxadiazol-2(3H)-one;

5-[6-(3-chlorophenyl)-7-[(trans-4-methylcyclohexyl)methyl]-8-(8-oxa-5-azaspiro[3.5]non-5-yl)-7H-purin-2-yl]-1,3,4-oxadiazol-2(3H)-one;

5-{6-(5-chloropyridin-3-yl)-8-[(4aR,7aR)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

5-{6-(5-chloropyridin-3-yl)-8-[(4aS,7aS)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

3-{6-(5-chloropyridin-3-yl)-8-[(3R)-3-(2-fluorophenyl)morpholin-4-yl]-7-[(trans-4-methylcyclohexyl)methyl]-7H-purin-2-yl}-1,2,4-oxadiazol-5(4H)-one;

3-{6-(5-chloropyridin-3-yl)-8-[(3R)-3-(4-fluorophenyl)morpholin-4-yl]-7-[(trans-4-methylcyclohexyl)methyl]-7H-purin-2-yl}-1,2,4-oxadiazol-5(4H)-one;

5-{6-(5-chloropyridin-3-yl)-8-[(3R)-3-(4-fluorophenyl)
morpholin-4-yl]-7-[(trans-4-methylcyclohexyl)methyl]-
7H-purin-2-yl}-1,3,4-oxadiazol-2(3H)-one;

5-{6-(5-chloropyridin-3-yl)-8-[(3R)-3-(2-fluorophenyl)
morpholin-4-yl]-7-[(trans-4-methylcyclohexyl)methyl]-
7H-purin-2-yl}-1,3,4-oxadiazol-2(3H)-one;

3-{6-(3-chlorophenyl)-7-[(trans-4-methylcyclohexyl)
methyl]-8-[(3R)-3-pyridin-4-ylmorpholin-4-yl]-7H-pu-
rin-2-yl}-1,2,4-oxadiazol-5(4H)-one;

5-{6-(3-chlorophenyl)-7-[(trans-4-methylcyclohexyl)
methyl]-8-[(3R)-3-pyridin-4-ylmorpholin-4-yl]-7H-pu-
rin-2-yl}-1,3,4-oxadiazol-2(3H)-one;

3-{6-(3-chlorophenyl)-7-[(trans-4-methylcyclohexyl)
methyl]-8-[(3R)-3-pyridin-2-ylmorpholin-4-yl]-7H-pu-
rin-2-yl}-1,2,4-oxadiazol-5(4H)-one;

5-{6-(3-chlorophenyl)-7-[(trans-4-methylcyclohexyl)
methyl]-8-[(3R)-3-pyridin-2-ylmorpholin-4-yl]-7H-pu-
rin-2-yl}-1,3,4-oxadiazol-2(3H)-one;

3-{6-(3-chlorophenyl)-8-[(cis)-2,3-dimethylmorpholin-4-
yl]-7-[(trans-4-methylcyclohexyl)methyl]-7H-purin-2-
yl}-1,2,4-oxadiazol-5(4H)-one;

5-{6-(3-chlorophenyl)-8-[(cis)-2,3-dimethylmorpholin-4-
yl]-7-[(trans-4-methylcyclohexyl)methyl]-7H-purin-2-
yl}-1,3,4-oxadiazol-2(3H)-one;

3-{6-(3-chlorophenyl)-8-[(trans)-2,3-dimethylmorpholin-4-
yl]-7-[(trans-4-methylcyclohexyl)methyl]-7H-purin-2-
yl}-1,2,4-oxadiazol-5(4H)-one;

5-{6-(5-chloropyridin-3-yl)-8-[(2S,3R)-2,3-dimethylmor-
pholin-4-yl]-7-[(trans-4-methylcyclohexyl)methyl]-7H-
purin-2-yl}-1,3,4-oxadiazol-2(3H)-one;

5-{6-(5-chloropyridin-3-yl)-8-[(2S)-2-(fluoromethyl)pyrro-
lidin-1-yl]-7-[(trans-4-methylcyclohexyl)methyl]-7H-pu-
rin-2-yl}-1,3,4-oxadiazol-2(3H)-one;

5-{6-(5-chloropyridin-3-yl)-8-[(3R,5R)-3,5-dimethylmor-
pholin-4-yl]-7-[(trans-4-methylcyclohexyl)methyl]-7H-
purin-2-yl}-1,3,4-oxadiazol-2(3H)-one;

5-{6-(5-chloropyridin-3-yl)-7-[(trans-4-methylcyclohexyl)
methyl]-8-[(2S)-2-(trifluoromethyl)pyrrolidin-1-yl]-7H-
purin-2-yl}-1,3,4-oxadiazol-2(3H)-one;

3-{6-(2,6-dichloropyridin-4-yl)-7-[(trans-4-methylcyclo-
hexyl)methyl]-8-[(3R)-3-phenylmorpholin-4-yl]-7H-pu-
rin-2-yl}-1,2,4-oxadiazol-5(4H)-one;

3-{6-(5-chloro-2-fluoropyridin-3-yl)-7-[(trans-4-methylcy-
clohexyl)methyl]-8-[(3R)-3-phenylmorpholin-4-yl]-7H-
purin-2-yl}-1,2,4-oxadiazol-5(4H)-one;

3-{6-(2-chloro-6-methoxypyridin-4-yl)-7-[(trans-4-methyl-
cyclohexyl)methyl]-8-[(3R)-3-phenylmorpholin-4-yl]-
7H-purin-2-yl}-1,2,4-oxadiazol-5(4H)-one;

3-{6-(2-chloropyridin-4-yl)-7-[(trans-4-methylcyclohexyl)
methyl]-8-[(3R)-3-phenylmorpholin-4-yl]-7H-purin-2-
yl}-1,2,4-oxadiazol-5(4H)-one;

3-{6-[3-chloro-5-(methylsulfonyl)phenyl]-7-[(trans-4-
methylcyclohexyl)methyl]-8-[(3R)-3-phenylmorpholin-
4-yl]-7H-purin-2-yl}-1,2,4-oxadiazol-5(4H)-one;

3-{7-[(trans-4-methylcyclohexyl)methyl]-6-[3-(5-methyl-1,
2,4-oxadiazol-3-yl)phenyl]-8-[(3R)-3-phenylmorpholin-
4-yl]-7H-purin-2-yl}-1,2,4-oxadiazol-5(4H)-one;

3-{6-(3-chloro-5-pyrrolidin-1-ylphenyl)-7-[(trans-4-meth-
ylcyclohexyl)methyl]-8-[(3R)-3-phenylmorpholin-4-yl]-
7H-purin-2-yl}-1,2,4-oxadiazol-5(4H)-one;

3-{6-(3-chloro-5-methylphenyl)-7-[(trans-4-methylcyclo-
hexyl)methyl]-8-[(3R)-3-phenylmorpholin-4-yl]-7H-pu-
rin-2-yl}-1,2,4-oxadiazol-5(4H)-one;

3-{7-[(trans-4-methylcyclohexyl)methyl]-6-(5-methylpyri-
din-3-yl)-8-[(3R)-3-phenylmorpholin-4-yl]-7H-purin-2-
yl}-1,2,4-oxadiazol-5(4H)-one;

3-{6-(3-chlorophenyl)-7-[(trans-4-methylcyclohexyl)
methyl]-8-[(3S)-3-(3-methyl-1,2,4-oxadiazol-5-yl)mor-
pholin-4-yl]-7H-purin-2-yl}-1,2,4-oxadiazol-5(4H)-one;

(3S)-4-[6-(3-chlorophenyl)-7-[(trans-4-methylcyclohexyl)
methyl]-2-(5-oxo-4,5-dihydro-1,2,4-oxadiazol-3-yl)-7H-
purin-8-yl]morpholine-3-carboxamide;

3-{6-(3-chlorophenyl)-8-(hexahydro-2H-pyrano[4,3-b]pyri-
din-1(5H)-yl)-7-[(trans-4-methylcyclohexyl)methyl]-7H-
purin-2-yl}-1,2,4-oxadiazol-5(4H)-one;

3-{6-(3-chlorophenyl)-7-[(trans-4-methylcyclohexyl)
methyl]-8-[(3S)-3-(4-methyl-1,3-thiazol-2-yl)morpholin-
4-yl]-7H-purin-2-yl}-1,2,4-oxadiazol-5(4H)-one;

5-{6-(3-chlorophenyl)-7-[(trans-4-methylcyclohexyl)
methyl]-8-[(3S)-3-(3-methyl-1,2,4-oxadiazol-5-yl)mor-
pholin-4-yl]-7H-purin-2-yl}-1,3,4-oxadiazol-2(3H)-one;

5-{6-(5-chloropyridin-3-yl)-8-(hexahydro-2H-pyrano[4,3-
b]pyridin-1(5H)-yl)-7-[(trans-4-methylcyclohexyl)
methyl]-7H-purin-2-yl}-1,3,4-oxadiazol-2(3H)-one;

5-{6-(5-chloropyridin-3-yl)-8-(hexahydro-2H-pyrano[4,3-b]pyri-
din-1(5H)-yl)-7-[(trans-4-methylcyclohexyl)methyl]-7H-
purin-2-yl}-1,3,4-oxadiazol-2(3H)-one;

3-{6-(3-chlorophenyl)-7-[(trans-4-methylcyclohexyl)
methyl]-8-[(2S,3R)-2-methyl-3-phenylmorpholin-4-yl]-
7H-purin-2-yl}-1,2,4-oxadiazol-5(4H)-one;

3-{6-(3-chlorophenyl)-7-[(trans-4-methylcyclohexyl)
methyl]-8-[(2R,3R)-2-methyl-3-phenylmorpholin-4-yl]-
7H-purin-2-yl}-1,2,4-oxadiazol-5(4H)-one;

5-{6-(5-chloropyridin-3-yl)-7-[(trans-4-methylcyclohexyl)
methyl]-8-[(cis)-octahydro-4H-1,4-benzoxazin-4-yl]-7H-
purin-2-yl}-1,3,4-oxadiazol-2(3H)-one;

3-{6-(5-chloropyridin-3-yl)-7-[(trans-4-methylcyclohexyl)
methyl]-8-[(2S,3R)-2-methyl-3-phenylmorpholin-4-yl]-
7H-purin-2-yl}-1,2,4-oxadiazol-5(4H)-one;

5-{6-(5-chloropyridin-3-yl)-7-[(trans-4-methylcyclohexyl)
methyl]-8-[(2S,3R)-2-methyl-3-phenylmorpholin-4-yl]-
7H-purin-2-yl}-1,3,4-oxadiazol-2(3H)-one;

3-{6-(5-chloropyridin-3-yl)-7-[(trans-4-methylcyclohexyl)
methyl]-8-[(cis)-octahydro-4H-1,4-benzoxazin-4-yl]-7H-
purin-2-yl}-1,2,4-oxadiazol-5(4H)-one;

5-{6-(3-chlorophenyl)-7-[(trans-4-methylcyclohexyl)
methyl]-8-[(2S,3R)-2-methyl-3-phenylmorpholin-4-yl]-
7H-purin-2-yl}-1,3,4-oxadiazol-2(3H)-one;

5-{6-(5-chloropyridin-3-yl)-7-[(trans-4-methylcyclohexyl)
methyl]-8-[(2R,3R)-2-methyl-3-phenylmorpholin-4-yl]-
7H-purin-2-yl}-1,3,4-oxadiazol-2(3H)-one;

5-{6-(3-chlorophenyl)-8-[(trans)-2,3-dimethylmorpholin-4-
yl]-7-[(trans-4-methylcyclohexyl)methyl]-7H-purin-2-
yl}-1,3,4-oxadiazol-2(3H)-one;

3-{6-(5-chloropyridin-3-yl)-7-[(trans-4-methylcyclohexyl)
methyl]-8-[(2R,3R)-2-methyl-3-phenylmorpholin-4-yl]-
7H-purin-2-yl}-1,2,4-oxadiazol-5(4H)-one;

3-{6-(5-chloropyridin-3-yl)-8-[(2R,3R)-2,3-dimethylmor-
pholin-4-yl]-7-[(trans-4-methylcyclohexyl)methyl]-7H-
purin-2-yl}-1,2,4-oxadiazol-5(4H)-one;

3-{6-(3-chlorophenyl)-8-[(3S)-3-(fluoromethyl)morpholin-
4-yl]-7-[(trans-4-methylcyclohexyl)methyl]-7H-purin-2-
yl}-1,2,4-oxadiazol-5(4H)-one;

3-{6-(3-chlorophenyl)-7-[(trans-4-methylcyclohexyl)
methyl]-8-[(3S)-3-(5-methyl-1,3,4-oxadiazol-2-yl)mor-
pholin-4-yl]-7H-purin-2-yl}-1,2,4-oxadiazol-5(4H)-one;

5-{6-(5-chloropyridin-3-yl)-8-[(3S)-3-(fluoromethyl)mor-
pholin-4-yl]-7-[(trans-4-methylcyclohexyl)methyl]-7H-
purin-2-yl}-1,3,4-oxadiazol-2(3H)-one;

5-{6-(5-chloropyridin-3-yl)-8-[(2R,3R)-2,3-dimethylmor-
pholin-4-yl]-7-[(trans-4-methylcyclohexyl)methyl]-7H-
purin-2-yl}-1,3,4-oxadiazol-2(3H)-one;

3-{6-(5-chloropyridin-3-yl)-7-[(trans-4-methylcyclohexyl)methyl]-8-[2-(5-methyl-1,3,4-oxadiazol-2-yl)pyrrolidin-1-yl]-7H-purin-2-yl}-1,2,4-oxadiazol-5(4H)-one;

5-{6-(3-chlorophenyl)-7-[(trans-4-methylcyclohexyl)methyl]-8-[(2R,3R)-2-methyl-3-phenylmorpholin-4-yl]-7H-purin-2-yl}-1,3,4-oxadiazol-2(3H)-one;

3-{6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purin-2-yl}-1,2,4-oxadiazol-5(4H)-one;

3-[6-(5-chloropyridin-3-yl)-7-[(trans-4-methylcyclohexyl)methyl]-8-(8-oxa-5-azaspiro[3.5]non-5-yl)-7H-purin-2-yl]-1,2,4-oxadiazol-5(4H)-one;

6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purine-2-carboxylic acid;

5-{6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purin-2-yl}-1,3,4-oxadiazol-2(3H)-one;

5-{6-(3-chlorophenyl)-8-[(3R,5R)-3,5-dimethylmorpholin-4-yl]-7-[(trans-4-methylcyclohexyl)methyl]-7H-purin-2-yl}-1,3,4-oxadiazol-2(3H)-one;

1-[6-(3-chlorophenyl)-7-[(trans-4-methylcyclohexyl)methyl]-2-(5-oxo-4,5-dihydro-1,2,4-oxadiazol-3-yl)-7H-purin-8-yl]-N,N-dimethyl-L-prolinamide;

3-{8-[(2S,5S)-2,5-bis(methoxymethyl)pyrrolidin-1-yl]-6-(3-chlorophenyl)-7-[(trans-4-methylcyclohexyl)methyl]-7H-purin-2-yl}-1,2,4-oxadiazol-5(4H)-one;

3-{6-(3-chlorophenyl)-8-(hexahydro-4H-furo[3,2-b]pyrrol-4-yl)-7-[(trans-4-methylcyclohexyl)methyl]-7H-purin-2-yl}-1,2,4-oxadiazol-5(4H)-one;

3-{6-(5-chloropyridin-3-yl)-7-[(trans-4-methylcyclohexyl)methyl]-8-[(trans)-3-methylhexahydrocyclopenta[b][1,4]oxazin-4(4aH)-yl]-7H-purin-2-yl}-1,2,4-oxadiazol-5(4H)-one;

3-{6-(5-chloropyridin-3-yl)-8-[(2R,3R)-3-ethyl-2-methylmorpholin-4-yl]-7-[(trans-4-methylcyclohexyl)methyl]-7H-purin-2-yl}-1,2,4-oxadiazol-5(4H)-one;

5-{6-(5-chloropyridin-3-yl)-8-[(2R,3R)-3-ethyl-2-methylmorpholin-4-yl]-7-[(trans-4-methylcyclohexyl)methyl]-7H-purin-2-yl}-1,3,4-oxadiazol-2(3H)-one;

5-{6-(5-chloropyridin-3-yl)-8-[(cis)-4-methoxy-2-methylpiperidin-1-yl]-7-[(trans-4-methylcyclohexyl)methyl]-7H-purin-2-yl}-1,3,4-oxadiazol-2(3H)-one;

5-{6-(5-chloropyridin-3-yl)-8-[(trans)-4-methoxy-2-methylpiperidin-1-yl]-7-[(trans-4-methylcyclohexyl)methyl]-7H-purin-2-yl}-1,3,4-oxadiazol-2(3H)-one;

3-{6-(5-chloro-2-methoxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(5-chloro-2-methoxypyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(5-chloro-2-methylpyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(5-chloro-2-methylpyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-[3-chloro-5-(2-methoxyethoxyl)phenyl]-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

3-{6-[2-(benzyloxy)-5-chloropyridin-3-yl]-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(5-chloro-2-methylpyridin-3-yl)-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

3-{6-cyclohexyl-7-[(trans-4-methylcyclohexyl)methyl]-8-[(3R)-3-phenylmorpholin-4-yl]-7H-purin-2-yl}-1,2,4-oxadiazol-5(4H)-one;

5-{6-cyclohexyl-7-[(trans-4-methylcyclohexyl)methyl]-8-[(3R)-3-phenylmorpholin-4-yl]-7H-purin-2-yl}-1,3,4-oxadiazol-2(3H)-one;

3-{7-[(trans-4-methylcyclohexyl)methyl]-8-[(3R)-3-phenylmorpholin-4-yl]-6-(tetrahydro-2H-pyran-4-yl)-7H-purin-2-yl}-1,2,4-oxadiazol-5(4H)-one;

5-{7-[(trans-4-methylcyclohexyl)methyl]-8-[(3R)-3-phenylmorpholin-4-yl]-6-(tetrahydro-2H-pyran-4-yl)-7H-purin-2-yl}-1,3,4-oxadiazol-2(3H)-one;

3-{6-(3-methylcyclohexyl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(3-methylcyclohexyl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(3-chlorophenyl)-7-[1-(trans-4-methylcyclohexyl)ethyl]-8-[(3R)-3-methylmorpholin-4-yl]-7H-purin-2-yl}-1,2,4-oxadiazol-5(4H)-one;

5-{6-(3-chlorophenyl)-7-[1-(trans-4-methylcyclohexyl)ethyl]-8-[(3R)-3-methylmorpholin-4-yl]-7H-purin-2-yl}-1,3,4-oxadiazol-2(3H)-one;

3-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one;

3-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,2,4-oxadiazol-5(4H)-one;

5-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,3,4-oxadiazol-2(3H)-one;

5-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,3,4-oxadiazol-2(3H)-one;

3-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,2,4-oxadiazol-5(4H)-one;

5-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,3,4-oxadiazol-2(3H)-one;

3-{6-(5-chloropyridin-3-yl)-7-[1-(trans-4-methylcyclohexyl)ethyl]-8-[(2S)-2-(trifluoromethyl)pyrrolidin-1-yl]-7H-purin-2-yl}-1,2,4-oxadiazol-5(4H)-one;

3-{6-(3-chlorophenyl)-8-[(3R)-3-ethylmorpholin-4-yl]-7-[1-(trans-4-methylcyclohexyl)ethyl]-7H-purin-2-yl}-1,2,4-oxadiazol-5(4H)-one;

3-{6-(5-chloropyridin-3-yl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one;

5-{6-(5-chloropyridin-3-yl)-8-(cyclopentylsulfanyl)-7-[(trans-4-methylcyclohexyl)methyl]-7H-purin-2-yl}-1,3,4-oxadiazol-2(3H)-one;

5-{6-(5-chloropyridin-3-yl)-8-(cyclopentylsulfonyl)-7-[(trans-4-methylcyclohexyl)methyl]-7H-purin-2-yl}-1,3,4-oxadiazol-2(3H)-one;

5-[6-(5-chloropyridin-3-yl)-7-[(trans-4-methylcyclohexyl)methyl]-8-(phenylsulfanyl)-7H-purin-2-yl]-1,3,4-oxadiazol-2(3H)-one;

3-[6-(5-chloropyridin-3-yl)-7-[(trans-4-methylcyclohexyl)methyl]-8-(1-phenylcyclobutyl)-7H-purin-2-yl]-1,2,4-oxadiazol-5(4H)-one;

5-[6-(5-chloropyridin-3-yl)-7-[(trans-4-methylcyclohexyl)methyl]-8-(1-phenylcyclobutyl)-7H-purin-2-yl]-1,3,4-oxadiazol-2(3H)-one;

5-[6-(5-chloro-1-oxidopyridin-3-yl)-7-[(trans-4-methylcyclohexyl)methyl]-8-(1-phenylcyclobutyl)-7H-purin-2-yl]-1,3,4-oxadiazol-2(3H)-one;

3-[6-(5-chloro-2-methoxypyridin-3-yl)-7-[(trans-4-methylcyclohexyl)methyl]-8-(1-phenylcyclobutyl)-7H-purin-2-yl]-1,2,4-oxadiazol-5(4H)-one;

3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-cyclohex-1-en-1-yl-7-[(trans-4-methylcyclohexyl)methyl]-7H-purin-2-yl)-1,2,4-oxadiazol-5(4H)-one;

6-{[(1R)-1-cyclobutylethyl]amino}-8-cyclohexyl-7-[(trans-4-methylcyclohexyl)methyl]-7H-purine-2-carboxylic acid;

3-(6-{[(1R)-1-cyclobutylethyl]amino}-8-cyclohexyl-7-[(trans-4-methylcyclohexyl)methyl]-7H-purin-2-yl)-1,2,4-oxadiazol-5(4H)-one;

5-(6-{[(1R)-1-cyclobutylethyl]amino}-8-cyclohexyl-7-[(trans-4-methylcyclohexyl)methyl]-7H-purin-2-yl)-1,3,4-oxadiazol-2(3H)-one;

3-(6-{[(1R)-1-cyclobutylethyl]amino}-8-[(1R or S)-2-methoxy-1-phenylethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-fluorocyclobutyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-methoxycyclobutyl)-7-[(trans-4-methylcyclohexyl)methyl]-7H-purin-2-yl)-1,2,4-oxadiazol-5(4H)-one;

3-(8-cyclobutyl-6-{[(1R)-1-cyclobutylethyl]amino}-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(1-pyridin-2-ylethyl)-7H-purin-2-yl]-1,2,4-oxadiazol-5(4H)-one;

3-(6-{[(1R)-1-cyclobutylethyl]amino}-8-[1-(2,5-dimethyl-1,3-thiazol-4-yl)cyclopropyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[1-(2,5-dimethyl-1,3-thiazol-4-yl)-1-fluoroethyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[methoxy(1,3-thiazol-4-yl)methyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-ethoxycyclobutyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1-fluoro-1-phenylethyl)-7-[(trans-4-methylcyclohexyl)methyl]-7H-purin-2-yl)-1,2,4-oxadiazol-5(4H)-one;

3-(6-{[(1R)-1-cyclobutylethyl]amino}-8-[difluoro(phenyl)methyl]-7-[(trans-4-methylcyclohexyl)methyl]-7H-purin-2-yl)-1,2,4-oxadiazol-5(4H)-one;

3-(6-{[(1R)-1-cyclobutylethyl]amino}-8-(1,3-dihydro-2-benzofuran-1-yl)-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(2-phenyloxetan-2-yl)-7H-purin-2-yl]-1,2,4-oxadiazol-5(4H)-one;

3-(6-{[(1R)-1-cyclobutylethyl]amino}-8-[1-(hydroxymethyl)propyl]-7-[(trans-4-methylcyclohexyl)methyl]-7H-purin-2-yl)-1,2,4-oxadiazol-5(4H)-one;

5-{6-(3-chlorophenyl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one;

3-{6-(3-chlorophenyl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one;

3-[6-(3-chlorophenyl)-7-[(trans-4-methylcyclohexyl)methyl]-8-(tetrahydro-2H-pyran-4-ylcarbonyl)-7H-purin-2-yl]-1,2,4-oxadiazol-5(4H)-one;

3-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,2,4-oxadiazol-5(4H)-one;

3-{6-(3-chlorophenyl)-8-[cyclohexyl(hydroxy)methyl]-7-[(trans-4-methylcyclohexyl)methyl]-7H-purin-2-yl}-1,2,4-oxadiazol-5(4H)-one;

3-{6-(3-chlorophenyl)-8-(cyclohexylcarbonyl)-7-[(trans-4-methylcyclohexyl)methyl]-7H-purin-2-yl}-1,2,4-oxadiazol-5(4H)-one;

5-{6-(3-chlorophenyl)-8-[cyclohexyl(hydroxy)methyl]-7-[(trans-4-methylcyclohexyl)methyl]-7H-purin-2-yl}-1,3,4-oxadiazol-2(3H)-one;

5-{6-(3-chlorophenyl)-8-(cyclohexylcarbonyl)-7-[(trans-4-methylcyclohexyl)methyl]-7H-purin-2-yl}-1,3,4-oxadiazol-2(3H)-one;

5-[6-(3-chlorophenyl)-7-[(trans-4-methylcyclohexyl)methyl]-8-(tetrahydro-2H-pyran-4-ylcarbonyl)-7H-purin-2-yl]-1,3,4-oxadiazol-2(3H)-one;

3-{6-(3-chlorophenyl)-8-(1-cyclohexyl-1-hydroxyethyl)-7-[(trans-4-methylcyclohexyl)methyl]-7H-purin-2-yl}-1,2,4-oxadiazol-5(4H)-one;

5-{6-(3-chlorophenyl)-8-(1-cyclohexyl-1-hydroxyethyl)-7-[(trans-4-methylcyclohexyl)methyl]-7H-purin-2-yl}-1,3,4-oxadiazol-2(3H)-one;

3-{6-(3-chlorophenyl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one;

5-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,3,4-oxadiazol-2(3H)-one;

3-{6-(3-chlorophenyl)-8-[cyclohexyl(methoxy)methyl]-7-[(trans-4-methylcyclohexyl)methyl]-7H-purin-2-yl}-1,2,4-oxadiazol-5(4H)-one;

5-{6-(3-chlorophenyl)-8-[cyclohexyl(methoxy)methyl]-7-[(trans-4-methylcyclohexyl)methyl]-7H-purin-2-yl}-1,3,4-oxadiazol-2(3H)-one;

5-{6-(3-chlorophenyl)-8-[methoxy(tetrahydro-2H-pyran-4-yl)methyl]-7-[(trans-4-methylcyclohexyl)methyl]-7H-purin-2-yl}-1,3,4-oxadiazol-2(3H)-one;

3-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one;

3-{6-(5-chloropyridin-3-yl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one;

5-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one;

5-{6-(5-chloropyridin-3-yl)-8-[methoxy(tetrahydro-2H-pyran-4-yl)methyl]-7-[(trans-4-methylcyclohexyl)methyl]-7H-purin-2-yl}-1,3,4-oxadiazol-2(3H)-one;

3-{6-(5-chloropyridin-3-yl)-8-[cyclohexyl(methoxy)methyl]-7-[(trans-4-methylcyclohexyl)methyl]-7H-purin-2-yl}-1,2,4-oxadiazol-5(4H)-one;

5-{6-(5-chloropyridin-3-yl)-8-[cyclohexyl(methoxy)methyl]-7-[(trans-4-methylcyclohexyl)methyl]-7H-purin-2-yl}-1,3,4-oxadiazol-2(3H)-one;

5-{6-(5-chloropyridin-3-yl)-8-[cyclopentyl(methoxy)methyl]-7-[(trans-4-methylcyclohexyl)methyl]-7H-purin-2-yl}-1,3,4-oxadiazol-2(3H)-one;

5-{6-(5-chloropyridin-3-yl)-8-[1-fluoro-1-(2-methoxyphenyl)ethyl]-7-[(trans-4-methylcyclohexyl)methyl]-7H-purin-2-yl}-1,3,4-oxadiazol-2(3H)-one;

3-{6-(5-chloropyridin-3-yl)-8-[1-fluoro-1-(2-methoxyphenyl)ethyl]-7-[(trans-4-methylcyclohexyl)methyl]-7H-purin-2-yl}-1,2,4-oxadiazol-5(4H)-one;

3-{6-(5-chloropyridin-3-yl)-8-(3-fluorooxetan-3-yl)-7-[(trans-4-methylcyclohexyl)methyl]-7H-purin-2-yl}-1,2,4-oxadiazol-5(4H)-one;

3-{6-(3-chlorophenyl)-8-[cyclohexyl(fluoro)methyl]-7-[(trans-4-methylcyclohexyl)methyl]-7H-purin-2-yl}-1,2,4-oxadiazol-5(4H)-one;

3-{6-(3-chlorophenyl)-8-(1-fluoro-1-pyridin-2-ylethyl)-7-[(trans-4-methylcyclohexyl)methyl]-7H-purin-2-yl}-1,2,4-oxadiazol-5(4H)-one;

5-{6-(5-chloropyridin-3-yl)-8-[1-fluoro-1-(2-fluorophenyl)ethyl]-7-[(trans-4-methylcyclohexyl)methyl]-7H-purin-2-yl}-1,3,4-oxadiazol-2(3H)-one;

3-{6-(5-chloropyridin-3-yl)-8-[1-fluoro-1-(2-fluorophenyl)ethyl]-7-[(trans-4-methylcyclohexyl)methyl]-7H-purin-2-yl}-1,2,4-oxadiazol-5(4H)-one;

5-{6-(3-chlorophenyl)-8-[1-fluoro-1-(pyridin-2-yl)ethyl]-7-[(trans-4-methylcyclohexyl)methyl]-7H-purin-2-yl}-1,3,4-oxadiazol-2(3H)-one;

5-{6-(5-chloropyridin-3-yl)-8-(1-fluorocyclobutyl)-7-[(trans-4-methylcyclohexyl)methyl]-7H-purin-2-yl}-1,3,4-oxadiazol-2(3H)-one;

3-{6-(5-chloropyridin-3-yl)-8-(1-fluorocyclohexyl)-7-[(trans-4-methylcyclohexyl)methyl]-7H-purin-2-yl}-1,2,4-oxadiazol-5(4H)-one;

5-{6-(5-chloropyridin-3-yl)-8-(1-fluorocyclopentyl)-7-[(trans-4-methylcyclohexyl)methyl]-7H-purin-2-yl}-1,3,4-oxadiazol-2(3H)-one;

3-{6-(3-chlorophenyl)-8-[hydroxy(phenyl)methyl]-7-[(trans-4-methylcyclohexyl)methyl]-7H-purin-2-yl}-1,2,4-oxadiazol-5(4H)-one;

3-[6-(3-chlorophenyl)-7-[(trans-4-methylcyclohexyl)methyl]-8-(phenylcarbonyl)-7H-purin-2-yl]-1,2,4-oxadiazol-5(4H)-one;

3-{6-(3-chlorophenyl)-8-[methoxy(phenyl)methyl]-7-[(trans-4-methylcyclohexyl)methyl]-7H-purin-2-yl}-1,2,4-oxadiazol-5(4H)-one;

3-{6-(3-chlorophenyl)-8-[methoxy(pyridin-2-yl)methyl]-7-[(trans-4-methylcyclohexyl)methyl]-7H-purin-2-yl}-1,2,4-oxadiazol-5(4H)-one;

3-{6-(5-chloropyridin-3-yl)-8-[methoxy(phenyl)methyl]-7-[(trans-4-methylcyclohexyl)methyl]-7H-purin-2-yl}-1,2,4-oxadiazol-5(4H)-one;

3-{6-(5-chloropyridin-3-yl)-8-[1-(2-fluorophenyl)-1-methoxyethyl]-7-[(trans-4-methylcyclohexyl)methyl]-7H-purin-2-yl}-1,2,4-oxadiazol-5(4H)-one;

5-{6-(5-chloropyridin-3-yl)-8-[1-methoxy-1-(2-methyl-1,3-thiazol-4-yl)ethyl]-7-[(trans-4-methylcyclohexyl)methyl]-7H-purin-2-yl}-1,3,4-oxadiazol-2(3H)-one;

3-{6-(3-chlorophenyl)-8-[1-methoxy-1-(pyridin-2-yl)ethyl]-7-[(trans-4-methylcyclohexyl)methyl]-7H-purin-2-yl}-1,2,4-oxadiazol-5(2H)-one;

5-{6-(3-chlorophenyl)-8-(1-methoxy-1-pyridin-2-ylethyl)-7-[(trans-4-methylcyclohexyl)methyl]-7H-purin-2-yl}-1,3,4-oxadiazol-2(3H)-one;

5-{6-(5-chloropyridin-3-yl)-8-(1-fluorocyclohexyl)-7-[(trans-4-methylcyclohexyl)methyl]-7H-purin-2-yl}-1,3,4-oxadiazol-2(3H)-one;

3-{6-(3-chlorophenyl)-8-[1-methoxy-1-(5-methyl-1,3-oxazol-4-yl)ethyl]-7-[(trans-4-methylcyclohexyl)methyl]-7H-purin-2-yl}-1,2,4-oxadiazol-5(4H)-one;

5-{6-(5-chloropyridin-3-yl)-8-(1-cyclopentyl-1-fluoroethyl)-7-[(trans-4-methylcyclohexyl)methyl]-7H-purin-2-yl}-1,3,4-oxadiazol-2(3H)-one;

5-{8-[1-(3-chloro-2-fluorophenyl)-1-fluoroethyl]-6-(5-chloropyridin-3-yl)-7-[(trans-4-methylcyclohexyl)methyl]-7H-purin-2-yl}-1,3,4-oxadiazol-2(3H)-one;

3-{6-(5-chloropyridin-3-yl)-8-[cyclopentyl(methoxy)methyl]-7-[(trans-4-methylcyclohexyl)methyl]-7H-purin-2-yl}-1,2,4-oxadiazol-5(4H)-one;

3-{6-(5-chloropyridin-3-yl)-8-(1-methoxycyclobutyl)-7-[(trans-4-methylcyclohexyl)methyl]-7H-purin-2-yl}-1,2,4-oxadiazol-5(4H)-one;

3-{6-(5-chloropyridin-3-yl)-8-(1-methoxy-2-methylcyclohexyl)-7-[(trans-4-methylcyclohexyl)methyl]-7H-purin-2-yl}-1,2,4-oxadiazol-5(4H)-one;

5-{6-(5-chloropyridin-3-yl)-8-(1-methoxy-2-methylcyclohexyl)-7-[(trans-4-methylcyclohexyl)methyl]-7H-purin-2-yl}-1,3,4-oxadiazol-2(3H)-one;

3-{6-(5-chloropyridin-3-yl)-8-(1-fluoro-2-methylcyclohexyl)-7-[(trans-4-methylcyclohexyl)methyl]-7H-purin-2-yl}-1,2,4-oxadiazol-5(4H)-one;

6-(5-chloropyridin-3-yl)-8-[1-fluoro-1-(2-fluorophenyl)ethyl]-7-[(trans-4-methylcyclohexyl)methyl]-7H-purine-2-carboxylic acid;

3-{6-(5-chloropyridin-3-yl)-8-[1-(2,6-difluorophenyl)-1-fluoroethyl]-7-[(trans-4-methylcyclohexyl)methyl]-7H-purin-2-yl}-1,2,4-oxadiazol-5(4H)-one;

3-{6-(5-chloropyridin-3-yl)-8-(3-methoxyoxetan-3-yl)-7-[(trans-4-methylcyclohexyl)methyl]-7H-purin-2-yl}-1,2,4-oxadiazol-5(4H)-one;

3-{6-(5-chloropyridin-3-yl)-8-(1-cyclopentyl-1-methoxyethyl)-7-[(trans-4-methylcyclohexyl)methyl]-7H-purin-2-yl}-1,2,4-oxadiazol-5(4H)-one;

5-{6-(5-chloropyridin-3-yl)-8-(1-cyclopentyl-1-methoxyethyl)-7-[(trans-4-methylcyclohexyl)methyl]-7H-purin-2-yl}-1,3,4-oxadiazol-2(3H)-one;

5-{8-[1-(3-chloro-2-fluorophenyl)-1-methoxyethyl]-6-(5-chloropyridin-3-yl)-7-[(trans-4-methylcyclohexyl)methyl]-7H-purin-2-yl}-1,3,4-oxadiazol-2(3H)-one;

3-{6-(5-chloropyridin-3-yl)-8-(1-methoxycyclohexyl)-7-[(trans-4-methylcyclohexyl)methyl]-7H-purin-2-yl}-1,2,4-oxadiazol-5(4H)-one;

5-{6-(5-chloropyridin-3-yl)-8-(1-methoxycyclohexyl)-7-[(trans-4-methylcyclohexyl)methyl]-7H-purin-2-yl}-1,3,4-oxadiazol-2(3H)-one;

3-{6-(5-chloropyridin-3-yl)-8-(1-methoxycyclopentyl)-7-[(trans-4-methylcyclohexyl)methyl]-7H-purin-2-yl}-1,2,4-oxadiazol-5(4H)-one;

5-{6-(5-chloropyridin-3-yl)-8-[1-methoxy-1-(2-methoxyphenyl)ethyl]-7-[(trans-4-methylcyclohexyl)methyl]-7H-purin-2-yl}-1,3,4-oxadiazol-2(3H)-one;

3-{6-(5-chloropyridin-3-yl)-8-[1-methoxy-1-(2-methoxyphenyl)ethyl]-7-[(trans-4-methylcyclohexyl)methyl]-7H-purin-2-yl}-1,2,4-oxadiazol-5(4H)-one;

5-{6-(5-chloropyridin-3-yl)-8-[1-(2,6-difluorophenyl)-1-fluoroethyl]-7-[(trans-4-methylcyclohexyl)methyl]-7H-purin-2-yl}-1,3,4-oxadiazol-2(3H)-one;

5-{6-(5-chloropyridin-3-yl)-8-(1-fluoro-2-methylcyclohexyl)-7-[(trans-4-methylcyclohexyl)methyl]-7H-purin-2-yl}-1,3,4-oxadiazol-2(3H)-one;

5-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,3,4-oxadiazol-2(3H)-one;

5-{6-(5-chloropyridin-3-yl)-8-[1-(3-fluoropyridin-2-yl)-1-methoxyethyl]-7-[(trans-4-methylcyclohexyl)methyl]-7H-purin-2-yl}-1,3,4-oxadiazol-2(3H)-one;

5-{6-(5-chloropyridin-3-yl)-8-[1-(2,6-difluorophenyl)-1-methoxyethyl]-7-[(trans-4-methylcyclohexyl)methyl]-7H-purin-2-yl}-1,3,4-oxadiazol-2(3H)-one;

5-{6-(5-chloropyridin-3-yl)-8-(4-methoxy-3,4-dihydro-2H-pyrano[3,2-b]pyridin-4-yl)-7-[(trans-4-methylcyclohexyl)methyl]-7H-purin-2-yl}-1,3,4-oxadiazol-2(3H)-one;

3-{6-(5-chloropyridin-3-yl)-8-(1-fluoro-1,2,2-trimethylpropyl)-7-[(trans-4-methylcyclohexyl)methyl]-7H-purin-2-yl}-1,2,4-oxadiazol-5(4H)-one;

5-{6-(5-chloropyridin-3-yl)-8-(4-fluoro-3,4-dihydro-2H-pyrano[3,2-b]pyridin-4-yl)-7-[(trans-4-methylcyclohexyl)methyl]-7H-purin-2-yl}-1,3,4-oxadiazol-2(3H)-one;

3-{6-(5-chloropyridin-3-yl)-8-[1-(2,6-difluorophenyl)-1-methoxyethyl]-7-[(trans-4-methylcyclohexyl)methyl]-7H-purin-2-yl}-1,2,4-oxadiazol-5(4H)-one;

3-{6-(5-chloropyridin-3-yl)-8-(4-fluoro-3-methyltetrahydro-2H-pyran-4-yl)-7-[(trans-4-methylcyclohexyl)methyl]-7H-purin-2-yl}-1,2,4-oxadiazol-5(4H)-one;

1,5-anhydro-3-C-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-2,4-dideoxy-2-methyl-3-O-methylpentitol;

3-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,2,4-oxadiazol-5(4H)-one;

3-{6-(5-chloropyridin-3-yl)-8-[1-(2-fluorophenyl)cyclopropyl]-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[1-(5-methyl-1,3-oxazol-4-yl)cyclopropyl]-7H-purin-2-yl}-1,2,4-oxadiazol-5(4H)-one;

3-[6-(3-chlorophenyl)-7-[(trans-4-methylcyclohexyl)methyl]-8-(1-pyridin-2-ylcyclopropyl)-7H-purin-2-yl]-1,2,4-oxadiazol-5(2H)-one;

5-{6-(5-chloropyridin-3-yl)-8-[(2-fluorophenyl)(methoxy)methyl]-7-[(trans-4-methylcyclohexyl)methyl]-7H-purin-2-yl}-1,3,4-oxadiazol-2(3H)-one;

3-{6-(5-chloropyridin-3-yl)-8-(3,4-dihydro-1H-isochromen-1-yl)-7-[(trans-4-methylcyclohexyl)methyl]-7H-purin-2-yl}-1,2,4-oxadiazol-5(4H)-one;

5-{6-(5-chloropyridin-3-yl)-8-(1-fluoro-2-methoxy-1-methylethyl)-7-[(trans-4-methylcyclohexyl)methyl]-7H-purin-2-yl}-1,3,4-oxadiazol-2(3H)-one;

3-{6-(5-chloropyridin-3-yl)-8-(1,2-dimethoxy-1-methylethyl)-7-[(trans-4-methylcyclohexyl)methyl]-7H-purin-2-yl}-1,2,4-oxadiazol-5(4H)-one;

3-{6-(5-chloropyridin-3-yl)-8-(1-fluoro-2-methoxy-1-methylethyl)-7-[(trans-4-methylcyclohexyl)methyl]-7H-purin-2-yl}-1,2,4-oxadiazol-5(4H)-one;

2-{[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl](methoxy)methyl}benzonitrile;

2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-fluoroethyl}benzonitrile;

2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-methoxyethyl}benzonitrile;

3-{6-(5-chloropyridin-3-yl)-8-[1-(2-fluorophenyl)ethyl]-7-[(trans-4-methylcyclohexyl)methyl]-7H-purin-2-yl}-1,2,4-oxadiazol-5(4H)-one;

5-{6-(5-chloropyridin-3-yl)-8-[1-(2-fluorophenyl)ethyl]-7-[(trans-4-methylcyclohexyl)methyl]-7H-purin-2-yl}-1,3,4-oxadiazol-2(3H)-one;

3-{6-(5-chloropyridin-3-yl)-8-[1-(2,6-difluorophenyl)ethyl]-7-[(trans-4-methylcyclohexyl)methyl]-7H-purin-2-yl}-1,2,4-oxadiazol-5(4H)-one;

2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]ethyl}benzonitrile;

5-{6-(3-chlorophenyl)-8-cyclopropyl-7-[(trans-4-methylcyclohexyl)methyl]-7H-purin-2-yl}-1,3,4-oxadiazol-2(3H)-one;

3-{6-(3-chlorophenyl)-8-cyclopropyl-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[1-(tetrahydro-2H-pyran-4-yl)ethyl]-7H-purin-2-yl}-1,2,4-oxadiazol-5(4H)-one;

5-chloro-1-{7-[(trans-4-methylcyclohexyl)methyl]-2-(5-oxo-4,5-dihydro-1,2,4-oxadiazol-3-yl)-8-[(3R)-3-phenylmorpholin-4-yl]-7H-purin-6-yl}pyridin-2(1H)-one;

3-{6-[(5-chloropyridin-2-yl)oxy]-7-[(trans-4-methylcyclohexyl)methyl]-8-[(3R)-3-phenylmorpholin-4-yl]-7H-purin-2-yl}-1,2,4-oxadiazol-5(4H)-one;

5-{6-[(5-chloropyridin-2-yl)oxy]-7-[(trans-4-methylcyclohexyl)methyl]-8-[(3R)-3-phenylmorpholin-4-yl]-7H-purin-2-yl}-1,3,4-oxadiazol-2(3H)-one;

{6-(3-chlorophenyl)-7-[(trans-4-methylcyclohexyl)methyl]-8-[(3R)-3-methylmorpholin-4-yl]-7H-purin-2-yl}acetic acid; and 3-{7-[(trans-4-methylcyclohexyl)methyl]-6-(2-methylmorpholin-4-yl)-8-[(3R)-3-phenylmorpholin-4-yl]-7H-purin-2-yl}-1,2,4-oxadiazol-5(4H)-one;

or a stereoisomer thereof;
or a pharmaceutically acceptable salt thereof;
or a pharmaceutically acceptable salt of the stereoisomer thereof.

CHEMICAL DEFINITIONS

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_6$ alkyl.

The term "cycloalkyl" means a monocyclic, bicyclic or spirocyclic saturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, and so on. "cycloalkyl" also includes cycloalkyl rings as described above wherein =$CH_2$ replaces two available hydrogens on the same ring carbon atom.

The term "cyclenyl" means a monocyclic, bicyclic or spirocyclic unsaturated aliphatic hydrocarbon group having the specified number of carbon atoms. The cyclenyl is optionally bridged (i.e., forming a bicyclic moiety), for example with a methylene, ethylene or propylene bridge. The cyclenyl may be fused with an aryl group such as phenyl, and it is understood that the cyclenyl substituent is attached via the cyclenyl group. For example, "cyclenyl" includes cyclopentenyl, cyclohexenyl and so on. "Cyclenyl" also includes cyclenyl rings as described above wherein =$CH_2$ replaces two available hydrogens on the same ring carbon atom.

In an embodiment, if the number of carbon atoms is not specified, "cycloalkyl" refers to $C_3$-$C_8$ cycloalkyl. In an embodiment, if the number of carbon atoms is not specified, "cyclenyl" refers to $C_5$-$C_8$ cyclenyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

"Alkenylene" means a diradical group of an alkenyl group that is defined above. For example, "alkenylene" includes —$CH_2$—$CH_2$—CH=CH—$CH_2$, —CH=CH—$CH_2$ and the like.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)CH_2CH(CH_3)$Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbon atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, in one embodiment, the attachment is via the heteroatom containing aromatic ring, respectively.

Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazolyl, 4-oxazolyl and 5-oxazolyl; isoxazolyl; pyrrolyl; pyridazinyl; pyrazinyl and the like.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyl and the like.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. Preferred heterocyclyls contain about 5 to about 6 ring atoms. The heterocycle may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

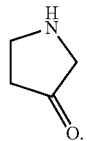

In describing the heteroatoms contained in a specified heterocyclyl group, the expression, "having one to x heteroatoms selected from the group of N, O, P and S" (wherein x is a specified integer), for example, means that each heteroatom in the specified heterocyclyl is independently selected from the specified selection of heteroatoms. Attachment of a heterocyclyl substituent can occur via a carbon atom or via a heteroatom. In cases where the heterocyclyl substituent is bicyclic and one ring is aromatic, unsaturated and/or contains no heteroatoms, in one embodiment, the attachment is via the heteroatom containing non-aromatic saturated ring.

"Heterocyclenyl" means a non-aromatic unsaturated monocyclic, bicyclic, tricyclic or spirocyclic ring system comprising up to 7 atoms in each ring. Preferably, the heterocyclenyl contains 3 to 14, or 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The heterocyclenyl is optionally bridged (i.e., forming a bicyclic moiety), for example with a methylene, ethylene or propylene bridge. The prefix aza, oxa or thia before the heterocyclenyl root name means that at least a nitrogen, oxygen, phosphor or sulfur atom respectively is present as a ring atom. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

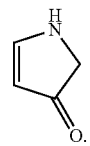

In describing the heteroatoms contained in a specified heterocyclenyl group, the expression, "having one to x heteroatoms selected from the group of N, O, P and S" (wherein x is an a specified integer), for example, means that each heteroatom in the specified heterocyclenyl is independently selected from the specified selection of heteroatoms. In cases where the heterocyclenyl substituent is bicyclic and one ring is aromatic, saturated and/or contains no heteroatoms, in one embodiment, the attachment is via the heteroatom containing non-aromatic unsaturated ring.

It should also be noted that tautomeric forms such as, for example, the moieties:

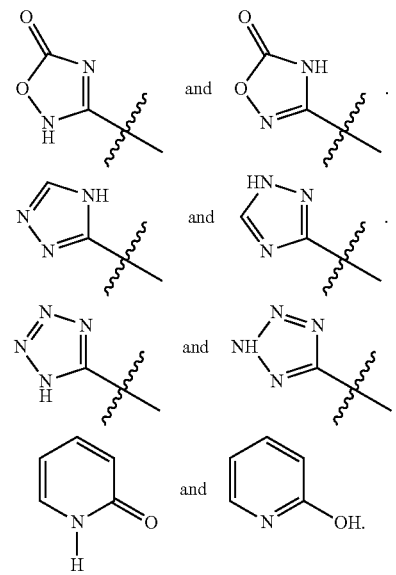

are considered equivalent in certain embodiments of this invention.

An "alkylaryl group" is an alkyl group substituted with an aryl group, for example, a phenyl group. Suitable aryl groups are described herein and suitable alkyl groups are described herein. The bond to the parent moiety is through the aryl group.

An "alkylheteroaryl group" is an alkyl group substituted with a heteroaryl group. Suitable heteroaryl groups are described herein and suitable alkyl groups are described herein. The bond to the parent moiety is through the heteroaryl group.

An "alkylheterocyclyl group" is an alkyl group substituted with a heterocyclyl group. Suitable heterocyclyl groups are described herein and suitable alkyl groups are described herein. The bond to the parent moiety is through the heterocyclyl group.

An "alkylheterocyclenyl group" is an alkyl group substituted with a heterocyclenyl group. Suitable heterocyclenyl groups are described herein and suitable alkyl groups are described herein. The bond to the parent moiety is through the heterocyclenyl group.

An "alkylcycloalkyl group" is an alkyl group substituted with a cycloalkyl group. Suitable cycloalkyl groups are described herein and suitable alkyl groups are described herein. The bond to the parent moiety is through the cycloalkyl group.

An "arylalkyl group" is an aryl group substituted with an alkyl group. Suitable aryl groups are described herein and suitable alkyl groups are described herein. The bond to the parent moiety is through the alkyl group.

A "heteroarylalkyl group" is a heteroaryl group substituted with an alkyl group. Suitable heteroaryl groups are described herein and suitable alkyl groups are described herein. The bond to the parent moiety is through the alkyl group.

A "heterocyclylalkyl group" is a heterocyclyl group substituted with an alkyl group. Suitable heterocyclyl groups are described herein and suitable alkyl groups are described herein. The bond to the parent moiety is through the alkyl group.

A "heterocyclenylalkyl group" is a heterocyclenyl group substituted with an alkyl group. Suitable heterocyclenyl groups are described herein and suitable alkyl groups are described herein. The bond to the parent moiety is through the alkyl group.

A "cycloalkylalkyl group" is a cycloalkyl group substituted with an alkyl group. Suitable cycloalkyl groups are described herein and suitable alkyl groups are described herein. The bond to the parent moiety is through the alkyl group.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

An "dialkylamino group" as used herein, is two alkyl groups that are attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

A "haloalkyl group" as used herein, is an alkyl group substituted with a halo group, which is attached to a compound via the alkyl group.

A "hydroxyalkyl group" as used herein, is an alkyl group substituted with a hydroxy group, which is attached to a compound via the alkyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase a group "optionally substituted with" substituent1, etc., or substituent2; substituent selected from the group consisting of substituent1, etc., and substituent2, means the group can be optionally substituted with one or more of the substituents, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

As used herein, the term "composition" is intended to encompass a product comprising the specified ingredients in the specified amounts, as well as any product which results, directly or indirectly, from combination of the specified ingredients in the specified amounts.

Isotopes In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Additionally, isotopic substitution of a compound at a site where epimerization occurs may slow or reduce the epimerization process and thereby retain the more active or efficacious form of the compound for a longer period of time.

Stereochemistry

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified planes in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

Solvates

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. Solvents to prepare solvates include but are not limited to acetic acid, acetone, anisole, 1-butanol, 2-butanol, butyl acetate, tert-butylmethyl ether, cumene, heptane, isobutyl acetate, methyl acetate, 3-methyl-1-butanol, methylethyl ketone, methylisobutyl ketone, 2-methyl-1-propanol, dimethyl sulfoxide, ethanol, ethyl acetate, ethyl ether, ethyl formate, formic acid, pentane, 1-pentanol, 1-propanol, 2-propanol, propyl acetate and propylene glycol. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

Pharmaceutically Acceptable Salts

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website).

Exemplary basic salts include ammonium salts, alkali metal salts such as sodium, lithium, and potassium salts, alkaline earth metal salts such as calcium and magnesium salts, zinc salts, salts with organic bases (for example, organic amines) such as N-Me-D-glucamine, Choline, tromethamine, dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention.

Compounds of Formula I, and salts, solvates thereof, may exist in their tautomeric form (for example, as an amide or imino ether). All such tautomeric forms are contemplated herein as part of the present invention.

Pharmaceutical Compositions

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described potential method of treating a patient by administering a pharmaceutical composition of the present invention is also intended to encompass the administration of the afore-said bulk composition and individual dosage units.

Isolation of the compound at various stages of the reaction may be achieved by standard techniques such as, for example, filtration, evaporation of solvent and the like. Purification of the product and the like, may also be performed by standard techniques such as recrystallization, distillation, sublimation, chromatography, conversion to a suitable derivative. Such techniques are well known to those skilled in the art. The compounds of this invention may be analyzed for their composition and purity as well as characterized by standard analytical techniques such as, for example, elemental analysis, NMR, mass spectroscopy, and IR spectra.

In another embodiment, this invention provides pharmaceutical compositions comprising the compounds of the invention as an active ingredient. The pharmaceutical compositions generally additionally comprise a pharmaceutically acceptable carrier diluent, excipient or carrier (collectively referred to herein as carrier materials).

In yet another embodiment, the present invention discloses methods for preparing pharmaceutical compositions comprising the compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Lubricants in these dosage forms include boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. For example, water or water-propylene glycol solutions may be included for parenteral injections or sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool to solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Another aspect of this invention is a kit comprising a therapeutically effective amount of at least one compound of Formula I, or a pharmaceutically acceptable salt of said compound and a pharmaceutically acceptable carrier, vehicle or diluent.

Yet another aspect of this invention is a kit comprising an amount of at least one compound of Formula I, or a pharmaceutically acceptable salt of said compound and an amount of at least one anticancer therapy and/or anti-cancer agent described below, wherein the amounts of the two or more ingredients result in desired therapeutic effect.

"Capsule"—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet"—refers to a compressed or molded solid dosage form containing the active ingredients with suitable diluents. The tablet can be prepared by compression of mixtures or granulations obtained by wet granulation, dry granulation or by compaction.

"Oral gels"—refer to the active ingredients dispersed or solubilized in a hydrophillic semi-solid matrix.

"Powders" for constitution refer to powder blends containing the active ingredients and suitable diluents which can be suspended in water or juices.

"Diluent"—refers to substances that usually make up the major portion of the composition or dosage form. Suitable diluents include but are not limited to sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition.

"Disintegrants"—refers to materials added to the composition to help it break apart (disintegrate) and release the medicaments. Suitable disintegrants include but are not limited to modified starches such as sodium carboxymethyl starch; methylcellulose, microcrystalline celluloses and sodium croscarmellose; and sodium alginate. The amount of disintegrant in the composition can range from about 2 to about 10% by weight of the composition.

"Lubricant"—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as high molecular weight polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition.

"Glidents"—materials that prevent caking and improve the flow characteristics of granulations, so that flow is smooth and uniform. Suitable glidents include silicon dioxide and talc. The amount of glident in the composition can range from about 0.1% to about 5% by weight of the total composition.

"Coloring agents"—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Method of Treatment

HDM2, Hdm2, hDM2, and hdm2 are all equivalent representations of the Human Double Minute 2 protein. Likewise, MDM2, Mdm2, mDM2, and mdm2 are all equivalent representations mouse Double Minute 2 protein.

The compounds of Formula I can be inhibitors or antagonists of the Human or Mouse Double Minute 2 protein interaction with p53 protein and it can be activators of the p53 protein in cells. Furthermore, the pharmacological properties of the compounds of Formula I may be useful to treat or prevent cancer, treat or prevent other disease states associated with abnormal cell proliferation, and treat or prevent diseases resulting from inadequate levels of p53 protein in cells.

Those skilled in the art will recognize that the term "cancer" is the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of Formula I may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer;

hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoetic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

Due to the key role of p53 in the regulation of cellular apoptosis (cell death), the compounds of Formula I could act as agents to induce cell death which may be useful in the treatment of any disease process which features abnormal celllular proliferation eg, cancers of various origin and tissue types, inflammation, immunological disorders.

Due to the key role of HDM2 and p53 in the regulation of cellular proliferation, the compounds of Formula I could act as reversible cytostatic agents which may be useful in the treatment of any disease process which features abnormal celllular proliferation, inhibitors could act as reversible cytostatic agents which may be useful in the treatment of any disease process which features abnormal cell proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty, or vascular surgery, hypertrophic scar formation, inflammatory bowel disease, transplantation rejection, endotoxic shock, and fungal infections.

Compounds of Formula I may also be useful in the chemoprevention of cancer. Chemoprevention is defined as inhibiting the development of invasive cancer by either blocking the initiating mutagenic event by blocking the progression of pre-malignant cells that have already suffered an insult or inhibiting tumor relapse.

Compounds of Formula I may also be useful in inhibiting tumor angiogenesis and metastasis.

Another aspect of this invention is a potential method of treating a mammal (e.g., human) having a disease or condition associated with HDM2 by administering a therapeutically effective amount of at least one compound of Formula I, or a pharmaceutically acceptable salt of said compound to the mammal.

The invention also provides a method of inhibiting one or more HDM2 proteins in a patient in need thereof, comprising administering to the patient a therapeutically effective amount of at least one compound of claim 1 or a pharmaceutically acceptable salt thereof.

Another aspect of the present invention is a potential method of treating, or slowing the progression of a disease associated with one or more HDM2 proteins in a patient, comprising administering to a patient in need thereof, a therapeutically effective amount of at least one compound of the present invention or a pharmaceutically acceptable salt thereof.

Another aspect of the present invention is a potential method of treating, or slowing the progression of a disease associated with inadequate p53 levels in a patient, comprising administering to a patient in need thereof, a therapeutically effective amount of at least one compound of the present invention or a pharmaceutically acceptable salt thereof.

Yet another aspect of the present invention is a potential method of treating one or more diseases associated with HDM2, comprising administering to a mammal in need of such treatment an amount of a first compound, which is a compound of the present invention, or a pharmaceutically acceptable salt thereof; and an amount of at least one second compound, the second compound being an anti-cancer agent, wherein the amounts of the first compound and the second compound result in a therapeutic effect.

Another aspect of the present invention is a potential method of treating one or more diseases associated with inadequate p53 levels, comprising administering to a mammal in need of such treatment an amount of a first compound, which is a compound of the present invention, or a pharmaceutically acceptable salt thereof; and an amount of at least one second compound, the second compound being an anti-cancer agent, wherein the amounts of the first compound and the second compound result in a therapeutic effect.

Another aspect of the present invention is a potential method of treating, or slowing the progression of, a disease associated with a HDM2 protein comprising administering to a patient in need thereof, a therapeutically effective amount of a pharmaceutical composition comprising in combination at least one pharmaceutically acceptable carrier and at least one compound according to the present invention, or a pharmaceutically acceptable salt thereof.

Another aspect of the present invention is a potential method of treating, or slowing the progression of, a disease associated with inadequate p53 levels in a patient, comprising administering to a patient in need thereof, a therapeutically effective amount of a pharmaceutical composition comprising in combination at least one pharmaceutically acceptable carrier and at least one compound according to the present invention, or a pharmaceutically acceptable salt thereof.

In one embodiment, the dosage is about 0.001 to 500 mg/kg of body weight/day of the compound of Formula I. In another embodiment, the dosage is about 0.01 to 25 mg/kg of body weight/day of a compound of Formula I, or a pharmaceutically acceptable salt of said compound.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"Patient" includes both human and animals.

"Mammal" means humans and other mammalian animals.

Combination Therapy

The instant compounds may also be useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, α-secretase inhibitors, agents that interfere with receptor tyrosine kinases (RTKs) and agents that interfere with cell cycle checkpoints. The instant compounds may also be useful when co-administered with radiation therapy. The compounds of the present invention can be present in the same dosage unit as the anticancer agent or in separate dosage units.

Another aspect of the present invention is a potential method of treating one or more diseases associated with HDM2, comprising administering to a mammal in need of such treatment an amount of a first compound, which is a compound of the present invention, or a pharmaceutically acceptable salt thereof; and an amount of at least one second compound, the second compound being an anti-cancer agent different from the compounds of the present invention, wherein the amounts of the first compound and the second compound result in a therapeutic effect.

Non-limiting examples of suitable anti-cancer agents include cytostatic agents, cytotoxic agents, targeted therapeutic agents (small molecules, biologics, siRNA and microRNA) against cancer and neoplastic diseases, 1) Anti-metabolites (such as methoxtrexate, 5-fluorouracil, gemcitabine, fludarabine, capecitabine);
2) Aalkylating agents, such as temozolomide, cyclophosphamide,
3) DNA interactive and DNA damaging agents, such as cisplatin, oxaliplatin, doxorubicin,
4) Ionizing irradiation, such as radiation therapy,
5) Topoisomerase II inhibitors, such as etoposide, doxorubicin,
6) Topoisomerase I inhibitors, such as irinotecan, topotecan,
7) Tubulin interacting agents, such as paclitaxel, docetaxel, Abraxane, epothilones,
8) Kinesin spindle protein inhibitors,
9) Spindle checkpoint inhibitors,
10) Poly(ADP-ribose) polymerase (PARP) inhibitors, such as olaparib, MK-4827 and veliparib
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant p53 to restore its wild-type p53 activity
15) Adenoviral-p53
16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) Sex hormone modulating agents,
   a. anti-estrogens, such as tamoxifen, fulvestrant,
   b. selective estrogen receptor modulators (SERM), such as raloxifene,
   c. anti-androgens, such as bicalutamide, flutamide
   d. LHRH agonists, such as leuprolide,
   e. 5α-reductase inhibitors, such as finasteride,
   f. Cytochrome P450 C17 lyase (CYP450c17, also called 17α-hydroxylase/17,20 lysase) inhibitors, such as Abiraterone acetate, VN/124-1, TAK-700
   g. aromatase inhibitors, such as letrozole, anastrozole, exemestane,
20) EGFR kinase inhibitors, such as geftinib, erlotinib, laptinib
21) dual erbB1 and erbB2 inhibitors, such as Lapatinib
22) multi-targeted kinases (serine/threonine and/or tyrosine kinase) inhibitors,
   a. ABL kinase inhibitors, imatinib and nilotinib, dasatinib b. VEGFR-1, VEGFR-2, PDGFR, KDR, FLT, c-Kit, Tie2, Raf, MEK and ERK inhibitors, such as sunitinib, sorafenib, Vandetanib, pazopanib, PLX-4032, Axitinib, PTK787, GSK-1120212
c. Polo-like kinase inhibitors
d. Aurora kinase inhibitors
e. JAK inhibitor
f. c-MET kinase inhibitors
g. Cyclin-dependent kinase inhibitors, such as CDK1 and CDK2 inhibitor SCH 727965
h. PI3K and mTOR inhibitors, such as GDC-0941, BEZ-235, BKM-120 and AZD-8055
i. Rapamycin and its analogs, such as Temsirolimus, everolimus, and deforolimus 23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide, Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar, Zevalin, Trisenox, Profimer, Thiotepa, Altretamine, Doxil, Ontak, Depocyt, Aranesp, Neupogen, Neulasta, Kepivance.
24) Farnesyl protein transferase inhibitors, such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron,
26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) Anti-CTLA-4 antibodies, such as ipilimumab
34) antibodies against CTA1, CEA, CD5, CD19, CD22, CD30, CD44, CD44V6, CD55, CD56, EpCAM, FAP, MHCII, HGF, IL-6, MUC1, PSMA, TAL6, TAG-72, TRAILR, VEGFR, IGF-2, FGF,
35) anti-IGF-1R antibodies, such as dalotuzumab (MK-0646) and robatumumab (SCH 717454).

If formulated as a fixed dose such combination products employ the compounds of this invention within the dosage range described herein and the other pharmaceutically active agent or treatment within its dosage range. Compounds of Formula I may also be administered sequentially with known anticancer or cytotoxic agents when a combination formulation is inappropriate. The invention is not limited in the sequence of administration; compounds of Formula I may be administered either concurrent with, prior to or after administration of the known anticancer or cytotoxic agent. Such techniques are within the skills of the persons skilled in the art as well as attending physicians.

Accordingly, in an aspect, this invention includes combinations comprising an amount of at least one compound of Formula I, or a pharmaceutically acceptable salt thereof, and an amount of one or more anti-cancer treatments and anti-cancer agents listed above wherein the amounts of the compounds/treatments result in potential therapeutic effect.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans, trans, trans)-bis-mu-(hexane-1,6-diamine)-mu-[diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'- morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, $BN_{80915}$, $BN_{80942}$, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors ofMKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, $ODN_{698}$, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. No. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652737, 60/670,469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598.

Inhibitors of COX-2 can be useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following:

parecoxib, BEXTRA® and CELEBREX® or a pharmaceutically acceptable salt thereof.

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_6\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the instantly claimed compounds with PPAR-γ (i.e., PPAR-gamma) agonists and PPAR-δ (i.e., PPAR-delta) agonists may be useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, $NN_{2344}$, KRP297, NP0110, DRF4158, $NN_{622}$, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxyl) phenoxy)propoxy)-2-ethylchromane-2-carboxylic acid.

Another embodiment of the instant invention is the use of the presently disclosed compounds in combination with gene therapy for the potential treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, may also be useful in combination with potassium salts, magnesium salts, beta-blockers (such as atenolol) and endothelin-α (ETa)antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, may also be useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors: olaparib, MK-4827 and veliparib.

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasuricase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742).

The invention disclosed herein is exemplified by the following preparations and examples which should not be construed to limit the scope of the disclosure.

EXAMPLES

Example 1

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below and then specific compounds of the Formula (I) are prepared in the Examples. Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations in parenthesis:

Me=methyl; Et=ethyl; Pr=propyl; iPr=isopropyl, Bu=butyl; t-Bu=tert-butyl; Ph=phenyl, and Ac=acetyl μl=microliters AcOH or HOAc=acetic acid ACN=acetonitrile
Ad=adamantyl
APCI or APC=atmospheric-pressure chemical ionization
aq=aqueous
BAIB=[bis(acetoxy)iodo]benzene
Bn=benzyl
Boc or BOC=tert-butoxycarbonyl
Bz=benzoyl
Cbz=benzyloxycarbonyl
CDI=1,1'-Carbonyldiimidazole
CEM MW=CEM Microwave Reaction System
DAST=diethylaminosulfur trifluoride
Dba=dibenzylideneacetone
DBU=1,8-Diaza-7-bicyclo[5.4.0]undecene
DCM=dichloromethane
DMAP=4-Dimethylaminopyridine
DIBAL=diisobutylaluminum hydride
DIEA or Hünig's Base=N,N-diisopropylethylamine
DMA=N,N-dimethylacetamide
DMF=dimethylformamide
DMSO=dimethyl sulfoxide
Dppf=1,1'-Bis(diphenylphosphino)ferrocene
DMT=Dimercaptotriazine
DTT=dithiothreitol
EDC or EDCI=1-ethyl-3-(3-dimethylaminopropyl)carbodiimide
EDTA=ethylenediamine tetraacetic acid
ESI or ES=Electrospray ionization
EtOAc=ethyl acetate
g=grams
GST=glutathione S-transferase
h=hour
HATU=N,N,N',N'-tetramethyl-O-(7-azabenzotriazol-1-yl)uronium hexafluorophosphate
HMDS=1,1,1,3,3,3-hexamethyldisilazane
HMPA=hexamethylphosphoramide
HOBt=1-hydroxybenzotriazole
HPLC=high-performance liquid chromatography
IPA=isopropanol
LAH=lithium aluminium hydride
LDA=lithium diisopropylamide
LC=liquid chromatography
LCMS=liquid chromatography mass spectrometry
min=minute
mg=milligrams
mL=milliliters
mmol=millimoles
mCPBA=meta-Chloroperoxybenzoic acid
Me=methyl
MeOH=methanol
MS=mass spectrometry
MTBE=methyl tert-butyl ether
NBS=N-bromosuccinimide
NMO=N-methylmorpholine-N-oxide
NMP=N-methylpyrrolidone
NMR=nuclear magnetic resonance spectroscopy
PTLC=preparative thin layer chromatography
p-TSA or PTSA=p-toluenesulfonic acid
rac=racemic mixture
$R_f$=retardation factor
RT or rt=room temperature (ambient, about 25° C.)
sat=saturated
SFC=supercritical fluid chromatography
TBAF=tetra-n-butylammonium fluoride
TBSC=t-butyldimethylsilyl chloride
TBS=t-butyldimethylsilyl
TEA=triethylamine ($Et_3N$)
TEMPO=(2,2,6,6-tetramethylpiperidin-1-yl)oxyl
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
Xantphos=4,5-Bis(diphenylphosphino)-9,9-dimethylxanthene Scheme 1. Synthetic methods to introduce substitutions at the 7 position of purine.

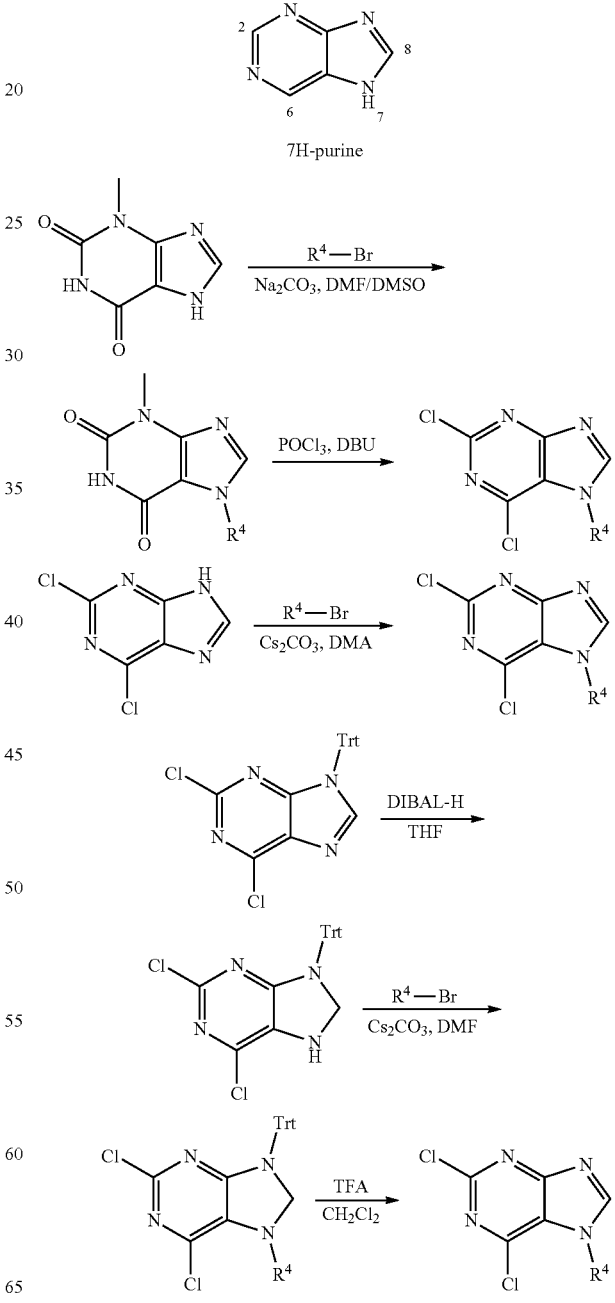

Scheme 2. Synthetic methods to introduce substitutions at the 6, 7 and 8 position of purine.
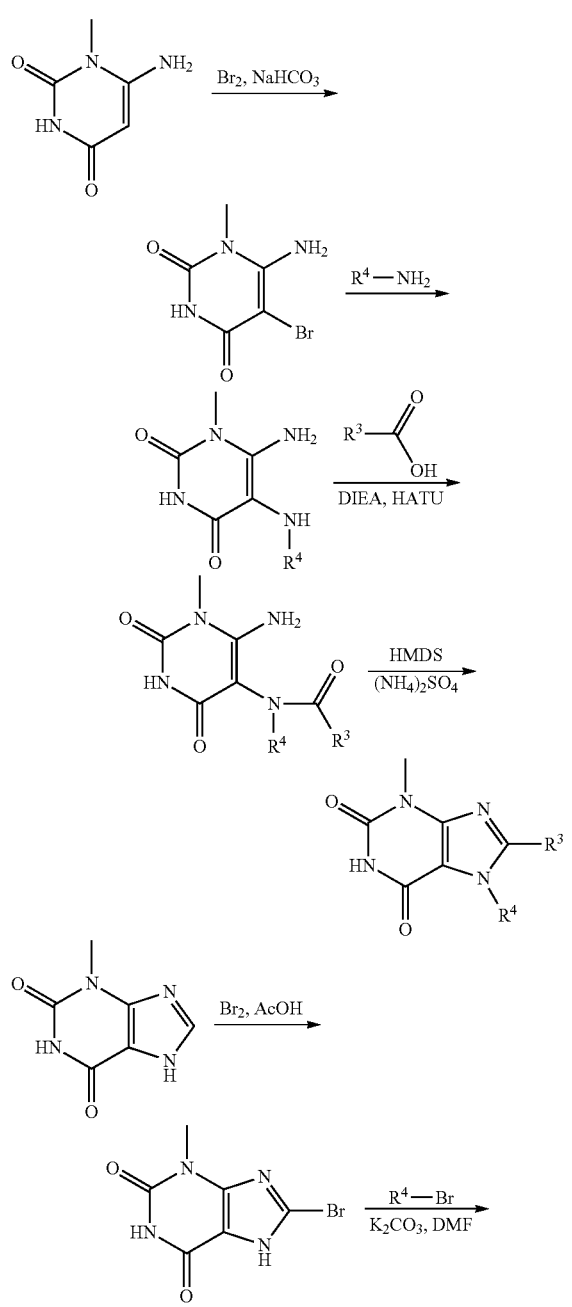
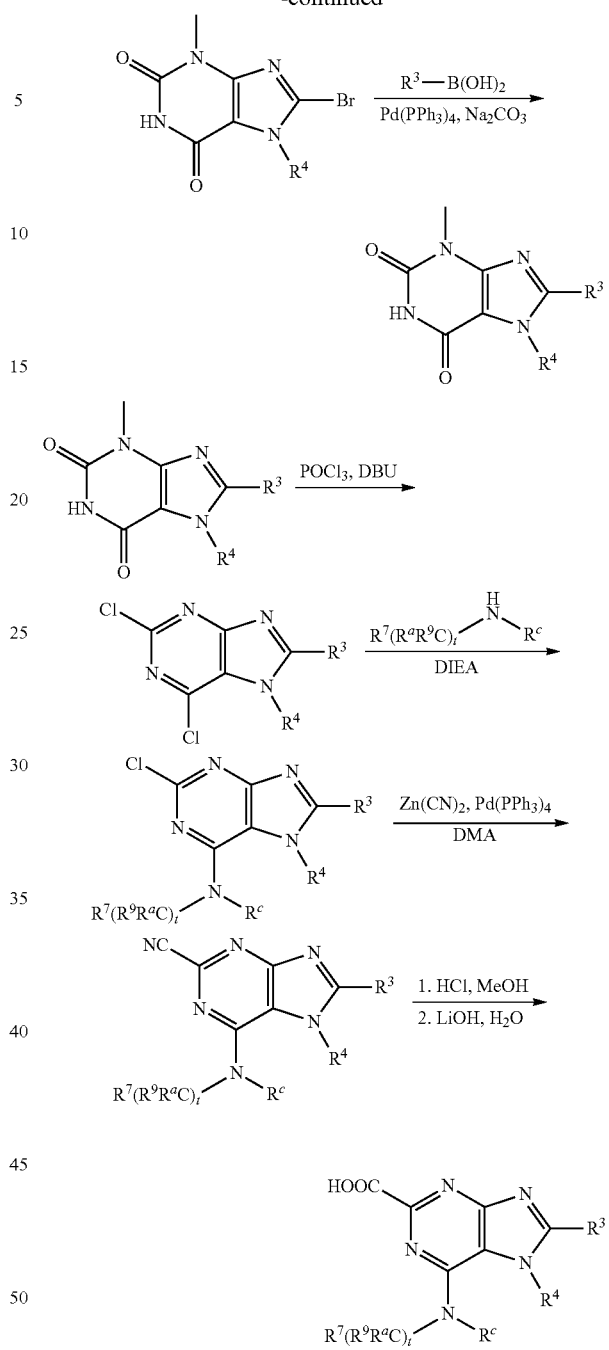
Scheme 3. Synthetic methods to introduce substitutions at the 6 and 8 position of purine.
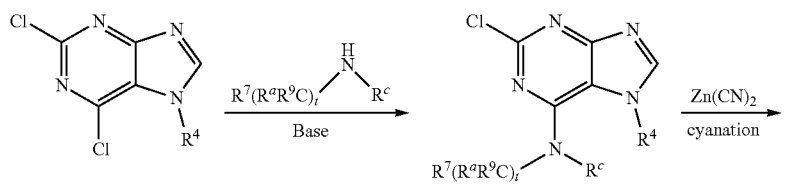

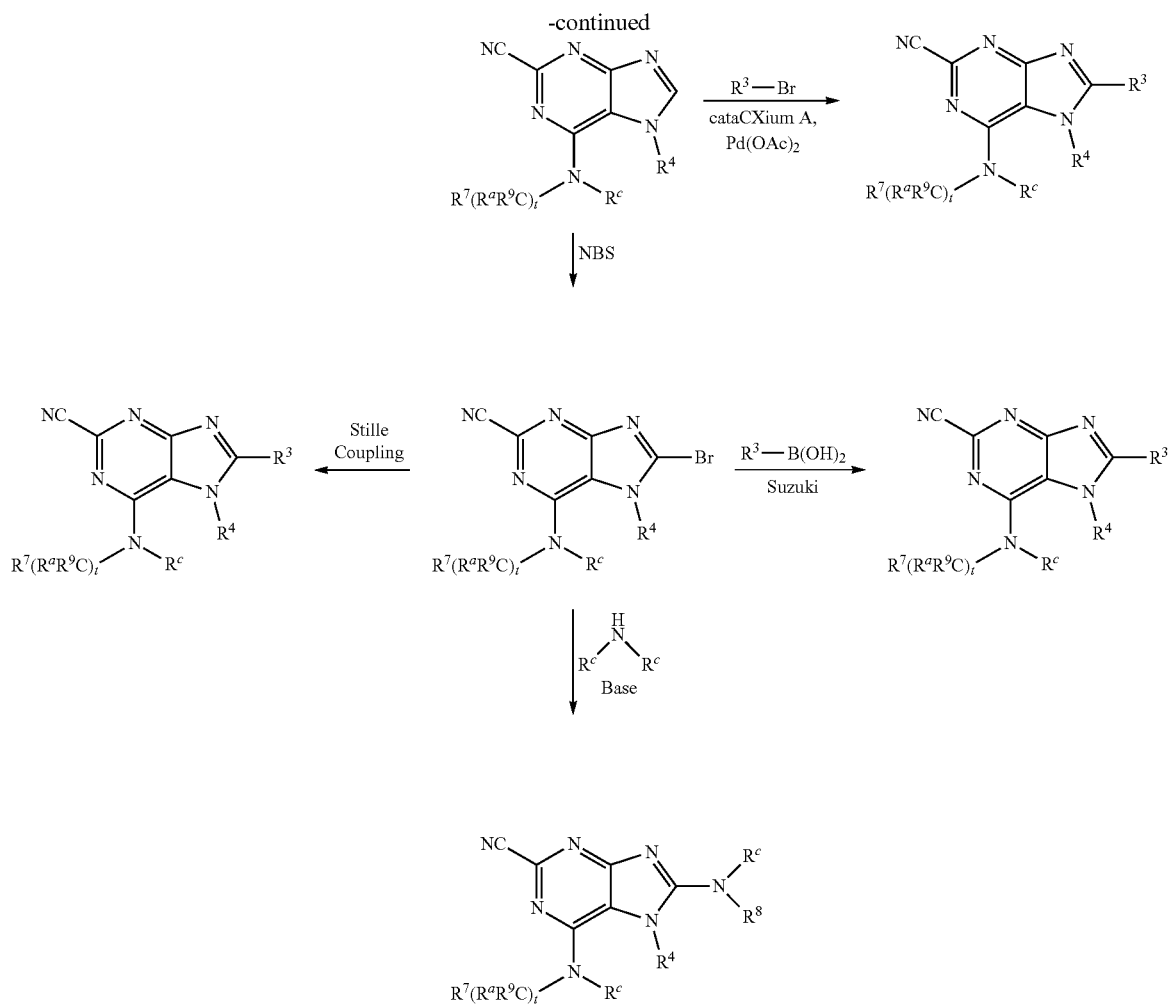
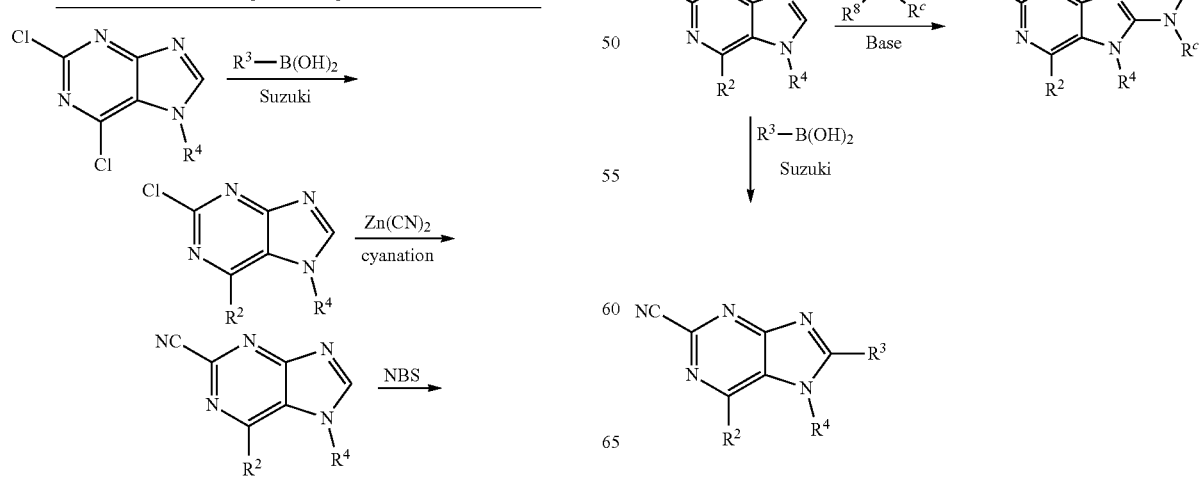
Scheme 4. Synthetic methods to introduce substitutions at the 6 and 8 position of purine.

Scheme 5. Synthetic methods to introduce substitutions at the 8 position of purine.
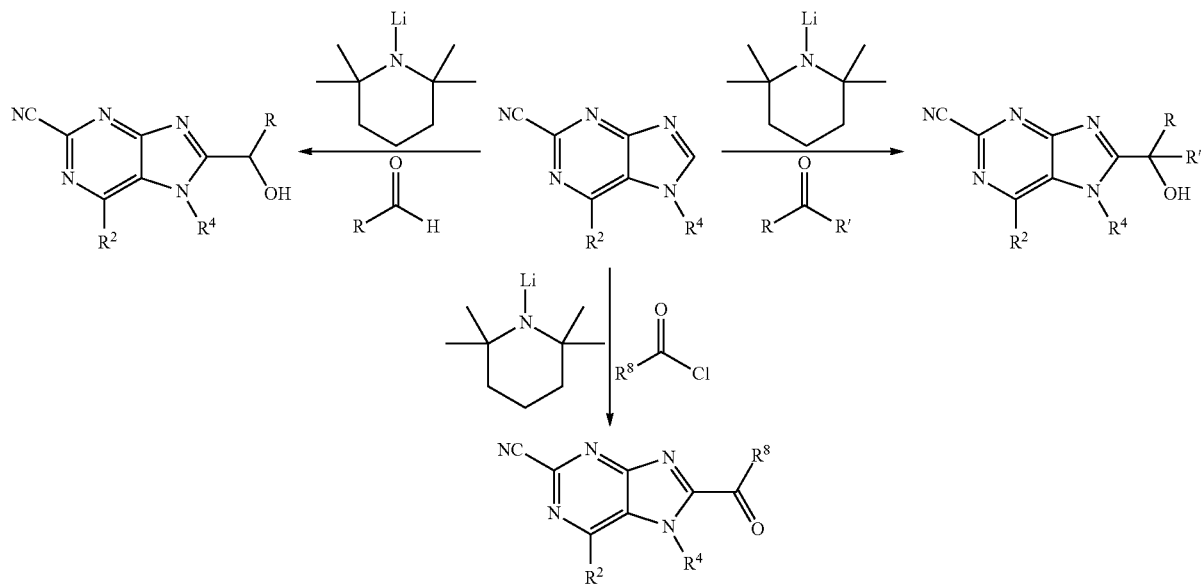
Scheme 6. Synthetic methods to introduce substitutions at the 6 and 8 position of purine.
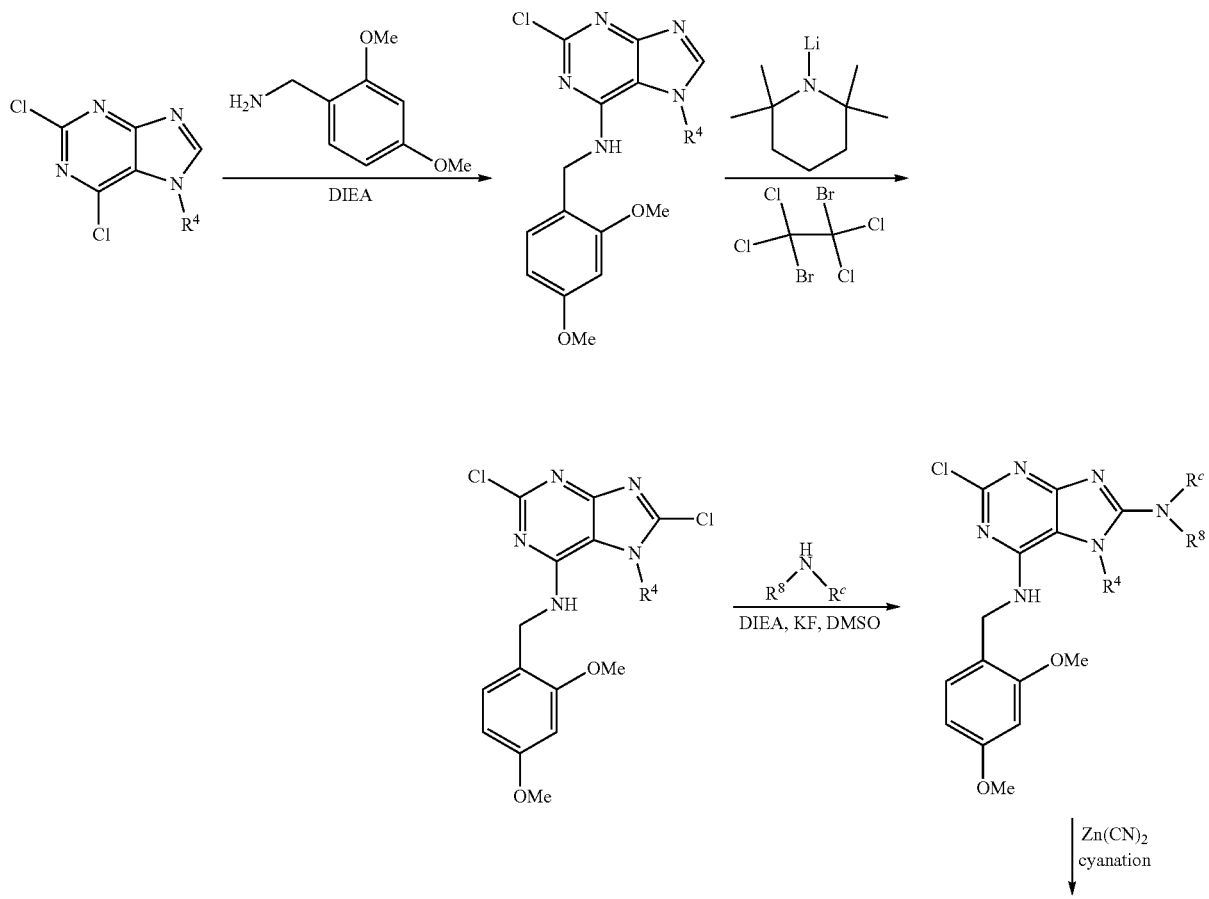

-continued

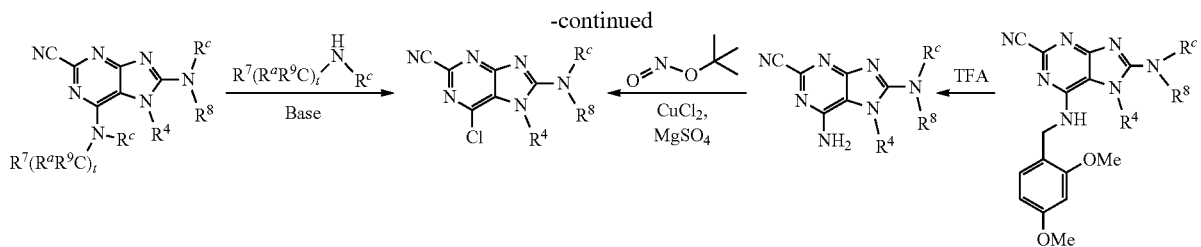

Scheme 7. Synthetic methods to convert nitrile at the 2 position to acid, 1,2,4-oxadiazol-5(4H)-one and 1,3,4-axadiazol-2(3H)-one.

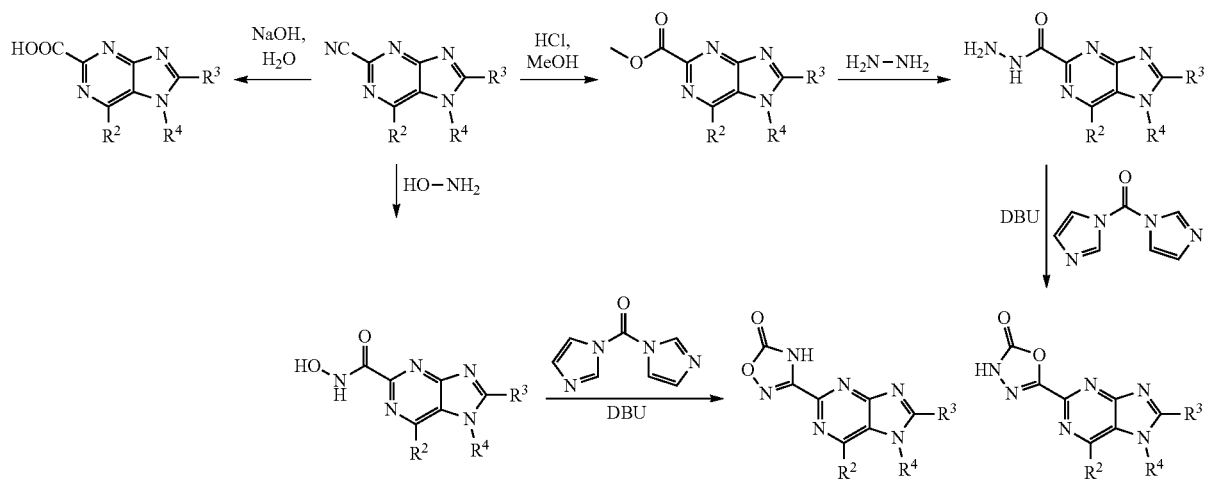

Preparative Example 1.0

(R)-1-cyclobutylethanamine hydrochloride

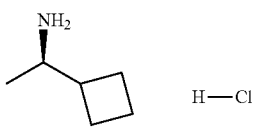

Step 1: Into a 20-L 4-necked round-bottom flask was placed a solution of cyclobutylmethanol (1000 g, 11.61 mol) in dichloromethane (10 L). This was followed by the addition of Dess-Martin periodinane (4683 g, 11.04 mol) in several batches at 10-15° C. over 120 min. The resulting solution was stirred for 2 h at room temperature and then quenched by the addition of 20 L of cold, saturated aqueous sodium bicarbonate solution. Solids were removed by filtration and washed with 5 L of dichloromethane. The filtrate was extracted with dichloromethane. The organic layers were combined, dried over anhydrous sodium sulfate and concentrated under vacuum. The residue was applied onto a silica gel column and eluted with DCM:PE (2:1). This resulted in 100 L of cyclobutanecarbaldehyde in dichloromethane and petroleum ether solution.

Step 2: Into a 50-L barrel was placed cyclobutanecarbaldehyde in dichloromethane and petroleum ether (33 L of the solution described at the end of Step 1), (S)-2-methylpropane-2-sulfinamide (500 g, 4.13 mol) and copper sulfate (2 kg, 13.33 mol). The resulting solution was stirred for 2 days at room temperature. Solids were removed by filtration. The filtrate was concentrated under vacuum. The residue was applied onto a silica gel column and eluted with ethyl acetate/petroleum ether (1:5) to afford (S)—N-[(1E)-cyclobutylmethylidene]-2-methylpropane-2-sulfinamide.

Step 3: Into a 10-L 4-neck round-bottom flask purged and maintained with an inert atmosphere of nitrogen was placed a solution of (S)—N-[(1E)-cyclobutylmethylidene]-2-methylpropane-2-sulfinamide (200 g, 1.07 mol) in tetrahydrofuran (3000 mL). This was followed by the addition of methylmagnesium bromide in ether (1070 mL, 3.00 equiv) dropwise with stirring at −78° C. over 1 hr. The resulting solution was stirred for 1 h at −70° C., 1 h at −60° C., 1 h at −50° C. and 2 h at −40° C. The reaction was then quenched by the addition of 10 L of saturated aqueous $NH_4Cl$ solution. The resulting solution was extracted with 2×3 L of ether. The organic layers were combined, washed with 2×3 L of brine, dried over anhydrous sodium sulfate, and concentrated under vacuum. The residue was diluted with 250 mL of n-hexane. The resulting solid was collected and washed with 2×100 mL of cold n-hexane to afford (S)—N-[(1R)-1-cyclobutylethyl]-2-methylpropane-2-sulfinamide.

Step 4: Into a 10-L 4-neck round-bottom flask was placed a solution of (S)—N-[(1R)-1-cyclobutylethyl]-2-methylpropane-2-sulfinamide (400 g, 1.97 mol) in methanol (2800 mL). This was followed by the addition of HCl/p-dioxane (5M, 1.6 L) dropwise with stirring at 0° C. over 60 min. The resulting solution was stirred for 60 min at room temperature. The solution was then concentrated under vacuum. The residue was diluted with 4 L of n-hexane and stirred for 30 min at room temperature. The solid was collected by filtration. The filtrate was diluted with 1200 mL of CH$_3$CN and stirred for 30 min at room temperature. The solid was collected by filtration. The combined solids were dried in an oven under reduced pressure to afford (1R)-1-cyclobutyle-than-1-amine as a hydrogen chloride salt. MS ESI calc'd for C$_6$H$_{13}$N [M+H]$^+$ 100. found 100. $^1$H NMR (400 MHz, DMSO-d$_6$): δ 7.95 (s, 3H), 3.11 (s, 1H), 2.32-2.42 (m, 1H), 1.75-2.01 (m, 6H), 1.10 (s, 3H).

Preparative Example 1.1

(R)-6-((1-cyclobutylethyl)amino)-7-(4-(trifluoromethyl)benzyl)-7H-purine-2-carbonitrile

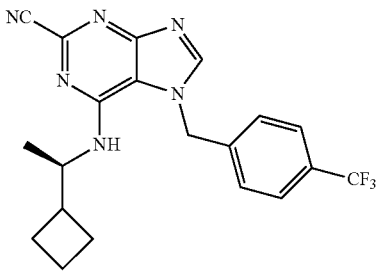 [SMILES: C[C@@H](Nc1nc(C#N)nc2ncn(Cc3ccc(C(F)(F)F)cc3)c12)C1CCC1]

Step 1: Into a 20-L 4-necked round-bottom flask purged and maintained with an inert atmosphere of nitrogen was placed a solution of sodium tert-butoxide (403 g, 4.19 mol) in tetrahydrofuran (6.5 L). This was followed by the addition of 2,6-dichloro-7H-purine (658 g, 3.48 mol) in several batches. To this was added dropwise a solution of 1-(bromomethyl)-4-(trifluoromethyl)benzene (1000 g, 4.18 mol) in tetrahydrofuran (3 L) with stirring over 3 hours while the reaction mixture was heated to reflux. The resulting solution was heated at reflux overnight in an oil bath. The reaction mixture was cooled to room temperature and then concentrated under vacuum. The residue was diluted with 5 L of water and then extracted with ethyl acetate (3×4 L). The organic layers were combined, washed with brine (3×4 L), dried over sodium sulfate and concentrated under vacuum. The residue was applied onto a silica gel column and eluted with ethyl acetate/petroleum ether (1:2) to give 2,6-dichloro-7-(4-(trifluoromethyl)benzyl)-7H-purine as the minor product and 2,6-dichloro-9-(4-(trifluoromethyl)benzyl)-9H-purine as the major product.

Step 2: Into a 5000-mL 4-necked round-bottom flask was placed 2,6-dichloro-7-(4-(trifluoromethyl)benzyl)-7H-purine (255 g, 734.61 mmol), isopropanol (2500 mL), (R)-1-cyclobutylethanamine hydrochloride (120 g, 888.89 mmol) and triethylamine (223 g, 2.20 mol). The resulting solution was stirred overnight at 50° C. in an oil bath. The resulting mixture was cooled and concentrated under vacuum. The residue was applied onto a silica gel column and eluted with ethyl acetate/petroleum ether (1:2) to give (R)-2-chloro-N-(1-cyclobutylethyl)-7-(4-(trifluoromethyl)benzyl)-7H-purin-6-amine.

Step 3: Into a 5-L 4-necked round-bottom flask purged and maintained with an inert atmosphere of nitrogen was placed (R)-2-chloro-N-(1-cyclobutylethyl)-7-(4-(trifluoromethyl)benzyl)-7H-purin-6-amine (191.1 g, 466.28 mmol), N,N-dimethylacetamide (3 L), 2-dicyclohexylphosphino-2',4',6'-triisopropylbiphenyl (33.4 g, 70.17 mmol) and allylpalladium(II) chloride dimer (8.6 g, 23.50 mmol). The resulting solution was stirred overnight at 120° C. in an oil bath. The reaction mixture was then cooled to room temperature, and quenched by the addition of water (5 L). The resulting solution was extracted with ethyl acetate (3×2 L). The organic layers were combined, washed with brine (3×1 L), dried over anhydrous sodium sulfate and concentrated under vacuum. The residue was applied onto a silica gel column and eluted with ethyl acetate/petroleum ether (1:2) to afford (R)-6-((1-cyclobutylethyl)amino)-7-(4-(trifluoromethyl) benzyl)-7H-purine-2-carbonitrile as an off-white solid. MS ESI calc'd. for C$_{20}$H$_{19}$F$_3$N$_6$ [M+H]$^+$ 401. found 401.

Example 1.1

(R)-6-((1-cyclobutylethyl)amino)-8-(5-(dimethylamino)-2-(trifluoromethoxy)phenyl)-7-(4-(trifluoromethyl)benzyl)-7H-purine-2-carboxylic acid

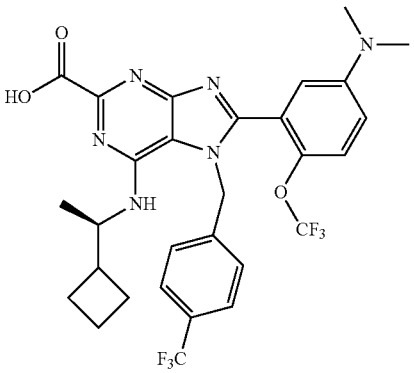 [SMILES: C[C@@H](Nc1nc(C(=O)O)nc2nc(-c3cc(N(C)C)ccc3OC(F)(F)F)n(Cc3ccc(C(F)(F)F)cc3)c12)C1CCC1]

Step 1: To a stirred solution of 3-bromo-4-(trifluoromethoxy)aniline (500 mg, 1.95 mmol) in acetic acid (10 mL) were added paraformaldehyde (585 mg, 19.52 mmol) and sodium cyanoborohydride (613 mg, 9.76 mmol). The reaction mixture was stirred at room temperature for 12 hours and then concentrated under reduced pressure. The resulting residue was taken up in ethyl acetate (25 mL) and washed with saturated sodium bicarbonate solution (20 mL). The organic layer was washed with brine (10 mL), dried over anhydrous sodium sulfate, filtered, and concentrated to dryness. Purification of the residue on a RediSep 12 g silica gel column (0 to 100% EtOAc/hexanes) afforded 3-bromo-N,N-dimethyl-4-(trifluoromethoxy)aniline. $^1$H NMR (300 MHz, CDCl$_3$) δ 7.13 (m, 1H), 6.87 (d, J=3.0 Hz, 1H), 6.57 (dd, J=9.3, 3.0 Hz, 1H), 2.94 (s, 6H). MS (ES)=284, 286 (M+1)$^+$.

Step 2: A microwave vial equipped with a stir bar was charged with di(1-adamantyl)-n-butylphosphine (cat-aCXium A, Strem) (36.0 mg, 0.10 mmol) and palladium(II) acetate (11.2 mg, 0.05 mmol). 1,4-Dioxane (2.0 mL) was added and the mixture was degassed with nitrogen. The vial was then sealed and heated at 50° C. for 30 minutes. The catalyst slurry was then cooled to room temperature and (R)-6-((1-cyclobutylethyl)amino)-7-(4-(trifluoromethyl) benzyl)-7H-purine-2-carbonitrile (100 mg, 0.25 mmol), 3-bromo-N,N-dimethyl-4-(trifluoromethoxy)aniline (110 mg, 0.35 mmol), cesium fluoride (114 mg, 0.75 mmol), and pivalic acid (36 mg, 0.32 mmol) were added. The reaction was degassed with nitrogen for 2 minutes, and then the vial was sealed and heated at 110° C. for 16 hours. The reaction mixture was then cooled to room temperature, diluted with hexanes (2.0 mL) and CH₂Cl₂ (2.0 mL), and loaded directly onto a Biotage 25 g silica gel column. Purification (0 to 100% EtOAc/hexanes) afforded (R)-6-((1-cyclobutylethyl)amino)-8-(5-(dimethylamino)-2-(trifluoromethoxy)phenyl)-7-(4-(trifluoromethyl)benzyl)-7H-purine-2-carbonitrile. MS ESI calc'd. for $C_{29}H_{27}F_6N_7O$ [M+H]$^+$ 604. found 604.

Step 3: NaOH (72 mg, 1.8 mmol) was added to a solution of (R)-6-((1-cyclobutylethyl)amino)-8-(5-(dimethylamino)-2-(trifluoromethoxy)phenyl)-7-(4-(trifluoromethyl)benzyl)-7H-purine-2-carbonitrile (60 mg, 0.10 mmol) in ethanol (2.0 mL) and water (0.5 mL) at room temperature. The reaction mixture was stirred at room temperature for 10 minutes and then heated at reflux for 2 hours. After cooling to room temperature, the reaction mixture was concentrated in vacuo. The residue was dissolved in water (1.5 mL) and neutralized to pH 7 with aqueous HCl solution (1M). The product precipitated and was collected by filtration, washed with water and dried under vacuum, to afford (R)-6-((1-cyclobutylethyl)amino)-8-(5-(dimethylamino)-2-(trifluoromethoxy)phenyl)-7-(4-(trifluoromethyl)benzyl)-7H-purine-2-carboxylic acid. MS ESI calc'd. for $C_{29}H_{28}F_6N_6O_3$ [M+H]$^+$ 623. found 623. $^1$H NMR (400 MHz, CD₃OD) δ 7.63 (d, J=7.8 Hz, 2H), 7.33 (d, J=9.1 Hz, 1H), 7.15 (d, J=7.8 Hz, 2H), 6.95 (dd, J=9.1, 2.9 Hz, 1H), 6.76 (d, J=2.9 Hz, 1H), 5.80 (d, J=18.2 Hz, 1H), 5.52 (d, J=18.2 Hz, 1H), 4.57 (m, 1H), 2.88 (s, 6H), 2.13 (m, 1H), 1.89 (m, 1H), 1.56-1.76 (m, 3H), 1.40-1.55 (m, 2H), 0.97 (d, J=6.3 Hz, 3H).

Preparative Example 1.2

2-bromo-1-chloro-4-ethylbenzene

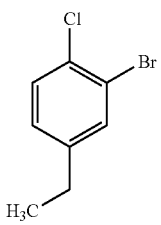

Step 1: To a stirred solution of 1-(3-bromo-4-chlorophenyl)ethanone (1.00 g, 4.28 mmol) in THF (10 mL) and MeOH (1.0 mL) was added sodium borohydride (0.19 g, 5.13 mmol) and then the reaction was heated at 70° C. for 1 hour. The reaction mixture was quenched by the addition of aqueous HCl (10 mL, 1N solution) and then diluted with EtOAc (100 mL). The organic layer was washed with water (30 mL) and brine (30 mL). The organic layer was dried over sodium sulfate, filtered, and concentrated to afford 1-(3-bromo-4-chlorophenyl)ethanol. $^1$H NMR (300 MHz, CDCl₃) δ 7.63 (d, J=1.8 Hz, 1H), 7.38 (d, J=8.4 Hz, 1H), 7.24 (m, 1H), 4.85 (q, J=6.6 Hz, 1H), 1.46 (d, J=6.3 Hz, 3H).

Step 2: To a stirred solution of 1-(3-bromo-4-chlorophenyl)ethanol (0.85 g, 3.60 mmol) in TFA (2.0 mL) was added triethylsilane (0.83 g, 7.21 mmol) and then the reaction was heated at 50° C. for 16 hours. The reaction mixture was quenched with saturated sodium bicarbonate solution (20 mL) and then diluted with dichloromethane (100 mL) and the organic layer was washed with water (30 mL) and brine (30 mL). The organic layer was dried over sodium sulfate, filtered, and concentrated. Purification of the residue on a RedisepR$_f$ 24 g silica gel column (0 to 10% EtOAc/hexanes) afforded 2-bromo-1-chloro-4-ethylbenzene. $^1$H NMR (400 MHz, CDCl₃) δ 7.44 (d, J=2.0 Hz, 1H), 7.33 (d, J=8.4 Hz, 1H), 7.05 (m, 1H), 2.59 (q, J=7.6 Hz, 2H), 1.23 (t, J=7.6 Hz, 3H).

Example 1.2

(R)-8-(2-chloro-5-ethylphenyl)-6-((1-cyclobutylethyl)amino)-7-(4-(trifluoromethyl)benzyl)-7H-purine-2-carboxylic acid

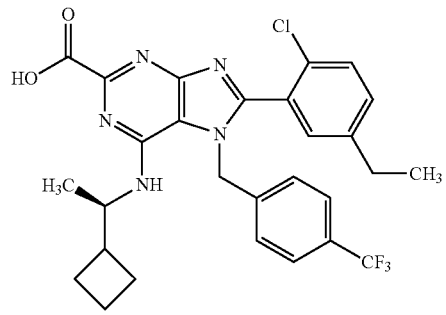 [SMILES: CCc1ccc(Cl)c(-c2nc3nc(C(=O)O)nc(N[C@H](C)C4CCC4)c3n2Cc2ccc(C(F)(F)F)cc2)c1]

Using a procedure analogous to that described in Example 1.1 (steps 2 and 3) and starting with (R)-6-((1-cyclobutylethyl)amino)-7-(4-(trifluoromethyl)benzyl)-7H-purine-2-carbonitrile and 2-bromo-1-chloro-4-ethylbenzene, (R)-8-(2-chloro-5-ethylphenyl)-6-((1-cyclobutylethyl)amino)-7-(4-(trifluoromethyl)benzyl)-7H-purine-2-carboxylic acid was prepared. MS ESI calc'd. for $C_{28}H_{27}ClF_3N_5O_2$ [M+H]$^+$ 558. found 558. $^1$H NMR (400 MHz, DMSO-d₆) δ 7.64 (d, J=8.4 Hz, 2H), 7.58 (d, J=8.0 Hz, 1H), 7.45 (d, J=8.0 Hz, 1H), 7.40 (s, 1H), 7.04 (d, J=8.4 Hz, 2H), 5.96 (br s, 2H), 4.36 (m, 1H), 2.60 (q, J=7.6 Hz, 2H), 2.18 (m, 1H), 1.84 (m, 1H), 1.47-1.66 (m, 3H), 1.31-1.44 (m, 2H), 1.10 (t, J=7.8 Hz, 3H), 0.93 (d, J=5.6 Hz, 3H).

Example 1.3

(R)-6-((1-cyclobutylethyl)amino)-7-(3-fluoro-4-(trifluoromethyl)benzyl)-7H-purine-2-carbonitrile

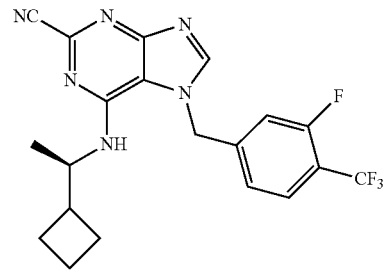 [SMILES: C[C@@H](Nc1nc(C#N)nc2ncn(Cc3ccc(C(F)(F)F)c(F)c3)c12)C1CCC1]

Step 1: Into a 500-mL 4-necked round-bottom flask purged and maintained with an inert atmosphere of nitrogen was placed a solution of 3-fluoro-4-(trifluoromethyl)benzoic acid (50 g, 240.26 mmol) in tetrahydrofuran (200 mL). This was followed by the addition of borane (300 g, 216.84 mmol) dropwise with stirring at room temperature over 2 hours. The resulting solution was stirred overnight at room temperature. The reaction was then quenched by the addition of 1 M aqueous HCl (500 mL). The resulting solution was diluted with water (500 mL) and extracted with ethyl acetate (3×600 mL). The organic layers were combined, washed with water (600 mL) and brine (600 mL), dried over anhydrous sodium sulfate and concentrated under vacuum. This resulted in [3-fluoro-4-(trifluoromethyl)phenyl]methanol as yellow oil.

Step 2: A mixture of [3-fluoro-4-(trifluoromethyl)phenyl]methanol (230 g, 1.18 mol) and HBr (1200 mL, 40%) was heated to reflux for 2 hours. The resulting solution was cooled and diluted with 2 L of water. The resulting solution was extracted with dichloromethane (3×1 L). The organic layers were combined, washed with water (1 L), aqueous sodium bicarbonate (1 L) and brine (1 L), dried over anhydrous sodium sulfate and concentrated under vacuum. This resulted in 4-(bromomethyl)-2-fluoro-1-(trifluoromethyl)benzene as yellow oil.

Step 3: Into a 5000-mL 4-necked round-bottom flask purged and maintained with an inert atmosphere of nitrogen was placed a solution of sodium tert-butoxide (300 g, 3.12 mol) in tetrahydrofuran (2000 mL). 2,6-Dichloro-7H-purine (183 g, 968.24 mmol) was added in several batches. The resulting solution was heated to reflux for 2 hours. This was followed by the addition of 4-(bromomethyl)-2-fluoro-1-(trifluoromethyl)benzene (98.1 g, 381.68 mmol) dropwise with stirring at 60° C. over 30 minutes. The resulting solution was heated to reflux for 2 hours. The reaction mixture was then cooled to room temperature. The solid was filtered out. The filtrate was concentrated under vacuum. The residue was applied onto a silica gel column and eluted with 0-10% ethyl acetate in dichloromethane to afford 2,6-dichloro-7-(3-fluoro-4-(trifluoromethyl)benzyl)-7H-purine as a white solid. MS ESI calc'd. for $C_{13}H_6Cl_2F_4N_4$ $[M+H]^+$ 365. found 365. $^1$H NMR (300 MHz, CDCl$_3$) δ 8.31 (s, 1H), 7.59-7.65 (m, 1H), 6.93-6.97 (m, 2H), 5.71 (s, 2H).

Step 4: Into a 5-L 3-necked round-bottom flask was placed propan-2-ol (2000 mL), 2,6-dichloro-7-(3-fluoro-4-(trifluoromethyl)benzyl)-7H-purine (200 g, 547.78 mmol), (R)-1-cyclobutylethanamine hydrochloride (89.5 g, 659.86 mmol), and triethylamine (166.4 g, 1.64 mol). The resulting solution was stirred overnight at 80° C. The resulting mixture was cooled and concentrated under vacuum. The residue was applied onto a silica gel column and eluted with 30-100% ethyl acetate in dichloromethane to afford (R)-2-chloro-N-(1-cyclobutylethyl)-7-(3-fluoro-4-(trifluoromethyl)benzyl)-7H-purin-6-amine as a white solid. MS ESI calc'd. for $C_{19}H_{18}ClF_4N_5$ $[M+H]^+$ 428. found 428. $^1$H NMR (300 MHz, CDCl$_3$) δ 7.97 (s, 1H), 7.58-7.72 (m, 1H), 6.88-7.01 (m, 2H), 5.52 (s, 2H), 4.08-4.26 (m, 2H), 1.33-1.96 (m, 7H), 0.85-0.88 (d, J=6.3 Hz, 3H).

Step 5: Into a 2-L 4-necked round-bottom flask purged and maintained with an inert atmosphere of nitrogen was placed N,N-dimethylacetamide (1000 mL), (R)-2-chloro-N-(1-cyclobutylethyl)-7-(3-fluoro-4-(trifluoromethyl)benzyl)-7H-purin-6-amine (100 g, 233.74 mmol), zinc(II) cyanide (35.7 g, 304.09 mmol), allylpalladium(II) chloride (4.3 g, 11.75 mmol), and 2-dicyclohexylphosphino-2',4',6'-triisopropylbiphenyl (16.7 g, 35.03 mmol). The resulting solution was stirred overnight at 120° C. The reaction mixture was then cooled to room temperature and diluted with water (3 L). The resulting solution was extracted with ethyl acetate (3×1 L). The organic layers were combined, washed with brine (4×1 L), dried over anhydrous sodium sulfate and concentrated under vacuum. The residue was applied onto a silica gel column and eluted with 50-100% ethyl acetate in dichloromethane to afford (R)-6-((1-cyclobutylethyl)amino)-7-(3-fluoro-4-(trifluoromethyl)benzyl)-7H-purine-2-carbonitrile as a white solid. MS ESI calc'd. for $C_{20}H_{18}F_4N_6$ $[M+H]^+$ 419. found 419. $^1$H NMR (300 MHz, CDCl$_3$) δ 8.13 (s, 1H), 7.68-7.73 (m, 1H), 6.96-7.03 (m, 2H), 5.60 (s, 2H), 4.20-4.25 (m, 2H), 1.33-1.99 (m, 7H), 0.87 (d, J=6.0 Hz, 3H).

Example 1.3

(R)-6-((1-cyclobutylethyl)amino)-7-(3-fluoro-4-(trifluoromethyl)benzyl)-8-(5-isopropyl-2-(trifluoromethoxy)phenyl)-7H-purine-2-carboxylic acid

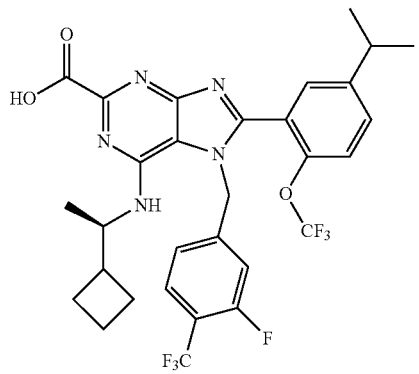 [SMILES: CC(C)c1ccc(OC(F)(F)F)c(-c2nc3nc(C(=O)O)nc(N[C@H](C)C4CCC4)c3n2Cc2ccc(C(F)(F)F)c(F)c2)c1]

Using a procedure analogous to that described in Example 1.1, and starting with (R)-6-((1-cyclobutylethyl)amino)-7-(3-fluoro-4-(trifluoromethyl)benzyl)-7H-purine-2-carbonitrile (Preparative Example 1.3), (R)-6-((1-cyclobutylethyl)amino)-7-(3-fluoro-4-(trifluoromethyl)benzyl)-8-(5-isopropyl-2-(trifluoromethoxy)phenyl)-7H-purine-2-carboxylic acid was prepared. MS ESI calc'd. for $C_{30}H_{28}F_7N_5O_3$ $[M+H]^+$ 640. found 640. $^1$H NMR (400 MHz, CD$_3$OD) δ 7.58-7.65 (m, 2H), 7.45 (d, J=7.6 Hz, 2H), 6.90 (dd, J=24.4, 7.6 Hz, 2H), 5.80 (d, J=16.8 Hz, 1H), 5.48 (d, J=16.8 Hz, 1H), 4.70 (m, 1H), 4.56 (m, 1H), 2.96 (s, 1H), 2.19 (m, 1H), 1.92 (m, 1H), 1.68-1.74 (m, 3H), 1.49-1.53 (m, 2H), 1.19 (t, J=6.4 Hz, 6H), 1.01 (d, J=6.4 Hz, 3H).

Preparative Example 1.4

4-bromo-2-isopropylpyridine

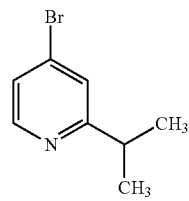

Step 1: To a suspension of 4-bromopyridine hydrochloride (1.0 g, 5.1 mmol) in THF (20 mL) was added isopropylmagnesium bromide (10.3 mL, 10.2 mmol) at −78° C. over 10 minutes. Phenyl chloroformate (0.81 g, 5.1 mmol) was then added drop-wise. The resulting mixture was stirred at −78° C. under a nitrogen atmosphere, for 10 minutes and then warmed to room temperature. After this time, the reaction mixture was quenched with 20% aqueous ammonium chloride (30 mL) and extracted with MTBE (3×50 mL). The combined organic layers were washed with water (50 mL), 10% aqueous HCl (50 mL), water (50 mL) and brine (50 mL). The organic layer was dried over sodium sulfate, filtered and concentrated under reduced pressure to afford phenyl 4-bromo-2-isopropylpyridine-1(2H)-carboxylate as a brown oil.

Step 2: To a solution of phenyl 4-bromo-2-isopropylpyridine-1(2H)-carboxylate (1.5 g, 4.8 mmol) in toluene (25 mL) was added 2,3,5,6-tetrachlorocyclohexa-2,5-diene-1,4-dione (1.4 g, 5.8 mmol) at room temperature and the reaction was stirred for 12 hours. The pH was then adjusted to pH=7 with 1 N aqueous sodium hydroxide and extracted with EtOAc (3×50 mL). The combined organic layers were washed with water (50 mL) and brine (50 mL). The organic layer was dried over sodium sulfate, filtered and concentrated under reduced pressure. The crude product was purified using a Redisep 120 g silica gel column (0 to 100% EtOAc/hexanes) to afford 4-bromo-2-isopropylpyridine as a colorless oil. $^1$H NMR (300 MHz, CDCl$_3$) δ 8.45 (d, J=5.4 Hz, 1H), 7.34 (d, J=1.5 Hz, 1H), 7.27 (d, J=5.7 Hz, 1H), 3.03 (m, 1H), 1.29 (d, J=7.2 Hz, 6H).

Example 1.4

(R)-6-((1-cyclobutylethyl)amino)-8-(2-isopropylpyridin-4-yl)-7-(4-(trifluoromethyl)benzyl)-7H-purine-2-carboxylic acid

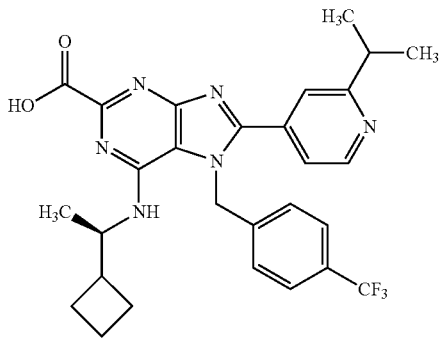 [SMILES: CC(C)c1cc(-c2nc3nc(C(=O)O)nc(N[C@H](C)C4CCC4)c3n2Cc2ccc(C(F)(F)F)cc2)ccn1]

Using a procedure analogous to that described in Example 1.1 (steps 2 and 3), and starting with (R)-6-((1-cyclobutylethyl)amino)-7-(4-(trifluoromethyl)benzyl)-7H-purine-2-carbonitrile and 4-bromo-2-isopropylpyridine, (R)-6-((1-cyclobutylethyl)amino)-8-(2-isopropylpyridin-4-yl)-7-(4-(trifluoromethyl)benzyl)-7H-purine-2-carboxylic acid, was prepared. MS ESI calc'd. for $C_{28}H_{29}F_3N_6O_2$ [M+H]$^+$ 539. found 539. $^1$H NMR (300 MHz, CD$_3$OD) δ 8.63 (d, J=10.2 Hz, 1H), 7.74 (d, J=8.1 Hz, 2H), 7.49-7.54 (m, 3H), 7.31 (d, J=8.1 Hz, 1H), 5.93 (d, J=18.6 Hz, 1H), 5.77 (d, J=18.6 Hz, 1H), 4.57 (m, 1H), 3.09 (m, 1H), 2.12 (m, 1H), 1.89 (m, 1H), 1.61-1.73 (m, 3H), 1.47-1.50 (m, 2H), 1.25 (d, J=0.6 Hz, 3H), 1.23 (d, J=0.6 Hz, 3H), 0.92 (d, J=6.3 Hz, 3H).

Preparative Example 1.5

2-bromo-6-methyl-4-(prop-1-en-2-yl)pyridine

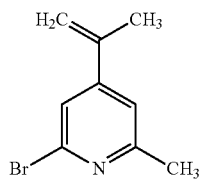

Step 1: To a room temperature solution of 2-bromo-6-methylpyridine (2.0 g, 1.17 mmol) in CH$_2$Cl$_2$ (150 mL) was added 3-chloroperoxybenzoic acid (4.5 g, 26.3 mmol). The resulting mixture was stirred at room temperature for 3 hours. After this time, the reaction mixture was diluted with dichloromethane (50 mL) and washed with 6N aqueous sodium hydroxide (2×40 mL). The organic layer was concentrated to afford 2-bromo-6-methylpyridine 1-oxide.

Step 2: To a solution of 2-bromo-6-methylpyridine 1-oxide (1.95 g, 10.4 mmol) in sulfuric acid (2.0 ml) was added 1:1 mixture of sulfuric acid and nitric acid, (5.0 ml) dropwise at 0° C. The reaction was then heated at 80° C. for 3 hours. After this time the reaction mixture was diluted with water (50 mL) and the pH was adjusted to pH 7 with saturated aqueous sodium bicarbonate. The resulting mixture was extracted with EtOAc (3×50 mL). The combined organic layers were dried over sodium sulfate, filtered and concentrated under reduced pressure to afford 2-bromo-6-methyl-4-nitropyridine as yellow solid.

Step 3: To a room temperature solution of 2-bromo-6-methyl-4-nitropyridine (1.5 g, 6.91 mmol) in acetic acid (10 mL) was added iron (1.34 g, 2.41 mmol). The reaction was then heated at 100° C. for 3 hours. After this time the reaction mixture was diluted with methanol (50 mL) and filtered through diatomaceous earth. The filtrate was concentrated and suspended in 6 N aqueous NaOH (50 mL). The resulting mixture was extracted with EtOAc (2×40 mL). The combined organic layers were dried over sodium sulfate, filtered and concentrated under reduced pressure to afford 2-bromo-6-methylpyridin-4-amine as a brown solid.

Step 4: To a solution of 2-bromo-6-methylpyridin-4-amine (1.0 g, 5.4 mmol) in 40% aqueous HBr (1.0 mL) cooled to −10° C. was added bromine (2.57 g, 16.2 mmol) followed by the slow solution of sodium nitrite (1.86 g, 27.0 mmol) in water (3.0 mL). The reaction mixture was warmed to room temperature and stirred for 3 hours. After this time saturated aqueous sodium bicarbonate was added and the reaction mixture was extracted with EtOAc (2×40 mL). The combined organic layers were washed with saturated aqueous sodium thiosulfate (2×40 mL) and water (2×40 mL). The organic layer was dried over sodium sulfate, filtered and concentrated. The resulting crude product was purified using a Redisep 12 g silica gel column (0 to 100% EtOAc/hexanes) to afford 2,4-dibromo-6-methylpyridine as a colorless oil. $^1$H NMR (300 MHz, CDCl$_3$) δ 7.49 (d, J=1.2 Hz, 1H), 7.28 (d, J=1.2 Hz, 1H), 2.51 (s, 3H).

Step 5: To a solution of 2,4-dibromo-6-methylpyridine (650 mg, 2.60 mmol) in diethyl ether (150 mL) was added n-BuLi (2.32 mL, 2 N) at −78° C. and the reaction was stirred for 15 minutes. Acetone (0.2 ml) was added and the resulting mixture was warmed to room temperature and stirred for 1 hour. After this time, the reaction mixture was quenched with saturated aqueous ammonium chloride (40 mL) and the reaction mixture was extracted with MTBE (3×50 mL). The combined organic layers were dried over sodium sulfate, filtered and concentrated under reduced pressure to afford 2-(2-bromo-6-methylpyridin-4-yl)propan-2-ol as a colorless oil.

Step 6: A solution of 2-(2-bromo-6-methylpyridin-4-yl)propan-2-ol (480 mg, 2.22 mmol) in thionyl chloride (2.0 mL) was stirred at 50° C. for 1 hour. After this time ice cooled water (20 mL) was added to the reaction mixture and the pH was adjusted to 7 using saturated aqueous sodium bicarbonate. The reaction mixture was extracted with MTBE (3×50 mL). The combined organic layers were dried over sodium sulfate, filtered and concentrated under reduced pressure to afford 2-bromo-6-methyl-4-(prop-1-en-2-yl)

pyridine as colorless oil. $^1$H NMR (300 MHz, CDCl$_3$) δ 7.37 (s, 1H), 7.17 (s, 1H), 5.57 (s, 1H), 5.31 (s, 1H), 2.11 (s, 3H), 1.92 (s, 3H).

Example 1.5

(R)-6-((1-cyclobutylethyl)amino)-8-(6-methyl-4-(prop-1-en-2-yl)pyridin-2-yl)-7-(4-(trifluoromethyl)benzyl)-7H-purine-2-carboxylic acid

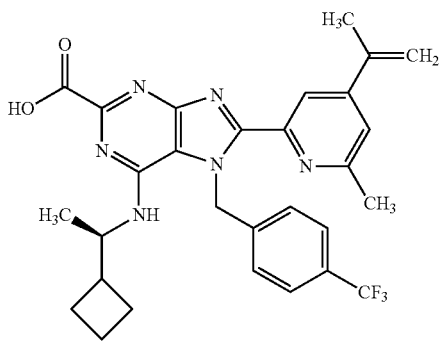 [SMILES: C=C(C)c1cc(C)nc(-c2nc3nc(C(=O)O)nc(N[C@H](C)C4CCC4)c3n2Cc2ccc(C(F)(F)F)cc2)c1]

Using a procedure analogous to that described in Example 1.1 (steps 2 and 3) and starting with (R)-6-((1-cyclobutylethyl)amino)-7-(4-(trifluoromethyl)benzyl)-7H-purine-2-carbonitrile and 2-bromo-6-methyl-4-(prop-1-en-2-yl)pyridine, (R)-6-((1-cyclobutylethyl)amino)-8-(6-methyl-4-(prop-1-en-2-yl)pyridin-2-yl)-7-(4-(trifluoromethyl)benzyl)-7H-purine-2-carboxylic acid was prepared. MS ESI calc'd. for $C_{29}H_{29}F_3N_6O_2$ [M+H]$^+$ 551. found 551. $^1$H NMR (300 MHz, CD$_3$OD) δ 8.24 (s, 1H), 7.67 (d, J=7.8 Hz, 2H), 7.31 (s, 1H), 7.32 (d, J=6.9 Hz, 2H), 6.90 (d, J=17.7 Hz, 1H), 6.29 (d, J=17.7 Hz, 1H), 5.73 (s, 1H), 5.36 (s, 1H), 4.60 (m, 1H), 2.45 (s, 3H), 2.19 (s, 3H), 2.16 (m, 1H), 1.91 (m, 1H), 1.58-1.72 (m, 3H), 1.42-1.52 (m, 2H), 1.00 (d, J=4.8 Hz, 3H).

Example 1.6

7-(4-chloro-3-fluorobenzyl)-6-{[(1R)-1-cyclobutylethyl]amino}-8-[4-(propan-2-yl)pyridin-2-yl]-7H-purine-2-carboxylic acid

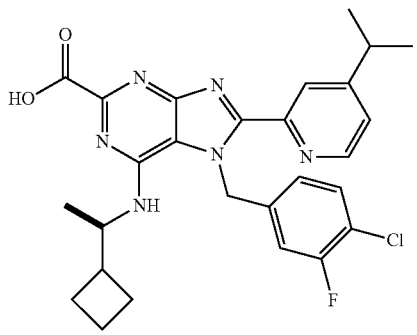

Step 1: 2-Iodo-6-chloropurine (2.5 g, 8.91 mmol) in N,N-dimethylacetamide (12 mL) was treated with 4-chloro-3-fluorobenzyl bromide (2.1 g, 9.4 mmol). Cesium carbonate (3.05 g, 9.4 mmol) was added and the mixture was stirred at room temperature for 2 hours. The reaction was quenched with water and extracted with ethyl acetate (2×). The combined organic layers were washed with brine, dried over sodium sulfate, filtered, and concentrated under reduced pressure to afford a 25:75 mixture of 6-chloro-7-(4-chloro-3-fluorobenzyl)-2-iodo-7H-purine:6-chloro-9-(4-chloro-3-fluorobenzyl)-2-iodo-9H-purine. The residue was purified by silica gel chromatography (0-80% ethyl acetate/hexanes, linear gradient) to afford 6-chloro-7-(4-chloro-3-fluorobenzyl)-2-iodo-7H-purine. MS ESI calc'd. for $C_{12}H_6Cl_2FIN_4$ [M+H]$^+$ 423. found 423.

Step 2: To a solution of 6-chloro-7-(4-chloro-3-fluorobenzyl)-2-iodo-7H-purine (883 mg, 2.09 mmol) in ethanol (25 mL) was added (1R)-1-cyclobutylethanamine hydrochloride (566 mg, 4.17 mmol) and N,N-diisopropylethylamine (1.46 mL, 8.35 mmol). The reaction mixture was stirred at 70° C. for 16 hours. The reaction was cooled to room temperature, diluted with ethyl acetate, and washed with hydrochloric acid (1.0 M in water, 2×). The organic layer was dried over sodium sulfate, filtered, and concentrated under reduced pressure. The residue was purified by silica gel chromatography (0-100% ethyl acetate/hexanes, and then 0-15% methanol/dichloromethane, linear gradient) to afford 7-(4-chloro-3-fluorobenzyl)-N-[(1R)-1-cyclobutylethyl]-2-iodo-7H-purin-6-amine. MS ESI calc'd. for $C_{18}H_{18}ClFIN_5$ [M+H]$^+$ 486. found 486.

Step 3: Tetrahydrofuran (0.10 mL) was added to tris(dibenzylideneacetone)dipalladium-chloroform adduct (20.5 mg, 0.019 mmol) and tri(2-furyl)phosphine (31.5 mg, 0.136 mmol) in a vial under a dry, nitrogen atmosphere. The solvent was removed under reduced pressure. 7-(4-chloro-3-fluorobenzyl)-N-[(1R)-1-cyclobutylethyl]-2-iodo-7H-purin-6-amine (60 mg, 0.124 mmol) and zinc cyanide (58 mg, 0.494 mmol) in N,N-dimethylacetamide (0.31 mL) were added to the preformed catalyst. The vial was capped and stirred at 70° C. for 16 hours. The mixture was cooled to room temperature, filtered, and concentrated. The residue was purified by silica gel chromatography (0-100% ethyl acetate/hexanes, and then 0-15% methanol/dichloromethane, linear gradient) to afford 7-(4-chloro-3-fluorobenzyl)-6-{[(1R)-1-cyclobutylethyl]amino}-7H-purine-2-carbonitrile. MS ESI calc'd. for $C_{19}H_{18}ClFN_6$ [M+H]$^+$ 385. found 385.

Step 4: Dioxane (0.35 mL) was added to palladium(II) acetate (6.9 mg, 0.031 mmol) and butyldi-1-adamantylphosphine (21.9 mg, 0.061 mmol) in an oven-dried, argon cooled vial. The vial was sealed and heated to 50° C. for 30 minutes. To a separate vial, added 7-(4-chloro-3-fluorobenzyl)-6-{[(1R)-1-cyclobutylethyl]amino}-7H-purine-2-carbonitrile (58.7 mg, 0.153 mmol), pivalic acid (17.1 mg, 0.17 mmol), cesium fluoride (69.5 mg, 0.46 mmol), 2-bromo-4-(isopropyl)pyridine (0.0427 mL, 0.305 mmol), and dioxane (0.35 mL). The activated catalyst solution was added to the reagents, the vial was evacuated and backfilled with argon (3×), sealed, and heated to 120° C. for 16 hours. The mixture was cooled to room temperature, filtered over celite, and the filtrate was concentrated under reduced pressure. The residue was purified by silica gel chromatography (0-70% ethyl acetate/hexanes, linear gradient) to afford 7-(4-chloro-3-fluorobenzyl)-6-{[(1R)-1-cyclobutylethyl]amino}-8-[4-(propan-2-yl)pyridin-2-yl]-7H-purine-2-carbonitrile. MS ESI calc'd. for $C_{27}H_{27}ClFN_7$ [M+H]$^+$ 504. found 504.

Step 5: Sodium hydroxide (5.0 M in water, 0.500 mL, 2.5 mmol) was added to 7-(4-chloro-3-fluorobenzyl)-6-{[(1R)-1-cyclobutylethyl]amino}-8-[4-(propan-2-yl)pyridin-2-yl]-7H-purine-2-carbonitrile (32.3 mg, 0.064 mmol) dissolved in ethanol (1.5 mL). The mixture was heated for 1 hour at 70° C. The reaction was cooled to room temperature, diluted with ethyl acetate, and washed with hydrochloric acid (1.0 M in water, 10 mL). The organic layer was dried over sodium sulfate, filtered, and concentrated under reduced pressure. The residue was dissolved in DMSO and purified by mass triggered, reverse phase (C-18) preparative HPLC (acetonitrile/water: 0.1% v/v trifluoroacetic acid modifier) to afford 7-(4-chloro-3-fluorobenzyl)-6-{[(1R)-1-cyclobutyl-ethyl]amino}-8-[4-(propan-2-yl)pyridin-2-yl]-7H-purine-2-carboxylic acid (as a TFA salt). MS ESI calc'd. for $C_{27}H_{28}ClFN_6O_2$ [M+H]$^+$523. found 523. $^1$H NMR (500 MHz, DMSO-$d_6$) δ 8.56 (d, J=5.1, 1H), 8.20 (s, 1H), 7.52-7.45 (m, 2H), 7.17-7.10 (m, 1H), 6.71 (dd, J=1.5, 8.4, 1H), 6.65 (d, J=17.8, 1H), 6.27 (d, J=17.7, 1H), 6.12 (d, J=8.5, 1H), 4.42-4.32 (m, 1H), 3.07-3.00 (m, 1H), 2.32-2.24 (m, 1H), 1.91-1.81 (m, 1H), 1.72-1.63 (m, 1H), 1.62-1.52 (m, 2H), 1.52-1.44 (m, 1H), 1.44-1.34 (m, 1H), 1.26 (d, J=6.9, 6H), 0.99 (d, J=6.5, 3H).

Preparative Example 1.6

6-{[(1R)-1-cyclobutylethyl]amino}-7-{[5-(trifluoromethyl)thiophen-2-yl]methyl}-7H-purine-2-carbonitrile

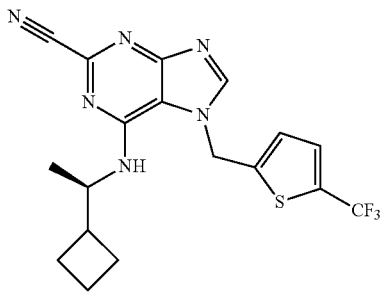 [SMILES: C[C@@H](Nc1nc(C#N)nc2ncn(Cc3ccc(C(F)(F)F)s3)c12)C1CCC1]

Step 1: 5-(trifluoromethyl)-2-thiophenecarboxylic acid (200 mg, 1.02 mmol) (purchased from Oakwood products) was dissolved in THF (10 ml) and $BH_3$.THF (3.06 ml of a 1M solution in THF, 3.06 mmol) was added dropwise. The reaction was stirred for 1.5 hours at room temperature and then heated to reflux for 3 hours. The reaction was then cooled to room temperature. Methanol (3 mL) was added dropwise and the reaction was stirred until the evolution of gas had ceased. The reaction was then diluted with EtOAc (75 mL) and the organics were washed with water (20 mL) and brine (20 mL). The organic layer was dried over sodium sulfate, filtered, and concentrated. Purification of the residue on a Biotage 25 g silica gel column with 0 to 50% EtOAc/hexanes afforded [5-trifluoromethyl)thiophen-2-yl]methanol. $^1$H NMR (600 MHz, CDCl$_3$) δ 7.29 (s, 1H), 6.94 (s, 1H), 4.84 (s, 2H), 1.91 (s, 1H).

Step 2: [5-trifluoromethyl)thiophen-2-yl]methanol (200 mg, 1.098 mmol) was dissolved in dichloromethane (10 ml) and cooled to 0° C. Carbon tetrabromide (546 mg, 1.65 mmol) was added as a solution in dichloromethane (2 mL). After stirring at 0° C. for 15 minutes, the reaction was warmed to room temperature for 2 hours. The reaction was then concentrated and the residue was purified on a Biotage 25 g silica gel column with 100% hexanes to afford 2-(bromomethyl)-5-(trifluoromethyl)thiophene $^1$H NMR (600 MHz, CDCl$_3$) δ 7.26 (d, J=3.0 Hz, 1H), 7.04 (d, J=3.0 Hz, 1H), 4.65 (s, 2H).

Step 3: To a solution of 2,6-dichloropurine (100 mg, 0.529 mmol) and 2-(bromomethyl)-5-(trifluoromethyl)thiophene (130 mg, 0.529 mmol) in N,N-dimethylacetamide (1 mL) was added cesium carbonate (172 mg, 0.529 mmol). The reaction was stirred at room temperature for 2 hours and then diluted with EtOAc (75 mL). The organics were washed with water (20 mL) and brine (20 mL). The organic layer was dried over sodium sulfate, filtered, and concentrated. Purification of the residue on a Biotage 25 g silica gel column with 0 to 100% EtOAc/hexanes afforded the faster eluting, undesired 2,6-dichloro-9-{[5-(trifluoromethyl)thiophen-2-yl]methyl}-9H-purine and the slower eluting, desired 2,6-dichloro-7-{[5-(trifluoromethyl)thiophen-2-yl]methyl}-7H-purine. $^1$H NMR (600 MHz, CDCl$_3$) δ 8.29 (s, 1H), 7.34 (d, J=3.0 Hz, 1H), 6.99 (d, J=3.0 Hz, 1H), 5.82 (s, 2H). MS(ES)=353 (M+1)$^+$.

Step 4: 2,6-dichloro-7-{[5-(trifluoromethyl)thiophen-2-yl]methyl}-7H-purine (42.3 mg, 0.120 mmol) and (1R)-1-cyclobutylethanamine hydrochloride (24.4 mg, 0.180 mmol) were placed in a vial. Ethanol (1 mL) was added, followed by triethylamine (50 uL, 0.36 mmol). The vial was sealed, and the reaction was heated to 85° C. for 4 hours. The reaction was then cooled to room temperature and concentrated. Purification of the residue by flash chromatography on a Biotage 25 g silica gel column with 0 to 100% EtOAc/hexanes followed by 10% MeOH/90% EtOAc afforded 2-chloro-N-[(1R)-1-cyclobutylethyl]-7-{[5-(trifluoromethyl)thiophen-2-yl]methyl}-7H-purin-6-amine. $^1$H NMR (600 MHz, CDCl$_3$) δ 7.96 (s, 1H), 7.41 (s, 1H), 6.89 (s, 1H), 5.59 (s, 2H), 4.35 (d, J=7.2 Hz, 1H), 4.26 (m, 1H), 1.48-2.04 (m, 7H), 0.93 (d, J=6.6 Hz, 3H). MS(ES)=416 (M+1)$^+$.

Step 5: A vial equipped with a stir bar, was charged with 2-dicyclohexylphosphino-2',4',6'-triisopropylbiphenyl (27 mg, 0.057 mmol), allylpalladium chloride dimer (6 mg, 0.016 mmol) and N,N-dimethylacetamide (1 mL). The mixture was degassed with $N_2$ and then the vial was sealed and heated at 60° C. for 1 hour. The catalyst solution was then cooled back to r.t., and 0.5 mL of this catalyst solution was added via syringe to a second vial equipped with a stir bar and containing a $N_2$ degassed solution of 2-chloro-N-[(1R)-1-cyclobutylethyl]-7-{[5-(trifluoromethyl)thiophen-2-yl]methyl}-7H-purin-6-amine (45 mg, 0.108 mmol) in N,N-dimethylacetamide (0.5 mL). Zinc cyanide (16.52 mg, 0.141 mmol) was added and the reaction was degassed with $N_2$ for an additional minute. The vial was then sealed and heated to 120° C. for 2.5 hours. After 2.5 hours, the reaction was cooled to room temperature. The reaction was partitioned between EtOAc (75 mL) and water (20 mL). The organic layer was washed with brine (20 mL), filtered through celite and concentrated. The residue was purified on a Biotage 25 g silica gel column with a gradient of 100% EtOAc to 5% MeOH/95% EtOAc to afford 6-{[(1R)-1-cyclobutylethyl]amino}-7-{[5-(trifluoromethyl)thiophen-2-yl]methyl}-7H-purine-2-carbonitrile. $^1$H NMR (600 MHz, CDCl$_3$) 8.09 (s, 1H), 7.42 (d, J=3.6 Hz, 1H), 6.91 (d, J=3.0 Hz, 1H), 5.65 (s, 2H), 4.46 (d, J=7.8 Hz, 1H), 4.30 (m, 1H), 1.48-2.08 (m, 7H), 0.94 (d, J=6.6 Hz, 3H). MS(ES)=407 (M+1)$^+$.

Example 1.7

6-{[(1R)-1-cyclobutylethyl]amino}-8-[4-(propan-2-yl)pyridin-2-yl]-7-{[5-(trifluoromethyl)thiophen-2-yl]methyl}-7H-purine-2-carboxylic acid

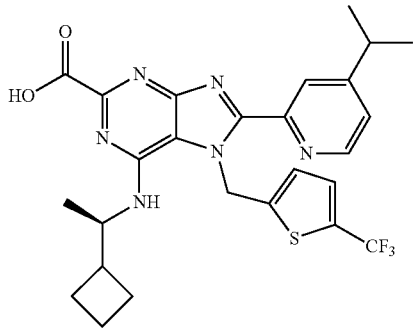 [SMILES: CC(C)c1ccnc(-c2nc3nc(C(=O)O)nc(N[C@H](C)C4CCC4)c3n2Cc2ccc(C(F)(F)F)s2)c1]

Using a procedure analogous to that described in Example 1.1 (steps 2 and 3) and starting with Preparative Example 1.6, 6-{[(1R)-1-cyclobutylethyl]amino}-7-{[5-(trifluoromethyl)thiophen-2-yl]methyl}-7H-purine-2-carbonitrile, and 2-bromo-4-(isopropyl)pyridine (purchased from Combiphos), 6-{[(1R)-1-cyclobutylethyl]amino}-8-[4-(propan-2-yl)pyridin-2-yl]-7-{[5-(trifluoromethyl)thiophen-2-yl]methyl}-7H-purine-2-carboxylic acid (TFA salt) was prepared. $^1$H NMR (600 MHz, d6-DMSO) δ 8.64 (d, J=5.4 Hz, 1H), 8.18 (s, 1H), 7.52 (d, J=3 Hz, 1H), 7.49 (dd, J=5.4, 1.2 Hz, 1H), 7.01 (d, J=3 Hz, 1H), 6.80 (d, J=17.4 Hz, 1H), 6.48-6.52 (m, 2H), 4.47 (m, 1H), 3.04 (m, 1H), 1.54-2.48 (m, 7H), 1.25 (d, J=6.6 Hz, 6H), 1.06 (d, J=6.6 Hz, 3H). MS(ES)=545 (M+1)$^+$.

Example 1.8

6-(((R)-1-cyclobutylethyl)amino)-8-(4-(hydroxy(phenyl)methyl)pyridin-2-yl)-7-(4-(trifluoromethyl)benzyl)-7H-purine-2-carboxylic acid

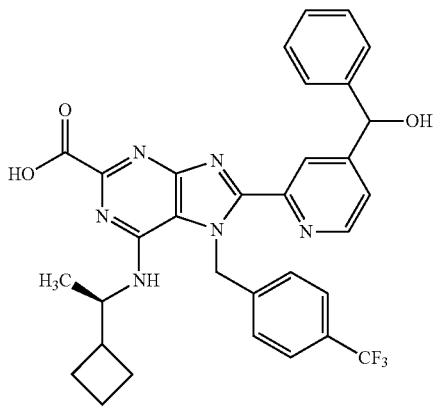 [SMILES: C[C@@H](Nc1nc(C(=O)O)nc2nc(-c3cc(C(O)c4ccccc4)ccn3)n(Cc3ccc(C(F)(F)F)cc3)c12)C1CCC1]

Using a procedure analogous to that described in Example 1.1 (steps 2 and 3), starting with (R)-6-((1-cyclobutylethyl)amino)-7-(4-(trifluoromethyl)benzyl)-7H-purine-2-carbonitrile (Preparative Example 1.1) and (2-bromopyridin-4-yl)(phenyl)methanol, 6-(((R)-1-cyclobutylethyl)amino)-8-(4-(hydroxy(phenyl)methyl)pyridin-2-yl)-7-(4-(trifluoromethyl)benzyl)-7H-purine-2-carboxylic acid was prepared. $^1$H NMR (300 MHz, CD$_3$OD) δ 8.56 (d, J=5.1 Hz, 1H), 8.39 (s, 1H), 7.66 (d, J=7.8 Hz, 2H), 7.55 (d, J=5.1 Hz, 1H), 7.23-7.42 (m, 7H), 6.69 (d, J=17.1 Hz, 1H), 6.28 (d, J=17.1 Hz, 1H), 5.86 (s, 1H), 4.58 (m, 1H), 2.13 (m, 1H), 1.90 (m, 1H), 1.61-1.73 (m, 3H), 1.22-1.35 (m, 2H), 1.00 (d, J=6.0 Hz, 3H). MS (ES)=603 (M+1)$^+$.

Example 1.9

(R)-8-(4-benzylpyridin-2-yl)-6-((1-cyclobutylethyl)amino)-7-(4-(trifluoromethyl)benzyl)-7H-purine-2-carboxylic acid

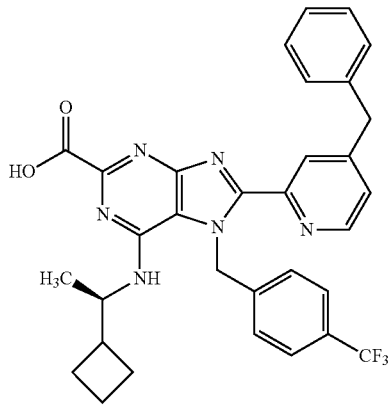 [SMILES: C[C@@H](Nc1nc(C(=O)O)nc2nc(-c3cc(Cc4ccccc4)ccn3)n(Cc3ccc(C(F)(F)F)cc3)c12)C1CCC1]

A mixture of 6-(((R)-1-cyclobutylethyl)amino)-8-(4-(hydroxy(phenyl)methyl)pyridin-2-yl)-7-(4-(trifluoromethyl)benzyl)-7H-purine-2-carboxylic acid (6.0 mg, 0.010 mmol), 10% palladium on carbon (6.0 mg) and TFA (0.1 mL, 1.13 mmol) in ethanol (2.0 mL) and EtOAc (0.1 mL) was stirred under an atmosphere of H$_2$ (balloon) at room temperature for 48 hours. After this time, the reaction mixture was filtered through diatomaceous earth and concentrated under reduced pressure. The residue was purified on a C18 reverse phase column chromatography to afford (R)-8-(4-benzylpyridin-2-yl)-6-((1-cyclobutylethyl)amino)-7-(4-(trifluoromethyl)benzyl)-7H-purine-2-carboxylic acid as an off-white solid. $^1$H NMR (300 MHz, CD$_3$OD) δ 8.55 (s, 1H), 8.05 (s, 1H), 7.78-7.52 (m, 2H), 7.42-7.03 (m 8H), 6.75-6.12 (m, 2H), 4.20-3.95 (m, 3H), 2.75 (m, 1H), 2.44 (m, 1H), 2.21-2.04 (m, 2H), 1.96-1.85 (m, 2H), 1.50-1.25 (m, 5H). MS (ES)=587 (M+1)$^+$.

Example 1.10

(R)-6-((1-cyclobutylethyl)amino)-8-(5-fluoro-4-isopropylpyridin-2-yl)-7-(4-(trifluoromethyl)benzyl)-7H-purine-2-carboxylic acid

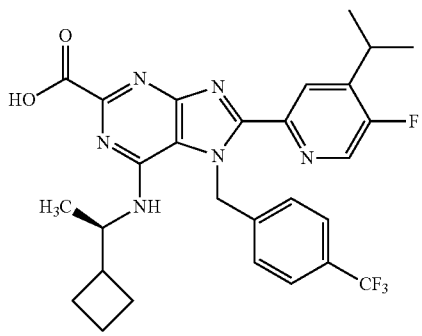 [SMILES: CC(C)c1cc(-c2nc3nc(C(=O)O)nc(N[C@H](C)C4CCC4)c3n2Cc2ccc(C(F)(F)F)cc2)ncc1F]

Using a procedure analogous to that described in Example 15.8, starting with (R)-6-((1-cyclobutylethyl)amino)-7-(4-(trifluoromethyl)benzyl)-7H-purine-2-carbonitrile (Preparative Example 1.1), (R)-6-((1-cyclobutylethyl)amino)-8-(5-fluoro-4-isopropylpyridin-2-yl)-7-(4-(trifluoromethyl) benzyl)-7H-purine-2-carboxylic acid was prepared. $^1$H NMR (300 MHz, CD$_3$OD) δ 8.41 (br s, 1H), 8.34 (d, J=5.6 Hz, 1H), 7.67 (d, J=7.6 Hz, 2H), 7.30 (d, J=7.6 Hz, 2H), 6.60 (d, J=18.0 Hz, 1H), 6.26 (d, J=18.0 Hz, 1H), 4.64 (m, 1H), 2.14 (m, 1H), 1.98 (m, 1H), 1.65-1.72 (m, 3H), 1.38-1.48 (m, 3H), 1.34 (d, J=6.8.0 Hz, 6H), 0.97 (d, J=6.4 Hz, 3H). MS (ES)=557 (M+1)$^+$.

Example 1.11

(R)-6-((1-cyclobutylethyl)amino)-8-(2-hydroxy-5-isopropylphenyl)-7-(4-(trifluoromethyl)benzyl)-7H-purine-2-carboxylic acid

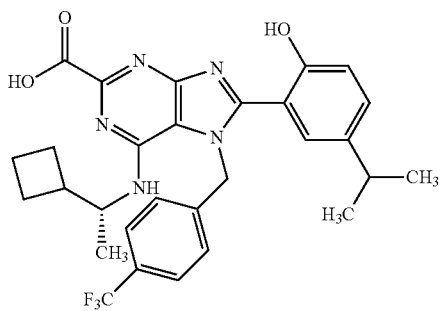 [SMILES: CC(C)c1ccc(O)c(-c2nc3nc(C(=O)O)nc(N[C@H](C)C4CCC4)c3n2Cc2ccc(C(F)(F)F)cc2)c1]

Using a procedure analogous to that described in Example 1.1 (steps 2 and 3), starting with (R)-6-((1-cyclobutylethyl) amino)-7-(4-(trifluoromethyl)benzyl)-7H-purine-2-carbonitrile and 2-bromo-4-isopropylphenol, (R)-6-((1-cyclobutylethyl)amino)-8-(2-hydroxy-5-isopropylphenyl)-7-(4-(trifluoromethyl)benzyl)-7H-purine-2-carboxylic acid was prepared. $^1$H NMR (400 MHz, CD$_3$OD) δ 7.63 (d, J=8.4 Hz, 2H), 7.22-7.29 (m, 4H), 6.91 (d, J=8.4 Hz, 1H), 5.75 (d, J=18.0 Hz, 1H), 5.60 (d, J=18.0 Hz, 1H), 4.60 (m, 1H), 2.82 (m, 1H), 2.09 (m, 1H), 1.90 (m, 1H), 1.62-1.72 (m, 3H), 1.53-1.46 (m, 2H), 1.15 (d, J=6.9 Hz, 6H), 0.94 (d, J=6.5 Hz, 3H). MS (ES)= 554 (M+1)$^+$.

Example 1.12

(R)-6-((1-cyclobutylethyl)amino)-8-(2-ethoxy-5-isopropylphenyl)-7-(4-(trifluoromethyl)benzyl)-7H-purine-2-carboxylic acid

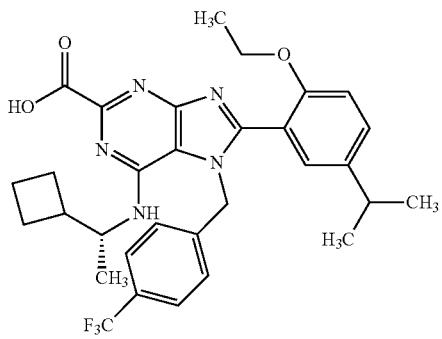 [SMILES: CCOc1ccc(C(C)C)cc1-c1nc2nc(C(=O)O)nc(N[C@H](C)C3CCC3)c2n1Cc1ccc(C(F)(F)F)cc1]

Step 1: Using a procedure analogous to Example 2.1 (step 2) and starting with (R)-6-((1-cyclobutylethyl)amino)-8-(2-hydroxy-5-isopropylphenyl)-7-(4-(trifluoromethyl)benzyl)-7H-purine-2-carbonitrile, (R)-methyl 6-((1-cyclobutylethyl) amino)-8-(2-hydroxy-5-isopropylphenyl)-7-(4-(trifluoromethyl)benzyl)-7H-purine-2-carboxylate was prepared. MS (ES)=568 (M+1)$^+$.

Step 2: A round bottom flask equipped with a stir bar was charged with (R)-methyl 6-((1-cyclobutylethyl)amino)-8-(2-hydroxy-5-isopropylphenyl)-7-(4-(trifluoromethyl)benzyl)-7H-purine-2-carboxylate (50 mg, 0.08 mmol) in DMF (2.0 mL). Potassium carbonate (24 mg, 0.17 mmol) was added to reaction mixture followed by the addition of ethyl iodide (20 mg, 0.13 mmol). The reaction mixture was stirred at room temperature for 1.5 hours. The reaction was then diluted with EtOAc (10 mL) and the organics were washed with brine (10 mL). The organic layer was dried over sodium sulfate, filtered, and concentrated. Purification of the residue on a RediSep 4 g silica gel column (0 to 70% EtOAc/hexanes) afforded (R)-methyl 6-((1-cyclobutylethyl)amino)-8-(2-ethoxy-5-isopropylphenyl)-7-(4-(trifluoromethyl)benzyl)-7H-purine-2-carboxylate. MS (ES)=596 (M+1)$^+$.

Step 3: Using a procedure analogous to that described in Example 2.1 (step 3) and starting with (R)-methyl 6-((1-cyclobutylethyl)amino)-8-(2-ethoxy-5-isopropylphenyl)-7-(4-(trifluoromethyl)benzyl)-7H-purine-2-carboxylate, (R)-6-((1-cyclobutylethyl)amino)-8-(2-ethoxy-5-isopropylphenyl)-7-(4-(trifluoromethyl)benzyl)-7H-purine-2-carboxylic acid was prepared. $^1$H NMR (400 MHz, CD$_3$OD) δ 7.61 (d, J=8.4 Hz, 2H), 7.41 (dd, J=8.4, 2.4 Hz, 1H), 7.30 (d, J=2.4 Hz, 1H), 7.14 (d, J=8.4 Hz, 2H), 7.08 (d, J=8.4 Hz, 1H), 5.71 (d, J=18.0 Hz, 1H), 5.50 (d, J=18.0 Hz, 1H), 4.62 (m, 1H), 4.02-4.08 (m, 2H), 2.87 (m, 1H), 2.07 (m, 1H), 1.88 (m, 1H), 1.62-1.70 (m, 3H), 1.47-1.51 (m, 2H), 1.17-1.23 (m, 9H), 0.96 (d, J=6.4 Hz, 3H). MS (ES)=582 (M+1)$^+$.

Example 1.13

(R)-6-((1-cyclobutylethyl)(methyl)amino)-7-(3-fluoro-4-(trifluoromethyl)benzyl)-8-(4-isopropylpyridin-2-yl)-7H-purine-2-carboxylic acid (TFA salt)

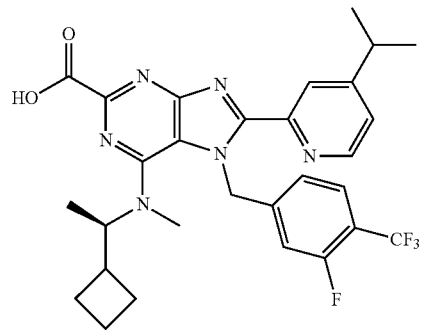 [SMILES: CC(C)c1ccnc(-c2nc3nc(C(=O)O)nc(N(C)[C@H](C)C4CCC4)c3n2Cc2ccc(C(F)(F)F)c(F)c2)c1]

Step 1: A solution of (R)-1-cycobutylethanamine hydrochloride salt (100 mg, 0.74 mmol) in methanol (0.7 mL) was added formaldehyde (0.061 ml, 0.811 mmol). The reaction mixture stirred at room temperature for 1 hour. Sodium cyanoborohydride (51.0 mg, 0.811 mmol) was then added and the clear solution became cloudy. The reaction was stirred overnight. The resulting solution was found to contain a 4:1 mixture of (R)-1-cyclobutylethanamine and (R)-1-cyclobutyl-N-methylethanamine. This mixture was used directly in next step.

Step 2: 6-Chloro-7-(3-fluoro-4-(trifluoromethyl)benzyl)-8-(4-isopropylpyridin-2-yl)-7H-purine-2-carbonitrile (30 mg, 0.063 mmol) was added to the 4:1 mixture of (R)-1-cyclobutylethanamine and (R)-1-cyclobutyl-N-methyl-ethanamine (110 mg, 0.147 mmol) in MeOH (2 ml) and the resulting solution was stirred at 80° C. for 1 hour to afford (R)-6-((1-cyclobutylethyl)(methyl)amino)-7-(3-fluoro-4-(trifluoromethyl)benzyl)-8-(4-isopropylpyridin-2-yl)-7H-purine-2-carbonitrile as major product. This solution was directly used for next step. MS ESI calc'd for $C_{29}H_{29}F_4N_7$ [M+H]$^+$ 552. found 552.

Step 3: To the solution of (R)-6-((1-cyclobutylethyl)(methyl)amino)-7-(3-fluoro-4-(trifluoromethyl)benzyl)-8-(4-isopropylpyridin-2-yl)-7H-purine-2-carbonitrile was added sodium hydroxide (1 ml, 5.0M in water, 5.00 mmol). The resulting suspension was heated at 80° C. for 3 hours. The reaction was then cooled to room temperature and the volatile organics were removed under reduced pressure. The resulting residue was purified via reverse phase HPLC (acetonitrile/water+0.1% TFA modifier) to afford (R)-6-((1-cyclobutylethyl)(methyl)amino)-7-(3-fluoro-4-(trifluoromethyl)benzyl)-8-(4-isopropylpyridin-2-yl)-7H-purine-2-carboxylic acid (TFA salt) as a white solid. MS ESI calc'd for $C_{29}H_{30}F_4N_6O_2$ [M+H]$^+$ 571. found 571. $^1$H NMR (500 MHz, CDCl$_3$): δ 8.58 (d, J=5.1 Hz, 1H), 8.16 (s, 1H), 7.30-7.34 (m, 2H), 6.54 (d, J=10.6 Hz, 1H), 6.48 (d, J=8.3 Hz, 1H), 6.41 (d, J=15.7 Hz, 1H), 5.89 (d, J=15.6 Hz, 1H), 4.13-4.17 (m, 1H), 3.09 (s, 3H), 2.97 (t, J=7.6 Hz, 1H), 2.60 (t, J=9.2 Hz, 1H), 1.98-2.05 (m, 1H), 1.77-1.80 (m, 1H), 1.64-1.72 (m, 3H), 1.25-1.28 (m, 10H).

Example 1.14

8-(4-(sec-butyl)pyridin-2-yl)-6-(((R)-1-cyclobutylethyl)amino)-7-(4-(trifluoromethyl)benzyl)-7H-purine-2-carboxylic acid

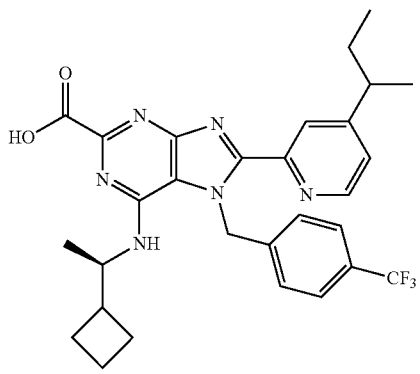 [SMILES: CCC(C)c1ccnc(-c2nc3nc(C(=O)O)nc(N[C@H](C)C4CCC4)c3n2Cc2ccc(C(F)(F)F)cc2)c1]

Step 1: Palladium acetate (II) (56 mg, 0.25 mmol) and butyldi-1-adamantylphosphine (179 mg, 0.5 mmol) in a 2 ml mw vial in 1,4-dioxane (2 mL) was evacuated and refilled with Ar (3×). The resulted solution was warmed to 70° C. for 20 minutes. In a separated 20 microwave vial were added pivalic acid (255 mg, 2.5 mmol), cesium fluoride (1138 mg, 7.49 mmol), 2-bromo-4-chloropyridine (481 mg, 2.5 mmol), (R)-6-((1-cyclobutylethyl)amino)-7-(4-(trifluoromethyl)benzyl)-7H-purine-2-carbonitrile (Preparative Example 1.1, 1.0 g, 2.5 mmol) and 1,4-dioxane (4 mL) and then was degassed with Ar for 15 minutes. Then cooled catalyst solution was added to the mixture. The resulting mixture was stirred at 130° C. for 2 days. The mixture was cooled down and concentrated. The residue was dissolved in DCM and loaded to column (40 g isco column), eluted with Ethyl acetate in hexane (0-100%) to give (R)-8-(4-chloropyridin-2-yl)-6-((1-cyclobutylethyl)amino)-7-(4-(trifluoromethyl)benzyl)-7H-purine-2-carbonitrile as a yellow solid. MS ESI calc'd For $C_{25}H_{21}ClF_3N_7$ [M+H]$^+$ 512. found 512.

Step 2: Palladium acetate (II) (2.2 mg, 0.0098 mmol), butyldi-1-adamantylphosphine (5.23 mg, 0.015 mmol), cesium carbonate (95 mg, 0.29 mmol), potassium (2Z)-2-buten-2-yltrifluoroborate (31.6 mg, 0.195 mmol) and (R)-8-(4-chloropyridin-2-yl)-6-((1-cyclobutylethyl)amino)-7-(4-(trifluoromethyl)benzyl)-7H-purine-2-carbonitrile (50 mg, 0.098 mmol) in a 2 ml mw vial in a mixture solvent of 1,4-dioxane (500 ul) and water (100 uL) was evacuated and refilled with Ar (3×). The resulted solution was heated by microwave irradiation to a temperature of 120° C. for 10 minutes. The mixture was cooled down and quenched with saturated sodium bicarbonate and ethyl acetate. The organic layer was collected and concentrated. The residue was dissolved in DCM and loaded to column (12 g isco column), eluted with Ethyl acetate in hexane (0-100%) to give (R,Z)-8-(4-(but-2-en-2-yl)pyridin-2-yl)-6-((1-cyclobutylethyl)amino)-7-(4-(trifluoromethyl)benzyl)-7H-purine-2-carbonitrile as a yellow solid. MS ESI calc'd For $C_{29}H_{28}F_3N_7$ [M+H]$^+$ 532. found 532.

Step 3: To an ethanol (1 ml) solution of (R,Z)-8-(4-(but-2-en-2-yl)pyridin-2-yl)-6-((1-cyclobutylethyl)amino)-7-(4-(trifluoromethyl)benzyl)-7H-purine-2-carbonitrile (50 mg, 0.094 mmol) was added sodium hydroxide (5.0 M in water, 1 mL, 5.0 mmol). Reaction was brought to 70° C. and stirred for 2 h. LCMS shows starting material consumed. The solution was used for next step directly. MS ESI calc'd For $C_{29}H_{29}F_3N_6O_2$ [M+H]$^+$ 551. found 551.

Step 4: A solution including (R,Z)-8-(4-(but-2-en-2-yl)pyridin-2-yl)-6-((1-cyclobutylethyl)amino)-7-(4-(trifluoromethyl)benzyl)-7H-purine-2-carboxylic acid (62.5 mg, 0.094 mmol) from last step was degassed with Ar (3×) and then added palladium (10% wt Carbon, 50 mg, 0.47 mmol). The reaction stirred at room temperature for 2 h and filtered through a pad of Celite and the filtrate was concentrated. The remaining residue was dissolved in Ethyl acetate (3 mL) and neutralized with HCl (1 N) to pH=7, and then washed with Brine. The organic layer was dried over sodium sulfate and concentrated to afford 8-(4-(sec-butyl)pyridin-2-yl)-6-(((R)-1-cyclobutylethyl)amino)-7-(4-(trifluoromethyl)benzyl)-7H-purine-2-carboxylic acid. It was used for next step without further purification. MS ESI calc'd For $C_{29}H_{31}F_3N_6O_2$ [M+H]$^+$ 553. found 553.

Step 5: To a solution of 8-(4-(sec-butyl)pyridin-2-yl)-6-(((R)-1-cyclobutylethyl)amino)-7-(4-(trifluoromethyl)benzyl)-7H-purine-2-carboxylic acid (60 mg, 0.109 mmol) in DCM (1.5 ml) at 0° C. was added drops of DMF and followed by Oxalyl chloride (0.039 ml, 0.434 mmol). Raise the temperature to room temperature and stirred for 15 min, lots of solid precipitated. Methanol (1 mL) was added to quench reaction. The mixture was concentrated and the residue dissolved in ethyl acetate and washed with saturated sodium bicarbonate and brine. The organic phase collected, dried with sodium sulfate and concentrated to form white solid which was purified with silica gel column (0-100% ethyl acetate/hex) to afford methyl 8-(4-(sec-butyl)pyridin-2-yl)-6-(((R)-1-cyclobutylethyl)amino)-7-(4-(trifluoromethyl)benzyl)-7H-purine-2-carboxylate as a white solid. MS ESI calc'd For $C_{30}H_{33}F_3N_6O_2$ [M+H]$^+$ 567. found 567. The product was then chiral separated to two isomers using the condition below: SFC Column: Chiral Technology Lux4 2.1×25 cm, 5 uM. MP: 30%/70% Ethanol+0.25% dimethyl ethylamine/CO2. Flow rate: 70 mL/Min, 16.5 min run time. WL: 220 nm. Submitted 42 mg, dissolved up in 2 ml methanol. Injections of 0.2 ml were performed on the Berger Multigram II SFC in 3-201. Elution was observed at 12.9 minutes (diastereoisomer 1) and 14.3 minutes (diastereoisomer 2).

Step 6: To a solution of methyl 8-(4-(sec-butyl)pyridin-2-yl)-6-(((R)-1-cyclobutylethyl)amino)-7-(4-(trifluoromethyl)benzyl)-7H-purine-2-carboxylate (diastereoisomer 1) in a mixture solvents of THF (0.5 mL), methanol (0.2 mL) and water (0.2 mL) was added lithium hydroxide (16.91 mg, 0.706 mmol). The reaction was stirred at room temperature for 2 hours. The solution was added TFA to adjust pH to 6 and purified to afford 8-(4-(sec-butyl)pyridin-2-yl)-6-(((R)-1-cyclobutylethyl)amino)-7-(4-(trifluoromethyl)benzyl)-7H-purine-2-carboxylic acid. MS ESI calc'd For $C_{29}H_{31}F_3N_6O_2$ [M+H]$^+$ 553. found 553. $^1$H NMR (500 MHz, CDCl$_3$): δ 0.90-0.86 (m, 3H); 1.33-1.29 (m, 3H); 1.40 (t, J=10.4 Hz, 1H); 1.72-1.56 (m, 7H); 1.99-1.87 (m, 3H); 2.74 (d, J=8.7 Hz, 1H); 3.18 (br s, 1H); 4.39 (d, J=8.9 Hz, 1H); 4.65 (d, J=7.7 Hz, 1H); 6.37 (d, J=17.3 Hz, 1H); 6.58 (d, J=17.1 Hz, 1H); 7.26-7.25 (m, 1H); 7.38 (d, J=7.7 Hz, 2H); 7.72 (d, J=7.6 Hz, 2H); 8.42 (d, J=25.7 Hz, 2H).

Preparative Example 1.7

2-Chloro-4-isopropyl-5-methylpyridine and 2-chloro-4-isopropyl-3-methylpyridine

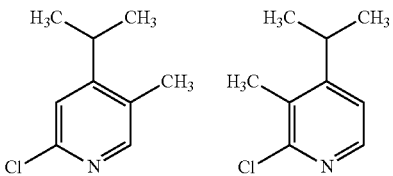

Step 1: To a solution of 3-methylpyridine (10.0 g, 107 mmol) in THF (100 mL) was added copper(I) iodide (0.67 g, 3.54 mmol). The mixture was stirred until homogeneous and then the mixture was cooled to −20° C. Ethyl chloroformate (8.1 g, 75.1 mmol) was added dropwise at −20° C. under a nitrogen atmosphere. A white precipitate formed. Isopropylmagnesium bromide (75.1 mL, 1 M solution) was then added dropwise at −20° C. and the resulting mixture was stirred at −20° C. for 15 minutes followed by warming to room temperature and stirring for 15 minutes. After this time, the reaction mixture quenched with 20% aqueous ammonium chloride (30 mL) and the reaction mixture was extracted with MTBE (3×50 mL). The combined organic layers were washed with water (1×50 mL), 10% aqueous HCl (50 mL), water (50 mL) and brine (50 mL). The resulting organic layer was dried over sodium sulfate, filtered and concentrated under reduced pressure to afford ethyl 4-isopropyl-3-methylpyridine-1(4H)-carboxylate as a yellow oil.

Step 2: To a room temperature solution of ethyl 4-isopropyl-3-methylpyridine-1(4H)-carboxylate (5.3 g, 25.3 mmol) in dichloromethane (50 mL) was added acetic acid (10 ml) and 2,3-dichloro-5,6-dicyanobenzoquinone (2.8 g, 12.6 mmol) and the reaction was stirred as such overnight. The pH was then adjusted to pH 7 using 1 N aqueous sodium hydroxide and the resulting mixture was extracted with EtOAc (3×50 mL). The combined organic layers were washed with water (50 mL) and brine (50 mL), dried over sodium sulfate, filtered and concentrated under reduced pressure. The resulting residue was purified using a Redisep 120 g silica gel column (0 to 100% EtOAc/hexanes) to afford 4-isopropyl-3-methylpyridine as colorless oil.

Step 3: To a room temperature solution of 4-isopropyl-3-methylpyridine (1.85 g, 13.6 mmol) in dichloromethane (150 mL) was added m-CPBA (4.73 g, 27.3 mmol). The resulting mixture was stirred at room temperature for 3 hours. After this time, the reaction mixture was diluted with dichloromethane (50 mL) and washed with 10% aqueous sodium hydroxide (2×40 mL). The organic layer was concentrated to afford 4-isopropyl-3-methylpyridine 1-oxide that was used for next step without further purification.

Step 4: A solution of 4-isopropyl-3-methylpyridine 1-oxide (500 mg, 3.3 mmol) in phosphorus oxychloride (10 mL) was subjected to microwave irradiation at 150° C. for 1 hour. After this time the reaction was carefully poured into stirring ice water (50 mL) and pH was adjusted to ~8 using ammonium hydroxide. The resulting mixture was extracted with EtOAc (2×100 mL). The combined organic layers were dried over sodium sulfate and concentrated under reduced pressure. The resulting residue was purified on a Redisep 120 g silica gel column (0 to 100% EtOAc/hexanes) to afford a mixture of 2-chloro-4-isopropyl-5-methylpyridine and 2-chloro-4-isopropyl-3-methylpyridine. MS (APCI)=170 (M+1)$^+$.

Preparative Example 1.8

2-Bromo-4-ethyl-1-(methoxymethoxy)benzene

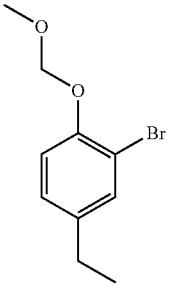

To a solution of 2-bromo-4-ethylphenol (500 mg, 2.49 mmol) in anhydrous dichloromethane (10 mL) was added chloro(methoxy)methane (400 mg, 4.98 mmol) at 0° C., followed by the addition of DIPEA (1.70 mL, 9.96 mmol). The reaction mixture was warmed slowly to room temperature and stirred at room temperature overnight. The reaction mixture was washed with water, brine and dried over sodium sulfate. The solvent was evaporated under vacuum. Purification of the residue on a Redisep 12 g silica gel column with 0 to 5% EtOAc/hexanes afforded 2-bromo-4-ethyl-1-(methoxymethoxy)benzene. $^1$H NMR (300 MHz, CDCl$_3$) δ 7.38 (s, 1H), 7.06 (d, J=1.2 Hz, 2H), 5.21 (s, 2H), 3.52 (s, 3H), 2.57 (q, J=7.8 Hz, 2H), 1.21 (d, J=6.8 Hz, 3H).

Preparative Example 1.9

2-Bromo-4-isopropyl-1-(methoxymethoxy)benzene

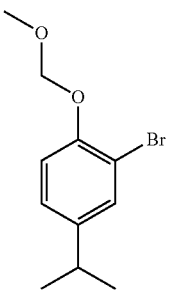

Using a procedure analogous to that described in Preparative Example 1.8 and starting with 2-bromo-4-isopropylphenol, 2-bromo-4-isopropyl-1-(methoxymethoxy)benzene was prepared. $^1$H NMR (300 MHz, CDCl$_3$) δ 7.38 (m, 1H), 7.04-7.11 (m, 2H), 5.21 (s, 2H), 3.52 (s, 3H), 2.83 (m, 1H), 1.21 (d, J=6.8 Hz, 6H).

The following compounds in Table 1 (other than Example 1.1 to 1.14 and Examples 1.32, 1.33, 1.85, 1.88 and 1.89) were prepared using procedures which are analogous to those described above in Example 1.1 (steps 2 and 3). Examples 1.32 and 1.33 were prepared analogously to Example 1.12. Examples 1.85, 1.88 and 1.89 were prepared analogously to Example 1.14.

TABLE 1

| Ex. | FRET IC$_{50}$ (nM) | Structure | Chemical Name | Salt Form | [M + H]$^+$ Calc'd | [M + H]$^+$ Obsv'd |
|-----|---------------------|-----------|---------------|-----------|---------------------|---------------------|
| 1.1 | 11.44 | 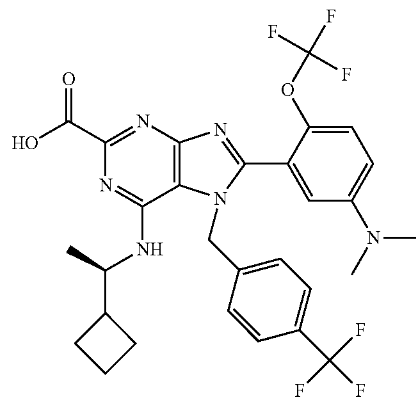 [SMILES: C[C@@H](Nc1nc(C(=O)O)nc2nc(-c3cc(N(C)C)ccc3OC(F)(F)F)n(Cc3ccc(C(F)(F)F)cc3)c12)C1CCC1] | (R)-6-((1-cyclobutylethyl)amino)-8-(5-(dimethylamino)-2-(trifluoromethoxy)phenyl)-7-(4-(trifluoromethyl)benzyl)-7H-purine-2-carboxylic acid | | 623 | 623 |
| 1.2 | 23.75 | 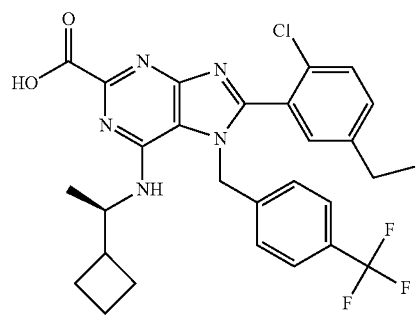 [SMILES: CCc1ccc(Cl)c(-c2nc3nc(C(=O)O)nc(N[C@H](C)C4CCC4)c3n2Cc2ccc(C(F)(F)F)cc2)c1] | (R)-8-(2-chloro-5-ethylphenyl)-6-((1-cyclobutylethyl)amino)-7-(4-(trifluoromethyl)benzyl)-7H-purine-2-carboxylic acid | | 558 | 558 |
| 1.3 | 15.25 | 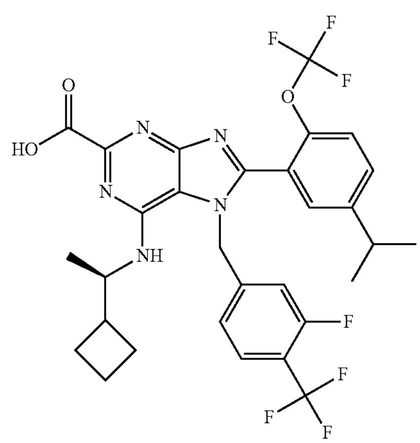 [SMILES: CC(C)c1ccc(OC(F)(F)F)c(-c2nc3nc(C(=O)O)nc(N[C@H](C)C4CCC4)c3n2Cc2ccc(C(F)(F)F)c(F)c2)c1] | (R)-6-((1-cyclobutylethyl)amino)-7-(3-fluoro-4-(trifluoromethyl)benzyl)-8-(5-isopropyl-2-(trifluoromethoxy)phenyl)-7H-purine-2-carboxylic acid | | 640 | 640 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.4 | 58.76 | 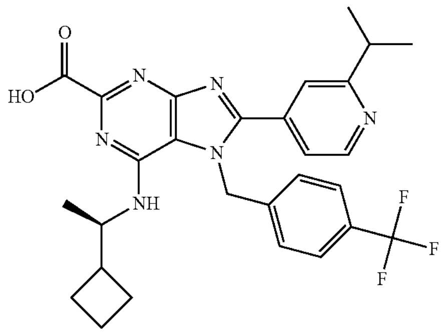 [SMILES: CC(C)c1cc(-c2nc3nc(C(=O)O)nc(N[C@H](C)C4CCC4)c3n2Cc2ccc(C(F)(F)F)cc2)ccn1] | (R)-6-((1-cyclobutylethyl)amino)-8-(2-isopropylpyridin-4-yl)-7-(4-(trifluoromethyl)benzyl)-7H-purine-2-carboxylic acid | | 539 | 539 |
| 1.5 | 50.18 | 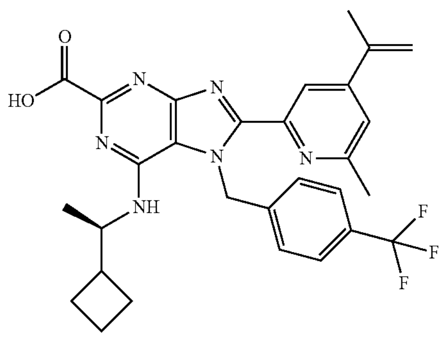 [SMILES: C=C(C)c1cc(C)nc(-c2nc3nc(C(=O)O)nc(N[C@H](C)C4CCC4)c3n2Cc2ccc(C(F)(F)F)cc2)c1] | (R)-6-((1-cyclobutylethyl)amino)-8-(6-methyl-4-(prop-1-en-2-yl)pyridin-2-yl)-7-(4-(trifluoromethyl)benzyl)-7H-purine-2-carboxylic acid | | 551 | 551 |
| 1.6 | 2.793 | 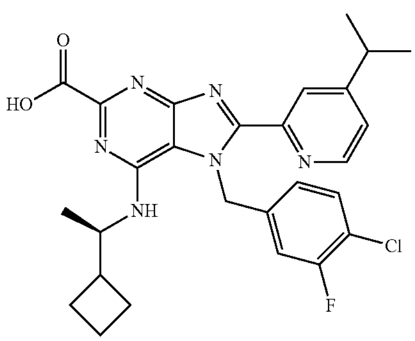 [SMILES: CC(C)c1ccnc(-c2nc3nc(C(=O)O)nc(N[C@H](C)C4CCC4)c3n2Cc2ccc(Cl)c(F)c2)c1] | 7-(4-chloro-3-fluorobenzyl)-6-{[(1R)-1-cyclobutylethyl]amino}-8-[4-(propan-2-yl)pyridin-2-yl]-7H-purine-2-carboxylic acid | TFA | 523 | 523 |
| 1.7 | 26.95 | 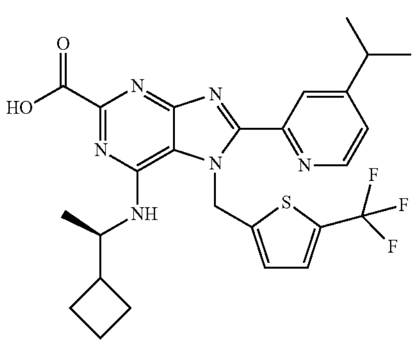 [SMILES: CC(C)c1ccnc(-c2nc3nc(C(=O)O)nc(N[C@H](C)C4CCC4)c3n2Cc2ccc(C(F)(F)F)s2)c1] | 6-{[(1R)-1-cyclobutylethyl]amino}-8-[4-(propan-2-yl)pyridin-2-yl]-7-{[5-(trifluoromethyl)thiophen-2-yl]methyl}-7H-purine-2-carboxylic acid | TFA | 545 | 545 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.8 | 20.05 | 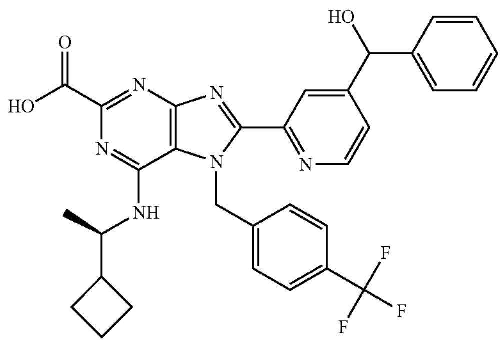 [SMILES: C[C@@H](Nc1nc(C(=O)O)nc2nc(-c3cc(C(O)c4ccccc4)ccn3)n(Cc3ccc(C(F)(F)F)cc3)c12)C1CCC1] | 6-(((R)-1-cyclobutylethyl)amino)-8-(4-(hydroxy(phenyl)methyl)pyridin-2-yl)-7-(4-(trifluoromethyl)benzyl)-7H-purine-2-carboxylic acid | | 603 | 603 |
| 1.9 | 37.35 | 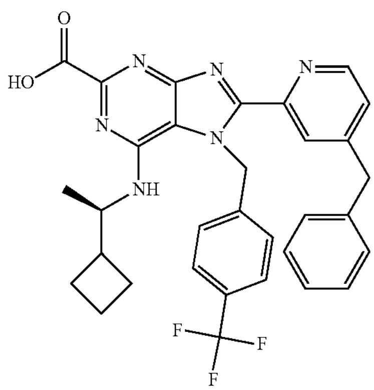 [SMILES: C[C@@H](Nc1nc(C(=O)O)nc2nc(-c3cc(Cc4ccccc4)ccn3)n(Cc3ccc(C(F)(F)F)cc3)c12)C1CCC1] | (R)-8-(4-benzylpyridin-2-yl)-6-((1-cyclobutylethyl)amino)-7-(4-(trifluoromethyl)benzyl)-7H-purine-2-carboxylic acid | | 587 | 587 |
| 1.10 | 3.958 | 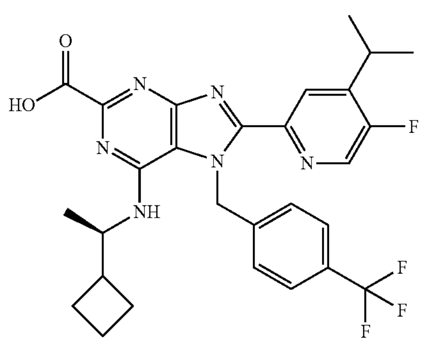 [SMILES: CC(C)c1cc(-c2nc3nc(C(=O)O)nc(N[C@H](C)C4CCC4)c3n2Cc2ccc(C(F)(F)F)cc2)ncc1F] | (R)-6-((1-cyclobutylethyl)amino)-8-(5-fluoro-4-isopropylpyridin-2-yl)-7-(4-(trifluoromethyl)benzyl)-7H-purine-2-carboxylic acid | | 557 | 557 |
| 1.11 | 50.33 | 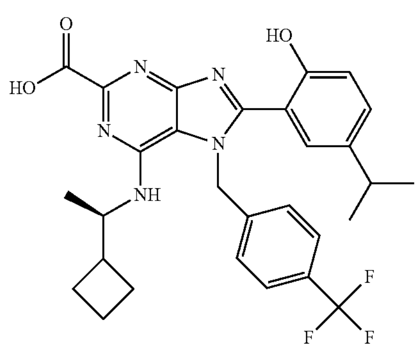 [SMILES: CC(C)c1ccc(O)c(-c2nc3nc(C(=O)O)nc(N[C@H](C)C4CCC4)c3n2Cc2ccc(C(F)(F)F)cc2)c1] | (R)-6-((1-cyclobutylethyl)amino)-8-(2-hydroxy-5-isopropylphenyl)-7-(4-(trifluoromethyl)benzyl)-7H-purine-2-carboxylic acid | | 554 | 554 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.12 | 29.43 | 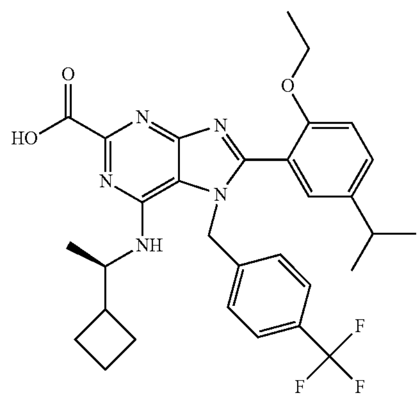 [SMILES: CCOc1ccc(C(C)C)cc1-c1nc2nc(C(=O)O)nc(N[C@H](C)C3CCC3)c2n1Cc1ccc(C(F)(F)F)cc1] | (R)-6-((1-cyclobutylethyl)amino)-8-(2-ethoxy-5-isopropylphenyl)-7-(4-(trifluoromethyl)benzyl)-7H-purine-2-carboxylic acid | | 582 | 582 |
| 1.13 | 157.7 | 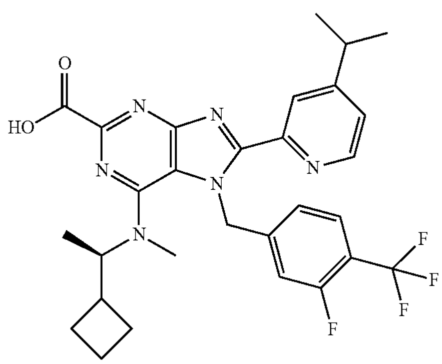 [SMILES: CC(C)c1ccnc(-c2nc3nc(C(=O)O)nc(N(C)[C@H](C)C4CCC4)c3n2Cc2ccc(C(F)(F)F)c(F)c2)c1] | (R)-6-((1-cyclobutylethyl)(methyl)amino)-7-(3-fluoro-4-(trifluoromethyl)benzyl)-8-(4-isopropylpyridin-2-yl)-7H-purine-2-carboxylic acid | TFA | 571 | 571 |
| 1.14 | 3.647 | 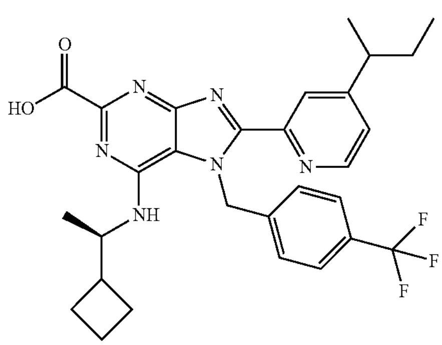 [SMILES: CCC(C)c1ccnc(-c2nc3nc(C(=O)O)nc(N[C@H](C)C4CCC4)c3n2Cc2ccc(C(F)(F)F)cc2)c1] | 8-(4-(sec-butyl)pyridin-2-yl)-6-(((R)-1-cyclobutylethyl)amino)-7-(4-(trifluoromethyl)benzyl)-7H-purine-2-carboxylic acid (diastereoisomer 1) | | 553 | 553 |
| 1.15 | 3.324 | 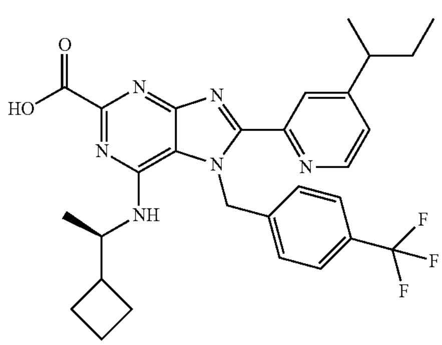 [SMILES: CCC(C)c1ccnc(-c2nc3nc(C(=O)O)nc(N[C@H](C)C4CCC4)c3n2Cc2ccc(C(F)(F)F)cc2)c1] | 8-(4-(sec-butyl)pyridin-2-yl)-6-(((R)-1-cyclobutylethyl)amino)-7-(4-(trifluoromethyl)benzyl)-7H-purine-2-carboxylic acid (diastereoisomer 2) | | 553 | 553 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.16 | 25.32 | 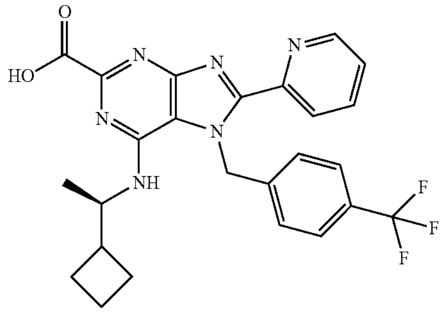 [SMILES: C[C@@H](Nc1nc(C(=O)O)nc2nc(-c3ccccn3)n(Cc3ccc(C(F)(F)F)cc3)c12)C1CCC1] | 6-{[(1R)-1-cyclobutylethyl]amino}-8-pyridin-2-yl-7-[4-(trifluoromethyl)benzyl]-7H-purine-2-carboxylic acid | TFA | 497 | 497 |
| 1.17 | 12.72 | 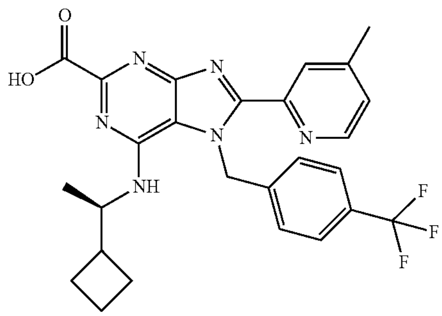 | 6-{[(1R)-1-cyclobutylethyl]amino}-8-(4-methylpyridin-2-yl)-(trifluoromethyl)benzyl]-7H-purine-2-carboxylic acid | TFA | 511 | 511 |
| 1.18 | 45.66 | 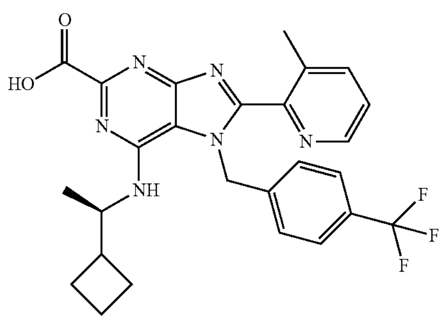 [SMILES: Cc1cccnc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(3-methylpyridin-2-yl)-7-[4-(trifluoromethyl)benzyl]-7H-purine-2-carboxylic acid | TFA | 511 | 511 |
| 1.19 | 42.46 | 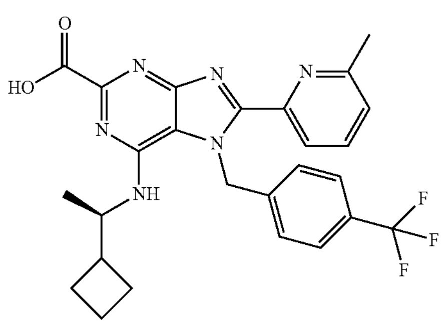 [SMILES: Cc1cccc(-c2nc3nc(C(=O)O)nc(N[C@H](C)C4CCC4)c3n2Cc2ccc(C(F)(F)F)cc2)n1] | 6-{[(1R)-1-cyclobutylethyl]amino}-8-(6-methylpyridin-2-yl)-7-[4-(trifluoromethyl)benzyl]-7H-purine-2-carboxylic acid | TFA | 511 | 511 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.20 | 24.1 | 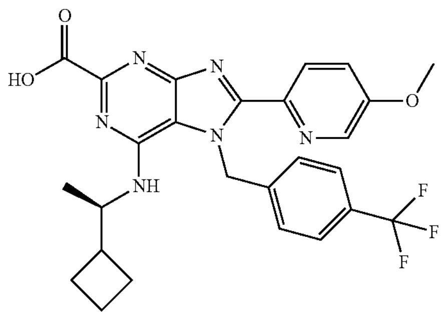 [SMILES: COc1ccc(-c2nc3nc(C(=O)O)nc(N[C@H](C)C4CCC4)c3n2Cc2ccc(C(F)(F)F)cc2)nc1] | 6-{[(1R)-1-cyclobutylethyl]amino}-8-(5-methoxypyridin-2-yl)-7-[4-(trifluoromethyl)benzyl]-7H-purine-2-carboxylic acid | TFA | 527 | 527 |
| 1.21 | 26.98 | 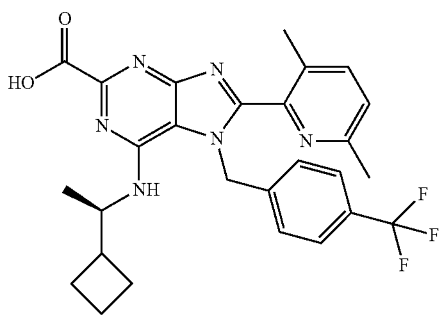 [SMILES: Cc1ccc(C)c(-c2nc3nc(C(=O)O)nc(N[C@H](C)C4CCC4)c3n2Cc2ccc(C(F)(F)F)cc2)n1] | 6-{[(1R)-1-cyclobutylethyl]amino}-8-(3,6-dimethylpyridin-2-yl)-7-[4-(trifluoromethyl)benzyl]-7H-purine-2-carboxylic acid | TFA | 525 | 525 |
| 1.22 | 4.217 | 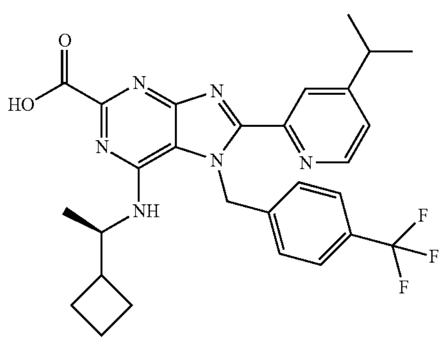 [SMILES: CC(C)c1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[4-(1-methylethyl)pyridin-2-yl]-7-[4-(trifluoromethyl)benzyl]-7H-purine-2-carboxylic acid | TFA | 539 | 539 |
| 1.23 | 13.12 | 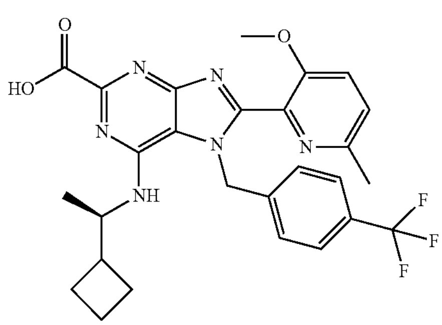 [SMILES: COc1ccc(C)nc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(3-methoxy-6-methylpyridin-2-yl)-7-[4-(trifluoromethyl)benzyl]-7H-purine-2-carboxylic acid | TFA | 541 | 541 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.24 | 112.2 | 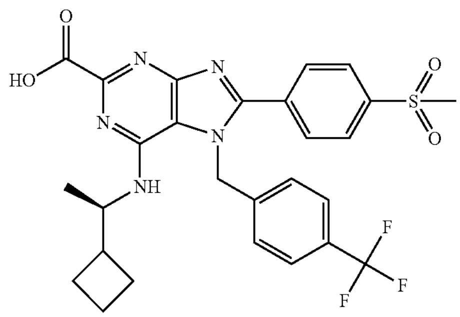 [SMILES: C[C@@H](Nc1nc(C(=O)O)nc2nc(-c3ccc(S(C)(=O)=O)cc3)n(Cc3ccc(C(F)(F)F)cc3)c12)C1CCC1] | 6-{[(1R)-1-cyclobutylethyl]amino}-8-[4-(methylsulfonyl)phenyl]-7-[4-(trifluoromethyl)benzyl]-7H-purine-2-carboxylic acid | | 574 | 574 |
| 1.25 | 1068 | 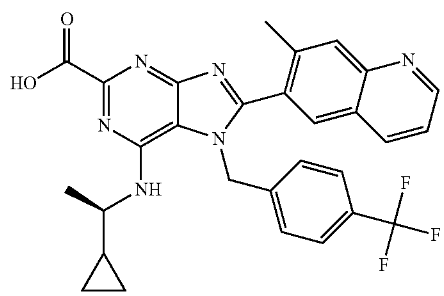 [SMILES: Cc1cc2ncccc2cc1-c1nc2nc(C(=O)O)nc(N[C@H](C)C3CC3)c2n1Cc1ccc(C(F)(F)F)cc1] | 6-{[(1R)-1-cyclopropylethyl]amino}-8-(7-methylquinolin-6-yl)-7-[4-(trifluoromethyl)benzyl]-7H-purine-2-carboxylic acid | | 547 | 547 |
| 1.26 | 12.12 | 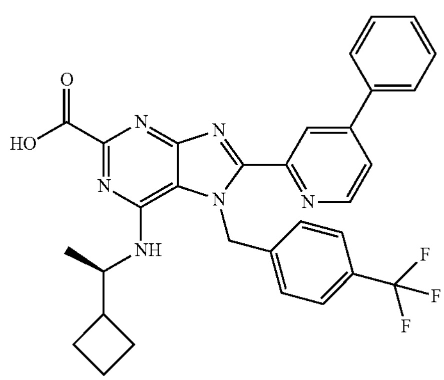 [SMILES: C[C@@H](Nc1nc(C(=O)O)nc2nc(-c3cc(-c4ccccc4)ccn3)n(Cc3ccc(C(F)(F)F)cc3)c12)C1CCC1] | 6-{[(1R)-1-cyclobutylethyl]amino}-8-(4-phenylpyridin-2-yl)-7-[4-(trifluoromethyl)benzyl]-7H-purine-2-carboxylic acid | TFA | 573 | 573 |
| 1.27 | 9.415 | 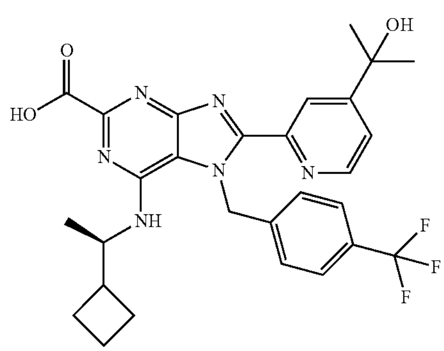 [SMILES: C[C@@H](Nc1nc(C(=O)O)nc2nc(-c3cc(C(C)(C)O)ccn3)n(Cc3ccc(C(F)(F)F)cc3)c12)C1CCC1] | 6-{[(1R)-1-cyclobutylethyl]amino}-8-[4-(1-hydroxy-1-methylethyl)pyridin-2-yl]-7-[4-(trifluoromethyl)benzyl]-7H-purine-2-carboxylic acid | TFA | 555 | 555 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.28 | 12.36 | 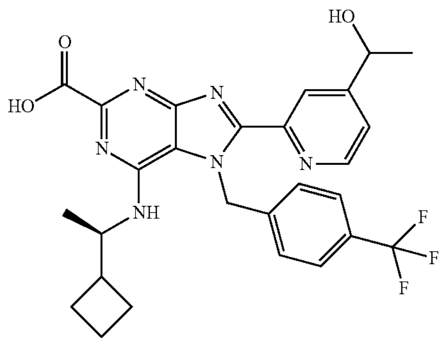 [SMILES: CC(O)c1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[4-(1-hydroxyethyl)pyridin-2-yl]-7-[4-(trifluoromethyl)benzyl]-7H-purine-2-carboxylic acid | TFA | 541 | 541 |
| 1.29 | 46.08 | 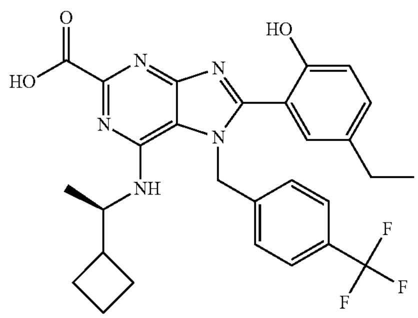 [SMILES: CCc1ccc(O)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(5-ethyl-2-hydroxyphenyl)-7-[4-(trifluoromethyl)benzyl]-7H-purine-2-carboxylic acid | | 540 | 540 |
| 1.30 | 54.41 | 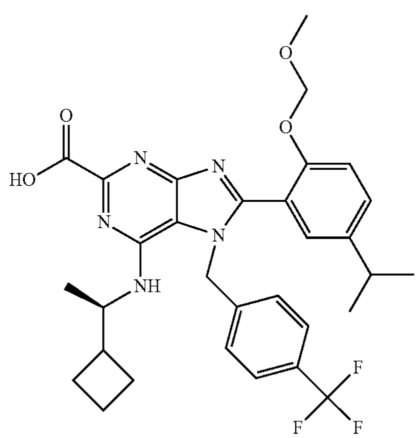 [SMILES: COCOc1ccc(C(C)C)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-(methoxymethoxy)-5-(1-methylethyl)phenyl]-7-[4-(trifluoromethyl)benzyl]-7H-purine-2-carboxylic acid | | 598 | 598 |
| 1.31 | 18.67 | 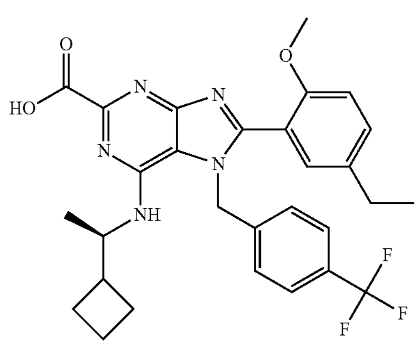 [SMILES: CCc1ccc(OC)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(5-ethyl-2-methoxyphenyl)-7-[4-(trifluoromethyl)benzyl]-7H-purine-2-carboxylic acid | | 554 | 554 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.32 | 23.62 | 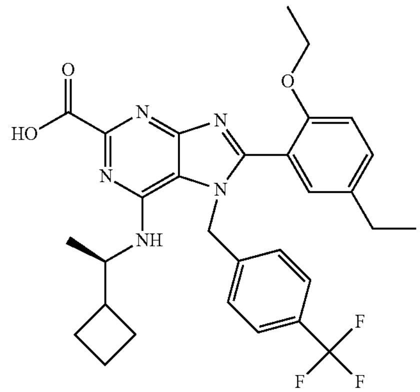 [SMILES: CCOc1ccc(CC)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(2-ethoxy-5-ethylphenyl)-7-[4-(trifluoromethyl)benzyl]-7H-purine-2-carboxylic acid | | 568 | 568 |
| 1.33 | 19.8 | 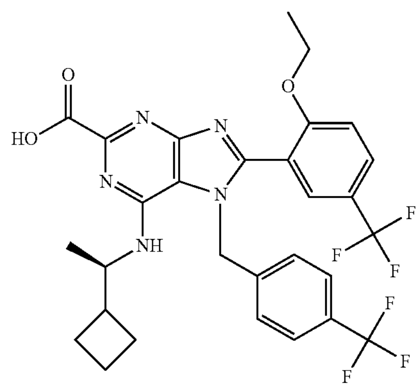 [SMILES: CCOc1ccc(C(F)(F)F)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-ethoxy-5-(trifluoromethyl)phenyl]-7-[4-(trifluoromethyl)benzyl]-7H-purine-2-carboxylic acid | | 608 | 608 |
| 1.35 | 27.75 | 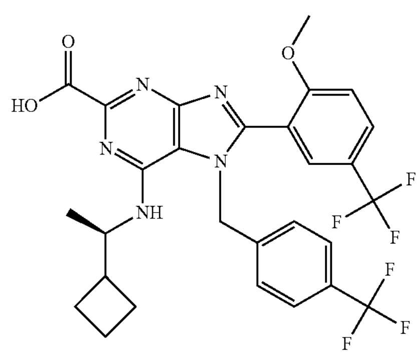 [SMILES: COc1ccc(C(F)(F)F)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-methoxy-5-(trifluoromethyl)phenyl]-7-[4-(trifluoromethyl)benzyl]-7H-purine-2-carboxylic acid | | 594 | 594 |
| 1.36 | 23.15 | 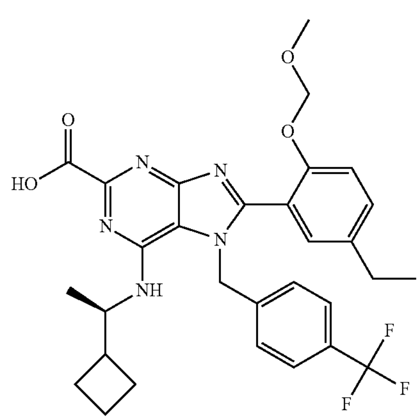 [SMILES: CCc1ccc(OCOC)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[5-ethyl-2-(methoxymethoxy)phenyl]-7-[4-(trifluoromethyl)benzyl]-7H-purine-2-carboxylic acid | | 584 | 584 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.37 | 49.38 | 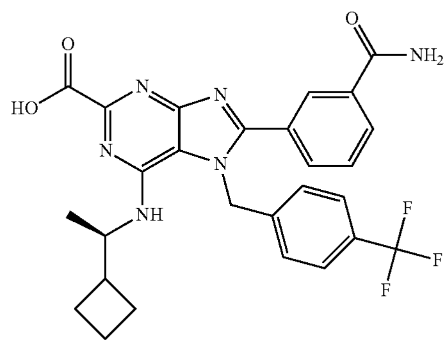 [SMILES: C[C@@H](Nc1nc(C(=O)O)nc2nc(-c3cccc(C(N)=O)c3)n(Cc3ccc(C(F)(F)F)cc3)c12)C1CCC1] | 8-(3-carbamoylphenyl)-6-{[(1R)-1-cyclobutylethyl]amino}-7-[4-(trifluoromethyl)benzyl]-7H-purine-2-carboxylic acid | | 539 | 539 |
| 1.38 | 27.51 | 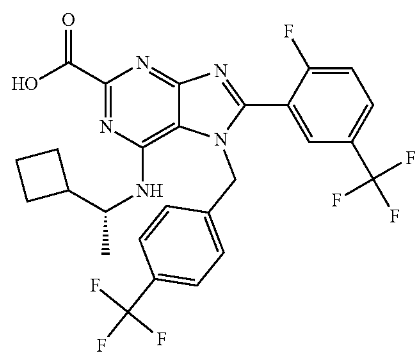 [SMILES: C[C@@H](Nc1nc(C(=O)O)nc2nc(-c3cc(C(F)(F)F)ccc3F)n(Cc3ccc(C(F)(F)F)cc3)c12)C1CCC1] | 6-{[(1R)-1-cyclobutylethyl]amino}-8-[2-fluoro-5-(trifluoromethyl)phenyl]-7-[4-(trifluoromethyl)benzyl]-7H-purine-2-carboxylic acid | | 582 | 582 |
| 1.39 | 58.5 | 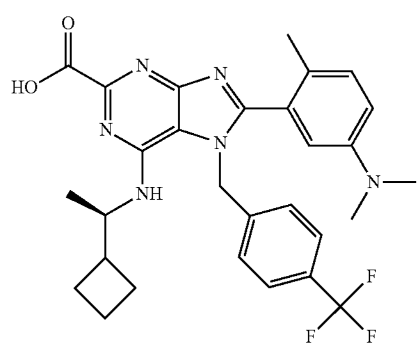 [SMILES: Cc1ccc(N(C)C)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[5-(dimethylamino)-2-methylphenyl]-7-[4-(trifluoromethyl)benzyl]-7H-purine-2-carboxylic acid | | 553 | 553 |
| 1.40 | 33.84 | 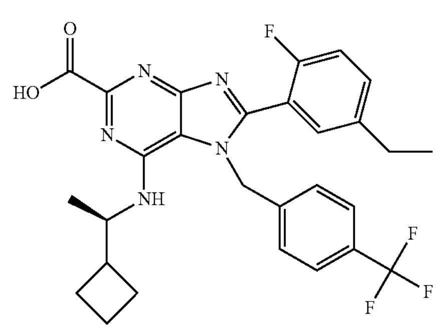 [SMILES: CCc1ccc(F)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(5-ethyl-2-fluorophenyl)-7-[4-(trifluoromethyl)benzyl]-7H-purine-2-carboxylic acid | | 542 | 542 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.41 | 27.54 | 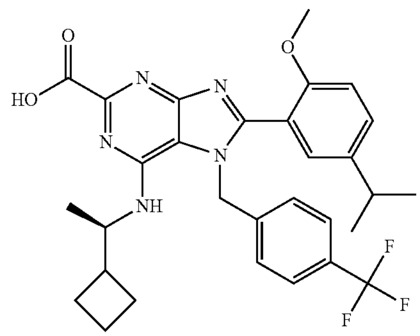 [SMILES: COc1ccc(C(C)C)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-methoxy-5-(1-methylethyl)phenyl]-7-[4-(trifluoromethyl)benzyl]-7H-purine-2-carboxylic acid | | 568 | 568 |
| 1.42 | 77.05 | 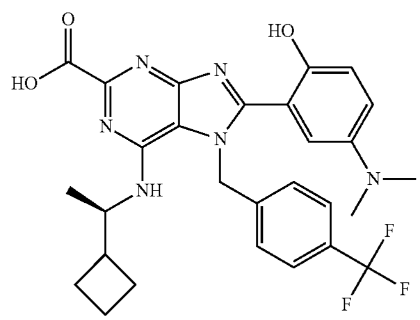 [SMILES: C[C@@H](Nc1nc(C(=O)O)nc2nc(-c3cc(N(C)C)ccc3O)n(Cc3ccc(C(F)(F)F)cc3)c12)C1CCC1] | 6-{[(1R)-1-cyclobutylethyl]amino}-8-[5-(dimethylamino)-2-hydroxyphenyl]-7-[4-(trifluoromethyl)benzyl]-7H-purine-2-carboxylic acid | | 555 | 555 |
| 1.43 | 11.77 | 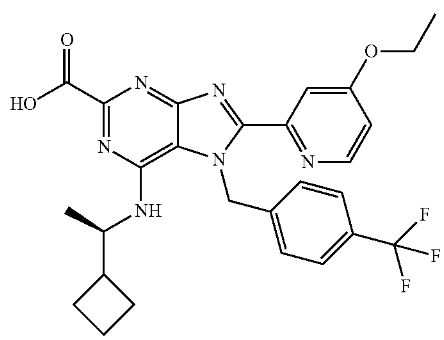 [SMILES: CCOc1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(4-ethoxypyridin-2-yl)-7-[4-(trifluoromethyl)benzyl]-7H-purine-2-carboxylic acid | TFA | 541 | 541 |
| 1.44 | 16.48 | 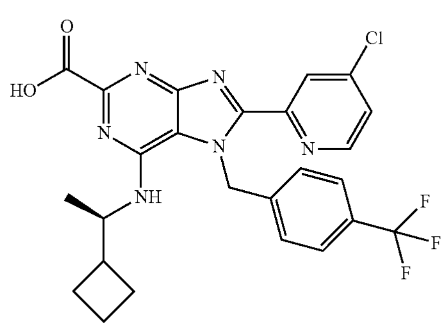 [SMILES: C[C@@H](Nc1nc(C(=O)O)nc2nc(-c3cc(Cl)ccn3)n(Cc3ccc(C(F)(F)F)cc3)c12)C1CCC1] | 8-(4-chloropyridin-2-yl)-6-{[(1R)-1-cyclobutylethyl]amino}-7-[4-(trifluoromethyl)benzyl]-7H-purine-2-carboxylic acid | TFA | 531 | 531 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.45 | 50.78 | 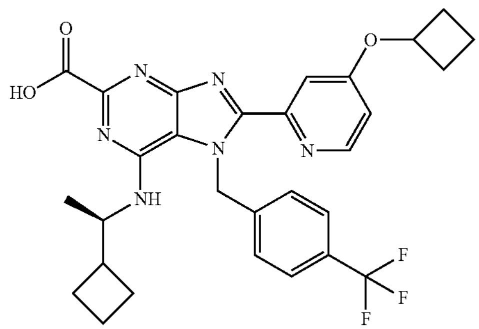 [SMILES: C[C@@H](Nc1nc(C(=O)O)nc2nc(-c3cc(OC4CCC4)ccn3)n(Cc3ccc(C(F)(F)F)cc3)c12)C1CCC1] | 6-{[(1R)-1-cyclobutylethyl]amino}-8-[4-(cyclobutyloxy)pyridin-2-yl]-7-[4-(trifluoromethyl)benzyl]-7H-purine-2-carboxylic acid | TFA | 567 | 567 |
| 1.46 | 12.28 | 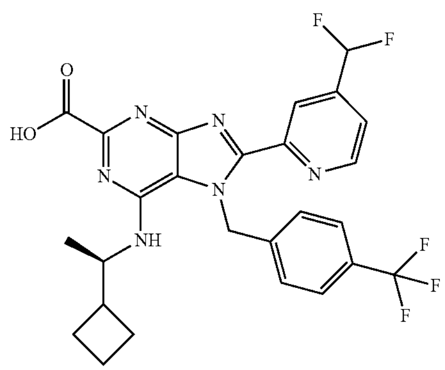 [SMILES: C[C@@H](Nc1nc(C(=O)O)nc2nc(-c3cc(C(F)F)ccn3)n(Cc3ccc(C(F)(F)F)cc3)c12)C1CCC1] | 6-{[(1R)-1-cyclobutylethyl]amino}-8-[4-(difluoromethyl)pyridin-2-yl]-7-[4-(trifluoromethyl)benzyl]-7H-purine-2-carboxylic acid | TFA | 547 | 547 |
| 1.47 | 16.35 | 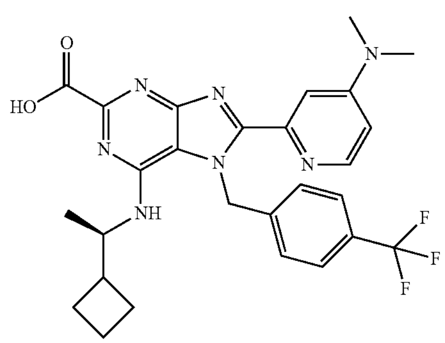 [SMILES: C[C@@H](Nc1nc(C(=O)O)nc2nc(-c3cc(N(C)C)ccn3)n(Cc3ccc(C(F)(F)F)cc3)c12)C1CCC1] | 6-{[(1R)-1-cyclobutylethyl]amino}-(dimethylamino)pyridin-2-yl]-7-[4-(trifluoromethyl)benzyl]-7H-purine-2-carboxylic acid | TFA | 540 | 540 |
| 1.48 | 2265 | 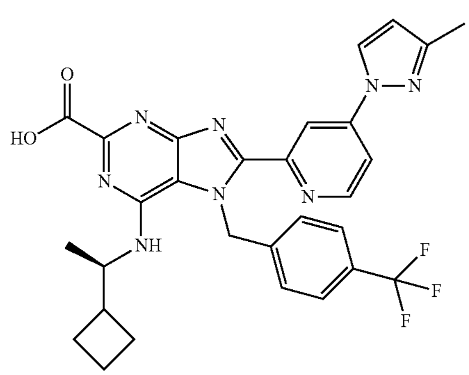 [SMILES: Cc1ccn(-c2ccnc(-c3nc4nc(C(=O)O)nc(N[C@H](C)C5CCC5)c4n3Cc3ccc(C(F)(F)F)cc3)c2)n1] | 6-{[(1R)-1-cyclobutylethyl]amino}-8-[4-(3-methyl-1H-pyrazol-1-yl)pyridin-2-yl]-7-[4-(trifluoromethyl)benzyl]-7H-purine-2-carboxylic acid | TFA | 577 | 577 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.49 | 3.521 | 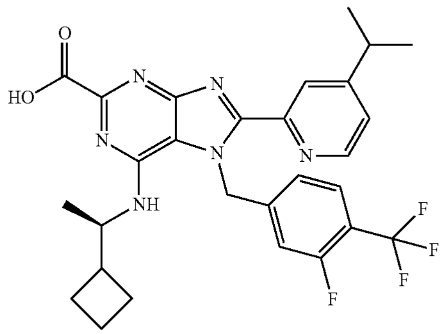 [SMILES: CC(C)c1ccnc(-c2nc3nc(C(=O)O)nc(N[C@H](C)C4CCC4)c3n2Cc2ccc(C(F)(F)F)c(F)c2)c1] | 6-{[(1R)-1-cyclobutylethyl]amino}-7-[3-fluoro-4-(trifluoromethyl)benzyl]-8-[4-(1-methylethyl)pyridin-2-yl]-7H-purine-2-carboxylic acid | TFA | 557 | 557 |
| 1.50 | 127.8 | 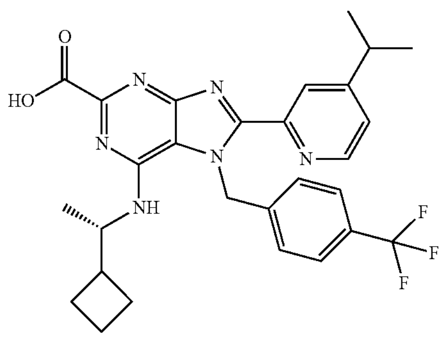 [SMILES: CC(C)c1ccnc(-c2nc3nc(C(=O)O)nc(N[C@@H](C)C4CCC4)c3n2Cc2ccc(C(F)(F)F)cc2)c1] | 6-{[(1S)-1-cyclobutylethyl]amino}-8-[4-(1-methylethyl)pyridin-2-yl]-7-[4-(trifluoromethyl)benzyl]-7H-purine-2-carboxylic acid | TFA | 539 | 539 |
| 1.51 | 8.389 | 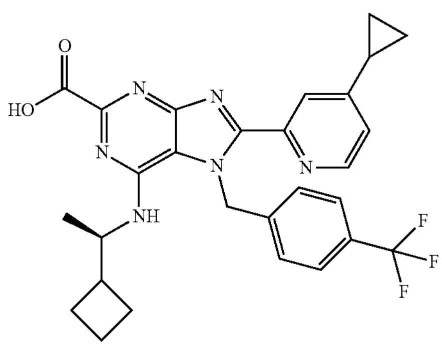 [SMILES: C[C@@H](Nc1nc(C(=O)O)nc2nc(-c3cc(C4CC4)ccn3)n(Cc3ccc(C(F)(F)F)cc3)c12)C1CCC1] | 6-{[(1R)-1-cyclobutylethyl]amino}-8-(4-cyclopropylpyridin-2-yl)-7-[4-(trifluoromethyl)benzyl]-7H-purine-2-carboxylic acid | TFA | 537 | 537 |
| 1.52 | 6.249 | 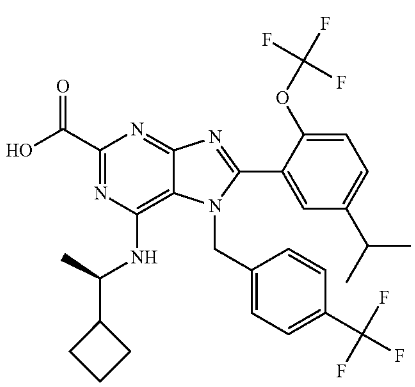 [SMILES: CC(C)c1ccc(OC(F)(F)F)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[5-(1-methylethyl)-2-(trifluoromethoxy)phenyl]-7-[4-(trifluoromethyl)benzyl]-7H-purine-2-carboxylic acid | | 622 | 622 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.53 | 4.364 | 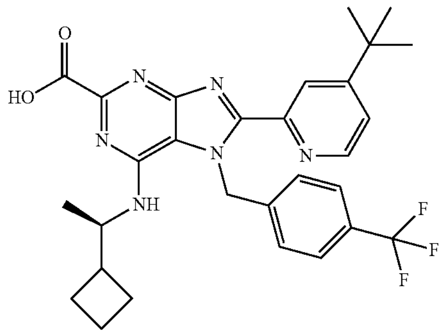 [SMILES: C[C@@H](Nc1nc(C(=O)O)nc2nc(-c3cc(C(C)(C)C)ccn3)n(Cc3ccc(C(F)(F)F)cc3)c12)C1CCC1] | 8-(4-tert-butylpyridin-2-yl)-6-{[(1R)-1-cyclobutylethyl]amino}-7-[4-(trifluoromethyl)benzyl]-7H-purine-2-carboxylic acid | TFA | 553 | 553 |
| 1.54 | 5.605 | 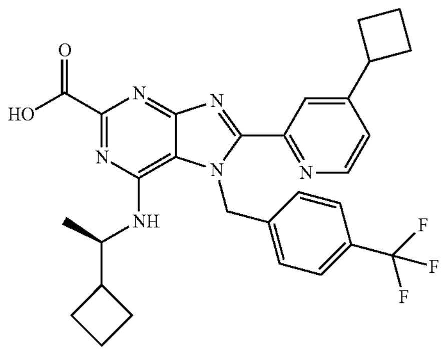 [SMILES: C[C@@H](Nc1nc(C(=O)O)nc2nc(-c3cc(C4CCC4)ccn3)n(Cc3ccc(C(F)(F)F)cc3)c12)C1CCC1] | 6-{[(1R)-1-cyclobutylethyl]amino}-8-(4-cyclobutylpyridin-2-yl)-7-[4-(trifluoromethyl)benzyl]-7H-purine-2-carboxylic acid | TFA | 551 | 551 |
| 1.55 | 4.771 | 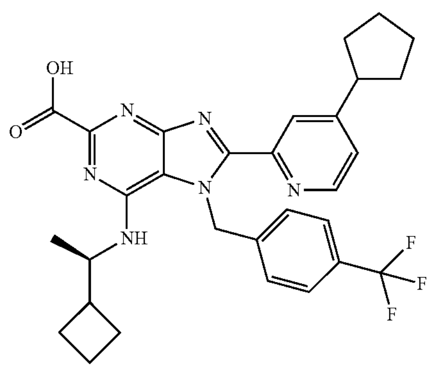 [SMILES: C[C@@H](Nc1nc(C(=O)O)nc2nc(-c3cc(C4CCCC4)ccn3)n(Cc3ccc(C(F)(F)F)cc3)c12)C1CCC1] | 6-{[(1R)-1-cyclobutylethyl]amino}-8-(4-cyclopentylpyridin-2-yl)-7-[4-(trifluoromethyl)benzyl]-7H-purine-2-carboxylic acid | TFA | 565 | 565 |
| 1.56 | 6.99 | 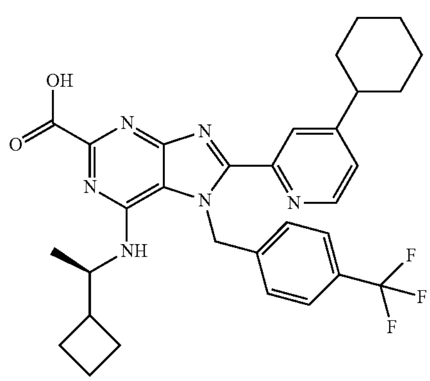 [SMILES: C[C@@H](Nc1nc(C(=O)O)nc2nc(-c3cc(C4CCCCC4)ccn3)n(Cc3ccc(C(F)(F)F)cc3)c12)C1CCC1] | 6-{[(1R)-1-cyclobutylethyl]amino}-8-(4-cyclohexylpyridin-2-yl)-7-[4-(trifluoromethyl)benzyl]-7H-purine-2-carboxylic acid | TFA | 579 | 579 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.57 | 5.954 | 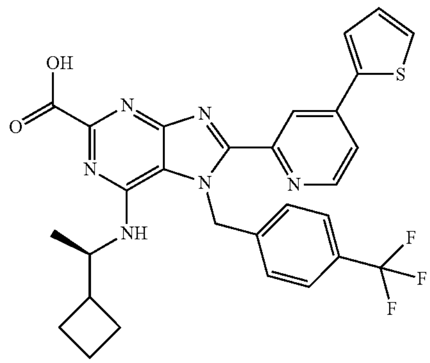 [SMILES: C[C@@H](Nc1nc(C(=O)O)nc2nc(-c3cc(-c4cccs4)ccn3)n(Cc3ccc(C(F)(F)F)cc3)c12)C1CCC1] | 6-{[(1R)-1-cyclobutylethyl]amino}-8-(4-thiophen-2-ylpyridin-2-yl)-7-[4-(trifluoromethyl)benzyl]-7H-purine-2-carboxylic acid | TFA | 579 | 579 |
| 1.58 | 16.93 | 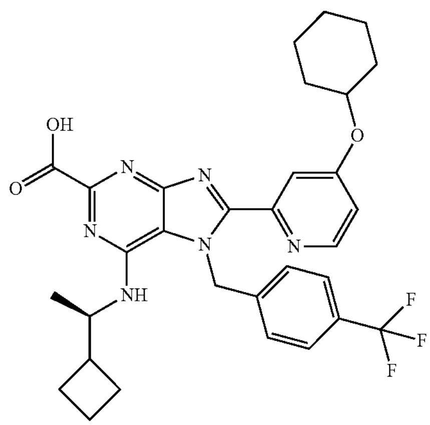 [SMILES: C[C@@H](Nc1nc(C(=O)O)nc2nc(-c3cc(OC4CCCCC4)ccn3)n(Cc3ccc(C(F)(F)F)cc3)c12)C1CCC1] | 6-{[(1R)-1-cyclobutylethyl]amino}-8-[4-(cyclohexyloxy)pyridin-2-yl]-7-[4-(trifluoromethyl)benzyl]-7H-purine-2-carboxylic acid | TFA | 595 | 595 |
| 1.59 | 7.047 | 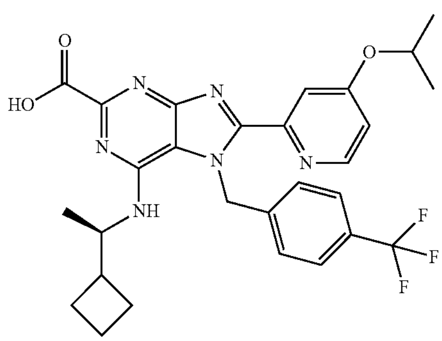 | 6-{[(1R)-1-cyclobutylethyl]amino}-8-[4-(1-methylethoxy))pyridin-2-yl]-7-[4-(trifluoromethyl)benzyl]-7H-purine-2-carboxylic acid | TFA | 555 | 555 |
| 1.60 | 15.18 | 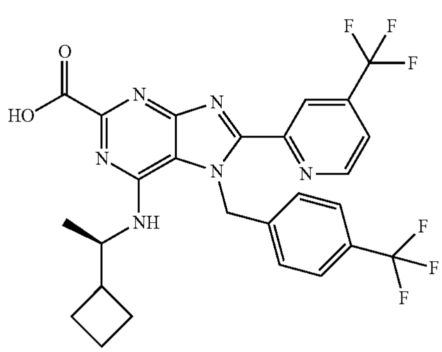 [SMILES: C[C@@H](Nc1nc(C(=O)O)nc2nc(-c3cc(C(F)(F)F)ccn3)n(Cc3ccc(C(F)(F)F)cc3)c12)C1CCC1] | 6-{[(1R)-1-cyclobutylethyl]amino}-7-[4-(trifluoromethyl)benzyl]-8-[4-(trifluoromethyl)pyridin-2-yl]-7H-purine-2-carboxylic acid | TFA | 565 | 565 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.61 | 51.4 | 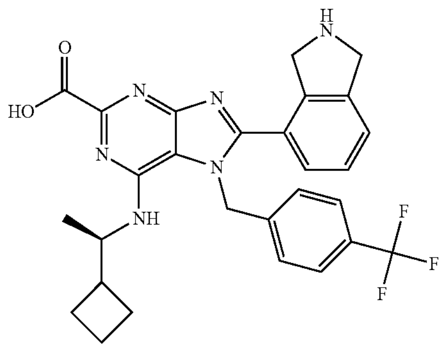 [SMILES: C[C@@H](Nc1nc(C(=O)O)nc2nc(-c3cccc4c3CNC4)n(Cc3ccc(C(F)(F)F)cc3)c12)C1CCC1] | 6-{[(1R)-1-cyclobutylethyl]amino}-8-(2,3-dihydro-1H-isoindol-4-yl)-7-[4-(trifluoromethyl)benzyl]-7H-purine-2-carboxylic acid | | 537 | 537 |
| 1.62 | 45.82 | 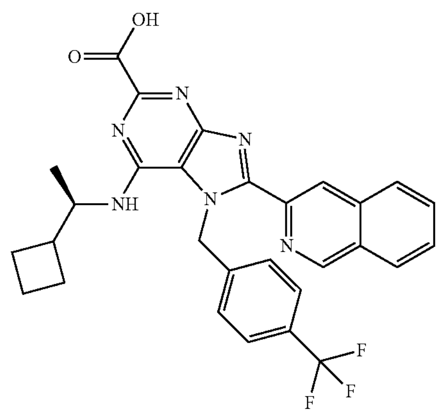 [SMILES: C[C@@H](Nc1nc(C(=O)O)nc2nc(-c3cc4ccccc4cn3)n(Cc3ccc(C(F)(F)F)cc3)c12)C1CCC1] | 6-{[(1R)-1-cyclobutylethyl]amino}-8-isoquinolin-3-yl-7-[4-(trifluoromethyl)benzyl]-7H-purine-2-carboxylic acid | TFA | 547 | 547 |
| 1.63 | 323.8 | 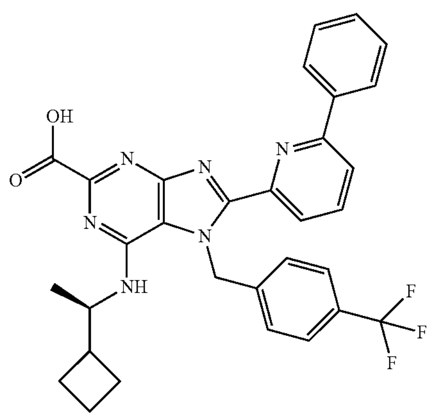 [SMILES: C[C@@H](Nc1nc(C(=O)O)nc2nc(-c3cccc(-c4ccccc4)n3)n(Cc3ccc(C(F)(F)F)cc3)c12)C1CCC1] | 6-{[(1R)-1-cyclobutylethyl]amino}-8-(6-phenylpyridin-2-yl)-7-[4-(trifluoromethyl)benzyl]-7H-purine-2-carboxylic acid | TFA | 573 | 573 |
| 1.64 | 22.85 | 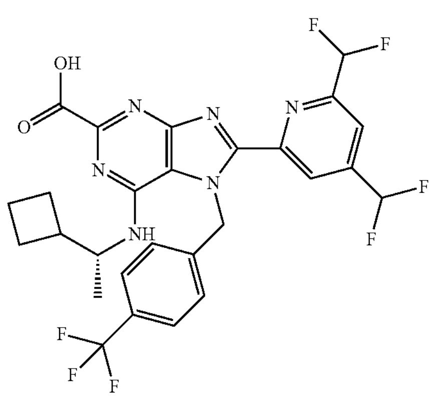 [SMILES: C[C@@H](Nc1nc(C(=O)O)nc2nc(-c3cc(C(F)F)cc(C(F)F)n3)n(Cc3ccc(C(F)(F)F)cc3)c12)C1CCC1] | 8-[4,6-bis(difluoromethyl)pyridin-2-yl]-6-{[(1R)-1-cyclobutylethyl]amino}-7-[4-(trifluoromethyl)benzyl]-7H-purine-2-carboxylic acid | TFA | 597 | 597 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.65 | 62.19 | 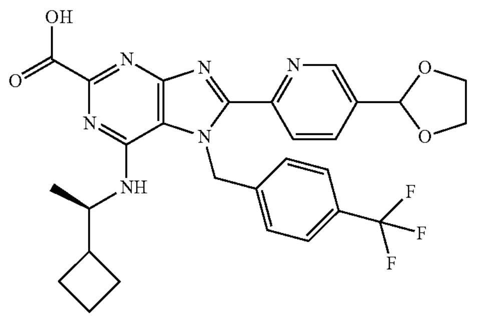 [SMILES: C[C@@H](Nc1nc(C(=O)O)nc2nc(-c3ccc(C4OCCO4)cn3)n(Cc3ccc(C(F)(F)F)cc3)c12)C1CCC1] | 6-{[(1R)-1-cyclobutylethyl]amino}-8-[5-(1,3-dioxolan-2-yl)pyridin-2-yl]-7-[4-(trifluoromethyl)benzyl]-7H-purine-2-carboxylic acid | TFA | 569 | 569 |
| 1.66 | 58.44 | 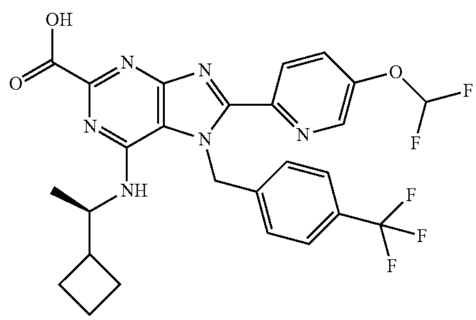 [SMILES: C[C@@H](Nc1nc(C(=O)O)nc2nc(-c3ccc(OC(F)F)cn3)n(Cc3ccc(C(F)(F)F)cc3)c12)C1CCC1] | 6-{[(1R)-1-cyclobutylethyl]amino}-8-[5-(difluoromethoxy)pyridin-2-yl]-7-[4-(trifluoromethyl)benzyl]-7H-purine-2-carboxylic acid | TFA | 563 | 563 |
| 1.67 | 14.19 | 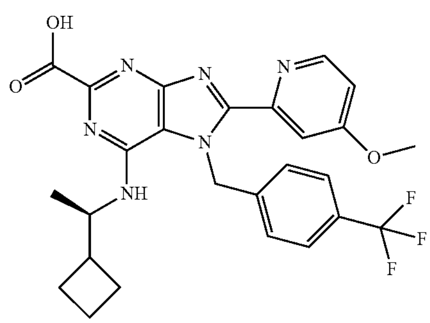 [SMILES: COc1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(4-methoxypyridin-2-yl)-7-[4-(trifluoromethyl)benzyl]-7H-purine-2-carboxylic acid | TFA | 527 | 527 |
| 1.68 | 5.618 | 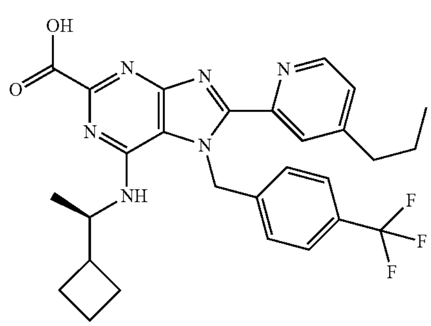 [SMILES: CCCc1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(4-propylpyridin-2-yl)-7-[4-(trifluoromethyl)benzyl]-7H-purine-2-carboxylic acid | TFA | 539 | 539 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.69 | 42.68 | 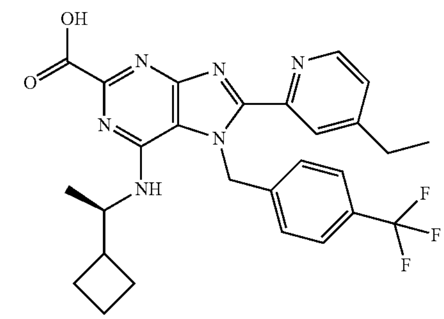 [SMILES: CCc1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(4-ethylpyridin-2-yl)-7-[4-(trifluoromethyl)benzyl]-7H-purine-2-carboxylic acid | TFA | 525 | 525 |
| 1.70 | 46.88 | 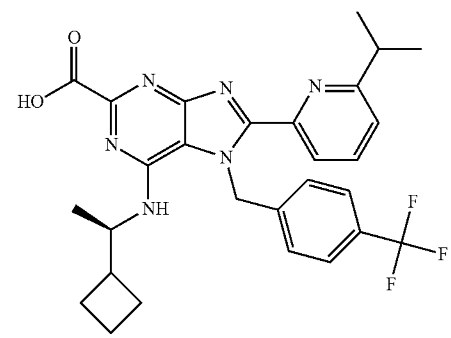 [SMILES: CC(C)c1cccc(-c2nc3nc(C(=O)O)nc(N[C@H](C)C4CCC4)c3n2Cc2ccc(C(F)(F)F)cc2)n1] | 6-{[(1R)-1-cyclobutylethyl]amino}-8-[6-(1-methylethyl)pyridin-2-yl]-7-[4-(trifluoromethyl)benzyl]-7H-purine-2-carboxylic acid | | 539 | 539 |
| 1.71 | 9.507 | 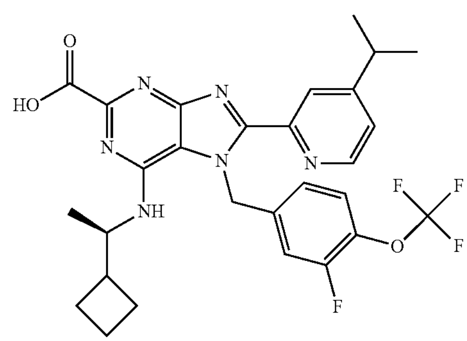 [SMILES: CC(C)c1ccnc(-c2nc3nc(C(=O)O)nc(N[C@H](C)C4CCC4)c3n2Cc2ccc(OC(F)(F)F)c(F)c2)c1] | 6-{[(1R)-1-cyclobutylethyl]amino}-7-[3-fluoro-4-(trifluoromethoxy)benzyl]-8-[4-(1-methylethyl)pyridin-2-yl]-7H-purine-2-carboxylic acid | TFA | 573 | 573 |
| 1.72 | 12.28 | 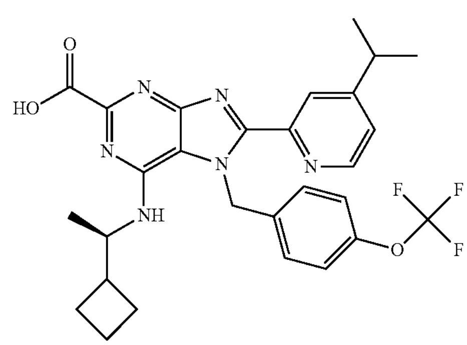 [SMILES: CC(C)c1ccnc(-c2nc3nc(C(=O)O)nc(N[C@H](C)C4CCC4)c3n2Cc2ccc(OC(F)(F)F)cc2)c1] | 6-{[(1R)-1-cyclobutylethyl]amino}-8-[4-(1-methylethyl)pyridin-2-yl]-7-[4-(trifluoromethoxy)benzyl]-7H-purine-2-carboxylic acid | TFA | 555 | 555 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.73 | 27.3 | 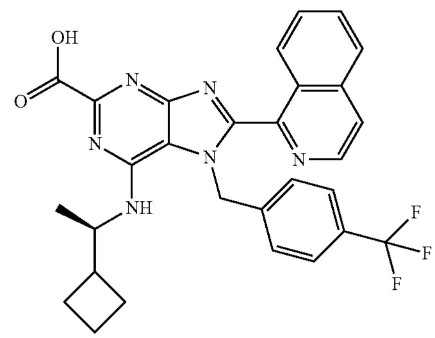 [SMILES: C[C@@H](Nc1nc(C(=O)O)nc2nc(-c3nccc4ccccc34)n(Cc3ccc(C(F)(F)F)cc3)c12)C1CCC1] | 6-{[(1R)-1-cyclobutylethyl]amino}-8-isoquinolin-1-yl-7-[4-(trifluoromethyl)benzyl]-7H-purine-2-carboxylic acid | TFA | 547 | 547 |
| 1.74 | 72.45 | 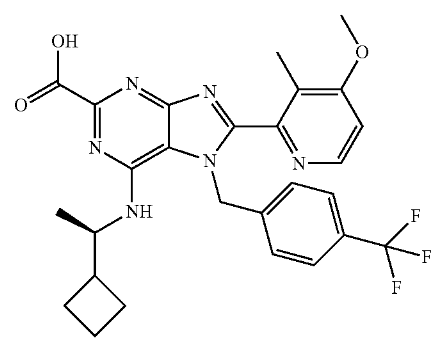 [SMILES: COc1ccnc(-c2nc3nc(C(=O)O)nc(N[C@H](C)C4CCC4)c3n2Cc2ccc(C(F)(F)F)cc2)c1C] | 6-{[(1R)-1-cyclobutylethyl]amino}-8-(4-methoxy-3-methylpyridin-2-yl)-7-[4-(trifluoromethyl)benzyl]-7H-purine-2-carboxylic acid | TFA | 541 | 541 |
| 1.75 | 6.118 | 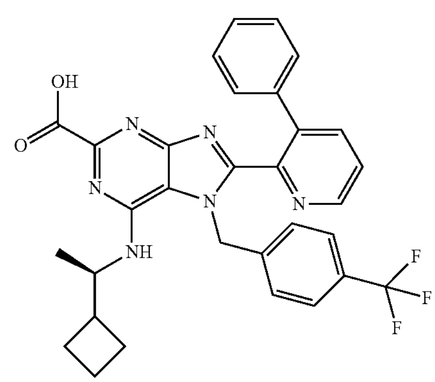 [SMILES: C[C@@H](Nc1nc(C(=O)O)nc2nc(-c3ncccc3-c3ccccc3)n(Cc3ccc(C(F)(F)F)cc3)c12)C1CCC1] | 6-{[(1R)-1-cyclobutylethyl]amino}-8-(3-phenylpyridin-2-yl)-7-[4-(trifluoromethyl)benzyl]-7H-purine-2-carboxylic acid | TFA | 573 | 573 |
| 1.76 | 8.493 | 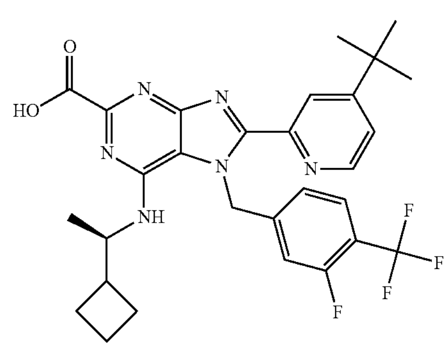 [SMILES: C[C@@H](Nc1nc(C(=O)O)nc2nc(-c3cc(C(C)(C)C)ccn3)n(Cc3ccc(C(F)(F)F)c(F)c3)c12)C1CCC1] | 8-(4-tert-butylpyridin-2-yl)-6-{[(1R)-1-cyclobutylethyl]amino}-7-[3-fluoro-4-(trifluoromethyl)benzyl]-7H-purine-2-carboxylic acid | TFA | 571 | 571 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.77 | 19.98 | 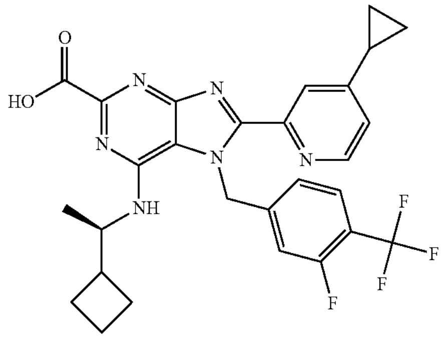 [SMILES: C[C@@H](Nc1nc(C(=O)O)nc2nc(-c3cc(C4CC4)ccn3)n(Cc3ccc(C(F)(F)F)c(F)c3)c12)C1CCC1] | 6-{[(1R)-1-cyclobutylethyl]amino}-8-(4-cyclopropylpyridin-2-yl)-7-[3-fluoro-4-(trifluoromethyl)benzyl]-7H-purine-2-carboxylic acid | TFA | 555 | 555 |
| 1.78 | 9.255 | 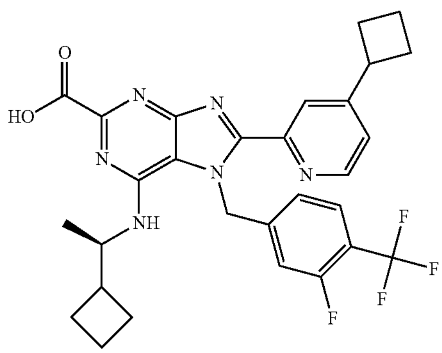 [SMILES: C[C@@H](Nc1nc(C(=O)O)nc2nc(-c3cc(C4CCC4)ccn3)n(Cc3ccc(C(F)(F)F)c(F)c3)c12)C1CCC1] | 6-{[(1R)-1-cyclobutylethyl]amino}-8-(4-cyclobutylpyridin-2-yl)-7-[3-fluoro-4-(trifluoromethyl)benzyl]-7H-purine-2-carboxylic acid | TFA | 569 | 569 |
| 1.79 | 10.21 | 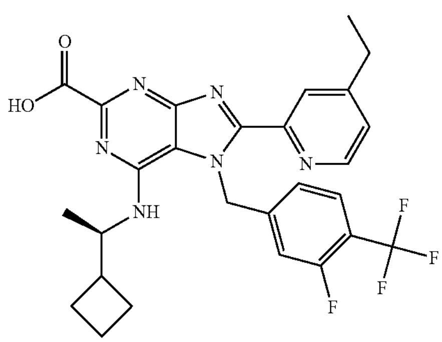 [SMILES: CCc1ccnc(-c2nc3nc(C(=O)O)nc(N[C@H](C)C4CCC4)c3n2Cc2ccc(C(F)(F)F)c(F)c2)c1] | 6-{[(1R)-1-cyclobutylethyl]amino}-8-(4-ethylpyridin-2-yl)-7-[3-fluoro-4-(trifluoromethyl)benzyl]-7H-purine-2-carboxylic acid | TFA | 543 | 543 |
| 1.80 | 7.445 | 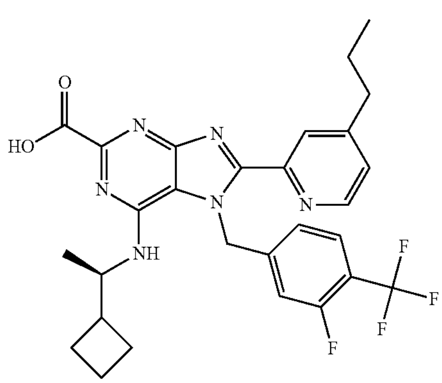 [SMILES: CCCc1ccnc(-c2nc3nc(C(=O)O)nc(N[C@H](C)C4CCC4)c3n2Cc2ccc(C(F)(F)F)c(F)c2)c1] | 6-{[(1R)-1-cyclobutylethyl]amino}-7-[3-fluoro-4-(trifluoromethyl)benzyl]-8-(4-propylpyridin-2-yl)-7H-purine-2-carboxylic acid | TFA | 557 | 557 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.81 | 74.4 | 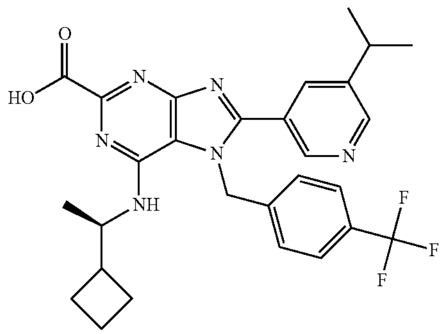 [SMILES: CC(C)c1cncc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[5-(1-methylethyl)pyridin-3-yl]-7-[4-(trifluoromethyl)benzyl]-7H-purine-2-carboxylic acid | | 539 | 539 |
| 1.82 | 48.98 | 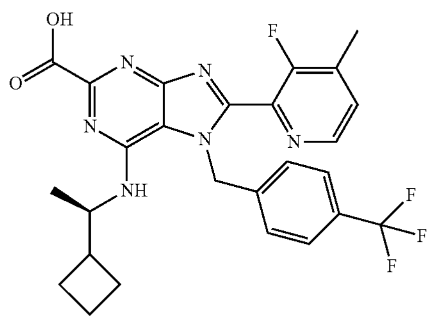 [SMILES: Cc1ccnc(-c2nc3nc(C(=O)O)nc(N[C@H](C)C4CCC4)c3n2Cc2ccc(C(F)(F)F)cc2)c1F] | 6-{[(1R)-1-cyclobutylethyl]amino}-8-(3-fluoro-4-methylpyridin-2-yl)-7-[4-(trifluoromethyl)benzyl]-7H-purine-2-carboxylic acid | TFA | 529 | 529 |
| 1.83 | 23.22 | 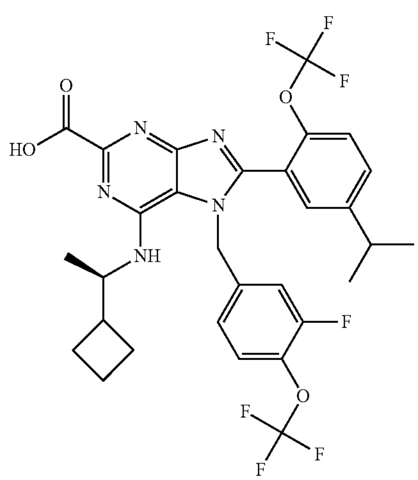 [SMILES: CC(C)c1ccc(OC(F)(F)F)c(-c2nc3nc(C(=O)O)nc(N[C@H](C)C4CCC4)c3n2Cc2ccc(OC(F)(F)F)c(F)c2)c1] | 6-{[(1R)-1-cyclobutylethyl]amino}-7-[3-fluoro-4-(trifluoromethoxy)benzyl]-8-[5-(1-methylethyl)-2-(trifluoromethoxy)phenyl]-7H-purine-2-carboxylic acid | | 656 | 656 |
| 1.84 | 9.676 | 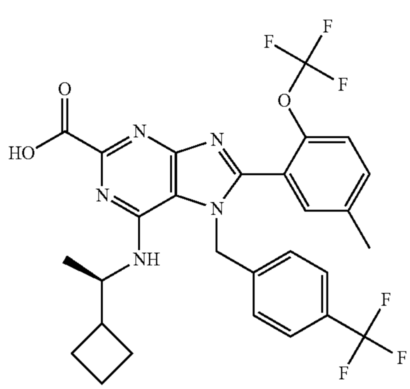 [SMILES: Cc1ccc(OC(F)(F)F)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[5-methyl-2-(trifluoromethoxy)phenyl]-7-[4-(trifluoromethyl)benzyl]-7H-purine-2-carboxylic acid | | 594 | 594 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.85 | 9.685 | 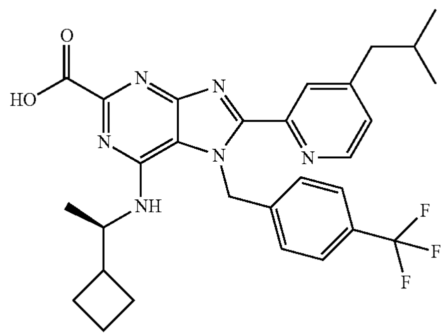 [SMILES: CC(C)Cc1ccnc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[4-(2-methylpropyl)pyridin-2-yl]-7-[4-(trifluoromethyl)benzyl]-7H-purine-2-carboxylic acid | | 553 | 553 |
| 1.86 | 24.8 | 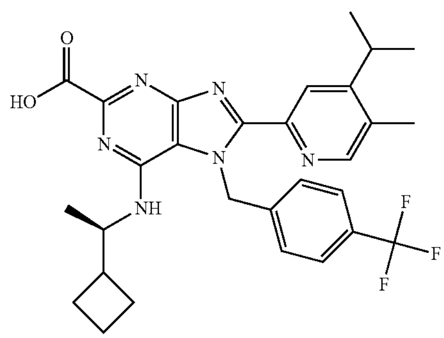 [SMILES: Cc1cnc(-c2nc3nc(C(=O)O)nc(N[C@H](C)C4CCC4)c3n2Cc2ccc(C(F)(F)F)cc2)cc1C(C)C] | 6-{[(1R)-1-cyclobutylethyl]amino}-8-[5-methyl-4-(1-methylethyl)pyridin-2-yl]-7-[4-(trifluoromethyl)benzyl]-7H-purine-2-carboxylic acid | | 553 | 553 |
| 1.87 | 58.98 | 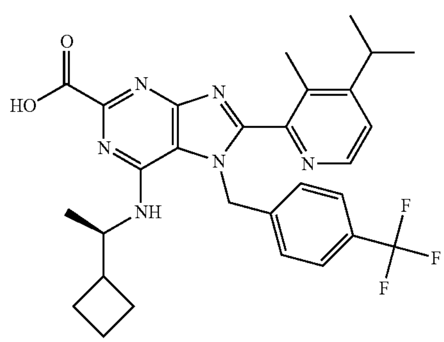 [SMILES: Cc1c(C(C)C)ccnc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[3-methyl-4-(1-methylethyl)pyridin-2-yl]-7-[4-(trifluoromethyl)benzyl]-7H-purine-2-carboxylic acid | | 553 | 553 |
| 1.88 | 19.57 | 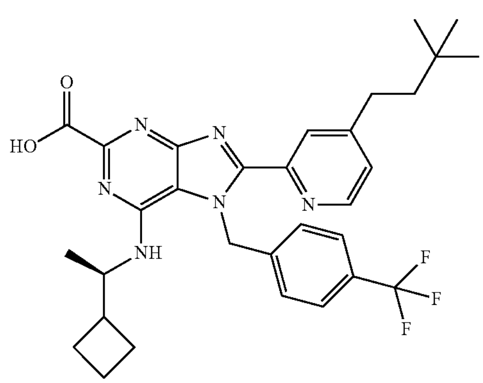 [SMILES: C[C@@H](Nc1nc(C(=O)O)nc2nc(-c3cc(CCC(C)(C)C)ccn3)n(Cc3ccc(C(F)(F)F)cc3)c12)C1CCC1] | 6-{[(1R)-1-cyclobutylethyl]amino}-8-[4-(3,3-dimethylbutyl)pyridin-2-yl]-7-[4-(trifluoromethyl)benzyl]-7H-purine-2-carboxylic acid | | 581 | 581 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.89 | 8.674 | 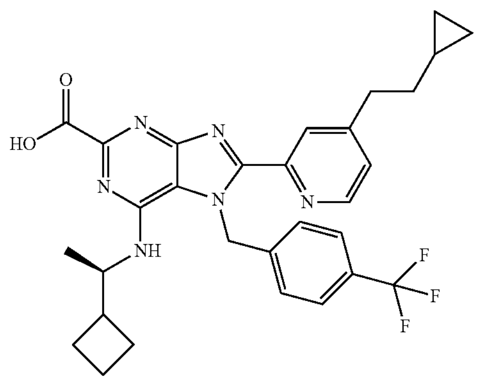 [SMILES: C[C@@H](Nc1nc(C(=O)O)nc2nc(-c3cc(CCC4CC4)ccn3)n(Cc3ccc(C(F)(F)F)cc3)c12)C1CCC1] | 6-{[(1R)-1-cyclobutylethyl]amino}-8-[4-(2-cyclopropylethyl)pyridin-2-yl]-7-[4-(trifluoromethyl)benzyl]-7H-purine-2-carboxylic acid | | 565 | 565 |
| 1.90 | 24.71 | 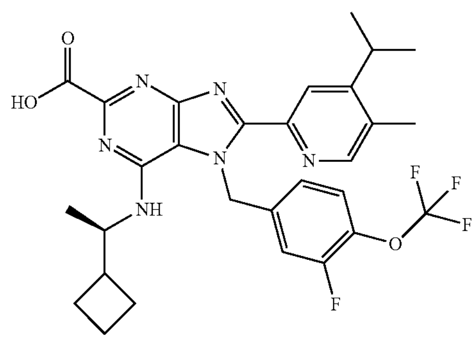 [SMILES: Cc1cnc(-c2nc3nc(C(=O)O)nc(N[C@H](C)C4CCC4)c3n2Cc2ccc(OC(F)(F)F)c(F)c2)cc1C(C)C] | 6-{[(1R)-1-cyclobutylethyl]amino}-7-[3-fluoro-4-(trifluoromethoxy)benzyl]-8-[5-methyl-4-(1-methylethyl)pyridin-2-yl]-7H-purine-2-carboxylic acid | | 587 | 587 |
| 1.91 | 22.32 | 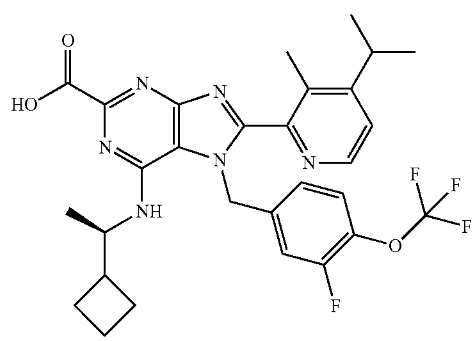 [SMILES: Cc1c(C(C)C)ccnc1-c1nc2nc(C(=O)O)nc(N[C@H](C)C3CCC3)c2n1Cc1ccc(OC(F)(F)F)c(F)c1] | 6-{[(1R)-1-cyclobutylethyl]amino}-7-[3-fluoro-4-(trifluoromethoxy)benzyl]-8-[3-methyl-4-(1-methylethyl)pyridin-2-yl]-7H-purine-2-carboxylic acid | | 587 | 587 |
| 1.92 | 15.91 | 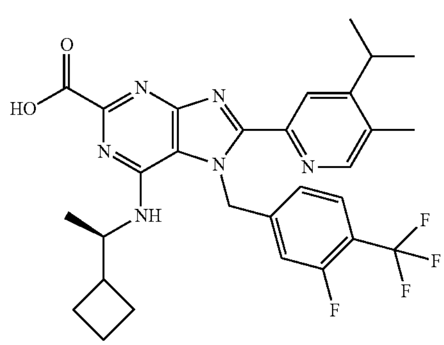 [SMILES: Cc1cnc(-c2nc3nc(C(=O)O)nc(N[C@H](C)C4CCC4)c3n2Cc2ccc(C(F)(F)F)c(F)c2)cc1C(C)C] | 6-{[(1R)-1-cyclobutylethyl]amino}-7-[3-fluoro-4-(trifluoromethyl)benzyl]-8-[5-methyl-4-(1-methylethyl)pyridin-2-yl]-7H-purine-2-carboxylic acid | | 571 | 571 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.93 | 19.05 | 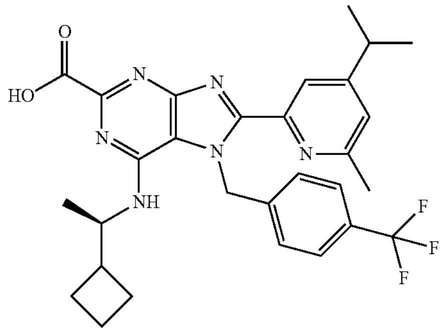 | 6-{[(1R)-1-cyclobutylethyl]amino}-8-[6-methyl-4-(1-methylethyl)pyridin-2-yl]-7-[4-(trifluoromethyl)benzyl]-7H-purine-2-carboxylic acid | | 553 | 553 |
| 1.94 | 172.9 | 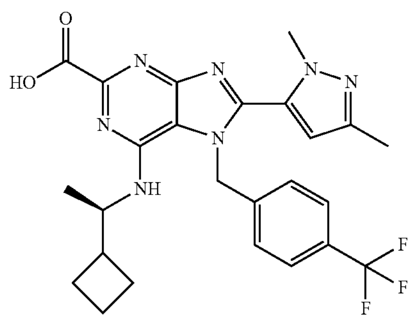 [SMILES: Cc1cc(-c2nc3nc(C(=O)O)nc(N[C@H](C)C4CCC4)c3n2Cc2ccc(C(F)(F)F)cc2)n(C)n1] | 6-{[(1R)-1-cyclobutylethyl]amino}-8-(1,3-dimethyl-1H-pyrazol-5-yl)-7-[4-(trifluoromethyl)benzyl]-7H-purine-2-carboxylic acid | | 514 | 514 |
| 1.95 | 138 | 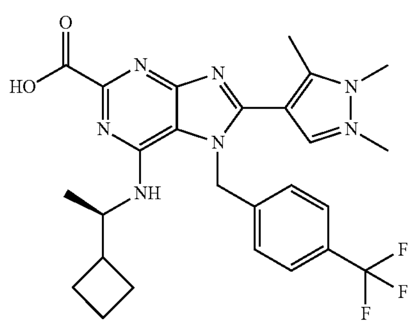 | 6-{[(1R)-1-cyclobutylethyl]amino}-8-(1,5-dimethyl-1H-pyrazol-4-yl)-7-[4-(trifluoromethyl)benzyl]-7H-purine-2-carboxylic acid | | 514 | 514 |
| 1.96 | 370.9 | 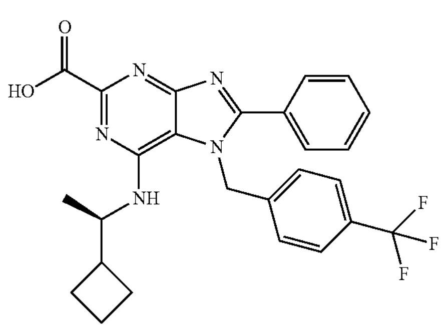 [SMILES: C[C@@H](Nc1nc(C(=O)O)nc2nc(-c3ccccc3)n(Cc3ccc(C(F)(F)F)cc3)c12)C1CCC1] | 6-{[(1R)-1-cyclopropylethyl]amino}-8-phenyl-7-[4-(trifluoromethyl)benzyl]-7H-purine-2-carboxylic acid | TFA | 482 | 482 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.97 | 1536 | 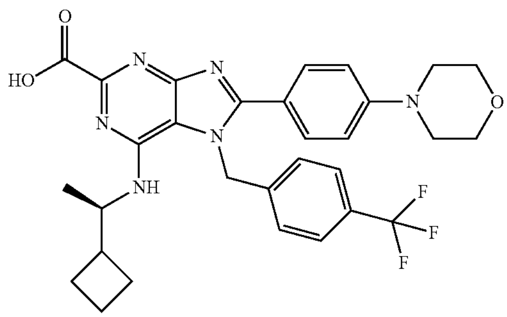 [SMILES: C[C@@H](Nc1nc(C(=O)O)nc2nc(-c3ccc(N4CCOCC4)cc3)n(Cc3ccc(C(F)(F)F)cc3)c12)C1CCC1] | 6-{[(1R)-1-cyclopropylethyl]amino}-8-(4-morpholin-4-ylphenyl)-7-[4-(trifluoromethyl)benzyl]-7H-purine-2-carboxylic acid | TFA | 567 | 567 |
| 1.98 | 316.1 | 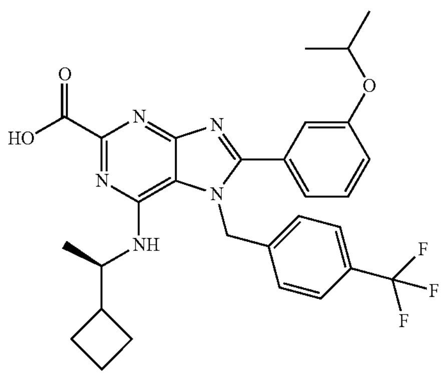 [SMILES: CC(C)Oc1cccc(-c2nc3nc(C(=O)O)nc(N[C@H](C)C4CCC4)c3n2Cc2ccc(C(F)(F)F)cc2)c1] | 6-{[(1R)-1-cyclopropylethyl]amino}-8-[3-(1-methylethoxy)phenyl]-7-[4-(trifluoromethyl)benzyl]-7H-purine-2-carboxylic acid | TFA | 540 | 540 |
| 1.99 | 14.87 | 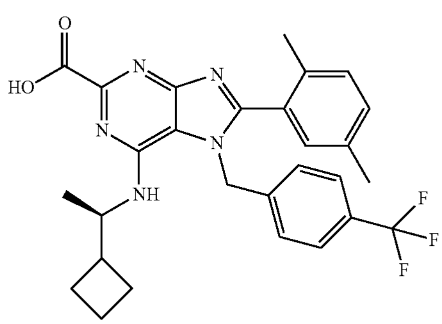 [SMILES: Cc1ccc(C)c(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(2,5-dimethylphenyl)-7-[4-(trifluoromethyl)benzyl]-7H-purine-2-carboxylic acid | TFA | 524 | 524 |
| 1.100 | 51.84 | 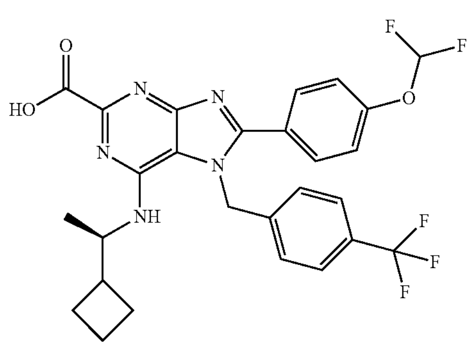 [SMILES: C[C@@H](Nc1nc(C(=O)O)nc2nc(-c3ccc(OC(F)F)cc3)n(Cc3ccc(C(F)(F)F)cc3)c12)C1CCC1] | 6-{[(1R)-1-cyclobutylethyl]amino}-8-[4-(difluoromethoxy)phenyl]-7-[4-(trifluoromethyl)benzyl]-7H-purine-2-carboxylic acid | TFA | 562 | 562 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.101 | 34.21 | 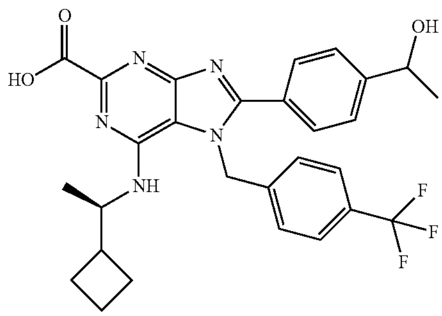 [SMILES: CC(O)c1ccc(-c2nc3nc(C(=O)O)nc(N[C@H](C)C4CCC4)c3n2Cc2ccc(C(F)(F)F)cc2)cc1] | 6-{[(1R)-1-cyclobutylethyl]amino}-8-[4-(1-hydroxyethyl)phenyl]-7-[4-(trifluoromethyl)benzyl]-7H-purine-2-carboxylic acid | TFA | 540 | 540 |
| 1.102 | 20.34 | 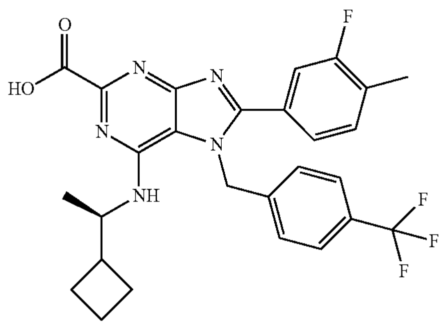 [SMILES: Cc1ccc(-c2nc3nc(C(=O)O)nc(N[C@H](C)C4CCC4)c3n2Cc2ccc(C(F)(F)F)cc2)cc1F] | 6-{[(1R)-1-cyclobutylethyl]amino}-8-(3-fluoro-4-methylphenyl)-7-[4-(trifluoromethyl)benzyl]-7H-purine-2-carboxylic acid | TFA | 528 | 528 |
| 1.103 | 10.79 | 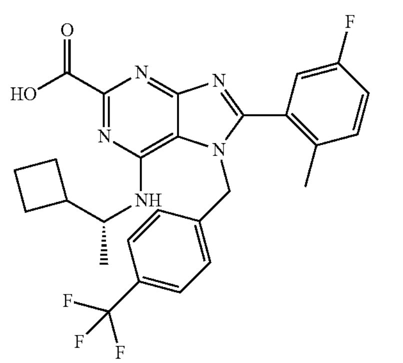 [SMILES: Cc1ccc(F)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(5-fluoro-2-methylphenyl)-7-[4-(trifluoromethyl)benzyl]-7H-purine-2-carboxylic acid | TFA | 528 | 528 |
| 1.104 | 17.41 | 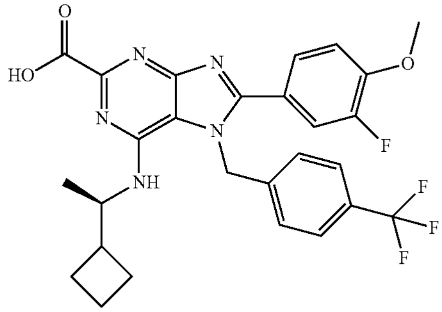 [SMILES: COc1ccc(-c2nc3nc(C(=O)O)nc(N[C@H](C)C4CCC4)c3n2Cc2ccc(C(F)(F)F)cc2)cc1F] | 6-{[(1R)-1-cyclobutylethyl]amino}-8-(3-fluoro-4-methoxyphenyl)-7-[4-(trifluoromethyl)benzyl]-7H-purine-2-carboxylic acid | TFA | 544 | 544 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.105 | 16.53 | 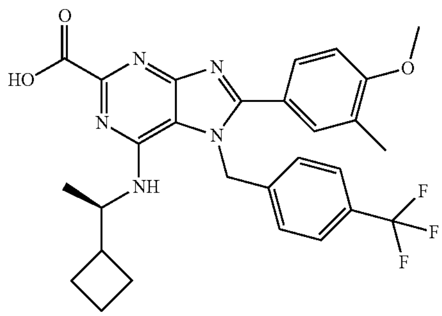 [SMILES: COc1ccc(-c2nc3nc(C(=O)O)nc(N[C@H](C)C4CCC4)c3n2Cc2ccc(C(F)(F)F)cc2)cc1C] | 6-{[(1R)-1-cyclobutylethyl]amino}-8-(4-methoxy-3-methylphenyl)-7-[4-(trifluoromethyl)benzyl]-7H-purine-2-carboxylic acid | TFA | 540 | 540 |
| 1.106 | 23.55 | 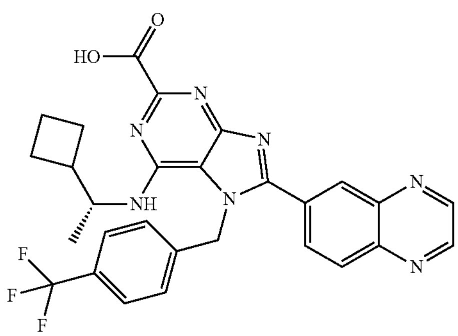 [SMILES: C[C@@H](Nc1nc(C(=O)O)nc2nc(-c3ccc4nccnc4c3)n(Cc3ccc(C(F)(F)F)cc3)c12)C1CCC1] | 6-{[(1R)-1-cyclobutylethyl]amino}-8-quinoxalin-6-yl-7-[4-(trifluoromethyl)benzyl]-7H-purine-2-carboxylic acid | TFA | 548 | 548 |
| 1.107 | 34.84 | 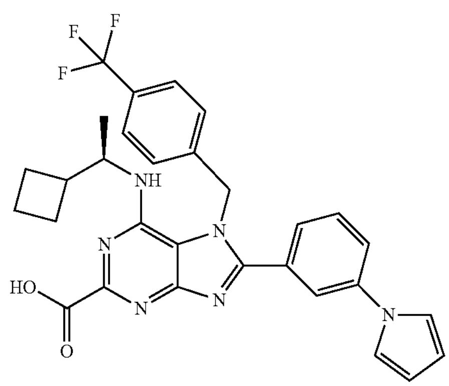 [SMILES: C[C@@H](Nc1nc(C(=O)O)nc2nc(-c3cccc(-n4cccc4)c3)n(Cc3ccc(C(F)(F)F)cc3)c12)C1CCC1] | 6-{[(1R)-1-cyclobutylethyl]amino}-8-[3-(1H-pyrrol-1-yl)phenyl]-7-[4-(trifluoromethyl)benzyl]-7H-purine-2-carboxylic acid | TFA | 561 | 561 |
| 1.108 | 60.86 | 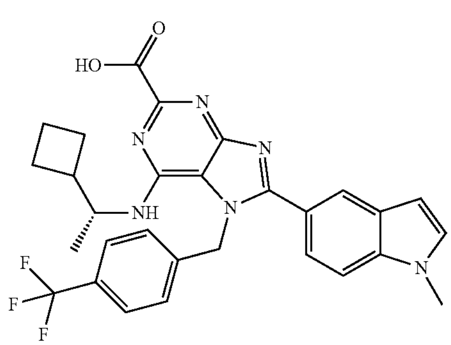 [SMILES: C[C@@H](Nc1nc(C(=O)O)nc2nc(-c3ccc4c(ccn4C)c3)n(Cc3ccc(C(F)(F)F)cc3)c12)C1CCC1] | 6-{[(1R)-1-cyclobutylethyl]amino}-8-(1-methyl-1H-indol-5-yl)-7-[4-(trifluoromethyl)benzyl]-7H-purine-2-carboxylic acid | TFA | 549 | 549 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.109 | 472.7 | 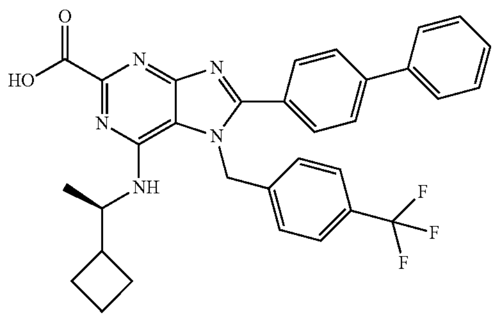 [SMILES: C[C@@H](Nc1nc(C(=O)O)nc2nc(-c3ccc(-c4ccccc4)cc3)n(Cc3ccc(C(F)(F)F)cc3)c12)C1CCC1] | 8-biphenyl-4-yl-6-{[(1R)-1-cyclobutylethyl]amino}-7-[4-(trifluoromethyl)benzyl]-7H-purine-2-carboxylic acid | TFA | 572 | 572 |
| 1.110 | 3702 | 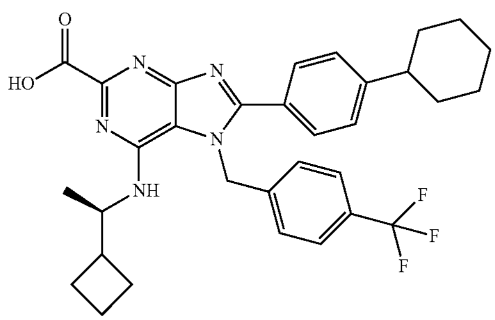 [SMILES: C[C@@H](Nc1nc(C(=O)O)nc2nc(-c3ccc(C4CCCCC4)cc3)n(Cc3ccc(C(F)(F)F)cc3)c12)C1CCC1] | 6-{[(1R)-1-cyclobutylethyl]amino}-8-(4-cyclohexylphenyl)-7-[4-(trifluoromethyl)benzyl]-7H-purine-2-carboxylic acid | TFA | 578 | 578 |
| 1.111 | 128.2 | 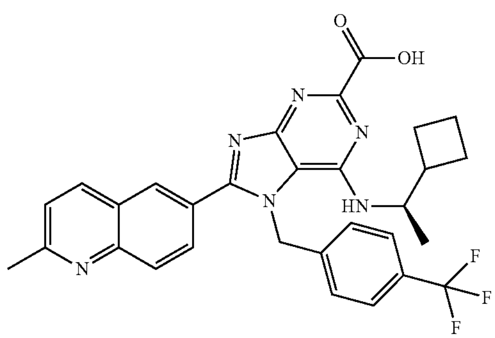 [SMILES: Cc1ccc2cc(-c3nc4nc(C(=O)O)nc(N[C@H](C)C5CCC5)c4n3Cc3ccc(C(F)(F)F)cc3)ccc2n1] | 6-{[(1R)-1-cyclobutylethyl]amino}-8-(2-methylquinolin-6-yl)-7-[4-(trifluoromethyl)benzyl]-7H-purine-2-carboxylic acid | TFA | 561 | 561 |
| 1.112 | 343.5 | 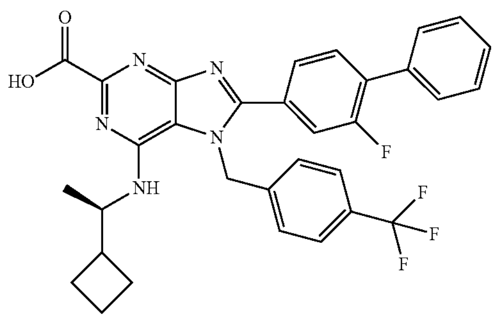 [SMILES: C[C@@H](Nc1nc(C(=O)O)nc2nc(-c3ccc(-c4ccccc4)c(F)c3)n(Cc3ccc(C(F)(F)F)cc3)c12)C1CCC1] | 6-{[(1R)-1-cyclobutylethyl]amino}-8-(2-fluorobiphenyl-4-yl)-7-[4-(trifluoromethyl)benzyl]-7H-purine-2-carboxylic acid | TFA | 590 | 590 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.113 | 715.9 | 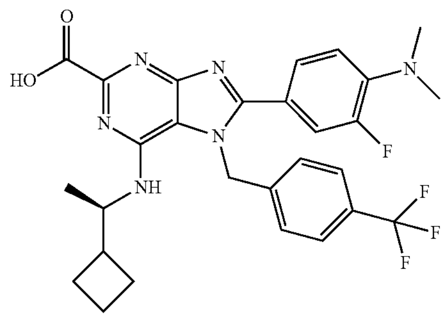 [SMILES: C[C@@H](Nc1nc(C(=O)O)nc2nc(-c3ccc(N(C)C)c(F)c3)n(Cc3ccc(C(F)(F)F)cc3)c12)C1CCC1] | 6-{[(1R)-1-cyclobutylethyl]amino}-8-[4-(dimethylamino)phenyl]-7-[4-(trifluoromethyl)benzyl]-7H-purine-2-carboxylic acid | TFA | 539 | 539 |
| 1.114 | 392.6 | 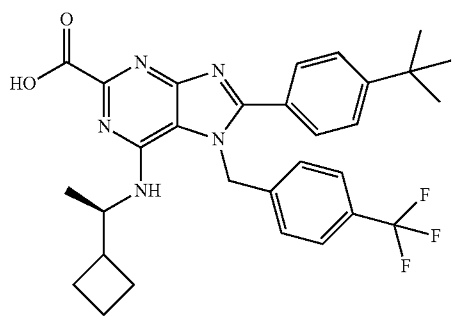 [SMILES: C[C@@H](Nc1nc(C(=O)O)nc2nc(-c3ccc(C(C)(C)C)cc3)n(Cc3ccc(C(F)(F)F)cc3)c12)C1CCC1] | 8-(4-tert-butylphenyl)-6-{[(1R)-1-cyclobutylethyl]amino}-7-[4-(trifluoromethyl)benzyl]-7H-purine-2-carboxylic acid | TFA | 552 | 552 |
| 1.115 | 17.29 | 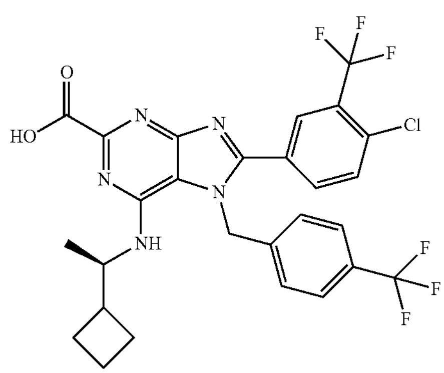 [SMILES: C[C@@H](Nc1nc(C(=O)O)nc2nc(-c3ccc(Cl)c(C(F)(F)F)c3)n(Cc3ccc(C(F)(F)F)cc3)c12)C1CCC1] | 8-[4-chloro-3-(trifluoromethyl)phenyl]-6-{[(1R)-1-cyclobutylethyl]amino}-7-[4-(trifluoromethyl)benzyl]-7H-purine-2-carboxylic acid | TFA | 598 | 598 |
| 1.116 | 66.26 | 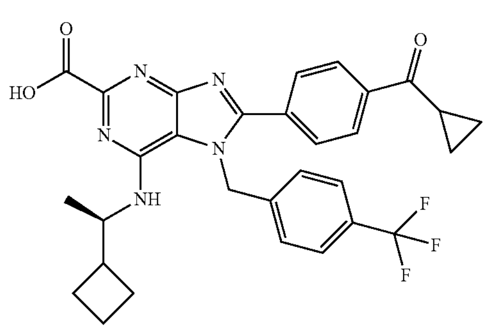 [SMILES: C[C@@H](Nc1nc(C(=O)O)nc2nc(-c3ccc(C(=O)C4CC4)cc3)n(Cc3ccc(C(F)(F)F)cc3)c12)C1CCC1] | 6-{[(1R)-1-cyclobutylethyl]amino}-8-[4-(cyclopropylcarbonyl)phenyl]-7-[4-(trifluoromethyl)benzyl]-7H-purine-2-carboxylic acid | TFA | 564 | 564 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.117 | 16.74 | 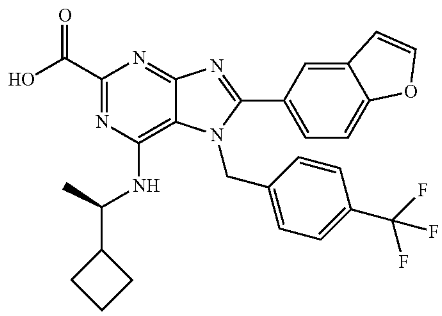 [SMILES: C[C@@H](Nc1nc(C(=O)O)nc2nc(-c3ccc4occc4c3)n(Cc3ccc(C(F)(F)F)cc3)c12)C1CCC1] | 8-(1-benzofuran-5-yl)-6-{[(1R)-1-cyclobutylethyl]amino}-7-[4-(trifluoromethyl)benzyl]-7H-purine-2-carboxylic acid | TFA | 536 | 536 |
| 1.118 | 1372 | 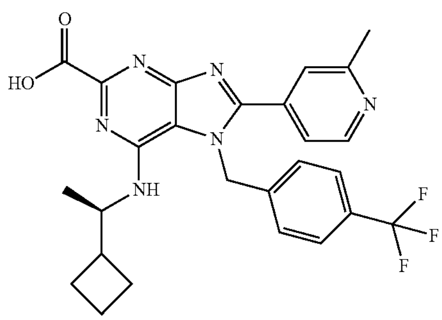 [SMILES: Cc1cc(-c2nc3nc(C(=O)O)nc(N[C@H](C)C4CCC4)c3n2Cc2ccc(C(F)(F)F)cc2)ccn1] | 6-{[(1R)-1-cyclopropylethyl]amino}-8-(2-methylpyridin-4-yl)-7-[4-(trifluoromethyl)benzyl]-7H-purine-2-carboxylic acid | TFA | 497 | 497 |
| 1.119 | 9.967 | 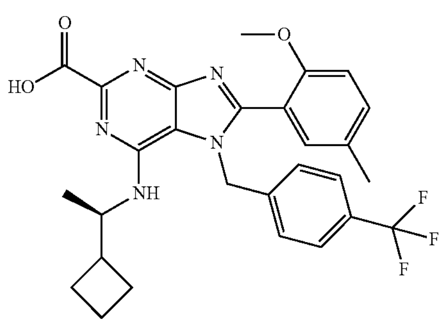 [SMILES: COc1ccc(C)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(2-methoxy-5-methylphenyl)-7-[4-(trifluoromethyl)benzyl]-7H-purine-2-carboxylic acid | TFA | 540 | 540 |
| 1.120 | 10.43 | 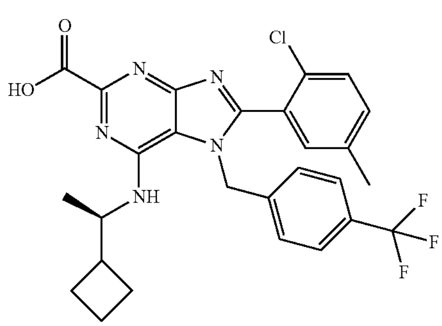 [SMILES: Cc1ccc(Cl)c(-c2nc3nc(C(=O)O)nc(N[C@H](C)C4CCC4)c3n2Cc2ccc(C(F)(F)F)cc2)c1] | 8-(2-chloro-5-methylphenyl)-6-{[(1R)-1-cyclobutylethyl]amino}-7-[4-(trifluoromethyl)benzyl]-7H-purine-2-carboxylic acid | TFA | 544 | 544 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.121 | 7.807 | 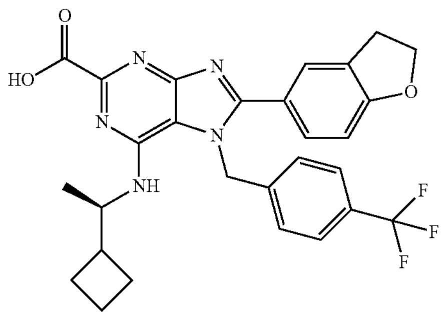 [SMILES: C[C@@H](Nc1nc(C(=O)O)nc2nc(-c3ccc4c(c3)CCO4)n(Cc3ccc(C(F)(F)F)cc3)c12)C1CCC1] | 6-{[(1R)-1-cyclobutylethyl]amino}-8-(2,3-dihydro-1-benzofuran-5-yl)-7-[4-(trifluoromethyl)benzyl]-7H-purine-2-carboxylic acid | TFA | 538 | 538 |
| 1.122 | 21.24 | 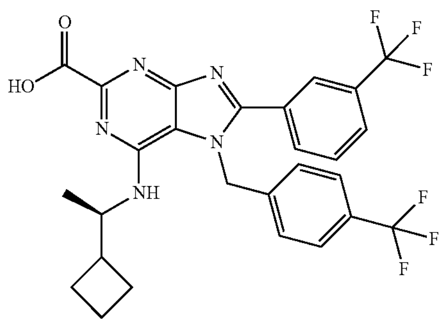 [SMILES: C[C@@H](Nc1nc(C(=O)O)nc2nc(-c3cccc(C(F)(F)F)c3)n(Cc3ccc(C(F)(F)F)cc3)c12)C1CCC1] | 6-{[(1R)-1-cyclobutylethyl]amino}-7-[4-(trifluoromethyl)benzyl]-8-[6-(trifluoromethyl)pyridin-2-yl]-7H-purine-2-carboxylic acid | TFA | 565 | 565 |
| 1.123 | 53.62 | 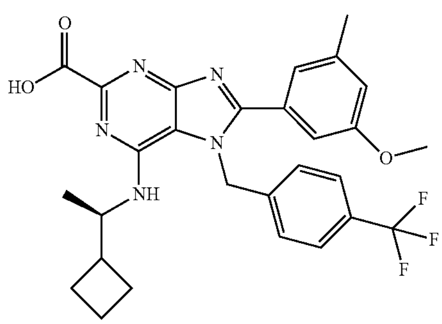 [SMILES: COc1cc(C)cc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(3-methoxy-5-methylphenyl)-7-[4-(trifluoromethyl)benzyl]-7H-purine-2-carboxylic acid | TFA | 540 | 540 |
| 1.124 | 26.41 | 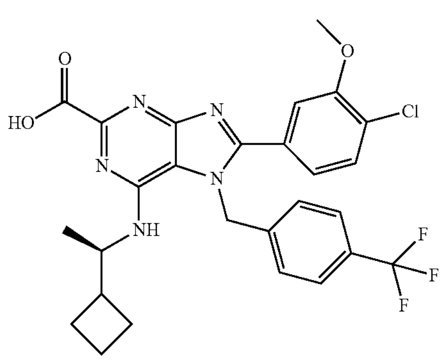 [SMILES: COc1cc(-c2nc3nc(C(=O)O)nc(N[C@H](C)C4CCC4)c3n2Cc2ccc(C(F)(F)F)cc2)ccc1Cl] | 8-(4-chloro-3-methoxyphenyl)-6-{[(1R)-1-cyclobutylethyl]amino}-7-[4-(trifluoromethyl)benzyl]-7H-purine-2-carboxylic acid | TFA | 560 | 560 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.125 | 116.4 | 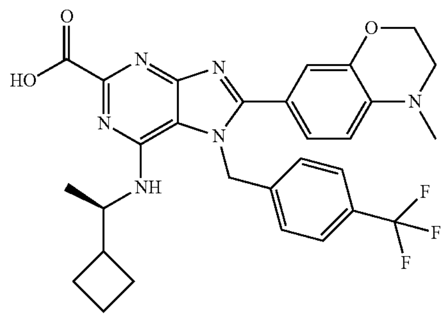 [SMILES: C[C@@H](Nc1nc(C(=O)O)nc2nc(-c3ccc4c(c3)OCCN4C)n(Cc3ccc(C(F)(F)F)cc3)c12)C1CCC1] | 6-{[(1R)-1-cyclobutylethyl]amino}-8-(4-methyl-3,4-dihydro-2H-1,4-benzoxazin-7-yl)-7-[4-(trifluoromethyl)benzyl]-7H-purine-2-carboxylic acid | TFA | 567 | 567 |
| 1.126 | 17.98 | 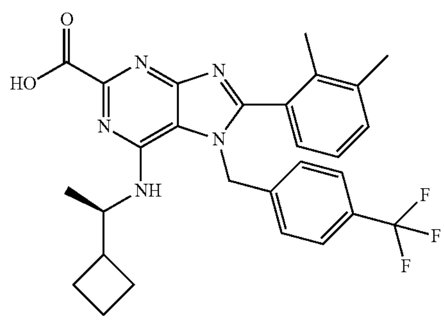 [SMILES: Cc1cccc(-c2nc3nc(C(=O)O)nc(N[C@H](C)C4CCC4)c3n2Cc2ccc(C(F)(F)F)cc2)c1C] | 6-{[(1R)-1-cyclobutylethyl]amino}-8-(2,3-dimethylphenyl)-7-[4-(trifluoromethyl)benzyl]-7H-purine-2-carboxylic acid | TFA | 524 | 524 |
| 1.127 | 38.7 | 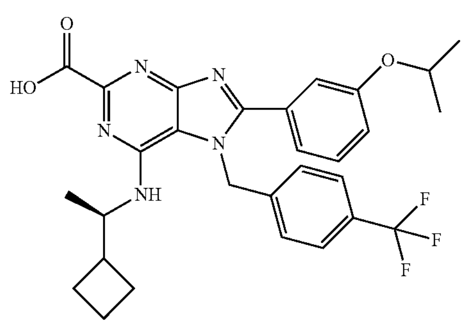 [SMILES: CC(C)Oc1cccc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-[3-(1-methylethoxy)phenyl]-7-[4-(trifluoromethyl)benzyl]-7H-purine-2-carboxylic acid | TFA | 554 | 554 |
| 1.128 | 224.5 | 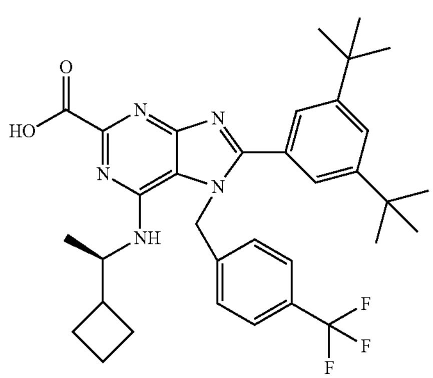 [SMILES: C[C@@H](Nc1nc(C(=O)O)nc2nc(-c3cc(C(C)(C)C)cc(C(C)(C)C)c3)n(Cc3ccc(C(F)(F)F)cc3)c12)C1CCC1] | 6-{[(1R)-1-cyclobutylethyl]amino}-8-(3,5-di-tert-butylphenyl)-7-[4-(trifluoromethyl)benzyl]-7H-purine-2-carboxylic acid | TFA | 608 | 608 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.129 | 46.0 | 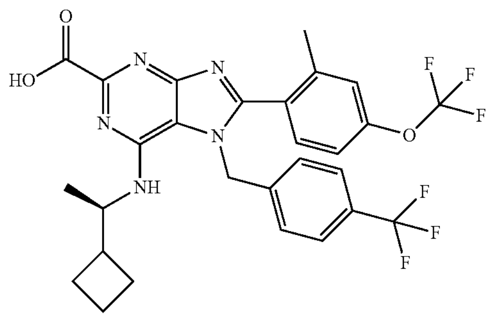 [SMILES: Cc1cc(OC(F)(F)F)ccc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-methyl-4-(trifluoromethoxy)phenyl]-7-[4-(trifluoromethyl)benzyl]-7H-purine-2-carboxylic acid | TFA | 594 | 594 |
| 1.130 | 76.29 | 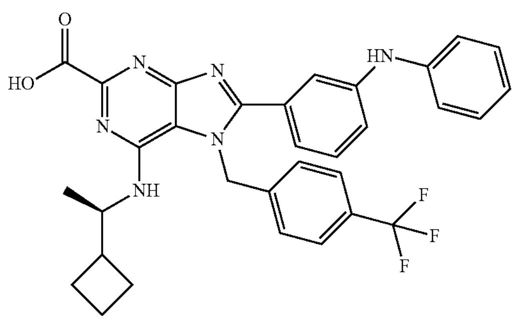 [SMILES: C[C@@H](Nc1nc(C(=O)O)nc2nc(-c3cccc(Nc4ccccc4)c3)n(Cc3ccc(C(F)(F)F)cc3)c12)C1CCC1] | 6-{[(1R)-1-cyclobutylethyl]amino}-8-[3-(phenylamino)phenyl]-7-[4-(trifluoromethyl)benzyl]-7H-purine-2-carboxylic acid | TFA | 587 | 587 |
| 1.131 | 369.0 | 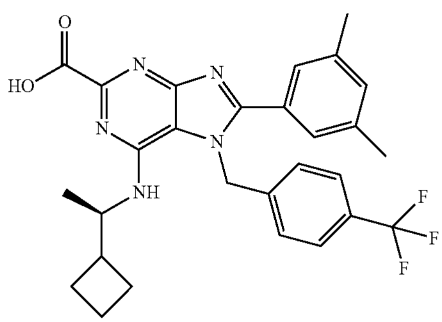 [SMILES: Cc1cc(C)cc(-c2nc3nc(C(=O)O)nc(N[C@H](C)C4CCC4)c3n2Cc2ccc(C(F)(F)F)cc2)c1] | 6-{[(1R)-1-cyclobutylethyl]amino}-8-(3,5-dimethylphenyl)-7-[4-(trifluoromethyl)benzyl]-7H-purine-2-carboxylic acid | TFA | 524 | 524 |
| 1.132 | 524.1 | 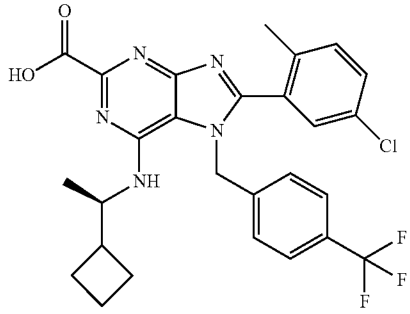 [SMILES: Cc1ccc(Cl)cc1-c1nc2nc(C(=O)O)nc(N[C@H](C)C3CCC3)c2n1Cc1ccc(C(F)(F)F)cc1] | 8-(5-chloro-2-methylphenyl)-6-{[(1R)-1-cyclobutylethyl]amino}-7-[4-(trifluoromethyl)benzyl]-7H-purine-2-carboxylic acid | TFA | 544 | 544 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.133 | 73.35 | 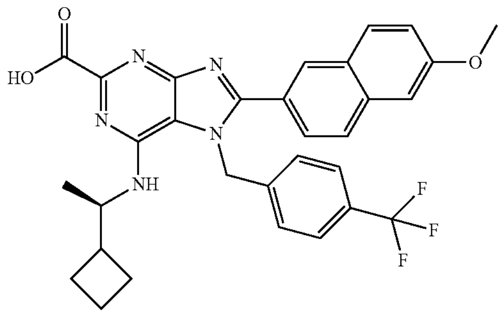 [SMILES: COc1ccc2cc(-c3nc4nc(C(=O)O)nc(N[C@H](C)C5CCC5)c4n3Cc3ccc(C(F)(F)F)cc3)ccc2c1] | 6-{[(1R)-1-cyclobutylethyl]amino}-8-(6-methoxynaphthalen-2-yl)-7-[4-(trifluoromethyl)benzyl]-7H-purine-2-carboxylic acid | TFA | 576 | 576 |
| 1.134 | 56.2 | 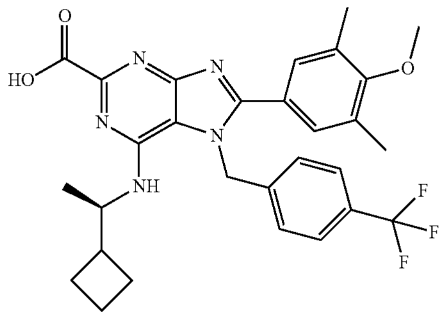 [SMILES: COc1c(C)cc(-c2nc3nc(C(=O)O)nc(N[C@H](C)C4CCC4)c3n2Cc2ccc(C(F)(F)F)cc2)cc1C] | 6-{[(1R)-1-cyclobutylethyl]amino}-8-(4-methoxy-3,5-dimethylphenyl)-7-[4-(trifluoromethyl)benzyl]-7H-purine-2-carboxylic acid | TFA | 554 | 554 |
| 1.135 | 47.9 | 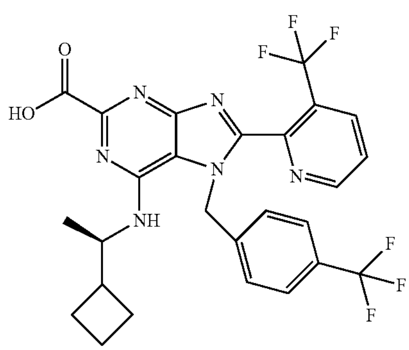 [SMILES: C[C@@H](Nc1nc(C(=O)O)nc2nc(-c3ncccc3C(F)(F)F)n(Cc3ccc(C(F)(F)F)cc3)c12)C1CCC1] | 6-{[(1R)-1-cyclobutylethyl]amino}-7-[4-(trifluoromethyl)benzyl]-8-[3-(trifluoromethyl)pyridin-2-yl]-7H-purine-2-carboxylic acid | TFA | 565 | 565 |
| 1.136 | 124.9 | 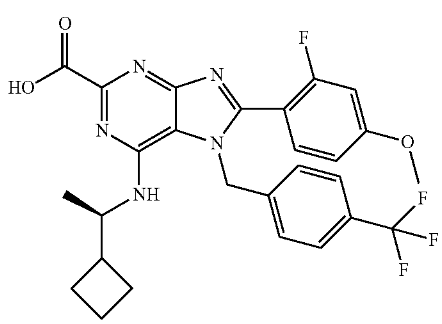 [SMILES: COc1ccc(-c2nc3nc(C(=O)O)nc(N[C@H](C)C4CCC4)c3n2Cc2ccc(C(F)(F)F)cc2)c(F)c1] | 6-{[(1R)-1-cyclobutylethyl]amino}-8-(2-fluoro-4-methoxyphenyl)-7-[4-(trifluoromethyl)benzyl]-7H-purine-2-carboxylic acid | TFA | 544 | 544 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.137 | 49.7 | 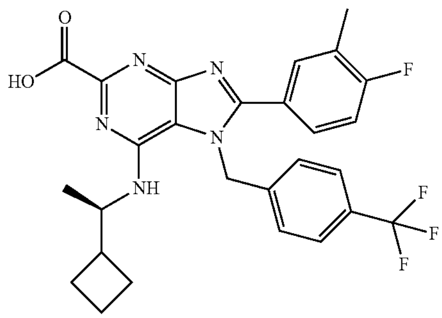 [SMILES: Cc1cc(-c2nc3nc(C(=O)O)nc(N[C@H](C)C4CCC4)c3n2Cc2ccc(C(F)(F)F)cc2)ccc1F] | 6-{[(1R)-1-cyclobutylethyl]amino}-8-(4-fluoro-3-methylphenyl)-7-[4-(trifluoromethyl)benzyl]-7H-purine-2-carboxylic acid | TFA | 528 | 528 |
| 1.138 | 15.81 | 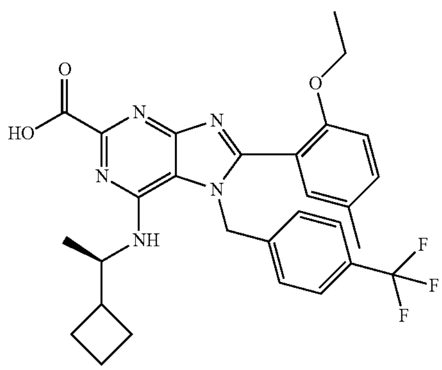 [SMILES: CCOc1ccc(C)cc1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(2-ethoxy-5-methylphenyl)-7-[4-(trifluoromethyl)benzyl]-7H-purine-2-carboxylic acid | TFA | 554 | 554 |

Preparative Example 2.1

(R)-8-bromo-6-((1-cyclobutylethyl)amino)-7-(4-(trifluoromethyl)benzyl)-7H-purine-2-carbonitrile

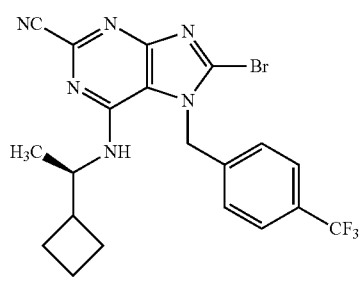 [SMILES: C[C@@H](Nc1nc(C#N)nc2nc(Br)n(Cc3ccc(C(F)(F)F)cc3)c12)C1CCC1]

(R)-6-((1-cyclobutylethyl)amino)-7-(4-(trifluoromethyl)benzyl)-7H-purine-2-carbonitrile (7.50 g, 18.7 mmol) was dissolved in anhydrous chloroform (250 mL) and NBS (recrystallized, 16.6 g, 93.6 mmol) was added. The reaction was heated at reflux for 3 hours. The reaction was then cooled to room temperature and was diluted with dichloromethane (100 mL). The organics were washed with saturated aqueous sodium sulfate solution (500 mL) and aqueous sodium hydroxide (0.05N, 500 mL). The organic layer was dried over sodium sulfate, filtered, and concentrated. Purification of the residue on RediSep 120 g silica gel column with 0 to 50% EtOAc/hexanes afforded (R)-8-bromo-6-((1-cyclobutylethyl)amino)-7-(4-(trifluoromethyl)benzyl)-7H-purine-2-carbonitrile. $^1$H NMR (300 MHz, CDCl$_3$) δ 7.74 (d, J=8.1 Hz, 2H), 7.28 (d, J=8.1 Hz, 2H), 5.66 (br s, 2H), 4.34 (d, J=8.1 Hz, 1H), 4.20-4.22 (m, 1H), 1.38-2.04 (m, 7H), 0.87 (d, J=6.6 Hz, 3H). MS (ES)=479 (M+1)$^+$.

Example 2.1

(R)-6-((1-cyclobutylethyl)amino)-8-(3-methoxyphenyl)-7-(4-(trifluoromethyl)benzyl)-7H-purine-2-carboxylic acid

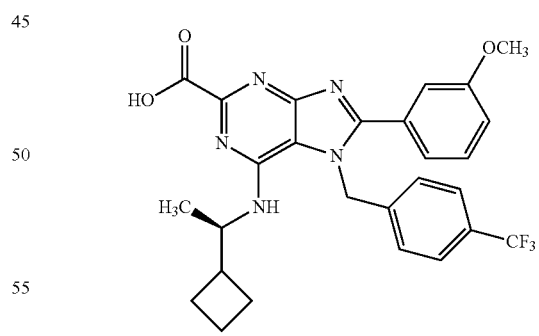

Step 1: A microwave vial (15 mL) was charged with (R)-8-bromo-6-((1-cyclobutylethyl)amino)-7-(4-(trifluoromethyl)benzyl)-7H-purine-2-carbonitrile (Preparative Example 2.1) (150 mg, 0.31 mmol), 3-methoxyphenyl boronic acid (94 mg, 0.62 mmol) and aqueous sodium carbonate (1.55 mL, 1 M). 1,4-Dioxane (4.5 mL) was added to the vial and the mixture was degassed using N$_2$ for 15 minutes. Pd(PPh$_3$)$_4$ (108 mg, 0.094 mmol) was then added to the vial. The reaction was heated at 120° C. in a CEM microwave for 15 minutes. The reaction was cooled and extracted with EtOAc (2×25 mL). The combined organic layers were washed with water and brine, and dried over sodium sulfate. The solvent was evaporated under reduced pressure and the crude product loaded onto a Redisep 12 g silica gel column. Purification with 0 to 100% EtOAc/hexanes afforded (R)-6-((1-cyclobutylethyl)amino)-8-(3-methoxyphenyl)-7-(4-(trifluoromethyl)benzyl)-7H-purine-2-carbonitrile. $^1$H NMR (400 MHz, CD$_3$OD) δ 7.80 (d, J=9.1 Hz, 2H), 7.35-7.39 (m, 3H), 7.26-7.28 (m, 1H), 7.11 (m, 2H), 5.61 (br s, 2H), 4.18-4.24 (m, 2H), 3.79 (s, 3H), 1.85 (m, 1H), 1.45-1.77 (m, 6H), 0.84 (d, J=8.1 Hz, 3H). MS (ES)=507 (M+1)$^+$.

Step 2: (R)-6-((1-cyclobutylethyl)amino)-8-(3-methoxyphenyl)-7-(4-(trifluoromethyl)benzyl)-7H-purine-2-carbonitrile (100 mg, 0.2 mmol) was suspended in anhydrous HCl (5.0 mL, 3.0 M in methanol) and heated at 75° C. for 4 hours. The solvent was evaporated under vacuum. The resulting residue was suspended in dichloromethane (40 mL) and washed with saturated aqueous sodium bicarbonate. The organic layer was separated and dried over sodium sulfate. The solvent was evaporated and the crude product loaded onto a Redisep 12 g silica gel column. Purification with 0 to 100% EtOAc/hexanes afforded (R)-methyl 6-((1-cyclobutylethyl)amino)-8-(3-methoxyphenyl)-7-(4-(trifluoromethyl)benzyl)-7H-purine-2-carboxylate. $^1$H NMR (300 MHz, CDCl$_3$) δ 7.75 (d, J=8.4 Hz, 2H), 7.23-7.41 (m, 4H), 7.11 (d, J=7.9 Hz, 1H), 7.03 (dd, J=8.4, 2.8 Hz, 1H), 5.69 (br s, 2H), 4.26-4.38 (m, 2H), 3.96 (s, 3H), 3.75 (s, 3H), 1.32-1.96 (m, 7H), 0.84 (d, J=5.6 Hz, 3H). MS (ES)=540 (M+1)$^+$.

Step 3: To a solution of (R)-methyl 6-((1-cyclobutylethyl)amino)-8-(3-methoxyphenyl)-7-(4-(trifluoromethyl)benzyl)-7H-purine-2-carboxylate (70 mg, 0.12 mmol) in THF (2.0 mL) was added aqueous lithium hydroxide solution (0.64 mL, 1 M) and the reaction was stirred for 2 hours at ambient temperature. Solvent was evaporated under vacuum and the residue was dissolved in water (2.0 mL). The pH for the solution was adjusted to 6.5 using aqueous HCl (2 N). The precipitate that formed was collected by filtration and air-dried to afford (R)-6-((1-cyclobutylethyl)amino)-8-(3-methoxyphenyl)-7-(4-(trifluoromethyl)benzyl)-7H-purine-2-carboxylic acid. $^1$H NMR (400 MHz, CD$_3$OD) δ 7.71 (d, J=8.2 Hz, 2H), 7.44 (t, J=8.1 Hz, 1H), 7.28 (d, J=8.2 Hz, 2H), 7.12-7.21 (m, 3H), 5.85 (d, J=19.0 Hz, 1H), 5.73 (d, J=18.7 Hz, 1H), 4.70 (m, 1H), 3.76 (s, 3H), 2.09 (m, 1H), 1.87 (m, 1H), 1.60-1.70 (m, 3H), 1.40-1.50 (m, 2H), 1.06 (d, J=6.4 Hz, 3H). MS (ES)=526 (M+1)$^+$.

Example 2.2

(R)-6-((1-cyclobutylethyl)amino)-8-(4-cyclopropyl-2-methylphenyl)-7-(4-(trifluoromethyl)benzyl)-7H-purine-2-carboxylic acid

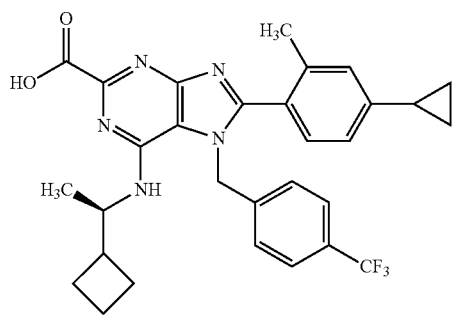 [SMILES: Cc1cc(C2CC2)ccc1-c1nc2nc(C(=O)O)nc(N[C@H](C)C3CCC3)c2n1Cc1ccc(C(F)(F)F)cc1]

Step 1: A microwave vial (15 mL) was charged with (R)-8-bromo-6-((1-cyclobutylethyl)amino)-7-(4-(trifluoromethyl)benzyl)-7H-purine-2-carbonitrile (Preparative Example 2.1) (300 mg, 0.62 mmol), 4-bromo-2-methylphenylboronic acid (161 mg, 0.75 mmol), aqueous sodium carbonate (1.25 mL, 2 M), toluene (3.5 mL), and ethanol (2.0 mL). The mixture was degassed using Ar for 15 minutes before Pd(PPh$_3$)$_4$ (36 mg, 0.031 mmol) was added to the vial. The reaction was heated at 105° C. for 18 hours. The reaction was then cooled to ambient temperature and extracted with EtOAc (2×10 mL). The combined organics were washed with water and brine, dried over sodium sulfate, filtered, and concentrated under reduced pressure. Purification of the residue on RediSep 12 g silica gel column with 0 to 40% EtOAc/hexanes afforded (R)-8-(4-bromo-2-methylphenyl)-6-((1-cyclobutylethyl)amino)-7-(4-(trifluoromethyl)benzyl)-7H-purine-2-carbonitrile. $^1$H NMR (300 MHz, CD$_3$OD) δ 7.73 (d, J=8.1 Hz, 2H), 7.55 (d, J=1.5 Hz, 1H), 7.38 (d, J=8.1 Hz, 1H), 7.18 (d, J=8.1 Hz, 2H), 7.12 (d, J=8.4 Hz, 1H), 5.39 (br s, 2H), 4.21-4.18 (m, 2H), 2.51 (s, 3H), 1.34-1.90 (m, 7H), 0.83 (d, J=6.0 Hz, 3H). MS (ES)=569 (M+1)$^+$, 571 (M+3)$^+$.

Step 2: A microwave vial equipped with a stir bar was charged with (R)-8-(4-bromo-2-methylphenyl)-6-((1-cyclobutylethyl)amino)-7-(4-(trifluoromethyl)benzyl)-7H-purine-2-carbonitrile (118 mg, 0.20 mmol), cyclopropylboronic acid (21 mg, 0.25 mmol), potassium phosphate (154 mg, 0.72 mmol), tricyclohexylphosphine (5 mg, 0.02 mmol), toluene (2 mL), and water (0.1 mL). The mixture was degassed with Ar for 25 minutes. Palladium acetate (2 mg, 0.01 mmol) was added and the vial was then sealed and heated at 100° C. for 18 hours. The reaction was then cooled to room temperature, diluted with ethyl acetate (10 mL) and the organics were washed with brine (10 mL). The organic layer was dried over sodium sulfate, filtered, and concentrated. Purification of the residue on a RediSep 12 g silica gel column with 0 to 70% EtOAc/hexanes afforded (R)-6-((1-cyclobutylethyl)amino)-8-(4-cyclopropyl-2-methylphenyl)-7-(4-(trifluoromethyl)benzyl)-7H-purine-2-carbonitrile. $^1$H NMR (300 MHz, CDCl$_3$) δ 7.70 (d, J=8.1 Hz, 2H), 7.19 (d, J=8.1 Hz, 2H), 7.12 (d, J=7.8 Hz, 1H), 7.04 (br s, 1H), 6.90 (dd, J=8.1, 1.5 Hz, 1H), 5.41 (br s, 2H), 4.20-4.31 (m, 2H), 2.27 (s, 3H), 1.28-1.90 (m, 7H), 0.98-1.03 (m, 2H), 0.82 (d, J=6.0 Hz, 3H), 0.56-0.76 (m, 2H). MS (ES)=531 (M+1)$^+$.

Step 3: Using a hydrolysis procedure analogous to that described in Example 2.1, and starting with (R)-6-((1-cyclobutylethyl)amino)-8-(4-cyclopropyl-2-methylphenyl)-7-(4-(trifluoromethyl)benzyl)-7H-purine-2-carbonitrile, (R)-6-((1-cyclobutylethyl)amino)-8-(4-cyclopropyl-2-methylphenyl)-7-(4-(trifluoromethyl)benzyl)-7H-purine-2-carboxylic acid was prepared. $^1$H NMR (400 MHz, CD$_3$OD) δ 7.63 (d, J=8.0 Hz, 2H), 7.22 (d, J=7.6 Hz, 1H), 7.10-7.12 (m, 3H), 6.98 (d, J=7.6, 1H), 5.69 (d, J=17.6, Hz, 1H), 5.43 (d, J=17.6, Hz, 1H), 4.64 (m, 1H), 2.17 (s, 3H), 2.09 (m, 1H), 1.85-1.97 (m, 2H), 1.56-1.71 (m, 3H), 1.41-1.51 (m, 2H), 0.99-1.04 (m, 2H), 0.95 (d, J=6.5 Hz, 3H), 0.72-0.79 (m, 2H). MS (ES)=550 (M+1)$^+$.

Example 2.3

(R)-8-benzyl-6-((1-cyclobutylethyl)amino)-7-(4-(trifluoromethyl)benzyl)-7H-purine-2-carboxylic acid (TFA salt)

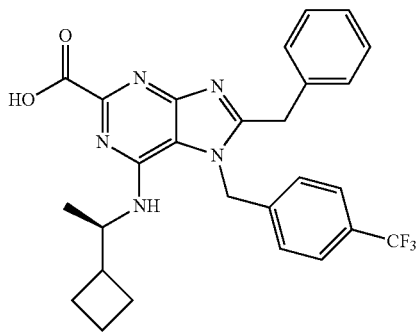 [SMILES: C[C@@H](Nc1nc(C(=O)O)nc2nc(Cc3ccccc3)n(Cc3ccc(C(F)(F)F)cc3)c12)C1CCC1]

Step 1: Palladium (II) acetate (2.342 mg, 10.43 μmol), Butyldi-1-adamantylphosphine (5.61 mg, 0.016 mmol), potassium benzyltrifluoroborate (83 mg, 0.417 mmol), and cesium carbonate (204 mg, 0.626 mmol) were added to a stirred, room temperature solution of (R)-8-bromo-6-((1-cyclobutylethyl)amino)-7-(4-(trifluoromethyl)benzyl)-7H-purine-2-carbonitrile (Preparative Example 2.1) (100 mg, 0.209 mmol) in toluene (1000 μl) and water (100 μl). The reaction vial was sealed, evacuated and backfilled with $N_2(g)$ (2×), heated to 100° C., and stirred overnight. The resulting mixture was cooled to room temperature and filtered through celite. The filtrate was purified by column chromatography on silica gel, eluting with EtOAc/isohexane to give (R)-8-benzyl-6-((1-cyclobutylethyl)amino)-7-(4-(trifluoromethyl)benzyl)-7H-purine-2-carbonitrile as a light brown solid. MS ESI calc'd. for $C_{27}H_{25}F_3N_6$ [M+H]$^+$ 491. found 491.

Step 2: A 5M aqueous solution of sodium hydroxide (500 μl, 2.500 mmol) was added to a stirred, room temperature solution of (R)-8-benzyl-6-((1-cyclobutylethyl)amino)-7-(4-(trifluoromethyl)benzyl)-7H-purine-2-carbonitrile (34.8 mg, 0.071 mmol) in ethanol (1 mL). The reaction vial was sealed under $N_2(g)$ and stirred at 70° C. for 2 hours. The mixture was then cooled to room temperature, diluted with EtOAc, and partitioned with 1N aqueous HCl in a separatory funnel. The aqueous layer was extracted with EtOAc (3×), and the combined organic layers were washed with brine, dried over sodium sulfate, filtered, and concentrated in vacuo. The residue was purified by automated mass triggered reverse phase HPLC (acetonitrile/water+0.1% TFA modifier) to afford (R)-8-benzyl-6-((1-cyclobutylethyl)amino)-7-(4-(trifluoromethyl)benzyl)-7H-purine-2-carboxylic acid (TFA salt) as a white solid. MS ESI calc'd. for $C_{27}H_{26}F_3N_5O_2$ [M+H]$^+$ 510. found 510. $^1$H NMR (500 MHz, DMSO-d$_6$) δ 7.59 (d, J=8.5 Hz, 2H), 7.25-7.19 (m, 4H), 7.16-7.13 (m, 1H), 6.97 (d, J=8.5 Hz, 2H), 6.04 (s, 1H), 6.00 (d, J=18 Hz, 1H), 5.83 (d, J=18 Hz, 1H), 4.36 (s, 2H), 4.31-4.26 (m, 1H), 2.17-2.12 (m, 1H), 1.79-1.75 (m, 1H), 1.60-1.54 (m, 1H), 1.50-1.44 (m, 2H), 1.34-1.26 (m, 2H), 0.90 (d, J=6.5 Hz, 3H).

Example 2.4

(R)-6-((1-cyclobutylethyl)amino)-8-cyclohexyl-7-(4-(trifluoromethyl)benzyl)-7H-purine-2-carboxylic acid (TFA salt)

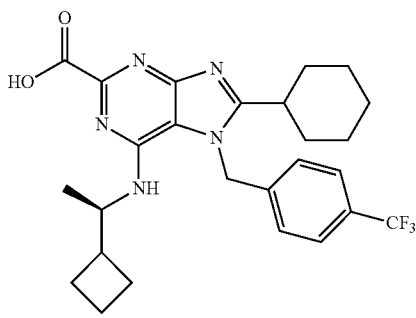 [SMILES: C[C@@H](Nc1nc(C(=O)O)nc2nc(C3CCCCC3)n(Cc3ccc(C(F)(F)F)cc3)c12)C1CCC1]

Step 1: A microwave vial was charged with (R)-8-bromo-6-((1-cyclobutylethyl)amino)-7-(4-(trifluoromethyl)benzyl)-7H-purine-2-carbonitrile (Preparative Example 2.1) (50 mg, 0.104 mmol), cyclohexene-1-boronic acid pinacol ester (43.4 mg, 0.21 mmol), PdCl$_2$(dppf)-CH$_2$Cl$_2$ adduct (8.52 mg, 0.0104 mmol), potassium phosphate (66.4 mg, 0.31 mmol), 1,4-dioxane (100 μL) and water (25 μL). The vial was evacuated and refilled with Ar (3×). The resulting solution was heated by microwave irradiation to a temperature of 120° C. for 10 minutes. The mixture was cooled to room temperature and partitioned between saturated aqueous sodium bicarbonate and ethyl acetate. The organic layer was collected and concentrated. The residue was purified via silica gel chromatography, eluting with 0-100% ethyl acetate in hexanes to give (R)-6-((1-cyclobutylethyl)amino)-8-(cyclohex-1-en-1-yl)-7-(4-(trifluoromethyl)benzyl)-7H-purine-2-carbonitrile as a white solid. MS ESI calc'd for $C_{26}H_{27}F_3N_6$ [M+H]$^+$ 481. found 481.

Step 2: To an ethanol (0.5 ml) solution of (R)-6-((1-cyclobutylethyl)amino)-8-(cyclohex-1-en-1-yl)-7-(4-(trifluoromethyl)benzyl)-7H-purine-2-carbonitrile (40 mg, 0.083 mmol) was added sodium hydroxide (5.0 M in water, 0.08 mL, 0.4 mmol). Reaction was brought to 70° C. and stirred for 2 h. The resulting solution was concentrated to afford (R)-6-((1-cyclobutylethyl)amino)-8-(cyclohex-1-en-1-yl)-7-(4-(trifluoromethyl)benzyl)-7H-purine-2-carboxylic acid which was used for next step directly. MS ESI calc'd for $C_{26}H_{28}F_3N_5O_2$ [M+H]$^+$ 500. found 500.

Step 3: A solution of (R)-6-((1-cyclobutylethyl)amino)-8-(cyclohex-1-en-1-yl)-7-(4-(trifluoromethyl)benzyl)-7H-purine-2-carboxylic acid (51 mg, 0.1) was taken up in ethanol (1.0 mL). The resulting solution was degassed with Ar, and palladium (10% wt Carbon, 50 mg, 0.47 mmol) was added. The reaction flask was evacuated and backfilled with hydrogen (3×) via balloon. The resulting mixture was heated to 50° C. for 4 h and then cooled to room temperature and stirred as such overnight. The reaction mixture was then filtered through a pad of celite and the filtrate was concentrated. The resulting residue was purified by reverse phase HPLC (acetonitrile/water+0.1% TFA modifier) to afford (R)-6-((1-cyclobutylethyl)amino)-8-cyclohexyl-7-(4-(trifluoromethyl)benzyl)-7H-purine-2-carboxylic acid (TFA salt). MS ESI calc'd for $C_{26}H_{30}F_3N_5O_2$ [M+H]$^+$ 502. found 502. $^1$H NMR (500 MHz, CDCl$_3$): δ 7.72 (d, J=8.0 Hz, 2H), 7.21 (d, J=8.0 Hz, 2H), 5.77 (d, J=18.2 Hz, 1H), 5.65 (d, J=18.2 Hz, 1H), 4.96 (s, 1H), 4.32-4.46 (br m, 2H), 2.87 (br s, 1H), 1.80-1.95 (br m, 8H), 1.68-1.70 (m, 1H), 1.53-1.56 (m, 2H), 1.30-1.41 (m, 5H), 0.87 (d, J=6.4 Hz, 3H).

The following compounds in Table 2 (other than Example 2.1 to 2.4 and Examples 2.42 and 2.43) were prepared using procedures which were analogous to those described above in Example 2.1. Examples 2.42 and 2.43 were prepared using procedures which were analogous to those described above in Example 2.3.

TABLE 2

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.1 | 37.48 | 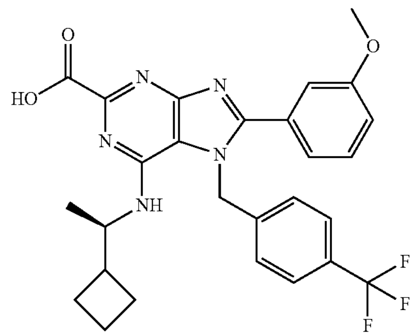 [SMILES: COc1cccc(-c2nc3nc(C(=O)O)nc(N[C@H](C)C4CCC4)c3n2Cc2ccc(C(F)(F)F)cc2)c1] | (R)-6-((1-cyclobutylethyl)amino)-8-(3-methoxyphenyl)-7-(4-(trifluoromethyl)benzyl)-7H-purine-2-carboxylic acid | | 526 | 526 |
| 2.2 | 151.1 | 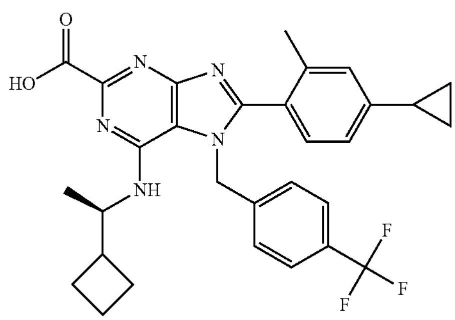 [SMILES: Cc1cc(C2CC2)ccc1-c1nc2nc(C(=O)O)nc(N[C@H](C)C3CCC3)c2n1Cc1ccc(C(F)(F)F)cc1] | (R)-6-((1-cyclobutylethyl)amino)-8-(4-cyclopropyl-2-methylphenyl)-7-(4-(trifluoromethyl)benzyl)-7H-purine-2-carboxylic acid | | 550 | 550 |
| 2.3 | 3.655 | 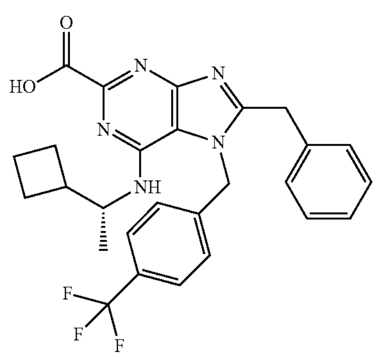 [SMILES: C[C@@H](Nc1nc(C(=O)O)nc2nc(Cc3ccccc3)n(Cc3ccc(C(F)(F)F)cc3)c12)C1CCC1] | (R)-8-benzyl-6-((1-cyclobutylethyl)amino)-7-(4-(trifluoromethyl)benzyl)-7H-purine-2-carboxylic acid | TFA | 510 | 510 |
| 2.4 | 11.47 | 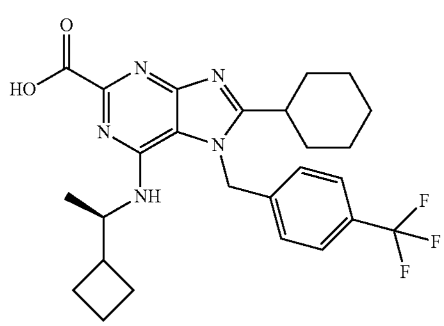 [SMILES: C[C@@H](Nc1nc(C(=O)O)nc2nc(C3CCCCC3)n(Cc3ccc(C(F)(F)F)cc3)c12)C1CCC1] | (R)-6-((1-cyclobutylethyl)amino)-8-cyclohexyl-7-(4-(trifluoromethyl)benzyl)-7H-purine-2-carboxylic acid | TFA | 502 | 502 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.5 | 217.5 | 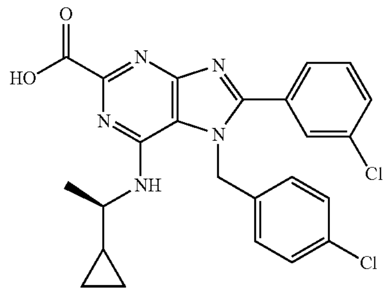 [SMILES: C[C@@H](Nc1nc(C(=O)O)nc2nc(-c3cccc(Cl)c3)n(Cc3ccc(Cl)cc3)c12)C1CC1] | 7-(4-chlorobenzyl)-8-(3-chlorophenyl)-6-{[(1R)-1-cyclopropylethyl]amino}-7H-purine-2-carboxylic acid | TFA | 482 | 482 |
| 2.6 | 209.1 | 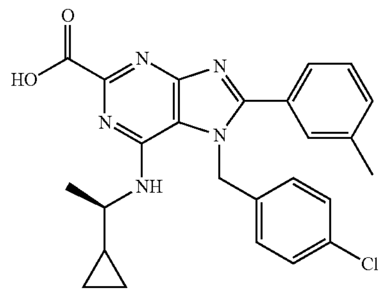 [SMILES: Cc1cccc(-c2nc3nc(C(=O)O)nc(N[C@H](C)C4CC4)c3n2Cc2ccc(Cl)cc2)c1] | 7-(4-chlorobenzyl)-6-{[(1R)-1-cyclopropylethyl]amino}-8-(3-methylphenyl)-7H-purine-2-carboxylic acid | TFA | 462 | 462 |
| 2.7 | 259.4 | 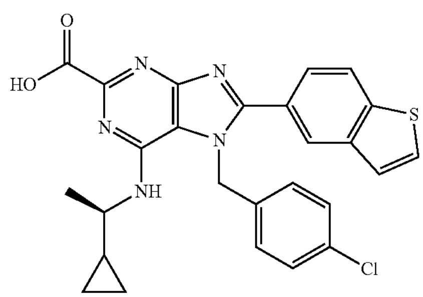 [SMILES: C[C@@H](Nc1nc(C(=O)O)nc2nc(-c3ccc4sccc4c3)n(Cc3ccc(Cl)cc3)c12)C1CC1] | 8-(1-benzothiophen-5-yl)-7-(4-chlorobenzyl)-6-{[(1R)-1-cyclopropylethyl]amino}-7H-purine-2-carboxylic acid | TFA | 504 | 504 |
| 2.8 | 28.4 | 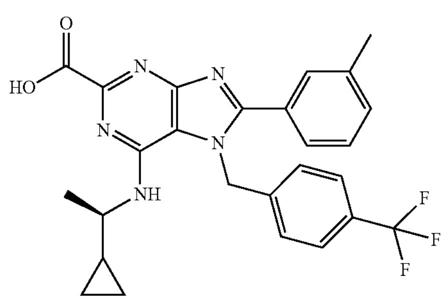 [SMILES: Cc1cccc(-c2nc3nc(C(=O)O)nc(N[C@H](C)C4CC4)c3n2Cc2ccc(C(F)(F)F)cc2)c1] | 6-{[(1R)-1-cyclopropylethyl]amino}-8-(3-methylphenyl)-7-[4-(trifluoromethyl)benzyl]-7H-purine-2-carboxylic acid | TFA | 496 | 496 |
| 2.9 | 43.8 | 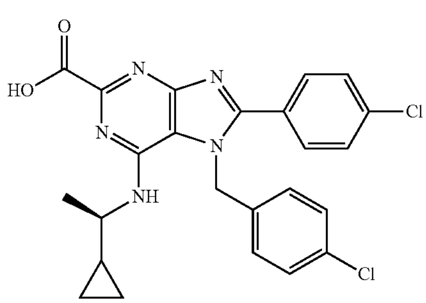 [SMILES: C[C@@H](Nc1nc(C(=O)O)nc2nc(-c3ccc(Cl)cc3)n(Cc3ccc(Cl)cc3)c12)C1CC1] | 7-(4-chlorobenzyl)-8-(4-chlorophenyl)-6-{[(1R)-1-cyclopropylethyl]amino}-7H-purine-2-carboxylic acid | | 482 | 482 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.10 | 7.2 | 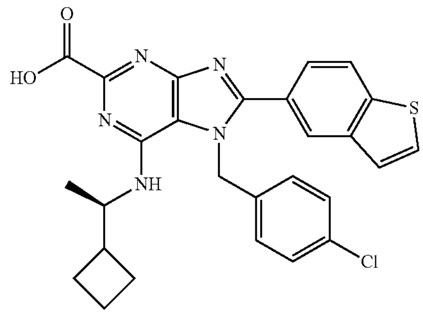 [SMILES: C[C@@H](Nc1nc(C(=O)O)nc2nc(-c3ccc4sccc4c3)n(Cc3ccc(Cl)cc3)c12)C1CCC1] | 8-(1-benzo-thiophen-5-yl)-7-(4-chloro-benzyl)-6-{[(1R)-1-cyclobutyl-ethyl]amino}-7H-purine-2-carboxylic acid | | 518 | 518 |
| 2.11 | 36.63 | 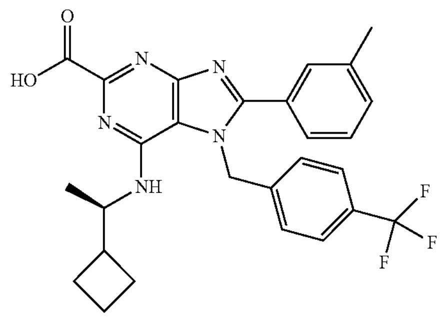 [SMILES: Cc1cccc(-c2nc3nc(C(=O)O)nc(N[C@H](C)C4CCC4)c3n2Cc2ccc(C(F)(F)F)cc2)c1] | 6-{[(1R)-1-cyclobutyl-ethyl]amino}-8-(3-methylphenyl)-7-[4-(trifluoromethyl)benzyl]-7H-purine-2-carboxylic acid | TFA | 510 | 510 |
| 2.12 | 198.9 | 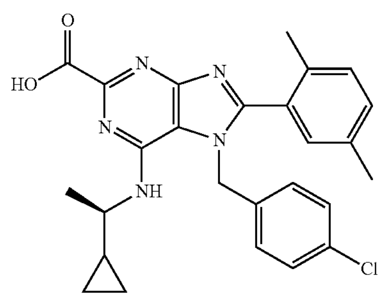 [SMILES: Cc1ccc(C)c(-c2nc3nc(C(=O)O)nc(N[C@H](C)C4CC4)c3n2Cc2ccc(Cl)cc2)c1] | 7-(4-chlorobenzyl)-6-{[(1R)-1-cyclopropyl-ethyl]amino}-8-(2,5-dimethyl-phenyl)-7H-purine-2-carboxylic acid | | 476 | 476 |
| 2.13 | 40.44 | 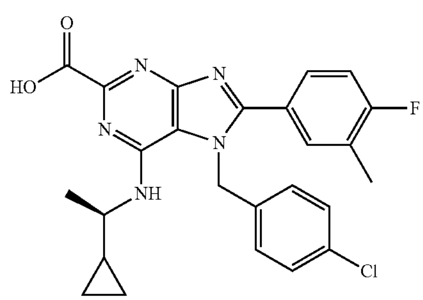 [SMILES: Cc1cc(-c2nc3nc(C(=O)O)nc(N[C@H](C)C4CC4)c3n2Cc2ccc(Cl)cc2)ccc1F] | 7-(4-chloro-benzyl)-6-{[(1R)-1-cyclopropyl-ethyl]amino}-8-(4-fluoro-3-methylphenyl)-7H-purine-2-carboxylic acid | | 480 | 480 |
| 2.14 | 339 | 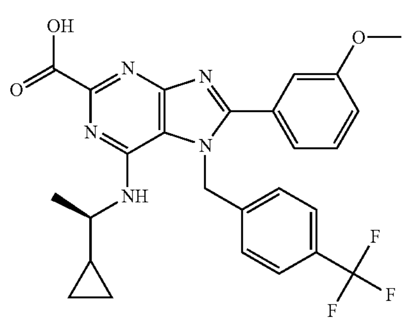 [SMILES: COc1cccc(-c2nc3nc(C(=O)O)nc(N[C@H](C)C4CC4)c3n2Cc2ccc(C(F)(F)F)cc2)c1] | 6-{[(1R)-1-cyclopropyl-ethyl]amino}-8-(3-methoxy-phenyl)-7-[4-(trifluoromethyl)benzyl]-7H-purine-2-carboxylic acid | | 512 | 512 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.15 | 304 | 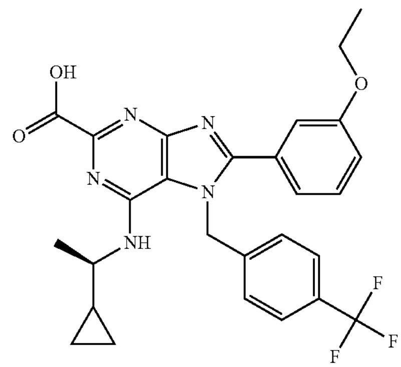 [SMILES: CCOc1cccc(-c2nc3nc(C(=O)O)nc(N[C@H](C)C4CC4)c3n2Cc2ccc(C(F)(F)F)cc2)c1] | 6-{[(1R)-1-cyclopropyl-ethyl]amino}-8-(3-ethoxy-phenyl)-7-[4-(trifluoromethyl)benzyl]-7H-purine-2-carboxylic acid | | 526 | 526 |
| 2.16 | 179.6 | 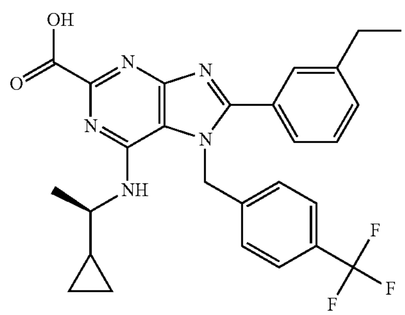 [SMILES: CCc1cccc(-c2nc3nc(C(=O)O)nc(N[C@H](C)C4CC4)c3n2Cc2ccc(C(F)(F)F)cc2)c1] | 6-{[(1R)-1-cyclopropyl-ethyl]amino}-8-(3-ethylphenyl)-7-[4-(trifluoro-methyl)benzyl]-7H-purine-2-carboxylic acid | | 510 | 510 |
| 2.17 | 40.16 | 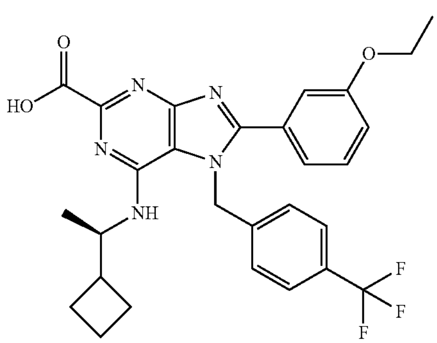 [SMILES: CCOc1cccc(-c2nc3nc(C(=O)O)nc(N[C@H](C)C4CCC4)c3n2Cc2ccc(C(F)(F)F)cc2)c1] | 6-{[(1R)-cyclobutyl-ethyl]amino}-8-(3-ethoxyphenyl)-7-[4-(trifluoro-methyl)benzyl]-7H-purine-2-carboxylic acid | | 540 | 540 |
| 2.18 | 122.9 | 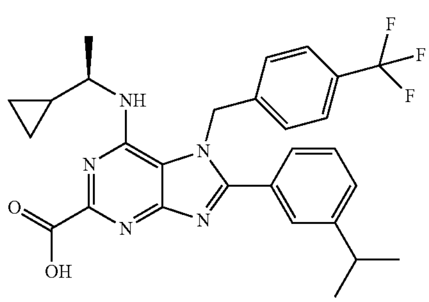 [SMILES: CC(C)c1cccc(-c2nc3nc(C(=O)O)nc(N[C@H](C)C4CC4)c3n2Cc2ccc(C(F)(F)F)cc2)c1] | 6-{[(1R)-1-cyclopropyl-ethyl]amino}-8-[3-(1-methylethyl)phenyl]-7-[4-(trifluoromethyl)benzyl]-7H-purine-2-carboxylic acid | | 524 | 524 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.19 | 144.8 | 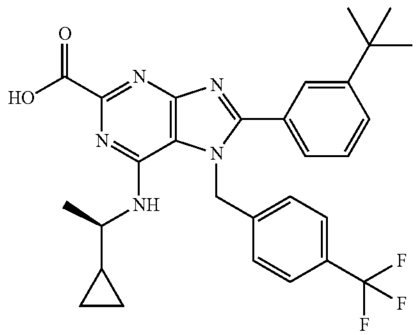 [SMILES: C[C@@H](Nc1nc(C(=O)O)nc2nc(-c3cccc(C(C)(C)C)c3)n(Cc3ccc(C(F)(F)F)cc3)c12)C1CC1] | 8-(3-tert-butyl-phenyl)-6-{[(1R)-1-cyclopropyl-ethyl]amino}-7-[4-(trifluoro-methyl)benzyl]-7H-purine-2-carboxylic acid | | 538 | 538 |
| 2.20 | 1407 | 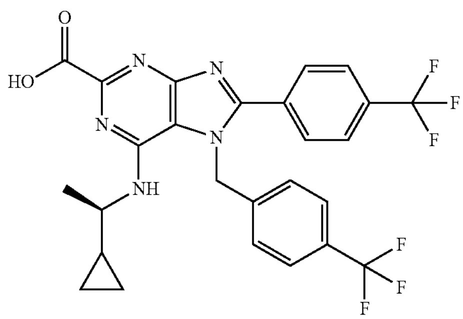 [SMILES: C[C@@H](Nc1nc(C(=O)O)nc2nc(-c3ccc(C(F)(F)F)cc3)n(Cc3ccc(C(F)(F)F)cc3)c12)C1CC1] | 6-{[(1R)-1-cyclopropyl-ethyl]amino}-7-[4-(trifluoro-methyl)benzyl]-8-[4-(trifluoro-methyl)phenyl]-7H-purine-2-carboxylic acid | | 550 | 550 |
| 2.21 | 253 | 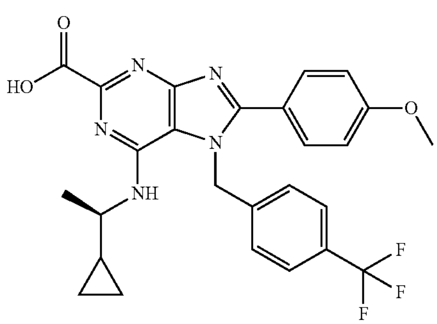 [SMILES: COc1ccc(-c2nc3nc(C(=O)O)nc(N[C@H](C)C4CC4)c3n2Cc2ccc(C(F)(F)F)cc2)cc1] | 6-{[(1R)-1-cyclopropyl-ethyl]amino}-8-(4-methoxy-phenyl)-7-[4-(trifluoromethyl)benzyl]-7H-purine-2-carboxylic acid | | 512 | 512 |
| 2.22 | 123.9 | 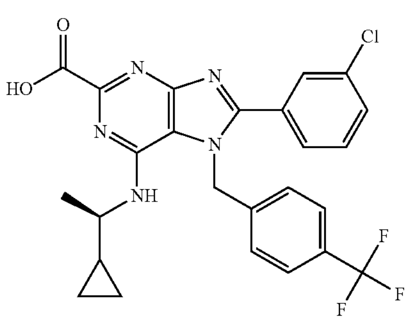 [SMILES: C[C@@H](Nc1nc(C(=O)O)nc2nc(-c3cccc(Cl)c3)n(Cc3ccc(C(F)(F)F)cc3)c12)C1CC1] | 8-(3-chlorophenyl)-6-{[(1R)-1-cyclopropyl-ethyl]amino}-7-[4-(trifluoro-methyl)benzyl]-7H-purine-2-carboxylic acid | | 516 | 516 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.23 | 16.74 | 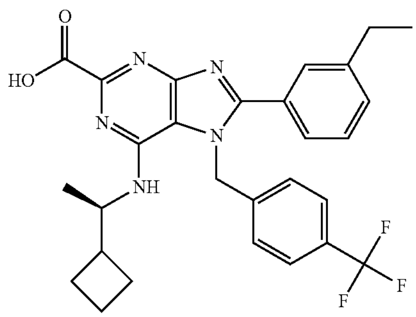 [SMILES: CCc1cccc(-c2nc3nc(C(=O)O)nc(N[C@H](C)C4CCC4)c3n2Cc2ccc(C(F)(F)F)cc2)c1] | 6-{[(1R)-1-cyclobutyl-ethyl]amino}-8-(3-ethylphenyl)-7-[4-(trifluoro-methyl)benzyl]-7H-purine-2-carboxylic acid | | 524 | 524 |
| 2.24 | 14.74 | 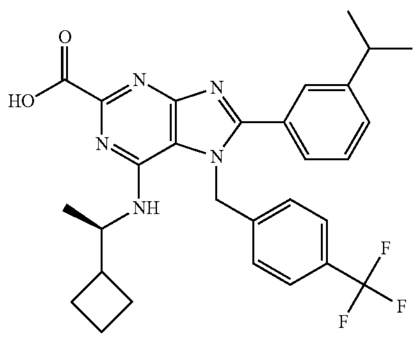 [SMILES: CC(C)c1cccc(-c2nc3nc(C(=O)O)nc(N[C@H](C)C4CCC4)c3n2Cc2ccc(C(F)(F)F)cc2)c1] | 6-{[(1R)-1-cyclobutyl-ethyl]amino}-8-[3-(1-methyl-ethyl)phenyl]-7-[4-(trifluoro-methyl)benzyl]-7H-purine-2-carboxylic acid | | 538 | 538 |
| 2.25 | 59.13 | 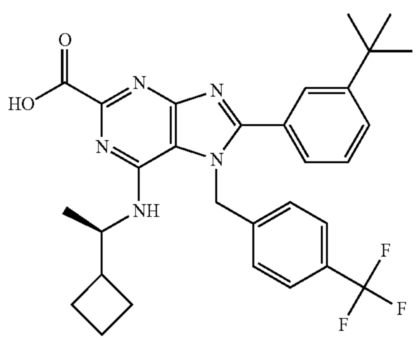 [SMILES: C[C@@H](Nc1nc(C(=O)O)nc2nc(-c3cccc(C(C)(C)C)c3)n(Cc3ccc(C(F)(F)F)cc3)c12)C1CCC1] | 8-(3-tert-butylphenyl)-6-{[(1R)-1-cyclobutyl-ethyl]amino}-7-[4-(trifluoro-methyl)benzyl]-7H-purine-2-carboxylic acid | | 552 | 552 |
| 2.26 | 550.3 | 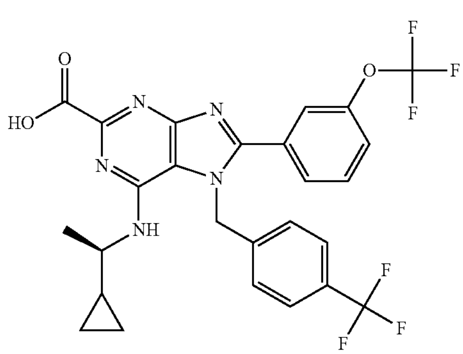 [SMILES: C[C@@H](Nc1nc(C(=O)O)nc2nc(-c3cccc(OC(F)(F)F)c3)n(Cc3ccc(C(F)(F)F)cc3)c12)C1CC1] | 6-{[(1R)-1-cyclopropyl-ethyl]amino}-8-[3-(trifluoro-methoxy)phenyl]-7-[4-(trifluoro-methyl)benzyl]-7H-purine-2-carboxylic acid | | 566 | 566 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.27 | 1144 | 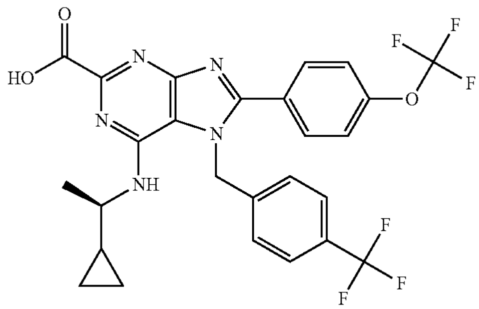 [SMILES: C[C@@H](Nc1nc(C(=O)O)nc2nc(-c3ccc(OC(F)(F)F)cc3)n(Cc3ccc(C(F)(F)F)cc3)c12)C1CC1] | 6-{[(1R)-1-cyclopropyl-ethyl]amino}-8-[4-(trifluoro-methoxy)phenyl]-7-[4-(trifluoro-methyl)benzyl]-7H-purine-2-carboxylic acid | | 566 | 566 |
| 2.28 | 454.6 | 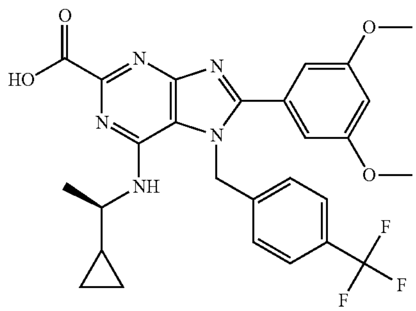 [SMILES: COc1cc(OC)cc(-c2nc3nc(C(=O)O)nc(N[C@H](C)C4CC4)c3n2Cc2ccc(C(F)(F)F)cc2)c1] | 6-{[(1R)-1-cyclopropyl-ethyl]amino}-8-(3,5-dimethoxy-phenyl)-7-[4-(trifluoromethyl)benzyl]-7H-purine-2-carboxylic acid | | 542 | 542 |
| 2.29 | 105.1 | 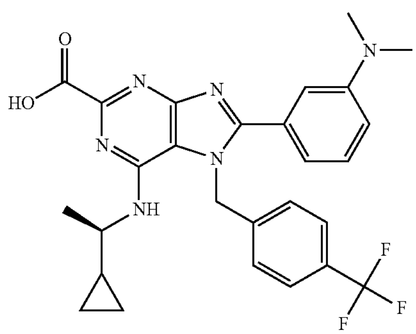 [SMILES: C[C@@H](Nc1nc(C(=O)O)nc2nc(-c3cccc(N(C)C)c3)n(Cc3ccc(C(F)(F)F)cc3)c12)C1CC1] | 6-{[(1R)-1-cyclopropyl-ethyl]amino}-8-[3-(dimethyl-amino)phenyl]-7-[4-(trifluoro-methyl)benzyl]-7H-purine-2-carboxylic acid | | 525 | 525 |
| 2.30 | 140 | 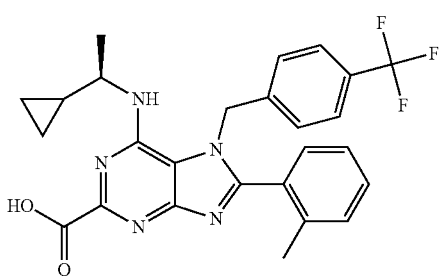 [SMILES: Cc1ccccc1-c1nc2nc(C(=O)O)nc(N[C@H](C)C3CC3)c2n1Cc1ccc(C(F)(F)F)cc1] | 6-{[(1R)-1-cyclopropyl-ethyl]amino}-8-(2-methyl-phenyl)-7-[4-(trifluoromethyl)benzyl]-7H-purine-2-carboxylic acid | | 496 | 496 |
| 2.31 | 153.6 | 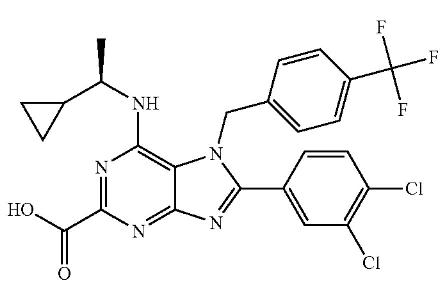 [SMILES: C[C@@H](Nc1nc(C(=O)O)nc2nc(-c3ccc(Cl)c(Cl)c3)n(Cc3ccc(C(F)(F)F)cc3)c12)C1CC1] | 6-{[(1R)-1-cyclopropyl-ethyl]amino}-8-(3,4-dichloro-phenyl)-7-(trifluoro-methyl)benzyl]-7H-purine-2-carboxylic acid | | 550 | 550 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.32 | 1950 | 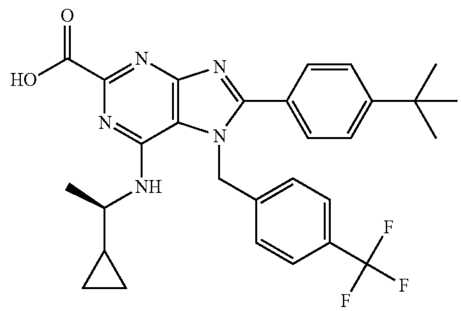 [SMILES: C[C@@H](Nc1nc(C(=O)O)nc2nc(-c3ccc(C(C)(C)C)cc3)n(Cc3ccc(C(F)(F)F)cc3)c12)C1CC1] | 8-(4-tert-butylphenyl)-6-{[(1R)-1-cyclopropyl-ethyl]amino}-7-[4-(trifluoro-methyl)benzyl]-7H-purine-2-carboxylic acid | | 538 | 538 |
| 2.33 | 400.8 | 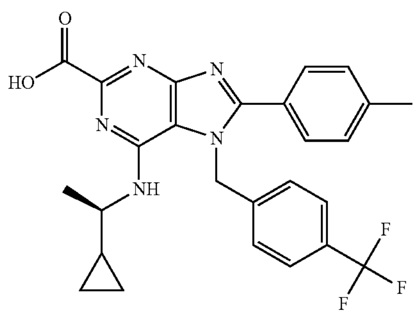 [SMILES: Cc1ccc(-c2nc3nc(C(=O)O)nc(N[C@H](C)C4CC4)c3n2Cc2ccc(C(F)(F)F)cc2)cc1] | 6-{[(1R)-1-cyclopropyl-ethyl]amino}-8-(4-methyl-phenyl)-7-[4-(trifluoro-methyl)benzyl]-7H-purine-2-carboxylic acid | | 496 | 496 |
| 2.34 | 21 | 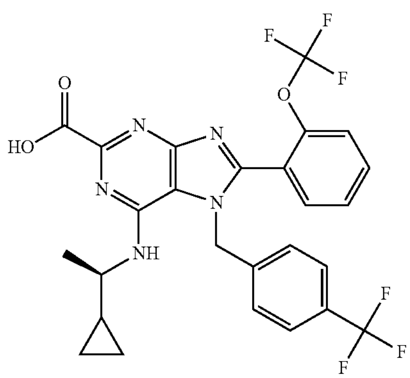 [SMILES: C[C@@H](Nc1nc(C(=O)O)nc2nc(-c3ccccc3OC(F)(F)F)n(Cc3ccc(C(F)(F)F)cc3)c12)C1CC1] | 6-{[(1R)-1-cyclopropyl-ethyl]amino}-8-[2-(trifluoro-methoxy)phenyl]-7-[4-(trifluoro-methyl)benzyl]-7H-purine-2-carboxylic acid | | 566 | 566 |
| 2.35 | 510 | 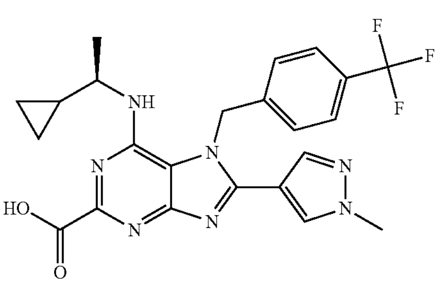 [SMILES: C[C@@H](Nc1nc(C(=O)O)nc2nc(-c3cnn(C)c3)n(Cc3ccc(C(F)(F)F)cc3)c12)C1CC1] | 6-{[(1R)-1-cyclopropyl-ethyl]amino}-8-(1-methyl-1H-pyrazol-4-yl)-7-[4-(trifluoro-methyl)benzyl]-7H-purine-2-carboxylic acid | | 486 | 486 |
| 2.36 | 1300 | 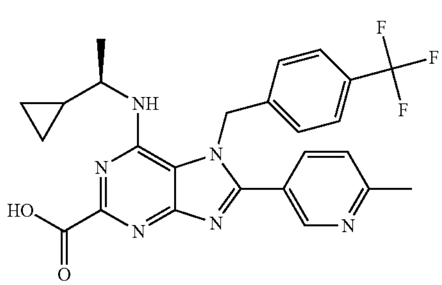 [SMILES: Cc1ccc(-c2nc3nc(C(=O)O)nc(N[C@H](C)C4CC4)c3n2Cc2ccc(C(F)(F)F)cc2)cn1] | 6-{[(1R)-1-cyclopropyl-ethyl]amino}-8-(6-methyl-pyridin-3-yl)-7-[4-(trifluoro-methyl)benzyl]-7H-purine-2-carboxylic acid | | 497 | 497 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.37 | 6.596 | 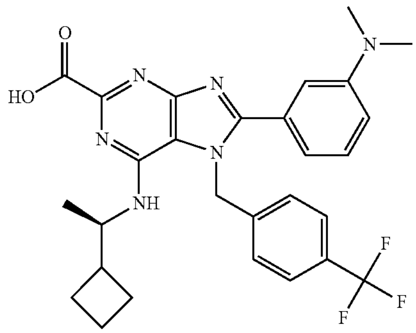 [SMILES: C[C@@H](Nc1nc(C(=O)O)nc2nc(-c3cccc(N(C)C)c3)n(Cc3ccc(C(F)(F)F)cc3)c12)C1CCC1] | 6-{[(1R)-1-cyclobutyl-ethyl]amino}-8-[3-(dimethyl-amino)phenyl]-7-[4-(trifluoro-methyl)benzyl]-7H-purine-2-carboxylic acid | | 539 | 539 |
| 2.38 | 11.23 | 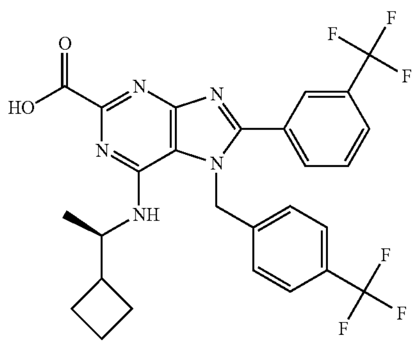 [SMILES: C[C@@H](Nc1nc(C(=O)O)nc2nc(-c3cccc(C(F)(F)F)c3)n(Cc3ccc(C(F)(F)F)cc3)c12)C1CCC1] | 6-{[(1R)-1-cyclobutyl-ethyl]amino}-7-[4-(trifluoro-methyl)benzyl]-8-[3-(trifluoro-methyl)phenyl]-7H-purine-2-carboxylic acid | | 564 | 564 |
| 2.39 | 52 | 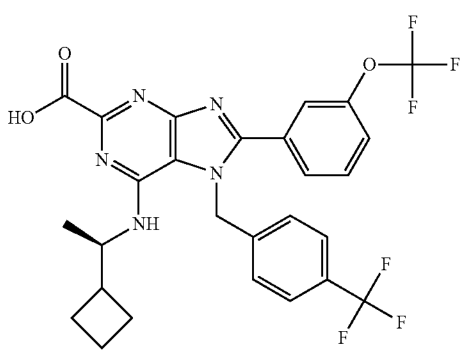 [SMILES: C[C@@H](Nc1nc(C(=O)O)nc2nc(-c3cccc(OC(F)(F)F)c3)n(Cc3ccc(C(F)(F)F)cc3)c12)C1CCC1] | 6-{[(1R)-1-cyclobutyl-ethyl]amino}-8-[3-(trifluoro-methoxy)phenyl]-7-[4-(trifluoro-methyl)benzyl]-7H-purine-2-carboxylic acid | | 580 | 580 |
| 2.40 | 30 | 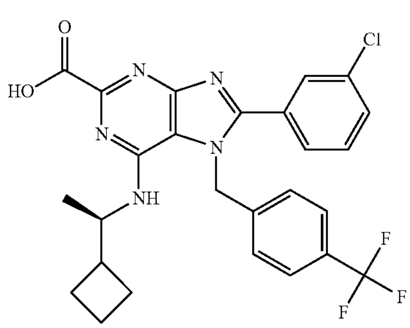 [SMILES: C[C@@H](Nc1nc(C(=O)O)nc2nc(-c3cccc(Cl)c3)n(Cc3ccc(C(F)(F)F)cc3)c12)C1CCC1] | 8-(3-chloro-phenyl)-6-{[(1R)-1-cyclobutyl-ethyl]amino}-7-[4-(trifluoro-methyl)benzyl]-7H-purine-2-carboxylic acid | | 530 | 530 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.41 | 44 | 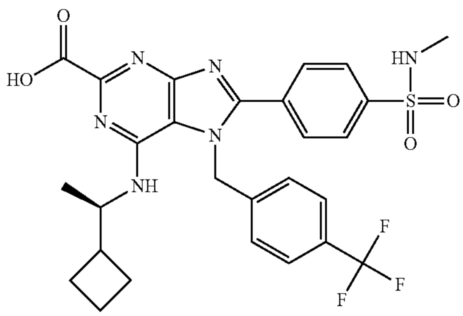 [SMILES: CNS(=O)(=O)c1ccc(-c2nc3nc(C(=O)O)nc(N[C@H](C)C4CCC4)c3n2Cc2ccc(C(F)(F)F)cc2)cc1] | 6-{[(1R)-1-cyclobutyl-ethyl]amino}-8-[4-(methyl-sulfamoyl)phenyl]-7-[4-(trifluoromethyl)benzyl]-7H-purine-2-carboxylic acid | | 589 | 589 |
| 2.42 | 264.9 | 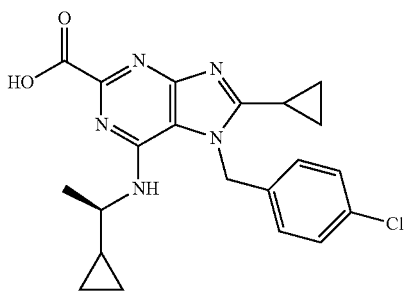 [SMILES: C[C@@H](Nc1nc(C(=O)O)nc2nc(C3CC3)n(Cc3ccc(Cl)cc3)c12)C1CC1] | 7-(4-chloro-benzyl)-8-cyclopropyl-6-{[(1R)-1-cyclopropyl-ethyl]amino}-7H-purine-2-carboxylic acid | TFA | 412 | 412 |
| 2.43 | 28.1 | 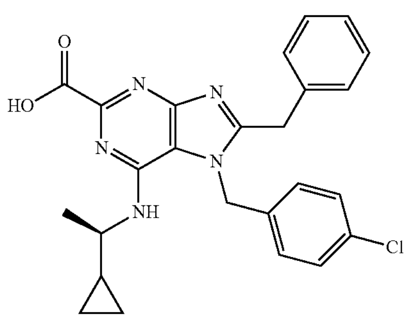 [SMILES: C[C@@H](Nc1nc(C(=O)O)nc2nc(Cc3ccccc3)n(Cc3ccc(Cl)cc3)c12)C1CC1] | 8-benzyl-7-(4-chlorobenzyl)-6-{[(1R)-1-cyclopropyl-ethyl]amino}-7H-purine-2-carboxylic acid | TFA | 462 | 462 |
| 2.44 | 640 | 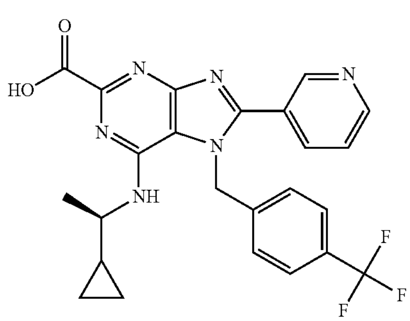 [SMILES: C[C@@H](Nc1nc(C(=O)O)nc2nc(-c3cccnc3)n(Cc3ccc(C(F)(F)F)cc3)c12)C1CC1] | 6-{[(1R)-1-cyclopropyl-ethyl]amino}-8-pyridin-3-yl-7-[4-(trifluoromethyl)benzyl]-7H-purine-2-carboxylic acid | | 483 | 483 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.45 | 63 | 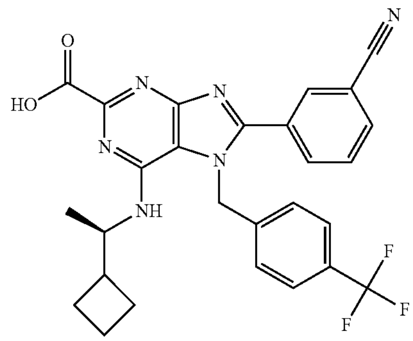 [SMILES: C[C@@H](Nc1nc(C(=O)O)nc2nc(-c3cccc(C#N)c3)n(Cc3ccc(C(F)(F)F)cc3)c12)C1CCC1] | 8-(3-cyano-phenyl)-6-{[(1R)-1-cyclobutyl-ethyl]amino}-7-[4-(trifluoro-methyl)benzyl]-7H-purine-2-carboxylic acid | | 521 | 521 |
| 2.46 | 51 | 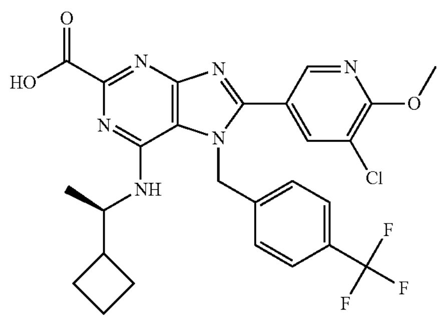 [SMILES: COc1ncc(-c2nc3nc(C(=O)O)nc(N[C@H](C)C4CCC4)c3n2Cc2ccc(C(F)(F)F)cc2)cc1Cl] | 8-(5-chloro-6-methoxy-pyridin-3-yl)-6-{[(1R)-1-cyclobutyl-ethyl]amino}-7-[4-(trifluoro-methyl)benzyl]-7H-purine-2-carboxylic acid | | 561 | 561 |
| 2.47 | 26 | 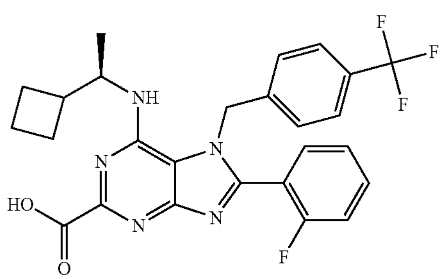 [SMILES: C[C@@H](Nc1nc(C(=O)O)nc2nc(-c3ccccc3F)n(Cc3ccc(C(F)(F)F)cc3)c12)C1CCC1] | 6-{[(1R)-1-cyclobutyl-ethyl]amino}-8-(2-fluoro-phenyl)-7-[4-(trifluoromethyl)benzyl]-7H-purine-2-carboxylic acid | | 514 | 514 |
| 2.48 | 680 | 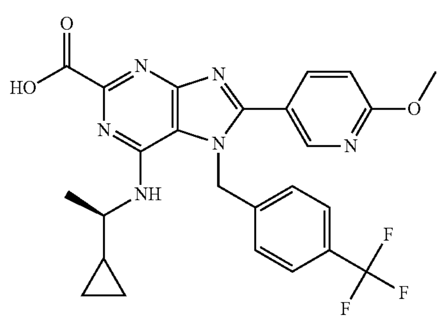 [SMILES: COc1ccc(-c2nc3nc(C(=O)O)nc(N[C@H](C)C4CC4)c3n2Cc2ccc(C(F)(F)F)cc2)cn1] | 6-{[(1R)-1-cyclopropyl-ethyl]amino}-8-(6-methoxy-pyridin-3-yl)-7-[4-(trifluoro-methyl)benzyl]-7H-purine-2-carboxylic acid | | 513 | 513 |
| 2.49 | 310 | 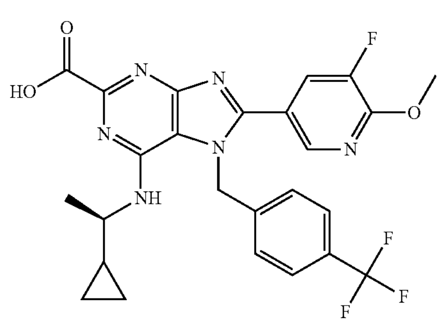 [SMILES: COc1ncc(-c2nc3nc(C(=O)O)nc(N[C@H](C)C4CC4)c3n2Cc2ccc(C(F)(F)F)cc2)cc1F] | 6-{[(1R)-1-cyclopropyl-ethyl]amino}-8-(5-fluoro-6-methoxy-pyridin-3-yl)-7-[4-(trifluoro-methyl)benzyl]-7H-purine-2-carboxylic acid | | 531 | 531 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.50 | 120.2 | 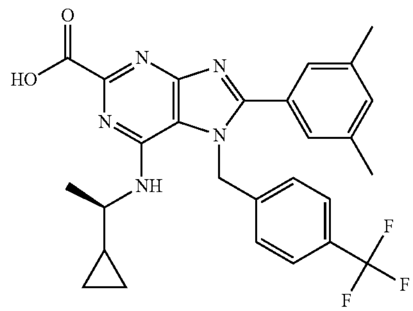 [SMILES: Cc1cc(C)cc(-c2nc3nc(C(=O)O)nc(N[C@H](C)C4CC4)c3n2Cc2ccc(C(F)(F)F)cc2)c1] | 6-{[(1R)-1-cyclopropylethyl]amino}-8-(3,5-dimethylphenyl)-7-[4-(trifluoromethyl)benzyl]-7H-purine-2-carboxylic acid | | 510 | 510 |
| 2.51 | 1232 | 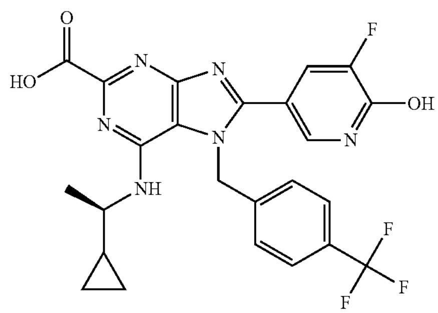 [SMILES: C[C@@H](Nc1nc(C(=O)O)nc2nc(-c3cnc(O)c(F)c3)n(Cc3ccc(C(F)(F)F)cc3)c12)C1CC1] | 6-{[(1R)-1-cyclopropylethyl]amino}-8-(5-fluoro-6-hydroxypyridin-3-yl)-7-[4-(trifluoromethyl)benzyl]-7H-purine-2-carboxylic acid | | 517 | 517 |
| 2.52 | 309 | 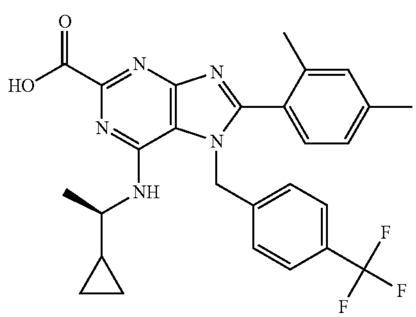 [SMILES: Cc1ccc(-c2nc3nc(C(=O)O)nc(N[C@H](C)C4CC4)c3n2Cc2ccc(C(F)(F)F)cc2)c(C)c1] | 6-{[(1R)-1-cyclopropylethyl]amino}-8-(2,4-dimethylphenyl)-7-[4-(trifluoromethyl)benzyl]-7H-purine-2-carboxylic acid | | 510 | 510 |
| 2.53 | 200.4 | 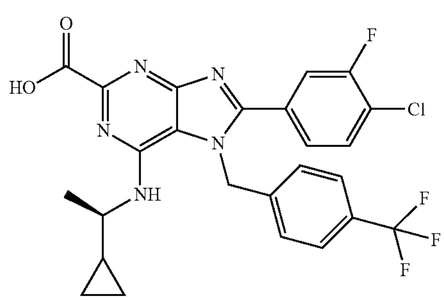 [SMILES: C[C@@H](Nc1nc(C(=O)O)nc2nc(-c3ccc(Cl)c(F)c3)n(Cc3ccc(C(F)(F)F)cc3)c12)C1CC1] | 8-(4-chloro-3-fluorophenyl)-6-{[(1R)-1-cyclopropylethyl]amino}-7-[4-(trifluoromethyl)benzyl]-7H-purine-2-carboxylic acid | | 534 | 534 |
| 2.54 | 825.6 | 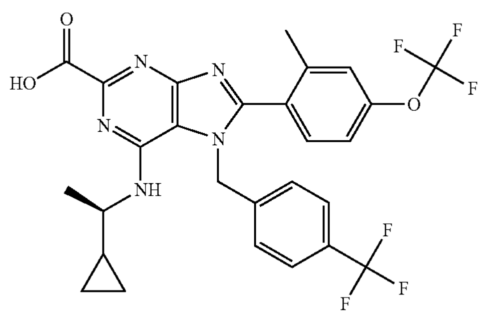 [SMILES: Cc1cc(OC(F)(F)F)ccc1-c1nc2nc(C(=O)O)nc(N[C@H](C)C3CC3)c2n1Cc1ccc(C(F)(F)F)cc1] | 6-{[(1R)-1-cyclopropylethyl]amino}-8-[2-methyl-4-(trifluoromethoxy)phenyl]-7-[4-(trifluoromethyl)benzyl]-7H-purine-2-carboxylic acid | | 580 | 580 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.55 | 98.32 | 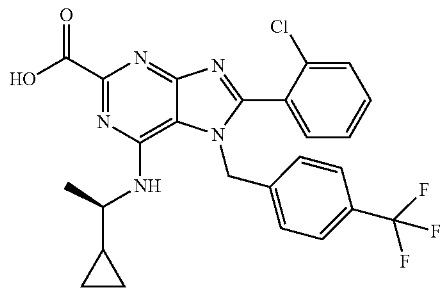 [SMILES: C[C@@H](Nc1nc(C(=O)O)nc2nc(-c3ccccc3Cl)n(Cc3ccc(C(F)(F)F)cc3)c12)C1CC1] | 8-(2-chloro-phenyl)-6-{[(1R)-1-cyclopropyl-ethyl]amino}-7-[4-(trifluoro-methyl)benzyl]-7H-purine-2-carboxylic acid | | 516 | 516 |
| 2.56 | 261.3 | 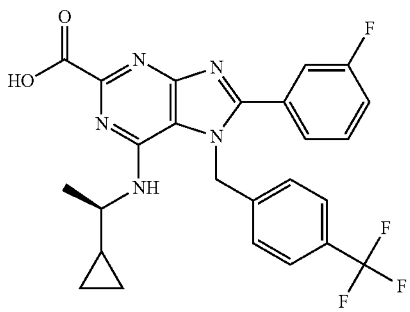 | 6-{[(1R)-1-cyclopropyl-ethyl]amino}-8-(3-fluoro-phenyl)-7-[4-(trifluoro-methyl)benzyl]-7H-purine-2-carboxylic acid | | 500 | 500 |
| 2.57 | 432.1 | 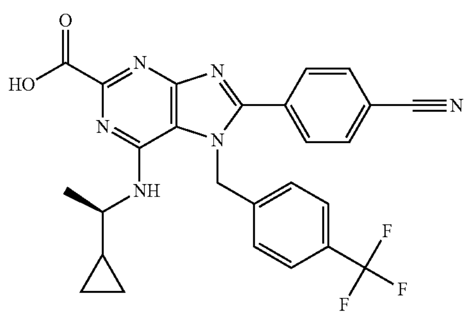 [SMILES: C[C@@H](Nc1nc(C(=O)O)nc2nc(-c3ccc(C#N)cc3)n(Cc3ccc(C(F)(F)F)cc3)c12)C1CC1] | 8-(4-cyano-phenyl)-6-{[(1R)-1-cyclopropyl-ethyl]amino}-7-[4-(trifluoro-methyl)benzyl]-7H-purine-2-carboxylic acid | | 507 | 507 |
| 2.58 | 212.9 | 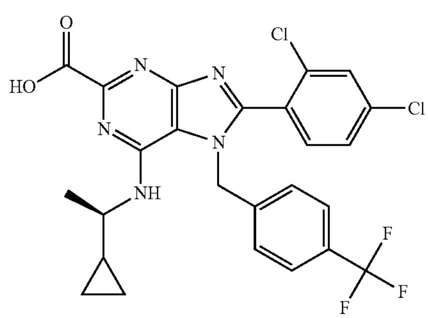 [SMILES: C[C@@H](Nc1nc(C(=O)O)nc2nc(-c3ccc(Cl)cc3Cl)n(Cc3ccc(C(F)(F)F)cc3)c12)C1CC1] | 6-{[(1R)-1-cyclopropyl-ethyl]amino}-8-(2,4-dichloro-phenyl)-7-[4-(trifluoromethyl)benzyl]-7H-purine-2-carboxylic acid | | 550 | 550 |
| 2.59 | 146.8 | 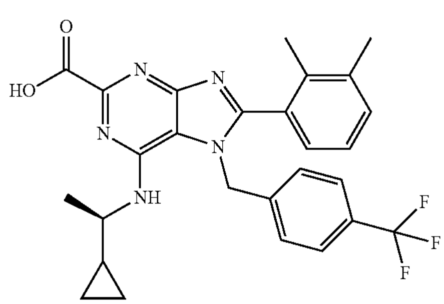 [SMILES: Cc1cccc(-c2nc3nc(C(=O)O)nc(N[C@H](C)C4CC4)c3n2Cc2ccc(C(F)(F)F)cc2)c1C] | 6-{[(1R)-1-cyclopropyl-ethyl]amino}-8-(2,3-dimethyl-phenyl)-7-[4-(trifluoromethyl)benzyl]-7H-purine-2-carboxylic acid | | 510 | 510 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.60 | 305.5 | 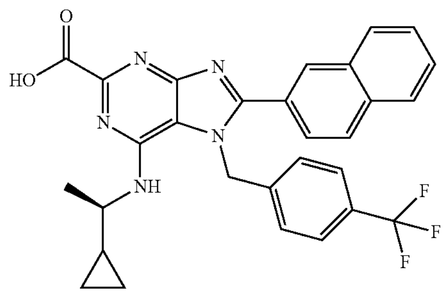 [SMILES: C[C@@H](Nc1nc(C(=O)O)nc2nc(-c3ccc4ccccc4c3)n(Cc3ccc(C(F)(F)F)cc3)c12)C1CC1] | 6-{[(1R)-1-cyclopropyl-ethyl]amino}-8-naphthalen-2-yl-7-[4-(trifluoromethyl)benzyl]-7H-purine-2-carboxylic acid | | 532 | 532 |
| 2.61 | 22.74 | 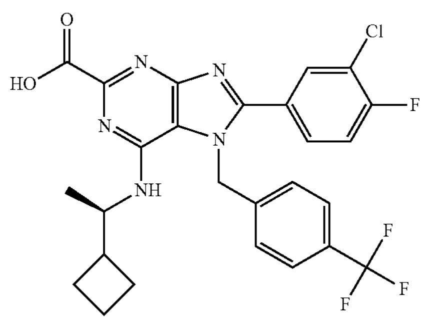 [SMILES: C[C@@H](Nc1nc(C(=O)O)nc2nc(-c3ccc(F)c(Cl)c3)n(Cc3ccc(C(F)(F)F)cc3)c12)C1CCC1] | 8-(3-chloro-4-fluorophenyl)-6-{[(1R)-1-cyclobutyl-ethyl]amino}-7-[4-(trifluoro-methyl)benzyl]-7H-purine-2-carboxylic acid | | 548 | 548 |
| 2.62 | 65.62 | 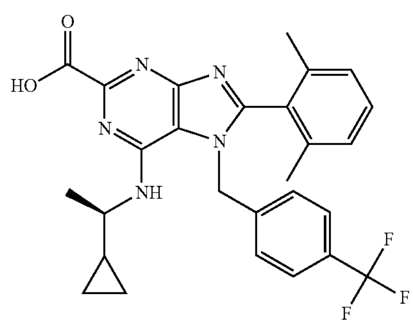 [SMILES: Cc1cccc(C)c1-c1nc2nc(C(=O)O)nc(N[C@H](C)C3CC3)c2n1Cc1ccc(C(F)(F)F)cc1] | 6-{[(1R)-1-cyclopropyl-ethyl]amino}-8-(2,6-dimethyl-phenyl)-7-[4-(trifluoromethyl)benzyl]-7H-purine-2-carboxylic acid | | 510 | 510 |
| 2.63 | 10.92 | 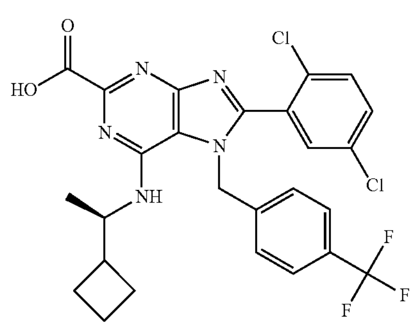 [SMILES: C[C@@H](Nc1nc(C(=O)O)nc2nc(-c3cc(Cl)ccc3Cl)n(Cc3ccc(C(F)(F)F)cc3)c12)C1CCC1] | 6-{[(1R)-1-cyclobutyl-ethyl]amino}-8-(2,5-dichloro-phenyl)-7-[4-(trifluoromethyl)benzyl]-7H-purine-2-carboxylic acid | | 564 | 564 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.64 | 89.1 | 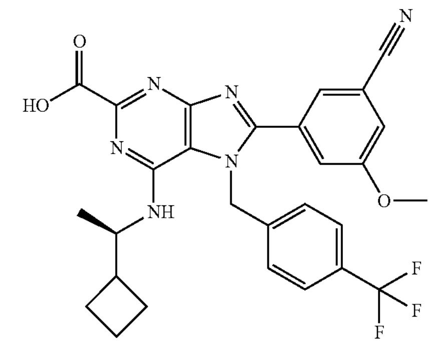 [SMILES: COc1cc(C#N)cc(-c2nc3nc(C(=O)O)nc(N[C@H](C)C4CCC4)c3n2Cc2ccc(C(F)(F)F)cc2)c1] | 8-(3-cyano-5-methoxyphenyl)-6-{[(1R)-1-cyclobutyl-ethyl]amino}-7-[4-(trifluoro-methyl)benzyl]-7H-purine-2-carboxylic acid | | 551 | 551 |
| 2.65 | 182.4 | 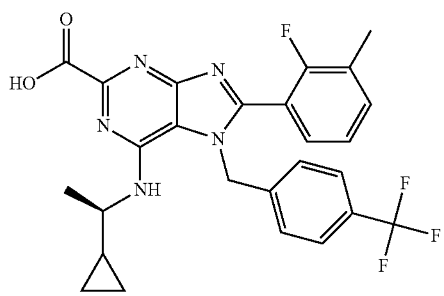 [SMILES: Cc1cccc(-c2nc3nc(C(=O)O)nc(N[C@H](C)C4CC4)c3n2Cc2ccc(C(F)(F)F)cc2)c1F] | 6-{[(1R)-1-cyclopropyl-ethyl]amino}-8-(2-fluoro-3-methylphenyl)-7-[4-(trifluoromethyl)benzyl]-7H-purine-2-carboxylic acid | | 514 | 514 |
| 2.66 | 111.8 | 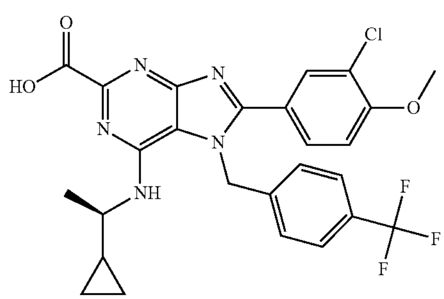 [SMILES: COc1ccc(-c2nc3nc(C(=O)O)nc(N[C@H](C)C4CC4)c3n2Cc2ccc(C(F)(F)F)cc2)cc1Cl] | 8-(3-chloro-4-methoxyphenyl)-6-{[(1R)-1-cyclopropyl-ethyl]amino}-7-[4-(trifluoro-methyl)benzyl]-7H-purine-2-carboxylic acid | | 546 | 546 |
| 2.67 | 41.71 | 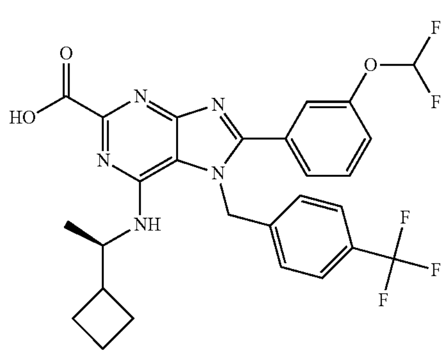 [SMILES: C[C@@H](Nc1nc(C(=O)O)nc2nc(-c3cccc(OC(F)F)c3)n(Cc3ccc(C(F)(F)F)cc3)c12)C1CCC1] | 6-{[(1R)-1-cyclobutyl-ethyl]amino}-8-[3-(difluoro-methoxy)phenyl]-7-[4-(trifluoro-methyl)benzyl]-7H-purine-2-carboxylic acid | | 562 | 562 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.68 | 22.44 | 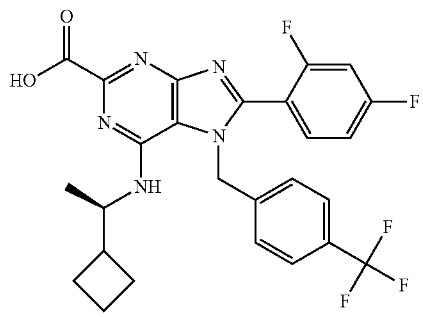 [SMILES: C[C@@H](Nc1nc(C(=O)O)nc2nc(-c3ccc(F)cc3F)n(Cc3ccc(C(F)(F)F)cc3)c12)C1CCC1] | 6-{[(1R)-1-cyclobutyl-ethyl]amino}-8-(2,4-difluoro-phenyl)-7-[4-(trifluoromethyl)benzyl]-7H-purine-2-carboxylic acid | | 532 | 532 |
| 2.69 | 295.6 | 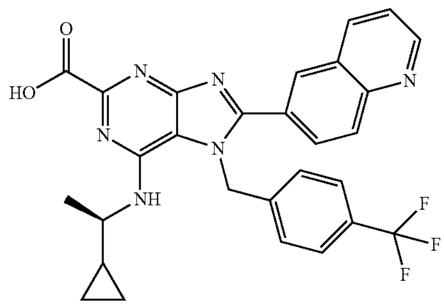 [SMILES: C[C@@H](Nc1nc(C(=O)O)nc2nc(-c3ccc4ncccc4c3)n(Cc3ccc(C(F)(F)F)cc3)c12)C1CC1] | 6-{[(1R)-1-cyclopropyl-ethyl]amino}-8-quinolin-6-yl-7-[4-(trifluoromethyl)benzyl]-7H-purine-2-carboxylic acid | | 533 | 533 |
| 2.70 | 1024 | 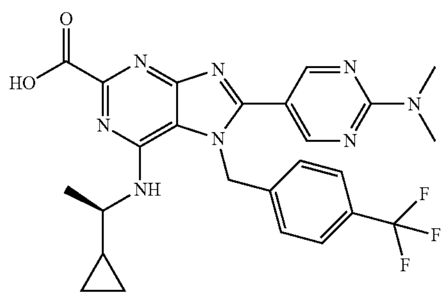 [SMILES: C[C@@H](Nc1nc(C(=O)O)nc2nc(-c3cnc(N(C)C)nc3)n(Cc3ccc(C(F)(F)F)cc3)c12)C1CC1] | 6-{[(1R)-1-cyclopropyl-ethyl]amino}-8-[2-(dimethyl-amino)pyrimidin-5-yl]-7-[4-(trifluoromethyl)benzyl]-7H-purine-2-carboxylic acid | | 527 | 527 |
| 2.71 | 588.6 | 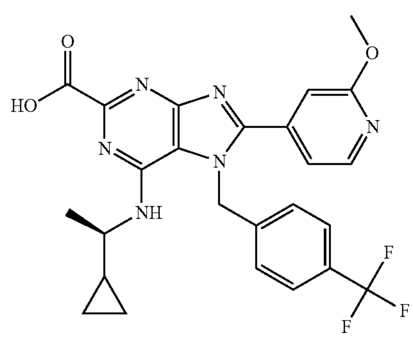 [SMILES: COc1cc(-c2nc3nc(C(=O)O)nc(N[C@H](C)C4CC4)c3n2Cc2ccc(C(F)(F)F)cc2)ccn1] | 6-{[(1R)-1-cyclopropyl-ethyl]amino}-8-(2-methoxy-pyridin-4-yl)-7-[4-(trifluoromethyl)benzyl]-7H-purine-2-carboxylic acid | | 513 | 513 |
| 2.72 | 612.9 | 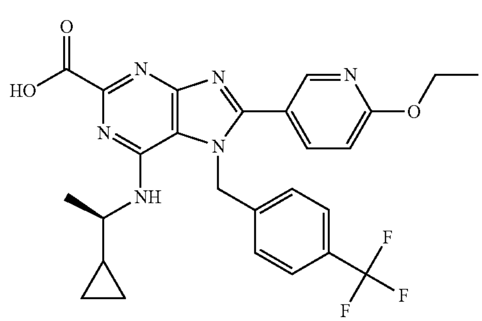 [SMILES: CCOc1ccc(-c2nc3nc(C(=O)O)nc(N[C@H](C)C4CC4)c3n2Cc2ccc(C(F)(F)F)cc2)cn1] | 6-{[(1R)-1-cyclopropyl-ethyl]amino}-8-(6-ethoxy-pyridin-3-yl)-7-[4-(trifluoromethyl)benzyl]-7H-purine-2-carboxylic acid | | 527 | 527 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.73 | 111.2 | 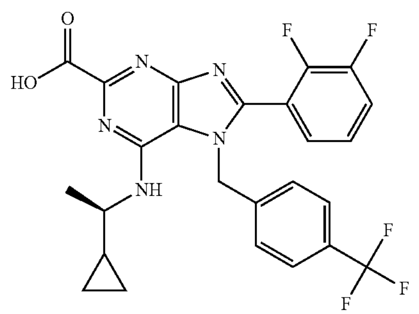 [SMILES: C[C@@H](Nc1nc(C(=O)O)nc2nc(-c3cccc(F)c3F)n(Cc3ccc(C(F)(F)F)cc3)c12)C1CC1] | 6-{[(1R)-1-cyclopropyl-ethyl]amino}-8-(2,3-difluoro-phenyl)-7-[4-(trifluoromethyl)benzyl]-7H-purine-2-carboxylic acid | | 518 | 518 |
| 2.74 | 204.6 | 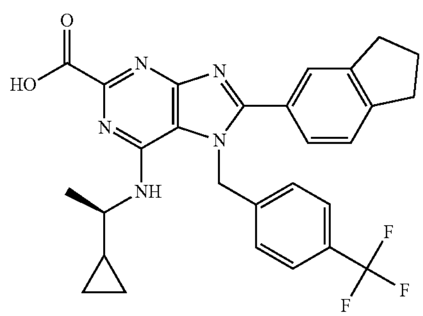 [SMILES: C[C@@H](Nc1nc(C(=O)O)nc2nc(-c3ccc4c(c3)CCC4)n(Cc3ccc(C(F)(F)F)cc3)c12)C1CC1] | 6-{[(1R)-1-cyclopropyl-ethyl]amino}-8-(2,3-dihydro-1H-inden-5-yl)-7-[4-(trifluoromethyl)benzyl]-7H-purine-2-carboxylic acid | | 522 | 522 |
| 2.75 | 204 | 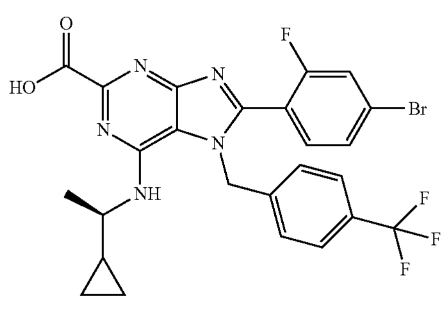 [SMILES: C[C@@H](Nc1nc(C(=O)O)nc2nc(-c3ccc(Br)cc3F)n(Cc3ccc(C(F)(F)F)cc3)c12)C1CC1] | 8-(4-bromo-2-fluorophenyl)-6-{[(1R)-1-cyclopropyl-ethyl]amino}-7-[4-(trifluoro-methyl)benzyl]-7H-purine-2-carboxylic acid | | 578 | 578 |
| 2.76 | 20.39 | 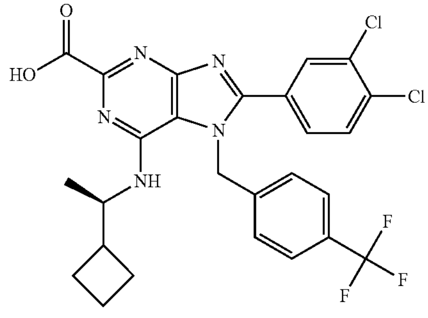 [SMILES: C[C@@H](Nc1nc(C(=O)O)nc2nc(-c3ccc(Cl)c(Cl)c3)n(Cc3ccc(C(F)(F)F)cc3)c12)C1CCC1] | 6-{[(1R)-1-cyclobutyl-ethyl]amino)-8-(3,4-dichloro-phenyl)-7-[4-(trifluoromethyl)benzyl]-7H-purine-2-carboxylic acid | | 564 | 564 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.77 | 72.55 | 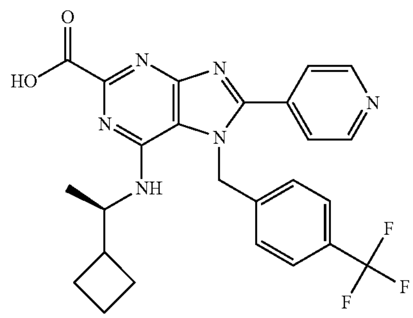 [SMILES: C[C@@H](Nc1nc(C(=O)O)nc2nc(-c3ccncc3)n(Cc3ccc(C(F)(F)F)cc3)c12)C1CCC1] | 6-{[(1R)-1-cyclobutyl-ethyl]amino}-8-pyridin-4-yl-7-[4-(trifluoromethyl)benzyl]-7H-purine-2-carboxylic acid | | 497 | 497 |
| 2.78 | 219.5 | 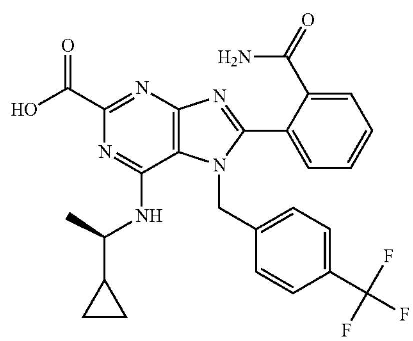 [SMILES: C[C@@H](Nc1nc(C(=O)O)nc2nc(-c3ccccc3C(N)=O)n(Cc3ccc(C(F)(F)F)cc3)c12)C1CC1] | 8-(2-carbamoyl-phenyl)-6-{[(1R)-1-cyclopropyl-ethyl]amino}-7-[4-(trifluoro-methyl)benzyl]-7H-purine-2-carboxylic acid | | 525 | 525 |
| 2.79 | 13.36 | 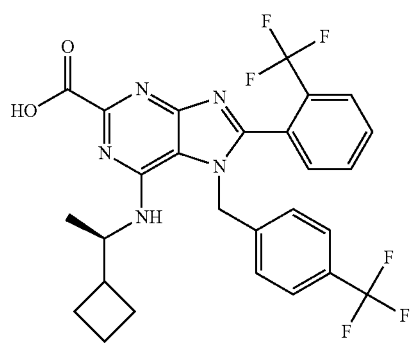 [SMILES: C[C@@H](Nc1nc(C(=O)O)nc2nc(-c3ccccc3C(F)(F)F)n(Cc3ccc(C(F)(F)F)cc3)c12)C1CCC1] | 6-{[(1R)-1-cyclobutyl-ethyl]amino}-7-[4-(trifluoro-methyl)benzyl]-8-[2-(trifluoro-methyl)phenyl]-7H-purine-2-carboxylic acid | | 564 | 564 |
| 2.80 | 11.11 | 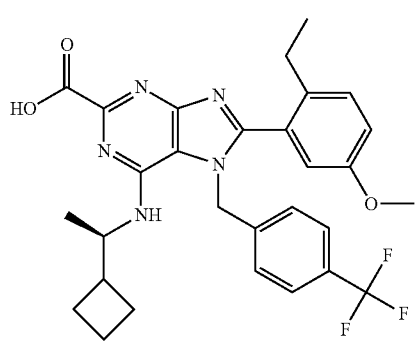 [SMILES: CCc1ccc(OC)cc1-c1nc2nc(C(=O)O)nc(N[C@H](C)C3CCC3)c2n1Cc1ccc(C(F)(F)F)cc1] | 6-{[(1R)-1-cyclobutyl-ethyl]amino}-8-(2-ethyl-5-methoxy-phenyl)-7-[4-(trifluoromethyl)benzyl]-7H-purine-2-carboxylic acid | | 554 | 554 |

TABLE 2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.81 | 18 | 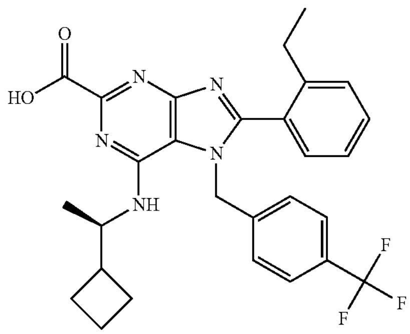 [SMILES: CCc1ccccc1-c1nc2nc(C(=O)O)nc(N[C@H](C)C3CCC3)c2n1Cc1ccc(C(F)(F)F)cc1] | 6-{[(1R)-1-cyclobutyl-ethyl]amino}-8-(2-ethyl-phenyl)-7-[4-(trifluoromethyl)benzyl]-7H-purine-2-carboxylic acid | | 524 | 524 |
| 2.82 | 13.65 | 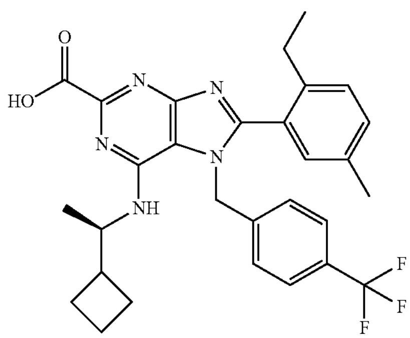 [SMILES: CCc1ccc(C)cc1-c1nc2nc(C(=O)O)nc(N[C@H](C)C3CCC3)c2n1Cc1ccc(C(F)(F)F)cc1] | 6-{[(1R)-1-cyclobutyl-ethyl]amino}-8-(2-ethyl-5-methylphenyl)-7-[4-(trifluoro-methyl)benzyl]-7H-purine-2-carboxylic acid | | 538 | 538 |
| 2.83 | 189.4 | 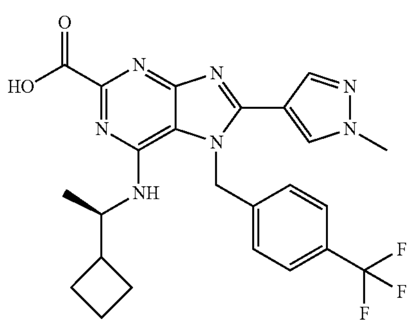 [SMILES: C[C@@H](Nc1nc(C(=O)O)nc2nc(-c3cnn(C)c3)n(Cc3ccc(C(F)(F)F)cc3)c12)C1CCC1] | 6-{[(1R)-1-cyclobutyl-ethyl]amino}-8-(1-methyl-1H-pyrazol-4-yl)-7-[4-(trifluoromethyl)benzyl]-7H-purine-2-carboxylic acid | | 500 | 500 |
| 2.84 | 79.4 | 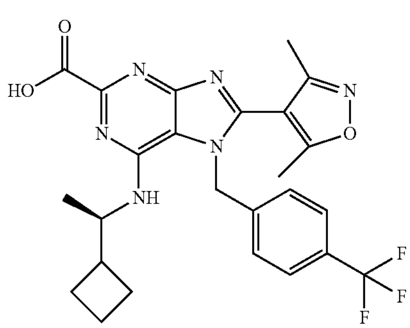 [SMILES: Cc1noc(C)c1-c1nc2nc(C(=O)O)nc(N[C@H](C)C3CCC3)c2n1Cc1ccc(C(F)(F)F)cc1] | 6-{[(1R)-1-cyclobutyl-ethyl]amino}-8-(3,5-dimethyl-isoxazol-4-yl)-7-[4-(trifluoromethyl)benzyl]-7H-purine-2-carboxylic acid | | 515 | 515 |

Example 3.1

(R)-6-((1-cyclobutylethyl)amino)-8-(1-methyl-1H-imidazol-2-yl)-7-(4-(trifluoromethyl)benzyl)-7H-purine-2-carboxylic acid

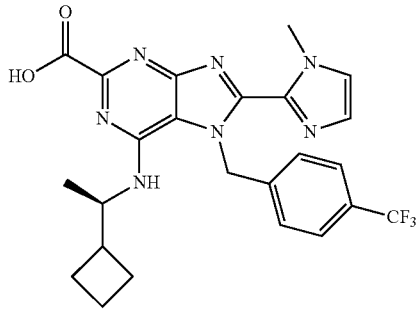 [SMILES: C[C@@H](Nc1nc(C(=O)O)nc2nc(-c3nccn3C)n(Cc3ccc(C(F)(F)F)cc3)c12)C1CCC1]

Step 1: A microwave vial was charged with (R)-8-bromo-6-((1-cyclobutylethyl)amino)-7-(4-(trifluoromethyl)benzyl)-7H-purine-2-carbonitrile (Preparative Example 2.1) (180 mg, 0.37 mmol), cesium fluoride (114 mg, 0.75 mmol), copper(I) iodide (14 mg, 0.075 mmol) and degassed DMF (3.0 mL). This reaction mixture was degassed with Ar before the addition of 1-methyl-2-(tributylstannyl)-1H-imidazole (209 mg, 0.56 mmol) and Pd(PPh$_3$)$_4$ (87 mg, 0.075 mmol). The vial was then sealed and heated at 110° C. for 12 hours. The reaction mixture was then concentrated under reduced pressure and the residue was purified on a RediSep 4 g silica gel column (0 to 100% EtOAc/hexanes) to afford (R)-6-(1-cyclobutylethylamino)-8-(1-methyl-1H-imidazol-2-yl)-7-(4-(trifluoromethyl)benzyl)-7H-purine-2-carbonitrile. MS (APCI)=481 (M+1)$^+$.

Step 2: Using a procedure analogous to that described in Example 1.1, Step 2 and 3, and starting with (R)-6-((1-cyclobutylethyl)amino)-8-(1-methyl-1H-imidazol-2-yl)-7-(4-(trifluoromethyl)benzyl)-7H-purine-2-carbonitrile, (R)-6-((1-cyclobutylethyl)amino)-8-(1-methyl-1H-imidazol-2-yl)-7-(4-(trifluoromethyl)benzyl)-7H-purine-2-carboxylic acid was prepared. $^1$H NMR (300 MHz, CD$_3$OD) δ 7.77 (s, 1H), 7.65-7.66 (m, 3H), 7.29 (d, J=7.8 Hz, 2H), 6.40 (br s, 2H), 4.67-4.72 (m, 1H), 4.10 (s, 3H), 2.34-2.39 (m, 1H), 1.71-1.80 (m, 3H), 1.46-1.52 (m, 2H), 1.23-1.28 (m, 2H), 1.12 (d, J=6.0 Hz, 3H). MS (ES)=500 (M+1)$^+$.

Example 3.2

(R)-6-((1-cyclobutylethyl)amino)-8-(4-isopropylpyrimidin-2-yl)-7-(4-(trifluoromethyl)benzyl)-7H-purine-2-carboxylic acid

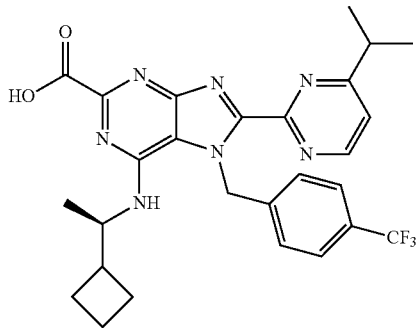 [SMILES: CC(C)c1ccnc(-c2nc3nc(C(=O)O)nc(N[C@H](C)C4CCC4)c3n2Cc2ccc(C(F)(F)F)cc2)n1]

Step 1: To a solution of tributyltin hydride (1.4 g, 4.8 mmol) in THF (12.0 mL) was added LDA (2.24 mL, 2.0 M) drop-wise at −78° C. and the reaction was stirred for 30 minutes. A solution of 2-chloro-4-isopropylpyrimidine (0.50 g, 3.2 mmol) in THF (2.0 mL) was added. The reaction mixture was warmed to rt and stirred overnight. After this time the reaction mixture was quenched with water (40 mL) and the reaction mixture was extracted with EtOAc (3×50 mL). The combined organic layers were dried over sodium sulfate, filtered and concentrated under reduced pressure to afford 4-isopropyl-2-(tributylstannyl)pyrimidine as a colorless oil, that was used without further purification.

Step 2: A solution of (R)-8-bromo-6-((1-cyclobutylethyl)amino)-7-(4-(trifluoromethyl)benzyl)-7H-purine-2-carbonitrile (60 mg, 0.125 mmol) in DMF (2.0 mL) was taken in a sealed tube and then degassed with nitrogen for 5 minutes. Cesium fluoride (37.8 mg, 0.25 mmol), copper(I) iodide (4.7 mg, 0.025 mmol), Pd(PPh$_3$)$_4$ (28.9 mg, 0.025 mmol) and 4-isopropyl-2-(tributylstannyl)pyrimidine (77 mg, 0.187 mmol) were added and the tube was sealed and stirred at 90° C. overnight. After this time water (20 mL) was added and the reaction mixture was extracted with EtOAc (3×50 mL). The combined organic layers were dried over sodium sulfate, filtered and concentrated under reduced pressure. Purification of the residue on a Redisep 12 g silica gel column (0 to 100% EtOAc/hexanes) afforded (R)-6-((1-cyclobutylethyl)amino)-8-(4-isopropylpyrimidin-2-yl)-7-(4-(trifluoromethyl)benzyl)-7H-purine-2-carbonitrile. $^1$H NMR (300 MHz, CDCl$_3$) δ 8.85 (d, J=6.6 Hz, 1H), 7.73 (d, J=8.1 Hz, 2H), 7.38 (d, J=7.8 Hz, 2H), 7.28 (d, J=5.1 Hz, 1H), 6.35 (d, J=17.4 Hz, 1H), 6.18 (d, J=17.4 Hz, 1H), 4.50 (d, J=8.1 Hz, 1H), 4.24 (m, 1H), 3.00 (m, 1H), 1.82-1.93 (m, 2H), 1.59-1.75 (m, 2H), 1.25-1.42 (m, 3H), 1.15 (d, J=6.9 Hz, 6H), 0.90 (d, J=7.5 Hz, 3H). MS (ES)=521 (M+1)$^+$.

Step 3: Using a procedure analogous to that described in Example 1.1, Step 2 and 3, and starting with (R)-6-((1-cyclobutylethyl)amino)-8-(4-isopropylpyrimidin-2-yl)-7-(4-(trifluoromethyl)benzyl)-7H-purine-2-carbonitrile, (R)-6-((1-cyclobutylethyl)amino)-8-(4-isopropylpyrimidin-2-yl)-7-(4-(trifluoromethyl)benzyl)-7H-purine-2-carboxylic acid was prepared: $^1$H NMR (300 MHz, CD$_3$OD) δ 9.13 (d, J=5.6 Hz, 1H), 7.81 (d, J=5.6 Hz, 1H), 7.71 (d, J=8.0 Hz, 2H), 7.34 (d, J=8.0 Hz, 2H), 7.07 (d, J=12.9 Hz, 1H), 6.54 (d, J=12.9 Hz, 1H), 4.51 (m, 2H), 3.14 (m, 1H), 2.08 (m, 1H), 1.81 (m, 1H), 1.63 (m, 1H), 1.52-1.55 (m, 2H), 1.32 (m, 1H), 1.19 (d, J=6.8 Hz, 3H), 0.91 (d, J=6.8 Hz, 3H), 0.91 (d, J=6.4 Hz, 3H). MS (ES)=540 (M+1)$^+$.

Example 3.3

(R)-6-((1-cyclobutylethyl)amino)-8-(5-isopropylthiazol-2-yl)-7-(4-(trifluoromethyl)benzyl)-7H-purine-2-carboxylic acid (TFA salt)

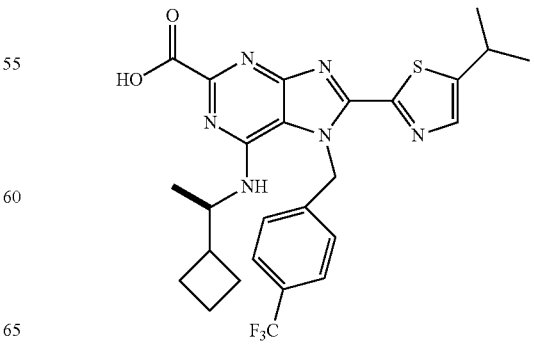

Step 1: To a solution of 2-bromo-5-(iso-propyl)thiazole (500 mg, 2.43 mmol) cooled at −78° C. was added N-butyllithium (4.55 mL, 7.28 mmol) via syringe. Stirring was continued for 2 h at −78° C. To the reaction mixture was added dropwise tributyltin chloride (2.06 mL, 7.28 mmol) in THF (3 mL). The resulting mixture was stirred an additional 2 h at room temperature and then quenched with water. The resulting mixture was stirred for 30 min, and then extracted with ethyl acetate (20 mL). The organic layer was dried over sodium sulfate and concentrated under vacuum to afford 5-isopropyl-2-(tributylstannyl)thiazole as yellow oil which was used without further purification.

Step 2: A microwave vial was charged with 5-isopropyl-2-(tributylstannyl)thiazole (434 mg, 0.21 mmol, 20%), Pd(PPh$_3$)$_4$ (12.0 mg, 0.0104 mmol) and (R)-8-bromo-6-((1-cyclobutylethyl)amino)-7-(4-(trifluoromethyl)benzyl)-7H-purine-2-carbonitrile (50 mg, 0.104 mmol) in 1,4-dioxane (0.6 mL). The resulting mixture was degassed with Ar. The vial was sealed and heated to 90° C. overnight. The reaction mixture was cooled to room temperature and saturated aqueous potassium fluoride solution (1 mL) and ethyl acetate (10 mL) were added. The resulting mixture was stirred for 5 min. The organic layer was separated, washed with brine, and concentrated under reduced pressure. The resulting residue was purified by silica gel chromatography (0-70% ethyl acetate in hexanes) to afford (R)-6-((1-cyclobutylethyl)amino)-8-(5-isopropylthiazol-2-yl)-7-(4-(trifluoromethyl)benzyl)-7H-purine-2-carbonitrile as yellow solid. MS ESI calc'd for $C_{26}H_{26}F_3N_7S$ [M+H]$^+$ 526. found 526.

Step 3: To a solution of (R)-6-((1-cyclobutylethyl)amino)-8-(5-isopropylthiazol-2-yl)-7-(4-(trifluoromethyl)benzyl)-7H-purine-2-carbonitrile (15 mg, 0.094 mmol) in ethanol (1 mL) was added sodium hydroxide (5.0 M in water, 0.29 mL, 0.14 mmol). The reaction was heated at 70° C. for 3 hours. The resulting solution was neutralized with TFA to pH 6 and purified via mass guided reverse phase HPLC (acetonitrile/water+0.1% TFA modifier) to afford (R)-6-((1-cyclobutylethyl)amino)-8-(5-isopropylthiazol-2-yl)-7-(4-(trifluoromethyl)benzyl)-7H-purine-2-carboxylic acid (TFA salt) as a white solid. MS ESI calc'd For $C_{26}H_{27}F_3N_6O_2S$ [M+H]$^+$ 545. found 545. $^1$H NMR (500 MHz, d6-dmso): δ 7.80 (d, J=10.5 Hz, 1H), 7.67 (d, J=8.1 Hz, 2H), 7.19 (d, J=8.1 Hz, 2H), 6.83 (d, J=17.9 Hz, 1H), 6.45 (d, J=17.8 Hz, 1H), 6.16 (d, J=8.4 Hz, 1H), 4.29-4.31 (m, 1H), 2.87 (t, J=7.5 Hz, 1H), 2.21 (q, J=8.2 Hz, 1H), 1.78-1.84 (m, 1H), 1.56-1.61 (m, 4H), 1.33 (m, 4H), 1.19-1.31 (br m, 1H), 0.95 (m, 4H).

The following compounds in Table 3 (other than Example 3.1 to 3.3) were prepared using procedures which are analogous to those described above in Example 3.1.

TABLE 3

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.1 | 160.6 | 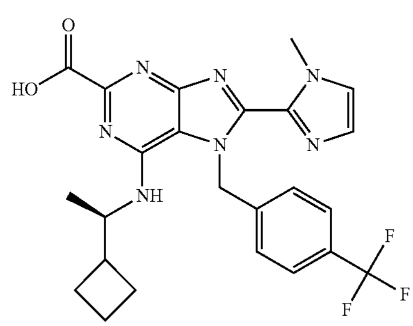 [SMILES: C[C@@H](Nc1nc(C(=O)O)nc2nc(-c3nccn3C)n(Cc3ccc(C(F)(F)F)cc3)c12)C1CCC1] | (R)-6-((1-cyclobutylethyl)amino)-8-(1-methyl-1H-imidazol-2-yl)-7-(4-(trifluoromethyl)benzyl)-7H-purine-2-carboxylic acid | | 500 | 500 |
| 3.2 | 21.97 | 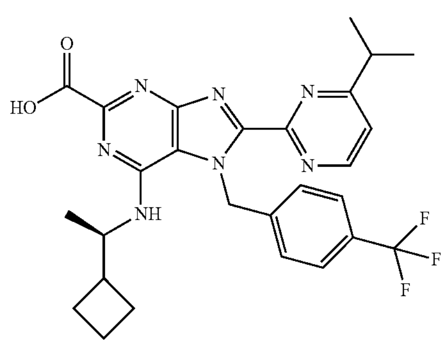 [SMILES: CC(C)c1ccnc(-c2nc3nc(C(=O)O)nc(N[C@H](C)C4CCC4)c3n2Cc2ccc(C(F)(F)F)cc2)n1] | (R)-6-((1-cyclobutylethyl)amino)-8-(4-isopropylpyrimidin-2-yl)-7-(4-(trifluoromethyl)benzyl)-7H-purine-2-carboxylic acid | | 540 | 540 |

TABLE 3-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.3 | 57.89 | 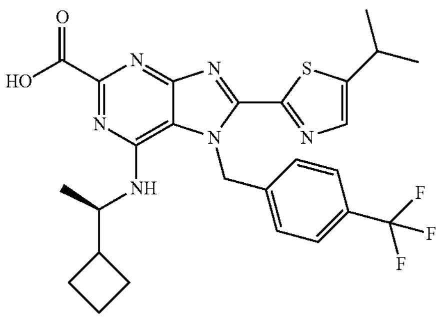 [SMILES: CC(C)c1cnc(-c2nc3nc(C(=O)O)nc(N[C@H](C)C4CCC4)c3n2Cc2ccc(C(F)(F)F)cc2)s1] | (R)-6-((1-cyclobutylethyl)amino)-8-(5-isopropylthiazol-2-yl)-7-(4-(trifluoromethyl)benzyl)-7H-purine-2-carboxylic acid | TFA | 545 | 545 |
| 3.4 | 69.82 | 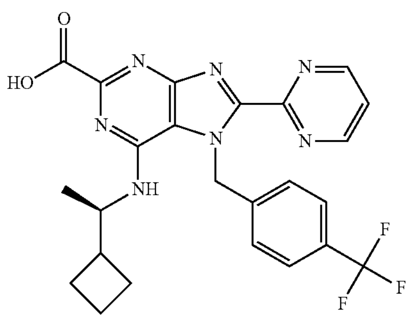 [SMILES: C[C@@H](Nc1nc(C(=O)O)nc2nc(-c3ncccn3)n(Cc3ccc(C(F)(F)F)cc3)c12)C1CCC1] | 6-{[(1R)-1-cyclobutylethyl]amino}-8-pyrimidin-2-yl-7-[4-(trifluoromethyl)benzyl]-7H-purine-2-carboxylic acid | | 498 | 498 |
| 3.5 | 30.04 | 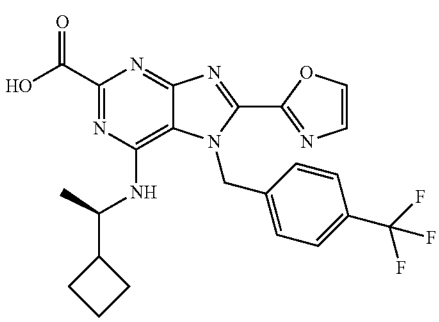 [SMILES: C[C@@H](Nc1nc(C(=O)O)nc2nc(-c3ncco3)n(Cc3ccc(C(F)(F)F)cc3)c12)C1CCC1] | 6-{[(1R)-1-cyclobutylethyl]amino}-8-(1,3-oxazol-2-yl)-7-[4-(trifluoromethyl)benzyl]-7H-purine-2-carboxylic acid | TFA | 487 | 487 |
| 3.6 | 312 | 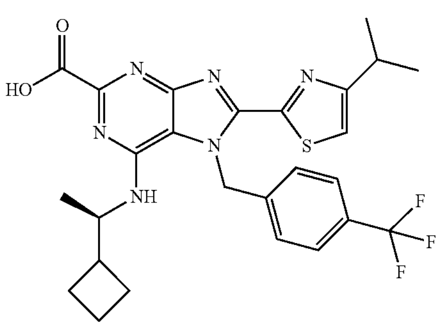 [SMILES: CC(C)c1csc(-c2nc3nc(C(=O)O)nc(N[C@H](C)C4CCC4)c3n2Cc2ccc(C(F)(F)F)cc2)n1] | 6-{[(1R)-1-cyclobutylethyl]amino}-8-[4-(1-methylethyl)-1,3-thiazol-2-yl]-7-[4-(trifluoromethyl)benzyl]-7H-purine-2-carboxylic acid | TFA | 545 | 545 |

TABLE 3-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 3.7 | 41.99 | 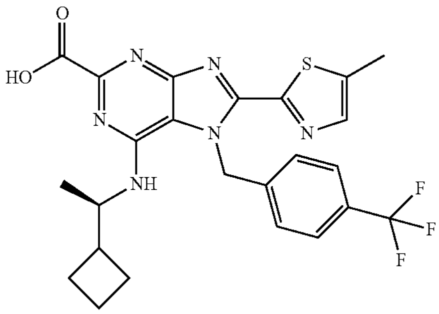 [SMILES: Cc1cnc(-c2nc3nc(C(=O)O)nc(N[C@H](C)C4CCC4)c3n2Cc2ccc(C(F)(F)F)cc2)s1] | 6-{[(1R)-1-cyclobutylethyl]amino}-8-(5-methyl-1,3-thiazol-2-yl)-7-[4-(trifluoromethyl)benzyl]-7H-purine-2-carboxylic acid | TFA | 517 | 517 |
| 3.8 | 98.8 | 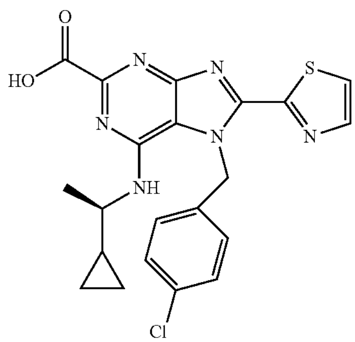 [SMILES: C[C@@H](Nc1nc(C(=O)O)nc2nc(-c3nccs3)n(Cc3ccc(Cl)cc3)c12)C1CC1] | 7-(4-chlorobenzyl)-6-{[(1R)-1-cyclopropylethyl]amino}-8-(1,3-thiazol-2-yl)-7H-purine-2-carboxylic acid | TFA | 455 | 455 |
| 3.9 | 7.86 | 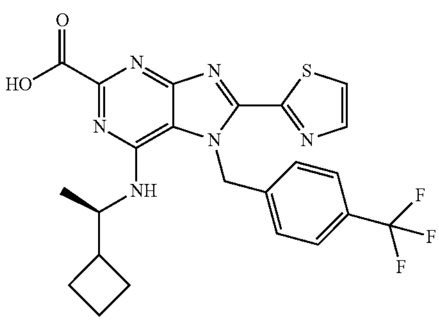 [SMILES: C[C@@H](Nc1nc(C(=O)O)nc2nc(-c3nccs3)n(Cc3ccc(C(F)(F)F)cc3)c12)C1CCC1] | 6-{[(1R)-1-cyclobutylethyl]amino}-8-(1,3-thiazol-2-yl)-7-[4-(trifluoromethyl)benzyl]-7H-purine-2-carboxylic acid | TFA | 503 | 503 |

Preparative Example 4.1

6-amino-5-((4-chlorobenzyl)amino)-1-methylpyrimidine-2,4(1H,3H)-dione

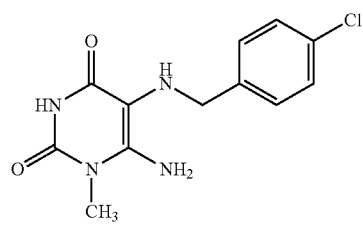 [SMILES: Cn1c(N)c(NCc2ccc(Cl)cc2)c(=O)[nH]c1=O]

Step 1: To a suspension of 6-amino-1-methylpyrimidine-2,4(1H,3H)-dione (20 g, 141.7 mmol) in methanol (200 mL) was added sodium bicarbonate (12.0 g, 141.7 mmol). The suspension was cooled to 0° C. and bromine (7.3 mL) was then added over 15 minutes. The suspension was stirred at room temperature for 12 hours. Then the resultant solid was collected by filtration and rinsed with cold water (500 mL) and methanol (200 mL). The solid was dried in vacuo to afford 6-amino-5-bromo-1-methylpyrimidine-2,4(1H,3H)-dione. $^1$H NMR (300 MHz, DMSO-d$_6$) δ10.89 (s, 1H), 7.01 (s, 2H), 3.29 (s, 3H).

Step 2: To a suspension of 6-amino-5-bromo-1-methyl-pyrimidine-2,4(1H,3H)-dione (17 g, 77.2 mmol) in NMP (150 mL) was added 4-chlorobenzylamine (16.3 g, 115.8 mmol). The suspension was heated at 120° C. for 30 minutes. Then the reaction mixture was cooled to room temperature, poured into ice water (500 mL) and stirred for 20 minutes when a solid precipitate formed. The solid was collected by filtration, washed with acetone (30 mL) and dried in vacuo to afford 6-amino-5-((4-chlorobenzyl)amino)-1-methylpyrimidine-2,4(1H,3H)-dione. $^1$H NMR (400 MHz, DMSO-d$_6$) δ 10.46 (s, 1H), 7.41-7.43 (m, 4H), 6.40 (s, 2H), 3.82 (s, 2H), 3.20 (s, 3H). MS (APCI)=281 (M+1)$^+$.

Example 4.1

(R)-7-(4-chlorobenzyl)-6-((1-cyclobutylethyl) amino)-8-(2-ethoxy-5-methylphenyl)-7H-purine-2-carboxylic acid

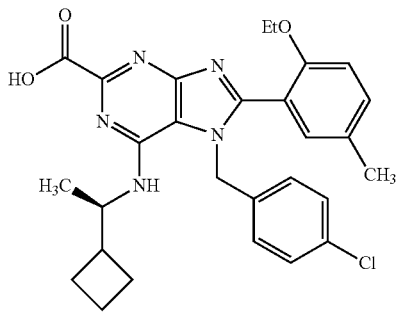 [SMILES: CCOc1ccc(C)cc1-c1nc2nc(C(=O)O)nc(N[C@H](C)C3CCC3)c2n1Cc1ccc(Cl)cc1]

Step 1: Methyl 2-hydroxy-5-methylbenzoate (5.00 g, 30.8 mmol), iodoethane (7.67 g, 45.1 mmol) and potassium carbonate (12.47 g, 90.2 mmol) were suspended in anhydrous DMF (50 mL). The reaction mixture was then heated at 70° C. for 3 hours. The reaction mixture was cooled to room temperature, diluted with water, and extracted with EtOAc (3×). The combined organic layers were washed with brine, dried over sodium sulfate, filtered and concentrated under reduced pressure. The residue was purified by column chromatography (5% EtOAc/hexanes) to afford methyl 2-ethoxy-5-methylbenzoate as white solid. $^1$H NMR (300 MHz, CD$_3$OD) δ 7.58 (d, J=3.0 Hz, 1H), 7.24 (dd, J=9.0, 3.0 Hz, 1H), 6.87 (d, J=9.0 Hz, 1H), 4.09 (q, J=6.0 Hz, 2H), 3.88 (s, 3H), 2.29 (s, 3H), 1.46 (t, J=7.5 Hz, 3H). MS (APCI)=195 (M+1)$^+$.

Step 2: Methyl 2-ethoxy-5-methylbenzoate (4.60 g, 23.6 mmol) was taken up in THF (20 mL), methanol (3.0 mL) and water (3.0 mL). Lithium hydroxide (2.83 g, 118 mmol) was added to the reaction and the resulting mixture was stirred at room temperature for 8 hours. The organic solvents were then removed under reduced pressure. The resulting mixture was quenched with aqueous HCl (1N) and extracted with EtOAc (2×100 mL). The combined organic layers were washed with brine (50 mL), dried over sodium sulfate, filtered, and concentrated under reduced pressure to afford 2-ethoxy-5-methylbenzoic acid as white solid. $^1$H NMR (300 MHz, CD$_3$OD) δ 12.40 (s, 1H), 7.42 (d, J=3.0 Hz, 1H), 7.28 (dd, J=9.0, 3.0 Hz, 1H), 6.87 (d, J=9.0 Hz, 1H), 4.05 (q, J=6.0 Hz, 2H), 2.25 (s, 3H), 1.46 (t, J=7.5 Hz, 3H). MS (APCI)=181 (M+1)$^+$.

Step 3: To a solution of 2-ethoxy-5-methylbenzoic acid (5.0 g, 27.7 mmol) in dichloromethane (50 mL) was added oxalyl chloride (5.28 g, 41.6 mmol) and DMF (catalytic) at 0° C. The reaction mixture was stirred for 1 hour under a N$_2$ atmosphere. The reaction mixture was evaporated to dryness under N$_2$ atmosphere. The crude acid chloride (2-ethoxy-5-methylbenzoyl chloride) was carried forward to the next step without further purification.

Step 4: To a solution of 6-amino-5-((4-chlorobenzyl)amino)-1-methylpyrimidine-2,4(1H,3H)-dione (5.0 g, 17.8 mmol) in dichloromethane (50 mL) was added DIPEA (10 mL). The suspension was cooled to 0° C. and a solution of 2-ethoxy-5-methylbenzoyl chloride (3.5 g, 17.8 mmol) in dichloromethane (20 mL) was added dropwise. The reaction mixture was brought to room temperature and stirred overnight. The reaction mixture was then diluted with saturated aqueous sodium bicarbonate solution and extracted with EtOAc. The organic layer was washed with brine, dried over sodium sulfate, filtered and concentrated under reduced pressure to afford N-(6-amino-1-methyl-2,4-dioxo-1,2,3,4-tetrahydropyrimidin-5-yl)-N-(4-chlorobenzyl)-2-ethoxy-5-methylbenzamide, which was used without purification in the next reaction. $^1$H NMR (300 MHz, CDCl$_3$) δ 7.49 (d, J=9.0 Hz, 2H), 7.44 (d, J=9.0 Hz, 2H), 7.05 (d, J=8.0 Hz, 1H), 6.94 (s, 1H), 6.81 (d, J=6.0 Hz, 1H), 4.92 (d, J=15.0 Hz, 1H), 4.49 (d, J=15.0 Hz, 1H), 4.05 (q, J=9.0 Hz, 2H), 2.99 (s, 3H), 2.12 (s, 3H), 1.29 (t, J=6.0 Hz, 3H). MS (APCI)=443 (M+1)$^+$ Step 5: N-(6-Amino-1-methyl-2,4-dioxo-1,2,3,4-tetrahydropyrimidin-5-yl)-N-(4-chlorobenzyl)-2-ethoxy-5-methylbenzamide (2.66 g, 6.0 mmol) was dissolved in ethanol (20 mL) and sodium hydroxide (2.61 g, 65.4 mmol) was added. The resultant reaction mixture was heated to reflux for 12 hours. The reaction mixture was then cooled to room temperature and the ethanol was removed in vacuo. The white residue was dissolved in water (50 mL) and the aqueous layer extracted EtOAc (100 mL). The organic layer was washed with water (50 mL), brine (50 mL), dried over anhydrous sodium sulfate, filtered and concentrated in vacuo. The residue was purified by silica gel chromatography (5% methanol/dichloromethane) to afford 7-(4-chlorobenzyl)-8-(2-ethoxy-5-methylphenyl)-3-methyl-1H-purine-2,6(3H,7H)-dione as white solid. $^1$H NMR (300 MHz, CDCl$_3$) δ 8.67 (s, 1H), 7.49 (d, J=9.0 Hz, 2H), 7.16-7.12 (m, 2H), 6.94-6.90 (m, 2H), 5.38 (s, 2H), 4.05 (q, J=9.0 Hz, 2H), 3.58 (s, 3H), 2.31 (s, 3H), 1.30 (t, J=6.0 Hz, 3H). MS (APCI)=425 (M+1)$^+$ Step 6: 7-(4-Chlorobenzyl)-8-(2-ethoxy-5-methylphenyl)-3-methyl-1H-purine-2,6(3H,7H)-dione (2.30 g, 5.41 mmol) was dissolved in phosphorus oxychloride (5.0 mL) and the mixture was heated to 60° C. 1,8-Diazabicyclo[5.4.0]undec-7-ene (1.64 mL, 10.8 mmol) was then added. The reaction was then heated to 120° C. for 3 hours. Then the reaction mixture was cooled to room temperature and poured into ice water. The resulting precipitate was collected by filtration and air-dried to afford 2,6-dichloro-7-(4-chlorobenzyl)-8-(2-ethoxy-5-methylphenyl)-7H-purine as brown solid. $^1$H NMR (300 MHz, CDCl$_3$) δ 7.33 (m, 4H), 6.94 (d, J=9.0 Hz, 1H), 6.77 (d, J=9.0 Hz, 2H), 5.52 (s, 2H), 4.07 (q, J=9.0 Hz, 2H), 2.30 (s, 3H), 1.28 (t, J=6.0 Hz, 3H). MS (APCI)=447 (M+1)$^+$ Step 7: A mixture of 2,6-dichloro-7-(4-chlorobenzyl)-8-(2-ethoxy-5-methylphenyl)-7H-purine (500 mg, 1.16 mmol) and (R)-1-cyclobutylethylamine (664 mg, 6.70 mmol) in ethanol (5.0 mL) was heated at reflux for 12 hours. Then the reaction mixture was cooled to room temperature and concentrated under reduced pressure. The residue was dissolved in EtOAc (30 mL) and washed with water (15 mL) and brine (15 mL). The organic layer was dried over anhydrous sodium sulfate, filtered, and concentrated in vacuo. Purification of the crude residue by column chromatography (45% EtOAc/hexanes) afforded (R)-2-chloro-7-(4-chlorobenzyl)-N-(1-cyclobutylethyl)-8-(2-ethoxy-5-methylphenyl)-7H-purin-6-amine as white solid. $^1$H NMR (300 MHz, CDCl$_3$) δ 7.33-7.40 (m, 3H), 7.21-7.25 (m, 1H), 7.09 (d, J=8.4 Hz, 2H), 6.83 (d, J=8.4 Hz, 1H), 4.20 (s, 2H), 3.95 (q, J=7.0 Hz, 2H), 2.30 (s, 3H), 1.85-1.88 (m, 2H), 1.58-1.70 (m, 4H), 1.41-1.49 (m, 2H), 1.11 (t, J=10.2 Hz, 3H), 0.82 (d, J=6.0 Hz, 3H). MS (APCI)=510 (M+1)$^+$.

Step 8: A mixture of (R)-2-chloro-7-(4-chlorobenzyl)-N-(1-cyclobutylethyl)-8-(2-ethoxy-5-methylphenyl)-7H-purin-6-amine (300 mg, 0.58 mmol) and sodium cyanide (57.6 mg, 1.17 mmol) were taken up in DMSO (4.0 mL) in a microwave tube. The tube was sealed and heated at 200° C. under microwave irradiation for 2 hours. Water (10 mL) was then added to the reaction and the aqueous layer was extracted with EtOAc (200 mL). The organic layer was washed with water (30 mL), brine (30 mL), dried over anhydrous sodium sulfate, filtered and concentrated in vacuo. The crude residue was purified by silica gel chromatography (45% EtOAc/hexanes) to afford (R)-7-(4-chlorobenzyl)-6-((1-cyclobutylethyl)amino)-8-(2-ethoxy-5-methylphenyl)-7H-purine-2-carbonitrile as white solid and (R)-7-(4-chlorobenzyl)-6-((1-cyclobutylethyl)amino)-8-(2-hydroxy-5-methylphenyl)-7H-purine-2-carbonitrile (a major by product) as a white solid. (R)-7-(4-chlorobenzyl)-6-((1-cyclobutylethyl)amino)-8-(2-ethoxy-5-methylphenyl)-7H-purine-2-carbonitrile: $^1$H NMR (300 MHz, CDCl$_3$) δ 7.41 (d, J=9.0 Hz, 2H), 7.23-7.31 (m, 2H), 7.09 (d, J=9.0 Hz, 2H), 6.85 (d, J=9.0 Hz, 1H), 5.31 (d, J=3.6 Hz, 2H), 4.19-4.26 (m, 1H), 4.00 (q, J=7.5 Hz, 2H), 2.32 (s, 3H), 1.60-1.91 (m, 7H), 1.16 (t, J=9.0 Hz, 3H), 0.82 (t, J=6.0 Hz, 3H). MS (ES)=501 (M+1)$^+$.

(R)-7-(4-chlorobenzyl)-6-((1-cyclobutylethyl)amino)-8-(2-hydroxy-5-methylphenyl)-7H-purine-2-carbonitrile: MS (ES)=473 (M+1)$^+$.

Step 9: A mixture of (R)-7-(4-chlorobenzyl)-6-((1-cyclobutylethyl)amino)-8-(2-ethoxy-5-methylphenyl)-7H-purine-2-carbonitrile (85.0 mg, 0.16 mmol) and sodium hydroxide (339 mg, 8.48 mmol) in ethanol (4.0 mL) and water (1.0 mL) were heated at reflux for 2 hours. The reaction mixture was then cooled to room temperature and acidified with aqueous HCl (1N) until pH 2. The aqueous layer was extracted with EtOAc (50 mL) and the organic layer was then washed with water (20 mL), brine (20 mL), dried over anhydrous sodium sulfate, filtered and concentrated in vacuo. Purification of the crude residue by silica gel chromatography (5% methanol/dichloromethane) afforded (R)-7-(4-chlorobenzyl)-6-((1-cyclobutylethyl)amino)-8-(2-ethoxy-5-methylphenyl)-7H-purine-2-carboxylic acid as white solid. $^1$H NMR (400 MHz, CD$_3$OD) δ 7.40 (d, J=8.0 Hz, 1H), 7.34 (d, J=8.0 Hz, 2H), 7.29 (s, 1H), 7.08 (d, J=8.0 Hz, 1H), 6.96 (d, J=8.0 Hz, 2H), 5.62 (d, J=16.0 Hz, 1H), 5.41 (d, J=16.0 Hz, 1H), 4.70 (s, 1H), 4.06 (t, J=8.0 Hz, 2H), 2.27 (s, 3H), 1.54-2.15 (m, 7H), 1.17 (m, 3H), 0.95 (d, J=8.0 Hz, 3H). MS (ES)=520 (M+1)$^+$.

Example 4.2

(R)-7-(4-chlorobenzyl)-6-((1-cyclobutylethyl)amino)-8-(2,5-dimethylphenyl)-7H-purine-2-carboxylic acid

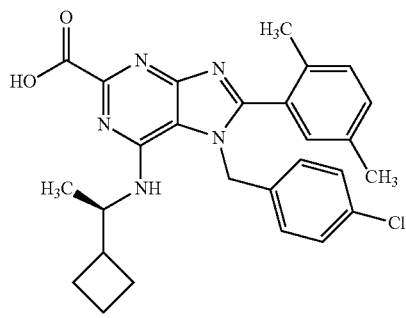 [SMILES: Cc1ccc(C)c(-c2nc3nc(C(=O)O)nc(N[C@H](C)C4CCC4)c3n2Cc2ccc(Cl)cc2)c1]

Using procedures analogous to that described in Example 4.1, (R)-7-(4-chlorobenzyl)-6-((1-cyclobutylethyl)amino)-8-(2,5-dimethylphenyl)-7H-purine-2-carboxylic acid was prepared. $^1$H NMR (400 MHz, CD$_3$OD) δ 7.19-7.37 (m, 3H), 7.19 (s, 1H), 6.93-6.95 (d, J=8.0 Hz, 2H), 5.36-5.63 (m, 2H), 4.61-4.65 (m, 1H), 2.30 (s, 3H), 2.05-2.28 (m, 1H), 2.16 (s, 3H), 1.94-1.98 (m, 2H), 1.68-1.73 (m, 3H), 1.55-1.61 (m, 2H), 1.00-1.02 (d, J=8.0 Hz, 3H). MS (ES)=490 (M+1)$^+$.

Preparative Example 4.2

8-(2-(but-3-en-1-yloxy)-5-methylphenyl)-7-(4-chlorobenzyl)-3-methyl-1H-purine-2,6(3H,7H)-dione

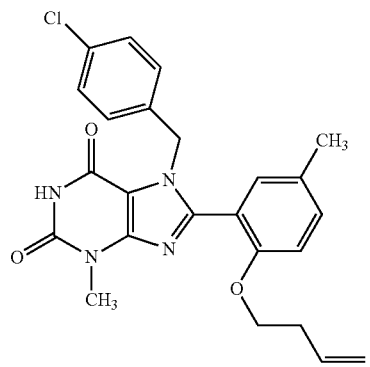 [SMILES: C=CCCOc1ccc(C)cc1-c1nc2c(c(=O)[nH]c(=O)n2C)n1Cc1ccc(Cl)cc1]

Step 1: Methyl 2-hydroxy-5-methylbenzoate (20.0 g, 120.3 mmol), 4-bromo-1-butene (24.3 g, 180.5 mmol) and cesium carbonate (117.6 g, 361.0 mmol) were suspended in anhydrous DMF (150 mL). The reaction mixture was heated at 80° C. for 14 hours. The reaction mixture was then brought to room temperature and diluted with EtOAc (100 mL). The resulting mixture was washed with water (3×150 mL) and the aqueous layers were back extracted with EtOAc (2×100 mL). The combined organic layers were washed with brine, dried over sodium sulfate, filtered and concentrated in vacuo. The resultant residue was purified by silica gel chromatography (5% EtOAc/hexanes) to afford methyl 2-(but-3-en-1-yloxy)-5-methylbenzoate as white solid. $^1$H NMR (300 MHz, CD$_3$OD) δ 7.58 (d, J=2.4 Hz, 1H), 7.22 (dd, J=6.8, 2.4 Hz, 1H), 6.86 (d, J=6.8 Hz, 1H), 5.89-5.96 (m, 1H), 5.08-5.18 (m, 2H), 4.04 (t, J=6.6 Hz, 2H), 3.86 (s, 3H), 2.59 (q, J=6.6 Hz, 2H), 2.28 (s, 3H).

Step 2: Methyl 2-(but-3-en-1-yloxy)-5-methylbenzoate (8.00 g, 36.3 mmol) was taken up in THF (15 mL), methanol (4.0 mL) and water (5.0 mL). Lithium hydroxide (4.34 g, 181.6 mmol) was then added and the reaction mixture was stirred at room temperature for 12 hours. Then the organic solvents were removed in vacuo. The resulting mixture was quenched with 1N aqueous HCl and extracted with EtOAc (2×100 mL). The combined organic layers were washed with brine (50 mL), dried over sodium sulfate, filtered, and concentrated under reduced pressure to afford 2-(but-3-en-1-yloxy)-5-methylbenzoic acid as white solid. $^1$H NMR (300 MHz, DMSO-d$_6$) δ 7.44 (d, J=3.0 Hz, 1H), 7.29 (dd, J=6.0, 3.0 Hz, 1H), 7.02 (d, J=6.0 Hz, 1H), 5.88-5.93 (m, 1H), 5.08-5.19 (m, 2H), 4.06 (t, J=6.0 Hz, 2H), 2.44 (q, J=9.0 Hz, 2H), 2.25 (s, 3H).

Step 3: To a solution of 2-(but-3-en-1-yloxy)-5-methylbenzoic acid (5.0 g, 24.0 mmol) in dichloromethane (20 mL) was added oxalyl chloride (4.61 g, 36.0 mmol) and DMF (catalytic) at 0° C. The reaction mixture was stirred for 1 hour under N$_2$ atmosphere. The reaction mixture was evaporated to dryness under N$_2$ atmosphere and the crude product (2-(but-3-en-1-yloxy)-5-methylbenzoyl chloride) was carried forward to the next reaction without further purification.

Step 4: To a solution of 6-amino-5-((4-chlorobenzyl)amino)-1-methylpyrimidine-2,4(1H,3H)-dione (5.0 g, 17.8 mmol) in dichloromethane (50 mL) was added DIPEA (10 mL). The suspension was cooled to 0° C. and a solution of 2-(but-3-en-1-yloxy)-5-methylbenzoyl chloride (3.5 g, 17.8 mmol) in dichloromethane (10 mL) was added dropwise. The reaction mixture was cooled to room temperature and stirred as such overnight. The solvent was then removed under reduced pressure and the residue partitioned between saturated aqueous sodium bicarbonate solution and EtOAc. The organic layer was separated and washed with brine, dried over sodium sulfate, filtered and concentrated under reduced pressure to afford crude N-(6-amino-1-methyl-2,4-dioxo-1,2,3,4-tetrahydropyrimidin-5-yl)-2-(but-3-en-1-yloxy)-N-(4-chlorobenzyl)-5-methylbenzamide, which was carried forward without further purification.

Step 5: N-(6-Amino-1-methyl-2,4-dioxo-1,2,3,4-tetrahydropyrimidin-5-yl)-2-(but-3-en-1-yloxy)-N-(4-chlorobenzyl)-5-methylbenzamide (8.07 g, 17.0 mmol) was taken up in ethanol (80 mL). Sodium hydroxide (6.82 g, 170 mmol) was added and the resultant reaction mixture was heated to reflux for 12 hours. Then the reaction mixture was cooled to room temperature and the ethanol was removed in vacuo. The resulting white residue was taken up in water (100 mL) and extracted with EtOAc (3×50 mL). The combined organic layers were washed with water (100 mL), brine (100 mL), dried over anhydrous sodium sulfate, filtered and concentrated in vacuo. The residue was purified by silica gel chromatography (3% methanol/dichloromethane) to afford 8-(2-(but-3-en-1-yloxy)-5-methylphenyl)-7-(4-chlorobenzyl)-3-methyl-1H-purine-2,6(3H,7H)-dione as white solid. $^1$H NMR (300 MHz, CDCl$_3$) δ9.36 (s, 1H), 7.31 (dd, J=9.0, 1.6 Hz, 1H), 7.16 (t, J=3.0 Hz, 1H), 7.13 (t, J=3.0 Hz, 2H), 6.94 (d, J=9.0 Hz, 3H), 5.68-5.82 (m, 1H), 5.38 (s, 2H), 5.11 (d, J=6.0 Hz, 2H), 4.03 (t, J=12.0 Hz, 2H), 3.58 (s, 3H), 2.44 (q, J=9.0 Hz, 2H), 2.17 (s, 3H). MS (ES)=451 (M+1)$^+$.

Example 4.3

(R)-8-(2-(but-3-en-1-yloxy)-5-methylphenyl)-7-(4-chlorobenzyl)-6-((1-cyclopropylethyl)amino)-7H-purine-2-carboxylic acid

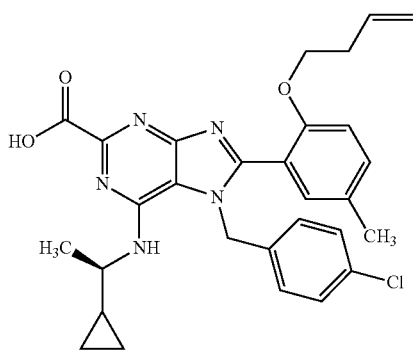 [SMILES: C=CCCOc1ccc(C)cc1-c1nc2nc(C(=O)O)nc(N[C@H](C)C3CC3)c2n1Cc1ccc(Cl)cc1]

Step 1: 8-(2-(But-3-en-1-yloxy)-5-methylphenyl)-7-(4-chlorobenzyl)-3-methyl-1H-purine-2,6(3H,7H)-dione (4.50 g, 8.87 mmol) was taken up in phosphorus oxychloride (5.0 mL) and the reaction mixture was heated to 60° C. 1,8-Diazabicyclo[5.4.0]undec-7-ene (2.65 mL, 17.7 mmol) was added and the temperature of the reaction was raised to 120° C. and stirred at the same temperature for 3 hours. Then the reaction mixture was cooled to room temperature and poured into ice water. The resulting brown precipitate was collected by filtration and air-dried. The brown residue was subjected to purification by silica gel column chromatography (45% EtOAc/hexanes) to afford 8-(2-(but-3-en-1-yloxy)-5-methylphenyl)-2,6-dichloro-7-(4-chlorobenzyl)-7H-purine as white solid. $^1$H NMR (300 MHz, CDCl$_3$) δ7.34 (dd, J=9.0, 3.0 Hz, 1H), 7.25 (s, 1H), 7.19 (d, J=9.0 Hz, 2H), 6.93 (s, 1H), 6.74 (d, J=9.0 Hz, 2H), 5.51-5.78 (m, 1H), 5.50 (m, 1H), 5.04 (s, 1H), 4.98-5.00 (m, 1H), 4.87 (br s, 1H), 4.04 (t, J=12.0 Hz, 2H), 2.41 (q, J=10.5 Hz, 2H) 2.30 (s, 3H). MS (ES)=473 (M+1)$^+$.

Step 2: A mixture of 8-(2-(but-3-en-1-yloxy)-5-methylphenyl)-2,6-dichloro-7-(4-chlorobenzyl)-7H-purine (4.0 g, 8.44 mmol) and (R)-1-cyclopropylethylamine (3.59 mL, 42.2 mmol) in ethanol (40 mL) was heated at reflux for 2 hours. Then the reaction mixture was cooled to room temperature and the ethanol was removed in vacuo. The resulting residue was dissolved in EtOAc (200 mL) and washed with water (50 mL) and brine (50 mL). The organic layer was dried over anhydrous sodium sulfate, filtered, and concentrated in vacuo. Purification of the crude material by column chromatography (45% EtOAc/hexanes) afforded (R)-8-(2-(but-3-en-1-yloxy)-5-methylphenyl)-2-chloro-7-(4-chlorobenzyl)-N-(1-cyclopropylethyl)-7H-purin-6-amine as white solid. $^1$H NMR (300 MHz, CDCl3) δ 7.34-7.38 (m, 3H), 7.24 (s, 1H), 7.06 (d, J=8.4 Hz, 2H), 6.92 (d, J=8.7 Hz, 1H), 5.60-5.73 (m, 1H), 5.29 (s, 2H), 5.02-5.03 (m, 1H), 4.96-4.98 (m, 1H), 4.55 (d, J=6.9 Hz, 1H), 3.99 (t, J=12.0 Hz, 2H), 3.58 (q, J=6.6 Hz, 1H), 2.31 (s, 3H), 2.26-2.28 (m, 1H), 1.02 (d, J=6.6 Hz, 3H), 0.43-0.52 (m, 2H), 0.19-0.26 (m, 3H). MS (ES)=522 (M+1)$^+$.

Step 3: A mixture of (R)-8-(2-(but-3-en-1-yloxy)-5-methylphenyl)-2-chloro-7-(4-chlorobenzyl)-N-(1-cyclopropylethyl)-7H-purin-6-amine (1.0 g, 1.91 mmol) and sodium cyanide (468 mg, 9.56 mmol) in DMSO (5.0 mL) was sealed in a microwave tube and heated at 200° C. under microwave irradiation for 2 hours. Water (10 mL) was then added to the reaction mixture and the aqueous layer was extracted with EtOAc (200 mL). Then the organic layer was washed with water (50 mL) and brine (50 mL), dried over anhydrous sodium sulfate, filtered and concentrated in vacuo. The crude residue was purified by column chromatography (45% EtOAc/hexanes) to afford (R)-8-(2-(but-3-en-1-yloxy)-5-methylphenyl)-7-(4-chlorobenzyl)-((1-cyclopropylethyl)amino)-7H-purine-2-carbonitrile as a white solid. $^1$H NMR (300 MHz, CDCl$_3$) δ7.37 (m, 3H), 7.25 (s, 1H), 7.03 (d, J=8.0 Hz, 2H), 6.99 (d, J=12.0 Hz, 1H), 5.59-5.72 (m, 1H), 4.95-5.03 (m, 2H), 4.57 (d, J=8.0 Hz, 1H), 3.66-3.98 (m, 6H), 2.26-2.32 (m, 5H), 1.05 (d, J=3.0 Hz, 2H), 0.38-0.50 (m, 2H), 0.15-0.24 (m, 3H). MS (ES)=513 (M+1)$^+$.

Step 4: A mixture of (R)-8-(2-(but-3-en-1-yloxy)-5-methylphenyl)-7-(4-chlorobenzyl)-((1-cyclopropylethyl)amino)-7H-purine-2-carbonitrile (250 mg, 0.48 mmol) and sodium hydroxide (974 mg, 24.35 mmol) in ethanol (4.0 mL) and water (0.5 mL) was heated at reflux for 30 minutes. The reaction mixture was then cooled to room temperature and acidified with 1M aqueous HCl until pH 2. The aqueous layer was extracted with EtOAc (150 mL) and the organic layer was washed with water (30 mL) and brine (30 mL), dried over anhydrous sodium sulfate, filtered and concentrated in vacuo. Purification of the resultant residue by silica gel column chromatography (2% methanol/dichloromethane) afforded (R)-8-(2-(but-3-en-1-yloxy)-5-methylphenyl)-7-(4-chlorobenzyl)-6-((1-cyclopropylethyl)amino)-7H-purine-2-carboxylic acid. $^1$H NMR (400 MHz, CD$_3$OD) δ 7.42 (dd, J=8.0, 4.0 Hz, 1H), 7.33-7.35 (m, 3H), 7.11 (d, J=8.0 Hz, 1H), 7.01 (d, J=8.0 Hz, 2H), 5.71-5.77 (m, 1H), 5.60 (d, J=16.0 Hz, 1H), 5.50 (d, J=16.0 Hz, 1H), 5.00-5.01 (m, 2H), 4.02-4.08 (m, 2H), 3.86-3.91 (m, 1H), 2.37 (t, J=6.0 Hz, 2H), 2.33 (s, 3H), 1.16 (d, J=6.6 Hz, 3H), 0.82-0.86 (m, 1H), 0.45-0.49 (m, 1H), 0.27 (m, 3H). MS (ES)=532 (M+1)$^+$.

Example 4.4

(R)-7-(4-chlorobenzyl)-6-((1-cyclobutylethyl)amino)-8-(2-(3-methoxypropoxy)-5-methylphenyl)-7H-purine-2-carboxylic acid

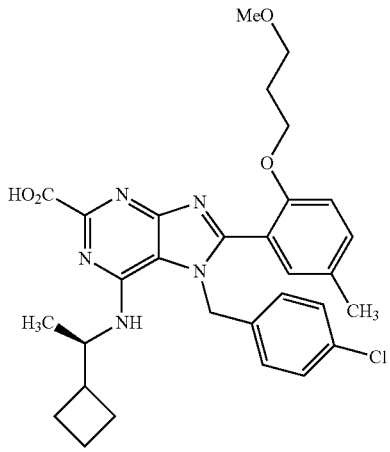 [SMILES: COCCCOc1ccc(C)cc1-c1nc2nc(C(=O)O)nc(N[C@H](C)C3CCC3)c2n1Cc1ccc(Cl)cc1]

Using a procedure analogous to that described in Example 4.1, starting with 6-amino-5-((4-chlorobenzyl)amino)-1-methylpyrimidine-2,4(1H,3H)-dione (Preparative Example 4.1), methyl 2-hydroxy-5-methylbenzoate and 1-iodo-3-methoxypropane, (R)-7-(4-chlorobenzyl)-6-((1-cyclobutylethyl)amino)-8-(2-(3-methoxypropoxy)-5-methylphenyl)-7H-purine-2-carboxylic acid was prepared. $^1$H NMR (300 MHz, CD$_3$OD) δ 7.37 (m, 4H), 7.09 (d, J=8.5 Hz, 1H), 6.98 (d, J=8.5 Hz, 2H), 5.62 (d, J=17.0 Hz, 1H), 5.44 (d, J=17.0 Hz, 1H), 4.61 (m, 1H), 4.10 (m, 2H), 3.34 (m, 3H), 3.19 (s, 3H), 2.30 (s, 3H), 2.19 (m, 1H), 1.98 (m, 1H), 1.87 (quintet, J=6.5 Hz, 2H), 1.63 (m, 2H), 1.55 (m, 2H), 0.98 (d, J=6.6 Hz, 3H). MS (ES)=564 (M+1)$^+$.

Example 4.5

(R)-7-(4-chlorobenzyl)-6-((1-cyclopropylethyl)amino)-8-(2-(3-methoxypropoxy)-5-methylphenyl)-7H-purine-2-carboxylic acid

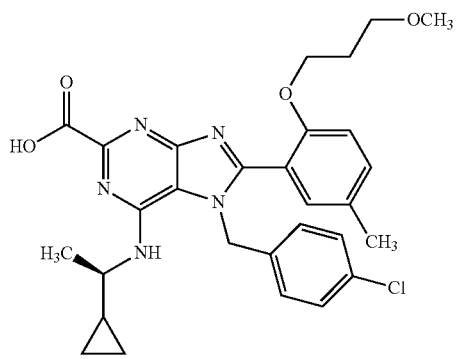 [SMILES: COCCCOc1ccc(C)cc1-c1nc2nc(C(=O)O)nc(N[C@H](C)C3CC3)c2n1Cc1ccc(Cl)cc1]

Using a procedure analogous to that described in Example 4.1, and starting with 6-amino-5-((4-chlorobenzyl)amino)-1-methylpyrimidine-2,4(1H,3H)-dione (Preparative Example 4.1), methyl 2-hydroxy-5-methylbenzoate and 1-iodo-3-methoxypropane, (R)-7-(4-chlorobenzyl)-6-((1-cyclopropylethyl)amino)-8-(2-(3-methoxypropoxy)-5-methylphenyl)-7H-purine-2-carboxylic acid was prepared. $^1$H NMR (300 MHz, CD$_3$OD) δ7.38 (m, 4H), 7.13 (d, J=8.4 Hz, 1H), 7.04 (d, J=8.4 Hz, 2H), 5.56 (m, 2H), 4.10 (m, 2H), 3.93 (m, 1H), 3.34 (m, 2H), 3.20 (s, 3H), 2.31 (s, 3H), 1.85 (p, J=6.2 Hz, 2H), 1.16 (d, J=6.5 Hz, 3H), 0.72 (m, 1H), 0.46 (m, 1H), 0.19 (m, 3H). MS (ES)=506 [M–CO$_2$]$^+$.

Example 4.6

(R)-7-(4-chlorobenzyl)-6-((1-cyclobutylethyl)amino)-8-(2-(3-hydroxypropoxy)-5-methylphenyl)-7H-purine-2-carboxylic acid

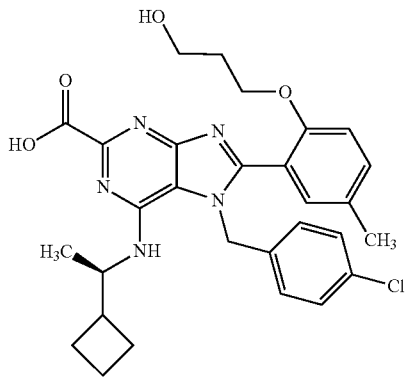 [SMILES: Cc1ccc(OCCCO)c(-c2nc3nc(C(=O)O)nc(N[C@H](C)C4CCC4)c3n2Cc2ccc(Cl)cc2)c1]

(R)-7-(4-chlorobenzyl)-6-((1-cyclobutylethyl)amino)-8-(2-(3-methoxypropoxy)-5-methylphenyl)-7H-purine-2-carboxylic acid, Example 4.4, (142 mg, 0.25 mmol) was dissolved in dichloromethane (2.0 mL) and cooled to 0° C. Iodotrimethylsilane (0.04 mL, 0.28 mmol) was added and the resulting solution was stirred at room temperature for 3 hours. The reaction was quenched by the addition of aqueous 1% sodium thiosulfate solution and extracted with EtOAc (100 mL). The organic layer was washed with water (20 mL) and brine (20 mL), dried over anhydrous sodium sulfate, filtered and concentrated in vacuo. Purification of the residue by silica gel column chromatography (8% methanol/dichloromethane) afforded (R)-7-(4-chlorobenzyl)-6-((1-cyclobutylethyl)amino)-8-(2-(3-hydroxypropoxy)-5-methylphenyl)-7H-purine-2-carboxylic acid. $^1$H NMR (400 MHz, CD$_3$OD) δ 7.37 (m, 4H), 7.10 (d, J=8.5 Hz, 1H), 6.97 (d, J=8.5 Hz, 2H), 5.62 (d, J=17.0 Hz, 1H), 5.42 (d, J=17.0 Hz, 1H), 4.64 (m, 1H), 4.10 (m, 2H), 3.35 (m, 3H), 2.37 (s, 3H), 2.19 (m, 1H), 1.98 (m, 1H), 1.87 (quintet, J=6.5 Hz, 2H), 1.63 (m, 2H), 1.55 (m, 2H), 0.98 (d, J=6.6 Hz, 3H). MS (ES)=550 (M+1)$^+$.

Example 4.7

(R)-7-(4-chlorobenzyl)-6-((1-cyclopropylethyl)amino)-8-(2-ethoxy-5-methylphenyl)-7H-purine-2-carboxylic acid

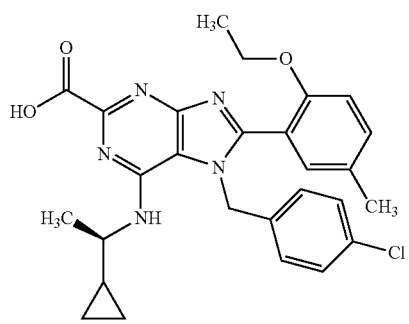 [SMILES: CCOc1ccc(C)cc1-c1nc2nc(C(=O)O)nc(N[C@H](C)C3CC3)c2n1Cc1ccc(Cl)cc1]

Using a procedure analogous to that described in Example 4.1, starting with 2,6-dichloro-7-(4-chlorobenzyl)-8-(2-ethoxy-5-methylphenyl)-7H-purine and (R)-1-cyclopropylethanamine, (R)-7-(4-chlorobenzyl)-6-((1-cyclopropylethyl)amino)-8-(2-ethoxy-5-methylphenyl)-7H-purine-2-carboxylic acid was prepared. $^1$H NMR (300 MHz, CD$_3$OD) δ 7.32-7.39 (m, 4H), 6.99-7.08 (m, 3H), 5.61 (d, J=15.0 Hz, 1H), 5.48 (d, J=15.0 Hz, 1H), 4.09 (q, J=7.2 Hz, 2H), 3.90-3.85 (m, 1H), 2.30 (s, 3H), 1.28 (t, J 7.2 Hz, 3H), 1.17 (d, J=6.0 Hz, 3H), 0.76-0.73 (m, 1H), 0.45-0.42 (m, 1H), 0.28-0.19 (m, 3H). MS (APCI)=504 (M−1)$^-$.

Example 4.8

(R)-7-(4-chlorobenzyl)-6-((1-cyclobutylethyl)amino)-8-(2-(2-methoxyethoxy)-5-methylphenyl)-7H-purine-2-carboxylic acid

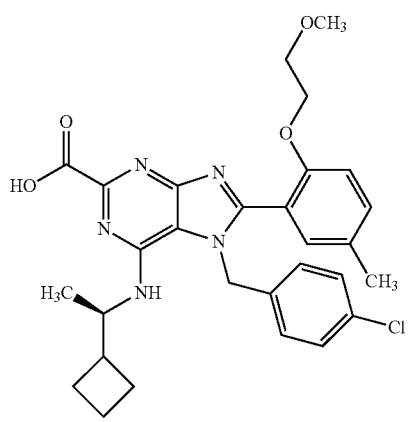 [SMILES: COCCOc1ccc(C)cc1-c1nc2nc(C(=O)O)nc(N[C@H](C)C3CCC3)c2n1Cc1ccc(Cl)cc1]

Using a procedure analogous to that described in Example 4.1, (R)-7-(4-chlorobenzyl)-6-((1-cyclobutylethyl)amino)-8-(2-(2-methoxyethoxy)-5-methylphenyl)-7H-purine-2-carboxylic acid was prepared. $^1$H NMR (300 MHz, CD$_3$OD) δ 7.30-7.39 (m, 4H), 7.13 (d, J=9.0 Hz, 1H), 6.99 (d, J=9.0 Hz, 2H), 5.60 (d, J=17.7 Hz, 1H), 5.44 (d, J=17.7 Hz, 1H), 4.66 (m, 1H), 4.09-4.18 (m, 2H), 3.54-3.57 (m, 2H), 3.24 (s, 3H), 2.31 (s, 3H), 2.11-2.19 (m, 1H), 1.93-1.98 (m, 1H), 1.51-1.81 (m, 5H), 0.98 (d, J=6.6 Hz, 3H). MS (ES)=550 (M+1)$^+$.

Example 4.9

(R)-7-(4-chlorobenzyl)-6-((1-cyclopropylethyl)amino)-8-(2-(2-methoxyethoxy)-5-methylphenyl)-7H-purine-2-carboxylic acid

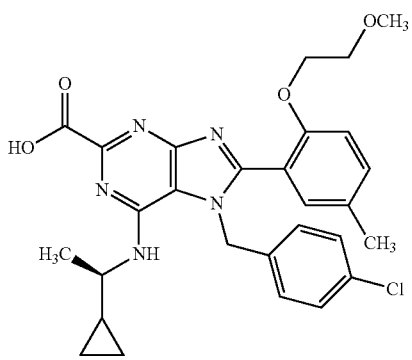 [SMILES: COCCOc1ccc(C)cc1-c1nc2nc(C(=O)O)nc(N[C@H](C)C3CC3)c2n1Cc1ccc(Cl)cc1]

Using a procedure analogous to that described in Example 4.1, (R)-7-(4-chlorobenzyl)-6-((1-cyclopropylethyl)amino)-8-(2-(2-methoxyethoxy)-5-methylphenyl)-7H-purine-2-carboxylic acid was prepared. $^1$H NMR (400 MHz, CD$_3$OD) δ7.38 (d, J=8.4 Hz, 1H), 7.32-7.34 (m, 3H), 7.11 (d, J=8.8 Hz, 1H), 7.01 (d, J=8.4 Hz, 2H), 5.49 (q, J=8.8 Hz, 2H), 4.15 (q, J=4.4 Hz, 2H), 3.87-3.91 (m, 1H), 3.58 (t, J=4.4 Hz, 2H), 3.26 (s, 3H), 2.32 (s, 3H), 1.15 (d, J=6.4 Hz, 3H), 0.69-0.80 (m, 1H), 0.42-0.45 (m, 1H), 0.20-0.27 (m, 3H). MS (APCI)=534 (M−1)$^-$.

Preparative Example 4.3

8-(2-(allyloxy)-5-methylphenyl)-2,6-dichloro-7-(4-chlorobenzyl)-7H-purine

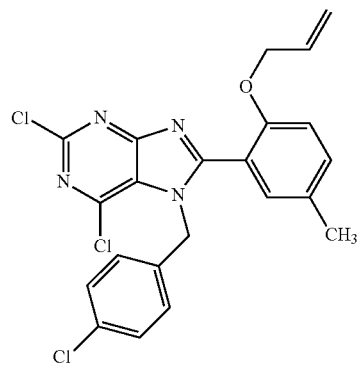 [SMILES: C=CCOc1ccc(C)cc1-c1nc2nc(Cl)nc(Cl)c2n1Cc1ccc(Cl)cc1]

Step 1: A mixture of methyl 5-methylsalicylate (8.80 g, 52.9 mmol), allyl bromide (9.2 mL, 106 mmol) and cesium carbonate (25.8 g, 79.3 mmol) in anhydrous DMF (80 mL) was heated at 70° C. for 14 hours. Then the reaction mixture was cooled to room temperature, diluted with water (200 mL) and extracted with EtOAc (500 mL). The organic layer was then washed with water (2×200 mL) and brine (100 mL), dried over anhydrous sodium sulfate, filtered, and concentrated in vacuo. The crude residue was purified by column chromatography (10% EtOAc/hexanes) to afford methyl 2-(allyloxy)-5-methylbenzoate as white solid. $^1$H NMR (300 MHz, CDCl$_3$) δ7.61 (d, J=2.2 Hz, 1H), 7.23 (dd, J=8.4, 2.2 Hz, 1H), 6.87 (d, J=8.4 Hz, 1H), 6.10 (m, 1H), 5.51 (dd, J=17.3, 4.5 Hz, 1H), 5.29 (dd, J=17.3, 4.5 Hz, 1H), 4.59 (d, J=4.5 Hz, 2H), 3.87 (s, 3H), 2.27 (s, 3H).

Step 2: Methyl 2-(allyloxy)-5-methylbenzoate (6.53 g, 31.7 mmol) was dissolved in a mixture of THF (72 mL), methanol (24 mL), and water (24 mL). Lithium hydroxide (3.80 g, 158 mmol) was added at room temperature and the resulting mixture was stirred for 12 hours. The solvents were then removed under reduced pressure and the white residue was taken up in a mixture of ethyl acetate (200 mL) and water (100 mL). The layers were separated and the aqueous layer was acidified with 1M aqueous HCl to pH 2 and then extracted with EtOAc (300 mL). The resulting organic layer was washed with water (100 mL) and brine (100 mL), dried over anhydrous sodium sulfate, filtered and concentrated in vacuo to afford 2-(allyloxy)-5-methylbenzoic acid which was used without further purification. $^1$H NMR (300 MHz, DMSO-d$_6$) δ12.47 (s, 1H), 7.44 (s, 1H), 7.28 (d, J=8.4 Hz, 1H), 7.01 (d, J=8.4 Hz, 1H), 6.05 (m, 1H), 5.49 (dd, J=17.3, 5.6 Hz, 1H), 5.45 (dd, J=17.3, 5.6 Hz, 1H), 4.59 (d, J=8.0 Hz, 2H), 2.25 (s, 3H).

Step 3: 2-(Allyloxy)-5-methylbenzoic acid (3.39 g, 17.6 mmol) was dissolved in anhydrous dichloromethane (40 mL) and cooled to 0° C. Oxalyl chloride (2.3 mL, 26.5 mmol) was added drop wise followed by the addition of 2 drops of anhydrous DMF. The reaction mixture was then stirred at room temperature for 1 hour and then the reaction was concentrated in vacuo. The resulting white residue (2-(allyloxy)-5-methylbenzoyl chloride) was used immediately without further purification.

Step 4: Preparative Example 4.1, 6-amino-5-((4-chlorobenzyl)amino)-1-methylpyrimidine-2,4(1H,3H)-dione, (3.30 g, 11.8 mmol) was suspended in anhydrous dichloromethane (50 mL) and N,N-diisopropylethylamine (9.0 mL, 53.0 mmol) was added to the stirring suspension. A solution of 2-(allyloxy)-5-methylbenzoyl chloride (from Step 3) in dichloromethane (40 mL) was added to the stirring suspension slowly over 10 minutes. The resulting reaction mixture was then stirred at room temperature for 12 hours. Water (100 mL) was then added to the reaction mixture and the organic layer was separated. The aqueous layer was further extracted with dichloromethane (200 mL) and the combined organic layers were washed with saturated aqueous sodium bicarbonate (100 mL), water (200 mL), and brine (100 mL), dried over anhydrous sodium sulfate, filtered and concentrated in vacuo. The intermediate brown residue was subjected to the next reaction without further purification. The intermediate was dissolved in ethanol (38 mL) and then sodium hydroxide (6.20 g, 155 mmol) was added and the resultant reaction mixture was heated at reflux for 12 hours. Then the reaction mixture was cooled to room temperature and ethanol was removed under reduced pressure. The resulting white residue was dissolved in water (100 mL). The aqueous layer was extracted with EtOAc (500 mL). The organic layer was washed with water (100 mL) and brine (100 mL), dried over anhydrous sodium sulfate, filtered and concentrated in vacuo. The resulting residue was purified by column chromatography (3% methanol/dichloromethane) to afford 8-(2-(allyloxy)-5-methylphenyl)-7-(4-chlorobenzyl)-3-methyl-1H-purine-2,6(3H,7H)-dione as white solid. $^1$H NMR (400 MHz, CDCl$_3$) δ7.29 (s, 1H), 7.16 (m, 3H), 6.91 (m, 3H), 5.88 (m, 1H), 5.37 (s, 2H), 5.34 (d, J=17.4 Hz, 2H), 4.51 (d, J=8.0 Hz, 2H), 3.59 (s, 3H), 2.30 (s, 3H). MS (ES)=437 (M+1)$^+$.

Step 5: 8-(2-(allyloxy)-5-methylphenyl)-7-(4-chlorobenzyl)-3-methyl-1H-purine-2,6(3H,7H)-dione (3.09 g, 7.07 mmol) was dissolved in phosphorus oxychloride (30 mL) and the mixture was heated to 60° C. 1,8-Diazabicyclo[5.4.0]undec-7-ene (2.11 mL, 14.1 mmol) was added, the temperature of the solution was raised to 120° C., and the reaction mixture was stirred at this temperature for 2 hours. Then the reaction mixture was cooled to room temperature and poured into ice water. The resulting brown precipitate was collected by filtration and air dried to afford 8-(2-(allyloxy)-5-methylphenyl)-2,6-dichloro-7-(4-chlorobenzyl)-7H-purine as a brown solid. $^1$H NMR (400 MHz, CDCl$_3$) δ7.31 (s, 1H), 7.29 (d, J=8.5 Hz, 1H), 7.20 (d, J=8.5 Hz, 2H), 6.93 (d, J=8.5 Hz, 1H), 6.76 (d, J=8.5 Hz, 2H), 5.86 (m, 1H), 5.52 (s, 2H), 5.25 (d, J=8.3 Hz, 1H), 5.21 (s, 1H), 4.49 (d, J=5.1 Hz, 2H), 2.29 (s, 3H). MS (ES)=459 (M+1)$^+$.

Example 4.10

(R)-7-(4-chlorobenzyl)-6-((1-cyclopropylethyl)amino)-8-(2-(2-hydroxyethoxy)-5-methylphenyl)-7H-purine-2-carboxylic acid

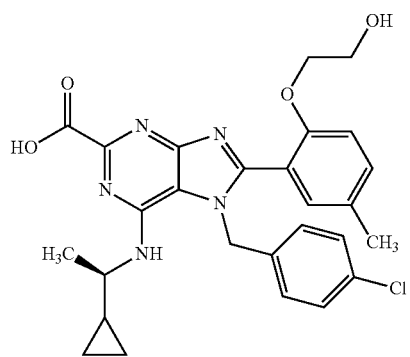 [SMILES: Cc1ccc(OCCO)c(-c2nc3nc(C(=O)O)nc(N[C@H](C)C4CC4)c3n2Cc2ccc(Cl)cc2)c1]

Step 1: A mixture of 8-(2-(allyloxy)-5-methylphenyl)-2,6-dichloro-7-(4-chlorobenzyl)-7H-purine (Preparative Example 4.3) (3.05 g, 6.63 mmol) and (R)-1-cyclopropylethylamine (3.61 mL, 33.17 mmol) in ethanol (25 mL) was heated to reflux for 2 hours. Then the reaction mixture was cooled to room temperature and the solvent was removed under reduced pressure. The residue was dissolved in EtOAc (300 mL) and then washed with water (50 mL) and brine (50 mL), dried over anhydrous sodium sulfate, filtered, and concentrated in vacuo. Purification of the resultant residue by column chromatography (10% EtOAc/dichloromethane) afforded (R)-8-(2-(allyloxy)-5-methylphenyl)-2-chloro-7-(4-chlorobenzyl)-N-(1-cyclopropylethyl)-7H-purin-6-amine as white solid. $^1$H NMR (300 MHz, CDCl$_3$) δ7.37 (m, 4H), 7.12 (d, J 7.9 Hz, 1H), 6.91 (d, J 8.5 Hz, 2H), 6.50 (d, J=7.9 Hz, 1H), 5.92 (m, 1H), 5.60 (d, J 17.4 Hz, 1H), 5.42 (d, J 17.4 Hz, 1H), 5.21 (m, 2H), 4.58 (d, J=6.5 Hz, 2H), 3.49 (q, J=6.6 Hz, 1H), 2.24 (s, 3H), 1.12 (d, J=6.6 Hz, 3H), 0.87 (m, 1H), 0.41 (m, 1H), 0.23 (m, 2H), 0.12 (m, 1H). MS (ES)=508 (M+1)$^+$.

Step 2: (R)-8-(2-(allyloxy)-5-methylphenyl)-2-chloro-7-(4-chlorobenzyl)-N-(1-cyclopropylethyl)-7H-purin-6-amine (700 mg, 1.38 mmol) was dissolved in a mixture of acetone (4.0 mL) and water (1.0 mL). Sodium periodate (589 mg, 2.76 mmol) was added. The reaction was stirred at room temperature for 10 minutes, and then osmium tetroxide (cat.) was added. The resulting reaction mixture was stirred at room temperature for 12 hours. The volatile organics were removed under reduced pressure and the resulting mixture was diluted with ethyl acetate. The organic layer was separated and washed with water and brine, dried over anhydrous sodium sulfate, filtered and concentrated in vacuo. The intermediate aldehyde was subjected to the next reaction without further purification. To the solution of crude aldehyde in anhydrous methanol (6.0 mL) at 0° C. was added sodium borohydride (104 mg, 2.76 mmol). The reaction mixture was then stirred at room temperature for 4 hours. Then the reaction mixture was quenched with 1% aqueous sodium hydroxide solution and extracted with EtOAc. The organic layer was washed with water and brine, dried over anhydrous sodium sulfate, filtered and concentrated in vacuo. Purification of the crude residue by column chromatography (2% methanol/dichloromethane) afforded (R)-2-(2-(2-chloro-7-(4-chlorobenzyl)-6-((1-cyclopropylethyl)amino)-7H-purin-8-yl)-4-methylphenoxy)ethanol as white solid. $^1$H NMR (300 MHz, CDCl$_3$) δ7.39 (d, J=8.5 Hz, 2H), 7.23 (s, 1H), 7.24 (d, J=8.5 Hz, 1H), 7.10 (d, J=8.5 Hz, 2H), 6.96 (d, J=8.5 Hz, 1H), 5.37 (s, 2H), 4.64 (d, J=7.0 Hz, 1H), 4.30 (br s, 1H), 4.12 (t, J=6.5 Hz, 2H), 3.75 (br s, 2H), 3.52 (q, J=6.5 Hz, 1H), 2.65 (s, 3H), 1.01 (d, J=6.5 Hz, 3H), 0.48 (m, 2H), 0.38 (m, 3H). MS (ES)=512 (M+1)$^+$.

Step 3: In a 5 mL microwave vial (R)-2-(2-(2-chloro-7-(4-chlorobenzyl)-6-((1-cyclopropylethyl)amino)-7H-purin-8-yl)-4-methylphenoxy)ethanol (440 mg, 0.86 mmol), zinc cyanide (50.0 mg, 0.43 mmol) and tetrakis(triphenylphosphine)palladium (0) (198 mg, 0.17 mmol) were mixed with degassed DMA (1.0 mL) and the vial was purged with Ar. Then the mixture was heated at 120° C. for 6 hours. Then the reaction was cooled to room temperature and water was added to the reaction. The resultant mixture was extracted with EtOAc, and the organic layer was washed with water and brine, dried over anhydrous sodium sulfate, filtered and concentrated in vacuo. Purification of the resultant residue by column chromatography (8% methanol/dichloromethane) afforded (R)-7-(4-chlorobenzyl)-6-((1-cyclopropylethyl)amino)-8-(2-(2-hydroxyethoxy)-5-methylphenyl)-7H-purine-2-carbonitrile as white solid. $^1$H NMR (300 MHz, CDCl$_3$) δ7.40 (d, J=8.4 Hz, 2H), 7.31 (d, J=8.4 Hz, 1H), 7.18 (s, 1H), 7.07 (d, J=8.4 Hz, 2H), 6.97 (d, J=8.4 Hz, 1H), 5.41 (s, 2H), 4.68 (d, J=6.9 Hz, 1H), 4.14 (t, J=8.8 Hz, 2H), 3.88 (t, J=6.2 Hz, 1H), 3.78 (m, 2H), 3.55 (q, J=6.6 Hz, 1H), 2.25 (s, 3H), 1.04 (d, J=6.6 Hz, 3H), 0.53 (m, 2H), 0.23 (m, 3H). MS (ES)=503 (M+1)$^+$.

Step 4: A mixture of (R)-7-(4-chlorobenzyl)-6-((1-cyclopropylethyl)amino)-8-(2-(2-hydroxyethoxy)-5-methylphenyl)-7H-purine-2-carbonitrile (120 mg, 0.24 mmol) and sodium hydroxide (480.0 mg, 12.0 mmol) in ethanol (2.5 mL) and water (0.5 mL) were heated at reflux for 30 minutes. Then the reaction mixture was cooled to room temperature and acidified with 1M aqueous HCl until pH 2. The aqueous layer was extracted with EtOAc (100 mL) and the organic layer was washed with water (10 mL) and brine (10 mL), dried over anhydrous sodium sulfate, filtered and concentrated in vacuo. Purification of the resultant residue by column chromatography (5% methanol/dichloromethane) afforded (R)-7-(4-chlorobenzyl)-6-((1-cyclopropylethyl)amino)-8-(2-(2-hydroxyethoxy)-5-methylphenyl)-7H-purine-2-carboxylic acid. $^1$H NMR (300 MHz, CD$_3$OD) δ7.39 (m, 4H), 7.12 (d, J=8.5 Hz, 1H), 7.02 (d, J=8.4 Hz, 2H), 5.61 (d, J=17.6 Hz, 1H), 5.51 (d, J=17.6 Hz, 1H), 4.08 (br s, 2H), 3.89 (m, 1H), 3.76 (br s, 2H), 2.31 (s, 3H), 1.16 (d, J=6.9 Hz, 3H), 0.75 (m, 1H), 0.44 (m, 1H), 0.02 (m, 3H). MS (ES)=522 (M+1)$^+$.

Preparative Example 4.4

(R)-3-(2-(7-(4-chlorobenzyl)-6-((1-cyclopropylethyl)amino)-2-(methoxycarbonyl)-7H-purin-8-yl)-4-methylphenoxy)propanoic acid

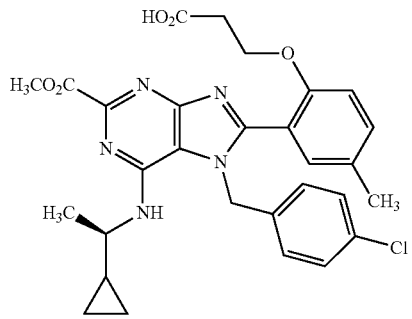 [SMILES: COC(=O)c1nc(N[C@H](C)C2CC2)c2c(n1)nc(-c1cc(C)ccc1OCCC(=O)O)n2Cc1ccc(Cl)cc1]

Step 1: (R)-8-(2-(but-3-en-1-yloxy)-5-methylphenyl)-7-(4-chlorobenzyl)-6-((1-cyclopropylethyl)amino)-7H-purine-2-carbonitrile (360 mg, 0.70 mmol) was suspended in HCl in methanol (5.0 mL, 3.0 M) and heated at 75° C. for 4 hours. The solvent was removed under reduced pressure. Then the crude product was suspended in dichloromethane (40 mL) and washed with aqueous saturated sodium bicarbonate. The organic layer was dried over sodium sulfate, filtered and concentrated in vacuo. The resultant residue was purified by column chromatography (0 to 100% EtOAc/hexanes) to afford (R)-methyl 8-(2-(but-3-en-1-yloxy)-5-methylphenyl)-7-(4-chlorobenzyl)-6-((1-cyclopropylethyl)amino)-7H-purine-2-carboxylate as a white solid. $^1$H NMR (300 MHz, CDCl$_3$) δ7.37 (m, 3H), 7.24 (s, 1H), 7.01 (d, J=8.0 Hz, 2H), 6.99 (d, J=12.0 Hz, 1H), 5.59-5.70 (m, 1H), 4.90-5.03 (m, 2H), 4.50 (d, J=8.0 Hz, 1H), 4.00 (s, 3H), 3.66-3.95 (m, 6H), 2.26-2.32 (m, 5H), 1.03 (d, J=3.0 Hz, 2H), 0.38-0.45 (m, 2H), 0.15-0.24 (m, 3H). MS (ES)=546 (M+1)$^+$.

Step 2: To a stirred solution (R)-methyl 8-(2-(but-3-en-1-yloxy)-5-methylphenyl)-7-(4-chlorobenzyl)-6-((1-cyclopropylethyl)amino)-7H-purine-2-carboxylate (200 mg, 0.36 mmol) in acetone (2.0 mL) and water (0.5 mL) was added sodium periodate (195 mg, 0.81 mmol) and the reaction mixture was stirred at room temperature for 10 minutes. Then ruthenium(III) chloride (cat.) was added and the reaction stirred for 12 hours at room temperature. The reaction mixture was passed through a pad of silica and washed with EtOAc (25 mL). The organic layer was washed with brine (10 mL) and water (10 mL), dried over sodium sulfate, filtered, and concentrated in vacuo to afford (R)-3-(2-(7-(4-chlorobenzyl)-6-((1-cyclopropylethyl)amino)-2-(methoxycarbonyl)-7H-purin-8-yl)-4-methylphenoxy)propanoic acid. $^1$H NMR (300 MHz, CD$_3$OD) δ 7.39-7.30 (m, 4H), 7.09 (d, J=8.4 Hz, 1H), 6.99 (d, J=8.4 Hz, 2H), 5.58 (d, J=16.5 Hz, 1H), 5.48 (d, J=16.5 Hz, 1H), 4.08 (m, 2H), 3.84 (m, 1H), 3.74-3.76 (m, 2H), 3.34 (s, 3H), 2.65 (s, 3H), 1.14 (d, J=4.2 Hz, 3H), 0.73-0.76 (m, 1H), 0.41-0.47 (m, 1H), 0.19-0.27 (m, 3H). MS (ES)=564 (M+1)$^+$.

Example 4.11

(R)-8-(2-(2-carboxyethoxy)-5-methylphenyl)-7-(4-chlorobenzyl)-6-((1-cyclopropylethyl)amino)-7H-purine-2-carboxylic acid

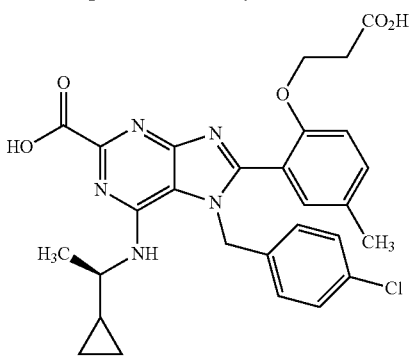

(R)-3-(2-(7-(4-chlorobenzyl)-6-((1-cyclopropylethyl)amino)-2-(methoxycarbonyl)-7H-purin-8-yl)-4-methylphenoxy)propanoic acid (Preparative Example 4.4) (78 mg, 0.14 mmol) was dissolved in a mixture of THF (1.5 mL), methanol (0.5 mL), and water (0.50 mL) and cooled to 0° C. Then lithium hydroxide (7.0 mg, 0.28 mmol) was added to the reaction. The reaction was stirred at 0° C. for 4 hours. Then the reaction was quenched with 1M aqueous HCl until pH 2 and then extracted with EtOAc (100 mL). The organic layer was washed with water (10 mL) and brine (10 mL), dried over anhydrous sodium sulfate, filtered and concentrated in vacuo. Purification of the resultant residue by column chromatography (4% methanol/dichloromethane) afforded (R)-8-(2-(2-carboxyethoxy)-5-methylphenyl)-7-(4-chlorobenzyl)-6-((1-cyclopropylethyl)amino)-7H-purine-2-carboxylic acid. $^1$H NMR (300 MHz, CD$_3$OD) δ7.41 (m, 4H), 7.14 (d, J=8.5 Hz, 1H), 7.01 (d, J=8.2 Hz, 2H), 5.54 (q, J=7.6 Hz, 2H), 4.27 (t, J=5.7 Hz, 2H), 3.88 (q, J=6.5 Hz, 1H), 2.65 (t, J=5.7 Hz, 2H), 2.28 (s, 3H), 1.17 (d, J=6.5 Hz, 3H), 0.76 (m, 1H), 0.47 (m, 1H), 0.24 (m, 3H). MS (ES)=550 (M+1)$^+$.

Example 4.12

(R)-7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylic acid

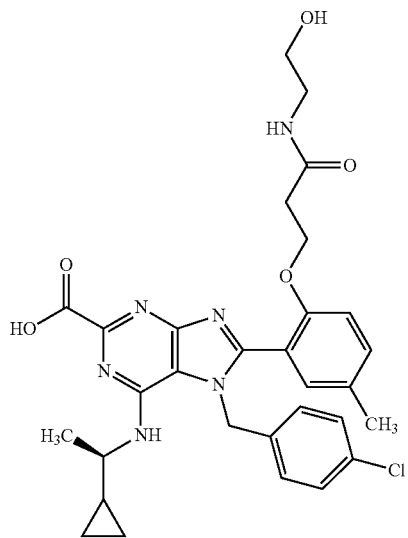 [SMILES: Cc1ccc(OCCC(=O)NCCO)c(-c2nc3nc(C(=O)O)nc(N[C@H](C)C4CC4)c3n2Cc2ccc(Cl)cc2)c1]

Step 1: A mixture of (R)-3-(2-(7-(4-chlorobenzyl)-6-((1-cyclopropylethyl)amino)-2-(methoxycarbonyl)-7H-purin-8-yl)-4-methylphenoxy)propanoic acid (Preparative Example 4.4) (140 mg, 0.248 mmol), DIPEA (64.1 mg, 0.496 mmol), 2-amino ethanol (0.496 mmol, 64 mg) and HATU (189 mg, 0.496 mmol) in DMF (2.0 mL) was stirred at 0° C. for 1 hour. Water (10 mL) was added to the reaction and the mixture was extracted with EtOAc (3×30 mL). The combined organic layers were washed with water (20 mL) and brine (20 mL), dried over anhydrous sodium sulfate, filtered and concentrated in vacuo. The crude residue was purified by silica gel column chromatography (45% EtOAc/hexanes) to afford (R)-methyl 7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylate as a white solid. $^1$H NMR (300 MHz, CDCl$_3$) δ7.35-7.38 (m, 3H), 7.14 (d, J=2.1 Hz, 1H), 7.04 (d, J=8.7 Hz, 2H), 6.94 (d, J=8.7 Hz, 1H), 5.38 (d, J=6.9 Hz, 2H), 7.52 (s, 1H), 5.29 (s, 1H), 4.92 (d, J=6.9 Hz, 2H), 4.24 (t, J=4.5 Hz, 2H), 3.98 (s, 3H), 3.62-3.64 (m, 1H), 3.43-3.44 (m, 2H), 3.08-3.17 (m, 2H), 2.95 (s, 1H), 2.53 (t, J=7.8 Hz, 2H), 2.26 (s, 1H), 1.10 (t, J=6.3 Hz, 3H), 0.60-0.62 (m, 1H), 0.39-0.42 (m, 1H), 0.14-0.24 (m, 3H). MS (ES)=607 (M+1)$^+$.

Step 2: Aqueous lithium hydroxide solution (3.78 mg, 0.15 mmol, 0.5 mL H$_2$O) was added to a solution of (R)-methyl 7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylate (48.0 mg, 0.07 mmol) in THF (2.0 mL) at room temperature. The reaction mixture was stirred at room temperature for 1.5 hours and was then concentrated in vacuo. The residue was dissolved in water (1.5 mL) and neutralized to pH=7 with aqueous HCl solution (1M). The product precipitated and was collected by filtration, washed with water and dried under vacuum, to afford (R)-7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylic acid. $^1$H NMR (400 MHz, CD3OD) δ 7.45 (d, J=8.0 Hz, 1H), 7.34 (d, J=8.4 Hz, 2H), 7.30 (s, 1H), 7.15 (d, J=8.4 Hz, 1H), 6.96 (d, J=8.0 Hz, 2H), 5.56 (d, J=17.2 Hz, 1H), 5.42 (d, J=17.2 Hz, 1H), 4.27-4.32 (m, 2H), 3.86-3.90 (m, 1H), 3.49 (t, J=5.6 Hz, 2H), 3.20 (t, J=5.6 Hz, 2H), 2.56 (t, J=6.8 Hz, 2H), 2.31 (s, 3H), 1.18 (d, J=8.0 Hz, 3H), 0.76-0.78 (m, 1H), 0.41-0.52 (m, 1H), 0.15-0.26 (m, 3H). MS (ES)=593 (M+1)$^+$.

Example 4.13

(R)-7-(4-chlorobenzyl)-6-((1-cyclopropylethyl)amino)-8-(5-methyl-2-(3-(methylamino)-3-oxopropoxy)phenyl)-7H-purine-2-carboxylic acid

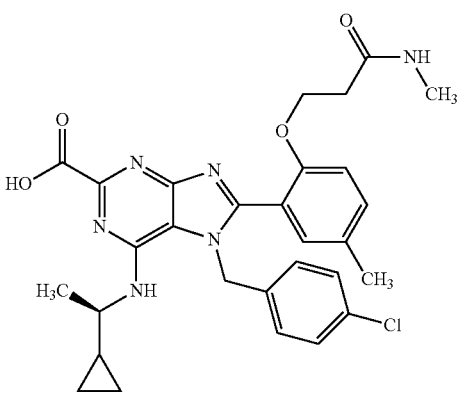 [SMILES: CNC(=O)CCOc1ccc(C)cc1-c1nc2nc(C(=O)O)nc(N[C@H](C)C3CC3)c2n1Cc1ccc(Cl)cc1]

Using a procedure analogous to that described in Example 4.12, (R)-7-(4-chlorobenzyl)-6-((1-cyclopropylethyl)amino)-8-(5-methyl-2-(3-(methylamino)-3-oxopropoxy)phenyl)-7H-purine-2-carboxylic acid was prepared. $^1$H NMR (300 MHz, CD$_3$OD) δ7.36 (m, 4H), 7.13 (d, J=8.5 Hz, 1H), 6.98 (d, J=8.5 Hz, 2H), 5.45 (m, 2H), 4.28 (t, J=5.2 Hz, 2H), 3.91 (q, J=6.4 Hz, 1H), 2.52 (d, J=4.5 Hz, 3H), 2.48 (t, J=5.2 Hz, 2H), 2.31 (s, 3H), 1.16 (d, J=6.4 Hz, 3H), 0.61 (m, 1H), 0.47 (m, 1H), 0.25 (m, 3H). MS (ES)=563 (M+1)$^+$.

Preparative Example 4.5

(R)-methyl 7-(4-chlorobenzyl)-6-((1-cyclopropylethyl)amino)-8-(5-methyl-2-(3-((methylsulfonyl)oxy)propoxy)phenyl)-7H-purine-2-carboxylate

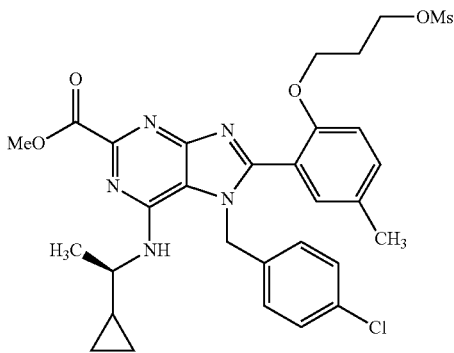 [SMILES: COC(=O)c1nc(N[C@H](C)C2CC2)c2c(n1)nc(-c1cc(C)ccc1OCCCOS(C)(=O)=O)n2Cc1ccc(Cl)cc1]

Step 1: A dry round-bottomed flask was charged with (R)-8-(2-(allyloxy)-5-methylphenyl)-2-chloro-7-(4-chlorobenzyl)-N-(1-cyclopropylethyl)-7H-purin-6-amine (1.36 g, 2.67 mmol) and THF (70 mL). The solution was cooled down to 0° C. and BH$_3$.THF (27 mL, 1M in THF) was added drop-wise. The reaction mixture was stirred at room temperature under a N$_2$ atmosphere for 1 hour. The reaction mixture was then quenched by the addition of hydrogen peroxide (30% aqueous) and extracted with EtOAc (300 mL). The organic layer was washed with brine (50 mL), dried over sodium sulfate, filtered, and concentrated in vacuo. The residue was purified by Combiflash chromatography to afford (R)-3-(2-(2-chloro-7-(4-chlorobenzyl)-6-((1-cyclopropylethyl)amino)-7H-purin-8-yl)-4-methylphenoxy)propan-1-ol. $^1$H NMR (300 MHz, CDCl$_3$) δ7.39 (d, J=8.4 Hz, 2H), 7.23-7.27 (m, 2H), 7.07 (d, J=8.4 Hz, 2H), 6.95 (d, J=8.4 Hz, 1H), 5.30 (s, 2H), 4.60 (d, J=6.9 Hz, 1H), 4.07-4.10 (m, 2H), 3.65 (t, J=5.7 Hz, 2H), 3.56 (q, J=6.9 Hz, 1H), 2.55 (br s, 1H), 2.28 (s, 3H), 1.86 (quintet, J=6.0 Hz, 2H), 1.02 (d, J=6.9 Hz, 3H), 0.36-0.54 (m, 2H), 0.18-0.25 (m, 1H), 0.05-0.16 (m, 2H).

Step 2: A microwave vial equipped with a stir bar was charged with (R)-3-(2-(2-chloro-7-(4-chlorobenzyl)-6-((1-cyclopropylethyl)amino)-7H-purin-8-yl)-4-methylphenoxy)propan-1-ol (330 mg, 0.63 mmol), zinc cyanide (59.0 mg, 0.51 mmol) and argon-degassed DMA (5.0 mL). Tetrakis(triphenylphosphine)palladium (0) (210 mg, 0.19 mmol) was then added to the reaction mixture. The mixture was degassed with Ar for 10 minutes and then the tube was sealed and heated at 120° C. for 12 hours. The reaction was partitioned between EtOAc (60 mL) and water (20 mL). The organic layer was separated and then washed with brine (20 mL), dried over sodium sulfate, filtered, and concentrated under reduced pressure. The residue was purified by Combiflash chromatography (80% EtOAc/hexanes) to afford (R)-7-(4-chlorobenzyl)-6-((1-cyclopropylethyl)amino)-8-(2-(3-hydroxypropoxy)-5-methylphenyl)-7H-purine-2-carbonitrile and (R)-7-(4-cyanobenzyl)-6-((1-cyclopropylethyl)amino)-8-(2-(3-hydroxypropoxy)-5-methylphenyl)-7H-purine-2-carbonitrile.

(R)-7-(4-chlorobenzyl)-6-((1-cyclopropylethyl)amino)-8-(2-(3-hydroxypropoxy)-5-methylphenyl)-7H-purine-2-carbonitrile: $^1$H NMR (300 MHz, CDCl$_3$) δ7.40 (d, J=8.4 Hz, 2H), 7.23-7.30 (m, 2H), 7.07 (d, J=8.4 Hz, 2H), 6.97 (d, J=8.7 Hz, 1H), 5.36 (s, 2H), 4.74 (d, J=6.9 Hz, 1H), 4.06-4.15 (m, 2H), 3.65 (t, J=5.4 Hz, 2H), 3.58 (q, J=7.3 Hz, 1H), 2.29 (s, 3H), 1.79-1.87 (m, 2H), 1.03 (d, J=6.3 Hz, 3H), 0.38-0.57 (m, 2H), 0.19-0.27 (m, 1H), 0.04-0.17 (m, 2H). MS (APCI)=517 (M+1)$^+$.

(R)-7-(4-cyanobenzyl)-6-((1-cyclopropylethyl)amino)-8-(2-(3-hydroxypropoxy)-5-methylphenyl)-7H-purine-2-carbonitrile: $^1$H NMR (400 MHz, CDCl$_3$): δ 7.71 (d, J=8.40 Hz, 2H), 7.31-7.26 (m, 2H), 7.22 (d, J=8.40 Hz, 2H), 6.97 (d, J=8.40 Hz, 1H), 5.45 (s, 2H), 4.55 (d, J=6.80 Hz, 1H), 4.11-4.06 (m, 2H), 3.65 (t, J=5.40 Hz, 2H), 3.61-3.54 (m, 1H), 2.30 (s, 3H), 1.85 (quintet, J=6.00 Hz, 2H), 1.03 (d, J=6.40 Hz, 3H), 0.56-0.39 (m, 2H), 0.25-0.19 (m, 1H), 0.17-0.08 (m, 2H). MS (APCI)=508 (M+1)$^+$.

Step 3: (R)-7-(4-chlorobenzyl)-6-((1-cyclopropylethyl)amino)-8-(2-(3-hydroxypropoxy)-5-methylphenyl)-7H-purine-2-carbonitrile (400 mg, 0.77 mmol) was dissolved in 3N HCl in methanol (16 mL). The reaction was heated to reflux for 3 hours. The reaction was cooled to room temperature and concentrated under reduced pressure. The reaction mixture was then diluted with dichloromethane (20 mL) and washed with saturated aqueous sodium bicarbonate solution (10 mL). The organic extracts were washed with brine (10 mL), dried over sodium sulfate, filtered, and concentrated in vacuo. The residue was purified by Combiflash chromatography (80% EtOAc/hexanes) to afford (R)-methyl 7-(4-chlorobenzyl)-6-((1-cyclopropylethyl)amino)-8-(2-(3-hydroxypropoxy)-5-methylphenyl)-7H-purine-2-carboxylate. $^1$H NMR (400 MHz, CDCl$_3$) δ7.37 (d, J=8.4 Hz, 2H), 7.25-7.28 (m, 2H), 7.05 (d, J=8.4 Hz, 2H), 6.96 (d, J=8.4 Hz, 1H), 5.34 (s, 2H), 4.60 (d, J=6.4 Hz, 1H), 4.07-4.11 (m, 2H), 3.97 (s, 3H), 3.66-3.73 (m, 1H), 3.64 (t, J=6.0 Hz, 2H), 2.29 (s, 3H), 1.85 (quintet, J=6.0 Hz, 2H), 1.05 (d, J=6.4 Hz, 3H), 0.47-0.56 (m, 1H), 0.35-0.42 (m, 1H), 0.09-0.26 (m, 3H). MS (APCI)=550 (M+1)$^+$.

Step 4: To a solution of (R)-methyl 7-(4-chlorobenzyl)-6-((1-cyclopropylethyl)amino)-8-(2-(3-hydroxypropoxy)-5-methylphenyl)-7H-purine-2-carboxylate (120 mg, 0.21 mmol) in dichloromethane (5.0 mL) was added triethylamine (66 mg, 0.65 mmol) and the reaction was cooled to 10° C. Methanesulfonyl chloride (60 mg, 0.52 mmol) was then added and the reaction was stirred as such for 3 hours. Then the reaction was diluted with dichloromethane (80 mL) and washed with saturated aqueous sodium bicarbonate solution (30 mL). The organic extracts were washed with brine (30 mL), dried over sodium sulfate, filtered, and concentrated under reduced pressure to afford (R)-methyl 7-(4-chlorobenzyl)-6-((1-cyclopropylethyl)amino)-8-(5-methyl-2-(3-((methylsulfonyl)oxy)propoxy)phenyl)-7H-purine-2-carboxylate. $^1$H NMR (300 MHz, CDCl$_3$) δ7.27-7.32 (m, 4H), 6.96 (m, 3H), 5.37 (s, 2H), 4.84 (d, J=7.2 Hz, 1H), 4.22 (t, J=6.0 Hz, 2H), 4.12 (t, J=5.4 Hz, 2H), 3.97 (s, 3H), 3.65-3.72 (m, 1H), 2.95 (s, 3H), 2.31 (s, 3H), 2.09 (t, J=6.0 Hz, 2H), 1.09 (d, J=6.3 Hz, 3H), 0.54-0.64 (m, 1H), 0.36-0.43 (m, 1H), 0.13-0.24 (m, 3H). MS (APCI)=628 (M+1)$^+$.

Example 4.14

(R)-7-(4-chlorobenzyl)-6-((1-cyclopropylethyl)amino)-8-(5-methyl-2-(3-morpholinopropoxyl)phenyl)-7H-purine-2-carboxylic acid

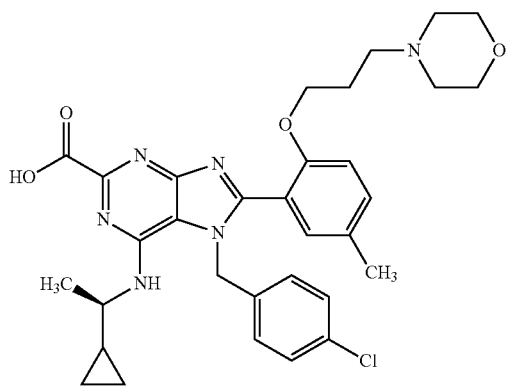 [SMILES: Cc1ccc(OCCCN2CCOCC2)c(-c2nc3nc(C(=O)O)nc(N[C@H](C)C4CC4)c3n2Cc2ccc(Cl)cc2)c1]

Step 1: To a solution of (R)-methyl 7-(4-chlorobenzyl)-6-((1-cyclopropylethyl)amino)-8-(5-methyl-2-(3-((methylsulfonyl)oxy)propoxy)phenyl)-7H-purine-2-carboxylate, Preparative Example 4.5, (150 mg, 0.24 mmol) in THF (5.0 mL) were added morpholine (25 mg, 0.28 mmol) and triethylamine (72 mg, 0.71 mmol). The reaction mixture was stirred at 50° C. for 12 hours. Then the solvent was removed under reduced pressure. The resultant residue was dissolved in dichloromethane (80 mL) and washed with water (30 mL). The organic extract was washed with brine (30 mL), dried over sodium sulfate, filtered, and concentrated in vacuo. The residue was purified by Combiflash chromatography (5% methanol/dichloromethane) to afford (R)-methyl 7-(4-chlorobenzyl)-6-((1-cyclopropylethyl)amino)-8-(5-methyl-2-(3-morpholinopropoxyl)phenyl)-7H-purine-2-carboxylate. $^1$H NMR (400 MHz, CDCl$_3$) δ7.37 (s, 1H), 7.34-7.35 (m, 2H), 7.24-7.27 (m, 1H), 7.06 (d, J=8.4 Hz, 2H), 6.92 (d, J=8.4 Hz, 1H), 5.32 (s, 2H), 4.58 (d, J=6.8 Hz, 1H), 3.97 (s, 3H), 3.90-3.95 (m, 2H), 3.66-3.72 (m, 1H), 3.65 (t, J=4.6 Hz, 4H), 2.31 (s, 3H), 2.28-2.30 (m, 4H), 2.25 (t, J=7.2 Hz, 2H), 1.72 (quintet, J=6.9 Hz, 2H), 1.04 (d, J=6.4 Hz, 3H), 0.45-0.54 (m, 1H), 0.35-0.41 (m, 1H), 0.10-0.25 (m, 3H). MS (APCI)=619 (M+1)$^+$.

Step 2: (R)-methyl 7-(4-chlorobenzyl)-6-((1-cyclopropylethyl)amino)-8-(5-methyl-2-(3-morpholinopropoxyl)phenyl)-7H-purine-2-carboxylate (90.0 mg, 0.14 mmol) was dissolved in THF (4.5 mL), methanol (1.9 mL) and water (2.3 mL). Lithium hydroxide (9.0 mg, 0.37 mmol) was then added into the reaction mixture and the reaction was stirred at room temperature for 45 minutes. The reaction mixture was then quenched with 1N aqueous HCl and extracted with EtOAc (2×50 mL). The combined organic layers were washed with brine (20 mL), dried over sodium sulfate, filtered, and concentrated in vacuo. The residue was purified by Combiflash chromatography (10% methanol/dichloromethane) to afford (R)-7-(4-chlorobenzyl)-6-((1-cyclopropylethyl)amino)-8-(5-methyl-2-(3-morpholinopropoxyl)phenyl)-7H-purine-2-carboxylic acid. $^1$H NMR (400 MHz, CD$_3$OD) δ 7.30-7.40 (m, 4H), 7.11 (d, J=8.4 Hz, 1H), 7.02 (d, J=8.4 Hz, 2H), 5.53 (d, J=17.2 Hz, 1H), 5.41 (d, J=17.2 Hz, 1H), 4.00-4.12 (m, 2H), 3.82-3.99 (m, 2H), 3.58-3.78 (m, 3H), 3.46-3.48 (m, 1H), 2.90-3.16 (m, 5H), 2.32 (s, 3H), 1.95-2.13 (m, 2H), 1.19 (d, J=6.4 Hz, 3H), 0.79-0.96 (m, 2H), 0.40-0.50 (m, 1H), 0.15-0.30 (m, 2H). MS (APCI)=605 (M+1)$^+$.

Example 4.15

(R)-8-(2-(3-(bis(2-methoxyethyl)amino)propoxy)-5-methylphenyl)-7-(4-chlorobenzyl)-6-((1-cyclopropylethyl)amino)-7H-purine-2-carboxylic acid

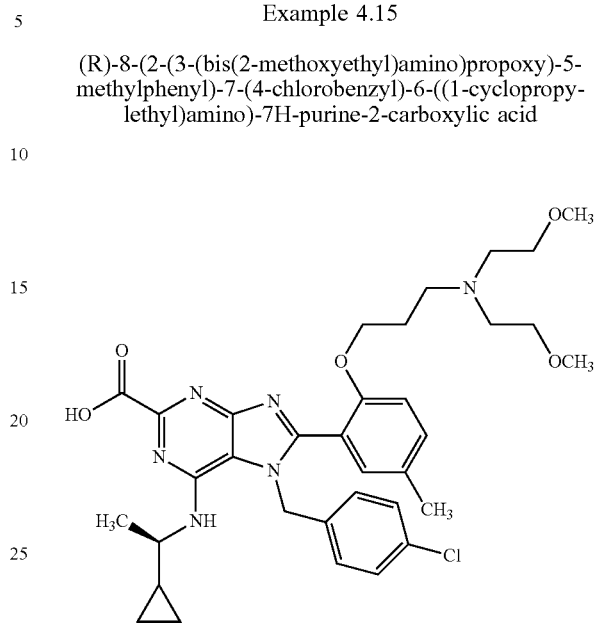

Using a procedure analogous to that described in Example 4.14, and starting with (R)-methyl 7-(4-chlorobenzyl)-6-((1-cyclopropylethyl)amino)-8-(5-methyl-2-(3-((methylsulfonyl)oxy)propoxy)phenyl)-7H-purine-2-carboxylate, Preparative Example 4.5, and bis(2-methoxyethyl)amine, (R)-8-(2-(3-(bis(2-methoxyethyl)amino)propoxy)-5-methylphenyl)-7-(4-chlorobenzyl)-6-((1-cyclopropylethyl)amino)-7H-purine-2-carboxylic acid was prepared. $^1$H NMR (400 MHz, CD$_3$OD) δ7.42 (dd, J=8.8, 1.6 Hz, 1H), 7.34 (m, 3H), 7.12 (d, J=8.8 Hz, 1H), 7.01 (d, J=8.0 Hz, 2H), 5.60 (d, J=17.2 Hz, 1H), 5.48 (d, J=17.2 Hz, 1H), 3.95-4.15 (m, 3H), 3.41 (m, 3H), 3.17 (s, 6H), 2.50-2.90 (m, 6H), 2.33 (s, 3H), 1.78-1.88 (m, 2H), 1.15-1.19 (m, 3H), 0.70-0.95 (m, 2H), 0.38-0.50 (m, 1H), 0.11-0.30 (m, 3H). MS (ES)=651 (M+1)$^+$.

Example 4.16

(R)-7-(4-cyanobenzyl)-6-((1-cyclopropylethyl)amino)-8-(2-(3-hydroxypropoxy)-5-methylphenyl)-7H-purine-2-carboxylic acid

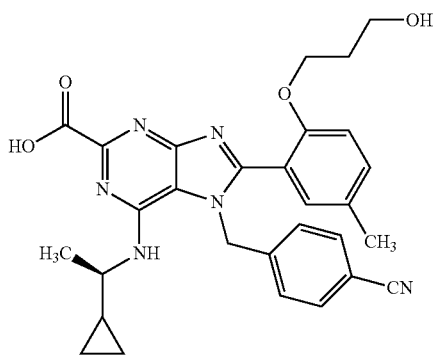 [SMILES: Cc1ccc(OCCCO)c(-c2nc3nc(C(=O)O)nc(N[C@H](C)C4CC4)c3n2Cc2ccc(C#N)cc2)c1]

Using procedures analogous to that described in Preparative Example 4.5 (step 3) and Example 4.14 (step 2), and starting with (R)-7-(4-cyanobenzyl)-6-((1-cyclopropylethyl)amino)-8-(2-(3-hydroxypropoxy)-5-methylphenyl)-7H-purine-2-carbonitrile, (R)-7-(4-cyanobenzyl)-6-((1-cyclopropylethyl)amino)-8-(2-(3-hydroxypropoxy)-5-methylphenyl)-7H-purine-2-carboxylic acid was prepared. $^1$H NMR (400 MHz, CD$_3$OD) δ7.69 (d, J=8.4 Hz, 2H), 7.39 (dd, J=8.4, 1.6 Hz, 1H), 7.30 (d, J=1.6 Hz, 1H), 7.14 (m, 3H), 5.73 (d, J=18.0 Hz, 1H), 5.61 (d, J=18.0 Hz, 1H), 4.06-4.13 (m, 2H), 3.85-3.89 (m, 1H), 3.55 (t, J=6.2 Hz, 2H), 2.31 (s, 3H), 1.79-1.84 (m, 2H), 1.18 (d, J=6.8 Hz, 3H), 0.80-0.91 (m, 1H), 0.76-0.79 (m, 1H), 0.43-0.47 (m, 1H), 0.14-0.24 (m, 2H). MS (ES)=527 (M+1)$^+$.

Example 4.17

(R)-7-(4-chlorobenzyl)-6-(1-cyclopropylethylamino)-8-(5-methyl-2-(3-(4-methylpiperazin-1-yl)propoxy)phenyl)-7H-purine-2-carboxylic acid

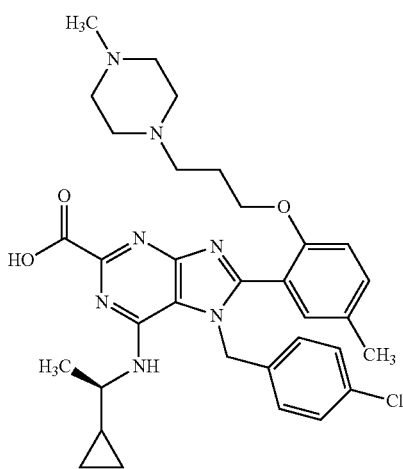 [SMILES: Cc1ccc(OCCCN2CCN(C)CC2)c(-c2nc3nc(C(=O)O)nc(N[C@H](C)C4CC4)c3n2Cc2ccc(Cl)cc2)c1]

Using a procedure analogous to that described in Example 4.14, and starting with (R)-methyl 7-(4-chlorobenzyl)-6-((1-cyclopropylethyl)amino)-8-(5-methyl-2-(3-((methylsulfonyl)oxy)propoxy)phenyl)-7H-purine-2-carboxylate, Preparative Example 4.5, and 1-methylpiperazine, (R)-7-(4-chlorobenzyl)-6-(1-cyclopropylethylamino)-8-(5-methyl-2-(3-(4-methylpiperazin-1-yl)propoxy)phenyl)-7H-purine-2-carboxylic acid was prepared. $^1$H NMR (400 MHz, CD$_3$OD) δ 7.27-7.37 (m, 4H), 7.00-7.06 (m, 3H), 5.38-5.55 (m, 2H), 4.00-4.01 (m, 2H), 3.91-3.96 (m, 1H), 3.22-3.25 (m, 1H), 3.11-3.21 (m, 3H), 2.76 (s, 3H), 2.73-2.74 (m, 1H), 2.63-2.72 (m, 3H), 2.41-2.44 (m, 2H), 2.32 (s, 3H), 1.77-1.80 (m, 2H), 1.13 (d, J=4.0 Hz, 3H), 0.69-0.78 (m, 1H), 0.39-0.44 (m, 1H), 0.18-0.24 (m, 3H). MS (APCI)=618 (M+1)$^+$.

Example 4.18

(R)-7-(4-chlorobenzyl)-6-((1-cyclopropylethyl)amino)-8-(2-hydroxy-5-methylphenyl)-7H-purine-2-carboxylic acid

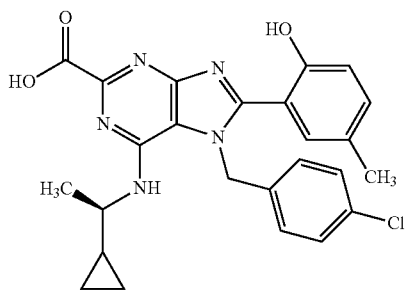 [SMILES: Cc1ccc(O)c(-c2nc3nc(C(=O)O)nc(N[C@H](C)C4CC4)c3n2Cc2ccc(Cl)cc2)c1]

Using a procedure analogous to that described in Example 4.14 (step 2), and starting with (R)-7-(4-chlorobenzyl)-6-((1-cyclobutylethyl)amino)-8-(2-hydroxy-5-methylphenyl)-7H-purine-2-carbonitrile (made using a procedure analogous to Example 4.1 steps 1-8), (R)-7-(4-chlorobenzyl)-6-((1-cyclopropylethyl)amino)-8-(2-hydroxy-5-methylphenyl)-7H-purine-2-carboxylic acid was prepared. $^1$HNMR (300 MHz, CD$_3$OD) δ 7.32-7.34 (d, J=8.0 Hz, 2H), 7.23-7.25 (m, 2H), 7.08-7.10 (d, J=8.0 Hz, 2H), 6.87-6.89 (d, J=6.0 Hz, 1H), 5.48-5.66 (m, 2H), 4.04-4.09 (m, 1H), 2.25 (s, 3H), 1.12-1.14 (d, J=8.0 Hz, 3H), 0.90-0.95 (m, 1H), 0.69-0.71 (m, 1H), 0.42-0.45 (m, 1H), 0.22-0.23 (m, 3H). MS (ES)=478 (M+1)$^+$.

Example 4.19

7-(4-chlorobenzyl)-6-(((R)-1-cyclopropylethyl)amino)-8-(2-(2,3-dihydroxypropoxy)-5-methylphenyl)-7H-purine-2-carboxylic acid

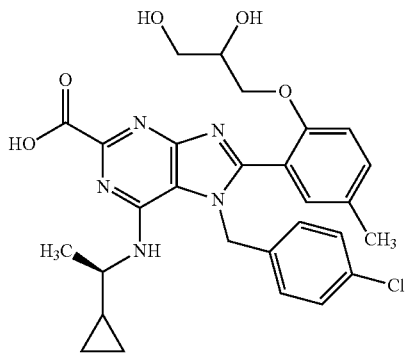 [SMILES: Cc1ccc(OCC(O)CO)c(-c2nc3nc(C(=O)O)nc(N[C@H](C)C4CC4)c3n2Cc2ccc(Cl)cc2)c1]

Step 1: To a solution of (R)-8-(2-(allyloxy)-5-methylphenyl)-2-chloro-7-(4-chlorobenzyl)-N-(1-cyclopropylethyl)-7H-purin-6-amine (508 mg, 1.0 mmol) in acetone (20 mL), were added osmium tetroxide (25.5 mg, 0.1 mmol), 4-methylmorpholine 4-oxide (140 mg, 1.2 mmol) and water (10 mL) at room temperature. The reaction mixture was stirred for 24 hours at room temperature then sodium thiosulphate (158 mg, 1.0 mmol) was added. The solvent was removed from the reaction under reduced pressure and the residue was extracted with EtOAc (3×50 mL). The combined organic layers were washed with water (20 mL) and brine (20 mL), dried over anhydrous sodium sulfate, filtered and concentrated in vacuo. The crude residue was purified by column chromatography (50% EtOAc/hexanes) to afford 3-(2-(2-chloro-7-(4-chlorobenzyl)-6-(((R)-1-cyclopropylethyl)amino)-7H-purin-8-yl)-4-methylphenoxy)propane-1,2-diol. MS (APCI)=542 (M+1)$^+$.

Step 2: Using a procedure analogous to that described in step 8 Example 4.1, and starting with 3-(2-(2-chloro-7-(4-chlorobenzyl)-6-(((R)-1-cyclopropylethyl)amino)-7H-purin-8-yl)-4-methylphenoxy)propane-1,2-diol, 7-(4-chlorobenzyl)-6-(((R)-1-cyclopropylethyl)amino)-8-(2-(2,3-dihydroxypropoxy)-5-methylphenyl)-7H-purine-2-carbonitrile was prepared. MS (APCI)=533 (M+1)$^+$.

Step 3: Using a procedure analogous to that described in Example 4.1 (step 9), and starting with 7-(4-chlorobenzyl)-6-(((R)-1-cyclopropylethyl)amino)-8-(2-(2,3-dihydroxypropoxy)-5-methylphenyl)-7H-purine-2-carbonitrile, 7-(4-chlorobenzyl)-6-(((R)-1-cyclopropylethyl)amino)-8-(2-(2,3-dihydroxypropoxy)-5-methylphenyl)-7H-purine-2-carboxylic acid was prepared. $^1$H NMR (400 MHz, CD$_3$OD) δ 7.41 (d, J=8.0 Hz, 1H), 7.20-7.35 (m, 3H), 7.13 (d, J=8.0 Hz, 1H), 6.90-7.03 (m, 2H), 5.65-5.93 (m, 2H), 3.80-4.13 (m, 4H), 3.40-3.56 (m, 2H), 2.33 (s, 3H), 1.18 (br s, 3H), 0.70-0.83 (m, 1H), 0.35-0.46 (m, 1H), 0.15-0.25 (m, 3H). MS (ES)=552 (M+1)$^+$.

Example 4.20

(R)-7-(4-chlorobenzyl)-6-((1-cyclopropylethyl)amino)-8-(2-(3-hydroxypropoxy)-5-methylphenyl)-7H-purine-2-carboxylic acid

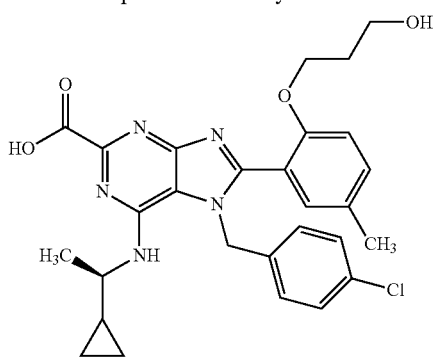

Using a procedure analogous to that described in Example 4.14 (step 2), and starting with (R)-methyl 7-(4-chlorobenzyl)-6-((1-cyclopropylethyl)amino)-8-(2-(3-hydroxypropoxy)-5-methylphenyl)-7H-purine-2-carboxylate, (R)-7-(4-chlorobenzyl)-6-((1-cyclopropylethyl)amino)-8-(2-(3-hydroxypropoxy)-5-methylphenyl)-7H-purine-2-carboxylic acid was prepared. $^1$H NMR (400 MHz, CDCl$_3$) δ7.39 (d, J=8.0 Hz, 2H), 7.27-7.30 (m, 2H), 7.07 (d, J=8.0 Hz, 2H), 6.97 (d, J=8.0 Hz, 1H), 5.40 (s, 2H), 4.83 (br s, 1H), 4.12 (br s, 2H), 3.61-3.80 (m, 3H), 2.30 (s, 3H), 1.85 (m, 2H), 1.06 (d, J=6.4 Hz, 3H), 0.86-0.94 (m, 1H), 0.53 (m, 1H), 0.41 (m, 1H), 0.07-0.23 (m, 3H). MS (ES)=536 (M+1)$^+$.

TABLE 4

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.1 | 32.05 | 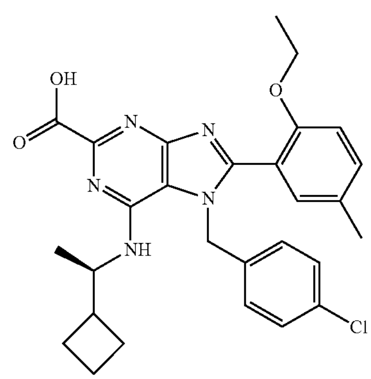 [SMILES: CCOc1ccc(C)cc1-c1nc2nc(C(=O)O)nc(N[C@H](C)C3CCC3)c2n1Cc1ccc(Cl)cc1] | (R)-7-(4-chlorobenzyl)-6-((1-cyclobutylethyl)amino)-8-(2-ethoxy-5-methylphenyl)-7H-purine-2-carboxylic acid | | 520 | 520 |
| 4.2 | 40.38 | 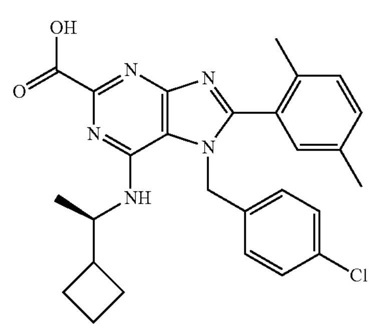 [SMILES: Cc1ccc(C)c(-c2nc3nc(C(=O)O)nc(N[C@H](C)C4CCC4)c3n2Cc2ccc(Cl)cc2)c1] | (R)-7-(4-chlorobenzyl)-6-((1-cyclobutylethyl)amino)-8-(2,5-dimethylphenyl)-7H-purine-2-carboxylic acid | | 490 | 490 |

TABLE 4-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.3 | 104.4 | 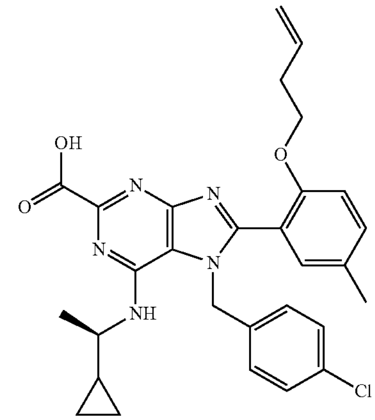 [SMILES: C=CCCOc1ccc(C)cc1-c1nc2nc(C(=O)O)nc(N[C@H](C)C3CC3)c2n1Cc1ccc(Cl)cc1] | (R)-8-(2-(but-3-en-1-yloxy)-5-methylphenyl)-7-(4-chlorobenzyl)-6-((1-cyclopropylethyl)amino)-7H-purine-2-carboxylic acid | | 532 | 532 |
| 4.4 | 48.69 | 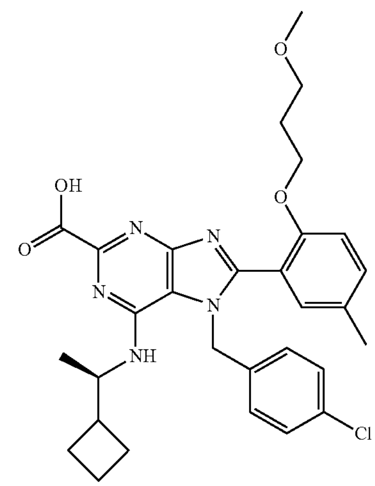 [SMILES: COCCCOc1ccc(C)cc1-c1nc2nc(C(=O)O)nc(N[C@H](C)C3CCC3)c2n1Cc1ccc(Cl)cc1] | (R)-7-(4-chlorobenzyl)-6-((1-cyclobutylethyl)amino)-8-(2-(3-methoxypropoxy)-5-methylphenyl)-7H-purine-2-carboxylic acid | | 564 | 564 |
| 4.5 | 161.7 | 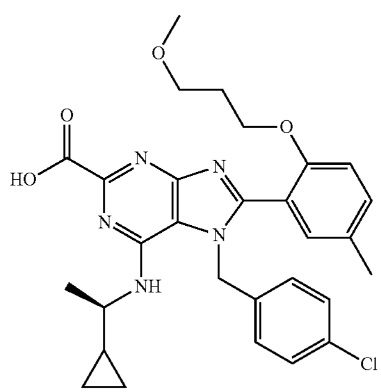 [SMILES: COCCCOc1ccc(C)cc1-c1nc2nc(C(=O)O)nc(N[C@H](C)C3CC3)c2n1Cc1ccc(Cl)cc1] | (R)-7-(4-chlorobenzyl)-6-((1-cyclopropylethyl)amino)-8-(2-(3-methoxypropoxy)-5-methylphenyl)-7H-purine-2-carboxylic acid | | 506 [M − CO$_2$]$^+$ | 506 [M − CO$_2$]$^+$ |

TABLE 4-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.6 | 33.68 | 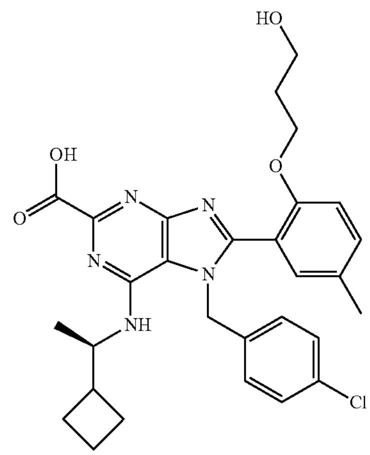 [SMILES: Cc1ccc(OCCCO)c(-c2nc3nc(C(=O)O)nc(N[C@H](C)C4CCC4)c3n2Cc2ccc(Cl)cc2)c1] | (R)-7-(4-chlorobenzyl)-6-((1-cyclobutylethyl)amino)-8-(2-(3-hydroxypropoxy)-5-methylphenyl)-7H-purine-2-carboxylic acid | | 550 | 550 |
| 4.7 | 123.3 | 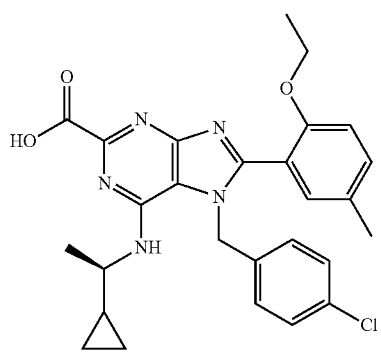 [SMILES: CCOc1ccc(C)cc1-c1nc2nc(C(=O)O)nc(N[C@H](C)C3CC3)c2n1Cc1ccc(Cl)cc1] | (R)-7-(4-chlorobenzyl)-6-((1-cyclopropylethyl)amino)-8-(2-ethoxy-5-methylphenyl)-7H-purine-2-carboxylic acid | | 504 [M − H]$^−$ | 504 [M − H]$^−$ |
| 4.8 | 55 | 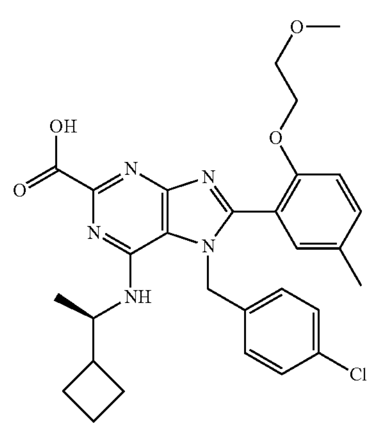 [SMILES: COCCOc1ccc(C)cc1-c1nc2nc(C(=O)O)nc(N[C@H](C)C3CCC3)c2n1Cc1ccc(Cl)cc1] | (R)-7-(4-chlorobenzyl)-6-((1-cydclobutylethyl)amino)-8-(2-(2-methoxyethoxy)-5-methylphenyl)-7H-purine-2-carboxylic acid | | 550 | 550 |

TABLE 4-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.9 | 27.3 | 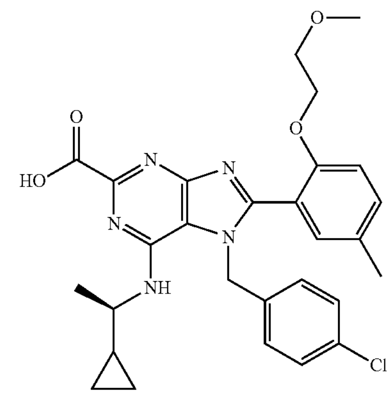 [SMILES: COCCOc1ccc(C)cc1-c1nc2nc(C(=O)O)nc(N[C@H](C)C3CC3)c2n1Cc1ccc(Cl)cc1] | (R)-7-(4-chlorobenzyl)-6-((1-cyclopropylethyl)amino)-8-(2-(2-methoxyethoxy)-5-methylphenyl)-7H-purine-2-carboxylic acid | | 534 [M − H]$^-$ | 534 [M − H]$^-$ |
| 4.10 | 238.2 | 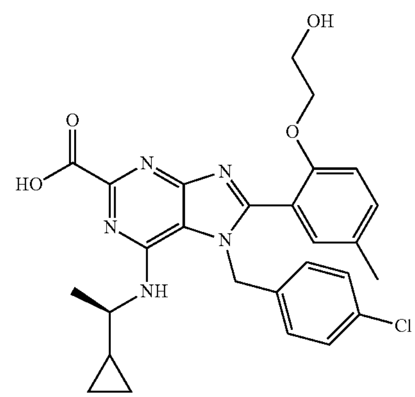 [SMILES: Cc1ccc(OCCO)c(-c2nc3nc(C(=O)O)nc(N[C@H](C)C4CC4)c3n2Cc2ccc(Cl)cc2)c1] | (R)-7-(4-chlorobenzyl)-6-((1-cyclopropylethyl)amino)-8-(2-(2-hydroxyethoxy)-5-methylphenyl)-7H-purine-2-carboxylic acid | | 522 | 522 |
| 4.11 | 312.2 | 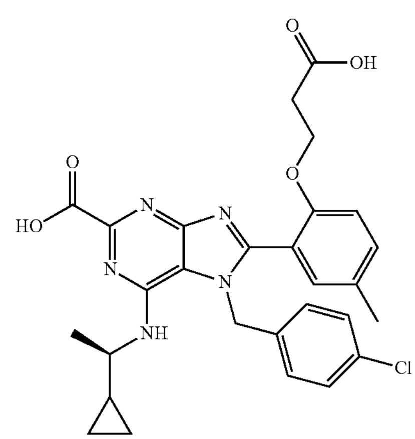 [SMILES: Cc1ccc(OCCC(=O)O)c(-c2nc3nc(C(=O)O)nc(N[C@H](C)C4CC4)c3n2Cc2ccc(Cl)cc2)c1] | (R)-8-(2-(2-carboxyethoxy)-5-methylphenyl)-7-(4-chlorobenzyl)-6-((1-cyclopropylethyl)amino)-7H-purine-2-carboxylic acid | | 550 | 550 |

TABLE 4-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.12 | 347.8 | 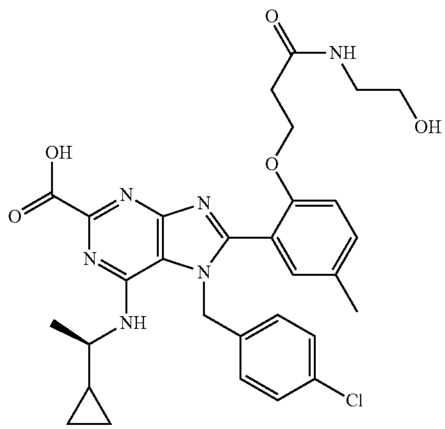 [SMILES: Cc1ccc(OCCC(=O)NCCO)c(-c2nc3nc(C(=O)O)nc(N[C@H](C)C4CC4)c3n2Cc2ccc(Cl)cc2)c1] | (R)-7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylic acid | | 593 | 593 |
| 4.13 | 486.9 | 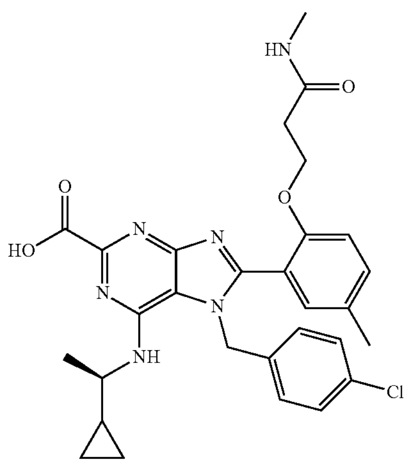 [SMILES: CNC(=O)CCOc1ccc(C)cc1-c1nc2nc(C(=O)O)nc(N[C@H](C)C3CC3)c2n1Cc1ccc(Cl)cc1] | (R)-7-(4-chlorobenzyl)-6-((1-cyclopropylethyl)amino)-8-(5-methyl-2-(3-(methylamino)-3-oxopropoxy)phenyl)-7H-purine-2-carboxylic acid | | 563 | 563 |
| 4.14 | 212.5 | 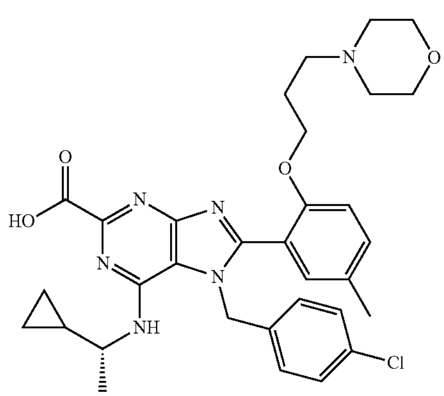 [SMILES: Cc1ccc(OCCCN2CCOCC2)c(-c2nc3nc(C(=O)O)nc(N[C@H](C)C4CC4)c3n2Cc2ccc(Cl)cc2)c1] | (R)-7-(4-chlorobenzyl)-6-((1-cyclopropylethyl)amino)-8-(5-methyl-2-(3-morpholinopropoxy)phenyl)-7H-purine-2-carboxylic acid | | 605 | 605 |

TABLE 4-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.15 | 667.1 | 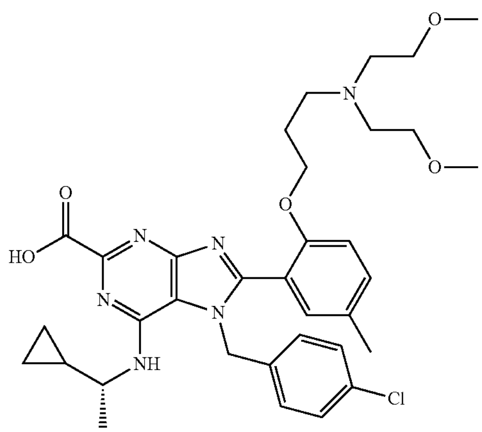 [SMILES: COCCN(CCCOc1ccc(C)cc1-c1nc2nc(C(=O)O)nc(N[C@H](C)C3CC3)c2n1Cc1ccc(Cl)cc1)CCOC] | (R)-8-(2-(3-(bis(2-methoxyethyl)amino)propoxy)-5-methyl-phenyl)-7-(4-chlorobenzyl)-6-((1-cyclopropylethyl)amino)-7H-purine-2-carboxylic acid | | 651 | 651 |
| 4.16 | 480.6 | 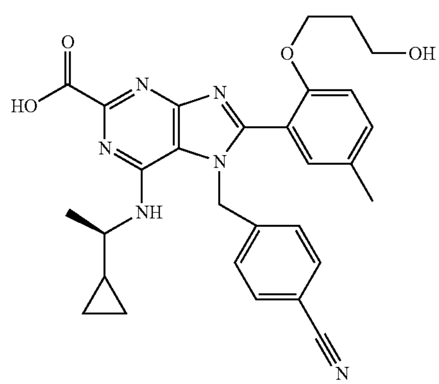 [SMILES: Cc1ccc(OCCCO)c(-c2nc3nc(C(=O)O)nc(N[C@H](C)C4CC4)c3n2Cc2ccc(C#N)cc2)c1] | (R)-7-(4-cyanobenzyl)-6-((1-cyclopropylethyl)amino)-8-(2-(3-hydroxy-propoxy)-5-methylphenyl)-7H-purine-2-carboxylic acid | | 527 | 527 |
| 4.17 | 506.7 | 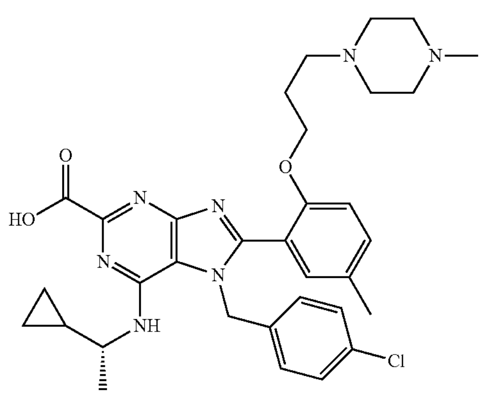 [SMILES: Cc1ccc(OCCCN2CCN(C)CC2)c(-c2nc3nc(C(=O)O)nc(N[C@H](C)C4CC4)c3n2Cc2ccc(Cl)cc2)c1] | (R)-7-(4-chlorobenzyl)-6-(1-cyclopropylethyl-amino)-8-(5-methyl-2-(3-(4-methylpiperazin-1-yl)propoxy)phenyl)-7H-purine-2-carboxylic acid | | 618 | 618 |
| 4.18 | 346.9 | 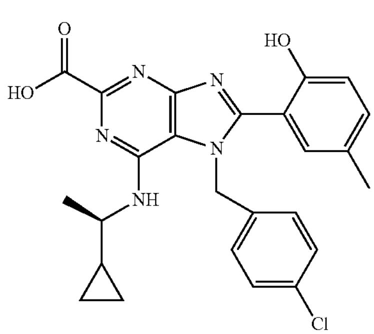 [SMILES: Cc1ccc(O)c(-c2nc3nc(C(=O)O)nc(N[C@H](C)C4CC4)c3n2Cc2ccc(Cl)cc2)c1] | (R)-7-(4-chlorobenzyl)-6-((1-cyclopropylethyl)amino)-8-(2-hydroxy-5-methylphenyl)-7H-purine-2-carboxylic acid | | 478 | 478 |

TABLE 4-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 4.19 | 585.8 | 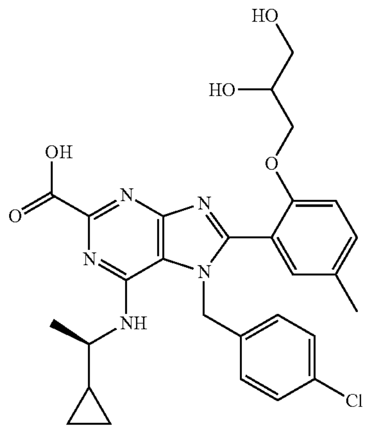 [SMILES: Cc1ccc(OCC(O)CO)c(-c2nc3nc(C(=O)O)nc(N[C@H](C)C4CC4)c3n2Cc2ccc(Cl)cc2)c1] | 7-(4-chlorobenzyl)-6-(((R)-1-cyclopropylethyl)amino)-8-(2-(2,3-dihydroxypropoxy)-5-methylphenyl)-7H-purine-2-carboxylic acid | | 552 | 552 |
| 4.20 | 111.8 | 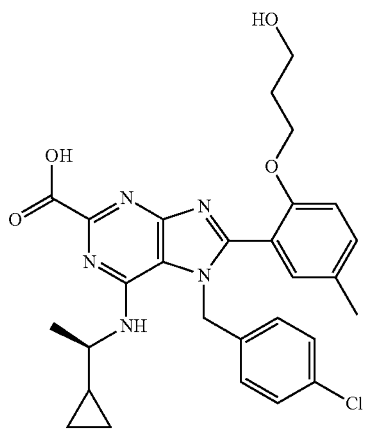 [SMILES: Cc1ccc(OCCCO)c(-c2nc3nc(C(=O)O)nc(N[C@H](C)C4CC4)c3n2Cc2ccc(Cl)cc2)c1] | (R)-7-(4-chlorobenzyl)-6-((1-cyclopropylethyl)amino)-8-(2-(3-hydroxypropoxy)-5-methylphenyl)-7H-purine-2-carboxylic acid | | 536 | 536 |

Preparative Example 5.1

2,6-dichloro-9-trityl-8,9-dihydro-7H-purine

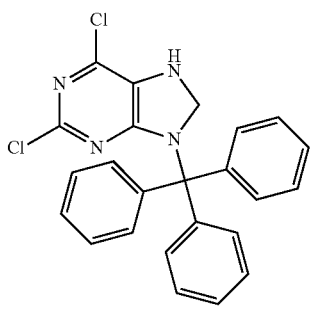 [SMILES: Clc1nc(Cl)c2c(n1)N(C(c1ccccc1)(c1ccccc1)c1ccccc1)CN2]

To a stirred solution of 2,6-dichloro-9-trityl-9H-purine (10.0 g, 23.1 mmol) in THF (115 mL) was added DIBAL (1M in THF, 27 mL, 27.8 mmol) and the resultant mixture was stirred at room temperature for 12 hours. The reaction mixture was quenched by slow addition of a saturated aqueous solution of sodium sulfate decahydrate at 0° C., filtered through celite, washed with hot EtOAc and concentrated in vacuo. Purification of the residue on a Redisep 120 g silica gel column (0 to 100% EtOAc/hexanes) afforded 2,6-dichloro-9-trityl-8,9-dihydro-7H-purine. $^1$H NMR (300 MHz, CDCl$_3$) δ 7.27-7.34 (m, 15H), 5.14 (s, 2H), 3.84 (br s, 1H). MS (APCI)=433 (M+1)$^+$.

Preparative Example 5.2

2,6-dichloro-7-(1-(4-chlorophenyl)ethyl)-9-trityl-9H-purine

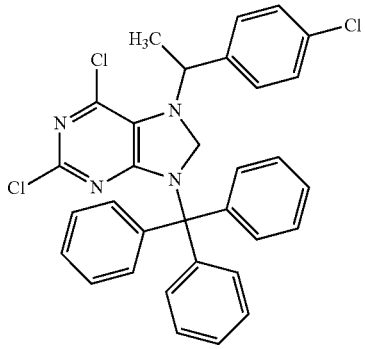 [SMILES: CC(c1ccc(Cl)cc1)N1CN(C(c2ccccc2)(c2ccccc2)c2ccccc2)c2nc(Cl)nc(Cl)c21]

To a stirred solution of 2,6-dichloro-9-trityl-8,9-dihydro-7H-purine (200 mg, 0.46 mmol) in DMF (2.0 mL) was added cesium carbonate (165 mg, 0.50 mmol) and 1-(1-bromoethyl)-4-chlorobenzene (11 mg, 0.50 mmol) and the reaction mixture was stirred for 1 hour under $N_2$ at room temperature. The reaction mixture was poured onto water and the pH was adjusted to 5 using acetic acid. The aqueous layer was extracted with $CH_2Cl_2$ (2×50 mL). The combined organic layers were washed with water and brine, dried over $Na_2SO_4$ and concentrated under reduced pressure. Purification of the residue on a Redisep 4 g silica gel column (0 to 50% EtOAc/hexanes) afforded 2,6-dichloro-7-(1-(4-chlorophenyl)ethyl)-9-trityl-9H-purine. $^1$H NMR (300 MHz, $CDCl_3$) δ 7.28-7.35 (m, 3H), 7.20-7.25 (m, 8H), 7.05-7.13 (m, 8H), 5.40 (q, J=7.2 Hz, 1H) 4.89 (d, J=5.8 Hz, 1H), 4.69 (d, J=5.8 Hz, 1H), 1.47 (d, J=7.2 Hz, 3H). MS (APCI)=571 (M+1)$^+$.

Preparative Example 5.3

2,6-dichloro-7-(1-(4-chlorophenyl)ethyl)-7H-purine

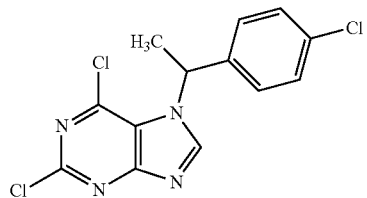 [SMILES: CC(c1ccc(Cl)cc1)n1cnc2nc(Cl)nc(Cl)c21]

TFA (0.3 mL, 4.56 mmol) was added slowly at 0° C. to a suspension of 2,6-dichloro-7-(1-(4-chlorophenyl)ethyl)-9-trityl-9H-purine (200 mg, 0.35 mmol) in dry $CH_2Cl_2$ (2.0 mL). The resultant mixture was stirred at room temperature for 12 hours. The reaction mixture was quenched by the addition of saturated aqueous $NaHCO_3$ solution and extracted with $CH_2Cl_2$ (2×30 mL). The combined organic layers were washed with water, brine, dried over $Na_2SO_4$ and concentrated under reduced pressure. Purification of the residue on a Redisep 4 g silica gel column (0 to 100% EtOAc/hexanes) afforded 2,6-dichloro-7-(1-(4-chlorophenyl)ethyl)-7H-purine. $^1$H NMR (300 MHz, $CDCl_3$) δ 8.32 (s, 1H), 7.36 (d, J=6.6 Hz, 2H), 7.13 (d, J=6.6 Hz, 2H), 6.22 (q, J=6.9 Hz, 1H), 2.02 (d, J=6.9 Hz, 3H). MS (APCI)=327 (M+1)$^+$.

Preparative Example 5.4

2-chloro-7-(1-(4-chlorophenyl)ethyl)-N—((R)-1-cyclopropylethyl)7H-purin-6-amine

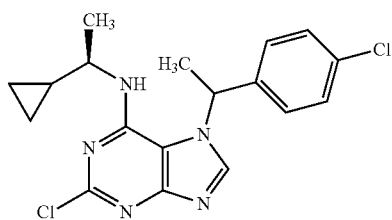 [SMILES: CC(c1ccc(Cl)cc1)n1cnc2nc(Cl)nc(N[C@H](C)C3CC3)c21]

DIPEA (0.56 mL, 3.22 mmol) and (R)-1-cyclopropylethylamine (18 mg, 2.14 mmol) were added to a solution of 2,6-dichloro-7-(1-(4-chlorophenyl)ethyl)-7H-purine (350 mg, 1.07 mmol) in ethanol (5.0 mL). The reaction mixture was heated at reflux for 2 hours. The reaction was then cooled to room temperature and concentrated in vacuo. Purification of the residue on a Redisep 4 g silica gel column (0 to 100% EtOAc/hexanes) to afford 2-chloro-7-(1-(4-chlorophenyl)ethyl)-N—((R)-1-cyclopropylethyl)7H-purin-6-amine as a mixture of diastereomers. $^1$H NMR (300 MHz, $CDCl_3$) δ 8.14 (d, J=4.8 Hz, 1H), 7.43 (dd, J=8.7, 2.7 Hz, 2H), 7.10 (q, J=5.8 Hz, 2H), 5.65-5.77 (m, 1H), 4.49 (m, 1H), 3.52 (m, 1H), 2.00 (d, J=2.7 Hz, 1.5H), 1.98 (d, J=2.7 Hz, 1.5H), 1.05 (d, J=6.3 Hz, 1.5H), 0.93 (d, J=6.3 Hz, 1.5H), 0.10-0.52 (m, 5H). MS (APCI)=376 (M+1)$^+$.

Preparative Example 5.5

7-(1-(4-chlorophenyl)ethyl)-6-((R)-1-cyclopropylethyl)amino)-7H-purine-2-carbonitrile

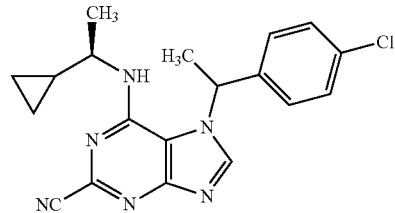 [SMILES: CC(c1ccc(Cl)cc1)n1cnc2nc(C#N)nc(N[C@H](C)C3CC3)c21]

2-Chloro-7-(1-(4-chlorophenyl)ethyl)-N—((R)-1-cyclopropylethyl)7H-purin-6-amine (100 mg, 0.26 mmol), zinc cyanide (18 mg, 0.15 mmol) and Pd(PPh$_3$)$_4$ (61 mg, 0.05 mmol) were placed in a microwave vial. Degassed DMA (1.5 mL) was added to the reaction and the reaction was evacuated with Ar and heated at 120° C. for 12 hours. The reaction was then cooled to room temperature and cold water was added slowly. The aqueous layer was extracted with EtOAc (2×20 mL), then the combined organic layers were dried over $Na_2SO_4$, filtered and concentrated under reduced pressure. Purification of the residue on a Redisep 4 g silica gel column (0 to 100% EtOAc/hexanes) afforded 7-(1-(4-chlorophenyl)ethyl)-6-((R)-1-cyclopropylethyl)amino-7H-purine-2-carbonitrile. MS (APCI)=367 (M+1)$^+$.

Preparative Example 5.6

8-bromo-7-(1-(4-chlorophenyl)ethyl)-6-(((R)-1-cyclopropylethyl)amino)-7H-purine-2-carbonitrile

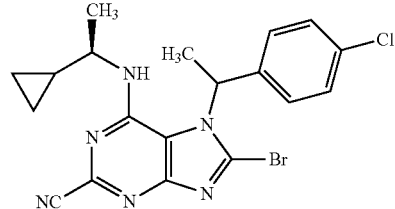 [SMILES: CC(c1ccc(Cl)cc1)n1c(Br)nc2nc(C#N)nc(N[C@H](C)C3CC3)c21]

NBS (17 mg, 1.0 mmol) was added to a solution of 7-(1-(4-chlorophenyl)ethyl)-6-((R)-1-cyclopropylethyl) amino-7H-purine-2-carbonitrile (75 mg, 0.20 mmol) in chloroform (2.0 mL) and the reaction mixture was heated at reflux for 3 hours. The reaction mixture was then cooled to room temperature, diluted with CH$_2$Cl$_2$ (2×30 mL) and quenched with saturated aqueous sodium thiosulphate solution (2×30 mL) and then 0.05% NaOH (2×30 mL) was added to the mixture. The aqueous layer was separated and washed with CH$_2$Cl$_2$ and then the combined organic layers were washed with brine, dried over Na$_2$SO$_4$, filtered and concentrated under reduced pressure. Purification of the residue on a Redisep 4 g silica gel column (0 to 100% EtOAc/hexanes) afforded 8-bromo-7-(1-(4-chlorophenyl)ethyl)-6-(((R)-1-cyclopropylethyl)amino)-7H-purine-2-carbonitrile as a mixture of diastereomers. $^1$H NMR (400 MHz, CDCl$_3$) δ 7.47-7.55 (m, 2H), 7.21-7.23 (m, 2H), 6.16 (m, 1H), 4.34 (m, 1H), 3.51 (m, 1H), 1.92 (t, J=6.8 Hz, 3H), 1.14 (d, J=6.8 Hz, 1.5H), 1.98 (d, J=6.8 Hz, 1.5H), 0.05-0.59 (m, 4H), 0.13 (m, 1H). MS (APCI)=447 (M+1)$^+$.

Preparative Example 5.7

7-(1-(4-chlorophenyl)ethyl)-6-(((R)-1-cyclopropylethyl)amino)-8-(m-tolyl)-7H-purine-2-carbonitrile

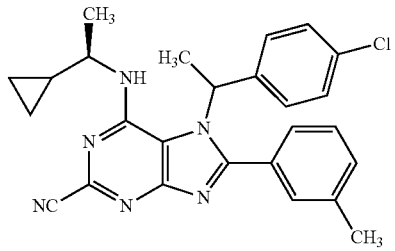 [SMILES: Cc1cccc(-c2nc3nc(C#N)nc(N[C@H](C)C4CC4)c3n2C(C)c2ccc(Cl)cc2)c1]

A microwave vial was charged with 8-bromo-7-(1-(4-chlorophenyl)ethyl)-6-(((R)-1-cyclopropylethyl)amino)-7H-purine-2-carbonitrile (150 mg, 0.33 mmol), m-tolylboronic acid (91 mg, 0.67 mmol), Na$_2$CO$_3$ (178 mg, 1.68 mmol), Pd(PPh$_3$)$_4$ (116 mg, 0.10 mmol), 1,4-dioxane (6.5 mL) and water (0.1 mL). The mixture was degassed with N$_2$ for 25 minutes. Palladium acetate (2.0 mg, 0.01 mmol) was added and the vial was then sealed and heated at 100° C. for 18 hours. The reaction was then cooled to room temperature and diluted with EtOAc (3.0 mL). The organic layer was washed with brine (5.0 mL), dried over Na$_2$SO$_4$, filtered, and concentrated under reduced pressure. Purification of the residue on a Redisep 4 g silica gel column (0 to 100% EtOAc/hexanes) afforded 7-(1-(4-chlorophenyl)ethyl)-6-(((R)-1-cyclopropylethyl)amino)-8-(m-tolyl)-7H-purine-2-carbonitrile. MS (APCI)=457 (M+1)$^+$.

Preparative Example 5.8 methyl 7-(1-(4-chlorophenyl)ethyl)-6-(((R)-1-cyclopropylethyl)amino)-8-(m-tolyl)-7H-purine-2-carboxylate

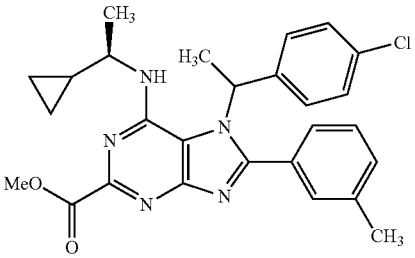 [SMILES: COC(=O)c1nc(N[C@H](C)C2CC2)c2c(n1)nc(-c1cccc(C)c1)n2C(C)c1ccc(Cl)cc1]

HCl (2 mL, 3N in methanol) was added to 7-(1-(4-chlorophenyl)ethyl)-6-(((R)-1-cyclopropylethyl)amino)-8-(m-tolyl)-7H-purine-2-carbonitrile (65 mg, 0.14 mmol) and the reaction mixture was heated at reflux for 3 hours. The reaction mixture was then cooled to room temperature and concentrated in vacuo. The residue was dissolved in aqueous saturated NaHCO$_3$ solution and extracted with EtOAc (3×30 mL). The combined organic layers were washed with brine, dried over Na$_2$SO$_4$ and concentrated under reduced pressure. Purification of the residue on a Redisep 4 g silica gel column (0 to 100% EtOAc/hexanes) afforded methyl 7-(1-(4-chlorophenyl)ethyl)-6-(((R)-1-cyclopropylethyl)amino)-8-(m-tolyl)-7H-purine-2-carboxylate as a mixture of diastereomers. $^1$H NMR (300 MHz, CDCl$_3$) δ 7.32-7.56 (m, 8H), 5.94 (m, 1H), 4.26 (d, J=6.3 Hz, 1H), 3.97 (s, 3H), 3.69 (m, 1H), 1.80 (q, J=5.4 Hz, 3H), 1.21-1.37 (m, 2H), 1.16 (d, J=6.3 Hz, 2H), 0.78-0.88 (m, 3H), 0.26-0.55 (m, 2H), 0.11 (m, 1H). MS (APCI)=490 (M+1)$^+$.

Example 5.1

7-(1-(4-chlorophenyl)ethyl)-6-(((R)-1-cyclopropylethyl)amino)-8-(3-methylphenyl)-7H-purine-2-carboxylic acid

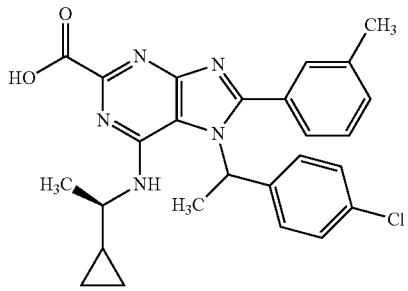 [SMILES: Cc1cccc(-c2nc3nc(C(=O)O)nc(N[C@H](C)C4CC4)c3n2C(C)c2ccc(Cl)cc2)c1]

Aqueous LiOH solution (0.8 mL, 0.80 mmol, 1M) was added to a solution of methyl-7-(1-(4-chlorophenyl)ethyl)-6-((R)-1-cyclopropylethyl)-8-(3-methylphenyl)-7H-purin-2-carboxylate (9.0 mg, 18 μmol) in THF (1.0 mL) at room temperature. The reaction mixture was stirred at room temperature for 1.5 hours and was then concentrated in vacuo. The residue was dissolved in water (1.5 mL) and neutralized to pH=7 with aqueous HCl solution (1M). The precipitated product was collected by filtration, washed with water and dried under vacuum, to afford 7-(1-(4-chlorophenyl)ethyl)-6-(((R)-1-cyclopropylethyl)amino)-8-(3-methylphenyl)-7H-purine-2-carboxylic acid. $^1$H NMR (400 MHz, CD$_3$OD) δ 7.56-7.59 (m, 3H), 7.45-7.50 (m, 5H), 5.97 (m, 1H), 2.42 (s, 3H), 1.87 (t, J=7.2 Hz, 3H), 1.18 (d, J=6.4 Hz, 2H), 0.79 (d, J=6.4 Hz, 2H), 0.60 (m, 1H), 0.32-0.36 (m, 2H), 0.20 (m, 1H), 0.12 (m, 1H). MS (APCI)=476 (M+1)$^+$.

Example 5.2

7-(1-(4-chlorophenyl)ethyl)-6-((cyclopropylmethyl)amino)-8-(m-tolyl)-7H-purine-2-carboxylic acid

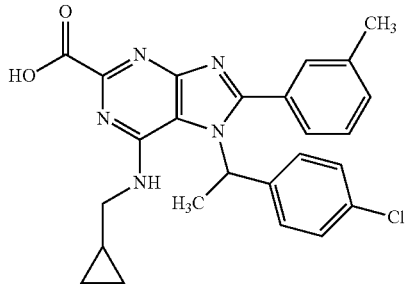 [SMILES: Cc1cccc(-c2nc3nc(C(=O)O)nc(NCC4CC4)c3n2C(C)c2ccc(Cl)cc2)c1]

Using a procedure analogous to that described in Example 5.1, and starting with 2,6-dichloro-7-(1-(4-chlorophenyl)ethyl)-7H-purine and cyclopropylmethanamine, 7-(1-(4-chlorophenyl)ethyl)-6-((cyclopropylmethyl)amino)-8-(m-tolyl)-7H-purine-2-carboxylic acid was prepared. ¹H NMR (400 MHz, DMSO-d₆) δ 7.57 (d, J=2.0 Hz, 2H), 7.41-7.49 (m, 6H), 5.89 (m, 1H), 4.55 (s, 1H), 3.06 (m, 1H), 2.37 (s, 3H), 1.82 (d, J=6.8 Hz, 3H), 0.84 (m, 1H), 0.68 (m, 1H), 0.28-0.32 (m, 2H), −0.09 (m, 1H). MS (ES)=462 (M+1)⁺.

Example 5.3

7-(1-(4-chlorophenyl)ethyl)-6-((S)-1-cyclopropylethylamino)-8-(3-methylphenyl)-7H-purine-2-carboxylic acid

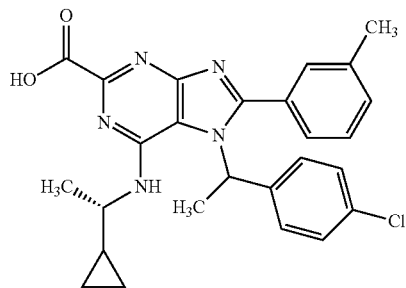 [SMILES: Cc1cccc(-c2nc3nc(C(=O)O)nc(N[C@@H](C)C4CC4)c3n2C(C)c2ccc(Cl)cc2)c1]

Using a procedure analogous to that described in Example 5.1, and starting with 2,6-dichloro-7-(1-(4-chlorophenyl)ethyl)-7H-purine and (S)-1-cyclopropylethanamine, 7-(1-(4-chlorophenyl)ethyl)-6-((S)-1-cyclopropylethylamino)-8-(3-methylphenyl)-7H-purine-2-carboxylic acid was prepared. ¹H NMR (300 MHz, CD₃OD) δ 7.45-7.60 (m, 8H), 5.99 (t, J=5.1 Hz, 1H), 2.42 (s, 3H), 1.85-1.90 (m, 3H), 1.29 (br s, 1H), 1.20 (d, J=6.3 Hz, 2H), 0.79-0.91 (m, 3H), 0.11-0.63 (m, 3H). MS (APCI)=476 (M+1)⁺.

Preparative Example 5.9

8-bromo-3-methyl-1H-purine-2,6(3H,9H)-dione

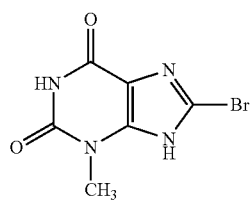

To a suspension of 3-methyl-1H-purine-2,6(3H,9H)-dione (10.0 g, 60.2 mmol) and NaHCO₃ (10.12 g, 120 mmol) in acetic acid (150 mL) at room temperature was added bromine (11.5 g, 72.2 mmol). The resulting mixture was stirred at 65° C. for 2 hours. The reaction mixture was cooled to room temperature and the resulting precipitate was collected by vacuum filtration and washed with acetic acid (2×50 mL) and water (4×100 mL) to afford 8-bromo-3-methyl-1H-purine-2,6(3H,9H)-dione. ¹H NMR (300 MHz, DMSO-d₆) δ 14.29 (bs, 1H), 11.18 (s, 1H), 3.32 (s, 3H).

Example 5.4

6-{[(1R)-1-cyclopropylethyl]amino}-7-[4-fluoro-3-(trifluoromethyl)benzyl]-8-(3-methylphenyl)-7H-purine-2-carboxylic acid

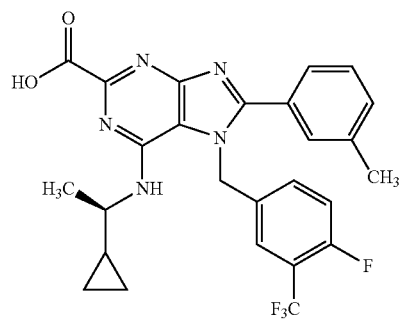 [SMILES: Cc1cccc(-c2nc3nc(C(=O)O)nc(N[C@H](C)C4CC4)c3n2Cc2ccc(F)c(C(F)(F)F)c2)c1]

Step 1: A suspension of 8-bromo-3-methyl-1H-purine-2,6(3H,9H)-dione (2.00 g, 8.16 mmol) and K₂CO₃ (1.12, 8.16 mmol) in DMF (80 mL) was stirred at room temperature for 1 hour before adding 4-(bromomethyl)-1-fluoro-2-(trifluoromethyl)benzene (1.90 g, 77.5 mmol) dropwise. The resulting mixture was stirred at room temperature under a nitrogen atmosphere for 16 hours and the reaction mixture was poured into cooled water (160 mL), stirred for 5 minutes and the precipitate product was collected by vacuum filtration, washed with water (2×50 mL) and diethyl ether (100 mL) to afford 8-bromo-7-(4-fluoro-3-(trifluoromethyl)benzyl)-3-methyl-1H-purine-2,6(3H,7H)-dione as a white solid: ¹H NMR (300 MHz, CDCl₃) δ 8.56 (s, 1H), 7.72 (dd, J=6.6, 2.1 Hz, 1H), 7.66 (m, 1H), 7.19 (t, J=9.0 Hz, 1H), 5.51 (s, 2H), 3.52 (s, 3H). MS (ES)=421 (M+1)⁺.

Step 2: A mixture of 8-bromo-7-(4-fluoro-3-(trifluoromethyl)benzyl)-3-methyl-1H-purine-2,6(3H,7H)-dione (500 mg, 1.18 mmol), m-tolylboronic acid (240 mg, 1.78 mmol), aq. Na₂CO₃ (1.55 mL, 2M) and 1,4-dioxane (10 mL) were placed in a microwave vial and degassed with nitrogen for 5 minutes. Pd(PPh₃)₄ (343 mg, 0.29 mmol) was added and the microwave tube sealed and subjected to microwave irradiation, at 120° C., for 15 min. The mixture was filtered through diatomaceous earth and the solid was washed with EtOAc (50 mL) and CH₂Cl₂/methanol (1:1, 2×50 mL). The filtrate was concentrated under reduced pressure and the crude product purified using a Redsep 80 g silica gel column (0 to 100% EtOAc/hexanes) to afford 7-(4-fluoro-3-(trifluoromethyl)benzyl)-3-methyl-8-(3-methylphenyl)-1H-purine-2,6(3H,7H)-dione as a white solid. ¹H NMR (300 MHz, CDCl₃) δ 8.71 (s, 1H), 7.30-7.41 (m, 5H), 7.07-7.17 (m, 2H), 5.58 (s, 2H), 3.60 (s, 3H), 2.41 (s, 3H). MS (ES)=433 (M+1)⁺.

Step 3: A suspension of 7-(4-fluoro-3-(trifluoromethyl)benzyl)-3-methyl-8-(3-methylphenyl)-1H-purine-2,6(3H,7H)-dione (450 mg, 0.37 mmol) and POCl₃ (750 mg, 4.9 mmol) was stirred at 60° C. DBU (1.10 g, 7.29 mmol) was added via syringe at 60° C. and the resulting mixture stirred at 120° C. for 3 hours. Then the reaction was cooled to room temperature, carefully poured into stirring ice water (50 mL) and the pH was adjusted to ~8 with 6N aq. NaOH. The resulting mixture was extracted with EtOAc (2×100 mL). The combined organic layers were dried over sodium sulfate, filtered and concentrated under reduced pressure to afford crude 2,6-dichloro-7-(4-fluoro-3-(trifluoromethyl)

benzyl)-8-(3-methylphenyl)-7H-purine as a brown solid which was used without further purification. $^1$H NMR (300 MHz, CDCl$_3$) δ7.48 (s, 1H), 7.39-7.43 (m, 3H), 7.11-7.25 (m, 3H), 5.74 (s, 2H), 2.40 (s, 3H). MS (ES)=455 (M+1)$^+$.

Step 4: To a suspension of 2,6-dichloro-7-(4-fluoro-3-(trifluoromethyl)benzyl)-8-(3-methylphenyl)-7H-purine (200 mg, 0.43 mmol) and (R)-1-cyclopropylethanamine (112 mg, 1.31 mmol) in ethanol (10 mL) was added DIEA (226 mg, 1.75 mmol). The reaction was stirred at 70° C. under a nitrogen atmosphere for 2 hours. Then the reaction mixture was cooled to room temperature, concentrated to dryness, diluted in EtOAc (100 mL) and washed with water (30 mL), and brine (40 mL). The organic layer was dried over sodium sulfate, filtered and concentrated under reduced pressure. The residue was purified on a Redisep 12 g silica gel column (0 to 100% EtOAc/hexanes) to afford (R)-2-chloro-N-(1-cyclopropylethyl)-7-(4-fluoro-3-(trifluoromethyl)benzyl)-8-(3-methylphenyl)-7H-purin-6-amine as an off-white solid: $^1$H NMR (300 MHz, CDCl$_3$) δ7.51-7.55 (m, 2H), 7.32-7.36 (m, 5H), 5.53 (s, 2H), 4.46 (d, J=6.9 Hz, 1H), 3.59 (m, 1H), 2.38 (s, 3H), 1.07 (d, J=6.6 Hz, 3H), 0.37-0.55 (m, 2H), 0.16-0.25 (m, 3H). MS (ES)=504 (M+1)$^+$.

Step 5: A mixture of (R)-2-chloro-N-(1-cyclopropylethyl)-7-(4-fluoro-3-(trifluoromethyl)benzyl)-8-(3-methylphenyl)-7H-purin-6-amine (350 mg, 0.69 mmol) and zinc cyanide (44.0 mg, 0.38 mmol) in DMA (2.0 ml) in a sealed tube was degassed with Ar for 30 minutes. Pd(PPh$_3$)$_4$ (0.06 g, 0.05 mmol) was then added to the reaction and the reaction was evacuated and refilled with Ar three times. The reaction was heated at 120° C. for 12 hours. After this time the reaction was cooled to room temperature and ice cold water (40 mL) was added slowly. The reaction mixture was extracted with EtOAc (3×50 mL) and the combined organic layers were dried over sodium sulfate, filtered and concentrated under reduced pressure. Purification of the residue on a Redisep 12 g silica gel column (0 to 100% EtOAc/hexanes) afforded (R)-6-((1-cyclopropylethyl)amino)-7-(4-fluoro-3-(trifluoromethyl)benzyl)-8-(3-methylphenyl)-7H-purine-2-carbonitrile as white solid: $^1$H NMR (400 MHz, CDCl$_3$) δ7.53 (d, J=6.4 Hz, 1H), 7.46 (s, 1H), 7.26-7.37 (m, 5H), 5.64 (s, 2H), 4.72 (d, J=5.1 Hz, 1H), 3.58 (m, 1H), 2.37 (s, 3H), 1.07 (d, J=4.8 Hz, 3H), 0.56 (m, 1H), 0.42 (m, 1H), 0.20 (m, 1H), 0.07-0.15 (m, 2H). MS (ES)=495 (M+1)$^+$.

Step 6: (R)-6-((1-cyclopropylethyl)amino)-7-(4-fluoro-3-(trifluoromethyl)benzyl)-8-(3-methylphenyl)-7H-purine-2-carbonitrile (105 mg, 0.21 mmol) was suspended in HCl in MeOH (4.0 mL, 3.0 M) and heated at 75° C. for 4 hours. The solvent was removed under reduced pressure and the crude residue was suspended in CH$_2$Cl$_2$ (40 mL) and washed with aqueous sat. NaHCO$_3$. The organic layer was separated and dried over Na$_2$SO$_4$, filtered and concentrated under reduced pressure. The resultant residue was purified on a Redisep 12 g silica gel column (0 to 100% EtOAc/hexanes) to afford (R)-methyl 6-((1-cyclopropylethyl)amino)-7-(4-fluoro-3-(trifluoromethyl)benzyl)-8-(m-tolyl)-7H-purine-2-carboxylate as white solid: $^1$H NMR (400 MHz, CDCl$_3$) δ7.52-7.54 (m, 2H), 7.32-7.35 (m, 5H), 5.59 (s, 2H), 4.50 (d, J=4.8 Hz, 1H), 3.98 (s, 3H), 3.72 (m, 1H), 2.38 (s, 3H), 1.10 (d, J=6.4 Hz, 3H), 0.53 (m, 1H), 0.40 (m, 1H), 0.18-0.24 (m, 3H). MS (ES) 528 (M+1)$^+$.

Step 7: To a solution of (R)-methyl 6-((1-cyclopropylethyl)amino)-7-(4-fluoro-3-(trifluoromethyl)benzyl)-8-(m-tolyl)-7H-purine-2-carboxylate (80 mg, 0.15 mmol) in THF (2.0 mL) was added aqueous LiOH solution (1N, 0.75 mL, 0.75 mmol) and the reaction mixture stirred for 2 hours at room temperature. The solvent was evaporated under reduced pressure and the residue was dissolved in water (2.0 mL). The pH was adjusted to 6.5 using aqueous HCl (2.0 N), the precipitate collected by filtration and air-dried to afford 6-{[(1R)-1-cyclopropylethyl]amino}-7-[4-fluoro-3-(trifluoromethyl)benzyl]-8-(3-methylphenyl)-7H-purine-2-carboxylic acid: $^1$H NMR (300 MHz, CD$_3$OD) δ7.47-7.52 (m, 5H), 7.33 (t, J=9.0 Hz, 1H), 7.23 (s, 1H), 5.87 (d, J=18.3 Hz, 1H), 5.80 (d, J=18.3 Hz, 1H), 3.96 (m, 1H), 2.43 (s, 3H), 1.26 (d, J=6.6 Hz, 3H), 0.86 (m, 1H), 0.48 (m, 1H), 0.26-0.32 (m, 3H). MS (ES)=514 (M+1)$^+$.

Example 5.19

6-{[(1R)-1-cyclobutylethyl]amino}-7-(4-methoxybenzyl)-8-(3-methylphenyl)-7H-purine-2-carboxylic acid

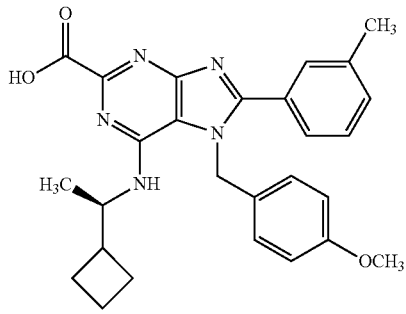 [SMILES: COc1ccc(Cn2c(-c3cccc(C)c3)nc3nc(C(=O)O)nc(N[C@H](C)C4CCC4)c32)cc1]

Step 1: 2,6-dichloro-7H-purine (3.78 g, 20 mmol) was dissolved in DMA (15 mL) then CsCO$_3$ (7.17 g, 22 mmol) was added and the reaction was stirred for 5 minutes and then 1-(bromomethyl)-4-methoxybenzene (3.4 g, 22 mmol) was added and the reaction mixture was stirred at room temperature for 3 hours. The reaction was diluted with EtOAc (60 mL) and the organic layer was washed with water (15 mL×4), dried over anhydrous Na$_2$SO$_4$, filtered, and concentrated in vacuo. Purification of the residue on a RF 40 g silica gel column (0 to 50% EtOAc/hexanes) afforded 2,6-dichloro-7-(4-methoxybenzyl)-7H-purine as white solid. $^1$H NMR (300 MHz, CDCl$_3$) δ 8.17 (br s, 1H), 7.14 (d, J=8.6 Hz, 2H), 6.92 (d, J=8.6 Hz, 2H), 5.58 (br s, 2H), 3.81 (s, 3H).

Step 2: A mixture of 2,6-dichloro-7-(4-methoxybenzyl)-7H-purine (2.08 mg, 6.73 mmol) and (R)-1-cyclobutylethylamine (1.33 g, 13.46 mmol) in ethanol (38 mL) was heated at reflux for 3 hours. The reaction mixture was cooled to room temperature and concentrated under reduced pressure. The residue was dissolved in EtOAc (30 mL) and the organic layer was washed with water (50 mL), brine (50 mL), dried over anhydrous Na$_2$SO$_4$, filtered, and concentrated in vacuo. Purification of the residue by on a RF 40 g silica gel column (0 to 50% EtOAc/hexanes) afforded (R)-2-chloro-N-(1-cyclobutylethyl)-7-(4-methoxybenzyl)-7H-purin-6-amine as a white solid. $^1$H NMR (300 MHz, CDCl$_3$) δ 7.96 (s, 1H), 7.05 (d, J=8.7 Hz, 2H), 6.96 (d, J=8.7 Hz, 2H), 5.37 (s, 2H), 4.39 (d, J=8.6 Hz, 1H), 4.18 (m, 1H), 3.82 (s, 3H), 1.64-1.96 (m, 5H), 1.50 (m, 2H), 0.82 (d, J=6.4 Hz, 3H). MS (ES)=372 (M+1)$^+$.

Step 3: Using a procedure analogous to that described in Preparative Example 5.5, and starting with (R)-2-chloro-N-(1-cyclobutylethyl)-7-(4-methoxybenzyl)-7H-purin-6-amine, (R)-6-(1-cyclobutylethylamino)-7-(4-methoxybenzyl)-7H-purine-2-carbonitrile was prepared. $^1$H NMR (400 MHz, CDCl$_3$) δ 8.09 (s, 1H), 7.07 (d, J=2.8 Hz, 2H), 7.05

(d, J=2.8 Hz, 2H), 5.45 (s, 2H), 4.52 (d, J=8.0 Hz, 1H), 4.20 (m, 1H), 3.83 (s, 3H), 1.64-1.96 (m, 5H), 1.50 (m, 2H), 0.83 (d, J=6.4 Hz, 3H). MS (ES)=363 (M+1)+.

Step 4: Using a procedure analogous to that described in Example 1.1 (Step 1), and starting with (R)-6-(1-cyclobutylethylamino)-7-(4-methoxybenzyl)-7H-purine-2-carbonitrile, (R)-6-((1-cyclobutylethyl)amino)-7-(4-methoxybenzyl)-8-(3-methylphenyl)-7H-purine-2-carbonitrile was prepared. ¹H NMR (400 MHz, CDCl₃) δ 7.59 (s, 1H), 7.33-7.34 (m, 3H), 7.14 (d, J=2.8 Hz, 2H), 7.04 (d, J=2.8 Hz, 2H), 5.45 (s, 2H), 4.55 (d, J=8.0 Hz, 1H), 4.20 (m, 1H), 3.85 (s, 3H), 2.38 (s, 3H), 1.64-1.96 (m, 5H), 1.50 (m, 2H), 0.87 (d, J=6.4 Hz, 3H).

Step 5: Using a procedure analogous to that described in Example 5.4, and starting with (R)-6-((1-cyclobutylethyl)amino)-7-(4-methoxybenzyl)-8-(3-methylphenyl)-7H-purine-2-carbonitrile, 6-{[(1R)-1-cyclobutylethyl]amino}-7-(4-methoxybenzyl)-8-(3-methylphenyl)-7H-purine-2-carboxylic acid was prepared. ¹H NMR (400 MHz, CD₃OD) δ 7.42-7.60 (m, 4H), 7.08 (d, J=8.0 Hz, 2H), 6.99 (d, J=8.4 Hz, 2H), 5.63 (d, J=7.8 Hz, 1H), 5.55 (d, J=7.8 Hz, 1H), 4.58 (m, 1H), 3.80 (s, 3H), 2.39 (s, 3H), 2.06 (m, 1H), 1.87 (m, 1H), 1.50-1.76 (m, 5H), 0.94 (d, J=6.4 Hz, 3H). MS (ES)=472 (M+1)⁺.

Example 5.20

6-{[(1R)-1-cyclopropylethyl]amino}-7-(4-ethylbenzyl)-8-(3-methylphenyl)-7H-purine-2-carboxylic acid

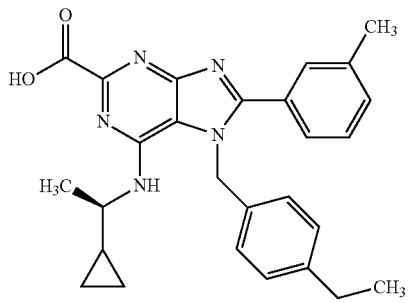 [SMILES: CCc1ccc(Cn2c(-c3cccc(C)c3)nc3nc(C(=O)O)nc(N[C@H](C)C4CC4)c32)cc1]

Using a procedure analogous to that described in Example 5.19, and starting with 2,6-dichloropurine and 4-ethylbenzyl bromide, 6-{[(1R)-1-cyclopropylethyl]amino}-7-(4-ethylbenzyl)-8-(3-methylphenyl)-7H-purine-2-carboxylic acid was prepared. ¹H NMR (300 MHz, CDCl₃) 7.62 (s, 1H), 7.29-7.46 (m, 5H), 7.17 (d, J=8.8 Hz, 2H), 5.60 (br s, 2H), 4.81 (d, J=5.8 Hz, 1H), 3.74 (m, 1H), 2.70 (d, J=7.4 Hz, 2H), 2.29 (s, 3H), 1.25 (t, J=7.4 Hz, 3H), 0.99 (d, J=5.9 Hz, 3H), 0.44 (m, 1H), 0.34 (m, 1H), 0.10-0.25 (m, 3H). MS (APCI)=456 (M+1)⁺

Example 5.21

6-{[(1R)-1-cyclopropylethyl]amino}-7-(4-methylbenzyl)-8-(3-methylphenyl)-7H-purine-2-carboxylic acid

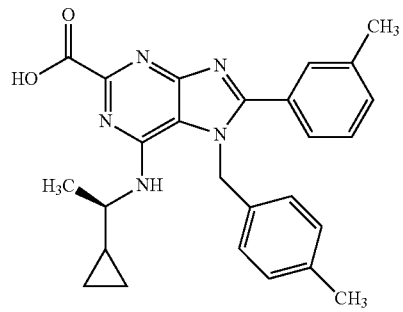 [SMILES: Cc1ccc(Cn2c(-c3cccc(C)c3)nc3nc(C(=O)O)nc(N[C@H](C)C4CC4)c32)cc1]

Using a procedure analogous to that described in Example 5.19, and starting with 2,6-dichloropurine and 4-methylbenzyl bromide, 6-{[(1R)-1-cyclopropylethyl]amino}-7-(4-methylbenzyl)-8-(3-methylphenyl)-7H-purine-2-carboxylic acid was prepared. ¹H NMR (400 MHz, CDCl₃) δ 7.41-7.60 (m, 4H), 7.27 (d, J=7.5 Hz, 2H), 7.06 (d, J=5.8 Hz, 2H), 5.67 (br s, 2H), 3.88 (m, 1H), 2.41 (s, 3H), 2.35 (s, 3H), 1.08 (d, J=7.6 Hz, 3H), 0.68 (m, 1H), 0.42 (m, 1H), 0.15-0.27 (m, 3H) MS (APCI)=442 (M+1)⁺.

The following compounds in Table 5 (other than Example 5.1 to 5.4, 5.19-5.21) were prepared using procedures which were analogous to those described above in Example 5.4.

TABLE 5

| Ex. | FRET IC₅₀ (nM) | Structure | Chemical Name | Salt Form | [M + H]⁺ Calc'd | [M + H]⁺ Obsv'd |
|---|---|---|---|---|---|---|
| 5.1 | 854.6 | 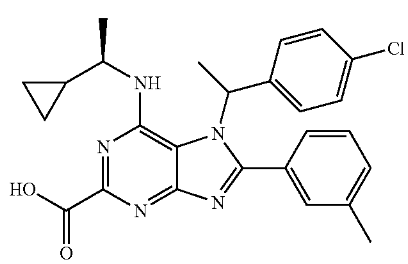 [SMILES: Cc1cccc(-c2nc3nc(C(=O)O)nc(N[C@H](C)C4CC4)c3n2C(C)c2ccc(Cl)cc2)c1] | 7-[1-(4-chlorophenyl)ethyl]-6-{[(1R)-1-cyclopropylethyl]amino}-8-(3-methylphenyl)-7H-purine-2-carboxylic acid | | 476 | 476 |

TABLE 5-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 5.2 | 984.4 | 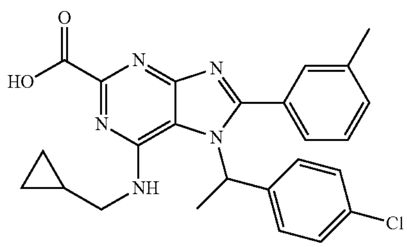 [SMILES: Cc1cccc(-c2nc3nc(C(=O)O)nc(NCC4CC4)c3n2C(C)c2ccc(Cl)cc2)c1] | 7-[1-4-chlorophenyl)ethyl]-6-[(cyclopropylmethyl)amino]-8-(3-methylphenyl)-7H-purine-2-carboxylic acid | | 462 | 462 |
| 5.3 | 601.2 | 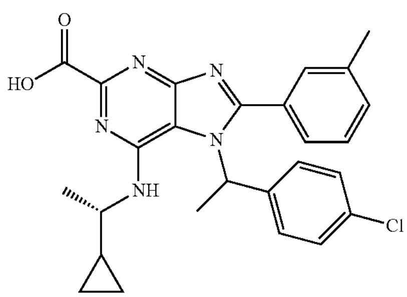 [SMILES: Cc1cccc(-c2nc3nc(C(=O)O)nc(N[C@@H](C)C4CC4)c3n2C(C)c2ccc(Cl)cc2)c1] | 7-[1-(4-chlorophenyl)ethyl]-6-{[(1S)-1-cyclopropylethyl]amino}-8-(3-methylphenyl)-7H-purine-2-carboxylic acid | | 476 | 476 |
| 5.4 | 4140 | 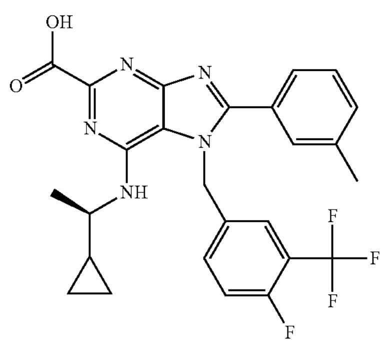 [SMILES: Cc1cccc(-c2nc3nc(C(=O)O)nc(N[C@H](C)C4CC4)c3n2Cc2ccc(F)c(C(F)(F)F)c2)c1] | 6-{[(1R)-1-cyclopropylethyl]amino}-7-[4-fluoro-3-(trifluoromethyl)benzyl]-8-(3-methylphenyl)-7H-purine-2-carboxylic acid | | 514 | 514 |
| 5.5 | 2736 | 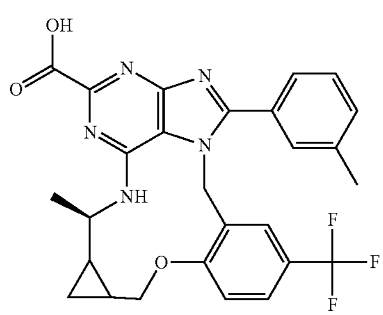 [SMILES: Cc1cccc(-c2nc3nc(C(=O)O)nc4c3n2Cc2cc(C(F)(F)F)ccc2OCC2CC2[C@@H](C)N4)c1] | 6-{[(1R)-1-cyclopropylethyl]amino}-7-(2-ethoxy-5-(trifluoromethyl)benzyl)-8-(3-methylphenyl)-7H-purine-2-carboxylic acid | | 540 | 540 |
| 5.6 | 1836 | 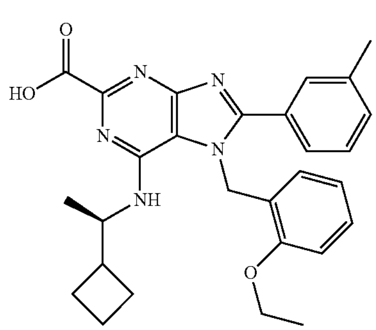 [SMILES: CCOc1ccccc1Cn1c(-c2cccc(C)c2)nc2nc(C(=O)O)nc(N[C@H](C)C3CCC3)c21] | 6-{[(1R)-1-cyclobutylethyl]amino}-7-(2-ethoxybenzyl)-8-(3-methylphenyl)-7H-purine-2-carboxylic acid | | 486 | 486 |

TABLE 5-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 5.7 | 3548 | 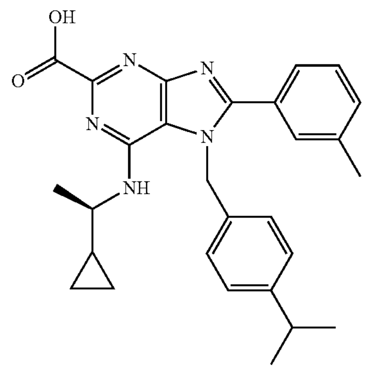 [SMILES: Cc1cccc(-c2nc3nc(C(=O)O)nc(N[C@H](C)C4CC4)c3n2Cc2ccc(C(C)C)cc2)c1] | 6-{[(1R)-1-cyclopropylethyl]amino}-7-[4-(1-methylethyl)benzyl]-8-(3-methylphenyl)-7H-purine-2-carboxylic acid | | 470 | 470 |
| 5.8 | 148.9 | 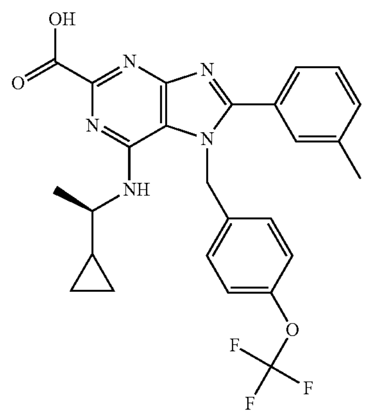 [SMILES: Cc1cccc(-c2nc3nc(C(=O)O)nc(N[C@H](C)C4CC4)c3n2Cc2ccc(OC(F)(F)F)cc2)c1] | 6-{[(1R)-1-cyclopropylethyl]amino}-8-(3-methylphenyl)-7[4-(trifluoromethoxy)benzyl]-7H-purine-2-carboxylic acid | | 512 | 512 |
| 5.9 | 118.9 | 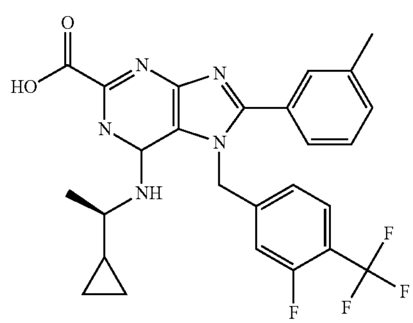 [SMILES: Cc1cccc(-c2nc3c(n2Cc2ccc(C(F)(F)F)c(F)c2)C(N[C@H](C)C2CC2)NC(C(=O)O)=N3)c1] | 6-{[(1R)-1-cyclopropylethyl]amino}-7-[3-fluoro-4-(trifluoromethyl)benzyl]-8-(3-methylphenyl)-7H-purine-2-carboxylic acid | | 514 | 514 |
| 5.10 | 270 | 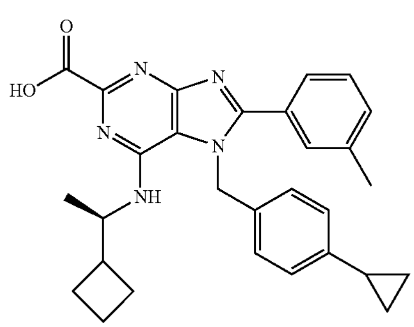 [SMILES: Cc1cccc(-c2nc3nc(C(=O)O)nc(N[C@H](C)C4CCC4)c3n2Cc2ccc(C3CC3)cc2)c1] | 6-{[(1R)-1-cyclobutylethyl]amino}-7-(4-cyclopropylbenzyl)-8-(3-methylphenyl)-7H-purine-2-carboxylic acid | | 482 | 482 |

TABLE 5-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 5.11 | 258.7 | 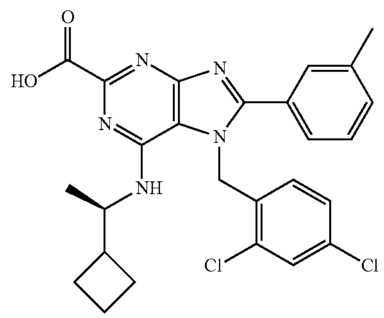 [SMILES: Cc1cccc(-c2nc3nc(C(=O)O)nc(N[C@H](C)C4CCC4)c3n2Cc2ccc(Cl)cc2Cl)c1] | 6-{[(1R)-1-cyclobutylethyl]amino}-7-(2,4-dichlorobenzyl)-8-(3-methylphenyl)-7H-purine-2-carboxylic acid | | 510 | 510 |
| 5.12 | 94.57 | 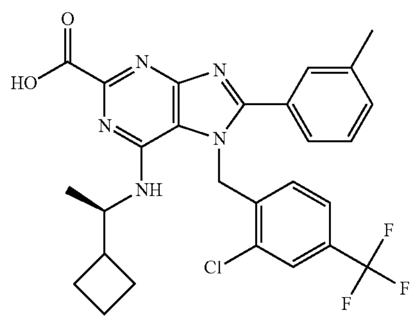 [SMILES: Cc1cccc(-c2nc3nc(C(=O)O)nc(N[C@H](C)C4CCC4)c3n2Cc2ccc(C(F)(F)F)cc2Cl)c1] | 7-[2-chloro-4-(trifluoromethyl)benzyl]-6-{[(1R)-1-cyclobutylethyl]amino}-8-(3-methylphenyl)-7H-purine-2-carboxylic acid | | 544 | 544 |
| 5.13 | 128.3 | 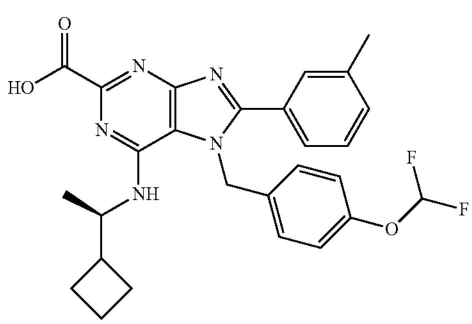 [SMILES: Cc1cccc(-c2nc3nc(C(=O)O)nc(N[C@H](C)C4CCC4)c3n2Cc2ccc(OC(F)F)cc2)c1] | 6-{[(1R)-1-cyclobutylethyl]amino}-7-[4-(difluoromethoxy)benzyl]-8-(3-methylphenyl)-7H-purine-2-carboxylic acid | | 508 | 508 |
| 5.14 | 36.44 | 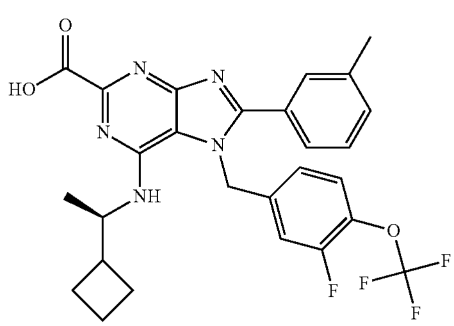 [SMILES: Cc1cccc(-c2nc3nc(C(=O)O)nc(N[C@H](C)C4CCC4)c3n2Cc2ccc(OC(F)(F)F)c(F)c2)c1] | 6-{[(1R)-1-cyclobutylethyl]aminol -7-[3-fluoro-4-(trifluoromethoxy)benzyl]-8-(3-methylphenyl)-7H-purine-2-carboxylic acid | | 544 | 544 |

TABLE 5-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 5.15 | 608.5 | 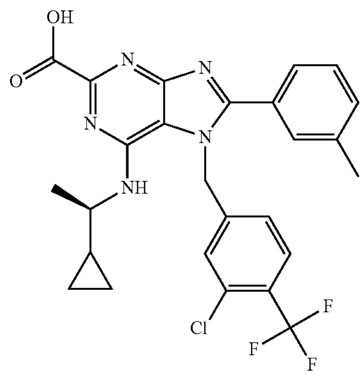 [SMILES: Cc1cccc(-c2nc3nc(C(=O)O)nc(N[C@H](C)C4CC4)c3n2Cc2ccc(C(F)(F)F)c(Cl)c2)c1] | 7-[3-chloro-4-(trifluoromethyl)benzyl]-6-{[(1R)-1-cyclopropylethyl]amino}-8-(3-methylphenyl)-7H-purine-2-carboxylic acid | | 530 | 530 |
| 5.16 | 8332 | 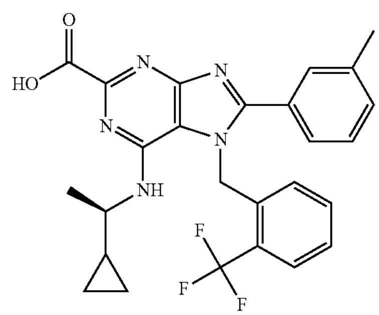 [SMILES: Cc1cccc(-c2nc3nc(C(=O)O)nc(N[C@H](C)C4CC4)c3n2Cc2ccccc2C(F)(F)F)c1] | 6-{[(1R)-1-cyclopropylethyl]amino}-8-(3-methylphenyl)-7-[2-(trifluoromethyl)benzyl]-7H-purine-2-carboxylic acid | | 496 | 496 |
| 5.17 | 74.35 | 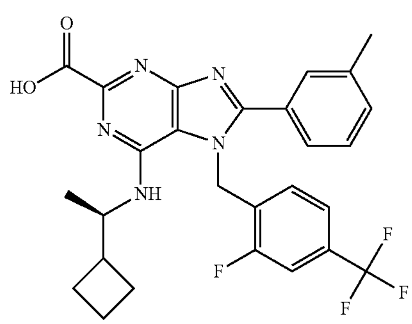 [SMILES: Cc1cccc(-c2nc3nc(C(=O)O)nc(N[C@H](C)C4CCC4)c3n2Cc2ccc(C(F)(F)F)cc2F)c1] | 6-{[(1R)-1-cyclobutylethyl]aminol-7-[2-fluoro-4-(trifluoromethyl)benzyl]-8-(3-methylphenyl)-7H-purine-2-carboxylic acid | | 528 | 528 |
| 5.18 | 206.7 | 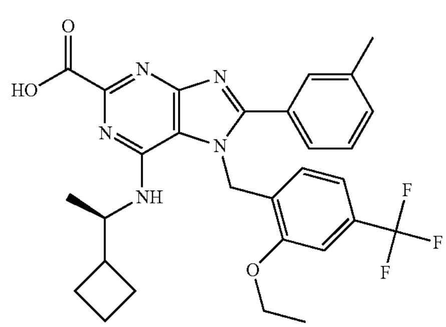 [SMILES: CCOc1cc(C(F)(F)F)ccc1Cn1c(-c2cccc(C)c2)nc2nc(C(=O)O)nc(N[C@H](C)C3CCC3)c21] | 6-{[(1R)-1-cyclobutylethyl]amino}-7-[2-ethoxy-4-(trifluoromethyl)benzyl]-8-(3-methylphenyl)-7H-purine-2-carboxylic acid | | 554 | 554 |

TABLE 5-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 5.19 | 581.7 | 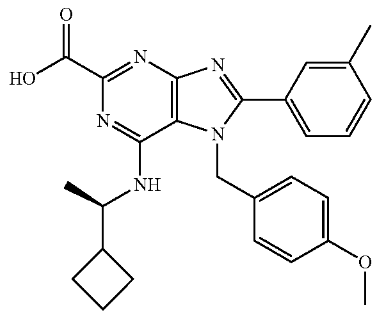 [SMILES: COc1ccc(Cn2c(-c3cccc(C)c3)nc3nc(C(=O)O)nc(N[C@H](C)C4CCC4)c32)cc1] | 6-{[(1R)-1-cyclobutylethyl]amino}-7-(4-methoxybenzyl)-8-(3-methylphenyl)-7H-purine-2-carboxylic acid | | 472 | 472 |
| 5.20 | 1197 | 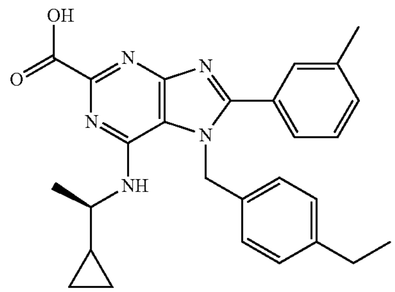 [SMILES: CCc1ccc(Cn2c(-c3cccc(C)c3)nc3nc(C(=O)O)nc(N[C@H](C)C4CC4)c32)cc1] | 6-{[(1R)-1-cyclopropylethyl]amino}-7-(4-ethylbenzyl)-8-(3-methylphenyl)-7H-purine-2-carboxylic acid | | 456 | 456 |
| 5.21 | 1198 | 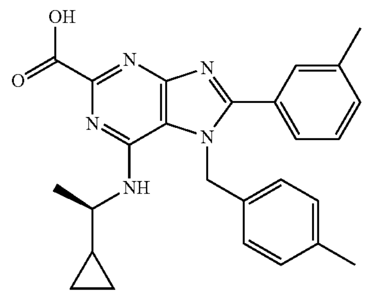 [SMILES: Cc1ccc(Cn2c(-c3cccc(C)c3)nc3nc(C(=O)O)nc(N[C@H](C)C4CC4)c32)cc1] | 6-{[(1R)-1-cyclopropylethyl]amino}-7-(4-methylbenzyl)-8-(3-methylphenyl)-7H-purine-2-carboxylic acid | | 442 | 442 |

Preparative Example 6.1

2,6-dichloro-8-(3-methylphenyl)-7-(4-(trifluoromethyl)benzyl)-7H-purine

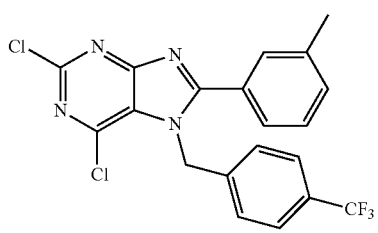 [SMILES: Cc1cccc(-c2nc3nc(Cl)nc(Cl)c3n2Cc2ccc(C(F)(F)F)cc2)c1]

Step 1: To a slurry of 6-amino-1-methylpyrimidine-2,4 (1H,3H)-dione (20 g, 142 mmol) and sodium bicarbonate (11.91 g, 142 mmol) in MeOH (200 mL) at 0° C. was added bromine (7.30 ml, 142 mmol) slowly. The reaction mixture stirred at room temperature overnight and filtered. The collected solids were washed with MeOH and DCM and air dried to afford 6-amino-5-bromo-1-methylpyrimidine-2,4 (1H,3H)-dione.

Step 2: To a slurry of 6-amino-5-bromo-1-methylpyrimidine-2,4(1H,3H)-dione (12 g, 54.5 mmol) in NMP (120 mL) was added 1-(bromomethyl)-4-(trifluoromethyl)benzene (19.2 g, 109.1 mmol). The slurry was heated to 120° C. for 2 h. The reaction was cooled to RT and poured into 400 mL ice-water. The precipitate was collected and washed with Et$_2$O to afford 6-amino-1-methyl-5-((4-(trifluoromethyl)benzyl)amino)pyrimidine-2,4(1H,3H)-dione.

Step 3: To the slurry of DIEA (4.17 mL, 23.87 mmol) and 6-amino-1-methyl-5-((4-(trifluoromethyl)benzyl)amino)pyrimidine-2,4(1H,3H)-dione (5 g, 15.91 mmol) at 0° C. was added m-toluoyl chloride (2.95 g, 19.1 mmol) slowly. The mixture was stirred at room temperature for 2 h and the solids were collected by filtration. The solids were washed with Et$_2$O and air dried to afford 3-methyl-N-(3-methyl-2,6-dioxo-5-((4-(trifluoromethyl)benzyl)amino)-1,2,3,6-tetrahydropyrimidin-4-yl)benzamide.

Step 4: To a slurry of 3-methyl-N-(3-methyl-2,6-dioxo-5-((4-(trifluoromethyl)benzyl)amino)-1,2,3,6-tetrahydropyrimidin-4-yl)benzamide (6.2 g, 14.34 mmol) in ethanol (50 mL) was added a solution of 1 M NaOH (21.5 mL). The reaction was stirred at 70° C. overnight and concentrated to remove ethanol. Et$_2$O was added and the precipitate was collected by filtration. The precipitate was washed with Et$_2$O and dried to afford 3-methyl-8-(3-methylphenyl)-7-(4-(trifluoromethyl)benzyl)-1H-purine-2,6(3H,7H)-dione as a white solid.

Step 5: To a slurry of 3-methyl-8-(3-methylphenyl)-7-(4-(trifluoromethyl)benzyl)-1H-purine-2,6(3H,7H)-dione (4.3 g, 10.38 mmol) in xylene (80 mL) at 60° C. was added POCl$_3$ (25.4 g, 166 mmol), and DBU (12.5 mL, 83 mmol) dropwise. The reaction temperature was brought to 120° C. for 24 h and then concentrated to remove the solvent. The residue was poured into ice-water and 3 M KOH was added to adjust the pH to 9. The mixture was extracted with EtOAc and the organics were concentrated. The residue was purified by column chromatography on silica gel to afford 2,6-dichloro-8-(3-methylphenyl)-7-(4-(trifluoromethyl)benzyl)-7H-purine. NMR (300 MHz, CDCl$_3$): δ7.65 (d, 2H), 7.52 (s, 1H), 7.39 (m, 3H), 7.12 (d, 2H), 5.78 (s, 2H), 2.37 (s, 3H). MS (ES)=437 (M+1)+.

Preparative Example 6.2

6-chloro-8-(3-methylphenyl)-7-(4-(trifluoromethyl)benzyl)-7H-purine-2-carbonitrile

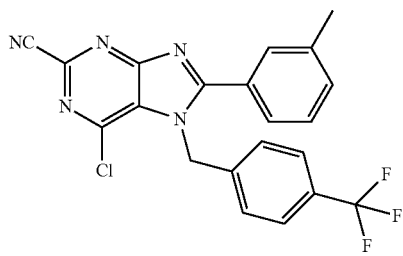 [SMILES: Cc1cccc(-c2nc3nc(C#N)nc(Cl)c3n2Cc2ccc(C(F)(F)F)cc2)c1]

Step 1: To a solution of 2,6-dichloro-8-(3-methylphenyl)-7-(4-(trifluoromethyl)benzyl)-7H-purine (3.77 g, 8.62 mmol) in THF (25 mL) at 0° C. was added NaSCH$_3$ (0.665 g, 9.48 mmol). The mixture was allowed to warm to room temperature and stirred overnight. The mixture was diluted with EtOAc and washed with water; the aqueous layer was extracted with EtOAc (3×). The combined organic layers were washed with brine, dried over anhydrous Na$_2$SO$_4$ and concentrated to give 2-chloro-6-(methylthio)-8-(3-methylphenyl)-7-(4-(trifluoromethyl)benzyl)-7H-purine.

Step 2: DMA (20 mL) was added to X-Phos (0.777 g, 1.631 mmol) and allylpalladium(II) chloride dimer (0.149 g, 0.408 mmol) in an oven-dried, N$_2$(g) cooled microwave vial. The vial was evacuated/backfilled with N$_2$ (3×) before heating to 60° C. for 1 h. In separate pressure vessel was placed zinc cyanide (1.245 g, 10.6 mmol), 2-chloro-6-(methylthio)-8-(3-methylphenyl)-7-(4-(trifluoromethyl)benzyl)-7H-purine (3.66 g, 8.15 mmol), and DMA (20 mL). This mixture was degassed with N$_2$ for 15 min before adding the catalyst solution described above and heating at 120° C. for 1 h. The reaction was then cooled to room temperature, and water was added slowly. The resulting precipitate was collected by filtration, dried, and then purified by column chromatography on silica gel, eluting with EtOAc/hexane to give 6-(methylthio)-8-(3-methylphenyl)-7-(4-(trifluoromethyl)benzyl)-7H-purine-2-carbonitrile.

Step 3: To a stirring solution of 6-(methylthio)-8-(3-methylphenyl)-7-(4-(trifluoromethyl)benzyl)-7H-purine-2-carbonitrile (3.25 g, 7.40 mmol) in THF (25 mL) at 0° C. was added m-CPBA (4.14 g, 18.49 mmol). The reaction was warmed to room temperature and stirred overnight before quenching with sodium thiosulfate and stirring for 10 min. Saturated aqueous sodium bicarbonate was added and the mixture was extracted with EtOAc. The organic layer was concentrated to give 6-(methylsulfonyl)-8-(3-methylphenyl)-7-(4-(trifluoromethyl)benzyl)-7H-purine-2-carbonitrile.

Step 4: TEA (3 mL, 21.52 mmol) was added to a mixture of 6-(methylsulfonyl)-8-(3-methylphenyl)-7-(4-(trifluoromethyl)benzyl)-7H-purine-2-carbonitrile (2.0 g, 3.18 mmol) in water (287 µL, 15.9 mmol) and the reaction was stirred at RT overnight. The mixture was concentrated, diluted with EtOAc, and washed with water and extracted with EtOAc (2×). The combined organic layers were dried over Na$_2$SO$_4$, filtered, and concentrated. The residue was purified by silica gel column chromatography to afford 6-hydroxy-8-(3-methylphenyl)-7-(4-(trifluoromethyl)benzyl)-7H-purine-2-carbonitrile.

Step 5: A suspension of 6-hydroxy-8-(3-methylphenyl)-7-(4-(trifluoromethyl)benzyl)-7H-purine-2-carbonitrile (7.68 g, 18.77 mmol) in POCl$_3$ (100 mL) was stirred at 90° C. for 1 h. The reaction mixture was cooled to RT, concentrated, and treated with aq.NaHCO$_3$. The mixture was extracted with EtOAc (30 mL) and the organic layer was dried over Na$_2$SO$_4$, filtered, and concentrated. The residue was purified by silica gel column chromatography to afford 6-chloro-8-(3-methylphenyl)-7-(4-(trifluoromethyl)benzyl)-7H-purine-2-carbonitrile. $^1$H NMR (300 MHz, CDCl$_3$) δ 7.65 (d, J=8.4, 2H), 7.54 (s, 1H), 7.39-7.44 (m, 3H), 7.11 (d, J=7.8, 2H), 5.85 (s, 2H), 2.39 (s, 3H). MS ESI calc'd. for C$_{21}$H$_{13}$ClF$_3$N$_5$ [M+H]$^+$ 428. found 428.

Example 6.1

6-(3-ethylpyrrolidin-1-yl)-8-(3-methylphenyl)-7-[4-(trifluoromethyl)benzyl]-7H-purine-2-carboxylic acid

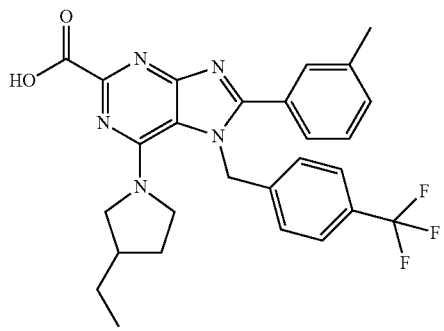 [SMILES: CCC1CCN(c2nc(C(=O)O)nc3nc(-c4cccc(C)c4)n(Cc4ccc(C(F)(F)F)cc4)c23)C1]

To a microwave vial was added 6-chloro-8-(3-methylphenyl)-7-(4-(trifluoromethyl)benzyl)-7H-purine-2-carbonitrile (0.020 g, 0.047 mmol), 3-ethylpyrrolidine (0.019 g, 0.19 mmol), DIEA (0.050 mL, 0.29 mmol), and NMP (0.50 mL, 0.093 M). The reaction vial was sealed and heated to 150° C. under microwave irradiation for 10 minutes. After cooling to room temperature, 5N NaOH (0.35 mL) was added and the reaction was heated at 80° C. for 3 hours. The reaction was neutralized with 6N HCl (0.30 mL) and was diluted with water and extracted with DCM. The organics were collected and concentrated under reduced pressure. The reaction residue was taken up in DMSO (1.0 mL), passed through a syringe filter, and purified by reverse phase preparative HPLC (0:100 to 95:5 acetonitrile:water: 0.1% v/v TFA modifier) to afford 6-(3-ethylpyrrolidin-1-yl)-8-(3- methylphenyl)-7-[4-(trifluoromethyl)benzyl]-7H-purine-2-carboxylic acid (TFA salt). $^1$H NMR (500 MHz, dmso-d$_6$) δ 7.54 (d, J=7.7, 2H), 7.49 (d, J=8.2, 2H), 7.36 (m, 2H), 6.79 (d, J=8.1, 2H), 5.73 (q, J=5.7, 2H), 3.78 (m, 3H), 3.36 (m, 1H), 2.33 (s, 3H), 2.02 (m, 2H), 1.49 (m, 1H), 1.35 (m, 2H), 0.86 (t, J=7.4, 3H). MS ESI calc'd. for C$_{27}$H$_{26}$F$_3$N$_5$O$_2$ [M+H]$^+$ 510. found 510.

The following compounds in Table 6 (other than Example 6.1) were prepared using procedures which were analogous to those described above in Example 6.1.

TABLE 6

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.1 | 41% inh. at 1000 nM | 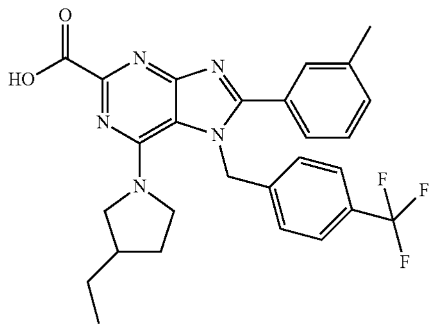 [SMILES: CCC1CCN(c2nc(C(=O)O)nc3nc(-c4cccc(C)c4)n(Cc4ccc(C(F)(F)F)cc4)c23)C1] | 6-(3-ethylpyrrolidin-1-yl)-8-(3-methylphenyl)-7-[4-(trifluoromethyl)benzyl]-1]-7H-purine-2-carboxylic acid | TFA | 510 | 510 |
| 6.2 | 13.9 | 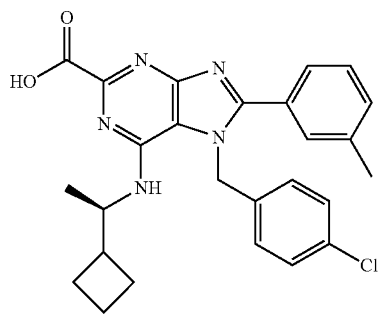 [SMILES: Cc1cccc(-c2nc3nc(C(=O)O)nc(N[C@H](C)C4CCC4)c3n2Cc2ccc(Cl)cc2)c1] | 7-(4-chlorobenzyl)-6-{[(1R)-1-cyclobutylethyl]amino}-8-(3-methylphenyl)-7H-purine-2-carboxylic acid | | 476 | 476 |
| 6.3 | 31.4 | 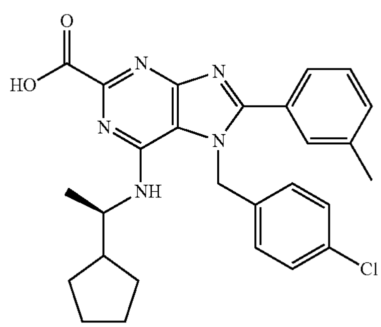 [SMILES: Cc1cccc(-c2nc3nc(C(=O)O)nc(N[C@H](C)C4CCCC4)c3n2Cc2ccc(Cl)cc2)c1] | 7-(4-chlorobenzyl)-6-{[(1R)-1-cyclopentylethyl]amino}-8-(3-methylphenyl)-7H-purine-2-carboxylic acid | | 490 | 490 |
| 6.4 | 1034 | 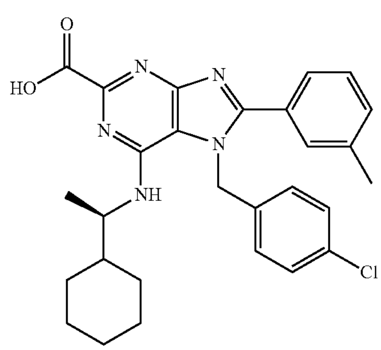 [SMILES: Cc1cccc(-c2nc3nc(C(=O)O)nc(N[C@H](C)C4CCCCC4)c3n2Cc2ccc(Cl)cc2)c1] | 7-(4-chlorobenzyl)-6-{[(1R)-1-cyclohexylethyl]amino}-8-(3-methylphenyl)-7H-purine-2-carboxylic acid | | 504 | 504 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.5 | 234 | 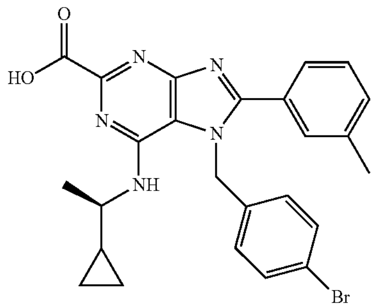 [SMILES: Cc1cccc(-c2nc3nc(C(=O)O)nc(N[C@H](C)C4CC4)c3n2Cc2ccc(Br)cc2)c1] | 7-(4-bromobenzyl)-6-{[(1R)-1-cyclopropylethyl]amino}-8-(3-methylphenyl)-7H-purine-2-carboxylic acid | | 506 | 506 |
| 6.6 | 1648 | 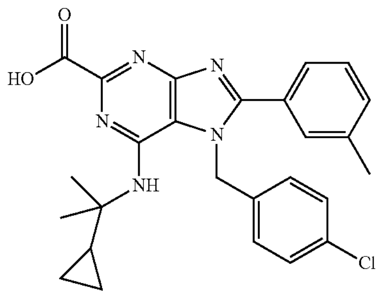 [SMILES: Cc1cccc(-c2nc3nc(C(=O)O)nc(NC(C)(C)C4CC4)c3n2Cc2ccc(Cl)cc2)c1] | 7-(4-chlorobenzyl)-6-[(1-cyclopropyl-1-methylethyl)amino]-8-(3-methylphenyl)-7H-purine-2-carboxylic acid | | 476 | 476 |
| 6.7 | 75.73 | 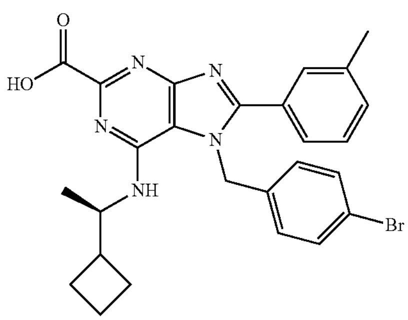 [SMILES: Cc1cccc(-c2nc3nc(C(=O)O)nc(N[C@H](C)C4CCC4)c3n2Cc2ccc(Br)cc2)c1] | 7-(4-bromobenzyl)-6-{[(1R)-1-cyclobutylethyl]amino}-8-(3-methylphenyl)-7H-purine-2-carboxylic acid | | 520 | 520 |
| 6.8 | 228 | 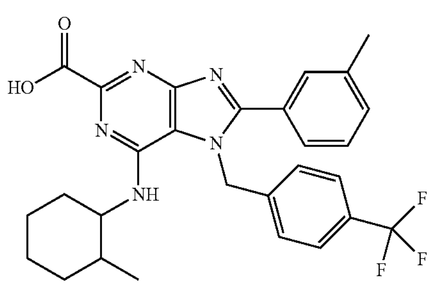 [SMILES: Cc1cccc(-c2nc3nc(C(=O)O)nc(NC4CCCCC4C)c3n2Cc2ccc(C(F)(F)F)cc2)c1] | 6-[(2-methylcyclohexyl)amino]-8-(3-methylphenyl)-7-[4-(trifluoromethyl)benzyl]-7H-purine-2-carboxylic acid | | 524 | 524 |
| 6.9 | 22.3 | 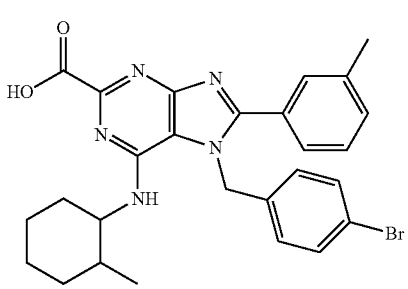 [SMILES: Cc1cccc(-c2nc3nc(C(=O)O)nc(NC4CCCCC4C)c3n2Cc2ccc(Br)cc2)c1] | 7-(4-bromobenzyl)-6-[(2-methylcyclohexyl)amino]-8-(3-methylphenyl)-7H-purine-2-carboxylic acid | | 534 | 534 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.10 | 1037 | 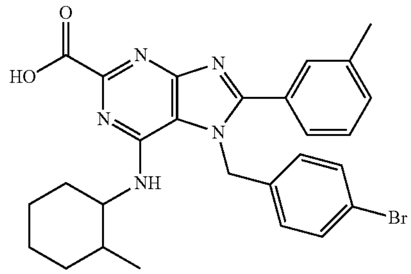 [SMILES: Cc1cccc(-c2nc3nc(C(=O)O)nc(NC4CCCCC4C)c3n2Cc2ccc(Br)cc2)c1] | 7-(4-bromobenzyl)-6-[(2-methylcyclohexyl)amino]-8-(3-methylphenyl)-7H-purine-2-carboxylic acid | | 534 | 534 |
| 6.11 | 1418 | 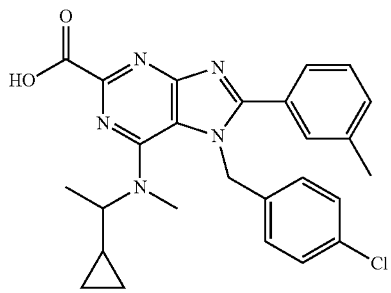 [SMILES: Cc1cccc(-c2nc3nc(C(=O)O)nc(N(C)C(C)C4CC4)c3n2Cc2ccc(Cl)cc2)c1] | 7-(4-chlorobenzyl)-6-[(1-cyclopropylethyl)(methyl)amino]-8-(3-methylphenyl)-7H-purine-2-carboxylic acid | | 476 | 476 |
| 6.12 | 4097 | 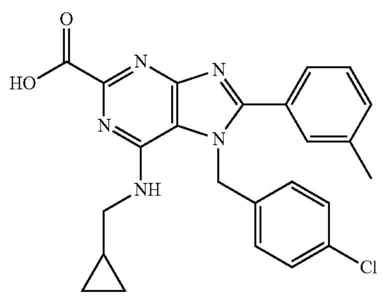 [SMILES: Cc1cccc(-c2nc3nc(C(=O)O)nc(NCC4CC4)c3n2Cc2ccc(Cl)cc2)c1] | 7-(4-chlorobenzyl)-8-(3-chlorophenyl)-6-[(cyclopropylmethyl)amino]-7H-purine-2-carboxylic acid | | 468 | 468 |
| 6.13 | 16.3 | 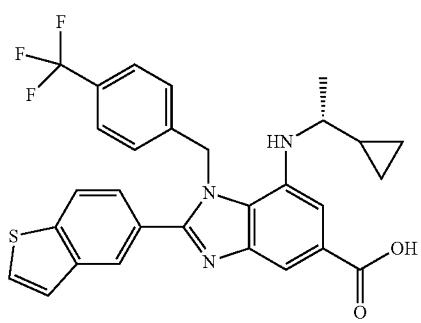 [SMILES: C[C@@H](Nc1cc(C(=O)O)cc2nc(-c3ccc4sccc4c3)n(Cc3ccc(C(F)(F)F)cc3)c12)C1CC1] | 8-(1-benzothiophen-5-yl)-6-{[(1R)-1-cyclopropylethyl]amino}-7-[4-(trifluoromethyl)benzyl]-7H-purine-2-carboxylic acid | | 538 | 538 |
| 6.14 | 35.3 | 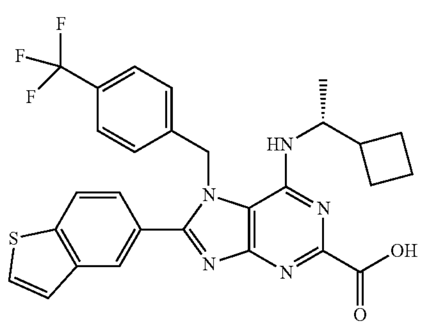 [SMILES: C[C@@H](Nc1nc(C(=O)O)nc2nc(-c3ccc4sccc4c3)n(Cc3ccc(C(F)(F)F)cc3)c12)C1CCC1] | 8-(1-benzothiophen-5-yl)-6-{[(1R)-1-cyclobutylethyl]amino}-7-[4-(trifluoromethyl)benzyl]-7H-purine-2-carboxylic acid | | 552 | 552 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.15 | 371.3 | 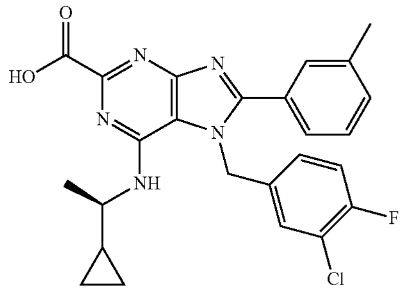 [SMILES: Cc1cccc(-c2nc3nc(C(=O)O)nc(N[C@H](C)C4CC4)c3n2Cc2ccc(F)c(Cl)c2)c1] | 7-(3-chloro-4-fluorobenzyl)-6-{[(1R)-1-cyclopropylethyl]amino}-8-(3-methylphenyl)-7H-purine-2-carboxylic acid | | 480 | 480 |
| 6.16 | 462.5 | 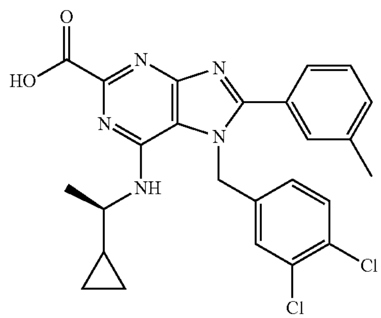 [SMILES: Cc1cccc(-c2nc3nc(C(=O)O)nc(N[C@H](C)C4CC4)c3n2Cc2ccc(Cl)c(Cl)c2)c1] | 6-{[(1R)-1-cyclopropylethyl]amino}-7-[3,4-dichlorobenzyl]-8-(3-methylphenyl)-7H-purine-2-carboxylic acid | TFA | 496 | 496 |
| 6.17 | 25.8 | 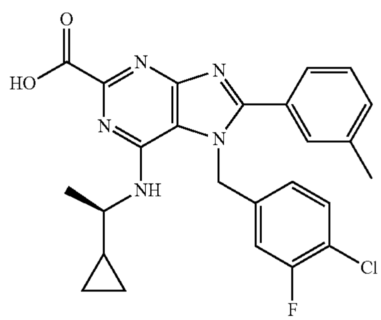 [SMILES: Cc1cccc(-c2nc3nc(C(=O)O)nc(N[C@H](C)C4CC4)c3n2Cc2ccc(Cl)c(F)c2)c1] | 7-(4-chloro-3-fluorobenzyl)-6-{[(1R)-1-cyclopropylethyl]amino}-8-[3-methylphenyl)-7H-purine-2-carboxylic acid | TFA | 480 | 480 |
| 6.18 | 5194 | 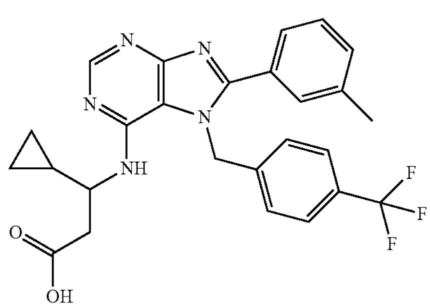 [SMILES: Cc1cccc(-c2nc3ncnc(NC(CC(=O)O)C4CC4)c3n2Cc2ccc(C(F)(F)F)cc2)c1] | 3-cyclopropyl-3-({8-(3-methylphenyl)-7-[4-(trifluoromethyl)benzyl]-7H-purin-6-yl}amino)propanoic acid | TFA | 496 | 496 |
| 6.19 | 869 | 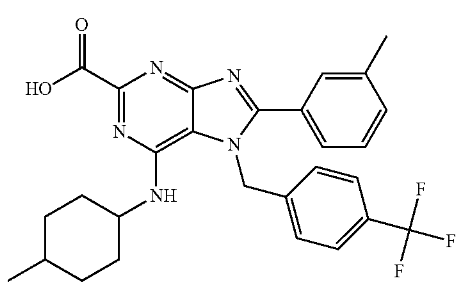 [SMILES: Cc1cccc(-c2nc3nc(C(=O)O)nc(NC4CCC(C)CC4)c3n2Cc2ccc(C(F)(F)F)cc2)c1] | 6-[(4-methylcyclohexyl)amino]-8-(3-methylphenyl)-7-[4-(trifluoromethyl)benzyl]-7H-purine-2-carboxylic acid | | 524 | 524 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.20 | 566.8 | 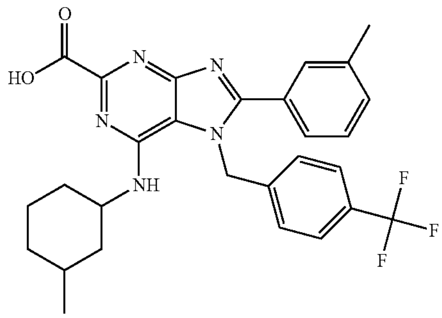 [SMILES: Cc1cccc(-c2nc3nc(C(=O)O)nc(NC4CCCC(C)C4)c3n2Cc2ccc(C(F)(F)F)cc2)c1] | 6-[(3-methylcyclohexyl)amino]-8-(3-methylphenyl)-7-[4-(trifluoromethyl)benzyl]-7H-purine-2-carboxylic acid | | 524 | 524 |
| 6.21 | 421.9 | 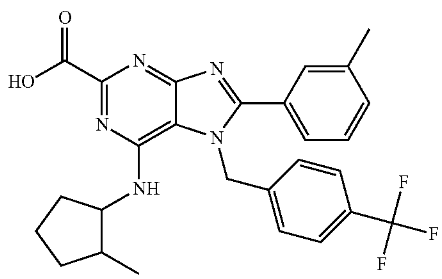 [SMILES: Cc1cccc(-c2nc3nc(C(=O)O)nc(NC4CCCC4C)c3n2Cc2ccc(C(F)(F)F)cc2)c1] | 6-[(2-methylcyclopentyl)amino]-8-(3-methylphenyl)-7-[4-(trifluoromethyl)benzyl]-7H-purine-2-carboxylic acid | | 510 | 510 |
| 6.22 | 649.1 | 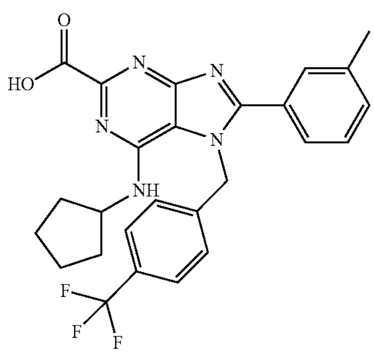 [SMILES: Cc1cccc(-c2nc3nc(C(=O)O)nc(NC4CCCC4)c3n2Cc2ccc(C(F)(F)F)cc2)c1] | 6-(cyclopentylamino)-8-(3-methylphenyl)-7-[4-(trifluoromethyl)benzyl]-7H-purine-2-carboxylic acid | TFA | 496 | 496 |
| 6.23 | 8267 | 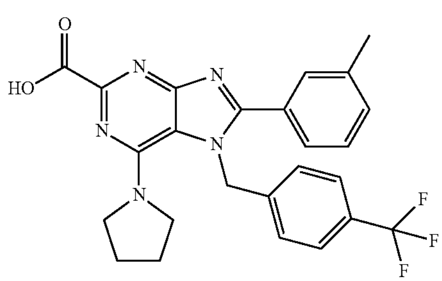 [SMILES: Cc1cccc(-c2nc3nc(C(=O)O)nc(N4CCCC4)c3n2Cc2ccc(C(F)(F)F)cc2)c1] | 8-(3-methylphenyl)-6-pyrrolidin-1-yl-7-[4-(trifluoromethyl)benzyl]-7H-purine-2-carboxylic acid | TFA | 482 | 482 |
| 6.24 | 328.7 | 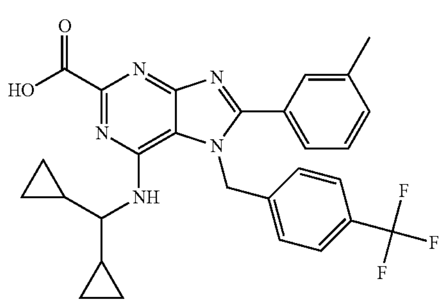 [SMILES: Cc1cccc(-c2nc3nc(C(=O)O)nc(NC(C4CC4)C4CC4)c3n2Cc2ccc(C(F)(F)F)cc2)c1] | 6-[(dicyclopropylmethyl)amino]-8-(3-methylphenyl)-7-[4-(trifluoromethyl)benzyl]-7H-purine-2-carboxylic acid | | 522 | 522 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.25 | 5078 | 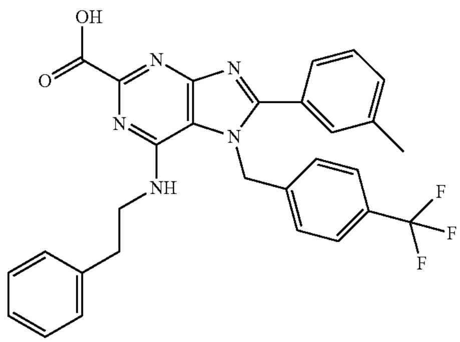 [SMILES: Cc1cccc(-c2nc3nc(C(=O)O)nc(NCCc4ccccc4)c3n2Cc2ccc(C(F)(F)F)cc2)c1] | 8-(3-methylphenyl)-6-[(2-phenylethyl)amino]-7-[4-(trifluoromethyl)benzyl]-7H-purine-2-carboxylic acid | TFA | 532 | 532 |
| 6.26 | 6973 | 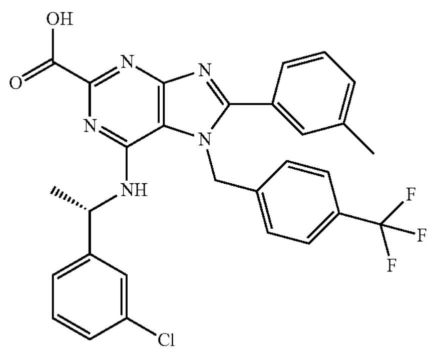 [SMILES: Cc1cccc(-c2nc3nc(C(=O)O)nc(N[C@@H](C)c4cccc(Cl)c4)c3n2Cc2ccc(C(F)(F)F)cc2)c1] | 6-{[1S]-1-(3-chlorophenyl)ethyl]amino}-8-(3-methylphenyl)-7-[4-(trifluoromethyl)benzyl]-7H-purine-2-carboxylic acid | TFA | 566 | 566 |
| 6.27 | 2359 | 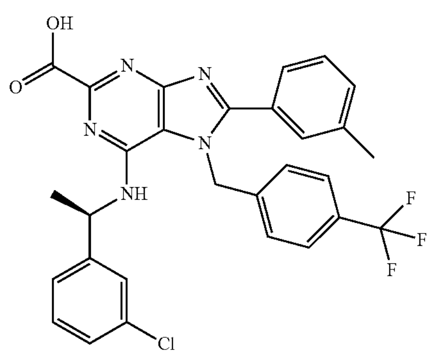 [SMILES: Cc1cccc(-c2nc3nc(C(=O)O)nc(N[C@H](C)c4cccc(Cl)c4)c3n2Cc2ccc(C(F)(F)F)cc2)c1] | 6-{[(1R)-1-(3-chlorophenyl)ethyl]amino}-8-(3-methylphenyl)-7[-4-(trifluoromethyl)benzyl]-7H-purine-2-carboxylic acid | TFA | 566 | 566 |
| 6.28 | 588.9 | 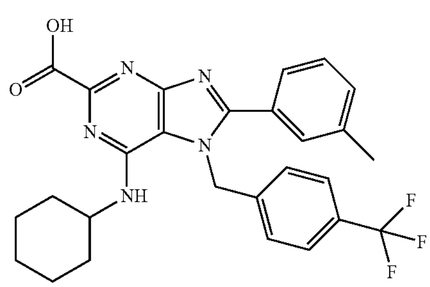 [SMILES: Cc1cccc(-c2nc3nc(C(=O)O)nc(NC4CCCCC4)c3n2Cc2ccc(C(F)(F)F)cc2)c1] | 6-(cyclohexylamino)-8-(3-methylphenyl)-7-[4-(trifluoromethyl)benzyl]-7H-purine-2-carboxylic acid | TFA | 510 | 510 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.29 | 1771 | 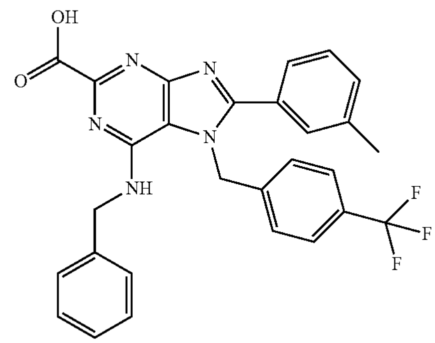 [SMILES: Cc1cccc(-c2nc3nc(C(=O)O)nc(NCc4ccccc4)c3n2Cc2ccc(C(F)(F)F)cc2)c1] | 6-(benzylamino)-8-(3-methylphenyl)-7-[4-(trifluoromethyl)benzyl]-7H-purine-2-carboxylic acid | TFA | 518 | 518 |
| 6.30 | 1488 | 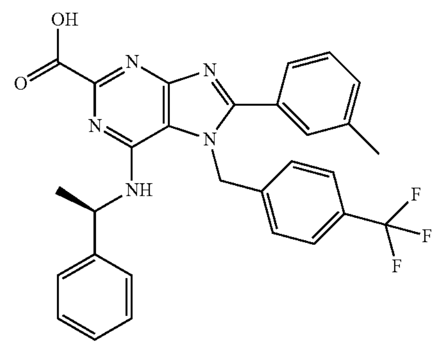 [SMILES: Cc1cccc(-c2nc3nc(C(=O)O)nc(N[C@H](C)c4ccccc4)c3n2Cc2ccc(C(F)(F)F)cc2)c1] | 8-(3-methylphenyl)-6-{[(1R)-1-phenylethyl]amino}-7-[4-(trifluoromethyl)benzyl]-7H-purine-2-carboxylic acid | TFA | 532 | 532 |
| 6.31 | 4304 | 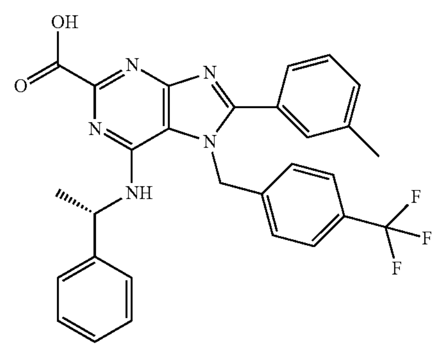 [SMILES: Cc1cccc(-c2nc3nc(C(=O)O)nc(N[C@@H](C)c4ccccc4)c3n2Cc2ccc(C(F)(F)F)cc2)c1] | 8-(3-methylphenyl)-6-{[(1S)-1-phenylethyl]amino}-7-[4-(trifluoromethyl)benzyl]-7H-purine-2-carboxylic acid | TFA | 532 | 532 |
| 6.32 | 373 | 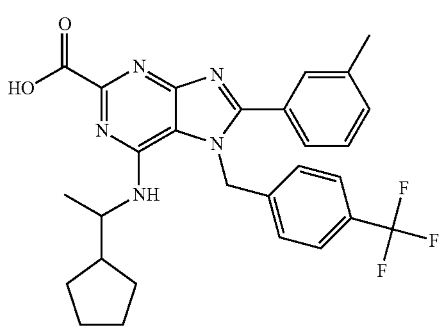 [SMILES: Cc1cccc(-c2nc3nc(C(=O)O)nc(NC(C)C4CCCC4)c3n2Cc2ccc(C(F)(F)F)cc2)c1] | 6-[(1-cyclopentylethyl)amino]-8-(3-methylphenyl)-7-[4-(trifluoromethyl)benzyl]-7H-purine-2-carboxylic acid | | 524 | 524 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.33 | 304.7 | 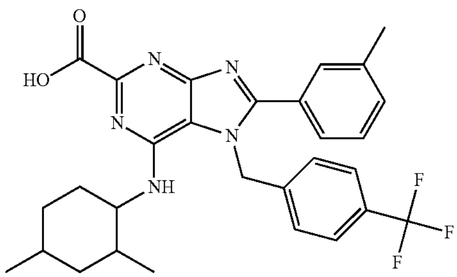 [SMILES: Cc1cccc(-c2nc3nc(C(=O)O)nc(NC4CCC(C)CC4C)c3n2Cc2ccc(C(F)(F)F)cc2)c1] | 6-[(2,4-dimethylcyclohexyl)amino]-8-(3-methylphenyl)-7[-4-(trifluoromethyl)benzyl]-7H-purine-2-carboxylic acid | | 538 | 538 |
| 6.34 | 1141 | 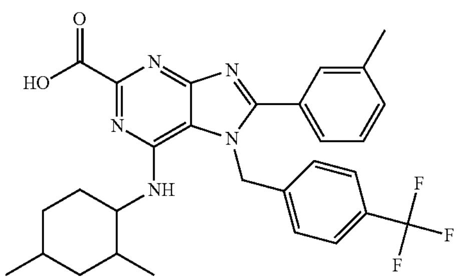 [SMILES: Cc1cccc(-c2nc3nc(C(=O)O)nc(NC4CCC(C)CC4C)c3n2Cc2ccc(C(F)(F)F)cc2)c1] | 6-[(2,4-dimethylcyclohexyl)amino]-8-(3-methylphenyl)-7[-4-(trifluoromethyl)benzyl]-7H-purine-2-carboxylic acid | | 538 | 538 |
| 6.35 | 2336 | 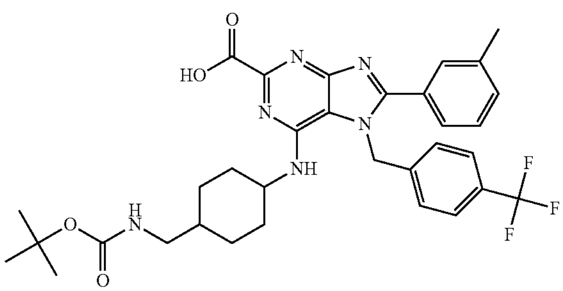 [SMILES: Cc1cccc(-c2nc3nc(C(=O)O)nc(NC4CCC(CNC(=O)OC(C)(C)C)CC4)c3n2Cc2ccc(C(F)(F)F)cc2)c1] | 6-[4-{[(tert-butoxycarbonyl)amino]methyl}cyclohexyl)amino]-8-(3-methylphenyl)-7-[4-(trifluoromethyl)benzyl]-7H-purine-2-carboxylic acid | | 639 | 639 |
| 6.36 | 670 | 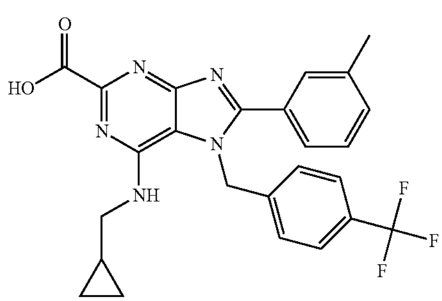 [SMILES: Cc1cccc(-c2nc3nc(C(=O)O)nc(NCC4CC4)c3n2Cc2ccc(C(F)(F)F)cc2)c1] | 6-[(cyclopropylmethyl)amino]-8-(3-methylphenyl)-7-[4-(trifluoromethyl)benzyl]-7H-purine-2-carboxylic acid | | 482 | 482 |
| 6.37 | 360 | 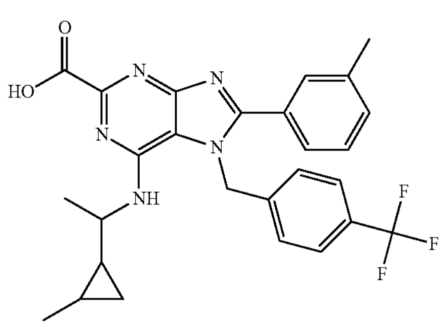 [SMILES: Cc1cccc(-c2nc3nc(C(=O)O)nc(NC(C)C4CC4C)c3n2Cc2ccc(C(F)(F)F)cc2)c1] | 6-{[1-(2-methylcyclopropyl)ethyl]amino}-8-(3-methylphenyl)-7-[4-(trifluoromethyl)benzyl]-7H-purine-2-carboxylic acid | | 510 | 510 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.38 | 530 | 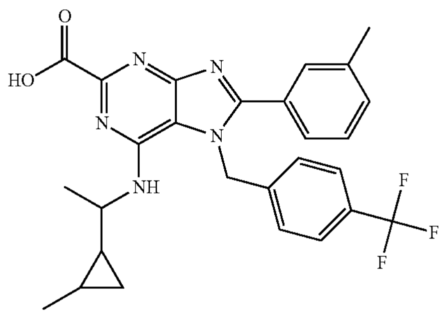 [SMILES: Cc1cccc(-c2nc3nc(C(=O)O)nc(NC(C)C4CC4C)c3n2Cc2ccc(C(F)(F)F)cc2)c1] | 6-{[1-(2-methylcyclopropyl)ethyl]amino}-8-(3-methylphenyl)-7-[4-(trifluoromethyl)benzyl]-7H-purine-2-carboxylic acid | | 510 | 510 |
| 6.39 | 2264 | 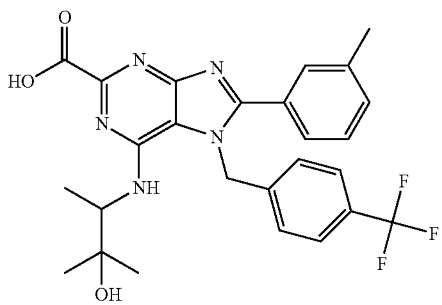 [SMILES: Cc1cccc(-c2nc3nc(C(=O)O)nc(NC(C)C(C)(C)O)c3n2Cc2ccc(C(F)(F)F)cc2)c1] | 6-[(2-hydroxy-1,2-dimethylpropyl)amino]-8-(3-methylphenyl)-7-[4-(trifluoromethyl)benzyl]-7H-purine-2-carboxylic acid | | 514 | 514 |
| 6.40 | 924.9 | 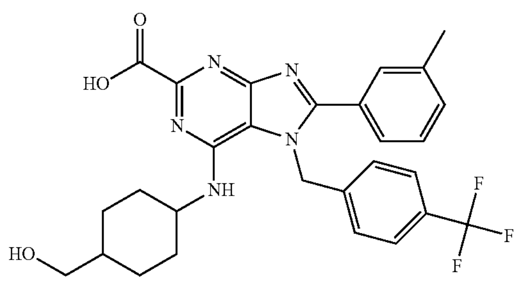 [SMILES: Cc1cccc(-c2nc3nc(C(=O)O)nc(NC4CCC(CO)CC4)c3n2Cc2ccc(C(F)(F)F)cc2)c1] | 6-{[4-(hydroxymethyl)cyclohexyl]amino}-8-(3-methylphenyl)-7-[4-(trifluoromethyl)benzyl]-7H-purine-2-carboxylic acid | | 540 | 540 |
| 6.41 | 637.6 | 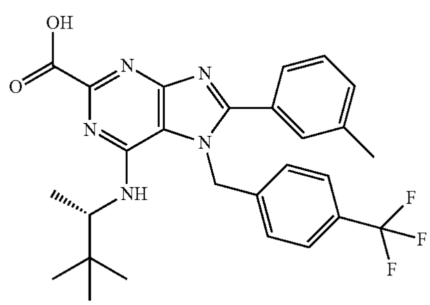 [SMILES: Cc1cccc(-c2nc3nc(C(=O)O)nc(N[C@@H](C)C(C)(C)C)c3n2Cc2ccc(C(F)(F)F)cc2)c1] | 8-3-methylphenyl)-7-[4-(trifluoromethyl)benzyl]-6-{[(1S)-1,2,2-trimethylpropyl]amino}-7H-purine-2-carboxylic acid | TFA | 512 | 512 |
| 6.42 | 564 | 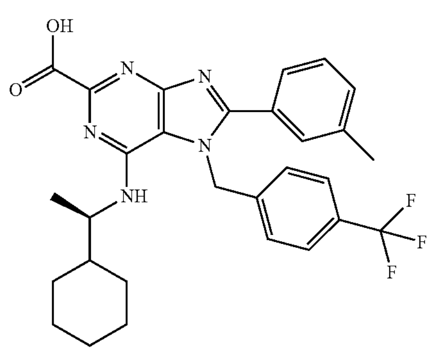 [SMILES: Cc1cccc(-c2nc3nc(C(=O)O)nc(N[C@H](C)C4CCCCC4)c3n2Cc2ccc(C(F)(F)F)cc2)c1] | 6-{[(1R)-1-cyclohexylethyl]amino}-8-(3-methylphenyl)-7-[4-(trifluoromethyl)benzyl]-7H-purine-2-carboxylic acid | TFA | 538 | 538 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.43 | 1709 | 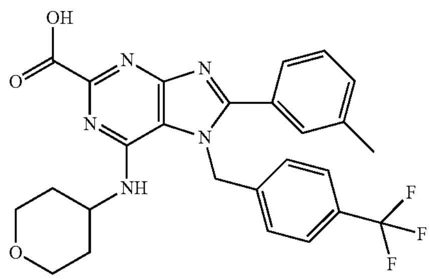 [SMILES: Cc1cccc(-c2nc3nc(C(=O)O)nc(NC4CCOCC4)c3n2Cc2ccc(C(F)(F)F)cc2)c1] | 8-(3-methylphenyl)-6-(tetrahydro-2H-pyran-4-ylamino)-7-[4-(trifluoromethyl)benzyl]-1]-7H-purine-2-carboxylic acid | TFA | 512 | 512 |
| 6.44 | 371.9 | 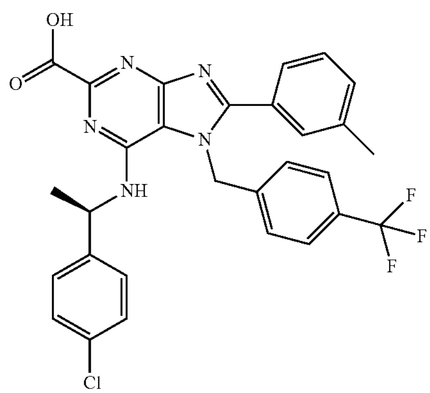 [SMILES: Cc1cccc(-c2nc3nc(C(=O)O)nc(N[C@H](C)c4ccc(Cl)cc4)c3n2Cc2ccc(C(F)(F)F)cc2)c1] | 6-{[(1R)-1-(4-chlorophenyl)ethyl]amino}-8-(3-methylphenyl)-7-[4-(trifluoromethyl)benzyl]-7H-purine-2-carboxylic acid | TFA | 566 | 566 |
| 6.45 | 1613 | 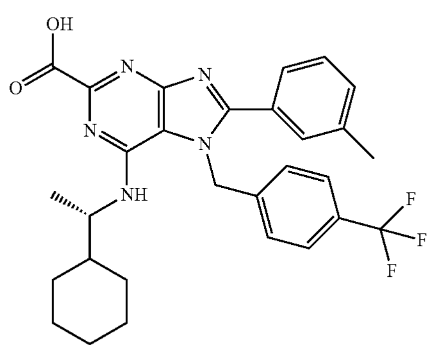 [SMILES: Cc1cccc(-c2nc3nc(C(=O)O)nc(N[C@@H](C)C4CCCCC4)c3n2Cc2ccc(C(F)(F)F)cc2)c1] | 6-{[(1S)-1-cyclohexylethyl]amino}-8-(3-methylphenyl)-7-[4-(trifluoromethyl)benzyl]-7H-purine-2-carboxylic acid | TFA | 538 | 538 |
| 6.46 | 4117 | 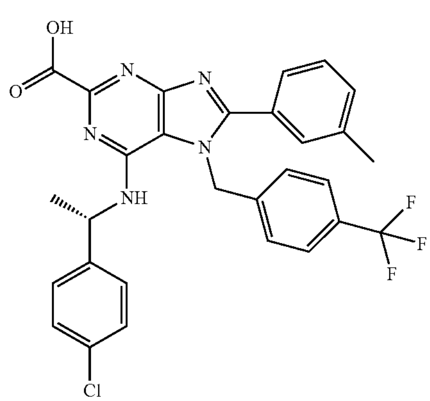 [SMILES: Cc1cccc(-c2nc3nc(C(=O)O)nc(N[C@@H](C)c4ccc(Cl)cc4)c3n2Cc2ccc(C(F)(F)F)cc2)c1] | 6-{[(1S)-1-(4-chlorophenyl)ethyl]amino}-8-(3-methylphenyl)-7-[4-(trifluoromethyl)benzyl]-7H-purine-2-carboxylic acid | TFA | 566 | 566 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.47 | 448.5 | 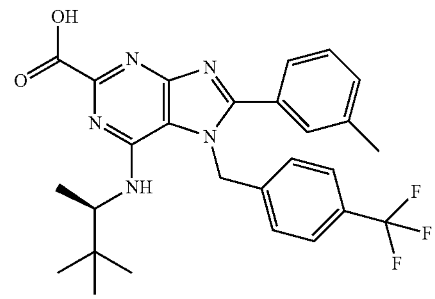 [SMILES: Cc1cccc(-c2nc3nc(C(=O)O)nc(N[C@H](C)C(C)(C)C)c3n2Cc2ccc(C(F)(F)F)cc2)c1] | 8-(3-methylphenyl)-7-[4-(trifluoromethyl)benzyl]-6-{[(1R)-1,2,2-trimethylpropyl]amino}-7H-purine-2-carboxylic acid | TFA | 512 | 512 |
| 6.48 | 145.2 | 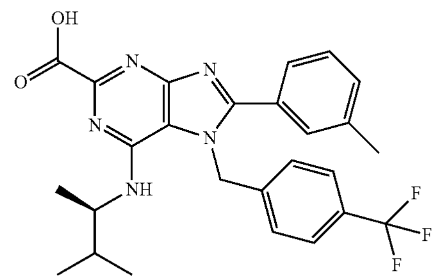 [SMILES: Cc1cccc(-c2nc3nc(C(=O)O)nc(N[C@H](C)C(C)C)c3n2Cc2ccc(C(F)(F)F)cc2)c1] | 6-{[(1R)-1,2-dimethylpropyl]amino}-8-(3-methylphenyl)-7-[4-(trifluoromethyl)benzyl]-7H-purine-2-carboxylic acid | TFA | 498 | 498 |
| 6.49 | 622.1 | 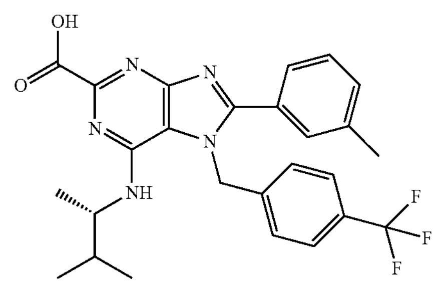 [SMILES: Cc1cccc(-c2nc3nc(C(=O)O)nc(N[C@@H](C)C(C)C)c3n2Cc2ccc(C(F)(F)F)cc2)c1] | 6-{[(1S)-1,2-dimethylpropyl]amino}-8-(3-methylphenyl)-7-[4-(trifluoromethyl)benzyl]-7H-purine-2-carboxylic acid | TFA | 498 | 498 |
| 6.50 | 1371 | 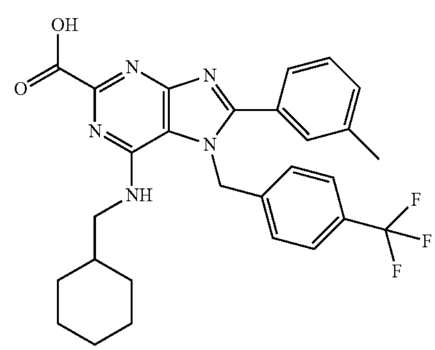 [SMILES: Cc1cccc(-c2nc3nc(C(=O)O)nc(NCC4CCCCC4)c3n2Cc2ccc(C(F)(F)F)cc2)c1] | 6-[(cyclohexylmethyl)amino]-8-(3-methylphenyl)-7-[4-(trifluoromethyl)benzyl]-7H-purine-2-carboxylic acid | TFA | 524 | 524 |
| 6.51 | 4596 | 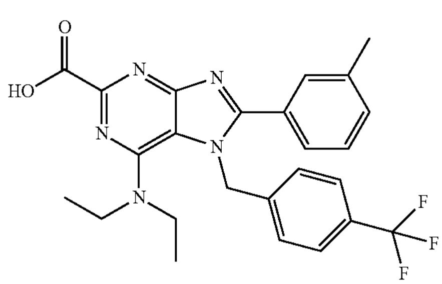 [SMILES: CCN(CC)c1nc(C(=O)O)nc2nc(-c3cccc(C)c3)n(Cc3ccc(C(F)(F)F)cc3)c12] | 6-(diethylamino)-8-(3-methylphenyl)-7-[-4-(trifluoromethyl)benzyl]-7H-purine-2-carboxylic acid | | 484 | 484 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.52 | 318.6 | 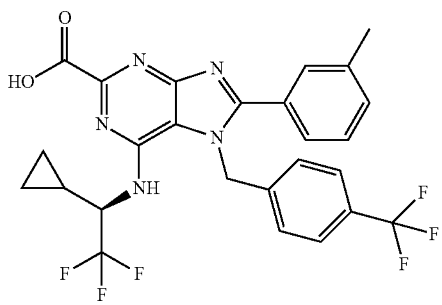 [SMILES: Cc1cccc(-c2nc3nc(C(=O)O)nc(N[C@H](C4CC4)C(F)(F)F)c3n2Cc2ccc(C(F)(F)F)cc2)c1] | 6-{[(1R)-1-cyclopropyl-2,2,2-trifluoroethyl]amino}-8-(3-methylphenyl)-7-[4-(trifluoromethyl)benzyl]-7H-purine-2-carboxylic acid | | 550 | 550 |
| 6.53 | 419.3 | 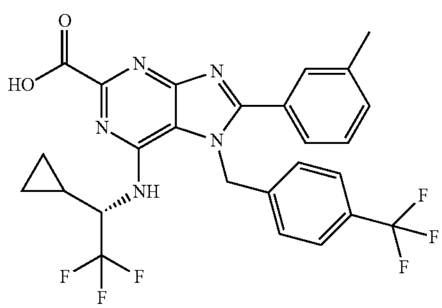 [SMILES: Cc1cccc(-c2nc3nc(C(=O)O)nc(N[C@@H](C4CC4)C(F)(F)F)c3n2Cc2ccc(C(F)(F)F)cc2)c1] | 6-{[(1S)-1-cyclopropyl-2,2,2-trifluoroethyl]amino}-8-(3-methylphenyl)-7-[4-(trifluoromethyl)benzyl]-7H-purine-2-carboxylic acid | | 550 | 550 |
| 6.54 | 203.3 | 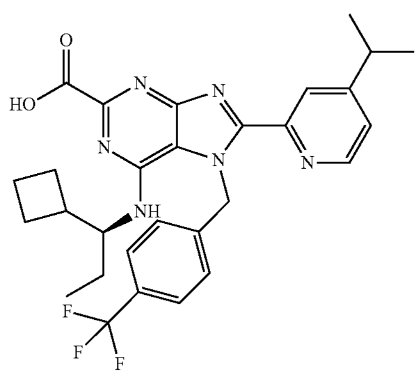 [SMILES: CC[C@H](Nc1nc(C(=O)O)nc2nc(-c3cc(C(C)C)ccn3)n(Cc3ccc(C(F)(F)F)cc3)c12)C1CCC1] | 6-{[(1S)-1-cyclobutylpropyl]amino}-8-[4-[1-methylethyl)pyridin-2-yl]-7-[4-(trifluoromethyl)benzyl]-7H-purine-2-carboxylic acid | TFA | 553 | 553 |
| 6.55 | 9.267 | 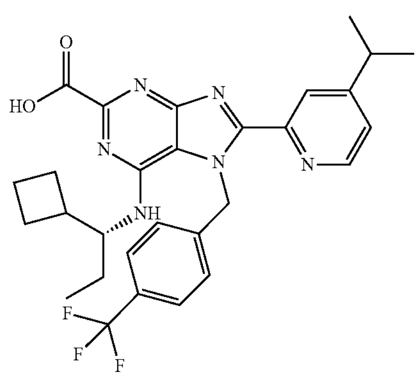 [SMILES: CC[C@@H](Nc1nc(C(=O)O)nc2nc(-c3cc(C(C)C)ccn3)n(Cc3ccc(C(F)(F)F)cc3)c12)C1CCC1] | 6-{[(1R)-1-cyclobutylpropyl]amino}-8-[4-[1-methylethyl)pyridin-2-yl]-7-[4-(trifluoromethyl)benzyl]-7H-purine-2-carboxylic acid | TFA | 553 | 553 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.56 | 1415 | 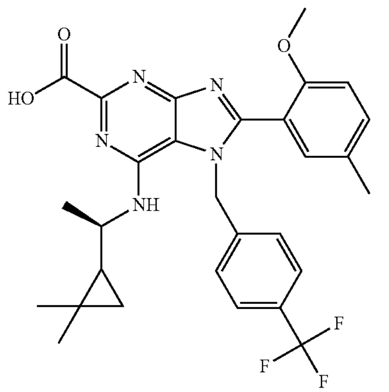 [SMILES: COc1ccc(C)cc1-c1nc2nc(C(=O)O)nc(N[C@H](C)C3CC3(C)C)c2n1Cc1ccc(C(F)(F)F)cc1] | 6-{[(1R)-1-(2,2-dimethylcyclopropyl)ethyl]amino}-8-(2-methoxy-5-methylphenyl)-7-[4-(trifluoromethyl)benzyl]-7H-purine-2-carboxylic acid | | 554 | 554 |
| 6.57 | 1061 | 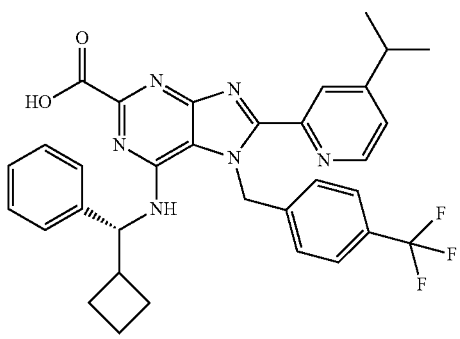 [SMILES: CC(C)c1ccnc(-c2nc3nc(C(=O)O)nc(N[C@@H](c4ccccc4)C4CCC4)c3n2Cc2ccc(C(F)(F)F)cc2)c1] | 6-{[(R)-cyclobutyl(phenyl)methyl]amino}-8-[4(1-methylethyl)pyridin-2-yl]-7-[4-(trifluoromethyl)benzyl]-7H-purine-2-carboxylic acid | TFA | 601 | 601 |
| 6.58 | 49.23 | 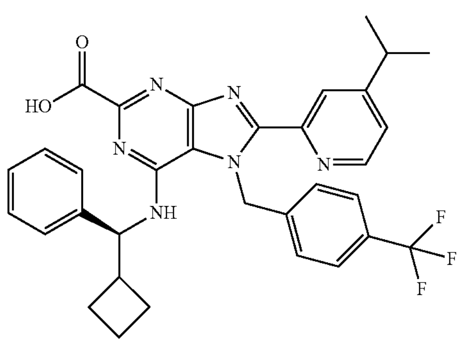 [SMILES: CC(C)c1ccnc(-c2nc3nc(C(=O)O)nc(N[C@H](c4ccccc4)C4CCC4)c3n2Cc2ccc(C(F)(F)F)cc2)c1] | 6-{[(S)-cyclobutyl(phenyl)methhyl]amino}-8-[4-(1-methylethyl)pyridin-2-yl]-7-[4-(trifluoromethyl)benzyl]-7H-purine-2-carboxylic acid | TFA | 601 | 601 |
| 6.59 | 1000 | 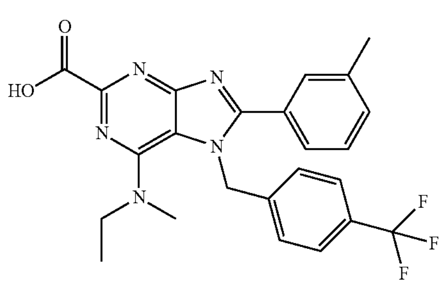 [SMILES: CCN(C)c1nc(C(=O)O)nc2nc(-c3cccc(C)c3)n(Cc3ccc(C(F)(F)F)cc3)c12] | 6-[ethyl(methyl)amino]-8-(3-methylphenyl)-7-[4-(trifluoromethyl)benzyl]-7H-purine-2-carboxylic acid | TFA | 470 | 470 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.60 | 583.2 | 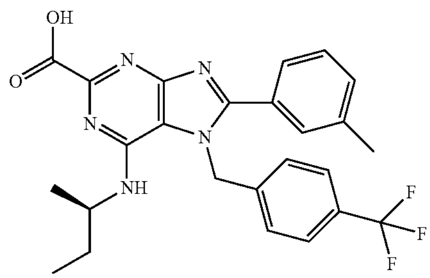 [SMILES: CC[C@@H](C)Nc1nc(C(=O)O)nc2nc(-c3cccc(C)c3)n(Cc3ccc(C(F)(F)F)cc3)c12] | 8-(3-methylphenyl)-6-{[(1R)-1-methylpropyl]amino}-7-[4-(trifluoromethyl)benzyl]-7H-purine-2-carboxylic acid | TFA | 484 | 484 |
| 6.61 | 41% inh. at 1000 nM | 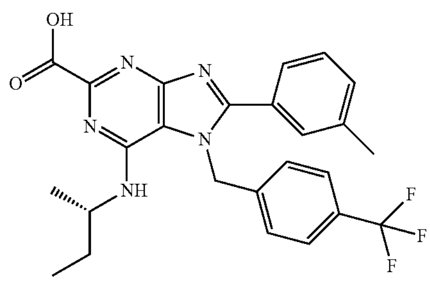 [SMILES: CC[C@H](C)Nc1nc(C(=O)O)nc2nc(-c3cccc(C)c3)n(Cc3ccc(C(F)(F)F)cc3)c12] | 8-(3-methylphenyl)-6-{[1S)-1-methylpropyl]amino}-7-[4-(trifluoromethyl)benzyl]-7H-purine-2-carboxylic acid | TFA | 484 | 484 |
| 6.62 | 34% inh. at 1000 nM | 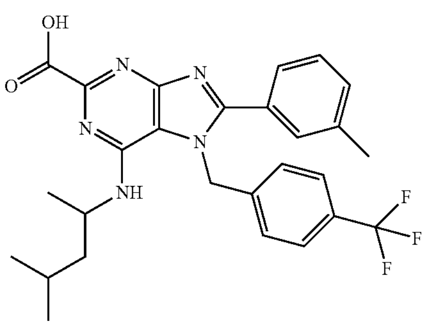 [SMILES: Cc1cccc(-c2nc3nc(C(=O)O)nc(NC(C)CC(C)C)c3n2Cc2ccc(C(F)(F)F)cc2)c1] | 6-[(1,3-dimethylbutyl)amino]-8-(3-methylphenyl)-7-[4-(trifluoromethyl)benzyl]-7H-purine-2-carboxylic acid | TFA | 512 | 512 |
| 6.63 | 719 | 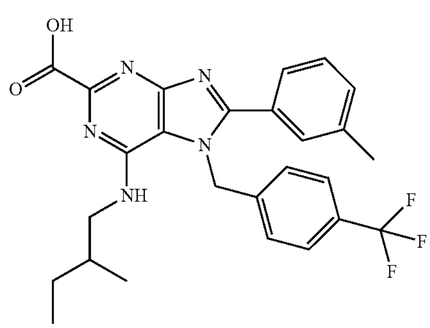 [SMILES: CCC(C)CNc1nc(C(=O)O)nc2nc(-c3cccc(C)c3)n(Cc3ccc(C(F)(F)F)cc3)c12] | 6-[(2-methylbutyl)amino]-8-(3-methylphenyl)-7-[4-(trifluoromethyl)benzyl]-7H-purine-2-carboxylic acid | TFA | 498 | 498 |
| 6.64 | 920.3 | 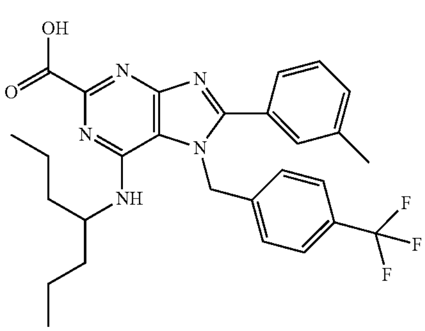 [SMILES: CCCC(CCC)Nc1nc(C(=O)O)nc2nc(-c3cccc(C)c3)n(Cc3ccc(C(F)(F)F)cc3)c12] | 8-(3-methylphenyl)-6-[(1-propylbutyl)amino]-7-[4-(trifluoromethyl)benzyl]-7H-purine-2-carboxylic acid | TFA | 526 | 526 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.65 | 35% inh. at 1000 nM | 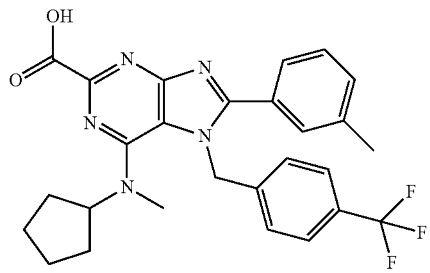 [SMILES: Cc1cccc(-c2nc3nc(C(=O)O)nc(N(C)C4CCCC4)c3n2Cc2ccc(C(F)(F)F)cc2)c1] | 6-[cyclopentyl(methyl)amino]-8-(3-methylphenyl)-7-[4-(trifluoromethyl)benzyl]-7H-purine-2-carboxylic acid | TFA | 510 | 510 |
| 6.66 | 46% inh. at 1000 nM | 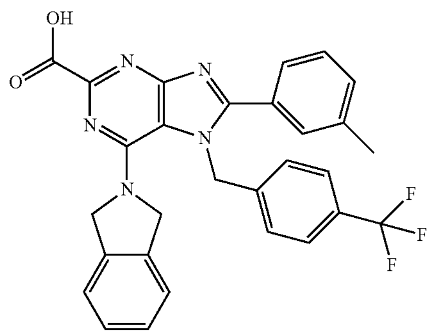 [SMILES: Cc1cccc(-c2nc3nc(C(=O)O)nc(N4Cc5ccccc5C4)c3n2Cc2ccc(C(F)(F)F)cc2)c1] | 6-(1,3-dihydro-2H-isoindol-2-yl)-8-(3-methylphenyl)-7-[4-(trifluoromethyl)benzyl]-7H-purine-2-carboxylic acid | TFA | 530 | 530 |
| 6.67 | 30% inh. at 1000 nM | 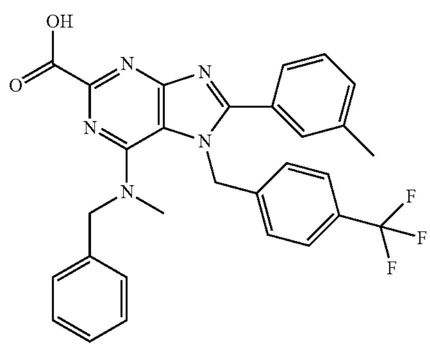 [SMILES: Cc1cccc(-c2nc3nc(C(=O)O)nc(N(C)Cc4ccccc4)c3n2Cc2ccc(C(F)(F)F)cc2)c1] | 6-[benzyl(methyl)amino]-8-(3-methylphenyl)-7-[4-(trifluoromethyl)benzyl]-7H-purine-2-carboxylic acid | TFA | 532 | 532 |
| 6.68 | 681.2 | 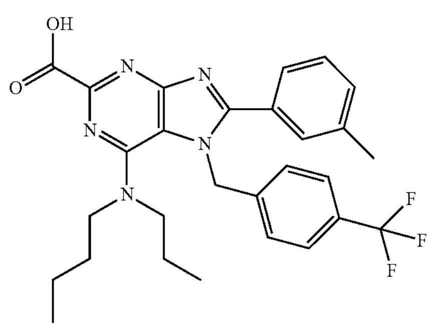 [SMILES: CCCCN(CCC)c1nc(C(=O)O)nc2nc(-c3cccc(C)c3)n(Cc3ccc(C(F)(F)F)cc3)c12] | 6-[butyl(propyl)amino]-8-(3-methylphenyl)-7-[4-(trifluoromethyl)benzyl]-7H-purine-2-carboxylic acid | TFA | 526 | 526 |
| 6.69 | 620.6 | 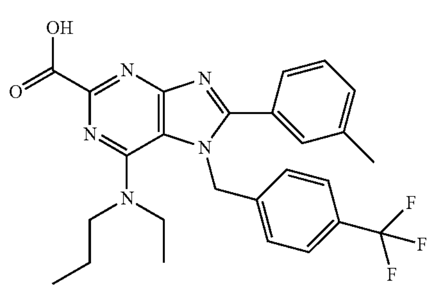 [SMILES: CCCN(CC)c1nc(C(=O)O)nc2nc(-c3cccc(C)c3)n(Cc3ccc(C(F)(F)F)cc3)c12] | 6-[butyl(ethyl)amino]-8-(3-methylphenyl)-7-[4-(trifluoromethyl)benzyl]-7H-purine-2-carboxylic acid | TFA | 512 | 512 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.70 | 39% inh. at 1000 nM | 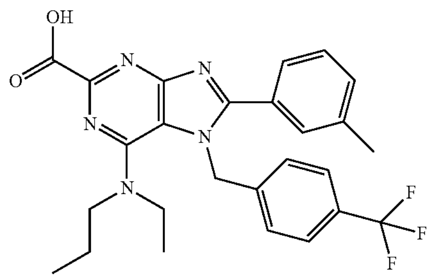 [SMILES: CCCN(CC)c1nc(C(=O)O)nc2nc(-c3cccc(C)c3)n(Cc3ccc(C(F)(F)F)cc3)c12] | 6-[ethyl(propyl)amino]-8-(3-methylphenyl)-7-[4-(trifluoromethyl)benzyl]-7H-purine-2-carboxylic acid | TFA | 498 | 498 |
| 6.71 | 940.4 | 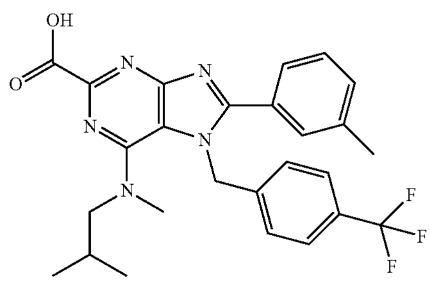 [SMILES: Cc1cccc(-c2nc3nc(C(=O)O)nc(N(C)CC(C)C)c3n2Cc2ccc(C(F)(F)F)cc2)c1] | 6-[methyl(2-methylpropyl)amino]-8-(3-methylphenyl)-7-[4-(trifluoromethyl)benzyl]-7H-purine-2-carboxylic acid | TFA | 498 | 498 |
| 6.72 | 40% inh. at 1000 nM | 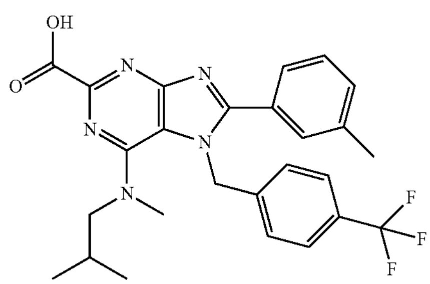 [SMILES: Cc1cccc(-c2nc3nc(C(=O)O)nc(N(C)CC(C)C)c3n2Cc2ccc(C(F)(F)F)cc2)c1] | 6-[methyl(2-methylpropyl)amino]-8-(3-methylphenyl)-7-[4-(trifluoromethyl)benzyl]-7H-purine-2-carboxylic acid | Ammonium salt | 498 | 498 |
| 6.73 | 437.3 | 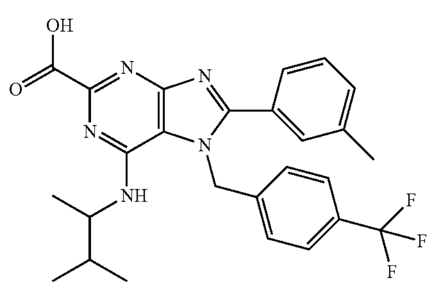 [SMILES: Cc1cccc(-c2nc3nc(C(=O)O)nc(NC(C)C(C)C)c3n2Cc2ccc(C(F)(F)F)cc2)c1] | 6-[(1,2-dimethylpropyl)amino]-8-(3-methylphenyl)-7-[4-(trifluoromethyl)benzyl]-7H-purine-2-carboxylic acid | TFA | 498 | 498 |
| 6.74 | 552.5 | 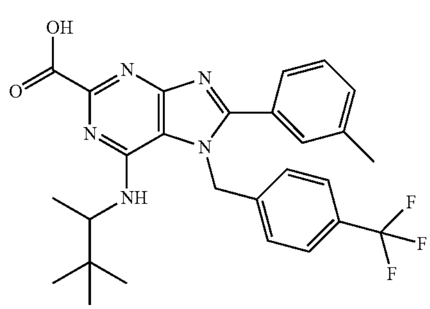 [SMILES: Cc1cccc(-c2nc3nc(C(=O)O)nc(NC(C)C(C)(C)C)c3n2Cc2ccc(C(F)(F)F)cc2)c1] | 8-(3-methylphenyl)-7-[4-(trifluoromethyl)benzy]-6-[(1,2,2-trimethylpropyl)amino]-7H-purine-2-carboxylic acid | TFA | 512 | 512 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.75 | 167.3 | 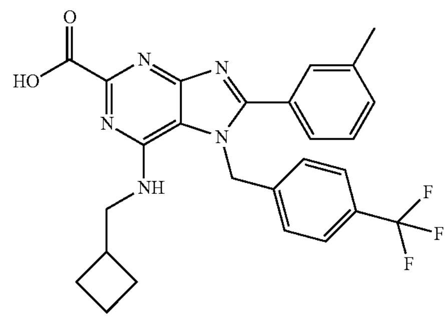 [SMILES: Cc1cccc(-c2nc3nc(C(=O)O)nc(NCC4CCC4)c3n2Cc2ccc(C(F)(F)F)cc2)c1] | 6-[(cyclobutylmethyl)amino]-8-(3-methylphenyl)-7-[4-(trifluoromethyl)benzyl]-7H-purine-2-carboxylic acid | TFA | 496 | 496 |
| 6.76 | 32% inh. at 1000 nM | 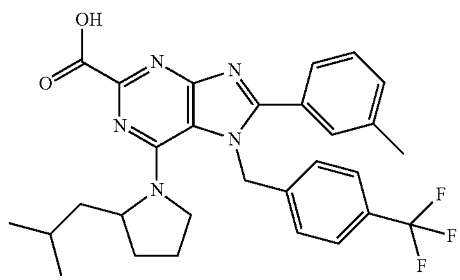 [SMILES: Cc1cccc(-c2nc3nc(C(=O)O)nc(N4CCCC4CC(C)C)c3n2Cc2ccc(C(F)(F)F)cc2)c1] | 8-(3-methylphenyl)-6-[2-(2-methylpropyl)pyrrolidin-1-yl]-7-[4-(trifluoromethyl)benzyl]-7H-purine-2-carboxylic acid | TFA | 538 | 538 |
| 6.77 | 36% inh. at 1000 nM | 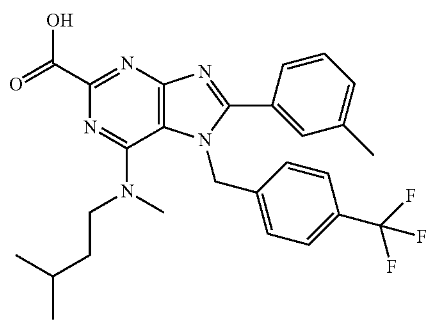 [SMILES: Cc1cccc(-c2nc3nc(C(=O)O)nc(N(C)CCC(C)C)c3n2Cc2ccc(C(F)(F)F)cc2)c1] | 6-[methyl(3-methylbutyl)amino]-8-(3-methylphenyl)-7-[4-(trifluoromethyl)benzyl]-7H-purine-2-carboxylic acid | TFA | 512 | 512 |
| 6.78 | 33% inh. at 1000 nM | 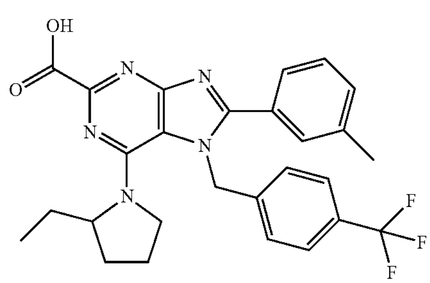 [SMILES: CCC1CCCN1c1nc(C(=O)O)nc2nc(-c3cccc(C)c3)n(Cc3ccc(C(F)(F)F)cc3)c12] | 6-(2-ethylpyrrolidin-1-yl)-8-(3-methylphenyl)-7-[4-(trifluoromethyl)benzyl]-7H-purine-2-carboxylic acid | TFA | 510 | 510 |
| 6.79 | 43% inh. at 1000 nM | 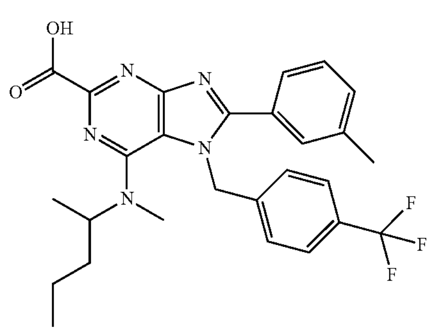 [SMILES: CCCC(C)N(C)c1nc(C(=O)O)nc2nc(-c3cccc(C)c3)n(Cc3ccc(C(F)(F)F)cc3)c12] | 6-[methyl(1-methylbutyl)amino]-8-(3-methylphenyl)-7-[4-(trifluoromethyl)benzyl]-7H-purine-2-carboxylic acid | TFA | 512 | 512 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.80 | 40% inh. at 1000 nM | 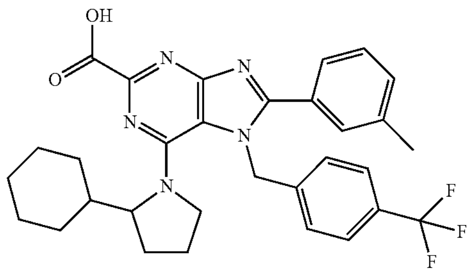 [SMILES: Cc1cccc(-c2nc3nc(C(=O)O)nc(N4CCCC4C4CCCCC4)c3n2Cc2ccc(C(F)(F)F)cc2)c1] | 6-(2-cyclohexylpyrrolidin-1-yl)-8-(3-methylphenyl)-7-[4-(trifluoromethyl)benzyl]-7H-purine-2-carboxylic acid | TFA | 564 | 564 |
| 6.81 | 46% inh. at 1000 nM | 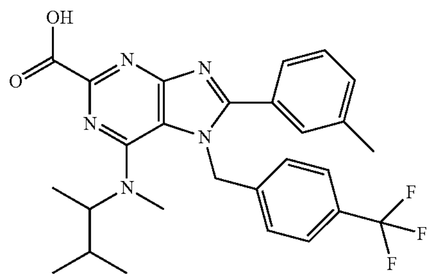 [SMILES: Cc1cccc(-c2nc3nc(C(=O)O)nc(N(C)C(C)C(C)C)c3n2Cc2ccc(C(F)(F)F)cc2)c1] | 6-[(1,2-dimethylpropyl)(methyl)amino]-8-(3-methylphenyl)-7-[4-(trifluoromethyl)benzyl]-7H-purine-2-carboxylic acid | TFA | 512 | 512 |
| 6.82 | 899.2 | 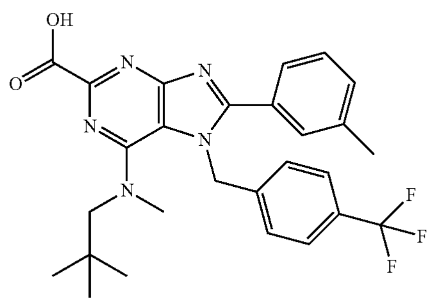 [SMILES: Cc1cccc(-c2nc3nc(C(=O)O)nc(N(C)CC(C)(C)C)c3n2Cc2ccc(C(F)(F)F)cc2)c1] | 6-[(2,2-dimethylpropyl)(methyl)amino]-8-(3-methylphenyl)-7-[4-(trifluoromethyl)benzyl]-7H-purine-2-carboxylic acid | TFA | 512 | 512 |
| 6.83 | 833.7 | 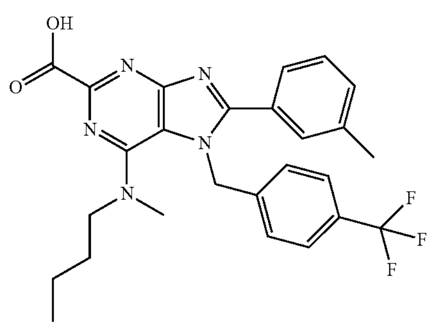 [SMILES: CCCCN(C)c1nc(C(=O)O)nc2nc(-c3cccc(C)c3)n(Cc3ccc(C(F)(F)F)cc3)c12] | 6-[butyl(methyl)amino]-8-(3-methylphenyl)-7-[4-(trifluoromethyl)benzyl]-7H-purine-2-carboxylic acid | TFA | 498 | 498 |
| 6.84 | 46% inh. at 1000 nM | 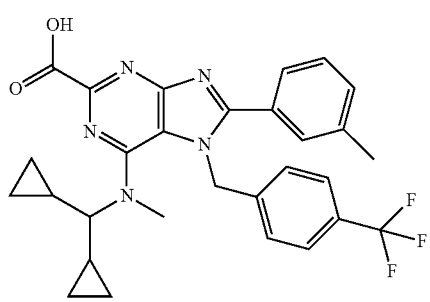 [SMILES: Cc1cccc(-c2nc3nc(C(=O)O)nc(N(C)C(C4CC4)C4CC4)c3n2Cc2ccc(C(F)(F)F)cc2)c1] | 6-[(dicyclopropylmethyl)(methyl)amino]-8-(3-methylphenyl)-7-[4-(trifluoromethyl)benzyl]-7H-purine-2-carboxylic acid | TFA | 536 | 536 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.85 | 722.9 | 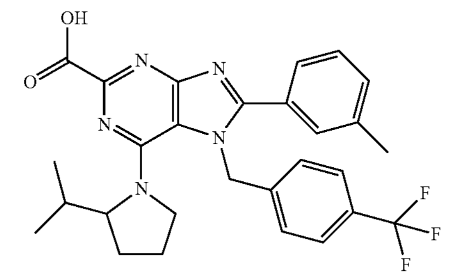 [SMILES: Cc1cccc(-c2nc3nc(C(=O)O)nc(N4CCCC4C(C)C)c3n2Cc2ccc(C(F)(F)F)cc2)c1] | 6-[2-(1-methylethyl)pyrrolidin-1-yl]-8-(3-methylphenyl)-7-[4-(trifluoromethyl)benzyl]-7H-purine-2-carboxylic acid | TFA | 524 | 524 |
| 6.86 | 754.2 | 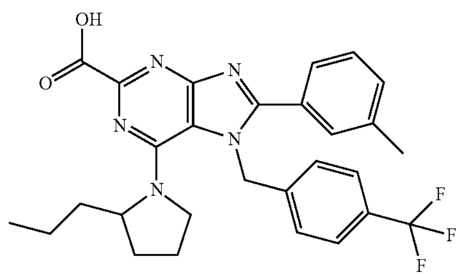 [SMILES: CCCC1CCCN1c1nc(C(=O)O)nc2nc(-c3cccc(C)c3)n(Cc3ccc(C(F)(F)F)cc3)c12] | 8-(3-methylphenyl)-6-(2-propylpyrrolidin-l-yl)-7-[4-(trifluoromethyl)benzyl]-7H-purine-2-carboxylic acid | TFA | 524 | 524 |
| 6.87 | 43% inh. at 1000 nM | 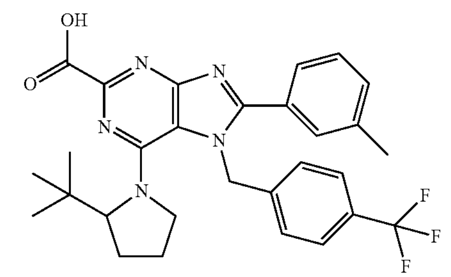 [SMILES: Cc1cccc(-c2nc3nc(C(=O)O)nc(N4CCCC4C(C)(C)C)c3n2Cc2ccc(C(F)(F)F)cc2)c1] | 6-(2-tert-butylpyrrolidin-l-yl)-8-(3-methylphenyl)-7-[4-(trifluoromethyl)benzyl]-7H-purine-2-carboxylic acid | TFA | 538 | 538 |
| 6.88 | 33% inh. at 1000 nM | 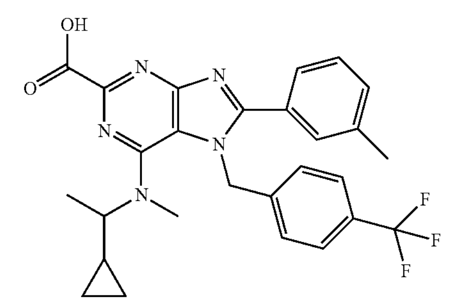 [SMILES: Cc1cccc(-c2nc3nc(C(=O)O)nc(N(C)C(C)C4CC4)c3n2Cc2ccc(C(F)(F)F)cc2)c1] | 6-[(1-cyclopropylethyl)(methyl)amino]-8-(3-methylphenyl)-7-[4-(trifluoromethyl)benzyl]-7H-purine-2-carboxylic acid | TFA | 510 | 510 |
| 6.89 | 729.9 | 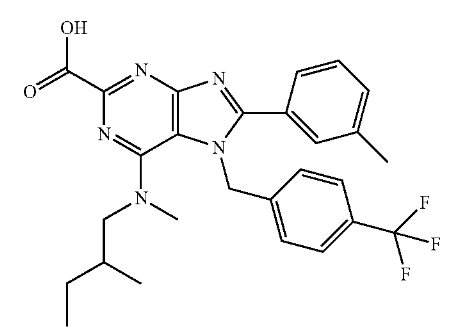 [SMILES: CCC(C)CN(C)c1nc(C(=O)O)nc2nc(-c3cccc(C)c3)n(Cc3ccc(C(F)(F)F)cc3)c12] | 6-[methyl(2-methylbutyl)amino]-8-(3-methylphenyl)-7-[4-(trifluoromethyl)benzyl]-7H-purine-2-carboxylic acid | TFA | 512 | 512 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.90 | 34% inh. at 1000 nM | 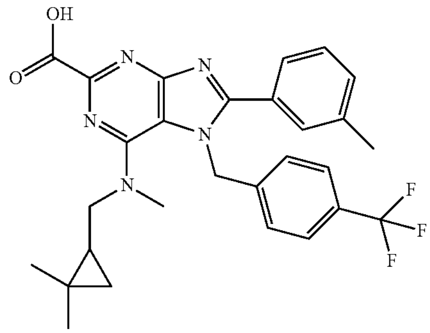 [SMILES: Cc1cccc(-c2nc3nc(C(=O)O)nc(N(C)CC4CC4(C)C)c3n2Cc2ccc(C(F)(F)F)cc2)c1] | 6-{[(2,2-dimethylcyclopropyl)methyl](methyl)amino}-8-(3-methylphenyl)-7-[4-(trifluoromethyl)benzyl]-7H-purine-2-carboxylic acid | TFA | 524 | 524 |
| 6.91 | 731.2 | 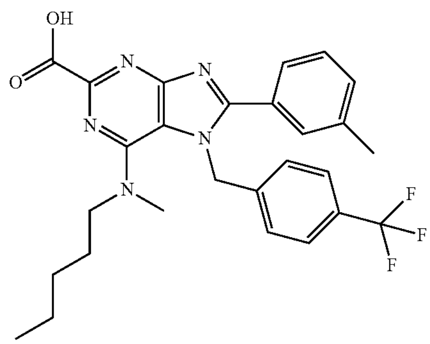 [SMILES: CCCCCN(C)c1nc(C(=O)O)nc2nc(-c3cccc(C)c3)n(Cc3ccc(C(F)(F)F)cc3)c12] | 6-[methyl(pentyl)amino]-8-(3-methylphenyl)-7-[4-(trifluoromethyl)benzyl]-7H-purine-2-carboxylic acid | TFA | 512 | 512 |
| 6.92 | 352.1 | 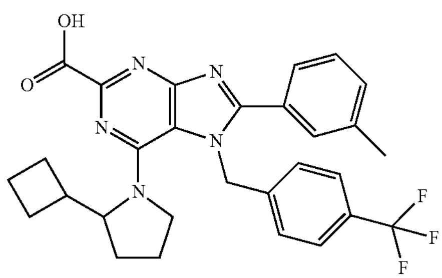 [SMILES: Cc1cccc(-c2nc3nc(C(=O)O)nc(N4CCCC4C4CCC4)c3n2Cc2ccc(C(F)(F)F)cc2)c1] | 6-(2-cyclobutylpyrrolidin-1-yl)-8-(3-methylphenyl)-7-[4-(trifluoromethyl)benzyl]-7H-purine-2-carboxylic acid | TFA | 536 | 536 |
| 6.93 | 805.6 | 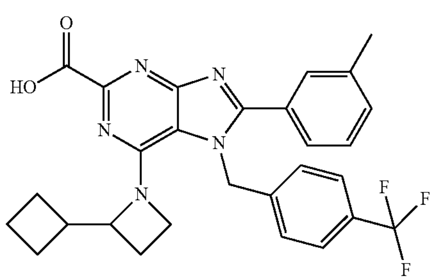 [SMILES: Cc1cccc(-c2nc3nc(C(=O)O)nc(N4CCC4C4CCC4)c3n2Cc2ccc(C(F)(F)F)cc2)c1] | 6-(2-cyclobutylazetidin-1-yl)-8-(3-methylphenyl)-7-[4-(trifluoromethyl)benzyl]-7H-purine-2-carboxylic acid | TFA | 522 | 522 |
| 6.94 | 32% inh. at 1000 nM | 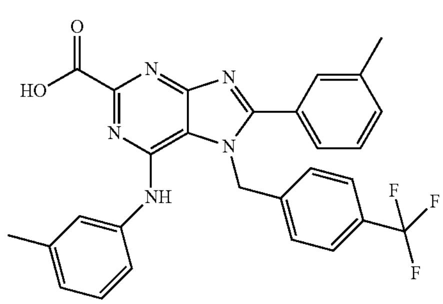 [SMILES: Cc1cccc(Nc2nc(C(=O)O)nc3nc(-c4cccc(C)c4)n(Cc4ccc(C(F)(F)F)cc4)c23)c1] | 8-(3-methylphenyl)-6-[(3-methylphenyl)amino]-7-[4-(trifluoromethyl)benzyl]-1]-7H-purine-2-carboxylic acid | TFA | 518 | 518 |

TABLE 6-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 6.95 | 270.6 | 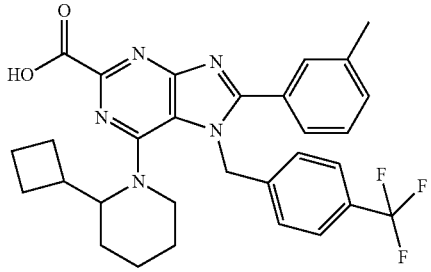 [SMILES: Cc1cccc(-c2nc3nc(C(=O)O)nc(N4CCCCC4C4CCC4)c3n2Cc2ccc(C(F)(F)F)cc2)c1] | 6-(2-cyclobutylpiperidin-1-yl)-8-(3-methylphenyl)-7-[4-(trifluoromethyl)benzyl]-7H-purine-2-carboxylic acid | TFA | 550 | 550 |

Preparative Example 7.1

(R)-1-cyclobutylbut-3-en-1-amine

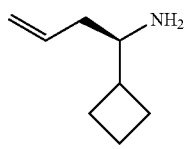

Step 1: Cyclobutanemethanol (10.0 g, 116 mmol) was dissolved in CH$_2$Cl$_2$ (600 mL). Dess-Martin periodinane (60.0 g, 141 mmol) was added portion wise at 0° C. under a nitrogen atmosphere. The reaction was raised to room temperature and was stirred for 3 h. The reaction mixture was filtered through celite. To the filtrate was added cesium carbonate (71.0 g, 218 mmol) and (R)-t-butyl sulfinamide (15.4 g, 127 mmol) and the reaction was stirred at room temperature for 12 h. The reaction mixture was quenched with sodium chloride solution and filtered through a pad of celite. The organic layer was washed with water and brine solution. The organic layer was then dried over sodium sulfate and concentrated under reduced pressure. The crude product was purified by silica gel chromatography to afford (E)-N-(cyclobutylmethylene)-2-methylpropane-2-sulfinamide. $^1$H NMR (300 MHz, CDCl$_3$) δ 8.12 (d, J=4.8 Hz, 1H), 3.33-3.40 (m, 1H), 2.18-2.28 (m, 4H), 2.00-2.06 (m, 2H), 1.20 (s, 9H).

Step 2: (E)-N-(cyclobutylmethylene)-2-methylpropane-2-sulfinamide (10.0 g, 53.4 mmol) was dissolved in HMPA (200 mL) and water (2.0 mL). Active zinc powder (4.0 g, 64 mmol) was added followed by allyl bromide (7.7 g, 64 mmol). The reaction mixture was stirred at room temperature for 24 hours under a nitrogen atmosphere. Then 1N aqueous HCl (5 mL) was added and the mixture was extracted with EtOAc, washed with brine solution and dried over anhydrous Na$_2$SO$_4$. The organic layer was concentrated under reduced pressure, and the resultant residue was purified by silica gel chromatography to afford N—((R)-1-cyclobutylbut-3-en-1-yl)-2-methylpropane-2-sulfinamide.
$^1$H NMR (300 MHz, CDCl$_3$) δ 5.77 (m, 1H), 5.04-5.17 (m, 2H), 3.22-3.40 (m, 2H), 2.18-2.38 (m, 5H), 2.00-2.06 (m, 3H), 1.20 (s, 9H).

Step 3: N—((R)-1-cyclobutylbut-3-en-1-yl)-2-methylpropane-2-sulfinamide (7.0 g, 30.5 mmol) was dissolved in methanol. HCl (30 mL, 4N solution in 1,4-dioxane) was added at 0° C. The reaction mixture was raised to room temperature and stirred for 3 hours. The reaction mixture was concentrated in vacuo and washed with aqueous sodium hydroxide to afford (R)-1-cyclobutylbut-3-en-1-amine hydrochloride. $^1$H NMR (300 MHz, CDCl$_3$) δ 5.79-5.88 (m, 1H), 5.19-5.28 (m, 2H), 3.17-3.22 (m, 1H), 2.63-2.66 (m, 1H), 2.41-2.45 (m, 2H), 1.77-2.12 (m, 6H).

Preparative Example 7.2

2,6-dichloro-7-(4-chlorobenzyl)-8-(3-methylphenyl)-7H-purine

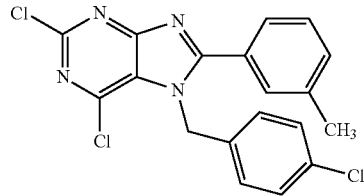 [SMILES: Cc1cccc(-c2nc3nc(Cl)nc(Cl)c3n2Cc2ccc(Cl)cc2)c1]

Step 1: 6-Amino-5-((4-chlorobenzyl)amino)-1-methylpyrimidine-2,4(1H,3H)-dione (Preparative Example 4.1, 10.2 g, 36.6 mmol) was suspended in anhydrous CH$_2$Cl$_2$ (150 mL) and N,N-diisopropyl ethylamine (9.5 g, 73 mmol) was added to the suspension. A solution of 3-methylbenzoyl chloride (8.5 g, 55 mmol) in CH$_2$Cl$_2$ (100 mL) was added to the amine slowly at 0° C. over 10 minutes. The reaction mixture was stirred at room temperature for 12 hours. The reaction mixture was then diluted with water (100 mL) and CH$_2$Cl$_2$ (300 mL) and the organic layer was separated. The aqueous layer was further extracted with CH$_2$Cl$_2$ (200 mL). The combined organic layers were washed with saturated aqueous NaHCO$_3$ (100 mL), water (200 mL), brine (100 mL), dried over anhydrous Na$_2$SO$_4$, filtered and concentrated in vacuo. The crude N-(6-amino-1-methyl-2,4-dioxo-1,2,3,4-tetrahydropyrimidin-5-yl)-N-(4-chlorobenzyl)-3-methylbenzamide was taken forward without further purification. $^1$H NMR (300 MHz, DMSO-d$_6$): δ10.30 (s, 1H), 7.90 (d, J=8.4 Hz, 1H), 7.08-7.44 (m, 9H), 4.95 (d, J=14.1 Hz, 1H), 4.30 (d, J=14.1 Hz, 1H), 3.09 (s, 3H), 2.23 (s, 3H).

Step 2: N-(6-amino-1-methyl-2,4-dioxo-1,2,3,4-tetrahydropyrimidin-5-yl)-N-(4-chlorobenzyl)-3-methylbenzamide (6.0 g, 15 mmol) was dissolved in ethanol (100 mL) and sodium hydroxide (3.0 g, 75 mmol) was added and the resultant reaction mixture was heated to reflux for 12 hours. The reaction mixture was cooled to room temperature and ethanol was removed under reduced pressure. The white residue was dissolved in water (10 mL) and the mixture was extracted with EtOAc (50 mL). The organic layer was washed with water and brine, dried over anhydrous $Na_2SO_4$, filtered and concentrated in vacuo. The residue was purified by silica gel chromatography (eluent 3% $MeOH/CH_2Cl_2$) to obtain 9-(4-chlorobenzyl)-3-methyl-8-(3-methylphenyl)-1H-purine-2,6(3H,9H)-dione as a white solid. $^1$H NMR (400 MHz, $CDCl_3$): δ7.33-7.43 (m, 6H), 7.03 (d, J=8.7 Hz, 2H), 5.60 (s, 2H), 3.40 (s, 3H), 2.30 (s, 3H).

Step 3: 9-(4-Chlorobenzyl)-3-methyl-8-(3-methylphenyl)-1H-purine-2,6(3H,9H)-dione (5.0 g, 13 mmol) was dissolved in $POCl_3$ (50 mL) and the mixture was heated at 60° C. before adding DBU (20 mL) and increasing the temperature to 120° C. for 2 hours. The reaction mixture was cooled to room temperature and poured into ice water and the resulting brown precipitate was collected by filtration and air-dried. The brown solid was purified by column chromatography (eluent 45% EtOAc/hexanes) to afford 2,6-dichloro-7-(4-chlorobenzyl)-8-(5-methylphenyl)-7H-purine as white solid. $^1$H NMR (300 MHz, $CDCl_3$): δ 7.37-7.51 (m, 6H), 7.15 (d, J=8.7 Hz, 2H), 5.70 (s, 2H), 2.30 (s, 3H).

Example 7.1

7-(4-chlorobenzyl)-6-{[(1R)-1-cyclobutyl-4-hydroxybutyl]amino}-8-(3-methylphenyl)-7H-purine-2-carboxylic acid

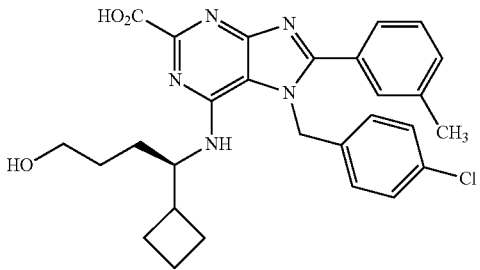 [SMILES: Cc1cccc(-c2nc3nc(C(=O)O)nc(N[C@H](CCCO)C4CCC4)c3n2Cc2ccc(Cl)cc2)c1]

Step 1: 2,6-Dichloro-7-(4-chlorobenzyl)-8-(5-methylphenyl)-7H-purine, (Preparative Example 7.2), (1.0 g, 2.48 mmol), R)-1-cyclobutylbut-3-en-1-amine, (Preparative Example 7.1) (930 mg, 7.4 mmol), and diisopropyl ethylamine (4.0 g, 31 mmol) were suspended in isopropanol (50 mL) and the reaction was heated to reflux for 2 hours. The reaction mixture was cooled to room temperature and the excess ethanol was removed under reduced pressure. The residue was dissolved in EtOAc (300 mL) and the organic layer was washed with water and brine, dried over anhydrous $Na_2SO_4$, filtered, and concentrated in vacuo. Purification of the crude material by silica gel column chromatography (45% EtOAc/hexanes) afforded (R)-2-chloro-7-(4-chlorobenzyl)-N-(1-cyclobutylbut-3-en-1-yl)-8-(3-methylphenyl)-7H-purin-6-amine as white solid. $^1$H NMR (300 MHz, DMSO-$d_6$): δ 7.37-7.48 (m, 6H), 6.92 (d, J=8.4 Hz, 1H), 6.14 (d, J=8.7 Hz, 1H), 5.51 (dd, J=18.3, 2H), 5.44-5.53 (m, 1H), 4.81-4.92 (m, 1H), 4.25-4.30 (m, 1H), 2.33 (s, 3H), 2.10-2.03 (m, 1H), 1.80-1.90 (m, 1H), 1.63-1.69 (m, 3H), 1.54-1.56 (m, 3H), 1.23-1.69 (m, 1H).

Step 2: (R)-2-Chloro-7-(4-chlorobenzyl)-N-(1-cyclobutylbut-3-en-1-yl)-8-(3-methylphenyl)-7H-purin-6-amine (500 mg, 1.01 mmol) was dissolved in THF (50 ml) and $BH_3$.THF (10 ml, 10 mmol) was added dropwise. The reaction was stirred for 12 hours at room temperature. Methanol (3.0 mL) was added dropwise and the reaction was stirred until the evolution of gas had ceased. The reaction was then diluted with EtOAc (75 mL) and the organics were washed with water (20 mL) and brine (20 mL). The organic layer was dried over $Na_2SO_4$, filtered, and concentrated in vacuo. Purification of the residue by silica gel chromatography (0 to 50% EtOAc/hexanes) afforded (R)-4-{[2-chloro-7-(4-chlorobenzyl)-8-(3-methylphenyl)-7H-purin-6-yl]amino}-4-cyclobutylbutan-1-ol$^1$H NMR (300 MHz, $CDCl_3$): δ7.48-7.60 (m, 3H), 7.20-7.33 (m, 3H), 6.91 (d, J=8.4 Hz, 2H), 5.51 (dd, J=18.3 Hz, 2H), 4.28-4.37 (m, 2H), 4.08-4.15 (m, 1H), 3.58-3.61 (m, 2H), 2.38 (s, 3H), 1.54-2.04 (m, 9H).

Step 3: (R)-4-{[2-chloro-7-(4-chlorobenzyl)-8-(3-methylphenyl)-7H-purin-6-yl]amino}-4-cyclobutylbutan-1-ol (250 mg, 0.49 mmol), zinc cyanide (28.7 mg, 0.245 mmol), and $Pd(PPh_3)_4$ (164 mg, 0.147 mmol) were suspended in anhydrous DMA (15 mL) and the reaction was heated at 120° C. for 3 hours. The reaction was then cooled to room temperature, diluted with water, and extracted with EtOAc. The organic layer was dried over $Na_2SO_4$, filtered, and concentrated in vacuo. The crude residue was purified by silica gel chromatography to afford (R)-7-(4-chlorobenzyl)-6-((1-cyclobutyl-4-hydroxybutyl)amino)-8-(3-methylphenyl)-7H-purine-2-carbonitrile. $^1$H NMR (300 MHz, $CDCl_3$): δ7.48-7.60 (m, 3H), 7.20-7.33 (m, 3H), 6.91 (d, J=8.4 Hz, 2H), 5.51 (dd, J=18.3 Hz, 2H), 4.28-4.37 (m, 2H), 4.05-4.15 (m, 1H), 3.58-3.61 (m, 2H), 2.38 (s, 3H), 1.54-2.04 (m, 9H).

Step 4: (R)-7-(4-chlorobenzyl)-6-((1-cyclobutyl-4-hydroxybutyl)amino)-8-(3-methylphenyl)-7H-purine-2-carbonitrile (220 mg, 0.44 mmol) was dissolved in anhydrous HCl (5 mL, 3N in methanol) and heated at reflux for 3 hours. The reaction mixture was cooled to room temperature and concentrated in vacuo. Purification of the crude residue by silica gel column chromatography (2% $MeOH/CH_2Cl_2$) afforded (R)-methyl7-(4-chlorobenzyl)-6-((1-cyclobutyl-4-hydroxybutyl)amino)-8-(3-methylphenyl)-7H-purine-2-carboxylate as white solid. $^1$H NMR (300 MHz, $CD_3OD$) δ 7.48-7.54 (m, 3H), 7.26-7.34 (m, 3H), 7.20 (d, J=8.1 Hz, 2H), 5.53 (dd, J=17 Hz, 2H), 5.52 (d, J=18.2 Hz, 1H), 4.11-4.13 (m, 2H), 3.99 (s, 3H), 3.65 (br s, 2H), 2.37 (s, 3H), 2.10-2.30 (m, 1H), 1.80-1.90 (m, 1H), 1.63-1.69 (m, 3H), 1.54-1.56 (m, 3H), 1.23-1.29 (m, 1H).

Step 5: (R)-Methyl-7-(4-chlorobenzyl)-6-((1-cyclobutyl-4-hydroxybutyl)amino)-8-(3-methylphenyl)-7H-purine-2-carboxylate (50 mg, 0.09 mmol) and lithium hydroxide (2.7 mg, 0.11 mmol) in THF (2.0 mL) and water (0.2 mL) were stirred at room temperature for 1 hour and then the reaction mixture was acidified to pH 2 with 1M HCl. The aqueous layer was extracted with EtOAc and the organic layer was washed with water and brine, dried over anhydrous $Na_2SO_4$, filtered and concentrated in vacuo. Purification of the crude residue by silica gel column chromatography (2% MeOH/$CH_2Cl_2$) afforded 7-(4-chlorobenzyl)-6-{[(1R)-1-cyclobutyl-4-hydroxybutyl]amino}-8-(3-methylphenyl)-7H-purine-2-carboxylic acid. $^1$H NMR (300 MHz, $CD_3OD$) δ 7.40-7.51 (m, 6H), 7.10 (d, J=8.1 Hz, 2H), 5.65 (dd, J=17 Hz, 1H), 5.62 (d, J=18.2 Hz, 1H), 4.74 (m, 1H), 3.42-3.47 (m, 2H), 2.3 (s, 3H), 2.10-2.30 (m, 1H), 1.80-1.90 (m, 1H), 1.63-1.69 (m, 3H), 1.54-1.56 (m, 3H), 1.28-1.33 (m, 2H), 1.00-1.20 (m, 1H). MS(ESI)=520 (M+1)$^+$.

Example 7.2

6-{[(1R)-1-cyclobutyl-4-hydroxybutyl]amino}-8-(3-methylphenyl)-7-[4-(trifluoromethyl)benzyl]-7H-purine-2-carboxylic acid

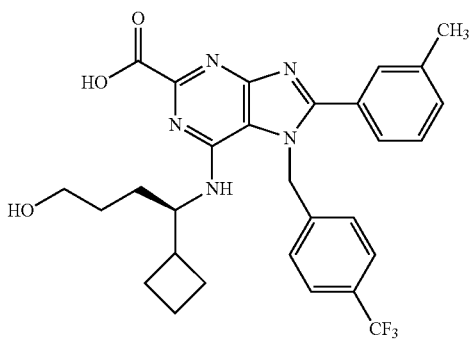 [SMILES: Cc1cccc(-c2nc3nc(C(=O)O)nc(N[C@H](CCCO)C4CCC4)c3n2Cc2ccc(C(F)(F)F)cc2)c1]

Step 1: 2,6-Dichloro-7-(4-(trifluoromethyl)benzyl)-7H-purine (Preparative Example 1.1, Step 1, 10.0 g, 28.8 mmol), R)-1-cyclobutylbut-3-en-1-amine hydrochloride salt, Preparative Example 7.1 (7.2 g, 44.5 mmol), and sodium bicarbonate (7.2 g, 85.7 mmol) were in suspended in isopropanol (20 mL) and the reaction was heated to reflux for 4 hours. The reaction mixture was cooled to room temperature and isopropanol was removed under reduced pressure. The residue was dissolved in EtOAc (300 mL) and the organic layer was washed with water and brine, dried over anhydrous $Na_2SO_4$, filtered, and concentrated in vacuo. Purification of the crude material by silica gel column chromatography (45% EtOAc/hexanes) afforded (R)-2-chloro-N-(1-cyclobutylbut-3-en-1-yl)-7-(4-(trifluoromethyl)benzyl)-7H-purin-6-amine as white solid. $^1$H NMR (300 MHz, $CD_3Cl$) δ 8.00 (s, 1H), 7.73 (d, J=8.2 Hz, 2H), 7.24 (d, J=8.2 Hz, 2H), 5.54 (d, J=9.5 Hz, 1H), 5.48 (d, J=9.5 Hz, 1H), 5.38-5.44 (m, 1H), 4.80-4.95 (m, 2H), 4.27-4.38 (m, 1H), 4.18 (d, J=8.8 Hz, 1H), 2.15-2.35 (m, 1H), 1.80-2.05 (m, 4H), 1.35-1.78 (m, 4H). MS (APCI)=436 $(M+1)^+$.

Step 2: (R)-2-Chloro-N-(1-cyclobutylbut-3-en-1-yl)-7-(4-(trifluoromethyl)benzyl)-7H-purin-6-amine (10.0 g, 22.9 mmol) was dissolved in THF (40 ml) and $BH_3$·THF (40 ml, 40 mmol) was added dropwise. The reaction was stirred for 6 hours at room temperature. The reaction was then cooled to 0° C. and an alkaline solution of hydrogen peroxide (10 ml 4M NaOH and 10 mL 30% $H_2O_2$) was added slowly and the mixture was stirred for 1 hour at room temperature. Excess $H_2O_2$ was quenched by addition of a saturated solution of sodium sulfite to the reaction mixture. The reaction was then diluted with EtOAc (200 mL) and the organics were washed with water (50 mL) and brine (20 mL). The organic layer was dried over $Na_2SO_4$, filtered, and concentrated in vacuo. Purification of the residue by silica gel chromatography (0 to 20% $CH_2Cl_2$/methanol) afforded (R)-4-((2-chloro-7-(4-(trifluoromethyl)benzyl)-7H-purin-6-yl)amino)-4-cyclobutylbutan-1-ol. $^1$H NMR (300 MHz, $CD_3Cl$) δ 7.95 (s, 1H), 7.72 (d, J=8.2 Hz, 2H), 7.27 (d, J=8.2 Hz, 2H), 5.63 (d, J 17.2 Hz, 1H), 5.53 (d, J=17.2 Hz, 1H), 4.48 (d, J=8.7 Hz, 1H), 4.22-4.33 (m, 1H), 3.70 (br s, 1H), 3.57 (dd, J=6.0 Hz, 6.1 Hz, 2H), 1.05-2.00 (11H, m). MS (APCI)=454 $(M+1)^+$.

Step 3: (R)-4-((2-Chloro-7-(4-(trifluoromethyl)benzyl)-7H-purin-6-yl)amino)-4-cyclobutylbutan-1-ol (600 mg, 1.32 mmol), zinc cyanide (117 mg, 1.0 mmol), and Pd(PPh$_3$)$_4$ (230 mg, 0.2 mmol) were suspended in anhydrous DMA (2.0 mL). The reaction was heated at 120° C. for 3 hours. The reaction was then cooled to room temperature, diluted with water and extracted with EtOAc. The organic layer was dried over $Na_2SO_4$, filtered, and concentrated in vacuo. Purification of the crude residue by silica gel chromatography with 50% EtOAc/hexanes afforded (R)-6-((1-cyclobutyl-4-hydroxybutyl)amino)-7-(4-(trifluoromethyl)benzyl)-7H-purine-2-carbonitrile. $^1$H NMR (400 MHz, $CD_3OD$) δ 8.51 (br s, 1H), 7.72 (d, J=8.2 Hz, 2H), 7.27 (d, J=8.2 Hz, 2H), 5.88-5.95 (m, 2H), 4.37 (dt, J=4.6 Hz, 3.5 Hz, 1H), 3.38-3.51 (m, 2H), 2.15-2.25 (m, 1H), 1.88-1.95 (m, 1H), 1.15-1.75 (m, 9H). MS (APCI)=445 $(M+1)^+$.

Step 4: To a solution of (R)-6-((1-cyclobutyl-4-hydroxybutyl)amino)-7-(4-(trifluoromethyl)benzyl)-7H-purine-2-carbonitrile (1.11 g, 2.50 mmol) in $CH_2Cl_2$ (20 mL) was added imidazole (340 mg, 5.0 mmol), tert-butylchlorodimethylsilane (452 mg, 3.0 mmol) and DMAP (10.0 mg, 0.08 mmol). The reaction mixture was stirred at room temperature for 1 hour. Then the reaction mixture was diluted with $CH_2Cl_2$ (200 mL) and washed with water (50 mL). The organic layer was washed with brine (20 mL), dried over $Na_2SO_4$, filtered, and concentrated in vacuo. The residue was purified by silica gel chromatography (20% EtOAc/hexanes) to afford (R)-6-((4-((tert-butyldimethylsilyl)oxy)-1-cyclobutylbutyl)amino)-7-(4-(trifluoromethyl)benzyl)-7H-purine-2-carbonitrile. MS (APCI): 559 $(M+1)^+$.

Step 5: A dry vial was charged with di(1-adamantyl)-n-butylphosphine (77.0 mg, 0.21 mmol) and palladium acetate (24.0 mg, 0.11 mmol). Toluene (2.0 mL) was added and the mixture was degassed with Ar for 10 minutes. The vial was sealed and heated at 50° C. for 30 minutes. The yellow catalyst slurry was then added via syringe to a second dry reaction vial containing (R)-6-((4-((tert-butyldimethylsilyl)oxy)-1-cyclobutylbutyl)amino)-7-(4-(trifluoromethyl)benzyl)-7H-purine-2-carbonitrile (600 mg, 1.07 mmol), 1-bromo-3-methylbenzene (275 mg, 1.61 mmol), potassium carbonate (442 mg, 3.20 mmol), and pivalic acid (110 mg, 1.11 mmol). The reaction was degassed with Ar for 10 minutes, and the vial was sealed and heated at 105° C. for 16 hours. The reaction was cooled to room temperature, diluted with EtOAc (100 mL), and washed with water (30 mL). The organic layer was washed with brine (20 mL), dried over $Na_2SO_4$, filtered, and concentrated in vacuo. The residue was purified by silica gel chromatography (20% EtOAc/hexanes) to afford (R)-6-((4-((tert-butyldimethylsilyl)oxy)-1-cyclobutylbutyl)amino)-8-(3-methylphenyl)-7-(4-(trifluoromethyl)benzyl)-7H-purine-2-carbonitrile. $^1$H NMR (300 MHz, $CDCl_3$) δ 7.79 (d, J=8.2 Hz, 2H), 7.56 (1H, s), 7.30-7.42 (m, 5H), 5.64 (d, J=9.1 Hz, 1H), 5.56 (d, J=9.0 Hz, 1H), 4.16-4.37 (m, 2H), 3.40-3.55 (m, 2H), 2.39 (s, 3H), 0.90-1.95 (m, 11H), 0.87 (s, 9H), 0.03 (s, 3H), 0.02 (s, 3H). MS (APCI)=649 $(M+1)^+$.

Step 6: (R)-6-((4-((tert-Butyldimethylsilyl)oxy)-1-cyclobutylbutyl)amino)-8-(3-methylphenyl)-7-(4-(trifluoromethyl)benzyl)-7H-purine-2-carbonitrile (550 mg, 0.85 mmol) was dissolved in HCl (10 mL, 3N in methanol) and heated to reflux for 4 hours. The reaction mixture was cooled to room temperature and concentrated in vacuo. Purification of the crude residue by silica gel column chromatography (2% MeOH/$CH_2Cl_2$) afforded (R)-methyl 6-((1-cyclobutyl-4-hydroxybutyl)amino)-8-(3-methylphenyl)-7-(4-(trifluoromethyl)benzyl)-7H-purine-2-carboxylate as white solid. MS (APCI)=568 $(M+1)^+$.

Step 7: To a solution of (R)-methyl 6-((1-cyclobutyl-4-hydroxybutyl)amino)-8-(3-methylphenyl)-7-(4-(trifluoromethyl)benzyl)-7H-purine-2-carboxylate (30.0 mg, 0.05 mmol) in THF (5.0 mL) and water (0.5 mL) was added lithium hydroxide (2.4 mg, 0.10 mmol). The reaction was stirred at room temperature for 1 hour. The reaction mixture was then acidified to pH 2 with 1M HCl. The aqueous layer was extracted with EtOAc and the organic layer was washed with water and brine, dried over anhydrous $Na_2SO_4$, filtered and concentrated in vacuo. Purification of the crude residue by silica gel column chromatography (2% MeOH/$CH_2Cl_2$) afforded 6-{[(1R)-1-cyclobutyl-4-hydroxybutyl]amino}-8-(3-methylphenyl)-7-[4-(trifluoromethyl)benzyl]-7H-purine-2-carboxylic acid. 1H NMR (300 MHz, $CD_3OD$) δ 7.70 (d, J=7.2 Hz, 2H), 7.20-7.50 (m, 6H), 5.65-5.90 (m, 2H), 4.89 (br s, 1H), 3.32-3.55 (m, 2H), 2.35 (br s, 3H), 2.05-2.22 (m, 1H), 1.08-1.95 (m, 10H). MS (ES)=554 (M+1)$^+$.

Example 7.3

(4R)-4-cyclobutyl-4-({8-(3-methylphenyl)-7-[4-(trifluoromethyl)benzyl]-7H-purin-6-yl}amino)butan-1-ol

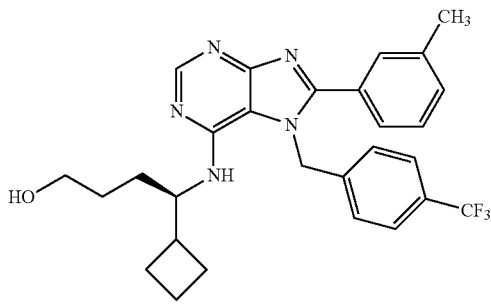 [SMILES: Cc1cccc(-c2nc3ncnc(N[C@H](CCCO)C4CCC4)c3n2Cc2ccc(C(F)(F)F)cc2)c1]

Step 1: To a solution of (R)-4-((2-chloro-7-(4-(trifluoromethyl)benzyl)-7H-purin-6-yl)amino)-4-cyclobutylbutan-1-ol (Example 7.2, Step 2) (300 mg, 0.66 mmol) in $CH_2Cl_2$ (15 mL) was added imidazole (90 mg, 1.32 mmol) and tert-butylchlorodimethylsilane (110 mg, 0.72 mmol). The reaction mixture was stirred at room temperature for 1 hour. Then the reaction mixture was washed with water (50 mL) and the aqueous layer was back extracted with $CH_2Cl_2$ (80 mL). The combined organic layers were washed with brine (20 mL), dried over $Na_2SO_4$, filtered, and concentrated in vacuo. The crude residue was purified by silica gel chromatography (80% EtOAc/hexanes) to afford (R)—N-(4-((tert-butyldimethylsilyl)oxy)-1-cyclobutylbutyl)-2-chloro-7-(4-(trifluoromethyl)benzyl)-7H-purin-6-amine. $^1$H NMR (400 MHz, $CDCl_3$): δ 7.99 (s, 1H), 7.72 (d, J=8.0 Hz, 2H), 7.26 (d, J=8.0 Hz, 2H), 5.53 (s, 2H), 4.21-4.28 (m, 1H), 4.07-4.13 (m, 1H), 3.40-3.51 (m, 2H), 1.80-1.97 (m, 2H), 1.68-1.76 (m, 1H), 1.57-1.61 (m, 1H), 1.43-1.56 (m, 2H), 1.32-1.41 (m, 1H), 1.08-1.21 (m, 2H), 0.88-1.00 (m, 1H), 0.87 (s, 9H), 0.10 (s, 3H), 0.09 (s, 3H). LCMS (APCI)=568 (M+1)$^+$.

Step 2: A dry vial was charged with di(1-adamantyl)-n-butylphosphine (cataCXium A, Strem, 25.2 mg, 0.07 mmol) and palladium acetate (7.90 mg, 0.03 mmol). Toluene (2.0 mL) was added and the mixture was degassed with Ar. The vial was then sealed and heated at 50° C. for 30 minutes. The catalyst slurry was then cooled to room temperature and added via syringe to a second dry vial containing (R)—N-(4-((tert-butyldimethylsilyl)oxy)-1-cyclobutylbutyl)-2-chloro-7-(4-(trifluoromethyl)benzyl)-7H-purin-6-amine (200 mg, 0.35 mmol), 1-bromo-3-methylbenzene (90 mg, 0.52 mmol), potassium carbonate (146 mg, 1.05 mmol), and pivalic acid (36 mg, 0.35 mmol). The reaction was degassed with Ar for 10 minutes, and the vial was sealed and heated at 105° C. for 16 hours. The reaction was then cooled to room temperature, diluted with EtOAc (50 mL), and washed with water (30 mL). The organic layer was washed with brine (20 mL), dried over $Na_2SO_4$, filtered, and concentrated in vacuo. The residue was purified by silica gel chromatography (50% EtOAc/hexanes) to afford (R)—N-(4-((tert-butyldimethylsilyl)oxy)-1-cyclobutylbutyl)-2-chloro-8-(3-methylphenyl)-7-(4-(trifluoromethyl)benzyl)-7H-purin-6-amine. $^1$H NMR (400 MHz, $CDCl_3$): δ 7.78 (d, J=7.8 Hz, 2H), 7.55 (s, 1H), 7.38 (d, J=7.8 Hz, 2H), 7.33 (s, 3H), 5.60 (d, J=18.2 Hz, 2H), 4.21-4.35 (m, 1H), 4.05-4.15 (m, 1H), 3.40-3.55 (m, 2H), 2.38 (s, 3H), 1.98-2.07 (m, 3H), 1.79-1.98 (m, 3H), 1.68-1.71 (m, 1H), 1.45-1.57 (m, 2H), 1.32-1.39 (m, 1H), 0.87 (s, 9H), 0.09 9s, 6H). LCMS (APCI)=658 (M+1)$^+$.

Step 3: (R)—N-(4-((tert-Butyldimethylsilyl)oxy)-1-cyclobutylbutyl)-2-chloro-8-(3-methylphenyl)-7-(4-(trifluoromethyl)benzyl)-7H-purin-6-amine (280 mg, 0.42 mmol) was dissolved in ethanol (10 mL) and degassed with Ar for 30 min. Palladium on carbon, loading 10 wt. % (225 mg) was added and the mixture was degassed for another 5 min. Degassed 5N NaOH (2.5 mL) was then added into the reaction mixture. The suspension was degassed with $H_2$ for 5 min and then stirred at 50° C. under a $H_2$ atmosphere for 12 hours. After 12 hours, the solid was removed by filtration and washed with methanol. The filtrate was concentrated in vacuo. The crude residue was purified by silica gel chromatography (10% MeOH/$CH_2Cl_2$) to afford (4R)-4-cyclobutyl-4-({8-(3-methylphenyl)-7-[4-(trifluoromethyl)benzyl]-7H-purin-6-yl}amino)butan-1-ol. $^1$H NMR (300 MHz, $CD_3OD$): δ 8.30 (s, 1H), 7.74 (d, J=8.1 Hz, 2H), 7.50 (s, 1H), 7.44 (m, 3H), 7.27 (d, J=8.1 Hz, 2H), 5.85 (dd, J=18.6 Hz, 2H), 4.38-4.44 (m, 1H), 3.40-3.46 (m, 2H), 2.38 (s, 3H), 2.03-2.19 (m, 1H), 1.80-1.89 (m, 1H), 1.56-1.77 (m, 3H), 1.48-1.54 (m, 3H), 1.28-1.45 (m, 3H), 1.06-1.19 (m, 1H). MS (ES)=510 (M+1)$^+$.

Example 7.5

6-{[(1R)-1-cyclobutylbutyl]amino}-8-(3-methylphenyl)-7-[4-(trifluoromethyl)benzyl]-7H-purine-2-carboxylic acid

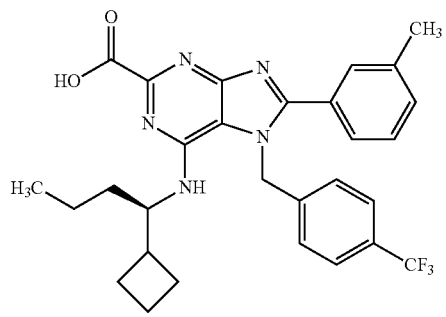 [SMILES: CCC[C@@H](Nc1nc(C(=O)O)nc2nc(-c3cccc(C)c3)n(Cc3ccc(C(F)(F)F)cc3)c12)C1CCC1]

Step 1: (R)-2-Chloro-N-(1-cyclobutylbut-3-en-1-yl)-7-(4-(trifluoromethyl)benzyl)-7H-purin-6-amine, Example 7.2 (Step 1), (250 mg, 0.57 mmol) was dissolved in ethanol (10 mL) and degassed with Ar for 30 minutes. Palladium on carbon, (320 mg, 10% by wt) was added into the reaction mixture and degassed for 5 minutes. The suspension was degassed with $H_2$ for 5 minutes and then stirred at 50° C. under a $H_2$ atmosphere for 2 hours. The solid was removed by filtration and the solid was washed with methanol. The filtrate was concentrated in vacuo. The crude (R)-2-chloro-N-(1-cyclobutylbutyl)-7- (4-(trifluoromethyl)benzyl)-7H- purin-6-amine was carried forward to the next step without further purification. LCMS (APCI)=438 (M+1)+

Step 2: Using a procedure analogous to that described in Example 7.1 (Step 3), and starting with (R)-2-chloro-N-(1-cyclobutylbutyl)-7-(4-(trifluoromethyl)benzyl)-7H-purin-6-amine, (R)-6-((1-cyclobutylbutyl)amino)-7-(4-(trifluoromethyl)benzyl)-7H-purine-2-carbonitrile was prepared. $^1$H NMR (300 MHz, CDCl$_3$): δ8.18 (s, 1H), 7.75 (d, J=8.3 Hz, 2H), 7.29 (d, J=8.3 Hz, 2H), 5.64 (s, 2H), 4.22-4.34 (m, 2H), 1.95-2.03 (m, 1H), 1.81-1.92 (m, 2H), 1.47-1.78 (m, 4H), 1.41-1.44 (m, 1H), 0.83-0.93 (m, 3H), 0.72-0.76 (m, 3H). LCMS (APCI)=429 (M+1)+.

Step 3: Using a procedure analogous to that described in Example 7.2 (Step 5), and starting with (R)-6-((1-cyclobutylbutyl)amino)-7-(4-(trifluoromethyl)benzyl)-7H-purine-2-carbonitrile and 1-bromo-3-methylbenzene, (R)-6-((1-cyclobutylbutyl)amino)-8-(3-methylphenyl)-7-(4-(trifluoromethyl)benzyl)-7H-purine-2-carbonitrile was prepared. $^1$H NMR (300 MHz, CDCl$_3$): δ7.80 (d, J=8.1 Hz, 2H), 7.55 (s, 1H), 7.39 (s, 1H), 7.35 (s, 4H), 5.67 (dd, J=18.60 Hz, 2H), 4.26-4.35 (m, 1H), 4.18-4.21 (m, 1H), 2.38 (s, 3H), 1.50-2.00 (m, 5H), 1.28-1.45 (m, 2H), 0.81-0.96 (m, 3H), 0.73-0.78 (m, 3H). LCMS (APCI)=519 (M+1)+.

Step 4: Using a procedure analogous to that described in Example 7.1 (Step 4), and starting with (R)-6-((1-cyclobutylbutyl)amino)-8-(3-methylphenyl)-7-(4-(trifluoromethyl)benzyl)-7H-purine-2-carbonitrile, (R)-methyl 6-((1-cyclobutylbutyl)amino)-8-(3-methylphenyl)-7-(4-(trifluoromethyl)benzyl)-7H-purine-2-carboxylate was prepared. $^1$H NMR (300 MHz, CD$_3$OD): δ 7.72 (d, J=6.9 Hz, 2H), 7.51 (s, 1H), 7.41 (s, 3H), 7.27 (d, J=6.9 Hz, 2H), 5.83 (br s, 2H), 4.54 (br s, 1H), 3.95 (s, 3H), 2.38 (s, 3H), 1.80-1.97 (m, 3H), 1.48-1.72 (m, 5H), 0.85-1.15 (m, 3H), 0.76-0.78 (m, 3H). LCMS (APCI)=552 (M+1)+.

Step 5: Using a procedure analogous to that described in Example 7.1 (Step 5), and starting with (R)-methyl 6-((1-cyclobutylbutyl)amino)-8-(3-methylphenyl)-7-(4-(trifluoromethyl)benzyl)-7H-purine-2-carboxylate, 6-{[(1R)-1-cyclobutylbutyl]amino}-8-(3-methylphenyl)-7-[4-(trifluoromethyl)benzyl]-7H-purine-2-carboxylic acid was prepared. $^1$H NMR (400 MHz, CD$_3$OD): δ 7.73 (d, J=8.0 Hz, 2H), 7.52 (s, 1H), 7.42-7.41 (m, 3H), 7.28 (d, J=8.0 Hz, 2H), 5.81 (s, 2H), 4.69-4.64 (m, 1H), 2.38 (s, 3H), 2.22-2.15 (m, 1H), 1.98-1.87 (m, 1H), 1.73-1.60 (m, 3H), 1.58-1.56 (m, 2H), 1.40-1.34 (m, 1H), 1.08-0.98 (m, 3H), 0.78 (t, J=6.8 Hz, 3H). LCMS: 538 (M+1)+.

Example 7.6

6-{[(1R)-3-carboxy-1-cyclobutylpropyl]amino}-8-(3-methylphenyl)-7-[4-(trifluoromethyl)benzyl]-7H-purine-2-carboxylic acid

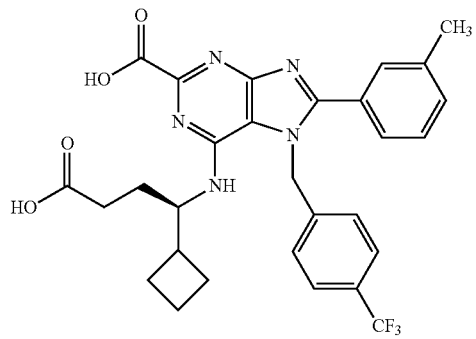 [SMILES: Cc1cccc(-c2nc3nc(C(=O)O)nc(N[C@H](CCC(=O)O)C4CCC4)c3n2Cc2ccc(C(F)(F)F)cc2)c1]

Step 1: To a solution of (R)-methyl 6-((1-cyclobutyl-4-hydroxybutyl)amino)-8-(3-methylphenyl)-7-(4-(trifluoromethyl)benzyl)-7H-purine-2-carboxylate, Example 7.2 (Step 6) (200 mg, 0.35 mmol) in acetonitrile (4.0 mL) and water (2.0 mL) were added TEMPO (10.0 mg, 0.06 mmol) and [bis(acetoxy)iodo]benzene (280 mg, 0.87 mmol) sequentially. The reaction mixture was stirred at room temperature for 12 hours. After 12 h, the reaction mixture was concentrated under reduced pressure. The solid residue was extracted with EtOAc (100 mL) and the organic layer was washed with water (20 mL) and brine (10 mL). The organic layer was then dried over Na$_2$SO$_4$ and concentrated in vacuo. The crude residue was purified by silica gel chromatography (70% EtOAc/hexanes) to afford (R)-4-cyclobutyl-4-((2-(methoxycarbonyl)-8-(3-methylphenyl)-7-(4-(trifluoromethyl)benzyl)-7H-purin-6-yl)amino)butanoic acid. MS (APCI)=582 (M+1)+.

Step 2: Using a procedure analogous to that described in Example 7.1 (Step 5), and starting with (R)-4-cyclobutyl-4-((2-(methoxycarbonyl)-8-(3-methylphenyl)-7-(4-(trifluoromethyl)benzyl)-7H-purin-6-yl)amino)butanoic acid, 6-{[(1R)-3-carboxy-1-cyclobutylpropyl]amino}-8-(3-methylphenyl)-7-[4-(trifluoromethyl)benzyl]-7H-purine-2-carboxylic acid was prepared. $^1$H NMR (400 MHz, CD$_3$OD) δ 7.73 (d, J=8.2 Hz, 2H), 7.53 (br s, 1H), 7.41-7.48 (m, 3H), 7.31 (d, J=8.2 Hz, 2H), 5.87 (d, J=18.4 Hz, 1H), 5.79 (d, J=18.4 Hz, 1H), 4.67 (dt, J=3.5, 9.2 Hz, 2H), 2.28 (3H, s), 2.01-2.26 (3H, m), 1.37-1.86 (8H, m). MS (APCI)=568 (M+1)+

Example 7.7

6-({(1R)-1-cyclobutyl-4-[(2-hydroxyethyl)amino]-4-oxobutyl}amino)-8-(3-methylphenyl)-7-[4-(trifluoromethyl)benzyl]-7H-purine-2-carboxylic acid

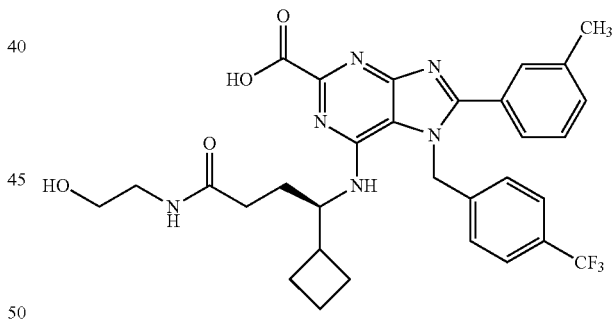

Step 1: To a solution of (R)-4-cyclobutyl-4-((2-(methoxycarbonyl)-8-(3-methylphenyl)-7-(4-(trifluoromethyl)benzyl)-7H-purin-6-yl)amino)butanoic acid Example 7.6 (Step 1) (40.0 mg, 0.07 mmol) and 2-aminoethanol (5.0 mg, 0.08 mmol) in DMF (5.0 mL) were added HATU (40.0 mg, 0.10 mmol) and DIPEA (17.7 mg, 0.14 mmol). The reaction mixture was stirred at room temperature for 30 minutes. After 30 minutes, the reaction mixture was poured into water (5.0 mL) and extracted with EtOAc (2×15 mL). The combined organic layers were washed with brine (5.0 mL), dried over Na$_2$SO$_4$, filtered and concentrated in vacuo. The crude (R)-methyl 6-((1-cyclobutyl-4-((2-hydroxyethyl)amino)-4-oxobutyl)amino)-8-(3-methylphenyl)-7-(4-(trifluoromethyl)benzyl)-7H-purine-2-carboxylate was carried forward to the next step without further purification. LCMS (APCI)=625 (M+1)+.

Step 2: Using a procedure analogous to that described in Example 7.1 (Step 5), and starting with (R)-methyl 6-((1-cyclobutyl-4-((2-hydroxyethyl)amino)-4-oxobutyl)amino)-8-(3-methylphenyl)-7-(4-(trifluoromethyl)benzyl)-7H-purine-2-carboxylate, 6-({(1R)-1-cyclobutyl-4-[(2-hydroxyethyl)amino]-4-oxobutyl}amino)-8-(3-methylphenyl)-7-[4-(trifluoromethyl)benzyl]-7H-purine-2-carboxylic acid was prepared. Purification of product was carried out by silica gel chromatography (10% MeOH/CH$_2$Cl$_2$) and by preparative HPLC (10-90% acetonitrile/water). $^1$H NMR (400 MHz, CD$_3$OD): δ 7.73 (d, J=8.0 Hz, 2H), 7.51 (s, 1H), 7.43 (s, 3H), 7.28 (d, J=8.0 Hz, 2H), 5.90 (d, J=18.3 Hz, 1H), 5.80 (d, J=16.8 Hz, 1H), 4.71 (td, J=9.6, 3.6 Hz, 1H), 3.73-3.82 (m, 2H), 3.49-3.69 (m, 2H), 2.39 (s, 3H), 2.16-2.24 (m, 2H), 2.08-2.16 (m, 1H), 1.77-1.94 (m, 2H), 1.65-1.75 (m, 2H), 1.58-1.64 (m, 1H), 1.35-1.52 (m, 3H). LCMS (APCI)=611 (M+1)$^+$.

Example 7.8

6-[(2R)-2-cyclobutylpyrrolidin-1-yl]-8-(3-methylphenyl)-7-[4-(trifluoromethyl)benzyl]-7H-purine-2-carboxylic acid

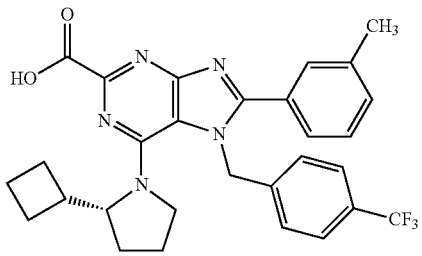 [SMILES: Cc1cccc(-c2nc3nc(C(=O)O)nc(N4CCC[C@@H]4C4CCC4)c3n2Cc2ccc(C(F)(F)F)cc2)c1]

Step 1: To a solution of (R)-methyl 6-((1-cyclobutyl-4-hydroxybutyl)amino)-8-(3-methylphenyl)-7-(4-(trifluoromethyl)benzyl)-7H-purine-2-carboxylate, Example 7.2 (Step 6), (60 mg, 0.11 mmol) in CH$_2$Cl$_2$ (5.0 mL), were added mesyl chloride (23 mg, 0.20 mmol) and triethylamine (0.30 ml, 22 mg, 0.22 mmol) sequentially. The reaction was stirred for 1 hour at room temperature and then diluted with CH$_2$Cl$_2$ (20 mL) and washed with water (5.0 mL). The organic layer was then dried over Na$_2$SO$_4$ and concentrated under reduced pressure to afford crude (R)-methyl 6-((1-cyclobutyl-4-((methylsulfonyl)oxy)butyl)amino)-8-(3-methylphenyl)-7-(4-(trifluoromethyl)benzyl)-7H-purine-2-carboxylate. MS (APCI)=646 (M+1)$^+$.

Step 2: To a solution of (R)-methyl 6-((1-cyclobutyl-4-((methylsulfonyl)oxy)butyl)amino)-8-(3-methylphenyl)-7-(4-(trifluoromethyl)benzyl)-7H-purine-2-carboxylate (100 mg, 0.15 mmol) in THF (3.0 mL), was added DBU (91 mg, 0.60 mmol). The reaction was stirred at 50° C. for 8 hours. The reaction mixture was cooled to room temperature and the solvent was removed under reduced pressure. The solid residue was dissolved in EtOAc (30 mL) and washed with saturated NaHCO$_3$ solution (5.0 mL) and water (5.0 mL). The organic layer was dried over Na$_2$SO$_4$ and concentrated in vacuo. The crude material was purified by silica gel column chromatography (50% EtOAc/hexanes) to afford (R)-methyl 6-(2-cyclobutylpyrrolidin-1-yl)-8-(3-methylphenyl)-7-(4-(trifluoromethyl)benzyl)-7H-purine-2-carboxylate. MS (APCI)=550 (M+1)$^+$.

Step 3: Using a procedure analogous to that described in Example 7.1 (Step 5), and starting with (R)-methyl 6-(2-cyclobutylpyrrolidin-1-yl)-8-(3-methylphenyl)-7-(4-(trifluoromethyl)benzyl)-7H-purine-2-carboxylate, 6-[(2R)-2-cyclobutylpyrrolidin-1-yl]-8-(3-methylphenyl)-7-[4-(trifluoromethyl)benzyl]-7H-purine-2-carboxylic acid was prepared. $^1$H NMR (300 MHz, CD$_3$OD) δ 7.68 (br s, 2H), 7.52 (d, J=7.8 Hz, 2H), 7.48 (d, J=6.3 Hz, 2H), 6.90 (d, J=7.9 Hz, 2H), 5.88 (d, J=17.0 Hz, 1H), 5.78 (d, J=17.0 Hz, 1H), 4.86-4.95 (m, 1H), 4.13 (br s, 1H), 3.97 (br s, 1H), 2.44 (s, 3H), 2.00-2.30 (m, 3H), 1.40-1.90 (m, 8H). MS (ESI)=536 (M+1)+.

Example 7.9

6-[(2R)-2-cyclobutylpyrrolidin-1-yl]-8-(3-methylphenyl)-7-[4-(trifluoromethyl)benzyl]-7H-purine

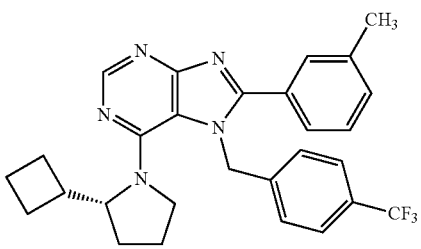 [SMILES: Cc1cccc(-c2nc3ncnc(N4CCC[C@@H]4C4CCC4)c3n2Cc2ccc(C(F)(F)F)cc2)c1]

To a solution of (R)-6-(2-cyclobutylpyrrolidin-1-yl)-8-(3-methylphenyl)-7-(4-(trifluoromethyl)benzyl)-7H-purine-2-carboxylic acid, Example 7.8, (16.0 mg, 0.03 mmol) in 1,4-dioxane (3.0 mL) was added HCl (3.0 mL, 3N in methanol) and the reaction mixture heated to reflux for 6 hours. The reaction was then cooled to room temperature and neutralized with NaHCO$_3$. EtOAc (50 mL) added was added and the organic layer was separated and washed with brine (5.0 mL) followed by water (5.0 mL). The organic layer was then dried over Na$_2$SO$_4$ and concentrated in vacuo. The crude material was purified by silica gel column chromatography (50% EtOAc/hexanes) to afford 6-[(2R)-2-cyclobutylpyrrolidin-1-yl]-8-(3-methylphenyl)-7-[4-(trifluoromethyl)benzyl]-7H-purine. $^1$H NMR (400 MHz, CD$_3$OD) δ 8.36 (s, 1H), 7.58 (s, 1H), 7.58 (d, J=7.6 Hz, 1H), 7.38-7.50 (m, 4H), 6.79 (d, J=7.6 Hz, 2H), 5.80 (d, J=16.9 Hz, 1H), 5.68 (d, J=16.9 Hz, 1H), 4.82-4.90 (m, 1H), 3.82-3.92 (m, 2H), 2.42 (s, 3H), 1.90-2.32 (m, 3H), 1.40-1.72 (m, 8H). MS (ESI)=492 (M+1)$^+$.

Example 7.10

6-{[(1R)-1-cyclobutyl-4-(4-methylpiperazin-1-yl)butyl]amino}-8-(3-methylphenyl)-7-[4-(trifluoromethyl)benzyl]-7H-purine-2-carboxylic acid

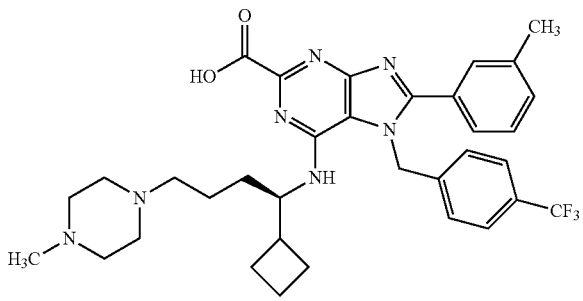 [SMILES: Cc1cccc(-c2nc3nc(C(=O)O)nc(N[C@H](CCCN4CCN(C)CC4)C4CCC4)c3n2Cc2ccc(C(F)(F)F)cc2)c1]

Step 1: To a solution of (R)-methyl 6-((1-cyclobutyl-4-((methylsulfonyl)oxy)butyl)amino)-8-(3-methylphenyl)-7-(4-(trifluoromethyl)benzyl)-7H-purine-2-carboxylate, Example 7.8 (Step 1), (50.0 mg, 0.08 mmol) in THF (3.0 mL), was added N-methylpiperazine (38.0 mg, 0.38 mmol) and the reaction was stirred at 50° C. for 6 hours. The reaction was then cooled to room temperature and the solvent was evaporated under reduced pressure. The solid residue was dissolved in EtOAc (20 mL) and washed with saturated NaHCO$_3$ solution (3.0 mL) and then water (3.0 mL). The organic layer was dried over Na$_2$SO$_4$ and concentrated in vacuo. The crude material was purified by silica gel chromatography (EtOAc) to afford (R)-methyl 6-((1-cyclobutyl-4-(4-methylpiperazin-1-yl)butyl)amino)-8-(3-methylphenyl)-7-(4-(trifluoromethyl)benzyl)-7H-purine-2-carboxylate. MS (APCI)=650 (M+1)+.

Step 2: Using a procedure analogous to that described in Example 7.1 (Step 5), and starting with (R)-methyl 6-((1-cyclobutyl-4-(4-methylpiperazin-1-yl)butyl)amino)-8-(3-methylphenyl)-7-(4-(trifluoromethyl)benzyl)-7H-purine-2-carboxylate, 6-{[(1R)-1-cyclobutyl-4-(4-methylpiperazin-1-yl)butyl]amino}-8-(3-methylphenyl)-7-[4-(trifluoromethyl)benzyl]-7H-purine-2-carboxylic acid was prepared. $^1$H NMR (300 MHz, CD$_3$OD) δ 7.72 (d, J=8.1 Hz, 2H), 7.52 (s, 1H), 7.43 (br s, 3H), 7.28 (d, J=8.1 Hz, 2H), 5.84 (d, J=18.6 Hz, 1H), 5.74 (d, J=18.6 Hz, 1H), 4.72-4.82 (m, 1H), 3.50-3.62 (m, 1H), 2.10-2.60 (m, 10H), 2.39 (s, 3H), 2.24 (s, 3H), 1.00-1.90 (m, 11H). MS (ESI)=636 (M+1)$^+$.

Example 7.11

6-{[(1R)-1-cyclobutyl-4-(dimethylamino)butyl]amino}-8-(3-methylphenyl)-7-[4-(trifluoromethyl)benzyl]-7H-purine-2-carboxylic acid

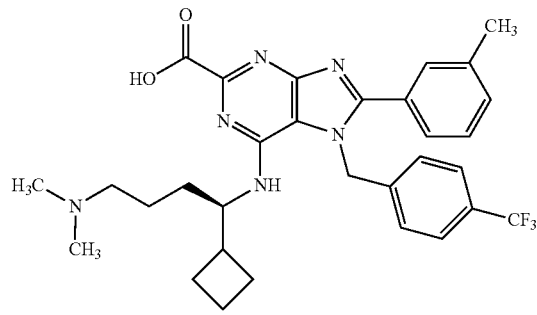 [SMILES: Cc1cccc(-c2nc3nc(C(=O)O)nc(N[C@H](CCCN(C)C)C4CCC4)c3n2Cc2ccc(C(F)(F)F)cc2)c1]

Step 1: To a solution of (R)-methyl 6-((1-cyclobutyl-4-((methylsulfonyl)oxy)butyl)amino)-8-(3-methylphenyl)-7-(4-(trifluoromethyl)benzyl)-7H-purine-2-carboxylate, Example 7.8 (Step 1), (35.0 mg, 0.05 mmol) in THF (3.0 mL), were added dimethylamine hydrochloride (26.0 mg, 0.32 mmol) and triethylamine (32 mg, 0.32 mmol). The reaction was stirred at room temperature for 6 hours and then the solvent was removed under reduced pressure. The solid residue was dissolved in EtOAc (20 mL) and washed with saturated NaHCO$_3$ solution (3.0 mL) and then water (3.0 mL). The organic layer was then dried over Na$_2$SO$_4$ and concentrated in vacuo. The crude material was purified by silica gel chromatography (80% EtOAc/hexanes) to afford (R)-methyl 6-((1-cyclobutyl-4-(dimethylamino)butyl)amino)-8-(3-methylphenyl)-7-(4-(trifluoromethyl)benzyl)-7H-purine-2-carboxylate. MS (APCI)=595 (M+1)$^+$.

Step 2: Using a procedure analogous to that described in Example 7.1 (Step 5), and starting with (R)-methyl 6-((1-cyclobutyl-4-(dimethylamino)butyl)amino)-8-(3-methylphenyl)-7-(4-(trifluoromethyl)benzyl)-7H-purine-2-carboxylate, 6-{[(1R)-1-cyclobutyl-4-(dimethylamino)butyl]amino}-8-(3-methylphenyl)-7-[4-(trifluoromethyl)benzyl]-7H-purine-2-carboxylic acid was prepared. $^1$H NMR (300 MHz, CD$_3$OD) δ 7.69 (d, J=7.8 Hz, 2H), 7.35-7.50 (m, 4H), 7.22 (d, J=7.8 Hz, 2H), 5.89 (d, J=18.7 Hz, 1H), 5.72 (d, J=18.7 Hz, 1H), 4.10-4.21 (m, 1H), 3.40-3.55 (m, 1H), 3.05-3.12 (m, 1H), 2.78-2.90 (m, 1H), 2.66 (s, 6H), 2.36 (s, 3H), 1.20-2.20 (m, 11H). MS (ESI)=581 (M+1)$^+$.

Example 7.12

6-{[(1R)-4-amino-1-cyclobutyl-4-oxobutyl]amino}-8-(3-methylphenyl)-7-[4-(trifluoromethyl)benzyl]-7H-purine-2-carboxylic acid

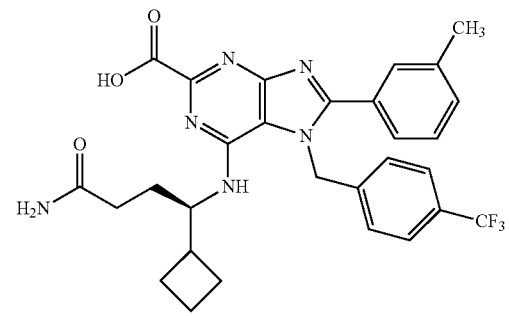 [SMILES: Cc1cccc(-c2nc3nc(C(=O)O)nc(N[C@H](CCC(N)=O)C4CCC4)c3n2Cc2ccc(C(F)(F)F)cc2)c1]

Step 1: To a solution of (R)-4-cyclobutyl-4-((2-(methoxycarbonyl)-8-(3-methylphenyl)-7-(4-(trifluoromethyl)benzyl)-7H-purin-6-yl)amino)butanoic acid, Example 7.6 (Step 1), (60.0 mg, 0.10 mmol) in CH$_2$Cl$_2$ (3.0 mL) were added ammonium carbonate (30.0 mg, 0.31 mmol), EDCl (38.0 mg, 0.20 mmol), DMAP (2.4 mg, 0.02 mmol) and triethylamine (30 mg, 0.30 mmol). The reaction mixture was stirred at room temperature for 6 hours. The reaction mixture was then diluted with CH$_2$Cl$_2$ (20.0 mL), washed with water (5.0 mL), dried over Na$_2$SO$_4$, filtered and concentrated under reduced pressure. The resulting residue was purified by silica gel column chromatography (5% MeOH in CH$_2$Cl$_2$) to afford (R)-methyl 6-((4-amino-1-cyclobutyl-4-oxobutyl)amino)-8-(3-methylphenyl)-7-(4-(trifluoromethyl)benzyl)-7H-purine-2-carboxylate. MS (APCI)=581 (M+1)$^+$.

Step 2: Using a procedure analogous to that described in Example 7.1 (Step 5), and starting with (R)-methyl 6-((4-amino-1-cyclobutyl-4-oxobutyl)amino)-8-(3-methylphenyl)-7-(4-(trifluoromethyl)benzyl)-7H-purine-2-carboxylate, 6-{[(1R)-4-amino-1-cyclobutyl-4-oxobutyl]amino}-8-(3-methylphenyl)-7-[4-(trifluoromethyl)benzyl]-7H-purine-2-carboxylic acid was prepared. $^1$H NMR (300 MHz, CD$_3$OD) δ 7.73 (d, J=7.8 Hz, 2H), 7.45-7.61 (m, 4H), 7.35 (d, J=7.8 Hz, 2H), 6.16 (d, J=18.0 Hz, 1H), 5.91 (d, J=18.0 Hz, 1H), 4.60-4.75 (m, 2H), 2.41 (s, 3H), 2.15-2.35 (m, 3H), 1.55-1.95 (m, 6H), 1.35-1.46 (m, 2H). MS (ESI)=567 (M+1)+.

Example 7.13

6-{[(1R)-1-cyclobutyl-4-(methylamino)-4-oxobutyl]amino}-8-(3-methylphenyl)-7-[4-(trifluoromethyl)benzyl]-7H-purine-2-carboxylic acid

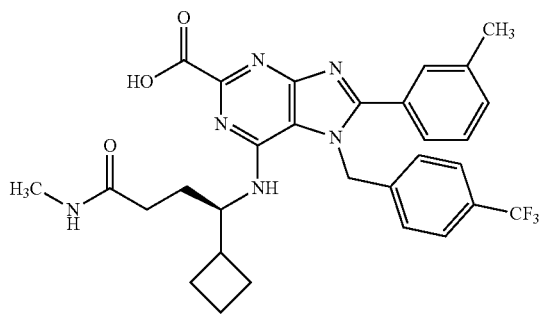 [SMILES: CNC(=O)CC[C@@H](Nc1nc(C(=O)O)nc2nc(-c3cccc(C)c3)n(Cc3ccc(C(F)(F)F)cc3)c12)C1CCC1]

Using a procedure analogous to that described in Example 7.12, and starting with (R)-4-cyclobutyl-4-((2-(methoxycarbonyl)-8-(3-methylphenyl)-7-(4-(trifluoromethyl)benzyl)-7H-purin-6-yl)amino)butanoic acid, Example 7.6 (Step 1) and methylamine hydrochloride, 6-{[(1R)-1-cyclobutyl-4-(methylamino)-4-oxobutyl]amino}-8-(3-methylphenyl)-7-[4-(trifluoromethyl)benzyl]-7H-purine-2-carboxylic acid was prepared. $^1$H NMR (300 MHz, CD$_3$OD) δ 7.71 (d, J=8.0 Hz, 2H), 7.45-7.61 (m, 4H), 7.34 (d, J=8.0 Hz, 2H), 6.26 (d, J=18.3 Hz, 1H), 5.94 (d, J=18.3 Hz, 1H), 4.68 (dt, J=9.4, 3.2 Hz, 1H), 2.70 (s, 3H), 2.41 (s, 3H), 2.18-2.30 (m, 3H), 1.60-1.95 (m, 6H), 1.35-1.48 (m, 2H). MS (ES)=581 (M+1)$^+$.

Example 7.14

(4R)-4-cyclobutyl-4-({8-[4-(1-methylethyl)pyridin-2-yl]-7-[4-(trifluoromethyl)benzyl]-7H-purin-6-yl}amino)butanoic acid

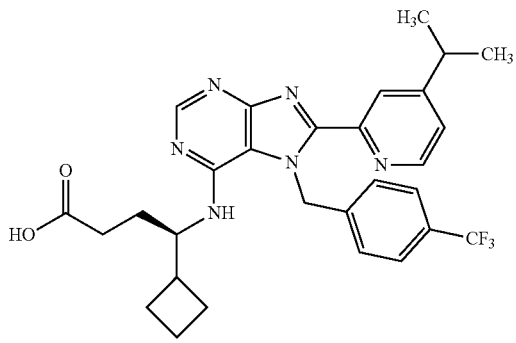 [SMILES: CC(C)c1ccnc(-c2nc3ncnc(N[C@H](CCC(=O)O)C4CCC4)c3n2Cc2ccc(C(F)(F)F)cc2)c1]

Step 1: To a solution of (R)-4-((2-chloro-7-(4-(trifluoromethyl)benzyl)-7H-purin-6-yl)amino)-4-cyclobutylbutan-1-ol, Example 7.2 (Step 2), (900 mg, 1.98 mmol) in acetonitrile (20.0 mL) and water (10.0 mL) were added TEMPO (65.0 mg, 0.42 mmol) and [bis(acetoxy)iodo]benzene (2.60 g, 8.07 mmol) sequentially. The reaction mixture was stirred at room temperature for 12 hours. The organics were removed under reduced pressure and the resulting residue was extracted with CH$_2$Cl$_2$ (20 mL). The organic layer was washed with water (10 mL) and brine (10 mL), then dried over Na$_2$SO$_4$, filtered and concentrated in vacuo. The resulting residue was purified by silica gel chromatography (10% MeOH/CH$_2$Cl$_2$) to afford (R)-4-((2-chloro-7-(4-(trifluoromethyl)benzyl)-7H-purin-6-yl)amino)-4-cyclobutylbutanoic acid. $^1$H NMR (300 MHz, CD$_3$Cl) δ 7.88 (s, 1H), 7.70 (d, J=7.8 Hz, 2H), 7.33 (d, J=7.8 Hz, 2H), 5.84 (d, J=17.3 Hz, 1H), 5.55 (d, J=17.3 Hz, 1H), 4.77 (d, J=8.8 Hz, 1H), 4.18-4.32 (m, 1H), 1.10-2.48 (m, 11H). MS (APCI)=468 (M+1)$^+$.

Step 2: To a solution of (R)-4-((2-chloro-7-(4-(trifluoromethyl)benzyl)-7H-purin-6-yl)amino)-4-cyclobutylbutanoic acid (700 mg, 1.50 mmol) in CH$_2$Cl$_2$ (10.0 mL), were added oxalyl chloride (450 mg, 3.54 mmol) and DMF (10.0 mg, 0.14 mmol). The reaction was stirred for 2 hours at room temperature. Then MeOH (0.5 mL) was added and the reaction was concentrated under reduced pressure and the resulting residue was purified by silica gel column chromatography (50% EtOAc/hexanes) to afford (R)-methyl 4-((2-chloro-7-(4-(trifluoromethyl)benzyl)-7H-purin-6-yl)amino)-4-cyclobutylbutanoate. MS (APCI) 482 (M+1)$^+$.

Step 3: A dry reaction vial was charged with di(1-adamantyl)-n-butylphosphine (104 mg, 0.29 mmol) and palladium acetate (33.0 mg, 0.15 mmol). 1,4-Dioxane (2.0 mL) was added and the mixture was degassed with Ar for 10 minutes. The vial was then sealed and heated at 70° C. for 30 minutes. The yellow catalyst slurry was then added via syringe to a second dry reaction vial containing (R)-methyl 4-((2-chloro-7-(4-(trifluoromethyl)benzyl)-7H-purin-6-yl)amino)-4-cyclobutylbutanoate (700 mg, 1.45 mmol), 4-isopropyl-2-bromopyridine (435 mg, 2.17 mmol), cesium fluoride (661 mg, 4.35 mmol), and pivalic acid (148 mg, 1.45 mmol). The reaction was degassed with Ar for 10 minutes, and then the vial was sealed and heated at 110° C. for 16 hours. The reaction was then cooled to room temperature, diluted with EtOAc (100 mL), and washed with water (30 mL). The organic layer was washed with brine (20 mL), dried over Na$_2$SO$_4$, filtered, and concentrated in vacuo. The residue was purified by silica gel chromatography (20% EtOAc/hexanes) to afford (R)-methyl 4-((2-chloro-8-(4-isopropylpyridin-2-yl)-7-(4-(trifluoromethyl)benzyl)-7H-purin-6-yl)amino)-4-cyclobutylbutanoate. $^1$H NMR (300 MHz, CD$_3$Cl) δ 8.43 (bs, 1H), 8.42 (d, J=3.4 Hz, 1H), 7.68 (d, J=8.2 Hz, 2H), 7.36 (d, J=8.2 Hz, 2H), 7.23 (dd, J=4.8, 1.6 Hz, 1H), 6.93 (d, J=17.3 Hz, 1H), 6.06 (d, J=17.3 Hz, 1H), 4.63 (d, J=8.8 Hz, 1H), 4.33 (dt, J=9.1, 6.0 Hz, 1H), 3.58 (s, 3H), 2.95-3.06 (m, 1H), 2.08-2.30 (m, 2H), 1.30-1.95 (9H, m), 1.32 (d, J=6.9 Hz, 6H). MS (APCI)=601 (M+1)$^+$.

Step 4: (R)-methyl 4-((2-chloro-8-(4-isopropylpyridin-2-yl)-7-(4-(trifluoromethyl)benzyl)-7H-purin-6-yl)amino)-4-cyclobutylbutanoate (100 mg, 0.17 mmol) was dissolved in ethanol (5.0 mL) and degassed with Ar for 30 minutes. Palladium on carbon, loading 10 wt. % (40.0 mg) and sodium acetate (41.0 mg, 0.5 mmol) were added to the reaction and the mixture was degassed for another 5 minutes. The suspension was stirred at 60° C. under a H$_2$ atmosphere for 6 hours. The reaction was then cooled to room temperature, and the solid was removed by filtration. The solid was washed with methanol. The filtrate was concentrated in vacuo and the crude residue was purified by silica gel chromatography (70% EtOAc/hexanes) to afford (R)-methyl 4-cyclobutyl-4-((8-(4-isopropylpyridin-2-yl)-7-(4-(trifluoromethyl)benzyl)-7H-purin-6-yl)amino)butanoate. MS (APCI)=567 (M+1)$^+$ Step 5: Using a procedure analogous to that described in Example 7.1 (Step 5), and starting with (R)-methyl 4-cyclobutyl-4-((8-(4-isopropylpyridin-2-yl)-7-(4-(trifluoromethyl)benzyl)-7H-purin-6-yl)amino)butanoate, (4R)-4-cyclobutyl-4-({8-[4-(1-methylethyl)pyridin-2-yl]-7-[4-(trifluoromethyl)benzyl]-7H-purin-6-yl}amino)butanoic acid was prepared. $^1$H NMR (400 MHz, CD$_3$OD) δ 8.51 (d, J=5.1 Hz, 1H), 8.32 (br s, 1H), 8.24 (br s, 1H), 7.69 (d, J=8.1 Hz, 2H), 7.39 (dd, J=5.1, 1.6 Hz, 1H), 7.33 (d, J=8.1 Hz, 2H), 6.78 (d, J=17.8 Hz, 1H), 6.15 (d, J=17.8 Hz, 1H), 4.45 (dt, J=9.8, 3.4 Hz, 1H), 2.96-3.10 (m, 1H), 2.05-2.25 (m, 3H), 1.30-1.92 (m, 9H), 1.32 (d, J=6.9 Hz, 6H). MS (ES)=553 (M+1)$^+$.

Example 7.15

6-{[(1R)-1-cyclobutyl-3,4-dihydroxybutyl]amino}-8-(3-methylphenyl)-7-[4-(trifluoromethyl)benzyl]-7H-purine-2-carboxylic acid

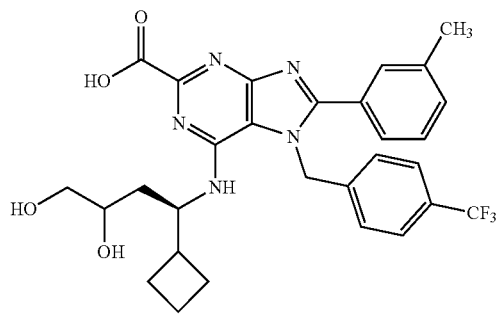 [SMILES: Cc1cccc(-c2nc3nc(C(=O)O)nc(N[C@H](CC(O)CO)C4CCC4)c3n2Cc2ccc(C(F)(F)F)cc2)c1]

Step 1: To a solution of (R)-2-chloro-N-(1-cyclobutylbut-3-en-1-yl)-7-(4-(trifluoromethyl)benzyl)-7H-purin-6-amine, (Example 7.2, Step 1, 1.50 g, 3.4 mmol) in acetone (150 mL), were added osmium tetroxide (89.0 mg, 0.35 mmol), NMO (484 mg, 4.1 mmol) and water (30 mL) at room temperature. The reaction mixture was stirred for 24 hours at room temperature and then sodium thiosulphate (790 mg, 5.0 mmol) was added. Next, the solvent was removed from the reaction by evaporation and the residue was extracted with EtOAc (3×100 mL). The combined organic layers were washed with water (50 mL) and brine (20 mL), dried over anhydrous Na$_2$SO$_4$, filtered and concentrated in vacuo. The crude residue was purified by silica gel column chromatography (10% MeOH/CH$_2$Cl$_2$) to afford (4R)-4-((2-chloro-7-(4-(trifluoromethyl)benzyl)-7H-purin-6-yl)amino)-4-cyclobutyl butane-1,2-diol. MS (APCI)=470 (M+1)$^+$.

Steps 2: Using a procedure analogous to that described in Example 7.2 (Steps 3, 5-7), and starting with (4R)-4-((2-chloro-7-(4-(trifluoromethyl)benzyl)-7H-purin-6-yl)amino)-4-cyclobutylbutane-1,2-diol, 6-{[(1R)-1-cyclobutyl-3,4-dihydroxybutyl]amino}-8-(3-methylphenyl)-7-[4-(trifluoromethyl)benzyl]-7H-purine-2-carboxylic acid was prepared. $^1$H NMR (400 MHz, CD$_3$OD) δ 7.70 (d, J=7.7 Hz, 2H), 7.24-7.50 (m, 4H), 7.23 (d, J=7.7 Hz, 2H), 5.88 (d, J=18.7 Hz, 1H), 5.73 (d, J=18.7 Hz, 1H), 4.65 (br s, 1H), 3.20-3.65 (m, 3H), 2.37 (s, 3H), 1.22-2.20 (m, 9H). MS (ES)=570 (M+1)$^+$.

Example 7.16

6-{[(S)-cyclobutyl(phenyl)methyl]amino}-8-[4-(1-methylethyl)pyridin-2-yl]-7-[4-(trifluoromethyl)benzyl]-7H-purine-2-carboxylic acid

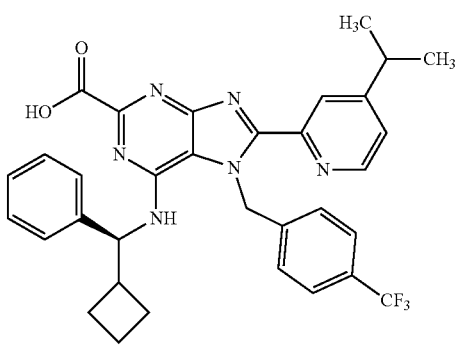 [SMILES: CC(C)c1ccnc(-c2nc3nc(C(=O)O)nc(N[C@H](c4ccccc4)C4CCC4)c3n2Cc2ccc(C(F)(F)F)cc2)c1]

Step 1: To a solution of (S,E)-N-(cyclobutylmethylene)-2-methylpropane-2-sulfinamide, prepared analogously to Preparative Example 7.1, Step 1, (1.20 g, 6.41 mmol) in CH$_2$Cl$_2$ (50 mL) was added phenyl magnesium bromide (7.7 mL, 7.70 mmol, 1M in THF) at −78° C. and the reaction was stirred at −78° C. for 5 hours. The reaction was slowly warmed to room temperature over 2 hours and then quenched by the addition of saturated ammonium chloride solution. EtOAc (200 mL) was added and the organic layer was separated, washed with brine (10 mL), dried over Na$_2$SO$_4$, filtered and concentrated in vacuo. The crude residue was purified by silica gel column chromatography to afford N-(1-cyclobutyl(phenyl)methyl)-2-methylpropane-2-sulfinamide. MS (APCI)=266 (M+1)$^+$.

Step 2: To a solution of N-(1-cyclobutyl(phenyl)methyl)-2-methylpropane-2-sulfinamide (1.48 g, 5.58 mmol) in 1,4-dioxane (10 mL) was added HCl (8 mL, 32 mmol, 4M in 1,4-dioxane) at 0° C. The reaction mixture was stirred at room temperature for 3 hours. After 3 h, the solvent was removed in vacuo. The solid was concentrated from hexanes three times to afford (S)-cyclobutyl(phenyl)methanamine hydrochloride which was carried forward to the next step without further purification. MS (APCI)=162 (M+1)$^+$.

Step 3: Using a procedure analogous to that described in Example 7.1 (Step 1 and 3) and Example 7.14 (Step 3), and starting with 2,6-dichloro-7-(4-(trifluoromethyl)benzyl)-7H-purine (Preparative Example 1.1, Step 1), and (S) cyclobutyl(phenyl) methanamine hydrochloride, (S)-6-((cyclobutyl(phenyl)methyl)amino)-8-(4-isopropylpyridin-2-yl)-7-(4-(trifluoromethyl)benzyl)-7H-purine-2-carbonitrile was prepared. $^1$H NMR (400 MHz, CD$_3$Cl) δ 8.43 (d, J=1.6 Hz, 1H), 8.42 (d, J=5.1 Hz, 1H), 7.72 (d, J=8.2 Hz, 2H), 7.37 (d, J=8.2 Hz, 2H), 7.25 (dd, J=1.6 Hz, 5.1 Hz, 1H), 7.20 (d, J=1.6 Hz, 1H), 7.17 (d, J=3.7 Hz, 1H), 6.82-6.90 (m, 2H), 6.66 (d, J=17.4 Hz, 1H), 6.31 (d, J=17.4 Hz, 1H), 5.21 (dd, J=9.5, 8.2 Hz, 1H), 5.04 (d, J=8.1 Hz, 1H), 2.95-3.05 (m, 1H), 2.28-2.40 (m, 1H), 1.56-1.82 (m, 6H), 1.32 (d, J=6.9 Hz, 6H), 1.24-1.30 (m, 1H). MS (APCI)=582 (M+1)$^+$.

Step 4: Using a procedure analogous to that described in Example 7.1 (Steps 4 and 5), and starting with (S)-6-((cyclobutyl(phenyl)methyl)amino)-8-(4-isopropylpyridin-2-yl)-7-(4-(trifluoromethyl)benzyl)-7H-purine-2-carbonitrile, 6-{[(S)-cyclobutyl(phenyl)methyl]amino}-8-[4-(1-methylethyl)pyridin-2-yl]-7-[4-(trifluoromethyl)benzyl]-7H-purine-2-carboxylic acid was prepared. $^1$H NMR (400

MHz, CD₃OD) δ 8.51 (d, J=5.1 Hz, 1H), 8.26 (br s, 1H), 7.66 (d, J=8.2 Hz, 2H), 7.40 (dd, J=5.1, 1.4 Hz, 1H), 7.32 (d, J=8.2 Hz, 2H), 7.05-7.20 (m, 5H), 6.58 (d, J=17.8 Hz, 1H), 6.45 (d, J=17.8 Hz, 1H), 5.54 (d, J=10.1 Hz, 1H), 4.83 (br s, 1H), 2.98-3.08 (m, 1H), 2.52-2.65 (m, 1H), 1.65-1.85 (m, 6H), 1.32 (d, J=6.9 Hz, 6H), 1.25-1.35 (m, 1H). MS (ES)=601 (M+1)⁺.

Preparative Example 7.3

(R)-1-(3,3-difluorocyclobutyl)ethanamine hydrochloride

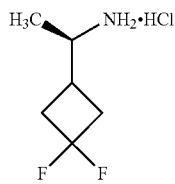

Step 1: N,O-Dimethylhydroxylamine (3.50 g, 43.0 mmol) was added at 0° C. to a solution of 3-oxocyclobutanecarboxylic acid (4.1 g, 36 mmol) in CH₂Cl₂ (200 mL). Propanephosphonic acid anhydride (T3P) (50% wt, 60.0 mL, 43.0 mmol) was added dropwise via addition funnel, and the reaction mixture was stirred at room temperature for 18 hours. After this time, the reaction mixture was partitioned between 1 N sodium hydroxide solution (200 mL) and CH₂Cl₂ (200 mL). The phases were separated and the aqueous layer was extracted with CH₂Cl₂ (200 mL). The combined organic phases were poured slowly at 0° C. into a stirring beaker of 1 N hydrochloric acid solution (200 mL). The layers were separated and the organic layer was washed with saturated sodium bicarbonate solution (200 mL), dried over anhydrous sodium sulfate, filtered, and concentrated under reduced pressure. The residue was dried under high vacuum overnight to afford N-methoxy-N-methyl-3-oxocyclobutanecarboxamide as a red oil: ¹H NMR (300 MHz, CDCl₃) δ 3.73 (s, 3H), 3.36-3.42 (m, 3H), 3.25 (s, 3H), 3.15-3.24 (m, 2H).

Step 2: N-methoxy-N-methyl-3-oxocyclobutanecarboxamide (4.54 g, 28.6 mmol) was added to a solution of diethylaminosulfur trifluoride (DAST) (8.20 mL, 61.0 mmol) in chloroform (200 mL) and the reaction mixture was heated at 40° C. for 72 hours. After this time, the mixture was cooled to room temperature and diluted with saturated sodium bicarbonate solution (200 mL). The resulting biphasic mixture was stirred vigorously for 15 minutes. The phases were separated and the organic phase was dried over anhydrous sodium sulfate, filtered, and concentrated under reduced pressure to afford 3,3-difluoro-N-methoxy-N-methylcyclobutanecarboxamide as an orange oil: ¹H NMR (300 MHz, CDCl₃) δ 3.69 (s, 3H), 3.22-3.30 (m, 1H), 3.21 (s, 3H), 2.69-2.93 (m, 4H). ¹⁹F NMR (282 MHz, CDCl₃) δ 66.57 (d, J=193 Hz, 1F), 83.54 (d, J=193 Hz, 1F).

Step 3: A solution of 3,3-difluoro-N-methoxy-N-methylcyclobutanecarboxamide (2.27 g, 12.7 mmol) in anhydrous diethyl ether (65 mL) was cooled to 78° C. Methyl magnesium bromide (12.6 mL, 38.0 mmol, 3M in diethyl ether) was added dropwise to the reaction via an addition funnel. After the addition, the reaction mixture was warmed to 15° C. and stirred for 3.5 hours. The reaction mixture was quenched at 15° C. with saturated ammonium chloride solution (80 mL). The resulting layers were separated, and the aqueous layer was back-extracted with chloroform (2×100 mL). The combined organic phases were dried over anhydrous sodium sulfate, filtered, and concentrated under reduced pressure to afford 1-(3,3-difluorocyclobutyl)ethanone as a red oil: ¹H NMR (300 MHz, CDCl₃) δ 3.01-3.09 (m, 1H), 2.61-2.83 (m, 4H), 2.18 (s, 3H); ¹⁹F NMR (282 MHz, CDCl₃) δ −67.63 (d, J=193 Hz, 1F), −81.25 (d, J=193 Hz, 1F).

Step 4: A solution of 1-(3,3-difluorocyclobutyl)ethanone (2.94 g, 22.0 mmol), (R)-2-methylpropane-2-sulfinamide (2.66 g, 22.0 mmol) and titanium(IV)ethoxide (11.0 g, 48.2 mmol) in anhydrous tetrahydrofuran (100 mL) was heated at 70° C. for 18 hours. After this time, the reaction mixture was cooled to −78° C. and lithium borohydride (44 mL, 88.0 mmol, 2M in tetrahydrofuran) was added via addition funnel over a period of 4 hours. The reaction mixture was stirred at −78° C. for 1 hour, and then stirred at room temperature for 18 hours. After this time, the reaction was quenched by addition of methanol (5.0 mL) and brine (150 mL). The resulting biphasic mixture was stirred vigorously for 20 min and then vacuum-filtered through diatomaceous earth. The filtrate phases were separated. The aqueous phase was back-extracted with EtOAc (100 mL). The combined organic phases were dried over anhydrous sodium sulfate, filtered, and concentrated under reduced pressure. The residue was purified by silica gel column chromatography (0-100% EtOAc/hexanes) to afford diastereomers of N-(1-(3,3-difluorocyclobutyl)ethyl)-2-methylpropane-2-sulfinamide: a: ¹H NMR (500 MHz, CDCl₃) δ 3.29-3.34 (m, 1H), 3.08 (d, J=4.5 Hz, 1H), 2.63-2.70 (m, 2H), 2.38-2.50 (m, 1H), 2.38-2.50 (m, 1H), 2.13-2.32 (m, 1H), 1.20 (s, 9H), 1.19 (d, J=6.5 Hz, 3H); ¹⁹F NMR (282 MHz, CDCl₃) δ −67.00 (d, J=194 Hz, 1F), −81.20 (d, J=194 Hz, 1F); and b: ¹H NMR (300 MHz, CDCl₃) δ 3.32-3.33 (m, 1H), 2.91 (d, J=7.5 Hz, 1H), 2.56-2.65 (m, 2H), 2.13-2.34 (m, 3H), 1.26 (d, J=6.6 Hz, 3H), 1.18 (s, 9H); ¹⁹F NMR (282 MHz, CDCl₃) δ 66.51 (d, J=193 Hz, 1F), −80.80 (d, J=193 Hz, 1F).

Step 5: A solution of HCl (4.0 mL, 16.2 mmol, 4 M in 1,4-dioxane) was added dropwise to a solution of N-(1-(3, 3-difluorocyclobutyl)ethyl)-2-methylpropane-2-(R)-sulfinamide (1.19 g, 4.97 mmol) in methanol (9.0 mL). The reaction mixture was stirred at room temperature for 6 hours. The mixture was then concentrated under reduced pressure and dried under high vacuum to afford (R)-1-(3,3-difluorocyclobutyl)ethanamine hydrochloride as a yellow solid: ¹H NMR (400 MHz, CD₃OD) δ 2.67-2.75 (m, 2H), 2.39-2.509 (m, 2H), 2.25-2.26 (m, 2H), 1.27 (d, J=8.0 Hz, 3H).

Example 7.17

6-{[(1R)-1-(3,3-difluorocyclobutyl)ethyl]amino}-8-(2-methoxy-5-methylphenyl)-7-[4-(trifluoromethyl)benzyl]-7H-purine-2-carboxylic acid

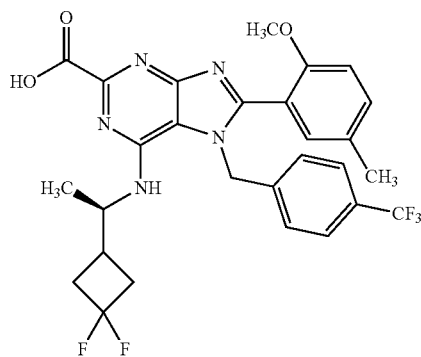 [SMILES: COc1ccc(C)cc1-c1nc2nc(C(=O)O)nc(N[C@H](C)C3CC(F)(F)C3)c2n1Cc1ccc(C(F)(F)F)cc1]

Step 1: Using a procedure analogous to that described in Example 7.2 (Step 1), and starting with 2,6-dichloro-7-(4-(trifluoromethyl)benzyl)-7H-purine and (R)-1-(3,3-difluorocyclobutyl)ethanamine hydrochloride, (R)-2-chloro-N-(1-(3,3-difluorocyclobutyl)ethyl)-7-(4-(trifluoromethyl)benzyl)-7H-purin-6-amine was prepared. $^{1}$H NMR (300 MHz, CDCl$_{3}$) δ 8.15 (s, 1H), 7.72-7.74 (d, J=6.0 Hz, 2H), 7.25-7.29 (m, 2H), 5.63-5.75 (m, 2H), 4.52-4.54 (d, J=6.0 Hz, 1H), 4.35-4.42 (m, 1H), 2.48-2.57 (m, 1H), 2.25-2.26 (m, 2H), 1.91-2.02 (m, 2H), 0.86-0.88 (d, J=6.0 Hz, 3H.). MS (ES)=446 (M+1)$^{+}$.

Step 2: Using a procedure analogous to that described in Example 7.2 (Step 3), and starting with (R)-2-chloro-N-(1-(3,3-difluorocyclobutyl)ethyl)-7-(4-(trifluoromethyl)benzyl)-7H-purin-6-amine, (R)-6-((1-(3,3-difluorocyclobutyl)ethyl)amino)-7-(4-(trifluoromethyl)benzyl)-7H-purine-2-carbonitrile was prepared. $^{1}$H NMR (400 MHz, CDCl$_{3}$) δ 8.19 (s, 1H), 7.74-7.76 (d, J 8.0 Hz, 2H), 7.27-7.31 (m, 2H), 5.63-5.57 (m, 2H), 4.54-4.56 (d, J=8.0 Hz, 1H), 4.35-4.42 (m, 1H), 2.48-2.59 (m, 1H), 2.25-2.27 (m, 2H), 1.91-2.02 (m, 2H), 0.86-0.88 (d, J=8.0 Hz, 3H.). MS (ES) 437 (M+1)$^{+}$.

Step 3: Using a procedure analogous to that described in Example 7.2 (Step 5), and starting with (R)-6-((1-(3,3-difluorocyclobutyl)ethyl)amino)-7-(4-(trifluoromethyl)benzyl)-7H-purine-2-carbonitrile and 2-bromo-1-methoxy-4-methylbenzene, (R)-6-((1-(3,3-difluorocyclobutyl)ethyl)amino)-8-(2-methoxy-5-methylphenyl)-7-(4-(trifluoromethyl)benzyl)-7H-purine-2-carbonitrile was prepared. $^{1}$H NMR (300 MHz, CDCl$_{3}$) δ 7.73-7.75 (d, J=6.0 Hz, 2H), 7.31-7.43 (m, 4H), 6.86-6.89 (d, J=9.0 Hz, 1H), 5.30-5.47 (m, 2H), 4.59 (m, 1H), 4.19-4.21 (d, J=6.0 Hz, 1H), 3.51 (s, 3H), 2.51-2.55 (m, 1H), 2.43 (s, 3H), 2.22-2.34 (m, 2H), 2.04-2.19 (m, 1H), 1.95, (br s, 1H), 0.75-0.77 (d, J=6.0 Hz, 3H). MS (ES)=557 (M+1)$^{+}$.

Step 4: Using a procedure analogous to that described in Example 7.1 (Steps 4 and 5), and starting with (R)-6-((1-(3,3-difluorocyclobutyl)ethyl)amino)-8-(2-methoxy-5-methylphenyl)-7-(4-(trifluoromethyl)benzyl)-7H-purine-2-carbonitrile, 6-{[(1R)-1-(3,3-difluorocyclobutyl)ethyl]amino}-8-(2-methoxy-5-methylphenyl)-7-[4-(trifluoromethyl)benzyl]-7H-purine-2-carboxylic acid was prepared. $^{1}$H NMR (400 MHz, CD$_{3}$OD) δ 7.75-7.77 (d, J=8.4 Hz, 2H), 7.35-7.44 (m, 4H), 6.88-6.90 (d, J=9.3 Hz, 2H), 5.65 (d, J=18.0 Hz, 1H), 5.45 (d, J=18.0 Hz, 1H), 4.57 (br s, 1H), 4.37 (br s, 1H), 3.52 (s, 3H), 2.47-2.53 (m, 1H), 2.35 (s, 3H), 2.17-2.21 (m, 2H), 1.97-2.04 (m, 1H), 1.88 (br s, 1H), 0.78 (d, J=7.1 Hz, 3H). MS (ES)=576 (M+1)$^{+}$.

Preparative Example 7.4

1-(3-methylcyclobutyl)ethanamine hydrochloride

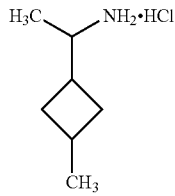

Step 1: A solution of 3-methylenecyclobutanecarbonitrile (9.31 g, 100 mmol), potassium hydroxide (25.2 g, 450 mmol), ethanol (80 mL) and water (80 mL) was heated at reflux for 12 hours. The reaction mixture was then cooled to room temperature and acidified to pH 2 with hydrochloric acid (6M in water). Ethanol was removed under reduced pressure. The remaining aqueous phase was extracted with diethyl ether (2×40 mL). The combined organic extracts were dried over anhydrous sodium sulfate, filtered, and concentrated under reduced pressure to afford 3-methylenecyclobutanecarboxylic acid: $^{1}$H NMR (300 MHz, CDCl$_{3}$) δ 4.78-4.83 (m, 2H), 2.80-3.25 (m, 5H).

Step 2: Thionyl chloride (23 mL) was added to a solution of 3-methylenecyclobutanecarboxylic acid (5.00 g, 44.6 mmol) in CH$_{2}$Cl$_{2}$ (23 mL) and the reaction mixture was heated at reflux for 5 hours. The reaction mixture was then cooled to room temperature and concentrated under reduced pressure. The residue was re-dissolved in methylene chloride (50 mL) and N,N-diisopropylethylamine (37 mL, 223 mmol) and N,O-dimethylhydroxylamine hydrochloride (8.68 g, 89.0 mmol) were added. The reaction mixture was stirred at room temperature 18 hours. After this time, the reaction mixture was washed with saturated sodium bicarbonate solution (15 mL), water (15 mL) and brine (15 mL). The organic phase was dried over anhydrous sodium sulfate, filtered, and concentrated under reduced pressure to yield a yellow syrup. The residue was purified by chromatography (5-15% EtOAc/heptane) to afford N-methoxy-N-methyl-3-methylenecyclobutanecarboxamide: $^{1}$H NMR (300 MHz, CDCl$_{3}$) δ 4.77-4.81 (m, 2H), 4.13-4.16 (m, 1H), 3.67 (s, 3H), 3.18 (s, 3H), 2.99-3.09 (m, 2H), 2.77-2.88 (m, 2H).

Step 3: Methylmagnesium bromide (7.90 mL, 23.7 mmol, 3M in diethyl ether) was added slowly at 0° C. to a solution of N-methoxy-N-methyl-3-methylenecyclobutanecarboxamide (1.84 g, 11.8 mmol) in anhydrous tetrahydrofuran (47 mL) and the reaction mixture was stirred at 0° C. for 2 hours. The reaction was carefully quenched at 0° C. with saturated ammonium chloride solution (1.0 mL). The reaction mixture was diluted with diethyl ether (50 mL) and washed with water (25 mL) and brine (25 mL). The organic phase was dried over anhydrous sodium sulfate, filtered, and concentrated under reduced pressure to afford 1-(3-methylenecyclobutyl)ethanone: $^{1}$H NMR (300 MHz, CDCl$_{3}$) δ 4.79-4.82 (m, 2H), 3.13-3.30 (m, 1H), 2.77-3.00 (m, 4H), 2.14 (s, 3H).

Step 4: A solution of 1-(3-methylenecyclobutyl)ethanone (1.04 g, 9.45 mmol), titanium(IV)ethoxide (6.82 g, 20.8 mmol), and (R)-2-methylpropane-2-sulfinamide (1.26 g, 10.4 mmol) in anhydrous tetrahydrofuan (38 mol) was heated at 75° C. for 5 hours. The reaction was cooled to −78° C. and sodium borohydride (1.41 g, 37.8 mmol) was added in small portions over several minutes. The reaction was stirred at −78° C. for 4 hours and then stirred at −30° C. for 1 hour. The reaction was quenched at −30° C. by addition of methanol (5 mL) and the resulting reaction mixture was stirred at room temperature for 0.5 hours. The reaction mixture was poured into water (150 mL) and extracted with diethyl ether (100 mL). The organic phase was dried over anhydrous sodium sulfate, filtered, and concentrated under reduced pressure. The residue was purified by silica gel chromatography (5-50% EtOAc/heptane) to afford 2-methyl-N-(1-(3-methylenecyclobutyl)ethyl)propane-2-sulfinamide: $^{1}$H NMR (300 MHz, CDCl$_{3}$) δ 4.76-4.78 (m, 2H), 3.28-3.40 (m, 1H), 3.05-3.12 (m, 1H), 2.65-2.83 (m, 2H), 2.20-2.60 (m, 3H), 1.19 (s, 9H), 1.12 (d, J=6.6 Hz, 3H).

Step 5: To a solution of 2-methyl-N-(1-(3-methylenecyclobutyl)ethyl)propane-2-sulfinamide (1.0 g, 4.65 mmol) in methanol (5.0 mL) was added Pd/C (5%)(100 mg) in a Parr hydrogenation flask and the reaction was run at 50 psi for 22 hours. After this time, the reaction mixture was filtered through Celite and the resulting filtrate was concentrated and purified by silica gel chromatography (10-70% EtOAc/hexanes) to afford 2-methyl-N-(1-(3-methylcyclobutyl)ethyl)propane-2-sulfinamide. $^{1}$H NMR (300 MHz, CDCl$_{3}$) δ 3.26-3.39 (m, 1H), 3.04-3.12 (m, 1H), 2.65-2.83 (m, 2H), 2.25-2.65 (m, 4H), 1.19 (s, 9H), 1.12 (d, J=6.6 Hz, 3H), 0.85-1.05 (m, 3H).

Step 6: A solution of 2-methyl-N-(1-(3-methylcyclobutyl)ethyl)propane-2-sulfinamide (0.480 g, 2.09 mmol) in methanol (2.0 mL) was treated with hydrogen chloride (1.0 mL, 4.00 mmol, 4M in 1,4-dioxane) and the reaction was stirred at room temperature 12 hours. The reaction was then concentrated under reduced pressure and the residue was dried under high vacuum to afford 1-(3-methylcyclobutyl)ethanamine hydrochloride as a light brown solid which was used directly in the next step without further purification.

Example 7.18

8-(2-methoxy-5-methylphenyl)-6-{[1-(3-methylcyclobutyl)ethyl]amino}-7-[4-(trifluoromethyl)benzyl]-7H-purine-2-carboxylic acid

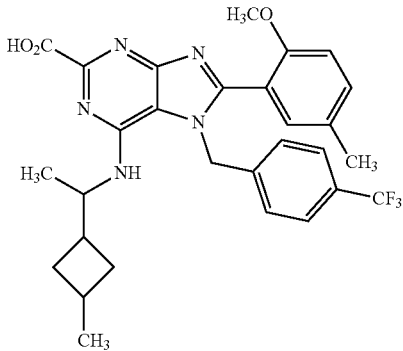 [SMILES: COc1ccc(C)cc1-c1nc2nc(C(=O)O)nc(NC(C)C3CC(C)C3)c2n1Cc1ccc(C(F)(F)F)cc1]

Step 1: Using a procedure analogous to that described in Example 7.2 (Step 1), and starting with 2,6-dichloro-7-(4-(trifluoromethyl)benzyl)-7H-purine and 1-(3-methylcyclobutyl) ethanamine hydrochloride, 2-chloro-N-(1-(3-methylcyclobutyl)ethyl)-7-(4-(trifluoromethyl)benzyl)-7H-purin-6-amine was prepared. $^1$H NMR (300 MHz, CDCl$_3$) δ 8.05 (s, 1H), 7.72-7.73 (d, J=6.0 Hz, 2H), 7.29-7.30 (d, J=6.0 Hz, 2H), 5.69 (m, 2H), 4.17-4.53 (m, 2H), 2.00-2.23 (m, 1H), 1.88-1.99 (m, 2H), 1.53-1.77 (m, 3H), 0.92-1.01 (m, 3H), 0.82-0.92 (m, 3H). MS (ES)=424 (M+1)$^+$.

Step 2: To a stirred solution of 2-chloro-N-(1-(3-methylcyclobutyl)ethyl)-7-(4-(trifluoromethyl)benzyl)-7H-purin-6-amine (250 mg, 0.59 mmol) in DMF (2.0 mL) was added sodium thiomethoxide (82.7 mg, 1.18 mmol) at room temperature. The reaction mixture was heated to 80° C. for 12 hours. After this time water was added to the reaction mixture and the mixture was extracted with EtOAc. The organic layer was dried over sodium sulfate and concentrated under reduced pressure. The crude residue was purified by combiflash (30% EtOAc/hexanes) to afford N-(1-(3-methylcyclobutyl)ethyl)-2-(methylthio)-7-(4-(trifluoromethyl)benzyl)-7H-purin-6-amine. $^1$H NMR (400 MHz, CDCl$_3$) δ 8.02 (s, 1H), 7.70-7.72 (d, J=6.0 Hz, 2H), 7.29 (d, J=6.0 Hz, 2H), 5.49 (m, 2H), 3.90-4.31 (m, 2H), 3.65-3.86 (m, 1H), 2.59 (s, 3H), 2.00-2.22 (m, 1H), 1.88-1.97 (m, 2H), 1.53-1.79 (m, 2H), 0.91-1.01 (m, 3H), 0.80-0.90 (m, 3H). MS (ES)=436 (M+1)$^+$.

Step 3: To a stirred solution of N-(1-(3-methylcyclobutyl)ethyl)-2-(methylthio)-7-(4-(trifluoromethyl)benzyl)-7H-purin-6-amine (200 mg, 0.45 mmol) in MeOH (2.0 mL) was added Oxone (565 mg, 0.91 mmol) in H$_2$O (1.0 mL) at 10° C. The resulting reaction mixture was stirred for 3 hours at room temperature. After this time the solvent was removed under reduced pressure and the residue was partitioned between water and EtOAc. The organic layer was dried over sodium sulfate, filtered, and concentrated under reduced pressure. The residue was purified by silica gel chromatography (30% EtOAc/hexanes) to afford N-(1-(3-methylcyclobutyl)ethyl)-2-(methylsulfonyl)-7-(4-(trifluoromethyl)benzyl)-7H-purin-6-amine as a white solid. $^1$H NMR (300 MHz, CDCl$_3$) δ 8.15 (s, 1H), 7.73-7.75 (d, J=6.0 Hz, 2H), 7.28-7.30 (d, J=6.0 Hz, 2H), 5.63 (m, 2H), 4.24-4.27 (m, 2H), 2.54 (s, 3H), 2.06-2.27 (m, 1H), 1.68-1.98 (m, 2H), 1.59-1.64 (m, 2H), 1.43-1.46 (m, 1H), 1.01-1.22 (m, 3H), 0.82-0.93 (m, 3H). MS (ES)=468 (M+1)$^+$.

Step 4: To a stirred solution of N-(1-(3-methylcyclobutyl)ethyl)-2-(methylsulfonyl)-7-(4-(trifluoromethyl)benzyl)-7H-purin-6-amine (200 mg, 0.42 mmol) in DMF (1.0 Ml) and IPA (1.0 mL) was added NaCN (62 mg, 1.28 mmol) at room temperature. The reaction mixture was stirred for 12 hours at 120° C. The reaction was cooled to room temperature and water was added to the reaction. The mixture was extracted with EtOAc and the organic layer was dried over sodium sulfate, filtered and concentrated under reduced pressure. The residue was purified by silica gel chromatography (30% EtOAc/hexane) to afford 6-((1-(3-methylcyclobutyl)ethyl)amino)-7-(4-(trifluoromethyl)benzyl)-7H-purine-2-carbonitrile as a white solid. $^1$H NMR (400 MHz, CDCl$_3$) δ 8.02 (s, 1H), 7.70-7.72 (d, J=6.0 Hz, 2H), 7.28-7.29 (d, J=6.0 Hz, 2H), 5.49 (m, 2H), 3.90-4.31 (m, 2H), 3.66-3.87 (m, 2H), 2.00-2.22 (m, 1H), 1.88-1.97 (m, 2H), 1.53-1.79 (m, 1H), 0.91-1.01 (m, 3H), 0.80-0.90 (m, 3H). MS (ES)=415 (M+1)$^+$.

Step 5: Using a procedure analogous to that described in Example 7.2 (Step 5), and starting with 6-((1-(3-methylcyclobutyl)ethyl)amino)-7-(4-(trifluoromethyl)benzyl)-7H-purine-2-carbonitrile and 2-bromo-1-methoxy-4-methylbenzene, 8-(2-methoxy-5-methylphenyl)-6-((1-(3-methylcyclobutyl)ethyl)amino)-7-(4-(trifluoromethyl)benzyl)-7H-purine-2-carbonitrile was prepared. $^1$H NMR (400 MHz, CDCl$_3$) δ 8.02 (s, 1H), 7.70-7.72 (d, J=6.0 Hz, 2H), 7.28-7.29 (d, J=6.0 Hz, 2H), 5.49 (m, 2H), 3.90-4.31 (m, 2H), 3.65-3.89 (m, 1H), 3.50 (s, 3H), 2.59 (s, 3H), 2.01-2.22 (m, 1H), 1.88-1.97 (m, 2H), 1.53-1.79 (m, 3H), 0.91-1.01 (m, 3H), 0.80-0.90 (m, 3H). MS (ES)=535 (M+1)$^+$.

Step 6: Using a procedure analogous to that described in Example 7.1 (Step 4), and starting with 8-(2-methoxy-5-methylphenyl)-6-((1-(3-methylcyclobutyl)ethyl)amino)-7-(4-(trifluoromethyl)benzyl)-7H-purine-2-carbonitrile, methyl 8-(2-methoxy-5-methylphenyl)-6-((1-(3-methylcyclobutyl)ethyl)amino)-7-(4-(trifluoromethyl)benzyl)-7H-purine-2-carboxylate was prepared. $^1$H NMR (300 MHz, CDCl$_3$) δ 8.01 (s, 1H), 7.71-7.72 (d, J=6.0 Hz, 2H), 7.28-7.29 (d, J=6.0 Hz, 2H), 5.49 (m, 2H), 3.90-4.31 (m, 2H), 3.68-3.88 (m, 1H), 3.86 (s, 3H), 3.48 (s, 3H), 2.58 (s, 3H), 2.00-2.22 (m, 1H), 1.88-1.97 (m, 2H), 1.52-1.78 (m, 2H), 0.89-1.01 (m, 3H), 0.87-0.90 (m, 3H). MS(ES)=568 (M+1)$^+$.

Step 7: Using a procedure analogous to that described in Example 7.1 (Step 5), and starting with methyl 8-(2-methoxy-5-methylphenyl)-6-((1-(3-methylcyclobutyl)ethyl)amino)-7-(4-(trifluoromethyl)benzyl)-7H-purine-2-carboxylate, 8-(2-methoxy-5-methylphenyl)-6-{[1-(3-methylcyclobutyl)ethyl]amino}-7-[4-(trifluoromethyl)benzyl]-7H-purine-2-carboxylic acid was prepared. $^1$H NMR (400 MHz, CD$_3$OD) δ 7.85-7.55 (m, 4H), 7.40-7.33 (m, 2H), 7.21 (d, J=8.3 Hz, 2H), 7.09 (d, J=7.8 Hz, 2H), 5.68 (d, J=18.0 Hz, 1H), 5.46 (d, J=18.0 Hz, 1H), 4.67 (br s, 1H), 4.99 (br s, 1H), 3.61 (s, 3H), 2.47-2.53 (m, 1H), 2.31 (s, 3H), 2.02-2.04 (m, 2H), 1.79-1.84, (m, 1H), 1.55-1.59, (m, 1H), 1.01-1.29, (m, 2H), 0.99-0.85, (m, 3H). MS (ES)=554 (M+1)$^+$.

Example 7.19

6-{[(1R)-1-(2,2-difluorocyclopropyl)ethyl]amino}-8-(2-methoxy-5-methylphenyl)-7-[4-(trifluoromethyl)benzyl]-7H-purine-2-carboxylic acid

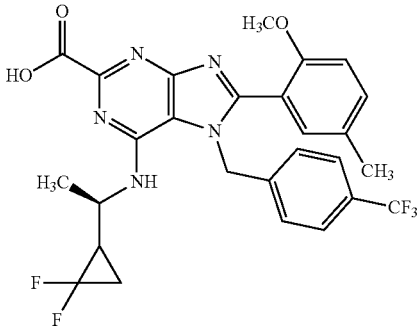 [SMILES: COc1ccc(C)cc1-c1nc2nc(C(=O)O)nc(N[C@H](C)C3CC3(F)F)c2n1Cc1ccc(C(F)(F)F)cc1]

Using a procedure analogous to that described in Example 7.17, and starting with 2,2-difluorocyclopropanecarboxylic acid, 6-{[(1R)-1-(2,2-difluorocyclopropyl)ethyl]amino}-8-(2-methoxy-5-methylphenyl)-7-[4-(trifluoromethyl)benzyl]-7H-purine-2-carboxylic acid was prepared. ¹H NMR (400 MHz, CD₃COCD₃) δ 7.69 (d, J=7.4 Hz, 2H), 7.40 (br s, 1H), 7.39 (d, J=7.8 Hz, 1H), 7.31 (d, J=7.4 Hz, 2H), 7.08 (d, J=7.8 Hz, 1H), 5.85-5.98 (m, 1H), 5.76 (d, J=16.8 Hz, 1H), 5.65 (d, J=16.8 Hz, 1H), 4.30-4.42 (m, 1H), 3.66 (s, 3H), 2.32 (s, 3H), 1.75-1.87 (m, 1H), 1.42-1.55 (m, 1H), 1.25-1.32 (m, 1H), 1.19 (d, J=6.1 Hz, 3H). MS (ES)=562

TABLE 7

| Ex. | FRET IC$_{50}$ (nM) | Structure | Chemical Name | Salt Form | [M + H]⁺ Calc'd | [M + H]⁺ Obsv'd |
|---|---|---|---|---|---|---|
| 7.1 | 104.9 | 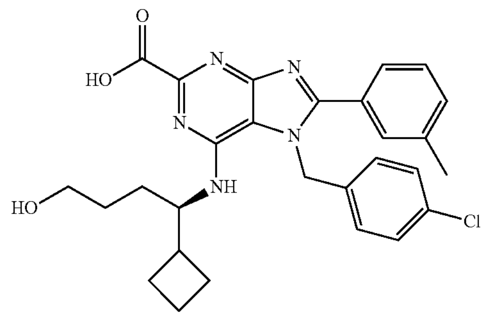 [SMILES: Cc1cccc(-c2nc3nc(C(=O)O)nc(N[C@H](CCCO)C4CCC4)c3n2Cc2ccc(Cl)cc2)c1] | (R)-Methyl-7-(4-chlorobenzyl)-6-{[(1R)-1-cyclobutyl-4-hydroxybutyl]amino}-8-(3-methylphenyl)-7H-purine-2-carboxylic acid | | 520 | 520 |
| 7.2 | 41 | 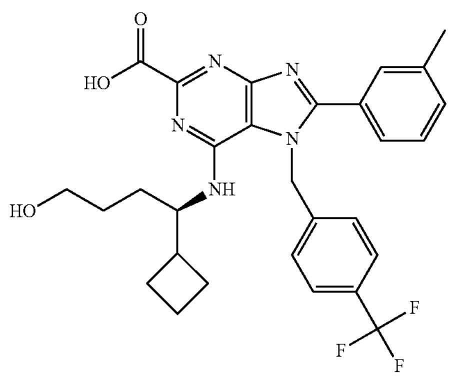 [SMILES: Cc1cccc(-c2nc3nc(C(=O)O)nc(N[C@H](CCCO)C4CCC4)c3n2Cc2ccc(C(F)(F)F)cc2)c1] | 6-{[(1R)-1-cyclobutyl-4-hydroxybutyl]amino}-8-(3-methylphenyl)-7-[4-(trifluoromethyl)benzyl]-7H-purine-2-carboxylic acid | | 554 | 554 |
| 7.3 | 3241 | 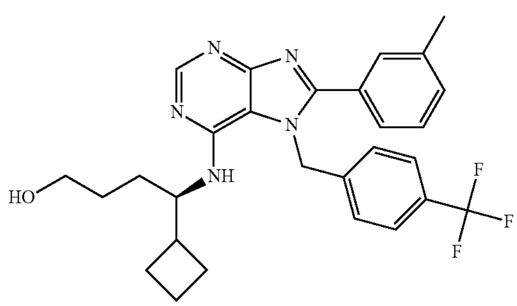 [SMILES: Cc1cccc(-c2nc3ncnc(N[C@H](CCCO)C4CCC4)c3n2Cc2ccc(C(F)(F)F)cc2)c1] | (4R)-4-cyclobutyl-4-({8-(3-methylphenyl)-7-[4-(trifluoromethyl)benzyl]-7H-purin-6-yl}amino)butan-1-ol | | 510 | 510 |
| 7.5 | 141.7 | 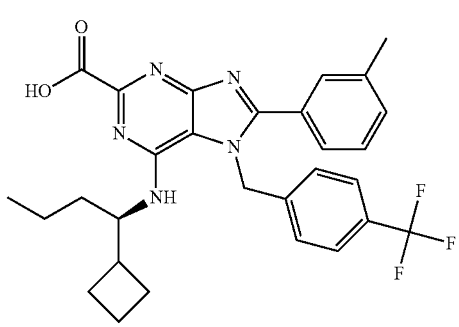 [SMILES: CCC[C@@H](Nc1nc(C(=O)O)nc2nc(-c3cccc(C)c3)n(Cc3ccc(C(F)(F)F)cc3)c12)C1CCC1] | 6-{[(1R)-1-cyclobutylbutyl]amino}-8-(3-methylphenyl)-7-[4-(trifluoromethyl)benzyl]-7H-purine-2-carboxylic acid | | 538 | 538 |

TABLE 7-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 7.7 | 832 | 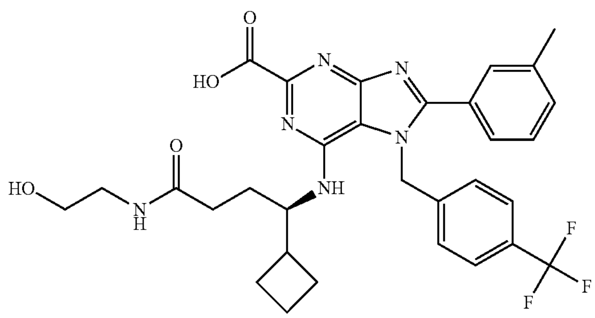 [SMILES: Cc1cccc(-c2nc3nc(C(=O)O)nc(N[C@H](CCC(=O)NCCO)C4CCC4)c3n2Cc2ccc(C(F)(F)F)cc2)c1] | 6-({(1R)-1-cyclobutyl-4-[(2-hydroxyethyl)amino]-4-oxobutyl}amino)-8-(3-methylphenyl)-7-[4-(trifluoromethyl)benzyl]-7H-purine-2-carboxylic acid | | 611 | 611 |
| 7.8 | 188 | 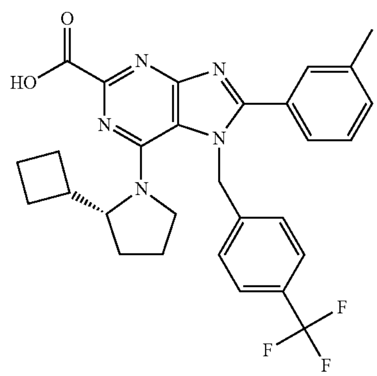 [SMILES: Cc1cccc(-c2nc3nc(C(=O)O)nc(N4CCC[C@@H]4C4CCC4)c3n2Cc2ccc(C(F)(F)F)cc2)c1] | 6-[(2R)-2-cyclobutylpyrrolidin-1-yl]-8-(3-methylphenyl)-7-[4-(trifluoromethyl)benzyl]-7H-purine-2-carboxylic acid | | 536 | 536 |
| 7.9 | 4475 | 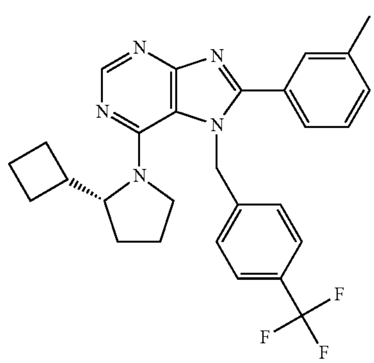 [SMILES: Cc1cccc(-c2nc3ncnc(N4CCC[C@@H]4C4CCC4)c3n2Cc2ccc(C(F)(F)F)cc2)c1] | 6-[(2R)-2-cyclobutylpyrrolidin-1-yl]-8-(3-methylphenyl)-7-[4-(trifluoromethyl)benzyl]-7H-purine | | 492 | 492 |
| 7.10 | 94.32 | 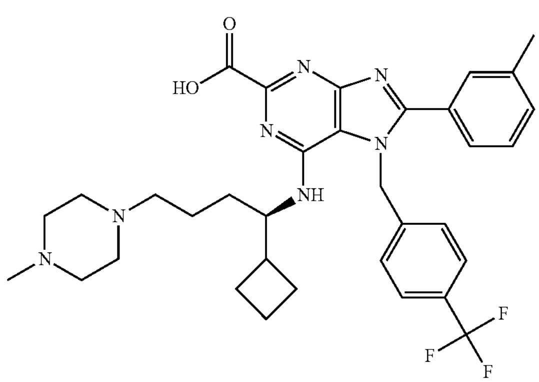 | 6-{[(1R)-1-cyclobutyl-4-(4-methylpiperazin-1-yl)butyl]amino}-8-(3-methylphenyl)-7-[4-(trifluoromethyl)benzyl]-7H-purine-2-carboxylic acid | | 636 | 636 |

TABLE 7-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 7.11 | 322.7 | 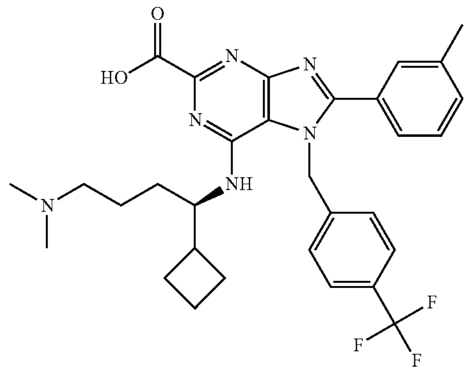 | 6-{[(1R)-1-cyclobutyl-4-(dimethylamino)butyl]amino}-8-(3-methylphenyl)-7-[4-(trifluoromethyl)benzyl]-7H-purine-2-carboxylic acid | | 581 | 581 |
| 7.12 | 55.32 | 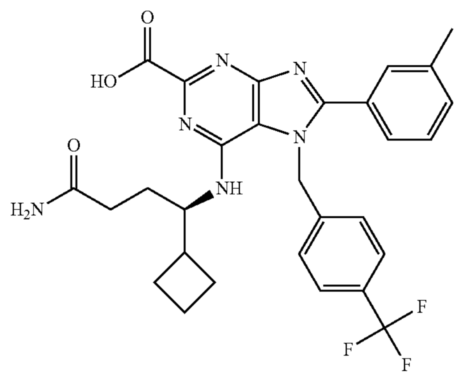 [SMILES: Cc1cccc(-c2nc3nc(C(=O)O)nc(N[C@H](CCC(N)=O)C4CCC4)c3n2Cc2ccc(C(F)(F)F)cc2)c1] | 6-{[(1R)-4-amino-1-cyclobutyl-4-oxobutyl]amino}-8-(3-methylphenyl)-7-[4-(trifluoromethyl)benzyl]-7H-purine-2-carboxylic acid | | 567 | 567 |
| 7.13 | 101.7 | 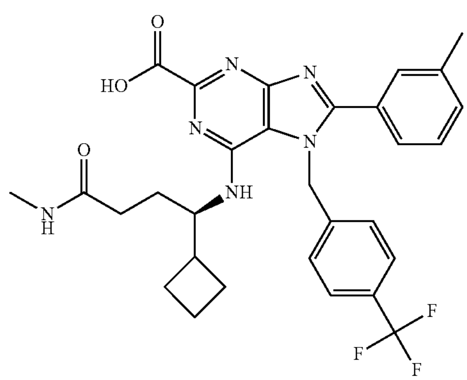 | 6-{[(1R)-1-cyclobutyl-4-(methylamino)-4-oxobutyl]amino}-8-(3-methylphenyl)-7-[4-(trifluoromethyl)benzyl]-7H-purine-2-carboxylic acid | | 581 | 581 |
| 7.15 | 26.5 | 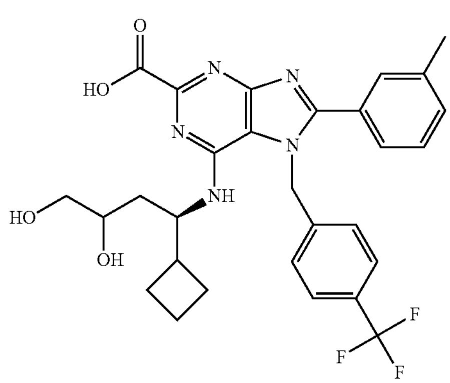 [SMILES: Cc1cccc(-c2nc3nc(C(=O)O)nc(N[C@H](CC(O)CO)C4CCC4)c3n2Cc2ccc(C(F)(F)F)cc2)c1] | 6-{[(1R)-1-cyclobutyl-3,4-dihydroxybutyl]amino}-8-(3-methylphenyl)-7-[4-(trifluoromethyl)benzyl]-7H-purine-2-carboxylic acid | | 570 | 570 |

TABLE 7-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 7.16 | 40.56 | 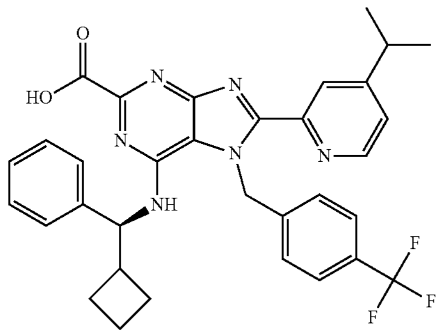 [SMILES: CC(C)c1ccnc(-c2nc3nc(C(=O)O)nc(N[C@H](c4ccccc4)C4CCC4)c3n2Cc2ccc(C(F)(F)F)cc2)c1] | 6-{[(S)-cyclobutyl(phenyl)methyl]amino}-8-[4-(1-methylethyl)pyridin-2-yl]-7-[4-(trifluoromethyl)benzyl]-7H-purine-2-carboxylic acid | | 601 | 601 |
| 7.17 | 58.89 | 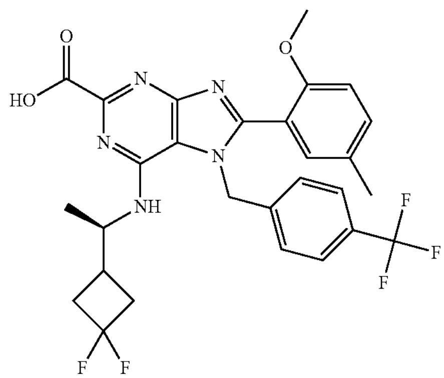 [SMILES: COc1ccc(C)cc1-c1nc2nc(C(=O)O)nc(N[C@H](C)C3CC(F)(F)C3)c2n1Cc1ccc(C(F)(F)F)cc1] | 6-{[(1R)-1-(3,3-difluorocyclobutyl)ethyl]amino}-8-(2-methoxy-5-methylphenyl)-7-[4-(trifluoromethyl)benzyl]-7H-purine-2-carboxylic acid | | 576 | 576 |
| 7.18 | 162.5 | 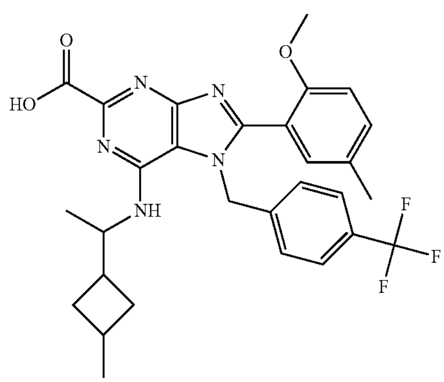 [SMILES: COc1ccc(C)cc1-c1nc2nc(C(=O)O)nc(NC(C)C3CC(C)C3)c2n1Cc1ccc(C(F)(F)F)cc1] | 8-2-methoxy-5-methylphenyl)-6-{[1-(3-methylcyclobutyl)ethyl]-amino}-7-[4-(trifluoromethyl)benzyl]-7H-purine-2-carboxylic acid | | 554 | 554 |
| 7.19 | 72.2 | 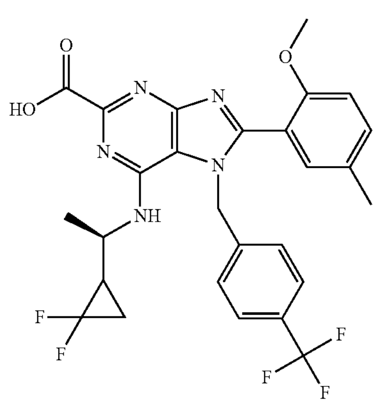 [SMILES: COc1ccc(C)cc1-c1nc2nc(C(=O)O)nc(N[C@H](C)C3CC3(F)F)c2n1Cc1ccc(C(F)(F)F)cc1] | 6-{[(1R)-1-(2,2-difluorocyclopropyl)ethyl]amino}-8-(2-methoxy-5-methylphenyl)-7-[4-(trifluoromethyl)benzyl]-7H-purine-2-carboxylic acid | | 562 | 562 |

Example 8.1

7-[2-amino-4-(trifluoromethyl)benzyl]-6-{[(1R)-1-cyclobutylethyl]amino}-8-[4-(propan-2-yl)pyridin-2-yl]-7H-purine-2-carboxylic acid

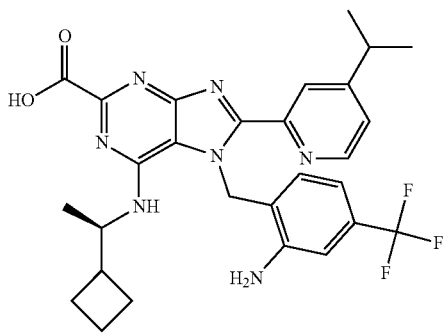 [SMILES: CC(C)c1ccnc(-c2nc3nc(C(=O)O)nc(N[C@H](C)C4CCC4)c3n2Cc2ccc(C(F)(F)F)cc2N)c1]

Step 1: 2,6-dichloropurine (3.2 g, 16.9 mmol) in N,N-dimethylacetamide (23 mL) was treated with 2-nitro-4-(trifluoromethyl)benzyl bromide (5.05 g, 17.8 mmol). Cesium carbonate (5.79 g, 17.8 mmol) was added and the mixture was stirred at room temperature for 2 hours. The reaction was quenched with water and extracted with ethyl acetate (2×). The combined organic layers were washed with brine, dried over sodium sulfate, filtered, and concentrated under reduced pressure. The residue was purified by silica gel chromatography (0-80% ethyl acetate/hexanes, linear gradient) to afford 2,6-dichloro-7-[2-nitro-4-(trifluoromethyl)benzyl]-7H-purine. MS ESI calc'd. for $C_{13}H_6Cl_2F_3N_5O_2$ [M+H]$^+$ 392. found 392.

Step 2: To a solution of 2,6-dichloro-7-[2-nitro-4-(trifluoromethyl)benzyl]-7H-purine (731.5 g, 1.86 mmol mmol) in ethanol (15 mL) was added (1R)-1-cyclobutylethanamine hydrochloride (506 mg, 3.73 mmol) and N,N-diisopropylethylamine (1.3 mL, 7.46 mmol). The reaction mixture was stirred at 70° C. for 16 hours. The reaction was cooled to room temperature, diluted with ethyl acetate, and washed with hydrochloric acid (1.0 M in water, 2×). The organic layer was dried over sodium sulfate, filtered, and concentrated under reduced pressure. The residue was purified by silica gel chromatography (0-100% ethyl acetate/hexanes, linear gradient) to afford 2-chloro-N-[(1R)-1-cyclobutylethyl]-7-[2-nitro-4-(trifluoromethyl)benzyl]-7H-purin-6-amine. MS ESI calc'd. for $C_{19}H_{18}ClF_3N_6O_2$ [M+H]$^+$ 455. found 455.

Step 3: Iron (266 mg, 4.77 mmol) was added to 2-chloro-N-[(1R)-1-cyclobutylethyl]-7-[2-nitro-4-(trifluoromethyl)benzyl]-7H-purin-6-amine (722.6 mg, 1.59 mmol) dissolved in ethanol (12.1 mL) and water (1.89 mL). Next, saturated aqueous ammonium chloride (1.89 mL) was added and the reaction was sealed and heated to 70° C. for 16 hours. The mixture was cooled to room temperature, diluted with ethyl acetate, and filtered over celite. The filter cake was washed with 1:1 ethyl acetate:ethanol (3×), the filtrate was concentrated, and the residue was purified by silica gel chromatography (0-70% ethyl acetate/hexanes, and then 0-15% methanol/dichloromethane, linear gradient) to afford 7-[2-amino-4-(trifluoromethyl)benzyl]-2-chloro-N-[(1R)-1-cyclobutylethyl]-7H-purin-6-amine. MS ESI calc'd. for $C_{19}H_{20}ClF_3N_6$ [M+H]$^+$ 425. found 425.

Step 4: Dioxane (2.2 mL) was added to 2-dicyclohexylphosphino-2',4',6'-triisopropylbiphenyl (128 mg, 0.27 mmol) and allylpalladium(II) chloride dimer (24.6 mg, 0.067 mmol) in an oven-dried, nitrogen cooled vial. The vial was evacuated and backfilled with argon (3×), and then sealed and heated at 60° C. for 1 hour. To a second vial, was added zinc cyanide (205 mg, 1.74 mmol), 7-[2-amino-4-(trifluoromethyl)benzyl]-2-chloro-N-[(1R)-1-cyclobutylethyl]-7H-purin-6-amine (570.4 mg, 1.34 mmol), and dioxane (2.2 mL). The mixture was degassed for 15 minutes. The activated catalyst solution from the first vial was added, the vial was sealed, and the reaction was stirred at 120° C. for 1 hour. The mixture was cooled to room temperature and diluted with water. The precipitate that formed was collected by filtration and further purified by silica gel chromatography (0-70% ethyl acetate/hexanes, linear gradient) to afford 7-[2-amino-4-(trifluoromethyl)benzyl]-6-{[(1R)-1-cyclobutylethyl]amino}-7H-purine-2-carbonitrile. MS ESI calc'd. for $C_{20}H_{20}F_3N_7$ [M+H]$^+$ 416. found 416.

Step 5: To a vial flushed with argon was added 7-[2-amino-4-(trifluoromethyl)benzyl]-6-{[(1R)-1-cyclobutylethyl]amino}-7H-purine-2-carbonitrile (50 mg, 0.12 mmol), phthalic anhydride (19.61 mg, 0.132 mmol), and acetic acid (1.34 mL). The vial was sealed and heated to 100° C. for 16 hours. The mixture was cooled to room temperature, diluted with water, and extracted with ethyl acetate. The organic layer was washed with brine, dried over sodium sulfate, filtered, and concentrated under reduced pressure. The residue was purified by silica gel chromatography (0-100% ethyl acetate/hexanes, linear gradient) to afford 6-{[(1R)-1-cyclobutylethyl]amino}-7-[2-(1,3-dioxo-1,3-dihydro-2H-isoindol-2-yl)-4-(trifluoromethyl)benzyl]-7H-purine-2-carbonitrile. MS ESI calc'd. for $C_{28}H_{22}F_3N_7O_2$ [M+H]$^+$ 546. found 546.

Step 6: Dioxane (0.2 mL) was added to palladium(II) acetate (2.9 mg, 0.013 mmol) and butyldi-1-adamantylphosphine (9.36 mg, 0.026 mmol) in an oven-dried, argon cooled vial. The vial was sealed and heated to 50° C. for 30 minutes. To a second vial, was added 6-{[(1R)-1-cyclobutylethyl]amino}-7-[2-(1,3-dioxo-1,3-dihydro-2H-isoindol-2-yl)-4-(trifluoromethyl)benzyl]-7H-purine-2-carbonitrile (35.6 mg, 0.065 mmol), pivalic acid (7.33 mg, 0.072 mmol), cesium fluoride (29.7 mg, 0.196 mmol), 2-bromo-4-(isopropyl)pyridine (0.0183 mL, 0.131 mmol), and dioxane (0.2 mL). The activated catalyst solution from the first vial was added, the second vial was evacuated and backfilled with argon (3×), sealed, and heated to 120° C. for 16 hours. The mixture was cooled to room temperature, filtered over celite, and the filtrate was concentrated under reduced pressure. The residue was purified by silica gel chromatography (0-70% ethyl acetate/hexanes, linear gradient) to afford 6-{[(1R)-1-cyclobutylethyl]amino}-7-[2-(1,3-dioxo-1,3-dihydro-2H-isoindol-2-yl)-4-(trifluoromethyl)benzyl]-8-[4-(propan-2-yl)pyridin-2-yl]-7H-purine-2-carbonitrile. MS ESI calc'd. for $C_{36}H_{31}F_3N_8O_2$ [M+H]$^+$ 665. found 665.

Step 7: Sodium hydroxide (5.0 M in water, 0.187 mL, 0.93 mmol) was added to 6-{[(1R)-1-cyclobutylethyl]amino}-7-[2-(1,3-dioxo-1,3-dihydro-2H-isoindol-2-yl)-4-(trifluoromethyl)benzyl]-8-[4-(propan-2-yl)pyridin-2-yl]-7H-purine-2-carbonitrile (15.9 mg, 0.024 mmol) dissolved in ethanol (1 mL). The mixture was heated for 2 hours at 70° C. The reaction was cooled to room temperature, diluted with ethyl acetate, and washed with hydrochloric acid (1.0 M in water, 10 mL). The organic layer was dried over sodium sulfate, filtered, and concentrated under reduced pressure to afford 7-[2-{[(2-carboxyphenyl)carbonyl]amino}-4-(trifluoromethyl)benzyl]-6-{[(1R)-1-cyclobutylethyl]amino}-8-[4-(propan-2-yl)pyridin-2-yl]-7H-purine-2-carboxylic acid. MS ESI calc'd. for $C_{36}H_{34}F_3N_7O_5$ [M+H]$^+$ 702. found 702.

Step 8: Hydrazine (0.088 mL, 0.99 mmol) was added to 7-[2-{[(2-carboxyphenyl)carbonyl]amino}-4-(trifluoromethyl)benzyl]-6-{[(1R)-1-cyclobutylethyl]amino}-8-[4-(propan-2-yl)pyridin-2-yl]-7H-purine-2-carboxylic acid (17.3 mg, 0.025 mmol) dissolved in ethanol (1 mL). The mixture was stirred at 70° C. for 6 days. The reaction was cooled to room temperature, washed with hydrochloric acid (1.0 M in water, 10 mL), and extracted with ethyl acetate. The organic layer was dried over sodium sulfate, filtered, and concentrated under reduced pressure to afford 7-[2-amino-4-(trifluoromethyl)benzyl]-6-{[(1R)-1-cyclobutylethyl]amino}-8-[4-(propan-2-yl)pyridin-2-yl]-7H-purine-2-carbohydrazide. MS ESI calc'd. for $C_{28}H_{32}F_3N_9O$ [M+H]$^+$ 568. found 568.

Step 9: Sodium hydroxide (5.0 M in water, 0.192 mL, 0.96 mmol) was added to 7-[2-amino-4-(trifluoromethyl)benzyl]-6-{[(1R)-1-cyclobutylethyl]amino}-8-[4-(propan-2-yl)pyridin-2-yl]-7H-purine-2-carbohydrazide (14 mg, 0.025 mmol) dissolved in ethanol (1 mL). The mixture was heated for 16 hours at 70° C. The reaction was cooled to room temperature, diluted with ethyl acetate, and washed with hydrochloric acid (1.0 M in water, 10 mL). The organic layer was dried over sodium sulfate, filtered, and concentrated under reduced pressure. The residue was purified by mass triggered, reverse phase (C-18) preparative HPLC (acetonitrile:water: 0.1% v/v trifluoroacetic acid modifier) to afford 7-[2-amino-4-(trifluoromethyl)benzyl]-6-{[(1R)-1-cyclobutylethyl]amino}-8-[4-(propan-2-yl)pyridin-2-yl]-7H-purine-2-carboxylic acid (as a TFA salt). MS ESI calc'd. for $C_{28}H_{30}F_3N_7O_2$ [M+H]$^+$ 554. found 554. $^1$H NMR (500 MHz, DMSO-d$_6$) δ 8.56 (d, J=5.1, 1H), 8.24 (s, 1H), 7.48 (dd, J=1.6, 5.1, 1H), 7.13 (d, J=1.5, 1H), 6.76 (d, J=8.3, 1H), 6.47 (d, J=8.1, 1H), 6.30 (d, J=17.6, 1H), 6.02 (d, J=17.8, 1H), 5.36 (d, J=8.4, 1H), 4.35-4.26 (m, 2H), 3.09-3.01 (m, 1H), 2.17-2.07 (m, 1H), 1.82-1.75 (m, 1H), 1.65-1.57 (m, 1H), 1.57-1.48 (m, 2H), 1.48-1.40 (m, 1H), 1.40-1.31 (m, 1H), 1.27 (d, J=6.9, 6H), 0.89 (d, J=6.5, 3H).

Example 9.1

6-{[(1R)-1-cyclobutylethyl]amino}-8-{[(1S)-1-(4-fluorophenyl)ethyl]amino}-7-[4-(trifluoromethyl)benzyl]-7H-purine-2-carboxylic acid

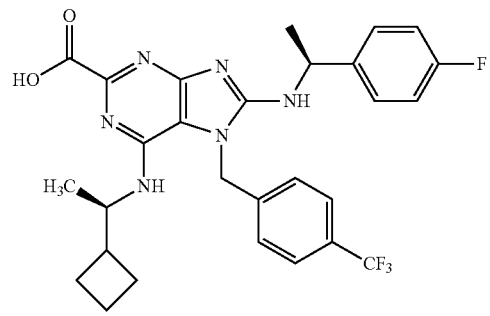 [SMILES: C[C@H](Nc1nc2nc(C(=O)O)nc(N[C@H](C)C3CCC3)c2n1Cc1ccc(C(F)(F)F)cc1)c1ccc(F)cc1]

Step 1: A microwave vial equipped with a stir bar was charged with Preparative Example 2.1 (R)-8-bromo-6-((1-cyclobutylethyl)amino)-7-(4-(trifluoromethyl)benzyl)-7H-purine-2-carbonitrile (50 mg, 0.10 mmol), (S)-1-(4-fluorophenyl)ethanamine (76 mg, 0.52 mmol), and 1,4 dioxane (1.0 mL). The vial was then sealed and heated at 50° C. for 24 hours. The reaction was concentrated and the residue was purified on a RediSep 4 g silica gel column with 0 to 100% EtOAc/hexanes to afford 6-(((R)-1-cyclobutylethyl)amino)-8-(((S)-1-(4-fluorophenyl)ethyl)amino)-7-(4-(trifluoromethyl)benzyl)-7H-purine-2-carbonitrile. LCMS=538 (M+1)$^+$.

Step 2: 6-(((R)-1-cyclobutylethyl)amino)-8-(((R)-1-(4-fluorophenyl)ethyl)amino)-7-(4-(trifluoromethyl)benzyl)-7H-purine-2-carbonitrile (35 mg, 0.060 mmol) was suspended in anhydrous HCl in MeOH (5.0 mL, 3.0 M) and was heated at 75° C. for 4 hours. The solvent was evaporated under vacuum, the crude product was suspended in $CH_2Cl_2$ (40 mL) and washed with aqueous saturated NaHCO$_3$. The organic layer was separated and dried over Na$_2$SO$_4$. The solvent was evaporated and purification of the residue on a RediSep 4 g silica gel column with 0 to 10% MeOH/CH$_2$Cl$_2$ afforded methyl 6-(((R)-1-cyclobutylethyl)amino)-8-(((S)-

TABLE 8

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 8.1 | 1.624 | 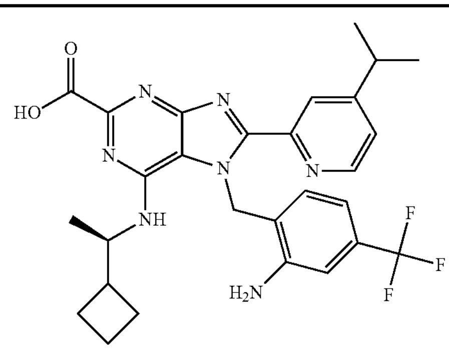 | 7-[2-amino-4-(trifluoromethyl)benzyl]-6-{[(1R)-1-cyclobutylethyl]amino}-8-[4-(1-methylethyl)pyridin-2-yl]-7H-purine-2-carboxylic acid | TFA | 554 | 554 |

1-(4-fluorophenyl)ethyl)amino)-7-(4-(trifluoromethyl)benzyl)-7H-purine-2-carboxylate. LCMS=571 (M+1)+.

Step 3: To a solution of methyl 6-(((R)-1-cyclobutylethyl)amino)-8-(((R)-1-(4-fluorophenyl)ethyl)amino)-7-(4-(trifluoromethyl)benzyl)-7H-purine-2-carboxylate (10 mg, 0.010 mmol) in THF (2.0 mL) was added aqueous LiOH solution (0.080 mL, 1.0 M) and the reaction was stirred at ambient temperature for 2 hours. Solvent was evaporated under vacuum and the residue was dissolved in water (2.0 mL). The pH for the solution was adjusted to 6.5 using aqueous HCl (2 N). The precipitate that formed was collected by filtration and air dried to afford 6-{[(1R)-1-cyclobutylethyl]amino}-8-{[(1S)-1-(4-fluorophenyl)ethyl]amino}-7-[4-(trifluoromethyl)benzyl]-7H-purine-2-carboxylic acid. $^1$H NMR (400 MHz, CD$_3$OD) δ 8.61 (d, J=8.4 Hz, 2H), 7.80 (q, J=5.6 Hz, 2H), 7.15 (d, J=8.0 Hz, 2H), 6.93 (t, J=8.8 Hz, 2H), 5.63 (d, J=18.4 Hz, 1H), 5.55 (d, J=18.4 Hz, 1H), 5.22 (q, J=6.8 Hz, 1H), 4.48-4.55 (m, 2H), 2.08 (m, 1H), 1.84 (m, 1H), 1.62-1.68 (m, 3H), 1.61 (d, J=8.0 Hz, 3H), 1.44-1.49 (m, 2H), 0.93 (d, J=6.4 Hz, 3H). LCMS=557 (M+1)+.

Example 9.2

6-{[(1R)-1-cyclobutylethyl]amino}-8-[methyl(phenyl)amino]-7-[4-(trifluoromethyl)benzyl]-7H-purine-2-carboxylic acid

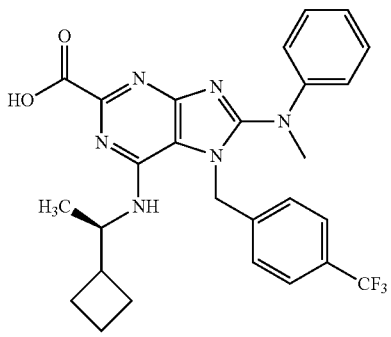 [SMILES: C[C@@H](Nc1nc(C(=O)O)nc2nc(N(C)c3ccccc3)n(Cc3ccc(C(F)(F)F)cc3)c12)C1CCC1]

Step 1: A microwave vial equipped with a stir bar was charged with Preparative Example 2.1, (R)-8-bromo-6-((1-cyclobutylethyl)amino)-7-(4-(trifluoromethyl)benzyl)-7H-purine-2-carbonitrile (100 mg, 0.20 mmol) and N-methylaniline (0.35 mL) and the vial was then sealed and heated at 150° C. in CEM MW for 15 minutes. The reaction was cooled to room temperature and concentrated to dryness. Purification of the residue on a RediSep 12 g silica gel column with 0 to 50% EtOAc/hexanes afforded (R)-6-((1-cyclobutylethyl)amino)-8-(methyl(phenyl)amino)-7-(4-(trifluoromethyl)benzyl)-7H-purine-2-carbonitrile. $^1$H NMR (400 MHz, CDCl$_3$) δ 7.52 (d, J=8.0 Hz, 2H), 7.17-7.21 (m, 2H), 7.04-7.06 (m, 3H), 6.96 (d, J=8.0 Hz, 2H), 5.02 (br s, 2H), 4.16 (m, 1H), 3.95 (d, J=8.0 Hz, 1H), 3.52 (s, 3H), 1.60-1.87 (m, 4H), 1.51-1.55 (m, 2H), 1.42 (m, 1H), 0.88 (d, J=6.2 Hz, 3H). LCMS=506 (M+1)+.

Step 2: Using a procedure analogous to that described in Step 2 and Step 3 of Example 9.1, 6-{[(1R)-1-cyclobutylethyl]amino}-8-[methyl(phenyl)amino]-7-[4-(trifluoromethyl)benzyl]-7H-purine-2-carboxylic acid was prepared. $^1$H NMR (400 MHz, CD$_3$OD) δ 7.54 (d, J=8.0 Hz, 2H), 7.35 (t, J=8.0 Hz, 2H), 7.17 (d, J=8.4 Hz, 3H), 7.00 (d, J=8.0 Hz, 2H), 5.28 (d, J=18.0 Hz, 1H), 5.20 (d, J=18.0 Hz, 1H), 4.62 (m, 1H), 3.57 (s, 3H), 2.16 (m, 1H), 1.90 (m, 1H), 1.63-1.73 (m, 3H), 1.53-1.59 (m, 2H), 0.97 (d, J=6.8 Hz, 3H). LCMS=525 (M+1)+.

Example 9.3

8-(2-benzylpiperidin-1-yl)-6-{[(1R)-1-cyclobutylethyl]amino}-7-[4-(trifluoromethyl)benzyl]-7H-purine-2-carboxylic acid

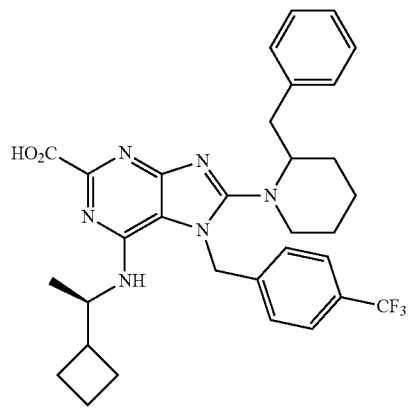 [SMILES: C[C@@H](Nc1nc(C(=O)O)nc2nc(N3CCCCC3Cc3ccccc3)n(Cc3ccc(C(F)(F)F)cc3)c12)C1CCC1]

Step 1: CsF (22 mg, 0.15 mmol) was added to a mixture of Preparative Example 2.1, (R)-8-bromo-6-((1-cyclobutylethyl)amino)-7-(4-(trifluoromethyl)benzyl)-7H-purine-2-carbonitrile (24 mg, 0.050 mmol) and 2-benzylpiperidine (35 mg, 0.20 mmol) in acetonitrile (1.0 mL). The reaction was heated at 100° C. for 2 hours and then cooled to room temperature, diluted with EtOAc (15 mL), and washed with water (10 mL) and brine (10 mL). The organic layer was separated and dried over Na$_2$SO$_4$. The solvent was evaporated and purification of the residue on a RediSep 4 g silica gel column with 0 to 5% MeOH/CH$_2$Cl$_2$ afforded 8-(2-benzylpiperidin-1-yl)-6-(((R)-1-cyclobutylethyl)amino)-7-(4-(trifluoromethyl)benzyl)-7H-purine-2-carbonitrile. $^1$H NMR (300 MHz, CD$_3$OD) 7.71 (d, d, J=9.0 Hz, 2H), 7.15-7.25 (m, 5H), 6.98-7.00 (m, 2H), 4.80-5.00 (m, 2H), 4.10 (m, 1H), 3.80-3.90 (m, 2H), 3.36-3.50 (m, 2H), 3.15 (m, 1H), 2.78 (m, 1H), 1.40-1.90 (m, 11H), 1.25-1.37 (m, 2H), 0.74-0.79 (m, 3H)). LCMS=574 (M+1)+.

Step 2: Using a procedure analogous to that described in Step 2 and Step 3 of Example 9.1, 8-(2-benzylpiperidin-1-yl)-6-{[(1R)-1-cyclobutylethyl]amino}-7-[4-(trifluoromethyl)benzyl]-7H-purine-2-carboxylic acid was prepared. $^1$H NMR (300 MHz, CD$_3$OD) 7.57-7.68 (m, 2H), 6.97-7.21 (m, 7H), 5.11-5.38 (m, 2H), 4.51 (m, 1H), 3.90 (m, 1H), 3.36-3.62 (m, 2H), 3.10 (m, 1H), 2.83 (m, 1H), 1.40-2.12 (m, 11H), 1.25-1.37 (m, 2H), 0.91 (d, J=5.9 Hz, 1.5H), 0.86 (d, J=5.9 Hz, 1.5H). LCMS=593 (M+1)+.

Example 9.4

3-{7-(4-chloro-3-fluorobenzyl)-6-{[(1R)-1-cyclobutylethyl]amino}-8-[(3R)-3-phenylmorpholin-4-yl]-7H-purin-2-yl}-1,2,4-oxadiazol-5(4H)-one

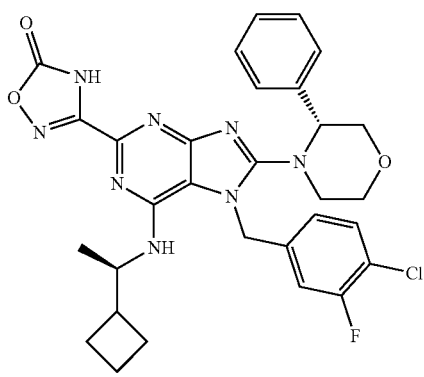 [SMILES: C[C@@H](Nc1nc(-c2noc(=O)[nH]2)nc2nc(N3CCOC[C@H]3c3ccccc3)n(Cc3ccc(Cl)c(F)c3)c12)C1CCC1]

Step 1: Using a procedure analogous to that described in Preparative Example 2.1, and starting from 7-(4-chloro-3-fluorobenzyl)-6-{[(1R)-1-cyclobutylethyl]amino}-7H-purine-2-carbonitrile (Example 1.6, Step 3), (R)-8-bromo-7-(4-chloro-3-fluorobenzyl)-6-((1-cyclobutylethyl)amino)-7H-purine-2-carbonitrile was prepared.

Step 2: Using a procedure analogous to that described in Example 9.3 (Step 1), and starting from (R)-8-bromo-7-(4-chloro-3-fluorobenzyl)-6-((1-cyclobutylethyl)amino)-7H-purine-2-carbonitrile and (R)-3-phenylmorpholine, followed by a procedure analogous to that described in Example 11.3 (Steps 1 and 2), 3-{7-(4-chloro-3-fluorobenzyl)-6-{[(1R)-1-cyclobutylethyl]amino}-8-[(3R)-3-phenylmorpholin-4-yl]-7H-purin-2-yl}-1,2,4-oxadiazol-5(4H)-one. $^1$H NMR (500 MHz, DMSO-$d_6$) δ 12.78 (s, 1H), 7.53 (t, J=8.1, 1H), 7.21-7.05 (m, 6H), 6.74 (dd, J=1.7, 10.2, 1H), 6.55 (d, J=8.3, 1H), 5.96 (d, J=8.6, 1H), 5.79 (d, J=17.6, 1H), 5.69 (d, J=17.4, 1H), 4.57 (dd, J=3.5, 9.9, 1H), 4.42-4.32 (m, 1H), 3.96-3.88 (m, 2H), 3.83 (dd, J=3.6, 11.7, 1H), 3.51 (dd, J=9.9, 11.6, 1H), 3.08-2.99 (m, 1H), 2.13-2.04 (m, 1H), 1.81-1.75 (m, 1H), 1.66-1.41 (m, 3H), 1.40-1.19 (m, 2H), 0.92 (d, J=6.5, 3H). MS ESI calc'd. for $C_{30}H_{30}ClFN_8O_3$ [M+H]$^+$ 605. found 605.

The following compounds in Table 9 (other than Example 9.1 to 9.4) were prepared using procedures which were analogous to those described above in Example 9.1, 9.2, 9.3 and 9.4.

TABLE 9

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.1 | 1.806 | 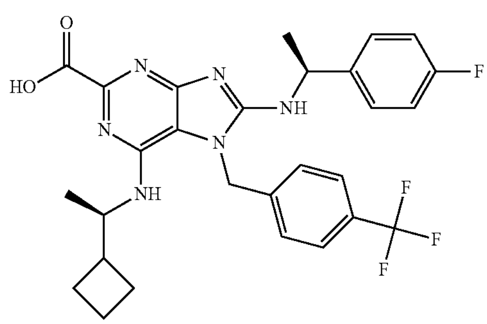 [SMILES: C[C@H](Nc1nc2nc(C(=O)O)nc(N[C@H](C)C3CCC3)c2n1Cc1ccc(C(F)(F)F)cc1)c1ccc(F)cc1] | 6-{[(1R)-1-cyclobutylethyl]amino}-8-{1(1S)-1-[4-fluorophenyl)ethyl]amino}-7-[4-(trifluoromethyl)benzyl]-7H-purine-2-carboxylic acid | | 557 | 557 |
| 9.2 | 20.73 | 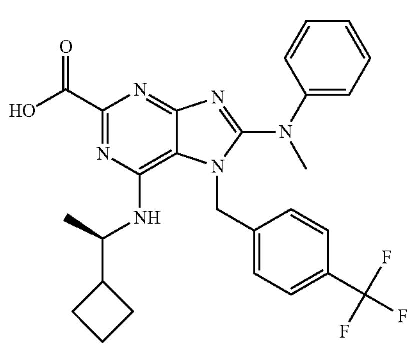 [SMILES: C[C@@H](Nc1nc(C(=O)O)nc2nc(N(C)c3ccccc3)n(Cc3ccc(C(F)(F)F)cc3)c12)C1CCC1] | 6-{[(1R)-1-cyclobutylethyl]amino}-8-[methyl(phenyl)amino]-7-[4-(trifluoromethyl)benzyl]-7H-purine-2-carboxylic acid | | 525 | 525 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.3 | 20.73 | 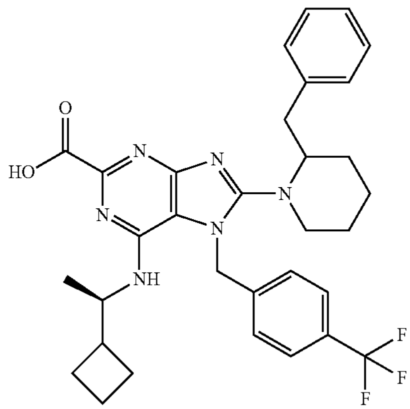 [SMILES: C[C@@H](Nc1nc(C(=O)O)nc2nc(N3CCCCC3Cc3ccccc3)n(Cc3ccc(C(F)(F)F)cc3)c12)C1CCC1] | 8-(2-benzylpiperidin-1-yl)-6-{[(1R)-1-cyclobutylethyl]amino]-7-[4-(trifluoromethyl)benzyl]-7H-purine-2-carboxylic acid | | 593 | 593 |
| 9.4 | 0.8475 | 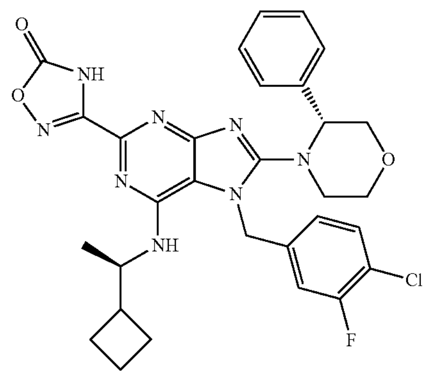 [SMILES: C[C@@H](Nc1nc(-c2noc(=O)[nH]2)nc2nc(N3CCOC[C@H]3c3ccccc3)n(Cc3ccc(Cl)c(F)c3)c12)C1CCC1] | 3-{7-(4-chloro-3-fluorobenzyl)-6-{[(1R)-1-cyclobutylethyl]amino}-8-[(3R)-3-phenylmorpholin-4-yl]-7H-purin-2-yl}-1,2,4-oxadiazol-5(4H)-one | TFA | 605 | 605 |
| 9.5 | 2350 | 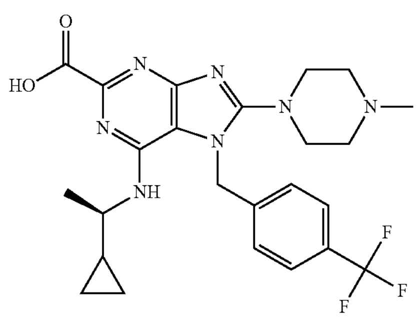 [SMILES: C[C@@H](Nc1nc(C(=O)O)nc2nc(N3CCN(C)CC3)n(Cc3ccc(C(F)(F)F)cc3)c12)C1CC1] | 6-{[(1R)-1-cyclopropylethyl]amino}-8-(4-methylpiperazin-1-yl)-7-[4-(trifluoromethyl)benzyl]-7H-purine-2-carboxylic acid | | 504 | 504 |
| 9.6 | 1.468 | 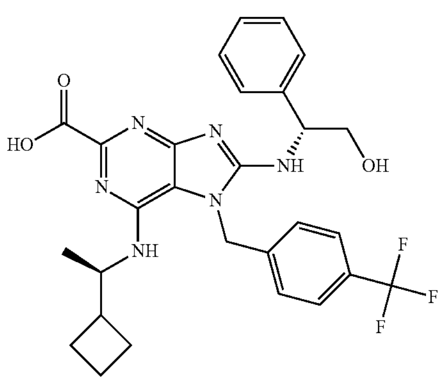 [SMILES: C[C@@H](Nc1nc(C(=O)O)nc2nc(N[C@@H](CO)c3ccccc3)n(Cc3ccc(C(F)(F)F)cc3)c12)C1CCC1] | 6-{[(1R)-1-cyclobutylethyl]amino}-8-}[(1R)-2-hydroxy-1-phenylethyl]amino}-7-[4-(trifluoromethyl)benzyl]-7H-purine-2-carboxylic acid | | 555 | 555 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.7 | 35.79 | 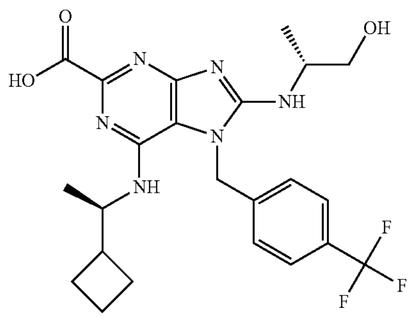 [SMILES: C[C@H](CO)Nc1nc2nc(C(=O)O)nc(N[C@H](C)C3CCC3)c2n1Cc1ccc(C(F)(F)F)cc1] | 6-{[(1R)-1-cyclobutylethyl]amino}-8-{[(1R)-2-hydroxy-1-methylethyl]amino}-7-[4-(trifluoromethyl)benzy]-7H-purine-2-carboxylic acid | | 493 | 493 |
| 9.8 | 15.2 | 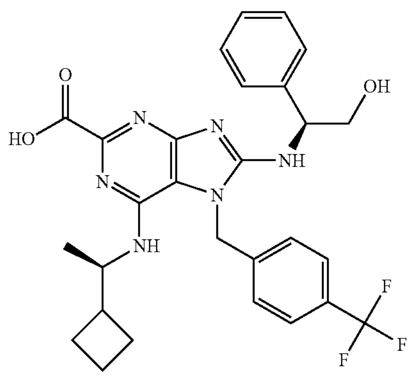 [SMILES: C[C@@H](Nc1nc(C(=O)O)nc2nc(N[C@H](CO)c3ccccc3)n(Cc3ccc(C(F)(F)F)cc3)c12)C1CCC1] | 6-{[(1R)-1-cyclobutylethyl]amino}-8-{[(1S)-2-hydroxy-1-phenylethyl]amino}-7-[4-(trifluoromethyl)benzyl]-7H-purine-2-carboxylic acid | | 555 | 555 |
| 9.9 | 574.1 | 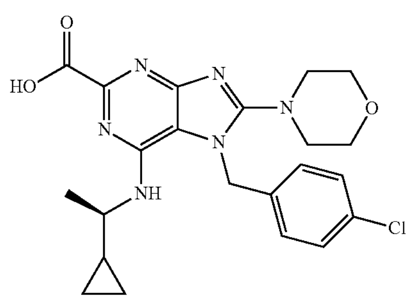 [SMILES: C[C@@H](Nc1nc(C(=O)O)nc2nc(N3CCOCC3)n(Cc3ccc(Cl)cc3)c12)C1CC1] | 7-(4-chlorobenzyl)-6-{[(1R)-1-cyclopropylethyl]amino}-8-morpholin-4-yl-7H-purine-2-carboxylic acid | TFA | 457 | 457 |
| 9.10 | 85.93 | 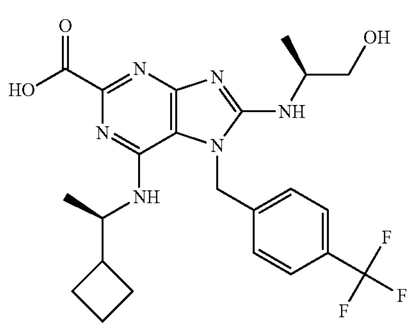 [SMILES: C[C@@H](CO)Nc1nc2nc(C(=O)O)nc(N[C@H](C)C3CCC3)c2n1Cc1ccc(C(F)(F)F)cc1] | 6-{[(1R)-1-cyclobutylethyl]amino}-8-{[(1 S)-2-hydroxy-1-methylethyl]amino}-7-[4-(trifluoromethyl)benzyl]-7H-purine-2-carboxylic acid | | 493 | 493 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.11 | 17.61 | 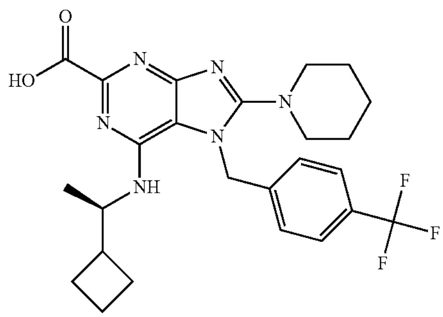 [SMILES: C[C@@H](Nc1nc(C(=O)O)nc2nc(N3CCCCC3)n(Cc3ccc(C(F)(F)F)cc3)c12)C1CCC1] | 6-{[(1R)-1-cyclobutylethyl]amino}-8-piperidin-1-yl-7-[4-(trifluoromethyl)benzyl]-7H-purine-2-carboxylic acid | | 503 | 503 |
| 9.12 | 7.653 | 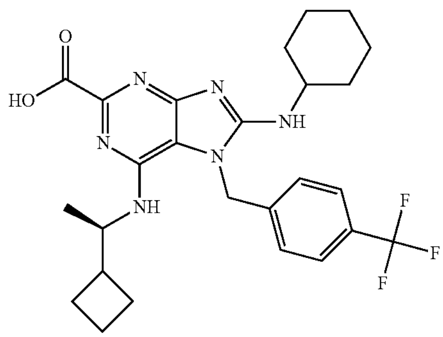 [SMILES: C[C@@H](Nc1nc(C(=O)O)nc2nc(NC3CCCCC3)n(Cc3ccc(C(F)(F)F)cc3)c12)C1CCC1] | 6-{[(1R)-1-cyclobutylethyl]amino}-8-(cyclohexylamino)-7-[4-(trifluoromethyl)benzyl]-7H-purine-2-carboxylic acid | | 517 | 517 |
| 9.13 | 3.07 | 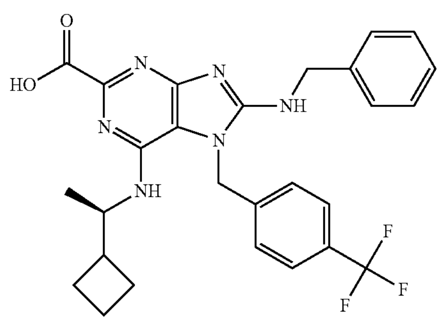 [SMILES: C[C@@H](Nc1nc(C(=O)O)nc2nc(NCc3ccccc3)n(Cc3ccc(C(F)(F)F)cc3)c12)C1CCC1] | 8-(benzylamino)-6-{[(1R)-1-cyclobutylethyl]amino}-7-[4-(trifluoromethyl)benzyl]-7H-purine-2-carboxylic acid | | 525 | 525 |
| 9.14 | 5.616 | 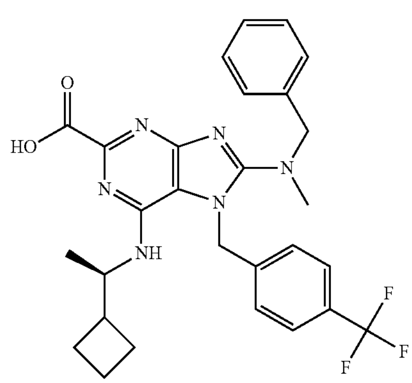 [SMILES: C[C@@H](Nc1nc(C(=O)O)nc2nc(N(C)Cc3ccccc3)n(Cc3ccc(C(F)(F)F)cc3)c12)C1CCC1] | 8-[benzyl(methyl)amino]-6-{[(1R)-1-cyclobutylethyl]amino}-7-[4-(trifluoromethyl)benzyl]-7H-purine-2-carboxylic acid | | 539 | 539 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.15 | 7.4 | 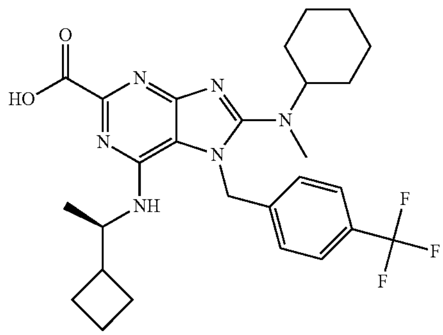 [SMILES: C[C@@H](Nc1nc(C(=O)O)nc2nc(N(C)C3CCCCC3)n(Cc3ccc(C(F)(F)F)cc3)c12)C1CCC1] | 6-{[(1R)-1-cyclobutylethyl]amino}-8-[cyclohexyl(methyl)amino]-7-[4-(trifluoromethyl)benzyl]-7H-purine-2-carboxylic acid | | 531 | 531 |
| 9.16 | 1.907 | 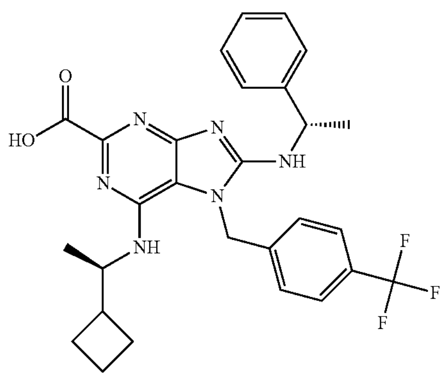 [SMILES: C[C@H](Nc1nc2nc(C(=O)O)nc(N[C@H](C)C3CCC3)c2n1Cc1ccc(C(F)(F)F)cc1)c1ccccc1] | 6-{[(1R)-1-cyclobutylethyl]amino}-8-{[(1S)-1-phenylethyl]amino}-7-[4-(trifluoromethyl)benzyl]-7H-purine-2-carboxylic acid | | 539 | 539 |
| 9.17 | 15.8 | 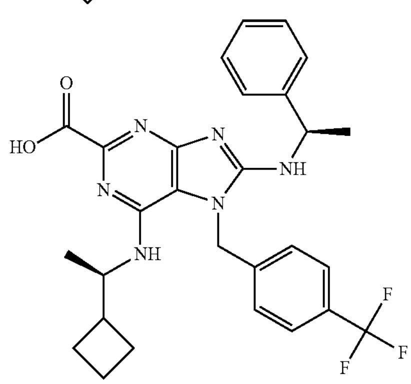 | 6-{[(1R)-1-cyclobutylethyl]amino}-8-{[(1R)-1-phenylethyl]amino}-7-[4-(trifluoromethyl)benzyl]-7H-purine-2-carboxylic acid | | 5.39 | 5.39 |
| 9.18 | 32.69 | 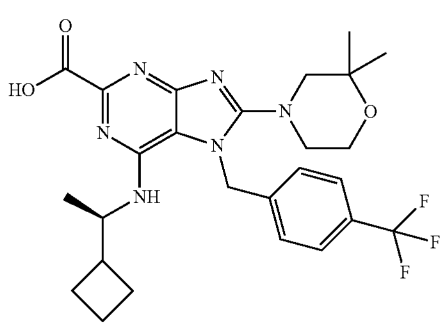 [SMILES: C[C@@H](Nc1nc(C(=O)O)nc2nc(N3CCOC(C)(C)C3)n(Cc3ccc(C(F)(F)F)cc3)c12)C1CCC1] | 6-{[(1R)-1-cyclobutylethyl]amino}-8-(2,2-dimethylmorpholin-4-yl)-7-[4-(trifluoromethyl)benzyl]-7H-purine-2-carboxylic acid | TFA | 533 | 533 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.19 | 12.4 | 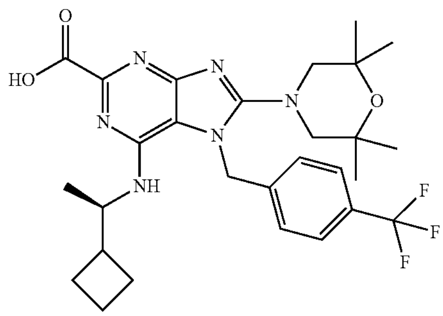 [SMILES: C[C@@H](Nc1nc(C(=O)O)nc2nc(N3CC(C)(C)OC(C)(C)C3)n(Cc3ccc(C(F)(F)F)cc3)c12)C1CCC1] | 6-{[(1R)-1-cyclobutylethyl]amino}-8-(2,2,6,6-tetramethylmorpholin-4-yl)-7-[4-(trifluoromethyl)benzyl]-7H-purine-2-carboxylic acid | TFA | 561 | 561 |
| 9.20 | 63.1 | 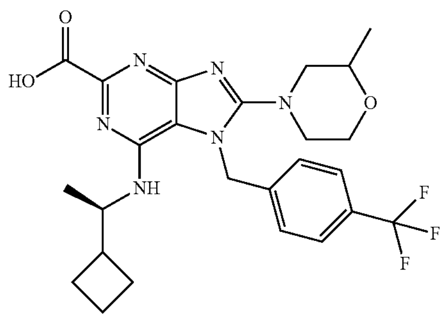 [SMILES: CC1CN(c2nc3nc(C(=O)O)nc(N[C@H](C)C4CCC4)c3n2Cc2ccc(C(F)(F)F)cc2)CCO1] | 6-{[(1R)-1-cyclobutylethyl]amino}-8-(2-methylmorpholin-4-yl)-7-[4-(trifluoromethyl)benzyl]-7H-purine-2-carboxylic acid | TFA | 519 | 519 |
| 9.21 | 9.439 | 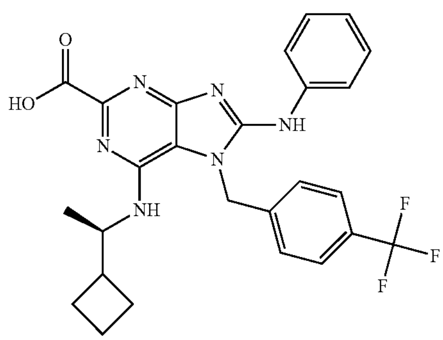 [SMILES: C[C@@H](Nc1nc(C(=O)O)nc2nc(Nc3ccccc3)n(Cc3ccc(C(F)(F)F)cc3)c12)C1CCC1] | 6-{[(1R)-1-cyclobutylethyl]amino}-8-(phenylamino)-7-[4-(trifluoromethyl)benzyl]-7H-purine-2-carboxylic acid | | 511 | 511 |
| 9.22 | 12.43 | 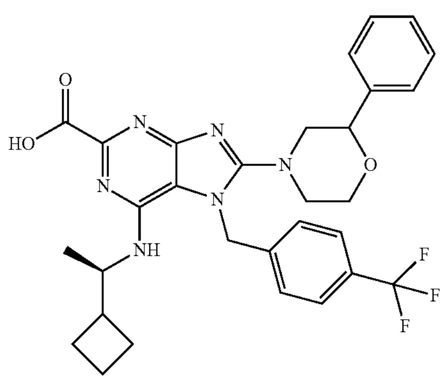 [SMILES: C[C@@H](Nc1nc(C(=O)O)nc2nc(N3CCOC(c4ccccc4)C3)n(Cc3ccc(C(F)(F)F)cc3)c12)C1CCC1] | 6-{[(1R)-1-cyclobutylethyl]amino}-8-(2-phenylmorpholin-4-yl)-7-[4-(trifluoromethyl)benzyl]-7H-purine-2-carboxylic acid | TFA | 581 | 581 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.23 | 25.23 | 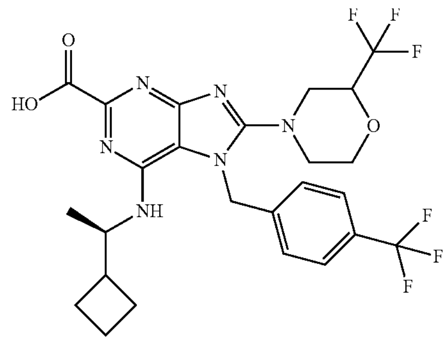 [SMILES: C[C@@H](Nc1nc(C(=O)O)nc2nc(N3CCOC(C(F)(F)F)C3)n(Cc3ccc(C(F)(F)F)cc3)c12)C1CCC1] | 6-{[(1R)-1-cyclobutylethyl]amino}-7-[4-(trifluoromethyl)benzyl]-8-[2-(trifluoromethyl) morpholin-4-yl]-7H-purine-2-carboxylic acid | TFA | 573 | 573 |
| 9.24 | 72.89 | 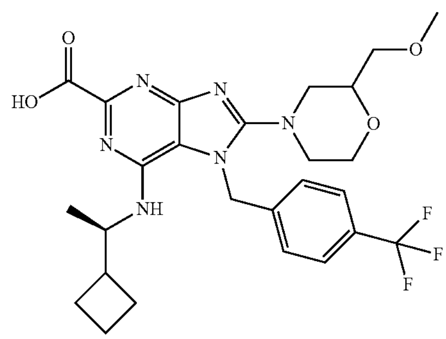 [SMILES: COCC1CN(c2nc3nc(C(=O)O)nc(N[C@H](C)C4CCC4)c3n2Cc2ccc(C(F)(F)F)cc2)CCO1] | 6-{[(1R)-1-cyclobutylethyl]amino}-8-[2-(methoxymethyl) morpholin-4-yl]-7-[4-(trifluoromethyl)benzyl]-7H-purine-2-carboxylic acid | TFA | 549 | 549 |
| 9.25 | 19.37 | 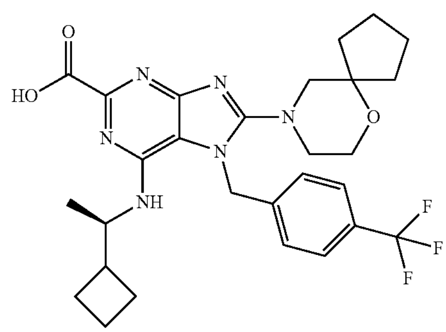 [SMILES: C[C@@H](Nc1nc(C(=O)O)nc2nc(N3CCOC4(CCCC4)C3)n(Cc3ccc(C(F)(F)F)cc3)c12)C1CCC1] | 6-{[(1R)-1-cyclobutylethyl]amino}-8-(6-oxa-9-azaspiro[4.5]dec-9-yl)-7-4-(trifluoromethyl)benzyl]-7H-purine-2-carboxylic acid | TFA | 559 | 559 |
| 9.26 | 34.24 | 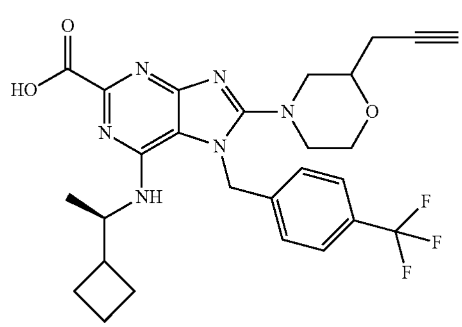 [SMILES: C#CCC1CN(c2nc3nc(C(=O)O)nc(N[C@H](C)C4CCC4)c3n2Cc2ccc(C(F)(F)F)cc2)CCO1] | 6-{[(1R)-1-cyclobutylethyl]amino}-8-(2-prop-2-yn-1-ylmorpholin-4-yl)-7-[4-(trifluoromethyl)benzyl]-7H-purine-2-carboxylic acid | TFA | 543 | 543 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.27 | 23.69 | 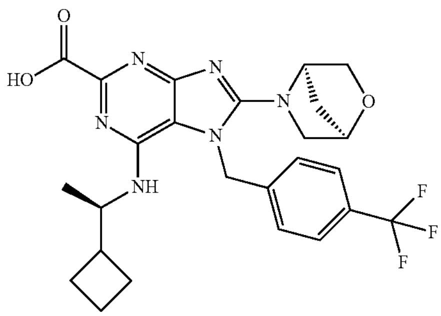 [SMILES: C[C@@H](Nc1nc(C(=O)O)nc2nc(N3C[C@H]4C[C@@H]3CO4)n(Cc3ccc(C(F)(F)F)cc3)c12)C1CCC1] | 6-{[(1R)-1-cyclobutylethyl]amino}-8-[(1R,4R)-2-oxa-5-azabicyclo[2.2.1]hept-5-yl]-7-[4-(trifluoromethyl)benzyl]-7H-purine-2-carboxylic acid | TFA | 517 | 517 |
| 9.28 | 142.8 | 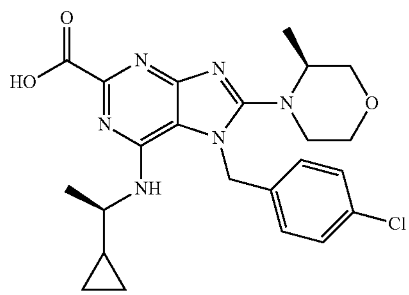 [SMILES: C[C@@H](Nc1nc(C(=O)O)nc2nc(N3CCOC[C@@H]3C)n(Cc3ccc(Cl)cc3)c12)C1CC1] | 7-(4-chlorobenzyl)-6-{[(1R)-1-cyclopropylethyl]amino}-8-[(3 S)-3-methylmorpholin-4-yl]-7H-purine-2-carboxylic acid | TFA | 471 | 471 |
| 9.29 | 4468 | 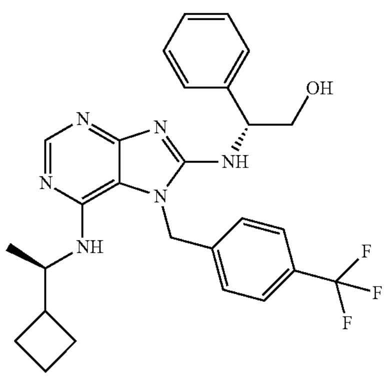 [SMILES: C[C@@H](Nc1ncnc2nc(N[C@@H](CO)c3ccccc3)n(Cc3ccc(C(F)(F)F)cc3)c12)C1CCC1] | (2R)-2-[(6- {[(1R)-1-cyclobutylethyl]amino}-7-[4-(trifluoromethyl)benzyl]-7H-purin-8-yl)amino]-2-phenylethanol | | 511 | 511 |
| 9.30 | 3.054 | 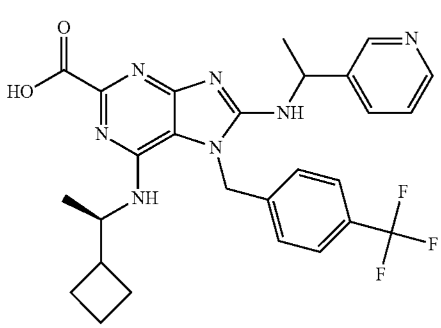 [SMILES: CC(Nc1nc2nc(C(=O)O)nc(N[C@H](C)C3CCC3)c2n1Cc1ccc(C(F)(F)F)cc1)c1cccnc1] | 6-{[(1R)-1-cyclobutylethyl]amino}-8-[(1-pyridin-3-ylethyl)amino]-7-[4-(trifluoromethyl)benzyl]-7H-purine-2-carboxylic acid | | 540 | 540 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.31 | 0.5259 | 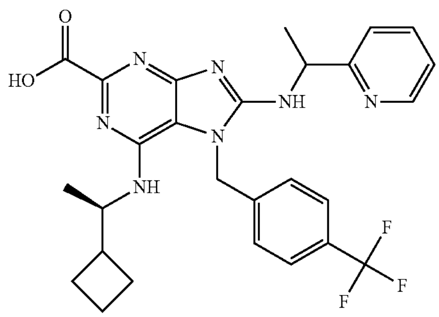 [SMILES: CC(Nc1nc2nc(C(=O)O)nc(N[C@H](C)C3CCC3)c2n1Cc1ccc(C(F)(F)F)cc1)c1ccccn1] | 6-{[(1R)-1-cyclobutylethyl]amino}-8-[(1-pyridin-2-ylethyl)amino]-7-[4-(trifluoromethyl)benzyl]-7H-purine-2-carboxylic acid | | 540 | 540 |
| 9.32 | 15.23 | 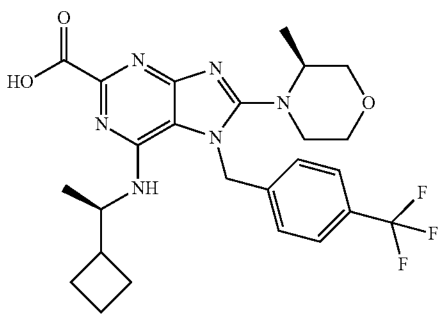 [SMILES: C[C@@H](Nc1nc(C(=O)O)nc2nc(N3CCOC[C@@H]3C)n(Cc3ccc(C(F)(F)F)cc3)c12)C1CCC1] | 6-{[(1R)-1-cyclobutylethyl]amino}-8-[(3S)-3-methylmorpholin-4-yl]-7-[4-(trifluoromethyl)benzyl]-7H-purine-2-carboxylic acid | TFA | 519 | 519 |
| 9.35 | 7.175 | 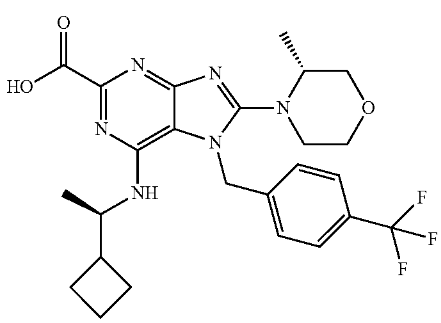 | 6-{[(1R)-1-cyclobutylethyl]amino}-8-[(3R)-3-methylmorpholin-4-yl]-7-[4-(trifluoromethyl)benzyl]-7H-purine-2-carboxylic acid | TFA | 519 | 519 |
| 9.36 | 0.8622 | 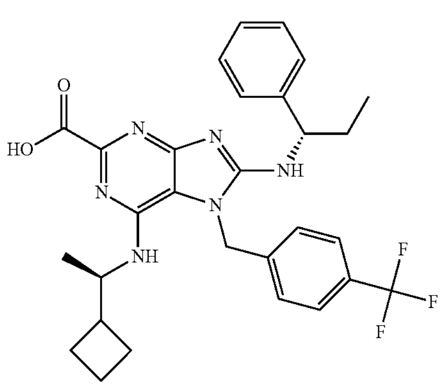 [SMILES: CC[C@H](Nc1nc2nc(C(=O)O)nc(N[C@H](C)C3CCC3)c2n1Cc1ccc(C(F)(F)F)cc1)c1ccccc1] | 6-{[(1R)-1-cyclobutylethyl]amino}-8-{[(1S)-1-phenylpropyl]amino}-7-[4-(trifluoromethyl)benzyl]-7H-purine-2-carboxylic acid | | 553 | 553 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.37 | 21.63 | 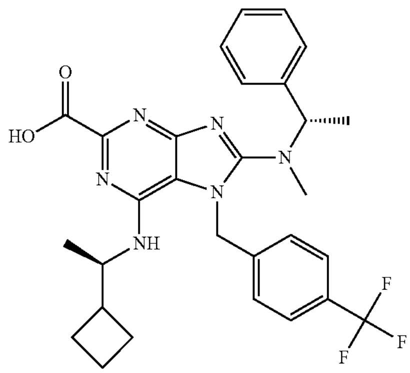 [SMILES: C[C@@H](Nc1nc(C(=O)O)nc2nc(N(C)[C@@H](C)c3ccccc3)n(Cc3ccc(C(F)(F)F)cc3)c12)C1CCC1] | 6-{[(1R)-1-cyclobutylethyl]amino}-8-{methyl[(1S)-1-phenylethyl]amino}-7-[4-(trifluoromethyl)benzyl]-7H-purine-2-carboxylic acid | | 553 | 553 |
| 9.38 | 656.8 | 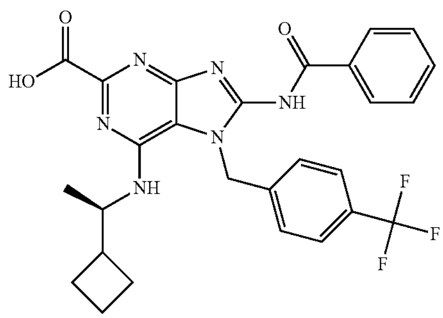 [SMILES: C[C@@H](Nc1nc(C(=O)O)nc2nc(NC(=O)c3ccccc3)n(Cc3ccc(C(F)(F)F)cc3)c12)C1CCC1] | 6-{[(1R)-1-cyclobutylethyl]amino}-8-[(phenylcarbonyl)amino]-7-[4-(trifluoromethyl)benzyl]-7H-purine-2-carboxylic acid | | 539 | 539 |
| 9.39 | 0.7528 | 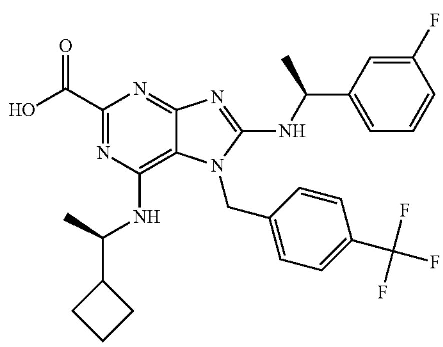 [SMILES: C[C@H](Nc1nc2nc(C(=O)O)nc(N[C@H](C)C3CCC3)c2n1Cc1ccc(C(F)(F)F)cc1)c1cccc(F)c1] | 6-{[(1R)-1-cyclobutylethyl]amino}-8-{[(1S)-1-(3-fluorophenyl)ethyl]amino}-7-[4-(trifluoromethyl)benzyl]-7H-purine-2-carboxylic acid | | 557 | 557 |
| 9.40 | 12.23 | 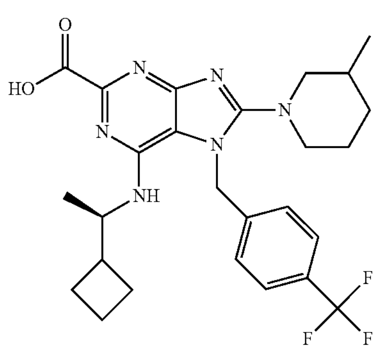 [SMILES: CC1CCCN(c2nc3nc(C(=O)O)nc(N[C@H](C)C4CCC4)c3n2Cc2ccc(C(F)(F)F)cc2)C1] | 6-{[(1R)-1-cyclobutylethyl]amino}-8-(3-methylpiperidin-1-yl)-7-[4-(trifluoromethyl)benzyl]-7H-purine-2-carboxylic acid | | 517 | 517 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.41 | 27.3 | 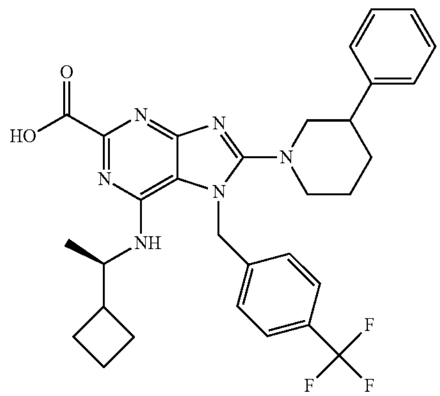 [SMILES: C[C@@H](Nc1nc(C(=O)O)nc2nc(N3CCCC(c4ccccc4)C3)n(Cc3ccc(C(F)(F)F)cc3)c12)C1CCC1] | 6-{[(1R)-1-cyclobutylethyl]amino}-8-[3-phenylpiperidin-1-yl)-7-[4-(trifluoromethyl)benzyl]-7H-purine-2-carboxylic acid | | 579 | 579 |
| 9.42 | 324 | 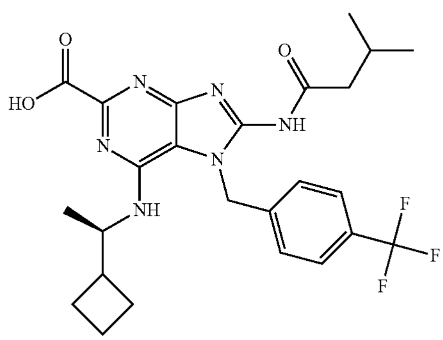 [SMILES: CC(C)CC(=O)Nc1nc2nc(C(=O)O)nc(N[C@H](C)C3CCC3)c2n1Cc1ccc(C(F)(F)F)cc1] | 6-{[(1R)-1-cyclobutylethyl]amino}-8-[(3-methylbutanoyl)amino]-7-[4-(trifluoromethyl)benzyl]-7H-purine-2-carboxylic acid | | 519 | 519 |
| 9.43 | 342.8 | 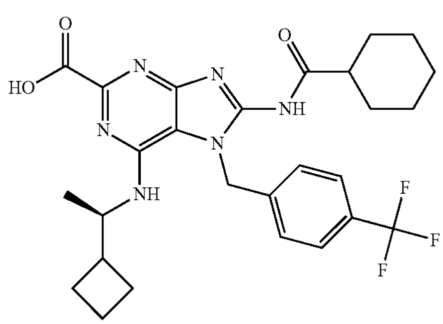 [SMILES: C[C@@H](Nc1nc(C(=O)O)nc2nc(NC(=O)C3CCCCC3)n(Cc3ccc(C(F)(F)F)cc3)c12)C1CCC1] | 6-{[(1R)-1-cyclobutylethyl]amino}-8-[(cyclohexylcarbonyl)amino]-7-[4-(trifluoromethyl)benzyl]-7H-purine-2-carboxylic acid | | 545 | 545 |
| 9.44 | 3.665 | 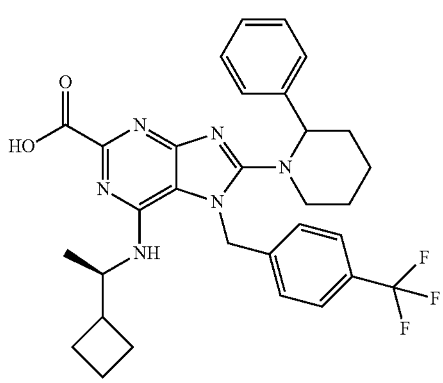 [SMILES: C[C@@H](Nc1nc(C(=O)O)nc2nc(N3CCCCC3c3ccccc3)n(Cc3ccc(C(F)(F)F)cc3)c12)C1CCC1] | 6-{[(1R)-1-cyclobutylethyl]amino}-8-(2-phenylpiperidin-1-yl)-7-[4-(trifluoromethyl)benzyl]-7H-purine-2-carboxylic acid | TFA | 579 | 579 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.45 | 7.566 | 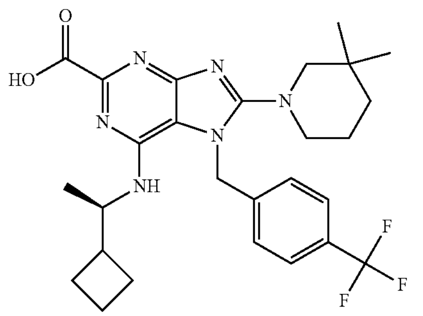 [SMILES: C[C@@H](Nc1nc(C(=O)O)nc2nc(N3CCCC(C)(C)C3)n(Cc3ccc(C(F)(F)F)cc3)c12)C1CCC1] | 6-{[(1R)-1-cyclobutylethyl]amino}-8-(3,3-dimethylpiperidin-1-yl)-7-[4-(trifluoromethyl)benzyl]-7H-purine-2-carboxylic acid | | 531 | 531 |
| 9.46 | 26.18 | 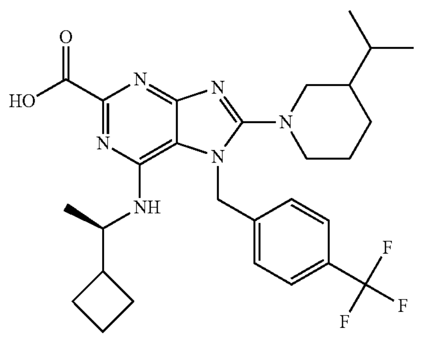 [SMILES: CC(C)C1CCCN(c2nc3nc(C(=O)O)nc(N[C@H](C)C4CCC4)c3n2Cc2ccc(C(F)(F)F)cc2)C1] | 6-{[(1R)-1-cyclobutylethyl]amino}-8-[3-(1-methylethyl)piperidin-1-yl]-7-[4-(trifluoromethyl)benzyl]-7H-purine-2-carboxylic acid | | 545 | 545 |
| 9.47 | 74.19 | 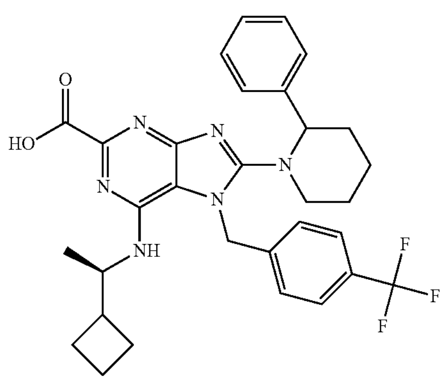 [SMILES: C[C@@H](Nc1nc(C(=O)O)nc2nc(N3CCCCC3c3ccccc3)n(Cc3ccc(C(F)(F)F)cc3)c12)C1CCC1] | 6-{[(1R)-1-cyclobutylethyl]amino}-7-[3-fluoro-4-(trifluoromethyl)benzyl]-8-[2-phenylpiperidin-1-yl)-7H-purine-2-carboxylic acid (enantiomer 1) | TFA | 597 | 597 |
| 9.48 | 6.559 | 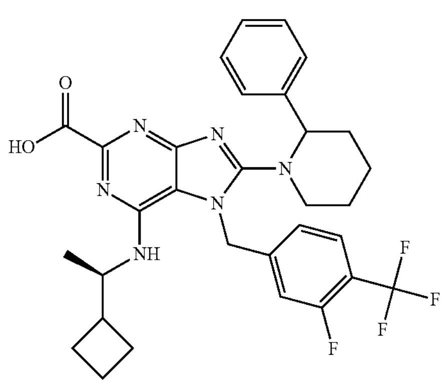 [SMILES: C[C@@H](Nc1nc(C(=O)O)nc2nc(N3CCCCC3c3ccccc3)n(Cc3ccc(C(F)(F)F)c(F)c3)c12)C1CCC1] | 6-{[(1R)-1-cyclobutylethyl]amino}-7-[3-fluoro-4-(trifluoromethyl)benzyl]-8-[2-phenylpiperidin-1-yl)-7H-purine-2-carboxylic acid (enantiomer 2) | TFA | 597 | 597 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.49 | 22.81 | 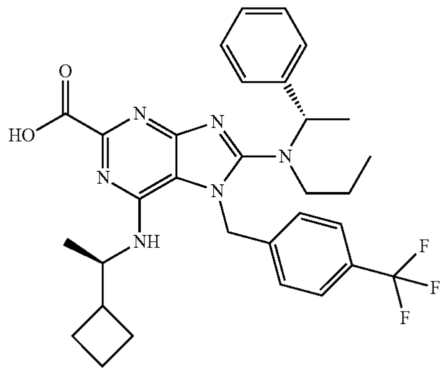 [SMILES: CCCN(c1nc2nc(C(=O)O)nc(N[C@H](C)C3CCC3)c2n1Cc1ccc(C(F)(F)F)cc1)[C@@H](C)c1ccccc1] | 6-{[(1R)-1-cyclobutylethyl]amino}-8-{[(1S)-1-phenylethyl](propyl)amino}-7-[4-(trifluoromethyl)benzyl]-7H-purine-2-carboxylic acid | | 581 | 581 |
| 9.50 | 1.756 | 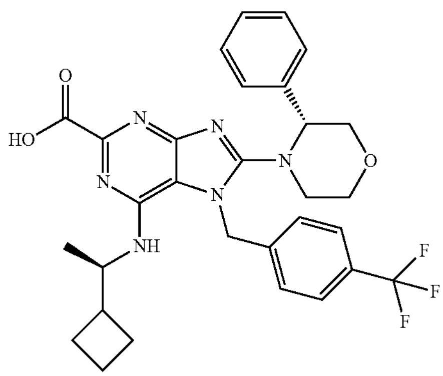 | 6-{[(1R)-1-cyclobutylethyl]amino}-8-[(3R)-3-phenylmorpholin-4-yl]-7-[4-(trifluoromethyl)benzy]-7H-purine-2-carboxylic acid | TFA | 581 | 581 |
| 9.51 | 120.5 | 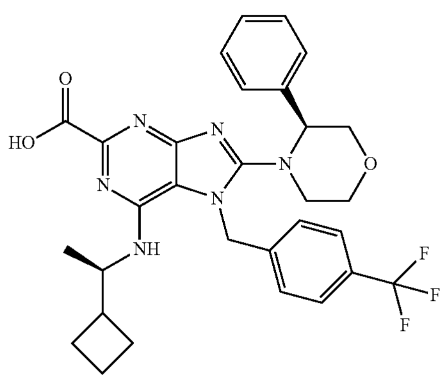 [SMILES: C[C@@H](Nc1nc(C(=O)O)nc2nc(N3CCOC[C@@H]3c3ccccc3)n(Cc3ccc(C(F)(F)F)cc3)c12)C1CCC1] | 6-{[(1R)-1-cyclobutylethyl]amino}-8-[(3S)-3-phenylmorpholin-4-yl]-7-[4-(trifluoromethyl)benzyl]-7H-purine-2-carboxylic acid | TFA | 581 | 581 |
| 9.52 | 31.88 | 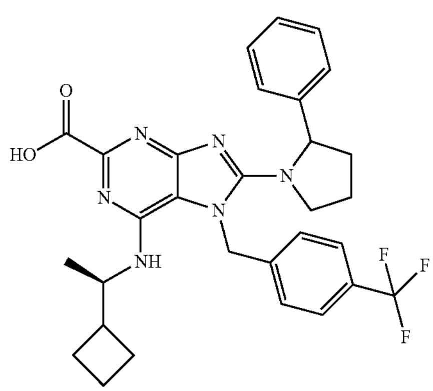 [SMILES: C[C@@H](Nc1nc(C(=O)O)nc2nc(N3CCCC3c3ccccc3)n(Cc3ccc(C(F)(F)F)cc3)c12)C1CCC1] | 6-{[(1R)-1-cyclobutylethyl]amino}-8-(2-phenylpyrrolidin-1-yl)-7-[4-(trifluoromethyl)benzyl]-7H-purine-2-carboxylic acid | | 565 | 565 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.53 | 26.38 | 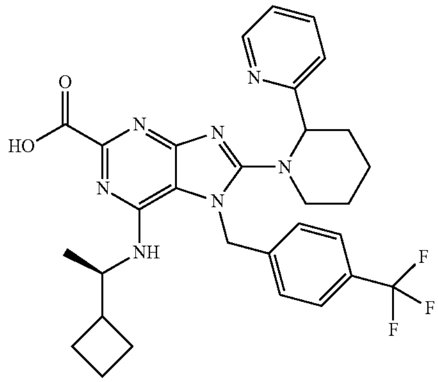 [SMILES: C[C@@H](Nc1nc(C(=O)O)nc2nc(N3CCCCC3c3ccccn3)n(Cc3ccc(C(F)(F)F)cc3)c12)C1CCC1] | 6-{[(1R)-1-cyclobutylethyl]amino}-8-(2-pyridin-2-ylpiperidin-1-yl)-7-[4-(trifluoromethyl)benzyl]-7H-purine-2-carboxylic acid | TFA | 580 | 580 |
| 9.54 | 23.86 | 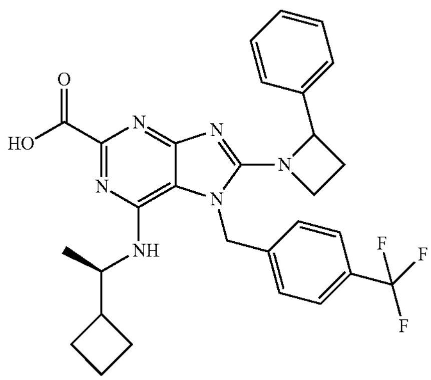 [SMILES: C[C@@H](Nc1nc(C(=O)O)nc2nc(N3CCC3c3ccccc3)n(Cc3ccc(C(F)(F)F)cc3)c12)C1CCC1] | 6-{[(1R)-1-cyclobutylethyl]amino}-8-(2-phenylazetidin-1-yl)-7-[4-(trifluoromethyl)benzyl]-7H-purine-2-carboxylic acid | | 551 | 551 |
| 9.55 | 3.053 | 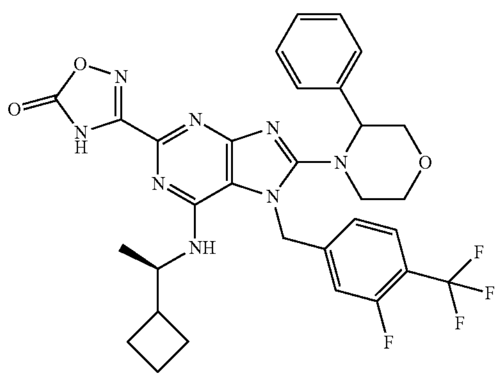 [SMILES: C[C@@H](Nc1nc(-c2noc(=O)[nH]2)nc2nc(N3CCOCC3c3ccccc3)n(Cc3ccc(C(F)(F)F)c(F)c3)c12)C1CCC1] | 3-[6-{[(1R)-1-cyclobutylethyl]amino}-7-[3-fluoro-4-(trifluoromethyl)benzyl]-8-[3-phenylmorpholin-4-yl]-7H-purin-2-yl]-1,2,4-oxadiazol-5(4H)-one (enantiomer 1) | | 639 | 639 |
| 9.56 | 2.249 | 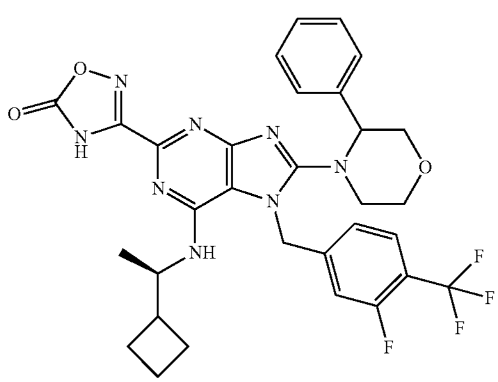 [SMILES: C[C@@H](Nc1nc(-c2noc(=O)[nH]2)nc2nc(N3CCOCC3c3ccccc3)n(Cc3ccc(C(F)(F)F)c(F)c3)c12)C1CCC1] | 3-[6-{[(1R)-1-cyclobutylethyl]amino}-7-[3-fluoro-4-(trifluoromethyl)benzyl]-8-(3-phenylmorpholin-4-yl)-7H-purin-2-yl]-1,2,4-oxadiazol-5(4H)-one (enantiomer 2) | | 639 | 639 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.57 | 1.718 | 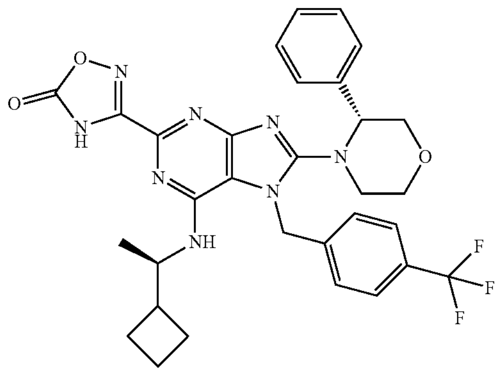 [SMILES: C[C@@H](Nc1nc(-c2noc(=O)[nH]2)nc2nc(N3CCOC[C@H]3c3ccccc3)n(Cc3ccc(C(F)(F)F)cc3)c12)C1CCC1] | 3-(6-{[(1R)-1-cyclobutylethyl]amino}-8-[(3R)-3-phenylmorpholin-4-yl]-7-[4-(trifluoromethyl)benzyl]-7H-purin-2-yl)-1,2,4-oxadiazol-5(4H)-one | TFA | 621 | 621 |
| 9.58 | 16.38 | 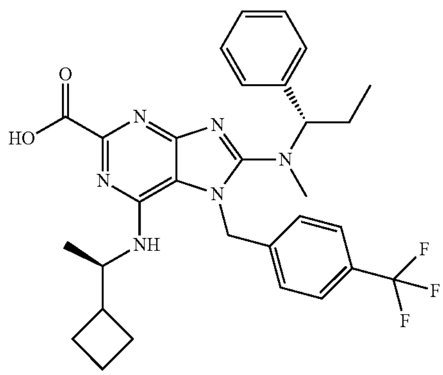 [SMILES: CC[C@@H](c1ccccc1)N(C)c1nc2nc(C(=O)O)nc(N[C@H](C)C3CCC3)c2n1Cc1ccc(C(F)(F)F)cc1] | 6-{[(1R)-1-cyclobutylethyl]amino}-8-{methyl[(1S)-1-phenylpropyl]amino}-7-[4-(trifluoromethyl)benzyl]-7H-purine-2-carboxylic acid | | 567 | 567 |
| 9.59 | 292.4 | 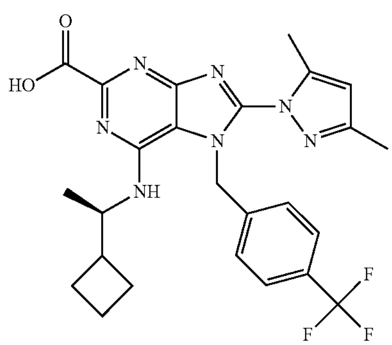 [SMILES: Cc1cc(C)n(-c2nc3nc(C(=O)O)nc(N[C@H](C)C4CCC4)c3n2Cc2ccc(C(F)(F)F)cc2)n1] | 6-{[(1R)-1-cyclobutylethyl]amino}-8-(3,5-dimethyl-1H-pyrazol-1-yl)-7-[4-(trifluoromethyl)benzyl]-7H-purine-2-carboxylic acid | | 514 | 514 |
| 9.60 | 10.16 | 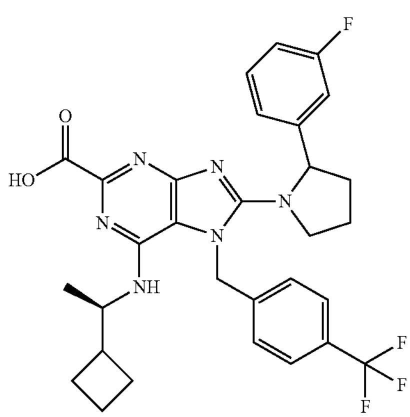 [SMILES: C[C@@H](Nc1nc(C(=O)O)nc2nc(N3CCCC3c3cccc(F)c3)n(Cc3ccc(C(F)(F)F)cc3)c12)C1CCC1] | 6-{[(1R)-1-cyclobutylethyl]amino}-8-[2-(3-fluorophenyl)pyrrolidin-1-yl]-7-[4-(trifluoromethyl)benzyl]-7H-purine-2-carboxylic acid | | 583 | 583 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.61 | 299.5 | 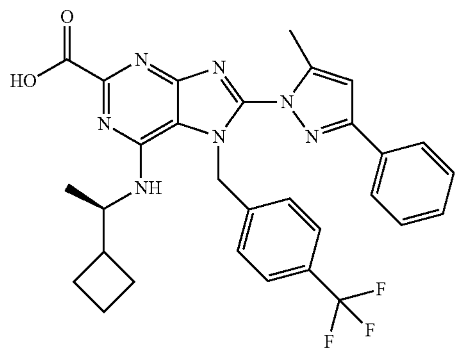 [SMILES: Cc1cc(-c2ccccc2)nn1-c1nc2nc(C(=O)O)nc(N[C@H](C)C3CCC3)c2n1Cc1ccc(C(F)(F)F)cc1] | 6-{[(1R)-1-cyclobutylethyl]amino}-8-(5-methyl-3-phenyl-1H-pyrazol-1-yl)-7-[4-(trifluoromethyl)benzyl]-7H-purine-2-carboxylic acid | | 576 | 576 |
| 9.62 | 17.27 | 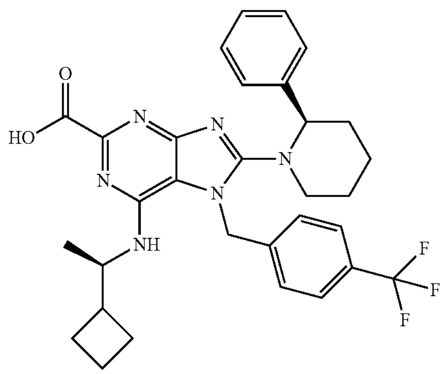 [SMILES: C[C@@H](Nc1nc(C(=O)O)nc2nc(N3CCCC[C@@H]3c3ccccc3)n(Cc3ccc(C(F)(F)F)cc3)c12)C1CCC1] | 6-{[(1R)-1-cyclobutylethyl]amino}-8-[(2R)-2-phenylpiperidin-1-yl]-7-[4-(trifluoromethyl)benzyl]-7H-purine-2-carboxylic acid | TFA | 579 | 579 |
| 9.63 | 3.065 | 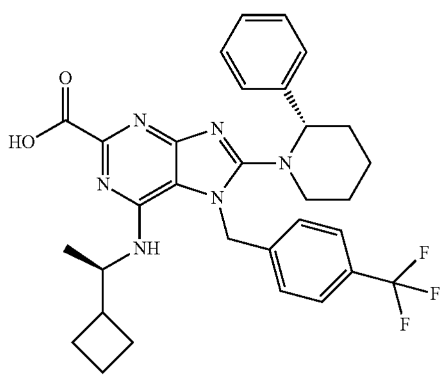 | 6-{[(1R)-1-cyclobutylethyl]amino}-8-[(2S)-2-phenylpiperidin-l-yl]-7-[4-(trifluoromethyl)benzyl]-7H-purine-2-carboxylic acid | TFA | 579 | 579 |
| 9.64 | 10.15 | 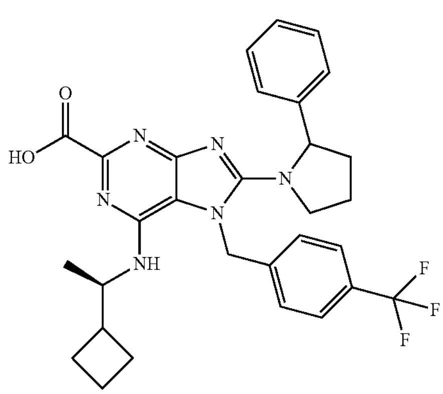 [SMILES: C[C@@H](Nc1nc(C(=O)O)nc2nc(N3CCCC3c3ccccc3)n(Cc3ccc(C(F)(F)F)cc3)c12)C1CCC1] | 6-{[(1R)-1-cyclobutylethyl]amino}-8-(2-phenylpyrrolidin-1-yl)-7-[4-(trifluoromethyl)benzyl]-7H-purine-2-carboxylic acid (enantiomer 1) | TFA | 565 | 565 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.65 | 11.38 | 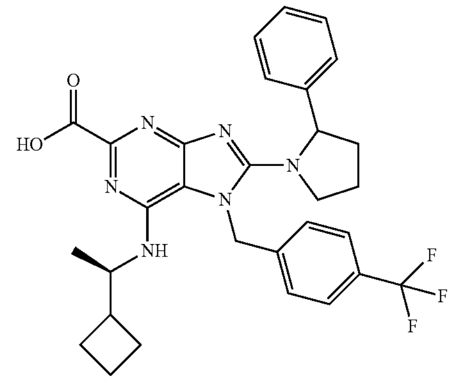 [SMILES: C[C@@H](Nc1nc(C(=O)O)nc2nc(N3CCCC3c3ccccc3)n(Cc3ccc(C(F)(F)F)cc3)c12)C1CCC1] | 6-{[(1R)-1-cyclobutylethyl]amino}-8-(2-phenylpyrrolidin-1-yl)-7-[4-(trifluoromethyl)benzyl]-7H-purine-2-carboxylic acid (enantiomer 2) | TFA | 565 | 565 |
| 9.66 | 6.067 | 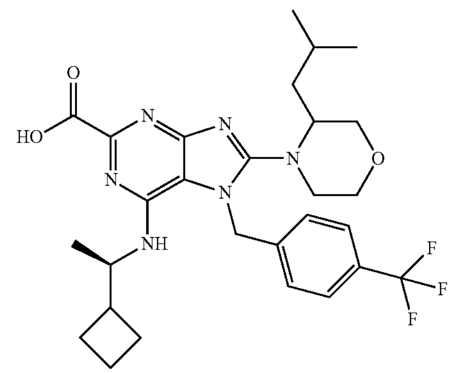 [SMILES: CC(C)CC1COCCN1c1nc2nc(C(=O)O)nc(N[C@H](C)C3CCC3)c2n1Cc1ccc(C(F)(F)F)cc1] | 6-{[(1R)-1-cyclobutylethyl]amino}-8-[3-[2-methylpropyl)morpholin-4-yl]-7-[4-(trifluoromethyl)benzyl]-7H-purine-2-carboxylic acid | TFA | 561 | 561 |
| 9.67 | 12.72 | 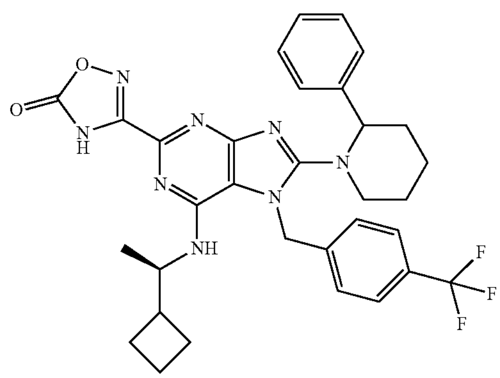 [SMILES: C[C@@H](Nc1nc(-c2noc(=O)[nH]2)nc2nc(N3CCCCC3c3ccccc3)n(Cc3ccc(C(F)(F)F)cc3)c12)C1CCC1] | 3-(6-{[(1R)-1-cyclobutylethyl]amino}-8-(2-phenylpiperidin-1-yl)-(trifluoromethyl)benzyl]-7H-purin-2-yl)-1,2,4-oxadiazol-5(4H)-one | TFA | 619 | 619 |
| 9.68 | 110.3 | 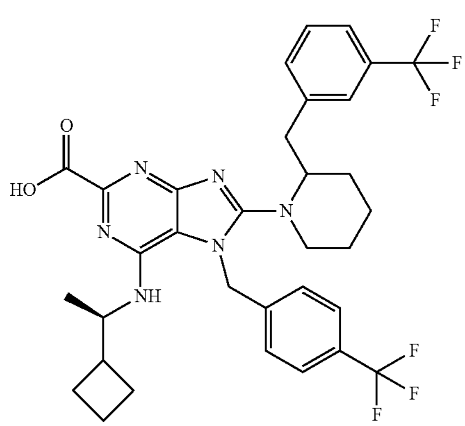 [SMILES: C[C@@H](Nc1nc(C(=O)O)nc2nc(N3CCCCC3Cc3cccc(C(F)(F)F)c3)n(Cc3ccc(C(F)(F)F)cc3)c12)C1CCC1] | 6-{[(1R)-1-cyclobutylethyl]amino}-7-[4-(trifluoromethyl)benzyl]-8-{2-[3-(trifluoromethyl)benzyl]-piperidin-1-yl}-7H-purine-2-carboxylic acid | | 661 | 661 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.69 | 7.916 | 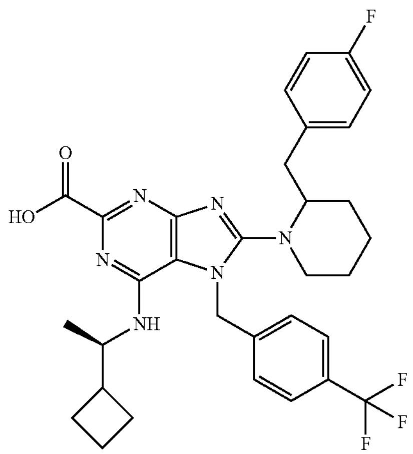 [SMILES: C[C@@H](Nc1nc(C(=O)O)nc2nc(N3CCCCC3Cc3ccc(F)cc3)n(Cc3ccc(C(F)(F)F)cc3)c12)C1CCC1] | 6-{[(1R)-1-cyclobutylethyl]amino}-8-[2-(4-fluorobenzyl)piperidin-1-yl]-7-[4-(trifluoromethyl)benzyl]-7H-purine-2-carboxylic acid | | 611 | 611 |
| 9.70 | 9.286 | 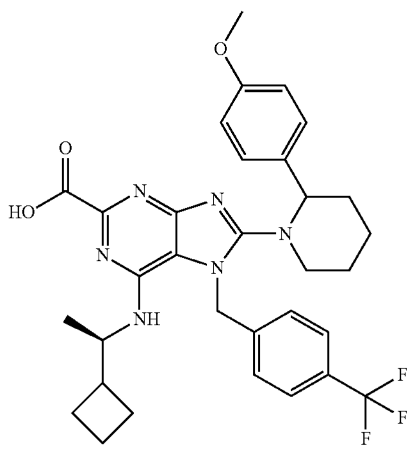 [SMILES: COc1ccc(C2CCCCN2c2nc3nc(C(=O)O)nc(N[C@H](C)C4CCC4)c3n2Cc2ccc(C(F)(F)F)cc2)cc1] | 6-{[(1R)-1-cyclobutylethyl]amino}-8-[2-(4-methoxyphenyl)piperidin-1-yl]-7-[4-(trifluoromethyl)benzyl]-7H-purine-2-carboxylic acid | | 609 | 609 |
| 9.71 | 18.14 | 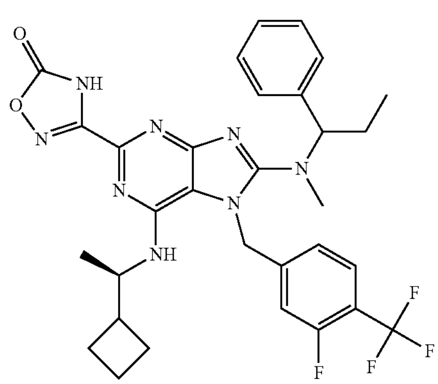 [SMILES: CCC(c1ccccc1)N(C)c1nc2nc(-c3noc(=O)[nH]3)nc(N[C@H](C)C3CCC3)c2n1Cc1ccc(C(F)(F)F)c(F)c1] | 3-(6-{[(1R)-1-cyclobutylethyl]amino}-7-[3-fluoro-4-(trifluoromethyl)benzyl]-8-[methyl(1-phenylpropyl)amino]-7H-purin-2-yl)-1,2,4-oxadiazol-5(4H)-one | TFA | 625 | 625 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.72 | 4.639 | 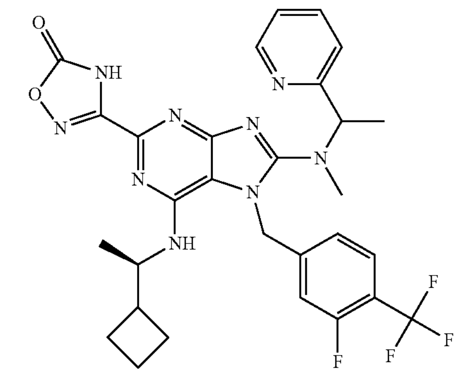 [SMILES: CC(c1ccccn1)N(C)c1nc2nc(-c3noc(=O)[nH]3)nc(N[C@H](C)C3CCC3)c2n1Cc1ccc(C(F)(F)F)c(F)c1] | 3-(6-{[(1R)-1-cyclobutylethyl]amino}-7-[3-fluoro-4-(trifluoromethyl)benzyl]-8-[methyl(1-pyridin-2-ylethyl)amino]-7H-purin-2-yl)-1,2,4-oxadiazol-5(4H)-one | TFA | 612 | 612 |
| 9.73 | 16.15 | 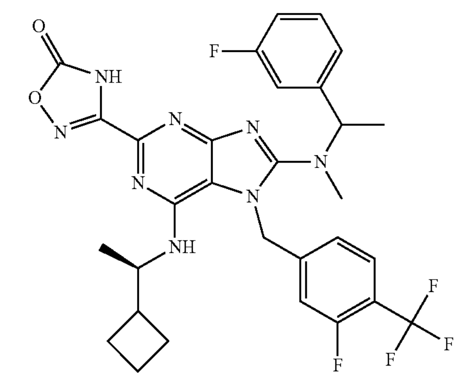 [SMILES: CC(c1cccc(F)c1)N(C)c1nc2nc(-c3noc(=O)[nH]3)nc(N[C@H](C)C3CCC3)c2n1Cc1ccc(C(F)(F)F)c(F)c1] | 3-(6-{[(1R)-1-cyclobutylethyl]amino}-8-{[1-(3-fluorophenyl)ethyl](methyl)amino}-7-[3-fluoro-4-(trifluoromethyl)benzyl]-1,2,4-oxadiazol-5(4H)-one | TFA | 629 | 629 |
| 9.74 | 12.89 | 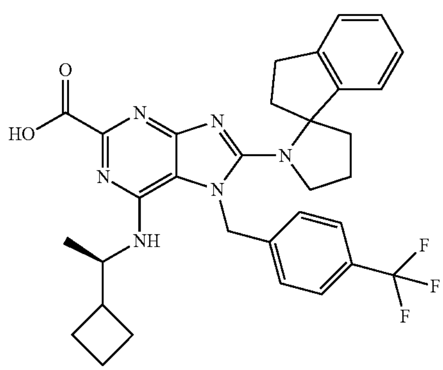 [SMILES: C[C@@H](Nc1nc(C(=O)O)nc2nc(N3CCCC34CCc3ccccc34)n(Cc3ccc(C(F)(F)F)cc3)c12)C1CCC1] | 6-{[(1R)-1-cyclobutylethyl]amino}-8-(2,3-dihydro-1'H-spiro[indene-1,2'-pyrrolidin]-1'-yl)-7-[4-(trifluoromethyl)benzyl]-7H-purine-2-carboxylic acid | TFA | 591 | 591 |
| 9.75 | 8.116 | 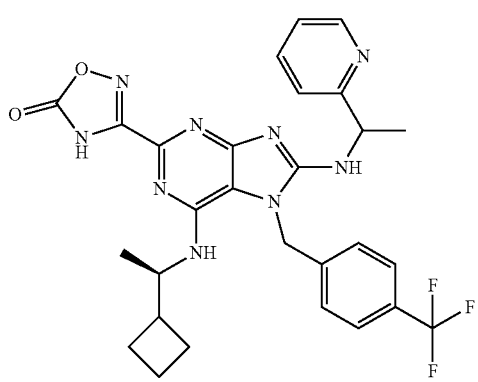 [SMILES: CC(Nc1nc2nc(-c3noc(=O)[nH]3)nc(N[C@H](C)C3CCC3)c2n1Cc1ccc(C(F)(F)F)cc1)c1ccccn1] | 3-(6-{[(1R)-1-cyclobutylethyl]amino}-8-[(1-pyridin-2-ylethyl)amino]-7-[4-(trifluoromethyl)benzyl]-7H-purin-2-yl)-1,2,4-oxadiazol-5(4H)-one | TFA | 580 | 580 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.76 | 15.93 | 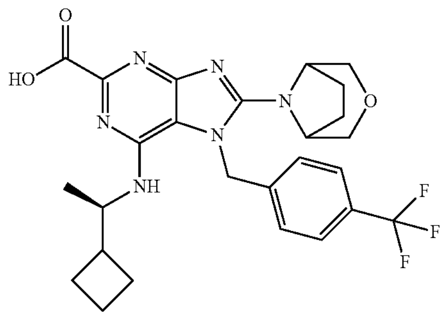 [SMILES: C[C@@H](Nc1nc(C(=O)O)nc2nc(N3C4CCC3COC4)n(Cc3ccc(C(F)(F)F)cc3)c12)C1CCC1] | 6-{[(1R)-1-cyclobutylethyl]amino}-8-(3-oxa-8-azabicyclo[3.2.1]oct-8-yl)-7-[4-(trifluoromethyl)benzyl]-7H-purine-2-carboxylic acid | TFA | 531 | 531 |
| 9.78 | 1.934 | 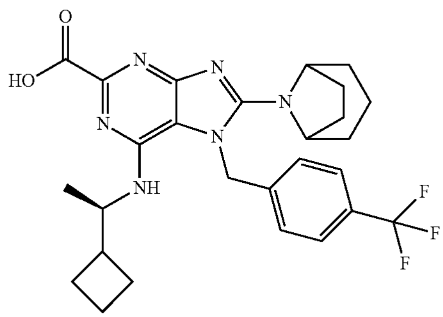 [SMILES: C[C@@H](Nc1nc(C(=O)O)nc2nc(N3C4CCCC3CC4)n(Cc3ccc(C(F)(F)F)cc3)c12)C1CCC1] | 8-(8-azabicyclo[3.2.1]oct-8-yl)-6-{[(1R)-1-cyclobutylethyl]amino}-7-[4-(trifluoromethyl)benzyl]-7H-purine-2-carboxylic acid | TFA | 529 | 529 |
| 9.79 | 7.803 | 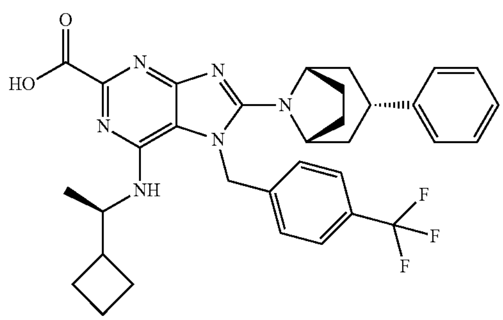 [SMILES: C[C@@H](Nc1nc(C(=O)O)nc2nc(N3[C@@H]4CC[C@H]3C[C@H](c3ccccc3)C4)n(Cc3ccc(C(F)(F)F)cc3)c12)C1CCC1] | 6-{[(1R)-1-cyclobutylethyl]amino}-8-[(3-exo)-3-phenyl-8-azabicyclo[3.2.1]oct-8-yl]-7-[4-(trifluoromethyl)benzyl]-7H-purine-2-carboxylic acid | TFA | 605 | 605 |
| 9.80 | 7.795 | 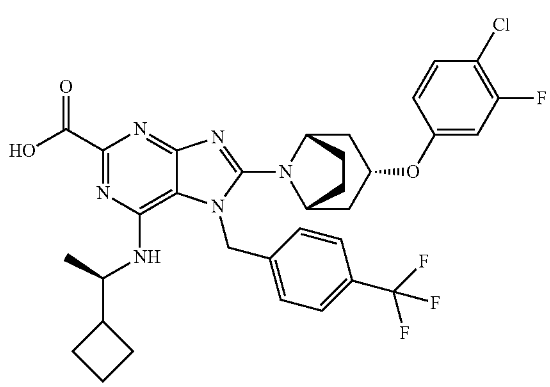 [SMILES: C[C@@H](Nc1nc(C(=O)O)nc2nc(N3[C@@H]4CC[C@H]3C[C@H](Oc3ccc(Cl)c(F)c3)C4)n(Cc3ccc(C(F)(F)F)cc3)c12)C1CCC1] | 8-[(3-exo)-3-(4-chloro-3-fluorophenoxy)-8-azabicyclo[3.2.1]oct-8-yl]-6-{[(1R)-1-cyclobutylethyl]amino}-7-[4-(trifluoromethyl)benzyl]-7H-purine-2-carboxylic acid | TFA | 673 | 673 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.81 | 11.63 | 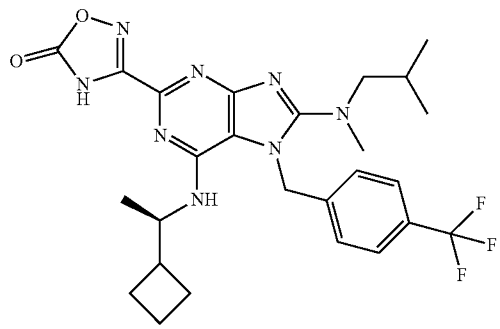 [SMILES: CC(C)CN(C)c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[methyl(2-methylpropyl)amino]-7-[4-(trifluoromethyl)benzyl]-7H-purin-2-1,2,4-oxadiazol-yl)-5(4H)-one | TFA | 545 | 545 |
| 9.82 | 13.74 | 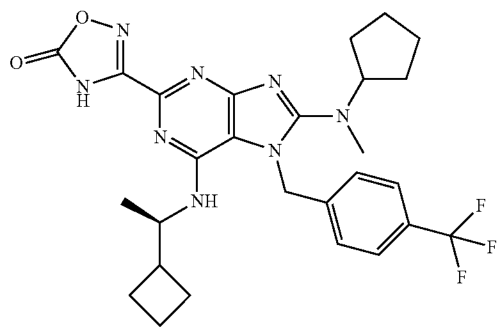 [SMILES: C[C@@H](Nc1nc(-c2noc(=O)[nH]2)nc2nc(N(C)C3CCCC3)n(Cc3ccc(C(F)(F)F)cc3)c12)C1CCC1] | 3-(6-{[(1R)-1-cyclobutylethyl]amino}-8-[cyclopentyl(methyl)amino]-7-[4-(trifluoromethyl)benzyl]-7H-purin-2-yl)-1,2,4-oxadiazol-5(4H)-one | TFA | 557 | 557 |
| 9.83 | 25.59 | 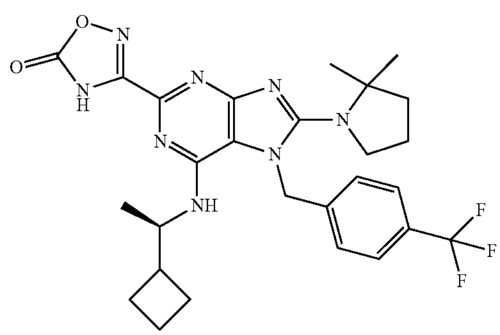 [SMILES: C[C@@H](Nc1nc(-c2noc(=O)[nH]2)nc2nc(N3CCCC3(C)C)n(Cc3ccc(C(F)(F)F)cc3)c12)C1CCC1] | 3-(6-{[(1R)-1-cyclobutylethyl]amino}-8-(2,2-dimethylpyrrolidin-1-yl)-7-[4-(trifluoromethyl)benzyl]-7H-purin-2-yl)-1,2,4-oxadiazol-5(4H)-one | TFA | 557 | 557 |
| 9.84 | 13.28 | 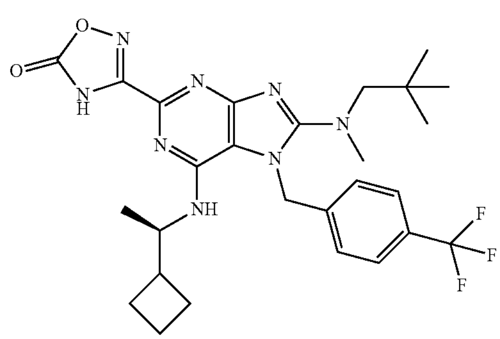 [SMILES: C[C@@H](Nc1nc(-c2noc(=O)[nH]2)nc2nc(N(C)CC(C)(C)C)n(Cc3ccc(C(F)(F)F)cc3)c12)C1CCC1] | 3-(6-{[(1R)-1-cyclobutylethyl]amino}-8-[(2,2-dimethylpropyl)(methyl)amino]-7-[4-(trifluoromethyl)benzyl]-7H-purin-2-yl)-1,2,4-oxadiazol-5(4H)-one | TFA | 559 | 559 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.85 | 9.84 | 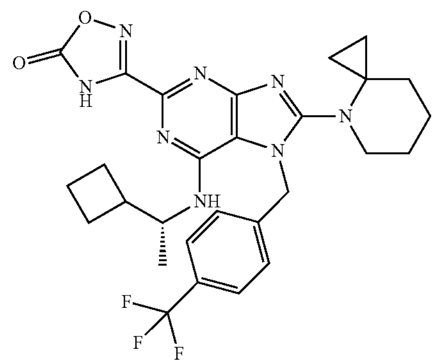 [SMILES: C[C@@H](Nc1nc(-c2noc(=O)[nH]2)nc2nc(N3CCCCC34CC4)n(Cc3ccc(C(F)(F)F)cc3)c12)C1CCC1] | 3-{8-(4-azaspiro[2.5]oct-4-yl)-6-{[(1R)-1-cyclobutylethyl]amino}-7-[4-(trifluoromethyl)benzyl]-7H-purin-2-yl)-1,2,4-oxadiazol-5(4H)-one | TFA | 569 | 569 |
| 9.86 | 10.21 | 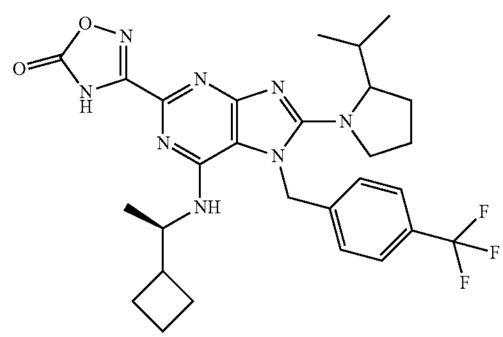 [SMILES: CC(C)C1CCCN1c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[2-[1-methylethyl)pyrrolidin-1-yl]-7-[4-(trifluoromethyl)benzyl]-7H-purin-2-yl)-1,2,4-oxadiazol-5(4H)-one | TFA | 571 | 571 |
| 9.87 | 23.37 | 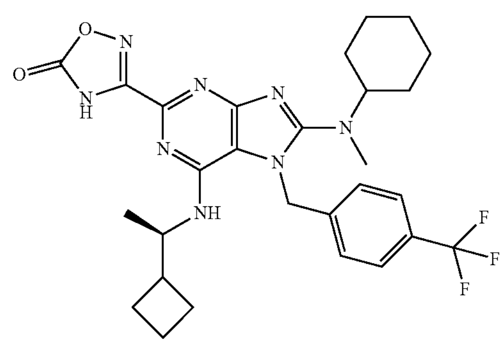 [SMILES: C[C@@H](Nc1nc(-c2noc(=O)[nH]2)nc2nc(N(C)C3CCCCC3)n(Cc3ccc(C(F)(F)F)cc3)c12)C1CCC1] | 3-(6-{[(1R)-1-cyclobutylethyl]amino}-8-[cyclohexyl(methyl)amino]-7-[4-(trifluoromethyl)benzyl]-7H-purin-2-yl)-1,2,4-oxadiazol-5(4H)-one | TFA | 571 | 571 |
| 9.88 | 12.23 | 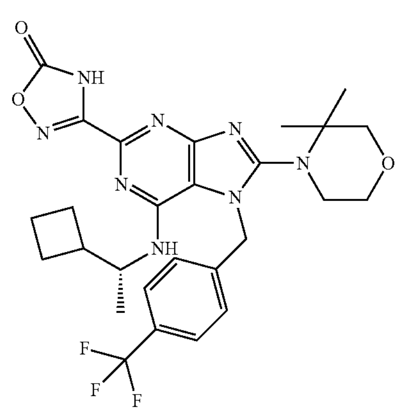 [SMILES: C[C@@H](Nc1nc(-c2noc(=O)[nH]2)nc2nc(N3CCOCC3(C)C)n(Cc3ccc(C(F)(F)F)cc3)c12)C1CCC1] | 3-(6-{[(1R)-1-cyclobutylethyl]amino}-8-(3,3-dimethylmorpholin-4-yl)-7-[4-(trifluoromethyl)benzyl]-7H-purin-2-yl)-1,2,4-oxadiazol-5(4H)-one | TFA | 573 | 573 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.89 | 22.65 | 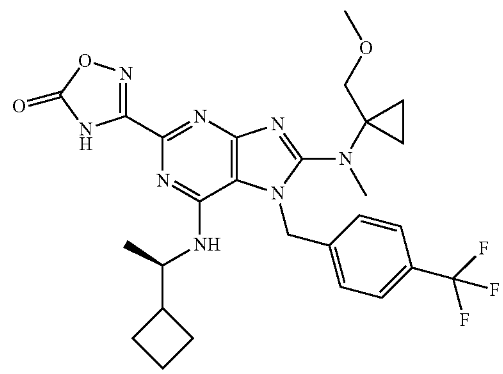 [SMILES: COCC1(N(C)c2nc3nc(-c4noc(=O)[nH]4)nc(N[C@H](C)C4CCC4)c3n2Cc2ccc(C(F)(F)F)cc2)CC1] | 3-(6-{[(1R)-1-cyclobutylethyl]amino}-8-{[1-(methoxymethyl)cyclopropyl](methyl)amino}-7-[4-(trifluoromethyl)benzyl]-7H-purin-2-yl)-1,2,4-oxadiazol-5(4H)-one | TFA | 573 | 573 |
| 9.90 | 12.1 | 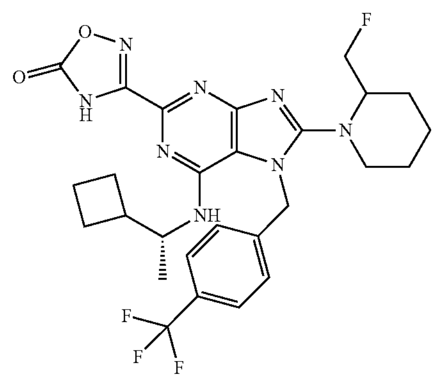 [SMILES: C[C@@H](Nc1nc(-c2noc(=O)[nH]2)nc2nc(N3CCCCC3CF)n(Cc3ccc(C(F)(F)F)cc3)c12)C1CCC1] | 3-(6-{[(1R)-1-cyclobutylethyl]amino}-8-[2-(fluoromethyl)piperidin-1-yl]-7-[4-(trifluoromethyl)benzyl]-7H-purin-2-yl)-1,2,4-oxadiazol-5(4H)-one | TFA | 575 | 575 |
| 9.91 | 19.45 | 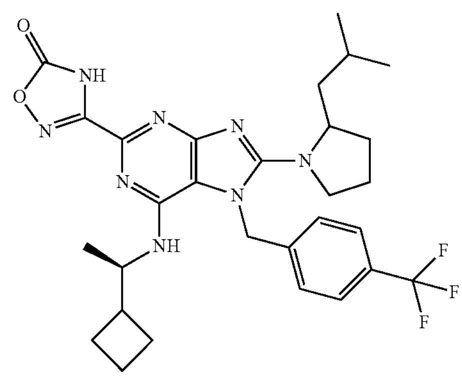 [SMILES: CC(C)CC1CCCN1c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[2-(2-methylpropyl)pyrrolidin-1-yl]-7-[4-(trifluoromethyl)benzyl]-7H-purin-2-yl)-1,2,4-oxadiazol-5(4H)-one | TFA | 585 | 585 |
| 9.92 | 478.4 | 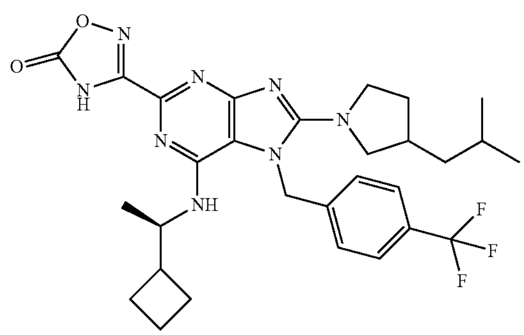 [SMILES: CC(C)CC1CCN(c2nc3nc(-c4noc(=O)[nH]4)nc(N[C@H](C)C4CCC4)c3n2Cc2ccc(C(F)(F)F)cc2)C1] | 3-(6-{[(1R)-1-cyclobutylethyl]amino}-8-[3-(2-methylpropyl)pyrrolidin-1-yl]-7-[4-(trifluoromethyl)benzyl]-7H-purin-2-yl)-1,2,4-oxadiazol-5(4H)-one | TFA | 585 | 585 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.93 | 46.97 | 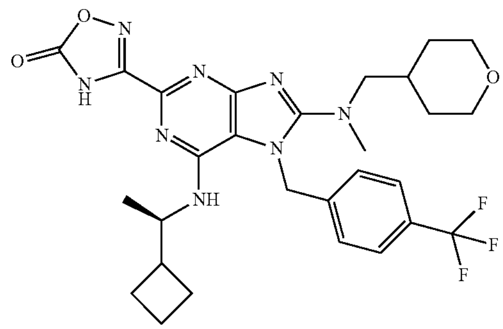 [SMILES: C[C@@H](Nc1nc(-c2noc(=O)[nH]2)nc2nc(N(C)CC3CCOCC3)n(Cc3ccc(C(F)(F)F)cc3)c12)C1CCC1] | 3-(6-{[(1R)-1-cyclobutylethyl]amino}-8-[methyl(tetrahydro-2H-pyran-4-ylmethyl)amino]-7-[4-(trifluoromethyl)benzyl]-7H-purin-2-yl)-1,2,4-oxadiazol-5(4H)-one | TFA | 587 | 587 |
| 9.94 | 96.74 | 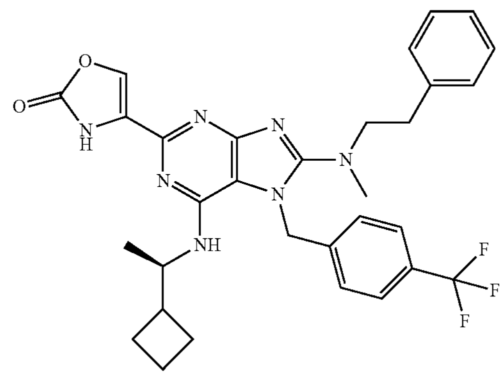 [SMILES: C[C@@H](Nc1nc(-c2coc(=O)[nH]2)nc2nc(N(C)CCc3ccccc3)n(Cc3ccc(C(F)(F)F)cc3)c12)C1CCC1] | 3-(6-{[(1R)-1-cyclobutylethyl]amino}-8-[methyl(2-phenylethyl)amino]-7-[4-(trifluoromethyl)benzyl]-7H-purin-2-yl)-1,2,4-oxadiazol-5(4H)-one | TFA | 593 | 593 |
| 9.95 | 27.18 | 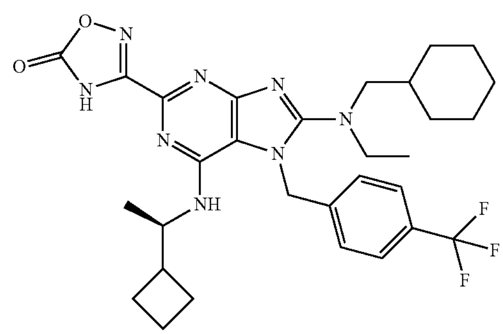 [SMILES: CCN(CC1CCCCC1)c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[(cyclohexylmethyl)(ethyl)amino]-7-[4-(trifluoromethyl)benzyl]-7H-purin-2-yl)-1,2,4-oxadiazol-5(4H)-one | TFA | 599 | 599 |
| 9.96 | 16.2 | 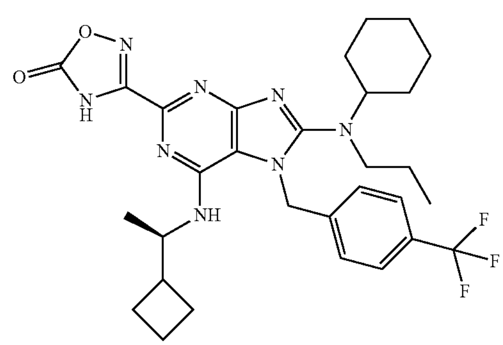 [SMILES: CCCN(c1nc2nc(-c3noc(=O)[nH]3)nc(N[C@H](C)C3CCC3)c2n1Cc1ccc(C(F)(F)F)cc1)C1CCCCC1] | 3-(6-{[(1R)-1-cyclobutylethyl]amino}-8-[cyclohexyl(propyl)amino]-7-[4-(trifluoromethyl)benzyl]-7H-purin-2-yl)-1,2,4-oxadiazol-5(4H)-one | TFA | 599 | 599 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.97 | 23.87 | 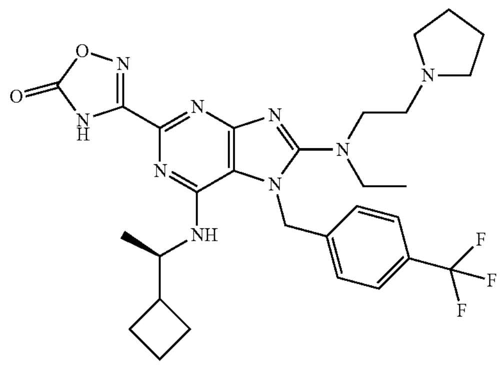 [SMILES: CCN(CCN1CCCC1)c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[ethyl(2-pyrrolidin-1-ylethyl)amino]-7-[4-(trifluoromethyl)benzyl]-7H-purin-2-yl)-1,2,4-oxadiazol-5(4H)-one | TFA | 600 | 600 |
| 9.98 | 71.05 | 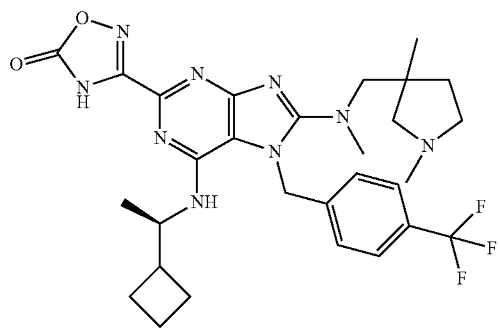 [SMILES: C[C@@H](Nc1nc(-c2noc(=O)[nH]2)nc2nc(N(C)CC3(C)CCN(C)C3)n(Cc3ccc(C(F)(F)F)cc3)c12)C1CCC1] | 3-(6-{[(1R)-1-cyclobutylethyl]amino}-8-{[(1,3-dimethylpyrrolidin-3-yl)methyl](methyl)amino}-7-[4-(trifluoromethyl)benzyl]-7H-purin-2-yl)-1,2,4-oxadiazol-5(4H)-one | TFA | 600 | 600 |
| 9.99 | 44.96 | 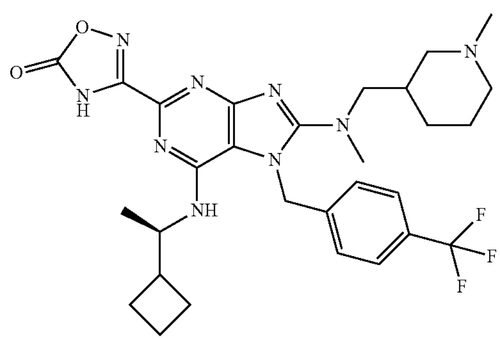 [SMILES: C[C@@H](Nc1nc(-c2noc(=O)[nH]2)nc2nc(N(C)CC3CCCN(C)C3)n(Cc3ccc(C(F)(F)F)cc3)c12)C1CCC1] | 3-(6-{[(1R)-1-cyclobutylethyl]amino}-8-{methyl[(1-methylpiperidin-3-yl)methyl]amino}-7-[4-(trifluoromethyl)benzyl]-7H-purin-2-yl)-1,2,4-oxadiazol-5(4H)-one | TFA | 600 | 600 |
| 9.100 | 148.4 | 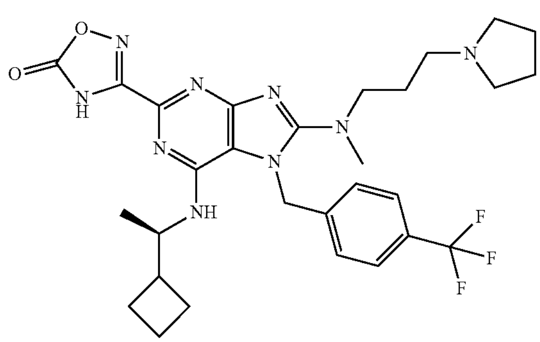 [SMILES: C[C@@H](Nc1nc(-c2noc(=O)[nH]2)nc2nc(N(C)CCCN3CCCC3)n(Cc3ccc(C(F)(F)F)cc3)c12)C1CCC1] | 3-(6-{[(1R)-1-cyclobutylethyl]amino}-8-[methyl(3-pyrrolidin-1-ylpropyl)amino]-7-[4-(trifluoromethyl)benzyl]-7H-purin-2-yl)-1,2,4-oxadiazol-5(4H)-one | TFA | 600 | 600 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.101 | 9.8 | 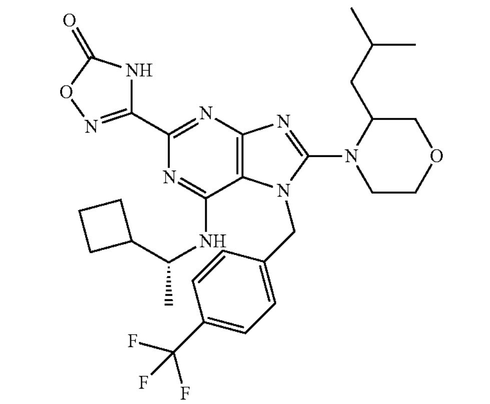 [SMILES: CC(C)CC1COCCN1c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[3-(2-methylpropyl)morpholin-4-yl]-7-[4-(trifluoromethyl)benzyl]-7H-purin-2-yl)-1,2,4-oxadiazol-5(4H)-one | TFA | 601 | 601 |
| 9.102 | 60.74 | 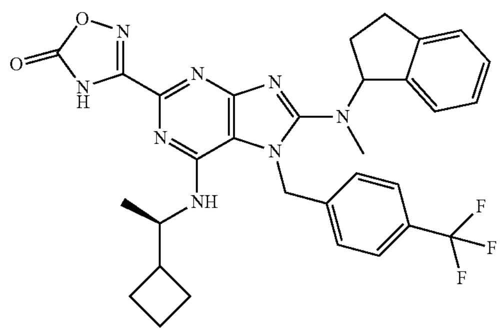 [SMILES: C[C@@H](Nc1nc(-c2noc(=O)[nH]2)nc2nc(N(C)C3CCc4ccccc43)n(Cc3ccc(C(F)(F)F)cc3)c12)C1CCC1] | 3-(6-{[(1R)-1-cyclobutylethyl]amino}-8-[2,3-dihydro-1H-inden-1-yl(methyl)amino]-7-[4-(trifluoromethyl)benzyl]-7H-purin-2-yl)-1,2,4-oxadiazol-5(4H)-one | TFA | 605 | 605 |
| 9.103 | 31.86 | 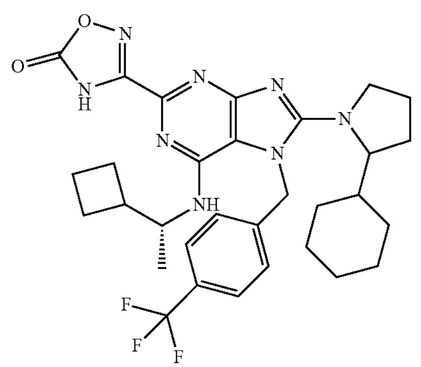 [SMILES: C[C@@H](Nc1nc(-c2noc(=O)[nH]2)nc2nc(N3CCCC3C3CCCCC3)n(Cc3ccc(C(F)(F)F)cc3)c12)C1CCC1] | 3-(6-{[(1R)-1-cyclobutylethyl]amino}-8-(2-cyclohexylpyrrolidin-1-yl)-7-[4-(trifluoromethyl)benzyl]-7H-purin-2-yl)-1,2,4-oxadiazol-5(4H)-one | TFA | 611 | 611 |
| 9.104 | 63.18 | 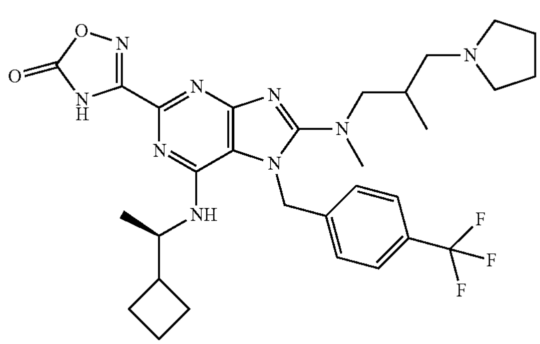 [SMILES: CC(CN1CCCC1)CN(C)c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[methyl(2-methyl-3-pyrrolidin-1-ylpropyl)amino]-7-[4-(trifluoromethyl)benzyl]-7H-purin-2-yl)-1,2,4-oxadiazol-5(4H)-one | TFA | 614 | 614 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.105 | 14.04 | 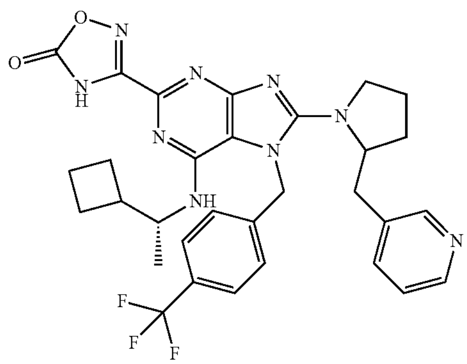 [SMILES: C[C@@H](Nc1nc(-c2noc(=O)[nH]2)nc2nc(N3CCCC3Cc3cccnc3)n(Cc3ccc(C(F)(F)F)cc3)c12)C1CCC1] | 3-(6-{[(1R)-1-cyclobutylethyl]amino}-8-[2-[2-3-ylmethyl)pyrrolidin-1-yl]-7-[4-(trifluoromethyl)benzyl]-7H-purin-2-yl)-1,2,4-oxadiazol-5(4H)-one | TFA | 620 | 620 |
| 9.106 | 11.49 | 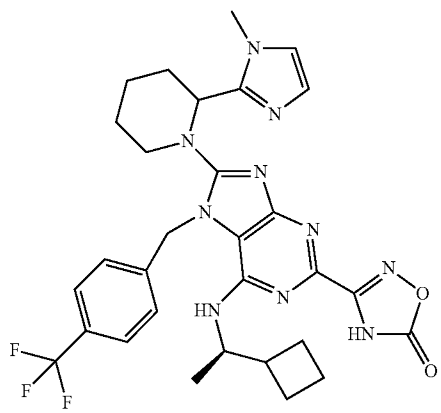 [SMILES: C[C@@H](Nc1nc(-c2noc(=O)[nH]2)nc2nc(N3CCCCC3c3nccn3C)n(Cc3ccc(C(F)(F)F)cc3)c12)C1CCC1] | 3-(6-{[(1R)-1-cyclobutylethyl]amino}-8-[2-(1-methyl-1H-imidazol-2-yl)piperidin-1-yl]-7-[4-(trifluoromethyl)benzyl]-7H-purin-2-yl)-1,2,4-oxadiazol-5(4H)-one | TFA | 623 | 623 |
| 9.107 | 5.18 | 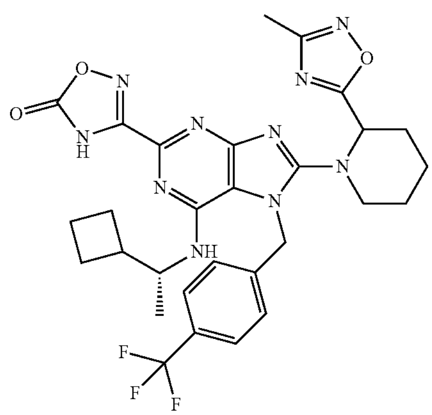 [SMILES: Cc1noc(C2CCCCN2c2nc3nc(-c4noc(=O)[nH]4)nc(N[C@H](C)C4CCC4)c3n2Cc2ccc(C(F)(F)F)cc2)n1] | 3-(6-{[(1R)-1-cyclobutylethyl]amino}-8-[2-[3-methyl-1,2,4-oxadiazol-5-yl)piperidin-1-yl]-7-[4-(trifluoromethyl)benzyl]-7H-purin-2-yl)-1,2,4-oxadiazol-5(4H)-one | TFA | 625 | 625 |
| 9.108 | 143.5 | 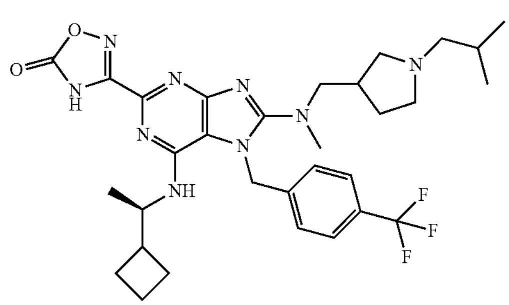 [SMILES: CC(C)CN1CCC(CN(C)c2nc3nc(-c4noc(=O)[nH]4)nc(N[C@H](C)C4CCC4)c3n2Cc2ccc(C(F)(F)F)cc2)C1] | 3-(6-{[(1R)-1-cyclobutylethyl]amino}-8-(methyl{[1-(2-methylpropyl)pyrrolidin-3-yl]methyl}amino)-7-[4-(trifluoromethyl)benzyl]-7H-purin-2-yl)-1,2,4-oxadiazol-5(4H)-one | TFA | 628 | 628 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.109 | 59.9 | 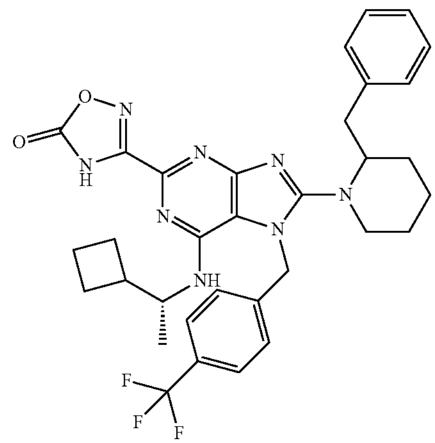 [SMILES: C[C@@H](Nc1nc(-c2noc(=O)[nH]2)nc2nc(N3CCCCC3Cc3ccccc3)n(Cc3ccc(C(F)(F)F)cc3)c12)C1CCC1] | 3-{8-(2-benzylpiperidin-1-yl)-6-{[(1R)-1-cyclobutylethyl]amino}-7-[4-(trifluoromethyl)benzyl]-7H-purin-2-yl}-1,2,4-oxadiazol-5(4H)-one | TFA | 633 | 633 |
| 9.110 | 10.32 | 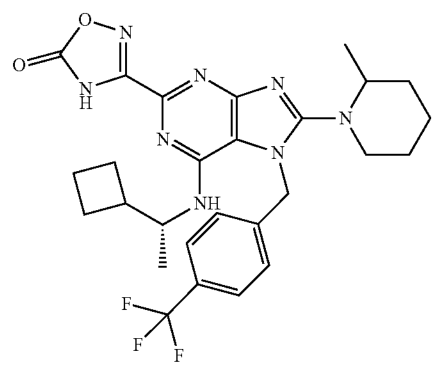 [SMILES: CC1CCCCN1c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-(2-methylpiperidin-1-yl)-7-[4-(trifluoromethyl)benzyl]-7H-purin-2-yl)-1,2,4-oxadiazol-5(4H)-one | TFA | 557 | 557 |
| 9.111 | 8.779 | 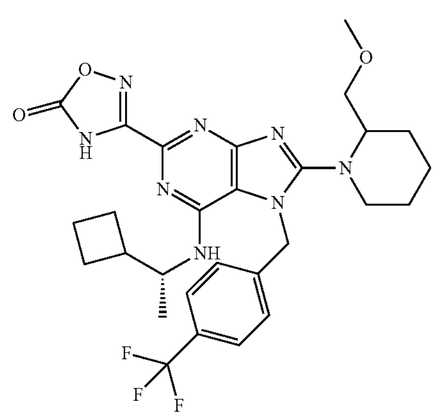 [SMILES: COCC1CCCCN1c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[2-(methoxymethyl)piperidin-1-yl]-7-[4-(trifluoromethyl)benzyl]-7H-purin-2-yl)-1,2,4-oxadiazol-5(4H)-one | TFA | 587 | 587 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.112 | 9.546 | 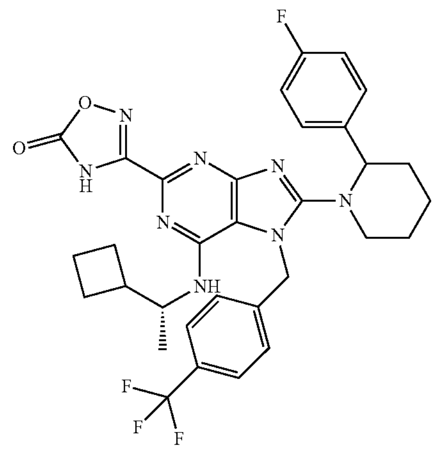 [SMILES: C[C@@H](Nc1nc(-c2noc(=O)[nH]2)nc2nc(N3CCCCC3c3ccc(F)cc3)n(Cc3ccc(C(F)(F)F)cc3)c12)C1CCC1] | 3-(6-{[(1R)-1-cyclobutylethyl]amino}-8-[2-(4-fluorophenyl)piperidin-1-yl]-7-[4-(trifluoromethyl)benzyl]-7H-purin-2-yl)-1,2,4-oxadiazol-5(4H)-one | TFA | 637 | 637 |
| 9.113 | 25.93 | 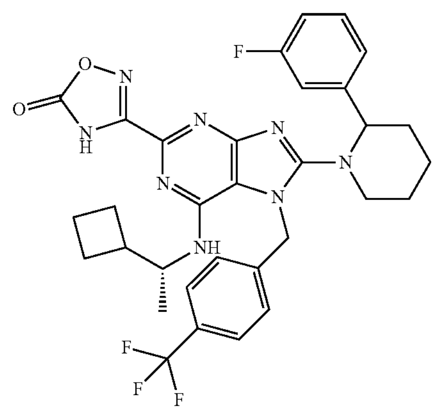 [SMILES: C[C@@H](Nc1nc(-c2noc(=O)[nH]2)nc2nc(N3CCCCC3c3cccc(F)c3)n(Cc3ccc(C(F)(F)F)cc3)c12)C1CCC1] | 3-(6-{[(1R)-1-cyclobutylethyl]amino}-8-[2-[3-fluorophenyl)piperidin-1-yl]-7-[4-(trifluoromethyl)benzyl]-7H-purin-2-yl)-1,2,4-oxadiazol-5(4H)-one | TFA | 637 | 637 |
| 9.114 | 110.5 | 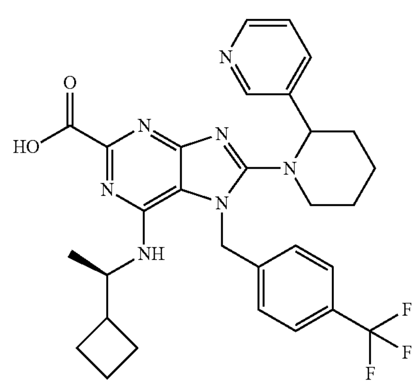 [SMILES: C[C@@H](Nc1nc(C(=O)O)nc2nc(N3CCCCC3c3cccnc3)n(Cc3ccc(C(F)(F)F)cc3)c12)C1CCC1] | 6-{[(1R)-1-cyclobutylethyl]amino}-8-(2-pyridin-3-ylpiperidin-1-yl)-7-[4-(trifluoromethyl)benzyl]-7H-purine-2-carboxylic acid | | 580 | 580 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.115 | 16.6 | 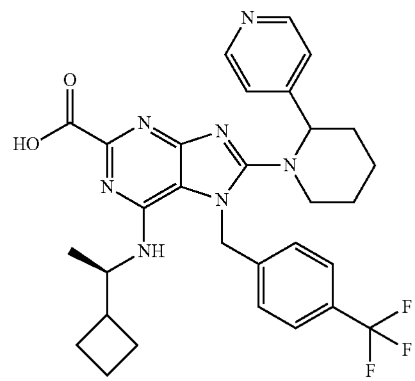 [SMILES: C[C@@H](Nc1nc(C(=O)O)nc2nc(N3CCCCC3c3ccncc3)n(Cc3ccc(C(F)(F)F)cc3)c12)C1CCC1] | 6-{[(1R)-1-cyclobutylethyl]amino}-8-(2-pyridin-4-ylpiperidin-1-yl)-7-[4-(trifluoromethyl)benzyl]-7H-purine-2-carboxylic acid | | 580 | 580 |
| 9.116 | 14.04 | 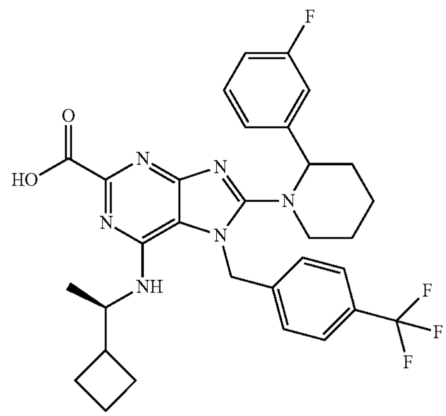 [SMILES: C[C@@H](Nc1nc(C(=O)O)nc2nc(N3CCCCC3c3cccc(F)c3)n(Cc3ccc(C(F)(F)F)cc3)c12)C1CCC1] | 6-{[(1R)-1-cyclobutylethyl]amino}-8-[2-(3-fluorophenyl)piperidin-1-yl]-7-[4-(trifluoromethyl)benzyl]-7H-purine-2-carboxylic acid | | 597 | 597 |
| 9.117 | 10.56 | 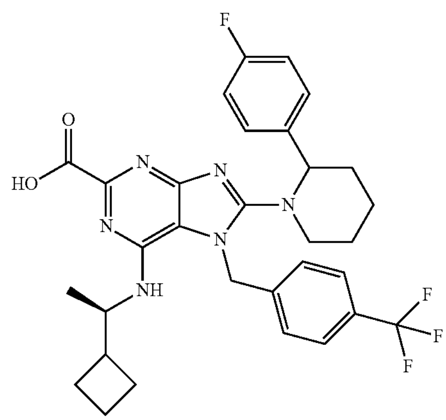 [SMILES: C[C@@H](Nc1nc(C(=O)O)nc2nc(N3CCCCC3c3ccc(F)cc3)n(Cc3ccc(C(F)(F)F)cc3)c12)C1CCC1] | 6-{[(1R)-1-cyclobutylethyl]amino}-8-[2-(4-fluorophenyl)piperidin-1-yl]-7-[4-(trifluoromethyl)benzyl]-7H-purine-2-carboxylic acid | | 597 | 597 |
| 9.118 | 51.8 | 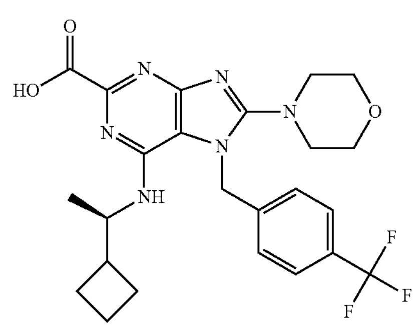 [SMILES: C[C@@H](Nc1nc(C(=O)O)nc2nc(N3CCOCC3)n(Cc3ccc(C(F)(F)F)cc3)c12)C1CCC1] | 6-{[(1R)-1-cyclobutylethyl]amino}-8-morpholin-4-yl-7-[4-(trifluoromethyl)benzyl]-7H-purine-2-carboxylic acid | | 505 | 505 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.119 | 9.158 | 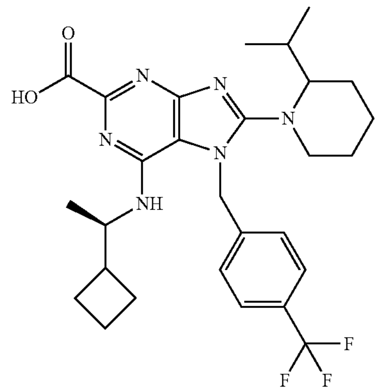 [SMILES: CC(C)C1CCCCN1c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-(1-methylethyl)piperidin-1-yl]-7-[4-(trifluoromethyl)benzyl]-7H-purine-2-carboxylic acid | | 545 | 545 |
| 9.120 | 5.319 | 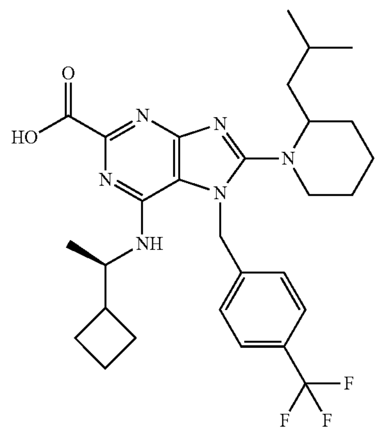 [SMILES: CC(C)CC1CCCCN1c1nc2nc(C(=O)O)nc(N[C@H](C)C3CCC3)c2n1Cc1ccc(C(F)(F)F)cc1] | 6-{[(1R)-1-cyclobutylethyl]amino}-8-[2-(2-methylpropyl)piperidin-1-yl]-7-[4-(trifluoromethyl)benzyl]-7H-purine-2-carboxylic acid | | 559 | 559 |
| 9.121 | 10.59 | 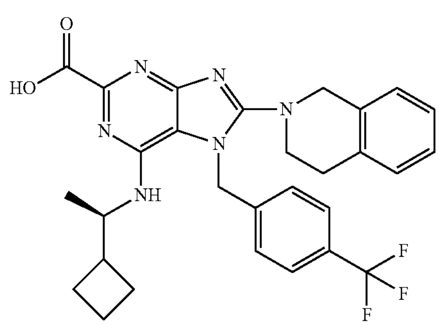 [SMILES: C[C@@H](Nc1nc(C(=O)O)nc2nc(N3CCc4ccccc4C3)n(Cc3ccc(C(F)(F)F)cc3)c12)C1CCC1] | 6-{[(1R)-1-cyclobutylethyl]amino}-8-(3,4-dihydroisoquinolin-2(1H)-yl)-7-[4-(trifluoromethyl)benzyl]-7H-purine-2-carboxylic acid | | 551 | 551 |
| 9.122 | 4.589 | 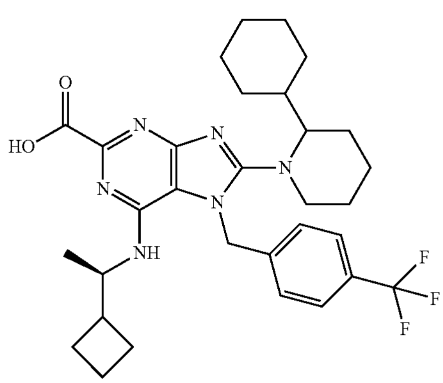 [SMILES: C[C@@H](Nc1nc(C(=O)O)nc2nc(N3CCCCC3C3CCCCC3)n(Cc3ccc(C(F)(F)F)cc3)c12)C1CCC1] | 6-{[(1R)-1-cyclobutylethyl]amino}-8-(2-cyclohexylpiperidin-1-yl)-7-[4-(trifluoromethyl)benzyl]-7H-purine-2-carboxylic acid | | 585 | 585 |

TABLE 9-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 9.123 | 1.854 | 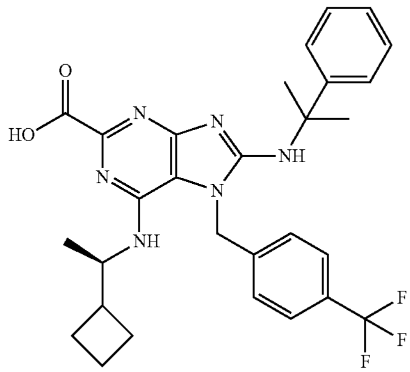 [SMILES: C[C@@H](Nc1nc(C(=O)O)nc2nc(NC(C)(C)c3ccccc3)n(Cc3ccc(C(F)(F)F)cc3)c12)C1CCC1] | 6-{[(1R)-1-cyclobutylethyl]amino}-8-[(1-methyl-1-phenylethyl)amino]-7-[4-(trifluoromethyl)benzyl]-7H-purine-2-carboxylic acid | | 553 | 553 |
| 9.124 | 10.36 | 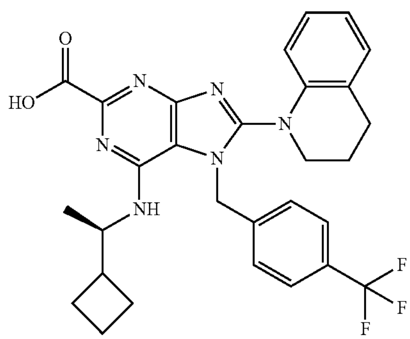 [SMILES: C[C@@H](Nc1nc(C(=O)O)nc2nc(N3CCCc4ccccc43)n(Cc3ccc(C(F)(F)F)cc3)c12)C1CCC1] | 6-{[(1R)-1-cyclobutylethyl]amino}-8-(3,4-dihydroquinolin-1(2H)-yl)-7-[4-(trifluoromethyl)benzyl]-7H-purine-2-carboxylic acid | | 551 | 551 |
| 9.125 | 6.717 | 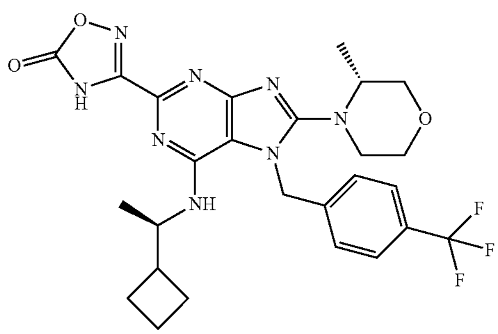 [SMILES: C[C@@H]1COCCN1c1nc2nc(-c3noc(=O)[nH]3)nc(N[C@H](C)C3CCC3)c2n1Cc1ccc(C(F)(F)F)cc1] | 3-(6-{[(1R)-1-cyclobutylethyl]amino}-8-[(3R)-3-methylmorpholin-4-yl]-7-[4-(trifluoromethyl)benzyl]-7H-purin-2-yl)-1,2,4-oxadiazol-5(4H)-one | TFA | 559 | 559 |

Preparative Example 10.1

8-(chloromethyl)-3-methyl-7-(4-(trifluoromethyl)benzyl)-1H-purine-2,6(3H,7H)-dione

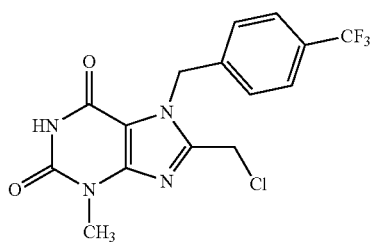 [SMILES: Cn1c(=O)[nH]c(=O)c2c1nc(CCl)n2Cc1ccc(C(F)(F)F)cc1]

Step 1: To a stirred solution of 8-(hydroxymethyl)-3-methyl-1H-purine-2,6(3H,7H)-dione (8.20 g, 41.8 mmol) in DMSO (60 mL) were added Na$_2$CO$_3$ (4.99 g, 20.9 mmol) and 1-(bromomethyl)-4-(trifluoromethyl)benzene (4.87 g, 20.9 mmol). The reaction mixture was stirred at room temperature for 1 hour. The reaction mixture was then quenched with ice water (500 mL) and the solution was adjusted to pH 2 using aqueous HCl (1N solution). The product precipitated, was collected by filtration, and the residual water was removed by azeotroping with toluene (4×200 mL). The crude solid was stirred with CH$_2$Cl$_2$ (50 mL) for 1 hour, collected by filtration, and air dried to afford 8-(hydroxymethyl)-3-methyl-7-(4-(trifluoromethyl)benzyl)-1H-purine-2,6(3H,7H)-dione. $^1$H NMR (300 MHz, DMSO-d$_6$) δ 11.12 (s, 1H), 7.69 (d, J=8.1 Hz, 2H), 7.42 (d, J=8.1 Hz, 2H), 5.75 (s, 1H), 5.66 (s, 2H), 4.57 (d, J=4.5 Hz, 2H), 3.37 (s, 3H). MS (ESI)=355 (M+1)$^+$.

Step 2: 8-(hydroxymethyl)-3-methyl-7-(4-(trifluoromethyl)benzyl)-1H-purine-2,6(3H, 7H)-dione (4.00 g, 11.28 mmol) was suspended in CHCl$_3$ (150 ml). SOCl$_2$ (53.7 g, 451.6 mmol) was added and reaction mixture was heated at reflux for 3 hours. The reaction mixture was then concentrated and azeotroped with toluene (2×200 mL) to afford 8-(chloromethyl)-3-methyl-7-(4-(trifluoromethyl)benzyl)-1H-purine-2,6(3H,7H)-dione. $^1$H NMR (300 MHz, DMSO-d$_6$) 7.66 (d, J=8.4 Hz, 2H), 7.42 (d, J=8.4 Hz, 2H), 6.76 (br s, 2H), 5.70 (s, 2H), 3.37 (s, 3H). MS (ESI)=373 (M+1)$^+$.

Example 10.1

(R)-6-((1-cyclobutylethyl)amino)-8-(phenoxymethyl)-7-(4-(trifluoromethyl)benzyl)-7H-purine-2-carboxylic acid

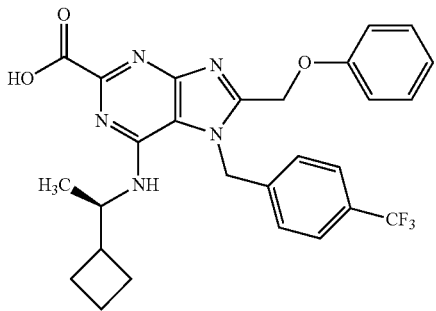 [SMILES: C[C@@H](Nc1nc(C(=O)O)nc2nc(COc3ccccc3)n(Cc3ccc(C(F)(F)F)cc3)c12)C1CCC1]

Step 1: To a stirred solution of 8-(chloromethyl)-3-methyl-7-(4-(trifluoromethyl)benzyl)1H-purine-2,6(3H,7H)-dione (50 mg, 0.13 mmol) in dry DMF (1.0 mL) was added NaH (26 mg, 0.67 mmol) and phenol (37 mg, 0.40 mmol) at 0° C. The reaction mixture was allowed to warm to room temperature and was stirred for 30 minutes. The reaction mixture was cooled and quenched by slow addition of NaOH (0.5 N). The aqueous layer was extracted with EtOAc (2×10 mL), and the combined organic layers were dried over Na$_2$SO$_4$, filtered and concentrated under reduced pressure. Purification of the residue on a Redisep 4 g silica gel column (0 to 100% EtOAc/hexanes) afforded 3-methyl-8-(phenoxymethyl)-7-(4-(trifluoromethyl)benzyl)-1H-purine-2,6(3H,7H)-dione. MS (ESI)=431 (M+1)$^+$.

Step 2: POCl$_3$ (0.5 mL) was added to 3-methyl-8-(phenoxymethyl)-7-(4-(trifluoromethyl)benzyl)-1H-purine-2,6 (3H,7H)-dione (50 mg, 0.11 mmol) and the reaction mixture was stirred at 60° C. for 30 minutes. Then DBU (0.1 mL) was added and the reaction mixture was heated at 120° C. for 4 hours. The reaction mixture was cooled to room temperature, poured into crushed ice, and slowly quenched with NH$_4$OH solution. The mixture was extracted with EtOAc (2×10 mL) and the combined organic layers were dried over Na$_2$SO$_4$, filtered and concentrated under reduced pressure. The resultant residue was purified on a Redisep 4 g silica gel column (0 to 100% EtOAc/hexanes) to afford 2,6-dichloro-8-(phenoxymethyl)-7-(4-(trifluoromethyl)benzyl)-7H-purine. $^1$H NMR (400 MHz, CDCl$_3$) δ 7.55 (d, J=8.0 Hz, 2H), 7.21-7.25 (m, 2H), 7.06 (d, J=8.4 Hz, 2H), 6.99 (m, 1H), 6.80-6.83 (m, 2H), 5.92 (s, 2H), 5.38 (s, 2H). MS (ESI)=453 (M+1)$^+$.

Step 3: A mixture of 2,6-dichloro-7-(4-chlorobenzyl)-8-(2-ethoxy-5-methylphenyl)-7H-purine (250 mg, 0.55 mmol) and (R)-1-cyclobutylethylamine (150 mg, 1.10 mmol) in ethanol (5.0 mL) was heated at reflux for 3 hours. The reaction mixture was cooled to room temperature and concentrated under reduced pressure. The residue was dissolved in EtOAc (30 mL) and the organic layer was washed with water (15 mL) and brine (15 mL), dried over anhydrous Na$_2$SO$_4$, filtered, and concentrated in vacuo. Purification of the crude residue by silica gel column chromatography (45% EtOAc/hexanes) afforded (R)-2-chloro-N-(1-cyclobutylethyl)-8-(phenoxymethyl)-7-(4-(trifluoromethyl)benzyl)-7H-purine-6-amine. MS (ESI)=516 (M+1)$^+$.

Step 4: A mixture of (R)-2-chloro-N-(1-cyclobutylethyl)-8-(phenoxymethyl)-7-(4-(trifluoromethyl)benzyl)-7H-purine-6-amine (100 mg, 0.19 mmol) and zinc cyanide (13.0 mg, 0.11 mmol) suspended in DMA (1.5 mL) was degassed in a sealable tube with Ar for 30 minutes. Pd(PPh$_3$)$_4$ (44 mg, 0.03 mmol) was added to the reaction and the reaction was evacuated and refilled with Ar three times, sealed, and then heated at 120° C. for 12 hours. The reaction was cooled to room temperature and ice water (40 mL) was added slowly. The reaction mixture was then extracted with EtOAc (3×50 mL). The combined organic layers were dried over sodium sulfate, filtered and concentrated under reduced pressure. Purification of the residue on a Redisep 12 g silica gel column (0 to 100% EtOAc/hexanes) afforded (R)-6-((1-cyclobutylethyl)amino)-8-(phenoxymethyl)-7-(4-(trifluoromethyl)benzyl)-7H-purine-2-carbonitrile. MS (ESI)=507 (M+1)$^+$.

Step 5: (R)-6-((1-cyclobutylethyl)amino)-8-(phenoxymethyl)-7-(4-(trifluoromethyl)benzyl)-7H-purine-2-carbonitrile (80 mg, 0.15 mmol) was suspended in anhydrous HCl in MeOH (5.0 mL, 3.0 M) and the reaction was heated at 75° C. for 4 hours. The reaction was concentrated and the crude product was taken up in CH$_2$Cl$_2$ (40 mL) and washed with aqueous saturated NaHCO$_3$. The organic layer was separated, dried over Na$_2$SO$_4$ and concentrated. The residue was purified on a RediSep 4 g silica gel column with 0 to 10% MeOH/CH$_2$Cl$_2$ to afford (R)-methyl6-((1-cyclobutylethyl)amino)-8-(phenoxymethyl)-7-(4-(trifluoromethyl)benzyl)-7H-purine-2-carboxylate. MS (ESI)=540 (M+1)$^+$.

Step 6: Aqueous LiOH solution (6.00 mg, 0.27 mmol, dissolved in 0.3 mL H$_2$O) was added to a solution of (R)-methyl6-((1-cyclobutylethyl)amino)-8-(phenoxymethyl)-7-(4-(trifluoromethyl)benzyl)-7H-purine-2-carboxylate (30.0 mg, 0.05 mmol) in THF (2.0 mL) at room temperature. The reaction mixture was stirred at room temperature for 1.5 hours and was then concentrated in vacuo. The residue was dissolved in water (1.5 mL) and neutralized to pH=7 with aqueous HCl solution (1M). The product precipitated and was collected by filtration, washed with water and dried under vacuum, to afford (R)-6-((1-cyclobutylethyl)amino)-8-(phenoxymethyl)-7-(4-(trifluoromethyl)benzyl)-7H-purine-2-carboxylic acid. $^1$H NMR (400 MHz, CD$_3$OD) δ 7.61 (d, J=8.0 Hz, 2H), 7.16-7.20 (m, 4H), 6.92 (t, J=7.6 Hz, 1H), 6.84 (t, J=7.6 Hz, 2H), 5.92 (d, J=18.4 Hz, 1H), 5.85 (d, J=18.4 Hz, 1H), 5.41 (d, J=12.8 Hz, 1H), 5.46 (d, J=12.8 Hz, 1H), 4.51-4.56 (m, 1H), 2.05 (m, 1H), 1.81-1.87 (m, 1H), 1.56-1.70 (m, 3H), 1.38-1.44 (m, 2H), 0.92 (d, J=6.8 Hz, 3H). MS (ESI)=526(M+1)$^+$.

Example 10.2

(R)-8-((benzyloxy)methyl)-6-((1-cyclobutylethyl)amino)-7-(4-(trifluoromethyl)benzyl)-7H-purine-2-carboxylic acid

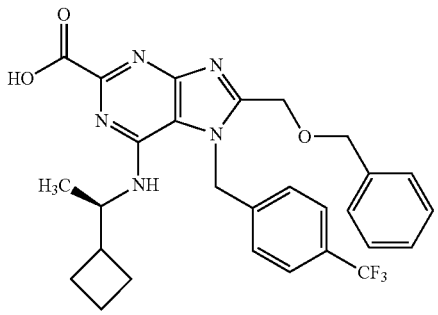 [SMILES: C[C@@H](Nc1nc(C(=O)O)nc2nc(COCc3ccccc3)n(Cc3ccc(C(F)(F)F)cc3)c12)C1CCC1]

Using a procedure analogous to that described in Example 10.1, and starting with 8-(chloromethyl)-3-methyl-7-(4-(trifluoromethyl)benzyl)-1H-purine-2,6(3H,7H)-dione, (R)-8-((benzyloxy)methyl)-6-((1-cyclobutylethyl)amino)-7-(4-(trifluoromethyl)benzyl)-7H-purine-2-carboxylic acid was prepared. $^1$H NMR (400 MHz, CD$_3$OD) δ 7.62 (d, J=8.0 Hz, 2H), 7.08-7.25 (m, 7H), 5.91 (d, J=18.4 Hz, 1H), 5.84 (d, J=18.4 Hz, 1H), 4.91 (m, 2H), 4.56 (m, 2H), 4.53 (m, 1H), 2.10 (m, 1H), 1.88 (m, 1H), 1.56-1.75 (m, 3H), 1.37-1.48 (m, 2H), 0.95 (d, J=6.4 Hz, 3H). MS (ES)=540 (M+1)$^+$.

Example 10.3

(R)-6-((1-cyclobutylethyl)amino)-8-(N,3-dimethylbutanamido)-7-(4-(trifluoromethyl)benzyl)-7H-purine-2-carboxylic acid

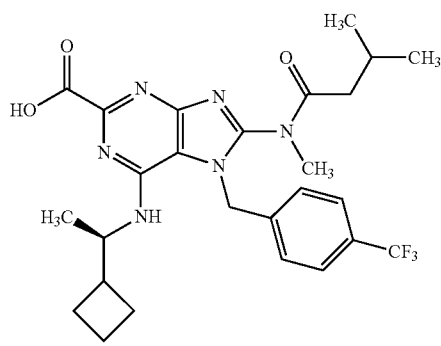 [SMILES: CC(C)CC(=O)N(C)c1nc2nc(C(=O)O)nc(N[C@H](C)C3CCC3)c2n1Cc1ccc(C(F)(F)F)cc1]

Step 1: Methylamine (2.0 mL, 33% in EtOH) was added to (R)-8-bromo-6-((1-cyclobutylethyl)amino)-7-(4-(trifluoromethyl)benzyl)-7H-purine-2-carbonitrile (Preparative Example 2.1; 250 mg, 0.52 mmol) and the reaction was stirred at room temperature for 30 minutes. The reaction mixture was then concentrated under reduced pressure and the resultant residue was purified on a Redisep 4 g silica gel column (0 to 100% EtOAc/hexanes) to afford (R)-6-((1-cyclobutylethyl)amino)-8-(methylamino)-7-(4-(trifluoromethyl)benzyl)-7H-purine-2-carbonitrile. $^1$H NMR (400 MHz, DMSO-d$_6$) δ 7.70 (d, J=8.0 Hz, 2H), 7.47 (m, 1H), 7.17 (d, J=8.0 Hz, 2H), 5.70-5.76 (m, 2H), 5.52 (d, J=18.4 Hz, 1H), 4.06 (m, 1H), 2.94 (s, 3H), 2.20 (m, 1H), 1.81 (m, 1H), 1.31-1.65 (m, 5H), 0.95 (d, J=6.4 Hz, 3H). MS (ESI)=430 (M+1).

Step 2: Using a procedure analogous to that described in Example 10.1 (Step 5), and starting with (R)-6-((1-cyclobutylethyl)amino)-8-(methylamino)-7-(4-(trifluoromethyl)benzyl)-7H-purine-2-carbonitrile, (R)-methyl 6-((1-cyclobutylethyl)amino)-8-(methylamino)-7-(4-(trifluoromethyl)benzyl)-7H-purine-2-carboxylate was prepared. MS (ESI)=463 (M+1)$^+$.

Step 3: To a stirred solution of (R)-methyl 6-((1-cyclobutylethyl)amino)-8-(methylamino)-7-(4-(trifluoromethyl)benzyl)-7H-purine-2-carboxylate (100 mg, 0.21 mmol) in pyridine (1.0 mL) was added isovaleryl chloride (130 mg, 1.08 mmol) and the reaction mixture was heated at 60° C. for 12 hours. Then the reaction mixture was concentrated under reduced pressure and the resultant residue was purified on a Redisep 4 g silica gel column (0 to 100% EtOAc/hexanes) to afford (R)-methyl 6-((1-cyclobutylethyl)amino)-8-(N,3-dimethylbutanamido)-7-(4-(trifluoromethyl)benzyl)-7H-purine-2-carboxylate. MS (ESI) 547 (M+1)$^+$.

Step 4: Using a procedure analogous to that described in Example 10.1 (Step 6), and starting with (R)-methyl 6-((1-cyclobutylethyl)amino)-8-(N,3-dimethylbutanamido)-7-(4-(trifluoromethyl)benzyl)-7H-purine-2-carboxylate, (R)-6-((1-cyclobutylethyl)amino)-8-(N,3-dimethylbutanamido)-7-(4-(trifluoromethyl)benzyl)-7H-purine-2-carboxylic acid was prepared. $^1$H NMR (400 MHz, CD$_3$OD) δ 7.69 (d, J=8.0 Hz, 2H), 7.29 (d, J=8.0 Hz, 2H), 5.61-5.77 (m, 2H), 4.55 (m, 1H), 2.10-2.15 (m, 3H), 1.87-1.92 (m, 2H), 1.65-1.70 (m, 3H), 1.49-1.58 (m, 2H), 1.24-1.35 (m, 2H), 0.84-0.98 (m, 10H). MS (ES)=533 (M+1)$^+$.

Example 10.4

(R)-6-((1-cyclobutylethyl)amino)-8-(N-methylcyclohexanecarboxamido)-7-(4-(trifluoromethyl)benzyl)-7H-purine-2-carboxylic acid

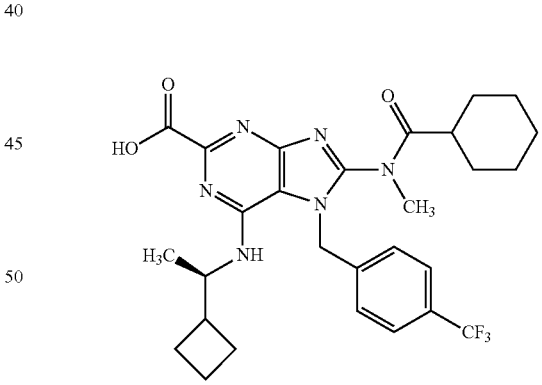

Using a procedure analogous to that described in Example 10.3, and starting with (R)-methyl-6-((1-cyclobutylethyl)amino)-8-(N-methylcyclohexanecarboxamido)-7-(4-(trifluoromethyl)benzyl)-7H-purine-2-carboxylate, (R)-6-((1-cyclobutylethyl)amino)-8-(N-methylcyclohexanecarboxamido)-7-(4-(trifluoromethyl)benzyl)-7H-purine-2-carboxylic acid was prepared. $^1$H NMR (400 MHz, CD$_3$OD) δ 7.71 (d, J=8.0 Hz, 2H), 7.30 (d, J=8.0 Hz, 2H), 5.69 (d, J=13.6 Hz, 1H), 5.84 (d, J=13.6 Hz, 1H), 4.59 (br s, 1H), 3.23-3.26 (m, 3H), 2.15 (br s, 1H), 1.82-2.20 (m, 2H), 1.54-1.72 (m, 9H), 1.28-1.37 (m, 4H), 0.98-1.14 (m, 6H). MS (ES)=559 (M+1)$^+$.

Example 10.5

6-(((R)-1-cyclobutylethyl)amino)-8-(1-isobutoxy-ethyl)-7-(4-(trifluoromethyl)benzyl)-7H-purine-2-carboxylic acid

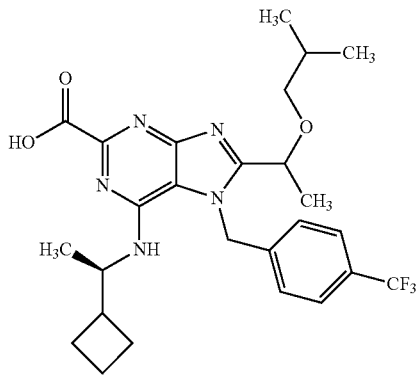 [SMILES: CC(C)COC(C)c1nc2nc(C(=O)O)nc(N[C@H](C)C3CCC3)c2n1Cc1ccc(C(F)(F)F)cc1]

Step 1: n-BuLi (2.5 mL, 5.0 mmol, 2M in hexanes) was added dropwise to a solution of 2,2,6,6-tetramethylpiperidine (0.85 mL, 5.0 mmol) in anhydrous THF (15 mL) at −10° C. The reaction mixture was stirred at −10° C. for 15 minutes and then cooled to −78° C. A solution of (R)-6-((1-cyclobutylethyl)amino)-7-(4-(trifluoromethyl)benzyl)-7H-purine-2-carbonitrile (Preparative Example 1.1; 500 mg, 1.25 mmol) in anhydrous THF (5.0 mL) was added to the reaction dropwise over 5 minutes. The reaction mixture was stirred at −78° C. for 30 minutes and acetaldehyde (excess) was then added in one portion. The reaction mixture was stirred at −78° C. for 40 minutes and then quenched with sat. aqueous NH$_4$Cl solution. The layers were separated and the aqueous layer was extracted with EtOAc (3×10 mL). The combined organic layers were washed with brine, dried over anhydrous Na$_2$SO$_4$, filtered and concentrated in vacuo. Purification of the residue on a Redisep 12 g silica gel column (0 to 50% EtOAc/hexanes) afforded 6-(((R)-1-cyclobutylethyl)amino)-8-(1-hydroxyethyl)-7-(4-(trifluoromethyl)benzyl)-7H-purine-2-carbonitrile as a mixture of diastereomers. MS (APCI)=445 (M+1)$^+$.

Step 2: NaH (14 mg, 0.33 mmol, 60%) was added to a solution of 6-(((R)-1-cyclobutylethyl)amino)-8-(1-hydroxyethyl)-7-(4-(trifluoromethyl)benzyl)-7H-purine-2-carbonitrile (50 mg, 0.11 mmol) in anhydrous DMF (2.0 mL) at room temperature. The reaction mixture was stirred at room temperature for 15 minutes and isobutyl bromide (25 μL, 0.22 mmol) was added. The resulting mixture was stirred at room temperature for 30 minutes and was then quenched with sat. aqueous NH$_4$Cl solution. The aqueous layer was extracted with EtOAc (3×10 mL). The combined organic layers were washed with brine, dried over anhydrous Na$_2$SO$_4$, filtered and concentrated in vacuo. Purification of the residue on a Redisep 4 g silica gel column (0 to 25% EtOAc/hexanes) afforded 6-(((R)-1-cyclobutylethyl)amino)-8-(1-isobutoxyethyl)-7-(4-(trifluoromethyl)benzyl)-7H-purine-2-carbonitrile as a mixture of diastereomers. $^1$H NMR (300 MHz, CDCl$_3$) δ 7.72 (d, J=8.1 Hz, 2H), 7.21 (d, J=8.1 Hz, 2H), 5.69-6.01 (m, 2H), 4.99 (q, J=6.9 Hz, 1H), 4.13-4.30 (m, 2H), 3.13-3.32 (m, 2H), 1.26-1.84 (m, 11H), 0.75-0.86 (m, 9H). MS (APCI)=501 (M+1)$^+$.

Step 3: NaOH (72 mg, 1.8 mmol) was added to a solution of 6-(((R)-1-cyclobutylethyl)amino)-8-(1-isobutoxyethyl)-7-(4-(trifluoromethyl)benzyl)-7H-purine-2-carbonitrile (30 mg, 0.06 mmol) in ethanol and water (2.0 mL: 0.5 mL) at room temperature. The reaction mixture was stirred at room temperature for 10 minutes and then heated at reflux for 2 hours. After cooling to room temperature, the reaction mixture was concentrated in vacuo. The residue was dissolved in water (1.5 mL) and neutralized to pH 7 with aqueous HCl solution (1M). The product precipitated and was collected by filtration, washed with water and dried under vacuum, to afford 6-(((R)-1-cyclobutylethyl)amino)-8-(1-isobutoxyethyl)-7-(4-(trifluoromethyl)benzyl)-7H-purine-2-carboxylic acid as a mixture of diastereomers. $^1$H NMR (400 MHz, CD$_3$OD) δ 7.70 (d, J=7.6 Hz, 2H), 7.22 (d, J=7.6 Hz, 2H), 6.05 (br s, 2H), 4.98 (m, 1H), 4.54 (dq, J=7.2, 7.2 Hz, 1H), 3.16-3.26 (m, 2H), 2.06 (m, 1H), 1.85 (m, 1H), 1.51-1.65 (m, 7H), 1.46 (m, 1H), 1.35 (m, 1H), 0.93 (d, J=6.4 Hz, 1.5H), 0.90 (d, J=6.4 Hz, 1.5H), 0.72-0.78 (m, 6H). MS (ES)=520 (M+1)$^+$.

Example 10.6

8-(1-(Benzyloxy)ethyl)-6-(((R)-1-cyclobutylethyl)amino)-7-(4-(trifluoromethyl)benzyl)-7H-purine-2-carboxylic acid

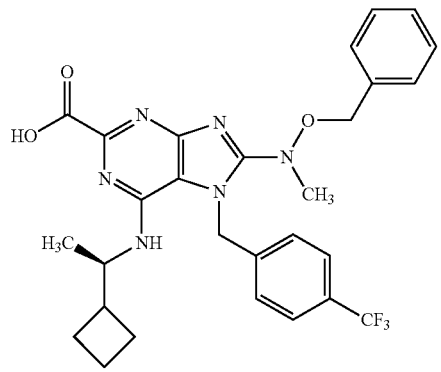 [SMILES: C[C@@H](Nc1nc(C(=O)O)nc2nc(N(C)OCc3ccccc3)n(Cc3ccc(C(F)(F)F)cc3)c12)C1CCC1]

Using a procedure analogous to that described in Example 10.5, 6-(((R)-1-cyclobutylethyl)amino)-8-(1-hydroxyethyl)-7-(4-(trifluoromethyl)benzyl)-7H-purine-2-carbonitrile, and benzylbromide, 8-(1-(benzyloxy)ethyl)-6-(((R)-1-cyclobutylethyl)amino)-7-(4-(trifluoromethyl)benzyl)-7H-purine-2-carboxylic acid was prepared as a mixture of diastereomers. $^1$H NMR (400 MHz, CD$_3$OD) δ 7.61 (d, J=7.2 Hz, 2H), 7.10-7.18 (m, 7H), 5.86-5.93 (m, 2H), 5.11 (m, 1H), 4.47-4.58 (m, 3H), 2.05 (m, 1H), 1.90 (m, 1H), 1.58-1.70 (m, 7H), 1.46 (m, 1H), 0.97 (d, J=6.4 Hz, 1.5H), 0.88 (d, J=6.4 Hz, 1.5H). MS (ES)=554 (M+1)$^+$.

Example 10.7

6-(((R)-1-Cyclobutylethyl)amino)-8-(1-hydroxyethyl)-7-(4-(trifluoromethyl)benzyl)-7H-purine-2-carboxylic acid

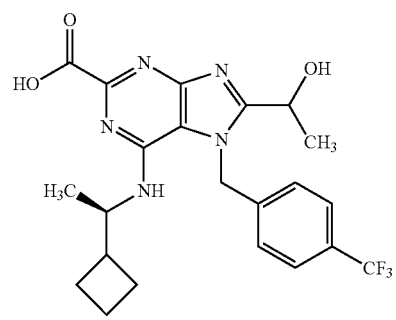 [SMILES: CC(O)c1nc2nc(C(=O)O)nc(N[C@H](C)C3CCC3)c2n1Cc1ccc(C(F)(F)F)cc1]

Using a procedure analogous to that described in Example 10.5 and starting with 6-(((R)-1-cyclobutylethyl)amino)-8-(1-hydroxyethyl)-7-(4-(trifluoromethyl)benzyl)-7H-purine-2-carbonitrile, 6-(((R)-1-cyclobutylethyl)amino)-8-(1-hydroxyethyl)-7-(4-(trifluoromethyl)benzyl)-7H-purine-2-carboxylic acid was prepared as a mixture of diastereomers. ¹H NMR (400 MHz, CD₃OD) δ 7.68 (d, J=8.0 Hz, 2H), 7.24 (t, J=6.4 Hz, 2H), 5.93-6.07 (m, 2H), 5.17 (m, 1H), 4.54 (m, 1H), 2.02 (m, 1H), 1.85 (m, 1H), 1.59-1.68 (m, 6H), 1.30-1.46 (m, 2H), 0.93 (d, J=6.4 Hz, 1.5H), 0.90 (d, J=6.4 Hz, 1.5H). MS (ES)=464 (M+1)⁺.

Example 10.8

6-(((R)-1-Cyclobutylethyl)amino)-8-(1-phenoxyethyl)-7-(4-(trifluoromethyl)benzyl)-7H-purine-2-carboxylic acid

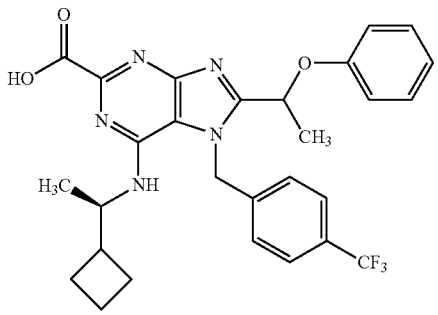 [SMILES: CC(Oc1ccccc1)c1nc2nc(C(=O)O)nc(N[C@H](C)C3CCC3)c2n1Cc1ccc(C(F)(F)F)cc1]

Using a procedure analogous to that described in Example 10.5, and starting with 8-(1-chloroethyl)-6-(((R)-1-cyclobutylethyl)amino)-7-(4-(trifluoromethyl)benzyl)-7H-purine-2-carbonitrile and phenol, 6-(((R)-1-cyclobutylethyl)amino)-8-(1-phenoxyethyl)-7-(4-(trifluoromethyl)benzyl)-7H-purine-2-carboxylic acid was prepared as a mixture of diastereomers. ¹H NMR (400 MHz, CD₃OD) δ 7.55 (d, J=8.2 Hz, 1H), 7.51 (d, J=8.2 Hz, 1H), 7.05-7.16 (m, 3H), 6.97 (d, J=8.4 Hz, 1H), 6.88 (m, 1H), 6.81 (d, J=8.0 Hz, 1H), 6.78 (d, J=8.0 Hz, 1H), 5.90-6.09 (m, 3H), 4.50 (dq, J=7.4, 7.4 Hz, 1H), 2.03 (m, 1H), 1.81-1.85 (m, 4H), 1.32-1.39 (m, 3H), 1.29-1.32 (m, 2H), 0.90-0.92 (m, 3H). MS (ES) 540 (M+1)⁺.

Example 10.9

6-(((R)-1-cyclobutylethyl)amino)-8-(1-(isobutyl(methyl)amino)ethyl)-7-(4-(trifluoromethyl)benzyl)-7H-purine-2-carboxylic acid

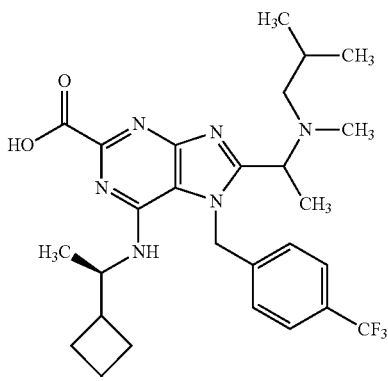 [SMILES: CC(C)CN(C)C(C)c1nc2nc(C(=O)O)nc(N[C@H](C)C3CCC3)c2n1Cc1ccc(C(F)(F)F)cc1]

Step 1: 6-(((R)-1-cyclobutylethyl)amino)-8-(1-hydroxyethyl)-7-(4-(trifluoromethyl)benzyl)-7H-purine-2-carbonitrile (Example 10.5, Step 1; 151 mg, 0.340 mmol) was dissolved in CH₂Cl₂ (2.0 mL). SOCl₂ (0.2 mL) was added and reaction was stirred at room temperature for 2 hours. The reaction was then concentrated under reduced pressure to afford 8-(1-chloroethyl)-6-(((R)-1-cyclobutylethyl)amino)-7-(4-(trifluoromethyl)benzyl)-7H-purine-2-carbonitrile as a mixture of diastereomers. MS (ES)=463 (M+1)⁺.

Step 2: (8-(1-chloroethyl)-6-(((R)-1-cyclobutylethyl)amino)-7-(4-(trifluoromethyl)benzyl)-7H-purine-2-carbonitrile (20 mg, 0.043 mmol) was dissolved in CH₃CN (1.0 mL) in a vial. K₂CO₃ (17 mg, 0.129 mmol) and N,2-dimethylpropan-1-amine (7.0 mg, 0.86 mmol) were added to the reaction followed by KI (10 mol %). The vial was sealed and the reaction was heated at 80° C. for 2 hours. The reaction was then cooled to room temperature and diluted with EtOAc (5.0 mL). The organic layer was washed with brine (5.0 mL), dried over Na₂SO₄, filtered, and concentrated under reduced pressure. Purification of the residue on a RediSep 4 g silica gel column (0 to 50% EtOAc/hexanes) afforded 6-(((R)-1-cyclobutylethyl)amino)-8-(1-(isobutyl(methyl)amino)ethyl)-7-(4-(trifluoromethyl)benzyl)-7H-purine-2-carbonitrile as a mixture of diastereomers. ¹H NMR (400 MHz, CDCl₃) δ 7.68 (d, J=8.1 Hz, 2H), 7.14-7.17 (m, 2H), 5.60-6.18 (m, 2H), 4.20-4.22 (m, 2H), 2.38 (m, 1H), 2.13-2.16 (m, 4H), 1.43-1.88 (m, 12H), 0.65-0.92 (m, 9H). MS (ES)=514 (M+1)⁺.

Step 3: Using a procedure analogous to that described in Example 10.5 (Step 3) and starting with 6-(((R)-1-cyclobutylethyl)amino)-8-(1-(isobutyl(methyl)amino)ethyl)-7-(4-(trifluoromethyl)benzyl)-7H-purine-2-carbonitrile, 6-(((R)-1-cyclobutylethyl)amino)-8-(1-(isobutyl(methyl)amino)ethyl)-7-(4-(trifluoromethyl)benzyl)-7H-purine-2-carboxylic acid was prepared as a mixture of diastereomers. ¹H NMR (400 MHz, CD₃OD) δ 7.68 (d, J=8.0 Hz, 2H), 7.18 (t, J=8.8 Hz, 2H), 6.00-6.20 (m, 1H), 6.59-6.61 (m, 1H), 4.59-4.61 (m, 2H), 4.31 (m, 1H), 2.36 (m, 1H), 2.23 (s, 1.8H), 2.15 (s, 1.2H), 2.06 (m, 1H), 1.89 (m, 1H), 1.59-1.68 (m, 4H), 1.51 (d, J=5.6 Hz, 3H), 1.37-1.46 (m, 2H), 0.90-0.97 (m, 3H), 0.76-0.80 (m, 5H), 0.58 (d, J=6.5 Hz, 1H). MS (ES)=533 (M+1)⁺.

Example 10.10

6-(((R)-1-cyclobutylethyl)amino)-8-(1-(methyl(phenyl)amino)ethyl)-7-(4-(trifluoromethyl)benzyl)-7H-purine-2-carboxylic acid

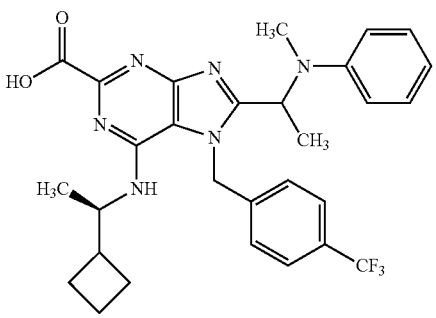 [SMILES: CC(c1nc2nc(C(=O)O)nc(N[C@H](C)C3CCC3)c2n1Cc1ccc(C(F)(F)F)cc1)N(C)c1ccccc1]

Using a procedure analogous to that described in Example 10.9, and starting with 8-(1-chloroethyl)-6-(((R)-1-cyclobutylethyl)amino)-7-(4-(trifluoromethyl)benzyl)-7H-purine-2- carbonitrile and N-methylaniline, 6-(((R)-1-cyclobutyl-ethyl)amino)-8-(1-(methyl(phenyl)amino)ethyl)-7-(4-(trifluoromethyl)benzyl)-7H-purine-2-carboxylic acid was prepared as a mixture of diastereomers. $^1$H NMR (400 MHz, CD$_3$OD) δ 7.58 (d, J=7.6 Hz, 1H), 7.49 (d, J=7.6 Hz, 1H), 7.16 (d, J=7.6 Hz, 1H), 7.12 (t, J=7.2 Hz, 1H), 6.99 (d, J=7.6 Hz, 1H), 6.89 (d, J=7.2 Hz, 1H), 6.66-6.80 (m, 3H), 5.46-5.84 (m, 3H), 4.64 (br s, 3H), 2.57 (s, 1.3H), 2.44 (s, 1.7H), 1.85-2.07 (m, 3H), 1.31-1.53 (m, 3H), 1.20 (m, 2H), 0.99 (d, J=6.0 Hz, 1.8H), 0.88 (d, J=6.0 Hz, 1.2H). MS (ES)=553 (M+1)$^+$.

Example 10.11

6-(((R)-1-cyclobutylethyl)amino)-8-(1-(cyclohexyl(methyl)amino)ethyl)-7-(4-(trifluoromethyl)benzyl)-7H-purine-2-carboxylic acid

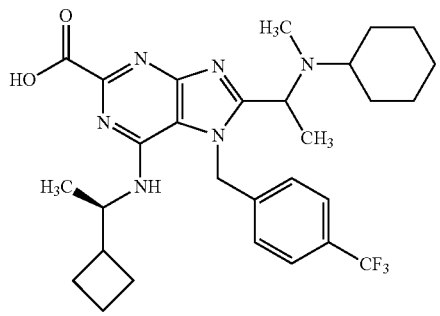 [SMILES: CC(c1nc2nc(C(=O)O)nc(N[C@H](C)C3CCC3)c2n1Cc1ccc(C(F)(F)F)cc1)N(C)C1CCCCC1]

Using a procedure analogous to that described in Example 10.9, and starting with 8-(1-chloroethyl)-6-(((R)-1-cyclobutylethyl)amino)-7-(4-(trifluoromethyl)benzyl)-7H-purine-2-carbonitrile and N-methylcyclohexanamine, 6-(((R)-1-cyclobutylethyl)amino)-8-(1-(cyclohexyl(methyl)amino)ethyl)-7-(4-(trifluoromethyl)benzyl)-7H-purine-2-carboxylic acid was prepared as a mixture of diastereomers. $^1$H NMR (400 MHz, CD$_3$OD) δ 7.69 (d, J=7.6 Hz, 2H), 7.21 (t, J=7.6 Hz, 2H), 5.98-6.17 (m, 2H), 4.64 (br s, 2H), 2.49 (m, 1H), 2.23 (s, 1.8H), 2.16 (s, 1.2H), 2.05-2.10 (m, 1H), 1.55-1.92 (m, 10H), 1.47-1.53 (m, 3H), 1.35 (m, 1H), 1.15-1.24 (m, 3H), 1.00-1.12 (m, 2H), 0.94 (d, J=6.4 Hz, 1H), 0.89 (d, J=6.4 Hz, 2H). MS (ES)=559 (M+1)$^+$.

Example 10.12

8-(1-(benzyl(methyl)amino)ethyl)-6-(((R)-1-cyclobutylethyl)amino)-7-(4-(trifluoromethyl)benzyl)-7H-purine-2-carboxylic acid

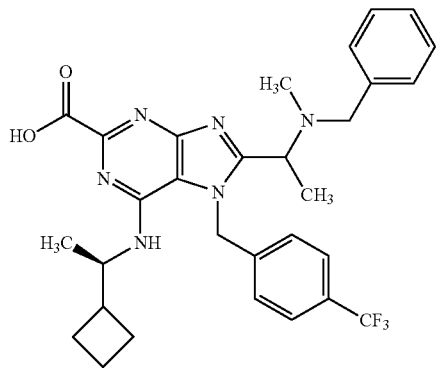 [SMILES: CC(c1nc2nc(C(=O)O)nc(N[C@H](C)C3CCC3)c2n1Cc1ccc(C(F)(F)F)cc1)N(C)Cc1ccccc1]

Using a procedure analogous to that described in Example 10.9, and starting with 8-(1-chloroethyl)-6-(((R)-1-cyclobutylethyl)amino)-7-(4-(trifluoromethyl)benzyl)-7H-purine-2-carbonitrile and N-methyl-1-phenylmethanamine, 8-(1-(benzyl(methyl)amino)ethyl)-6-(((R)-1-cyclobutylethyl)amino)-7-(4-(trifluoromethyl)benzyl)-7H-purine-2-carboxylic acid was prepared as a mixture of diastereomers. $^1$H NMR (400 MHz, CD$_3$OD) δ 7.62-7.68 (m, 2H), 6.91-7.16 (m, 7H), 5.79-5.87 (m, 2H), 4.64 (m, 1H), 4.37 (m, 1H), 3.56-3.76 (m, 2H), 2.19 (s, 1.3H), 2.09 (s, 1.7H), 1.60-1.94 (m, 6H), 1.42 (m, 1H), 1.28-1.32 (m, 4H), 0.93 (d, J=6.4 Hz, 1.2H), 0.89 (d, J=6.4 Hz, 1.9H). MS (ES)=567 (M+1)$^+$.

Preparative Example 10.2

(R)-ethyl-2-cyano-6-((1-cyclobutylethyl)amino)-7-(4-(trifluoromethyl)benzyl)-7H-purine-8-carboxylate

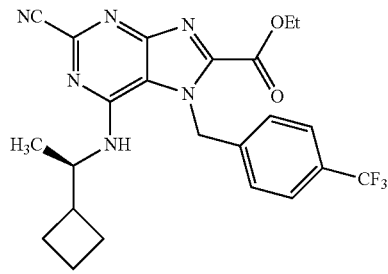 [SMILES: CCOC(=O)c1nc2nc(C#N)nc(N[C@H](C)C3CCC3)c2n1Cc1ccc(C(F)(F)F)cc1]

n-BuLi (3.75 mL, 7.5 mmol, 2M in hexanes) was added dropwise to a solution of 2,2,6,6-tetramethylpiperidine (1.27 mL, 7.50 mmol) in anhydrous THF (30 mL) at −10° C. The reaction mixture was stirred at −10° C. for 15 minutes and then cooled to −78° C. A solution of (R)-6-((1-cyclobutylethyl)amino)-7-(4-(trifluoromethyl)benzyl)-7H-purine-2-carbonitrile (Preparative Example 1.1; 1.0 g, 2.5 mmol) in anhydrous THF (8.0 mL) was then added dropwise over 10 minutes. The reaction mixture was stirred at −78° C. for 30 minutes and then cyano ethyl formate (0.74 mL, 7.5 mmol) was added in one portion. The reaction mixture was then stirred at −78° C. for 40 minutes and then quenched with sat. aqueous NH$_4$Cl solution. The layers were separated and the aqueous layer was extracted with EtOAc (3×20 mL). The combined organic layers were washed with brine, dried over anhydrous Na$_2$SO$_4$, filtered and concentrated in vacuo. Purification of the residue on a Redisep 24 g silica gel column (0 to 50% EtOAc/hexanes) afforded (R)-ethyl 2-cyano-6-((1-cyclobutylethyl)amino)-7-(4-(trifluoromethyl)benzyl)-7H-purine-8-carboxylate. $^1$H NMR (400 MHz, CDCl$_3$) δ 7.73 (d, J=8.4 Hz, 2H), 7.24 (d, J=8.4 Hz, 2H), 6.21 (d, J=17.6 Hz, 1H), 6.05 (d, J=17.6 Hz, 1H), 4.57 (d, J=8.0 Hz, 1H), 4.51 (q, J=7.0 Hz, 2H), 4.26 (m, 1H), 1.47 (t, J=7.0 Hz, 3H), 1.34-2.00 (m, 7H), 0.89 (d, J=6.4 Hz, 3H). MS (ES)=473 (M+1)$^+$.

Example 10.13

(R)-8-((benzyl(methyl)amino)methyl)-6-((1-cyclobutylethyl)amino)-7-(4-(trifluoromethyl)benzyl)-7H-purine-2-carboxylic acid

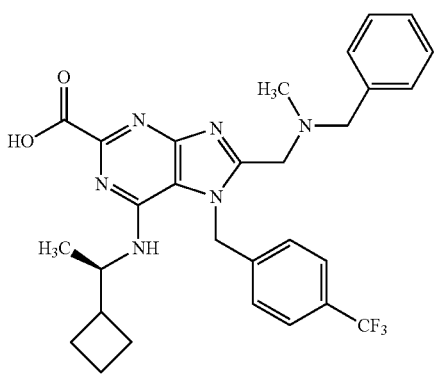 [SMILES: C[C@@H](Nc1nc(C(=O)O)nc2nc(CN(C)Cc3ccccc3)n(Cc3ccc(C(F)(F)F)cc3)c12)C1CCC1]

Step 1: (R)-ethyl 2-cyano-6-((1-cyclobutylethyl)amino)-7-(4-(trifluoromethyl)benzyl)-7H-purine-8-carboxylate (Preparative Example 10.2) (238 mg, 0.50 mmol) was dissolved in MeOH (2 mL) and cooled to 0° C. NaBH$_4$ (20 mg, 0.55 mmol) was added portion wise and the reaction was stirred at 0° C. for 1 hour. The reaction was then concentrated and residue was purified on RediSep12 g silica gel column (100% EtOAc) to afford (R)-6-((1-cyclobutylethyl)amino)-8-(hydroxymethyl)-7-(4-(trifluoromethyl)benzyl)-7H-purine-2-carbonitrile. $^1$H NMR (400 MHz, CDCl$_3$) δ 7.73 (d, J=8.1 Hz, 2H), 7.28 (d, J=8.1 Hz, 2H), 5.93 (d, J=18.0 Hz, 1H), 5.74 (d, J=18.0 Hz, 1H), 4.42 (t, J=6.4 Hz, 1H), 4.97-5.07 (m, 2H), 4.35 (d, J=8.0 Hz, 1H), 4.12 (m, 1H), 1.39-1.91 (m, 7H), 0.91 (d, J=6.4 Hz, 3H).

Step 2: (R)-6-((1-cyclobutylethyl)amino)-8-(hydroxymethyl)-7-(4-(trifluoromethyl)benzyl)-7H-purine-2-carbonitrile (152 mg, 0.353 mmol) was dissolved in CH$_2$Cl$_2$ (2.0 mL). SOCl$_2$ (0.5 mL) was added and reaction was stirred at room temperature for 2 hours. The reaction was then concentrated under reduced pressure to afford (R)-8-(chloromethyl)-6-((1-cyclobutylethyl)amino)-7-(4-(trifluoromethyl)benzyl)-7H-purine-2-carbonitrile. MS (ES) 449 (M+1)$^+$.

Step 3: (R)-8-(chloromethyl)-6-((1-cyclobutylethyl)amino)-7-(4-(trifluoromethyl)benzyl)-7H-purine-2-carbonitrile (80 mg, 0.178 mmol) was dissolved in CH$_3$CN (3.0 mL) in a vial. Cs$_2$CO$_3$ (116 mg, 0.356 mmol) and N-methyl-1-phenylmethanamine (32 mg, 0.267 mmol) were added to the vial followed by addition of KI (cat.). The vial was sealed and the reaction was heated at 80° C. for 2 hours. The reaction was then cooled to room temperature and was diluted with EtOAc (10 mL). The organics were washed with brine (10 mL), dried over Na$_2$SO$_4$, filtered, and concentrated under reduced pressure. Purification of the residue on RediSep 12 g silica gel column (0 to 100% EtOAc/hexanes) afforded (R)-8-((benzyl(methyl)amino)methyl)-6-((1-cyclobutylethyl)amino)-7-(4-(trifluoromethyl)benzyl)-7H-purine-2-carbonitrile. $^1$H NMR (300 MHz, CDCl$_3$) δ 7.68 (d, J=8.1 Hz, 2H), 7.17-7.19 (m, 3H), 7.06-7.11 (m, 4H), 5.49-5.56 (m, 2H), 4.18 (br s, 2H), 3.79 (s, 2H), 3.55 (s, 2H), 2.30 (s, 3H), 1.43-1.85 (m, 7H), 0.81 (d, J=6.0 Hz, 3H). MS (ES)=534 (M+1)$^+$.

Step 4: Using a procedure analogous to that described in Example 10.1 (Step 5 and 6) and starting with (R)-8-((benzyl(methyl)amino)methyl)-6-((1-cyclobutylethyl)amino)-7-(4-(trifluoromethyl)benzyl)-7H-purine-2-carbonitrile, (R)-8-((benzyl(methyl)amino)methyl)-6-((1-cyclobutylethyl)amino)-7-(4-(trifluoromethyl)benzyl)-7H-purine-2-carboxylic acid was prepared. $^1$H NMR (400 MHz, CD$_3$OD) δ 7.65 (d, J=8.0 Hz, 2H), 7.11-7.17 (m, 7H), 5.83 (s, 2H), 4.52-4.56 (m, 2H), 3.81-3.91 (m, 2H), 3.60 (q, J=12.8 Hz, 2H), 2.25 (s, 3H), 2.05 (m, 1H), 1.87 (m, 1H), 1.56-1.68 (m, 3H), 1.38-1.42 (m, 2H), 0.92 (d, J=6.6 Hz, 3H). MS (ES)=553 (M+1)$^+$.

Example 10.14

(R)-6-((1-cyclobutylethyl)amino)-8-((cyclohexyl(methyl)amino)methyl)-7-(4-(trifluoromethyl)benzyl)-7H-purine-2-carboxylic acid

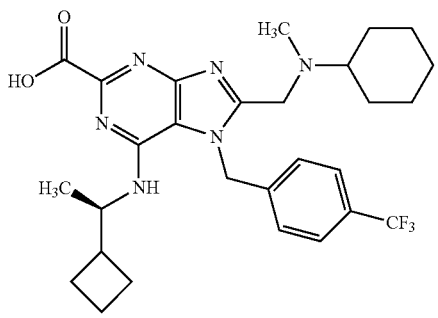 [SMILES: C[C@@H](Nc1nc(C(=O)O)nc2nc(CN(C)C3CCCCC3)n(Cc3ccc(C(F)(F)F)cc3)c12)C1CCC1]

Using a procedure analogous to that described in Example 10.13, and starting with (R)-8-(chloromethyl)-6-((1-cyclobutylethyl)amino)-7-(4-(trifluoromethyl)benzyl)-7H-purine-2-carbonitrile, (R)-6-((1-cyclobutylethyl)amino)-8-((cyclohexyl(methyl)amino)methyl)-7-(4-(trifluoromethyl)benzyl)-7H-purine-2-carboxylic acid was prepared. $^1$H NMR (400 MHz, CD$_3$OD) δ 7.66 (d, J=8.0 Hz, 2H), 7.20 (d, J=8.0 Hz, 2H), 5.89-6.01 (m, 2H), 4.54-4.58 (m, 2H), 4.16 (br s, 2H), 2.76 (m, 1H), 2.45 (br s, 3H), 2.07 (m, 1H), 1.60-1.83 (m, 9H), 1.24-1.46 (m, 7H), 0.94 (d, J=6.4 Hz, 3H). MS (ES)=545 (M+1)$^+$.

Example 10.15

6-(((R)-1-cyclobutylethyl)amino)-8-(((R)-2-hydroxy-1-phenylethyl)carbamoyl)-7-(4-(trifluoromethyl)benzyl)-7H-purine-2-carboxylic acid

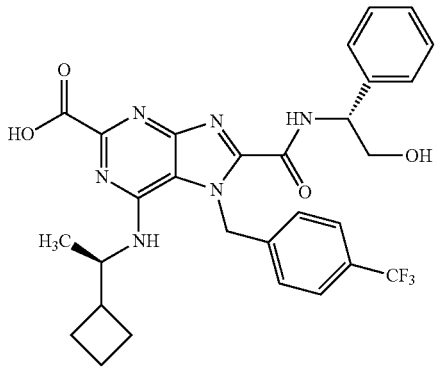 [SMILES: C[C@@H](Nc1nc(C(=O)O)nc2nc(C(=O)N[C@@H](CO)c3ccccc3)n(Cc3ccc(C(F)(F)F)cc3)c12)C1CCC1]

Step 1: A mixture of (R)-ethyl 2-cyano-6-((1-cyclobutylethyl)amino)-7-(4-(trifluoromethyl)benzyl)-7H-purine-8-carboxylate (Preparative Example 10.2, 100 mg, 0.21 mmol) and (R)-2-amino-2-phenylethanol (145 mg, 1.06 mmol) was dissolved in toluene (4.0 mL) at room temperature. The resulting mixture was stirred at room temperature overnight. After concentration in vacuo, purification of the residue on a Redisep 4 g silica gel column (0 to 35% EtOAc/hexanes) afforded 2-cyano-6-(((R)-1-cyclobutylethyl)amino)-N—((R)-2-hydroxy-1-phenylethyl)-7-(4-(trifluoromethyl)benzyl)-7H-purine-8-carboxamide. MS (ES)=564 (M+1)+.

Step 2: 2-Cyano-6-(((R)-1-cyclobutylethyl)amino)-N—((R)-2-hydroxy-1-phenylethyl)-7-(4-(trifluoromethyl)benzyl)-7H-purine-8-carboxamide (28 mg, 0.05 mmol) was dissolved in HCl (3.0 M in MeOH, 2.0 mL). The resulting mixture was heated at reflux for 2.5 hours and then concentrated in vacuo. The residue was dissolved in $CH_2Cl_2$ and quenched with sat. aqueous $NaHCO_3$ solution. The layers were separated and the aqueous layer was extracted with $CH_2Cl_2$ (3×5 mL). The combined organic layers were washed with brine, dried over anhydrous $Na_2SO_4$, filtered and concentrated in vacuo. Purification of the residue on a Redisep 4 g silica gel column (0 to 70% EtOAc/hexanes) afforded methyl 6-(((R)-1-cyclobutylethyl)amino)-8-(((R)-2-hydroxy-1-phenylethyl) carbamoyl)-7-(4-(trifluoromethyl)benzyl)-7H-purine-2-carboxylate. MS (APCI)=597 (M+1)+.

Step 3: Using a procedure analogous to that described in Example 10.1 (Step 6) and starting with methyl 6-(((R)-1-cyclobutylethyl)amino)-8-(((R)-2-hydroxy-1-phenylethyl) carbamoyl)-7-(4-(trifluoromethyl)benzyl)-7H-purine-2-carboxylate, 6-(((R)-1-cyclobutylethyl)amino)-8-(((R)-2-hydroxy-1-phenylethyl)carbamo-yl)-7-(4-(trifluoromethyl) benzyl)-7H-purine-2-carboxylic acid was prepared. $^1$H NMR (400 MHz, $CD_3OD$) δ 7.65 (d, J=8.4 Hz, 2H), 7.42 (d, J=7.2 Hz, 2H), 7.33 (t, J=7.2 Hz, 2H), 7.23-7.28 (m, 3H), 6.57 (d, J=17.4 Hz, 1H), 6.16 (d, J=17.4 Hz, 1H), 5.15 (t, J=6.4 Hz, 1H), 4.57 (dq, J=9.2, 6.6 Hz, 1H), 3.84-3.92 (m, 2H), 2.16 (m, 1H), 1.91 (m, 1H), 1.62-1.73 (m, 3H), 1.43-1.50 (m, 2H), 1.00 (d, J=6.6 Hz, 3H). MS (ES)=583 (M+1)+.

Example 10.16

(R)-6-((1-Cyclobutylethyl)amino)-8-(isobutylcarbamoyl)-7-(4-(trifluoromethyl)benzyl)-7H-purine-2-carboxylic acid

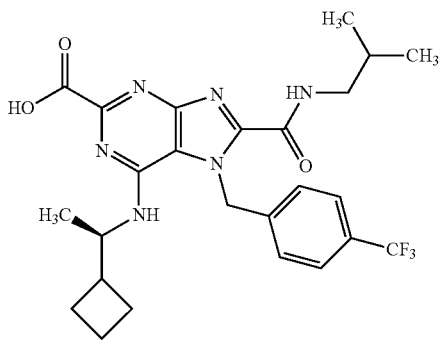 [SMILES: CC(C)CNC(=O)c1nc2nc(C(=O)O)nc(N[C@H](C)C3CCC3)c2n1Cc1ccc(C(F)(F)F)cc1]

Using a procedure analogous to that described in Example 10.15 and starting with (R)-ethyl 2-cyano-6-((1-cyclobutylethyl)amino)-7- (4-(trifluoromethyl)benzyl)-7H-purine-8-carboxylate (Preparative Example 10.2), and 2-methylpropan-1-amine, (R)-6-((1-cyclobutylethyl)amino)-8-(isobutylcarbamoyl)-7-(4-(trifluoromethyl)benzyl)-7H-purine-2-carboxylic acid was prepared. $^1$H NMR (400 MHz, $CD_3OD$) δ 7.68 (d, J=8.2 Hz, 2H), 7.25 (d, J=8.2 Hz, 2H), 6.59 (d, J=17.6 Hz, 1H), 6.21 (d, J=17.6 Hz, 1H), 4.57 (dq, J=9.2, 6.7 Hz, 1H), 3.21 (d, J=7.0 Hz, 2H), 2.17 (m, 1H), 1.88-1.93 (m, 2H), 1.62-1.73 (m, 3H), 1.40-1.50 (m, 2H), 1.00 (d, J=6.7 Hz, 3H), 0.96 (d, J=1.3 Hz, 6H). MS (ES)=519 (M+1)+.

Example 10.17

(R)-6-((1-Cyclobutylethyl)amino)-8-((cyclopropylmethyl)carbamoyl)-7-(4-(trifluoromethyl)benzyl)-7H-purine-2-carboxylic acid

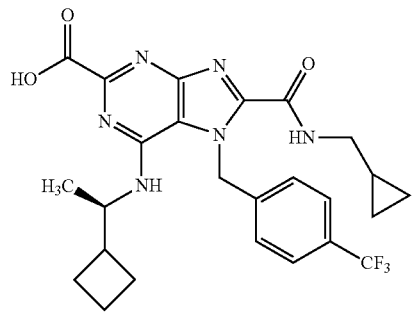 [SMILES: C[C@@H](Nc1nc(C(=O)O)nc2nc(C(=O)NCC3CC3)n(Cc3ccc(C(F)(F)F)cc3)c12)C1CCC1]

Using a procedure analogous to that described in Example 10.15 and starting with (R)-ethyl 2-cyano-6-((1-cyclobutylethyl)amino)-7-(4-(trifluoro-methyl)benzyl)-7H-purine-8-carboxylate (Preparative Example 10.2), and cyclopropylmethanamine, (R)-6-((1-cyclobutylethyl)amino)-8-((cyclopropylmethyl)carbamoyl)-7-(4-(trifluoromethyl) benzyl)-7H-purine-2-carboxylic acid was prepared. $^1$H NMR (400 MHz, $CD_3OD$) δ 7.67 (d, J=8.0 Hz, 2H), 7.25 (d, J=8.0 Hz, 2H), 6.59 (d, J=17.4 Hz, 1H), 6.20 (d, J=17.4 Hz, 1H), 4.59 (dq, J=9.2, 6.4 Hz, 1H), 3.25 (d, J=7.2 Hz, 2H), 2.16 (m, 1H), 1.90 (m, 1H), 1.49-1.61 (m, 3H), 1.44-1.49 (m, 2H), 1.10 (m, 1H), 1.00 (d, J=6.4 Hz, 3H), 0.51-0.54 (m, 2H), 0.28-0.31 (m, 2H). MS (ES)=517 (M+1)+.

Example 10.18

(R)-8-(Benzylcarbamoyl)-6-((1-cyclobutylethyl) amino)-7-(4-(trifluoromethyl)benzyl)-7H-purine-2-carboxylic acid

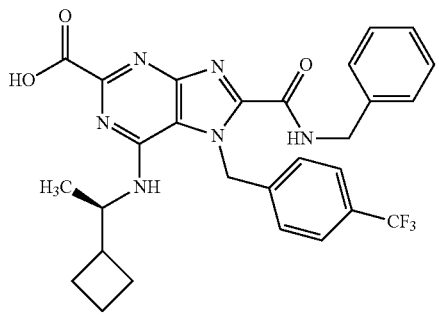 [SMILES: C[C@@H](Nc1nc(C(=O)O)nc2nc(C(=O)NCc3ccccc3)n(Cc3ccc(C(F)(F)F)cc3)c12)C1CCC1]

Using a procedure analogous to that described in Example 10.15 and starting with (R)-ethyl 2-cyano-6-((1-cyclobutylethyl)amino)-7-(4-(trifluoromethyl)benzyl)-7H-purine-8-carboxylate (Preparative Example 10.2), and benzylamine, (R)-8-(benzyl carbamoyl)-6-((1-cyclobutylethyl)amino)-7-(4-(trifluoromethyl)benzyl)-7H-purine-2-carboxylic acid was prepared. $^1$H NMR (400 MHz, CD$_3$OD) δ 7.66 (d, J=8.4 Hz, 2H), 7.22-7.35 (m, 7H), 6.59 (d, J=17.6 Hz, 1H), 6.20 (d, J=17.6 Hz, 1H), 4.54-4.58 (m, 3H), 2.17 (m, 1H), 1.90 (m, 1H), 1.59-1.74 (m, 3H), 1.44-1.52 (m, 2H), 0.99 (d, J=6.4 Hz, 3H). MS (ES)=553 (M+1)$^+$.

Example 10.19

(R)-6-((1-Cyclobutylethyl)amino)-8-(cyclohexylcarbamoyl)-7-(4-(trifluoromethyl)benzyl)-7H-purine-2-carboxylic acid

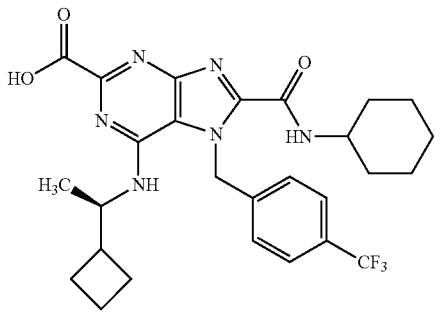 [SMILES: C[C@@H](Nc1nc(C(=O)O)nc2nc(C(=O)NC3CCCCC3)n(Cc3ccc(C(F)(F)F)cc3)c12)C1CCC1]

Using a procedure analogous to that described in Example 10.15 and starting with (R)-ethyl 2-cyano-6-((1-cyclobutylethyl)amino)-7-(4-(trifluoromethyl)benzyl)-7H-purine-8-carboxylate (Preparative Example 10.2), and cyclohexanamine, (R)-6-((1-cyclobutylethyl)amino)-8-(cyclohexylcarbamoyl)-7-(4-(trifluoromethyl)benzyl)-7H-purine-2-carboxylic acid was prepared. $^1$H NMR (400 MHz, CD$_3$OD) δ 7.67 (d, J=8.0 Hz, 2H), 7.25 (d, J=8.0 Hz, 2H), 6.56 (d, J=17.6 Hz, 1H), 6.18 (d, J=17.6 Hz, 1H), 4.59 (dq, J=8.8, 6.4 Hz, 1H), 3.82 (br s, 1H), 2.14 (m, 1H), 1.61-1.94 (m, 8H), 1.28-1.49 (m, 8H), 0.99 (d, J=6.4 Hz, 3H). MS (ES)=545 (M+1)$^+$.

Example 10.20

(R)-6-((1-Cyclobutylethyl)amino)-8-(phenylcarbamoyl)-7-(4-(trifluoromethyl)benzyl)-7H-purine-2-carboxylic acid

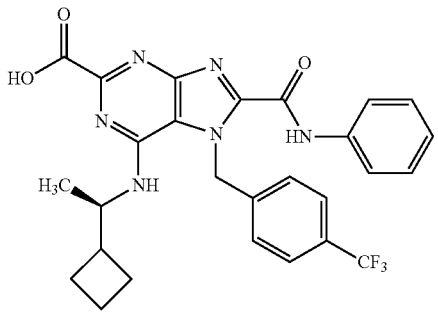 [SMILES: C[C@@H](Nc1nc(C(=O)O)nc2nc(C(=O)Nc3ccccc3)n(Cc3ccc(C(F)(F)F)cc3)c12)C1CCC1]

Using a procedure analogous to that described in Example 10.15 and starting with (R)-ethyl 2-cyano-6-((1-cyclobutylethyl)amino)-7-(4-(trifluoromethyl)benzyl)-7H-purine-8-carboxylate (Preparative Example 10.2), and aniline, (R)-6-((1-Cyclobutylethyl)amino)-8-(phenylcarbamoyl)-7-(4-(trifluoromethyl)benzyl)-7H-purine-2-carboxylic acid was prepared. $^1$H NMR (400 MHz, CD$_3$OD) δ 7.76 (d, J=7.6 Hz, 2H), 7.69 (d, J=8.0 Hz, 2H), 7.37 (t, J=7.6 Hz, 2H), 7.31 (d, J=8.0 Hz, 2H), 7.17 (t, J=7.6 Hz, 1H), 6.65 (d, J=17.4 Hz, 1H), 6.26 (d, J=17.4 Hz, 1H), 4.58 (dq, J=9.6, 6.4 Hz, 1H), 2.17 (m, 1H), 1.90 (m, 1H), 1.65-1.77 (m, 3H), 1.29-1.49 (m, 2H), 1.00 (d, J=6.4 Hz, 3H). MS (ES)=539 (M+1)$^+$.

Example 10.21

(R)-6-((1-Cyclobutylethyl)amino)-8-(3,3-dimethylpiperidine-1-carbonyl)-7-(4-(trifluoromethyl)benzyl)-7H-purine-2-carboxylic acid

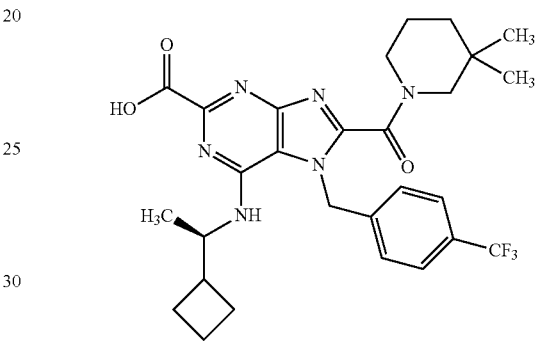

Using a procedure analogous to that described in Example 10.15 and starting with (R)-ethyl 2-cyano-6-((1-cyclobutylethyl)amino)-7-(4-(trifluoromethyl)benzyl)-7H-purine-8-carboxylate (Preparative Example 10.2), and 3,3-dimethylpiperidine, (R)-6-((1-cyclobutylethyl)amino)-8-(3,3-dimethylpiperidine-1-carbonyl)-7-(4-(trifluoromethyl)benzyl)-7H-purine-2-carboxylic acid was prepared. $^1$H NMR (400 MHz, CD$_3$OD) δ 7.70 (d, J=8.0 Hz, 2H), 7.33 (d, J=8.0 Hz, 2H), 5.87-5.96 (m, 2H), 4.69 (m, 1H), 3.46-3.49 (m, 2H), 3.26-3.38 (m, 2H), 2.19 (m, 1H), 1.90 (m, 1H), 1.55-1.73 (m, 5H), 1.40-1.58 (m, 4H), 0.82-1.02 (m, 9H). MS (ES)=559 (M+1)$^+$.

Example 10.22

6-(((R)-1-Cyclobutylethyl)amino)-8-((R)-4-phenyl-4,5-dihydrooxazol-2-yl)-7-(4-(trifluoromethyl)benzyl)-7H-purine-2-carboxylic acid

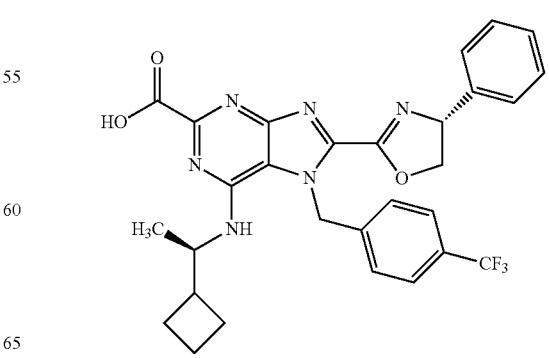

Step 1: Burgess reagent (16 mg, 0.067 mmol) was added to a solution of methyl 6-(((R)-1-cyclobutylethyl)amino)-8-(((R)-2-hydroxy-1-phenylethyl)carbamoyl)-7-(4-(trifluoromethyl)benzyl)-7H-purine-2-carboxylate (Example 10.15, Step 2) (20 mg, 0.03 mmol) in THF (2.0 mL) at room temperature. The reaction mixture was heated at reflux for 3 hours and then cooled to room temperature. The reaction mixture was diluted into EtOAc and water. The layers were separated and the aqueous layer was extracted with EtOAc (3×5 mL). The combined organic layers were washed with brine, dried over anhydrous $Na_2SO_4$, filtered and concentrated in vacuo. Purification of the residue on a Redisep 4 g silica gel column (0 to 50% EtOAc/hexanes) to afford methyl 6-(((R)-1-cyclobutyl ethyl)amino)-8-((R)-4-phenyl-4,5-dihydrooxazol-2-yl)-7-(4-(trifluoromethyl)benzyl)-7H-purine-2-carboxylate. $^1$H NMR (300 MHz, $CDCl_3$) δ 7.66 (d, J=8.1 Hz, 2H), 7.16-7.36 (m, 7H), 6.63 (d, J=17.7 Hz, 1H), 6.26 (d, J=17.7 Hz, 1H), 5.46 (t, J=9.0 Hz, 1H), 4.86 (t, J=9.0 Hz, 1H), 4.55 (d, J=8.1 Hz, 1H), 4.32-4.57 (m, 2H), 3.99 (s, 3H), 3.87-4.05 (m, 2H), 1.30-2.00 (m, 5H), 0.92 (d, J=6.6 Hz, 3H). MS (ES)=579 (M+1)$^+$.

Step 2: Using a procedure analogous to that described in Example 10.1 (Step 6) and starting with 6-(((R)-1-cyclobutylethyl)amino)-8-((R)-4-phenyl-4,5-dihydrooxazol-2-yl)-7-(4-(trifluoro-methyl)benzyl)-7H-purine-2-carboxylate, 6-(((R)-1-cyclobutylethyl)amino)-8-((R)-4-phenyl-4,5-dihydrooxazol-2-yl)-7-(4-(trifluoromethyl)benzyl)-7H-purine-2-carboxylic acid was prepared. $^1$H NMR (400 MHz, $CD_3OD$) δ 7.65 (d, J=8.0 Hz, 2H), 7.30-7.34 (m, 3H), 7.22-7.30 (m, 4H), 6.65 (d, J=17.8 Hz, 1H), 6.31 (d, J=17.8 Hz, 1H), 5.51 (t, J=9.4 Hz, 1H), 4.89 (t, J=9.4 Hz, 1H), 4.63 (dq, J=9.0, 6.7 Hz, 1H), 4.28 (t, J=9.4 Hz, 1H), 2.14 (m, 1H), 1.89 (m, 1H), 1.61-1.71 (m, 3H), 1.45-1.51 (m, 2H), 0.98 (d, J=6.7 Hz, 3H). MS (ES)=565 (M+1)$^+$.

Example 10.23

6-(((R)-1-Cyclobutylethyl)amino)-8-(1-methylpiperidin-2-yl)-7-(4-(trifluoro methyl)benzyl)-7H-purine-2-carboxylic acid

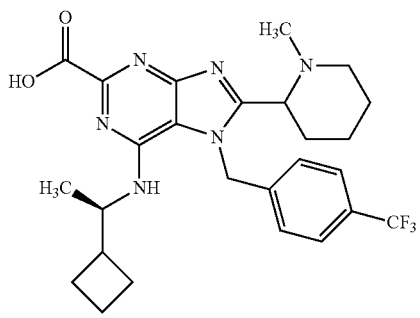 [SMILES: C[C@@H](Nc1nc(C(=O)O)nc2nc(C3CCCCN3C)n(Cc3ccc(C(F)(F)F)cc3)c12)C1CCC1]

Step 1: A solution of palladium acetate (68 mg, 0.3 mmol) and Catacxium®A (215 mg, 0.6 mmol) in 1,4-dioxane (3.0 mL) under Ar was heated at 50° C. for 30 minutes then cooled to room temperature. The above catalyst mixture was then added to a mixture of (R)-6-((1-cyclobutylethyl)amino)-7-(4-(trifluoromethyl)benzyl)-7H-purine-2-carbonitrile (Preparative Example 1.1; 300 mg, 0.75 mmol), 2-bromopyridine (143 µL, 1.50 mmol), CsF (342 mg, 2.25 mmol) and pivalic acid (100 mg, 0.98 mmol) in 1,4-dioxane (6.0 mL) under Ar. The reaction mixture was heated at 110° C. overnight in a sealed tube. After evaporation of solvent, the residue was diluted with water (5.0 mL) and extracted with EtOAc (3×10 mL). The combined organic layers were washed with water and brine, dried over anhydrous $Na_2SO_4$, filtered and concentrated in vacuo. Purification of the residue on a Redisep 4 g silica gel column (0 to 50% EtOAc/hexanes) afforded (R)-6-((1-cyclobutylethyl)amino)-8-(pyridin-2-yl)-7-(4-(trifluoromethyl)benzyl)-7H-purine-2-carbonitrile. $^1$H NMR (300 MHz, $CDCl_3$) δ 8.54-8.58 (m, 2H), 7.92 (m, 1H), 7.72 (d, J=8.1 Hz, 2H), 7.34-7.43 (m, 3H), 6.53 (d, J=17.9 Hz, 1H), 6.33 (d, J=17.9 Hz, 1H), 4.50 (d, J=8.4 Hz, 1H), 4.26 (m, 1H), 1.40-1.98 (m, 7H), 0.90 (d, J=6.0 Hz, 3H). MS (APCI)=478 (M+1)$^+$.

Step 2: (R)-6-((1-cyclobutylethyl)amino)-8-(pyridin-2-yl)-7-(4-(trifluoromethyl)benzyl)-7H-purine-2-carbonitrile (60 mg, 0.126 mmol) was dissolved in HCl (3.0 M in MeOH, 3.0 mL). The resulting mixture was heated at reflux for 4 hours and then concentrated in vacuo. The residue was dissolved in $CH_2Cl_2$ and neutralized with sat. aqueous $NaHCO_3$ solution. The aqueous layer was extracted with $CH_2Cl_2$ (3×5.0 mL). The combined organic layers were washed with brine, dried over anhydrous $Na_2SO_4$, filtered and concentrated in vacuo. Purification of the residue on a Redisep 4 g silica gel column (0 to 70% EtOAc/hexanes) afforded (R)-methyl 6-((1-cyclobutylethyl)amino)-8-(pyridin-2-yl)-7-(4-(trifluoromethyl)benzyl)-7H-purine-2-carboxylate. $^1$H NMR (300 MHz, $CDCl_3$) δ 8.52 8.60 (m, 2H), 7.89 (m, 1H), 7.72 (d, J=8.1 Hz, 2H), 7.33-7.39 (m, 3H), 6.54 (d, J=17.3 Hz, 1H), 6.36 (d, J=17.3 Hz, 1H), 4.35-4.36 (m, 2H), 4.00 (s, 3H), 1.21-2.09 (m, 7H), 0.88 (d, J=6.3 Hz, 3H). MS(APCI)=511 (M+1)$^+$.

Step 3: A round bottom flask was charged with $PtO_2$ (40 mg, 0.18 mmol) under $N_2$. A solution of (R)-methyl 6-((1-cyclobutylethyl)amino)-8-(pyridin-2-yl)-7-(4-(trifluoromethyl)benzyl)-7H-purine-2-carboxylate (170 mg, 0.33 mmol) in AcOH (4.0 mL) was added. The reaction mixture was stirred at room temperature under $H_2$ (40 psi) for 1 hour and then filtered through celite and washing the celite pad with MeOH. The filtrate was concentrated in vacuo and the residue was diluted with $CH_2Cl_2$ and water. The aqueous layer was extracted with $CH_2Cl_2$ (3×5.0 mL). The combined organic layers were washed with brine, dried over anhydrous $Na_2SO_4$, filtered and concentrated in vacuo. Purification of the residue on a Redisep 4 g silica gel column (0 to 10% MeOH/$CH_2Cl_2$) afforded methyl 6-(((R)-1-cyclobutylethyl)amino)-8-(piperidin-2-yl)-7-(4-(trifluoromethyl)benzyl)-7H-purine-2-carboxylate as a mixture of diastereomers. MS (APCI)=517 (M+1)$^+$.

Step 4: Formaldehyde (10 µL, 37% aqueous solution) was added to a solution of methyl 6-(((R)-1-cyclobutylethyl)amino)-8-(piperidin-2-yl)-7-(4-(trifluoromethyl)benzyl)-7H-purine-2-carboxylate (10.0 mg, 19 µmol) in acetonitrile (0.9 mL), followed by the addition of HOAc (50 µL) and $NaCNBH_3$ (6.7 mg, 0.11 mmol). The reaction mixture was stirred at room temperature for 3 hours. After evaporation of solvent, the residue was dissolved in $CH_2Cl_2$ and neutralized with sat. aqueous $NaHCO_3$ solution. The two layers were separated and the aqueous layer was extracted with $CH_2Cl_2$ (3×5 mL). The combined organic layers were washed with brine, dried over anhydrous $Na_2SO_4$, filtered and concentrated in vacuo. Purification of the residue on a Redisep 4 g silica gel column (0 to 10% MeOH/$CH_2Cl_2$) afforded methyl 6-(((R)-1-cyclobutylethyl)amino)-8-(1-methylpiperidin-2-yl)-7-(4-(trifluoromethyl)benzyl)-7H-purine-2-carboxylate as a mixture of diastereomers. MS (APCI)=531 (M+1)$^+$.

Step 5: Using a procedure analogous to that described in Example 10.1 (Step 6) and starting with methyl 6-(((R)-1-cyclobutylethyl)amino)-8- (1-methylpiperidin-2-yl)-7-(4-(trifluoromethyl)benzyl)-7H-purine-2-carboxylate, 6-(((R)-1-cyclobutylethyl)amino)-8-(1-methylpiperidin-2-yl)-7-(4-(trifluoromethyl)benzyl)-7H-purine-2-carboxylic acid was prepared as a mixture of diastereomers. $^1$H NMR (400 MHz, $CD_3OD$) δ 7.71 (d, J=8.0 Hz, 2H), 7.22 (d, J=8.0 Hz, 2H), 6.31 (m, 1H), 6.01 (d, J=18.8 Hz, 1H), 4.54 (m, 1H), 4.09 (m, 1H), 3.40 (m, 1H), 2.64 (m, 1H), 2.35-2.45 (m, 3H), 1.26-2.13 (m, 13H), 0.96 (d, J=6.4 Hz, 1.5H), 0.88 (d, J=6.4 Hz, 1.5H). MS (ES)=517 (M+1)+.

Example 10.24

6-(((R)-1-Cyclobutylethyl)amino)-8-(piperidin-2-yl)-7-(4-(trifluoromethyl)benzyl)-7H-purine-2-carboxylic acid

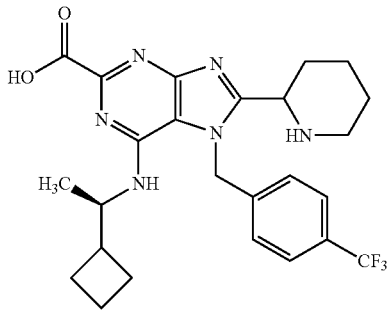 [SMILES: C[C@@H](Nc1nc(C(=O)O)nc2nc(C3CCCCN3)n(Cc3ccc(C(F)(F)F)cc3)c12)C1CCC1]

Using a procedure analogous to that described in Example 10.23, and starting with methyl 6-(((R)-1-cyclobutylethyl) amino)-8-(piperidin-2-yl)-7-(4-(trifluoromethyl)benzyl)-7H-purine-2-carboxylate, 6-(((R)-1-cyclobutylethyl) amino)-8-(piperidin-2-yl)-7-(4-(trifluoromethyl)benzyl)-7H-purine-2-carboxylic acid was prepared. 1H NMR (400 MHz, CD3OD) δ 7.70 (d, J=8.4 Hz, 1H), 7.68 (d, J=8.4 Hz, 1H), 7.06 (d, J=8.4 Hz, 1H), 7.03 (d, J=8.4 Hz, 1H), 5.87 (d, J=18.8 Hz, 1H), 5.62 (d, J=18.8 Hz, 1H), 4.43 (m, 1H), 3.66 (m, 1H), 1.09-2.50 (m, 15H), 0.95 (d, J=6.4 Hz, 1.5H), 0.79 (d, J=6.4 Hz, 1.5H). MS (ES)=503 (M+1)+.

Example 10.25

6-(((R)-1-Cyclobutylethyl)amino)-8-(1-ethylpiperidin-2-yl)-7-(4-(trifluoromethyl)benzyl)-7H-purine-2-carboxylic acid

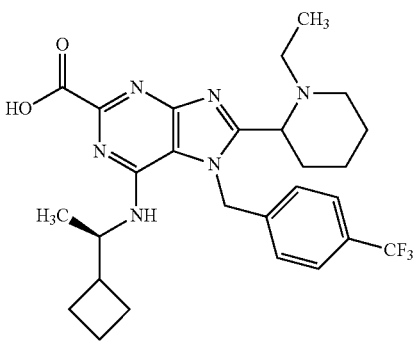 [SMILES: CCN1CCCCC1c1nc2nc(C(=O)O)nc(N[C@H](C)C3CCC3)c2n1Cc1ccc(C(F)(F)F)cc1]

Using a procedure analogous to that described in Example 10.23, and starting with methyl 6-(((R)-1-cyclobutylethyl) amino)-8-(piperidin-2-yl)-7-(4-(trifluoromethyl)benzyl)-7H-purine-2-carboxylate, 6-(((R)-1-cyclobutylethyl) amino)-8-(1-ethylpiperidin-2-yl)-7-(4-(trifluoromethyl) benzyl)-7H-purine-2-carboxylic acid was prepared. 1H NMR (400 MHz, CD3OD) δ 7.73 (d, J=7.9 Hz, 2H), 7.27 (d, J=7.9 Hz, 1H), 7.24 (d, J=7.9 Hz, 1H), 5.94-6.06 (m, 2H), 4.54 (dq, J=9.2, 6.4 Hz, 1H), 3.85 (m, 1H), 2.95-3.25 (m, 2H), 1.89-2.17 (m, 7H), 1.54-1.72 (m, 4H), 1.40-1.48 (m, 2H), 1.23-1.42 (m, 5H), 0.99 (d, J=6.4 Hz, 1.5H), 0.97 (d, J=6.4 Hz, 1.5H). MS (ES)=531 (M+1)+.

Example 10.26

6-{[(1R)-1-cyclobutylethyl]amino}-8-{[(1S)-1-(3-fluorophenyl)ethyl](propyl)amino}-7-[4-(trifluoromethyl)benzyl]-7H-purine-2-carboxylic acid

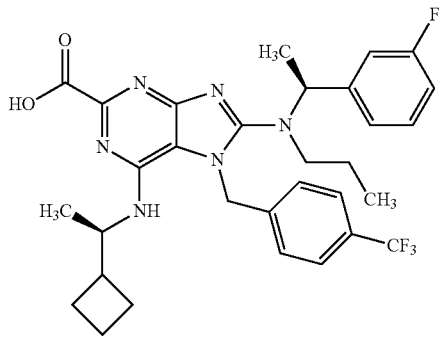 [SMILES: CCCN(c1nc2nc(C(=O)O)nc(N[C@H](C)C3CCC3)c2n1Cc1ccc(C(F)(F)F)cc1)[C@@H](C)c1cccc(F)c1]

Step 1: Cs2CO3 (78 mg, 0.24 mmol) was added to a solution of 6-(((R)-1-cyclobutylethyl)amino)-8-(((S)-1-(3-fluorophenyl)ethyl)amino)-7-(4-(trifluoromethyl)benzyl)-7H-purine-2-carbonitrile (64 mg, 0.12 mmol) in anhydrous DMF (3.0 mL) at 0° C. Allylbromide (21 μL, 0.24 mmol) was added dropwise. The reaction mixture was stirred at 0° C. for 1 hour and was then warmed to room temperature and stirred for 1 hour. The reaction mixture was quenched with water and extracted with EtOAc (3×10 mL). The combined organic layers were washed with water and brine, dried over anhydrous Na2SO4, filtered and concentrated in vacuo. Purification of the residue on a Redisep 4 g silica gel column (0 to 50% EtOAc/hexanes) afforded 6-(allyl((R)-1-cyclobutylethyl)amino)-8-(((S)-1-(3-fluorophenyl)ethyl)amino)-7-(4-(trifluoromethyl)benzyl)-7H-purine-2-carbonitrile and 8-(allyl((S)-1-(3-fluorophenyl)ethyl)amino)-6-(((R)-1-cyclobutylethyl)amino)-7-(4-(trifluoromethyl)benzyl)-7H-purine-2-carbonitrile. 6-(allyl((R)-1-cyclobutylethyl)amino)-8-(((S)-1-(3-fluorophenyl)ethyl)amino)-7-(4-(trifluoromethyl)benzyl)-7H-purine-2-carbonitrile: 1H NMR (300 MHz, CDCl3) δ 7.71 (d, J=8.1 Hz, 2H), 7.43 (d, J=8.1 Hz, 2H), 7.24 (m, 1H), 6.84-7.10 (m, 3H), 5.60 (m, 1H), 4.95-5.40 (m, 5H), 3.77 (dd, J=15.2, 6.1 Hz, 1H), 3.67 (dd, J=15.2, 6.1 Hz, 1H), 3.90-4.08 (m, 2H), 1.39 (d, J=6.3 Hz, 3H), 1.26-1.94 (m, 7H), 0.84 (d, J=6.3 Hz, 3H). MS (ES)=578 (M+1)+.

8-(allyl((S)-1-(3-fluorophenyl)ethyl)amino)-6-(((R)-1-cyclobutylethyl)amino)-7-(4-(trifluoromethyl)benzyl)-7H-purine-2-carbonitrile: 1H NMR (300 MHz, CDCl3) δ 7.70 (d, J=8.1 Hz, 2H), 6.94-7.33 (m, 6H), 5.75 (m, 1H), 5.52 (d, J=17.4 Hz, 1H), 5.43 (d, J=17.4 Hz, 1H), 5.03-5.10 (m, 2H), 4.79 (q, J=6.6 Hz, 1H), 4.15 (m, 1H), 4.01 (d, J=8.1 Hz, 1H), 3.77 (dd, J=15.2, 6.1 Hz, 1H), 3.67 (dd, J=15.2, 6.1 Hz, 1H), 1.54 (d, J=6.6 Hz, 3H), 1.17-1.90 (m, 7H), 0.80 (d, J=6.3 Hz, 3H). MS (ES)=578 (M+1)+.

Step 2: A round bottom flask was charged with Pd/C (10 mg) under N2. A solution of 8-(allyl((S)-1-(3-fluorophenyl) ethyl)amino)-6-(((R)-1-cyclobutylethyl)amino)-7-(4-(trifluoromethyl)benzyl)-7H-purine-2-carbonitrile (25 mg, 0.04 mmol) in EtOH (3.0 mL) was added. The reaction mixture was stirred at room temperature under H2 (1 atm) for 20 minutes and then filtered through celite. The filtrate was concentrated in vacuo. Purification of the residue on a Redisep 4 g silica gel column (0 to 30% EtOAc/hexanes) afforded 6-(((R)-1-cyclobutylethyl)amino)-8-(((S)-1-(3-fluorophenyl)ethyl)(propyl)amino)-7-(4-(trifluoromethyl) benzyl)-7H-purine-2-carbonitrile. 1H NMR (400 MHz, CDCl3) δ 7.71 (d, J=8.0 Hz, 2H), 7.25-7.35 (m, 3H), 6.94-7.01 (m, 3H), 5.48 (d, J=19.0 Hz, 1H), 5.41 (d, J=19.0 Hz, 1H), 4.67 (q, J=6.8 Hz, 1H), 4.16 (m, 1H), 3.98 (d, J=8.0 Hz, 1H), 3.12 (m, 1H), 3.00 (m, 1H), 1.52 (d, J=6.8 Hz, 3H), 1.31-1.87 (m, 9H), 0.81 (d, J=6.4 Hz, 3H), 0.72 (t, J=7.4 Hz, 3H). MS (APCI)=580 (M+1)+.

Step 3: Using a procedure analogous to that described in Example 10.5 (Step 3), and starting with 6-(((R)-1-cyclobutylethyl)amino)-8-(((S)-1-(3-fluorophenyl)ethyl) (propyl)amino)-7-(4-(trifluoromethyl)benzyl)-7H-purine-2-carbonitrile, 6-{[(1R)-1-cyclobutylethyl]amino}-8-{[(1S)-1-(3-fluorophenyl)ethyl](propyl)amino}-7-[4-(trifluoromethyl)benzyl]-7H-purine-2-carboxylic acid was prepared. $^1$H NMR (400 MHz, CD$_3$OD) δ 7.65 (d, J=8.0 Hz, 2H), 7.29 (m, 1H), 7.16 (d, J=8.0 Hz, 2H), 6.96-7.09 (m, 3H), 5.71 (d, J=18.4 Hz, 1H), 5.65 (d, J=18.4 Hz, 1H), 4.57 (dq, J=8.8, 6.4 Hz, 1H), 3.10-3.31 (m, 2H), 2.11 (m, 1H), 1.89 (m, 1H), 1.44-1.78 (m, 10H), 0.96 (d, J=6.4 Hz, 3H), 0.74 (t, J=7.2 Hz, 3H). MS (ES)=599 (M+1)$^+$.

Example 10.27

8-(Allyl((S)-1-(3-fluorophenyl)ethyl)amino)-6-(((R)-1-cyclobutylethyl)amino)-7-(4-(trifluoromethyl)benzyl)-7H-purine-2-carboxylic acid

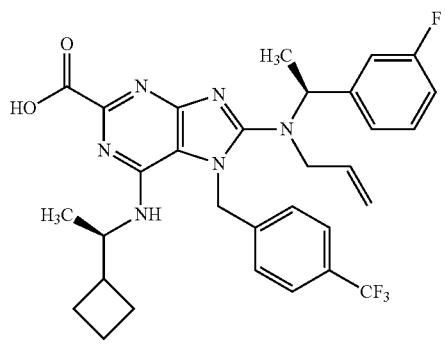 [SMILES: C=CCN(c1nc2nc(C(=O)O)nc(N[C@H](C)C3CCC3)c2n1Cc1ccc(C(F)(F)F)cc1)[C@@H](C)c1cccc(F)c1]

Using a procedure analogous to that described in Example 10.5 (Step 3), and starting with 8-(allyl((S)-1-(3-fluorophenyl)ethyl)amino)-6-(((R)-1-cyclobutylethyl)amino)-7-(4-(trifluoromethyl)benzyl)-7H-purine-2-carbonitrile (prepared in Example 10.26, Step 1), 8-(allyl((S)-1-(3-fluorophenyl)ethyl)amino)-6-(((R)-1-cyclobutylethyl)amino)-7-(4-(trifluoromethyl)benzyl)-7H-purine-2-carboxylic acid was prepared. $^1$H NMR (400 MHz, CD$_3$OD) δ 7.65 (d, J=8.0 Hz, 2H), 7.28 (m, 1H), 7.13 (d, J=8.0 Hz, 2H), 7.00-7.11 (m, 2H), 6.96 (m, 1H), 5.80 (m, 1H), 5.69 (br s, 2H), 5.19-5.17 (m, 2H), 4.92 (m, 1H), 4.60 (m, 1H), 3.80-3.90 (m, 2H), 2.10 (m, 1H), 1.90 (m, 1H), 1.60-1.75 (m, 6H), 1.42-1.50 (m, 2H), 0.97 (d, J=6.5 Hz, 3H). MS (ES)=597 (M+1)$^+$.

Example 10.28

6-(Allyl((R)-1-cyclobutylethyl)amino)-8-(((S)-1-(3-fluorophenyl)ethyl)amino)-7-(4-(trifluoromethyl)benzyl)-7H-purine-2-carboxylic acid

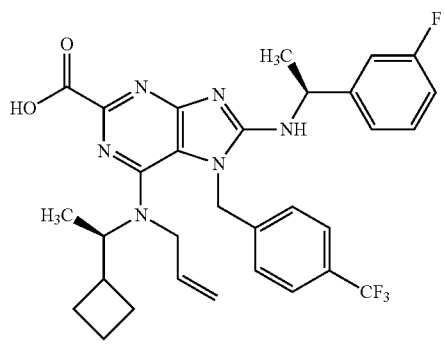 [SMILES: C=CCN(c1nc(C(=O)O)nc2nc(N[C@@H](C)c3cccc(F)c3)n(Cc3ccc(C(F)(F)F)cc3)c12)[C@H](C)C1CCC1]

Using a procedure analogous to that described in Example 10.5 (Step 3), and starting with 6-(allyl((R)-1-cyclobutylethyl)amino)-8-(((S)-1-(3-fluorophenyl)ethyl)amino)-7-(4-(trifluoromethyl)benzyl)-7H-purine-2-carbonitrile (prepared in Example 10.26, Step 1), 6-(allyl((R)-1-cyclobutylethyl)amino)-8-(((S)-1-(3-fluorophenyl)ethyl)amino)-7-(4-(trifluoromethyl)benzyl)-7H-purine-2-carboxylic acid was prepared. $^1$H NMR (400 MHz, CD$_3$OD) δ 7.70 (d, J=8.2 Hz, 2H), 7.33 (d, J=8.2 Hz, 2H), 7.28 (m, 1H), 6.98-7.05 (m, 3H), 6.06 (m, 1H), 5.63 (d, J=18.0 Hz, 1H), 5.52 (d, J=18.0 Hz, 1H), 5.18-5.33 (m, 2H), 4.97-5.05 (m, 2H), 4.49-4.55 (m, 2H), 2.02 (m, 1H), 1.83 (m, 1H), 1.59-1.68 (m, 6H), 1.28-1.40 (m, 2H), 0.95 (d, J=6.5 Hz, 3H). MS (ES)=597 (M+1)$^+$.

Example 10.29

6-(((R)-1-Cyclobutylethyl)amino)-8-((cyclopropylmethyl)((S)-1-phenylethyl)amino)-7-(4-(trifluoromethyl)benzyl)-7H-purine-2-carboxylic acid

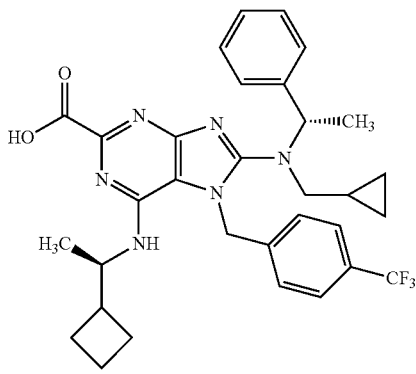 [SMILES: C[C@@H](Nc1nc(C(=O)O)nc2nc(N(CC3CC3)[C@@H](C)c3ccccc3)n(Cc3ccc(C(F)(F)F)cc3)c12)C1CCC1]

Using a procedure analogous to that described in Example 10.26 and starting with 6-(((R)-1-cyclobutylethyl)amino)-8-(((S)-1-phenylethyl)amino)-7-(4-(trifluoromethyl)benzyl)-7H-purine-2-carbonitrile and (bromomethyl)cyclopropane, 6-(((R)-1-cyclobutylethyl)amino)-8-((cyclopropylmethyl)((S)-1-phenylethyl)amino)-7-(4-(trifluoromethyl)benzyl)-7H-purine-2-carboxylic acid was prepared. $^1$H NMR (400 MHz, CD$_3$OD) δ 7.74 (d, J=8.1 Hz, 2H), 7.25-7.33 (m, 7H), 5.66 (d, J=18.5 Hz, 1H), 5.51 (d, J=18.5 Hz, 1H), 4.98 (m, 1H), 4.48 (dq, J=8.6, 6.6 Hz, 1H), 4.26-4.30 (m, 2H), 2.01 (m, 1H), 1.84 (m, 1H), 1.68 (d, J=6.7 Hz, 3H), 1.58-1.66 (m, 3H), 1.29-1.43 (m, 3H), 0.94 (d, J=6.4 Hz, 3H), 0.91 (m, 1H), 0.53-0.60 (m, 3H). MS (ES)=593 (M+1)$^+$.

Example 10.30

8-(Allyl(1-(pyridin-2-yl)ethyl)amino)-6-(((R)-1-cyclobutylethyl)amino)-7-(4-(trifluoromethyl)benzyl)-7H-purine-2-carboxylic acid

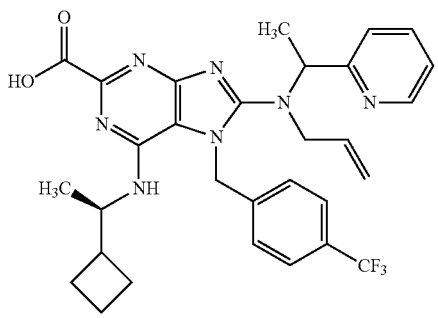 [SMILES: C=CCN(c1nc2nc(C(=O)O)nc(N[C@H](C)C3CCC3)c2n1Cc1ccc(C(F)(F)F)cc1)C(C)c1ccccn1]

Using a procedure analogous to that described in Example 10.26, and starting with 6-(((R)-1-cyclobutylethyl)amino)-8-((1-(pyridin-2-yl)ethyl)amino)-7-(4-(trifluoromethyl)benzyl)-7H-purine-2-carbonitrile, 8-(Allyl(1-(pyridin-2-yl)ethyl)amino)-6-(((R)-1-cyclobutylethyl)amino)-7-(4-(trifluoromethyl)benzyl)-7H-purine-2-carboxylic acid was prepared. $^1$H NMR (400 MHz, CD$_3$OD) δ 8.48 (m, 1H), 7.77 (m, 1H), 7.65-7.69 (m, 2H), 7.49 (m, 1H), 7.20-7.31 (m, 3H), 5.73-5.89 (m, 3H), 5.01-5.14 (m, 3H), 4.57 (m, 1H), 3.88-3.98 (m, 2H), 2.11 (m, 1H), 1.88 (m, 1H), 1.61-1.73 (m, 6H), 1.42-1.54 (m, 2H), 0.88-0.96 (m, 3H). MS (ES)=580 (M+1)$^+$.

Example 10.31

6-(allyl((R)-1-cyclobutylethyl)amino)-8-((1-(pyridin-2-yl)ethyl)amino)-7-(4-(trifluoromethyl)benzyl)-7H-purine-2-carboxylic acid

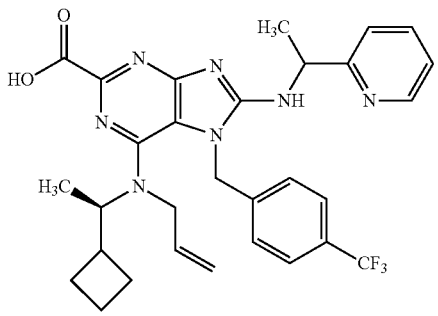 [SMILES: C=CCN(c1nc(C(=O)O)nc2nc(NC(C)c3ccccn3)n(Cc3ccc(C(F)(F)F)cc3)c12)[C@H](C)C1CCC1]

Using a procedure analogous to that described in Example 10.26, and starting with 6-(((R)-1-cyclobutylethyl)amino)-8-((1-(pyridin-2-yl)ethyl)amino)-7-(4-(trifluoromethyl)benzyl)-7H-purine-2-carbonitrile, 6-(allyl((R)-1-cyclobutylethyl)amino)-8-((1-(pyridin-2-yl)ethyl)amino)-7-(4-(trifluoromethyl)benzyl)-7H-purine-2-carboxylic acid was prepared. $^1$H NMR (400 MHz, CD$_3$OD) δ 8.40 (m, 1H), 7.41-7.78 (m, 3H), 7.21-7.41 (m, 4H), 6.13 (m, 1H), 5.89 (d, J=18.4 Hz, 1H), 5.81 (d, J=18.4 Hz, 1H), 4.95-5.34 (m, 5H), 4.52 (m, 1H), 2.11 (m, 1H), 1.86 (m, 1H), 1.64-1.70 (m, 6H), 1.61-1.63 (m, 2H), 0.90-0.96 (m, 3H). MS (ES)=580 (M+1)$^+$.

Example 10.32

6-(((R)-1-cyclobutylethyl)amino)-8-(propyl(1-(pyridin-2-yl)ethyl)amino)-7-(4-(trifluoromethyl)benzyl)-7H-purine-2-carboxylic acid

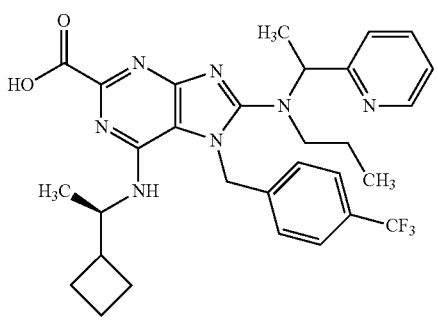 [SMILES: CCCN(c1nc2nc(C(=O)O)nc(N[C@H](C)C3CCC3)c2n1Cc1ccc(C(F)(F)F)cc1)C(C)c1ccccn1]

Using a procedure analogous to that described in Example 10.26, and starting with 6-(((R)-1-cyclobutylethyl)amino)-8-((1-(pyridin-2-yl)ethyl)amino)-7-(4-(trifluoromethyl)benzyl)-7H-purine-2-carbonitrile, 6-(((R)-1-cyclobutylethyl)amino)-8-(propyl(1-(pyridin-2-yl)ethyl)amino)-7-(4-(trifluoromethyl)benzyl)-7H-purine-2-carboxylic acid was prepared. $^1$H NMR (400 MHz, CD$_3$OD) δ 8.49 (m, 1H), 7.78 (m, 1H), 7.66-7.68 (m, 2H), 7.45 (m, 1H), 7.24-7.32 (m, 3H), 5.81-5.89 (m, 2H), 4.95 (m, 1H), 4.58 (m, 1H), 3.27 (m, 1H), 3.12 (m, 1H), 2.12 (m, 1H), 1.91 (m, 1H), 1.62-1.71 (m, 6H), 1.29-1.56 (m, 4H), 0.94-0.98 (m, 3H), 0.66-0.71 (m, 3H). MS (ES)=582 (M+1)$^+$.

Example 10.33

6-(((R)-1-Cyclobutylethyl)amino)-8-(1,4-dimethylpiperidin-2-yl)-7-((trans-4-methylcyclohexyl)methyl)-7H-purine-2-carboxylic acid

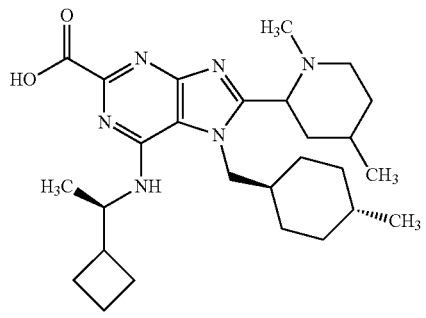 [SMILES: CC1CCN(C)C(c2nc3nc(C(=O)O)nc(N[C@H](C)C4CCC4)c3n2C[C@H]2CC[C@H](C)CC2)C1]

Using a procedure analogous to that described in Example 10.23, and starting with 6-(((R)-1-cyclobutylethyl)amino)-7-((trans-4-methylcyclohexyl)methyl)-7H-purine-2-carbonitrile (Preparative Example 11.6) and 2-bromo-4-methylpyridine, 6-(((R)-1-cyclobutylethyl)amino)-8-(1,4-dimethylpiperidin-2-yl)-7-((trans-4-methylcyclohexyl)methyl)-7H-purine-2-carboxylic acid was prepared. $^1$H NMR (400 MHz, CD$_3$OD) δ 4.45 (m, 1H), 4.22 (m, 1H), 3.40 (m, 1H), 2.91 (m, 1H), 2.39-2.61 (m, 3H), 1.54-2.11 (m, 14H), 1.13-1.40 (m, 10H), 1.01-1.08 (m, 3H), 0.80-0.91 (m, 6H). MS (ES)=483 (M+1)$^+$.

Example 10.34

6-(((R)-1-Cyclobutylethyl)amino)-8-(1-ethyl-4-methylpiperidin-2-yl)-7-((trans-4-methylcyclohexyl)methyl)-7H-purine-2-carboxylic acid

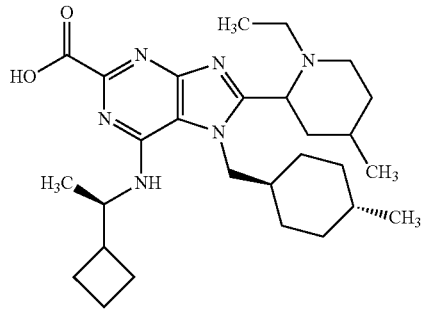 [SMILES: CCN1CCC(C)CC1c1nc2nc(C(=O)O)nc(N[C@H](C)C3CCC3)c2n1C[C@H]1CC[C@H](C)CC1]

Using a procedure analogous to that described in Example 10.23, and starting with 6-(((R)-1-cyclobutylethyl)amino)-7-((trans-4-methylcyclohexyl)methyl)-7H-purine-2-carbonitrile (Preparative Example 11.6) and 2-bromo-4-methylpyridine, 6-(((R)-1-cyclobutylethyl)amino)-8-(1-ethyl-4- methylpiperidin-2-yl)-7-((trans-4-methylcyclohexyl) methyl)-7H-purine-2-carboxylic acid was prepared. ¹H NMR (400 MHz, CD₃OD) δ 4.70 (m, 1H), 4.49 (m, 1H), 4.25 (m, 1H), 3.79 (m, 1H), 3.12 (m, 1H), 2.88 (m, 1H), 2.55 (m, 1H), 1.55-2.15 (m, 14H), 1.14-1.40 (m, 12H), 1.03-1.41 (m, 3H), 0.86-0.91 (m, 6H). MS (ES)=497 (M+1)⁺.

TABLE 10

| Ex. | FRET IC$_{50}$ (nM) | Structure | Chemical Name | Salt Form | [M + H]⁺ Calc'd | [M + H]⁺ Obsv'd |
|---|---|---|---|---|---|---|
| 10.1 | 37.53 | 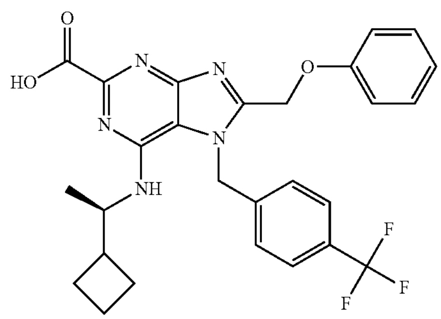 [SMILES: C[C@@H](Nc1nc(C(=O)O)nc2nc(COc3ccccc3)n(Cc3ccc(C(F)(F)F)cc3)c12)C1CCC1] | 6-{[(1R)-1-cyclobutylethyl]amino}-8-(phenoxymethyl)-7-[4-(trifluoromethyl)benzyl]-7H-purine-2-carboxylic acid | | 526 | 526 |
| 10.2 | 21.55 | 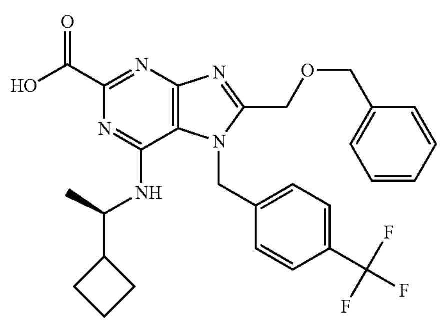 [SMILES: C[C@@H](Nc1nc(C(=O)O)nc2nc(COCc3ccccc3)n(Cc3ccc(C(F)(F)F)cc3)c12)C1CCC1] | 8-[(benzyloxy)methyl]-6-{[(1R)-1-cyclobutylethyl]amino}-7-[4-(trifluoromethyl)benzyl]-7H-purine-2-carboxylic acid | | 540 | 540 |
| 10.3 | 69.79 | 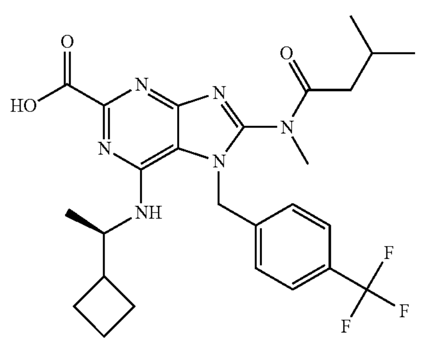 [SMILES: CC(C)CC(=O)N(C)c1nc2nc(C(=O)O)nc(N[C@H](C)C3CCC3)c2n1Cc1ccc(C(F)(F)F)cc1] | 6-{[(1R)-1-cyclobutylethyl]amino}-8-[methyl(3-methylbutanoyl)amino]-7-[4-(trifluoromethyl)benzyl]-7H-purine-2-carboxylic acid | | 533 | 533 |
| 10.4 | 14.07 | 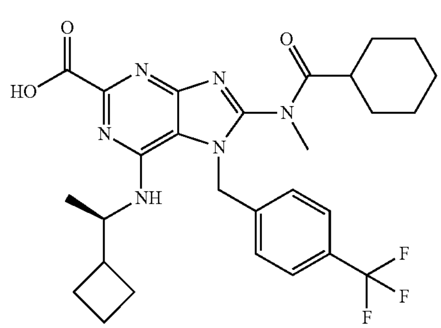 [SMILES: C[C@@H](Nc1nc(C(=O)O)nc2nc(N(C)C(=O)C3CCCCC3)n(Cc3ccc(C(F)(F)F)cc3)c12)C1CCC1] | 6-{[(1R)-1-cyclobutylethyl]amino}-8-[(cyclohexylcarbonyl)(methyl)amino]-7-[4-(trifluoromethyl)benzyl]-7H-purine-2-carboxylic acid | | 559 | 559 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.5 | 39.42 | 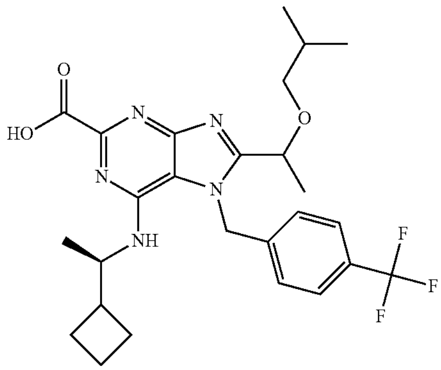 [SMILES: CC(C)COC(C)c1nc2nc(C(=O)O)nc(N[C@H](C)C3CCC3)c2n1Cc1ccc(C(F)(F)F)cc1] | 6-{[(1R)-1-cyclobutylethyl]amino}-8-[1-(2-methylpropoxy)ethyl]-7-[4-(trifluoromethyl)benzyl]-7H-purine-2-carboxylic acid | | 520 | 520 |
| 10.6 | 19.27 | 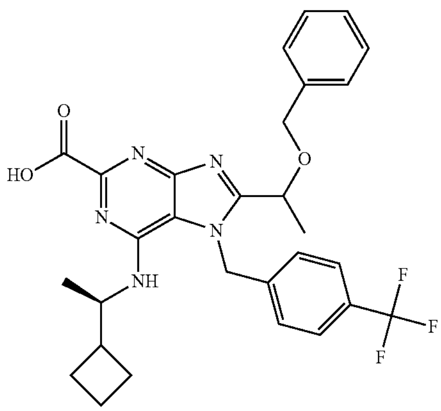 [SMILES: CC(OCc1ccccc1)c1nc2nc(C(=O)O)nc(N[C@H](C)C3CCC3)c2n1Cc1ccc(C(F)(F)F)cc1] | 8-[1-(benzyloxy)ethyl]-6-{[(1R)-1-cyclobutylethyl]amino}-7-[4-(trifluoromethyl)benzyl]-7H-purine-2-carboxylic acid | | 554 | 554 |
| 10.7 | 139.6 | 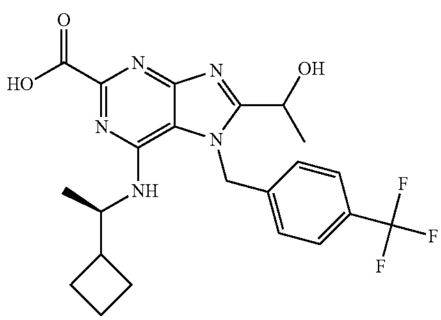 [SMILES: CC(O)c1nc2nc(C(=O)O)nc(N[C@H](C)C3CCC3)c2n1Cc1ccc(C(F)(F)F)cc1] | 6-{[(1R)-1-cyclobutylethyl]amino}-8-(1-hydroxyethyl)-7-[4-(trifluoromethyl)benzyl]-7H-purine-2-carboxylic acid | | 464 | 464 |
| 10.8 | 28.95 | 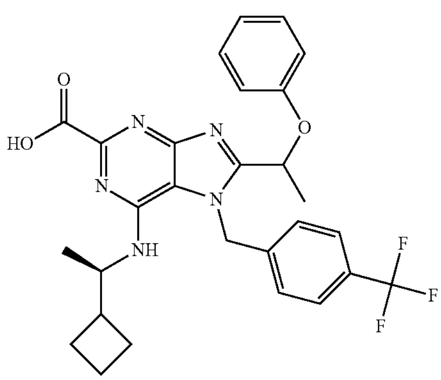 [SMILES: CC(Oc1ccccc1)c1nc2nc(C(=O)O)nc(N[C@H](C)C3CCC3)c2n1Cc1ccc(C(F)(F)F)cc1] | 6-{[(1R)-1-cyclobutylethyl]amino}-8-(1-phenoxyethyl)-7-[4-[4(trifluoromethyl)benzyl]-7H-purine-2-carboxylic acid | | 540 | 540 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.9 | 21.24 | 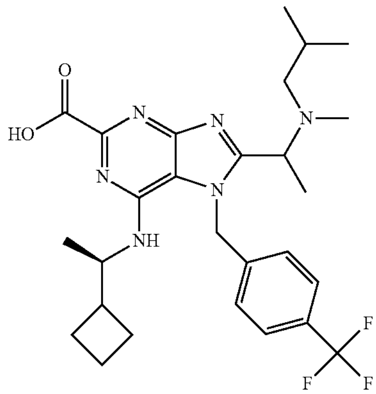 [SMILES: CC(C)CN(C)C(C)c1nc2nc(C(=O)O)nc(N[C@H](C)C3CCC3)c2n1Cc1ccc(C(F)(F)F)cc1] | 6-{[(1R)-1-cyclobutylethyl]amino}-8-{1-[methyl(2-methylpropyl)amino]ethyl}-7-[4-(trifluoromethyl)benzyl]-7H-purine-2-carboxylic acid | | 533 | 533 |
| 10.10 | 68.76 | 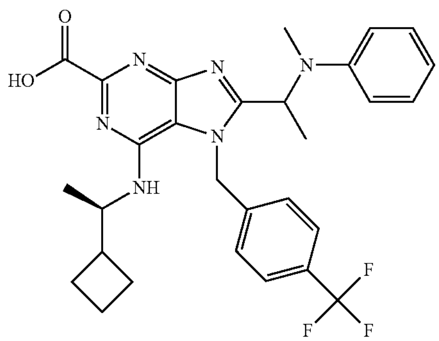 [SMILES: CC(c1nc2nc(C(=O)O)nc(N[C@H](C)C3CCC3)c2n1Cc1ccc(C(F)(F)F)cc1)N(C)c1ccccc1] | 6-{[(1R)-1-cyclobutylethyl]amino}-8-{1-[methyl(phenyl)amino]ethyl}-7-[4-(trifluoromethyl)benzyl]-7H-purine-2-carboxylic acid | | 553 | 553 |
| 10.11 | 22.1 | 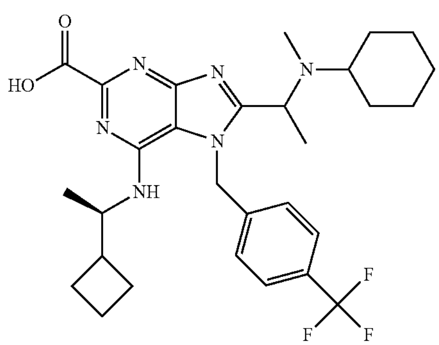 [SMILES: CC(c1nc2nc(C(=O)O)nc(N[C@H](C)C3CCC3)c2n1Cc1ccc(C(F)(F)F)cc1)N(C)C1CCCCC1] | 6-{[(1R)-1-cyclobutylethyl]amino}-8-{1-[cyclohexyl(methyl)amino]ethyl}-7-[4-(trifluoromethyl)benzyl]-7H-purine-2-carboxylic acid | | 559 | 559 |
| 10.12 | 138.8 | 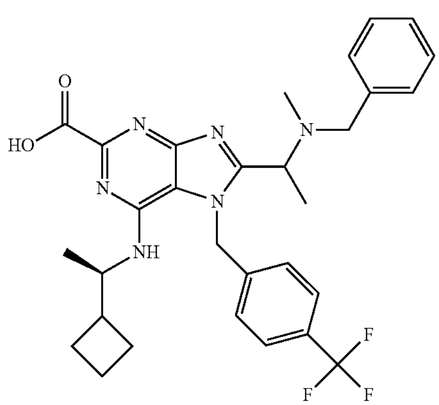 [SMILES: CC(c1nc2nc(C(=O)O)nc(N[C@H](C)C3CCC3)c2n1Cc1ccc(C(F)(F)F)cc1)N(C)Cc1ccccc1] | 8-{1-[benzyl(methyl)amino]ethyl}-6-{[(1R)-1-cyclobutylethyl]amino}-7-[4-(trifluoromethyl)benzyl]-7H-purine-2-carboxylic acid | | 567 | 567 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.13 | 47.73 | 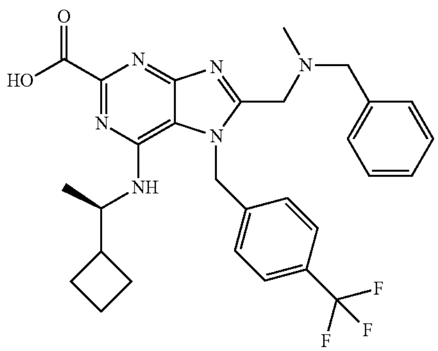 [SMILES: C[C@@H](Nc1nc(C(=O)O)nc2nc(CN(C)Cc3ccccc3)n(Cc3ccc(C(F)(F)F)cc3)c12)C1CCC1] | 8-{[benzyl(methyl)amino]methyl}-6-{[(1R)-1-cyclobutylethyl]amino}-7-[4-(trifluoromethyl)benzyl]-7H-purine-2-carboxylic acid | | 553 | 553 |
| 10.14 | 4.532 | 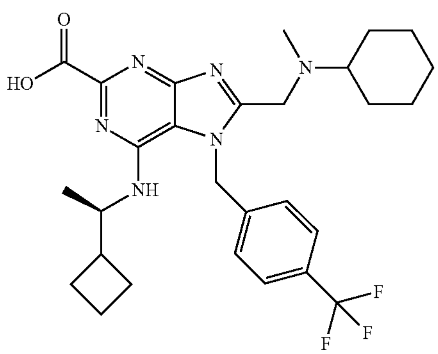 [SMILES: C[C@@H](Nc1nc(C(=O)O)nc2nc(CN(C)C3CCCCC3)n(Cc3ccc(C(F)(F)F)cc3)c12)C1CCC1] | 6-{[(1R)-1-cyclobutylethyl]amino}-8-{[cyclohexyl(methyl)amino]methyl}-7-[4-(trifluoromethyl)benzyl]-7H-purine-2-carboxylic acid | | 545 | 545 |
| 10.15 | 201.6 | 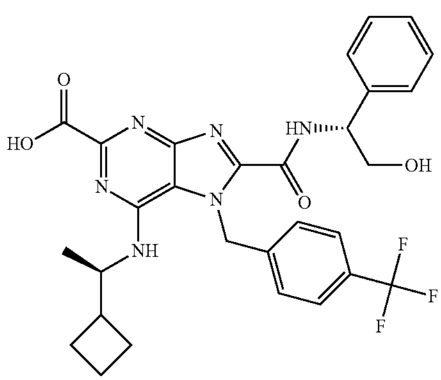 [SMILES: C[C@@H](Nc1nc(C(=O)O)nc2nc(C(=O)N[C@@H](CO)c3ccccc3)n(Cc3ccc(C(F)(F)F)cc3)c12)C1CCC1] | 6-{[(1R)-1-cyclobutylethyl]amino}-8-{[(1R)-2-hydroxy-1-phenylethyl]carbamoyl}-7-[4-(trifluoromethyl)benzyl]-7H-purine-2-carboxylic acid | | 583 | 583 |
| 10.16 | 37.05 | 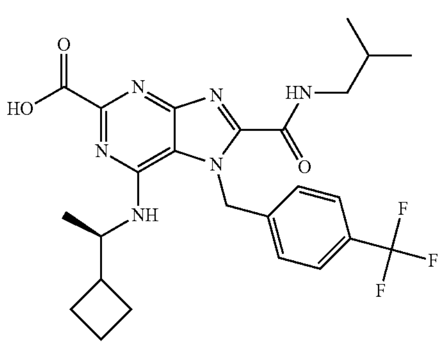 [SMILES: CC(C)CNC(=O)c1nc2nc(C(=O)O)nc(N[C@H](C)C3CCC3)c2n1Cc1ccc(C(F)(F)F)cc1] | 6-{[(1R)-1-cyclobutylethyl]amino}-8-[(2-methylpropyl)carbamoyl]-7-[4-(trifluoromethyl)benzyl]-7H-purine-2-carboxylic acid | | 519 | 519 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.17 | 67.67 | 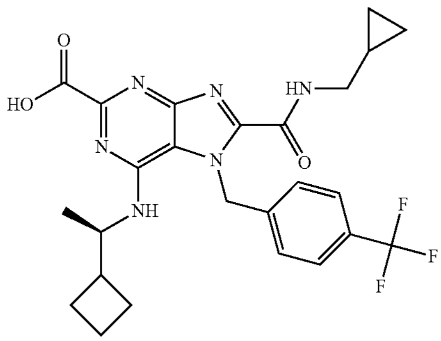 [SMILES: C[C@@H](Nc1nc(C(=O)O)nc2nc(C(=O)NCC3CC3)n(Cc3ccc(C(F)(F)F)cc3)c12)C1CCC1] | 6-{[(1R)-1-cyclobutylethyl]amino}-8-[(cyclopropylmethyl)carbamoyl]-7-[4-(trifluoromethyl)benzyl]-7H-purine-2-carboxylic acid | | 517 | 517 |
| 10.18 | 58.92 | 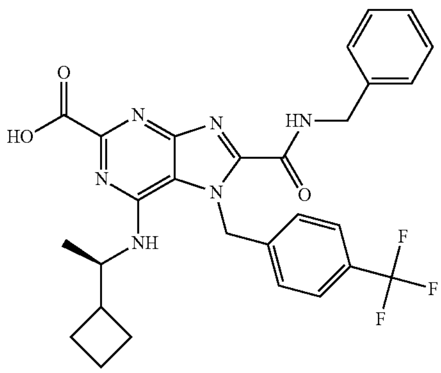 [SMILES: C[C@@H](Nc1nc(C(=O)O)nc2nc(C(=O)NCc3ccccc3)n(Cc3ccc(C(F)(F)F)cc3)c12)C1CCC1] | 8-(benzylcarbamoyl)-6-{[(1R)-1-cyclobutylethyl]amino}-7-[4-(trifluoromethyl)benzyl]-7H-purine-2-carboxylic acid | | 553 | 553 |
| 10.19 | 68.04 | 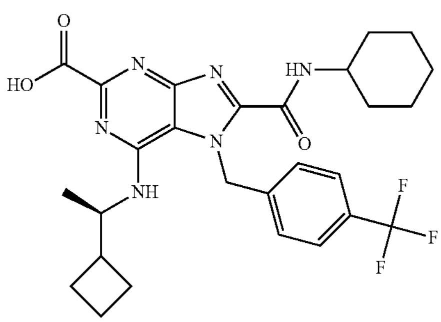 [SMILES: C[C@@H](Nc1nc(C(=O)O)nc2nc(C(=O)NC3CCCCC3)n(Cc3ccc(C(F)(F)F)cc3)c12)C1CCC1] | 6-{[(1R)-1-cyclobutylethyl]amino}-8-(cyclohexylcarbamoyl)-7-[4-(trifluoromethyl)benzyl]-7H-purine-2-carboxylic acid | | 545 | 545 |
| 10.20 | 188.9 | 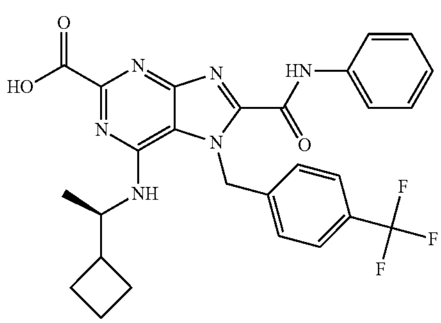 [SMILES: C[C@@H](Nc1nc(C(=O)O)nc2nc(C(=O)Nc3ccccc3)n(Cc3ccc(C(F)(F)F)cc3)c12)C1CCC1] | 6-{[(1R)-1-cyclobutylethyl]amino}-8-(phenylcarbamoyl)-7-[4-(trifluoromethyl)benzyl]-7H-purine-2-carboxylic acid | | 539 | 539 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.21 | 22.29 | 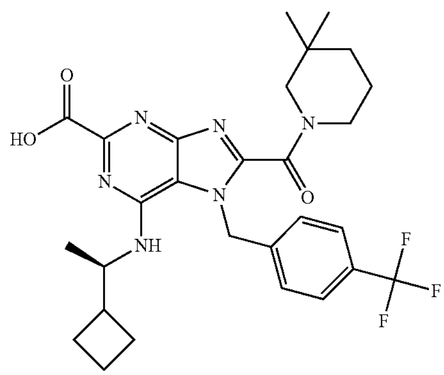 [SMILES: C[C@@H](Nc1nc(C(=O)O)nc2nc(C(=O)N3CCCC(C)(C)C3)n(Cc3ccc(C(F)(F)F)cc3)c12)C1CCC1] | 6-{[(1R)-1-cyclobutylethyl]amino}-8-[(3,3-dimethylpiperidin-1-yl)carbonyl]-7-[4-(trifluoromethyl)benzyl]-7H-purine-2-carboxylic acid | | 559 | 559 |
| 10.22 | 28.35 | 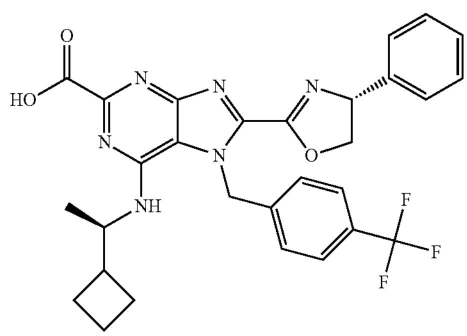 [SMILES: C[C@@H](Nc1nc(C(=O)O)nc2nc(C3=N[C@H](c4ccccc4)CO3)n(Cc3ccc(C(F)(F)F)cc3)c12)C1CCC1] | 6-{[(1R)-1-cyclobutylethyl]amino}-8-[(4R)-4-phenyl-4,5-dihydro-1,3-oxazol-2-yl]-7-[4-(trifluoromethyl)benzyl]-7H-purine-2-carboxylic acid | | 565 | 565 |
| 10.23 | 48.03 | 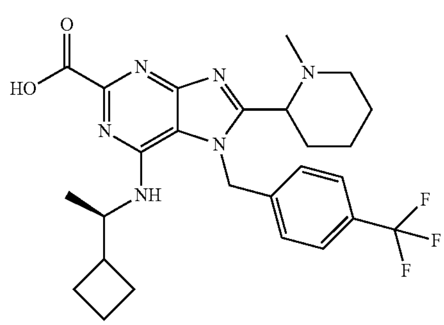 [SMILES: C[C@@H](Nc1nc(C(=O)O)nc2nc(C3CCCCN3C)n(Cc3ccc(C(F)(F)F)cc3)c12)C1CCC1] | 6-{[(1R)-1-cyclobutylethyl]amino}-8-(1-methylpiperidin-2-yl)-7-[4-(trifluoromethyl)benzyl]-7H-purine-2-carboxylic acid | | 517 | 517 |
| 10.24 | 96.29 | 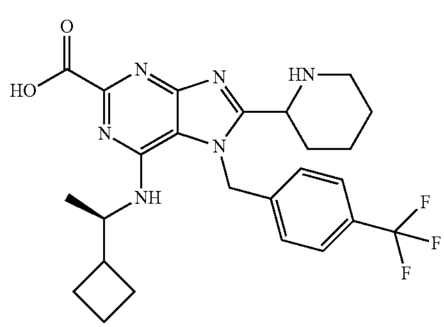 [SMILES: C[C@@H](Nc1nc(C(=O)O)nc2nc(C3CCCCN3)n(Cc3ccc(C(F)(F)F)cc3)c12)C1CCC1] | 6-{[(1R)-1-cyclobutylethyl]amino}-8-piperidin-2-yl-7-[4-(trifluoromethyl)benzyl]-7H-purine-2-carboxylic acid | | 503 | 503 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.25 | 35.38 | 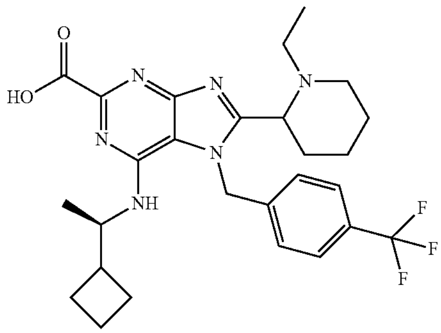 [SMILES: CCN1CCCCC1c1nc2nc(C(=O)O)nc(N[C@H](C)C3CCC3)c2n1Cc1ccc(C(F)(F)F)cc1] | 6-{[(1R)-1-cyclobutylethyl]amino}-8-(1-ethylpiperidin-2-yl)-7-[4-(trifluoromethyl)benzyl]-7H-purine-2-carboxylic acid | | 531 | 531 |
| 10.26 | 1.937 | 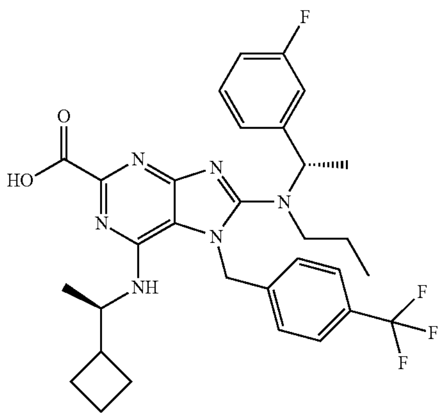 [SMILES: CCCN(c1nc2nc(C(=O)O)nc(N[C@H](C)C3CCC3)c2n1Cc1ccc(C(F)(F)F)cc1)[C@@H](C)c1cccc(F)c1] | 6-{[(1R)-1-cyclobutylethyl]amino}-8-{[(1S)-1-(3-fluorophenyl)ethyl](propyl)amino}-7-[4-(trifluoromethyl)benzyl]-7H-purine-2-carboxylic acid | | 599 | 599 |
| 10.27 | 9.844 | 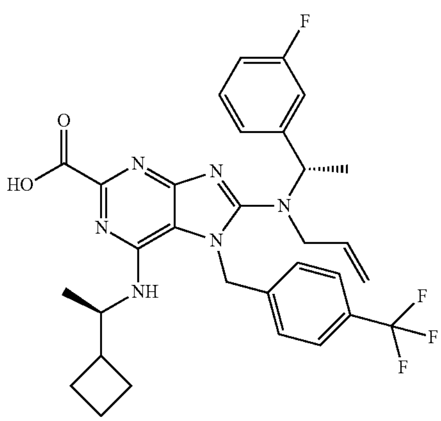 [SMILES: C=CCN(c1nc2nc(C(=O)O)nc(N[C@H](C)C3CCC3)c2n1Cc1ccc(C(F)(F)F)cc1)[C@@H](C)c1cccc(F)c1] | 6-{[(1R)-1-cyclobutylethyl]amino}-8-{[(1S)-1-(3-fluorophenyl)ethyl](prop-2-en-1-yl)amino}-7-[4-(trifluoromethyl)benzyl]-7H-purine-2-carboxylic acid | | 597 | 597 |
| 10.28 | 22.17 | 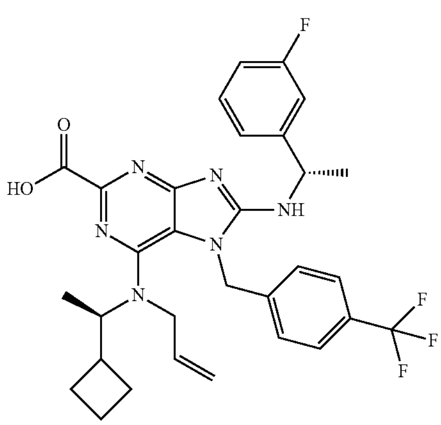 [SMILES: C=CCN(c1nc(C(=O)O)nc2nc(N[C@@H](C)c3cccc(F)c3)n(Cc3ccc(C(F)(F)F)cc3)c12)[C@H](C)C1CCC1] | 6-{[(1R)-1-cyclobutylethyl](prop-2-en-1-yl)amino}-8-{[(1S)-1-(3-fluorophenyl)ethyl]amino}-7-[4-(trifluoromethyl)benzyl]-7H-purine-2-carboxylic acid | | 597 | 597 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.29 | 35.27 | 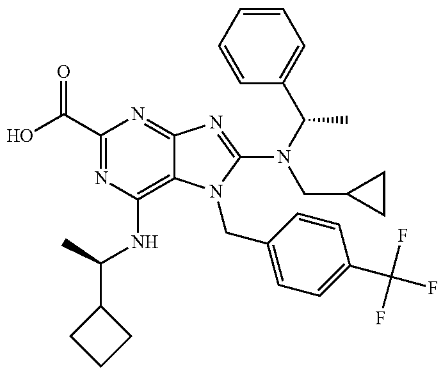 [SMILES: C[C@@H](Nc1nc(C(=O)O)nc2nc(N(CC3CC3)[C@@H](C)c3ccccc3)n(Cc3ccc(C(F)(F)F)cc3)c12)C1CCC1] | 6-{[(1R)-1-cyclobutylethyl]amino}-8-{(cyclopropylmethyl)[(1S)-1-phenylethyl]amino}-7-[4-(trifluoromethyl)benzyl]-7H-purine-2-carboxylic acid | | 593 | 593 |
| 10.30 | 9.072 | 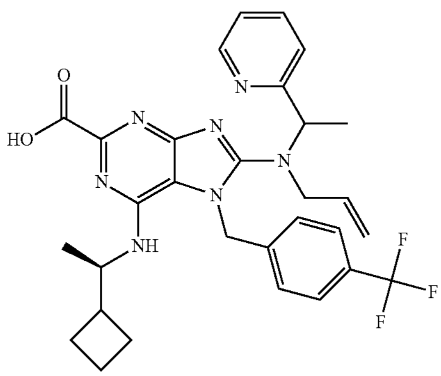 [SMILES: C=CCN(c1nc2nc(C(=O)O)nc(N[C@H](C)C3CCC3)c2n1Cc1ccc(C(F)(F)F)cc1)C(C)c1ccccn1] | 6-{[(1R)-1-cyclobutylethyl]amino}-8-[prop-2-en-1-yl(1-pyridin-2-ylethyl)amino]-7-[4-(trifluoromethyl)benzyl]-7H-purine-2-carboxylic acid | | 580 | 580 |
| 10.31 | 54.93 | 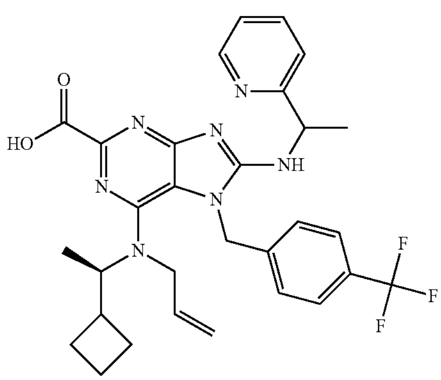 [SMILES: C=CCN(c1nc(C(=O)O)nc2nc(NC(C)c3ccccn3)n(Cc3ccc(C(F)(F)F)cc3)c12)[C@H](C)C1CCC1] | 6-{[(1R)-1-cyclobutylethyl](prop-2-en-1-yl)amino}-8-[(1-pyridin-2-ylethyl)amino]-7[4-(trifluoromethyl)benzyl]-7H-purine-2-carboxylic acid | | 580 | 580 |
| 10.32 | 3.719 | 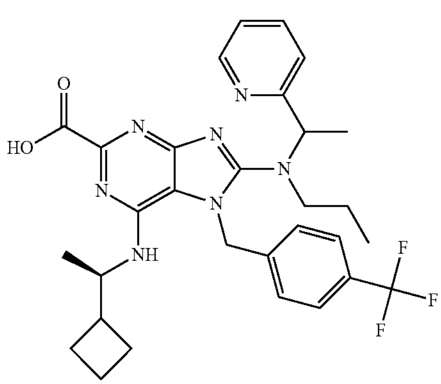 [SMILES: CCCN(c1nc2nc(C(=O)O)nc(N[C@H](C)C3CCC3)c2n1Cc1ccc(C(F)(F)F)cc1)C(C)c1ccccn1] | 6-{[(1R)-1-cyclobutylethyl]amino}-8-[propyl(1-pyridin-2-ylethyl)amino]-7-[4-(trifluoromethyl)benzyl]-7H-purine-2-carboxylic acid | | 582 | 582 |

TABLE 10-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 10.33 | 17.74 | 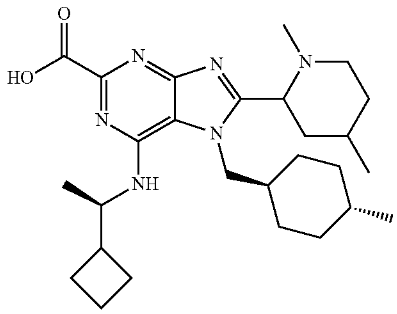 [SMILES: CC1CCN(C)C(c2nc3nc(C(=O)O)nc(N[C@H](C)C4CCC4)c3n2C[C@H]2CC[C@H](C)CC2)C1] | 6-{[(1R)-1-cyclobutylethyl]amino}-8-(1,4-dimethylpiperidin-2-yl)-7-[(trans-4-methylcyclohexyl)methyl]-7H-purine-2-carboxylic acid | | 483 | 483 |
| 10.34 | 5.983 | 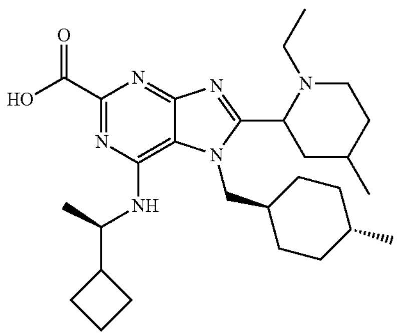 [SMILES: CCN1CCC(C)CC1c1nc2nc(C(=O)O)nc(N[C@H](C)C3CCC3)c2n1C[C@H]1CC[C@H](C)CC1] | 6-{[(1R)-1-cyclobutylethyl]amino}-8-(1-ethyl-4-methylpiperidin-2-yl)-7-[(trans-4-methylcyclohexyl)methyl]-7H-purine-2-carboxylic acid | | 497 | 497 |

Preparative Example 11.1

(trans-4-methylcyclohexyl)methanol

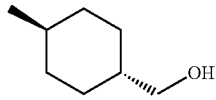

To a solution of trans-4-methylcyclohexanecarboxylic acid (113.6 g, 0.8 mmol) in dry tetrahydrofuran (800 mL) was added borane in tetrahydrofuran (1M, 800 mL, 0.8 mol) dropwise at 0° C. under nitrogen atmosphere over 1 h. Then the reaction mixture was warmed to room temperature and stirred for 8 h. The reaction solution was quenched with NH$_4$Cl solution at 0° C., diluted with water (2 L) and then extracted with ethyl acetate (1 L×3). The organic layer was washed with water (2×1 L) and brine (1 L), dried over anhydrous Na$_2$SO$_4$, filtered and concentrated to give (trans-4-methylcyclohexyl)methanol, which was used for next step without further purification.

Preparative Example 11.2 trans-1-(bromomethyl)-4-methylcyclohexane

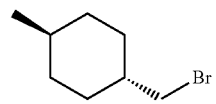

To a solution of (trans-4-methylcyclohexyl)methanol (150 g, 1.17 mol) and CBr$_4$ (450 g, 1.35 mol) in dichloromethane (1.0 L) was added PPh$_3$ (300 g, 1.17 mol) dissolved in dichloromethane (0.5 L) dropwise at 0° C. over 1 h. The mixture was stirred at room temperature for 12 h. The reaction mixture was filtered and the filtrate was concentrated. The residue was diluted with hexane:EtOAc (9:1) (3 L) and stirred for 1 h. The solids were filtered off and the filtrate was concentrated to give trans-1-(bromomethyl)-4-methylcyclohexane, which was used for next step without further purification.

Preparative Example 11.3

3-methyl-7-((trans-4-methylcyclohexyl)methyl)-1H-purine-2,6(3H,7H)-dione

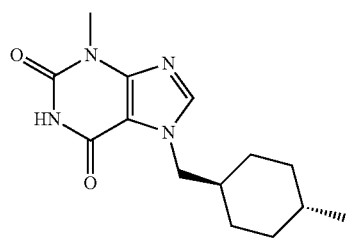 [SMILES: Cn1c(=O)[nH]c(=O)c2c1ncn2C[C@H]1CC[C@H](C)CC1]

A suspension of 3-methyl-1H-purine-2,6(3H,7H)-dione (100 g, 0.60 mol), trans-1-(bromomethyl)-4-methylcyclohexane (160 g, 0.84 mol) and sodium carbonate (192 g, 1.81 mol) in anhydrous DMF (900 mL) and DMSO (900 mL) was stirred at 100° C. for 24 h. The reaction mixture was cooled to room temperature and poured into ice water. The mixture was filtered and the filter cake was washed with cold water and dried to give 3-methyl-7-((trans-4-methylcyclohexyl)methyl)-1H-purine-2,6(3H,7H)-dione. $^1$H NMR (400 MHz, DMSO-d$_6$) δ: 11.04 (s, 1H), 7.96 (s, 1H), 4.02-4.00 (d, J=7.2 Hz, 2H), 3.32 (s, 3H), 1.69-0.79 (m, 13H).

Preparative Example 11.4

2,6-dichloro-7-((trans-4-methylcyclohexyl)methyl)-7H-purine

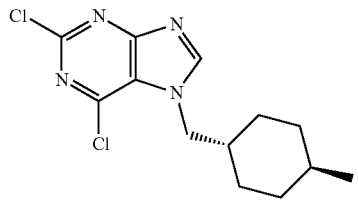 [SMILES: C[C@H]1CC[C@H](Cn2cnc3nc(Cl)nc(Cl)c32)CC1]

To a suspension of 3-methyl-7-((trans-4-methylcyclohexyl)methyl)-1H-purine-2,6(3H,7H)-dione (150 g, 0.54 mol) in POCl$_3$ (900 mL) was added DBU (300 mL) at 60° C. The reaction mixture was heated at 120° C. for 5 h. Reaction mixture was cooled to ambient temperature and excess POCl$_3$ was removed by evaporation under reduced pressure. The residue was poured into water slowly and the pH of the solution was adjusted to neutral using NaOH. The aqueous solution was then extracted with dichloromethane, the combined organic layers were dried over Na$_2$SO$_4$, filtered, and concentrated. The residue was purified by silica gel column chromatography to afford 2,6-dichloro-7-((trans-4-methylcyclohexyl)methyl)-7H-purine. $^1$H NMR (400 MHz, CDCl$_3$) δ: 8.19 (s, 1H), 4.27-4.25 (d, J=7.6 Hz, 2H), 1.78-0.83 (m, 13H).

Preparative Example 11.5

2-chloro-N-[(1R)-1-cyclobutylethyl]-7-[(trans-4-methylcyclohexyl)methyl]-5,7-dihydro-4H-purin-6-amine

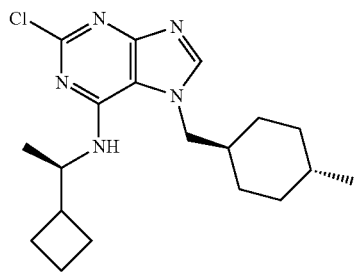 [SMILES: C[C@@H](Nc1nc(Cl)nc2ncn(C[C@H]3CC[C@H](C)CC3)c12)C1CCC1]

Into a 3000-mL 3-necked round-bottom flask was placed a solution of 2,6-dichloro-7-[(trans-4-methylcyclohexyl)methyl]-7H-purine (129 g, 418.22 mmol, 97%) in IPA (1000 mL). This was followed by the addition of triethylamine (52.4 g, 517.84 mmol) at 25° C. Next was added (1R)-1-cyclobutylethan-1-amine hydrochloride (62 g, 457.11 mmol) at 25° C. The resulting solution was stirred overnight at 90° C. in an oil bath. The reaction was then cooled and concentrated under vacuum. The residue was diluted with 1000 mL of water. The resulting mixture was extracted with ethyl acetate (3×1000 mL). The organic layers were combined, washed with brine (1×1000 mL), dried over anhydrous sodium sulfate and concentrated under vacuum. The residue was purified via silica gel column chromatography eluting with dichloromethane:methanol (40:1) to afford 2-chloro-N-[(1R)-1-cyclobutylethyl]-7-[(trans-4-methylcyclohexyl)methyl]-5,7-dihydro-4H-purin-6-amine.

Preparative Example 11.6

6-[[(1R)-1-cyclobutylethyl]amino]-7-[(trans-4-methylcyclohexyl)methyl]-7H-purine-2-carbonitrile

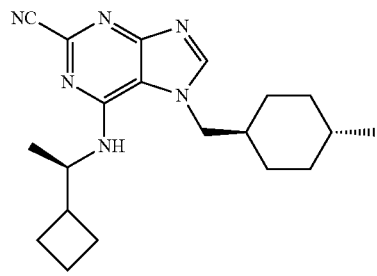 [SMILES: C[C@@H](Nc1nc(C#N)nc2ncn(C[C@H]3CC[C@H](C)CC3)c12)C1CCC1]

Into each of twenty 20-mL vials purged and maintained with an inert atmosphere of nitrogen was added a solution of 2-chloro-N-[(1R)-1-cyclobutylethyl]-7-[(trans-4-methylcyclohexyl)methyl]-7H-purin-6-amine (3 g, 8.04 mmol, 97%) in DMA (18 mL), followed by the addition of Zn(CN)$_2$ (1.26 g, 10.77 mmol) at 25° C. To the suspension was added X-phos (1.025 g, 2.15 mmol) at 25° C. and allylpalladium (II) chloride dimer (303 mg, 0.83 mmol) at 25° C. The reaction mixtures were irradiated in a microwave for 1 hr at 150° C. and then cooled to room temperature. The 20 batches were combined and diluted with 200 mL of EA and 100 mL of aq. sodium bicarbonate. The solids were removed by filtration. The filtrate was extracted with 3×500 mL of ethyl acetate. The organic layers were combined, washed with brine (1×1000 mL), dried over anhydrous sodium sulfate, and concentrated under vacuum. The residue was purified via column chromatography on silica gel eluting with ethyl acetate:petroleum ether (1:2) to afford 6-[[(1R)-1-cyclobutylethyl]amino]-7-[(trans-4-methylcyclohexyl)methyl]-7H-purine-2-carbonitrile. MS ESI calc'd. for C$_{20}$H$_{28}$N$_6$ [M+H]$^+$ 353. found 353. $^1$H NMR (400 MHz, DMSO-d6): δ 8.45 (1H, s), 6.68-6.71 (1H, d, J=11.6 Hz), 4.58-4.65 (1H, m), 4.31-4.33 (1H, m), 4.13-4.20 (1H, m), 2.54-2.59 (1H, m), 1.49-2.03 (10H, m), 1.12-1.25 (5H, m), 0.91-1.02 (2H, m), 0.64-0.81 (5H, m).

Preparative Example 11.7

8-bromo-6-(((R)-1-cyclobutylethyl)amino)-7-((trans-4-methylcyclohexyl)methyl)-7H-purine-2-carbonitrile

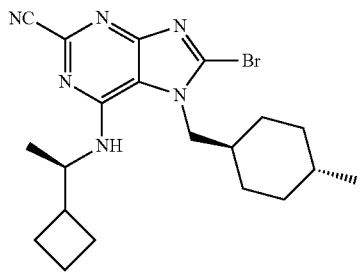 [SMILES: C[C@@H](Nc1nc(C#N)nc2nc(Br)n(C[C@H]3CC[C@H](C)CC3)c12)C1CCC1]

Into a 500-mL 3-necked round-bottom flask purged and maintained with an inert atmosphere of nitrogen was placed a solution of 6-(((R)-1-cyclobutylethyl)amino)-7-((trans-4-methylcyclohexyl)methyl)-7H-purine-2-carbonitrile (16 g, 45.5 mmol) in chloroform (200 mL), and NBS (40.4 g, 227 mmol) was added. The resulting solution was heated to reflux for 6 hr. The reaction was cooled to room temperature and diluted with 500 mL of DCM. The resulting mixture was washed with Na$_2$SO$_3$ (aq) (1×500 mL) and brine (1×500 mL). The organic layer was dried over anhydrous sodium sulfate and concentrated under vacuum. The residue was purified via column chromatography on silica gel eluting with ethyl acetate:petroleum ether (1:10-1:2) to afford 8-bromo-6-(((R)-1-cyclobutylethyl)amino)-7-((trans-4-methylcyclohexyl)methyl)-7H-purine-2-carbonitrile. MS ESI calc'd. for C$_{20}$H$_{27}$BrN$_6$ [M+H]$^+$ 431. found 431.

Preparative Example 11.8

8-bromo-6-(((R)-1-cyclobutylethyl)amino)-N-hydroxy-7-((trans-4-methylcyclohexyl)methyl)-7H-purine-2-carboximidamide

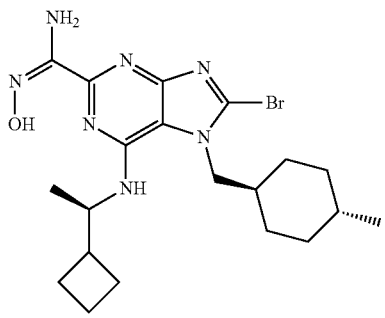 [SMILES: C[C@@H](Nc1nc(/C(N)=N\O)nc2nc(Br)n(C[C@H]3CC[C@H](C)CC3)c12)C1CCC1]

Into a 1000-mL pressure reactor was placed a solution of hydroxylamine hydrochloride (4.8 g, 69.07 mmol) in water (120 mL), sodium methoxide (8.7 g, 103.56 mmol), and a solution of 8-bromo-6-(((R)-1-cyclobutylethyl)amino)-7-((trans-4-methylcyclohexyl)methyl)-7H-purine-2-carbonitrile (15 g, 34.85 mmol) in ethanol (360 mL). The reaction was stirred for 3 h at 100° C. The reaction was then cooled to room temperature and diluted with 500 mL of DCM. The resulting mixture was washed with water (1×500 mL) and brine (1×500 mL). The organic phase was dried over anhydrous sodium sulfate and concentrated under vacuum to afford 8-bromo-6-(((R)-1-cyclobutylethyl)amino)-N-hydroxy-7-((trans-4-methylcyclohexyl)methyl)-7H-purine-2-carboximidamide.

Preparative Example 11.9

3-(8-bromo-6-(((R)-1-cyclobutylethyl)amino)-7-((trans-4-methylcyclohexyl)methyl)-7H-purin-2-yl)-1,2,4-oxadiazol-5(4H)-one

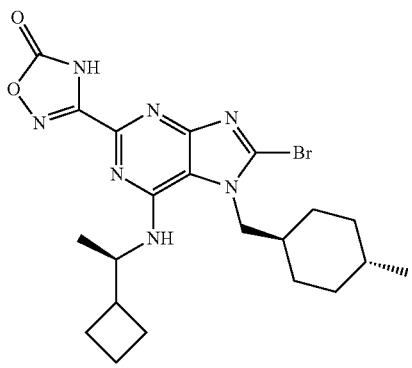 [SMILES: C[C@@H](Nc1nc(-c2noc(=O)[nH]2)nc2nc(Br)n(C[C@H]3CC[C@H](C)CC3)c12)C1CCC1]

Into a 1000-mL 4-necked round-bottom flask purged and maintained with an inert atmosphere of nitrogen was placed a solution of 8-bromo-6-(((R)-1-cyclobutylethyl)amino)-N-hydroxy-7-((trans-4-methylcyclohexyl)methyl)-7H-purine-2-carboximidamide (14.2 g, 30.6 mmol) in CH$_3$CN (430 mL), CDI (7.43 g, 45.8 mmol), and DBU (18.6 g, 122.4 mmol). The resulting solution was stirred overnight at room temperature. The reaction was diluted with DCM (500 mL), and then washed with HCl (1 M) (1×500 mL), H$_2$O (1×500 mL) and brine (1×500 mL). The organics were dried over anhydrous sodium sulfate and concentrated under vacuum to afford 3-(8-bromo-6-(((R)-1-cyclobutylethyl)amino)-7-((trans-4-methylcyclohexyl)methyl)-7H-purin-2-yl)-1,2,4-oxadiazol-5(4H)-one. MS ESI calc'd. for C$_{21}$H$_{28}$BrN$_7$O$_2$ [M+H]$^+$ 490. found 490. $^1$H NMR (300 MHz, CDCl$_3$) δ 0.6-0.9 (5H, m), 1.0-1.2 (5H, m), 1.2-1.3 (2H, m), 1.5-2.1 (11H, m), 4.1-4.2 (1H, m), 4.5-4.6 (2H, m), 6.6 (1H, d), 12.9 (1H, s).

Example 11.1

6-(((R)-1-cyclobutylethyl)amino)-8-(2,3-dimethylpiperidin-1-yl)-7-((trans-4-methylcyclohexyl)methyl)-7H-purine-2-carboxylic acid

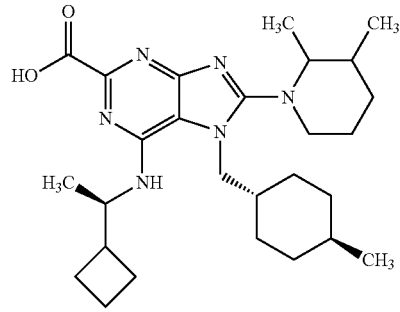 [SMILES: CC1CCCN(c2nc3nc(C(=O)O)nc(N[C@H](C)C4CCC4)c3n2C[C@H]2CC[C@H](C)CC2)C1C]

Step 1: To a stirred solution of 2,3 lutidine (3.00 g, 27.9 mmol) in acetic acid (25 mL) was added PtO$_2$ (600 mg, 2.60 mmol) and the reaction was degassed with H$_2$ for 30 minutes then held under 50 psi of H$_2$ for 16 hours at ambient temperature. The reaction mixture was then diluted with water, basified with 40% aq NaOH, and extracted with diethyl ether (30 mL). The organic layer was dried over anhydrous Na$_2$SO$_4$, filtered, and concentrated to afford 2,3-dimethylpiperidine (crude). $^1$H NMR (400 MHz, CDCl$_3$) δ 3.44 (m, 1H), 2.98-3.11 (m, 2H), 1.78-1.87 (m, 2H), 1.59-1.74 (m, 3H), 1.50 (m, 1H), 1.32 (d, J=6.8 Hz, 3H), 0.97 (d, J=6.8 Hz, 3H).

Step 2: Using a procedure analogous to that described in Example 9.3, and starting with Preparative Example 11.7, 8-bromo-6-(((R)-1-cyclobutylethyl)amino)-7-((trans-4-methylcyclohexyl)methyl)-7H-purine-2-carbonitrile, 6-(((R)-1-cyclobutylethyl)amino)-8-(2,3-dimethylpiperidin-1-yl)-7-((trans-4-methylcyclohexyl)methyl)-7H-purine-2-carboxylic acid was prepared. $^1$H NMR (400 MHz, CD$_3$OD) δ 4.15 (m, 1H), 3.82-3.95 (m, 2H), 3.40-3.56 (m, 2H), 2.51 (m, 1H), 1.86-2.18 (m, 7H), 1.45-1.86 (m, 7H), 1.06-1.22 (m, 7H), 0.62-1.03 (m, 13H). MS (ES)=483 (M+1)$^+$.

Example 11.2

6-(((R)-1-cyclobutylethyl)amino)-8-(2-isobutylpiperidin-1-yl)-7-((trans-4-methylcyclohexyl)methyl)-7H-purine-2-carboxylic acid

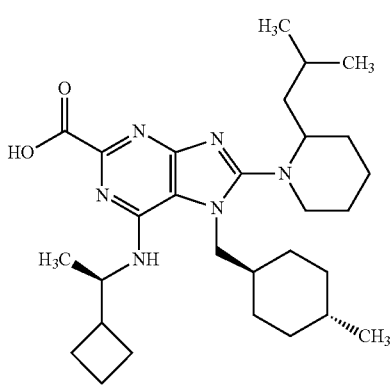 [SMILES: CC(C)CC1CCCCN1c1nc2nc(C(=O)O)nc(N[C@H](C)C3CCC3)c2n1C[C@H]1CC[C@H](C)CC1]

Step 1: Isopropyl magnesium chloride (2 M in hexanes; 44.8 mL, 89.7 mmol) was added dropwise to a solution of pyridine-2-aldehyde (14.9 mL, 89.7 mmol) in anhydrous THF (75 mL) at −10° C. The reaction mixture was stirred at −10° C. for 30 minutes and then warmed to room temperature. The reaction mixture was stirred at room temperature for 12 hours and then quenched with a saturated aqueous NH$_4$Cl solution. The layers were separated and the aqueous layer was extracted with EtOAc (3×100 mL). The combined organic layers were washed with brine (100 mL), dried over anhydrous Na$_2$SO$_4$, filtered and concentrated in vacuo. The crude residue was stirred with hexanes (20 mL) and filtered. The filtrate was concentrated to afford 2-methyl-1-(pyridin-2-yl)propan-1-ol. MS (APCI)=152 (M+1)$^+$.

Step 2: 2-methyl-1-(pyridin-2-yl)propan-1-ol (10 g, 66 mmol) was dissolved in anhydrous THF. SOCl$_2$ was added and the reaction was heated to reflux for 2 hours. The reaction was cooled, concentrated and quenched with crushed ice/water. The mixture was extracted with EtOAc (3×100 mL). The combined organic layers were washed with brine (100 mL), dried over anhydrous Na$_2$SO$_4$, filtered and concentrated in vacuo. The crude residue was stirred with hexanes (20 mL), filtered and then the filtrate was concentrated to afford 2-(2-methylprop-1-en-1-yl)pyridine. MS (APCI)=134 (M+1)$^+$ Step 3: To a stirred solution of 2-(2-methylprop-1-en-1-yl)pyridine (2.1 g, 17.3 mmol) in acetic acid (25 mL) was added PtO$_2$ (197 mg) and the reaction mixture was held under 50 psi of H$_2$ for 16 hours at ambient temperature. The reaction mixture was filtered through celite, the filtrate was concentrated, and the residue was dissolved in EtOAc (200 mL). The organic layer was washed with 20% NaOH solution (2×100 mL) and brine (100 mL). The organic layer was dried over Na$_2$SO$_4$, filtered, and concentrated to afford 2-isobutylpiperidine. $^1$H NMR (300 MHz, CDCl$_3$) δ 4.79 (m, 1H), 4.12 (m, 2H), 2.63-2.66 (m, 2H), 2.40-2.48 (m, 2H), 2.01-2.13 (m, 4H), 1.20-1.26 (m, 1H), 1.07 (d, J=4.5 Hz, 6H).

Step 4: Using a procedure analogous to that described for the synthesis of Example 9.3, and starting with Preparative Example 11.7, 8-bromo-6-(((R)-1-cyclobutylethyl)amino)-7-((trans-4-methylcyclohexyl)methyl)-7H-purine-2-carbonitrile, 6-(((R)-1-cyclobutylethyl)amino)-8-(2-isobutylpiperidin-1-yl)-7-((trans-4-methylcyclohexyl)methyl)-7H-purine-2-carbonitrile was prepared. $^1$H NMR (300 MHz, CDCl$_3$) δ 4.39-4.42 (m, 1H), 4.24-4.26 (m, 1H), 3.72-3.79 (m, 3H), 3.55-3.57 (m, 1H), 3.31-3.33 (m, 1H), 2.47-2.53 (m, 1H), 2.01-2.10 (m, 3H), 1.81-1.88 (m, 5H), 1.51-1.58 (m, 6H), 1.42-1.78 (m, 5H), 1.11-1.21 (m, 2H), 1.19 (d, J=6.0 Hz, 3H), 0.96-1.04 (m, 1H), 0.88-0.98 (m, 6H), 0.81-0.84 (m, 3H), 0.63-0.75 (m, 2H). MS (ES)=492 (M+1)$^+$.

Step 5: To a solution of 6-(((R)-1-cyclobutylethyl)amino)-8-(2-isobutylpiperidin-1-yl)-7-((trans-4-methylcyclohexyl)methyl)-7H-purine-2-carbonitrile (50 mg, 0.10 mmol) in ethanol (2.0 mL) and water (0.2 mL) was added sodium hydroxide (80 mg, 2.0 mmol) and the reaction was heated at reflux for 4 hours. The reaction mixture was cooled to room temperature and acidified with aqueous HCl (1 M) to pH 2. The aqueous layer was extracted with EtOAc and the organic layer was washed with water and brine, dried over anhydrous Na$_2$SO$_4$, filtered, and concentrated in vacuo. Purification of the resultant residue by silica gel chromatography (0 to 2% MeOH/CH$_2$Cl$_2$) afforded 6-(((R)-1-cyclobutylethyl)amino)-8-(2-isobutylpiperidin-1-yl)-7-((trans-4-methylcyclohexyl)methyl)-7H-purine-2-carboxylic acid. $^1$H NMR (300 MHz, CD$_3$OD) δ 4.29 (m, 0.5H), 3.94-4.12 (m, 2H), 3.68-3.77 (m, 0.5H), 3.38-3.56 (m, 2H), 2.47-2.53 (m, 1H), 1.90-2.11 (m, 2H), 1.81-1.88 (m, 5H), 1.72-1.79 (m, 6H), 1.62-1.78 (m, 5H), 1.23-1.28 (m, 2H), 1.19 (d, J=6.0 Hz, 3H), 0.96-1.04 (m, 1H), 0.88-0.98 (m, 6H), 0.81-0.84 (m, 6H), 0.63-0.75 (m, 2H). MS (ES)=511 (M+1)$^+$.

Example 11.3

3-(6-(((R)-1-cyclobutylethyl)amino)-8-(2-isobutylpiperidin-1-yl)-7-((trans-4-methylcyclohexyl)methyl)-7H-purine-2-yl)-1,2,4-oxadiazol-5(4H)-one

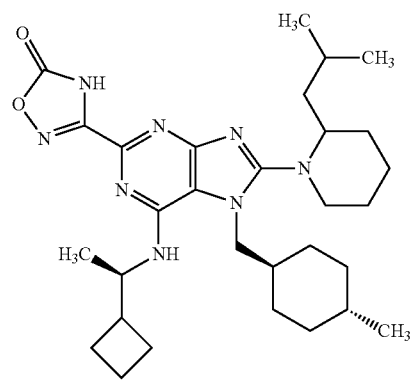 [SMILES: CC(C)CC1CCCCN1c1nc2nc(-c3noc(=O)[nH]3)nc(N[C@H](C)C3CCC3)c2n1C[C@H]1CC[C@H](C)CC1]

Step 1: To a solution of hydroxylamine hydrochloride (55 mg, 0.79 mmol) and water (0.7 mL) was added NaHCO$_3$ (87 mg, 1.04 mmol) and the mixture was stirred for 10 minutes. Next was added a solution of 6-(((R)-1-cyclobutylethyl)amino)-8-(2-isobutylpiperidin-1-yl)-7-((trans-4-methylcyclohexyl)methyl)-7H-purine-2-carbonitrile (Example 11.2, Step 4; 299 mg, 0.61 mmol) in EtOH (1.0 mL) and the reaction was then heated at 100° C. for 1 hour. The reaction mixture was concentrated to dryness. Water (10 mL) was added and the solids were collected by filtration. Air drying of the solids afforded 6-(((R)-1-cyclobutylethyl)amino)-N'- hydroxy-8-(2-isobutylpiperidin-1-yl)-7-((trans-4-methylcyclohexyl)methyl)-7H-purine-2-carboximidamide. MS (APCI)=525 (M+1)$^+$.

Step 2: CDI (94 mg, 0.58 mmol) was added to a solution of 6-(((R)-1-cyclobutylethyl)amino)-N-hydroxy-8-(2-isobutylpiperidin-1-yl)-7-((trans-4-methylcyclohexyl)methyl)-7H-purine-2-carboximidamide (250 mg, 0.53 mmol) in acetonitrile (4.0 mL) at room temperature. The reaction mixture was stirred at room temperature for 1 hour, and then concentrated to dryness. The residue was dissolved in CH$_2$Cl$_2$ (10 mL) and the organic layer was washed with brine, dried over anhydrous Na$_2$SO$_4$, filtered and concentrated. Purification of the residue on a RediSep 12 g silica gel column (0 to 5% MeOH/CH$_2$Cl$_2$) afforded 3-(6-(((R)-1-cyclobutylethyl)amino)-8-(2-isobutylpiperidin-1-yl)-7-((trans-4-methyl cyclohexyl)methyl)-7H-purine-2-yl)-1,2,4-oxadiazol-5(4H)-one. $^1$H NMR (300 MHz, CD$_3$OD) δ 4.57-4.67 (m, 2H), 4.31 (dd, J=15.0, 6.0 Hz, 0.5H), 4.15-4.05 (m, 0.5H), 3.85-3.94 (m, 1H), 3.68-3.76 (m, 1H), 3.37-3.41 (m, 2H), 2.47-2.53 (m, 1H), 2.04-2.08 (m, 1H), 1.78-1.96 (m, 7H), 1.45-1.75 (m, 12H), 1.16 (t, J=6.0 Hz, 3H), 0.95-1.04 (m, 8H), 0.84 (d, J=6.0 Hz, 3H), 0.69-0.73 (m, 2H). MS (APCI)=551 (M+1)$^+$.

Example 11.4

6-(((R)-1-cyclobutylethyl)amino)-8-(2-cyclohexylpiperidin-1-yl)-7-((trans-4-methylcyclohexyl)methyl)-7H-purine-2-carboxylic acid

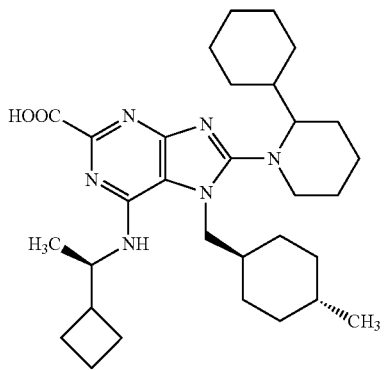 [SMILES: C[C@@H](Nc1nc(C(=O)O)nc2nc(N3CCCCC3C3CCCCC3)n(C[C@H]3CC[C@H](C)CC3)c12)C1CCC1]

Step 1: A microwave vial (15 mL) was charged with 2-bromo pyridine (500 mg, 3.16 mmol), cyclohexene boronic acid (398 mg, 3.16 mmol) and aqueous Na$_2$CO$_3$ (1.55 mL, 1 M). 1,4-dioxane (4.5 mL) was added to the vial and the mixture was degassed using N$_2$ for 15 minutes before Pd(PPh$_3$)$_4$ (36.5 mg, 0.031 mmol) was added to the vial. The reaction was heated at 120° C. under microwave irradiation for 15 minutes. The reaction was cooled to room temperature and extracted with EtOAc (100 mL). The organic layer was washed with water and brine, and dried over anhydrous Na$_2$SO$_4$ and concentrated to dryness. The crude product was purified on a RediSep 12 g silica gel column (0 to 100% EtOAc/hexanes) to afford 2-(cyclohex-1-en-1-yl)pyridine. MS (APCI)=160 (M+1)$^+$.

Step 2: To a stirred solution of 2-(cyclohex-1-en-1-yl) pyridine (2.76 g, 17.4 mmol) in acetic acid (25 mL) was added PtO$_2$ (197 mg) and reaction mixture was held under 50 psi of H$_2$ for 16 hours. The reaction mixture was filtered through celite, the filtrate was concentrated, and the residue was dissolved in EtOAc (200 mL). The organic layer was washed with 20% NaOH solution (2×100 mL) and brine (100 mL). The organic layer was dried over anhydrous Na$_2$SO$_4$, filtered, and concentrated to afford 2-cyclohexylpiperidine. $^1$H NMR (300 MHz, CDCl$_3$) δ3.51-3.53 (m, 1H), 2.69-2.79 (m, 2H), 1.50-1.52 (m, 10H), 1.44-1.49 (m, 6H), 1.02-1.08 (m, 2H).

Step 3: Using a procedure analogous to that described for the synthesis of Example 9.3 and starting with Preparative Example 11.7, 8-bromo-6-(((R)-1-cyclobutylethyl)amino)-7-((trans-4-methylcyclohexyl)methyl)-7H-purine-2-carbonitrile, 6-(((R)-1-cyclobutylethyl)amino)-8-(2-cyclohexylpiperidin-1-yl)-7-((trans-4-methylcyclohexyl)methyl)-7H-purine-2-carbonitrile was prepared. $^1$H NMR (400 MHz, CD$_3$OD) δ 4.61-4.79 (m, 2H), 4.05-4.12 (m, 4H), 3.61-3.79 (m, 2H), 3.58 (m, 1H), 3.43 (m, 1H), 2.58 (m, 1H), 2.41 (m, 1H), 1.81-1.97 (m, 6H), 1.42-1.78 (m, 8H), 1.39-1.42 (m, 2H), 1.25-1.32 (m, 3H), 1.16-1.25 (m, 12H), 0.79-0.85 (m, 3H). MS (ES)=518 (M+1)$^+$.

Step 4: Using a procedure analogous to that described for the synthesis of Example 11.2, and starting with 6-(((R)-1-cyclobutylethyl)amino)-8-(2-cyclohexylpiperidin-1-yl)-7-((trans-4-methylcyclohexyl)methyl)-7H-purine-2-carbonitrile, 6-(((R)-1-cyclobutylethyl)amino)-8-(2-cyclohexylpiperidin-1-yl)-7-((trans-4-methylcyclohexyl)methyl)-7H-purine-2-carboxylic acid was prepared. $^1$H NMR (400 MHz, CD$_3$OD) δ 4.25-4.48 (m, 2H), 3.59-3.83 (m, 3H), 3.34-3.41 (m, 1H), 2.40-2.53 (m, 2H), 2.05-2.10 (m, 3H), 1.84-2.05 (m, 6H), 1.67-1.81 (m, 9H), 1.52-1.58 (m, 3H), 1.23-1.37 (m, 4H), 1.15-1.17 (m, 12H), 0.84 (m, 3H). MS (ES)=537 (M+1)$^+$.

Example 11.5

3-(6-(((R)-1-cyclobutylethyl)amino)-8-(2-cyclohexylpiperidin-1-yl)-7-((trans-4-methylcyclohexyl)methyl)-7H-purine-2-yl)-1,2,4-oxadiazol-5(4H)-one

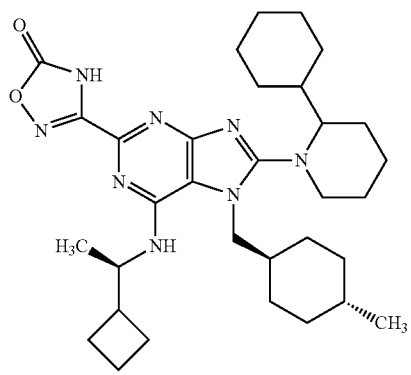 [SMILES: C[C@@H](Nc1nc(-c2noc(=O)[nH]2)nc2nc(N3CCCCC3C3CCCCC3)n(C[C@H]3CC[C@H](C)CC3)c12)C1CCC1]

Step 1: Using a procedure analogous to that described for the synthesis of Example 11.3, and starting from 6-(((R)-1-cyclobutylethyl)amino)-8-(2-cyclohexylpiperidin-1-yl)-7-((trans-4-methylcyclohexyl)methyl)-7H-purine-2-carbonitrile, 6-(((R)-1-cyclobutylethyl)amino)-N-hydroxy-8-(2-cyclohexylpiperidin-1-yl)-7-((trans-4-methylcyclohexyl) methyl)-7H-purine-2-carboximidamide was prepared. MS (ES)=551 (M+1)$^+$.

Step 2: Using a procedure analogous to that described for the synthesis of Example 11.3, and starting from 6-(((R)-1-cyclobutylethyl)amino)-N'-hydroxy-8-(2-cyclohexylpiperidin-1-yl)-7-((trans-4-methylcyclohexyl)methyl)-7H-purine-2-carboximidamide, 3-(6-(((R)-1-cyclobutylethyl)amino)-8-(2-cyclohexylpiperidin-1-yl)-7-((trans-4-methylcyclohexyl)methyl)-7H-purine-2-yl)-1,2,4-oxadiazol-5(4H)-one was prepared. $^1$H NMR (400 MHz, CD$_3$OD) δ 4.61-4.79 (m, 2H), 4.05-4.12 (m, 2H), 3.61-3.79 (m, 2H), 3.58 (m, 1H), 3.43 (m, 1H), 2.58 (m, 1H), 2.41 (m, 1H), 1.81-1.97 (m, 7H), 1.42-1.78 (m, 8H), 1.39-1.42 (m, 3H), 1.25-1.32 (m, 3H), 1.16-1.25 (m, 12H), 0.79-0.85 (m, 3H). MS (APCI)=577 (M+1)$^+$.

Example 11.6

6-(((R)-1-cyclobutylethyl)amino)-8-(3-methyl-2-phenylpiperidin-1-yl)-7-((trans-4-methylcyclohexyl)methyl)-7H-purine-2-carboxylic acid

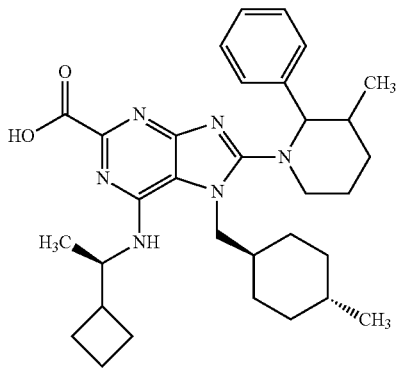 [SMILES: CC1CCCN(c2nc3nc(C(=O)O)nc(N[C@H](C)C4CCC4)c3n2C[C@H]2CC[C@H](C)CC2)C1c1ccccc1]

Step 1: To a stirred solution of 3-methyl-2-phenylpyridine (1.0 g, 6.0 mmol) in acetic acid (25 mL) was added PtO$_2$ (50.0 mg) and reaction mixture was held under 60 psi of H$_2$ for 16 hours. The reaction mixture was filtered through celite, and the filtrate was concentrated. The residue was dissolved in EtOAc (200 mL) and the organic layer was washed with 20% NaOH solution (2×100 mL) and brine (100 mL). The organic layer was dried over anhydrous Na$_2$SO$_4$, filtered, and concentrated to dryness to afford 3-methyl-2-phenylpiperidine. MS (ES)=176 (M+1)$^+$.

Step 2: Using a procedure analogous to that described in Example 11.2, and starting with 8-bromo-6-(((R)-1-cyclobutylethyl)amino)-7-((trans-4-methylcyclohexyl)methyl)-7H-purine-2-carbonitrile (Preparative Example 11.7), 6-(((R)-1-cyclobutylethyl)amino)-8-(3-methyl-2-phenylpiperidin-1-yl)-7-((trans-4-methylcyclohexyl)methyl)-7H-purine-2-carboxylic acid was prepared. $^1$H NMR (400 MHz, CD$_3$OD) δ 7.33-7.38 (m, 2H), 7.19-7.27 (m, 3H), 4.93-4.94 (m, 1H), 4.19-4.33 (m, 0.5H), 4.05-4.17 (m, 0.5H), 3.84-3.98 (m, 0.5H), 3.69-3.82 (m, 1.5H), 3.47-3.51 (m, 0.5H), 2.46-2.50 (m, 1H), 2.36-2.39 (m, 0.5H), 1.94-2.06 (m, 2H), 1.79-1.92 (m, 7H), 1.42-1.60 (m, 6H), 1.15 (d, J=8.0 Hz, 4H), 0.89-0.92 (m, 6H), 0.78-0.85 (m, 5H), 0.51-0.72 (m, 3H). MS (ES)=545 (M+1)$^+$.

Example 11.7

3-(6-(((R)-1-cyclobutylethyl)amino)-8-(3-methyl-2-phenylpiperidin-1-yl)-7-((trans-4-methylcyclohexyl)methyl)-7H-purin-2-yl)-1,2,4-oxadiazol-5(4H)-one

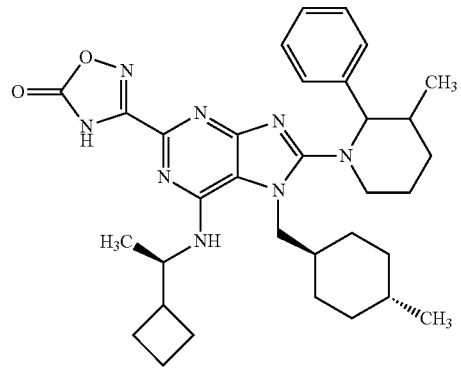 [SMILES: CC1CCCN(c2nc3nc(-c4noc(=O)[nH]4)nc(N[C@H](C)C4CCC4)c3n2C[C@H]2CC[C@H](C)CC2)C1c1ccccc1]

Step 1: Using a procedure analogous to that described in Example 11.3, and starting with 6-(((R)-1-cyclobutylethyl)amino)-8-(3-methyl-2-phenylpiperidin-1-yl)-7-((trans-4-methylcyclohexyl)methyl)-7H-purine-2-carbonitrile, 6-(((R)-1-cyclobutylethyl)amino)-N'-hydroxy-8-(3-methyl-2-phenylpiperidin-1-yl)-7-((trans-4-methylcyclohexyl)methyl)-7H-purine-2-carboximidamide was prepared. MS (ES)=559 (M+1)$^+$.

Step 2: Using a procedure analogous to that described in Example 11.3, and starting with 6-(((R)-1-cyclobutylethyl)amino)-N'-hydroxy-8-(3-methyl-2-phenylpiperidin-1-yl)-7-((trans-4-methylcyclohexyl)methyl)-7H-purine-2-carboximidamide, 3-(6-(((R)-1-cyclobutylethyl)amino)-8-(3-methyl-2-phenylpiperidin-1-yl)-7-((trans-4-methylcyclohexyl)methyl)-7H-purin-2-yl)-1,2,4-oxadiazol-5(4H)-one was prepared. $^1$H NMR (300 MHz, CDCl$_3$) δ 7.32-7.36 (m, 2H), 7.18-7.24 (m, 3H), 4.89-4.90 (m, 1H), 4.62-4.77 (m, 1H), 4.10-4.25 (m, 1H), 3.67-3.85 (m, 2H), 3.59-3.61 (m, 2H), 3.25-3.28 (m, 2H), 2.65-2.67 (m, 2H), 2.47-2.49 (m, 1H), 2.38-2.42 (m, 0.5H), 2.28-2.34 (m, 0.5H), 2.00-2.06 (m, 4H), 1.73-1.95 (m, 4H), 1.28-1.70 (m, 3H), 1.15 (d, J=8.0 Hz, 3H), 0.69-0.86 (m, 5H), 0.59-0.67 (m, 3H). MS (ES)=585 (M+1)$^+$.

Example 11.8

3-(6-{[(1R)-1-cyclobutylethyl]amino}-8-[(2S)-2-(fluoromethyl)pyrrolidin-1-yl]-7-[(trans-4-methylcyclohexyl)methyl]-7H-purin-2-yl)-1,2,4-oxadiazol-5(4H)-one

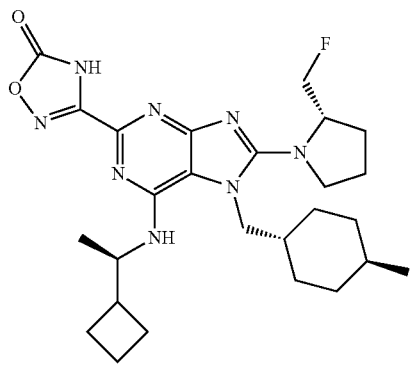 [SMILES: C[C@@H](Nc1nc(-c2noc(=O)[nH]2)nc2nc(N3CCC[C@H]3CF)n(C[C@H]3CC[C@H](C)CC3)c12)C1CCC1]

To a reaction vessel was added cesium fluoride (0.075 g, 0.49 mmol). The reaction vessel was sealed and heated to 100° C. for 3 hours with stirring, under high vacuum. The vial was cooled to ambient temperature under high vacuum. The reaction vessel was backfilled with argon and next was added a solution of (S)-2-(fluoromethyl)pyrrolidine hydrochloride (0.011 g, 0.076 mmol) and 3-(8-bromo-6-(((R)-1-cyclobutylethyl)amino)-7-((trans-4-methylcyclohexyl)methyl)-7H-purin-2-yl)-1,2,4-oxadiazol-5(4H)-one (Preparative Example 11.9; 0.025 g, 0.051 mmol) in DMSO (0.50 mL). The reaction was heated to 100° C. for 12 hours. The reaction was cooled, diluted with DMSO (0.50 mL), passed through a syringe filter, and purified by reverse phase preparative HPLC (0:100 to 95:5 acetonitrile:water: 0.1% v/v TFA modifier) to afford 3-(6-{[(1R)-1-cyclobutylethyl]amino}-8-[(2S)-2-(fluoromethyl)pyrrolidin-1-yl]-7-[(trans-4-methylcyclohexyl)methyl]-7H-purin-2-yl)-1,2,4-oxadiazol-5(4H)-one (TFA salt). MS ESI calc'd. for $C_{26}H_{37}FN_8O_2$ [M+H]$^+$ 513. found 513. $^1$H NMR (500 MHz, dmso) δ 12.78 (s, 1H), 6.40 (d, J=8.7, 1H), 4.49 (m, 6H), 3.74 (q, J=6.2, 2H), 3.40 (t, 1H), 2.13 (m, 1H), 2.00 (m, 2H), 1.85 (m, 4H), 1.74 (m, 3H), 1.58 (d, 1H), 1.45 (d, 2H), 1.35 (d, 1H), 1.15 (m, 1H), 1.05 (d, J=6.4, 3H), 0.88 (m, 2H), 0.81 (m, 1H), 0.74 (d, J=6.5, 3H), 0.66 (m, 1H), 0.54 (m, 1H).

Preparative Example 11.10

6-chloro-7-((trans-4-methylcyclohexyl)methyl)-8-((R)-3-phenylmorpholino)-7H-purine-2-carbonitrile

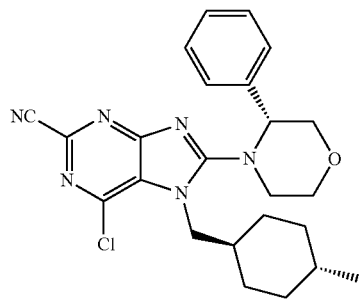 [SMILES: C[C@H]1CC[C@H](Cn2c(N3CCOC[C@H]3c3ccccc3)nc3nc(C#N)nc(Cl)c32)CC1]

Step 1: A mixture of 2,6-dichloro-7-((trans-4-methylcyclohexyl)methyl)-7H-purine (Preparative Example 11.4; 50 g, 167.1 mmol), (2,4-dimethoxyphenyl)methanamine (30 g, 175.5 mmol) and DIPEA (129.7 g, 1 mol) in i-PrOH (500 mL) was heated to 85° C. for 2 h. The reaction was then concentrated and water (200 mL) and CH$_2$Cl$_2$ (500 mL×2) were added. The organic layer was washed with brine, dried over Na$_2$SO$_4$ and concentrated to give the crude product, which was washed with MTBE to afford 2-chloro-N-(2,4-dimethoxybenzyl)-7-((trans-4-methylcyclohexyl)methyl)-7H-purin-6-amine. MS ESI calc'd. for $C_{22}H_{29}ClN_5O_2$ [M+H]$^+$ 430.2. found 430.2.

Step 2: To the solution of 2,2,6,6-tetramethylpiperidine (120 mL, 690 mmol) in THF (750 mL) was added n-BuLi (270 mL, 660 mmol, 2.5M) dropwise at −15° C. under N$_2$. After the addition was complete, the mixture was stirred for 30 min at −15° C. 2-Chloro-N-(2,4-dimethoxybenzyl)-7-((trans-4-methylcyclohexyl)methyl)-7H-purin-6-amine (57 g, 133 mmol) in THF (500 mL) was added dropwise at −15° C. After the addition was complete, the mixture was stirred for 2 h at −15° C. Next, 1,2-dibromo-1,1,2,2-tetrachloroethane (90 g, 276 mmol) in THF (250 mL) was added dropwise at −15° C. After the addition was complete, the mixture was stirred for 30 min at room temperature. The reaction was then quenched with Na$_2$S$_2$O$_3$ solution. The organic layer was concentrated and the residue was extracted with CH$_2$Cl$_2$ (400 mL×2). The combined organic layers were washed with brine, dried over Na$_2$SO$_4$ and concentrated. The crude product was purified via column chromatography on silica gel (petroleum ether:ethyl acetate, 50:1) to afford 2,8-dichloro-N-(2,4-dimethoxybenzyl)-7-((trans-4-methylcyclohexyl)methyl)-7H-purin-6-amine. $^1$H NMR (400 MHz, CDCl$_3$) δ: 0.75-0.81 (m, 2H), 0.86-0.87 (d, J=6.4 Hz, 3H), 1.05-1.10 (m, 2H), 1.25-1.27 (m, 1H), 1.50-1.54 (m, 2H), 1.67-1.74 (m, 3H), 3.81 (s, 3H), 3.88 (s, 3H), 3.97-4.03 (m, 2H) 4.72-4.74 (d, J=5.6 Hz, 2H), 5.44-5.45 (m, 1H), 6.46-6.50 (m, 2H), 7.30-7.32 (d, J=8.4 Hz, 1H).

Step 3: A mixture of 2,8-dichloro-N-(2,4-dimethoxybenzyl)-7-((trans-4-methylcyclohexyl)methyl)-7H-purin-6-amine (17 g, 36.6 mmol), (R)-3-phenylmorpholine (7.8 g, 47.6 mmol), KF (17 g, 292.8 mmol) and DIEA (37.8 g, 292.8 mmol) in DMSO (170 mL) was heated to 140° C. and stirred for 48 hr. Water (200 mL) was added, the precipitate was collected by filtration, washed with water, and dried to afford 2-chloro-N-(2,4-dimethoxybenzyl)-7-((trans-4-methylcyclohexyl)methyl)-8-((R)-3-phenylmorpholino)-7H-purin-6-amine, which was used directly without further purification.

Step 4: A mixture of 2-chloro-N-(2,4-dimethoxybenzyl)-7-((trans-4-methylcyclohexyl)methyl)-8-((R)-3-phenylmorpholino)-7H-purin-6-amine (1 g, 1.7 mmol), [(allyl)PdCl]$_2$ (0.2 g, 0.55 mmol), XPhos (0.3 g, 0.63 mmol) and zinc cyanide (0.4 g, 3.4 mmol) in DMA (15 mL) was purged with N$_2$ and heated to 125° C. with stirring for 25 min under microwave irradiation. The solvent was removed and water (200 mL) was added. The mixture was extracted with CH$_2$Cl$_2$ (400 mL×2) and the combined organic layers were washed with brine, dried over Na$_2$SO$_4$ and concentrated to give 6-((2,4-dimethoxybenzyl)amino)-7-((trans-4-methylcyclohexyl)methyl)-8-((R)-3-phenylmorpholino)-7H-purine-2-carbonitrile, which was used directly without further purification.

Step 5: To a solution of 6-((2,4-dimethoxybenzyl)amino)-7-((trans-4-methylcyclohexyl)methyl)-8-((R)-3-phenylmorpholino)-7H-purine-2-carbonitrile (10 g, 17.2 mmol) in CH$_2$Cl$_2$ (200 mL) was added TFA (100 mL) dropwise at 0° C. After the addition was complete, the solution was stirred at room temperature overnight. The solvent was evaporated and the residue was treated with saturated Na$_2$CO$_3$ (200 mL). The mixture was extracted with CH$_2$Cl$_2$ (200 mL×3), and the combined organic layers were washed with saturated sodium bicarbonate and brine, dried over Na$_2$SO$_4$ and concentrated to give 6-amino-7-((trans-4-methylcyclohexyl)methyl)-8-((R)-3-phenylmorpholino)-7H-purine-2-carbonitrile, which was used directly without further purification.

Step 6: A mixture of 6-amino-7-((trans-4-methylcyclohexyl)methyl)-8-((R)-3-phenylmorpholino)-7H-purine-2-carbonitrile (10 g, 23.2 mmol), tert-butyl nitrite (4.7 g, 45.2 mmol), MgSO$_4$ (0.36 g, 3.0 mmol) and CuCl$_2$ (4.9 g, 36.2 mmol) in CH$_3$CN (100 mL) was heated to reflux and stirred overnight. The mixture was filtered and the filtrate was concentrated to give the crude product which was purified by preparative HPLC (acetonitrile/water) to afford 6-chloro-7-((trans-4-methylcyclohexyl)methyl)-8-((R)-3-phenylmorpholino)-7H-purine-2-carbonitrile. $^1$H NMR (400 MHz, CD$_3$OD) δ 0.75-0.99 (m, 7H), 1.23-1.26 (d, J=11.2 Hz, 3H), 1.60-1.67 (m, 3H), 3.56-3.56 (m, 1H), 3.69-3.71 (m, 1H), 3.92-3.92 (m, 1H), 4.06-4.12 (m, 3H), 4.18-4.19 (m, 1H), 4.21-4.22 (m, 1H), 5.07-5.09 (m, 1H), 7.28-7.34 (m, 3H), 7.52-7.54 (d, J=7.2 Hz, 2H).

Example 11.9

3-(6-((R)-2-Cyclobutylazetidin-1-yl)-7-((trans-4-methylcyclohexyl)methyl)-8-((R)-3-phenylmorpholino)-7H-purin-2-yl)-1,2,4-oxadiazol-5(4H)-one

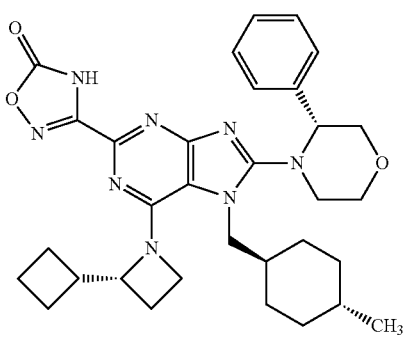 [SMILES: C[C@H]1CC[C@H](Cn2c(N3CCOC[C@H]3c3ccccc3)nc3nc(-c4noc(=O)[nH]4)nc(N4CC[C@@H]4C4CCC4)c32)CC1]

Step 1: Using a procedure analogous to that described for Preparative Example 11.5, and starting with 6-chloro-7-((trans-4-methylcyclohexyl)methyl)-8-((R)-3-phenylmorpholino)-7H-purine-2-carbonitrile (Preparative Example 11.10) and (R)-2-cyclobutylazetidine hydrochloride, 6-((R)-2-cyclobutylazetidin-1-yl)-7-((trans-4-methylcyclohexyl)methyl)-8-((R)-3-phenylmorpholino)-7H-purine-2-carbonitrile was prepared. $^1$H NMR (400 MHz, CDCl$_3$) δ 7.43 (dd, J=8.0, 1.6 Hz, 2H), 7.18-7.27 (m, 3H), 4.95 (dd, J=6.4, 3.6 Hz, 1H), 4.85 (dt, J=8.8, 5.6 Hz, 1H), 4.15-4.25 (m, 1H), 4.11 (dd, J=9.0, 4.0 Hz, 1H), 3.50-3.77 (m, 6H), 3.39-3.49 (m, 1H), 3.16-3.25 (m, 1H), 2.71-2.84 (m, 1H), 2.32-2.46 (m, 1H), 2.09-2.19 (m, 1H), 1.98-2.07 (m, 2H), 1.86-1.98 (m, 3H), 1.65-1.85 (m, 3H), 1.44-1.52 (m, 1H), 1.10-1.18 (m, 1H), 0.86-1.04 (m, 2H), 0.85 (d, J=6.8 Hz, 3H), 0.78-0.84 (m, 1H), 0.69-0.77 (m, 2H), 0.53-0.66 (m, 1H). MS (ES)=526 (M+1)$^+$.

Step 2: Using a procedure analogous to that described for Preparative Example 11.8 and 11.9, and starting with 6-((R)-2-cyclobutylazetidin-1-yl)-7-((trans-4-methylcyclohexyl)methyl)-8-((R)-3-phenylmorpholino)-7H-purine-2-carbonitrile, 3-(6-((R)-2-Cyclobutylazetidin-1-yl)-7-((trans-4-methylcyclohexyl)methyl)-8-((R)-3-phenylmorpholino)-7H-purin-2-yl)-1,2,4-oxadiazol-5(4H)-one was prepared. $^1$H NMR (300 MHz, CDCl$_3$) δ 7.43 (dd, J=8.0, 1.6 Hz, 2H), 7.19-7.29 (m, 3H), 4.87-4.99 (m, 2H), 4.25 (m, 1H), 4.13 (dd, J=12.0, 3.6 Hz, 1H), 3.78-4.09 (m, 6H), 3.40-3.55 (m, 1H), 3.18-3.29 (m, 1H), 2.75-2.89 (m, 1H), 2.35-2.49 (m, 1H), 2.12-2.21 (m, 1H), 2.01-2.12 (m, 2H), 1.84-2.00 (m, 4H), 1.66-1.82 (m, 4H), 0.94-1.07 (m, 1H), 0.81-0.93 (m, 2H), 0.85 (d, J=6.4 Hz, 3H), 0.71-0.79 (m, 2H), 0.53-0.69 (m, 1H). MS (ES)=585 (M+1)$^+$.

The following compounds in Table 11 (other than Example 11.1 to 11.9) were prepared using procedures which were analogous to those described above in Example 11.1 to 11.9.

TABLE 11

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.1 | 4.547 | (structure) | 6-{[(1R)-1-cyclobutylethyl]amino}-8-(2,3-dimethylpiperidin-1-yl)-7-[(trans-4-methylcyclohexyl)methyl]-7H-purine-2-carboxylic acid | | 483 | 483 |
| 11.2 | 1.817 | (structure) | 6-{[(1R)-1-cyclobutylethyl]amino}-7-[(trans-4-methylcyclohexyl)methyl]-8-[2-(2-methylpropyl)piperidin-1-yl]-7H-purine-2-carboxylic acid | | 511 | 511 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.3 | 6.139 | 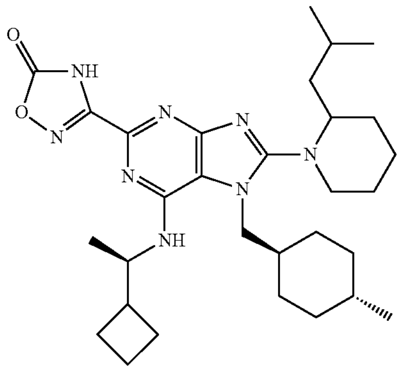 [SMILES: CC(C)CC1CCCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[2-(2-methylpropyl)piperidin-1-yl]-7H-purin-2-yl)-1,2,4-oxadiazol-5(4H)-one | | 551 | 551 |
| 11.4 | 1.558 | 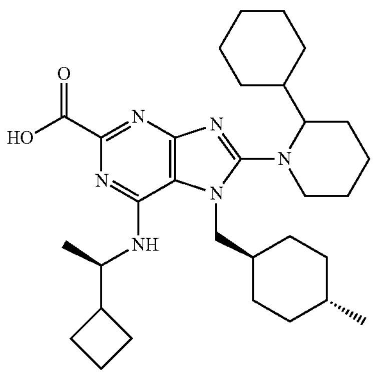 [SMILES: C[C@@H](Nc1nc(C(=O)O)nc2nc(N3CCCCC3C3CCCCC3)n(C[C@H]3CC[C@H](C)CC3)c12)C1CCC1] | 6-{[(1R)-1-cyclobutylethyl]amino}-8-(2-cyclohexylpiperidin-1-yl)-7-[(trans-4-methylcyclohexyl)methyl]-7H-purine-2-carboxylic acid | | 537 | 537 |
| 11.5 | 449.9 | 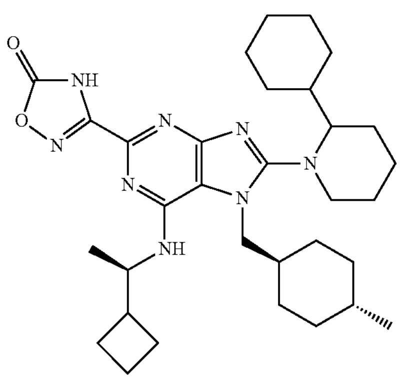 [SMILES: C[C@@H](Nc1nc(-c2noc(=O)[nH]2)nc2nc(N3CCCCC3C3CCCCC3)n(C[C@H]3CC[C@H](C)CC3)c12)C1CCC1] | 3-(6-{[(1R)-1-cyclobutylethyl]amino}-8-(2-cyclohexylpiperidin-1-yl)-7-[(trans-4-methylcyclohexyl)methyl]-7H-purin-2-yl)-1,2,4-oxadiazol-5(4H)-one | | 577 | 577 |
| 11.6 | 1.818 | 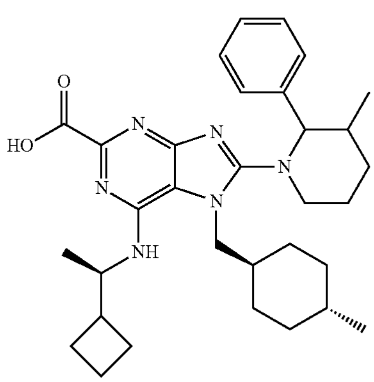 [SMILES: CC1CCCN(c2nc3nc(C(=O)O)nc(N[C@H](C)C4CCC4)c3n2C[C@H]2CC[C@H](C)CC2)C1c1ccccc1] | 6-{[(1R)-1-cyclobutylethyl]amino}-7-[(trans-4-methylcyclohexyl)methyl]-8-(3-methyl-2-phenylpiperidin-1-yl)-7H-purine-2-carboxylic acid | | 545 | 545 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.7 | 6.337 | 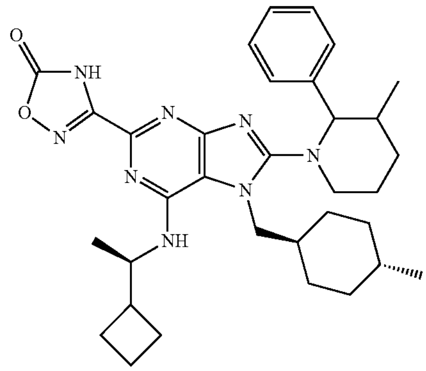 [SMILES: CC1CCCN(c2nc3nc(-c4noc(=O)[nH]4)nc(N[C@H](C)C4CCC4)c3n2C[C@H]2CC[C@H](C)CC2)C1c1ccccc1] | 3-[6-{[(1R)-1-cyclobutylethyl]amino}-7-[(trans-4-methylcyclohexyl)methyl]-8-(3-methyl-2-phenylpiperidin-1-yl)-7H-purin-2-yl]-1,2,4-oxadiazol-5(4H)-one | | 585 | 585 |
| 11.8 | 2.364 | 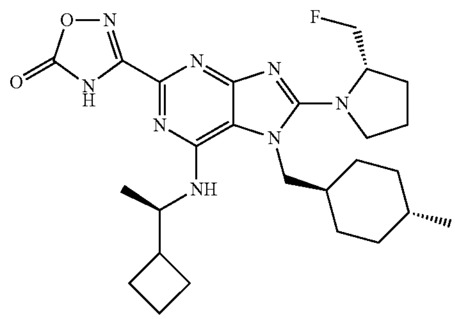 [SMILES: C[C@@H](Nc1nc(-c2noc(=O)[nH]2)nc2nc(N3CCC[C@H]3CF)n(C[C@H]3CC[C@H](C)CC3)c12)C1CCC1] | 3-(6-{[(1R)-1-cyclobutylethyl]amino}-8-[(2S)-2-(fluoromethyl)pyrrolidin-1-yl]-7-[(trans-4-methylcyclohexyl)methyl]-7H-purin-2-yl)-1,2,4-oxadiazol-5(4H)-one | TFA | 513 | 513 |
| 11.9 | 27.34 | 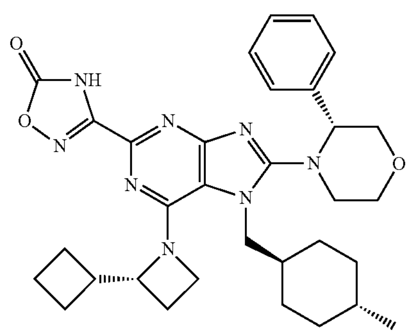 [SMILES: C[C@H]1CC[C@H](Cn2c(N3CCOC[C@H]3c3ccccc3)nc3nc(-c4noc(=O)[nH]4)nc(N4CC[C@@H]4C4CCC4)c32)CC1] | 3-{6-[(2R)-2-cyclobutylazetidin-1-yl]-7-[(trans-4-methylcyclohexyl)methyl]-8-[(3R)-3-phenylmorpholin-4-yl]-7H-purin-2-yl}-1,2,4-oxadiazol-5(4H)-one | | 585 | 585 |
| 11.10 | 0.2019 | 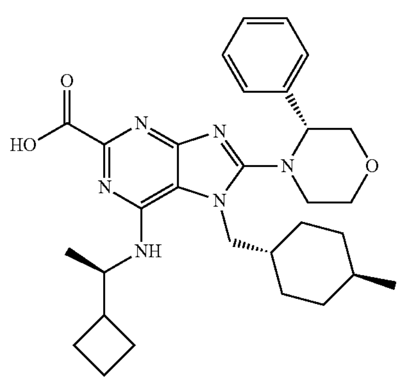 | 6-{[(1R)-1-cyclobutylethyl]amino}-7-[(trans-4-methylcyclohexyl)methyl]-8-[(3R)-3-phenylmorpholin-4-yl]-7H-purine-2-carboxylic acid | TFA | 533 | 533 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.11 | 0.6257 | 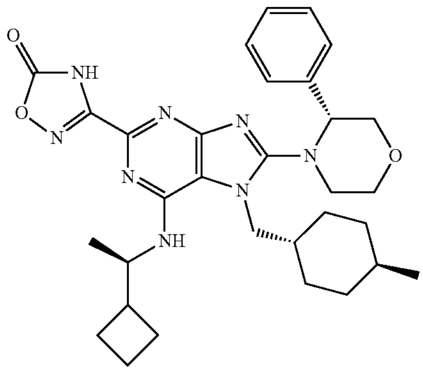 [SMILES: C[C@@H](Nc1nc(-c2noc(=O)[nH]2)nc2nc(N3CCOC[C@H]3c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(3R)-3-phenylmorpholin-4-yl]-7H-purin-2-yl)-1,2,4-oxadiazol-5(4H)-one | TFA | 573 | 573 |
| 11.12 | 2.819 | 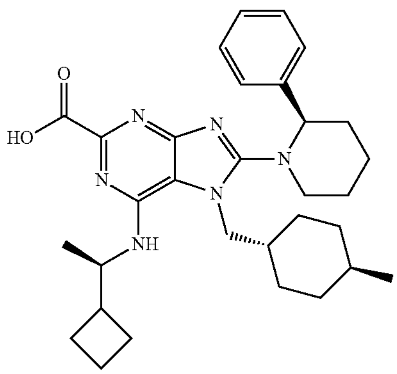 [SMILES: C[C@@H](Nc1nc(C(=O)O)nc2nc(N3CCCC[C@@H]3c3ccccc3)n(C[C@H]3CC[C@H](C)CC3)c12)C1CCC1] | 6-{[(1R)-1-cyclobutylethyl]amino}-7-[(trans-4-methylcyclohexyl)methyl]-8-[(2R)-2-phenylpiperidin-1-yl]-7H-purine-2-carboxylic acid | TFA | 531 | 531 |
| 11.13 | 26.75 | 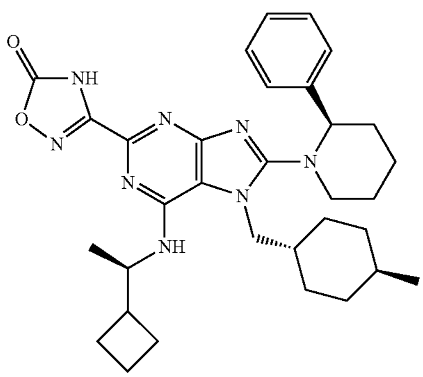 [SMILES: C[C@@H](Nc1nc(-c2noc(=O)[nH]2)nc2nc(N3CCCC[C@@H]3c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(2R)-2-phenylpiperidin-1-yl]-7H-purin-2-yl)-1,2,4-oxadiazol-5(4H)-one | TFA | 571 | 571 |
| 11.14 | 0.3806 | 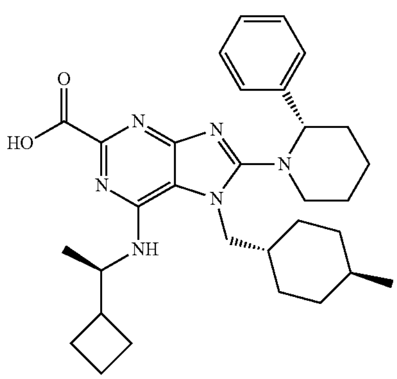 [SMILES: C[C@@H](Nc1nc(C(=O)O)nc2nc(N3CCCC[C@H]3c3ccccc3)n(C[C@H]3CC[C@H](C)CC3)c12)C1CCC1] | 6-{[(1R)-1-cyclobutylethyl]amino}-7-[(trans-4-methylcyclohexyl)methyl]-8-[(2S)-2-phenylpiperidin-1-yl]-7H-purine-2-carboxylic acid | TFA | 531 | 531 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.15 | 2.815 | 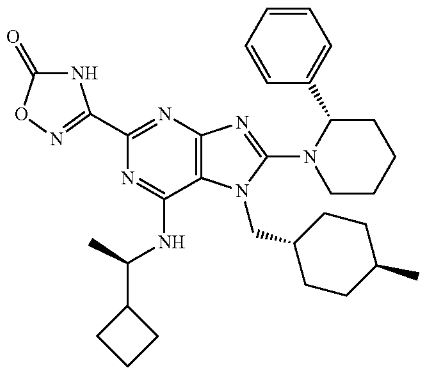 [SMILES: C[C@@H](Nc1nc(-c2noc(=O)[nH]2)nc2nc(N3CCCC[C@H]3c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(2S)-2-phenylpiperidin-1-yl]-7H-purin-2-yl)-1,2,4-oxadiazol-5(4H)-one | TFA | 571 | 571 |
| 11.16 | 2.843 | 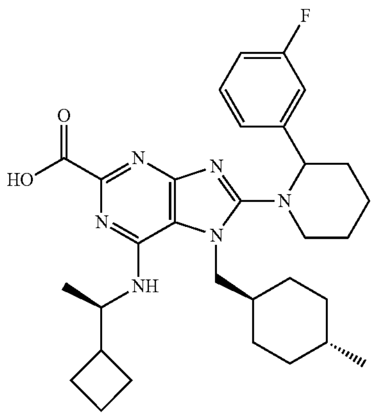 [SMILES: C[C@@H](Nc1nc(C(=O)O)nc2nc(N3CCCCC3c3cccc(F)c3)n(C[C@H]3CC[C@H](C)CC3)c12)C1CCC1] | 6-{[(1R)-1-cyclobutylethyl]amino}-8-[2-(3-fluorophenyl)piperidin-1-yl]-7-[(trans-4-methylcyclohexyl)methyl]-7H-purine-2-carboxylic acid | | 549 | 549 |
| 11.17 | 17.91 | 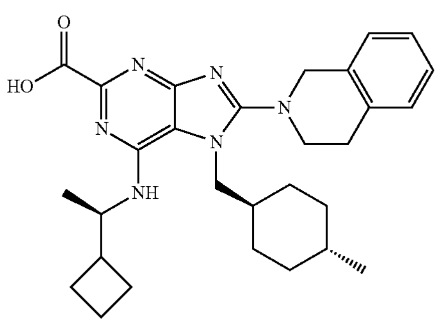 [SMILES: C[C@@H](Nc1nc(C(=O)O)nc2nc(N3CCc4ccccc4C3)n(C[C@H]3CC[C@H](C)CC3)c12)C1CCC1] | 6-{[(1R)-1-cyclobutylethyl]amino}-8-(3,4-dihydroisoquinolin-2(1H)-yl)-7-[(trans-4-methylcyclohexyl)methyl]-7H-purine-2-carboxylic acid | | 503 | 503 |
| 11.18 | 4.423 | 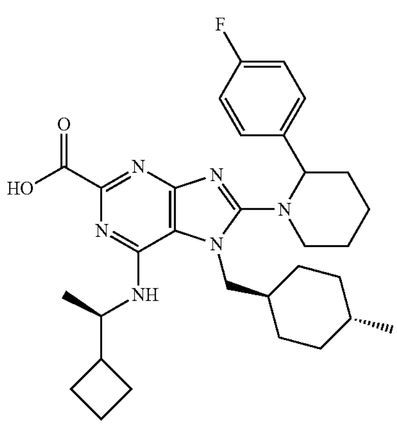 [SMILES: C[C@@H](Nc1nc(C(=O)O)nc2nc(N3CCCCC3c3ccc(F)cc3)n(C[C@H]3CC[C@H](C)CC3)c12)C1CCC1] | 6-{[(1R)-1-cyclobutylethyl]amino}-8-[2-(4-fluorophenyl)piperidin-1-yl]-7-[(trans-4-methylcyclohexyl)methyl]-7H-purine-2-carboxylic acid | | 549 | 549 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.19 | 0.8947 | 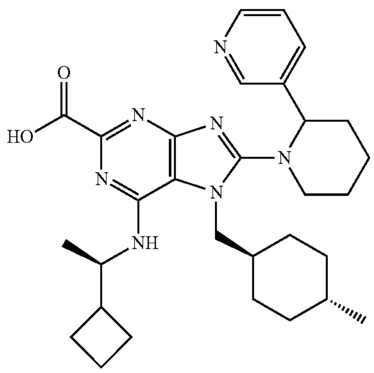 [SMILES: C[C@@H](Nc1nc(C(=O)O)nc2nc(N3CCCCC3c3cccnc3)n(C[C@H]3CC[C@H](C)CC3)c12)C1CCC1] | 6-{[(1R)-1-cyclobutylethyl]amino}-7-[(trans-4-methylcyclohexyl)methyl]-8-(2-pyridin-3-ylpiperidin-1-yl)-7H-purine-2-carboxylic acid | | 532 | 532 |
| 11.20 | 1.339 | 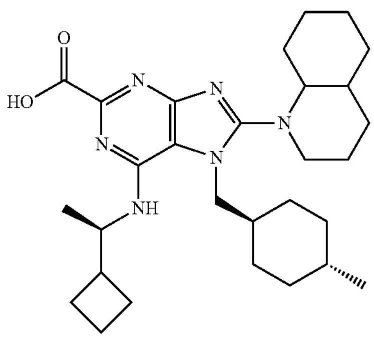 [SMILES: C[C@@H](Nc1nc(C(=O)O)nc2nc(N3CCCC4CCCCC43)n(C[C@H]3CC[C@H](C)CC3)c12)C1CCC1] | 6-{[(1R)-1-cyclobutylethyl]amino}-7-[(trans-4-methylcyclohexyl)methyl]-8-(octahydroquinolin-1(2H)-yl)-7H-purine-2-carboxylic acid | | 509 | 509 |
| 11.21 | 2.716 | 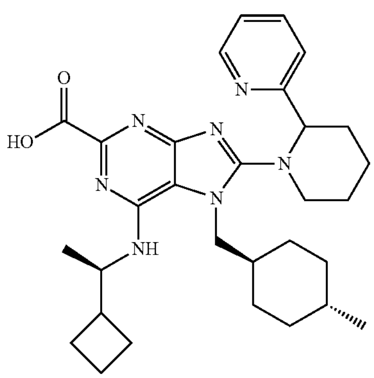 [SMILES: C[C@@H](Nc1nc(C(=O)O)nc2nc(N3CCCCC3c3ccccn3)n(C[C@H]3CC[C@H](C)CC3)c12)C1CCC1] | 6-{[(1R)-1-cyclobutylethyl]amino}-7-[(trans-4-methylcyclohexyl)methyl]-8-(2-pyridin-2-ylpiperidin-1-yl)-7H-purine-2-carboxylic acid | | 532 | 532 |
| 11.22 | 17.99 | 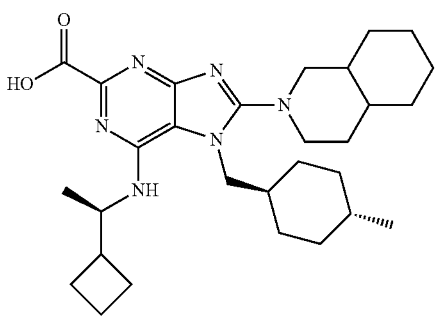 [SMILES: C[C@@H](Nc1nc(C(=O)O)nc2nc(N3CCC4CCCCC4C3)n(C[C@H]3CC[C@H](C)CC3)c12)C1CCC1] | 6-{[(1R)-1-cyclobutylethyl]amino}-7-[(trans-4-methylcyclohexyl)methyl]-8-(octahydroisoquinolin-2(1H)-yl)-7H-purine-2-carboxylic acid | | 509 | 509 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.23 | 3.111 | 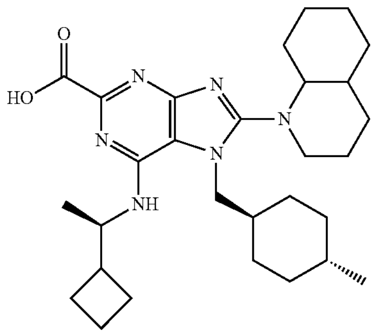 [SMILES: C[C@@H](Nc1nc(C(=O)O)nc2nc(N3CCCC4CCCCC43)n(C[C@H]3CC[C@H](C)CC3)c12)C1CCC1] | 6-{[(1R)-1-cyclobutylethyl]amino}-7-[(trans-4-methylcyclohexyl)methyl]-8-(octahydroquinolin-1(2H)-yl)-7H-purine-2-carboxylic acid | | 509 | 509 |
| 11.24 | 11.6 | 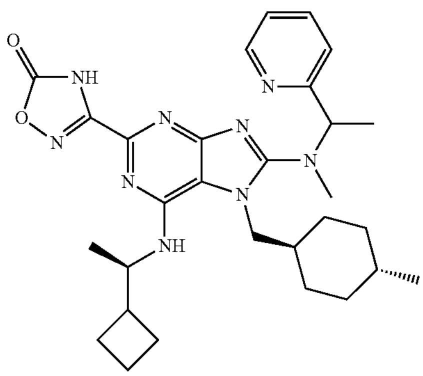 [SMILES: CC(c1ccccn1)N(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[methyl(1-pyridin-2-ylethyl)amino]-7H-purin-2-yl)-1,2,4-oxadiazol-5(4H)-one (diastereomer 1) | TFA | 546 | 546 |
| 11.25 | 10.47 | 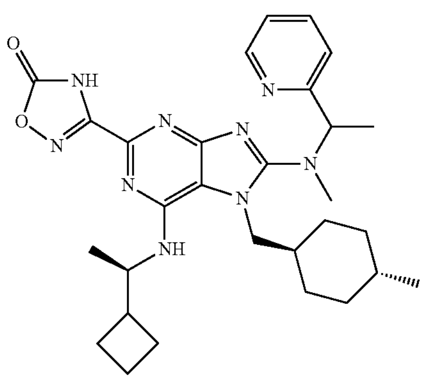 [SMILES: CC(c1ccccn1)N(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[methyl(1-pyridin-2-ylethyl)amino]-7H-purin-2-yl)-1,2,4-oxadiazol-5(4H)-one (diastereomer 2) | TFA | 546 | 546 |
| 11.26 | 3.57 | 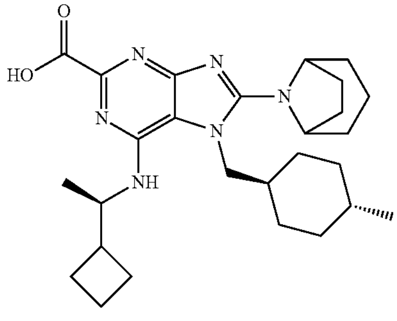 [SMILES: C[C@@H](Nc1nc(C(=O)O)nc2nc(N3C4CCCC3CC4)n(C[C@H]3CC[C@H](C)CC3)c12)C1CCC1] | 8-(8-azabicyclo[3.2.1]oct-8-yl)-6-{[(1R)-1-cyclobutylethyl]amino}-7-[(trans-4-methylcyclohexyl)methyl]-7H-purine-2-carboxylic acid | TFA | 481 | 481 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.27 | 11.62 | 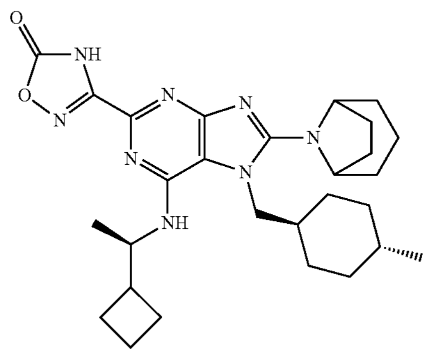 [SMILES: C[C@@H](Nc1nc(-c2noc(=O)[nH]2)nc2nc(N3C4CCCC3CC4)n(C[C@H]3CC[C@H](C)CC3)c12)C1CCC1] | 3-{8-(8-azabicyclo[3.2.1]oct-8-yl)-6-{[(1R)-1-cyclobutylethyl]amino}-7-[(trans-4-methylcyclohexyl)methyl]-7H-purin-2-yl}-1,2,4-oxadiazol-5(4H)-one | TFA | 521 | 521 |
| 11.28 | 1.521 | 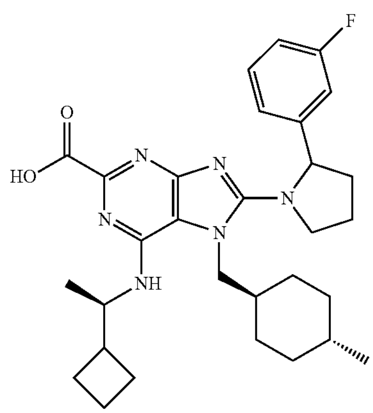 [SMILES: C[C@@H](Nc1nc(C(=O)O)nc2nc(N3CCCC3c3cccc(F)c3)n(C[C@H]3CC[C@H](C)CC3)c12)C1CCC1] | 6-{[(1R)-1-cyclobutylethyl]amino}-8-[2-(3-fluorophenyl)pyrrolidin-1-yl]-7-[(trans-4-methylcyclohexyl)methyl]-7H-purine-2-carboxylic acid | | 535 | 535 |
| 11.29 | 2.231 | 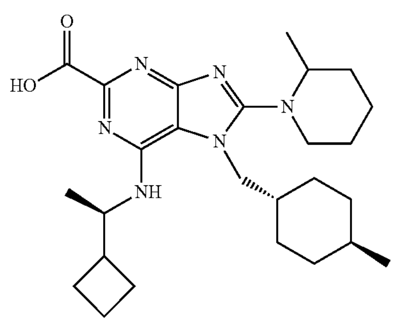 [SMILES: CC1CCCCN1c1nc2nc(C(=O)O)nc(N[C@H](C)C3CCC3)c2n1C[C@H]1CC[C@H](C)CC1] | 6-{[(1R)-1-cyclobutylethyl]amino}-7-[(trans-4-methylcyclohexyl)methyl]-8-(2-methylpiperidin-1-yl)-7H-purine-2-carboxylic acid | TFA | 469 | 469 |
| 11.30 | 1.648 | 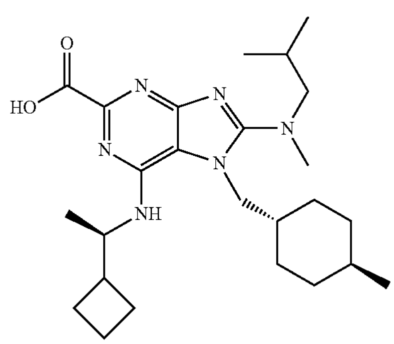 [SMILES: CC(C)CN(C)c1nc2nc(C(=O)O)nc(N[C@H](C)C3CCC3)c2n1C[C@H]1CC[C@H](C)CC1] | 6-{[(1R)-1-cyclobutylethyl]amino}-7-[(trans-4-methylcyclohexyl)methyl]-8-[methyl(2-methylpropyl)amino]-7H-purine-2-carboxylic acid | TFA | 457 | 457 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.31 | 2.256 | 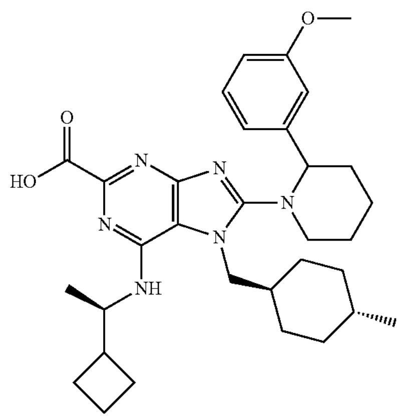 [SMILES: COc1cccc(C2CCCCN2c2nc3nc(C(=O)O)nc(N[C@H](C)C4CCC4)c3n2C[C@H]2CC[C@H](C)CC2)c1] | 6-{[(1R)-1-cyclobutylethyl]amino}-8-[2-(3-methoxyphenyl)piperidin-1-yl]-7-[(trans-4-methylcyclohexyl)methyl]-7H-purine-2-carboxylic acid | | 561 | 561 |
| 11.32 | 7.995 | 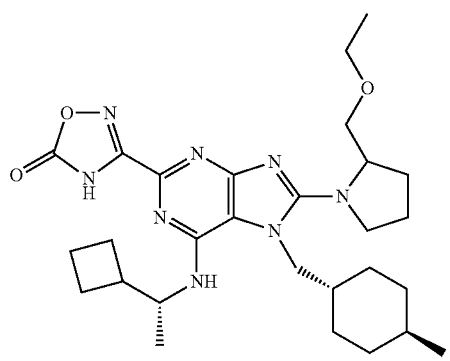 [SMILES: CCOCC1CCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[2-(ethoxymethyl)pyrrolidin-1-yl]-7-[(trans-4-methylcyclohexyl)methyl]-7H-purin-2-yl)-1,2,4-oxadiazol-5(2H)-one | TFA | 539 | 539 |
| 11.33 | 5.368 | 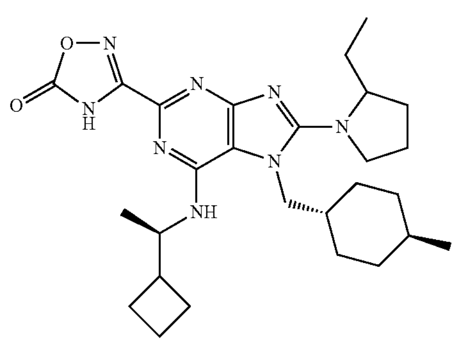 [SMILES: CCC1CCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-(2-ethylpyrrolidin-1-yl)-7-[(trans-4-methylcyclohexyl)methyl]-7H-purin-2-yl)-1,2,4-oxadiazol-5(2H)-one | TFA | 509 | 509 |
| 11.34 | 25.37 | 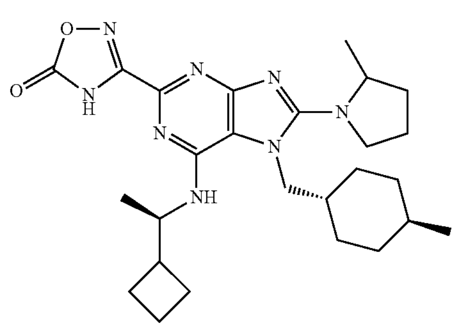 [SMILES: CC1CCCN1c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(2-methylpyrrolidin-1-yl)-7H-purin-2-yl]-1,2,4-oxadiazol-5(2H)-one | TFA | 495 | 495 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.35 | 4.396 | 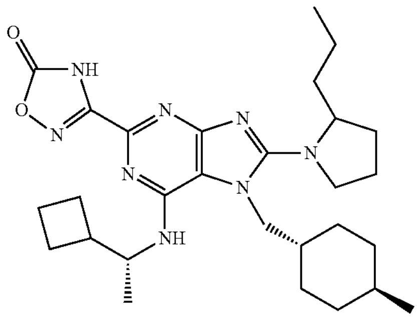 [SMILES: CCCC1CCCN1c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(2-propylpyrrolidin-1-yl)-7H-purin-2-yl]-1,2,4-oxadiazol-5(2H)-one | TFA | 523 | 523 |
| 11.36 | 3.931 | 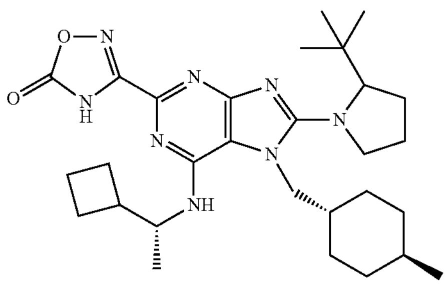 [SMILES: C[C@@H](Nc1nc(-c2noc(=O)[nH]2)nc2nc(N3CCCC3C(C)(C)C)n(C[C@H]3CC[C@H](C)CC3)c12)C1CCC1] | 3-{8-(2-tert-butylpyrrolidin-1-yl)-6-{[(1R)-1-cyclobutylethyl]amino}-7-[(trans-4-methylcyclohexyl)methyl]-7H-purin-2-yl}-1,2,4-oxadiazol-5(2H)-one | TFA | 537 | 537 |
| 11.37 | 6.976 | 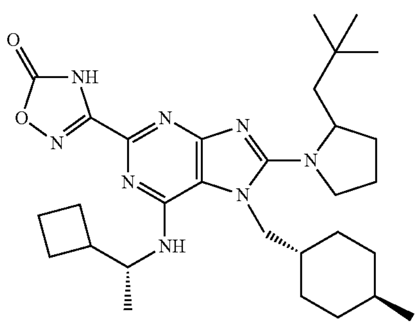 [SMILES: C[C@@H](Nc1nc(-c2noc(=O)[nH]2)nc2nc(N3CCCC3CC(C)(C)C)n(C[C@H]3CC[C@H](C)CC3)c12)C1CCC1] | 3-(6-{[(1R)-1-cyclobutylethyl]amino}-8-[2-(2,2-dimethylpropyl)pyrrolidin-1-yl]-7-[(trans-4-methylcyclohexyl)methyl]-7H-purin-2-yl)-1,2,4-oxadiazol-5(2H)-one | TFA | 551 | 551 |
| 11.38 | 4.86 | 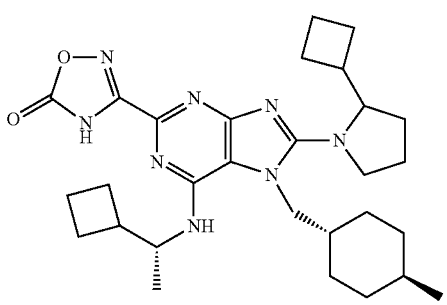 [SMILES: C[C@@H](Nc1nc(-c2noc(=O)[nH]2)nc2nc(N3CCCC3C3CCC3)n(C[C@H]3CC[C@H](C)CC3)c12)C1CCC1] | 3-(6-{[(1R)-1-cyclobutylethyl]amino}-8-(2-cyclobutylpyrrolidin-1-yl)-7-[(trans-4-methylcyclohexyl)methyl]-7H-purin-2-yl)-1,2,4-oxadiazol-5(2H)-one | TFA | 535 | 535 |
| 11.39 | 9.706 | 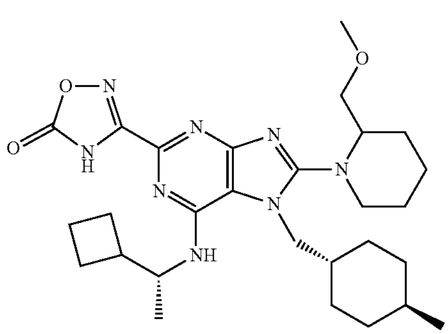 [SMILES: COCC1CCCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[2-(methoxymethyl)piperidin-1-yl]-7-[(trans-4-methylcyclohexyl)methyl]-7H-purin-2-yl)-1,2,4-oxadiazol-5(2H)-one | TFA | 539 | 539 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.40 | 8.524 | 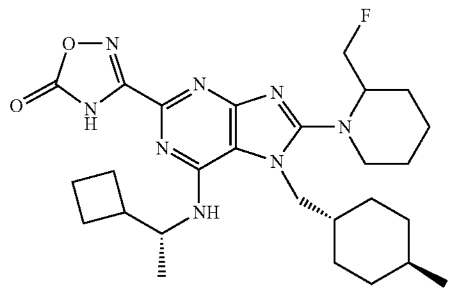 [SMILES: C[C@@H](Nc1nc(-c2noc(=O)[nH]2)nc2nc(N3CCCCC3CF)n(C[C@H]3CC[C@H](C)CC3)c12)C1CCC1] | 3-(6-{[(1R)-1-cyclobutylethyl]amino}-8-[2-(fluoromethyl)piperidin-1-yl]-7-[(trans-4-methylcyclohexyl)methyl]-7H-purin-2-yl)-1,2,4-oxadiazol-5(2H)-one | TFA | 527 | 527 |
| 11.41 | 14.67 | 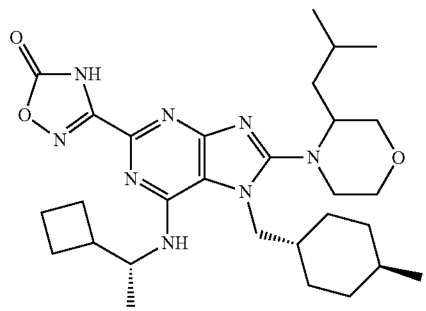 [SMILES: CC(C)CC1COCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[3-(2-methylpropyl)morpholin-4-yl]-7H-purin-2-yl)-1,2,4-oxadiazol-5(2H)-one | TFA | 553 | 553 |
| 11.42 | 5.341 | 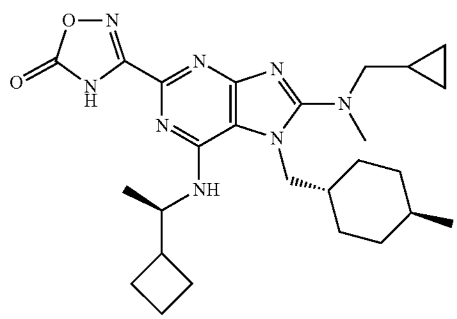 [SMILES: C[C@@H](Nc1nc(-c2noc(=O)[nH]2)nc2nc(N(C)CC3CC3)n(C[C@H]3CC[C@H](C)CC3)c12)C1CCC1] | 3-(6-{[(1R)-1-cyclobutylethyl]amino}-8-[(cyclopropylmethyl)(methyl)amino]-7-[(trans-4-methylcyclohexyl)methyl]-7H-purin-2-yl)-1,2,4-oxadiazol-5(2H)-one | TFA | 495 | 495 |
| 11.43 | 19.43 | 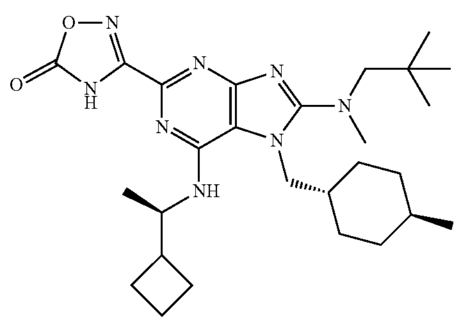 [SMILES: C[C@@H](Nc1nc(-c2noc(=O)[nH]2)nc2nc(N(C)CC(C)(C)C)n(C[C@H]3CC[C@H](C)CC3)c12)C1CCC1] | 3-(6-{[(1R)-1-cyclobutylethyl]amino}-8-[(2,2-dimethylpropyl)(methyl)amino]-7-[(trans-4-methylcyclohexyl)methyl]-7H-purin-2-yl)-1,2,4-oxadiazol-5(2H)-one | TFA | 511 | 511 |
| 11.44 | 9.974 | 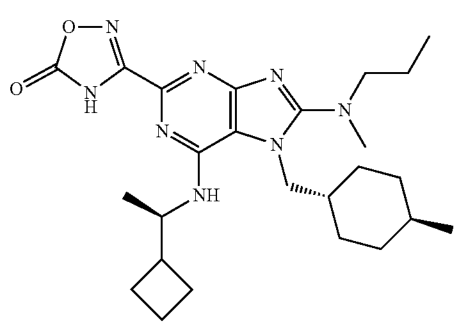 [SMILES: CCCN(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[methyl(propyl)amino]-7H-purin-2-yl)-1,2,4-oxadiazol-5(2H)-one | TFA | 483 | 483 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.45 | 81.86 | 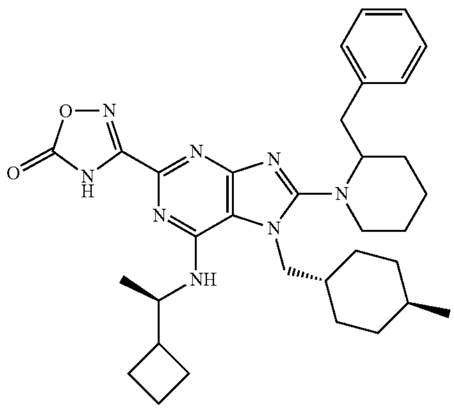 [SMILES: C[C@@H](Nc1nc(-c2noc(=O)[nH]2)nc2nc(N3CCCCC3Cc3ccccc3)n(C[C@H]3CC[C@H](C)CC3)c12)C1CCC1] | 3-{8-(2-benzylpiperidin-1-yl)-6-{[(1R)-1-cyclobutylethyl]amino}-7-[(trans-4-methylcyclohexyl)methyl]-7H-purin-2-yl}-1,2,4-oxadiazol-5(2H)-one | TFA | 585 | 585 |
| 11.46 | 4.455 | 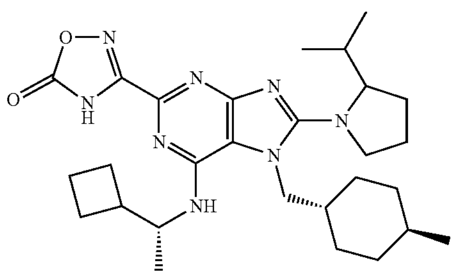 [SMILES: CC(C)C1CCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[2-(1-methylethyl)pyrrolidin-1-yl]-7H-purin-2-yl)-1,2,4-oxadiazol-5(2H)-one | TFA | 523 | 523 |
| 11.47 | 7.272 | 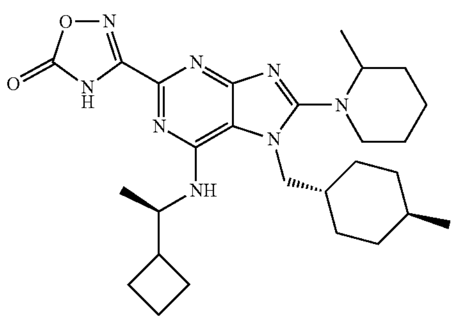 [SMILES: CC1CCCCN1c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(2-methylpiperidin-1-yl)-7H-purin-2-yl]-1,2,4-oxadiazol-5(4H)-one | TFA | 509 | 509 |
| 11.48 | 6.708 | 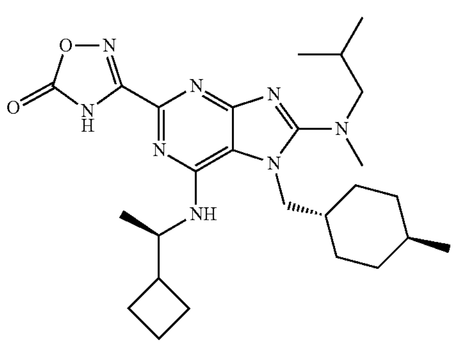 [SMILES: CC(C)CN(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[methyl(2-methylpropyl)amino]-7H-purin-2-yl)-1,2,4-oxadiazol-5(4H)-one | TFA | 497 | 497 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.49 | 2.429 | 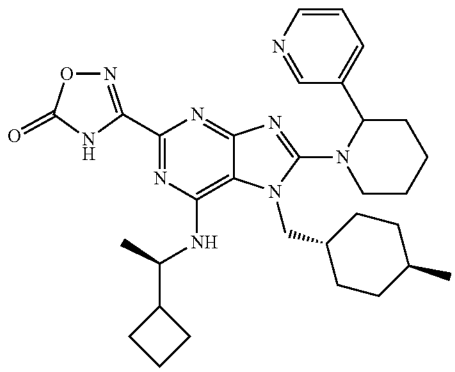 [SMILES: C[C@@H](Nc1nc(-c2noc(=O)[nH]2)nc2nc(N3CCCCC3c3cccnc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-pyridin-3-ylpiperidin-1-yl)-7H-purin-2-yl]-1,2,4-oxadiazol-5(4H)-one (diastereomer 1) | TFA | 572 | 572 |
| 11.50 | 14.33 | 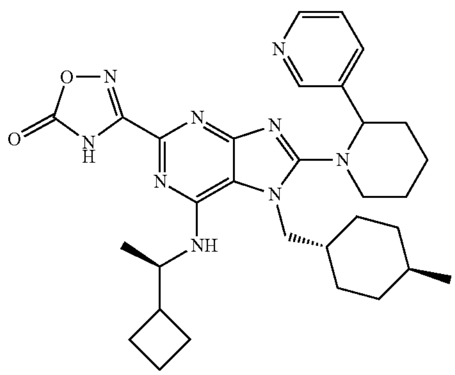 [SMILES: C[C@@H](Nc1nc(-c2noc(=O)[nH]2)nc2nc(N3CCCCC3c3cccnc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-pyridin-3-ylpiperidin-1-yl)-7H-purin-2-yl]-1,2,4-oxadiazol-5(4H)-one (diastereomer 2) | TFA | 572 | 572 |
| 11.51 | 2.262 | 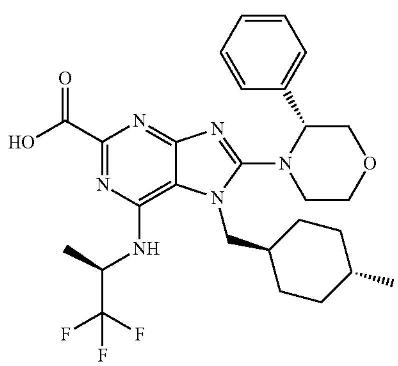 [SMILES: C[C@@H](Nc1nc(C(=O)O)nc2nc(N3CCOC[C@H]3c3ccccc3)n(C[C@H]3CC[C@H](C)CC3)c12)C(F)(F)F] | 7-[(trans-4-methylcyclohexyl)methyl]-8-[(3R)-3-phenylmorpholin-4-yl]-6-{[(1R)-2,2,2-trifluoro-1-methylethyl]amino}-7H-purine-2-carboxylic acid | TFA | 547 | 547 |
| 11.52 | 3.427 | 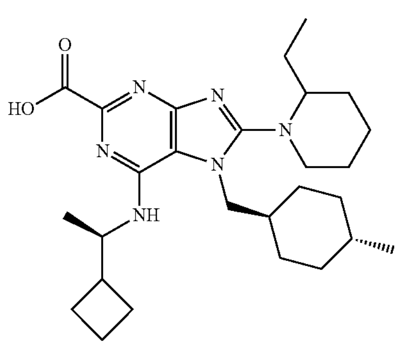 [SMILES: CCC1CCCCN1c1nc2nc(C(=O)O)nc(N[C@H](C)C3CCC3)c2n1C[C@H]1CC[C@H](C)CC1] | 6-{[(1R)-1-cyclobutylethyl]amino}-8-(2-ethylpiperidin-1-yl)-7-[(trans-4-methylcyclohexyl)methyl]-7H-purine-2-carboxylic acid | | 483 | 483 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.53 | 4.682 | 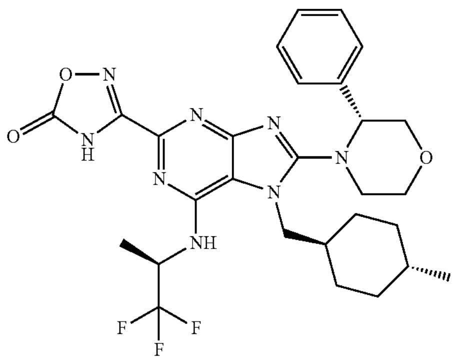 [SMILES: C[C@@H](Nc1nc(-c2noc(=O)[nH]2)nc2nc(N3CCOC[C@H]3c3ccccc3)n(C[C@H]3CC[C@H](C)CC3)c12)C(F)(F)F] | 3-(7-[(trans-4-methylcyclohexyl)methyl]-8-[(3R)-3-phenylmorpholin-4-yl]-6-{[(1R)-2,2,2-trifluoro-1-methylethyl]amino}-7H-purin-2-yl)-1,2,4-oxadiazol-5(4H)-one | TFA | 587 | 587 |
| 11.54 | 3.309 | 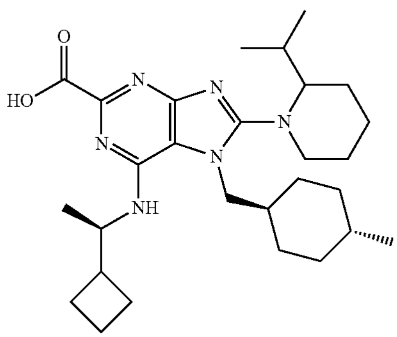 [SMILES: CC(C)C1CCCCN1c1nc2nc(C(=O)O)nc(N[C@H](C)C3CCC3)c2n1C[C@H]1CC[C@H](C)CC1] | 6-{[(1R)-1-cyclobutylethyl]amino}-7-[(trans-4-methylcyclohexyl)methyl]-8-[2-(1-methylethyl)piperidin-1-yl]-7H-purine-2-carboxylic acid | | 497 | 497 |
| 11.55 | 2.137 | 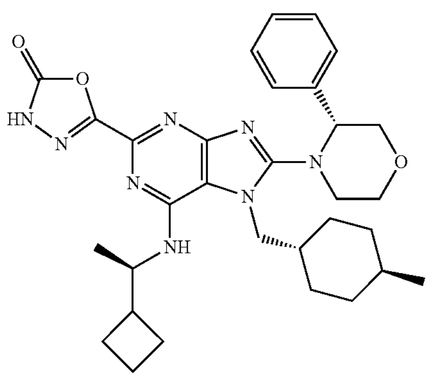 [SMILES: C[C@@H](Nc1nc(-c2n[nH]c(=O)o2)nc2nc(N3CCOC[C@H]3c3ccccc3)n(C[C@H]3CC[C@H](C)CC3)c12)C1CCC1] | 5-(6-{[(1R)-1-cyclobutylethyl]amino}-7-[(trans-4-methylcyclohexyl)methyl]-8-[(3R)-3-phenylmorpholin-4-yl]-7H-purin-2-yl)-1,3,4-oxadiazol-2(3H)-one | TFA | 573 | 573 |
| 11.56 | 11.57 | 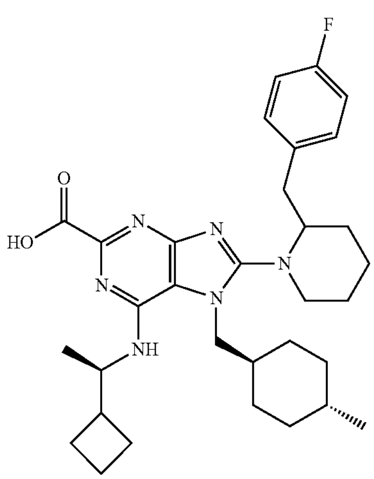 [SMILES: C[C@@H](Nc1nc(C(=O)O)nc2nc(N3CCCCC3Cc3ccc(F)cc3)n(C[C@H]3CC[C@H](C)CC3)c12)C1CCC1] | 6-{[(1R)-1-cyclobutylethyl]amino}-8-[2-(4-fluorobenzyl)piperidin-1-yl]-7-[(trans-4-methylcyclohexyl)methyl]-7H-purine-2-carboxylic acid | | 563 | 563 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.57 | 16.45 | 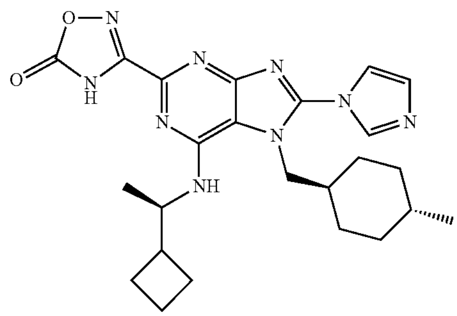 [SMILES: C[C@@H](Nc1nc(-c2noc(=O)[nH]2)nc2nc(-n3ccnc3)n(C[C@H]3CC[C@H](C)CC3)c12)C1CCC1] | 3-(6-{[(1R)-1-cyclobutylethyl]amino}-8-(1H-imidazol-1-yl)-7-[(trans-4-methylcyclohexyl)methyl]-7H-purin-2-yl)-1,2,4-oxadiazol-5(4H)-one | TFA | 478 | 478 |
| 11.58 | 5.372 | 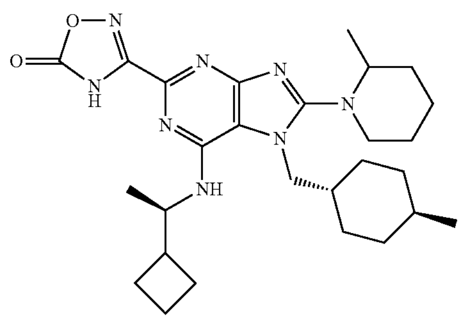 [SMILES: CC1CCCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(2R)-2-methylpiperidin-1-yl]-7H-purin-2-yl)-1,2,4-oxadiazol-5(2H)-one (diastereomer 1) | | 509 | 509 |
| 11.59 | 13.48 | 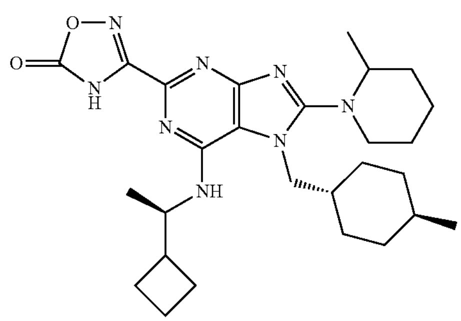 [SMILES: CC1CCCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(2S)-2-methylpiperidin-1-yl]-7H-purin-2-yl)-1,2,4-oxadiazol-5(2H)-one (diastereomer 2) | | 509 | 509 |
| 11.60 | 10.46 | 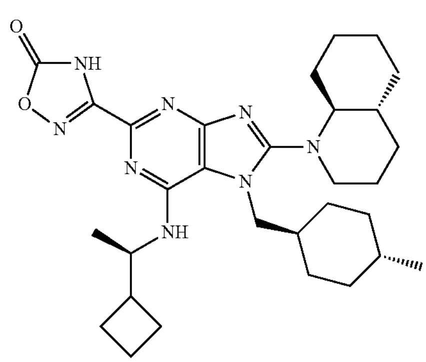 [SMILES: C[C@@H](Nc1nc(-c2noc(=O)[nH]2)nc2nc(N3CCC[C@H]4CCCC[C@@H]43)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(4aR,8aS)-octahydroquinolin-1(2H)-yl]-7H-purin-2-yl)-1,2,4-oxadiazol-5(4H)-one | TFA | 549 | 549 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.61 | 5.128 | 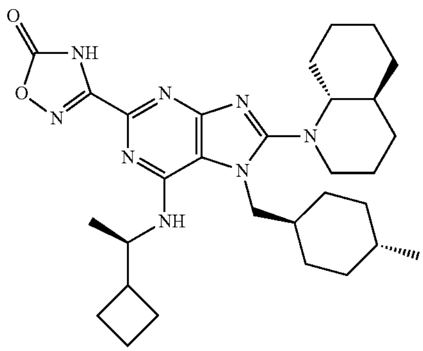 [SMILES: C[C@@H](Nc1nc(-c2noc(=O)[nH]2)nc2nc(N3CCC[C@@H]4CCCC[C@H]43)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(4aS,8aR)-octahydroquinolin-1(2H)-yl]-7H-purin-2-yl)-1,2,4-oxadiazol-5(4H)-one | TFA | 549 | 549 |
| 11.62 | 7.84 | 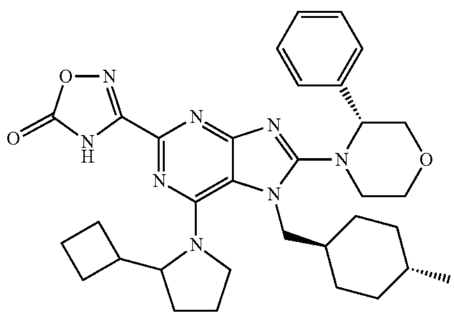 [SMILES: C[C@H]1CC[C@H](Cn2c(N3CCOC[C@H]3c3ccccc3)nc3nc(-c4noc(=O)[nH]4)nc(N4CCCC4C4CCC4)c32)CC1] | 3-{6-(2-cyclobutylpyrrolidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 599 | 599 |
| 11.63 | 3.706 | 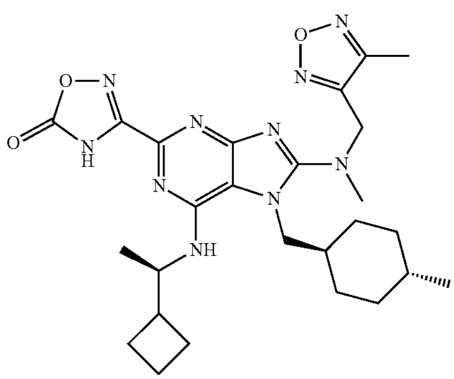 [SMILES: Cc1nonc1CN(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-{methyl[(4-methyl-1,2,5-oxadiazol-3-yl)methyl]amino}-7H-purin-2-yl)-1,2,4-oxadiazol-5(4H)-one | TFA | 537 | 537 |
| 11.64 | 5.773 | 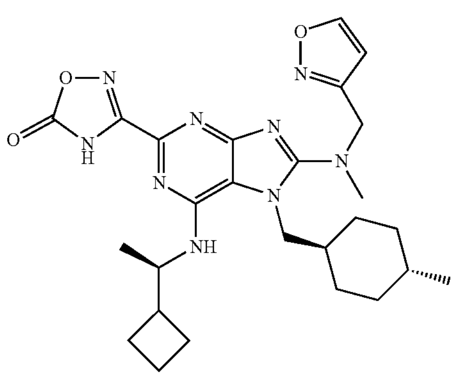 [SMILES: C[C@@H](Nc1nc(-c2noc(=O)[nH]2)nc2nc(N(C)Cc3ccon3)n(C[C@H]3CC[C@H](C)CC3)c12)C1CCC1] | 3-(6-{[(1R)-1-cyclobutylethyl]amino}-8-[(isoxazol-3-ylmethyl)(methyl)amino]-7-[(trans-4-methylcyclohexyl)methyl]-7H-purin-2-yl)-1,2,4-oxadiazol-5(4H)-one | TFA | 522 | 522 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.65 | 1.446 | 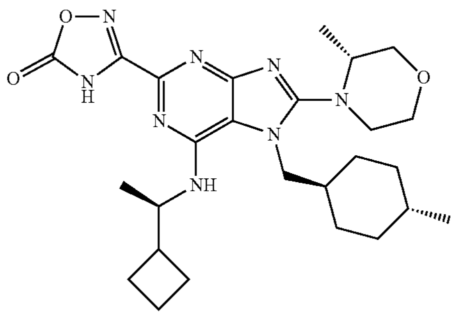 [SMILES: C[C@@H]1COCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(3R)-3-methylmorpholin-4-yl]-7H-purin-2-yl)-1,2,4-oxadiazol-5(4H)-one | TFA | 511 | 511 |
| 11.66 | 5.799 | 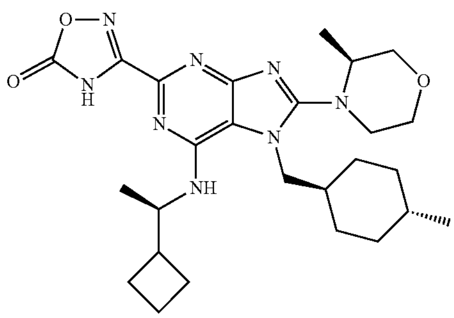 [SMILES: C[C@@H](Nc1nc(-c2noc(=O)[nH]2)nc2nc(N3CCOC[C@@H]3C)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(3S)-3-methylmorpholin-4-yl]-7H-purin-2-yl)-1,2,4-oxadiazol-5(4H)-one | TFA | 511 | 511 |
| 11.67 | 10.84 | 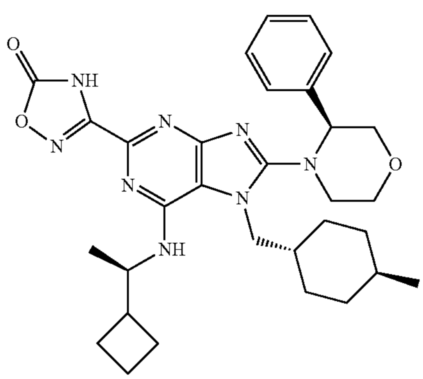 [SMILES: C[C@@H](Nc1nc(-c2noc(=O)[nH]2)nc2nc(N3CCOC[C@@H]3c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(3S)-3-phenylmorpholin-4-yl]-7H-purin-2-yl)-1,2,4-oxadiazol-5(4H)-one | TFA | 573 | 573 |
| 11.68 | 2.039 | 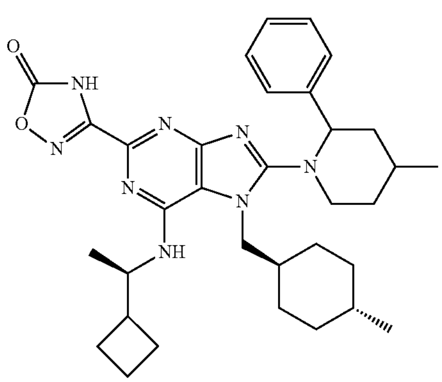 [SMILES: CC1CCN(c2nc3nc(-c4noc(=O)[nH]4)nc(N[C@H](C)C4CCC4)c3n2C[C@H]2CC[C@H](C)CC2)C(c2ccccc2)C1] | 3-[6-{[(1R)-1-cyclobutylethyl]amino}-7-[(trans-4-methylcyclohexyl)methyl]-8-(4-methyl-2-phenylpiperidin-1-yl)-7H-purin-2-yl]-1,2,4-oxadiazol-5(4H)-one (stereoisomer 1) | TFA | 585 | 585 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.69 | 17.34 | 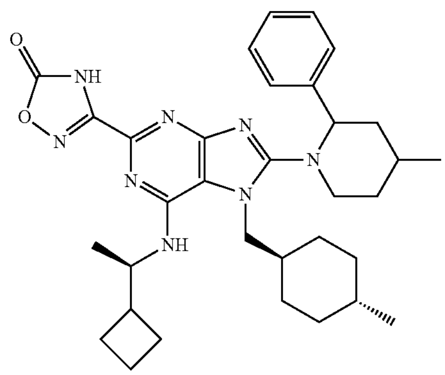 [SMILES: CC1CCN(c2nc3nc(-c4noc(=O)[nH]4)nc(N[C@H](C)C4CCC4)c3n2C[C@H]2CC[C@H](C)CC2)C(c2ccccc2)C1] | 3-[6-{[(1R)-1-cyclobutylethyl]amino}-7-[(trans-4-methylcyclohexyl)methyl]-8-(4-methyl-2-phenylpiperidin-1-yl)-7H-purin-2-yl]-1,2,4-oxadiazol-5(4H)-one (stereoisomer 2) | TFA | 585 | 585 |
| 11.70 | 22.76 | 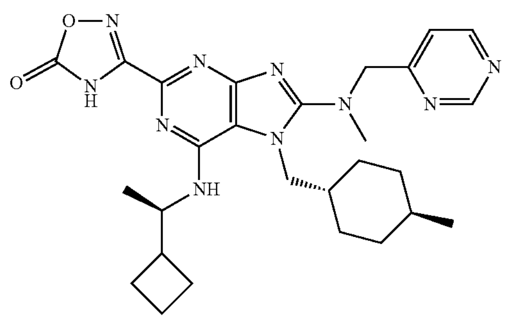 [SMILES: C[C@@H](Nc1nc(-c2noc(=O)[nH]2)nc2nc(N(C)Cc3ccncn3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[methyl(pyrimidin-4-ylmethyl)amino]-7H-purin-2-yl)-1,2,4-oxadiazol-5(2H)-one | TFA | 533 | 533 |
| 11.71 | 24.34 | 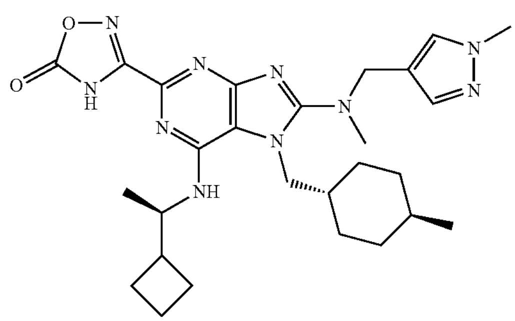 [SMILES: C[C@@H](Nc1nc(-c2noc(=O)[nH]2)nc2nc(N(C)Cc3cnn(C)c3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-{methyl[(1-methyl-1H-pyrazol-4-yl)methyl]amino}-7H-purin-2-yl)-1,2,4-oxadiazol-5(2H)-one | TFA | 535 | 535 |
| 11.72 | 5.983 | 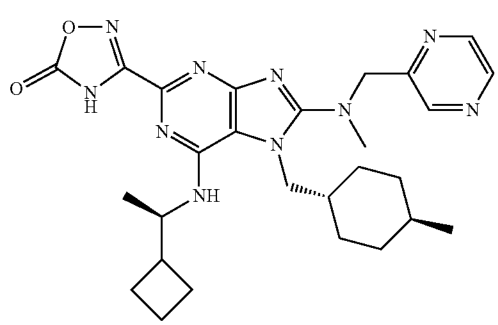 [SMILES: C[C@@H](Nc1nc(-c2noc(=O)[nH]2)nc2nc(N(C)Cc3cnccn3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[methyl(pyrazin-2-ylmethyl)amino]-7H-purin-2-yl)-1,2,4-oxadiazol-5(2H)-one | TFA | 533 | 533 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.73 | 11.49 | 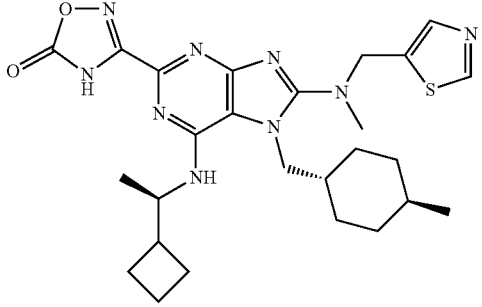 [SMILES: C[C@@H](Nc1nc(-c2noc(=O)[nH]2)nc2nc(N(C)Cc3cncs3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[methyl(1,3-thiazol-5-ylmethyl)amino]-7H-purin-2-yl)-1,2,4-oxadiazol-5(2H)-one | TFA | 538 | 538 |
| 11.74 | 133.3 | 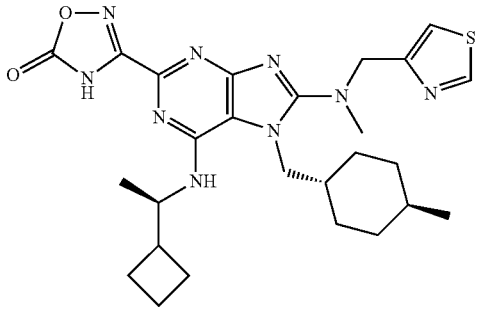 [SMILES: C[C@@H](Nc1nc(-c2noc(=O)[nH]2)nc2nc(N(C)Cc3cscn3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[methyl(1,3-thiazol-4-ylmethyl)amino]-7H-purin-2-yl)-1,2,4-oxadiazol-5(2H)-one | TFA | 538 | 538 |
| 11.75 | 9.577 | 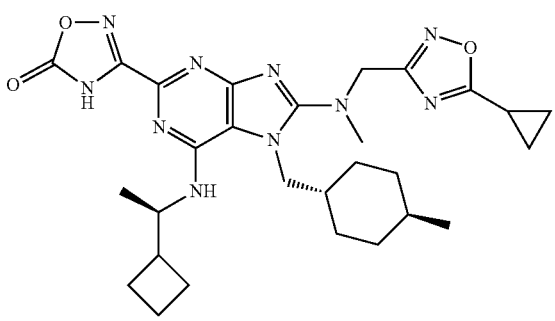 [SMILES: C[C@@H](Nc1nc(-c2noc(=O)[nH]2)nc2nc(N(C)Cc3noc(C4CC4)n3)n(C[C@H]3CC[C@H](C)CC3)c12)C1CCC1] | 3-(6-{[(1R)-1-cyclobutylethyl]amino}-8-{[(5-cyclopropyl-1,2,4-oxadiazol-3-yl)methyl](methyl)amino)}-7-[(trans-4-methylcyclohexyl)methyl]-7H-purin-2-yl)-1,2,4-oxadiazol-5(2H)-one | TFA | 563 | 563 |
| 11.76 | 8.187 | 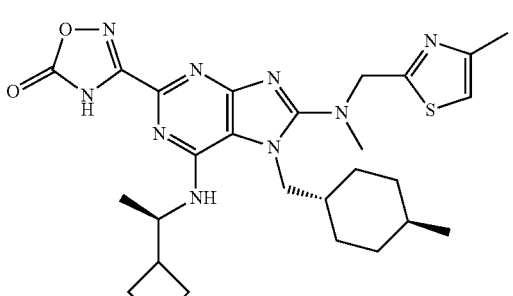 | 3-(6-{[(1R)-1-cyclobutylethyl]amino}-7-[(trans-4-methylcyclohexyl)methyl]-8-{methyl[(4-methyl-1,3-thiazol-2-y)methyl]amino}-7H-purin-2-yl)-1,2,4-oxadiazol-5(2H)-one | TFA | 552 | 552 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.77 | 12.63 | 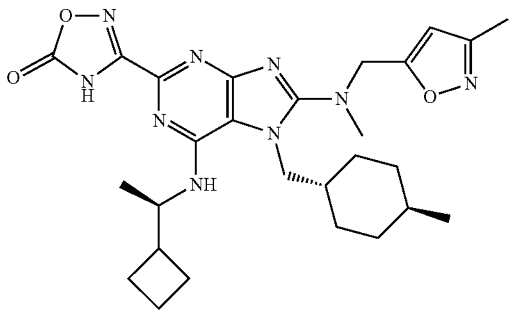 [SMILES: Cc1cc(CN(C)c2nc3nc(-c4noc(=O)[nH]4)nc(N[C@H](C)C4CCC4)c3n2C[C@H]2CC[C@H](C)CC2)on1] | 3-(6-{[(1R)-1-cyclobutylethyl]amino}-7-[(trans-4-methylcyclohexyl)methyl]-8-{methyl[(3-methylisoxazol-5-yl)methyl]amino}-7H-purin-2-yl)-1,2,4-oxadiazol-5(2H)-one | TFA | 536 | 536 |
| 11.78 | 37.11 | 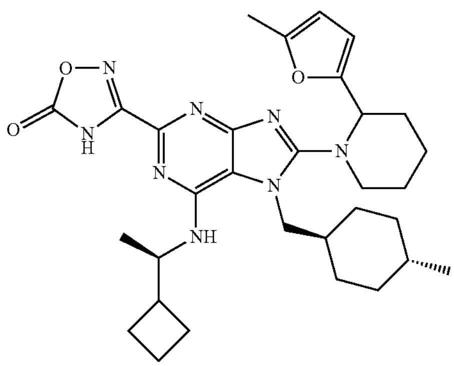 [SMILES: Cc1ccc(C2CCCCN2c2nc3nc(-c4noc(=O)[nH]4)nc(N[C@H](C)C4CCC4)c3n2C[C@H]2CC[C@H](C)CC2)o1] | 3-(6-{[(1R)-1-cyclobutylethyl]amino}-7-[(trans-4-methylcyclohexyl)methyl]-8-[2-(5-methylfuran-2-yl)piperidin-1-yl]-7H-purin-2-yl)-1,2,4-oxadiazol-5(4H)-one | TFA | 575 | 575 |
| 11.79 | 33.34 | 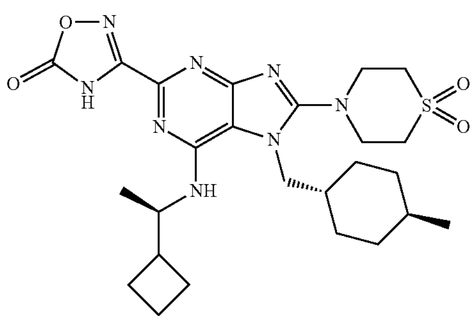 [SMILES: C[C@@H](Nc1nc(-c2noc(=O)[nH]2)nc2nc(N3CCS(=O)(=O)CC3)n(C[C@H]3CC[C@H](C)CC3)c12)C1CCC1] | 3-(6-{[(1R)-1-cyclobutylethyl]amino}-8-(1,1-dioxidothiomorpholin-4-yl)-7-[(trans-4-methylcyclohexyl)methyl]-7H-purin-2-yl)-1,2,4-oxadiazol-5(2H)-one | | 545 | 545 |
| 11.80 | 25.86 | 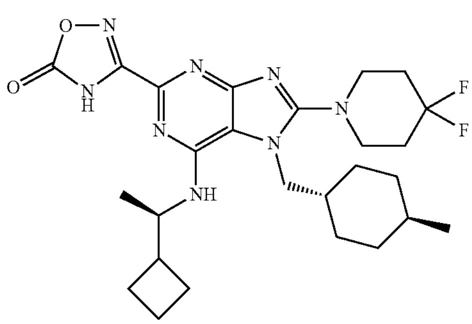 [SMILES: C[C@@H](Nc1nc(-c2noc(=O)[nH]2)nc2nc(N3CCC(F)(F)CC3)n(C[C@H]3CC[C@H](C)CC3)c12)C1CCC1] | 3-(6-{[(1R)-1-cyclobutylethyl]amino}-8-(4,4-difluoropiperidin-1-yl)-7-[(trans-4-methylcyclohexyl)methyl]-7H-purin-2-yl)-1,2,4-oxadiazol-5(2H)-one | | 531 | 531 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.81 | 482.7 | 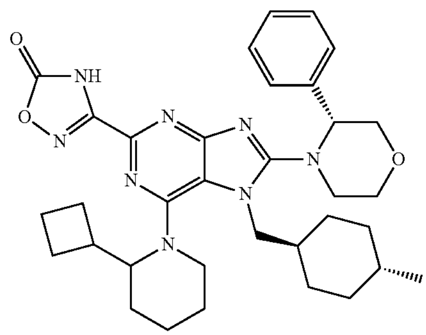 [SMILES: C[C@H]1CC[C@H](Cn2c(N3CCOC[C@H]3c3ccccc3)nc3nc(-c4noc(=O)[nH]4)nc(N4CCCCC4C4CCC4)c32)CC1] | 3-{6-(2-cyclobutylpiperidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 613 | 613 |
| 11.82 | 6.452 | 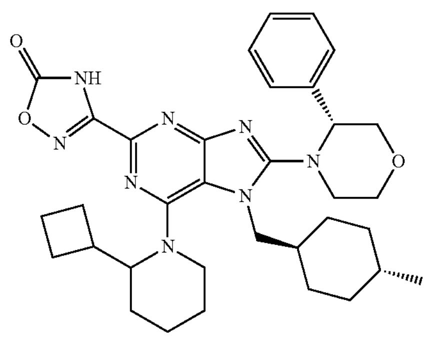 [SMILES: C[C@H]1CC[C@H](Cn2c(N3CCOC[C@H]3c3ccccc3)nc3nc(-c4noc(=O)[nH]4)nc(N4CCCCC4C4CCC4)c32)CC1] | 3-{6-(2-cyclobutylpiperidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 613 | 613 |
| 11.83 | 11.47 | 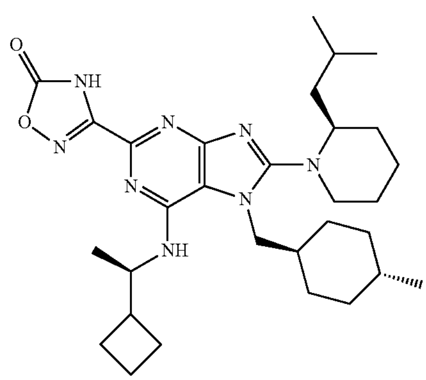 [SMILES: CC(C)C[C@H]1CCCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(2R)-2-(2-methylpropyl)piperidin-1-yl]-7H-purin-2-yl)-1,2,4-oxadiazol-5(4H)-one | TFA | 551 | 551 |
| 11.84 | 3.066 | 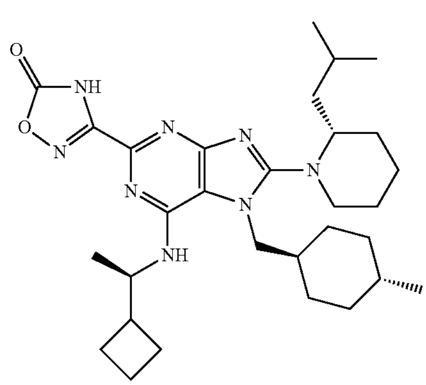 [SMILES: CC(C)C[C@@H]1CCCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(2S)-2-(2-methylpropyl)piperidin-1-yl]-7H-purin-2-yl)-1,2,4-oxadiazol-5(4H)-one | TFA | 551 | 551 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.85 | 4.967 | 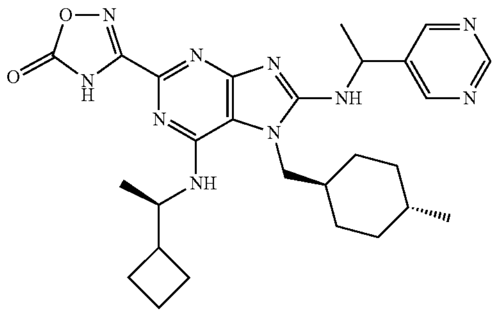 | 3-(6-{[(1R)-1-cyclobutylethyl]amino}-7-[(trans-4-methylcyclohexyl)methyl]-8-[(1-pyrimidin-5-ylethyl)amino]-7H-purin-2-yl)-1,2,4-oxadiazol-5(2H)-one | TFA | 533 | 533 |
| 11.86 | 3.388 | 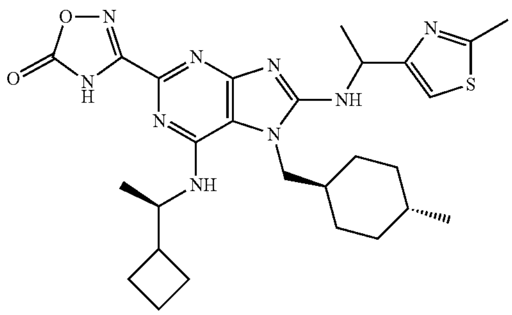 [SMILES: Cc1nc(C(C)Nc2nc3nc(-c4noc(=O)[nH]4)nc(N[C@H](C)C4CCC4)c3n2C[C@H]2CC[C@H](C)CC2)cs1] | 3-(6-{[(1R)-1-cyclobutylethyl]amino}-7-[(trans-4-methylcyclohexyl)methyl]-8-{[1-(2-methyl-1,3-thiazol-4-yl)ethyl]amino}-7H-purin-2-yl)-1,2,4-oxadiazol-5(2H)-one | TFA | 552 | 552 |
| 11.87 | 105.5 | 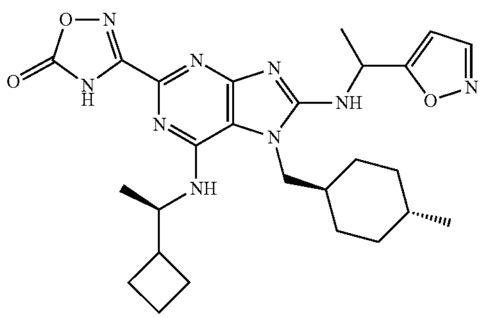 [SMILES: CC(Nc1nc2nc(-c3noc(=O)[nH]3)nc(N[C@H](C)C3CCC3)c2n1C[C@H]1CC[C@H](C)CC1)c1ccno1] | 3-(6-{[(1R)-1-cyclobutylethyl]amino}-8-[(1-isoxazol-5-ylethyl)amino]-7-[(trans-4-methylcyclohexyl)methyl]-7H-purin-2-yl)-1,2,4-oxadiazol-5(2H)-one | TFA | 522 | 522 |
| 11.88 | 3.826 | 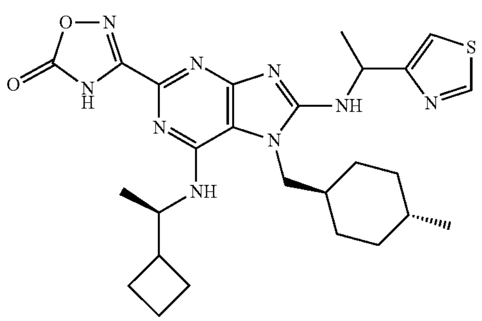 [SMILES: CC(Nc1nc2nc(-c3noc(=O)[nH]3)nc(N[C@H](C)C3CCC3)c2n1C[C@H]1CC[C@H](C)CC1)c1cscn1] | 3-(6-{[(1R)-1-cyclobutylethyl]amino}-7-[(trans-4-methylcyclohexyl)methyl]-8-{[1-(1,3-thiazol-4-yl)ethyl]amino}-7H-purin-2-yl)-1,2,4-oxadiazol-5(2H)-one | TFA | 538 | 538 |
| 11.89 | 13.82 | 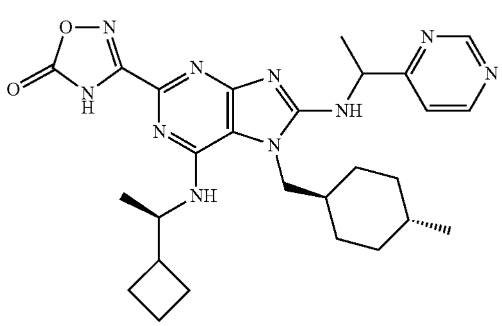 [SMILES: CC(Nc1nc2nc(-c3noc(=O)[nH]3)nc(N[C@H](C)C3CCC3)c2n1C[C@H]1CC[C@H](C)CC1)c1ccncn1] | 3-(6-{[(1R)-1-cyclobutylethyl]amino}-7-[(trans-4-methylcyclohexyl)methyl]-8-[(1-pyrimidin-4-ylethyl)amino]-7H-purin-2-yl)-1,2,4-oxadiazol-5(2H)-one | TFA | 533 | 533 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.90 | 4.044 | 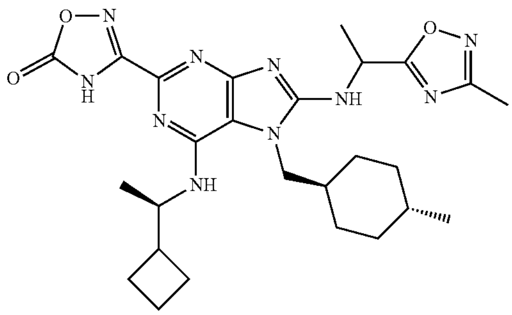 [SMILES: Cc1noc(C(C)Nc2nc3nc(-c4noc(=O)[nH]4)nc(N[C@H](C)C4CCC4)c3n2C[C@H]2CC[C@H](C)CC2)n1] | 3-(6-{[(1R)-1-cyclobutylethyl]amino}-7-[(trans-4-methylcyclohexyl)methyl]-8-{[1-(3-methyl-1,2,4-oxadiazol-5-yl)ethyl]amino}-7H-purin-2-yl)-1,2,4-oxadiazol-5(2H)-one | TFA | 537 | 537 |
| 11.91 | 3.67 | 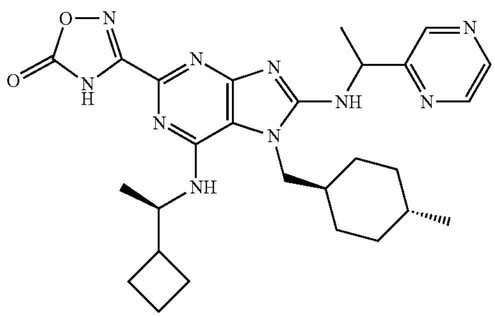 [SMILES: CC(Nc1nc2nc(-c3noc(=O)[nH]3)nc(N[C@H](C)C3CCC3)c2n1C[C@H]1CC[C@H](C)CC1)c1cnccn1] | 3-(6-{[(1R)-1-cyclobutylethyl]amino}-7-[(trans-4-methylcyclohexyl)methyl]-8-[(1-pyrazin-2-ylethyl)amino]-7H-purin-2-yl)-1,2,4-oxadiazol-5(2H)-one (diastereomer 1) | TFA | 533 | 533 |
| 11.92 | 11.74 | 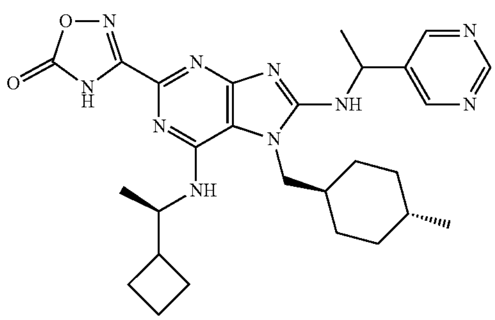 [SMILES: CC(Nc1nc2nc(-c3noc(=O)[nH]3)nc(N[C@H](C)C3CCC3)c2n1C[C@H]1CC[C@H](C)CC1)c1cncnc1] | 3-(6-{[(1R)-1-cyclobutylethyl]amino}-7-[(trans-4-methylcyclohexyl)methyl]-8-[(1-pyrimidin-5-ylethyl)amino]-7H-purin-2-yl)-1,2,4-oxadiazol-5(2H)-one | TFA | 533 | 533 |
| 11.93 | 11.95 | 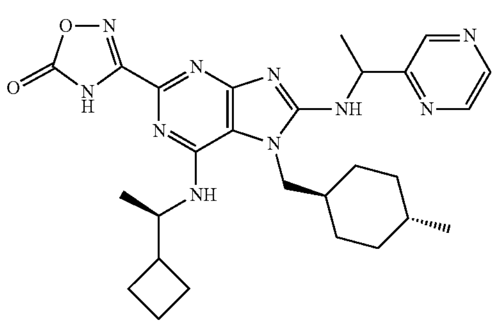 | 3-(6-{[(1R)-1-cyclobutylethyl]amino}-7-[(trans-4-methylcyclohexyl)methyl]-8-[(1-pyrazin-2-ylethyl)amino]-7H-purin-2-yl)-1,2,4-oxadiazol-5(2H)-one (diastereomer 2) | TFA | 533 | 533 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.94 | 9.398 | 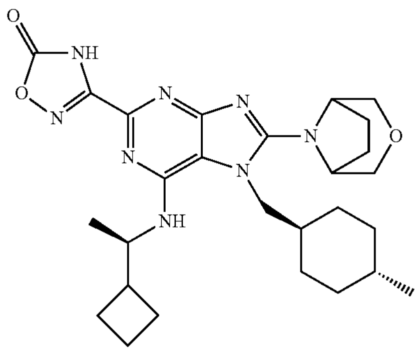 [SMILES: C[C@@H](Nc1nc(-c2noc(=O)[nH]2)nc2nc(N3C4CCC3COC4)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(3-oxa-8-azabicyclo[3.2.1]oct-8-yl)-7H-purin-2-yl]-1,2,4-oxadiazol-5(4H)-one | TFA | 523 | 523 |
| 11.95 | 0.791 | 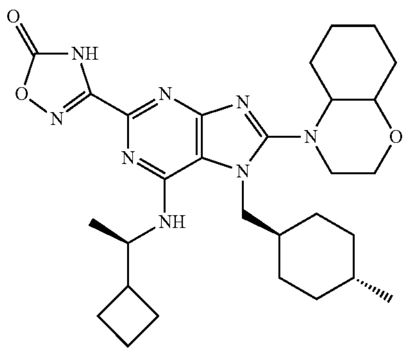 [SMILES: C[C@@H](Nc1nc(-c2noc(=O)[nH]2)nc2nc(N3CCOC4CCCCC43)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,2,4-oxadiazol-5(4H)-one (diastereomer 1) | | 551 | 551 |
| 11.96 | 4.173 | 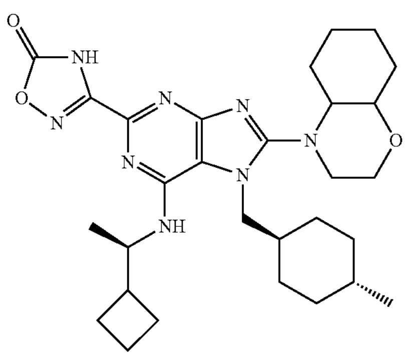 [SMILES: C[C@@H](Nc1nc(-c2noc(=O)[nH]2)nc2nc(N3CCOC4CCCCC43)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,2,4-oxadiazol-5(4H)-one (diastereomer 2) | | 551 | 551 |
| 11.97 | 1.943 | 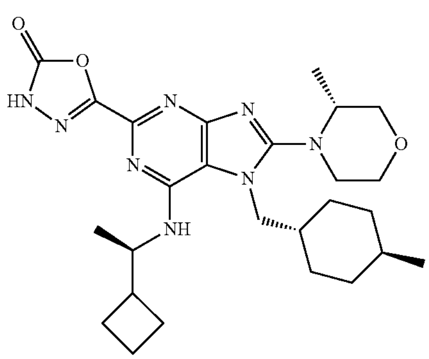 [SMILES: C[C@@H]1COCCN1c1nc2nc(-c3n[nH]c(=O)o3)nc(N[C@H](C)C3CCC3)c2n1C[C@H]1CC[C@H](C)CC1] | 5-(6-{[(1R)-1-cyclobutylethyl]amino}-7-[(trans-4-methylcyclohexyl)methyl]-8-[(3R)-3-methylmorpholin-4-yl]-7H-purin-2-yl)-1,3,4-oxadiazol-2(3H)-one | TFA | 511 | 511 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.98 | 2.524 | 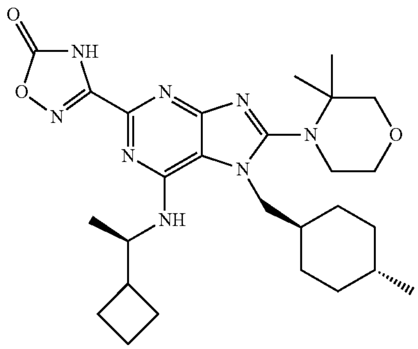 [SMILES: C[C@@H](Nc1nc(-c2noc(=O)[nH]2)nc2nc(N3CCOCC3(C)C)n(C[C@H]3CC[C@H](C)CC3)c12)C1CCC1] | 3-(6-{[(1R)-1-cyclobutylethyl]amino}-8-(3,3-dimethylmorpholin-4-yl)-7-[(trans-4-methylcyclohexyl)methyl]-7H-purin-2-yl)-1,2,4-oxadiazol-5(4H)-one | TFA | 525 | 525 |
| 11.99 | 3.43 | 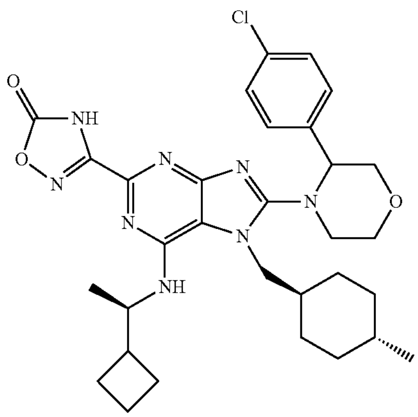 [SMILES: C[C@@H](Nc1nc(-c2noc(=O)[nH]2)nc2nc(N3CCOCC3c3ccc(Cl)cc3)n(C[C@H]3CC[C@H](C)CC3)c12)C1CCC1] | 3-{8-[3-(4-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one | TFA | 607 | 607 |
| 11.100 | 0.9358 | 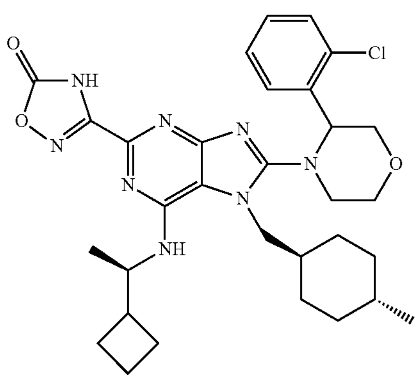 [SMILES: C[C@@H](Nc1nc(-c2noc(=O)[nH]2)nc2nc(N3CCOCC3c3ccccc3Cl)n(C[C@H]3CC[C@H](C)CC3)c12)C1CCC1] | 3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one | TFA | 607 | 607 |
| 11.101 | 16.21 | 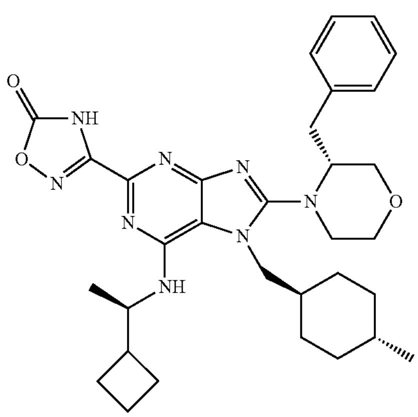 [SMILES: C[C@@H](Nc1nc(-c2noc(=O)[nH]2)nc2nc(N3CCOC[C@H]3Cc3ccccc3)n(C[C@H]3CC[C@H](C)CC3)c12)C1CCC1] | 3-{8-[(3R)-3-benzylmorpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one | TFA | 587 | 587 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.102 | 20.77 | 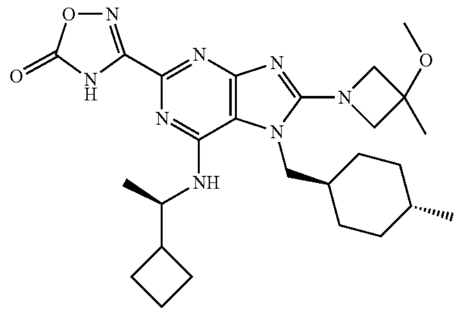 [SMILES: COC1(C)CN(c2nc3nc(-c4noc(=O)[nH]4)nc(N[C@H](C)C4CCC4)c3n2C[C@H]2CC[C@H](C)CC2)C1] | 3-(6-{[(1R)-1-cyclobutylethyl]amino}-8-(3-methoxy-3-methylazetidin-1-yl)-7-[(trans-4-methylcyclohexyl)methyl]-7H-purin-2-yl)-1,2,4-oxadiazol-5(2H)-one | TFA | 511 | 511 |
| 11.103 | 36.21 | 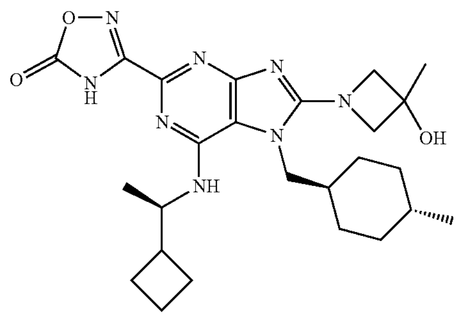 [SMILES: C[C@@H](Nc1nc(-c2noc(=O)[nH]2)nc2nc(N3CC(C)(O)C3)n(C[C@H]3CC[C@H](C)CC3)c12)C1CCC1] | 3-(6-{[(1R)-1-cyclobutylethyl]amino}-8-(3-hydroxy-3-methylazetidin-1-yl)-7-[(trans-4-methylcyclohexyl)methyl]-7H-purin-2-yl)-1,2,4-oxadiazol-5(2H)-one | TFA | 497 | 497 |
| 11.104 | 9.236 | 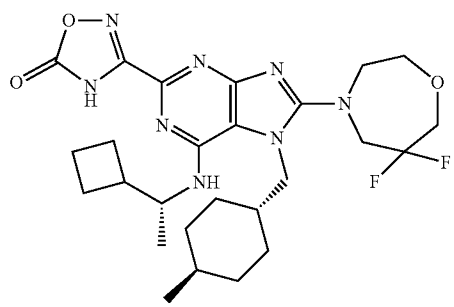 [SMILES: C[C@@H](Nc1nc(-c2noc(=O)[nH]2)nc2nc(N3CCOCC(F)(F)C3)n(C[C@H]3CC[C@H](C)CC3)c12)C1CCC1] | 3-(6-{[(1R)-1-cyclobutylethyl]amino}-8-(6,6-difluoro-1,4-oxazepan-4-yl)-7-[(trans-4-methylcyclohexyl)methyl]-7H-purin-2-yl)-1,2,4-oxadiazol-5(2H)-one | TFA | 547 | 547 |
| 11.105 | 42.59 | 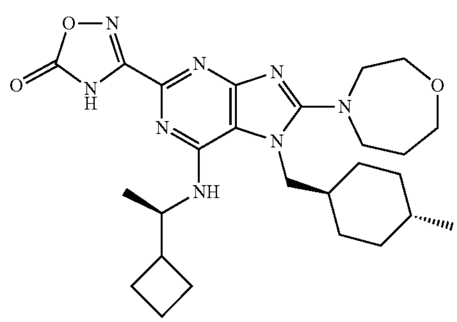 [SMILES: C[C@@H](Nc1nc(-c2noc(=O)[nH]2)nc2nc(N3CCCOCC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(1,4-oxazepan-4-yl)-7H-purin-2-yl]-1,2,4-oxadiazol-5(2H)-one | TFA | 511 | 511 |
| 11.106 | 3.217 | 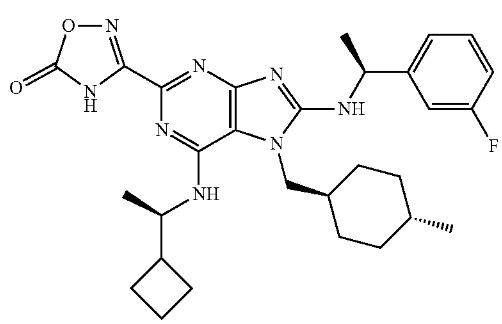 [SMILES: C[C@H](Nc1nc2nc(-c3noc(=O)[nH]3)nc(N[C@H](C)C3CCC3)c2n1C[C@H]1CC[C@H](C)CC1)c1cccc(F)c1] | 3-(6-{[(1R)-1-cyclobutylethyl]amino}-8-{[(1S)-1-(3-fluorophenyl)ethyl]amino}-7-[(trans-4-methylcyclohexyl)methyl]-7H-purin-2-yl)-1,2,4-oxadiazol-5(2H)-one | TFA | 549 | 549 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.107 | 0.5071 | 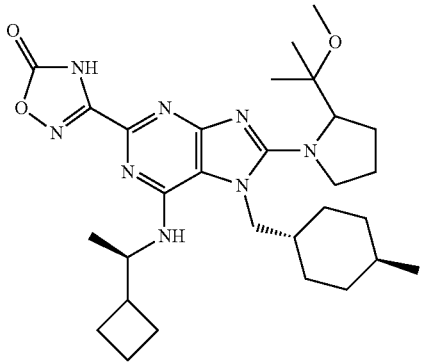 [SMILES: COC(C)(C)C1CCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[2-(1-methoxy-1-methylethyl)pyrrolidin-1-yl]-7-[(trans-4-methylcyclohexyl)methyl]-7H-purin-2-yl)-1,2,4-oxadiazol-5(2H)-one | TFA | 553 | 553 |
| 11.108 | 1.598 | 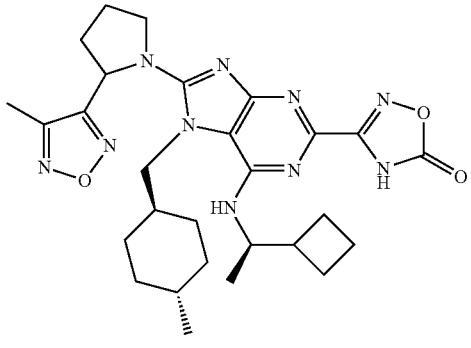 [SMILES: Cc1nonc1C1CCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[2-(4-methyl-1,2,5-oxadiazol-3-yl)pyrrolidin-1-yl]-7H-purin-2-yl)-1,2,4-oxadiazol-5(2H)-one | TFA | 563 | 563 |
| 11.109 | 55.62 | 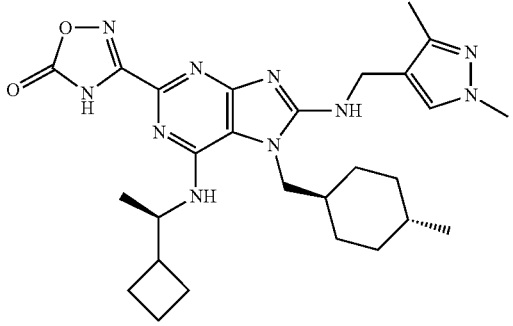 [SMILES: Cc1nn(C)cc1CNc1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-{[(1,3-dimethyl-1H-pyrazol-4-yl)methyl]amino}-7-[(trans-4-methylcyclohexyl)methyl]-7H-purin-2-yl)-1,2,4-oxadiazol-5(2H)-one | TFA | 535 | 535 |
| 11.110 | 6.762 | 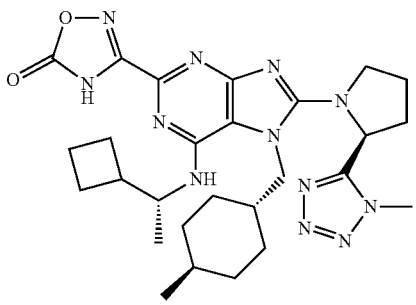 [SMILES: C[C@@H](Nc1nc(-c2noc(=O)[nH]2)nc2nc(N3CCC[C@H]3c3nnnn3C)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(2S)-2-(1-methyl-1H-tetrazol-5-yl)pyrrolidin-1-yl]-7H-purin-2-yl)-1,2,4-oxadiazol-5(2H)-one | TFA | 563 | 563 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.111 | 6.341 | 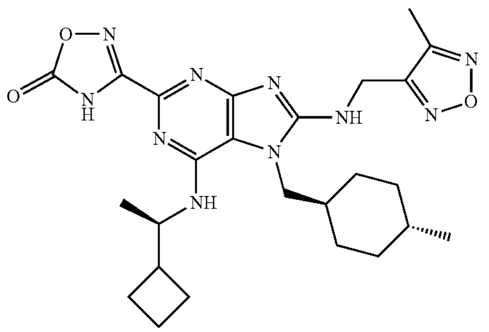 [SMILES: Cc1nonc1CNc1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-{[(4-methyl-1,2,5-oxadiazol-3-yl)methyl]amino}-7H-purin-2-yl)-1,2,4-oxadiazol-5(2H)-one | TFA | 523 | 523 |
| 11.112 | 214.6 | 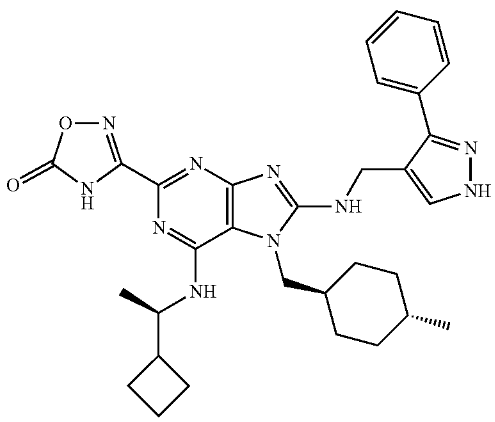 [SMILES: C[C@@H](Nc1nc(-c2noc(=O)[nH]2)nc2nc(NCc3c[nH]nc3-c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-{[(3-phenyl-1H-pyrazol-4-yl)methyl]amino}-7H-purin-2-yl)-1,2,4-oxadiazol-5(2H)-one | TFA | 583 | 583 |
| 11.113 | 57.74 | 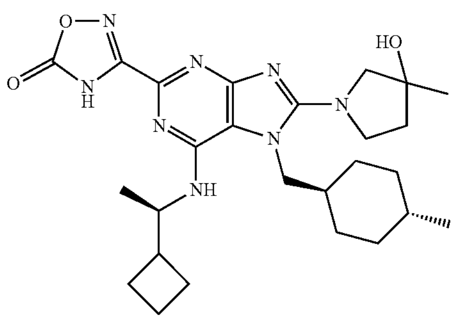 [SMILES: C[C@@H](Nc1nc(-c2noc(=O)[nH]2)nc2nc(N3CCC(C)(O)C3)n(C[C@H]3CC[C@H](C)CC3)c12)C1CCC1] | 3-(6-{[(1R)-1-cyclobutylethyl]amino}-8-(3-hydroxy-3-methylpyrrolidin-1-yl)-7-[(trans-4-methylcyclohexyl)methyl]-7H-purin-2-yl)-1,2,4-oxadiazol-5(2H)-one | TFA | 511 | 511 |
| 11.114 | 52.95 | 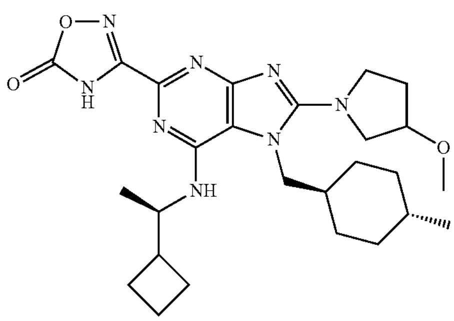 [SMILES: COC1CCN(c2nc3nc(-c4noc(=O)[nH]4)nc(N[C@H](C)C4CCC4)c3n2C[C@H]2CC[C@H](C)CC2)C1] | 3-(6-{[(1R)-1-cyclobutylethyl]amino}-8-(3-methoxypyrrolidin-1-yl)-7-[(trans-4-methylcyclohexyl)methyl]-7H-purin-2-yl)-1,2,4-oxadiazol-5(2H)-one | TFA | 511 | 511 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.115 | 8.132 | 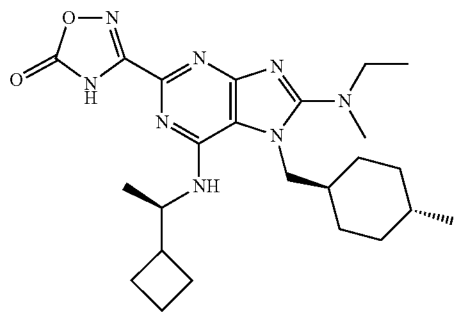 [SMILES: CCN(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[ethyl(methyl)amino]-7-[(trans-4-methylcyclohexyl)methyl]-7H-purin-2-yl)-1,2,4-oxadiazol-5(2H)-one | TFA | 469 | 469 |
| 11.116 | 21.04 | 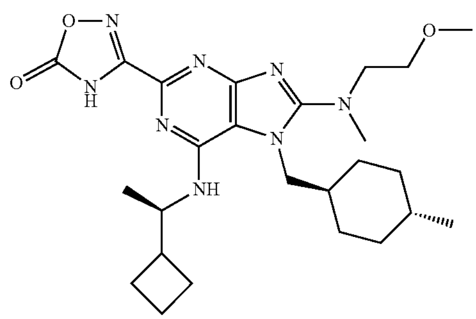 [SMILES: COCCN(C)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(2-methoxyethyl)(methyl)amino]-7-[(trans-4-methylcyclohexyl)methyl]-7H-purin-2-yl)-1,2,4-oxadiazol-5(2H)-one | TFA | 499 | 499 |
| 11.117 | 3.77 | 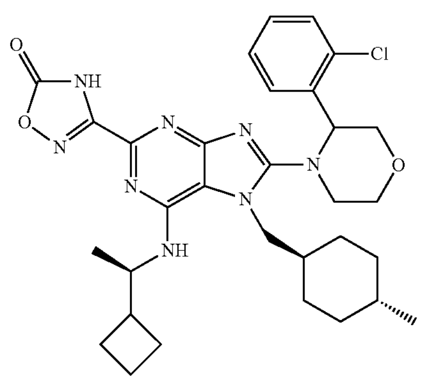 [SMILES: C[C@@H](Nc1nc(-c2noc(=O)[nH]2)nc2nc(N3CCOCC3c3ccccc3Cl)n(C[C@H]3CC[C@H](C)CC3)c12)C1CCC1] | 3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one (diastereomer 1) | | 607 | 607 |
| 11.118 | 0.5682 | 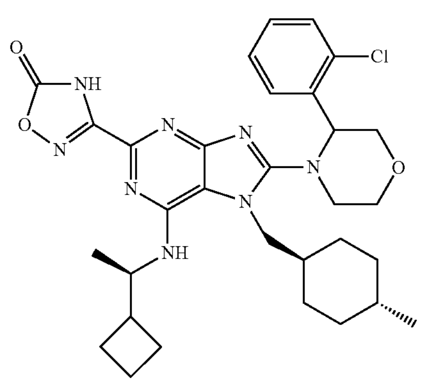 [SMILES: C[C@@H](Nc1nc(-c2noc(=O)[nH]2)nc2nc(N3CCOCC3c3ccccc3Cl)n(C[C@H]3CC[C@H](C)CC3)c12)C1CCC1] | 3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one (diastereomer 2) | | 607 | 607 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.119 | 24.83 | 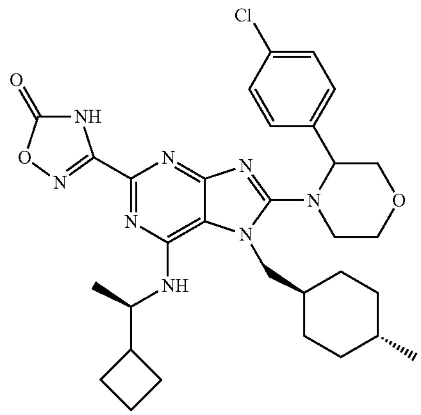 [SMILES: C[C@@H](Nc1nc(-c2noc(=O)[nH]2)nc2nc(N3CCOCC3c3ccc(Cl)cc3)n(C[C@H]3CC[C@H](C)CC3)c12)C1CCC1] | 3-{8-[3-(4-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one | | 607 | 607 |
| 11.120 | 5.569 | 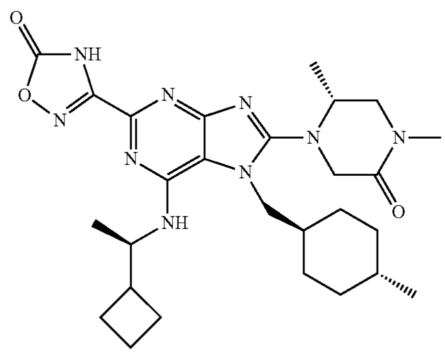 [SMILES: C[C@@H]1CN(C)C(=O)CN1c1nc2nc(-c3noc(=O)[nH]3)nc(N[C@H](C)C3CCC3)c2n1C[C@H]1CC[C@H](C)CC1] | (5R)-4-[6-{[(1R)-1-cyclobutylethyl]amino}-7-[(trans-4-methylcyclohexyl)methyl]-2-(5-oxo-4,5-dihydro-1,2,4-oxadiazol-3-yl)-7H-purin-8-yl]-1,5-dimethylpiperazin-2-one | TFA | 538 | 538 |
| 11.121 | 40.13 | 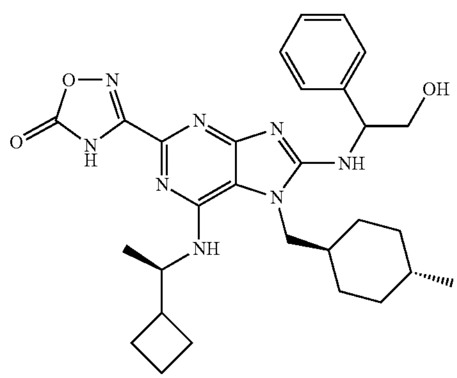 [SMILES: C[C@@H](Nc1nc(-c2noc(=O)[nH]2)nc2nc(NC(CO)c3ccccc3)n(C[C@H]3CC[C@H](C)CC3)c12)C1CCC1] | 3-(6-{[(1R)-1-cyclobutylethyl]amino}-8-[(2-hydroxy-1-phenylethyl)amino]-7-[(trans-4-methylcyclohexyl)methyl]-7H-purin-2-yl)-1,2,4-oxadiazol-5(4H)-one (diastereomer 1) | TFA | 547 | 547 |
| 11.122 | 4.173 | 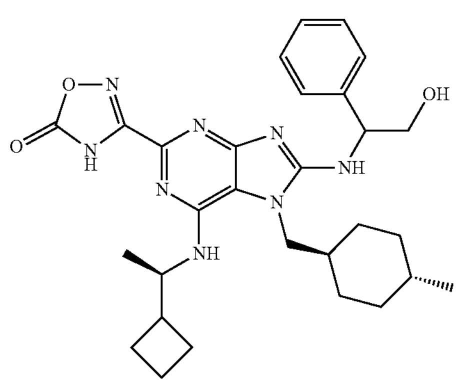 [SMILES: C[C@@H](Nc1nc(-c2noc(=O)[nH]2)nc2nc(NC(CO)c3ccccc3)n(C[C@H]3CC[C@H](C)CC3)c12)C1CCC1] | 3-(6-{[(1R)-1-cyclobutylethyl]amino}-8-[(2-hydroxy-1-phenylethyl)amino]-7-[(trans-4-methylcyclohexyl)methyl]-7H-purin-2-yl)-1,2,4-oxadiazol-5(4H)-one (diastereomer 2) | TFA | 547 | 547 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.123 | 4.392 | 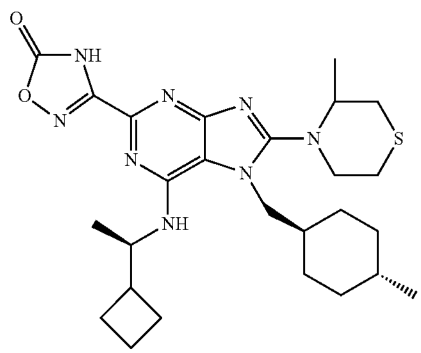 [SMILES: CC1CSCCN1c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(3-methylthiomorpholin-4-yl)-7H-purin-2-yl]-1,2,4-oxadiazol-5(2H)-one | TFA | 527 | 527 |
| 11.124 | 9.616 | 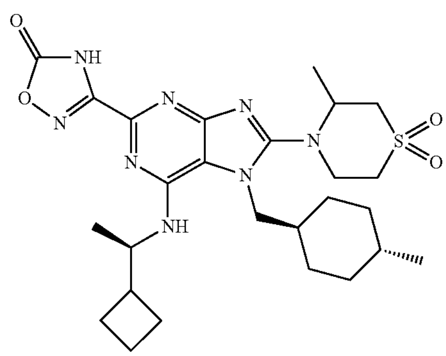 [SMILES: CC1CS(=O)(=O)CCN1c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(3-methyl-1,1-dioxidothiomorpholin-4-yl)-7H-purin-2-yl]-1,2,4-oxadiazol-5(2H)-one | | 559 | 559 |
| 11.125 | 7.488 | 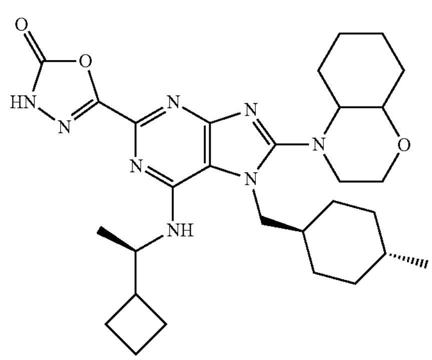 [SMILES: C[C@@H](Nc1nc(-c2n[nH]c(=O)o2)nc2nc(N3CCOC4CCCCC43)n(C[C@H]3CC[C@H](C)CC3)c12)C1CCC1] | 5-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,3,4-oxadiazol-2(3H)-one (diastereomer 1) | | 551 | 551 |
| 11.126 | 1.46 | 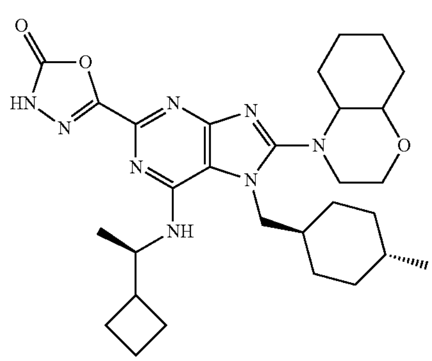 [SMILES: C[C@@H](Nc1nc(-c2n[nH]c(=O)o2)nc2nc(N3CCOC4CCCCC43)n(C[C@H]3CC[C@H](C)CC3)c12)C1CCC1] | 5-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,3,4-oxadiazol-2(3H)-one (diastereomer 2) | | 551 | 551 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.127 | 26.23 | 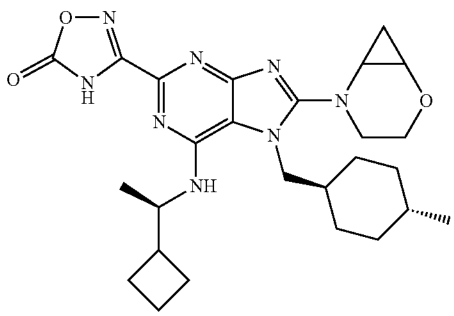 [SMILES: C[C@@H](Nc1nc(-c2noc(=O)[nH]2)nc2nc(N3CCOC4CC43)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-oxa-5-azabicyclo[4.1.0]hept-5-yl)-7H-purin-2-yl]-1,2,4-oxadiazol-5(4H)-one | TFA | 509 | 509 |
| 11.128 | 0.6423 | 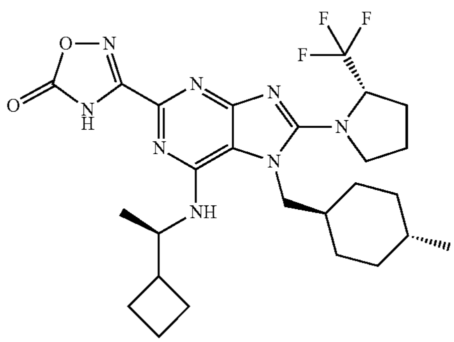 [SMILES: C[C@@H](Nc1nc(-c2noc(=O)[nH]2)nc2nc(N3CCC[C@H]3C(F)(F)F)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(2S)-2-(trifluoromethyl)pyrrolidin-1-yl]-7H-purin-2-yl)-1,2,4-oxadiazol-5(4H)-one | TFA | 549 | 549 |
| 11.129 | 0.7883 | 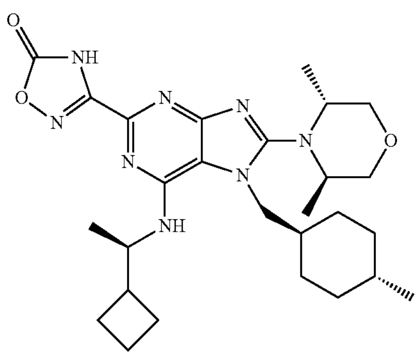 [SMILES: C[C@@H]1COC[C@@H](C)N1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(3R,5R)-3,5-dimethylmorpholin-4-yl]-7-[(trans-4-methylcyclohexyl)methyl]-7H-purin-2-yl)-1,2,4-oxadiazol-5(4H)-one | TFA | 525 | 525 |
| 11.130 | 2.052 | 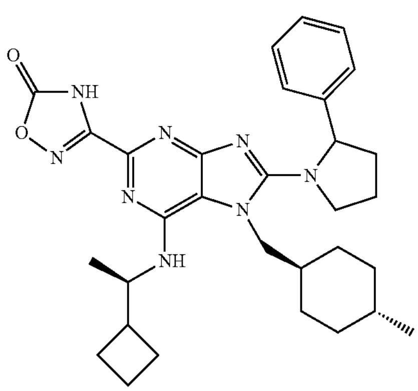 [SMILES: C[C@@H](Nc1nc(-c2noc(=O)[nH]2)nc2nc(N3CCCC3c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenylpyrrolidin-1-yl)-7H-purin-2-yl]-1,2,4-oxadiazol-5(4H)-one | TFA | 557 | 557 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.131 | 7.015 | 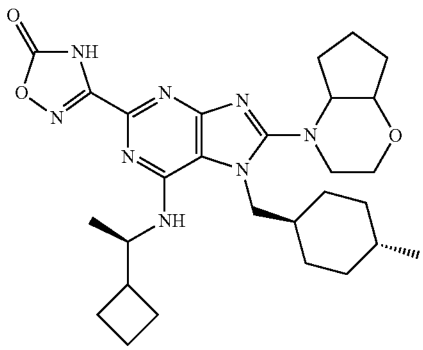 [SMILES: C[C@@H](Nc1nc(-c2noc(=O)[nH]2)nc2nc(N3CCOC4CCCC43)n(C[C@H]3CC[C@H](C)CC3)c12)C1CCC1] | 3-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,2,4-oxadiazol-5(2H)-one (diastereomer 1) | | 537 | 537 |
| 11.132 | 25.63 | 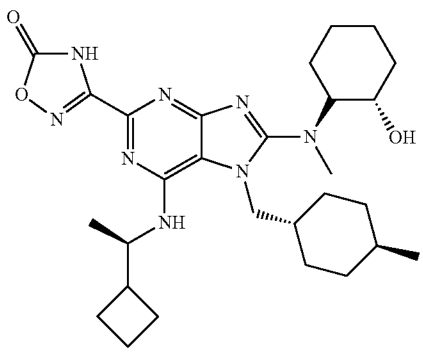 | 3-(6-{[(1R)-1-cyclobutylethyl]amino}-8-{[(1R,2S)-2-hydroxycyclohexyl](methyl)amino}-7-[(trans-4-methylcyclohexyl)methyl]-7H-purin-2-yl)-1,2,4-oxadiazol-5(4H)-one | | 539 | 539 |
| 11.133 | 0.3439 | 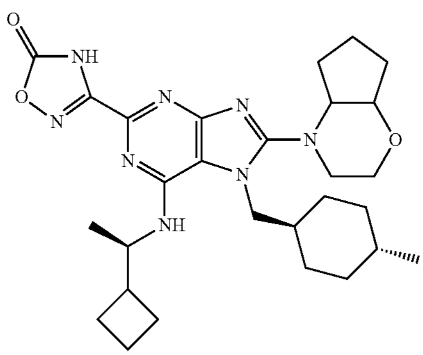 [SMILES: C[C@@H](Nc1nc(-c2noc(=O)[nH]2)nc2nc(N3CCOC4CCCC43)n(C[C@H]3CC[C@H](C)CC3)c12)C1CCC1] | 3-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,2,4-oxadiazol-5(2H)-one (diastereomer 2) | | 537 | 537 |
| 11.134 | 9.456 | 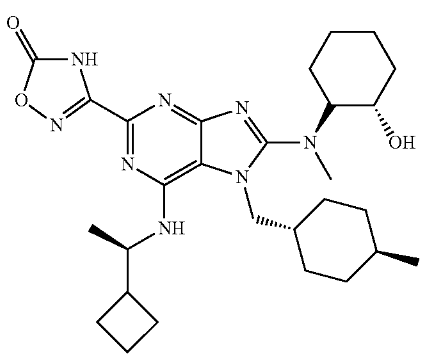 | 3-(6-{[(1R)-1-cyclobutylethyl]amino}-8-{[(1R,2S)-2-hydroxycyclohexyl](methyl)amino}-7-[(trans-4-methylcyclohexyl)methyl]-7H-purin-2-yl)-1,2,4-oxadiazol-5(4H)-one | | 539 | 539 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.135 | 2.079 | 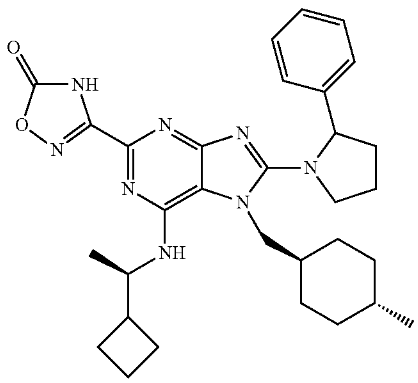 [SMILES: C[C@@H](Nc1nc(-c2noc(=O)[nH]2)nc2nc(N3CCCC3c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenylpyrrolidin-1-yl)-7H-purin-2-yl]-1,2,4-oxadiazol-5(4H)-one (diastereomer 1) | | 557 | 557 |
| 11.136 | 513.6 | 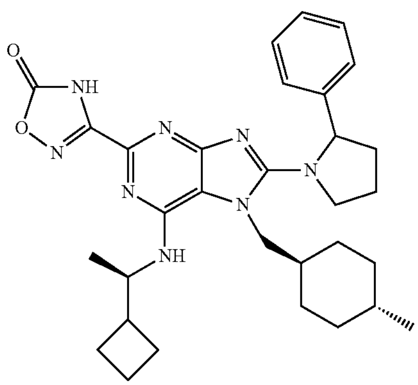 [SMILES: C[C@@H](Nc1nc(-c2noc(=O)[nH]2)nc2nc(N3CCCC3c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenylpyrrolidin-1-yl)-7H-purin-2-yl]-1,2,4-oxadiazol-5(4H)-one (diastereomer 2) | | 557 | 557 |
| 11.137 | 0.8813 | 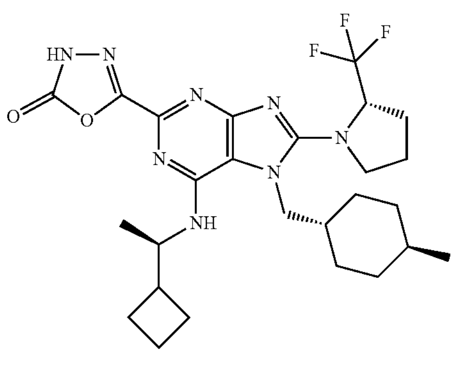 [SMILES: C[C@@H](Nc1nc(-c2n[nH]c(=O)o2)nc2nc(N3CCC[C@H]3C(F)(F)F)n(C[C@H]3CC[C@H](C)CC3)c12)C1CCC1] | 5-(6-{[(1R)-1-cyclobutylethyl]amino}-7-[(trans-4-methylcyclohexyl)methyl]-8-[(2S)-2-(trifluoromethyl)pyrrolidin-1-yl]-7H-purin-2-yl)-1,3,4-oxadiazol-2(3H)-one | TFA | 549 | 549 |
| 11.140 | 9.871 | 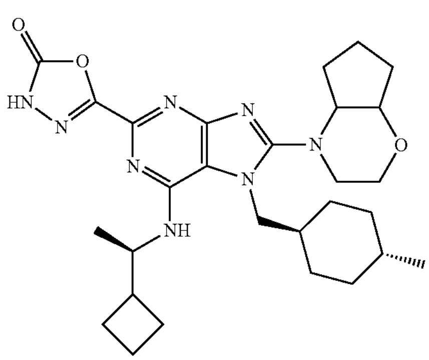 [SMILES: C[C@@H](Nc1nc(-c2n[nH]c(=O)o2)nc2nc(N3CCOC4CCCC43)n(C[C@H]3CC[C@H](C)CC3)c12)C1CCC1] | 5-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,3,4-oxadiazol-2(3H)-one (diastereomer 1) | | 537 | 537 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.141 | 0.841 | 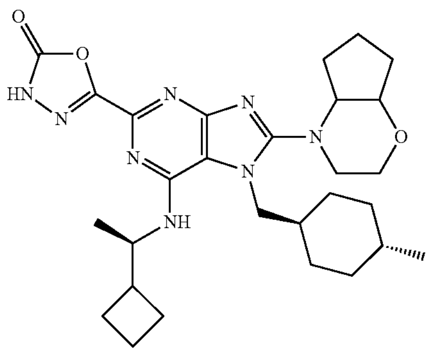 [SMILES: C[C@@H](Nc1nc(-c2n[nH]c(=O)o2)nc2nc(N3CCOC4CCCC43)n(C[C@H]3CC[C@H](C)CC3)c12)C1CCC1] | 5-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,3,4-oxadiazol-2(3H)-one (diastereomer 2) | | 537 | 537 |
| 11.142 | 0.774 | 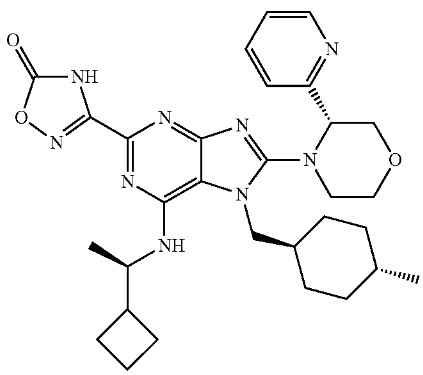 [SMILES: C[C@@H](Nc1nc(-c2noc(=O)[nH]2)nc2nc(N3CCOC[C@H]3c3ccccn3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(3R)-3-pyridin-2-ylmorpholin-4-yl]-7H-purin-2-yl)-1,2,4-oxadiazol-5(4H)-one | | 574 | 574 |
| 11.143 | 12.61 | 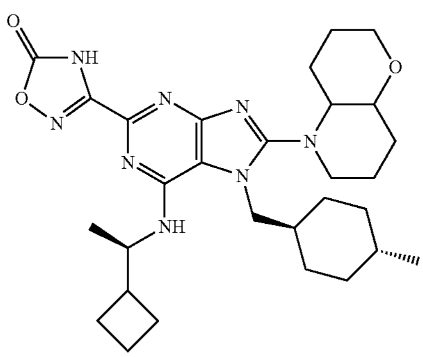 [SMILES: C[C@@H](Nc1nc(-c2noc(=O)[nH]2)nc2nc(N3CCCC4OCCCC43)n(C[C@H]3CC[C@H](C)CC3)c12)C1CCC1] | 3-(6-{[(1R)-1-cyclobutylethyl]amino}-8-(hexahydro-2H-pyrano[4,3-b]pyridin-1(5H)-yl)-7-[(trans-4-methylcyclohexyl)methyl]-7H-purin-2-yl)-1,2,4-oxadiazol-5(4H)-one (diastereomer 1) | | 551 | 551 |
| 11.144 | 5.665 | 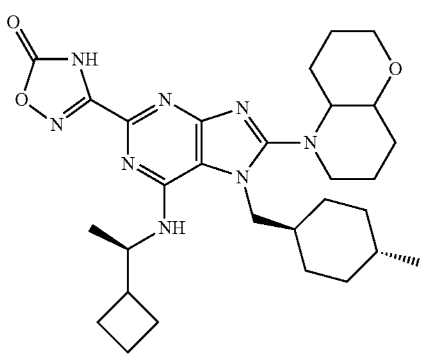 [SMILES: C[C@@H](Nc1nc(-c2noc(=O)[nH]2)nc2nc(N3CCCC4OCCCC43)n(C[C@H]3CC[C@H](C)CC3)c12)C1CCC1] | 3-(6-{[(1R)-1-cyclobutylethyl]amino}-8-(hexahydro-2H-pyrano[4,3-b]pyridin-1(5H)-yl)-7-[(trans-4-methylcyclohexyl)methyl]-7H-purin-2-yl)-1,2,4-oxadiazol-5(4H)-one (diastereomer 2) | | 551 | 551 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.145 | 1.312 | 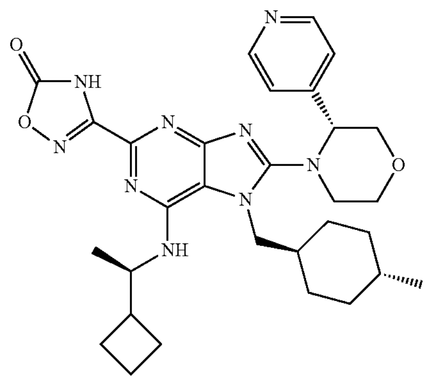 [SMILES: C[C@@H](Nc1nc(-c2noc(=O)[nH]2)nc2nc(N3CCOC[C@H]3c3ccncc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(3R)-3-pyridin-4-ylmorpholin-4-yl]-7H-purin-2-yl)-1,2,4-oxadiazol-5(4H)-one | | 574 | 574 |
| 11.146 | 20.06 | 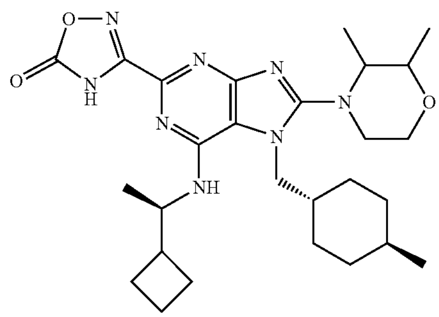 [SMILES: CC1OCCN(c2nc3nc(-c4noc(=O)[nH]4)nc(N[C@H](C)C4CCC4)c3n2C[C@H]2CC[C@H](C)CC2)C1C] | 3-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,2,4-oxadiazol-5(4H)-one (diastereomer 1) | | 525 | 525 |
| 11.147 | 9.194 | 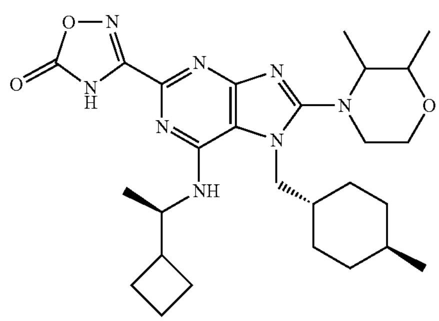 [SMILES: CC1OCCN(c2nc3nc(-c4noc(=O)[nH]4)nc(N[C@H](C)C4CCC4)c3n2C[C@H]2CC[C@H](C)CC2)C1C] | 3-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,2,4-oxadiazol-5(4H)-one (diastereomer 2) | | 525 | 525 |
| 11.148 | 23.82 | 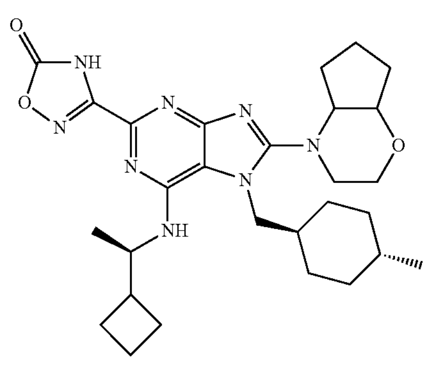 [SMILES: C[C@@H](Nc1nc(-c2noc(=O)[nH]2)nc2nc(N3CCOC4CCCC43)n(C[C@H]3CC[C@H](C)CC3)c12)C1CCC1] | 3-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,2,4-oxadiazol-5(4H)-one (diastereomer 3) | | 537 | 537 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.149 | 3.578 | 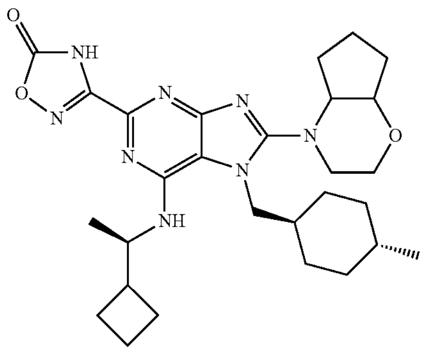 [SMILES: C[C@@H](Nc1nc(-c2noc(=O)[nH]2)nc2nc(N3CCOC4CCCC43)n(C[C@H]3CC[C@H](C)CC3)c12)C1CCC1] | 3-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,2,4-oxadiazol-5(4H)-one (diastereomer 4) | | 537 | 537 |
| 11.150 | 6.727 | 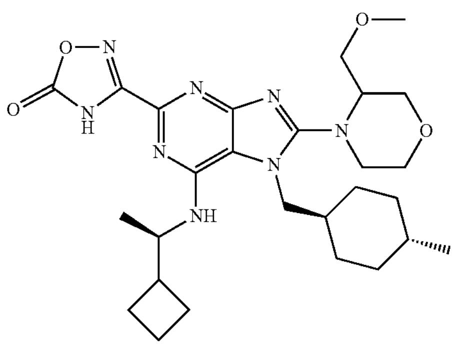 [SMILES: COCC1COCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[3-(methoxymethyl)morpholin-4-yl]-7-[(trans-4-methylcyclohexyl)methyl]-7H-purin-2-yl)-1,2,4-oxadiazol-5(4H)-one (diastereomer 1) | TFA | 541 | 541 |
| 11.151 | 20.86 | 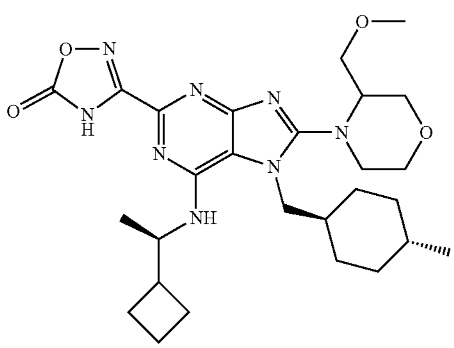 [SMILES: COCC1COCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[3-(methoxymethyl)morpholin-4-yl]-7-[(trans-4-methylcyclohexyl)methyl]-7H-purin-2-yl)-1,2,4-oxadiazol-5(4H)-one (diastereomer 2) | TFA | 541 | 541 |
| 11.152 | 3.088 | 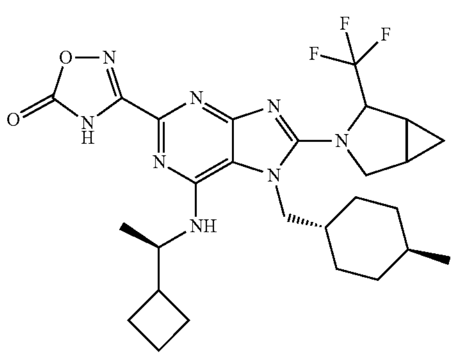 [SMILES: C[C@@H](Nc1nc(-c2noc(=O)[nH]2)nc2nc(N3CC4CC4C3C(F)(F)F)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[2-(trifluoromethyl)-3-azabicyclo[3.1.0]hex-3-yl]-7H-purin-2-yl)-1,2,4-oxadiazol-5(4H)-one | TFA | 561 | 561 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.153 | 65.57 | 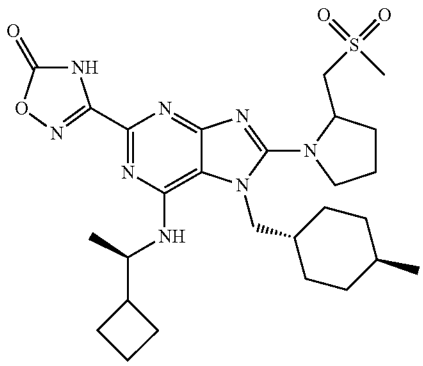 [SMILES: C[C@@H](Nc1nc(-c2noc(=O)[nH]2)nc2nc(N3CCCC3CS(C)(=O)=O)n(C[C@H]3CC[C@H](C)CC3)c12)C1CCC1] | 3-(6-{[(1R)-1-cyclobutylethyl]amino}-7-[(trans-4-methylcyclohexyl)methyl]-8-{2-[(methylsulfonyl)methyl]pyrrolidin-1-yl}-7H-purin-2-yl)-1,2,4-oxadiazol-5(4H)-one | TFA | 573 | 573 |
| 11.154 | 70.69 | 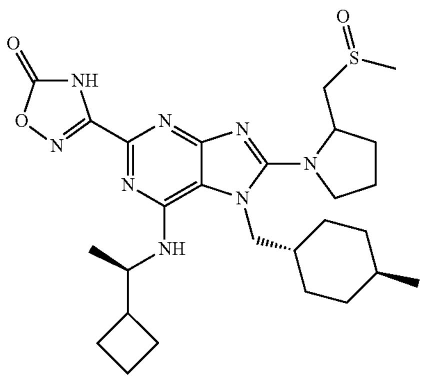 [SMILES: C[C@@H](Nc1nc(-c2noc(=O)[nH]2)nc2nc(N3CCCC3CS(C)=O)n(C[C@H]3CC[C@H](C)CC3)c12)C1CCC1] | 3-(6-{[(1R)-1-cyclobutylethyl]amino}-7-[(trans-4-methylcyclohexyl)methyl]-8-{2-[(methylsulfinyl)methyl]pyrrolidin-1-yl}-7H-purin-2-yl)-1,2,4-oxadiazol-5(4H)-one (stereoisomer 1) | TFA | 557 | 557 |
| 11.155 | 165.4 | 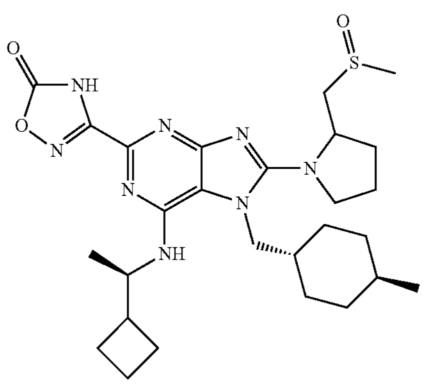 [SMILES: C[C@@H](Nc1nc(-c2noc(=O)[nH]2)nc2nc(N3CCCC3CS(C)=O)n(C[C@H]3CC[C@H](C)CC3)c12)C1CCC1] | 3-(6-{[(1R)-1-cyclobutylethyl]amino}-7-[(trans-4-methylcyclohexyl)methyl]-8-{2-[(methylsulfinyl)methyl]pyrrolidin-1-yl}-7H-purin-2-yl)-1,2,4-oxadiazol-5(4H)-one (stereoisomer 2) | TFA | 557 | 557 |
| 11.157 | 46.96 | 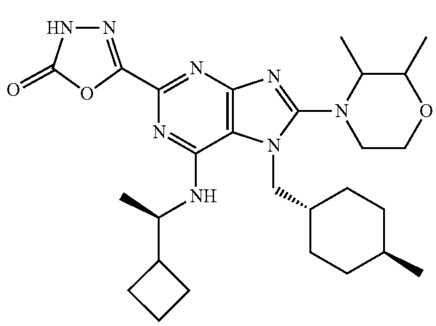 [SMILES: CC1OCCN(c2nc3nc(-c4n[nH]c(=O)o4)nc(N[C@H](C)C4CCC4)c3n2C[C@H]2CC[C@H](C)CC2)C1C] | 5-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,3,4-oxadiazol-2(3H)-one (diastereomer 1) | | 525 | 525 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.158 | 12.93 | 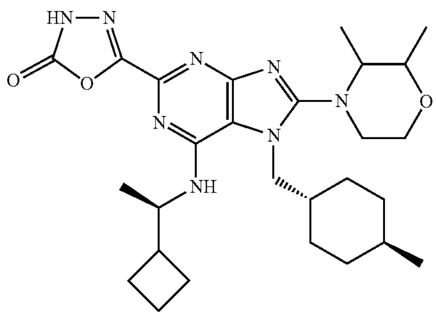 [SMILES: CC1OCCN(c2nc3nc(-c4n[nH]c(=O)o4)nc(N[C@H](C)C4CCC4)c3n2C[C@H]2CC[C@H](C)CC2)C1C] | 5-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,3,4-oxadiazol-2(3H)-one (diastereomer 2) | | 525 | 525 |
| 11.159 | 12.13 | 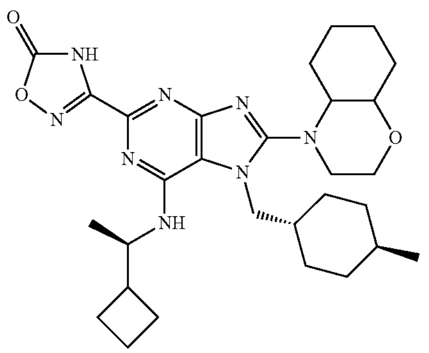 [SMILES: C[C@@H](Nc1nc(-c2noc(=O)[nH]2)nc2nc(N3CCOC4CCCCC43)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,2,4-oxadiazol-5(4H)-one (diastereomer 1) | | 551 | 551 |
| 11.160 | 3.929 | 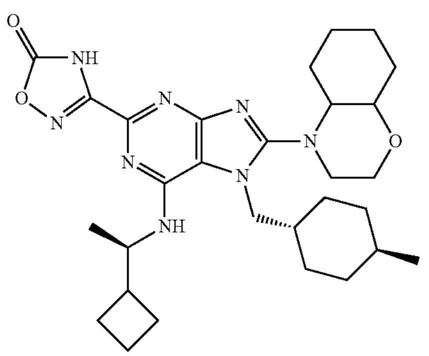 [SMILES: C[C@@H](Nc1nc(-c2noc(=O)[nH]2)nc2nc(N3CCOC4CCCCC43)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,2,4-oxadiazol-5(4H)-one (diastereomer 2) | | 551 | 551 |
| 11.161 | 29.54 | 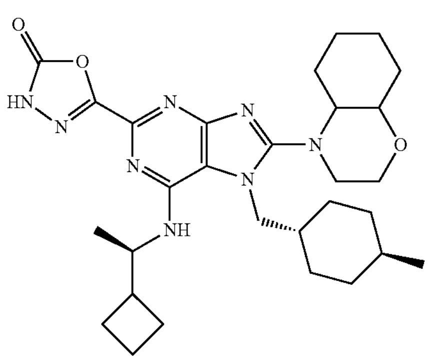 [SMILES: C[C@@H](Nc1nc(-c2n[nH]c(=O)o2)nc2nc(N3CCOC4CCCCC43)n(C[C@H]3CC[C@H](C)CC3)c12)C1CCC1] | 5-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,3,4-oxadiazol-2(3H)-one (diastereomer 1) | | 551 | 551 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.162 | 7.402 | 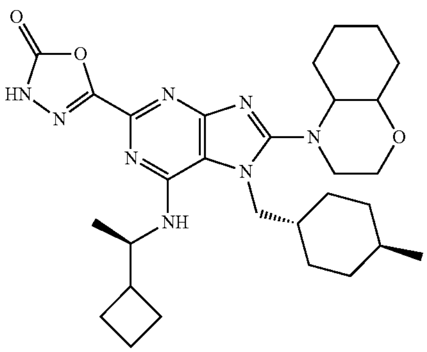 [SMILES: C[C@@H](Nc1nc(-c2n[nH]c(=O)o2)nc2nc(N3CCOC4CCCCC43)n(C[C@H]3CC[C@H](C)CC3)c12)C1CCC1] | 5-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,3,4-oxadiazol-2(3H)-one (diastereomer 2) | | 551 | 551 |
| 11.163 | 21.19 | 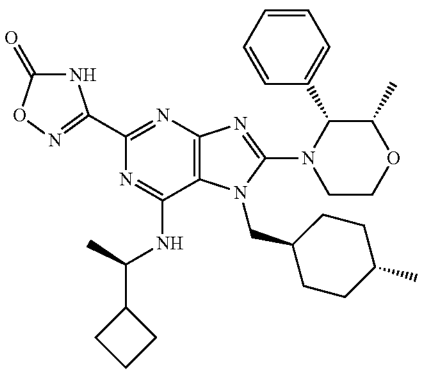 [SMILES: C[C@@H]1OCCN(c2nc3nc(-c4noc(=O)[nH]4)nc(N[C@H](C)C4CCC4)c3n2C[C@H]2CC[C@H](C)CC2)[C@@H]1c1ccccc1] | 3-(6-{[(1R)-1-cyclobutylethyl]amino}-7-[(trans-4-methylcyclohexyl)methyl]-8-[(2S,3R)-2-methyl-3-phenylmorpholin-4-yl]-7H-purin-2-yl)-1,2,4-oxadiazol-5(4H)-one | | 587 | 587 |
| 11.164 | 30.95 | 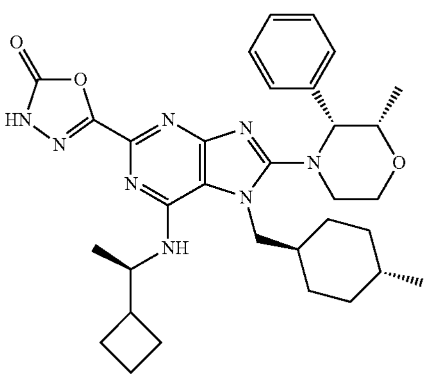 [SMILES: C[C@@H]1OCCN(c2nc3nc(-c4n[nH]c(=O)o4)nc(N[C@H](C)C4CCC4)c3n2C[C@H]2CC[C@H](C)CC2)[C@@H]1c1ccccc1] | 5-(6-{[(1R)-1-cyclobutylethyl]amino}-7-[(trans-4-methylcyclohexyl)methyl]-8-[(2S,3R)-2-methyl-3-phenylmorpholin-4-yl]-7H-purin-2-yl)-1,3,4-oxadiazol-2(3H)-one | | 587 | 587 |
| 11.165 | 0.767 | 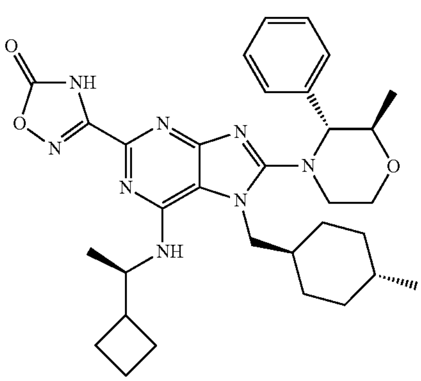 [SMILES: C[C@@H](Nc1nc(-c2noc(=O)[nH]2)nc2nc(N3CCO[C@H](C)[C@H]3c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(2R,3R)-2-methyl-3-phenylmorpholin-4-yl]-7H-purin-2-yl)-1,2,4-oxadiazol-5(4H)-one | | 587 | 587 |

TABLE 11-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 11.166 | 0.790 | 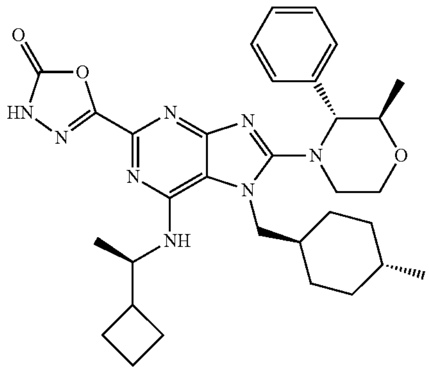 [SMILES: C[C@@H](Nc1nc(-c2n[nH]c(=O)o2)nc2nc(N3CCO[C@H](C)[C@H]3c3ccccc3)n(C[C@H]3CC[C@H](C)CC3)c12)C1CCC1] | 5-(6-{[(1R)-1-cyclobutylethyl]amino}-7-[(trans-4-methylcyclohexyl)methyl]-8-[(2R,3R)-2-methyl-3-phenylmorpholin-4-yl]-7H-purin-2-yl)-1,3,4-oxadiazol-2(3H)-one | | 587 | 587 |
| 11.167 | 2.156 | 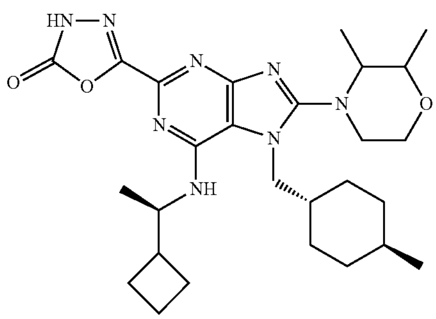 [SMILES: CC1OCCN(c2nc3nc(-c4n[nH]c(=O)o4)nc(N[C@H](C)C4CCC4)c3n2C[C@H]2CC[C@H](C)CC2)C1C] | 5-(6-{[(1R)-1-cyclobutylethyl]amino}-8-[(trans)-2,3-dimethylmorpholin-4-yl]-7-[(trans-4-methylcyclohexyl)methyl]-7H-purin-2-yl)-1,3,4-oxadiazol-2(3H)-one (mixture of diastereomers) | | 525 | 525 |

Preparative Example 12.1

6-{[(1R)-1-cyclobutylethyl]amino}-8-[4-(propan-2-yl)pyridin-2-yl]-7-[4-(trifluoromethyl)benzyl]-7H-purine-2-carbonitrile

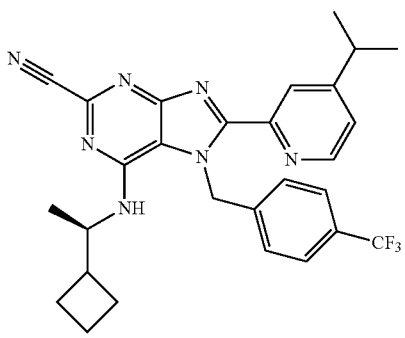 [SMILES: CC(C)c1ccnc(-c2nc3nc(C#N)nc(N[C@H](C)C4CCC4)c3n2Cc2ccc(C(F)(F)F)cc2)c1]

Using a procedure analogous to that described in Step 2 of Example 1.1, 6-{[(1R)-1-cyclobutylethyl]amino}-8-[4-(propan-2-yl)pyridin-2-yl]-7-[4-(trifluoromethyl)benzyl]-7H-purine-2-carbonitrile was prepared starting from 6-{[(1R)-1-cyclobutylethyl]amino}-7-[4-(trifluoromethyl)benzyl]-7H-purine-2-carbonitrile (Preparative Example 1.1) and 2-bromo-4-(isopropyl)pyridine (purchased from Combiphos). $^1$H NMR (600 MHz, CDCl$_3$) δ 8.44 (s, 1H), 8.39 (d, J=4.2 Hz, 1H), 7.69 (d, J=7.2 Hz, 2H), 7.33 (d, J=7.8 Hz, 2H), 7.23 (m, 1H), 6.53 (d, J=17.4 Hz, 1H), 6.31 (d, J=17.4 Hz, 1H), 4.47 (d, J=8.4 Hz, 1H), 4.22 (m, 1H), 2.99 (m, 1H), 1.34-1.94 (m, 7H), 1.31 (d, J=7.2 Hz, 6H), 0.85 (d, J=5.4 Hz, 3H). MS(ES)=520.2 (M+1)$^+$.

Example 12.1

N-[(1R)-1-cyclobutylethyl]-8-[4-(propan-2-yl)pyridin-2-yl]-2-(1H-tetrazol-5-yl)-7-[4-(trifluoromethyl)benzyl]-7H-purin-6-amine

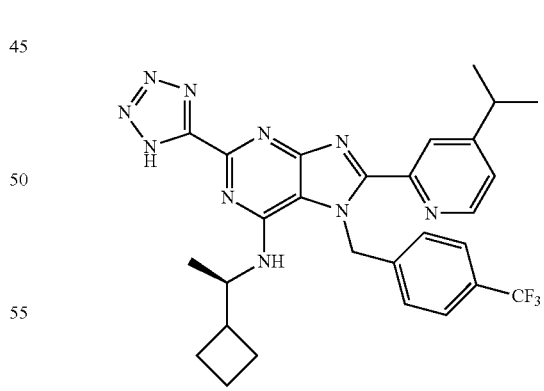

A vial equipped with a stir bar was charged with 6-{[(1R)-1-cyclobutylethyl]amino}-8-[4-(propan-2-yl)pyridin-2-yl]-7-[4-(trifluoromethyl)benzyl]-7H-purine-2-carbonitrile (31.4 mg, 0.060 mmol), sodium azide (39.3 mg, 0.604 mmol), and ammonium chloride (32.7 mg, 0.610 mmol). DMF (0.5 mL) was added and the mixture was degassed with N$_2$. The vial was then sealed and heated at 120° C. for 16 hours. The reaction was then cooled to room temperature, diluted with EtOAc (40 mL) and washed with water (10 mL) and brine (10 mL). The organic layer was dried over Na₂SO₄, filtered, and concentrated. Purification of the residue by mass triggered reverse phase HPLC (C-18), eluting with acetonitrile/water containing 0.1% TFA afforded N-[(1R)-1-cyclobutylethyl]-8-[4-(propan-2-yl)pyridin-2-yl]-2-(1H-tetrazol-5-yl)-7-[4-(trifluoromethyl)benzyl]-7H-purin-6-amine (TFA salt). $^1$H NMR (600 MHz, d6-DMSO) δ 8.56 (d, J=6.6 Hz, 1H), 8.23 (s, 1H), 7.66 (d, J=10.2 Hz, 2H), 7.47 (dd, J=6.6, 1.8 Hz, 1H), 7.19 (d, J=10.2 Hz, 2H), 6.82 (d, J=22.2 Hz, 1H), 6.43 (d, J=20.4 Hz, 1H), 6.18 (d, J=10.2 Hz, 1H), 4.54 (m, 1H), 3.04 (m, 1H), 1.32-2.24 (m, 7H), 1.26 (d, J=8.4 Hz, 6H), 0.98 (d, J=7.8 Hz, 3H). MS(ES)=563.3 (M+1)$^+$.

Example 12.2

(6-{[(1R)-1-cyclobutylethyl]amino}-8-[4-(propan-2-yl)pyridin-2-yl]-7-[4-(trifluoromethyl)benzyl]-7H-purin-2-yl)methanol

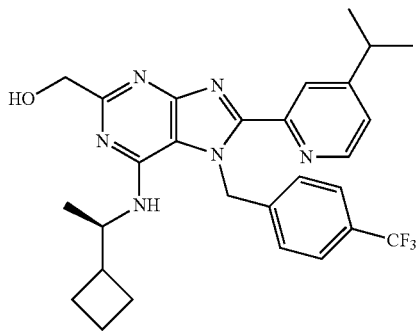 [SMILES: CC(C)c1ccnc(-c2nc3nc(CO)nc(N[C@H](C)C4CCC4)c3n2Cc2ccc(C(F)(F)F)cc2)c1]

CDI (47.0 mg, 0.290 mmol) was added to a solution of (6-{[(1R)-1-cyclobutylethyl]amino}-8-[(4-(propan-2-yl)pyridin-2-yl)-7-[4-(trifluoromethyl)benxyl]-7H-purin-2-yl) carboxylic acid (Example 1.22, 104 mg, 0.193 mmol) in THF (3 ml) and the reaction was stirred at ambient temperature for 45 minutes before quickly adding NaBH₄ (21.92 mg, 0.579 mmol) in water (2 mL) and stirring at ambient temperature for 1 hr. The reaction was diluted with EtOAc and the organics were washed with 2N aq. HCl and brine. The organic layer was dried over Na₂SO₄, filtered, and concentrated. Purification of the residue on a silica gel column with 2 to 15% MeOH/DCM afforded (6-{[(1R)-1-cyclobutylethyl]amino}-8-[4-(propan-2-yl)pyridin-2-yl]-7-[4-(trifluoromethyl)benzyl]-7H-purin-2-yl)methanol. $^1$H NMR (600 MHz, cd3od) δ 8.53 (d, J=5.1, 1H), 8.31 (s, 1H), 7.65 (d, J=8.3, 2H), 7.42 (dd, J=5.1, 1.6, 1H), 7.27 (d, J=8.1, 2H), 6.90 (d, J=17.7, 1H), 6.38 (d, J=17.9, 1H), 4.76 (d, J=1.9, 2H), 4.55-4.42 (m, 1H), 3.08-2.98 (m, 1H), 2.27-2.17 (m, 1H), 1.98-1.88 (m, 1H), 1.78-1.67 (m, 1H), 1.68-1.57 (m, 2H), 1.47-1.33 (m, 2H), 1.31 (d, J=6.9, 6H), 1.03 (d, J=6.6, 3H). LCMS=525 (M+1)$^+$.

Example 12.3

N-[(1R)-1-cyclobutylethyl]-8-[4-(propan-2-yl)pyridin-2-yl]-2-(1H-1,2,3-triazol-5-yl)-7-[4-(trifluoromethyl)benzyl]-7H-purin-6-amine

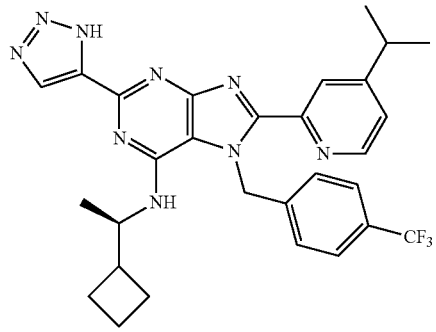 [SMILES: CC(C)c1ccnc(-c2nc3nc(-c4cnn[nH]4)nc(N[C@H](C)C4CCC4)c3n2Cc2ccc(C(F)(F)F)cc2)c1]

Step 1: Dess-MartinPeriodinane (97 mg, 0.229 mmol) was added to a solution of (6-{[(1R)-1-cyclobutylethyl]amino}-8-[4-(propan-2-yl)pyridin-2-yl]-7-[4-(trifluoromethyl)benzyl]-7H-purin-2-yl)methanol (Example 12.2) (48 mg, 0.092 mmol) in DCM (915 μL) and the suspension was stirred at ambient temperature for 2 hr. The reaction was quenched by addition of 0.1 N Na₂S₂O₃ and the aqueous layer was extracted with DCM (3×). The organic layer was dried over Na₂SO₄, filtered, and concentrated. Purification of the residue on a Biotage silica gel column with 0 to 15% MeOH/DCM afforded 6-{[(1R)-1-cyclobutylethyl]amino}-8-[4-(propan-2-yl)pyridin-2-yl]-7-[4-(trifluoromethyl)benzyl]-7H-purine-2-carbaldehyde. $^1$H NMR (600 MHz, CDCl₃) δ 9.98 (s, 1H), 8.49 (s, 1H), 8.40 (d, J=5.1, 1H), 7.68 (d, J=8.1, 2H), 7.34 (d, J=8.1, 2H), 7.22 (d, J=1.6, 1H), 6.46 (dd, J=118.7, 16.3, 2H), 4.42-4.36 (m, 1H), 3.00 (td, J=13.9, 7.0, 1H), 1.98-1.37 (m, 7H), 1.31 (d, J=6.9, 6H), 0.87 (d, J=6.4, 3H). LCMS=541 (M+18)$^+$.

Step 2: Dry methanol (702 μL) (dried over molecular sieves) was added to a flask containing 6-{[(1R)-1-cyclobutylethyl]amino}-8-[4-(propan-2-yl)pyridin-2-yl]-7-[4-(trifluoromethyl)benzyl]-7H-purine-2-carbaldehyde (22 mg, 0.042 mmol) and potassium carbonate (11.64 mg, 0.084 mmol) and dimethyl (1-diazo-2-oxopropyl)phosphonate (7.58 μL, 0.051 mmol) added before sealing the flask and stirring at ambient temperature for 2 hr. The reaction was diluted with EtOAc and the organics were washed with saturated aqueous sodium bicarbonate (3×). The aqueous layers were combined and back-extracted with EtOAc (3×). The combined organic layers were washed with brine, dried over Na₂SO₄, filtered, and concentrated. Purification of the residue on a Biotage silica gel column with 0 to 40% EtOAc/DCM afforded N-[(1R)-1-cyclobutylethyl]-2-ethynyl-8-[4-(propan-2-yl)pyridin-2-yl]-7-[4-(trifluoromethyl)benzyl]-7H-purin-6-amine. $^1$H NMR (600 MHz, CDCl₃) δ 8.43 (s, 1H), 8.38 (d, J=5.0, 1H), 7.67 (d, J=8.1, 2H), 7.32 (d, J=8.0, 2H), 7.21-7.16 (m, 1H), 6.39 (dd, J=113.4, 16.6, 2H), 4.30-4.26 (m, 1H), 3.03-2.94 (m, 1H), 2.90 (s, 1H), 1.95-1.76 (m, 2H), 1.76-1.65 (m, 1H), 1.66-1.44 (m, 3H), 1.44-1.34 (m, 1H), 1.30 (d, J=6.9, 6H), 0.84 (d, J=5.8, 3H). LCMS=519 (M+1)$^+$.

Step 3: N-[(1R)-1-cyclobutylethyl]-2-ethynyl-8-[4-(propan-2-yl)pyridin-2-yl]-7-[4-(trifluoromethyl)benzyl]-7H-purin-6-amine (17 mg, 0.033 mmol) was dissolved in DMF (295 μL)/Methanol (32.8 L) in a sealable tube and degassed for 10 minutes before adding copper(I) iodide (0.312 mg, 1.639 mol) and degassing for an additional 5 minutes before adding TMS-N₃ (6.53 L, 0.049 mmol). The reaction was sealed and heated to 100° C. for 1.75 hr. The reaction was cooled to ambient temperature and diluted with EtOAc and the organics were washed with saturated aqueous sodium bicarbonate and brine. The aqueous layer was extracted with DCM (3×) and the organic layers were combined and washed with brine, dried over Na₂SO₄, filtered, and concentrated. Purification of the residue by mass triggered reverse phase HPLC (C-18), eluting with acetonitrile/water containing 0.1% TFA afforded N-[(1R)-1-cyclobutylethyl]-8-[4-(propan-2-yl)pyridin-2-yl]-2-(1H-1,2,3-triazol-5-yl)-7-[4-(trifluoromethyl)benzyl]-7H-purin-6-amine (TFA salt). $^1$H NMR (600 MHz, dmso) δ 8.54 (s, 1H), 8.34 (s, 1H), 8.20 (s, 1H), 7.64 (d, J=8.2, 2H), 7.44 (s, 1H), 7.18 (d, J=8.0, 2H), 6.77 (d, J=17.9, 1H), 6.41 (d, J=17.9, 1H), 6.24 (s, 1H), 4.54-4.43 (m, 1H), 3.07-2.96 (m, 1H), 2.25-2.16 (m, 1H), 1.86-1.78 (m, 1H), 1.65-1.49 (m, 3H), 1.39-1.29 (m, 2H), 1.24 (d, J=6.9, 6H), 0.96 (d, J=6.4, 3H). LCMS=562 (M+1)⁺.

Preparative Example 12.2

6-{[(1R)-1-cyclobutylethyl]amino}-7-[(trans-4-methylcyclohexyl)methyl]-8-[4-(propan-2-yl)pyridin-2-yl]-7H-purine-2-carbonitrile

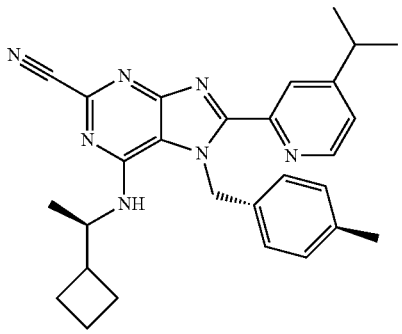

Using a procedure analogous to that described in Step 2 of Example 1.1, 6-{[(1R)-1-cyclobutylethyl]amino}-7-[(trans-4-methylcyclohexyl)methyl]-8-[4-(propan-2-yl)pyridin-2-yl]-7H-purine-2-carbonitrile was prepared starting from 6-{[(1R)-1-cyclobutylethyl]amino}-7-[(trans-4-methylcyclohexyl)methyl]-7H-purine-2-carbonitrile and 2-bromo-4-(isopropyl)pyridine. $^1$H NMR (600 MHz, CDCl₃) δ 8.52 (d, J=4.8 Hz, 1H), 8.33 (s, 1H), 7.23 (d, J=1.8 Hz, 1H), 4.80 (d, J=7.8 Hz, 1H), 4.48 (m, 1H), 2.98 (m, 1H), 2.42 (m, 1H), 1.30 (d, J=7.2 Hz, 6H), 1.19 (d, J=6.6 Hz, 3H), 0.80 (d, J=6.6 Hz, 3H), 0.70-2.10 (m, 18H). MS(ES)=472.3 (M+1)⁺.

Example 12.4

2-(aminomethyl)-N-[(1R)-1-cyclobutylethyl]-7-[(trans-4-methylcyclohexyl)methyl]-8-[4-(propan-2-yl)pyridin-2-yl]-7H-purin-6-amine

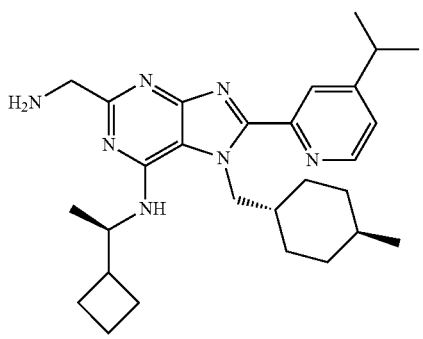 [SMILES: CC(C)c1ccnc(-c2nc3nc(CN)nc(N[C@H](C)C4CCC4)c3n2C[C@H]2CC[C@H](C)CC2)c1]

A solution of 6-{[(1R)-1-cyclobutylethyl]amino}-7-[(trans-4-methylcyclohexyl)methyl]-8-[4-(propan-2-yl)pyridin-2-yl]-7H-purine-2-carbonitrile (58 mg, 0.123 mmol) in dichloromethane (2 mL) was cooled to −78° C. and DIBAL-H (0.369 mL of a 1M solution in hexanes, 0.369 mmol) was added. The reaction was warmed to room temperature. After 15 minutes at room temperature, the reaction was cooled back to −78° C. and MeOH (200 µL) was added. The reaction was warmed to room temperature and a solution of Rochelle's salt (2 mL of a 1.5 M aqueous solution) was added. Additional dichloromethane (2 mL) was added, and the mixture was stirred vigorously at room temperature for 16 hours. Water (15 mL) was added and the mixture was extracted with dichloromethane (2×30 mL). The organic extracts were combined, dried over Na₂SO₄, filtered, and concentrated. Purification of the residue by mass triggered reverse phase HPLC (C-18), eluting with acetonitrile/water containing 0.1% TFA afforded 2-(aminomethyl)-N-[(1R)-1-cyclobutylethyl]-7-[(trans-4-methylcyclohexyl)methyl]-8-[4-(propan-2-yl)pyridin-2-yl]-7H-purin-6-amine (TFA salt). $^1$H NMR (600 MHz, d6-DMSO) δ 8.61 (d, J=4.8 Hz, 1H), 8.19 (bs, 2H), 8.05 (s, 1H), 7.43 (d, J=4.8 Hz, 1H), 6.56 (d, J=9.0 Hz, 1H), 5.16 (bs, 1H), 4.82 (bs, 1H), 4.47 (m, 1H), 4.08 (m, 2H), 3.00 (m, 1H), 2.55 (m, 1H), 2.01 (m, 1H), 1.92 (m, 1H), 1.81 (m, 1H) 1.70-1.79 (m, 3H), 1.52 (m, 1H), 1.36-1.44 (m, 3H), 1.23 (d, J=7.2 Hz, 6H), 1.10 (d, J=6.6 Hz, 3H), 1.08 (m, 1H), 0.99 (bs, 1H), 0.84 (m, 1H), 0.69 (d, J=6.0 Hz, 3H), 0.61 (m, 2H), 0.50 (m, 1H). MS(ES)=476.4 (M+1)⁺.

Preparative Example 12.3

2-chloro-N-[(1R)-1-cyclobutylethyl]-7-[(trans-4-methylcyclohexyl)methyl]-8-[4-(propan-2-yl)pyridin-2-yl]-7H-purin-6-amine

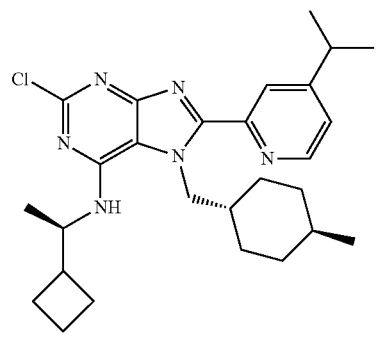 [SMILES: CC(C)c1ccnc(-c2nc3nc(Cl)nc(N[C@H](C)C4CCC4)c3n2C[C@H]2CC[C@H](C)CC2)c1]

Using a procedure analogous to that described in Step 2 of Example 1.1, 2-chloro-N-[(1R)-1-cyclobutylethyl]-7-[(trans-4-methylcyclohexyl)methyl]-8-[4-(propan-2-yl)pyridin-2-yl]-7H-purin-6-amine was prepared starting from 2-chloro-N-[(1R)-1-cyclobutylethyl]-7-[(trans-4-methylcyclohexyl)methyl]-7H-purin-6-amine (Preparative Example 11.5) and 2-bromo-4-(isopropyl)pyridine (purchased from Combiphos). $^1$H NMR (600 MHz, CDCl₃) δ 8.50 (d, J=5.4 Hz, 1H), 8.30 (s, 1H), 7.20 (dd, J=5.4, 1.2 Hz, 1H), 4.72 (d, J=8.4 Hz, 1H), 4.44 (m, 1H), 2.96 (m, 1H), 2.39 (m, 1H), 1.98-2.10 (m, 2H), 1.29 (d, J=6.6 Hz, 6H), 1.19 (d, J=6.6 Hz, 3H), 0.80 (d, J=6.6 Hz, 3H), 0.68-1.94 (m, 16H). MS(ES)=481.3 (M+1)⁺.

Example 12.5

1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanone

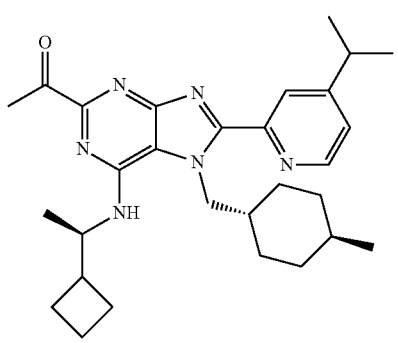 [SMILES: CC(=O)c1nc(N[C@H](C)C2CCC2)c2c(n1)nc(-c1cc(C(C)C)ccn1)n2C[C@H]1CC[C@H](C)CC1]

Step 1: A vial was charged with 2-chloro-N-[(1R)-1-cyclobutylethyl]-7-[(trans-4-methylcyclohexyl)methyl]-8-[4-(propan-2-yl)pyridin-2-yl]-7H-purin-6-amine (51 mg, 0.106 mmol), bis(triphenylphosphine)palladium(II)dichloride (14.9 mg, 0.021 mmol), DMA (0.7 mL), and tributyl (1-ethoxyvinyl)tin (0.054 mL, 0.159 mmol). The solution was degassed with $N_2$, the vial was sealed, and the reaction was heated to 110° C. for 16 hours. The reaction was then cooled to room temperature, diluted with EtOAc (1 mL) and added to a solution of potassium fluoride (1.65 g) in water (2 mL). The mixture was stirred vigorously at room temperature for 45 minutes and then filtered through a pad of celite, washing the pad with EtOAc (50 mL). The filtrate was washed with water (15 mL) and brine (15 mL), dried over $Na_2SO_4$, filtered, and concentrated. Purification of the residue on a Biotage 10 g silica gel column using 0 to 100% EtOAc/hexanes afforded N-[(1R)-1-cyclobutylethyl]-2-(1-ethoxyethenyl)-7-[(trans-4-methylcyclohexyl)methyl]-8-[4-(propan-2-yl)pyridin-2-yl]-7H-purin-6-amine. MS(ES)=517.4 (M+1)$^+$.

Step 2: To a solution of N-[(1R)-1-cyclobutylethyl]-2-(1-ethoxyethenyl)-7-[(trans-4-methylcyclohexyl)methyl]-8-[4-(propan-2-yl)pyridin-2-yl]-7H-purin-6-amine (51.3 mg, 0.99 mmol) in acetone (2 mL) was added 2N HCl (0.67 mL, 1.340 mmol). The reaction was stirred vigorously at room temperature for 18 hours. The reaction was then diluted with EtOAc (50 mL) and washed with saturated NaHCO$_3$ (15 mL) and brine (15 mL). The organic layer was dried over Na$_2$SO$_4$, filtered, and concentrated. Purification of the residue on a Biotage 25 g silica gel column using 0 to 100% EtOAc/hexanes afforded 1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanone. $^1$H NMR (600 MHz, CDCl$_3$) δ 8.52 (d, J=4.8 Hz, 1H), 8.39 (d, J=1.8 Hz, 1H), 7.22 (dd, J=4.8, 1.8 Hz, 1H), 4.73 (d, J=7.8 Hz, 1H), 4.59 (m, 1H), 2.97 (m, 1H), 2.80 (s, 3H), 2.43 (m, 1H), 2.06 (m, 1H), 2.01 (m, 1H), 1.81-1.93 (m, 4H), 1.30 (d, J=7.2 Hz, 6H), 1.21 (d, J=6.6 Hz, 3H), 0.79 (d, J=6.6 Hz, 3H), 0.70-1.70 (m, 12H). MS(ES)=489.3 (M+1)$^+$.

Example 12.6

1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanol

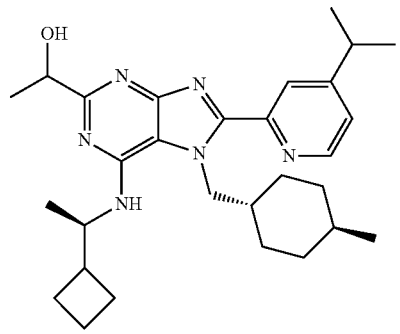 [SMILES: CC(C)c1ccnc(-c2nc3nc(C(C)O)nc(N[C@H](C)C4CCC4)c3n2C[C@H]2CC[C@H](C)CC2)c1]

To a solution of 1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanone (Example 12.5) (17 mg, 0.035 mmol) in MeOH (0.5 mL) and THF (0.1 mL) was added NaBH$_4$ (6.6 mg, 0.174 mmol). After 15 minutes at room temperature, the reaction was quenched with saturated NH$_4$Cl (1 mL) and diluted with EtOAc (30 mL). The organic layer was washed with water (10 mL) and brine (10 mL). The organic layer was then dried over Na$_2$SO$_4$, filtered, and concentrated. Purification of the residue by mass triggered reverse phase HPLC (C-18), eluting with acetonitrile/water containing 0.1% TFA afforded 1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanol (TFA salt) as a mixture of diastereomers. $^1$H NMR (600 MHz, d6-DMSO) δ 8.66 (d, J=5.4 Hz, 1H), 8.06 (s, 1H), 7.66 (bs, 1H), 7.50 (d, J=4.8 Hz, 1H), 5.23 (bs, 1H), 4.94 (bs, 1H), 4.77 (m, 1H), 4.47 (m, 1H), 3.02 (m, 1H), 2.61 (m, 1H), 2.46 (m, 1H), 2.03 (m, 1H), 1.92 (m, 1H), 1.70-1.86 (m, 4H), 1.39-1.55 (m, 7H), 1.24 (d, J=7.2 Hz, 6H), 1.07-1.24 (m, 5H), 0.87 (m, 1H), 0.71 (d, J=6.0 Hz, 3H), 0.53-0.70 (m, 3H). MS(ES)=491.4 (M+1)$^+$.

Example 12.7

2-(6-{[(1R)-1-cyclobutylethyl]amino}-7-[(trans-4-methylcyclohexyl)methyl]-8-[4-(propan-2-yl)pyridin-2-yl]-7H-purin-2-yl)propan-2-ol

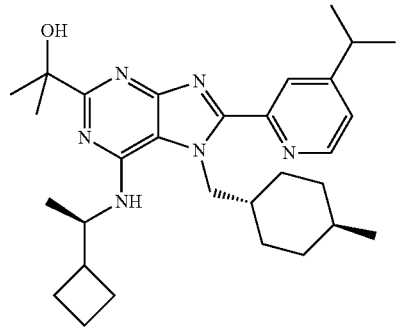 [SMILES: CC(C)c1ccnc(-c2nc3nc(C(C)(C)O)nc(N[C@H](C)C4CCC4)c3n2C[C@H]2CC[C@H](C)CC2)c1]

To a 0° C. solution of 1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanone (Example 12.5) (12 mg, 0.025 mmol) in THF (1 mL) was added MeMgBr (8 μL of a 3M solution in Et$_2$O, 0.025 mmol). After 15 minutes, a second addition of MeMgBr (8 μL of a 3M solution in Et$_2$O, 0.025 mmol) was carried out, and then 15 minutes later a third portion of MeMgBr (8 μL of a 3M solution in Et$_2$O, 0.025 mmol) was added. 15 minutes later, the reaction was quenched with saturated NH$_4$Cl (1 mL) and diluted with EtOAc (30 mL). The organic layer was washed with water (10 mL) and brine (10 mL). The organic layer was then dried over Na$_2$SO$_4$, filtered, and concentrated. Purification of the residue by PTLC with 75% EtOAc/hexanes afforded 2-(6-{[(1R)-1-cyclobutylethyl]amino}-7-[(trans-4-methylcyclohexyl)methyl]-8-[4-(propan-2-yl)pyridin-2-yl]-7H-purin-2-yl)propan-2-ol. $^1$H NMR (600 MHz, d6-DMSO) δ 8.59 (d, J=5.4 Hz, 1H), 8.08 (s, 1H), 7.40 (dd, J=5.4, 1.2 Hz, 1H), 6.34 (d, J=8.4 Hz, 1H), 5.15 (bs, 1H), 4.91 (s, 1H), 4.83 (bs, 1H), 4.40 (m, 1H), 2.99 (m, 1H), 2.55 (m, 1H), 1.98 (m, 1H), 1.91 (m, 1H), 1.70-1.83 (m, 4H), 1.44 (d, J=4.8 Hz, 6H), 1.23 (dd, J=6.6, 1.8 Hz, 6H), 1.12 (d, J=6.6 Hz, 3H), 0.69 (d, J=6.6 Hz, 3H), 0.51-1.53 (m, 10H). MS(ES)=505.4 (M+1)$^+$.

Example 12.8

N-[(1R)-1-cyclobutylethyl]-7-[(trans-4-methylcyclohexyl)methyl]-8-[4-(propan-2-yl)pyridin-2-yl]-2-(1H-tetrazol-5-yl)-7H-purine-6-amine

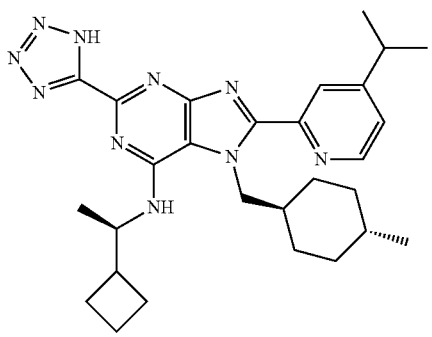 [SMILES: CC(C)c1ccnc(-c2nc3nc(-c4nnn[nH]4)nc(N[C@H](C)C4CCC4)c3n2C[C@H]2CC[C@H](C)CC2)c1]

6-{[(1R)-1-cyclobutylethyl]amino}-7-[(trans-4-methylcyclohexyl)methyl]-8-[4-(propan-2-yl)pyridin-2-yl]-7H-purine-2-carbonitrile (Preparative Example 12.2) (25 mg, 0.053 mmol), sodium azide (34.5 mg, 0.530 mmol) and ammonium chloride (28.6 mg, 0.535 mmol) were placed in a vial. DMF (530 μL) was added and the solution was degassed before sealing and heating at 120° C. overnight. The reaction was cooled to ambient temperature, diluted with EtOAc and the organics were washed with water and brine. The organic layer was dried over Na$_2$SO$_4$, filtered, and concentrated. Purification of the residue by mass triggered reverse phase HPLC (C-18), eluting with acetonitrile/water containing 0.1% TFA afforded N-[(1R)-1-cyclobutylethyl]-7-[(trans-4-methylcyclohexyl)methyl]-8-[4-(propan-2-yl)pyridin-2-yl]-2-(1H-tetrazol-5-yl)-7H-purine-6-amine (TFA salt). $^1$H NMR (600 MHz, cd3od) δ 8.64 (d, J=5.0, 1H), 8.12 (s, 1H), 7.47 (d, J=4.3, 1H), 5.49-4.70 (m, 3H), 3.13-3.00 (m, 1H), 2.73-2.48 (m, 1H), 2.17-1.99 (m, 2H), 1.99-1.89 (m, 3H), 1.89-1.82 (m, 1H), 1.67-1.48 (m, 4H), 1.34 (dd, J=6.8, 1.7, 6H), 1.28-1.07 (m, 5H), 1.02-0.85 (m, 1H), 0.82-0.55 (m, 6H). LCMS=515 (M+1)$^+$.

Example 12.9

N-[(6-{[(1R)-1-cyclobutylethyl]amino}-7-[(trans-4-methylcyclohexyl)methyl]-8-[4-(propan-2-yl)pyridin-2-yl]-7H-purine-2-yl)methyl]methane sulfonamide

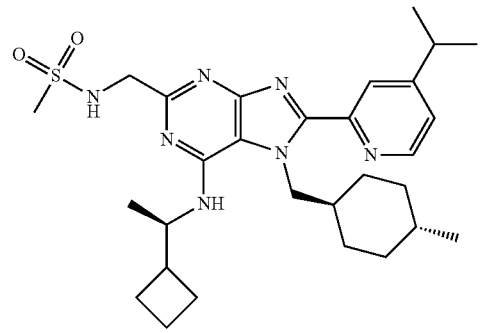 [SMILES: CC(C)c1ccnc(-c2nc3nc(CNS(C)(=O)=O)nc(N[C@H](C)C4CCC4)c3n2C[C@H]2CC[C@H](C)CC2)c1]

2-(aminomethyl)-N-[(1R)-1-cyclobutylethyl]-7-[(trans-4-methylcyclohexyl)methyl]-8-[4-(propan-2-yl)pyridin-2-yl]-7H-purine-6-amine (Example 12.4) (21 mg, 0.044 mmol) and Hunig's Base (38.6 μL, 0.221 mmol) were dissolved in DCM (441 μL) and cooled to 0° C. before adding methanesulfonyl chloride (23.37 μL, 0.040 mmol) and stirring for 30 minutes. The reaction mixture was allowed to warm to ambient temperature before diluting with DCM and washing with saturated sodium bicarbonate solution and brine. The organic layer was dried over Na$_2$SO$_4$, filtered, and concentrated. Purification of the residue by mass triggered reverse phase HPLC (C-18), eluting with acetonitrile/water containing 0.1% TFA afforded N-[(6-{[(1R)-1-cyclobutylethyl]amino}-7-[(trans-4-methylcyclohexyl)methyl]-8-[4-(propan-2-yl)pyridin-2-yl]-7H-purine-2-yl)methyl]methane sulfonamide (TFA salt). $^1$H NMR (600 MHz, cd3od) δ 8.63 (d, J=5.1, 1H), 8.16 (s, 1H), 7.45 (d, J=5.0, 1H), 5.35-5.22 (m, 1H), 4.85-4.72 (m, 2H), 4.47 (s, 2H), 3.10-2.99 (m, 4H), 2.69-2.57 (m, 1H), 2.18-1.98 (m, 2H), 1.96-1.80 (m, 4H), 1.62 (d, J=13.1, 1H), 1.52 (t, J=12.2, 3H), 1.32 (d, J=6.9, 6H), 1.24-1.10 (m, 5H), 0.95 (q, J=13.0, 1H), 0.82-0.70 (m, 5H), 0.65 (dd, J=24.5, 10.3, 1H). LCMS=554 (M+1)$^+$.

Example 12.10

N-[(6-{[(1R)-1-cyclobutylethyl]amino}-7-[(trans-4-methylcyclohexyl)methyl]-8-[4-(propan-2-yl)pyridin-2-yl]-7H-purine-2-yl)methyl]-2,2,2-trifluoroacetamide

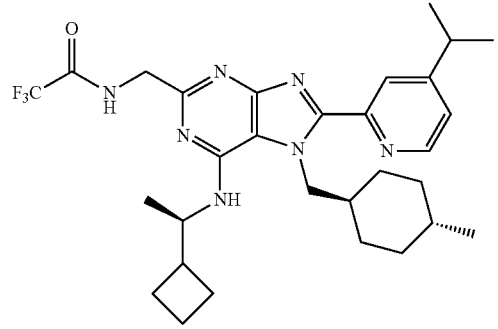 [SMILES: CC(C)c1ccnc(-c2nc3nc(CNC(=O)C(F)(F)F)nc(N[C@H](C)C4CCC4)c3n2C[C@H]2CC[C@H](C)CC2)c1]

2-(aminomethyl)-N-[(1R)-1-cyclobutylethyl]-7-[(trans-4-methylcyclohexyl)methyl]-8-[4-(propan-2-yl)pyridin-2-yl]-7H-purine-6-amine (Example 12.4) (21 mg, 0.044 mmol) and Hunig's Base (38.6 µL, 0.221 mmol) were dissolved in DCM (441 µL) and cooled to 0° C. before adding trifluoroacetic anhydride (7.01 µL, 0.050 mmol) (125 µL of a solution of 56 µL in 100 mL DCM) and stirring for 1 hr. The reaction mixture was allowed to warm to ambient temperature before diluting with DCM and washing with saturated sodium bicarbonate solution and brine. The organic layer was dried over Na₂SO₄, filtered, and concentrated. Purification of the residue by mass triggered reverse phase HPLC (C-18), eluting with acetonitrile/water containing 0.1% TFA afforded N-[(6-{[(1R)-1-cyclobutylethyl]amino}-7-[(trans-4-methylcyclohexyl)methyl]-8-[4-(propan-2-yl)pyridin-2-yl]-7H-purine-2-yl)methyl]-2,2,2-trifluoroacetamide (TFA salt). ¹H NMR (600 MHz, cd3od) δ 8.62 (d, J=3.8, 1H), 8.13 (s, 1H), 7.45 (3, 1H), 5.29-5.16 (m, 1H), 4.83-4.75 (m, 1H), 4.67-4.58 (m, 3H), 3.04 (dd, J=13.1, 6.5, 1H), 2.61 (dd, J=16.1, 8.1, 1H), 2.17-2.06 (m, 1H), 2.07-1.97 (m, 1H), 1.98-1.87 (m, 1H), 1.87-1.75 (m, 3H), 1.65-1.46 (m, 4H), 1.32 (d, J=6.9, 6H), 1.19 (d, J=6.5, 5H), 0.93 (dd, J=24.1, 11.5, 1H), 0.81-00.68 (m, 5H), 0.64 (dd, J=24.9, 21.9, 1H). LCMS=572 (M+1)⁺.

Example 12.11 and 12.12

N-[(1R)-1-cyclobutylethyl]-7-[(trans-4-methylcyclohexyl)methyl]-2-(2-methyl-2H-tetrazol-5-yl)-8-[(3R)-3-phenylmorpholin-4-yl]-7H-purin-6-amine and N-[(1R)-1-cyclobutylethyl]-7-[(trans-4-methylcyclohexyl)methyl]-2-(1-methyl-1H-tetrazol-5-yl)-8-[(3R)-3-phenylmorpholin-4-yl]-7H-purin-6-amine

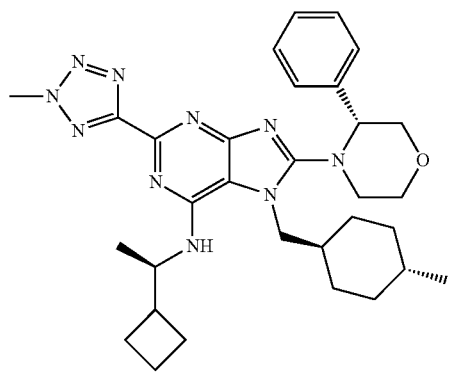

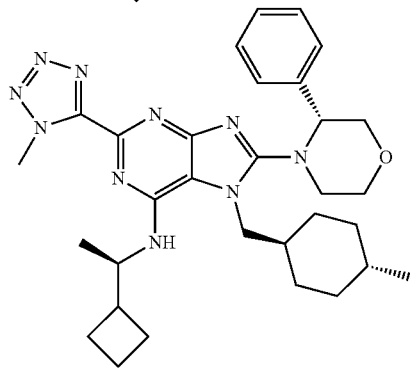

Step 1: Using a procedure analogous to that described in Example 12.1, 6-{[(1R)-1-cyclobutylethyl]amino}-7-[(trans-4-methylcyclohexyl)methyl]-8-[(3R)-3-phenylmorpholin-4-yl]-7H-purine-2-carbonitrile (prepared by using a procedure analogous to that described in Example 9.3, and starting with Preparative Example 11.7) was converted to N-[(1R)-1-cyclobutylethyl]-7-[(trans-4-methylcyclohexyl)methyl]-8-[(3R)-3-phenylmorpholin-4-yl]-2-(1H-tetrazol-5-yl)-7H-purin-6-amine. ¹H NMR (600 MHz, d6-DMSO) δ 7.38 (d, J=7.2 Hz, 2H), 7.12-7.21 (m, 3H), 4.58 (m, 1H), 4.46 (m, 1H), 4.32 (m, 1H), 3.76-3.92 (m, 5H), 3.26-3.80 (m, 2H), 2.99 (m, 1H), 2.42-2.48 (m, 1H), 1.20-1.98 (m, 11H), 1.02 (d, J=6.6 Hz, 3H), 1.00 (m, 1H), 0.87 (m, 1H), 0.76 (d, J=6.6 Hz, 3H), 0.70 (m, 1H), 0.52 (m, 1H). MS(ES)=557.3 (M+1)⁺

Step 2: To a solution of N-[(1R)-1-cyclobutylethyl]-7-[(trans-4-methylcyclohexyl)methyl]-8-[(3R)-3-phenylmorpholin-4-yl]-2-(1H-tetrazol-5-yl)-7H-purin-6-amine (20 mg, 0.0396 mmol) in toluene (750 µL) and MeOH (100 µL) was added TMS diazomethane (17 µL of a 2M solution in Et₂O). The reaction was stirred at room temperature for 30 minutes and then concentrated. Purification by PTLC with 10% MeOH/DCM (2 elutions) followed by further purification by PTLC with 100% EtOAc (2 elutions) afforded the desired products. N-[(1R)-1-cyclobutylethyl]-7-[(trans-4-methylcyclohexyl)methyl]-2-(1-methyl-1H-tetrazol-5-yl)-8-[(3R)-3-phenylmorpholin-4-yl]-7H-purin-6-amine. ¹H NMR (600 MHz, d6-DMSO) δ 7.39 (d, J=7.8 Hz, 2H), 7.21 (t, J=7.2 Hz, 2H), 7.15 (d, J=7.2 Hz, 1H), 6.36 (d, J=8.4 Hz, 1H), 4.63 (m, 1H), 4.30-4.40 (m, 2H), 4.33 (s, 3H), 3.80-3.94 (m, 5H), 3.39 (m, 1H), 3.03 (m, 1H), 1.19-2.52 (m, 13H), 1.07 (d, J=6.0 Hz, 3H), 1.01 (m, 1H), 0.88 (m, 1H), 0.76 (d, J=6.6 Hz, 3H), 0.70 (m, 1H), 0.52 (m, 1H). MS(ES)=571.4 (M+1)⁺. N-[(1R)-1-cyclobutylethyl]-7-[(trans-4-methylcyclohexyl)methyl]-2-(2-methyl-2H-tetrazol-5-yl)-8-[(3R)-3-phenylmorpholin-4-yl]-7H-purin-6-amine. ¹H NMR (600 MHz, d6-DMSO) δ 7.39 (d, J=7.8 Hz, 2H), 7.21 (t, J=7.2 Hz, 2H), 7.14 (d, J=7.2 Hz, 1H), 6.16 (d, J=9.0 Hz, 1H), 4.60 (m, 1H), 4.33-4.41 (m, 2H), 4.38 (s, 3H), 3.78-3.91 (m, 5H), 3.38 (m, 1H), 3.00 (m, 1H), 1.16-2.50 (m, 13H), 1.06 (d, J=6.6 Hz, 3H), 1.02 (m, 1H), 0.88 (m, 1H), 0.76 (d, J=6.6 Hz, 3H), 0.72 (m, 1H), 0.52 (m, 1H). MS(ES)=571.3 (M+1)⁺.

Example 12.13

Methyl-6-{[(1R)-1-cyclobutylethyl]amino}-7-[(trans-4-methylcyclohexyl)methyl]-8-[(3R)-3-phenylmorpholin-4-yl]-7H-purine-2-carboxylate

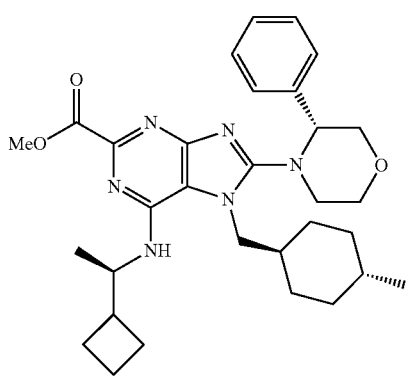 [SMILES: COC(=O)c1nc(N[C@H](C)C2CCC2)c2c(n1)nc(N1CCOC[C@H]1c1ccccc1)n2C[C@H]1CC[C@H](C)CC1]

Using a procedure analogous to that described in Step 2 of Example 9.1, 6-{[(1R)-1-cyclobutylethyl]amino}-7-[(trans-4-methylcyclohexyl)methyl]-8-[(3R)-3-phenylmorpholin-4-yl]-7H-purine-2-carbonitrile was converted to methyl-6-{[(1R)-1-cyclobutylethyl]amino}-7-[(trans-4-methylcyclohexyl)methyl]-8-[(3R)-3-phenylmorpholin-4-yl]-7H-purine-2-carboxylate. MS(ES)=547.3 (M+1)+.

Example 12.14

2-(6-{[(1R)-1-cyclobutylethyl]amino}-7-[(trans-4-methylcyclohexyl)methyl]-8-[(3R)-3-phenylmorpholin-4-yl]-7H-purine-2-yl)propan-2-ol

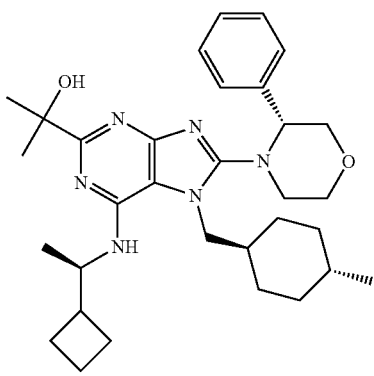 [SMILES: C[C@@H](Nc1nc(C(C)(C)O)nc2nc(N3CCOC[C@H]3c3ccccc3)n(C[C@H]3CC[C@H](C)CC3)c12)C1CCC1]

Methyl-6-{[(1R)-1-cyclobutylethyl]amino}-7-[(trans-4-methylcyclohexyl)methyl]-8-[(3R)-3-phenylmorpholin-4-yl]-7H-purine-2-carboxylate (Example 12.13) (25.0 mg, 0.046 mmol) was dissolved in THF (1 mL) in a vial under nitrogen and cooled to 0° C. before adding methylmagnesium bromide (76 µL, 0.228 mmol) and stirring for 10 minutes. Additional methylmagnesium bromide (76 µL, 0.228 mmol) was added (at 0° C.) and stirred for 20 minutes. The reaction was quenched with saturated NH4Cl and allowed to warm to ambient temperature. The reaction mixture was diluted with EtOAc and washed with water and brine. The organic layer was dried over Na2SO4, filtered, and concentrated. Purification of the residue by mass triggered reverse phase HPLC (C-18), eluting with acetonitrile/water containing 0.1% TFA afforded 2-(6-{[(1R)-1-cyclobutylethyl]amino}-7-[(trans-4-methylcyclohexyl)methyl]-8-[(3R)-3-phenylmorpholin-4-yl]-7H-purine-2-yl)propan-2-ol (TFA salt). 1H NMR (600 MHz, CD3OD) δ 7.47-7.43 (m, 2H), 7.27-7.19 (m, 3H), 4.80 (t, J=5.3, 1H), 4.51 (dq, J=9.7, 6.6, 1H), 4.28 (dd, J=14.5, 5.8, 1H), 4.02-3.97 (m, 4H), 3.91 (ddd, J=11.6, 5.8, 3.1, 1H), 3.53 (ddd, J=12.6, 5.7, 2.8, 1H), 3.24 (ddd, J=10.6, 7.3, 2.8, 1H), 2.61-2.50 (m, 1H), 2.16-2.07 (m, 1H), 2.07-1.98 (m, 1H), 1.98-1.89 (m, 1H), 1.89-1.74 (m, 3H), 1.72-1.63 (m, 2H), 1.57 (d, J=14.2, 6H), 1.48 (dd, J=14.3, 11.5, 2H), 1.34-1.24 (m, 1H), 1.17 (d, J=6.6, 3H), 1.04 (ddd, J=25.1, 12.7, 3.3, 1H), 0.91 (td, J=9.3, 3.2, 2H), 0.83 (d, J=6.5, 3H), 0.78 (ddd, J=25.2, 13.0, 3.5, 1H), 0.69-0.58 (m, 1H). LCMS=547 (M+1)+.

Example 12.15

5-(6-{[(1R)-1-cyclobutylethyl]amino}-7-[(trans-4-methylcyclohexyl)methyl]-8-[(3R)-3-phenylmorpholin-4-yl]-7H-purin-2-yl)-4-methyl-2,4-dihydro-3H-1,2,4-triazol-3-one

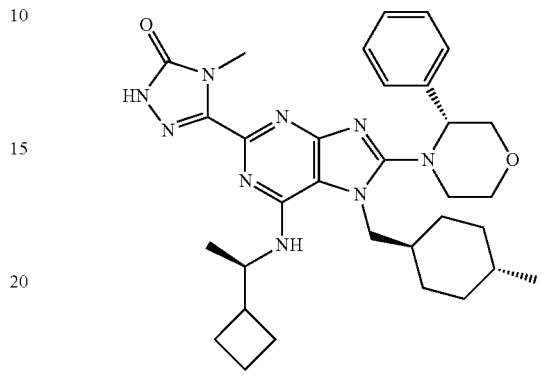

Step 1: CDI (22.8 mg, 0.141 mmol) was added to a solution of 6-{[(1R)-1-cyclobutylethyl]amino}-7-[(trans-4-methylcyclohexyl)methyl]-8-[(3R)-3-phenylmorpholin-4-yl]-7H-purine-2-carboxylic acid (50.0 mg, 0.094 mmol) in THF (2 mL) and the reaction was stirred at ambient temperature for 40 minutes before adding hydrazine (58.9 µL, 1.88 mmol). After stirring at ambient temperature for 1.5 hr, the reaction mixture was diluted with EtOAc and washed with water and brine. The organic layer was dried over Na2SO4, filtered, and concentrated to afford crude 6-{[(1R)-1-cyclobutylethyl]amino}-7-[(trans-4-methylcyclohexyl)methyl]-8-[(3R)-3-phenylmorpholin-4-yl]-7H-purine-2-carbohydrazide. 1H NMR (600 MHz, CDCl3) δ 8.98-8.87 (m, 1H), 7.71 (s, 1H), 7.39-7.35 (m, 2H), 7.23-7.17 (m, 3H), 7.14-7.07 (m, 2H), 4.71-3.21 (m, 10H), 2.37-2.28 (m, 1H), 2.09-1.97 (m, 1H), 1.97-1.90 (m, 1H), 1.91-1.84 (m, 1H), 1.85-1.75 (m, 3H), 1.75-1.52 (m, 4H), 1.35-1.25 (m, 1H), 1.12 (d, J=6.4, 3H), 1.07-0.96 (m, 1H), 0.94 (d, J=6.7, 1H), 0.93-0.88 (m, 1H), 0.85-0.83 (m, 3H), 0.81-0.73 (m, 1H), 0.72-0.64 (m, 1H). LCMS=547 (M+1)+. This material was used in Step 2 without further purification.

Step 2: Crude 6-{[(1R)-1-cyclobutylethyl]amino}-7-[(trans-4-methylcyclohexyl)methyl]-8-[(3R)-3-phenylmorpholin-4-yl]-7H-purine-2-carbohydrazide (50 mg, 0.091 mmol) was dissolved in THF (915 µL) and methyl isocyanate (5.31 µL, 0.101 mmol) was added dropwise. The reaction mixture was allowed to stir at ambient temperature overnight. An additional 50 µL of the isocyanate solution was then added and the reaction was stirred for 1.5 hr to afford a solution of crude 2-[(6-{[(1R)-1-cyclobutylethyl]amino}-7-[(trans-4-methylcyclohexyl)methyl]-8-[(3R)-3-phenylmorpholin-4-yl]-7H-purin-2-yl)carbonyl]-N-methylhydrazinecarboxamide in THF (915 µL). LCMS=604 (M+1)+. This material was used in Step 3 without further purification.

Step 3: A solution of crude 2-[(6-{[(1R)-1-cyclobutylethyl]amino}-7-[(trans-4-methylcyclohexyl)methyl]-8-[(3R)-3-phenylmorpholin-4-yl]-7H-purin-2-yl)carbonyl]-N-methylhydrazinecarboxamide (915 µL, 0.091 mmol) in THF was transferred to a vial and 1N NaOH (500 µL, 0.500 mmol) was added. The vial was sealed and allowing to stir at 100° C. for 2.5 hr. The reaction was then cooled to room temperature and diluted with EtOAc. The organics were washed with 1N aq HCl and brine, dried over Na$_2$SO$_4$, filtered, and concentrated. Purification of the residue by mass triggered reverse phase HPLC (C-18), eluting with acetonitrile/water containing 0.1% TFA afforded 5-(6-{[(1R)-1-cyclobutylethyl]amino}-7-[(trans-4-methylcyclohexyl)methyl]-8-[(3R)-3-phenylmorpholin-4-yl]-7H-purin-2-yl)-4-methyl-2,4-dihydro-3H-1,2,4-triazol-3-one (TFA salt). $^1$H NMR (600 MHz, CD$_3$OD) δ 7.45 (d, J=7.1, 2H), 7.26-7.18 (m, 3H), 4.82 (t, J=5.0, 1H), 4.49 (dq, J=9.4, 6.5, 1H), 4.30 (dd, J=14.5, 5.7, 1H), 4.04-3.95 (m, 4H), 3.90 (ddd, J=11.6, 6.3, 3.0, 1H), 3.67 (s, 3H), 3.55 (ddd, J=12.5, 6.2, 2.8, 1H), 3.25 (ddd, J=12.4, 6.9, 2.9, 1H), 2.57 (dp, J=16.4, 8.2, 1H), 2.16-2.02 (m, 2H), 1.99-1.88 (m, 1H), 1.88-1.78 (m, 3H), 1.70-1.44 (m, 4H), 1.33-1.23 (m, 1H), 1.18 (d, J=6.5, 3H), 1.04 (qd, J=12.8, 3.5, 1H), 0.97-0.86 (m, 2H), 0.82 (d, J=6.5, 3H), 0.80-0.73 (m, 1H), 0.63 (ddd, J=24.9, 12.1, 4.8, 1H). LCMS=586 (M+1)$^+$.

Example 12.16

N-[(1R)-1-cyclobutylethyl]-7-[(trans-4-methylcyclohexyl)methyl]-8-[(3R)-3-phenylmorpholin-4-yl]-2-(4H-1,2,4-triazol-3-yl)-7H-purin-6-amine

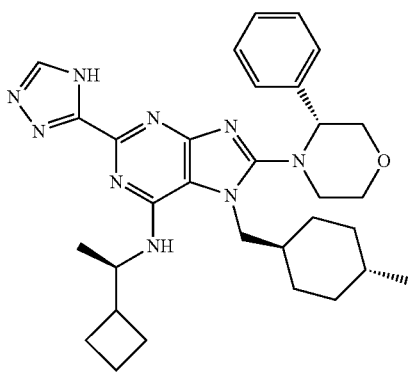 [SMILES: C[C@@H](Nc1nc(-c2nnc[nH]2)nc2nc(N3CCOC[C@H]3c3ccccc3)n(C[C@H]3CC[C@H](C)CC3)c12)C1CCC1]

6-{[(1R)-1-cyclobutylethyl]amino}-7-[(trans-4-methylcyclohexyl)methyl]-8-[(3R)-3-phenylmorpholin-4-yl]-7H-purine-2-carbonitrile (25.0 mg, 0.049 mmol) and formic acid hydrazide (11.46 μL, 0.195 mmol) were dissolved in DMA (487 μL) in a vial and the vial was sealed and heated at 100° C. overnight. The reaction was then cooled to room temperature and diluted with EtOAc. The organics were washed with deionized water (2×) and brine, dried over Na$_2$SO$_4$, filtered, and concentrated. Purification of the residue by mass triggered reverse phase HPLC (C-18), eluting with acetonitrile/water containing 0.1% NH$_4$OH afforded N-[(1R)-1-cyclobutylethyl]-7-[(trans-4-methylcyclohexyl)methyl]-8-[(3R)-3-phenylmorpholin-4-yl]-2-(4H-1,2,4-triazol-3-yl)-7H-purin-6-amine. $^1$H NMR (600 MHz, CD$_3$OD) δ 8.08 (s, 1H), 7.42 (d, J=7.0, 2H), 7.23-7.15 (m, J=20.8, 7.0, 3H), 4.81-4.70 (m, J=12.9, 6.5, 1H), 4.62 (dd, J=6.5, 3.7, 1H), 4.27 (dd, J=14.3, 5.5, 1H), 4.04-3.89 (m, 5H), 3.48-3.41 (m, J=8.6, 4.0, 1H), 3.19-3.10 (m, 1H), 2.53-2.46 (m, J=16.1, 8.4, 1H), 2.14-1.96 (m, 2H), 1.93-1.78 (m, J=25.1, 13.1, 9.9, 4H), 1.74-1.64 (m, J=13.2, 2H), 1.61-1.54 (m, J=7.5, 2H), 1.34-1.27 (m, 1H), 1.13 (d, J=6.4, 3H), 1.11-1.01 (m, 1H), 1.00-0.90 (m, J=16.9, 10.2, 2H), 0.85-0.77 (m, 5H), 0.70-0.60 (m, 1H). LCMS=556 (M+1)$^+$.

Example 12.17

6-{[(1R)-1-cyclobutylethyl]amino}-N-ethyl-7-[(trans-4-methylcyclohexyl)methyl]-8-[(3R)-3-phenylmorpholin-4-yl]-7H-purine-2-carboxamide

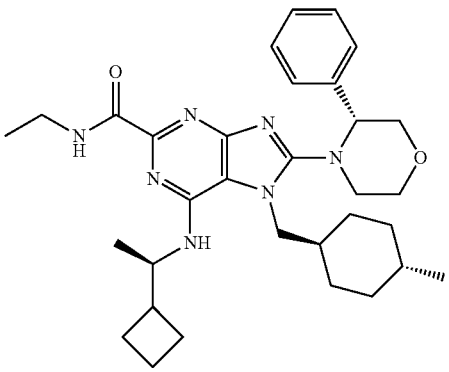 [SMILES: CCNC(=O)c1nc(N[C@H](C)C2CCC2)c2c(n1)nc(N1CCOC[C@H]1c1ccccc1)n2C[C@H]1CC[C@H](C)CC1]

CDI (22.30 mg, 0.141 mmol) was added to a solution of 6-{[(1R)-1-cyclobutylethyl]amino}-7-[(trans-4-methylcyclohexyl)methyl]-8-[(3R)-3-phenylmorpholin-4-yl]-7H-purine-2-carboxylic acid (50.0 mg, 0.094 mmol) in THF (3 ml) and stirred at ambient temperature for 40 minutes before adding ethylamine (70.4 μL, 0.141 mmol) and stirring at ambient temperature for 20 minutes. The reaction was diluted with EtOAc and the organics were washed with water and brine. The organic layer was dried over Na$_2$SO$_4$, filtered, and concentrated. Purification of the residue by mass triggered reverse phase HPLC (C-18), eluting with acetonitrile/water containing 0.1% TFA afforded 6-{[(1R)-1-cyclobutylethyl]amino}-N-ethyl-7-[(trans-4-methylcyclohexyl)methyl]-8-[(3R)-3-phenylmorpholin-4-yl]-7H-purine-2-carboxamide (TFA salt). $^1$H NMR (600 MHz, CD$_3$OD) 7.44 (d, J=7.2, 2H), 7.26-7.17 (m, 3H), 4.80 (t, J=5.0, 1H), 4.74 (ddd, J=13.2, 9.7, 6.6, 1H), 4.28 (dd, J=14.4, 5.6, 1H), 4.01 (d, J=5.3, 2H), 4.00-3.93 (m, 2H), 3.93-3.87 (m, 1H), 3.57-3.51 (m, 1H), 3.43 (q, J=7.2, 2H), 3.27-3.20 (m, 1H), 2.58-2.47 (m, 1H), 2.14-2.06 (m, 1H), 2.06-1.98 (m, 1H), 1.98-1.80 (m, 4H), 1.69-1.44 (m, 4H), 1.32-1.24 (m, 1H), 1.21 (t, J=7.2, 3H), 1.15 (d, J=6.5, 3H), 1.07-1.00 (m, 1H), 0.93-0.86 (m, 2H), 0.82 (d, J=6.6, 3H), 0.80-0.72 (m, 1H), 0.67-0.55 (m, 1H). LCMS=560 (M+1)$^+$.

Example 12.18

6-{[(1R)-1-cyclobutylethyl]amino}-7-[(trans-4-methylcyclohexyl)methyl]-Nethylsulfonyl)-8-[(3R)-3-phenylmorpholin-4-yl]-7H-purine-2-carboxamide

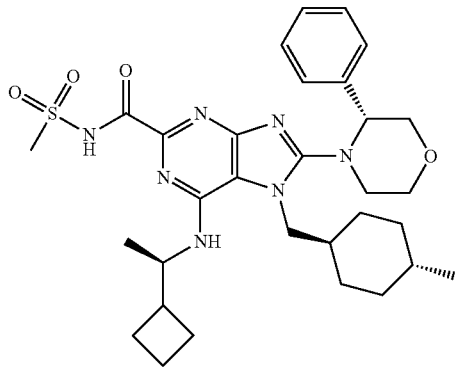 [SMILES: C[C@@H](Nc1nc(C(=O)NS(C)(=O)=O)nc2nc(N3CCOC[C@H]3c3ccccc3)n(C[C@H]3CC[C@H](C)CC3)c12)C1CCC1]

DMAP (6.88 mg, 0.056 mmol), EDC (10.80 mg, 0.056 mmol) and methanesulfonamide (8.93 mg, 0.094 mmol) were added to a stirring solution of 6-{[(1R)-1-cyclobutylethyl]amino}-7-[(trans-4-methylcyclohexyl)methyl]-8-[(3R)-3-phenylmorpholin-4-yl]-7H-purine-2-carboxylic acid (25.0 mg, 0.047 mmol) in DCM (235 L) and the reaction allowed to stir at ambient temperature under nitrogen overnight. The reaction was diluted with DCM and the organics were washed with water, 2N aq. HCl, and brine. The organic layer was dried over $Na_2SO_4$, filtered, and concentrated. Purification of the residue by mass triggered reverse phase HPLC (C-18), eluting with acetonitrile/water containing 0.1% TFA afforded 6-{[(1R)-1-cyclobutylethyl]amino}-7-[(trans-4-methylcyclohexyl)methyl]-N-ethylsulfonyl)-8-[(3R)-3-phenylmorpholin-4-yl]-7H-purine-2-carboxamide (TFA salt). $^1$H NMR (600 MHz, $CD_3OD$) δ 7.45-7.41 (m, 2H), 7.25-7.17 (m, 3H), 4.75 (t, J=5.2, 1H), 4.70 (dq, J=9.6, 6.5, 1H), 4.29 (dd, J=14.5, 5.7, 1H), 4.04-3.94 (m, 4H), 3.91 (ddd, J=11.6, 6.0, 3.0, 1H), 3.52 (ddd, J=12.6, 5.9, 2.8, 1H), 3.34 (s, 3H), 3.21 (ddd, J=12.4, 7.3, 2.9, 1H), 2.58-2.46 (m, 1H), 2.13-2.06 (m, 1H), 2.06-1.98 (m, 1H), 1.98-1.88 (m, 1H), 1.89-1.81 (m, 3H), 1.71-1.43 (m, 4H), 1.34-1.22 (m, 1H), 1.14 (d, J=6.5, 3H), 1.04 (qd, J=12.9, 3.6, 1H), 0.94-0.84 (m, 2H), 0.82 (d, J=6.6, 3H), 0.80-0.72 (m, 1H), 0.60 (ddd, J=24.9, 12.6, 4.3, 1H). LCMS=610 (M+1)$^+$.

Example 12.19

5-(6-{[(1R)-1-cyclobutylethyl]amino}-7-[(trans-4-methylcyclohexyl)methyl]-8-[(3R)-3-phenylmorpholin-4-yl]-7H-purine-2-yl)-2-methyl-2,4-dihydro-3H-1,2,4-triazol-3-one

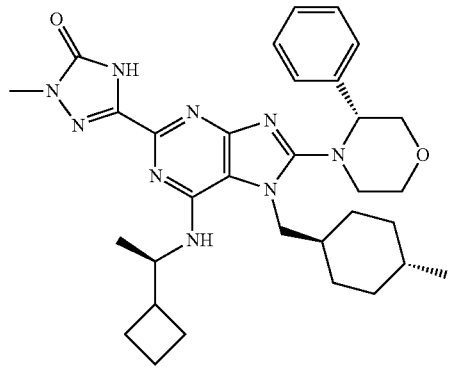

Step 1: Sodium methoxide (1.052 mg, 0.019 mmol) was added to a solution of 6-{[(1R)-1-cyclobutylethyl]amino}-7-[(trans-4-methylcyclohexyl)methyl]-8-[(3R)-3-phenylmorpholin-4-yl]-7H-purine-2-carbonitrile (100 mg, 0.195 mmol) in methanol (195 μL) and the vial capped and allowed to stir at ambient temperature overnight. The reaction was concentrated to afford crude methyl 6-{[(1R)-1-cyclobutylethyl]amino}-7-[(trans-4-methylcyclohexyl)methyl]-8-[(3R)-3-phenylmorpholin-4-yl]-7H-purine-2-carboximidoate. LCMS=546 (M+1)$^+$. This material was taken on to Step 2 without further purification.

Step 2: Methylhydrazine (56.4 μL, 1.072 mmol) was added to a solution of methyl 6-{[(1R)-1-cyclobutylethyl]amino}-7-[(trans-4-methylcyclohexyl)methyl]-8-[(3R)-3-phenylmorpholin-4-yl]-7H-purine-2-carboximidoate (117 mg, 0.214 mmol) in methanol (2144 μL) and the reaction vial was then capped and stirred at 50° C. for 1 hr. The reaction was then diluted with EtOAc and washed with water and brine. The organic layer was dried over $Na_2SO_4$, filtered, and concentrated to afford crude 6-{[(1R)-1-cyclobutylethyl]amino}-N'-methyl-7-[(trans-4-methylcyclohexyl)methyl]-8-[(3R)-3-phenylmorpholin-4-yl]-7H-purine-2-carboximidohydrazide. LCMS=560 (M+1)$^+$. This material was taken on to Step 3 without further purification.

Step 3: CDI (41.3 mg, 0.255 mmol) and DBU (153 μL, 1.018 mmol) were added to a solution of crude 6-{[(1R)-1-cyclobutylethyl]amino}-N'-methyl-7-[(trans-4-methylcyclohexyl)methyl]-8-[(3R)-3-phenylmorpholin-4-yl]-7H-purine-2-carboximidohydrazide (95.0 mg, 0.170 mmol) in ACN (360 μL) and the reaction was stirred at ambient temperature overnight. The reaction was then diluted with DCM and the organics were washed with 2N HCl and brine. The organic layer was dried over $Na_2SO_4$, filtered, and concentrated. Purification of the residue by mass triggered reverse phase HPLC (C-18), eluting with acetonitrile/water containing 0.1% TFA afforded impure 5-(6-{[(1R)-1-cyclobutylethyl]amino}-7-[(trans-4-methylcyclohexyl)methyl]-8-[(3R)-3-phenylmorpholin-4-yl]-7H-purine-2-yl)-2-methyl-2,4-dihydro-3H-1,2,4-triazol-3-one. The material was repurified by PTLC (DCM/5% MeOH) to afford pure 5-(6-{[(1R)-1-cyclobutylethyl]amino}-7-[(trans-4-methylcyclohexyl)methyl]-8-[(3R)-3-phenylmorpholin-4-yl]-7H-purine-2-yl)-2-methyl-2,4-dihydro-3H-1,2,4-triazol-3-one. $^1$H NMR (600 MHz, cd3od) δ 7.44 (d, J=7.9, 2H), 7.27-7.17 (m, 3H), 4.79-4.70 (m, 2H), 4.27 (dd, J=14.6, 5.5, 1H), 4.01 (d, J=4.8, 2H), 4.01-3.88 (m, 4H), 3.51 (s, 3H), 3.23-3.19 (m, 1H), 2.55-2.45 (m, 1H), 2.08 (d, J=8.7, 1H), 2.06-1.97 (m, 1H), 1.94-1.80 (m, 4H), 1.72-1.45 (m, 4H), 1.33-1.21 (m, 1H), 1.14 (d, J=6.5, 3H), 1.09-1.00 (m, 1H), 0.96-0.86 (m, 2H), 0.82 (d, J=6.6, 3H), 0.79-0.74 (m, 1H), 0.66-0.59 (m, 1H). LCMS=586 (M+1)$^+$ Preparative Example 12.4

(R)-3-phenylmorpholine

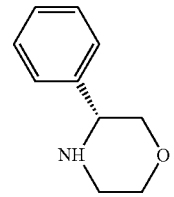 [SMILES: c1ccc([C@@H]2COCCN2)cc1]

Step 1: To a solution of (R)-2-amino-2-phenylethanol (205 g, 1.496 mol) and $Et_3N$ (226 g, 2.24 mol) in THF (2.0 L) was added 2-chloroacetyl chloride (177 g, 1.57 mol) dropwise at 0° C. Then the mixture was stirred at room temperature for 12 h. The reaction mixture was poured into ice water and extracted with dichloromethane. The organic phase was washed with brine, dried over anhydrous $Na_2SO_4$, filtered and concentrated to give (R)-2-chloro-N-(2-hydroxy-1-phenylethyl)acetamide, which was used in the next step without further purification.

Step 2: NaH (18 g, 0.45 mol, 60%) was suspended in tetrahydrofuran (0.6 L) at 0° C. A solution of (R)-2-chloro-N-(2-hydroxy-1-phenylethyl)acetamide (80 g, 0.374 mol) in tetrahydrofuran (0.6 L) was added dropwise to the solution at 0° C. under $N_2$. Then the mixture was stirred at room temperature for 12 h. The reaction mixture was poured into ice water and extracted with DCM. The organic phase was washed with brine, dried over anhydrous $Na_2SO_4$, filtered and concentrated to give a crude product as yellow solid, which was washed by methyl tertiary butyl ether to give (R)-5-phenylmorpholin-3-one.

Step 3: To a suspension of LiAlH₄ (19.3 g, 0.508 mol) in tetrahydrofuran (0.45 L) was added dropwise a solution of (R)-5-phenylmorpholin-3-one (45 g, 0.254 mol) in tetrahydrofuran (0.45 L) at 0° C. under N₂. Then the reaction was stirred at room temperature for 12 h. Aqueous NaOH (20 mL, 10%) was added dropwise to the mixture at 0° C., and then H₂O (20 mL) was added. The mixture was filtered and the cake was washed with tetrahydrofuran. The filtrate was concentrated to give (R)-3-phenylmorpholine, which was used without further purification. ¹H NMR (400 MHz, CDCl₃) δ: 7.50-7.048 (m, 5H), 3.85-3.73 (m, 3H), 3.57-3.55 (m, 1H), 3.34-3.29 (t, J=10.4 Hz, 1H), 3.05-3.04 (m, 1H), 2.93-2.90 (d, J=10.4 Hz, 1H).

Preparative Example 12.5

(R)-4-(2,6-dichloro-7-((trans-4-methylcyclohexyl)methyl)-7H-purin-8-yl)-3-phenylmorpholine

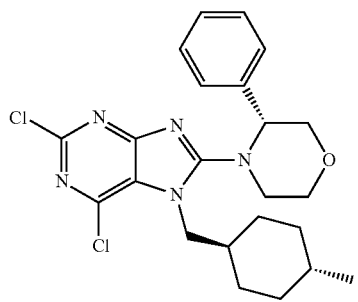 [SMILES: C[C@H]1CC[C@H](Cn2c(N3CCOC[C@H]3c3ccccc3)nc3nc(Cl)nc(Cl)c32)CC1]

Step 1: A suspension of 3-methyl-7-((trans-4-methylcyclohexyl)methyl)-1H-purine-2,6(3H,7H)-dione (Preparative Example 11.3, 65 g, 0.235 mol) and NBS (125 g, 0.706 mol) dissolved in CHCl₃ (500 mL) and acetonitrile (500 mL) was stirred at 90° C. for 5 h. The reaction mixture was then cooled, diluted with CH₂Cl₂ and quenched with aqueous sodium thiosulfate. The organic phase was washed with aqueous NaOH (0.5 mol/L) and brine, dried over Na₂SO₄, filtered and concentrated to give 8-bromo-3-methyl-7-((trans-4-methylcyclohexyl)methyl)-1H-purine-2,6(3H,7H)-dione. ¹H NMR (400 MHz, CDCl₃) δ: 9.01 (s, 1H), 4.14-4.12 (d, J=7.6 Hz, 2H), 3.53 (s, 3H), 1.87-0.86 (m, 13H).

Step 2: A mixture of 8-bromo-3-methyl-7-((trans-4-methylcyclohexyl)methyl)-1H-purine-2,6(3H,7H)-dione (60 g, 0.17 mol), (R)-3-phenylmorpholine (33.3 g, 0.204 mol) and potassium fluoride (90 g, 1.53 mol) in anhydrous DMSO (300 mL) was stirred at 140° C. for 24 h. The reaction mixture was cooled to room temperature, poured into ice water, and then extracted with ethyl acetate. The combined organic layers were washed with brine, dried over Na₂SO₄, filtered and concentrated. The residue was purified by silica gel column chromatography (petroleum ether/ethyl acetate=2/1) to give 3-methyl-7-((trans-4-methylcyclohexyl)methyl)-8-((R)-3-phenylmorpholino)-1H-purine-2,6(3H,7H)-dione.

Step 3: To a suspension of 3-methyl-7-((trans-4-methylcyclohexyl)methyl)-8-((R)-3-phenylmorpholino)-1H-purine-2,6(3H,7H)-dione (77 g, 0.176 mol) in POCl₃ (350 mL) was added DBU (120 mL) at room temperature. The reaction mixture was heated at 120° C. for 3 h. The reaction mixture was cooled to ambient temperature and the excess POCl₃ was removed under vacuum. The residue was poured into ice water slowly and the pH of the solution was adjusted to neutral using NaHCO₃. The aqueous mixture was extracted with dichloromethane, and the organic layers were dried over Na₂SO₄, filtered and concentrated. The residue was purified by silica gel column chromatography (petroleum ether/ethyl acetate=5/1) to afford (R)-4-(2,6-dichloro-7-((trans-4-methylcyclohexyl)methyl)-7H-purin-8-yl)-3-phenylmorpholine. MS ESI calc'd. for C₂₃H₂₇Cl₂N₅O [M+H]⁺ 460. found 460. ¹H NMR (400 MHz, CDCl₃) δ: 7.49-7.48 (m, 2H), 7.34-7.26 (m, 3H), 5.01-4.99 (m, 1H), 4.18-4.12 (m, 3H), 3.99-3.97 (m, 2H), 3.87-3.85 (m, 1H), 3.57-3.51 (m, 2H), 1.69-1.63 (m, 3H), 1.31-1.24 (m, 3H), 0.94-0.76 (m, 7H).

Preparative Example 12.6

2-chloro-N-[(1R)-1-cyclobutylethyl]-7-[(trans-4-methylcyclohexyl)methyl]-8-[(3R)-3-phenylmorpholin-4-yl]-7H-purin-6-amine

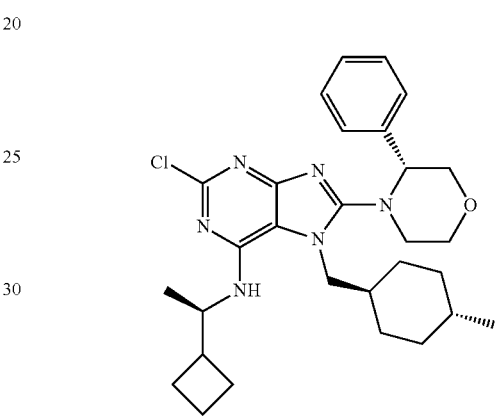

Using a procedure analogous to that described in Preparative Example 11.5, and starting with Preparative Example 12.5 and (1R)-1-cyclobutylethan-1-amine hydrochloride, 2-chloro-N-[(1R)-1-cyclobutylethyl]-7-[(trans-4-methylcyclohexyl)methyl]-8-[(3R)-3-phenylmorpholin-4-yl]-7H-purin-6-amine was prepared. MS ESI calc'd. for C₂₉H₃₉ClN₆O [M+H]⁺ 523. found 523.

Example 12.20

1-(6-(((R)-1-cyclobutylethyl)amino)-7-((trans-4-methylcyclohexyl)methyl)-8-((R)-3-phenylmorpholino)-7H-purin-2-yl)ethane-1,2-diol

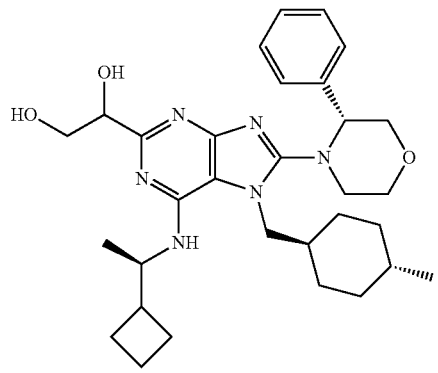 [SMILES: C[C@@H](Nc1nc(C(O)CO)nc2nc(N3CCOC[C@H]3c3ccccc3)n(C[C@H]3CC[C@H](C)CC3)c12)C1CCC1]

Step 1: (Ph₃P)₄Pd (5.52 mg, 4.78 μmol), 4,4,5,5-tetramethyl-2-vinyl-1,3,2-dioxaborolane (0.012 ml, 0.072 mmol) and 2.0 M aqueous Na₂CO₃ (0.072 ml, 0.143 mmol) was added into a solution of 2-chloro-N-[(1R)-1-cyclobutylethyl]-7-[(trans-4-methylcyclohexyl)methyl]-8-[(3R)-3-phenylmorpholin-4-yl]-7H-purin-6-amine (Preparative Example 12.6) (25 mg, 0.048 mmol) in 1,4-Dioxane (1 ml). The reaction mixture was heated at 120° C. under Ar for 18 h. The mixture was cooled to room temperature, filtered through Celite and concentrated by rotary evaporation. The residue was taken up in CH₂Cl₂, brine was added and the mixture was extracted. The organic layer was dried over Na₂SO₄, filtered and the solvent was removed by rotary evaporation. N—((R)-1-cyclobutylethyl)-7-((trans-4-methylcyclohexyl)methyl)-8-((R)-3-phenylmorpholino)-2-vinyl-7H-purin-6-amine was isolated by flash chromatography on silica gel using 10:90 to 90:10 EtOAc-hexanes as eluent. MS ESI calc'd. for C₃₁H₄₂N₆O [M+H]⁺ 515. found 515.

Step 2: To a solution of N—((R)-1-cyclobutylethyl)-7-((trans-4-methylcyclohexyl)methyl)-8-((R)-3-phenylmorpholino)-2-vinyl-7H-purin-6-amine (20 mg, 0.039 mmol) in a mixture of acetone (1.2 ml), water (0.4 ml) and acetonitrile (0.4 ml) was added 4-methylmorpholine N-oxide monohydrate (10.50 mg, 0.078 mmol), followed by osmium tetroxide (0.610 μl, 1.943 μmol) at room temperature. The resulting mixture was stirred for 6 hrs at room temperature. Organic solvents were evaporated and the aqueous residue was extracted with ethyl acetate (50 ml, three times), dried over Na₂SO₄, and concentrated. The residue was purified by preparative reverse phase HPLC (C-18), eluting with acetonitrile/water+0.1% TFA, to give 1-(6-(((R)-1-cyclobutylethyl)amino)-7-((trans-4-methylcyclohexyl)methyl)-8-((R)-3-phenylmorpholino)-7H-purin-2-yl)ethane-1,2-diol as TFA salt. MS ESI calc'd. for C₃₁H₄₄N₆O₃ [M+H]⁺ 549. found 549. ¹H NMR (DMSO-d₆): δ 0.79 (3H, d, J=6.77 Hz), 1.09 (3H, d, J=6.61 Hz), 1.27-0.71 (4H, m), 1.84-1.42 (8H, m), 2.53-2.50 (1H, m), 3.18-3.10 (1H, m), 3.49-3.43 (1H, m), 3.69-3.75 (5H, m), 3.93-3.85 (6H, m), 4.49-4.38 (2H, m), 4.55 (1H, t, J=5.26 Hz), 4.74-4.70 (1H, m), 7.26-7.24 (3H, m), 7.40 (2H, d, J=7.56 Hz), 7.59-7.57 (2H, m).

The following compounds in Table 12 (other than Example 12.1 to 12.20) were prepared using procedures which were analogous to those described above.

TABLE 12

| Ex. | FRET IC₅₀ (nM) | Structure | Chemical Name | Salt Form | [M + H]⁺ Calc'd | [M + H]⁺ Obsv'd |
|---|---|---|---|---|---|---|
| 12.1 | 8.348 | 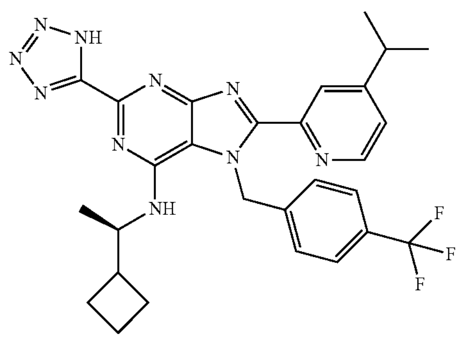 [SMILES: CC(C)c1ccnc(-c2nc3nc(-c4nnn[nH]4)nc(N[C@H](C)C4CCC4)c3n2Cc2ccc(C(F)(F)F)cc2)c1] | N-[(1R)-1-cyclobutylethyl]-8-[4-(propan-2-yl)pyridin-2-yl]-2-(1H-tetrazol-5-yl)-7-[4-(trifluoromethyl)benzyl]-7H-purin-6-amine | TFA | 563 | 563 |
| 12.2 | 597.3 | 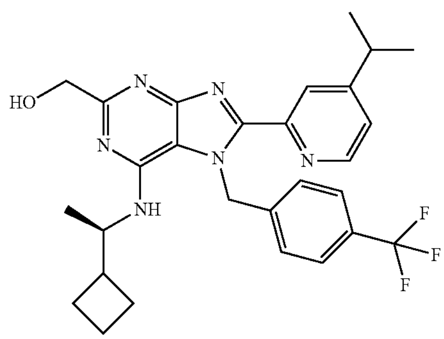 [SMILES: CC(C)c1ccnc(-c2nc3nc(CO)nc(N[C@H](C)C4CCC4)c3n2Cc2ccc(C(F)(F)F)cc2)c1] | (6-{[(1R)-1-cyclobutylethyl]amino}-8-[4-(propan-2-yl)pyridin-2-yl]-7-[4-(trifluoromethyl)benzyl]-7H-purin-2-yl)methanol | TFA | 525 | 525 |
| 12.3 | 535.1 | 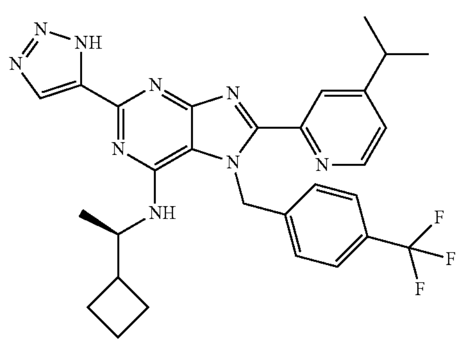 | N-[(1R)-1-cyclobutylethyl]-8-[4-(propan-2-yl)pyridin-2-yl]-2-(1H-1,2,3-triazol-5-yl)-7-[4-(trifluoromethyl)benzyl]-7H-purin-6-amine | TFA | 562 | 562 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.4 | 39% inh. at 1000 nM | 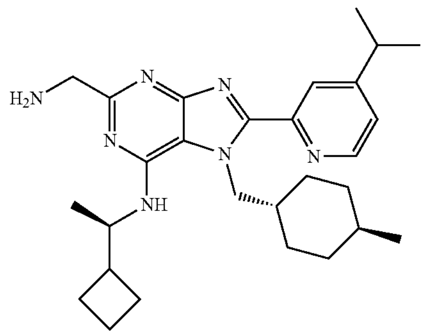 [SMILES: CC(C)c1ccnc(-c2nc3nc(CN)nc(N[C@H](C)C4CCC4)c3n2C[C@H]2CC[C@H](C)CC2)c1] | 2-(aminomethyl)-N-[(1R)-1-cyclobutylethyl]-7-[(trans-4-methylcyclohexyl)methyl]-8-[4-(propan-2-yl)pyridin-2-yl]-7H-purin-6-amine | TFA | 476 | 476 |
| 12.5 | 471 | 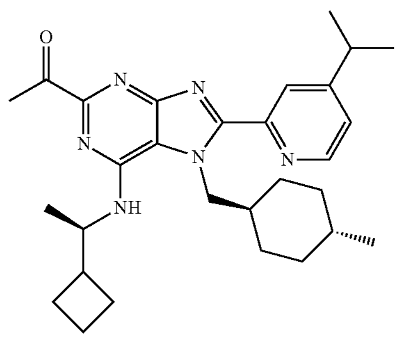 [SMILES: CC(=O)c1nc(N[C@H](C)C2CCC2)c2c(n1)nc(-c1cc(C(C)C)ccn1)n2C[C@H]1CC[C@H](C)CC1] | 1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanone | | 489 | 489 |
| 12.6 | 420.5 | 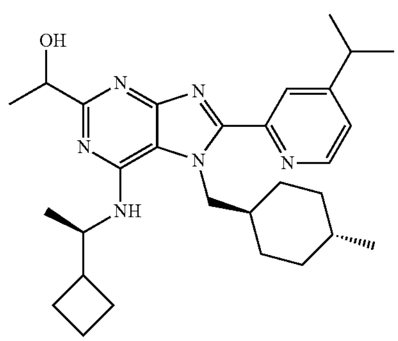 [SMILES: CC(C)c1ccnc(-c2nc3nc(C(C)O)nc(N[C@H](C)C4CCC4)c3n2C[C@H]2CC[C@H](C)CC2)c1] | 1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanol | TFA | 491 | 491 |
| 12.7 | 730.8 | 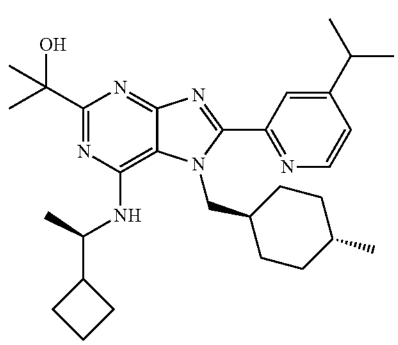 [SMILES: CC(C)c1ccnc(-c2nc3nc(C(C)(C)O)nc(N[C@H](C)C4CCC4)c3n2C[C@H]2CC[C@H](C)CC2)c1] | 2-(6-{[(1R)-1-cyclobutylethyl]amino}-7-[(trans-4-methylcyclohexyl)methyl]-8-[4-(propan-2-yl)pyridin-2-yl]-7H-purin-2-yl)propan-2-ol | | 505 | 505 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.8 | 1.914 | 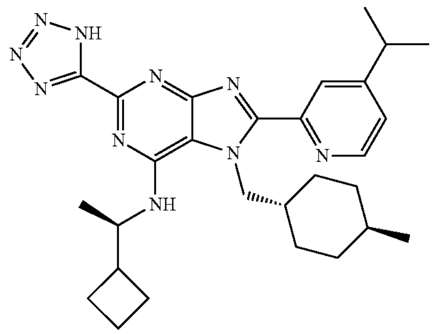 [SMILES: CC(C)c1ccnc(-c2nc3nc(-c4nnn[nH]4)nc(N[C@H](C)C4CCC4)c3n2C[C@H]2CC[C@H](C)CC2)c1] | N-[(1R)-1-cyclobutylethyl]-7-[(trans-4-methylcyclohexyl)methyl]-8-[4-(propan-2-yl)pyridin-2-yl]-2-(1H-tetrazol-5-yl)-7H-purin-6-amine | TFA | 515 | 515 |
| 12.9 | 374 | 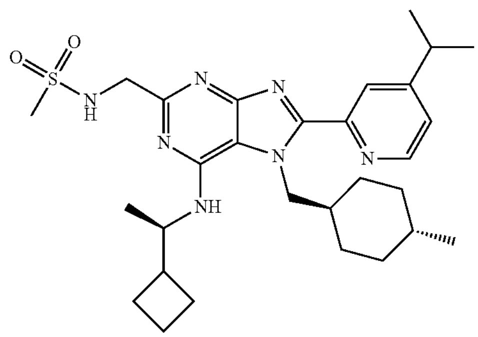 [SMILES: CC(C)c1ccnc(-c2nc3nc(CNS(C)(=O)=O)nc(N[C@H](C)C4CCC4)c3n2C[C@H]2CC[C@H](C)CC2)c1] | N-[(6-{[(1R)-1-cyclobutylethyl]amino}-7-[(trans-4-methylcyclohexyl)methyl]-8-[4-(propan-2-yl)pyridin-2-yl]-7H-purin-2-yl)methyl]methanesulfonamide | TFA | 554 | 554 |
| 12.10 | 30% inh. at 1000 nM | 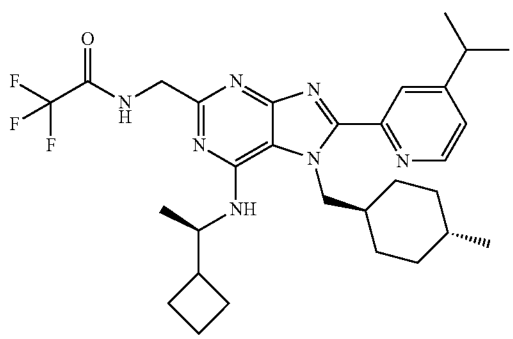 [SMILES: CC(C)c1ccnc(-c2nc3nc(CNC(=O)C(F)(F)F)nc(N[C@H](C)C4CCC4)c3n2C[C@H]2CC[C@H](C)CC2)c1] | N-[(6-{[(1R)-1-cyclobutylethyl]amino}-7-[(trans-4-methylcyclohexyl)methyl]-8-[4-(propan-2-yl)pyridin-2-yl]-7H-purin-2-yl)methyl]-2,2,2-trifluoroacetamide | TFA | 572 | 572 |
| 12.11 | 32.47 | 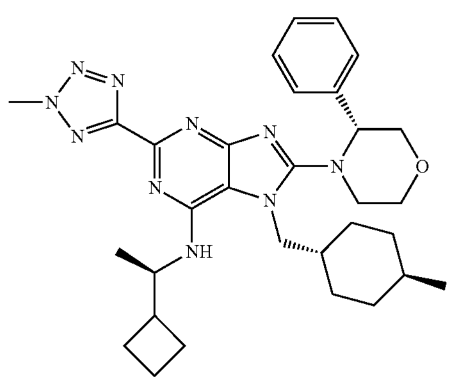 | N-[(1R)-1-cyclobutylethyl]-7-[(trans-4-methylcyclohexyl)methyl]-2-(2-methyl-2H-tetrazol-5-yl)-8-[(3R)-3-phenylmorpholin-4-yl]-7H-purin-6-amine | | 571 | 571 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.12 | 27.27 | 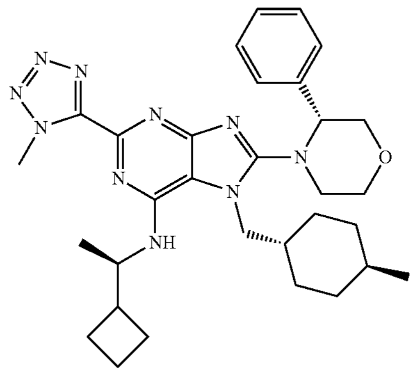 [SMILES: C[C@@H](Nc1nc(-c2nnnn2C)nc2nc(N3CCOC[C@H]3c3ccccc3)n(C[C@H]3CC[C@H](C)CC3)c12)C1CCC1] | N-[(1R)-1-cyclobutylethyl]-7-[(trans-4-methylcyclohexyl)methyl]-2-(1-methyl-1H-tetrazol-5-yl)-8-[(3R)-3-phenylmorpholin-4-yl]-7H-purin-6-amine | | 571 | 571 |
| 12.13 | 49.38 | 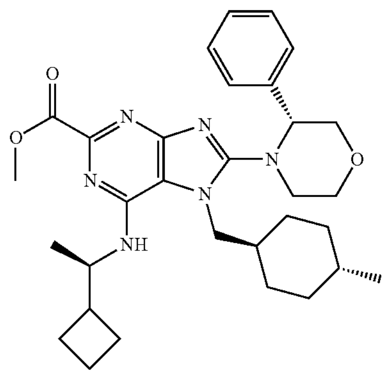 [SMILES: COC(=O)c1nc(N[C@H](C)C2CCC2)c2c(n1)nc(N1CCOC[C@H]1c1ccccc1)n2C[C@H]1CC[C@H](C)CC1] | methyl 6-{[(1R)-1-cyclobutylethyl]amino}-7-[(trans-4-methylcyclohexyl)methyl]-8-[(3R)-3-phenylmorpholin-4-yl]-7H-purine-2-carboxylate | | 547 | 547 |
| 12.14 | 107.4 | 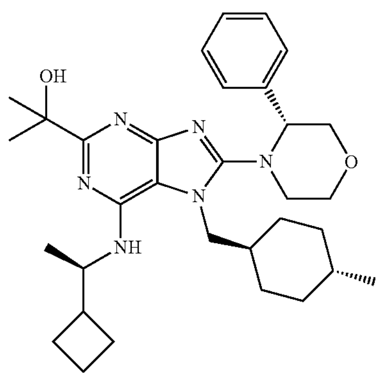 [SMILES: C[C@@H](Nc1nc(C(C)(C)O)nc2nc(N3CCOC[C@H]3c3ccccc3)n(C[C@H]3CC[C@H](C)CC3)c12)C1CCC1] | 2-(6-{[(1R)-1-cyclobutylethyl]amino}-7-[(trans-4-methylcyclohexyl)methyl]-8-[(3R)-3-phenylmorpholin-4-yl]-7H-purin-2-yl)propan-2-ol | TFA | 547 | 547 |
| 12.15 | 14.5 | 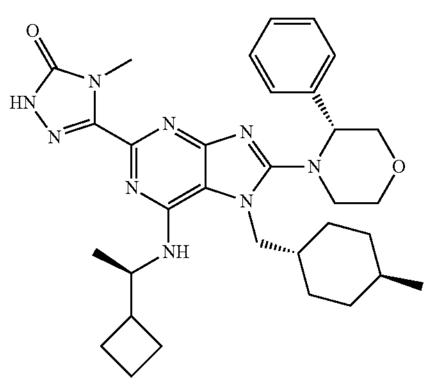 [SMILES: C[C@@H](Nc1nc(-c2n[nH]c(=O)n2C)nc2nc(N3CCOC[C@H]3c3ccccc3)n(C[C@H]3CC[C@H](C)CC3)c12)C1CCC1] | 5-(6-{[(1R)-1-cyclobutylethyl]amino}-7-[(trans-4-methylcyclohexyl)methyl]-8-[(3R)-3-phenylmorpholin-4-yl]-7H-purin-2-yl)-4-methyl-2,4-dihydro-3H-1,2,4-triazol-3-one | TFA | 586 | 586 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.16 | 10.76 | 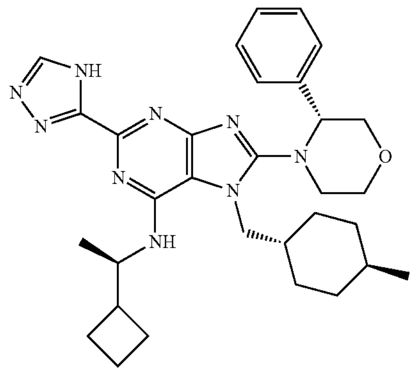 [SMILES: C[C@@H](Nc1nc(-c2nnc[nH]2)nc2nc(N3CCOC[C@H]3c3ccccc3)n(C[C@H]3CC[C@H](C)CC3)c12)C1CCC1] | N-[(1R)-1-cyclobutylethyl]-7-[(trans-4-methylcyclohexyl)methyl]-8-[(3R)-3-phenylmorpholin-4-yl]-2-(4H-1,2,4-triazol-3-yl)-7H-purin-6-amine | | 556 | 556 |
| 12.17 | 1.632 | 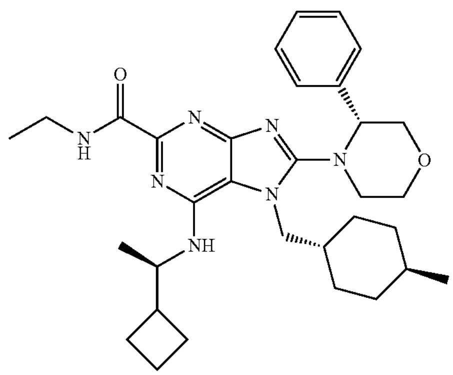 [SMILES: CCNC(=O)c1nc(N[C@H](C)C2CCC2)c2c(n1)nc(N1CCOC[C@H]1c1ccccc1)n2C[C@H]1CC[C@H](C)CC1] | 6-{[(1R)-1-cyclobutylethyl]amino}-N-ethyl-7-[(trans-4-methylcyclohexyl)methyl]-8-[(3R)-3-phenylmorpholin-4-yl]-7H-purine-2-carboxamide | TFA | 560 | 560 |
| 12.18 | 0.5847 | 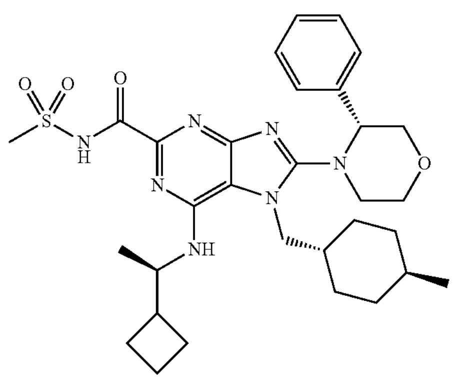 | 6-{[(1R)-1-cyclobutylethyl]amino}-7-[(trans-4-methylcyclohexyl)methyl]-N-(methylsulfonyl)-8-[(3R)-3-phenylmorpholin-4-yl]-7H-purine-2-carboxamide | TFA | 610 | 610 |
| 12.19 | 1.608 | 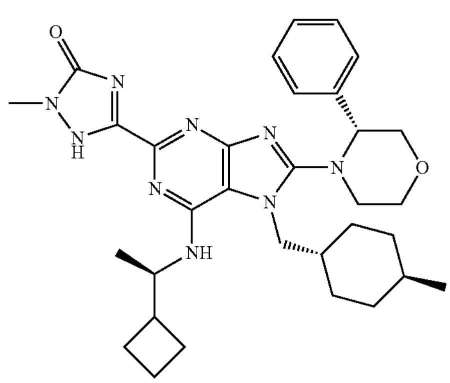 | 5-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methyl-1,2-dihydro-3H-1,2,4-triazol-3-one | TFA | 586 | 586 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.20 | 49.39 | 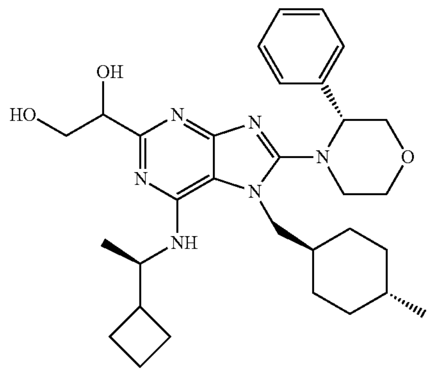 [SMILES: C[C@@H](Nc1nc(C(O)CO)nc2nc(N3CCOC[C@H]3c3ccccc3)n(C[C@H]3CC[C@H](C)CC3)c12)C1CCC1] | 1-(6-(((R)-1-cyclobutylethyl)amino)-7-((trans-4-methylcyclohexyl)methyl)-8-((R)-3-phenylmorpholino)-7H-purin-2-yl)ethane-1,2-diol | TFA | 549 | 549 |
| 12.21 | 53.28 | 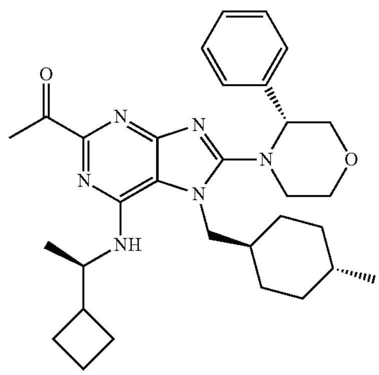 [SMILES: CC(=O)c1nc(N[C@H](C)C2CCC2)c2c(n1)nc(N1CCOC[C@H]1c1ccccc1)n2C[C@H]1CC[C@H](C)CC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)ethanone | | 531 | 531 |
| 12.22 | 78.61 | 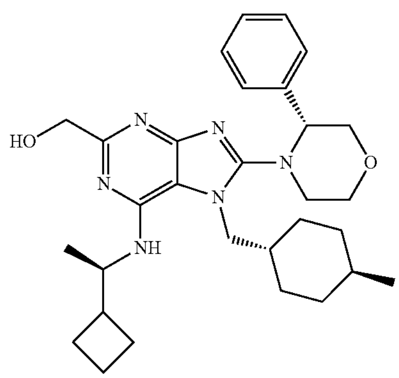 [SMILES: C[C@@H](Nc1nc(CO)nc2nc(N3CCOC[C@H]3c3ccccc3)n(C[C@H]3CC[C@H](C)CC3)c12)C1CCC1] | (6-{[(1R)-1-cyclobutylethyl]amino}-7-[(trans-4-methylcyclohexyl)methyl]-8-[(3R)-3-phenylmorpholin-4-yl]-7H-purin-2-yl)methanol | TFA | 519 | 519 |
| 12.23 | 53.28 | 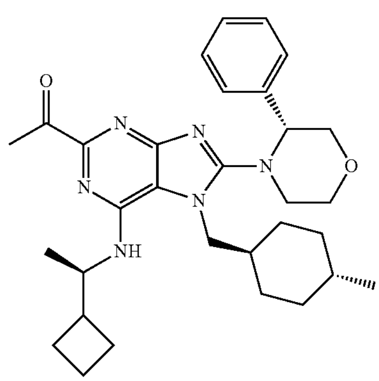 [SMILES: CC(=O)c1nc(N[C@H](C)C2CCC2)c2c(n1)nc(N1CCOC[C@H]1c1ccccc1)n2C[C@H]1CC[C@H](C)CC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)ethanone | | 531 | 531 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.24 | 1.413 | 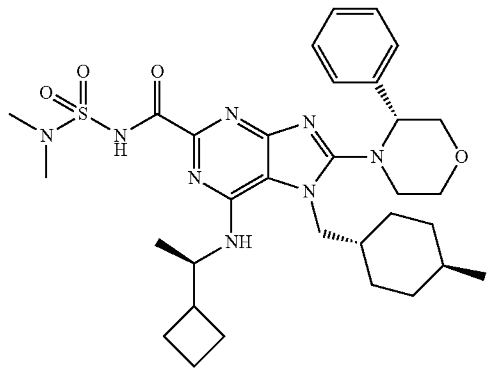 | 6-{[(1R)-1-cyclobutylethyl]amino}-N-(dimethylsulfamoyl)-7-[(trans-4-methylcyclohexyl)methyl]-8-[(3R)-3-phenylmorpholin-4-yl]-7H-purine-2-carboxamide | TFA | 639 | 639 |
| 12.25 | 1067 | 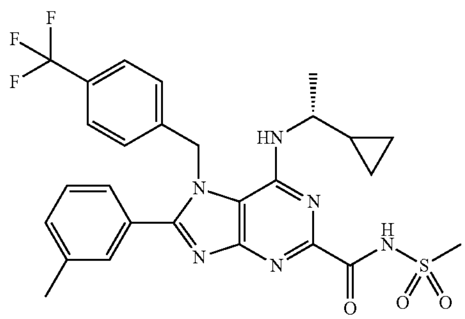 [SMILES: Cc1cccc(-c2nc3nc(C(=O)NS(C)(=O)=O)nc(N[C@H](C)C4CC4)c3n2Cc2ccc(C(F)(F)F)cc2)c1] | 6-{[(1R)-1-cyclopropylethyl]amino}-8-(3-methylphenyl)-N-(methylsulfonyl)-7-[4-(trifluoromethyl)benzyl]-7H-purine-2-carboxamide | | 573 | 573 |
| 12.26 | 53 | 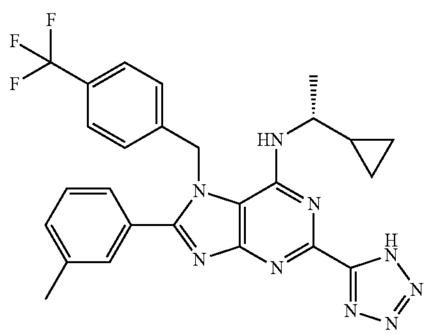 [SMILES: Cc1cccc(-c2nc3nc(-c4nnn[nH]4)nc(N[C@H](C)C4CC4)c3n2Cc2ccc(C(F)(F)F)cc2)c1] | N-[(1R)-1-cyclopropylethyl]-8-(3-methylphenyl)-2-(1H-tetrazol-5-yl)-7-[4-(trifluoromethyl)benzyl]-7H-purin-6-amine | | 520 | 520 |
| 12.27 | 2043 | 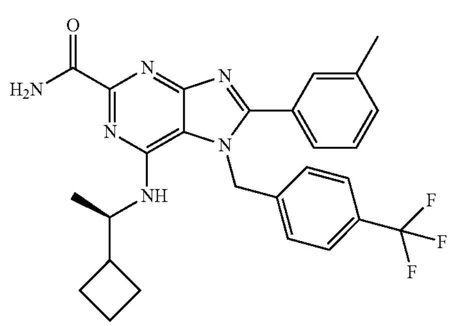 [SMILES: Cc1cccc(-c2nc3nc(C(N)=O)nc(N[C@H](C)C4CCC4)c3n2Cc2ccc(C(F)(F)F)cc2)c1] | 6-{[(1R)-1-cyclopropylethyl]amino}-8-(3-methylphenyl)-7-[4-(trifluoromethyl)benzyl]-7H-purine-2-carboxamide | TFA | 495 | 495 |

TABLE 12-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.28 | 314.3 | 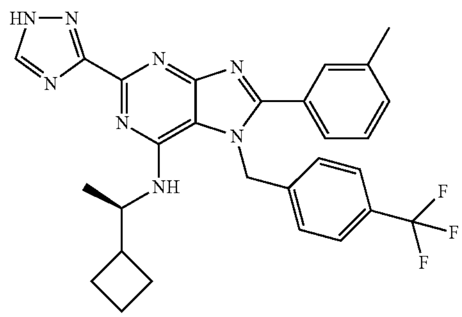 [SMILES: Cc1cccc(-c2nc3nc(-c4nc[nH]n4)nc(N[C@H](C)C4CCC4)c3n2Cc2ccc(C(F)(F)F)cc2)c1] | N-[(1R)-1-cyclopropylethyl]-8-(3-methylphenyl)-2-(1H-1,2,4-triazol-3-yl)-7-[4-(trifluoromethyl)benzyl]-7H-purin-6-amine | TFA | 519 | 519 |
| 12.29 | 1415 | 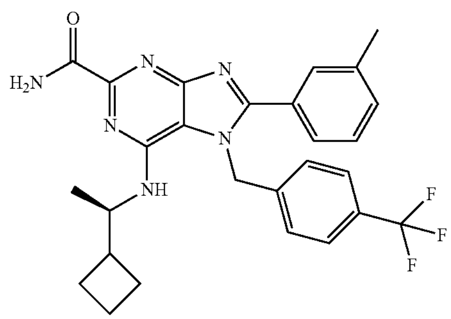 [SMILES: Cc1cccc(-c2nc3nc(C(N)=O)nc(N[C@H](C)C4CCC4)c3n2Cc2ccc(C(F)(F)F)cc2)c1] | 6-{[(1R)-1-cyclobutylethyl]amino}-8-(3-methylphenyl)-7-[4-(trifluoromethyl)benzyl]-7H-purine-2-carboxamide | TFA | 509 | 509 |
| 12.30 | 873.4 | 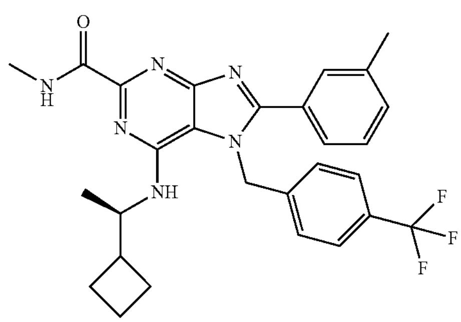 [SMILES: CNC(=O)c1nc(N[C@H](C)C2CCC2)c2c(n1)nc(-c1cccc(C)c1)n2Cc1ccc(C(F)(F)F)cc1] | 6-{[(1R)-1-cyclobutylethyl]amino}-N-methyl-8-(3-methylphenyl)-7-[4-(trifluoromethyl)benzyl]-7H-purine-2-carboxamide | TFA | 523 | 523 |
| 12.31 | 37.73 | 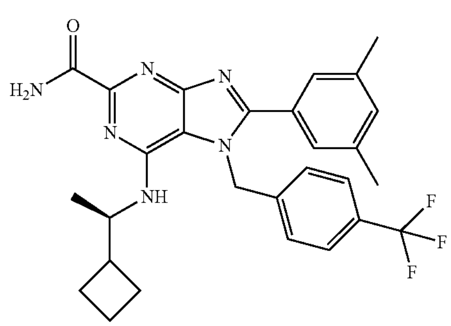 [SMILES: Cc1cc(C)cc(-c2nc3nc(C(N)=O)nc(N[C@H](C)C4CCC4)c3n2Cc2ccc(C(F)(F)F)cc2)c1] | 6-{[(1R)-1-cyclobutylethyl]amino}-8-(2,5-dimethylphenyl)-7-[4-(trifluoromethyl)benzyl]-7H-purine-2-carboxamide | TFA | 523 | 523 |

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 12.32 | 42.46 | 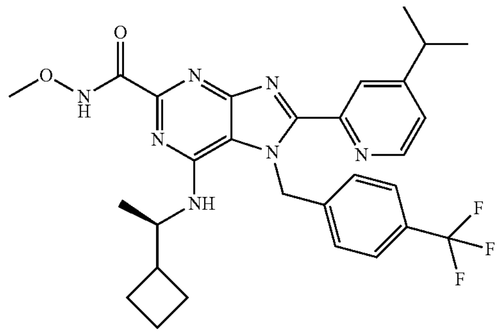 [SMILES: CONC(=O)c1nc(N[C@H](C)C2CCC2)c2c(n1)nc(-c1cc(C(C)C)ccn1)n2Cc1ccc(C(F)(F)F)cc1] | 6-{[(1R)-1-cyclobutylethyl]amino}-N-methoxy-8-[4-(1-methylethyl)pyridin-2-yl]-7-[4-(trifluoromethyl)benzyl]-7H-purine-2-carboxamide | TFA | 568 | 568 |
| 12.33 | 150.5 | 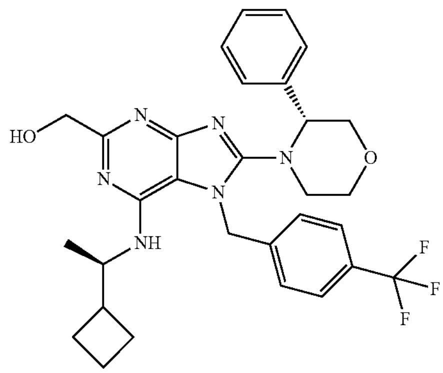 [SMILES: C[C@@H](Nc1nc(CO)nc2nc(N3CCOC[C@H]3c3ccccc3)n(Cc3ccc(C(F)(F)F)cc3)c12)C1CCC1] | (6-{[(1R)-1-cyclobutylethyl]amino}-8-[(3R)-3-phenylmorpholin-4-yl]-7-[4-(trifluoromethyl)benzyl]-7H-purin-2-yl)methanol | | 567 | 567 |
| 12.34 | 300.5 | 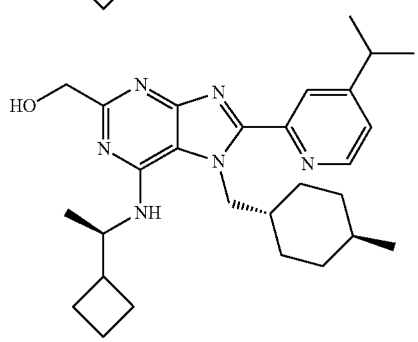 | (6-{[(1R)-1-cyclobutylethyl]amino}-7-[(trans-4-methylcyclohexyl)methyl]-8-[4-(1-methylethyl)pyridin-2-yl]-7H-purin-2-yl)methanol | | 477 | 477 |

Example 13.1

2-((6-(((R)-1-cyclobutylethyl)amino)-7-((trans-4-methylcyclohexyl)methyl)-8-((R)-3-phenylmorpholino)-7H-purin-2-yl)amino)ethanol

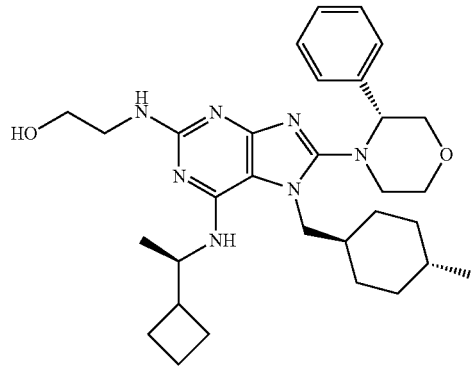 [SMILES: C[C@@H](Nc1nc(NCCO)nc2nc(N3CCOC[C@H]3c3ccccc3)n(C[C@H]3CC[C@H](C)CC3)c12)C1CCC1]

Ethanolamine (11.68 mg, 0.191 mmol) was added to a stirred mixture of 2-chloro-N—((R)-1-cyclobutylethyl)-7-((trans-4-methylcyclohexyl)methyl)-8-((R)-3-phenylmorpholino)-7H-purin-6-amine (Preparative Example 12.6; 25 mg, 0.048 mmol) and DIEA (0.067 ml, 0.382 mmol) in NMP (0.2 ml) and the mixture was stirred at 150° C. for 16 h. The mixture was cooled to room temperature, diluted with ethyl acetate (30 mL), washed with brine (5 mL), dried (Na$_2$SO$_4$), filtered, and concentrated. The residue was purified by preparative reverse phase HPLC (C-18), eluting with Acetonitrile/Water+0.1% TFA, to give 2-((6-(((R)-1-cyclobutylethyl)amino)-7-((trans-4-methylcyclohexyl)methyl)-8-((R)-3-phenylmorpholino)-7H-purin-2-yl)amino)ethanol as a TFA salt. MS ESI calc'd. for C$_{31}$H$_{45}$N$_7$O$_2$ [M+H]$^+$ 548. found 548. $^1$H NMR (500 MHz, dmso): δ 0.79 (3H, d, J=6.47 Hz), 1.07 (3H, d, J=6.51 Hz), 1.07-0.75 (m, 6H); 1.30-1.20 (m, 1H); 1.56-1.43 (br m, 3H); 1.99-1.62 (m, 8H); 2.53 (d, J=8.4 Hz, 1H); 3.07-3.03 (m, 1H); 3.52 (t, J=5.7 Hz, 2H); 3.89-3.86 (m, 5H); 4.36-4.29 (m, 2H); 4.58 (dd, J=6.8, 3.7 Hz, 1H); 7.24-7.22 (m, 4H); 7.36 (d, J=7.5 Hz, 2H).

The following compounds in Table 13 (other than Example 13.1) were prepared using procedures which were analogous to those described above in Example 13.1.

TABLE 13

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 13.1 | 885.2 | 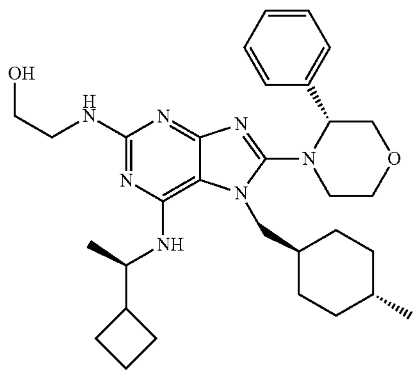 [SMILES: C[C@@H](Nc1nc(NCCO)nc2nc(N3CCOC[C@H]3c3ccccc3)n(C[C@H]3CC[C@H](C)CC3)c12)C1CCC1] | 2-((6-(((R)-1-cyclobutylethyl)amino)-7-((trans-4-methylcyclohexyl)methyl)-8-((3R)-3-phenylmorpholino)-7H-purin-2-yl)amino)ethanol | TFA | 548 | 548 |
| 13.2 | 986.8 | 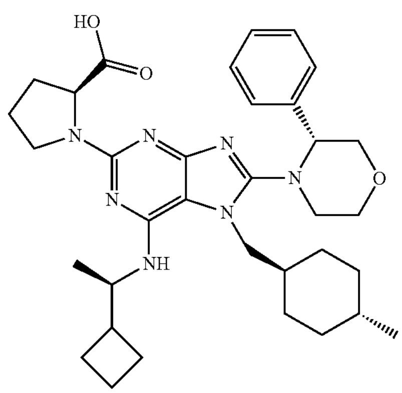 [SMILES: C[C@@H](Nc1nc(N2CCC[C@H]2C(=O)O)nc2nc(N3CCOC[C@H]3c3ccccc3)n(C[C@H]3CC[C@H](C)CC3)c12)C1CCC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)-L-proline | TFA | 602 | 602 |
| 13.3 | 46% inh. at 1000 nM | 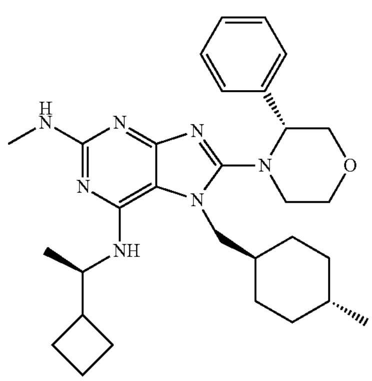 | N$^6$-[(1R)-1-cyclobutylethyl]-N$^2$-methyl-7-[(trans-4-methylcyclohexyl)methyl]-8-[(3R)-3-phenylmorpholin-4-yl]-7H-purin-2,6-diamine | TFA | 518 | 518 |

TABLE 13-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 13.4 | 96.07 | 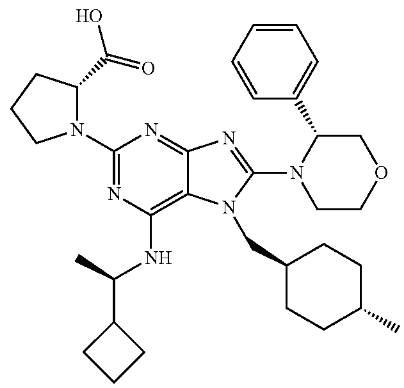 [SMILES: C[C@@H](Nc1nc(N2CCC[C@@H]2C(=O)O)nc2nc(N3CCOC[C@H]3c3ccccc3)n(C[C@H]3CC[C@H](C)CC3)c12)C1CCC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)-D-proline | TFA | 602 | 602 |
| 13.5 | 259.6 | 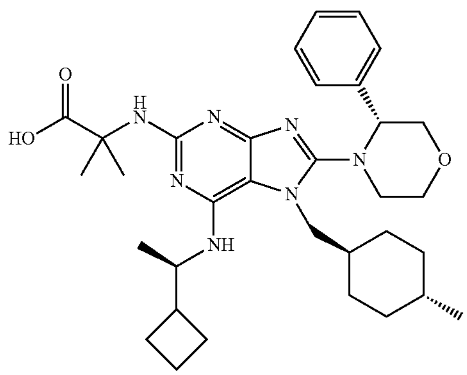 [SMILES: C[C@@H](Nc1nc(NC(C)(C)C(=O)O)nc2nc(N3CCOC[C@H]3c3ccccc3)n(C[C@H]3CC[C@H](C)CC3)c12)C1CCC1] | N-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methylalanine | TFA | 590 | 590 |
| 13.6 | 146.4 | 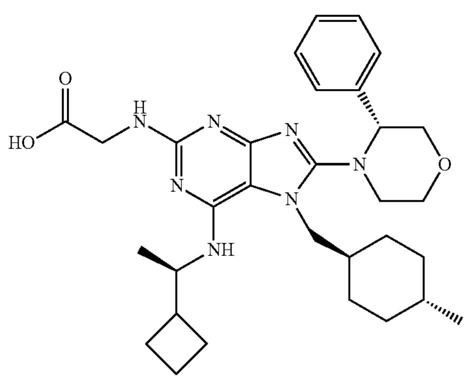 [SMILES: C[C@@H](Nc1nc(NCC(=O)O)nc2nc(N3CCOC[C@H]3c3ccccc3)n(C[C@H]3CC[C@H](C)CC3)c12)C1CCC1] | N-(6-{[(1R)-1-cyclobutylethyl]amino}-7-[(trans-4-methylcyclohexyl)methyl]-8-[(3R)-3-phenylmorpholin-4-yl]-7H-purin-2-yl)glycine | TFA | 562 | 562 |
| 13.7 | 224.5 | 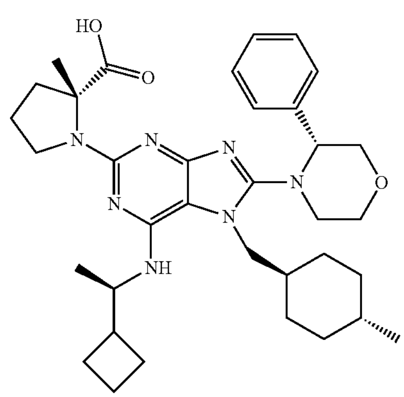 [SMILES: C[C@@H](Nc1nc(N2CCC[C@]2(C)C(=O)O)nc2nc(N3CCOC[C@H]3c3ccccc3)n(C[C@H]3CC[C@H](C)CC3)c12)C1CCC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methyl-D-proline | TFA | 616 | 616 |

TABLE 13-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 13.8 | 119.7 | 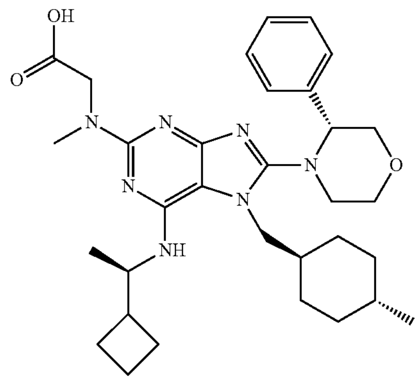 [SMILES: C[C@@H](Nc1nc(N(C)CC(=O)O)nc2nc(N3CCOC[C@H]3c3ccccc3)n(C[C@H]3CC[C@H](C)CC3)c12)C1CCC1] | N-(6-{[(1R)-1-cyclobutylethyl]amino}-7-[(trans-4-methylcyclohexyl)methyl]-8-[(3R)-3-phenylmorpholin-4-yl]-7H-purin-2-yl)-N-methylglycine | TFA | 576 | 576 |
| 13.9 | 199.3 | 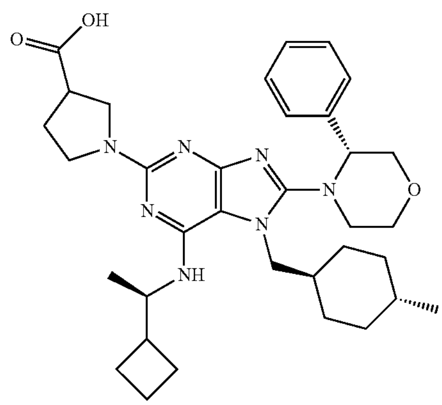 [SMILES: C[C@@H](Nc1nc(N2CCC(C(=O)O)C2)nc2nc(N3CCOC[C@H]3c3ccccc3)n(C[C@H]3CC[C@H](C)CC3)c12)C1CCC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)pyrrolidine-3-carboxylic acid | TFA | 602 | 602 |
| 13.10 | 248.4 | 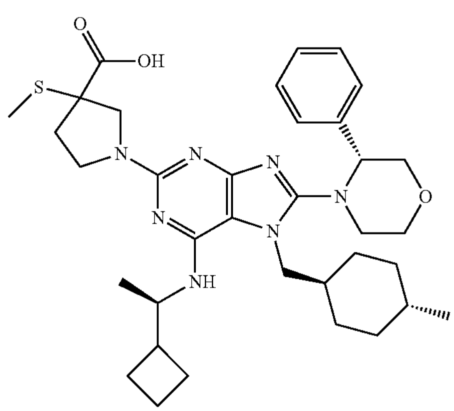 | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)-3-(methylsulfanyl)pyrrolidine-3-carboxylic acid | TFA | 648 | 648 |

TABLE 13-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 13.11 | 95.94 | 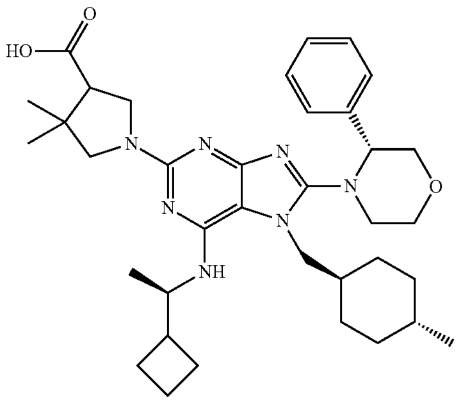 [SMILES: C[C@@H](Nc1nc(N2CC(C(=O)O)C(C)(C)C2)nc2nc(N3CCOC[C@H]3c3ccccc3)n(C[C@H]3CC[C@H](C)CC3)c12)C1CCC1] | 1-(6-{[(1R)-1-cyclobutylethyl]amino}-7-[(trans-4-methylcyclohexyl)methyl]-8-[(3R)-3-phenylmorpholin-4-yl]-7H-purin-2-yl)-4,4-dimethylpyrrolidine-3-carboxylic acid | TFA | 630 | 630 |

Preparative Example 14.1

N—((R)-1-cyclobutylethyl)-7-((trans-4-methylcyclohexyl)methyl)-2-(methylthio)-8-((R)-3-phenylmorpholino)-7H-purin-6-amine

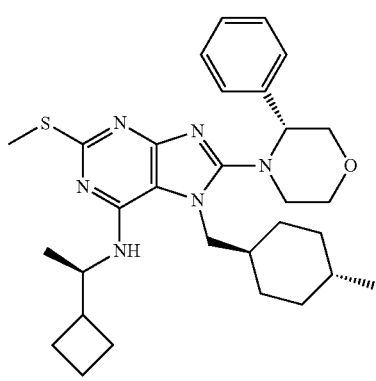

Sodium thiomethoxide (32.2 mg, 0.459 mmol) and aluminum oxide (117 mg, 1.147 mmol) were added to a stirred mixture of 2-chloro-N—((R)-1-cyclobutylethyl)-7-((trans-4-methylcyclohexyl)methyl)-8-((R)-3-phenylmorpholino)-7H-purin-6-amine (Preparative Example 12.6; 60 mg, 0.115 mmol) in 1,4-Dioxane (1 ml) and the reaction was stirred at 120° C. for 2 h. The reaction was cooled to room temperature, diluted with ethyl acetate (30 mL), washed with brine (5 mL), dried (Na$_2$SO$_4$), filtered and the solvent was evaporated under reduced pressure. The residue was purified by column chromatography on silica gel, eluting with EtOAc/isohexane (0:100% to 100%:0) to give N—((R)-1-cyclobutylethyl)-7-((trans-4-methylcyclohexyl)methyl)-2-(methylthio)-8-((R)-3-phenylmorpholino)-7H-purin-6-amine. MS ESI calc'd. for C$_{30}$H$_{42}$N$_6$OS [M+H]$^+$ 535. found 535.

Example 14.1

N—((R)-1-cyclobutylethyl)-7-((trans-4-methylcyclohexyl)methyl)-2-(methylsulfonyl)-8-((R)-3-phenylmorpholino)-7H-purin-6-amine

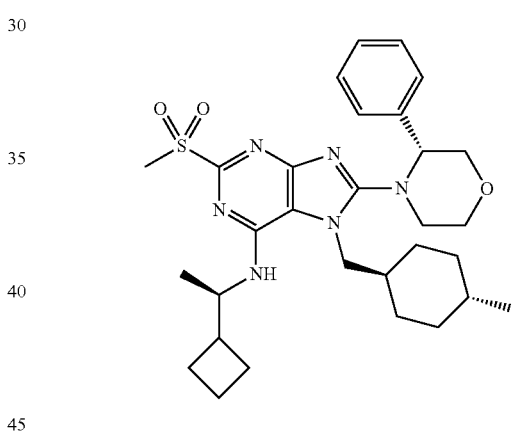

N—((R)-1-cyclobutylethyl)-7-((trans-4-methylcyclohexyl)methyl)-2-(methylthio)-8-((R)-3-phenylmorpholino)-7H-purin-6-amine (48 mg, 0.074 mmol) was dissolved in CH$_2$Cl$_2$ (1.6 ml) and mCPBA (51.1 mg, 0.296 mmol) was added at room temperature. The mixture was stirred at room temperature for 2 h. The reaction was concentrated and the residue was purified by preparative reverse phase HPLC (C-18), eluting with acetonitrile/water+0.1% TFA, to give N—((R)-1-cyclobutylethyl)-7-((trans-4-methylcyclohexyl)methyl)-2-(methylsulfonyl)-8-((R)-3-phenylmorpholino)-7H-purin-6-amine as TFA salt. MS ESI calc'd. for C$_{30}$H$_{42}$N$_6$O$_3$S [M+H]$^+$ 567. found 567. $^1$H NMR (500 MHz, DMSO-d$_6$): 0.77 (3 H, d, J=6.42 Hz), 1.07 (3H, d, J=6.43 Hz), 1.24-0.93 (7H, m), 1.45-1.99 (10H, m), 3.04 (1H, br s), 3.24 (3H, s), 3.40 (1H, d, J=12.54 Hz), 3.90-3.85 (6H, m), 4.29-4.23 (1H, m), 4.42-4.36 (1H, m), 4.63 (1H, d, J=6.35 Hz), 6.60 (1H, d, J=8.32 Hz), 7.23-7.21 (3H, m), 7.40 (2H, d, J=7.55 Hz).

Example 14.2 and 14.3

N—((R)-1-cyclobutylethyl)-7-((trans-4-methylcyclohexyl)methyl)-2-(methylsulfinyl)-8-((R)-3-phenylmorpholino)-7H-purin-6-amine (two diastereoisomers)

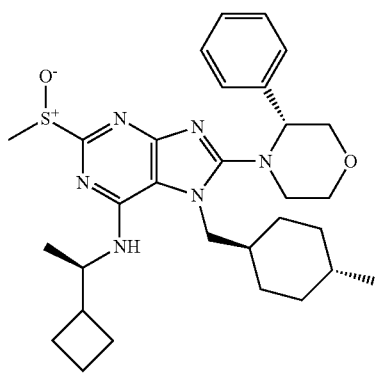

N—((R)-1-cyclobutylethyl)-7-((trans-4-methylcyclohexyl)methyl)-2-(methylthio)-8-((R)-3-phenylmorpholino)-7H-purin-6-amine (10 mg, 0.015 mmol) was dissolved in $CH_2Cl_2$ (0.4 ml) and mCPBA (4.26 mg, 0.025 mmol) was added at room temperature. The mixture was stirred at room temperature for 2 h. The reaction was concentrated and the residue was purified by preparative reverse phase HPLC (C-18), eluting with acetonitrile/water+0.1% TFA, to give N—((R)-1-cyclobutylethyl)-7-((trans-4-methylcyclohexyl)methyl)-2-(methylsulfinyl)-8-((R)-3-phenylmorpholino)-7H-purin-6-amine as a TFA salt. Two stereoisomers were separated by preparative HPLC. Diastereoisomer 1 (Example 14.2): $^1$H NMR (500 MHz, DMSO-$d_6$): 0.79 (3H, d, J=6.37 Hz), 1.07 (3H, d, J=6.45 Hz), 1.25-0.89 (5H, m), 1.81-1.69 (12H, br m), 2.74 (3H, s), 3.01 (1H, br s), 3.38 (1H, m), 3.90-3.81 (5H, m), 4.38-4.29 (2H, m), 4.60 (1H, s), 6.43 (1H, d, J=8.39 Hz), 7.22-7.20 (3H, m), 7.40 (2H, d, J=7.51 Hz); Diastereoisomer 2 (Example 14.3): $^1$H NMR (500 MHz, DMSO-$d_6$): 0.77 (3H, d, J=6.51 Hz), 1.05 (3H, d, J=6.31 Hz), 1.25-0.75 (5H, m), 2.00-1.45 (12H, m), 2.74 (3H, s), 3.01 (1H, m), 3.37 (1H, m), 3.93-3.78 (5H, m), 4.36-4.26 (2H, m), 4.60 (1H, s), 6.43 (1H, d, J=8.21 Hz), 7.23-7.17 (3H, m), 7.40 (2H, d, J=7.31 Hz). MS ESI calc'd. for $C_{30}H_{42}N_6O_2S$ $[M+H]^+$ 551. found 551.

The following compounds in Table 14 (other than Example 14.1 to 14.3) were prepared using procedures which were analogous to those described above.

TABLE 14

| Ex. | FRET IC$_{50}$ (nM) | Structure | Chemical Name | Salt Form | $[M + H]^+$ Calc'd | $[M + H]^+$ Obsv'd |
|---|---|---|---|---|---|---|
| 14.1 | 23.47 | 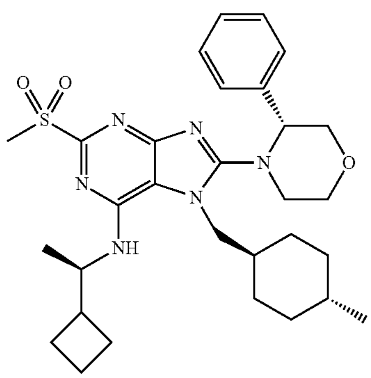 | N-((R)-1-cyclobutylethyl)-7-((trans-4-methylcyclohexyl)methyl)-2-(methylsulfonyl)-8-((R)-3-phenylmorpholino)-7H-purin-6-amine | TFA | 567 | 567 |
| 14.2 | 10.5 | 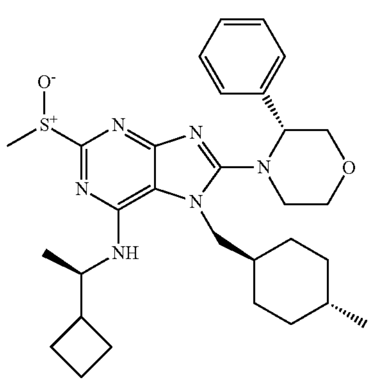 | N-((R)-1-cyclobutylethyl)-7-((trans-4-methylcyclohexyl)methyl)-2-(methylsulfinyl)-8-((R)-3-phenylmorpholino)-7H-purin-6-amine (diastereoisomer 1) | TFA | 551 | 551 |

TABLE 14-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 14.3 | 57.38 | 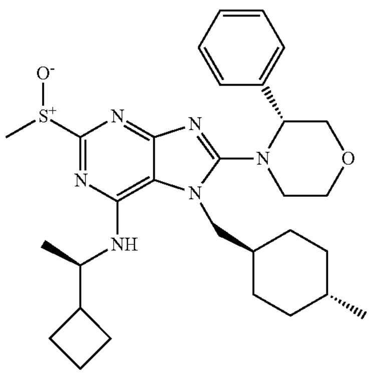 | N-((R)-1-cyclobutylethyl)-7-((trans-4-methylcyclohexyl)methyl)-2-(methylsulfinyl)-8-((R)-3-phenylmorpholino)-7H-purin-6-amine (diastereoisomer 2) | TFA | 551 | 551 |
| 14.4 | 72.44 | 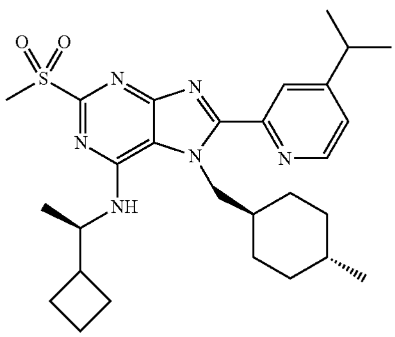 [SMILES: CC(C)c1ccnc(-c2nc3nc(S(C)(=O)=O)nc(N[C@H](C)C4CCC4)c3n2C[C@H]2CC[C@H](C)CC2)c1] | N-[(1R)-1-cyclobutylethyl]-7-[(trans-4-methylcyclohexyl)methyl]-8-[4-(1-methylethyl)pyridin-2-yl]-2-(methylsulfonyl)-7H-purin-6-amine | TFA | 525 | 525 |
| 14.5 | 20.09 | 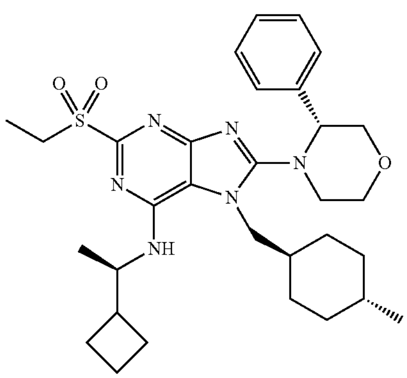 [SMILES: CCS(=O)(=O)c1nc(N[C@H](C)C2CCC2)c2c(n1)nc(N1CCOC[C@H]1c1ccccc1)n2C[C@H]1CC[C@H](C)CC1] | N-[(1R)-1-cyclobutylethyl]-2-(ethylsulfonyl)-7-[(trans-4-methylcyclohexyl)methyl]-8-[(3R)-3-phenylmorpholin-4-yl]-7H-purin-6-amine | TFA | 581 | 581 |
| 14.6 | 21.07 | 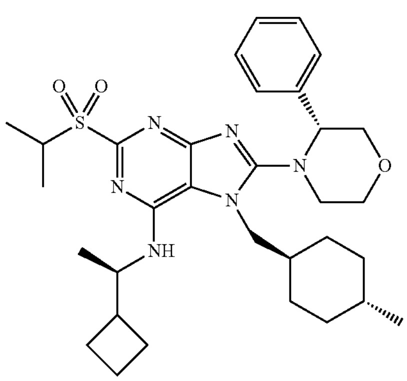 | N-[(1R)-1-cyclobutylethyl]-7-[(trans-4-methylcyclohexyl)methyl]-2-[(1-methylethyl)sulfonyl]-8-[(3R)-3-phenylmorpholin-4-yl]-7H-purin-6-amine | TFA | 595 | 595 |

TABLE 14-continued

| Ex. | FRET IC$_{50}$ (nM) | Structure | Chemical Name | Salt Form | [M + H]$^+$ Calc'd | [M + H]$^+$ Obsv'd |
| --- | --- | --- | --- | --- | --- | --- |
| 14.7 | 12.19 | 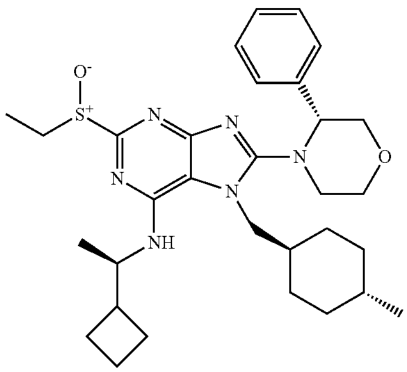 [SMILES: CC[S+]([O-])c1nc(N[C@H](C)C2CCC2)c2c(n1)nc(N1CCOC[C@H]1c1ccccc1)n2C[C@H]1CC[C@H](C)CC1] | N-[(1R)-1-cyclobutylethyl]-2-(ethylsulfinyl)-7-[(trans-4-methylcyclohexyl)methyl]-8-[(3R)-3-phenylmorpholin-4-yl]-7H-purin-6-amine | TFA | 565 | 565 |
| 14.8 | 15.46 | 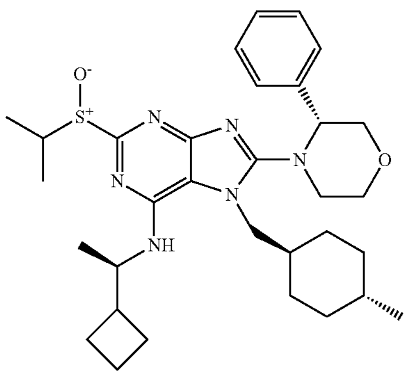 [SMILES: CC(C)[S+]([O-])c1nc(N[C@H](C)C2CCC2)c2c(n1)nc(N1CCOC[C@H]1c1ccccc1)n2C[C@H]1CC[C@H](C)CC1] | N-[(1R)-1-cyclobutylethyl]-7-[(trans-4-methylcyclohexyl)methyl]-2-[(1-methylethyl)sulfinyl]-8-[(3R)-3-phenylmorpholin-4-yl]-7H-purin-6-amine | TFA | 579 | 579 |
| 14.9 | 46% inh. at 1000 nM | 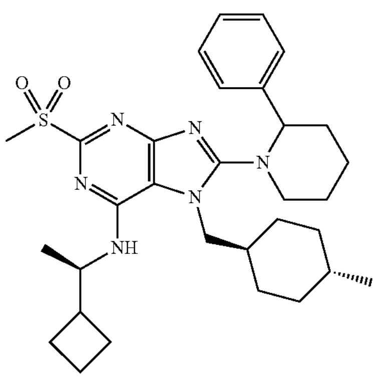 | N-[(1R)-1-cyclobutylethyl]-7-[(trans-4-methylcyclohexyl)methyl]-2-(methylsulfonyl)-8-(2-phenylpiperidin-1-yl)-7H-purin-6-amine (diastereoisomer 1) | | 565 | 565 |
| 14.10 | 109.4 | 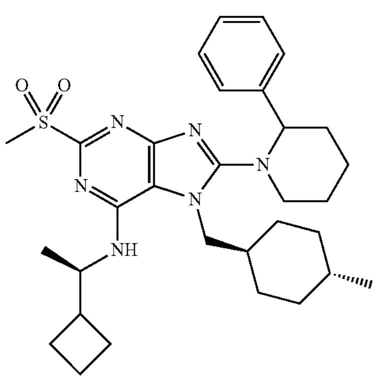 | N-[(1R)-1-cyclobutylethyl]-7-[(trans-4-methylcyclohexyl)methyl]-2-(methylsulfonyl)-8-(2-phenylpiperidin-1-yl)-7H-purin-6-amine (diastereoisomer 2) | | 565 | 565 |

TABLE 14-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 14.11 | 417 | 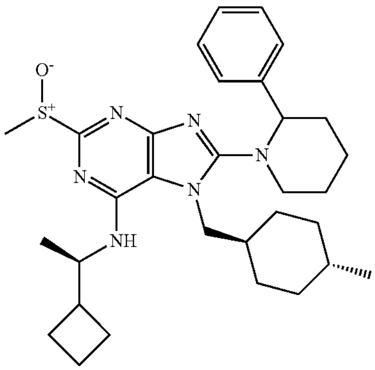 | N-[(1R)-1-cyclobutylethyl]-7-[(trans-4-methylcyclohexyl)methyl]-2-(methylsulfinyl)-8-(2-phenylpiperidin-1-yl)-7H-purin-6-amine (diastereoisomer 1) | | 549 | 549 |
| 14.12 | 25.89 | 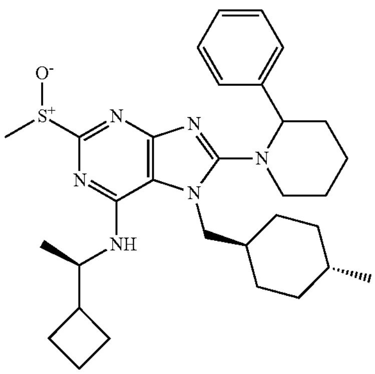 | N-[(1R)-1-cyclobutylethyl]-7-[(trans-4-methylcyclohexyl)methyl]-2-(methylsulfinyl)-8-(2-phenylpiperidin-1-yl)-7H-purin-6-amine (diastereoisomer 2) | | 549 | 549 |
| 14.13 | 645.5 | 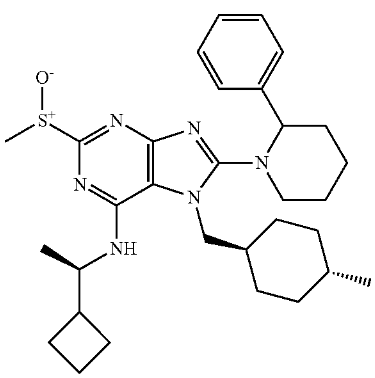 | N-[(1R)-1-cyclobutylethyl]-7-[(trans-4-methylcyclohexyl)methyl]-2-(methylsulfinyl)-8-(2-phenylpiperidin-1-yl)-7H-purin-6-amine (diastereoisomer 3) | | 549 | 549 |
| 14.14 | 185.5 | 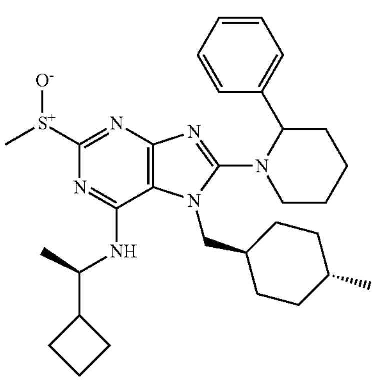 | N-[(1R)-1-cyclobutylethyl]-7-[(trans-4-methylcyclohexyl)methyl]-2-(methylsulfinyl)-8-(2-phenylpiperidin-1-yl)-7H-purin-6-amine (diastereoisomer 4) | | 549 | 549 |

TABLE 14-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 14.15 | 220.5 | 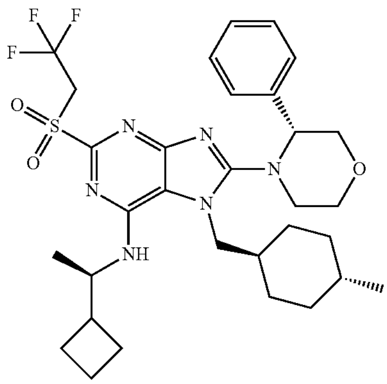 [SMILES: C[C@@H](Nc1nc(S(=O)(=O)CC(F)(F)F)nc2nc(N3CCOC[C@H]3c3ccccc3)n(C[C@H]3CC[C@H](C)CC3)c12)C1CCC1] | N-[(1R)-1-cyclobutylethyl]-7-[(trans-4-methylcyclohexyl)methyl]-8-[(3R)-3-phenylmorpholin-4-yl]-2-[(2,2,2-trifluoroethyl)sulfonyl]-7H-purin-6-amine | TFA | 635 | 635 |
| 14.16 | 17.43 | 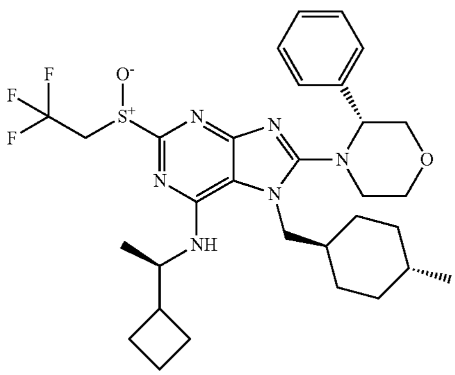 [SMILES: C[C@@H](Nc1nc([S+]([O-])CC(F)(F)F)nc2nc(N3CCOC[C@H]3c3ccccc3)n(C[C@H]3CC[C@H](C)CC3)c12)C1CCC1] | (6-{[(1R)-1-cyclobutylethyl]amino}-7-[(trans-4-methylcyclohexyl)methyl]-8-[(3R)-3-phenylmorpholin-4-yl]-7H-purin-2-yl)(2,2,2-trifluoroethyl)sulfonium olate (diastereoisomer 1) | TFA | 619 | 619 |
| 14.17 | 320.8 | 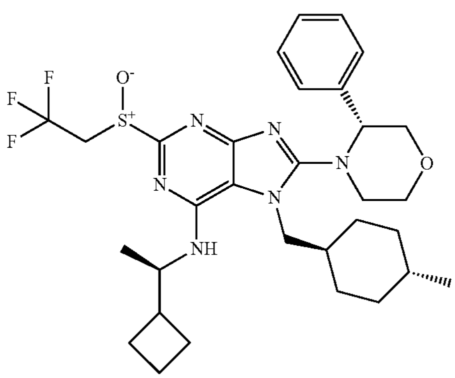 [SMILES: C[C@@H](Nc1nc([S+]([O-])CC(F)(F)F)nc2nc(N3CCOC[C@H]3c3ccccc3)n(C[C@H]3CC[C@H](C)CC3)c12)C1CCC1] | (6-{[(1R)-1-cyclobutylethyl]amino}-7-[(trans-4-methylcyclohexyl)methyl]-8-[(3R)-3-phenylmorpholin-4-yl]-7H-purin-2-yl)(2,2,2-trifluoroethyl)sulfonium olate (diastereoisomer 2) | TFA | 619 | 619 |
| 14.18 | 6.937 | 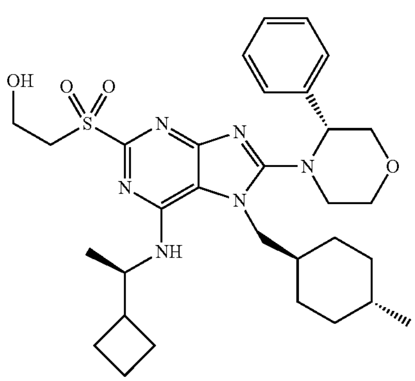 [SMILES: C[C@@H](Nc1nc(S(=O)(=O)CCO)nc2nc(N3CCOC[C@H]3c3ccccc3)n(C[C@H]3CC[C@H](C)CC3)c12)C1CCC1] | 2-[(6-{[(1R)-1-cyclobutylethyl]amino}-7-[(trans-4-methylcyclohexyl)methyl]-8-[(3R)-3-phenylmorpholin-4-yl]-7H-purin-2-yl)sulfonyl]ethanol | TFA | 597 | 597 |

Example 15.1

6-(((R)-1-cyclobutylethyl)amino)-8-(4-isopropylpyridin-2-yl)-7-((trans-4-methylcyclohexyl)methyl)-7H-purine-2-carboxylic acid

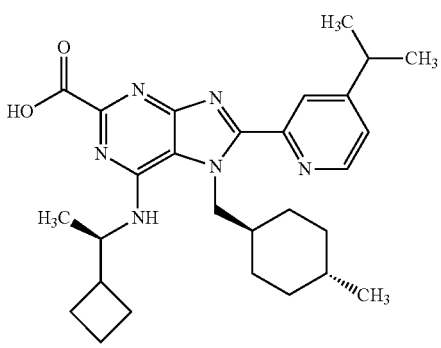 [SMILES: CC(C)c1ccnc(-c2nc3nc(C(=O)O)nc(N[C@H](C)C4CCC4)c3n2C[C@H]2CC[C@H](C)CC2)c1]

Using a procedure analogous to that described in Example 1.1, and starting with 6-(((R)-1-cyclobutylethyl)amino)-7-((trans-4-methylcyclohexyl)methyl)-7H-purine-2-carbonitrile (Preparative Example 11.6), 6-(((R)-1-cyclobutylethyl)amino)-8-(4-isopropylpyridin-2-yl)-7-((trans-4-methylcyclohexyl)methyl)-7H-purine-2-carboxylic acid was prepared. $^1$H NMR (300 MHz, CD$_3$OD) δ8.64 (d, J=5.1 Hz, 1H), 8.15 (s, 1H), 7.45 (d, J=5.1 Hz, 1H), 5.32-5.39 (m, 1H), 5.15-5.22 (m, 1H), 3.01-3.13 (m, 1H), 2.51-2.67 (m, 1H), 2.16-2.21 (m, 1H), 1.85-2.08 (m, 7H), 1.43-1.68 (m, 2H), 1.38-1.25 (m, 8H), 1.20-1.35 (m, 6H), 0.85-0.94 (m, 2H), 0.79 (d, J=6.60 Hz, 3H). MS (ES)=491 (M+1)$^+$.

Example 15.2

6-(((R)-1-cyclobutylethyl)(methyl)amino)-8-(4-isopropylpyridin-2-yl)-7-((trans-4-methylcyclohexyl)methyl)-7H-purine-2-carboxylic acid

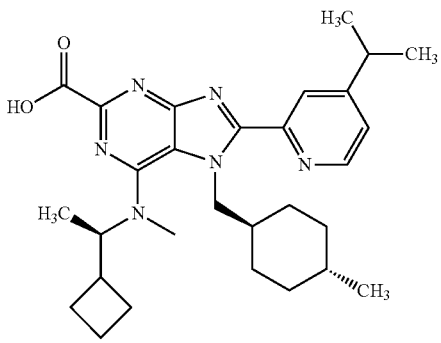 [SMILES: CC(C)c1ccnc(-c2nc3nc(C(=O)O)nc(N(C)[C@H](C)C4CCC4)c3n2C[C@H]2CC[C@H](C)CC2)c1]

Cs$_2$CO$_3$ (51.6 mg, 0.15 mmol) was added to a solution of 6-(((R)-1-cyclobutylethyl)amino)-8-(4-isopropylpyridin-2-yl)-7-((trans-4-methylcyclohexyl)methyl)-7H-purine-2-carbonitrile (50 mg, 0.12 mmol) in anhydrous DMF (2.0 mL) at 0° C. Methyl iodide (20 µL, 0.31 mmol) was added drop-wise. The reaction mixture was then stirred at room temperature for 2 hours. The reaction mixture was quenched with water and then extracted with EtOAc (3×10 mL). The combined organic layers were washed with water and brine, dried over anhydrous Na$_2$SO$_4$, filtered and concentrated in vacuo. Purification of the residue on a Redisep 4 g silica gel column (0 to 50% EtOAc/hexanes) afforded 6-(((R)-1-cyclobutylethyl)(methyl)amino)-8-(4-isopropylpyridin-2-yl)-7-((trans-4-methylcyclohexyl)methyl)-7H-purine-2-carbonitrile as a light yellow solid. This compound was taken up in ethanol (1.0 mL). Sodium hydroxide (18.0 mg, 0.45 mmol) was added and then the reaction was heated to reflux for 2 hours. The reaction mixture was cooled to room temperature, acidified with aq. 1N HCl, and extracted with EtOAc (3×10 mL). The combined organic layers were washed with water and brine, dried over anhydrous Na$_2$SO$_4$, filtered and concentrated in vacuo. Purification of the residue on a Redisep 4 g silica gel column (0 to 10% CH$_2$Cl$_2$/methanol) afforded 6-(((R)-1-cyclobutylethyl)(methyl)amino)-8-(4-isopropylpyridin-2-yl)-7-((trans-4-methylcyclohexyl)methyl)-7H-purine-2-carboxylic acid as a white solid. $^1$H NMR (400 MHz, CD$_3$OD): δ8.68 (s, 1H), 8.21 (s, 1H), 7.52 (s, 1H), 4.95-5.20 (m, 2H), 4.52-4.56 (m, 1H), 4.42-4.39 (m, 1H), 3.16 (s, 3H), 3.15-3.07 (m, 1H), 2.74-2.81 (m, 1H), 2.09-2.15 (m, 1H), 2.15-2.11 (m, 1H), 1.77-1.92 (m, 4H), 1.53-1.48 (m, 4H), 1.37 (d, J=4.0 Hz, 3H), 1.35 (d, J=4.0 Hz, 3H), 1.03-1.12 (m, 4H), 0.91-0.89 (m, 1H), 0.65 (d, J=12.0 Hz, 3H), 0.69-0.55 (m, 3H). MS (ES)=505 (M+1)$^+$.

Example 15.3

6-(((R)-1-cyclobutylethyl)amino)-8-(4-isopropyl-6-oxo-1,6-dihydropyridin-2-yl)-7-((trans-4-methylcyclohexyl)methyl)-7H-purine-2-carboxylic acid

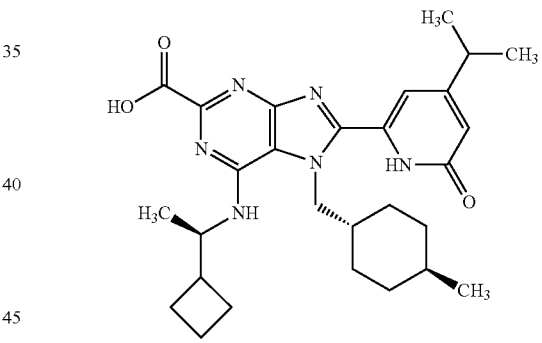

Step 1: To a degassed solution of 4-bromo-2-fluoropyridine (500 mg, 2.81 mmol) in 1,4-dioxane and water (5.0 mL, 3:1) was added 4,4,5,5-tetramethyl-2-(prop-1-en-2-yl)-1,3,2-dioxaborolane (490 mg, 5.74 mmol), tetrakis(triphenylphosphine)palladium(0) (660 mg, 0.57 mmol) and K$_2$CO$_3$ (1.18 g, 8.62 mmol). The resulting mixture was stirred at 100° C. for overnight. The reaction mixture was then poured into water (50 mL) and extracted with 10% CH$_2$Cl$_2$ inhexanes (3×10 mL). The organic layer was concentrated to dryness to afford crude 2-fluoro-4-(prop-1-en-2-yl)pyridine, that was used without further purification. To a solution of 2-fluoro-4-(prop-1-en-2-yl)pyridine (crude) in MeOH (2 ml) was added 10% Pd/C (80 mg) and the reaction was stirred under 1 atm of H$_2$ at room temperature for 12 hours. The reaction mixture was filtered through diatomaceous earth and water (6 mL) was added to the filtrate, which was extracted with 10% CH$_2$Cl$_2$ in hexanes (3×10 mL). The organic layer was concentrated to dryness to afford crude 2-fluoro-4-isopropylpyridine as colorless oil. MS (ES)=140 (M+1)$^+$.

Step 2: To a solution of 2-fluoro-4-isopropylpyridine (1.00 g, 7.19 mmol) in dichloromethane (15 mL) was added urea hydrogen peroxide (1.40 g, 15.1 mmol) and the reaction mixture was cooled to 0° C. Trifluoroacetic anhydride (3.17 g, 15.1 mmol) was added dropwise over 10 minutes. The resulting mixture was stirred at room temperature for 4 hours. The reaction mixture was then diluted with $CH_2Cl_2$ (50 mL), and washed with aq. $Na_2S_2O_3$ (2×40 mL), and the organic layer was concentrated to dryness to afford crude 2-fluoro-4-isopropylpyridine 1-oxide as colorless oil that was used without further purification. A solution of 2-fluoro-4-isopropylpyridine 1-oxide (0.21 g, 1.35 mmol) in $POCl_3$ (3 mL) was stirred at 90° C. for 3 hours. After this time, the reaction was carefully poured into stirring ice water (5 mL) and the pH was adjusted to ~8 using $NH_4OH$. The resulting mixture was extracted with $CH_2Cl_2$ (2×100 mL), the combined organic layers were dried over anhydrous $Na_2SO_4$ and concentrated under reduced pressure, and the crude product was loaded onto a RediSep 120 g silica gel column. Purification with 0 to 100% EtOAc/hexanes afforded 2-chloro-6-fluoro-4-isopropylpyridine as colorless oil. $^1$H NMR (300 MHz, $CDCl_3$) δ 7.08 (s, 1H), 6.70 (s, 1H), 2.93 (m, 1H), 1.26 (d, J=6.9 Hz, 6H). MS (ES)=174 (M+1)$^+$.

Step 3: Using a procedure analogous to that in Example 1.1 and starting with Preparative Example 11.6, 6-(((R)-1-cyclobutylethyl)amino)-7-((trans-4-methylcyclohexyl)methyl)-7H-purine-2-carbonitrile and 2-chloro-6-fluoro-4-isopropylpyridine, 6-(((R)-1-cyclobutylethyl)amino)-8-(4-isopropyl-6-oxo-1,6-dihydropyridin-2-yl)-7-((trans-4-methylcyclohexyl)methyl)-7H-purine-2-carboxylic acid was prepared. $^1$H NMR (300 MHz, $CD_3OD$) δ 7.15 (s, 1H), 6.62 (s, 1H), 4.61-4.85 (m, 2H), 2.90-2.96 (m, 2H), 2.57-2.59 (m, 1H), 1.90-2.12 (m, 6H), 1.49-1.65 (m, 4H), 1.29 (d, J=6.8 Hz, 6H), 1.10-1.26 (m, 5H) 0.85-1.02 (m, 1H), 0.79 (d, J=6.4 Hz, 3H), 0.65-0.76 (m, 3H). MS (ES)=507 (M+1)$^+$.

Example 15.4

6-(((R)-1-cyclobutylethyl)amino)-8-(6-ethoxy-4-isopropylpyridin-2-yl)-7-((trans-4-methyl cyclohexyl)methyl)-7H-purine-2-carboxylic acid

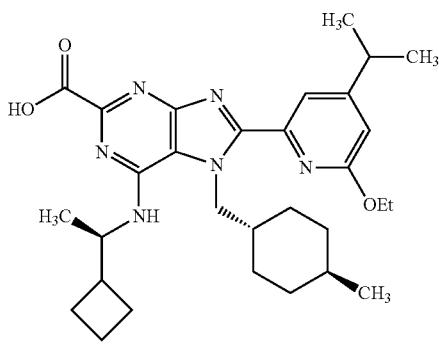 [SMILES: CCOc1cc(C(C)C)cc(-c2nc3nc(C(=O)O)nc(N[C@H](C)C4CCC4)c3n2C[C@H]2CC[C@H](C)CC2)n1]

Using a procedure analogous to that in Example 1.1, and starting with Preparative Example 11.6, 6-(((R)-1-cyclobutylethyl)amino)-7-((trans-4-methylcyclohexyl)methyl)-7H-purine-2-carbonitrile and 2-chloro-6-fluoro-4-isopropylpyridine, 6-(((R)-1-cyclobutylethyl)amino)-8-(6-ethoxy-4-isopropylpyridin-2-yl)-7-((trans-4-methyl cyclohexyl)methyl)-7H-purine-2-carboxylic acid was prepared. $^1$H NMR (300 MHz, $CD_3OD$) δ 7.79 (d, J=0.8 Hz, 1H), 6.79 (d, J=0.8 Hz, 1H), 5.25-5.35 (m, 1H), 4.78-4.85 (m, 2H), 4.42 (q, J=6.9 Hz, 2H), 2.95-3.02 (m, 1H), 2.53-2.60 (m, 1H), 2.04-2.11 (m, 2H), 1.87-1.97 (m, 4H), 1.47-1.68 (m, 4H), 1.42 (t, J=6.8 Hz, 3H), 1.31 (d, J=7.2 Hz, 6H), 1.15-1.28 (m, 5H), 0.91-1.04 (m, 1H), 0.75-0.88 (m, 5H), 0.65-0.76 (m, 1H). MS (ES)=535 (M+1)$^+$.

Example 15.5

3-(6-(((R)-1-cyclobutylethyl)amino)-8-(6-fluoro-4-isopropylpyridin-2-yl)-7-((trans-4-methylcyclohexyl)methyl)-7H-purin-2-yl)-1,2,4-oxadiazol-5 (2H)-one

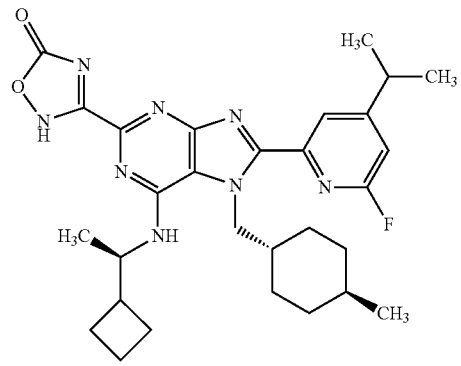 [SMILES: CC(C)c1cc(F)nc(-c2nc3nc(-c4nc(=O)o[nH]4)nc(N[C@H](C)C4CCC4)c3n2C[C@H]2CC[C@H](C)CC2)c1]

Using a procedure analogous to that described in the synthesis of Example 1.1 and starting with Preparative Example 11.6, 6-(((R)-1-cyclobutylethyl)amino)-7-((trans-4-methylcyclohexyl)methyl)-7H-purine-2-carbonitrile and 2-chloro-6-fluoro-4-isopropylpyridine, followed by a procedure similar to that described in Example 11.3, 3-(6-(((R)-1-cyclobutylethyl)amino)-8-(6-fluoro-4-isopropylpyridin-2-yl)-7-((trans-4-methyl cyclohexyl)methyl)-7H-purin-2-yl)-1,2,4-oxadiazol-5(2H)-one was prepared. $^1$H NMR (400 MHz, $CD_3OD$) δ 8.11 (br s, 1H), 7.13 (br s, 1H), 5.10-5.25 (m, 1H), 4.71-4.85 (m, 2H), 3.01-3.13 (m, 1H), 2.51-2.62 (m, 1H), 2.00-2.18 (m, 3H), 1.82-2.00 (m, 2H), 1.78-1.81 (m, 1H), 1.51-1.69 (m, 5H), 1.11-1.42 (m, 9H), 0.95-1.10 (m, 1H), 0.61-0.95 (m, 7H). MS (ES)=549 (M+1)$^+$.

Example 15.6

6-(((R)-1-Cyclobutylethyl)amino)-8-(3-fluoro-4-isopropylpyridin-2-yl)-7-((trans-4-methylcyclohexyl)methyl)-7H-purine-2-carboxylic acid

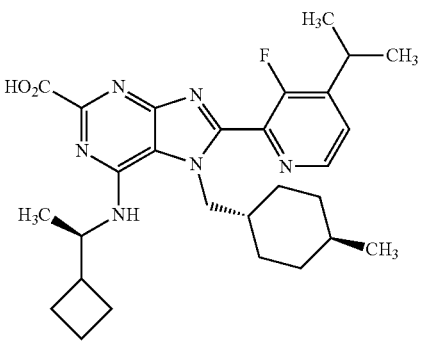 [SMILES: CC(C)c1ccnc(-c2nc3nc(C(=O)O)nc(N[C@H](C)C4CCC4)c3n2C[C@H]2CC[C@H](C)CC2)c1F]

Step 1: A sealed tube was charged with 2-chloro-3-fluoro-4-iodopyridine (500 mg, 1.94 mmol) and K$_2$CO$_3$ (616 mg, 4.47 mmol) in degassed THF and H$_2$O (10 mL: 2 mL) under argon. PdCl$_2$(PPh$_3$)$_2$ (27 mg, 0.038 mmol) was added, followed by the addition of 4,4,5,5-tetramethyl-2-(prop-1-en-2-yl)-1,3,2-dioxaborolane (365 µL, 1.94 mmol). The reaction mixture was heated at 95° C. for 4 hours. The reaction was cooled to room temperature and extracted with EtOAc (3×5 mL). The combined organic layers were washed with water and brine and dried over anhydrous Na$_2$SO$_4$. The solvent was evaporated under vacuum. Purification of the residue on a RediSep 24 g silica gel column with 0 to 2% EtOAc/hexanes afforded 2-chloro-3-fluoro-4-(prop-1-en-2-yl)pyridine as a colorless oil. $^1$H NMR (300 MHz, CDCl$_3$) δ 8.14 (d, J=5.0 Hz, 1H), 7.18 (t, J=5.0 Hz, 1H), 5.45 (br s, 2H), 2.16 (d, J=0.9 Hz, 3H). MS (APCI)=172 (M+1)$^+$.

Step 2: Using a procedure analogous to that in Example 1.1, and starting with Preparative Example 11.6, 6-(((R)-1-cyclobutylethyl)amino)-7-((trans-4-methylcyclohexyl)methyl)-7H-purine-2-carbonitrile, and 2-chloro-3-fluoro-4-isopropylpyridine (prepared from 2-chloro-3-fluoro-4-(prop-1-en-2-yl)pyridine using standard methods), 6-(((R)-1-cyclobutylethyl)amino)-8-(3-fluoro-4-isopropylpyridin-2-yl)-7-((trans-4-methylcyclohexyl)methyl)-7H-purine-2-carboxylic acid was prepared. $^1$H NMR (400 MHz, CD$_3$OD) δ 8.54 (d, J=5.2 Hz, 1H), 7.64 (d, J=5.2 Hz, 1H), 4.80 (m, 1H), 4.56 (dd, J=15.2, 6.0 Hz, 1H), 4.33 (dd, J=15.2, 8.6 Hz, 1H), 3.39 (m, 1H), 2.59 (m, 1H), 1.91-2.13 (m, 6H), 1.51-1.65 (m, 4H), 1.37 (d, J=6.6 Hz, 3H), 1.35 (d, J=6.6 Hz, 3H), 1.23 (d, J=6.4 Hz, 3H), 1.10-1.23 (m, 2H), 0.79 (d, J=6.4 Hz, 3H), 0.58-0.73 (m, 4H). MS (ES)=509 (M+1)$^+$.

Example 15.7

3-(6-((R)-1-cyclobutylethylamino)-8-(3-fluoro-4-isopropylpyridin-2-yl)-7-((trans-4-methylcyclohexyl)methyl)-7H-purin-2-yl)-1,2,4-oxadiazol-5 (4H)-one

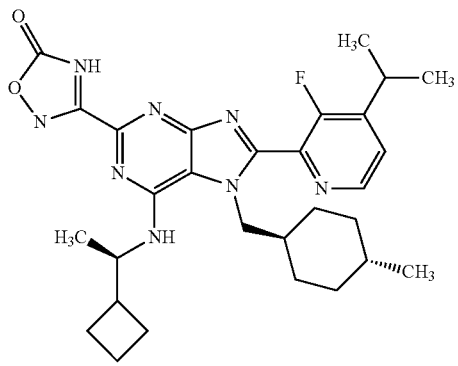 [SMILES: CC(C)c1ccnc(-c2nc3nc(-c4nc(=O)o[nH]4)nc(N[C@H](C)C4CCC4)c3n2C[C@H]2CC[C@H](C)CC2)c1F]

Following a procedure analogous to that described in the synthesis of Example 1.1, and starting with Preparative Example 11.6, 6-(((R)-1-cyclobutylethyl)amino)-7-((trans-4-methylcyclohexyl)methyl)-7H-purine-2-carbonitrile and 2-chloro-3-fluoro-4-isopropylpyridine, followed by a procedure similar to that described in Example 11.3, 3-(6-((R)-1-cyclobutylethylamino)-8-(3-fluoro-4-isopropylpyridin-2-yl)-7-((trans-4-methylcyclohexyl)methyl)-7H-purin-2-yl)-1,2,4-oxadiazol-5(4H)-one was prepared. $^1$H NMR (400 MHz, CD$_3$OD) δ 8.52 (d, J=5.0 Hz, 1H), 7.62 (t, J=5.0 Hz, 1H), 4.82 (m, 1H), 4.52 (m, 1H), 4.23 (m, 1H), 2.53 (m, 1H), 1.53-2.00 (m, 13H), 1.36 (d, J=7.2, 3H), 1.35 (d, J=7.2 Hz, 3H), 1.21 (d, J=6.4 Hz, 3H), 0.78-0.82 (m, 5H), 0.58-0.69 (m, 2H). MS (ES)=549 (M+1)$^+$.

Example 15.8

6-(((R)-1-cyclobutylethyl)amino)-8-(5-fluoro-4-isopropylpyridin-2-yl)-7-((trans-4-methylcyclohexyl)methyl)-7H-purine-2-carboxylic acid

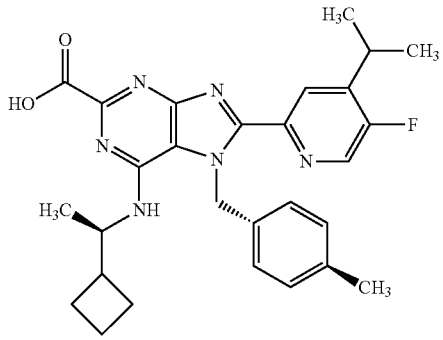

Step 1: To the solution of n-BuLi (3.75 mL, 7.5 mmol, 2 M in hexanes) in THF (25 mL) was added 2-chloro-5-fluoropyridine (3.75 mL, 7.5 mmol, 2 M in hexanes) dropwise at −78° C. The reaction mixture was stirred at −78° C. for 15 minutes. Acetone (1.0 g, 2.5 mmol) was then added dropwise over 10 minutes. The reaction mixture was stirred at −78° C. for 30 minutes and then quenched with sat. aqueous NH$_4$Cl solution. The layers were separated and the aqueous layer was extracted with EtOAc (3×20 mL). The combined organic layers were washed with brine, dried over anhydrous Na$_2$SO$_4$, filtered and concentrated in vacuo. Purification of the residue on a RediSep 24 g silica gel column (0 to 50% EtOAc/hexanes) afforded 2-(2-chloro-5-fluoropyridin-4-yl)propan-2-ol. $^1$H NMR (300 MHz, CDCl$_3$) δ 8.12 (d, J=2.7 Hz, 1H), 7.65 (d, J=5.7 Hz, 1H), 2.91 (br s, 1H), 1.65 (s, 3H), 1.64 (s, 3H).

Step 2: Following a procedure analogous to that described in the synthesis of Example 1.1, and starting with Preparative Example 11.6, 6-(((R)-1-cyclobutylethyl)amino)-7-((trans-4-methylcyclohexyl)methyl)-7H-purine-2-carbonitrile and 2-(2-chloro-5-fluoropyridin-4-yl)propan-2-ol, 6-(((R)-1-cyclobutylethyl)amino)-8-(5-fluoro-4-(2-hydroxypropan-2-yl)pyridin-2-yl)-7-((trans-4-methylcyclohexyl)methyl)-7H-purine-2-carbonitrile was prepared. This compound, 6-(((R)-1-cyclobutylethyl)amino)-8-(5-fluoro-4-(2-hydroxypropan-2-yl)pyridin-2-yl)-7-((trans-4-methylcyclohexyl)methyl)-7H-purine-2-carbonitrile (261 mg, 0.51 mmol) was dissolved in 3 N HCl in methanol (10 mL) and heated at reflux for 4 hours. The reaction mixture was cooled to room temperature and concentrated in vacuo. To the crude residue, SOCl$_2$ (10 mL) was added and the reaction was heated at 50° C. for 5 hours. The reaction was cooled to room temperature, concentrated in vacuo, and diluted with EtOAc. The organic layer was washed with sat. NaHCO$_3$ and brine, dried over anhydrous Na$_2$SO$_4$, filtered and concentrated in vacuo to give mixture of methyl 6-((R)-1-cyclobutylethylamino)-8-(5-fluoro-4-(prop-1-en-2-yl)pyridin-2-yl)-7-((trans-4-methylcyclohexyl)methyl)-7H-purine-2-carboxylate; MS (ES)=521 (M+1)$^+$ and methyl 8-(4-(2-chloropropan-2-yl)-5-fluoropyridin-2-yl)-6-((R)-1-cyclobutylethylamino)-7-((trans-4-methylcyclohexyl)methyl)-7H-purine-2-carboxylate. MS (ES)=557 (M+1)$^+$.

Step 3: To a degassed mixture of methyl 6-((R)-1-cyclobutylethylamino)-8-(5-fluoro-4-(prop-1-en-2-yl)pyridin-2-yl)-7-((trans-4-methylcyclohexyl)methyl)-7H-purine-2-carboxylate and methyl 8-(4-(2-chloropropan-2-yl)-5-fluoropyridin-2-yl)-6-  ((R)-1-cyclobutylethylamino)-7-

((trans-4-methylcyclohexyl)methyl)-7H-purine-2-carboxylate (130 mg) in MeOH/EtOAc (1:1, 10 mL) was added 10% Pd/C (13 mg). The reaction was stirred under a hydrogen atmosphere (1 atm) for 18 hours. Reaction mixture was filtered through celite. The filtrate was concentrated under vacuum. Purification of the residue on a RediSep 12 g silica gel column (0 to 20% MeOH/CH$_2$Cl$_2$) afforded methyl 6-((R)-1-cyclobutylethylamino)-8-(5-fluoro-4-isopropylpyridin-2-yl)-7-((trans-4-methylcyclohexyl)methyl)-7H-purine-2-carboxylate. MS (ES)=523 (M+1)$^+$.

Step 4: Using a procedure analogous to that in Example 5.1, and starting with methyl 6-((R)-1-cyclobutylethylamino)-8-(5-fluoro-4-isopropylpyridin-2-yl)-7-((trans-4-methylcyclohexyl)methyl)-7H-purine-2-carboxylate, 6-(((R)-1-cyclobutylethyl)amino)-8-(5-fluoro-4-isopropylpyridin-2-yl)-7-((trans-4-methylcyclohexyl)methyl)-7H-purine-2-carboxylic acid was prepared. $^1$H NMR (300 MHz, DMSO-d$_6$) δ 8.66 (br s, 1H), 8.21 (d, J=6.0 Hz, 1H), 5.15 (m, 1H), 4.83 (m, 1H), 4.49 (br s, 1H), 4.11 (m, 2H), 2.67 (m, 1H), 1.69-1.94 (m, 6H), 1.49-1.57 (m, 5H), 1.30 (m, 6H), 1.12-1.29 (m, 4H), 0.73 (d, J=6.3 Hz, 3H), 0.60-0.66 (m, 4H). MS (ES)=509 (M+1)$^+$.

Example 15.9

3-(6-(((R)-1-cyclobutylethyl)amino)-8-(5-fluoro-4-(2-hydroxypropan-2-yl)pyridin-2-yl)-7-((trans-4-methylcyclohexyl)methyl)-7H-purin-2-yl)-1,2,4-oxadiazol-5(4H)-one

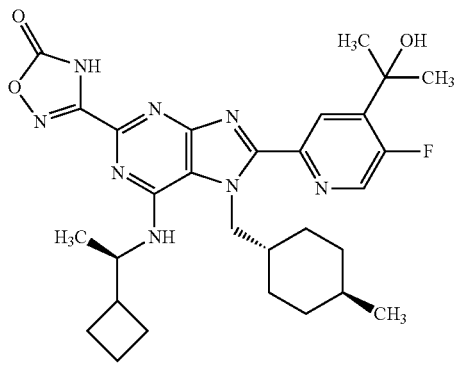 [SMILES: C[C@@H](Nc1nc(-c2noc(=O)[nH]2)nc2nc(-c3cc(C(C)(C)O)c(F)cn3)n(C[C@H]3CC[C@H](C)CC3)c12)C1CCC1]

Following a procedure analogous to that described in the synthesis of Example 1.1, and starting with Preparative Example 11.6, 6-(((R)-1-cyclobutylethyl)amino)-7-((trans-4-methylcyclohexyl)methyl)-7H-purine-2-carbonitrile and 2-(2-chloro-5-fluoropyridin-4-yl)propan-2-ol, followed by a procedure similar to that described in Example 11.3, 3-(6-(((R)-1-cyclobutylethyl)amino)-8-(5-fluoro-4-(2-hydroxypropan-2-yl)pyridin-2-yl)-7-((trans-4-methylcyclohexyl)methyl)-7H-purin-2-yl)-1,2,4-oxadiazol-5(4H)-one was prepared. $^1$H NMR (300 MHz, DMSO-d$_6$) δ 12.89 (br s, 1H), 8.65 (br s, 1H), 8.56 (d, J=6.6 Hz, 1H), 6.67 (br s, 1H), 5.75 (br s, 1H), 5.20 (m, 1H), 4.91 (m, 1H), 4.66 (m, 1H), 2.67 (m, 1H), 1.81-2.06 (m, 7H), 1.49-1.69 (m, 9H), 1.30 (m, 3H), 1.14 (d, J=6.3 Hz, 3H), 0.89 (m, 1H), 0.73 (d, J=6.4 Hz, 3H), 0.60-0.66 (m, 2H). MS (ES)=565 (M+1)$^+$.

Example 15.10

3-(6-(((R)-1-cyclobutylethyl)amino)-8-(5-fluoro-4-isopropylpyridin-2-yl)-7-((trans-4-methylcyclohexyl)methyl)-7H-purin-2-yl)-1,2,4-oxadiazol-5(4H)-one

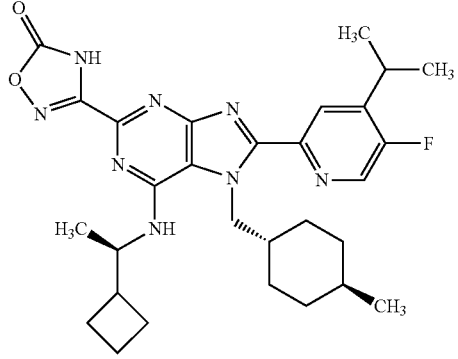 [SMILES: CC(C)c1cc(-c2nc3nc(-c4noc(=O)[nH]4)nc(N[C@H](C)C4CCC4)c3n2C[C@H]2CC[C@H](C)CC2)ncc1F]

Step 1: A microwave vial was charged with 3-(6-(((R)-1-cyclobutylethyl)amino)-8-(5-fluoro-4-(2-hydroxypropan-2-yl)pyridin-2-yl)-7-((trans-4-methylcyclohexyl)methyl)-7H-purin-2-yl)-1,2,4-oxadiazol-5(4H)-one (Example 15.9; 12 mg, 0.02 mmol) and thionyl chloride (0.5 mL). The vial was sealed and heated at 80° C. for 18 hours. The reaction was concentrated and the residue was dissolved in CH$_2$Cl$_2$ (20 mL). The organic layer was washed with aqueous NaHCO$_3$ solution (2 mL) and brine (2 mL), dried over anhydrous Na$_2$SO$_4$, filtered and concentrated in vacuo. The crude product was use for next step without any purification. MS (ES)=547 (M+1)$^+$.

Step 2: 3-(6-(((R)-1-cyclobutylethyl)amino)-8-(5-fluoro-4-(prop-1-en-2-yl)pyridin-2-yl)-7-((trans-4-methylcyclohexyl)methyl)-7H-purin-2-yl)-1,2,4-oxadiazol-5(4H)-one (12.0 mg, crude) was dissolved in THF (0.5 mL) and cooled to 0° C. NaBH$_4$ (1.0 mg, 0.61 mmol) was added and the reaction mixture was stirred at room temperature for 18 hours. The reaction was concentrated and the residue was purified by preparative HPLC (acetonitrile/water) to afford 3-(6-(((R)-1-cyclobutylethyl)amino)-8-(5-fluoro-4-isopropylpyridin-2-yl)-7-((trans-4-methylcyclohexyl)methyl)-7H-purin-2-yl)-1,2,4-oxadiazol-5(4H)-one. $^1$H NMR (400 MHz, CD$_3$OD) δ 8.55 (d, J=1.6 Hz, 1H), 8.24 (d, J=6.0 Hz, 1H), 5.17 (m, 2H), 3.38 (m, 1H), 2.58 (m, 1H), 2.03-2.18 (m, 3H), 1.89-1.93 (m, 4H), 1.50-1.65 (m, 5H), 1.38 (d, J=2.6 Hz, 3H), 1.36 (d, J=2.6 Hz, 3H), 1.25 (m, 1H), 1.22 (d, J=6.4 Hz, 3H), 1.00 (m, 1H), 0.75 (d, J=6.4 Hz, 3H), 0.61-0.71 (m, 3H). MS (ES)=549 (M+1)$^+$.

Example 15.11

6-(((R)-1-cyclobutylethyl)amino)-7-((trans-4-methylcyclohexyl)methyl)-8-(thiazol-2-yl)-7H-purine-2-carboxylic acid

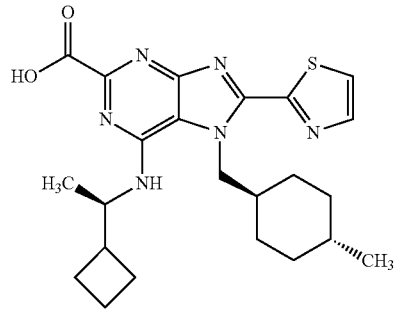 [SMILES: C[C@@H](Nc1nc(C(=O)O)nc2nc(-c3nccs3)n(C[C@H]3CC[C@H](C)CC3)c12)C1CCC1]

Step 1: 8-bromo-6-(((R)-1-cyclobutylethyl)amino)-7-((trans-4-methylcyclohexyl)methyl)-7H-purine-2-carbonitrile (Preparative Example 11.7; 100 mg, 0.232 mmol), 2-(tributylstannyl)thiazole (0.12 mL, 0.35 mmol), and copper(I) iodide (9.00 mg, 0.046 mmol) were dissolved in Ar-degassed 1,4-dioxane and the reaction vessel was evacuated and refilled with argon (3 times). Tetrakis(triphenylphosphine)palladium(0) (27.0 mg, 0.023 mmol) was then added and the mixture was degassed with argon for another 2 minutes. N,N-Diisopropylethylamine (0.08 mL, 0.46 mmol) was then added, the vial was sealed, and the reaction was heated at 100° C. for 4 hours. The reaction mixture was quenched with KF solution, extracted with EtOAc (2×50 mL), and washed with water (50 mL). The combined organic extracts were dried over anhydrous $Na_2SO_4$, filtered, and concentrated. The residue was purified on a RediSep 4 g silica gel column (0 to 100% EtOAc/hexanes) to afford 6-(((R)-1-cyclobutylethyl)amino)-7-((trans-4-methylcyclohexyl)methyl)-8-(thiazol-2-yl)-7H-purine-2-carbonitrile. $^1$H NMR (300 MHz, $CDCl_3$) δ 7.98 (d, J=3.3 Hz, 1H), 7.57 (d, J=3.3 Hz, 1H), 4.87 (d, J=7.8 Hz, 1H), 4.53 (m, 1H), 2.40-2.48 (m, 1H), 2.02-2.14 (m, 3H), 1.85-1.99 (m, 5H), 1.43-1.73 (m, 7H), 1.00-1.20 (m, 3H), 0.86 (d, J=6.6 Hz, 3H), 0.73-0.81 (m, 2H). MS (APCI)=436 (M+1)$^+$.

Step 2: A solution of 6-(((R)-1-cyclobutylethyl)amino)-7-((trans-4-methylcyclohexyl)methyl)-8-(thiazol-2-yl)-7H-purine-2-carbonitrile (30.0 mg, 0.065 mmol) and sodium hydroxide (78 mg, 1.94 mmol) in ethanol (1 mL) and water (0.25 mL) was stirred at reflux for 1 hour. The reaction was then concentrated. The residue was dissolved in water, acidified with 1.0 M HCl solution to pH 5-6, and extracted with $CH_2Cl_2$ (2×50 mL). The combined organic extracts were dried over anhydrous $Na_2SO_4$, filtered, and concentrated. The residue was purified on a RediSep 4 g silica gel column (0 to 100% MeOH/$CH_2Cl_2$) to afford 6-(((R)-1-cyclobutylethyl)amino)-7-((trans-4-methylcyclohexyl)methyl)-8-(thiazol-2-yl)-7H-purine-2-carboxylic acid. $^1$H NMR (300 MHz, $CD_3OD$) δ 8.07 (d, J=4.0 Hz, 1H), 7.81 (d, J=4.0 Hz, 1H), 4.88-5.00 (m, 1H), 2.46-2.47 (m, 1H), 2.03-2.16 (m, 1H), 1.99-2.02 (m, 1H), 1.80-1.98 (m, 5H), 1.60-1.87 (m, 3H), 1.50-1.60 (m, 2H), 1.25-1.37 (m, 5H), 1.19 (d, J=6.0 Hz, 3H), 0.85-0.98 (m, 3H), 0.81 (d, J=6.6 Hz, 3H). MS (ES)=455 (M+1)$^+$.

Example 15.12

3-(6-(((R)-1-cyclobutylethyl)amino)-7-((trans-4-methylcyclohexyl)methyl)-8-(thiazol-2-yl)-7H-purin-2-yl)-1,2,4-oxadiazol-5(4H)-one

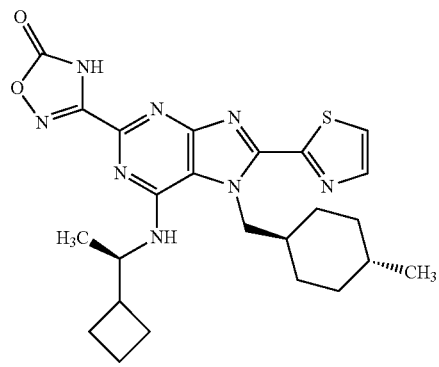 [SMILES: C[C@@H](Nc1nc(-c2noc(=O)[nH]2)nc2nc(-c3nccs3)n(C[C@H]3CC[C@H](C)CC3)c12)C1CCC1]

Using a procedure similar to that described in Example 11.3, and starting with 6-(((R)-1-cyclobutylethyl)amino)-7-((trans-4-methylcyclohexyl)methyl)-8-(thiazol-2-yl)-7H-purine-2-carbonitrile, 3-(6-(((R)-1-cyclobutylethyl)amino)-7-((trans-4-methylcyclohexyl)methyl)-8-(thiazol-2-yl)-7H-purin-2-yl)-1,2,4-oxadiazol-5(4H)-one was prepared. $^1$H NMR (400 MHz, $CD_3OD$) δ 8.09 (d, J=4.0 Hz, 1H), 7.88 (d, J=4.0 Hz, 1H), 5.24-5.43 (m, 1H), 4.71-4.75 (m, 1H), 2.57-2.63 (m, 1H), 2.04-2.15 (m, 2H), 1.86-1.99 (m, 5H), 1.66-1.73 (m, 4H), 1.30-1.32 (m, 3H), 1.23 (d, J=4.0 Hz, 3H), 0.99-1.32 (m, 2H), 0.83 (d, J=8.0 Hz, 3H), 0.70-0.74 (m, 1H). MS (ES)=495 (M+1)$^+$.

The following compounds in Table 15 (other than Example 15.1 to 15.12) were prepared using procedures which were analogous to those described above.

TABLE 15

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.1 | 1.299 | 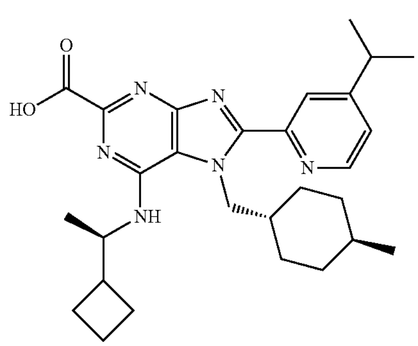 [SMILES: CC(C)c1ccnc(-c2nc3nc(C(=O)O)nc(N[C@H](C)C4CCC4)c3n2C[C@H]2CC[C@H](C)CC2)c1] | 6-(((R)-1-cyclobutylethyl)amino)-8-(4-isopropylpyridin-2-yl)-7-((trans-4-methylcyclohexyl)methyl)-7H-purine-2-carboxylic acid | TFA | 491 | 491 |

TABLE 15-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.2 | 10.46 | 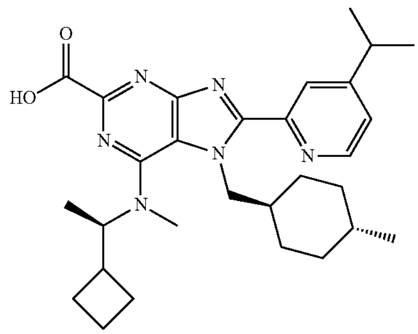 [SMILES: CC(C)c1ccnc(-c2nc3nc(C(=O)O)nc(N(C)[C@H](C)C4CCC4)c3n2C[C@H]2CC[C@H](C)CC2)c1] | 6-(((R)-1-cyclobutylethyl)(methyl)amino)-8-(4-isopropylpyridin-2-yl)-7-((trans-4-methylcyclohexyl)methyl)-7H-purine-2-carboxylic acid | | 505 | 505 |
| 15.3 | 15.55 | 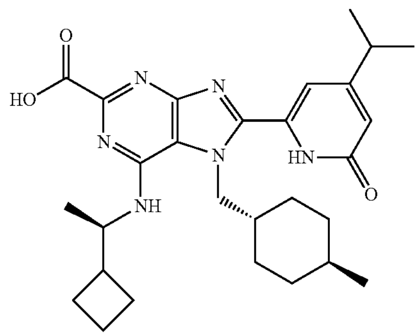 [SMILES: CC(C)c1cc(-c2nc3nc(C(=O)O)nc(N[C@H](C)C4CCC4)c3n2C[C@H]2CC[C@H](C)CC2)[nH]c(=O)c1] | 6-(((R)-1-cyclobutylethyl)amino)-8-(4-isopropyl-6-oxo-1,6-dihydropyridin-2-yl)-7-((trans-4-methylcyclohexyl)methyl)-7H-purine-2-carboxylic acid | | 507 | 507 |
| 15.4 | 4.438 | 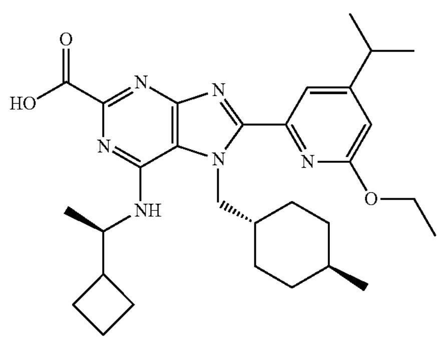 [SMILES: CCOc1cc(C(C)C)cc(-c2nc3nc(C(=O)O)nc(N[C@H](C)C4CCC4)c3n2C[C@H]2CC[C@H](C)CC2)n1] | 6-(((R)-1-cyclobutylethyl)amino)-8-(6-ethoxy-4-isopropylpyridin-2-yl)-7-((trans-4-methyl-cyclohexyl)methyl)-7H-purine-2-carboxylic acid | | 535 | 535 |
| 15.5 | 33.49 | 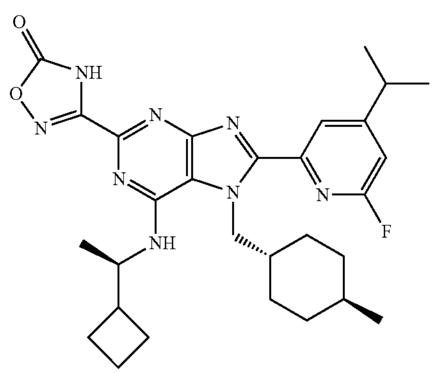 [SMILES: CC(C)c1cc(F)nc(-c2nc3nc(-c4noc(=O)[nH]4)nc(N[C@H](C)C4CCC4)c3n2C[C@H]2CC[C@H](C)CC2)c1] | 3-(6-(((R)-1-cyclobutylethyl)amino)-8-(6-fluoro-4-isopropylpyridin-2-yl)-7-((trans-4-methylcyclohexyl)methyl)-7H-purin-2-yl)-1,2,4-oxadiazol-5(2H)-one | | 549 | 549 |

TABLE 15-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.6 | 6.016 | 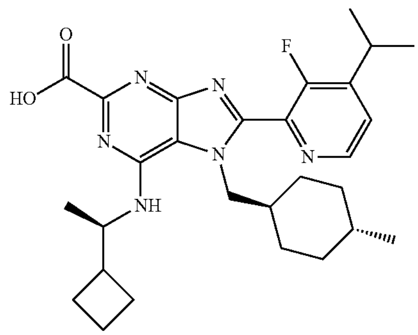 [SMILES: CC(C)c1ccnc(-c2nc3nc(C(=O)O)nc(N[C@H](C)C4CCC4)c3n2C[C@H]2CC[C@H](C)CC2)c1F] | 6-(((R)-1-Cyclobutylethyl)amino)-8-(3-fluoro-4-isopropylpyridin-2-yl)-7-((trans-4-methylcyclohexyl)methyl)-7H-purine-2-carboxylic acid | | 509 | 509 |
| 15.7 | 5.131 | 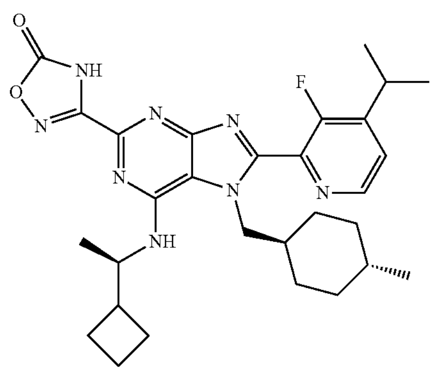 [SMILES: CC(C)c1ccnc(-c2nc3nc(-c4noc(=O)[nH]4)nc(N[C@H](C)C4CCC4)c3n2C[C@H]2CC[C@H](C)CC2)c1F] | 3-(6-((R)-1-cyclobutylethylamino)-8-(3-fluoro-4-isopropylpyridin-2-yl)-7-((trans-4-methylcyclohexyl)methyl)-7H-purin-2-yl)-1,2,4-oxadiazol-5(4H)-one | | 549 | 549 |
| 15.8 | 1.139 | 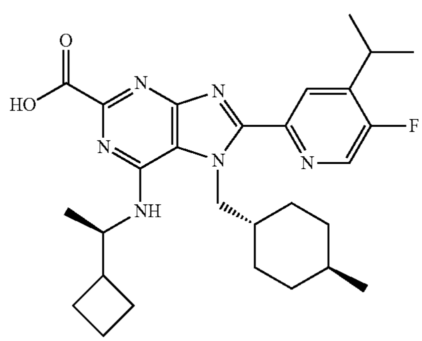 [SMILES: CC(C)c1cc(-c2nc3nc(C(=O)O)nc(N[C@H](C)C4CCC4)c3n2C[C@H]2CC[C@H](C)CC2)ncc1F] | 6-(((R)-1-cyclobutylethyl)amino)-8-(5-fluoro-4-isopropylpyridin-2-yl)-7-((trans-4-methylcyclohexyl)methyl)-7H-purine-2-carboxylic acid | | 509 | 509 |
| 15.9 | 3.954 | 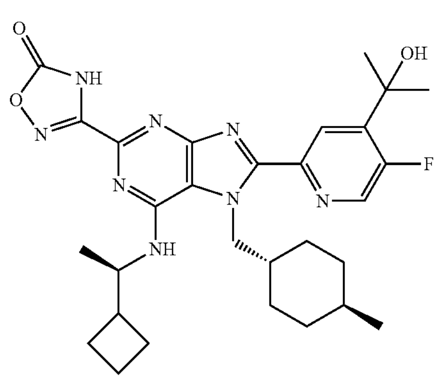 [SMILES: C[C@@H](Nc1nc(-c2noc(=O)[nH]2)nc2nc(-c3cc(C(C)(C)O)c(F)cn3)n(C[C@H]3CC[C@H](C)CC3)c12)C1CCC1] | 3-(6-(((R)-1-cyclobutylethyl)amino)-8-(5-fluoro-4-(2-hydroxypropan-2-yl)pyridin-2-yl)-7-((trans-4-methylcyclohexyl)methyl)-7H-purin-2-yl)-1,2,4-oxadiazol-5(4H)-one | | 565 | 565 |

TABLE 15-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.10 | 11.77 | 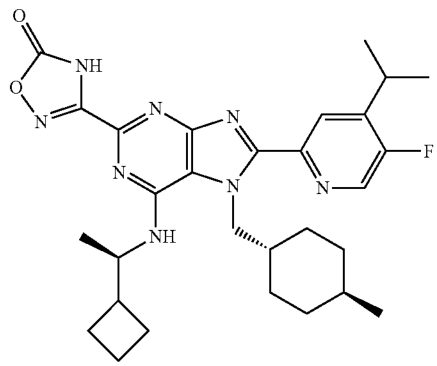 [SMILES: CC(C)c1cc(-c2nc3nc(-c4noc(=O)[nH]4)nc(N[C@H](C)C4CCC4)c3n2C[C@H]2CC[C@H](C)CC2)ncc1F] | 3-(6-(((R)-1-cyclobutylethyl)amino)-8-(5-fluoro-4-isopropylpyridin-2-yl)-7-((trans-4-methylcyclohexyl)methyl)-7H-purin-2-yl)-1,2,4-oxadiazol-5(4H)-one | | 549 | 549 |
| 15.11 | 2.451 | 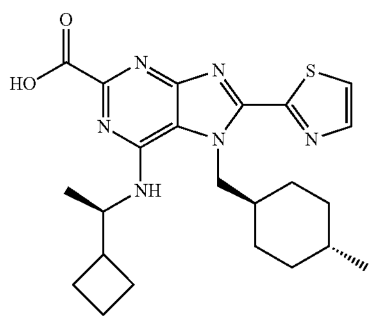 [SMILES: C[C@@H](Nc1nc(C(=O)O)nc2nc(-c3nccs3)n(C[C@H]3CC[C@H](C)CC3)c12)C1CCC1] | 6-(((R)-1-cyclobutylethyl)amino)-7-((trans-4-methylcyclohexyl)methyl)-8-(thiazol-2-yl)-7H-purine-2-carboxylic acid | | 455 | 455 |
| 15.12 | 6.279 | 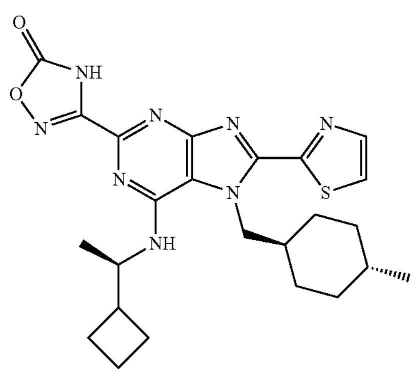 [SMILES: C[C@@H](Nc1nc(-c2noc(=O)[nH]2)nc2nc(-c3nccs3)n(C[C@H]3CC[C@H](C)CC3)c12)C1CCC1] | 3-(6-(((R)-1-cyclobutylethyl)amino)-7-((trans-4-methylcyclohexyl)methyl)-8-(thiazol-2-yl)-7H-purin-2-yl)-1,2,4-oxadiazol-5(4H)-one | | 495 | 495 |
| 15.13 | 4.961 | 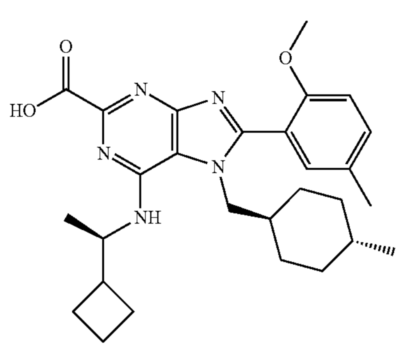 [SMILES: COc1ccc(C)cc1-c1nc2nc(C(=O)O)nc(N[C@H](C)C3CCC3)c2n1C[C@H]1CC[C@H](C)CC1] | 6-{[(1R)-1-cyclobutylethyl]amino}-8-(2-methoxy-5-methylphenyl)-7-[(trans-4-methylcyclohexyl)methyl]-7H-purine-2-carboxylic acid | | 492 | 492 |

TABLE 15-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.14 | 2.913 | 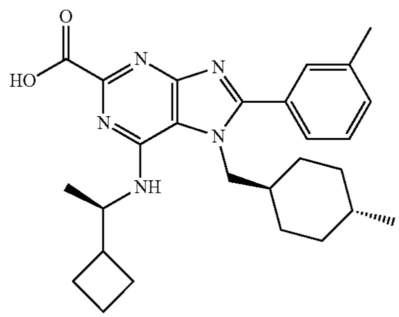 [SMILES: Cc1cccc(-c2nc3nc(C(=O)O)nc(N[C@H](C)C4CCC4)c3n2C[C@H]2CC[C@H](C)CC2)c1] | 6-{[(1R)-1-cyclobutylethyl]amino}-7-[(trans-4-methylcyclohexyl)methyl]-8-(3-methylphenyl)-7H-purine-2-carboxylic acid | TFA | 462 | 462 |
| 15.15 | 2.548 | 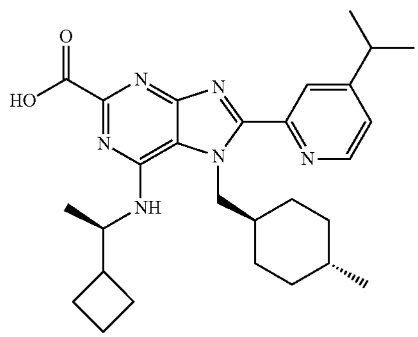 [SMILES: CC(C)c1ccnc(-c2nc3nc(C(=O)O)nc(N[C@H](C)C4CCC4)c3n2C[C@H]2CC[C@H](C)CC2)c1] | 6-{[(1R)-1-cyclobutylethyl]amino}-7-[(trans-4-methylcyclohexyl)methyl]-8-[4-(1-methylethyl)pyridin-2-yl]-7H-purine-2-carboxylic acid | | 491 | 491 |
| 15.16 | 1.037 | 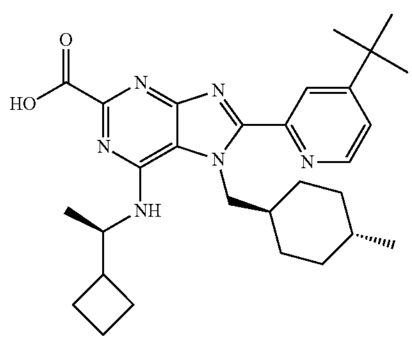 [SMILES: C[C@@H](Nc1nc(C(=O)O)nc2nc(-c3cc(C(C)(C)C)ccn3)n(C[C@H]3CC[C@H](C)CC3)c12)C1CCC1] | 8-(4-tert-butylpyridin-2-yl)-6-{[(1R)-1-cyclobutylethyl]amino}-7-[(trans-4-methylcyclohexyl)methyl]-7H-purine-2-carboxylic acid | TFA | 505 | 505 |
| 15.17 | 2.091 | 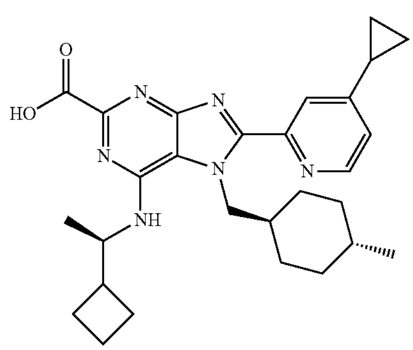 [SMILES: C[C@@H](Nc1nc(C(=O)O)nc2nc(-c3cc(C4CC4)ccn3)n(C[C@H]3CC[C@H](C)CC3)c12)C1CCC1] | 6-{[(1R)-1-cyclobutylethyl]amino}-8-(4-cyclopropylpyridin-2-yl)-7-[(trans-4-methylcyclohexyl)methyl]-7H-purine-2-carboxylic acid | TFA | 489 | 489 |

TABLE 15-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.18 | 1.802 | 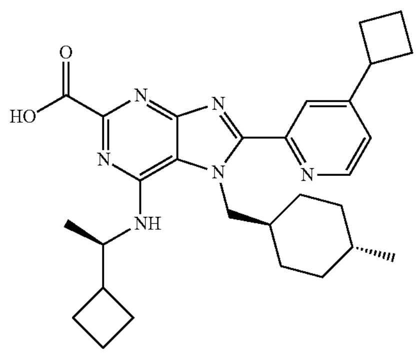 [SMILES: C[C@@H](Nc1nc(C(=O)O)nc2nc(-c3cc(C4CCC4)ccn3)n(C[C@H]3CC[C@H](C)CC3)c12)C1CCC1] | 6-{[(1R)-1-cyclobutylethyl]amino}-8-(4-cyclobutylpyridin-2-yl)-7-[(trans-4-methylcyclohexyl)methyl]-7H-purine-2-carboxylic acid | TFA | 503 | 503 |
| 15.19 | 2.283 | 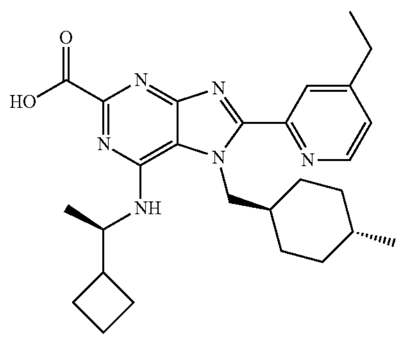 [SMILES: CCc1ccnc(-c2nc3nc(C(=O)O)nc(N[C@H](C)C4CCC4)c3n2C[C@H]2CC[C@H](C)CC2)c1] | 6-{[(1R)-1-cyclobutylethyl]amino}-8-(4-ethylpyridin-2-yl)-7-[(trans-4-methylcyclohexyl)methyl]-7H-purine-2-carboxylic acid | TFA | 477 | 477 |
| 15.20 | 17.86 | 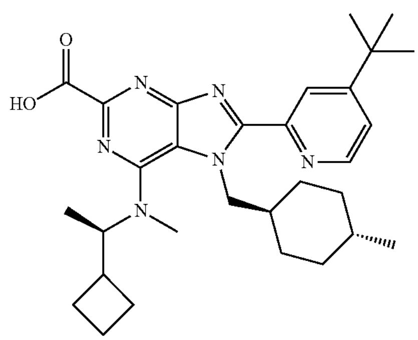 [SMILES: C[C@H](C1CCC1)N(C)c1nc(C(=O)O)nc2nc(-c3cc(C(C)(C)C)ccn3)n(C[C@H]3CC[C@H](C)CC3)c12] | 8-(4-tert-butylpyridin-2-yl)-6-{[(1R)-1-cyclobutylethyl](methyl)amino}-7-[(trans-4-methylcyclohexyl)methyl]-7H-purine-2-carboxylic acid | TFA | 519 | 519 |
| 15.21 | 8.44 | 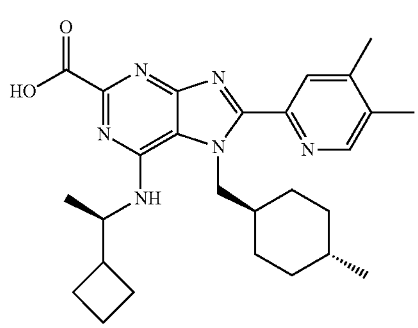 [SMILES: Cc1cnc(-c2nc3nc(C(=O)O)nc(N[C@H](C)C4CCC4)c3n2C[C@H]2CC[C@H](C)CC2)cc1C] | 6-{[(1R)-1-cyclobutylethyl]amino}-8-(4,5-dimethylpyridin-2-yl)-7-[(trans-4-methylcyclohexyl)methyl]-7H-purine-2-carboxylic acid | | 477 | 477 |

TABLE 15-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 15.22 | 17.88 | 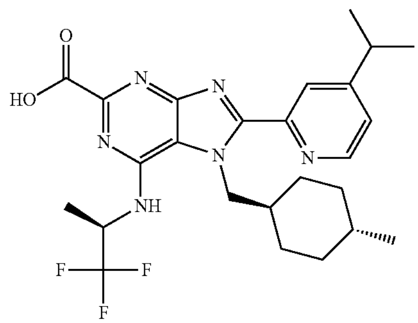 [SMILES: CC(C)c1ccnc(-c2nc3nc(C(=O)O)nc(N[C@H](C)C(F)(F)F)c3n2C[C@H]2CC[C@H](C)CC2)c1] | 7-[(trans-4-methylcyclohexyl)methyl]-8-[4-(1-methylethyl)pyridin-2-yl]-6-{[(1R)-2,2,2-trifluoro-1-methylethyl]amino}-7H-purine-2-carboxylic acid | TFA | 505 | 505 |
| 15.23 | 4.745 | 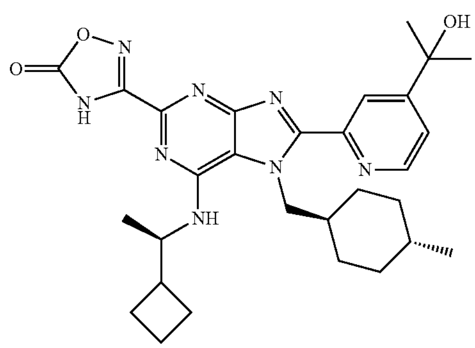 [SMILES: C[C@@H](Nc1nc(-c2noc(=O)[nH]2)nc2nc(-c3cc(C(C)(C)O)ccn3)n(C[C@H]3CC[C@H](C)CC3)c12)C1CCC1] | 3-(6-{[(1R)-1-cyclobutylethyl]amino}-8-[4-(1-hydroxy-1-methylethyl)pyridin-2-yl]-7-[(trans-4-methylcyclohexyl)methyl]-7H-purin-2-yl)-1,2,4-oxadiazol-5(4H)-one | TFA | 547 | 547 |
| 15.24 | 715.5 | 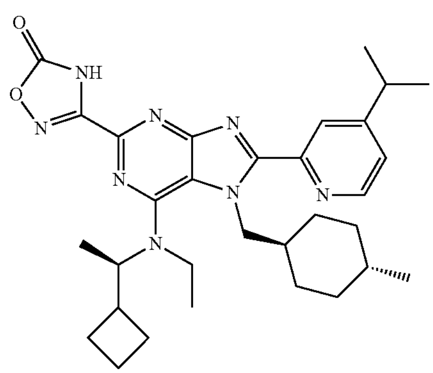 [SMILES: CCN(c1nc(-c2noc(=O)[nH]2)nc2nc(-c3cc(C(C)C)ccn3)n(C[C@H]3CC[C@H](C)CC3)c12)[C@H](C)C1CCC1] | 3-(6-{[(1R)-1-cyclobutylethyl](ethyl)amino}-7-[(trans-4-methylcyclohexyl)methyl]-8-[4-(1-methylethyl)pyridin-2-yl]-7H-purin-2-yl)-1,2,4-oxadiazol-5(4H)-one | | 559 | 559 |
| 15.25 | 6.742 | 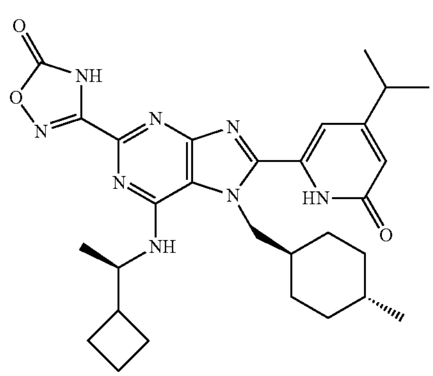 [SMILES: CC(C)c1cc(-c2nc3nc(-c4noc(=O)[nH]4)nc(N[C@H](C)C4CCC4)c3n2C[C@H]2CC[C@H](C)CC2)[nH]c(=O)c1] | 6-[6-{[(1R)-1-cyclobutylethyl]amino}-7-[(trans-4-methylcyclohexyl)methyl]-2-(5-oxo-2,5-dihydro-1,2,4-oxadiazol-3-yl)-7H-purin-8-yl]-4-(1-methylethyl)pyridin-2(1H)-one | TFA | 547 | 547 |

Preparative Example 16.1

8-bromo-2-chloro-6-(3-chlorophenyl)-7-(((trans)-4-methylcyclohexyl)methyl)-7H-purine

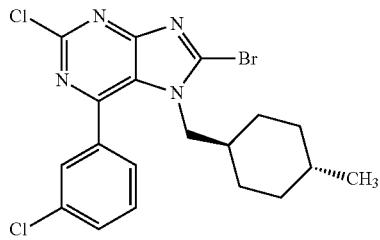 [SMILES: C[C@H]1CC[C@H](Cn2c(Br)nc3nc(Cl)nc(-c4cccc(Cl)c4)c32)CC1]

Step 1: 2,6-dichloro-7-(((trans)-4-methylcyclohexyl)methyl)-7H-purine (Preparative Example 11.4; 500 mg, 1.7 mmol), 3-chlorophenyl boronic acid (288 mg, 1.8 mmol), aqueous 1M $Na_2CO_3$ (2.5 mL, 2.5 mmol), and toluene (4.5 mL) were taken in sealed tube vial (25 mL) and the mixture was degassed using $N_2$ for 15 minutes before $Pd(PPh_3)_4$ (207 mg, 0.18 mmol) was added. The vial was sealed and the reaction was heated at 100° C. for 15 minutes. The reaction was cooled to room temperature and extracted with EtOAc (2×25 mL). The combined organic layers were washed with water and brine, and dried over anhydrous $Na_2SO_4$. The solvent was evaporated under vacuum. The crude product was loaded onto a Redisep 12 g silica gel column. Purification with 0 to 10% EtOAc/hexanes afforded 2-chloro-6-(3-chlorophenyl)-7-(((trans)-4-methylcyclohexyl)methyl)-7H-purine. $^1$H NMR (300 MHz, $CDCl_3$): δ 8.16 (s, 1H), 7.48-7.60 (m, 4H), 3.80 (d, J=6.9 Hz, 2H), 1.08-1.29 (m, 3H), 0.87-1.08 (m, 4H), 0.80 (d, J=6.6 Hz, 3H), 0.56-0.75 (m, 3H). MS (APCI)=375 $(M+1)^+$.

Step 2: 2-chloro-6-(3-chlorophenyl)-7-(((trans)-4-methylcyclohexyl)methyl)-7H-purine (200 mg, 0.5 mmol) was dissolved in anhydrous $CHCl_3$ (20 mL) and NBS (recrystallized, 365 mg, 2.1 mmol) was added. The reaction was heated at reflux for 3 hours. The reaction was then cooled to room temperature and was diluted with $CH_2Cl_2$ (50 mL). The organics were washed with saturated aqueous $Na_2S_2O_4$ solution (20 mL) and aqueous 0.05 N NaOH solution (10 mL). The organic layer was dried over anhydrous $Na_2SO_4$, filtered, and concentrated. Purification of the residue on RediSep 120 g silica gel column with 0 to 50% EtOAc/hexanes afforded 8-bromo-2-chloro-6-(3-chlorophenyl)-7-(((trans)-4-methylcyclohexyl)methyl)-7H-purine. $^1$H NMR (300 MHz, $CDCl_3$): δ 7.44-7.59 (m, 4H), 3.95 (d, J=6.9 Hz, 2H), 1.50-1.55 (m, 2H), 1.08-1.29 (m, 2H), 0.85-1.01 (m, 4H), 0.78 (d, J=6.6 Hz, 3H), 0.52-0.56 (m, 2H). MS (APCI)=453 $(M+1)^+$.

Example 16.1

3-(6-(3-chlorophenyl)-7-(((trans)-4-methylcyclohexyl)methyl)-8-morpholino-7H-purin-2-yl)-1,2,4-oxadiazol-5(4H)-one

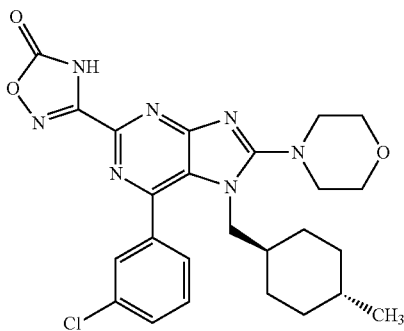 [SMILES: C[C@H]1CC[C@H](Cn2c(N3CCOCC3)nc3nc(-c4noc(=O)[nH]4)nc(-c4cccc(Cl)c4)c32)CC1]

Step 1: 8-bromo-2-chloro-6-(3-chlorophenyl)-7-(((trans)-4-methylcyclohexyl)methyl)-7H-purine (Preparative Example 16.1, 150 mg, 0.33 mmol) and morpholine (86.2 mg, 0.99 mmol) were dissolved in acetonitrile (9 mL) and heated at reflux for 12 hours. The reaction was cooled to room temperature, diluted with water (20 mL), and extracted with EtOAc (2×50 mL). The combined organic extracts were dried over anhydrous $Na_2SO_4$, filtered and concentrated under vacuum. The residue was purified on a RediSep 12 g silica gel column (0 to 100% EtOAc/Hexanes) to afford 4-(2-chloro-6-(3-chlorophenyl)-7-(((trans)-4-methylcyclohexyl)methyl)-7H-purin-8-yl)morpholine. $^1$H NMR (300 MHz, $CDCl_3$): δ 7.65 (s, 1H), 7.46-7.56 (m, 3H), 3.85-3.88 (m, 4H), 3.55-3.59 (m, 6H), 1.39-1.44 (m, 3H), 0.88-0.95 (m, 4H), 0.83 (d, J=6.3 Hz, 3H), 0.59-0.63 (m, 3H). MS (APCI)=460 $(M+1)^+$.

Step 2: 4-(2-chloro-6-(3-chlorophenyl)-7-(((trans)-4-methylcyclohexyl)methyl)-7H-purin-8-yl)morpholine (120 mg, 0.26 mmol) and zinc cyanide (18.3 mg, 0.15 mmol) were added to DMA (4.0 mL) and the mixture was degassed with argon for 20 minutes. Tetrakis(triphenylphosphine)palladium (0) (30.3 mg, 0.02 mmol) was then added and the mixture was degassed for another 5 minutes. The vial was sealed and the reaction was heated at 120° C. for 12 hours. The reaction was cooled to room temperature, diluted with water (15 mL), and extracted with EtOAc (2×25 mL). The combined organic extracts were dried over anhydrous $Na_2SO_4$, filtered, and concentrated. The residue was purified on a RediSep 12 g silica gel column (0 to 100% EtOAc/hexanes) to afford 6-(3-chlorophenyl)-7-(((trans)-4-methylcyclohexyl)methyl)-8-morpholino-7H-purine-2-carbonitrile. $^1$H NMR (400 MHz, $CDCl_3$): δ 7.64-7.61 (m, 1H), 7.51-7.56 (m, 3H), 3.87-3.90 (m, 4H), 3.61-3.63 (m, 6H), 1.45-1.48 (m, 2H), 1.05-1.14 (m, 1H), 0.95-0.99 (m, 1H), 0.86-0.90 (m, 1H), 0.76 (d, J=8.0 Hz, 3H), 0.72-0.73 (m, 1H), 0.56-0.66 (m, 2H), 0.45-0.51 (m, 2H). MS (APCI)=450 $(M+1)^+$.

Step 3: Hydroxylamine hydrochloride (9.24 mg, 0.13 mmol) and sodium bicarbonate (16.7 mg, 0.19 mmol) were dissolved in water (0.5 mL) and stirred at room temperature for 15 minutes. This solution was added into a solution of 6-(3-chlorophenyl)-7-(((trans)-4-methylcyclohexyl)methyl)-8-morpholino-7H-purine-2-carbonitrile (30.0 mg, 0.06 mmol) in ethanol (2.0 mL). The vial was sealed and the reaction mixture was stirred at 100° C. for 1 hour. The reaction was then diluted with EtOAc (20 mL) and washed with water (20 mL). The organic extract was dried over anhydrous $Na_2SO_4$ and concentrated to afford crude (Z)-6-(3-chlorophenyl)-N-hydroxy-7-(((trans)-4-methylcyclohexyl)methyl)-8-morpholino-7H-purine-2-carboximidamide. MS (APCI)=483 $(M+1)^+$.

Step 4: To a solution of (Z)-6-(3-chlorophenyl)-N'-hydroxy-7-(((trans)-4-methylcyclohexyl)methyl)-8-morpholino-7H-purine-2-carboximidamide (30.0 mg, 0.06 mmol) and 1,1'-carbonyldiimidazole (50.2 mg, 0.30 mmol) in acetonitrile (2.0 mL) was added DBU (0.13 mL, 0.74 mmol) dropwise. The reaction was stirred at room temperature for 2 hours. The reaction was then concentrated, and the residue was diluted with $CH_2Cl_2$ (30 mL) and washed with water (30 mL). The organic layer was dried over anhydrous $Na_2SO_4$ and concentrated. The residue was purified on a RediSep 4 g silica gel column (0 to 100% EtOAc/hexanes) to afford 3-(6-(3-chlorophenyl)-7-(((trans)-4-methylcyclohexyl)methyl)-8-morpholino-7H-purin-2-yl)-1,2,4-oxadiazol-5(4H)-one. $^1$H NMR (400 MHz, $CD_3OD$): δ 7.89 (s, 1H), 7.71-7.72 (m, 1H), 7.59-7.62 (m, 2H), 3.85-3.87 (m, 4H), 3.75 (d, J=7.2 Hz, 2H), 3.61-3.62 (m, 4H), 1.44-1.47

(m, 2H), 1.01-1.12 (m, 3H), 0.75-0.77 (m, 1H), 0.74 (d, J=6.4 Hz, 3H), 0.65-0.71 (m, 2H), 0.43-0.53 (m, 2H). MS (ES)=510 (M+1)+.

Example 16.2

3-(6-(3-chlorophenyl)-7-(((trans)-4-methylcyclohexyl)methyl)-8-((S)-3-methylmorpholino)-7H-purin-2-yl)-1,2,4-oxadiazol-5(4H)-one

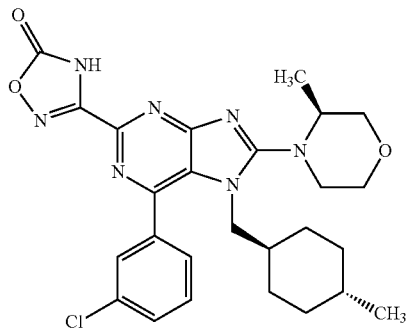 [SMILES: C[C@H]1COCCN1c1nc2nc(-c3noc(=O)[nH]3)nc(-c3cccc(Cl)c3)c2n1C[C@H]1CC[C@H](C)CC1]

Step 1: 8-bromo-2-chloro-6-(3-chlorophenyl)-7-(((trans)-4-methylcyclohexyl)methyl)-7H-purine, (Preparative Example 16.1, 300 mg, 0.66 mmol), (S)-3-methylmorpholine (202 mg, 2.0 mmol), and potassium fluoride (383 mg, 6.60 mmol) were suspended in DMSO (25 mL) and the reaction was heated at 85° C. for 12 hours. The reaction was then cooled to room temperature, diluted with water (50 mL), and extracted with EtOAc (2×50 mL). The organic layer was dried over anhydrous $Na_2SO_4$, filtered and concentrated. The residue was purified on a RediSep 4 g silica gel column (0 to 10% EtOAc/Hexanes) to afford (S)-4-(2-chloro-6-(3-chlorophenyl)-7-(((trans)-4-methylcyclohexyl)methyl)-7H-purin-8-yl)-3-methylmorpholine. $^1H$ NMR (400 MHz, $CDCl_3$): δ 7.64-7.65 (m, 1H), 7.45-7.55 (m, 3H), 3.97-4.02 (m, 1H), 3.86-3.94 (m, 2H), 3.82 (m, 2.8 Hz, 1H), 3.69 (dd, $J_1$=11.3, 3.0 Hz, 1H), 3.59-3.64 (m, 1H), 3.46-3.57 (m, 3H), 1.43-1.50 (m, 2H), 1.41 (d, J=6.7 Hz, 2H), 1.04-1.13 (m, 1H), 0.91-1.01 (m, 1H), 0.83 (d, J=6.3 Hz, 3H), 0.75 (d, J=6.5 Hz, 3H), 0.42-0.65 (m, 4H). MS (APCI)=474 (M+1)+.

Step 2: (S)-4-(2-chloro-6-(3-chlorophenyl)-7-(((trans)-4-methylcyclohexyl)methyl)-7H-purin-8-yl)-3-methylmorpholine (260 mg, 0.55 mmol) and zinc cyanide (32.2 mg, 0.28 mmol) were added to DMA (4.0 mL) and the mixture was degassed with argon for 20 minutes. Tetrakis(triphenylphosphine) palladium(0) (127 mg, 0.109 mmol) was added and the mixture was degassed for another 5 minutes. The vial was sealed and the reaction was heated at 120° C. for 12 hours. The reaction was then cooled to room temperature, diluted with water (20 mL), and extracted with EtOAc (2×50 mL). The combined organic extracts were dried over anhydrous $Na_2SO_4$, filtered, and concentrated. The residue was purified on a RediSep 4 g silica gel column (0 to 100% EtOAc/hexanes) to afford 6-(3-chlorophenyl)-7-(((trans)-4-methylcyclohexyl)methyl)-8-((S)-3-methylmorpholino)-7H-purine-2-carbonitrile. MS (APCI)=465 (M+1)+.

Step 3: Using a procedure analogous to that described in Example 16.1 (Step 3) and starting with (S)-4-(2-chloro-6-(3-chlorophenyl)-7-(((trans)-4-methylcyclohexyl)methyl)-7H-purin-8-yl)-3-methylmorpholine, (Z)-6-(3-chlorophenyl)-N'-hydroxy-7-(((trans)-4-methylcyclohexyl)methyl)-8-((S)-3-methylmorpholino)-7H-purine-2-carboximidamide was prepared. MS (APCI)=498 (M+1)+.

Step 4: Using a procedure analogous to that described in Example 16.1 (Step 4) and starting with (Z)-6-(3-chlorophenyl)-N'-hydroxy-7-(((trans)-4-methylcyclohexyl)methyl)-8-((S)-3-methylmorpholino)-7H-purine-2-carboximidamide, 3-(6-(3-chlorophenyl)-7-(((trans)-4-methylcyclohexyl)methyl)-8-((S)-3-methylmorpholino)-7H-purin-2-yl)-1,2,4-oxadiazol-5(4H)-one was prepared. $^1H$ NMR (300 MHz, $CD_3OD$): δ 7.90 (s, 1H), 7.70-7.74 (m, 1H), 7.59-7.61 (m, 2H), 4.03-4.09 (m, 1H), 3.87-3.96 (m, 2H), 3.66-3.82 (m, 5H), 3.46-3.53 (m, 1H), 1.44-1.48 (m, 2H), 1.40 (d, J=6.6 Hz, 3H), 0.99-1.20 (m, 2H), 0.72-0.85 (m, 3H), 0.75 (d, J=6.6 Hz, 3H), 0.60-0.71 (m, 1H), 0.43-0.55 (m, 2H). MS (ES)=524 (M+1)+.

Preparative Example 16.2

8-bromo-2-chloro-7-(((trans)-4-methylcyclohexyl)methyl)-6-(m-tolyl)-7H-purine

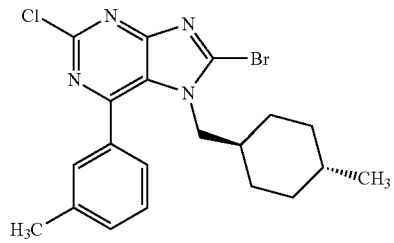 [SMILES: Cc1cccc(-c2nc(Cl)nc3nc(Br)n(C[C@H]4CC[C@H](C)CC4)c23)c1]

Step 1: 2,6-dichloro-7-(((trans)-4-methylcyclohexyl)methyl)-7H-purine (Preparative Example 11.4; 2.00 g, 6.68 mmol), 3-methylphenyl boronic acid (1.00 g, 7.35 mmol), aqueous $Na_2CO_3$ (2.0 mL, 1 M) and toluene (20 mL) were taken in a sealed tube vial (25 mL) and the mixture was degassed using $N_2$ for 15 minutes before $Pd(PPh_3)_4$ (770 mg, 0.66 mmol) was added. The vial was sealed and the reaction was heated at 100° C. for 12 hours. The reaction was then cooled to room temperature and extracted with EtOAc (2×75 mL). The combined organic layers were washed with water and brine and dried over anhydrous $Na_2SO_4$. The solvent was evaporated under vacuum. The crude product was purified on a Redisep 24 g silica gel column (0 to 100% EtOAc/hexanes) to afford 2-chloro-7-(((trans)-4-methylcyclohexyl)methyl)-6-(m-tolyl)-7H-purine. $^1H$ NMR (400 MHz, $CDCl_3$) δ 8.13 (s, 1H), 7.40-7.44 (m, 2H), 7.34-7.39 (m, 2H), 3.82 (d, J=6.0 Hz, 2H), 2.46 (s, 3H), 1.50-1.55 (m, 2H), 0.98-1.16 (m, 4H), 0.79 (d, J=6.0 Hz, 3H), 0.60-0.68 (m, 2H), 0.47-0.52 (m, 2H), MS (APCI)=355 (M+1)+.

Step 2: n-BuLi (2.4 mL, 2.4 mmol, 1 M in hexanes) was added dropwise to a solution of 2,2,6,6-tetramethylpiperidine (0.38 mL, 2.28 mmol) in anhydrous THF (4.0 mL) at 78° C. The reaction mixture was stirred at 78° C. for 2 hours. A solution of 2-chloro-7-(((trans)-4-methylcyclohexyl)methyl)-6-(m-tolyl)-7H-purine (270 mg, 0.76 mmol) in anhydrous THF (3.0 mL) was added dropwise over 5 minutes. The reaction mixture was stirred at 78° C. for 2 hours and then 1,3-dibromo-5,5-dimethylhydantoin (651 mg, 2.28 mmol) in THF (2.0 mL) was added dropwise. The reaction mixture was stirred at 78° C. for 2 hours and then quenched with saturated aqueous $NH_4Cl$ solution (15 mL). The layers were separated and the aqueous layer was extracted with EtOAc (3×10 mL). The combined organic layers were washed with brine, dried over anhydrous Na₂SO₄, filtered and concentrated in vacuo. The residue was purified on a RediSep 12 g silica gel column (0 to 100% EtOAc/hexanes) to afford 8-bromo-2-chloro-7-(((trans)-4-methylcyclohexyl)methyl)-6-(m-tolyl)-7H-purine. $^1$H NMR (400 MHz, CDCl₃): δ 7.42-7.46 (m, 1H), 7.36-7.39 (m, 2H), 7.30-7.34 (m, 1H), 3.95 (d, J=8.0 Hz, 2H), 2.46 (s, 3H), 1.42-1.51 (m, 2H), 1.13-1.17 (m, 1H), 0.93-1.07 (m, 3H), 0.77 (d, J=8.0 Hz, 3H), 0.68-0.72 (m, 2H), 0.48-0.54 (m, 2H), MS (APCI)=433 (M+1)⁺.

Example 16.3

5-(7-(((trans)-4-methylcyclohexyl)methyl)-8-morpholino-6-(m-tolyl)-7H-purin-2-yl)-1,3,4-oxadiazol-2(3H)-one

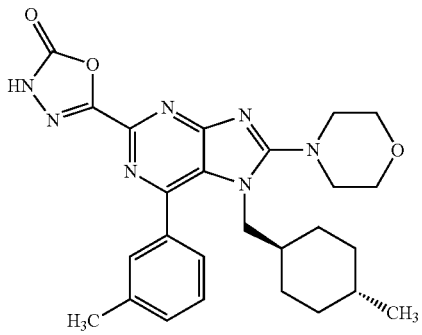 [SMILES: Cc1cccc(-c2nc(-c3n[nH]c(=O)o3)nc3nc(N4CCOCC4)n(C[C@H]4CC[C@H](C)CC4)c23)c1]

Step 1: Using a procedure analogous to that described in Example 16.2 (Step 1), and starting with 8-bromo-2-chloro-7-(((trans)-4-methylcyclohexyl)methyl)-6-(m-tolyl)-7H-purine (Preparative Example 16.2), 4-(2-chloro-7-(((trans)-4-methylcyclohexyl)methyl)-6-(m-tolyl)-7H-purin-8-yl)morpholine was prepared. $^1$H NMR (400 MHz, CDCl₃): δ 7.48 (s, 1H), 7.36-7.41 (m, 2H), 7.29-7.34 (m, 1H), 3.87 (t, J=4.7 Hz, 4H), 3.51-3.58 (m, 6H), 2.44 (s, 3H), 1.40-1.48 (m, 2H), 1.19-1.35 (m, 2H), 1.02-1.14 (m, 1H), 0.91-1.01 (m, 1H), 0.75 (d, J=6.5 Hz, 3H), 0.39-0.63 (m, 4H). MS (APCI)=440 (M+1)⁺.

Step 2: Using a procedure analogous to that described in Example 16.2 (Step 2), and starting with 4-(2-chloro-7-(((trans)-4-methylcyclohexyl)methyl)-6-(m-tolyl)-7H-purin-8-yl)morpholine, 7-(((trans)-4-methylcyclohexyl)methyl)-8-morpholino-6-(m-tolyl)-7H-purine-2-carbonitrile was prepared. MS (APCI)=431 (M+1)⁺.

Step 3: 7-(((trans)-4-methylcyclohexyl)methyl)-8-morpholino-6-(m-tolyl)-7H-purine-2-carbonitrile (180 mg, 0.42 mmol) was dissolved in 3N HCl in MeOH (18 mL) and stirred at 78° C. for 4 hours. The reaction mixture was quenched with saturated aqueous NaHCO₃ solution and extracted with EtOAc (2×80 mL). The combined organic extracts were dried over anhydrous Na₂SO₄, filtered and concentrated. The residue was purified on a RediSep 4 g silica gel column (0 to 100% EtOAc/Hexanes) to afford methyl 7-(((trans)-4-methylcyclohexyl)methyl)-8-morpholino-6-(m-tolyl)-7H-purine-2-carboxylate. MS (APCI)=464 (M+1)⁺.

Step 4: Using a procedure analogous to that described in Example 2.1 (Step 3), and starting with methyl 7-(((trans)-4-methylcyclohexyl)methyl)-8-morpholino-6-(m-tolyl)-7H-purine-2-carboxylate, 7-(((trans)-4-methylcyclohexyl)methyl)-8-morpholino-6-(m-tolyl)-7H-purine-2-carboxylic acid was prepared. $^1$H NMR (400 MHz, CDCl₃): δ 7.54 (s, 1H), 7.39-7.43 (m, 2H), 7.33-7.38 (m, 1H), 3.90 (t, J=9.2 Hz, 4H), 3.72-3.76 (m, 1H), 3.57-3.63 (m, 5H), 2.46 (s, 3H), 1.83-1.86 (m, 1H), 1.40-1.48 (m, 2H), 0.91-1.12 (m, 2H), 0.74 (d, J=6.5 Hz, 3H), 0.65-0.71 (m, 1H), 0.53-0.63 (m, 2H), 0.41-0.52 (m, 2H). MS (APCI)=450 (M+1)⁺.

Step 5: To a solution of 7-(((trans)-4-methylcyclohexyl)methyl)-8-morpholino-6-(m-tolyl)-7H-purine-2-carboxylic acid (40.0 mg, 0.08 mmol) in CH₂Cl₂ (3.0 mL) was added oxalyl chloride (0.04 mL, 0.44 mmol) dropwise. One drop of DMF was added to the reaction mixture and the reaction was stirred at room temperature for 45 minutes. The reaction was concentrated and dried under vacuum for 10 minutes. The residue was dissolved in THF (3.0 mL) and was added into a solution of 1.0 M hydrazine in THF (1.6 mL, 1.6 mmol) at room temperature and stirred for 2 hours. The reaction mixture was quenched with saturated aqueous NaHCO₃ solution and extracted with EtOAc (2×30 mL). The combined organic extracts were dried over anhydrous Na₂SO₄, filtered, and concentrated to afford 7-(((trans)-4-methylcyclohexyl)methyl)-8-morpholino-6-(m-tolyl)-7H-purine-2-carbohydrazide. MS (APCI)=464 (M+1)⁺.

Step 6: Using a procedure analogous to that described in Example 16.1 (Step 4) and starting with 7-(((trans)-4-methylcyclohexyl)methyl)-8-morpholino-6-(m-tolyl)-7H-purine-2-carbohydrazide, 5-(7-(((trans)-4-methylcyclohexyl)methyl)-8-morpholino-6-(m-tolyl)-7H-purin-2-yl)-1,3,4-oxadiazol-2(3H)-one was prepared. $^1$H NMR (300 MHz, CD₃OD): δ 7.61 (s, 1H), 7.40-7.56 (m, 3H), 3.86 (t, J=4.5 Hz, 4H), 3.73 (d, J=7.0 Hz, 2H), 3.55-3.59 (m, 4H), 2.48 (s, 3H), 1.39-1.48 (m, 2H), 1.25-1.36 (m, 1H), 0.94-1.20 (m, 2H), 0.73 (d, J=6.5 Hz, 3H), 0.60-0.69 (m, 3H), 0.38-0.52 (m, 2H). MS (ESI)=490 (M+1)⁺.

Preparative Example 16.3

8-bromo-6-(3-chlorophenyl)-7-(((trans)-4-methylcyclohexyl)methyl)-7H-purine-2-carbonitrile

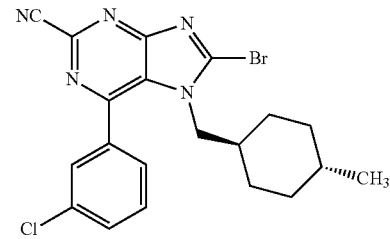 [SMILES: C[C@H]1CC[C@H](Cn2c(Br)nc3nc(C#N)nc(-c4cccc(Cl)c4)c32)CC1]

Step 1: 2-chloro-6-(3-chlorophenyl)-7-(((trans)-4-methylcyclohexyl)methyl)-7H-purine (200 mg, 0.53 mmol) and zinc cyanide (31.2 mg, 0.26 mmol) were suspended in DMA and degassed with argon for 20 minutes. Tetrakis(triphenylphosphine)palladium(0) (123 mg, 0.10 mmol) was then added and the mixture was degassed for another 5 minutes. The reaction was sealed and heated at 120° C. for 4 hours. The reaction was then diluted with water (20 mL) and extracted with EtOAc (2×50 mL). The combined organic extracts were dried over anhydrous Na₂SO₄, filtered, and concentrated. The residue was purified on a RediSep 12 g silica gel column (0 to 10% EtOAc/Hexanes) to afford 6-(3-chlorophenyl)-7-(((trans)-4-methylcyclohexyl)methyl)-7H-purine-2-carbonitrile. $^1$H NMR (300 MHz, CDCl₃): δ 8.15 (s, 1H), 7.44-7.59 (m, 4H), 3.95 (d, J=6.9 Hz, 2H), 1.50-1.55 (m, 2H), 1.08-1.29 (m, 2H), 0.85-1.01 (m, 4H), 0.78 (d, J=6.6 Hz, 3H), 0.52-0.56 (m, 2H). MS (APCI)=366 (M+1)⁺.

Step 2: 6-(3-chlorophenyl)-7-(((trans)-4-methylcyclohexyl)methyl)-7H-purine-2-carbonitrile (2.40 g, 6.57 mmol) was dissolved in anhydrous THF (100 mL) and cooled to −78° C. 2,2,6,6-tetramethylpiperidinylmagnesium chloride, lithium chloride complex 1.0 M in anhydrous THF/toluene (20 mL, 20 mmol) was added slowly into the solution at −78° C. This reaction mixture was stirred at −78° C. for 2 hours. A solution of 1,3-dibromo-5,5-dimethylhydantoin (5.70 g, 19.7 mmol) in THF (20 mL) was added into the reaction mixture at −78° C. The reaction was allowed to warm to room temperature and stirred for 2 hours. The reaction was quenched with saturated NH₄Cl solution at −78° C. and extracted with CH₂Cl₂ (2×200 mL). The combined organic extracts were dried over anhydrous Na₂SO₄ and concentrated. The residue was purified on a RediSep 40 g silica gel column (0 to 10% EtOAc/hexanes) to afford 8-bromo-6-(3-chlorophenyl)-7-(((trans)-4-methylcyclohexyl)methyl)-7H-purine-2-carbonitrile. ¹H NMR (300 MHz, CDCl₃): δ 7.51-7.65 (m, 3H), 7.43-7.51 (m, 1H), 4.02 (d, J=7.0 Hz, 2H), 2.41-2.54 (m, 1H), 2.09-2.36 (m, 2H), 1.83-2.05 (m, 1H), 0.90-1.02 (m, 3H), 0.78 (d, J=6.5 Hz, 3H), 0.66-0.75 (m, 1H), 0.43-0.63 (m, 2H).

Example 16.4

3-(6-(3-chlorophenyl)-8-(((R)-1-hydroxypropan-2-yl)amino)-7-(((trans)-4-methylcyclohexyl)methyl)-7H-purin-2-yl)-1,2,4-oxadiazol-5(4H)-one

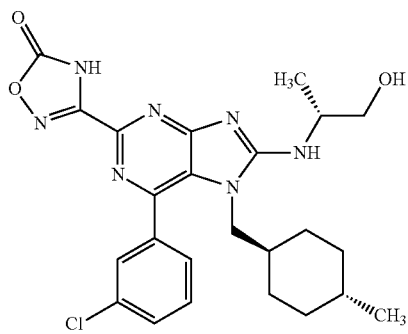 [SMILES: C[C@H](CO)Nc1nc2nc(-c3noc(=O)[nH]3)nc(-c3cccc(Cl)c3)c2n1C[C@H]1CC[C@H](C)CC1]

Step 1: Using a procedure analogous to that described in Example 16.2 (Step 1), and starting with 8-bromo-6-(3-chlorophenyl)-7-(((trans)-4-methylcyclohexyl)methyl)-7H-purine-2-carbonitrile (Preparative Example 16.3), 6-(3-chlorophenyl)-8-(((R)-1-hydroxypropan-2-yl)amino)-7-(((trans)-4-methylcyclohexyl)methyl)-7H-purine-2-carbonitrile was prepared. MS (APCI)=439 (M+1)⁺.

Step 2: 6-(3-chlorophenyl)-8-(((R)-1-hydroxypropan-2-yl)amino)-7-(((trans)-4-methylcyclohexyl)methyl)-7H-purine-2-carbonitrile (50.0 mg, 0.11 mmol), tert-butyldimethylsilyl chloride (68.0 mg, 0.45 mmol), and imidazole (62.0 mg, 0.91 mmol) were dissolved in CH₂Cl₂ and stirred at room temperature for 4 hours. The reaction mixture was quenched with water (20 mL) and extracted with EtOAc (2×50 mL). The combined organic extracts were dried over anhydrous Na₂SO₄, filtered, and concentrated to afford crude 8-(((R)-1-((tert-butyldimethylsilyl)oxy)propan-2-yl)amino)-6-(3-chlorophenyl)-7-(((trans)-4-methylcyclohexyl)methyl)-7H-purine-2-carbonitrile. MS (APCI)=553 (M+1)⁺.

Step 3: Using a procedure analogous to that described in Example 16.1 (Step 3), and starting with 8-(((R)-1-((tert-butyldimethylsilyl)oxy)propan-2-yl)amino)-6-(3-chlorophenyl)-7-(((trans)-4-methylcyclohexyl)methyl)-7H-purine-2-carbonitrile, (Z)-8-(((R)-1-((tert-butyldimethylsilyl)oxy)propan-2-yl)amino)-6-(3-chlorophenyl)-N'-hydroxy-7-(((trans)-4-methylcyclohexyl)methyl)-7H-purine-2-carboximidamide was prepared. MS (ESI)=586 (M+1)⁺.

Step 4: Using a procedure analogous to that described in Example 16.1 (Step 4), and starting with (Z)-8-(((R)-1-((tert-butyldimethylsilyl)oxy)propan-2-yl)amino)-6-(3-chlorophenyl)-N'-hydroxy-7-(((trans)-4-methylcyclohexyl)methyl)-7H-purine-2-carboximidamide, 3-(8-(((R)-1-((tert-butyldimethylsilyl)oxy)propan-2-yl)amino)-6-(3-chlorophenyl)-7-(((trans)-4-methylcyclohexyl)methyl)-7H-purin-2-yl)-1,2,4-oxadiazol-5(4H)-one was prepared. MS (ESI)=612 (M+1)⁺.

Step 5: To a solution of 3-(8-(((R)-1-((tert-butyldimethylsilyl)oxy)propan-2-yl)amino)-6-(3-chlorophenyl)-7-(((trans)-4-methylcyclohexyl)methyl)-7H-purin-2-yl)-1,2,4-oxadiazol-5(4H)-one (70.0 mg, 0.11 mmol) in THF (4.0 mL) was added tetra-n-butylammonium fluoride (0.17 mL, 1 M in THF, 0.17 mmol) dropwise. The reaction mixture was stirred at room temperature for 15 minutes and then quenched with water (20 mL). The mixture was extracted with EtOAc (2×50 mL), dried over anhydrous Na₂SO₄, filtered and concentrated. The residue was purified on a RediSep 4 g silica gel column (0 to 10% MeOH/CH₂Cl₂) to afford 3-(6-(3-chlorophenyl)-8-(((R)-1-hydroxypropan-2-yl)amino)-7-(((trans)-4-methylcyclohexyl)methyl)-7H-purin-2-yl)-1,2,4-oxadiazol-5(4H)-one. ¹H NMR (400 MHz, CD₃OD): δ 7.72 (s, 1H), 7.55-7.61 (m, 3H), 4.28 (q, J=6.2 Hz, 1H), 3.71 (d, J=7.2 Hz, 2H), 3.67 (d, J=5.8 Hz, 2H), 1.56-1.70 (m, 1H), 1.46-1.55 (m, 2H), 1.38-1.44 (m, 1H), 1.33 (d, J=6.7 Hz, 3H), 1.05-1.20 (m, 2H), 0.95-1.00 (m, 1H), 0.77 (d, J=6.5 Hz, 3H), 0.68-0.75 (m, 1H), 0.50-0.65 (m, 2H). MS (ESI)=498 (M+1)⁺

Example 16.5

3-(6-(3-chlorophenyl)-8-(((S)-1-hydroxy-2-phenylpropan-2-yl)amino)-7-(((trans)-4-methylcyclohexyl)methyl)-7H-purin-2-yl)-1,2,4-oxadiazol-5(4H)-one

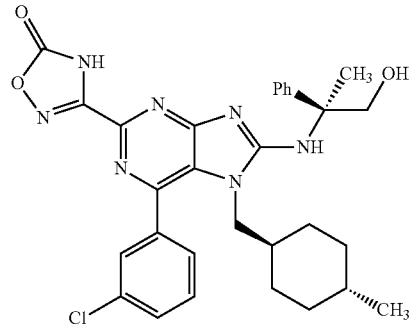 [SMILES: C[C@](CO)(Nc1nc2nc(-c3noc(=O)[nH]3)nc(-c3cccc(Cl)c3)c2n1C[C@H]1CC[C@H](C)CC1)c1ccccc1]

Step 1: To a solution of (R)-2-amino-2-phenylpropanoic acid (250 mg, 1.51 mmol) in THF (10 mL) was added borane-tetrahydrofuran complex solution 1.0 M in THF (6.0 mL, 6.0 mmol) dropwise. The reaction mixture was stirred at room temperature for 12 hours. The reaction mixture was quenched with saturated aqueous NH₄Cl solution and stirred with chloroform-methanol-ammonia (1:1:1, 100 mL) solution for 1 hour. The organic extract was dried over anhydrous Na₂SO₄, filtered and concentrated. The residue was purified on a RediSep 4 g silica gel column (0 to 100% EtOAc/hexanes) to afford (R)-2-amino-2-phenylpropan-1-ol. ¹H NMR (400 MHz, CDCl₃): δ 7.43-7.49 (m, 2H), 7.29-7.35 (m, 2H), 7.22-7.28 (m, 1H), 3.87 (dd, J=15.2, 11.8, 2H), 1.62 (s, 3H). MS (APCI)=152 (M+1)⁺.

Step 2: Using a procedure analogous to that described in Example 16.4, and starting with 8-bromo-6-(3-chlorophenyl)-7-(((trans)-4-methylcyclohexyl)methyl)-7H-purine-2-carbonitrile (Preparative Example 16.3) and (R)-2-amino-2-phenylpropan-1-ol, 3-(6-(3-chlorophenyl)-8-(((S)-1-hydroxy-2-phenylpropan-2-yl)amino)-7-(((trans)-4-methylcyclohexyl)methyl)-7H-purin-2-yl)-1,2,4-oxadiazol-5(4H)-one was prepared. ¹H NMR (400 MHz, CD₃OD): δ 7.73 (s, 1H), 7.55-7.62 (m, 3H), 7.43 (d, J=7.6 Hz, 2H), 7.32 (t, J=7.6 Hz, 2H), 7.19-7.26 (m, 1H), 4.06 (m, 1H), 3.76-3.89 (m, 3H), 1.88 (s, 3H), 1.52-1.60 (m, 2H), 1.01-1.25 (m, 4H), 0.83-0.92 (m, 1H), 0.81 (d, J=6.5 Hz, 3H), 0.73-0.78 (m, 1H), 0.58-0.71 (m, 2H). MS (ESI)=574 (M+1)⁺.

Example 16.6

3-(6-(3-chlorophenyl)-7-(((trans)-4-methylcyclohexyl)methyl)-8-((R)-3-methylmorpholino)-7H-purin-2-yl)-1,2,4-oxadiazol-5(4H)-one

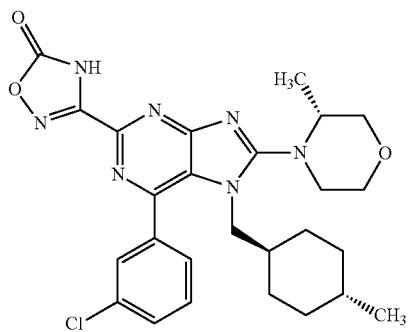 [SMILES: C[C@@H]1COCCN1c1nc2nc(-c3noc(=O)[nH]3)nc(-c3cccc(Cl)c3)c2n1C[C@H]1CC[C@H](C)CC1]

Step 1: 8-bromo-2-chloro-6-(3-chlorophenyl)-7-(((trans)-4-methylcyclohexyl)methyl)-7H-purine (Preparative Example 16.1, 300 mg, 0.66 mmol), (R)-3-methylmorpholine (133 mg, 1.32 mmol), and potassium fluoride (306 mg, 6.60 mmol) were dissolved in DMSO (5.0 mL) and heated at 85° C. for 12 hours. The reaction was cooled to room temperature, diluted with water (50 mL), and extracted with EtOAc (2×50 mL). The combined organic extracts were dried over anhydrous Na₂SO₄, filtered and concentrated. The residue was purified on a RediSep 12 g silica gel column (0 to 100% EtOAc/Hexanes) to afford (R)-4-(2-chloro-6-(3-chlorophenyl)-7-(((trans)-4-methylcyclohexyl)methyl)-7H-purin-8-yl)-3-methylmorpholine. ¹H NMR (300 MHz, CDCl₃): δ 7.65 (s, 1H), 7.47-7.52 (m, 3H), 3.76-4.01 (m, 4H), 3.46-3.69 (m, 5H), 1.45-1.48 (m, 2H), 1.41 (d, J=6.0 Hz, 3H), 0.97-1.10 (m, 3H), 0.77-0.79 (m, 1H), 0.76 (d, J=6.0 Hz, 3H), 0.46-0.67 (m, 4H). MS (APCI) 474 (M+1)⁺.

Step 2: Using a procedure analogous to that described in Example 16.1 (Step 2), and starting with (R)-4-(2-chloro-6-(3-chlorophenyl)-7-(((trans)-4-methylcyclohexyl)methyl)-7H-purin-8-yl)-3-methylmorpholine, 6-(3-chlorophenyl)-7-(((trans)-4-methylcyclohexyl)methyl)-8-((R)-3-methylmorpholino)-7H-purine-2-carbonitrile was prepared. ¹H NMR (400 MHz, CDCl₃): δ 7.66 (s, 1H), 7.53-7.55 (m, 3H), 4.07-4.05 (m, 1H), 3.88-3.96 (m, 2H), 3.80-3.83 (m, 1H), 3.51-3.67 (m, 5H), 1.45-1.46 (m, 2H), 1.45 (d, J=8.0 Hz, 3H), 1.09-1.14 (m, 1H), 0.86-0.90 (m, 2H), 0.76 (d, J=8.0 Hz, 3H), 0.53-0.65 (m, 3H), 0.47-0.52 (m, 2H). MS (APCI)=465 (M+1)⁺.

Step 3: Using a procedure analogous to that described in Example 16.1 (Step 3), and starting with 6-(3-chlorophenyl)-7-(((trans)-4-methylcyclohexyl)methyl)-8-((R)-3-methylmorpholino)-7H-purine-2-carbonitrile, (Z)-6-(3-chlorophenyl)-N'-hydroxy-7-(((trans)-4-methylcyclohexyl)methyl)-8-((R)-3-methylmorpholino)-7H-purine-2-carboximidamide was prepared. MS (APCI)=498 (M+1)⁺.

Step 4: Using a procedure analogous to that described in Example 16.1 (Step 4), and starting with (Z)-6-(3-chlorophenyl)-N'-hydroxy-7-(((trans)-4-methylcyclohexyl)methyl)-8-((R)-3-methylmorpholino)-7H-purine-2-carboximidamide, 3-(6-(3-chlorophenyl)-7-(((trans)-4-methylcyclohexyl)methyl)-8-((R)-3-methylmorpholino)-7H-purin-2-yl)-1,2,4-oxadiazol-5(4H)-one was prepared. ¹H NMR (400 MHz, CD₃OD): δ 7.91-7.90 (s, 1H), 7.71-7.74 (m, 1H), 7.58-7.63 (m, 2H), 4.06-4.08 (m, 1H), 3.81-3.88 (m, 2H), 3.69-3.78 (m, 5H), 3.47-3.51 (m, 1H), 1.45-1.48 (m, 2H), 1.41 (d, J=8.0 Hz, 3H), 1.00-1.13 (m, 2H), 0.77-0.80 (m, 2H), 0.72 (d, J=8.0 Hz, 3H), 0.66-0.69 (m, 2H), 0.47-0.51 (m, 2H). MS (ES)=524 (M+1)⁺.

Example 16.7

5-(6-(3-chlorophenyl)-7-(((trans)-4-methylcyclohexyl)methyl)-8-((R)-3-methylmorpholino)-7H-purin-2-yl)-1,3,4-oxadiazol-2(3H)-one

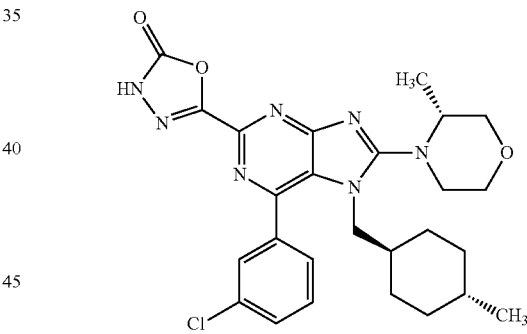

Step 1: 6-(3-chlorophenyl)-7-(((trans)-4-methylcyclohexyl)methyl)-8-((R)-3-methylmorpholino)-7H-purine-2-carbonitrile (115 mg, 0.24 mmol) was dissolved in 3N HCl in MeOH (4.0 mL) and refluxed for 4 hours. The reaction mixture was quenched with saturated aqueous NaHCO₃ solution and extracted with EtOAc (2×30 mL). The combined organic extracts were dried over anhydrous Na₂SO₄, filtered and concentrated. The residue was purified on a RediSep 12 g silica gel column (0 to 100% EtOAc/Hexanes) to afford methyl 6-(3-chlorophenyl)-7-(((trans)-4-methylcyclohexyl)methyl)-8-((R)-3-methylmorpholino)-7H-purine-2-carboxylate. MS (APCI)=498 (M+1)⁺.

Step 2: To a solution of methyl 6-(3-chlorophenyl)-7-(((trans)-4-methylcyclohexyl)methyl)-8-((R)-3-methylmorpholino)-7H-purine-2-carboxylate (75.0 mg, 0.15 mmol) in methanol (0.7 mL) was added 1.0 M hydrazine in THF (6.0 mL, 6.0 mmol) at room temperature and the reaction was stirred for 2 hours. The reaction mixture was quenched with water (20 mL) and extracted with EtOAc (2×20 mL). The combined organic extracts were dried over anhydrous Na₂SO₄, filtered, and concentrated to afford crude 6-(3-chlorophenyl)-7-(((trans)-4-methylcyclohexyl)methyl)-8-((R)-3-methylmorpholino)-7H-purine-2-carbohydrazide. MS (APCI)=498 (M+1)⁺.

Step 3: Using a procedure analogous to that described in Example 16.1 (Step 4), and starting with 6-(3-chlorophenyl)-7-(((trans)-4-methylcyclohexyl)methyl)-8-((R)-3-methylmorpholino)-7H-purine-2-carbohydrazide, 5-(6-(3-chlorophenyl)-7-(((trans)-4-methylcyclohexyl)methyl)-8-((R)-3-methylmorpholino)-7H-purin-2-yl)-1,3,4-oxadiazol-2(3H)-one was prepared. ¹H NMR (400 MHz, CD₃OD): δ 7.86 (s, 1H), 7.70-7.72 (m, 1H), 7.60-7.62 (m, 2H), 4.06-4.08 (m, 1H), 3.87-3.94 (m, 2H), 3.69-3.80 (m, 5H), 3.47-3.51 (m, 1H), 1.45-1.48 (m, 2H), 1.40 (d, J=8.0 Hz, 3H), 1.01-1.13 (m, 2H), 0.77-0.80 (m, 2H), 0.71 (d, J=8.0 Hz, 3H), 0.66-0.69 (m, 2H), 0.45-0.51 (m, 2H). MS (ES)=524 (M+1)⁺

Preparative Example 16.4

(Z)-6-(3-chlorophenyl)-N'-hydroxy-8-(((1R,2S)-2-hydroxy-1-phenylpropyl)amino)-7-(((trans)-4-methylcyclohexyl)methyl)-7H-purine-2-carboximidamide

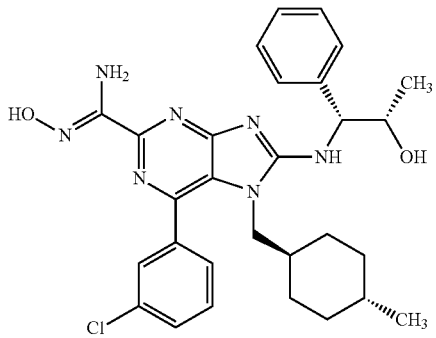 [SMILES: C[C@H](O)[C@H](Nc1nc2nc(/C(N)=N/O)nc(-c3cccc(Cl)c3)c2n1C[C@H]1CC[C@H](C)CC1)c1ccccc1]

Step 1: Using a procedure analogous to that described in Example 16.6 (Step 1), and starting with Preparative Example 16.3, 8-bromo-6-(3-chlorophenyl)-7-(((trans)-4-methylcyclohexyl)methyl)-7H-purine-2-carbonitrile and (1R,2S)-1-amino-1-phenylpropan-2-ol hydrochloride, 6-(3-chlorophenyl)-8-(((1R,2S)-2-hydroxy-1-phenylpropyl)amino)-7-(((trans)-4-methylcyclohexyl)methyl)-7H-purine-2-carbonitrile was prepared. ¹H NMR (400 MHz, CDCl₃): δ 7.45-7.51 (m, 3H), 7.31-7.40 (m, 6H), 5.99 (d, J=8.0 Hz, 1H), 5.32-5.30 (br s, 1H), 5.26 (dd, J=4.0, 8.0 Hz, 1H), 4.31-4.36 (br s, 1H), 3.55 (d, J=4.0 Hz, 2H), 2.44-2.51 (m, 1H), 2.16-2.34 (m, 3H), 1.92-1.98 (m, 1H), 1.12 (d, J=8.0 Hz, 3H), 1.03-1.06 (m, 2H), 0.86 (d, J=8.0 Hz, 3H), 0.58-0.70 (m, 3H). MS (APCI)=515 (M+1)⁺.

Step 2: Using a procedure analogous to that described in Example 16.1 (Step 3), and starting with 6-(3-chlorophenyl)-8-(((1R,2S)-2-hydroxy-1-phenylpropyl)amino)-7-(((trans)-4-methylcyclohexyl)methyl)-7H-purine-2-carbonitrile, (Z)-6-(3-chlorophenyl)-N'-hydroxy-8-(((1R,2S)-2-hydroxy-1-phenylpropyl)amino)-7-(((trans)-4-methylcyclohexyl)methyl)-7H-purine-2-carboximidamide was prepared. MS (APCI)=548 (M+1)⁺.

Example 16.8

3-(6-(3-chlorophenyl)-8-(((1R,2S)-2-hydroxy-1-phenylpropyl)amino)-7-(((trans)-4-methylcyclohexyl)methyl)-7H-purin-2-yl)-1,2,4-oxadiazol-5(4H)-one and Example 16.9

3-(6-(3-chlorophenyl)-8-((4R,5S)-5-methyl-2-oxo-4-phenyloxazolidin-3-yl)-7-(((trans)-4-methylcyclohexyl)methyl)-7H-purin-2-yl)-1,2,4-oxadiazol-5(4H)-one

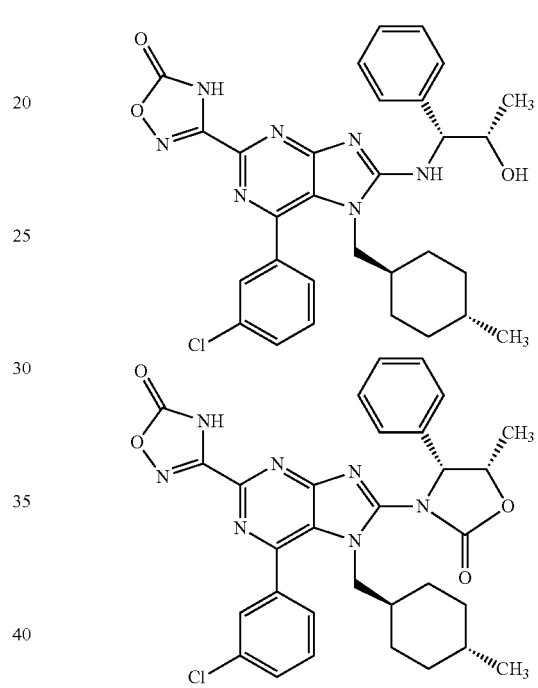

Using a procedure analogous to that described in Example 16.1 (Step 4), and starting with (Z)-6-(3-chlorophenyl)-N'-hydroxy-8-(((trans)-2-hydroxy-1-phenylpropyl)amino)-7-(((trans)-4-methylcyclohexyl)methyl)-7H-purine-2-carboximidamide, 3-(6-(3-chlorophenyl)-8-(((1R,2S)-2-hydroxy-1-phenylpropyl)amino)-7-(((trans)-4-methylcyclohexyl)methyl)-7H-purin-2-yl)-1,2,4-oxadiazol-5(4H)-one, Example 16.8 was prepared. 3-(6-(3-chlorophenyl)-8-((4R,5S)-5-methyl-2-oxo-4-phenyloxazolidin-3-yl)-7-(((trans)-4-methylcyclohexyl)methyl)-7H-purin-2-yl)-1,2,4-oxadiazol-5(4H)-one (Example 16.9) was also isolated from the reaction. Example 16.8: ¹H NMR (400 MHz, CD₃OD): δ 7.86 (s, 1H), 7.63-7.68 (m, 3H), 7.36-7.42 (m, 5H), 6.01 (d, J=8.0 Hz, 1H), 5.40 (quint, 7.0 Hz, 1H), 4.16 (dd, J=8.0, 12.0 Hz, 1H), 3.97 (dd, J=8.0, 12.0 Hz, 1H), 1.45-1.48 (m, 1H), 1.26-1.37 (m, 2H), 1.15 (d, J=8.0 Hz, 3H), 0.87-0.97 (m, 3H), 0.75 (d, J=8.0 Hz, 3H), 0.65-0.71 (m, 2H), 0.49-0.56 (m, 2H). MS (APCI)=574 (M+1)⁺. Example 16.9: ¹H NMR (400 MHz, CD₃OD): δ 7.70-7.72 (m, 1H), 7.49-7.58 (m, 4H), 7.30-7.34 (m, 3H), 7.07 (s, 1H), 5.08 (d, J=8.0 Hz, 1H), 4.30 (quint, 7.0 Hz, 1H), 3.76 (d, J=8.0 Hz, 2H), 1.42-1.51 (m, 2H), 1.27 (d, J=8.0 Hz, 3H), 1.03-1.12 (m, 1H), 0.85-1.00 (m, 3H), 0.75 (d, J=8.0 Hz, 3H), 0.64-0.71 (m, 2H), 0.50-0.58 (m, 2H). MS (APCI)=600 (M+1)⁺

Preparative Example 16.5

8-bromo-2-chloro-6-(5-chloropyridin-3-yl)-7-(((trans)-4-methylcyclohexyl)methyl)-7H-purine

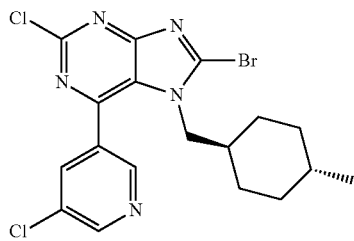 [SMILES: C[C@H]1CC[C@H](Cn2c(Br)nc3nc(Cl)nc(-c4cncc(Cl)c4)c32)CC1]

Step 1: 2,6-dichloro-7-(((trans)-4-methylcyclohexyl)methyl)-7H-purine (Preparative Example 11.4; 200 mg, 0.67 mmol), (5-chloropyridin-3-yl)boronic acid (126 mg, 0.80 mmol), aqueous $K_3PO_4$ (0.5 mL, 1 M), and dioxane (2.0 mL) were taken in sealable tube and the mixture was degassed using $N_2$ for 15 minutes before Pd(dppf)Cl$_2$ (98.1 mg, 0.13 mmol) was added. The tube was sealed and the reaction was heated at 100° C. for 15 minutes. The reaction was cooled to room temperature and extracted with EtOAc (2×25 mL), the combined organic layers were washed with water and brine and dried over $Na_2SO_4$. The solvent was evaporated under vacuum. The crude product was loaded onto a Redisep 12 g silica gel column. Purification with 0 to 10% EtOAc/hexanes afforded 2-chloro-6-(5-chloropyridin-3-yl)-7-(((trans)-4-methylcyclohexyl)methyl)-7H-purine. MS (APCI)=375 (M+1)$^+$.

Step 2: 2-chloro-6-(5-chloropyridin-3-yl)-7-(((trans)-4-methylcyclohexyl)methyl)-7H-purine (2.40 g, 6.57 mmol) was dissolved in THF (100 mL) and cooled to −78° C. 2,2,6,6-tetramethylpiperidinylmagnesium chloride, lithium chloride complex 1.0M in THF/toluene (20 mL, 20 mmol) was added slowly into the solution at −78° C. This reaction mixture was stirred at −78° C. for 2 hours. A solution of 1,3-dibromo-5,5-dimethylhydantoin (5.70 g, 19.7 mmol) in THF (20 mL) was added into the reaction mixture at −78° C. The reaction was allowed to warm up to room temperature and stirred for 2 hours. The reaction was then quenched with saturated $NH_4Cl$ solution at −78° C. and extracted with $CH_2Cl_2$ (2×200 mL). The combined organic extracts were dried over anhydrous $Na_2SO_4$ and concentrated. The residue was purified on a RediSep 40 g silica gel column (0 to 100% EtOAc/hexanes) to afford 8-bromo-2-chloro-6-(5-chloropyridin-3-yl)-7-(((trans)-4-methylcyclohexyl)methyl)-7H-purine. $^1$H NMR (300 MHz, CDCl$_3$): δ 8.81 (d, J=2.4 Hz, 1H), 8.72 (d, J=2.1 Hz, 1H), 8.03 (t, J=2.1 Hz, 1H), 3.86 (d, J=6.9 Hz, 2H), 1.59-1.60 (m, 2H), 1.19-1.29 (m, 1H), 1.10-1.18 (m, 2H), 0.91-1.02 (m, 1H), 0.79 (d, J=6.6 Hz, 3H), 0.74-0.75 (m, 2H), 0.66-0.72 (m, 1H), 0.53-0.65 (m, 1H).

Example 16.10

3-(6-(5-chloropyridin-3-yl)-7-(((trans)-4-methylcyclohexyl)methyl)-8-((R)-3-methylmorpholino)-7H-purin-2-yl)-1,2,4-oxadiazol-5(4H)-one

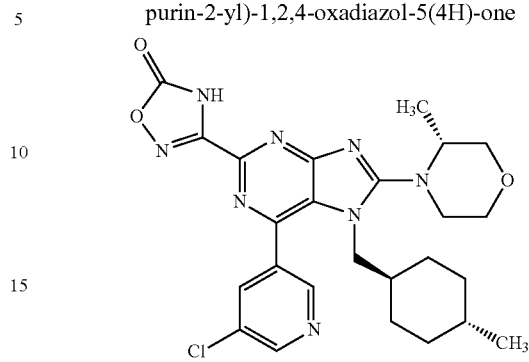

Step 1: Using a procedure analogous to that described in Example 16.2 (Step 1), and starting with 8-bromo-2-chloro-6-(5-chloropyridin-3-yl)-7-(((trans)-4-methylcyclohexyl)methyl)-7H-purine (Preparative Example 16.5) and (R)-3-methylmorpholine, (R)-4-(2-chloro-6-(5-chloropyridin-3-yl)-7-(((trans)-4-methylcyclohexyl)methyl)-7H-purin-8-yl)-3-methylmorpholine was prepared. MS (APCI)=475 (M+1)$^+$.

Step 2: (R)-4-(2-chloro-6-(5-chloropyridin-3-yl)-7-(((trans)-4-methylcyclohexyl)methyl)-7H-purin-8-yl)-3-methylmorpholine (200 mg, 0.42 mmol) and zinc cyanide (22.2 mg, 0.18 mmol) were suspended in DMA (2 mL) and the mixture was degassed with argon for 20 minutes. Tetrakis(triphenylphosphine)palladium(0) (48.7 mg, 0.04 mmol) was added and the reaction mixture was degassed for another 5 minutes. The vial was sealed and the reaction was heated at 120° C. for 2 hours. The reaction was cooled to room temperature, diluted with water (20 mL), and extracted with EtOAc (2×50 mL). The combined organic extracts were dried over anhydrous $Na_2SO_4$, filtered, and concentrated. The residue was purified on a RediSep 15 g C18 silica gel column (0 to 100% water/acetonitrile) to afford 6-(5-chloropyridin-3-yl)-7-(((trans)-4-methylcyclohexyl)methyl)-8-((R)-3-methylmorpholino)-7H-purine-2-carbonitrile. $^1$H NMR (300 MHz, CDCl$_3$): δ 8.75 (d, J=2.1 Hz, 1H), 8.73 (d, J=1.8 Hz, 1H), 8.13 (t, J=2.1 Hz, 1H), 4.09-4.11 (m, 1H), 3.67-3.99 (m, 8H), 1.51 (m, 2H), 1.45 (d, J=6.6 Hz, 3H), 1.12-1.19 (m, 2H), 0.95-1.01 (m, 2H), 0.75 (d, J=6.6 Hz, 3H), 0.44-0.68 (m, 4H). MS (APCI)=466 (M+1)$^+$.

Step 3: Using a procedure analogous to that described in Example 16.1 (Step 3), and starting 6-(5-chloropyridin-3-yl)-7-(((trans)-4-methylcyclohexyl)methyl)-8-((R)-3-methylmorpholino)-7H-purine-2-carbonitrile, (Z)-6-(5-chloropyridin-3-yl)-N'-hydroxy-7-(((trans)-4-methylcyclohexyl)methyl)-8-((R)-3-methylmorpholino)-7H-purine-2-carboximidamide was prepared. MS (APCI)=499 (M+1)$^+$.

Step 4: Using a procedure analogous to that described in Example 16.1 (Step 4), and starting with (Z)-6-(5-chloropyridin-3-yl)-N'-hydroxy-7-(((trans)-4-methylcyclohexyl)methyl)-8-((R)-3-methylmorpholino)-7H-purine-2-carboximidamide, 3-(6-(5-chloropyridin-3-yl)-7-(((trans)-4-methylcyclohexyl)methyl)-8-((R)-3-methylmorpholino)-7H-purin-2-yl)-1,2,4-oxadiazol-5(4H)-one was prepared. $^1$H NMR (300 MHz, CD$_3$OD): δ 8.92 (d, J=1.5 Hz, 1H), 8.78 (d, J=2.1 Hz, 1H), 8.44 (t, J=1.8 Hz, 1H), 4.10-4.13 (m, 1H), 3.88-3.96 (m, 2H), 3.79-3.87 (m, 4H), 3.54-3.74 (m, 2H), 1.45-1.49 (m, 2H), 1.41 (d, J=6.6 Hz, 3H), 1.18-1.28 (m, 2H), 1.08-1.14 (m, 2H), 0.74 (d, J=6.3 Hz, 3H), 0.43-0.68 (m, 4H). MS (ESI)=525 (M+1)$^+$. (m,

Example 16.11

5-(6-(5-chloropyridin-3-yl)-7-(((trans)-4-methylcyclohexyl)methyl)-8-((R)-3-methylmorpholino)-7H-purin-2-yl)-1,3,4-oxadiazol-2(3H)-one

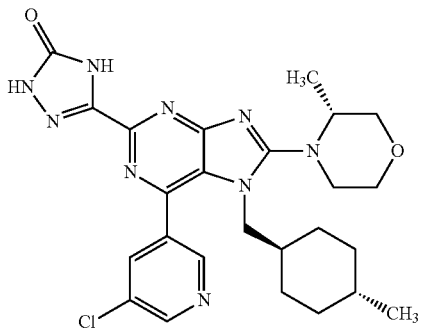 [SMILES: C[C@@H]1COCCN1c1nc2nc(-c3n[nH]c(=O)[nH]3)nc(-c3cncc(Cl)c3)c2n1C[C@H]1CC[C@H](C)CC1]

Step 1: Using a procedure analogous to that described in Example 16.3 (Step 3), and starting with 6-(5-chloropyridin-3-yl)-7-(((trans)-4-methylcyclohexyl)methyl)-8-((R)-3-methylmorpholino)-7H-purine-2-carbonitrile, methyl 6-(5-chloropyridin-3-yl)-7-(((trans)-4-methylcyclohexyl)methyl)-8-((R)-3-methylmorpholino)-7H-purine-2-carboxylate was prepared. MS (APCI)=499 (M+1)+.

Step 2: To a solution of methyl 6-(5-chloropyridin-3-yl)-7-(((trans)-4-methylcyclohexyl)methyl)-8-((R)-3-methylmorpholino)-7H-purine-2-carboxylate (45.0 mg, 0.09 mmol) in $CH_3OH$ (0.5 mL) was added 1.0 M hydrazine in THF (3.6 mL, 3.6 mmol). The reaction mixture was stirred at room temperature for 2 hours. The reaction was quenched with water (30 mL) and extracted with $CH_2Cl_2$ (2×50 mL). The combined organic extracts were dried over anhydrous $Na_2SO_4$, filtered, and concentrated to afford crude 6-(5-chloropyridin-3-yl)-7-(((trans)-4-methylcyclohexyl)methyl)-8-((R)-3-methylmorpholino)-7H-purine-2-carbohydrazide. MS (APCI)=499 (M+1)+.

Step 3: Using a procedure analogous to that described in Example 16.1 (Step 4), and starting 6-(5-chloropyridin-3-yl)-7-(((trans)-4-methylcyclohexyl)methyl)-8-((R)-3-methylmorpholino)-7H-purine-2-carbohydrazide, 5-(6-(5-chloropyridin-3-yl)-7-(((trans)-4-methylcyclohexyl)methyl)-8-((R)-3-methylmorpholino)-7H-purin-2-yl)-1,3,4-oxadiazol-2(3H)-one was prepared. $^1$H NMR (400 MHz, $CD_3OD$): δ 8.91 (d, J=1.6 Hz, 1H), 8.79 (d, J=2.4 Hz, 1H), 8.42 (t, J=2.0 Hz, 1H), 4.09-4.11 (m, 1H), 3.79-3.93 (m, 2H), 3.74-3.79 (m, 4H), 3.55-3.74 (m, 2H), 1.46-1.49 (m, 2H), 1.40 (d, J=6.4 Hz, 3H), 1.17-1.27 (m, 2H), 1.07-1.15 (m, 2H), 0.74 (d, J=6.8 Hz, 3H), 0.45-0.67 (m, 4H). MS (ES)=525 (M+1)+

Preparative Example 16.6

4-isopropylpicolinaldehyde

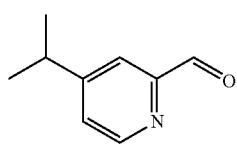

Step 1: To a solution of $Ph_3PCH_3Br$ (307 g, 0.86 mol) in THF (1500 mL) was added t-BuOK (96 g, 0.86 mol) at 0° C. under $N_2$. The mixture was stirred at 0° C. for 30 min and a solution of 1-(pyridin-4-yl)ethanone (80 g, 0.66 mol) in THF (500 mL) was added. The reaction mixture was warmed to room temperature and stirred for 2 h. The reaction was quenched by addition of aqueous $NH_4Cl$ (500 mL) and the organic layer was concentrated. The residue was extracted with EtOAc (1000 mL×3). The organic phase was washed with brine, dried over $Na_2SO_4$ and concentrated to give a crude product which was purified by silica gel column chromatography (petroleum/EtOAc=50:1 to petroleum/EtOAc 5:1) to give 4-(prop-1-en-2-yl)pyridine. $^1$H NMR (400 MHz, $CDCl_3$) δ 8.54-8.52 (m, 2H), 7.30-7.28 (m, 2H), 5.54-5.53 (m, 1H), 5.24-5.22 (m, 1H), 2.13-2.10 (m, 3H).

Step 2: A mixture of 4-(prop-1-en-2-yl)pyridine (100 g, 0.84 mol) and $Pd(OH)_2$ (10 g) in MeOH (1000 mL) was stirred under $H_2$ (50 psi) at room temperature for 12 h. The mixture was filtered through a pad of Celite and the filtrate was concentrated to afford 4-isopropylpyridine. $^1$H NMR (400 MHz, $CDCl_3$) δ 8.46-8.44 (m, 2H), 7.10-7.08 (m, 2H), 2.85-2.82 (m, 1H), 1.23-1.20 (m, 6H).

Step 3: To a solution of 4-isopropylpyridine (50 g, 0.413 mol) in $CH_2Cl_2$ (500 mL) was added m-CPBA (101 g, 0.496 mol) at 0° C. under $N_2$. The reaction was stirred overnight at room temperature. To the reaction was added aqueous $Na_2SO_3$, and then the organic layer was washed with $NaHCO_3$ and brine, dried over $Na_2SO_4$ and concentrated to give a crude 4-isopropylpyridine 1-oxide.

Step 4: To a solution of 4-isopropylpyridine 1-oxide (60 g, 0.44 mol) in $CH_2Cl_2$ (300 mL) was added trimethylsilyl cyanide (57 g, 0.58 mol) and a solution of dimethylcarbamic chloride (62 g, 0.58 mol) in $CH_2Cl_2$ (100 mL) below 10° C. under $N_2$. The mixture was stirred overnight at room temperature. To the reaction was added dropwise aqueous $K_2CO_3$ (10% solution). The mixture was extracted with $CH_2Cl_2$. The organic phase was washed with brine, dried over $Na_2SO_4$ and concentrated to give a crude product, which was purified by silica gel column to afford 4-isopropylpicolinonitrile. $^1$H NMR (400 MHz, $CDCl_3$) δ 8.59-8.58 (d, 1H), 7.55-7.54 (m, 1H), 7.36-7.35 (m, 1H), 2.97-2.93 (m, 1H), 1.29-1.26 (m, 6H).

Step 5: A mixture of 4-isopropylpicolinonitrile (60 g, 0.41 mol) and Pd/C (18 g) in 15% $H_2SO_4$ (645 g) was heated to 60° C. overnight. The mixture was filtered through a pad of Celite and the filtrate was adjusted to pH >8 with $Na_2CO_3$ and extracted with EtOAc. The organic phase was washed with brine, dried over $Na_2SO_4$ and concentrated to afford (4-isopropylpyridin-2-yl)methanol.

Step 6: A mixture of (4-isopropylpyridin-2-yl)methanol (70 g, 0.46 mol) and $MnO_2$ (202 g, 2.32 mol) in THF (500 mL) was heated to reflux for 5 h. The mixture was filtered through a pad of Celite and the filtrate was concentrated to afford 4-isopropylpicolinaldehyde. $^1$H NMR (400 MHz, $CDCl_3$) δ 10.06 (s, 1H), 8.66-8.65 (d, 1H), 7.83 (s, 1H), 7.37-7.36 (d, 1H), 3.01-2.94 (m, 1H), 1.30-1.21 (m, 6H).

Preparative Example 16.7

2,6-dichloro-8-(4-isopropylpyridin-2-yl)-7-((trans-4-methylcyclohexyl)methyl)-7H-purine

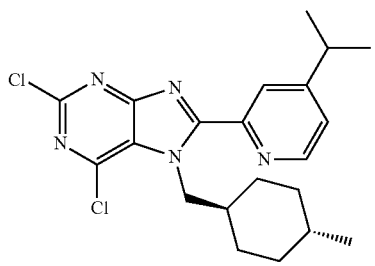 [SMILES: CC(C)c1ccnc(-c2nc3nc(Cl)nc(Cl)c3n2C[C@H]2CC[C@H](C)CC2)c1]

Step 1: Sodium (122.4 g, 5.32 mol) was added to ethanol (600 mL) carefully at 45° C. to give a colorless solution. After stirring for half an hour, 1-benzylurea (400 g, 2.66 mol) and ethyl 2-cyanoacetate (301.6 g, 2.67 mol) were added in turns at 45° C. The reaction mixture was heated at reflux under nitrogen for 16 h. The reaction mixture was then cooled to room temperature. Most of ethanol was removed under vacuum and the residue was dissolved in $H_2O$ (2 L). The solution was adjusted to pH=5-6 with hydrochloric acid to give a yellow solid that was isolated by filtration to give crude product as a yellow solid, which was triturated with $H_2O$ (1 L) and dried under vacuum to give 6-amino-1-benzylpyrimidine-2,4(1H,3H)-dione.

Step 2: To the suspension of 6-amino-1-benzylpyrimidine-2,4(1H,3H)-dione (250 g, 1.15 mol) in methanol (3.16 L) was added NBS (208 g, 1.17 mol) in portions over 30 minutes. The reaction mixture was stirred at room temperature for 20 hours. The solids were collected by filtration, washed with methanol, and dried under vacuum to give 6-amino-1-benzyl-5-bromopyrimidine-2,4(1H,3H)-dione.

Step 3: A mixture of 6-amino-1-benzyl-5-bromopyrimidine-2,4(1H,3H)-dione (40 g, 136 mmol), (trans-4-methylcyclohexyl)methanamine (34.4 g, 270.4 mmol) and $Na_2CO_3$ (30.08 g, 284 mmol) in water (80 mL) and DMSO (80 mL) was stirred at 95° C. for 8 h. The mixture was cooled to 20° C. and water (200 mL) was added to give a precipitate. The precipitate was collected by filtration, washed with water (100 mL×2), and dried under vacuum for 24 h to give crude 6-amino-1-benzyl-5-(((trans-4-methylcyclohexyl)methyl) amino)dihydropyrimidine-2,4(1H,3H)-dione.

Step 4: To a mixture of 6-amino-1-benzyl-5-(((trans-4-methylcyclohexyl)methyl)amino)dihydropyrimidine-2,4 (1H,3H)-dione (41 g, 120 mmol) and 4-isopropylpicolinaldehyde (23.2 g, 160 mmol) in DMF (328 mL) was added AcOH (21.6 g, 360 mmol) dropwise at 0° C. The reaction was stirred at room temperature overnight. Water was added to the reaction and the mixture was extracted with $CH_2Cl_2$. The organic phase was washed with brine, dried over $Na_2SO_4$ and concentrated to give a crude product which was purified by silica gel chromatography to afford 3-benzyl-8-(4-isopropylpyridin-2-yl)-7-((trans-4-methylcyclohexyl) methyl)-1H-purine-2,6(3H,7H)-dione.

Step 5: A mixture of 3-benzyl-8-(4-isopropylpyridin-2-yl)-7-((trans-4-methylcyclohexyl)methyl)-1H-purine-2,6 (3H,7H)-dione (60 g, 0.127 mol), $POCl_3$ (178 mL, 1.9 mol) and DBU (58 mL) was stirred at 100° C. overnight. The mixture was concentrated and the residue was added to water, the pH was adjusted to >8 with $Et_3N$, and the mixture was extracted with $CH_2Cl_2$. The organic phase was washed with brine, dried over $Na_2SO_4$ and concentrated to give a crude product which was purified on a silica gel column to afford 2,6-dichloro-8-(4-isopropylpyridin-2-yl)-7-((trans-4-methylcyclohexyl)methyl)-7H-purine. MS ESI calc'd. for $C_{21}H_{25}Cl_2N_5$ $[M+H]^+$ 418.1. found 418.1. $^1$H NMR (400 MHz, $CDCl_3$) δ 8.62-8.60 (m, 1H), 8.40 (s, 1H), 7.33-7.31 (m, 1H), 5.20 (s, 2H), 3.06-2.99 (m, 1H), 1.72-1.67 (m, 1H), 1.62-1.59 (m, 2H), 1.46-1.43 (m, 2H), 1.35-1.32 (m, 6H), 1.27-1.22 (m, 2H), 1.03-0.97 (m, 2H), 0.80-0.70 (m, 5H).

Example 16.12

3-(7-(((trans)-4-methylcyclohexyl)methyl)-6-phenyl-8-((R)-3-phenylmorpholino)-7H-purin-2-yl)-1,2,4-oxadiazol-5(4H)-one

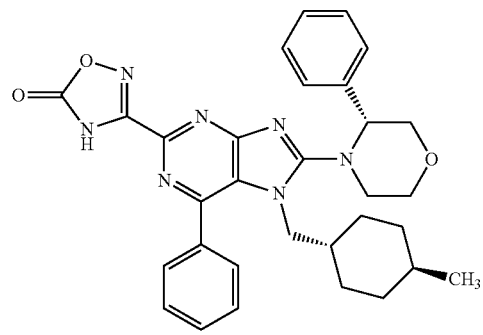 [SMILES: C[C@H]1CC[C@H](Cn2c(N3CCOC[C@H]3c3ccccc3)nc3nc(-c4noc(=O)[nH]4)nc(-c4ccccc4)c32)CC1]

Step 1: In a microwave vial (R)-4-(2,6-dichloro-7-((trans-4-methylcyclohexyl)methyl)-7H-purin-8-yl)-3-phenylmorpholine (Preparative Example 12.5, 230 mg, 0.50 mmol), phenyl boronic acid (75.6 mg, 0.60 mmol), sodium carbonate (106 mg, 2.00 mmol) and 1,1'-Bis(diphenylphosphino) ferrocene-palladium(II)dichloride dichloromethane complex (62.0 mg, 0.08 mmol) were added. Dioxane (4.5 mL) and water (0.5 mL) were added and the reaction mixture was degassed with argon for 5 minutes. Then the reaction was irradiated in a microwave at 100° C. for 2 hours. The reaction mixture was cooled to room temperature, diluted with EtOAc (50 mL), and the organic layer was washed with water (10 mL). The organic layer was concentrated under reduced pressure and the residue was purified on a RediSep 80 g silica gel column (0 to 100% EtOAc/Hexanes) to afford (R)-4-(2-chloro-7-(((trans)-4-methylcyclohexyl)methyl)-6-phenyl-7H-purin-8-yl)-3-phenylmorpholine. MS (APCI)= 502 $(M+1)^+$.

Step 2: Using a procedure analogous to that described in Example 16.1 (Step 2) and starting with (R)-4-(2-chloro-7-(((trans)-4-methylcyclohexyl)methyl)-6-phenyl-7H-purin-8-yl)-3-phenyl morpholine, 7-(((trans)-4-methylcyclohexyl) methyl)-6-phenyl-8-((R)-3-phenylmorpholino)-7H-purine-2-carbonitrile was prepared. MS (APCI)=493 $(M+1)^+$.

Step 3: Using a procedure analogous to that described in Example 16.1 (Step 3 and 4) and starting with 7-(((trans)-4-methylcyclohexyl)methyl)-6-phenyl-8-((R)-3-phenylmorpholino)-7H-purine-2-carbonitrile, 3-(7-(((trans)-4-methylcyclohexyl)methyl)-6-phenyl-8-((R)-3-phenylmorpholino)-7H-purin-2-yl)-1,2,4-oxadiazol-5(4H)-one was prepared. $^1$H NMR (400 MHz, $CDCl_3$) δ 7.25-7.55 (m, 10H), 5.05-5.10 (m, 1H), 4.10-4.25 (m, 2H), 3.95-4.02 (m, 2H), 3.50-3.68 (m, 4H), 0.30-1.70 (m, 10H), 0.72 (d, J=6.5 Hz, 3H); MS (ES)=552 $(M+1)^+$.

Preparative Example 16.8

8-bromo-6-(5-chloropyridin-3-yl)-7-(((trans)-4-methylcyclohexyl)methyl)-7H-purine-2-carbonitrile

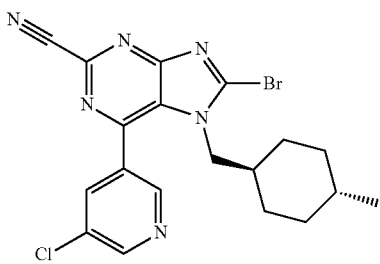 [SMILES: C[C@H]1CC[C@H](Cn2c(Br)nc3nc(C#N)nc(-c4cncc(Cl)c4)c32)CC1]

Step 1: Into a 3000-mL 4-necked round-bottom flask purged and maintained with an inert atmosphere of nitrogen, was placed 2-chloro-6-(5-chloropyridin-3-yl)-7-(((trans)-4-methylcyclohexyl)methyl)-7H-purine (Preparative Example 16.5, Step 1; 50 g, 130.22 mmol), DABCO (4.5 g, 40.18 mmol), potassium cyanide (17.3 g, 265.68 mmol), and DMA (950 mL). The reaction mixture was stirred overnight at 110° C. in an oil bath and then poured into 5000 mL of water/ice. The mixture was extracted with 3×800 mL of dichloromethane. The combined organic layers were washed with 1500 mL of water and 1000 mL of brine, dried over anhydrous magnesium sulfate, and concentrated under vacuum. The residue was purified on a silica gel column with EtOAc: petroleum ether: DCM (4:4:1) to afford 6-(5-chloropyridin-3-yl)-7-(((trans)-4-methylcyclohexyl)methyl)-7H-purine-2-carbonitrile. MS (ES)=367 (M+1)$^+$.

Step 2: Into a 1000-mL 4-necked round-bottom flask purged and maintained with an inert atmosphere of nitrogen, was placed 6-(5-chloropyridin-3-yl)-7-(((trans)-4-methylcyclohexyl)methyl)-7H-purine-2-carbonitrile (18.5 g, 48.41 mmol), NBS (27 g, 458.41 mmol), and chloroform (280 mL). The resulting solution was heated to reflux overnight in an oil bath and then poured into 1000 mL of aq. Na$_2$S$_2$O$_3$. The mixture was extracted with 2×500 mL of dichloromethane. The combined organic layers were washed with 5×500 mL of water, dried over anhydrous magnesium sulfate, and concentrated under vacuum. The residue was purified on a silica gel column with DCM: EtOAc: petroleum ether (1:1: 5). Further purification by re-crystallization from petroleum ether afforded 8-bromo-6-(5-chloropyridin-3-yl)-7-(((trans)-4-methylcyclohexyl)methyl)-7H-purine-2-carbonitrile. MS (ES)=445 (M+1)$^+$. $^1$H NMR (300 MHz, CDCl$_3$) δ 8.85 (d, J=3.2 Hz, 1H), 8.70 (d, J=2.4 Hz, 1H), 8.03 (t, 1H), 4.04 (d, J=9.2 Hz, 2H), 1.57 (m, 2H), 0.77-1.25 (m, 11H).

Preparative Example 16.9 trans-2,3-dimethylmorpholine hydrochloride (racemic)

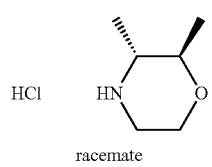

racemate

Step 1: N-benzylethanolamine (5.00 g, 33.0 mmol) was added slowly to a 0° C. suspension of 60% NaH (1.60 g, 40.0 mmol) in THF (100 mL). After stirring for 15 minutes at 0° C., methyl 2-bromopropanoate (5.50 g, 32.9 mmol) was added in a dropwise manner. The reaction mixture was then warmed to room temperature and stirred for 2 hours. Methanol (1 mL) was added, followed by addition of saturated aqueous NH$_4$Cl (20 mL). The mixture was then extracted with EtOAc (2×100 mL) and the combined organic layers were washed with water (50 mL), dried over anhydrous Na$_2$SO$_4$, filtered, and concentrated. The residue was purified on a silica gel column (0 to 50% EtOAc/hexanes) to afford 4-benzyl-2-methylmorpholin-3-one.

Step 2: A solution of 4-benzyl-2-methylmorpholin-3-one (1.80 g, 8.77 mmol) in THF (50.0 mL) was cooled to −78° C. and methyl lithium (4.4 mL of a 3M solution in dimethoxyethane, 13.2 mmol) was added. The reaction mixture was slowly warmed to 0° C. and stirred at that temperature for 1 hour. Next, acetic acid (0.80 mL, 840 mg, 14.0 mmol) was added to the reaction dropwise at 0° C. and the reaction was stirred for 10 minutes. Next, BH$_3$ (15.0 mL, 1.0 M solution in THF, 15.0 mmol) was added to the reaction at 0° C. and the reaction was stirred for 30 minutes. Methanol (2 mL) was added followed by saturated aqueous NH$_4$Cl (20 mL). The mixture was then extracted with EtOAc (2×50 mL) and the combined organic extracts were washed with water (20 mL), dried over anhydrous Na$_2$SO$_4$, filtered, and concentrated. Purification of the residue on a silica gel column (0 to 20% EtOAc/hexanes) afforded cis-N-benzyl-2,3-dimethylmorpholine and trans-N-benzyl-2,3-dimethylmorpholine.

cis-N-benzyl-2,3-dimethylmorpholine (first eluting): $^1$H NMR (300 MHz, CD$_3$Cl) δ 7.20-7.38 (m, 5H), 3.75-3.84 (m, 2H), 3.65 (dt, J=3.1 Hz, 11.0 Hz, 1H), 3.60 (bs, 2H), 2.56-2.72 (m, 2H), 2.27 (td, J=2.3 Hz, 11.6 Hz, 1H), 1.08 (d, J=6.6 Hz, 3H), 0.95 (d, J=6.6 Hz, 3H; MS (APCI)=206 (M+1)$^+$.

trans-N-benzyl-2,3-dimethylmorpholine (second eluting): $^1$H NMR (300 MHz, CDCl$_3$) δ 7.20-7.38 (m, 5H), 4.13 (d, J=13.4 Hz, 1H), 3.55-3.76 (m, 2H), 3.25-3.36 (m, 1H), 3.10 (d, J=13.4 Hz, 1H), 2.58 (td, J=2.0 Hz, 11.7 Hz, 1H), 2.23 (dt, J=3.5 Hz, 11.5 Hz, 1H), 2.04-2.14 (m, 1H), 1.20 (d, J=6.2 Hz, 3H), 1.15 (d, J=6.1 Hz, 3H); MS (APCI)=206 (M+1)$^+$.

Step 3: Palladium hydroxide (30 mg of 10% w/w in carbon) was added to a solution of trans-N-benzyl-2,3-dimethylmorpholine (570 mg, 2.78 mmol) in methanol (10.0 mL). The reaction mixture was flushed with hydrogen and then stirred under an atmosphere of hydrogen for two hours at room temperature. Next, aqueous HCl (2.0 mL of 2.0 M solution) was added to the reaction and the reaction filtered through a pad of celite, rinsing with MeOH. The filtrate was concentrated in vacuo to afford trans-2,3-dimethylmorpholine hydrochloride (racemate). $^1$H NMR (300 MHz, CDCl$_3$) δ 10.00 (bs, 1H), 9.82 (bs, 1H), 3.92-4.15 (m, 2H), 3.70-3.82 (m, 1H), 2.85-3.40 (m, 3H), 1.46 (d, J=6.2 Hz, 3H), 1.22 (d, J=6.1 Hz, 3H).

Cis-2,3-dimethylmorpholine hydrochloride (racemate) was prepared starting with cis-N-benzyl-2,3-dimethylmorpholine (Step 2 above) and following a procedure similar to that described in Step 3.

Example 16.107

3-{6-(2,6-dichloropyridin-4-yl)-7-[(trans-4-methyl-cyclohexyl)methyl]-8-[(3R)-3-phenylmorpholin-4-yl]-7H-purin-2-yl}-1,2,4-oxadiazol-5(4H)-one

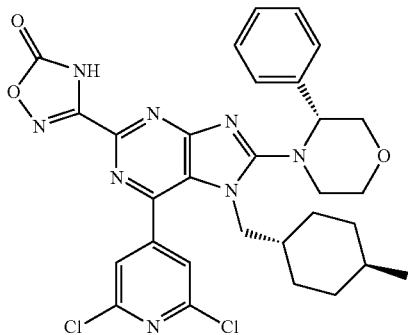 [SMILES: C[C@H]1CC[C@H](Cn2c(N3CCOC[C@H]3c3ccccc3)nc3nc(-c4noc(=O)[nH]4)nc(-c4cc(Cl)nc(Cl)c4)c32)CC1]

Step 1: To a sealable tube was added 6-chloro-7-((trans-4-methylcyclohexyl)methyl)-8-((R)-3-phenylmorpholino)-7H-purine-2-carbonitrile (Preparative Example 11.10, 0.030 g, 0.067 mmol), PdCl$_2$(dppf)-CH$_2$Cl$_2$ adduct (0.011 g, 0.013 mmol), 2,6-dichloro-4-(4,4,5,5-tetramethyl-1,3,2-dioxaborolan-2-yl)pyridine (0.019 g, 0.067 mmol), K$_2$CO$_3$ (0.046 g, 0.33 mmol), dioxane (1.0 mL) and water (0.050 mL). The reaction vessel was purged with argon, sealed, and warmed to 100° C. for 6 hours. The reaction was then cooled to room temperature and filtered. The filtrate was concentrated under reduced pressure to afford crude 6-(2,6-dichloropyridin-4-yl)-7-[(trans-4-methylcyclohexyl)methyl]-8-[(3R)-3-phenylmorpholin-4-yl]-7H-purine-2-carbonitrile. MS ESI calc'd. for C$_{29}$H$_{29}$Cl$_2$N$_7$O [M+H]$^+$ 562. found 562.

Step 2: To the crude 6-(2,6-dichloropyridin-4-yl)-7-[(trans-4-methylcyclohexyl)methyl]-8-[(3R)-3-phenylmorpholin-4-yl]-7H-purine-2-carbonitrile (0.038 g, 0.067 mmol) was added EtOH (1.0 mL) and hydroxylamine (0.10 mL, 50% w/w solution in H$_2$O). The reaction was stirred at ambient temperature for 1 hour and then concentrated under reduced pressure to afford crude 6-(2,6-dichloropyridin-4-yl)-N-hydroxy-7-[(trans-4-methylcyclohexyl)methyl]-8-[(3R)-3-phenylmorpholin-4-yl]-7H-purine-2-carboximidamide.

Step 3: To the crude 6-(2,6-dichloropyridin-4-yl)-N-hydroxy-7-[(trans-4-methylcyclohexyl)methyl]-8-[(3R)-3-phenylmorpholin-4-yl]-7H-purine-2-carboximidamide (0.040 g, 0.067 mmol), was added acetonitrile (1 mL), 1,1'-carbonyldiimidazole (0.022 g, 0.13 mmol), and DBU (0.25 mL, 0.17 mmol). The reaction vessel was sealed and allowed to stir for 4 hours at ambient temperature. The reaction was then diluted with water and extracted with DCM. The organic layer was collected and concentrated under reduced pressure. The residue was purified by reverse phase preparative HPLC (0:100 to 95:5 acetonitrile:water: 0.1% v/v TFA modifier) to afford 3-{6-(2,6-dichloropyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one. $^1$H NMR (600 MHz, DMSO): δ 8.08 (s, 2H); 7.47 (d, J=7.7 Hz, 2H); 7.29 (t, J=7.6 Hz, 2H); 7.23 (t, J=7.4 Hz, 1H); 5.09 (t, J=4.3 Hz, 1H); 4.05-4.08 (m, 1H); 3.93-3.96 (m, 2H); 3.80-3.83 (m, 2H); 3.65-3.67 (m, 2H); 3.51-3.54 (m, 2H); 1.36 (t, J=15.5 Hz, 2H); 1.02-1.05 (m, 1H); 0.78-0.81 (m, 1H); 0.66-0.69 (m, 6H); 0.28-0.50 (m, 3H). MS ESI calc'd. for C$_{30}$H$_{30}$Cl$_2$N$_8$O$_3$ [M+H]$^+$ 621. found 621.

Preparative Example 16.10

(2S,3R)-2-methyl-3-phenylmorpholine hydrochloride

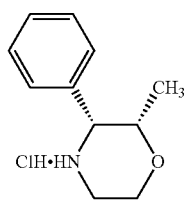

Step 1: To a solution of benzaldehyde (1.12 g, 10.6 mmol) and (1R,2S)-1-amino-1-phenylpropan-2-ol hydrochloride (2.00 g, 10.6 mmol) in dichloroethane (40 mL) was added sodium cyanoborohydride (1.34 g, 21.2 mmol) followed by acetic acid (100 μL, 1.75 mmol). Methanol (1 mL) was added and the reaction mixture was stirred at room temperature overnight and then concentrated in vacuo. The residue was dissolved in dichloromethane and washed with saturated aqueous NaHCO$_3$ solution. The layers were separated and the aqueous layer was extracted with dichloromethane (3×40 mL). The combined organic layers were washed with brine, dried over anhydrous Na$_2$SO$_4$, filtered, and concentrated in vacuo to afford (1R,2S)-1-(benzylamino)-1-phenylpropan-2-ol. MS (APCI)=242 (M+1)$^+$.

Step 2: To a solution of (1R,2S)-1-(benzylamino)-1-phenylpropan-2-ol (2.40 g, 9.94 mmol) in dichloromethane (30 mL) at −40° C., was added triethylamine (4.20 mL, 29.8 mmol) followed by dropwise addition of 2-chloroacetyl chloride (2.14 mL, 9.94 mmol). The reaction was stirred at −40° C. for 1 hour and then quenched with saturated NaHCO$_3$ solution. The layers were separated and the aqueous layer was extracted with dichloromethane (3×40 mL). The combined organic layers were washed with brine, dried over anhydrous Na$_2$SO$_4$, filtered, and concentrated in vacuo. Purification of the residue on a silica gel column (0 to 50% EtOAc/hexanes) afforded N-benzyl-2-chloro-N-((1R,2S)-2-hydroxy-1-phenylpropyl)acetamide. MS (ES)=318 (M+1)$^+$.

Step 3: A solution of N-benzyl-2-chloro-N-((1R,2S)-2-hydroxy-1-phenylpropyl)acetamide (1.20 g, 3.78 mmol) in THF (10 mL) was added to a suspension of 60% NaH (272 mg, 11.35 mmol) in THF (10 mL) at 0° C. The reaction mixture was stirred at 0° C. for 1 hour and then quenched with saturated aqueous NH$_4$Cl solution. The layers were separated and the aqueous layer was extracted with EtOAc (3×15 mL). The combined organic layers were washed with brine, dried over anhydrous Na$_2$SO$_4$, filtered, and concentrated in vacuo. Purification of the residue on a silica gel column (0 to 50% EtOAc/hexanes) afforded (5R,6S)-4-benzyl-6-methyl-5-phenylmorpholin-3-one. MS (ES)=282 (M+1)$^+$.

Step 4: LiAlH$_4$ (296 mg, 7.80 mmol) was added to a solution of (5R,6S)-4-benzyl-6-methyl-5-phenylmorpholin-3-one (440 mg, 1.56 mmol) in THF (10 mL). The reaction mixture was heated at 70° C. for 3 hours and then cooled to 0° C. At 0° C. was added aqueous sodium sulphate (15 mL) to quench the reaction. The reaction mixture was stirred at room temperature for 10 minutes and the white solid was removed by filtration. The filtrate was extracted with EtOAc (3×15 mL). The combined organics were dried over anhydrous Na$_2$SO$_4$, filtered, and concentrated in vacuo. Purification of the residue on a silica gel column (0 to 30% EtOAc/hexanes) afforded (2S,3R)-4-benzyl-2-methyl-3-phenylmorpholine. MS (APCI)=268 (M+1)$^+$.

Step 5: Pd(OH)$_2$ (25% on carbon, 42.0 mg) was added to a solution of (2S,3R)-4-benzyl-2-methyl-3-phenylmorpholine (420 mg, 1.57 mmol) in MeOH (10 mL) under N$_2$. Hydrogen was bubbled through the reaction for one minute and then the reaction was stirred at rt under hydrogen (1 atm) for 2 hours. The reaction was then sparged with N$_2$ and a solution of 3M HCl in methanol (3 mL) was added. The reaction was stirred at room temperature for 30 minutes and then concentrated in vacuo to afford (2S,3R)-2-methyl-3-phenylmorpholine hydrochloride. $^1$H NMR (300 MHz, CD$_3$OD) δ 7.68-7.75 (m, 2H), 7.45-7.53 (m, 3H), 3.97-4.47 (m, 4H), 3.39-3.46 (m, 1H), 3.08-3.13 (m, 1H), 1.11 (d, J=6.3 Hz, 3H), MS (APCI)=178 (M–HCl+1)$^+$.

Preparative Example 16.11

(cis)-octahydro-2H-benzo[b][1,4]oxazine hydrochloride

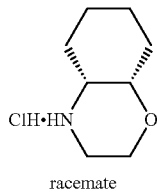

racemate

Step 1: To a solution of benzyaldehyde (560 mg, 5.3 mmol) and (cis)-2-aminocyclohexanol hydrochloride (800 mg, 5.3 mmol) in dichloroethane (25 mL) was added sodium cyanoborohydride (666 mg, 10.6 mmol) followed by acetic acid (50 μL, 0.87 mmol). Methanol (0.5 mL) was added and the reaction mixture was stirred at room temperature overnight and then concentrated in vacuo. The residue was dissolved in dichloromethane and washed with saturated aqueous NaHCO$_3$ solution. The layers were separated and the aqueous layer was extracted with dichloromethane (3×10 mL). The combined organic layers were washed with brine, dried over anhydrous Na$_2$SO$_4$, filtered, and concentrated in vacuo. Purification of the residue on a silica gel column (0 to 10% MeOH/CH$_2$Cl$_2$) afforded (cis)-2-(benzylamino)cyclohexanol. MS (APCI)=206 (M+1)$^+$.

Step 2: Triethylamine (0.90 mL, 6.42 mmol) was added to a solution of (cis)-2-(benzylamino)cyclohexanol (440 mg, 2.14 mmol) in dichloromethane (15 mL) at −40° C., followed by dropwise addition of 2-chloroacetyl chloride (0.17 mL, 2.14 mmol). The reaction mixture was stirred at −40° C. for 1 hour and then quenched with saturated aqueous NaHCO$_3$ solution. The layers were separated and the aqueous layer was extracted with dichloromethane (3×8 mL). The combined organic layers were washed with brine, dried over anhydrous Na$_2$SO$_4$, filtered, and concentrated in vacuo. Purification of the residue on a silica gel column (0 to 50% EtOAc/hexanes) afforded N-benzyl-2-chloro-N-((cis)-2-hydroxycyclohexyl)acetamide. MS (APCI)=282 (M+1)$^+$.

Step 3: A solution of N-benzyl-2-chloro-N-((cis)-2-hydroxycyclohexyl)acetamide (380 mg, 1.35 mmol) in THF (5 mL) was added to a suspension of 60% NaH (162 mg, 4.83 mmol) in THF (10 mL) at 0° C. The reaction mixture was stirred at 0° C. for 1 hour and then quenched with saturated aqueous NH$_4$Cl solution. The layers were separated and the aqueous layer was extracted with EtOAc (3×8 mL). The combined organic layers were washed with brine, dried over anhydrous Na$_2$SO$_4$, filtered, and concentrated in vacuo. Purification of the residue on a silica gel column (0 to 50% EtOAc/hexanes) afforded (cis)-4-benzylhexahydro-2H-benzo[b][1,4]oxazin-3(4H)-one. MS (APCI)=246 (M+1)$^+$.

Step 4: LiAlH$_4$ (176 mg, 4.63 mmol) was added to a solution of (cis)-4-benzylhexahydro-2H-benzo[b][1,4]oxazin-3(4H)-one (370 mg, 1.50 mmol) in THF (10 mL). The reaction mixture was heated at 70° C. for 2 hours and then cooled to room temperature. Water (1 mL) was added to quench the reaction. The reaction mixture was stirred at room temperature for 15 minutes and the white solid was removed by filtration. The filtrate was dried over anhydrous Na$_2$SO$_4$, filtered, and concentrated in vacuo. Purification of the residue on a silica gel column (0 to 30% EtOAc/hexanes) afforded (cis)-4-benzyloctahydro-2H-benzo[b][1,4]oxazine. MS (APCI)=232 (M+1)$^+$.

Step 5: Pd(OH)$_2$ (25% on carbon, 280 mg) was added to a solution of (cis)-4-benzyloctahydro-2H-benzo[b][1,4]oxazine (280 mg, 1.21 mmol) in MeOH (10 mL) under N$_2$. H$_2$ was bubbled through the reaction mixture for one minute and then the reaction was stirred at rt under H$_2$ (1 atm) for 1 hour. The reaction was sparged with N$_2$ for 1 minute and then a solution of 3M HCl in MeOH (3 mL) was added. The reaction mixture was stirred at room temperature for 30 minutes and then filtered through celite. The filtrate was concentrated in vacuo to afford (cis)-octahydro-2H-benzo[b][1,4]oxazine hydrochloride (racemate). $^1$H NMR (300 MHz, CD3OD) δ 4.07 (m, 1H), 3.83-3.90 (m, 2H), 3.32-3.37 (m, 2H), 3.03 (m, 1H), 2.10 (m, 1H), 1.78-1.91 (m, 3H), 1.55-1.47 (m, 4H). MS (APCI)=142 (M+1)$^+$.

Preparative Example 16.12

(S)-3-(5-methyl-1,3,4-oxadiazol-2-yl)morpholine hydrochloride

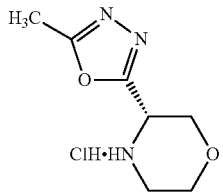

Step 1: To a solution of (S)-4-(tert-butoxycarbonyl)morpholine-3-carboxylic acid (400 mg, 1.73 mmol) in anhydrous THF (2 mL) was added acetyl hydrazine (256 mg, 3.46 mmol) and triethyl amine (0.4 mL, 3.46 mmol) followed by HATU (855 mg, 2.25 mmol). After being stirred for 3 hours at room temperature, the reaction mixture was diluted with EtOAc (10 mL) and washed with water (10 mL) and brine (10 mL). The organic layer was dried over Na$_2$SO$_4$, filtered, and concentrated. The residue was purified on a silica gel column (50% EtOAc/hexane) to afford (S)-tert-butyl 3-(2-acetylhydrazinecarbonyl)morpholine-4-carboxylate.

Step 2: Burgess reagent (530 mg, 2.22 mmol) was added to a solution of (S)-tert-butyl 3-(2-acetylhydrazinecarbonyl)morpholine-4-carboxylate (320 mg, 1.11 mmol) in CH$_2$Cl$_2$ (2 mL). The reaction was stirred at room temperature for 12 hours and then diluted with water (100 mL) and extracted with EtOAc (100 mL). The organic layer was washed with brine, dried over Na₂SO₄, filtered, and concentrated. The residue was purified on a silica gel column (50% EtOAc/hexane) to afford (S)-tert-butyl 3-(5-methyl-1,3,4-oxadiazol-2-yl)morpholine-4-carboxylate.

Step 3: To a solution of (S)-tert-butyl 3-(5-methyl-1,3,4-oxadiazol-2-yl)morpholine-4-carboxylate (210 mg, 0.78 mmol), was added 3M HCl in 1,4 dioxane (2.0 mL). The reaction was stirred at room temperature for 1 hour and then concentrated to afford (S)-3-(5-methyl-1,3,4-oxadiazol-2-yl)morpholine hydrochloride. $^1$H NMR (300 MHz, CD₃OD) δ 4.96-5.00 (m, 1H), 4.33-4.37 (m, 1H), 4.03-4.11 (m, 2H), 3.77-3.84 (m, 1H), 3.54-3.60 (m, 1H), 3.30-3.42 (m, 1H), 2.59 (s, 3H).

Preparative Example 16.13 trans-3-methyloctahydrocyclopenta[b][1,4]oxazine hydrochloride

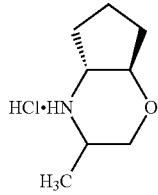

Step 1: Cyclopentene oxide (5.0 g, 59.1 mmol), benzylamine (7.0 g, 65.3 mmol) and titanium isopropoxide (3.40 g, 12.0 mmol) were taken in a microwave vial and microwaved at 150° C. for 3 hours. The reaction mixture was then cooled and diluted with EtOAc (100 mL). The organic layer was washed with water and dried over anhydrous Na₂SO₄. Evaporation of the solvent in vacuo and purification on a silica gel column (0 to 20% MeOH/CH₂Cl₂) afforded trans-2-(benzylamino)cyclopentanol. MS APCI calc'd for C₁₂H₁₇NO [M+H]⁺ 192. found 192.

Step 2: To a suspension of NaH (6.0 g of 60% w/w in oil, 150 mmol) in THF (300 mL) cooled at 0° C., trans-2-(benzylamino)cyclopentanol (9.6 g, 50 mmol) was added slowly. After stirring for 15 minutes at 0° C., ethyl bromoacetate (10 g, 60 mmol) was added slowly. The reaction mixture was then warmed to room temperature and stirred for 2 hours. Methanol (5.0 mL) was added slowly to the reaction followed by addition of saturated aqueous NH₄Cl (100 mL). The reaction mixture was then extracted with EtOAc (2×300 mL), and the combined organic layers were washed with water (100 mL) and dried over anhydrous Na₂SO₄. Evaporation of solvent in vacuo followed by purification on a silica gel column (0 to 50% EtOAc/Hexanes) afforded trans-4-benzylhexahydrocyclopenta[b][1,4]oxazin-3(2H)-one. MS APCI calc'd for C₁₄H₁₇NO₂ [M+H]⁺ 232. found 232.

Step 3: To -78° C. solution of trans-4-benzylhexahydrocyclopenta[b][1,4]oxazin-3(2H)-one (5.0 g, 21.6 mmol) in THF (200.0 mL), methyl lithium (11.0 mL of 3.00 M solution in dimethoxyethane, 33.0 mmol) was added. The reaction mixture was slowly warmed to 0° C. and stirred at that temperature for 2 hours. Acetic acid (2.00 mL, 2.00 g, 33.3 mmol) was added to the reaction dropwise at 0° C. and stirred for 10 minutes. Then BH₃ (33.0 mL, 1.0 M solution in THF, 33.0 mmol) was added to the reaction at 0° C. and stirred for 30 minutes. After slow addition of methanol (5.0 mL), saturated aqueous NH₄Cl (50.0 mL) solution was added. The reaction mixture was then extracted with EtOAc (2×200 mL), and the combined organic layers were washed with water (100 mL) and dried over anhydrous Na₂SO₄. Evaporation of solvent in vacuo and purification on a silica gel column (0 to 20% EtOAc/Hexanes) afforded trans-4-benzyl-3-methyloctahydrocyclopenta[b][1,4]oxazine as a mixture of diastereomers.

Step 4: To a solution of trans-4-benzyl-3-methyloctahydrocyclopenta[b][1,4]oxazine (1.0 g, 4.3 mmol) in methanol (20 mL), palladium hydroxide (50 mg of 10% w/w in carbon) was added. The reaction mixture was flushed with hydrogen and then stirred under an atmosphere of hydrogen for two hours at room temperature. Aqueous HCl (2.0 mL of a 2.0 M solution) was added to the reaction, and the reaction mixture was filtered through a pad of celite, rinsing with MeOH. The filtrate was concentrated in vacuo to afford trans-3-methyloctahydrocyclopenta[b][1,4]oxazine hydrochloride (mixture of diastereomers).

Preparative Example 16.14

(2R,3R)-3-ethyl-2-methylmorpholine hydrochloride

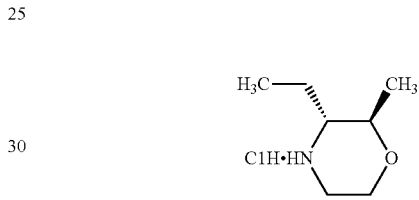

Step 1: To a solution of (2R,3R)-3-aminopentan-2-ol hydrochloride (1.00 g, 7.2 mmol) in DCM (20 mL) at rt was added sodium bicarbonate solution (604 mg, 7.2 mmol dissolved in 3.0 mL of water), dropwise. The reaction mixture was stirred for 1 hour, and the solvent was evaporated under reduced pressure. The residue and sodium cyanoborohydride (600 mg, 10.7 mmol) were added to a solution of benzyaldehyde 877 mg, 8.6 mmol) in DCM (20 mL). The reaction mixture was stirred at room temperature overnight and then concentrated in vacuo. 30.0 mL water was added to this mixture, and the aqueous layer was extracted with dichloromethane (3×10 mL). The combined organic layers were washed with brine, dried over anhydrous Na₂SO₄, filtered and concentrated in vacuo. Purification of the residue on a silica gel column (0 to 50% EtOAc/hexanes) afforded (2R,3R)-3-(benzylamino)pentan-2-ol. MS APCI calc'd for C₁₂H₁₉NO [M+H]⁺ 194. found 194.

Step 2: Triethylamine (0.43 mL, 3.4 mmol) was added to a -40° C. solution of (2R,3R)-3-(benzylamino)pentan-2-ol (220 mg, 1.1 mmol) in dichloromethane (100 mL), followed by the addition of 2-chloroacetyl chloride (0.10 mL, 1.1 mmol) dropwise. The reaction mixture was stirred at -40° C. for 1 hour and then quenched with saturated NaHCO₃ solution. The layers were separated, and the aqueous layer was extracted with dichloromethane (3×10 mL). The combined organic layers were washed with brine, dried over anhydrous Na₂SO₄, filtered and concentrated in vacuo. Purification of the residue on a silica gel column (0 to 50% EtOAc/hexanes) afforded N-benzyl-2-chloro-N-((2R,3R)-2-hydroxypentan-3-yl)acetamide. MS APCI calc'd for C₁₄H₂₀ClNO₂ [M+H]⁺ 270. found 270.

Step 3: A solution of of N-benzyl-2-chloro-N-((2R,3R)-2-hydroxypentan-3-yl)acetamide (210 mg, 0.7 mmol) in THF (5 mL) was added to a suspension of NaH (89 mg, 3.7 mmol) in THF (5 mL) at 0° C. The reaction mixture was stirred at 0° C. for 1 hour and then quenched with saturated NH₄Cl solution. The layers were separated and the aqueous layer was extracted with EtOAc (2×10 mL). The combined organic layers were washed with brine, dried over anhydrous Na₂SO₄, filtered and concentrated in vacuo. Purification of the residue on a silica gel column (0 to 50% EtOAc/hexanes) afforded (5R,6R)-4-benzyl-5-ethyl-6-methylmorpholin-3-one. MS APCI calc'd for $C_{14}H_{19}NO_2$ [M+H]⁺ 234. found 234.

Step 4: LiAlH₄ (217 mg, 37.95 mmol) was added to a solution of (5R,6R)-4-benzyl-5-ethyl-6-methylmorpholin-3-one (200 mg, 0.85 mmol) in THF (10 mL). The reaction mixture was heated at 70° C. for 3 hours and then cooled to 0° C. At 0° C., was added aqueous sodium sulfate (15 mL). The mixture was stirred at room temperature for 10 minutes, and the white solid was removed by filtration. The filtrate was extracted with EtOAc (3×15 mL), dried over anhydrous Na₂SO₄, filtered and concentrated in vacuo. Purification of the residue on a silica gel column (0 to 30% EtOAc/hexanes) afforded (2R,3R)-4-benzyl-3-ethyl-2-methylmorpholine. MS APCI calc'd for $C_{14}H_{21}NO$ [M+H]⁺ 220. found 220.

Step 5: Pd(OH)₂ (15.0 mg, 10% on carbon) was added to a solution of (2R,3R)-4-benzyl-3-ethyl-2-methylmorpholine (110 mg, 0.50 mmol) in MeOH (10 mL) under N₂. Hydrogen was bubbled through the reaction mixture for one minute and then the reaction was stirred at rt under hydrogen (1 atm) for 2 hours. Then, N₂ was bubbled through the reaction for 1 minute. A solution of HCl (3M, 3 mL, 9 mmol) in methanol was added. The reaction mixture was stirred at room temperature for 30 minutes and concentrated in vacuo to afford (2R,3R)-3-ethyl-2-methylmorpholine hydrochloride. ¹H NMR (300 MHz, DMSO-d₆) δ 9.45-9.34 (br s, 1H), 3.84-3.91 (m, 1H), 3.68-3.78 (m, 1H), 3.53-3.61 (m, 1H), 3.08-3.21 (m, 1H), 2.93-3.01 (m, 1H), 2.70-2.85 (m, 1H), 1.45-1.81 (m, 2H), 1.13 (d, J=6.3 Hz, 3H), 0.90-1.05 (m, 3H). MS APCI calc'd for $C_7H_{15}NO$ [M+H]⁺ 130. found 130.

Preparative Example 16.15

(cis)-4-methoxy-2-methylpiperidine hydrochloride (racemate)

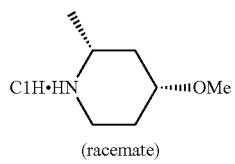

(racemate)

Step 1: To a 0° C. solution of tert-butyl 2-methyl-4-oxopiperidine-1-carboxylate (2.0 g, 9.3 mmol) in methanol (20 mL) was added sodium borohydride (707 mg, 18.6 mmol). The reaction was stirred at room temperature for 1 hour, then concentrated, diluted with CH₂Cl₂ (20 mL), and washed with water (10 mL) and brine (10 mL). The organic layer was dried over sodium sulfate, filtered, and concentrated. Purification of the residue on a silica gel column (0 to 60% EtOAc/hexanes) afforded both (cis)-tert-butyl 4-hydroxy-2-methylpiperidine-1-carboxylate and (trans)-tert-butyl 4-hydroxy-2-methylpiperidine-1-carboxylate. Data for (cis)-tert-butyl 4-hydroxy-2-methylpiperidine-1-carboxylate (faster eluting): NMR (300 MHz, CDCl₃) δ 4.27 (m, 1H), 4.15 (m, 1H), 3.81 (m, 1H), 3.26 (m, 1H), 1.84 (m, 1H), 1.60-1.74 (m, 3H), 1.59 (m, 1H), 1.45 (s, 9H), 1.32 (d, J=6.9 Hz, 3H). Data for (trans)-tert-butyl 4-hydroxy-2-methylpiperidine-1-carboxylate (slower eluting): NMR (300 MHz, CDCl₃) δ 4.48 (m, 1H), 4.04 (m, 1H), 3.94 (m, 1H), 2.86 (m, 1H), 1.80-1.96 (m, 2H), 1.66-1.79 (m, 2H), 1.53 (m, 1H), 1.45 (s, 9H), 1.13 (d, J=7.2 Hz, 3H).

Step 2: To a 0° C. solution of (cis)-tert-butyl 4-hydroxy-2-methylpiperidine-1-carboxylate (705 mg, 3.2 mmol) in DMF (10 mL) was added sodium hydride (216 mg, 6.5 mmol) at and the reaction was stirred for 20 minutes. Methyl iodide (1.39 g, 9.8 mmol) was added and stirring was continued for 2 hours, warming slowly from 0° C. to rt. Water (10 mL) was added and the mixture was extracted with EtOAc (3×10 mL). The combined organic extracts were washed with water (10 mL) and brine (10 mL), dried over sodium sulfate, filtered, and concentrated to afford racemic (cis)-tert-butyl 4-methoxy-2-methylpiperidine-1-carboxylate. NMR (400 MHz, CDCl₃) δ 4.24 (m, 1H), 3.80 (m, 1H), 3.54 (m, 3H), 3.32 (s, 1H), 3.31 (m, 1H), 1.77-1.84 (m, 2H), 1.60-1.71 (m, 2H), 1.45 (s, 9H), 1.25 (d, J=6.8 Hz, 3H).

Step 3: Racemic (cis)-tert-butyl 4-methoxy-2-methylpiperidine-1-carboxylate (818 mg, 3.57 mmol) was dissolved in CH₂Cl₂ (3 mL). 4M HCl in dioxane (3 mL, 12 mmol) was added dropwise at 0° C. and the reaction was stirred for 2 hours at room temperature. The reaction was then concentrated to dryness to afford (cis)-4-methoxy-2-methylpiperidine hydrochloride (racemate).

Preparative Example 16.16

5-chloro-2-methyl-3-(4,4,5,5-tetramethyl-1,3,2-dioxaborolan-2-yl)pyridine

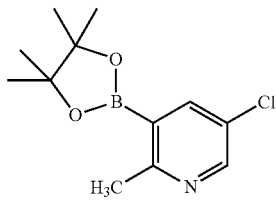 [SMILES: Cc1ncc(Cl)cc1B1OC(C)(C)C(C)(C)O1]

Step 1: MeMgBr (4.40 mL, 8.80 mmol) was added dropwise to a 0° C. solution of 2,3-dibromo-5-chloropyridine (2.00 g, 7.40 mmol) and Ni(dppf)Cl₂ (0.40 g, 0.740 mmol) in THF (25 mL). After 2 hours, a second addition of MeMgBr (4.40 mL, 8.80 mmol) was carried out and the reaction was stirred at 0° C. for 2 more hours. The reaction was then quenched with saturated aqueous NH₄Cl (50 ml) and extracted with EtOAc (2×50 mL). The combined organic layers were dried over anhydrous Na₂SO₄, and concentrated under reduced pressure. The residue was purified on a silica gel column (0 to 50% EtOAc/hexanes) to afford 3-bromo-5-chloro-2-methylpyridine. ¹H NMR (300 MHz, CDCl₃) δ 8.38 (d, J=2.1 Hz, 1H), 7.80 (d, J=2.1 Hz, 1H), 2.63 (s, 3H).

Step 2: To a solution of 3-bromo-5-chloro-2-methylpyridine (0.60 g, 2.91 mmol) in 1,4-dioxane (12 mL) was added bis(pinacolato)diboron (1.47 g, 5.82 mmol), Pd(dppf)Cl₂ (0.106 g, 0.145 mmol) and KOAc (0.857, 8.73 mmol). The mixture was sparged with Ar for 5 minutes and then the reaction was sealed and heated at 90° C. for 1 hour. The reaction was then diluted with water (30 ml) and extracted with EtOAc (2×50 mL). The combined organic extracts

Example 16.160

3-{6-[3-chloro-5-(2-methoxyethoxyl)phenyl]-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one (racemate)

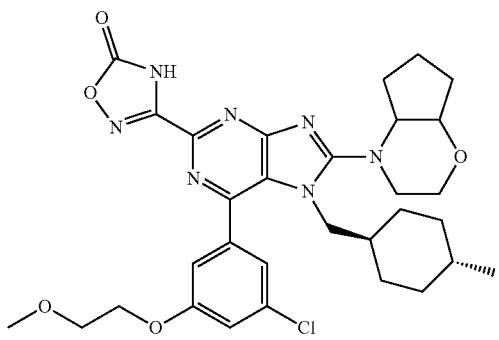

Step 1: 2,6-dichloro-7-((trans-4-methylcyclohexyl)methyl)-7H-purine (Preparative Example 11.4; 3.44 g, 7.49 mmol), 3-chloro-5-hydroxyphenylboronic acid (1.32 g, 8.39 mmol), potassium phosphate (12.2 g, 37.4 mmol), and 1,1'-Bis(diphenylphosphino) ferrocene-palladium(II)dichloride (1.1 g, 1.49 mmol) were combined in a vial that had been oven-dried and flushed with nitrogen. Dioxane (75 mL) was added and the vial was sealed and heated at 90° C. for 4 hours. The reaction mixture was cooled to room temperature, filtered through celite, and the filtrate was concentrated under reduced pressure. The residue was purified by silica gel chromatography (0-100% ethyl acetate/hexanes, linear gradient) to afford 3-chloro-5-(2-chloro-7-(((trans)-4-methyl cyclohexyl)methyl)-7H-purin-6-yl)phenol. MS (ES)=391 (M+1)$^+$.

Step 2: 3-chloro-5-(2-chloro-7-(((trans)-4-methylcyclohexyl)methyl)-7H-purin-6-yl)phenol (3.44 g, 7.49 mmol), cesium carbonate (12.2 g, 37.4 mmol), and 1-bromo-2-methoxy ethane (1.03 g, 74.8 mmol) were combined in a vial that had been oven-dried and flushed with nitrogen. DMF (75 mL) was added and the vial was sealed and heated to 60° C. for 3 hours. The reaction mixture was cooled to room temperature, filtered through celite, and the filtrate was concentrated under reduced pressure. The residue was purified by silica gel chromatography (0-100% ethyl acetate/hexanes, linear gradient) to afford 2-chloro-6-(3-chloro-5-(2-methoxyethoxyl)phenyl)-7-(((trans)-4-methylcyclohexyl)methyl)-7H-purine. MS (ES)=449 (M+1)$^+$.

Step 3: An oven-dried, nitrogen cooled flask was charged with palladium(II) acetate (70 mg, 0.312 mmol) and (R)-(+)-2,2'-bis(diphenylphosphino)-1,1'-binaphthyl (195 mg, 0.313 mmol). N,N-Dimethylacetamide (18.7 mL) was added and the mixture was degassed for three minutes with nitrogen (sparge). Sulfuric acid (0.017 mL, 0.32 mmol) was added and the mixture was degassed for three minutes with nitrogen (sparge). The flask was sealed and heated to 80° C. for 30 minutes. This catalyst solution was then cooled to room temperature, and added to a second separate nitrogen purged flask containing 2-chloro-6-(3-chloro-5-(2-methoxyethoxyl)phenyl)-7-(((trans)-4-methylcyclohexyl)methyl)-7H-purine (1.68 g, 3.14 mmol), zinc cyanide (0.184 g, 1.57 mmol), and zinc (21 mg, 0.32 mmol). The flask was purged with nitrogen for five minutes, sealed, and heated to 100° C. for 3.5 hours. The reaction was then cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford 6-(3-chloro-5-(2-methoxyethoxy)phenyl)-7-(((trans)-4-methylcyclohexyl)methyl)-7H-purine-2-carbonitrile. MS (ES)=440 (M+1)$^+$.

Step 4: 6-(3-chloro-5-(2-methoxyethoxy)phenyl)-7-(((trans)-4-methylcyclohexyl)methyl)-7H-purine-2-carbonitrile (100 mg, 0.24 mmol) was dissolved in THF (10 mL) and the solution was cooled to -78° C. under a nitrogen atmosphere. 2,2,6,6-tetramethylpiperidinylmagnesium chloride, lithium chloride complex (1M in THF/toluene, 0.72 mL, 0.72 mmol) was added slowly at -78° C. The reaction was stirred at -78° C. for 2 hours and then a solution of 1,3-dibromo-5,5-dimethylhydantoin (340 mg, 1.2 mmol) in THF (2 mL) was added at -78° C. The reaction was allowed to warm up to room temperature and stirred for 8 hours. The reaction was then cooled back to -78° C., quenched with saturated NH$_4$Cl solution (10 mL), and extracted with EtOAc (3×20 mL). The combined organic extracts were dried over anhydrous Na$_2$SO$_4$, filtered, and concentrated. The residue was purified on a silica gel column (0 to 100% EtOAc/hexanes) to afford 8-bromo-6-(3-chloro-5-(2-methoxyethoxyl)phenyl)-7-(((trans)-4-methylcyclohexyl)methyl)-7H-purine-2-carbonitrile. MS (APCI)=520 (M+1)$^+$.

Step 5: A dry reaction vial was charged with 8-bromo-6-(3-chloro-5-(2-methoxyethoxyl)phenyl)-7-(((trans)-4-methylcyclohexyl)methyl)-7H-purine-2-carbonitrile (60.0 mg, 0.11 mmol), trans-octahydrocyclopenta[b][1,4]oxazine hydrochloride (90.0 mg, 0.55 mmol), potassium fluoride (58 mg, 1.0 mmol), DIEA (192 µL, 1.1 mmol), and DMSO (2.0 mL). The vial was sealed and heated to 85° C. for 2 hours. The reaction was then cooled to room temperature, diluted with ethyl acetate, and washed with water and then brine. The organic layer was dried over sodium sulfate, filtered, and concentrated under reduced pressure. The residue was purified by silica gel chromatography (0-60% ethyl acetate/hexanes, linear gradient) to afford 6-[3-chloro-5-(2-methoxyxyl)phenyl]-8-[(trans)-hexahydrocyclopenta[b][1,4]oxazin-4(4aH)-yl]-7-[(trans-4-methylcyclohexyl)methyl]-7H-purine-2-carbonitrile (racemate). MS (APCI)=565 (M+1)$^+$.

Steps 6-7: Using procedures similar to those described in Example 16.1 (Steps 3 and 4), 6-[3-chloro-5-(2-methoxyethoxyl)phenyl]-8-[(trans)-hexahydrocyclopenta[b][1,4]oxazin-4(4aH)-yl]-7-[(trans-4-methylcyclohexyl)methyl]-7H-purine-2-carbonitrile (racemate) was converted to 3-{6-[3-chloro-5-(2-methoxyethoxyl)phenyl]-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one (racemate). $^1$H NMR (400 MHz, CDCl$_3$) δ 7.11 (brs, 1H), 7.15 (brs, 1H), 7.19 (brs, 1H), 4.09-4.22 (m, 3H), 3.91-3.92 (m, 1H), 3.73-3.79 (m, 2H), 3.50-3.56 (m, 1H), 3.46 (s, 3H), 3.14-3.28 (m, 1H), 3.02-3.05 (m, 1H), 2.55-2.60 (m, 1H), 2.00-2.17 (m, 2H), 1.61-1.86 (m, 8H), 1.18-

1.20 (m, 1H), 1.06-1.09 (m, 2H), 0.83-0.86 (m, 3H), 0.78 (d, J=8.0 Hz, 3H), 0.59-0.63 (m, 2H). MS (APCI)=624 (M+1)+.

Example 16.161

3-{6-[2-(benzyloxy)-5-chloropyridin-3-yl]-7-[(trans-4-methylcyclohexyl)methyl]-8-[(3R)-3-phenylmorpholin-4-yl]-7H-purin-2-yl}-1,2,4-oxadiazol-5(4H)-one

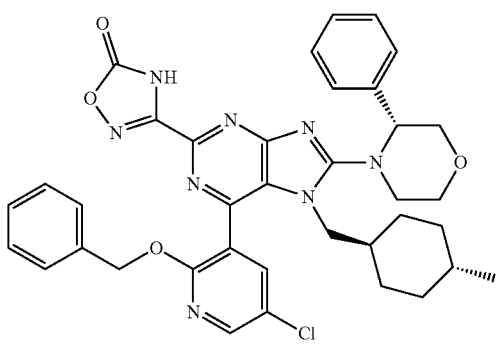 [SMILES: C[C@H]1CC[C@H](Cn2c(N3CCOC[C@H]3c3ccccc3)nc3nc(-c4noc(=O)[nH]4)nc(-c4cc(Cl)cnc4OCc4ccccc4)c32)CC1]

Step 1: (R)-4-(2,6-dichloro-7-((trans-4-methylcyclohexyl)methyl)-7H-purin-8-yl)-3-phenylmorpholine (Preparative Example 12.5; 1.00 g, 2.17 mmol), (2-(benzyloxy)-5-chloropyridin-3-yl)boronic acid (603 mg, 2.17 mmol) and Na₂CO₃ (3.26 mL, 2 M) were added to a vial containing degassed DME (12 mL), followed by the addition of PdCl₂(dppf) (318 mg, 0.43 mmol). The vial was sealed and the reaction was heated at 100° C. for 1.5 hours. The reaction was then diluted with EtOAc (20 mL) and washed with H₂O (2×5 mL) and brine (5 mL). The organic layer was dried over anhydrous Na₂SO₄, filtered, and concentrated in vacuo. The residue was purified on a silica gel column (0 to 30% EtOAc/hexanes) to afford (R)-4-(4-(2-(benzyloxy)-5-chloropyridin-3-yl)-6-chloro-3-(((trans)-4-methylcyclohexyl)methyl)-3H-imidazo[4,5-c]pyridin-2-yl)-3-phenylmorpholine. MS (ES)=642 (M+1)+.

Steps 2-4: Following procedures similar to those described in Example 16.160 (Step 3), and Example 16.1 (Steps 3 and 4), (R)-4-(4-(2-(benzyloxy)-5-chloropyridin-3-yl)-6-chloro-3-(((trans)-4-methylcyclohexyl)methyl)-3H-imidazo[4,5-c]pyridin-2-yl)-3-phenylmorpholine was converted to 3-{6-[2-(benzyloxy)-5-chloropyridin-3-yl]-7-[(trans-4-methylcyclohexyl)methyl]-8-[(3R)-3-phenylmorpholin-4-yl]-7H-purin-2-yl}-1,2,4-oxadiazol-5(4H)-one. NMR shows 8:2 mixture of rotamers. ¹H NMR (400 MHz, CD₃OD) (for major rotamer) δ 8.42 (s, 1H), 8.23 (s, 1H), 7.34-7.44 (m, 4H), 7.20-7.28 (m, 6H), 5.63 (d, J=12.4 Hz, 1H), 5.19 (d, J=12.4 Hz, 1H), 4.90 (m, 2H), 4.52 (m, 1H), 4.01 (m, 1H), 3.83 (m, 1H), 3.43-3.61 (m, 2H), 3.12 (m, 1H), 2.72 (m, 1H), 1.43 (d, J=11.6 Hz, 2H), 0.99-1.05 (m, 4H), 0.73-0.89 (m, 4H), 0.45-0.56 (m, 3H). MS (ES)=693 (M+1)+.

Example 16.162

3-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one

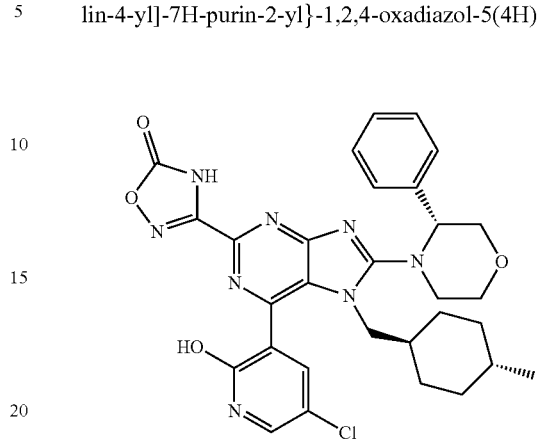

Et₃SiH (22.0 mg, 0.18 mmol) and PdCl₂ (2 mg, 0.01 mmol) were added to a 0° C. solution of 3-{6-[2-(benzyloxy)-5-chloropyridin-3-yl]-7-[(trans-4-methylcyclohexyl)methyl]-8-[(3R)-3-phenylmorpholin-4-yl]-7H-purin-2-yl}-1,2,4-oxadiazol-5(4H)-one (Example 16.161; 25 mg, 0.03 mmol) in anhydrous CH₂Cl₂ (1.5 mL). The reaction was stirred at 0° C. for 30 minutes and then concentrated. The residue was purified on a C-18 column (0 to 100% acetonitrile/water) to afford 3-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one. ¹H NMR (400 MHz, CD₃OD) δ 8.15 (br s, 1H), 7.83 (d, J=2.8 Hz, 1H), 7.52-7.54 (m, 2H), 7.24-7.30 (m, 3H), 5.04 (m, 1H), 4.01-4.20 (m, 2H), 3.87-3.95 (m, 3H), 3.64-3.78 (m, 2H), 3.47 (m, 1H), 1.48-1.53 (m, 2H), 1.31 (m, 1H), 1.28 (m, 1H), 0.88-1.17 (m, 2H), 0.72-0.79 (m, 5H), 0.54-0.60 (m, 2H). MS (ES)=603 (M+1)+.

Example 16.165

3-{6-cyclohexyl-7-[(trans-4-methylcyclohexyl)methyl]-8-[(3R)-3-phenylmorpholin-4-yl]-7H-purin-2-yl}-1,2,4-oxadiazol-5(4H)-one

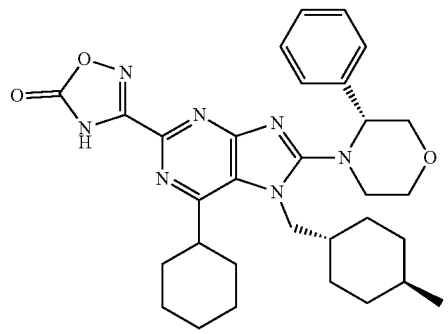 [SMILES: C[C@H]1CC[C@H](Cn2c(N3CCOC[C@H]3c3ccccc3)nc3nc(-c4noc(=O)[nH]4)nc(C4CCCCC4)c32)CC1]

Step 1: A 1M solution of cyclohexyl magnesiumbromide in THF (2.0 mL, 2.0 mmol) was added dropwise to a −40° C. suspension of CuI (190 mg, 1.0 mmol) in THF (10 mL). The resulting mixture was warmed to 0° C. and stirred for 1 hour. Next, a solution of (R)-4-(2,6-dichloro-7-((trans-4- methylcyclohexyl)methyl)-7H-purin-8-yl)-3-phenylmorpholine (Preparative Example 12.5; 230 mg, 0.5 mmol) in THF (3 mL) was added slowly at 0° C. and then the reaction was warmed to room temperature. After stirring at room temperature for 2 hours, the reaction was quenched with saturated aqueous NH$_4$Cl (5.0 mL) solution and then extracted with EtOAc (50 mL). The organic layer was dried over anhydrous Na$_2$SO$_4$, filtered, and concentrated. Purification of the residue on a silica gel column (0 to 50% EtOAc/hexanes) afforded (R)-4-(2-chloro-6-cyclohexyl-7-(((trans)-4-methylcyclohexyl)methyl)-7H-purin-8-yl)-3-phenylmorpholine. MS (APCI)=508 (M+1)$^+$.

Steps 2-4: Following procedures similar to those described in Example 16.160 (Step 3), and Example 16.1 (Steps 3 and 4), (R)-4-(2-chloro-6-cyclohexyl-7-(((trans)-4-methylcyclohexyl)methyl)-7H-purin-8-yl)-3-phenylmorpholine was converted to 3-{6-cyclohexyl-7-[(trans-4-methylcyclohexyl)methyl]-8-[(3R)-3-phenylmorpholin-4-yl]-7H-purin-2-yl}-1,2,4-oxadiazol-5(4H)-one. $^1$H NMR (300 MHz, CDCl$_3$) δ 7.39-7.45 (m, 2H), 7.22-7.31 (m, 3H), 4.84 (t, J=4.8 Hz, 1H), 4.11 (d, J=5.2 Hz, 2H), 3.90-4.05 (m, 3H), 3.75-3.82 (m, 1H), 3.46 (t, J=4.8 Hz, 2H), 2.80-2.90 (m, 1H), 1.42-2.0 (m, 10H), 1.15-1.42 (m, 6H), 0.85-1.12 (m, 2H), 0.85 (d, J=6.5 Hz, 3H), 0.62-0.80 (m, 2H). MS (ES)=558 (M+1)$^+$.

The following compounds in Table 16 were described above or were prepared using procedures which are analogous to those described above.

TABLE 16

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.1 | 71.75 | 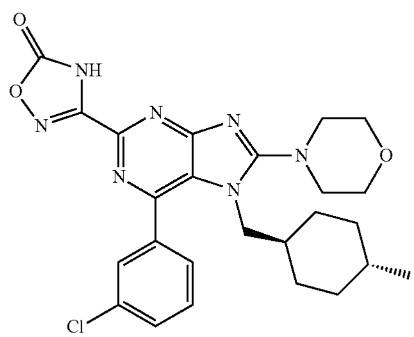 [SMILES: C[C@H]1CC[C@H](Cn2c(N3CCOCC3)nc3nc(-c4noc(=O)[nH]4)nc(-c4cccc(Cl)c4)c32)CC1] | 3-(6-(3-chlorophenyl)-7-(((trans)-4-methylcyclohexyl)methyl)-8-morpholino-7H-purin-2-yl)-1,2,4-oxadiazol-5(4H)-one | | 510 | 510 |
| 16.2 | 106.1 | 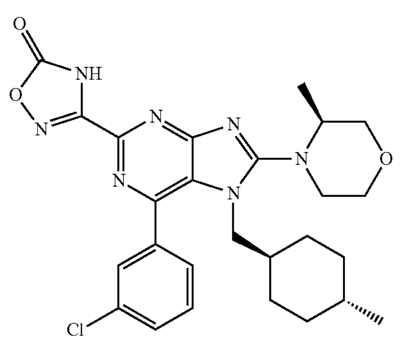 [SMILES: C[C@H]1COCCN1c1nc2nc(-c3noc(=O)[nH]3)nc(-c3cccc(Cl)c3)c2n1C[C@H]1CC[C@H](C)CC1] | 3-(6-(3-chlorophenyl)-7-(((trans)-4-methylcyclohexyl)methyl)-8-((S)-3-methylmorpholino)-7H-purin-2-yl)-1,2,4-oxadiazol-5(4H)-one | | 524 | 524 |
| 16.3 | 563.1 | 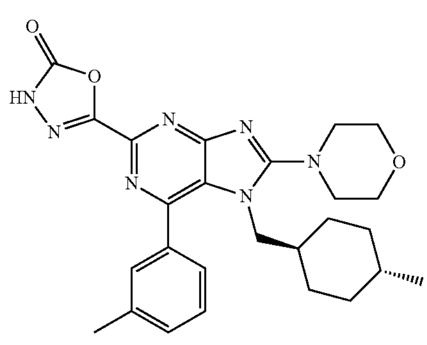 [SMILES: Cc1cccc(-c2nc(-c3n[nH]c(=O)o3)nc3nc(N4CCOCC4)n(C[C@H]4CC[C@H](C)CC4)c23)c1] | 5-(7-(((trans)-4-methylcyclohexyl)methyl)-8-morpholino-6-(m-tolyl)-7H-purin-2-yl)-1,3,4-oxadiazol-2(3H)-one | | 490 | 490 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.4 | 29.77 | 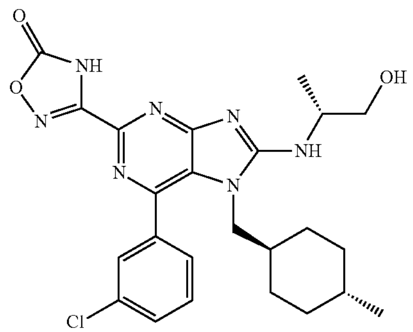 [SMILES: C[C@H](CO)Nc1nc2nc(-c3noc(=O)[nH]3)nc(-c3cccc(Cl)c3)c2n1C[C@H]1CC[C@H](C)CC1] | 3-(6-(3-chlorophenyl)-8-(((R)-1-hydroxypropan-2-yl)amino)-7-(((trans)-4-methylcyclohexyl)methyl)-7H-purin-2-yl)-1,2,4-oxadiazol-5(4H)-one | | 498 | 498 |
| 16.5 | 1.594 | 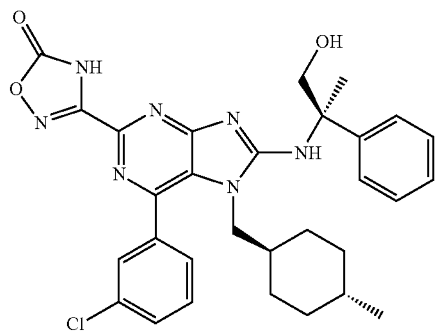 [SMILES: C[C@@](CO)(Nc1nc2nc(-c3noc(=O)[nH]3)nc(-c3cccc(Cl)c3)c2n1C[C@H]1CC[C@H](C)CC1)c1ccccc1] | 3-(6-(3-chlorophenyl)-8-(((S)-1-hydroxy-2-phenylpropan-2-yl)amino)-7-(((trans)-4-methylcyclohexyl)methyl)-7H-purin-2-yl)-1,2,4-oxadiazol-5(4H)-one | | 574 | 574 |
| 16.6 | 8.05 | 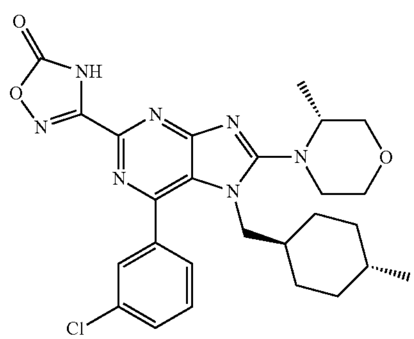 [SMILES: C[C@@H]1COCCN1c1nc2nc(-c3noc(=O)[nH]3)nc(-c3cccc(Cl)c3)c2n1C[C@H]1CC[C@H](C)CC1] | 3-(6-(3-chlorophenyl)-7-(((trans)-4-methylcyclohexyl)methyl)-8-((R)-3-methylmorpholino)-7H-purin-2-yl)-1,2,4-oxadiazol-5(4H)-one | | 524 | 524 |
| 16.7 | 14.48 | 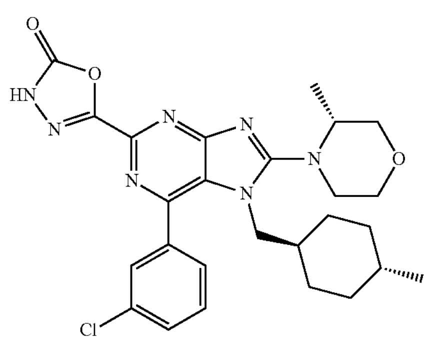 [SMILES: C[C@@H]1COCCN1c1nc2nc(-c3n[nH]c(=O)o3)nc(-c3cccc(Cl)c3)c2n1C[C@H]1CC[C@H](C)CC1] | 5-(6-(3-chlorophenyl)-7-(((trans)-4-methylcyclohexyl)methyl)-8-((R)-3-methylmorpholino)-7H-purin-2-yl)-1,3,4-oxadiazol-2(3H)-one | | 524 | 524 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.8 | 1.493 | 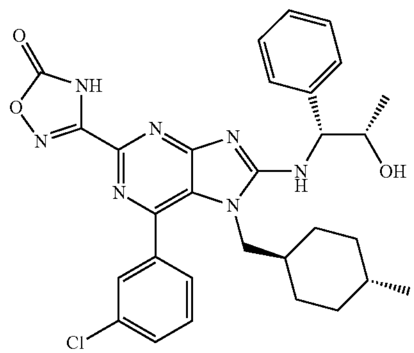 [SMILES: C[C@H](O)[C@H](Nc1nc2nc(-c3noc(=O)[nH]3)nc(-c3cccc(Cl)c3)c2n1C[C@H]1CC[C@H](C)CC1)c1ccccc1] | 3-(6-(3-chlorophenyl)-8-(((1R,2S)-2-hydroxy-1-phenylpropyl)amino)-7-(((trans)-4-methylcyclohexyl)methyl)-7H-purin-2-yl)-1,2,4-oxadiazol-5(4H)-one | | 574 | 574 |
| 16.9 | 3.007 | 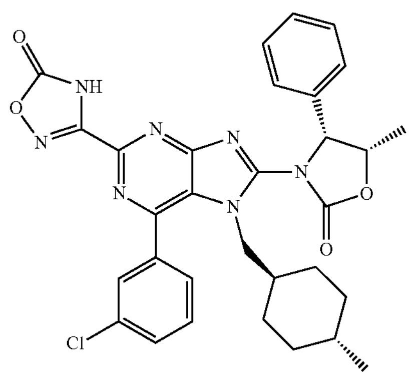 [SMILES: C[C@@H]1OC(=O)N(c2nc3nc(-c4noc(=O)[nH]4)nc(-c4cccc(Cl)c4)c3n2C[C@H]2CC[C@H](C)CC2)[C@@H]1c1ccccc1] | 3-(6-(3-chlorophenyl)-8-((4R,5S)-5-methyl-2-oxo-4-phenyloxazolidin-3-yl)-7-(((trans)-4-methylcyclohexyl)methyl)-7H-purin-2-yl)-1,2,4-oxadiazol-5(4H)-one | | 600 | 600 |
| 16.10 | 18.12 | 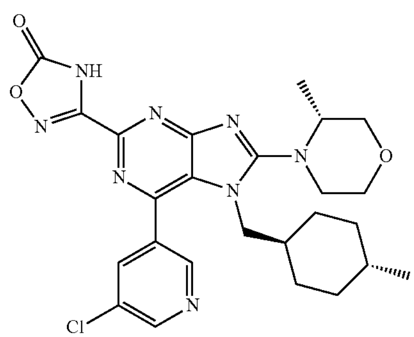 [SMILES: C[C@@H]1COCCN1c1nc2nc(-c3noc(=O)[nH]3)nc(-c3cncc(Cl)c3)c2n1C[C@H]1CC[C@H](C)CC1] | 3-(6-(5-chloropyridin-3-yl)-7-(((trans)-4-methylcyclohexyl)methyl)-8-((R)-3-methylmorpholino)-7H-purin-2-yl)-1,2,4-oxadiazol-5(4H)-one | | 525 | 525 |
| 16.11 | 27.71 | 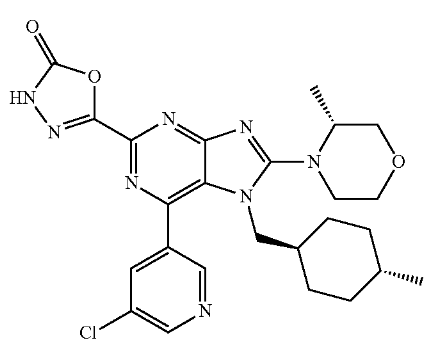 [SMILES: C[C@@H]1COCCN1c1nc2nc(-c3n[nH]c(=O)o3)nc(-c3cncc(Cl)c3)c2n1C[C@H]1CC[C@H](C)CC1] | 5-(6-(5-chloropyridin-3-yl)-7-(((trans)-4-methylcyclohexyl)methyl)-8-((R)-3-methylmorpholino)-7H-purin-2-yl)-1,3,4-oxadiazol-2(3H)-one | | 525 | 525 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.12 | 10.11 | 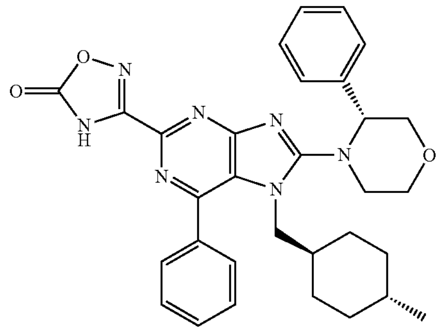 [SMILES: C[C@H]1CC[C@H](Cn2c(N3CCOC[C@H]3c3ccccc3)nc3nc(-c4noc(=O)[nH]4)nc(-c4ccccc4)c32)CC1] | 3-(7-(((trans)-4-methylcyclohexyl)methyl)-6-phenyl-8-((R)-3-phenylmorpholino)-7H-purin-2-yl)-1,2,4-oxadiazol-5(4H)-one | | 552 | 552 |
| 16.13 | 401.3 | 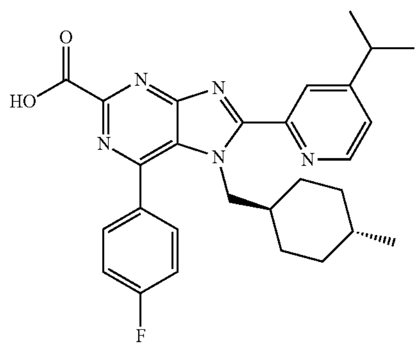 [SMILES: CC(C)c1ccnc(-c2nc3nc(C(=O)O)nc(-c4ccc(F)cc4)c3n2C[C@H]2CC[C@H](C)CC2)c1] | 6-(4-fluorophenyl)-7-[(trans-4-methylcyclohexyl)methyl]-8-[4-(1-methylethyl)pyridin-2-yl]-7H-purine-2-carboxylic acid | TFA | 488 | 488 |
| 16.14 | 35.46 | 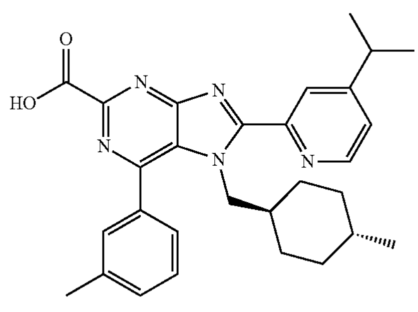 [SMILES: Cc1cccc(-c2nc(C(=O)O)nc3nc(-c4cc(C(C)C)ccn4)n(C[C@H]4CC[C@H](C)CC4)c23)c1] | 7-[(trans-4-methylcyclohexyl)methyl]-8-[4-(1-methylethyl)pyridin-2-yl]-6-(3-methylphenyl)-7H-purine-2-carboxylic acid | TFA | 484 | 484 |
| 16.15 | 30.03 | 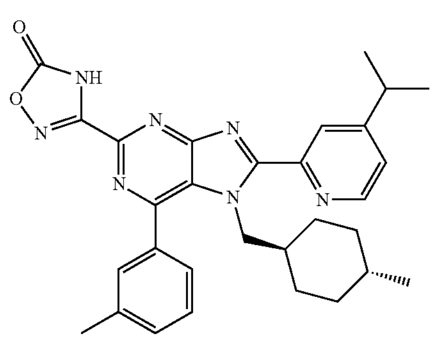 [SMILES: Cc1cccc(-c2nc(-c3noc(=O)[nH]3)nc3nc(-c4cc(C(C)C)ccn4)n(C[C@H]4CC[C@H](C)CC4)c23)c1] | 3-{7-[(trans-4-methylcyclohexyl)methyl]-8-[4-(1-methylethyl)pyridin-2-yl]-6-(3-methylphenyl)-7H-purin-2-yl}-1,2,4-oxadiazol-5(4H)-one | TFA | 524 | 524 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.16 | 11.44 | 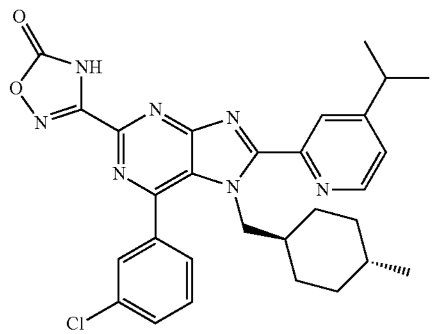 [SMILES: CC(C)c1ccnc(-c2nc3nc(-c4noc(=O)[nH]4)nc(-c4cccc(Cl)c4)c3n2C[C@H]2CC[C@H](C)CC2)c1] | 3-{6-(3-chlorophenyl)-7-[(trans-4-methylcyclohexyl)methyl]-8-[4-(1-methylethyl)pyridin-2-yl]-7H-purin-2-yl}-1,2,4-oxadiazol-5(4H)-one | TFA | 544 | 544 |
| 16.17 | 3.955 | 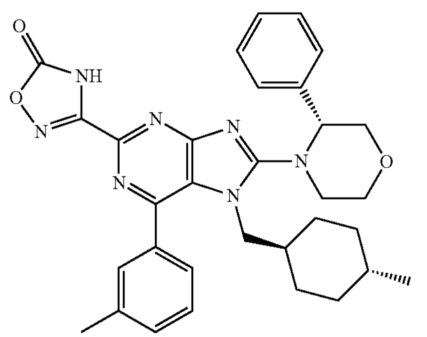 [SMILES: Cc1cccc(-c2nc(-c3noc(=O)[nH]3)nc3nc(N4CCOC[C@H]4c4ccccc4)n(C[C@H]4CC[C@H](C)CC4)c23)c1] | 3-{7-[(trans-4-methylcyclohexyl)methyl]-6-(3-methylphenyl)-8-[(3R)-3-phenylmorpholin-4-yl]-7H-purin-2-yl}-1,2,4-oxadiazol-5(4H)-one | | 566 | 566 |
| 16.18 | 1.266 | 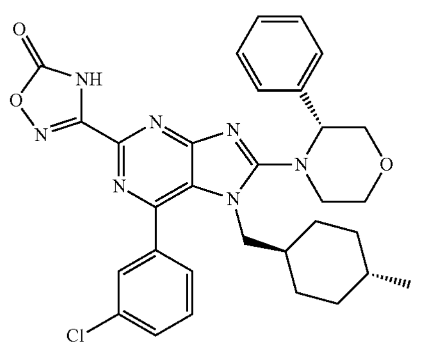 [SMILES: C[C@H]1CC[C@H](Cn2c(N3CCOC[C@H]3c3ccccc3)nc3nc(-c4noc(=O)[nH]4)nc(-c4cccc(Cl)c4)c32)CC1] | 3-{6-(3-chlorophenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 586 | 586 |
| 16.19 | 0.9953 | 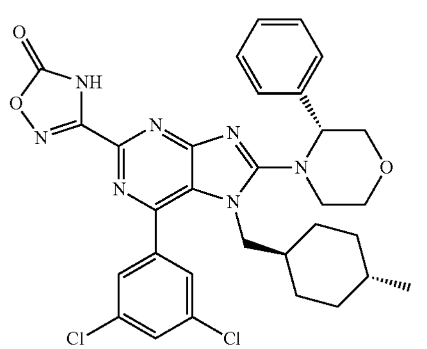 [SMILES: C[C@H]1CC[C@H](Cn2c(N3CCOC[C@H]3c3ccccc3)nc3nc(-c4noc(=O)[nH]4)nc(-c4cc(Cl)cc(Cl)c4)c32)CC1] | 3-{6-(3,5-dichlorophenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 620 | 620 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.20 | 1.21 | 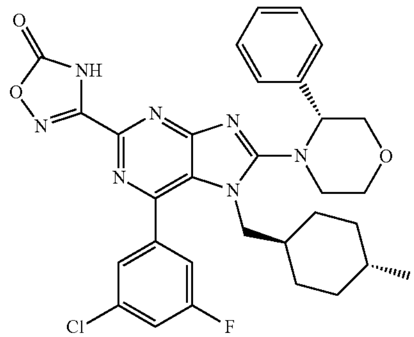 [SMILES: C[C@H]1CC[C@H](Cn2c(N3CCOC[C@H]3c3ccccc3)nc3nc(-c4noc(=O)[nH]4)nc(-c4cc(F)cc(Cl)c4)c32)CC1] | 3-{6-(3-chloro-5-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 604 | 604 |
| 16.21 | 2.249 | 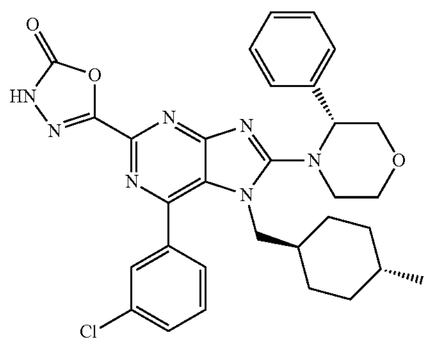 [SMILES: C[C@H]1CC[C@H](Cn2c(N3CCOC[C@H]3c3ccccc3)nc3nc(-c4n[nH]c(=O)o4)nc(-c4cccc(Cl)c4)c32)CC1] | 5-{6-(3-chlorophenyl)-7-[(trans-4-methylcyclohexyl)methyl]-8-[(3R)-3-phenylmorpholin-4-yl]-7H-purin-2-yl}-1,3,4-oxadiazol-2(3H)-one | TFA | 586 | 586 |
| 16.22 | 0.68 | 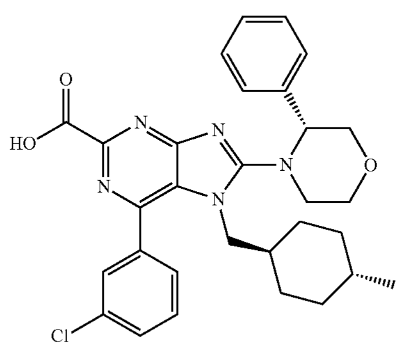 [SMILES: C[C@H]1CC[C@H](Cn2c(N3CCOC[C@H]3c3ccccc3)nc3nc(C(=O)O)nc(-c4cccc(Cl)c4)c32)CC1] | 6-(3-chlorophenyl)-7-[(trans-4-methylcyclohexyl)methyl]-8-[(3R)-3-phenylmorpholin-4-yl]-7H-purine-2-carboxylic acid | TFA | 546 | 546 |
| 16.23 | 1.44 | 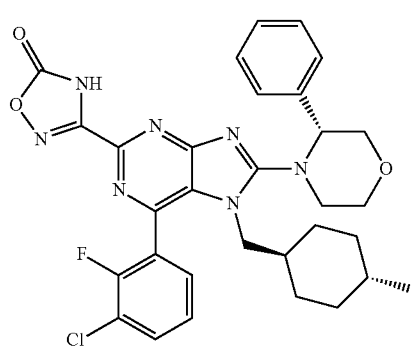 [SMILES: C[C@H]1CC[C@H](Cn2c(N3CCOC[C@H]3c3ccccc3)nc3nc(-c4noc(=O)[nH]4)nc(-c4cccc(Cl)c4F)c32)CC1] | 3-{6-(3-chloro-2-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 604 | 604 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.24 | 5.625 | 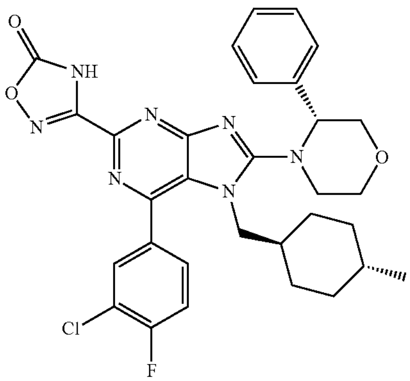 [SMILES: C[C@H]1CC[C@H](Cn2c(N3CCOC[C@H]3c3ccccc3)nc3nc(-c4noc(=O)[nH]4)nc(-c4ccc(F)c(Cl)c4)c32)CC1] | 3-{6-(3-chloro-4-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 604 | 604 |
| 16.25 | 1.63 | 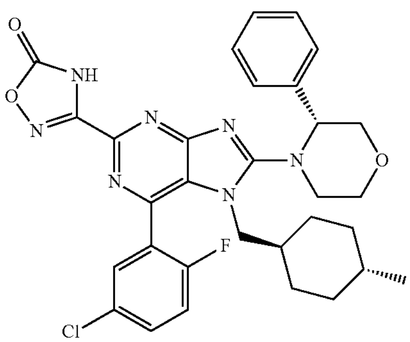 [SMILES: C[C@H]1CC[C@H](Cn2c(N3CCOC[C@H]3c3ccccc3)nc3nc(-c4noc(=O)[nH]4)nc(-c4cc(Cl)ccc4F)c32)CC1] | 3-{6-(5-chloro-2-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 604 | 604 |
| 16.26 | 0.5167 | 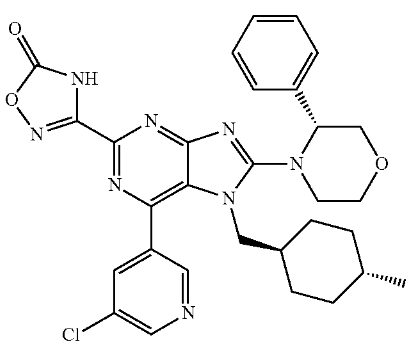 [SMILES: C[C@H]1CC[C@H](Cn2c(N3CCOC[C@H]3c3ccccc3)nc3nc(-c4noc(=O)[nH]4)nc(-c4cncc(Cl)c4)c32)CC1] | 3-{6-(5-chloropyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 587 | 587 |
| 16.27 | 333.7 | 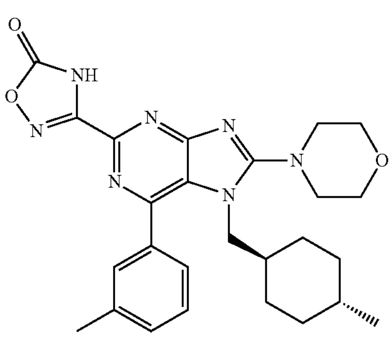 [SMILES: Cc1cccc(-c2nc(-c3noc(=O)[nH]3)nc3nc(N4CCOCC4)n(C[C@H]4CC[C@H](C)CC4)c23)c1] | 3-{7-[(trans-4-methylcyclohexyl)methyl]-6-(3-methylphenyl)-8-morpholin-4-yl-7H-purin-2-yl}-1,2,4-oxadiazol-5(4H)-one | | 490 | 490 |

TABLE 16-continued

| Ex. | FRET IC$_{50}$ (nM) | Chemical Name | Salt Form | [M + H]$^+$ Calc'd | [M + H]$^+$ Obsv'd |
|---|---|---|---|---|---|
| 16.28 | 38.7 | 3-{7-[(trans-4-methylcyclohexyl)methyl]-8-[(3R)-3-methylmorpholin-4-yl]-6-(3-methylphenyl)-7H-purin-2-yl}-1,2,4-oxadiazol-5(4H)-one | | 504 | 504 |
| 16.29 | 5.199 | 3-{6-(3-chlorophenyl)-8-(3,3-dimethylmorpholin-4-yl)-7-[(trans-4-methylcyclohexyl)methyl]-7H-purin-2-yl}-1,2,4-oxadiazol-5(4H)-one | TFA | 538 | 538 |
| 16.30 | 2.767 | 3-{6-(3-ethylphenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 580 | 580 |
| 16.31 | 7.108 | 3-{6-[3-(difluoromethyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one | TFA | 602 | 602 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.32 | 60.54 | 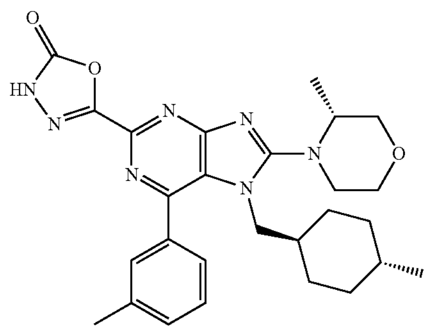 [SMILES: Cc1cccc(-c2nc(-c3n[nH]c(=O)o3)nc3nc(N4CCOC[C@H]4C)n(C[C@H]4CC[C@H](C)CC4)c23)c1] | 5-{7-[(trans-4-methylcyclohexyl)methyl]-8-[(3R)-3-methylmorpholin-4-yl]-6-(3-methylphenyl)-7H-purin-2-yl}-1,3,4-oxadiazol-2(3H)-one | | 504 | 504 |
| 16.33 | 162.9 | 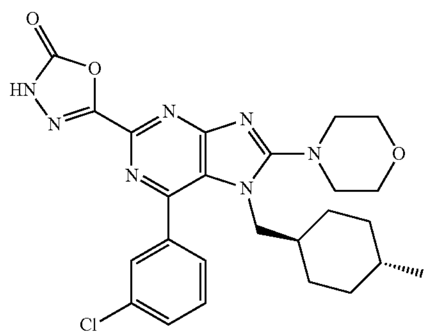 [SMILES: C[C@H]1CC[C@H](Cn2c(N3CCOCC3)nc3nc(-c4n[nH]c(=O)o4)nc(-c4cccc(Cl)c4)c32)CC1] | 5-{6-(3-chlorophenyl)-7-[(trans-4-methylcyclohexyl)methyl]-8-morpholin-4-yl-7H-purin-2-yl}-1,3,4-oxadiazol-2(3H)-one | | 510 | 510 |
| 16.34 | 503.1 | 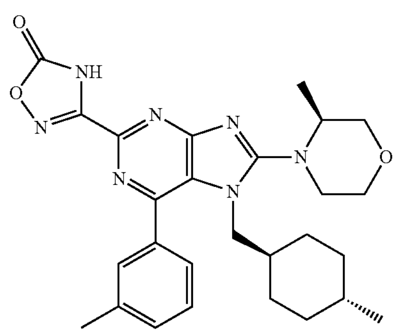 [SMILES: Cc1cccc(-c2nc(-c3noc(=O)[nH]3)nc3nc(N4CCOC[C@@H]4C)n(C[C@H]4CC[C@H](C)CC4)c23)c1] | 3-{7-[(trans-4-methylcyclohexyl)methyl]-8-[(3S)-3-methylmorpholin-4-yl]-6-(3-methylphenyl)-7H-purin-2-yl}-1,2,4-oxadiazol-5(4H)-one | | 504 | 504 |
| 16.35 | 0.8238 | 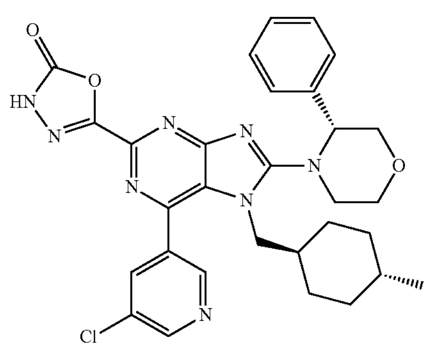 [SMILES: C[C@H]1CC[C@H](Cn2c(N3CCOC[C@H]3c3ccccc3)nc3nc(-c4n[nH]c(=O)o4)nc(-c4cncc(Cl)c4)c32)CC1] | 5-{6-(5-chloropyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one | | 587 | 587 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.36 | 26.17 | 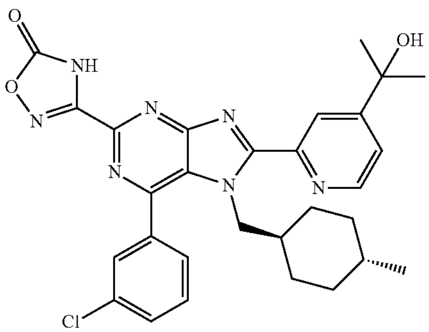 [SMILES: CC(C)(O)c1ccnc(-c2nc3nc(-c4noc(=O)[nH]4)nc(-c4cccc(Cl)c4)c3n2C[C@H]2CC[C@H](C)CC2)c1] | 3-{6-(3-chlorophenyl)-8-[4-(1-hydroxy-1-methylethyl)pyridin-2-yl]-7-[(trans-4-methylcyclohexyl)methyl]-7H-purin-2-yl}-1,2,4-oxadiazol-5(4H)-one | | 560 | 560 |
| 16.37 | 1000 | 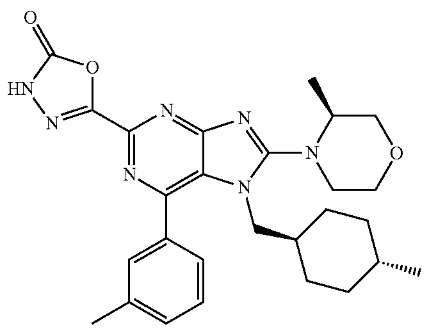 [SMILES: Cc1cccc(-c2nc(-c3n[nH]c(=O)o3)nc3nc(N4CCOC[C@@H]4C)n(C[C@H]4CC[C@H](C)CC4)c23)c1] | 5-{7-[(trans-4-methylcyclohexyl)methyl]-8-[(3S)-3-methylmorpholin-4-yl]-6-(3-methylphenyl)-7H-purin-2-yl}-1,3,4-oxadiazol-2(3H)-one | | 504 | 504 |
| 16.38 | 1.951 | 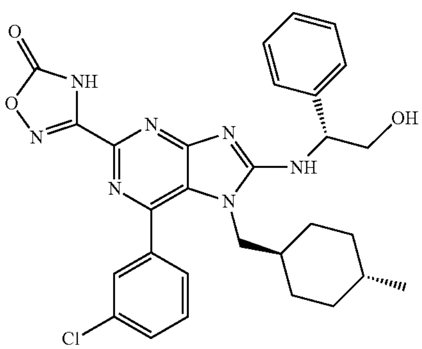 [SMILES: C[C@H]1CC[C@H](Cn2c(N[C@@H](CO)c3ccccc3)nc3nc(-c4noc(=O)[nH]4)nc(-c4cccc(Cl)c4)c32)CC1] | 3-{6-(3-chlorophenyl)-8-{[(1R)-2-hydroxy-1-phenylethyl]amino}-7-[(trans-4-methylcyclohexyl)methyl]-7H-purin-2-yl}-1,2,4-oxadiazol-5(4H)-one | | 560 | 560 |
| 16.39 | 47.47 | 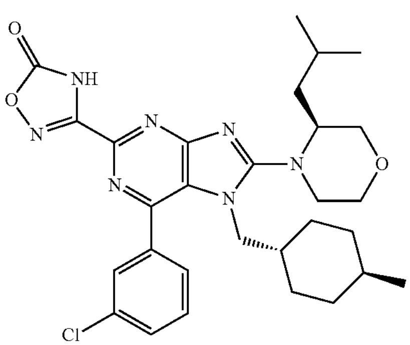 [SMILES: CC(C)C[C@H]1COCCN1c1nc2nc(-c3noc(=O)[nH]3)nc(-c3cccc(Cl)c3)c2n1C[C@H]1CC[C@H](C)CC1] | 3-{6-(3-chlorophenyl)-7-[(trans-4-methylcyclohexyl)methyl]-8-[(3S)-3-(2-methylpropyl)morpholin-4-yl]-7H-purin-2-yl}-1,2,4-oxadiazol-5(4H)-one | TFA | 566 | 566 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.40 | 4.589 | 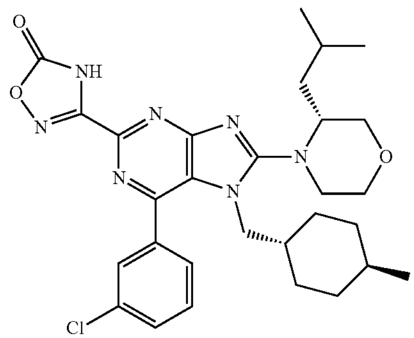 [SMILES: CC(C)C[C@@H]1COCCN1c1nc2nc(-c3noc(=O)[nH]3)nc(-c3cccc(Cl)c3)c2n1C[C@H]1CC[C@H](C)CC1] | 3-{6-(3-chlorophenyl)-7-[(trans-4-methylcyclohexyl)methyl]-8-[(3R)-3-(2-methylpropyl)morpholin-4-yl]-7H-purin-2-yl}-1,2,4-oxadiazol-5(4H)-one | TFA | 566 | 566 |
| 16.41 | 17.81 | 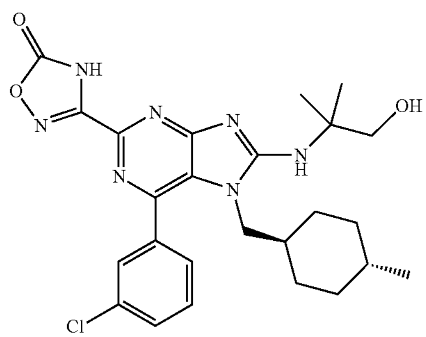 [SMILES: CC(C)(CO)Nc1nc2nc(-c3noc(=O)[nH]3)nc(-c3cccc(Cl)c3)c2n1C[C@H]1CC[C@H](C)CC1] | 3-{6-(3-chlorophenyl)-8-[(2-hydroxy-1,1-dimethylethyl)amino]-7-[(trans-4-methylcyclohexyl)methyl]-7H-purin-2-yl}-1,2,4-oxadiazol-5(4H)-one | | 512 | 512 |
| 16.42 | 3.624 | 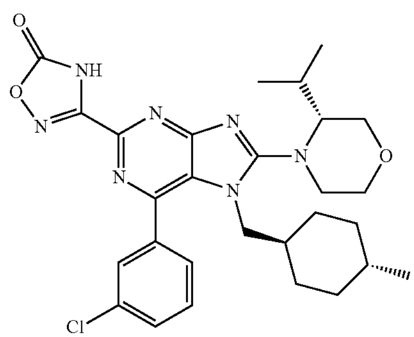 [SMILES: CC(C)[C@@H]1COCCN1c1nc2nc(-c3noc(=O)[nH]3)nc(-c3cccc(Cl)c3)c2n1C[C@H]1CC[C@H](C)CC1] | 3-{6-(3-chlorophenyl)-7-[(trans-4-methylcyclohexyl)methyl]-8-[(3R)-3-(1-methylethyl)morpholin-4-yl]-7H-purin-2-yl}-1,2,4-oxadiazol-5(4H)-one | | 552 | 552 |
| 16.43 | 238.8 | 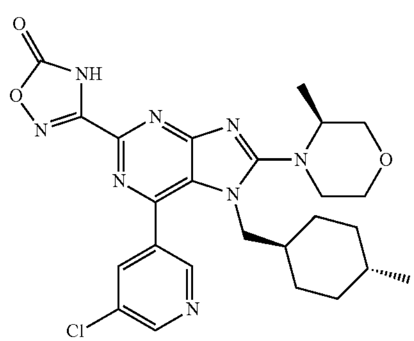 [SMILES: C[C@H]1COCCN1c1nc2nc(-c3noc(=O)[nH]3)nc(-c3cncc(Cl)c3)c2n1C[C@H]1CC[C@H](C)CC1] | 3-{6-(5-chloropyridin-3-yl)-7-[(trans-4-methylcyclohexyl)methyl]-8-[(3S)-3-methylmorpholin-4-yl]-7H-purin-2-yl}-1,2,4-oxadiazol-5(2H)-one | | 525 | 525 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.44 | 0.2052 | 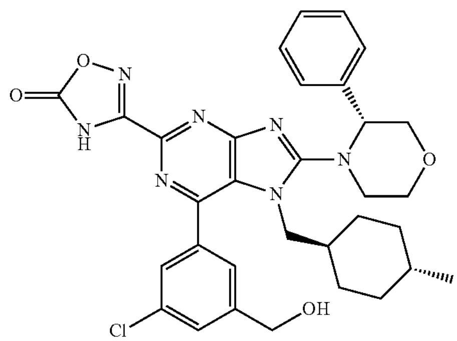 [SMILES: C[C@H]1CC[C@H](Cn2c(N3CCOC[C@H]3c3ccccc3)nc3nc(-c4noc(=O)[nH]4)nc(-c4cc(Cl)cc(CO)c4)c32)CC1] | 3-{6-[3-chloro-5-(hydroxymethyl)phen-yl]-7-[(trans-4-methylcyclohexyl)methyl]-8-[(3R)-3-phenylmorpholin-4-yl]-7H-purin-2-yl}-1,2,4-oxadiazol-5(4H)-one | TFA | 616 | 616 |
| 16.45 | 47.5 | 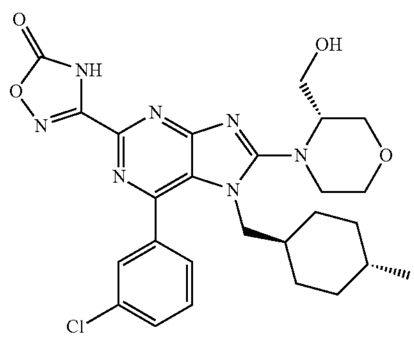 [SMILES: C[C@H]1CC[C@H](Cn2c(N3CCOC[C@H]3CO)nc3nc(-c4noc(=O)[nH]4)nc(-c4cccc(Cl)c4)c32)CC1] | 3-{6-(3-chlorophenyl)-8-[(3R)-3-(hydroxymethyl)morpholin-4-yl]-7-[(trans-4-methylcyclohexyl)methyl]-7H-purin-2-yl}-1,2,4-oxadiazol-5(4H)-one | | 540 | 540 |
| 16.46 | 71.01 | 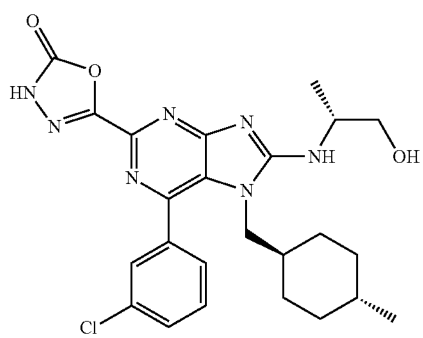 [SMILES: C[C@H](CO)Nc1nc2nc(-c3n[nH]c(=O)o3)nc(-c3cccc(Cl)c3)c2n1C[C@H]1CC[C@H](C)CC1] | 5-{6-(3-chlorophenyl)-8-{[(1R)-2-hydroxy-1-methylethyl]amino}-7-[(trans-4-methylcyclohexyl)methyl]-7H-purin-2-yl}-1,3,4-oxadiazol-2(3H)-one | | 498 | 498 |
| 16.47 | 11.15 | 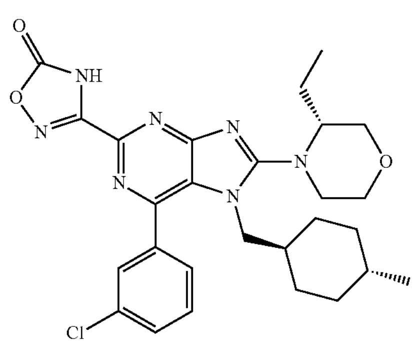 [SMILES: CC[C@@H]1COCCN1c1nc2nc(-c3noc(=O)[nH]3)nc(-c3cccc(Cl)c3)c2n1C[C@H]1CC[C@H](C)CC1] | 3-{6-(3-chlorophenyl)-8-[(3R)-3-ethylmorpholin-4-yl]-7-[(trans-4-methylcyclohexyl)methyl]-7H-purin-2-yl}-1,2,4-oxadiazol-5(4H)-one | | 538 | 538 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.48 | 88.3 | 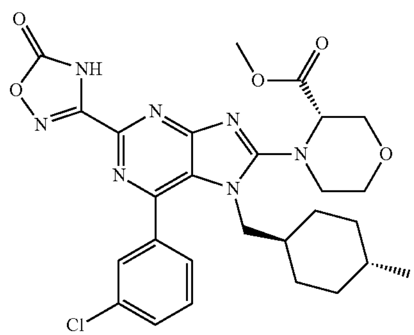 [SMILES: COC(=O)[C@@H]1COCCN1c1nc2nc(-c3noc(=O)[nH]3)nc(-c3cccc(Cl)c3)c2n1C[C@H]1CC[C@H](C)CC1] | methyl (3S)-4-[6-(3-chlorophenyl)-7-[(trans-4-methylcyclohexyl)methyl]-2-(5-oxo-4,5-dihydro-1,2,4-oxadiazol-3-yl)-7H-purin-8-yl]morpholine-3-carboxylate | | 568 | 568 |
| 16.49 | 1.632 | 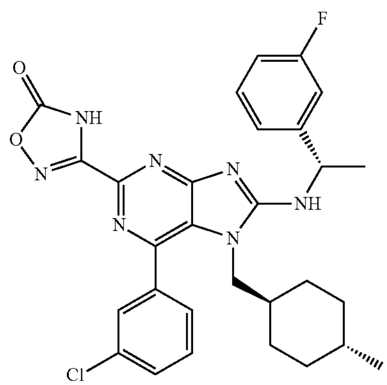 [SMILES: C[C@H](Nc1nc2nc(-c3noc(=O)[nH]3)nc(-c3cccc(Cl)c3)c2n1C[C@H]1CC[C@H](C)CC1)c1cccc(F)c1] | 3-{6-(3-chlorophenyl)-8-{[(1S)-1-(3-fluorophenyl)ethyl]amino}-7-[(trans-4-methylcyclohexyl)methyl]-7H-purin-2-yl}-1,2,4-oxadiazol-5(4H)-one | | 562 | 562 |
| 16.50 | 2.671 | 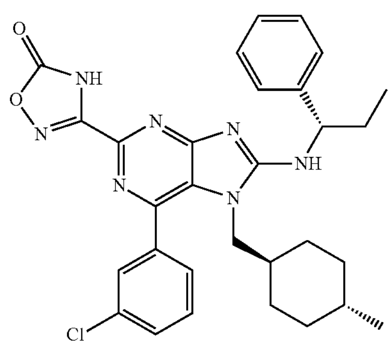 [SMILES: CC[C@H](Nc1nc2nc(-c3noc(=O)[nH]3)nc(-c3cccc(Cl)c3)c2n1C[C@H]1CC[C@H](C)CC1)c1ccccc1] | 3-(6-(3-chlorophenyl)-7-[(trans-4-methylcyclohexyl)methyl]-8-{[(1S)-1-phenylpropyl]amino}-7H-purin-2-yl]-1,2,4-oxadiazol-5(4H)-one | | 558 | 558 |
| 16.51 | 30.15 | 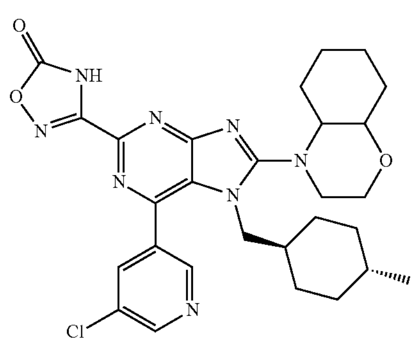 [SMILES: C[C@H]1CC[C@H](Cn2c(N3CCOC4CCCCC43)nc3nc(-c4noc(=O)[nH]4)nc(-c4cncc(Cl)c4)c32)CC1] | 3-[6-(5-chloropyridin-3-yl)-7-[(trans-4-methylcyclohexyl)methyl]-8-(octahydro-4H-1,4-benzoxazin-4-yl)-7H-purin-2-yl]-1,2,4-oxadiazol-5(4H)-one (enantiomer 1) | TFA | 565 | 565 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.52 | 1.002 | 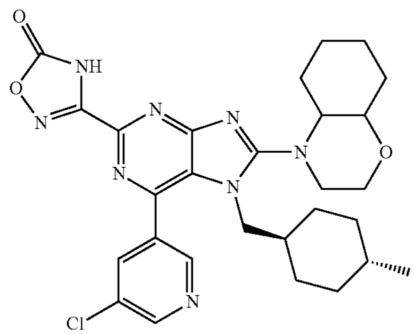 [SMILES: C[C@H]1CC[C@H](Cn2c(N3CCOC4CCCCC43)nc3nc(-c4noc(=O)[nH]4)nc(-c4cncc(Cl)c4)c32)CC1] | 3-[6-(5-chloropyridin-3-yl)-7-[(trans-4-methylcyclohexyl)methyl]-8-(octahydro-4H-1,4-benzoxazin-4-yl)-7H-purin-2-yl]-1,2,4-oxadiazol-5(4H)-one (enantiomer 2) | TFA | 565 | 565 |
| 16.53 | 42.84 | 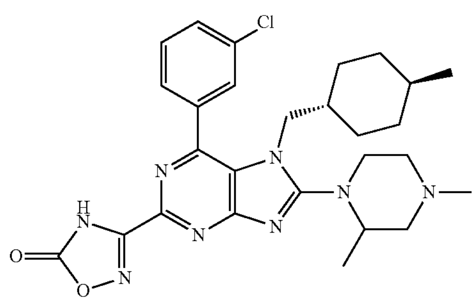 [SMILES: CC1CN(C)CCN1c1nc2nc(-c3noc(=O)[nH]3)nc(-c3cccc(Cl)c3)c2n1C[C@H]1CC[C@H](C)CC1] | 3-{6-(3-chlorophenyl)-8-(2,4-dimethylpiperazin-1-yl)-7-[(trans-4-methylcyclohexyl)methyl]-7H-purin-2-yl}-1,2,4-oxadiazol-5(4H)-one | TFA | 537 | 537 |
| 16.54 | 58.97 | 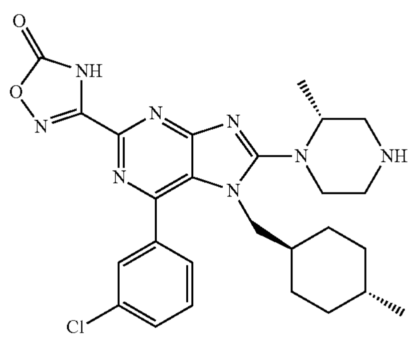 [SMILES: C[C@@H]1CNCCN1c1nc2nc(-c3noc(=O)[nH]3)nc(-c3cccc(Cl)c3)c2n1C[C@H]1CC[C@H](C)CC1] | 3-{6-(3-chlorophenyl)-7-[(trans-4-methylcyclohexyl)methyl]-8-[(2R)-2-methylpiperazin-1-yl]-7H-purin-2-yl}-1,2,4-oxadiazol-5(4H)-one | TFA | 523 | 523 |
| 16.55 | 5.042 | 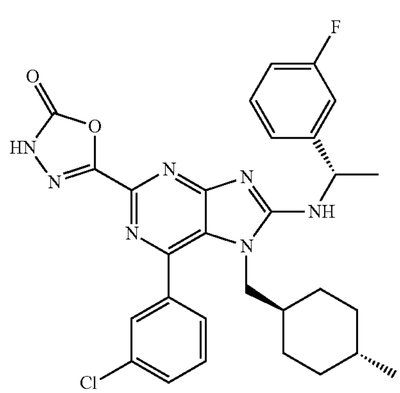 [SMILES: C[C@H](Nc1nc2nc(-c3n[nH]c(=O)o3)nc(-c3cccc(Cl)c3)c2n1C[C@H]1CC[C@H](C)CC1)c1cccc(F)c1] | 5-{6-(3-chlorophenyl)-8-{[(1S)-1-(3-fluorophenyl)ethyl]amino}-7-[(trans-4-methylcyclohexyl)methyl]-7H-purin-2-yl}-1,3,4-oxadiazol-2(3H)-one | | 562 | 562 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.56 | 42.94 | 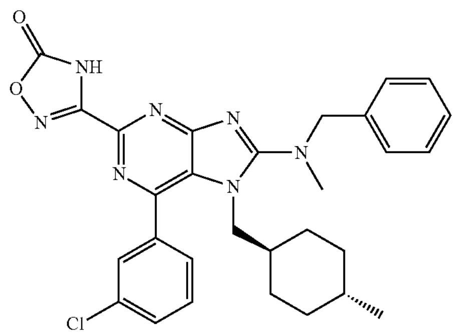 [SMILES: CN(Cc1ccccc1)c1nc2nc(-c3noc(=O)[nH]3)nc(-c3cccc(Cl)c3)c2n1C[C@H]1CC[C@H](C)CC1] | 3-{8-[benzyl(methyl)amino]-6-(3-chlorophenyl)-7-[(trans-4-methylcyclohexyl)methyl]-7H-purin-2-yl}-1,2,4-oxadiazol-5(4H)-one | | 544 | 544 |
| 16.57 | 5.536 | 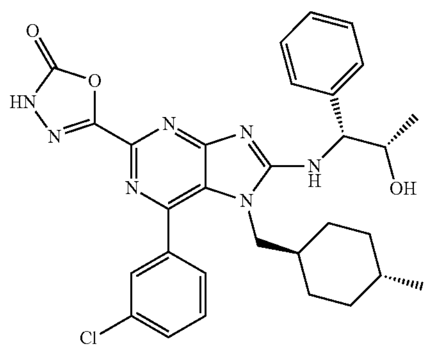 [SMILES: C[C@H](O)[C@H](Nc1nc2nc(-c3n[nH]c(=O)o3)nc(-c3cccc(Cl)c3)c2n1C[C@H]1CC[C@H](C)CC1)c1ccccc1] | 5-{6-[3-chlorophenyl)-8-{[(1R,2S)-2-hydroxy-1-phenylpropyl]amino}-7-[(trans-4-methylcyclohexyl)methyl]-7H-purin-2-yl}-1,3,4-oxadiazol-2(3H)-one | | 574 | 574 |
| 16.58 | 21.45 | 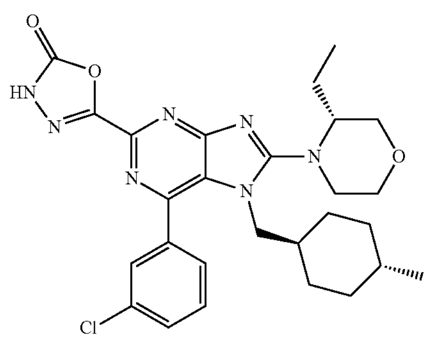 | 5-{6-(3-chlorophenyl)-8-[(3R)-3-ethylmorpholin-4-yl]-7-[(trans-4-methylcyclohexyl)methyl]-7H-purin-2-yl}-1,3,4-oxadiazol-2(3H)-one | | 538 | 538 |
| 16.59 | 19 | 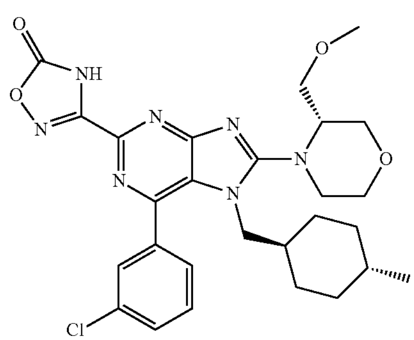 [SMILES: COC[C@@H]1COCCN1c1nc2nc(-c3noc(=O)[nH]3)nc(-c3cccc(Cl)c3)c2n1C[C@H]1CC[C@H](C)CC1] | 3-{6-(3-chlorophenyl)-8-[(3R)-3-(methoxymethyl)morpholin-4-yl]-7-[(trans-4-methylcyclohexyl)methyl]-7H-purin-2-yl}-1,2,4-oxadiazol-5(4H)-one | | 554 | 554 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.60 | 2.235 | 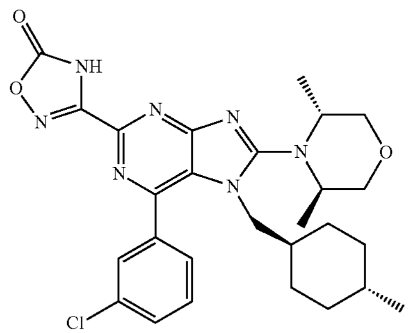 [SMILES: C[C@@H]1COC[C@@H](C)N1c1nc2nc(-c3noc(=O)[nH]3)nc(-c3cccc(Cl)c3)c2n1C[C@H]1CC[C@H](C)CC1] | 3-{6-(3-chlorophenyl)-8-[(3R,5R)-3,5-dimethylmorpholin-4-yl]-7-[(trans-4-methylcyclohexyl)methyl]-7H-purin-2-yl}-1,2,4-oxadiazol-5(4H)-one | TFA | 538 | 538 |
| 16.61 | 9.667 | 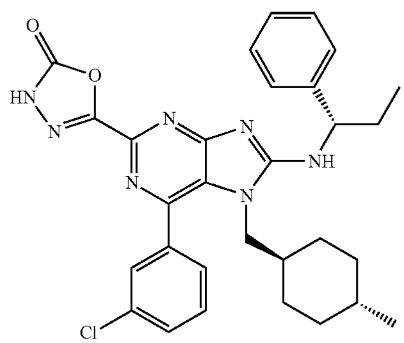 [SMILES: CC[C@H](Nc1nc2nc(-c3n[nH]c(=O)o3)nc(-c3cccc(Cl)c3)c2n1C[C@H]1CC[C@H](C)CC1)c1ccccc1] | 5-[6-(3-chlorophenyl)-7-[(trans-4-methylcyclohexyl)methyl]-8-{[(1S)-1-phenylpropyl]amino}-7H-purin-2-yl]-1,3,4-oxadiazol-2(3H)-one | | 558 | 558 |
| 16.62 | 136.1 | 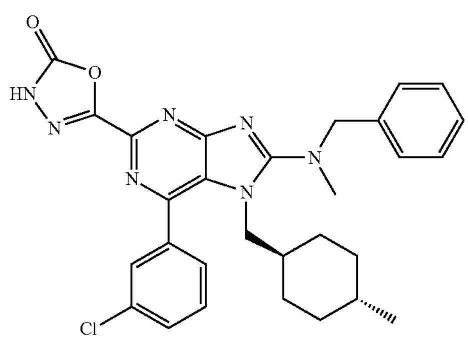 [SMILES: CN(Cc1ccccc1)c1nc2nc(-c3n[nH]c(=O)o3)nc(-c3cccc(Cl)c3)c2n1C[C@H]1CC[C@H](C)CC1] | 5-{8-[benzyl(methyl)amino]-6-(3-chlorophenyl)-7-[(trans-4-methylcyclohexyl)methyl]-7H-purin-2-yl}-1,3,4-oxadiazol-2(3H)-one | | 544 | 544 |
| 16.63 | 19.68 | 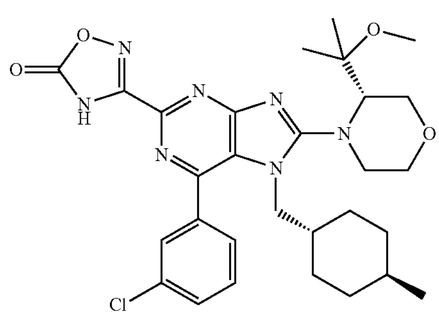 [SMILES: COC(C)(C)[C@@H]1COCCN1c1nc2nc(-c3noc(=O)[nH]3)nc(-c3cccc(Cl)c3)c2n1C[C@H]1CC[C@H](C)CC1] | 3-{6-(3-chlorophenyl)-8-[(3S)-3-(1-methoxy-1-methylethyl)morpholin-4-yl]-7-[(trans-4-methylcyclohexyl)methyl]-7H-purin-2-yl}-1,2,4-oxadiazol-5(4H)-one | | 582 | 582 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.64 | 3.158 | 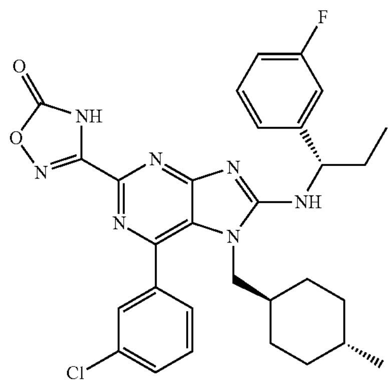 [SMILES: CC[C@H](Nc1nc2nc(-c3noc(=O)[nH]3)nc(-c3cccc(Cl)c3)c2n1C[C@H]1CC[C@H](C)CC1)c1cccc(F)c1] | 3-{6-(3-chlorophenyl)-8-{[(1S)-1-(3-fluorophenyl)propyl]amino}-7-[(trans-4-methylcyclohexyl)methyl]-7H-purin-2-yl}-1,2,4-oxadiazol-5(4H)-one | | 576 | 576 |
| 16.65 | 0.6578 | 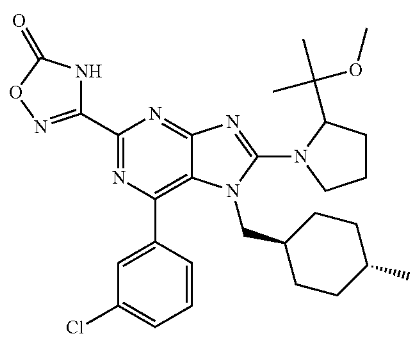 [SMILES: COC(C)(C)C1CCCN1c1nc2nc(-c3noc(=O)[nH]3)nc(-c3cccc(Cl)c3)c2n1C[C@H]1CC[C@H](C)CC1] | 3-{6-(3-chlorophenyl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one (enantiomer 1) | TFA | 566 | 566 |
| 16.66 | 1.238 | 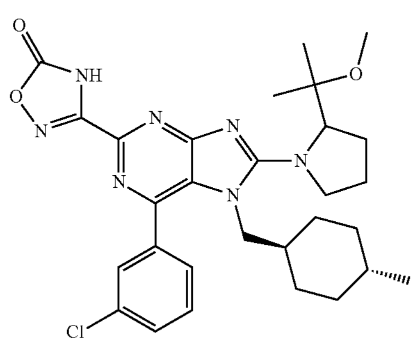 [SMILES: COC(C)(C)C1CCCN1c1nc2nc(-c3noc(=O)[nH]3)nc(-c3cccc(Cl)c3)c2n1C[C@H]1CC[C@H](C)CC1] | 3-{6-(3-chlorophenyl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one (enantiomer 2) | TFA | 566 | 566 |
| 16.67 | 6.356 | 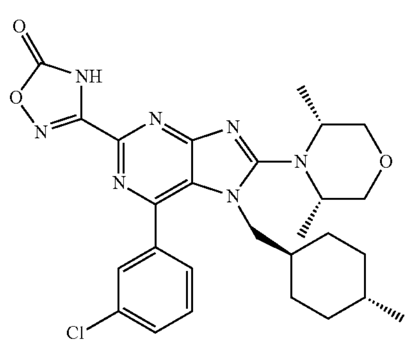 [SMILES: C[C@@H]1COC[C@H](C)N1c1nc2nc(-c3noc(=O)[nH]3)nc(-c3cccc(Cl)c3)c2n1C[C@H]1CC[C@H](C)CC1] | 3-{6-(3-chlorophenyl)-8-[(3R,5S)-3,5-dimethylmorpholin-4-yl]-7-[(trans-4-methylcyclohexyl)methyl]-7H-purin-2-yl}-1,2,4-oxadiazol-5(4H)-one | TFA | 538 | 538 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.68 | 11.54 | 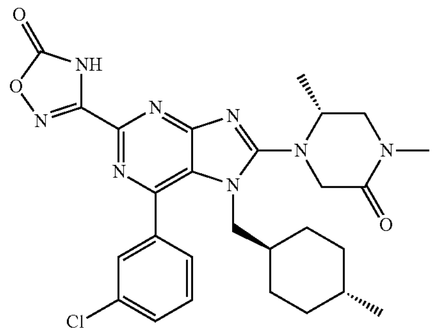 [SMILES: C[C@@H]1CN(C)C(=O)CN1c1nc2nc(-c3noc(=O)[nH]3)nc(-c3cccc(Cl)c3)c2n1C[C@H]1CC[C@H](C)CC1] | (5R)-4-[6-(3-chlorophenyl)-7-[(trans-4-methylcyclohexyl)methyl]-2-(5-oxo-4,5-dihydro-1,2,4-oxadiazol-3-yl)-7H-purin-8-yl]-1,5-dimethylpiperazin-2-one | TFA | 551 | 551 |
| 16.69 | 0.9185 | 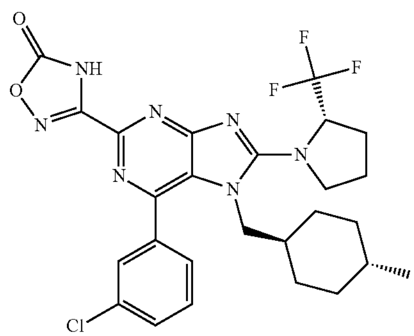 [SMILES: C[C@H]1CC[C@H](Cn2c(N3CCC[C@H]3C(F)(F)F)nc3nc(-c4noc(=O)[nH]4)nc(-c4cccc(Cl)c4)c32)CC1] | 3-{6-(3-chlorophenyl)-7-[(trans-4-methylcyclohexyl)methyl]-8-[(2S)-2-(trifluoromethyl)pyrrolidin-1-yl]-7H-purin-2-yl}-1,2,4-oxadiazol-5(4H)-one | TFA | 562 | 562 |
| 16.70 | 2.293 | 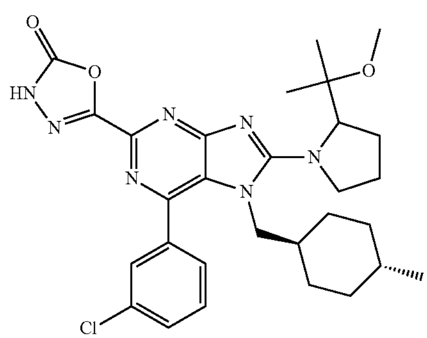 [SMILES: COC(C)(C)C1CCCN1c1nc2nc(-c3n[nH]c(=O)o3)nc(-c3cccc(Cl)c3)c2n1C[C@H]1CC[C@H](C)CC1] | 5-{6-(3-chlorophenyl)-8-[2-(1-methoxy-1-methylethyl)pyrrolidin-1-yl]-7-[(trans-4-methylcyclohexyl)methyl]-7H-purin-2-yl}-1,3,4-oxadiazol-2(3H)-one (enantiomer 1) | TFA | 566 | 566 |
| 16.71 | 2.47 | 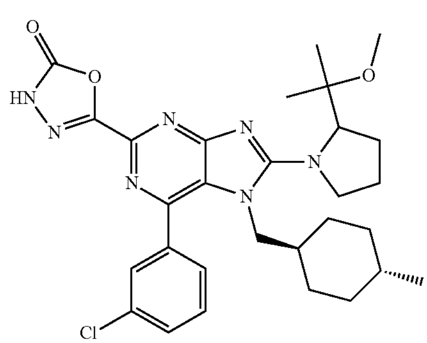 [SMILES: COC(C)(C)C1CCCN1c1nc2nc(-c3n[nH]c(=O)o3)nc(-c3cccc(Cl)c3)c2n1C[C@H]1CC[C@H](C)CC1] | 5-{6-(3-chlorophenyl)-8-[2-(1-methoxy-1-methylethyl)pyrrolidin-1-yl]-7-[(trans-4-methylcyclohexyl)methyl]-7H-purin-2-yl}-1,3,4-oxadiazol-2(3H)-one (enantiomer 2) | TFA | 566 | 566 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.72 | 0.985 | 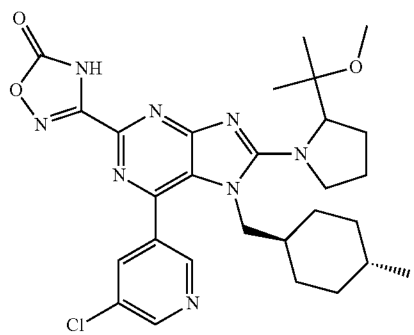 [SMILES: COC(C)(C)C1CCCN1c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one (enantiomer 1) | TFA | 567 | 567 |
| 16.73 | 1.968 | 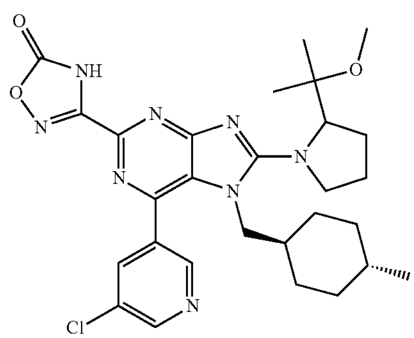 [SMILES: COC(C)(C)C1CCCN1c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one (enantiomer 2) | TFA | 567 | 567 |
| 16.74 | 0.585 | 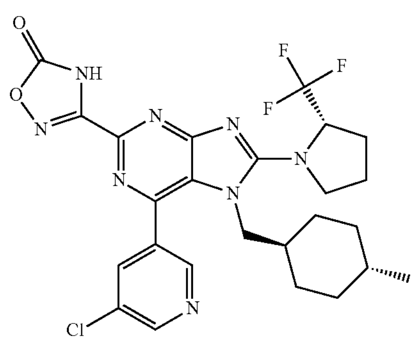 [SMILES: C[C@H]1CC[C@H](Cn2c(N3CCC[C@H]3C(F)(F)F)nc3nc(-c4noc(=O)[nH]4)nc(-c4cncc(Cl)c4)c32)CC1] | 3-{6-(5-chloropyridin-3-yl)-7-[(trans-4-methylcyclohexyl)methyl]-8-[(2S)-2-(trifluoromethyl)pyrrolidin-1-yl]-7H-purin-2-yl}-1,2,4-oxadiazol-5(4H)-one | TFA | 563 | 563 |
| 16.75 | 14.69 | 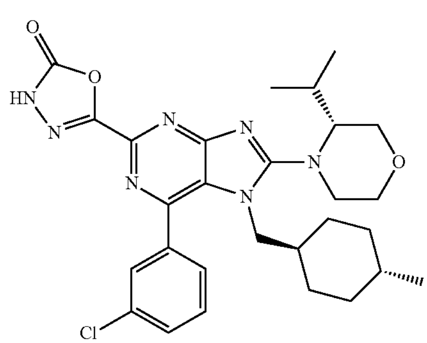 [SMILES: CC(C)[C@@H]1COCCN1c1nc2nc(-c3n[nH]c(=O)o3)nc(-c3cccc(Cl)c3)c2n1C[C@H]1CC[C@H](C)CC1] | 5-{6-(3-chlorophenyl)-7-[(trans-4-methylcyclohexyl)methyl]-8-[(3R)-3-(1-methylethyl)morpholin-4-yl]-7H-purin-2-yl}-1,3,4-oxadiazol-2(3H)-one | | 552 | 552 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.76 | 13.23 | 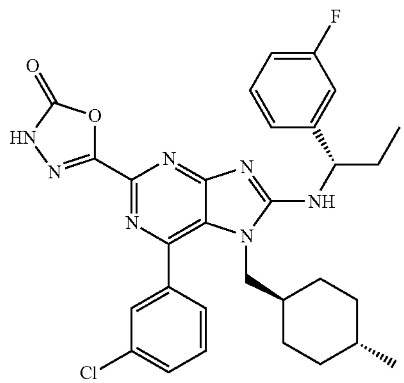 [SMILES: CC[C@H](Nc1nc2nc(-c3n[nH]c(=O)o3)nc(-c3cccc(Cl)c3)c2n1C[C@H]1CC[C@H](C)CC1)c1cccc(F)c1] | 5-{6-(3-chlorophenyl)-8-{[(1S)-1-(3-fluorophenyl)propyl]amino}-7-[(trans-4-methylcyclohexyl)methyl]-7H-purin-2-yl}-1,3,4-oxadiazol-2(3H)-one | | 576 | 576 |
| 16.77 | 29.7 | 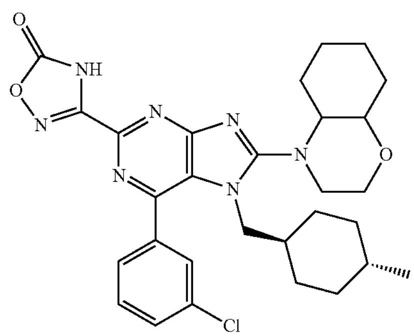 [SMILES: C[C@H]1CC[C@H](Cn2c(N3CCOC4CCCCC43)nc3nc(-c4noc(=O)[nH]4)nc(-c4cccc(Cl)c4)c32)CC1] | 3-(6-(3-chlorophenyl)-7-[(trans-4-methylcyclohexyl)methyl]-8-(octahydro-4H-1,4-benzoxazin-4-yl)-7H-purin-2-yl]-1,2,4-oxadiazol-5(4H)-one (enantiomer 1) | | 564 | 564 |
| 16.78 | 1.396 | 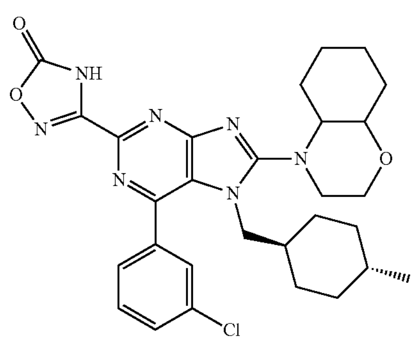 [SMILES: C[C@H]1CC[C@H](Cn2c(N3CCOC4CCCCC43)nc3nc(-c4noc(=O)[nH]4)nc(-c4cccc(Cl)c4)c32)CC1] | 3-(6-(3-chlorophenyl)-7-[(trans-4-methylcyclohexyl)methyl]-8-(octahydro-4H-1,4-benzoxazin-4-yl)-7H-purin-2-yl]-1,2,4-oxadiazol-5(4H)-one (enantiomer 2) | | 564 | 564 |
| 16.79 | 21.55 | 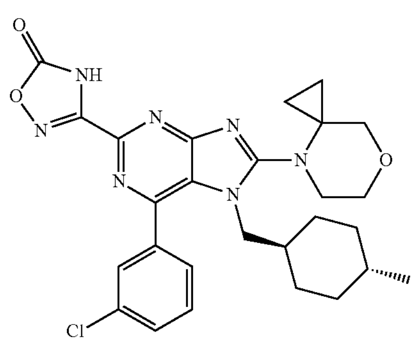 [SMILES: C[C@H]1CC[C@H](Cn2c(N3CCOCC34CC4)nc3nc(-c4noc(=O)[nH]4)nc(-c4cccc(Cl)c4)c32)CC1] | 3-(6-(3-chlorophenyl)-7-[(trans-4-methylcyclohexyl)methyl]-8-(7-oxa-4-azaspiro[2.5]oct-4-yl)-7H-purin-2-yl]-1,2,4-oxadiazol-5(4H)-one | | 536 | 536 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.80 | 8.703 | 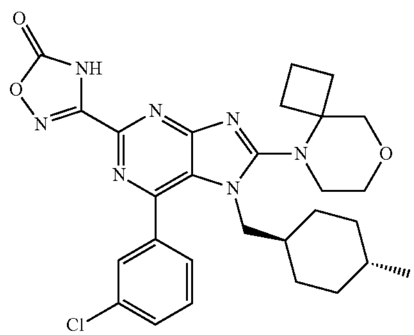 [SMILES: C[C@H]1CC[C@H](Cn2c(N3CCOCC34CCC4)nc3nc(-c4noc(=O)[nH]4)nc(-c4cccc(Cl)c4)c32)CC1] | 3-(6-(3-chlorophenyl)-7-[(trans-4-methylcyclohexyl)methyl]-8-(8-oxa-5-azaspiro[3.5]non-5-yl)-7H-purin-2-yl]-1,2,4-oxadiazol-5(4H)-one | | 550 | 550 |
| 16.81 | 105.4 | 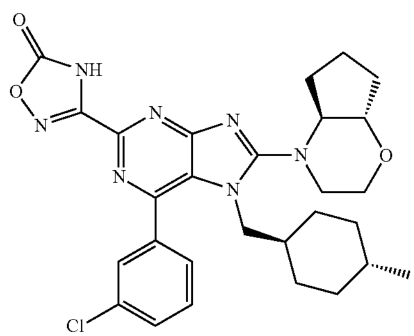 [SMILES: C[C@H]1CC[C@H](Cn2c(N3CCO[C@H]4CCC[C@@H]43)nc3nc(-c4noc(=O)[nH]4)nc(-c4cccc(Cl)c4)c32)CC1] | 3-{6-(3-chlorophenyl)-8-[(4aS,7aS)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one | | 550 | 550 |
| 16.82 | 1.10 | 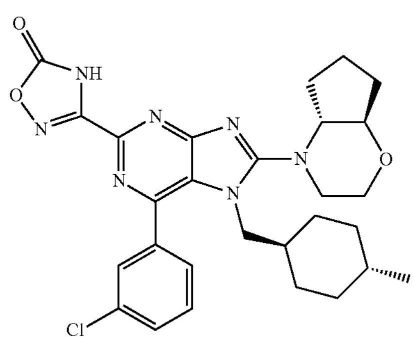 [SMILES: C[C@H]1CC[C@H](Cn2c(N3CCO[C@@H]4CCC[C@H]43)nc3nc(-c4noc(=O)[nH]4)nc(-c4cccc(Cl)c4)c32)CC1] | 3-{6-(3-chlorophenyl)-8-[(4aR,7aR)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one | | 550 | 550 |
| 16.83 | 186.2 | 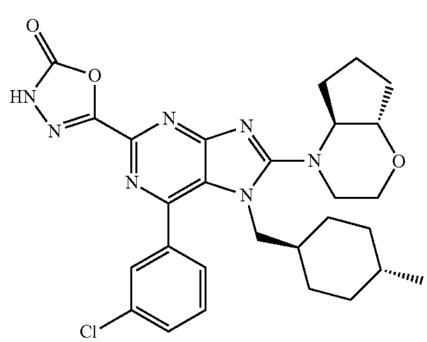 [SMILES: C[C@H]1CC[C@H](Cn2c(N3CCO[C@H]4CCC[C@@H]43)nc3nc(-c4n[nH]c(=O)o4)nc(-c4cccc(Cl)c4)c32)CC1] | 5-{6-(3-chlorophenyl)-8-[(4aS,7aS)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one | | 550 | 550 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.84 | 2.472 | 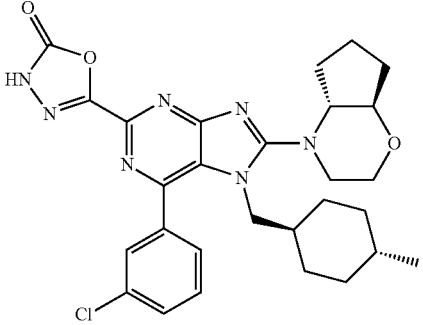 [SMILES: C[C@H]1CC[C@H](Cn2c(N3CCO[C@@H]4CCC[C@H]43)nc3nc(-c4n[nH]c(=O)o4)nc(-c4cccc(Cl)c4)c32)CC1] | 5-{6-(3-chlorophenyl)-8-[(4aR,7aR)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one | | 550 | 550 |
| 16.85 | 2.874 | 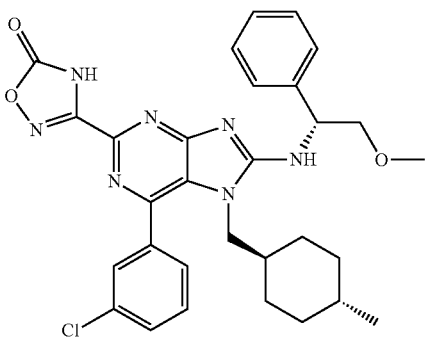 [SMILES: COC[C@H](Nc1nc2nc(-c3noc(=O)[nH]3)nc(-c3cccc(Cl)c3)c2n1C[C@H]1CC[C@H](C)CC1)c1ccccc1] | 3-{6-(3-chlorophenyl)-8-{[(1R)-2-methoxy-1-phenylethyl]amino}-7-[(trans-4-methylcyclohexyl)methyl]-7H-purin-2-yl}-1,2,4-oxadiazol-5(4H)-one | | 574 | 574 |
| 16.86 | 344.4 | 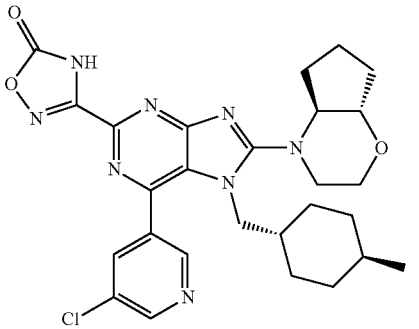 [SMILES: C[C@H]1CC[C@H](Cn2c(N3CCO[C@H]4CCC[C@@H]43)nc3nc(-c4noc(=O)[nH]4)nc(-c4cncc(Cl)c4)c32)CC1] | 3-{6-(5-chloropyridin-3-yl)-8-[(4aS,7aS)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one | | 551 | 551 |
| 16.87 | 1.563 | 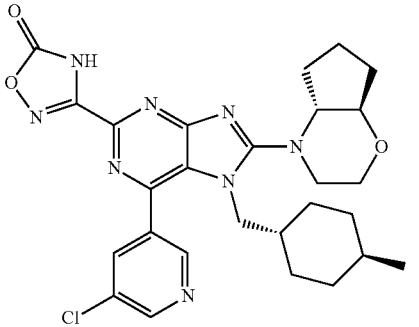 [SMILES: C[C@H]1CC[C@H](Cn2c(N3CCO[C@@H]4CCC[C@H]43)nc3nc(-c4noc(=O)[nH]4)nc(-c4cncc(Cl)c4)c32)CC1] | 3-{6-(5-chloropyridin-3-yl)-8-[(4aR,7aR)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one | | 551 | 551 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.88 | 39.14 | 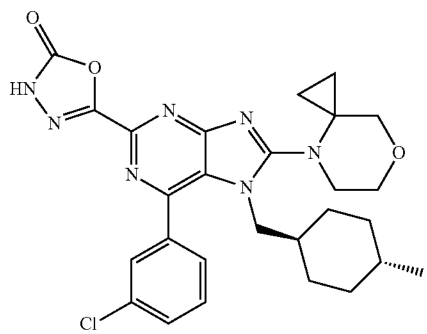 [SMILES: C[C@H]1CC[C@H](Cn2c(N3CCOCC34CC4)nc3nc(-c4n[nH]c(=O)o4)nc(-c4cccc(Cl)c4)c32)CC1] | 5-[6-(3-chlorophenyl)-7-[(trans-4-methylcyclohexyl)methyl]-8-(7-oxa-4-azaspiro[2.5]oct-4-yl)-7H-purin-2-yl]-1,3,4-oxadiazol-2(3H)-one | | 536 | 536 |
| 16.89 | 25.01 | 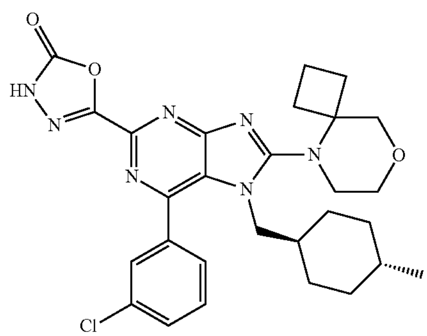 [SMILES: C[C@H]1CC[C@H](Cn2c(N3CCOCC34CCC4)nc3nc(-c4n[nH]c(=O)o4)nc(-c4cccc(Cl)c4)c32)CC1] | 5-[6-(3-chlorophenyl)-7-[(trans-4-methylcyclohexyl)methyl]-8-(8-oxa-5-azaspiro[3.5]non-5-yl)-7H-purin-2-yl]-1,3,4-oxadiazol-2(3H)-one | | 550 | 550 |
| 16.90 | 2.283 | 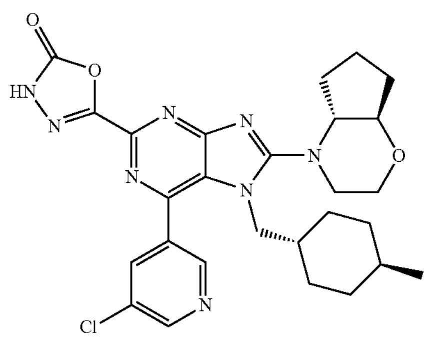 [SMILES: C[C@H]1CC[C@H](Cn2c(N3CCO[C@@H]4CCC[C@H]43)nc3nc(-c4n[nH]c(=O)o4)nc(-c4cncc(Cl)c4)c32)CC1] | 5-{6-(5-chloropyridin-3-yl)-8-[(4aR,7aR)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one | | 551 | 551 |
| 16.91 | 402.5 | 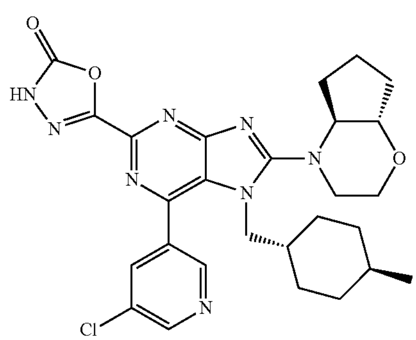 [SMILES: C[C@H]1CC[C@H](Cn2c(N3CCO[C@H]4CCC[C@@H]43)nc3nc(-c4n[nH]c(=O)o4)nc(-c4cncc(Cl)c4)c32)CC1] | 5-{6-(5-chloropyridin-3-yl)-8-[(4aS,7aS)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one | | 551 | 551 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.92 | 0.5846 | 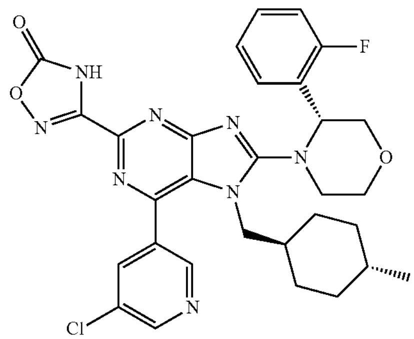 [SMILES: C[C@H]1CC[C@H](Cn2c(N3CCOC[C@H]3c3ccccc3F)nc3nc(-c4noc(=O)[nH]4)nc(-c4cncc(Cl)c4)c32)CC1] | 3-{6-(5-chloropyridin-3-yl)-8-[(3R)-3-(2-fluorophenyl)morpholin-4-yl]-7-[(trans-4-methylcyclohexyl)methyl]-7H-purin-2-yl}-1,2,4-oxadiazol-5(4H)-one | | 605 | 605 |
| 16.93 | 1.374 | 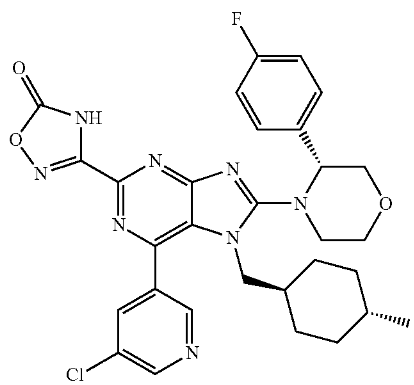 [SMILES: C[C@H]1CC[C@H](Cn2c(N3CCOC[C@H]3c3ccc(F)cc3)nc3nc(-c4noc(=O)[nH]4)nc(-c4cncc(Cl)c4)c32)CC1] | 3-{6-(5-chloropyridin-3-yl)-8-[(3R)-3-(4-fluorophenyl)morpholin-4-yl]-7-[(trans-4-methylcyclohexyl)methyl]-7H-purin-2-yl}-1,2,4-oxadiazol-5(4H)-one | | 605 | 605 |
| 16.94 | 1.975 | 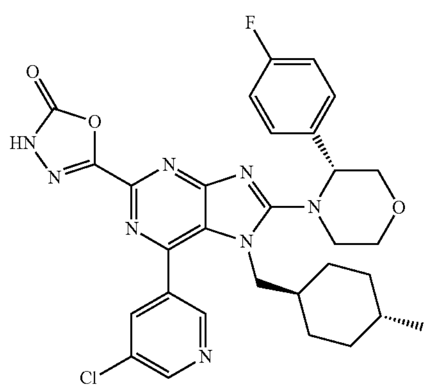 [SMILES: C[C@H]1CC[C@H](Cn2c(N3CCOC[C@H]3c3ccc(F)cc3)nc3nc(-c4n[nH]c(=O)o4)nc(-c4cncc(Cl)c4)c32)CC1] | 5-{6-(5-chloropyridin-3-yl)-8-[(3R)-3-(4-fluorophenyl)morpholin-4-yl]-7-[(trans-4-methylcyclohexyl)methyl]-7H-purin-2-yl}-1,3,4-oxadiazol-2(3H)-one | | 605 | 605 |
| 16.95 | 0.4938 | 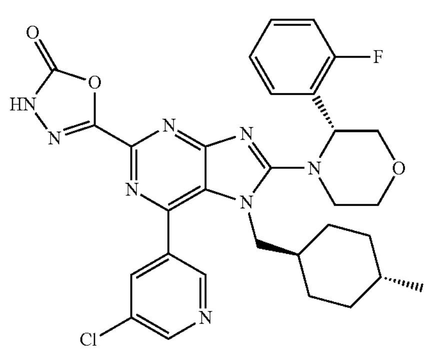 [SMILES: C[C@H]1CC[C@H](Cn2c(N3CCOC[C@H]3c3ccccc3F)nc3nc(-c4n[nH]c(=O)o4)nc(-c4cncc(Cl)c4)c32)CC1] | 5-{6-(5-chloropyridin-3-yl)-8-[(3R)-3-(2-fluorophenyl)morpholin-4-yl]-7-[(trans-4-methylcyclohexyl)methyl]-7H-purin-2-yl}-1,3,4-oxadiazol-2(3H)-one | | 605 | 605 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.96 | 3.291 | 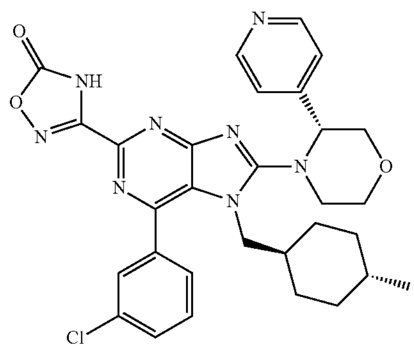 [SMILES: C[C@H]1CC[C@H](Cn2c(N3CCOC[C@H]3c3ccncc3)nc3nc(-c4noc(=O)[nH]4)nc(-c4cccc(Cl)c4)c32)CC1] | 3-{6-(3-chlorophenyl)-7-[(trans-4-methylcyclohexyl)methyl]-8-[(3R)-3-pyridin-4-ylmorpholin-4-yl]-7H-purin-2-yl}-1,2,4-oxadiazol-5(4H)-one | | 587 | 587 |
| 16.97 | 3.807 | 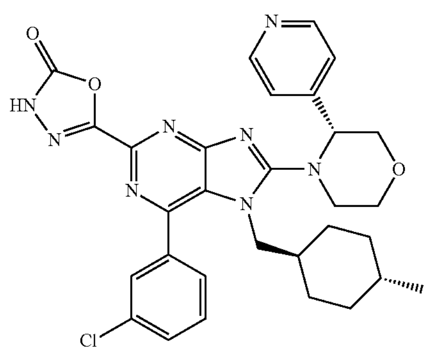 [SMILES: C[C@H]1CC[C@H](Cn2c(N3CCOC[C@H]3c3ccncc3)nc3nc(-c4n[nH]c(=O)o4)nc(-c4cccc(Cl)c4)c32)CC1] | 5-{6-(3-chlorophenyl)-7-[(trans-4-methylcyclohexyl)methyl]-8-[(3R)-3-pyridin-4-ylmorpholin-4-yl]-7H-purin-2-yl}-1,3,4-oxadiazol-2(3H)-one | | 587 | 587 |
| 16.98 | 1.608 | 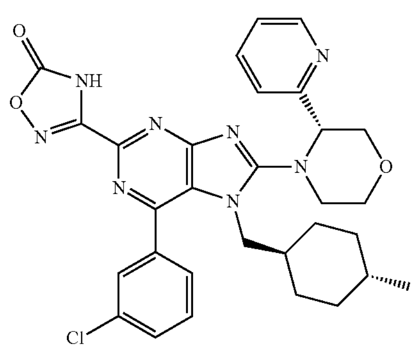 [SMILES: C[C@H]1CC[C@H](Cn2c(N3CCOC[C@H]3c3ccccn3)nc3nc(-c4noc(=O)[nH]4)nc(-c4cccc(Cl)c4)c32)CC1] | 3-{6-(3-chlorophenyl)-7-[(trans-4-methylcyclohexyl)methyl]-8-[(3R)-3-pyridin-2-ylmorpholin-4-yl]-7H-purin-2-yl}-1,2,4-oxadiazol-5(4H)-one | | 587 | 587 |
| 16.99 | 1.984 | 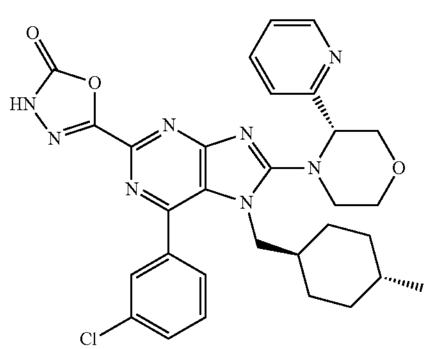 [SMILES: C[C@H]1CC[C@H](Cn2c(N3CCOC[C@H]3c3ccccn3)nc3nc(-c4n[nH]c(=O)o4)nc(-c4cccc(Cl)c4)c32)CC1] | 5-{6-(3-chlorophenyl)-7-[(trans-4-methylcyclohexyl)methyl]-8-[(3R)-3-pyridin-2-ylmorpholin-4-yl]-7H-purin-2-yl}-1,3,4-oxadiazol-2(3H)-one | | 587 | 587 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.100 | 51.01 | 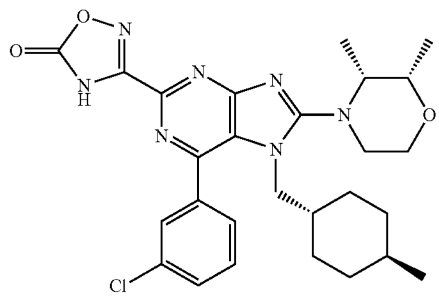 [SMILES: C[C@@H]1OCCN(c2nc3nc(-c4noc(=O)[nH]4)nc(-c4cccc(Cl)c4)c3n2C[C@H]2CC[C@H](C)CC2)[C@@H]1C] | 3-{6-(3-chlorophenyl)-8-[(cis)-2,3-dimethylmorpholin-4-yl]-7-[(trans-4-methylcyclohexyl)methyl]-7H-purin-2-yl}-1,2,4-oxadiazol-5(4H)-one (racemate) | | 538 | 538 |
| 16.101 | 41.33 | 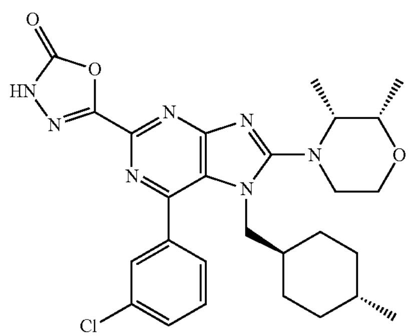 [SMILES: C[C@@H]1OCCN(c2nc3nc(-c4n[nH]c(=O)o4)nc(-c4cccc(Cl)c4)c3n2C[C@H]2CC[C@H](C)CC2)[C@@H]1C] | 5-{6-(3-chlorophenyl)-8-[(cis)-2,3-dimethylmorpholin-4-yl]-7-[(trans-4-methylcyclohexyl)methyl]-7H-purin-2-yl}-1,3,4-oxadiazol-2(3H)-one (racemate) | | 538 | 538 |
| 16.102 | 7.802 | 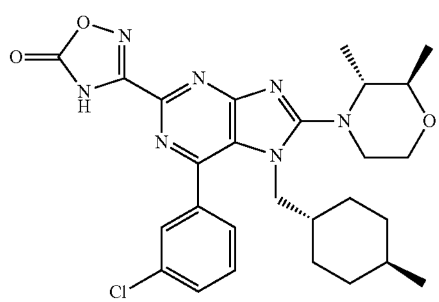 [SMILES: C[C@@H]1[C@@H](C)OCCN1c1nc2nc(-c3noc(=O)[nH]3)nc(-c3cccc(Cl)c3)c2n1C[C@H]1CC[C@H](C)CC1] | 3-{6-(3-chlorophenyl)-8-[(trans)-2,3-dimethylmorpholin-4-yl]-7-[(trans-4-methylcyclohexyl)methyl]-7H-purin-2-yl}-1,2,4-oxadiazol-5(4H)-one (racemate) | | 538 | 538 |
| 16.103 | 139.8 | 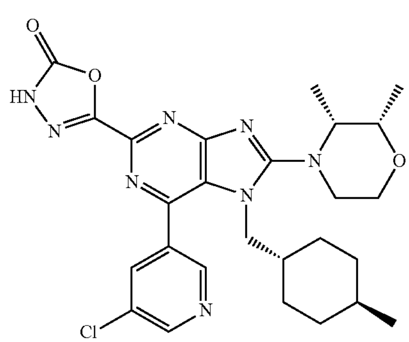 [SMILES: C[C@@H]1OCCN(c2nc3nc(-c4n[nH]c(=O)o4)nc(-c4cncc(Cl)c4)c3n2C[C@H]2CC[C@H](C)CC2)[C@@H]1C] | 5-{6-(5-chloropyridin-3-yl)-8-[(2S,3R)-2,3-dimethylmorpholin-4-yl]-7-[(trans-4-methylcyclohexyl)methyl]-7H-purin-2-yl}-1,3,4-oxadiazol-2(3H)-one | | 539 | 539 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.104 | 3.912 | 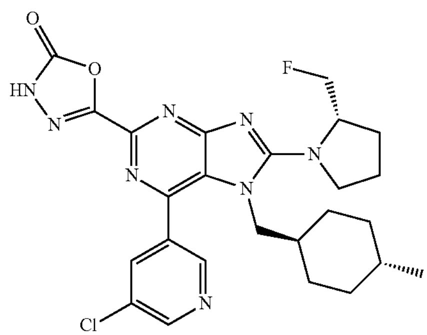 [SMILES: C[C@H]1CC[C@H](Cn2c(N3CCC[C@H]3CF)nc3nc(-c4n[nH]c(=O)o4)nc(-c4cncc(Cl)c4)c32)CC1] | 5-{6-(5-chloropyridin-3-yl)-8-[(2S)-2-(fluoromethyl)pyrrolidin-1-yl]-7-[(trans-4-methylcyclohexyl)methyl]-7H-purin-2-yl}-1,3,4-oxadiazol-2(3H)-one | | 527 | 527 |
| 16.105 | 10.99 | 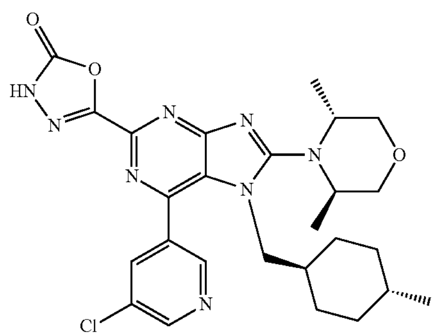 [SMILES: C[C@@H]1COC[C@@H](C)N1c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[(3R,5R)-3,5-dimethylmorpholin-4-yl]-7-[(trans-4-methylcyclohexyl)methyl]-7H-purin-2-yl}-1,3,4-oxadiazol-2(3H)-one | | 539 | 539 |
| 16.106 | 0.825 | 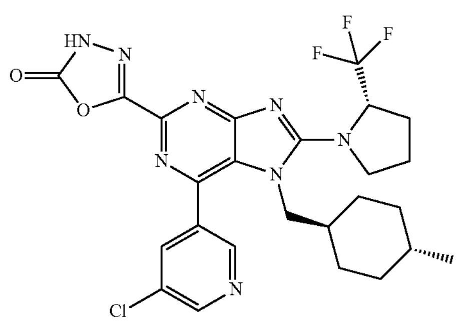 [SMILES: C[C@H]1CC[C@H](Cn2c(N3CCC[C@H]3C(F)(F)F)nc3nc(-c4n[nH]c(=O)o4)nc(-c4cncc(Cl)c4)c32)CC1] | 5-{6-(5-chloropyridin-3-yl)-7-[(trans-4-methylcyclohexyl)methyl]-8-[(2S)-2-[(trifluoromethyl)pyrrolidin-1-yl]-7H-purin-2-yl}-1,3,4-oxadiazol-2(3H)-one | | 563 | 563 |
| 16.107 | 1.658 | 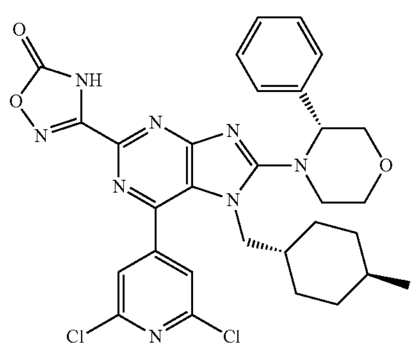 [SMILES: C[C@H]1CC[C@H](Cn2c(N3CCOC[C@H]3c3ccccc3)nc3nc(-c4noc(=O)[nH]4)nc(-c4cc(Cl)nc(Cl)c4)c32)CC1] | 3-{6-(2,6-dichloropyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 621 | 621 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.108 | 1.160 | 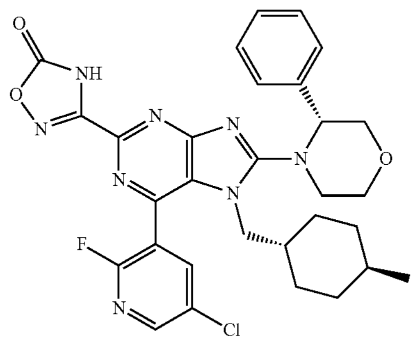 [SMILES: C[C@H]1CC[C@H](Cn2c(N3CCOC[C@H]3c3ccccc3)nc3nc(-c4noc(=O)[nH]4)nc(-c4cc(Cl)cnc4F)c32)CC1] | 3-{6-(5-chloro-2-fluoropyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 605 | 605 |
| 16.109 | 1.213 | 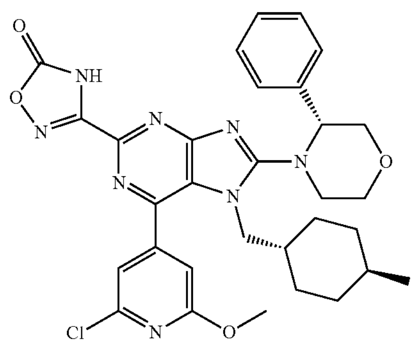 [SMILES: COc1cc(-c2nc(-c3noc(=O)[nH]3)nc3nc(N4CCOC[C@H]4c4ccccc4)n(C[C@H]4CC[C@H](C)CC4)c23)cc(Cl)n1] | 3-{6-(2-chloro-6-methoxypyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one | | 617 | 617 |
| 16.110 | 1.139 | 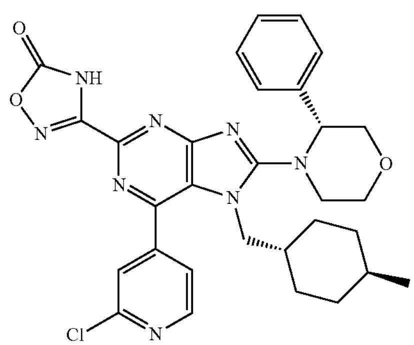 [SMILES: C[C@H]1CC[C@H](Cn2c(N3CCOC[C@H]3c3ccccc3)nc3nc(-c4noc(=O)[nH]4)nc(-c4ccnc(Cl)c4)c32)CC1] | 3-{6-(2-chloropyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 587 | 587 |
| 16.111 | 2.903 | 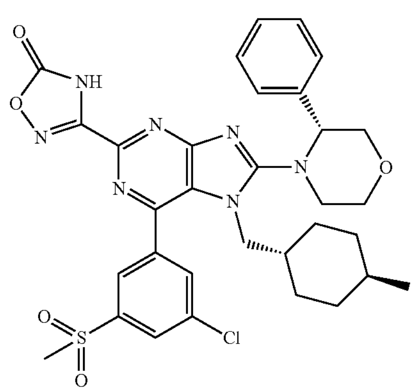 [SMILES: CS(=O)(=O)c1cc(Cl)cc(-c2nc(-c3noc(=O)[nH]3)nc3nc(N4CCOC[C@H]4c4ccccc4)n(C[C@H]4CC[C@H](C)CC4)c23)c1] | 3-{6-[3-chloro-5-(methylsulfonyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one | TFA | 664 | 664 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.112 | 18.05 | 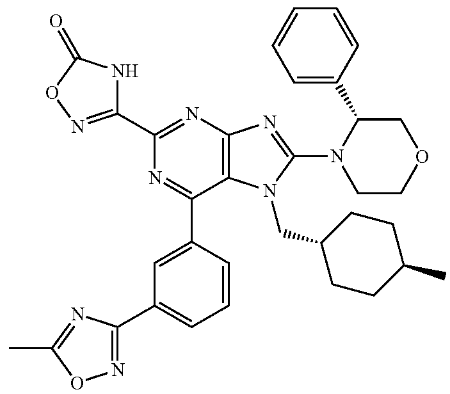 | 3-{7-[(trans-4-methylcyclohexyl)methyl]-6-[3-(5-methyl-1,2,4-oxadiazol-3-yl)phenyl]-8-[(3R)-3-phenylmorpholin-4-yl]-7H-purin-2-yl}-1,2,4-oxadiazol-5(4H)-one | TFA | 634 | 634 |
| 16.113 | 14.91 | 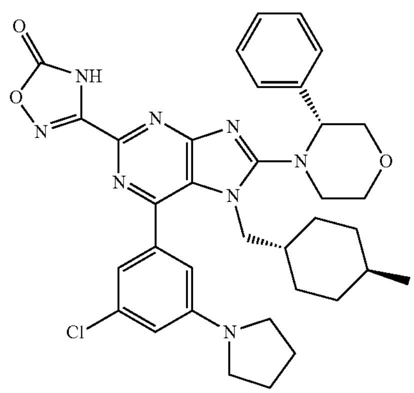 [SMILES: C[C@H]1CC[C@H](Cn2c(N3CCOC[C@H]3c3ccccc3)nc3nc(-c4noc(=O)[nH]4)nc(-c4cc(Cl)cc(N5CCCC5)c4)c32)CC1] | 3-{6-(3-chloro-5-pyrrolidin-1-ylphenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 655 | 655 |
| 16.114 | 1.561 | 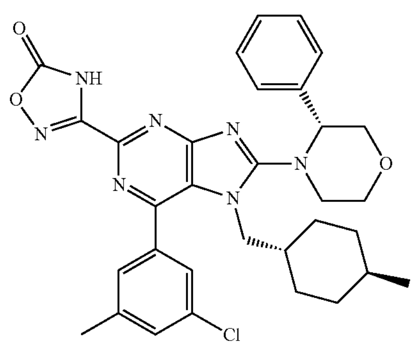 [SMILES: Cc1cc(Cl)cc(-c2nc(-c3noc(=O)[nH]3)nc3nc(N4CCOC[C@H]4c4ccccc4)n(C[C@H]4CC[C@H](C)CC4)c23)c1] | 3-{6-(3-chloro-5-methylphenyl)-7-[(trans-4-methylcyclohexyl)methyl]-8-[(3R)-3-phenylmorpholin-4-yl]-7H-purin-2-yl}-1,2,4-oxadiazol-5(4H)-one | TFA | 600 | 600 |
| 16.115 | 3.919 | 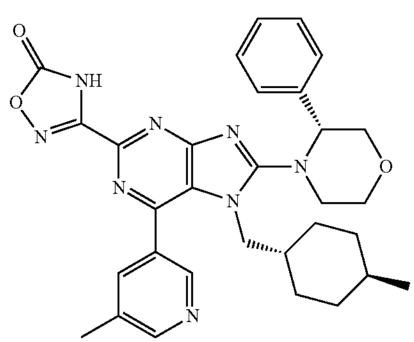 [SMILES: Cc1cncc(-c2nc(-c3noc(=O)[nH]3)nc3nc(N4CCOC[C@H]4c4ccccc4)n(C[C@H]4CC[C@H](C)CC4)c23)c1] | 3-{7-[(trans-4-methylcyclohexyl)methyl]-6-(5-methylpyridin-3-yl)-8-[(3R)-3-phenylmorpholin-4-yl]-7H-purin-2-yl}-1,2,4-oxadiazol-5(4H)-one | TFA | 567 | 567 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.116 | 7.264 | 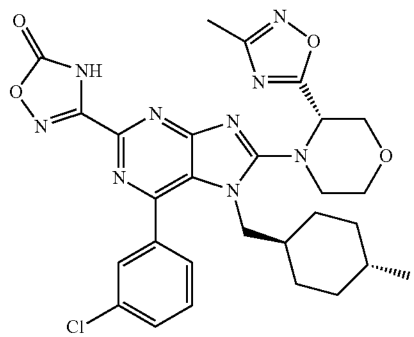 [SMILES: Cc1noc([C@@H]2COCCN2c2nc3nc(-c4noc(=O)[nH]4)nc(-c4cccc(Cl)c4)c3n2C[C@H]2CC[C@H](C)CC2)n1] | 3-{6-(3-chlorophenyl)-7-[(trans-4-methylcyclohexyl)methyl]-8-[(3S)-3-(3-methyl-1,2,4-oxadiazol-5-yl)morpholin-4-yl]-7H-purin-2-yl}-1,2,4-oxadiazol-5(4H)-one | | 592 | 592 |
| 16.117 | 105.5 | 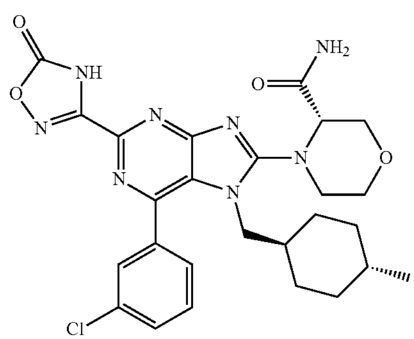 [SMILES: C[C@H]1CC[C@H](Cn2c(N3CCOC[C@H]3C(N)=O)nc3nc(-c4noc(=O)[nH]4)nc(-c4cccc(Cl)c4)c32)CC1] | (3S)-4-[6-(3-chlorophenyl)-7-[(trans-4-methylcyclohexyl)methyl]-2-(5-oxo-4,5-dihydro-1,2,4-oxadiazol-3-yl)-7H-purin-8-yl]morpholine-3-carboxamide | | 553 | 553 |
| 16.118 | 22.21 | 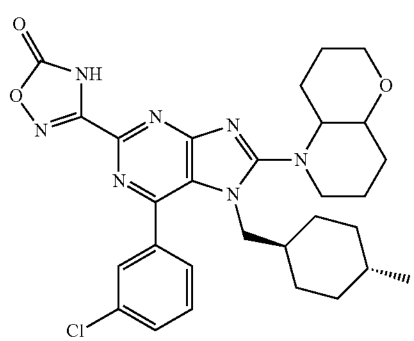 | 3-{6-[3-chlorophenyl)-8-(hexahydro-2H-pyrano[4,3-b]pyridin-1(5H)-yl)-7-[(trans-4-methylcyclohexyl)methyl]-7H-purin-2-yl}-1,2,4-oxadiazol-5(4H)-one (stereoisomer 1) | | 564 | 564 |
| 16.119 | 60.86 | 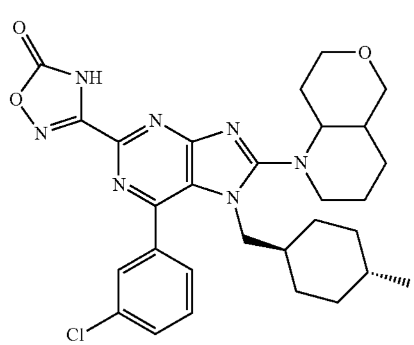 [SMILES: C[C@H]1CC[C@H](Cn2c(N3CCCC4COCCC43)nc3nc(-c4noc(=O)[nH]4)nc(-c4cccc(Cl)c4)c32)CC1] | 3-{6-[3-chlorophenyl)-8-(hexahydro-2H-pyrano[4,3-b]pyridin-1(5H)-yl)-7-[(trans-4-methylcyclohexyl)methyl]-7H-purin-2-yl}-1,2,4-oxadiazol-5(4H)-one, (stereoisomer 2) | | 564 | 564 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.120 | 9.145 | 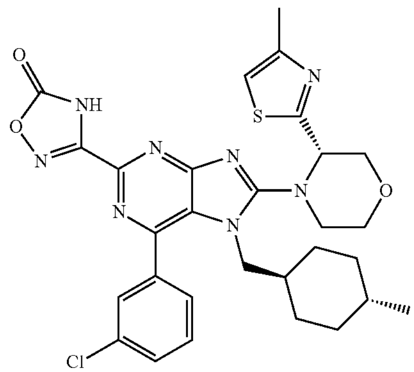 [SMILES: Cc1csc([C@@H]2COCCN2c2nc3nc(-c4noc(=O)[nH]4)nc(-c4cccc(Cl)c4)c3n2C[C@H]2CC[C@H](C)CC2)n1] | 3-{6-(3-chlorophenyl)-7-[(trans-4-methylcyclohexyl)methyl]-8-[(3S)-3-(4-methyl-1,3-thiazol-2-yl)morpholin-4-yl]-7H-purin-2-yl}-1,2,4-oxadiazol-5(4H)-one | | 607 | 607 |
| 16.121 | 9.177 | 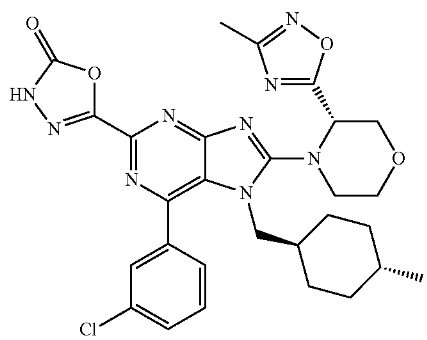 [SMILES: Cc1noc([C@@H]2COCCN2c2nc3nc(-c4n[nH]c(=O)o4)nc(-c4cccc(Cl)c4)c3n2C[C@H]2CC[C@H](C)CC2)n1] | 5-{6-(3-chlorophenyl)-7-[(trans-4-methylcyclohexyl)methyl]-8-[(3S)-3-(3-methyl-1,2,4-oxadiazol-5-yl)morpholin-4-yl]-7H-purin-2-yl}-1,3,4-oxadiazol-2(3H)-one | | 592 | 592 |
| 16.122 | 202.6 | 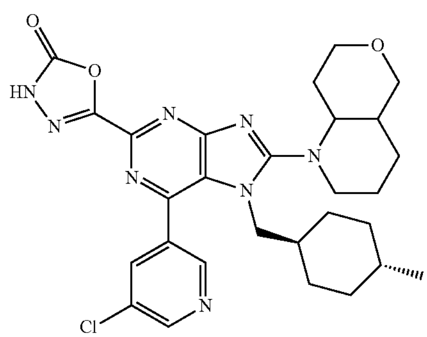 [SMILES: C[C@H]1CC[C@H](Cn2c(N3CCCC4COCCC43)nc3nc(-c4n[nH]c(=O)o4)nc(-c4cncc(Cl)c4)c32)CC1] | 5-{6-(5-chloropyridin-3-yl)-8-(hexahydro-2H-pyrano[4,3-b]pyridin-1(5H)-yl)-7-[(trans-4-methylcyclohexyl)methyl]-7H-purin-2-yl}-1,3,4-oxadiazol-2(3H)-one (stereoisomer 1) | | 565 | 565 |
| 16.123 | 59.15 | 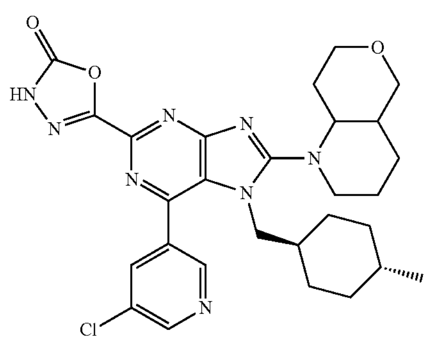 [SMILES: C[C@H]1CC[C@H](Cn2c(N3CCCC4COCCC43)nc3nc(-c4n[nH]c(=O)o4)nc(-c4cncc(Cl)c4)c32)CC1] | 5-{6-(5-chloropyridin-3-yl)-8-(hexahydro-2H-pyrano[4,3-b]pyridin-1(5H)-yl)-7-[(trans-4-methylcyclohexyl)methyl]-7H-purin-2-yl}-1,3,4-oxadiazol-2(3H)-one (stereoisomer 2) | | 565 | 565 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.124 | 263.3 | 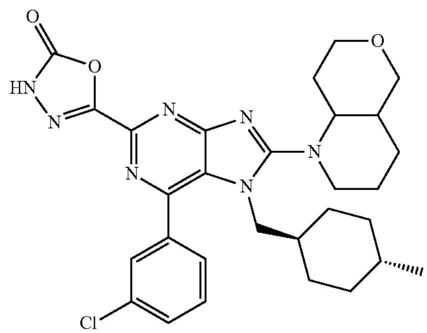 [SMILES: C[C@H]1CC[C@H](Cn2c(N3CCCC4COCCC43)nc3nc(-c4n[nH]c(=O)o4)nc(-c4cccc(Cl)c4)c32)CC1] | 5-{6-(3-chlorophenyl)-8-(hexahydro-2H-pyrano[4,3-b]pyridin-1(5H)-yl)-7-[(trans-4-methylcyclohexyl)methyl]-7H-purin-2-yl}-1,3,4-oxadiazol-2(3H)-one (stereoisomer 1) | | 564 | 564 |
| 16.125 | 56.69 | 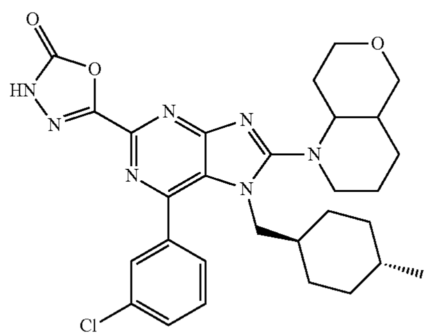 [SMILES: C[C@H]1CC[C@H](Cn2c(N3CCCC4COCCC43)nc3nc(-c4n[nH]c(=O)o4)nc(-c4cccc(Cl)c4)c32)CC1] | 5-{6-(3-chlorophenyl)-8-(hexahydro-2H-pyrano[4,3-b]pyridin-1(5H)-yl)-7-[(trans-4-methylcyclohexyl)methyl]-7H-purin-2-yl}-1,3,4-oxadiazol-2(3H)-one (stereoisomer 2) | | 564 | 564 |
| 16.126 | 85.61 | 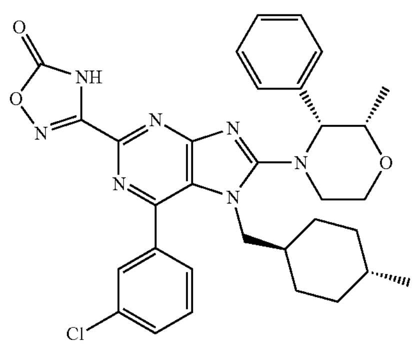 [SMILES: C[C@@H]1OCCN(c2nc3nc(-c4noc(=O)[nH]4)nc(-c4cccc(Cl)c4)c3n2C[C@H]2CC[C@H](C)CC2)[C@@H]1c1ccccc1] | 3-{6-(3-chlorophenyl)-7-[(trans-4-methylcyclohexyl)methyl]-8-[(2S,3R)-2-methyl-3-phenylmorpholin-4-yl]-7H-purin-2-yl}-1,2,4-oxadiazol-5(4H)-one | | 600 | 600 |
| 16.127 | 1.057 | 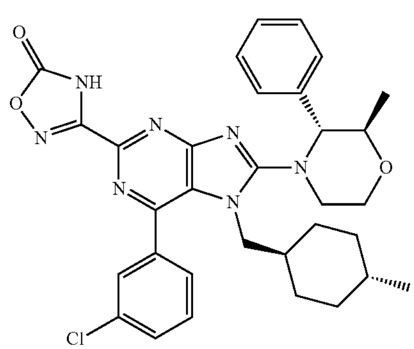 [SMILES: C[C@H]1OCCN(c2nc3nc(-c4noc(=O)[nH]4)nc(-c4cccc(Cl)c4)c3n2C[C@H]2CC[C@H](C)CC2)[C@@H]1c1ccccc1] | 3-{6-(3-chlorophenyl)-7-[(trans-4-methylcyclohexyl)methyl]-8-[(2R,3R)-2-methyl-3-phenylmorpholin-4-yl]-7H-purin-2-yl}-1,2,4-oxadiazol-5(4H)-one | | 600 | 600 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.128 | 75.61 | 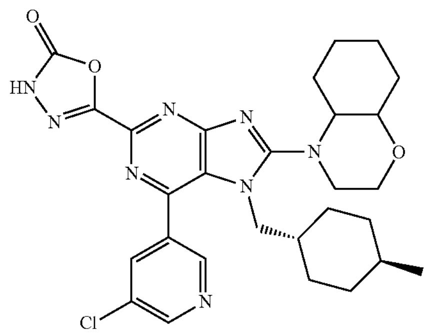 [SMILES: C[C@H]1CC[C@H](Cn2c(N3CCOC4CCCCC43)nc3nc(-c4n[nH]c(=O)o4)nc(-c4cncc(Cl)c4)c32)CC1] | 5-{6-(5-chloropyridin-3-yl)-7-[(trans-4-methylcyclohexyl)methyl]-8-[(cis)-octahydro-4H-1,4-benzoxazin-4-yl]-7H-purin-2-yl}-1,3,4-oxadiazol-2(3H)-one (racemate) | | 565 | 565 |
| 16.129 | 21.86 | 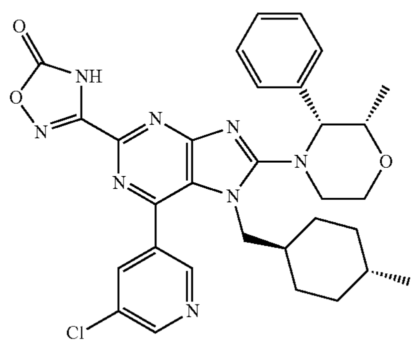 [SMILES: C[C@@H]1OCCN(c2nc3nc(-c4noc(=O)[nH]4)nc(-c4cncc(Cl)c4)c3n2C[C@H]2CC[C@H](C)CC2)[C@@H]1c1ccccc1] | 3-{6-(5-chloropyridin-3-yl)-7-[(trans-4-methylcyclohexyl)methyl]-8-[(2S,3R)-2-methyl-3-phenylmorpholin-4-yl]-7H-purin-2-yl}-1,2,4-oxadiazol-5(4H)-one | | 601 | 601 |
| 16.130 | 28.86 | 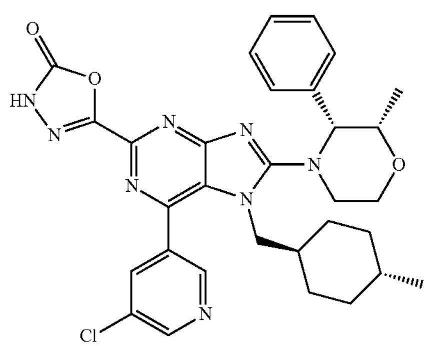 | 5-{6-(5-chloropyridin-3-yl)-7-[(trans-4-methylcyclohexyl)methyl]-8-[(2S,3R)-2-methyl-3-phenylmorpholin-4-yl]-7H-purin-2-yl}-1,3,4-oxadiazol-2(3H)-one | | 601 | 601 |
| 16.131 | 35.02 | 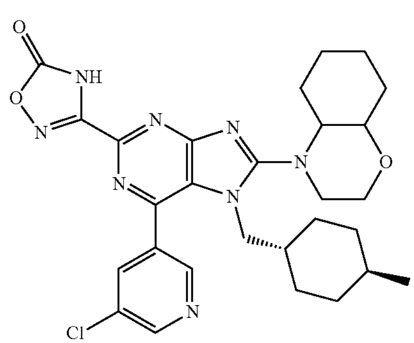 [SMILES: C[C@H]1CC[C@H](Cn2c(N3CCOC4CCCCC43)nc3nc(-c4noc(=O)[nH]4)nc(-c4cncc(Cl)c4)c32)CC1] | 3-{6-(5-chloropyridin-3-yl)-7-[(trans-4-methylcyclohexyl)methyl]-8-[(cis)-octahydro-4H-1,4-benzoxazin-4-yl]-7H-purin-2-yl}-1,2,4-oxadiazol-5(4H)-one (racemate) | | 565 | 565 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.132 | 89.53 | 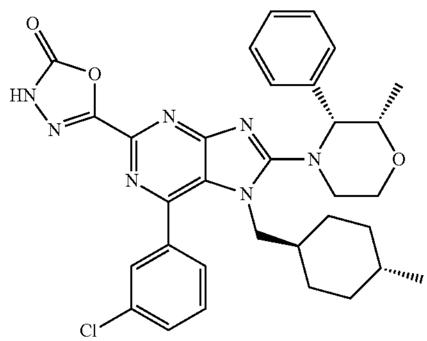 [SMILES: C[C@@H]1OCCN(c2nc3nc(-c4n[nH]c(=O)o4)nc(-c4cccc(Cl)c4)c3n2C[C@H]2CC[C@H](C)CC2)[C@@H]1c1ccccc1] | 5-{6-(3-chlorophenyl)-7-[(trans-4-methylcyclohexyl)methyl]-8-[(2S,3R)-2-methyl-3-phenylmorpholin-4-yl]-7H-purin-2-yl}-1,3,4-oxadiazol-2(3H)-one | | 600 | 600 |
| 16.133 | 0.569 | 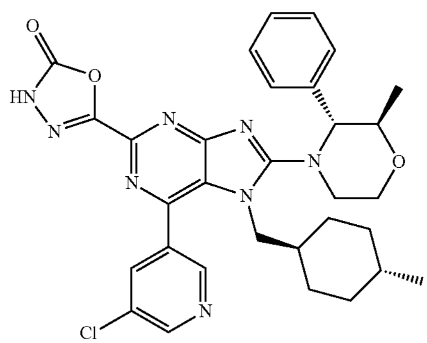 [SMILES: C[C@H]1OCCN(c2nc3nc(-c4n[nH]c(=O)o4)nc(-c4cncc(Cl)c4)c3n2C[C@H]2CC[C@H](C)CC2)[C@@H]1c1ccccc1] | 5-{6-(5-chloropyridin-3-yl)-7-[(trans-4-methylcyclohexyl)methyl]-8-[(2R,3R)-2-methyl-3-phenylmorpholin-4-yl]-7H-purin-2-yl}-1,3,4-oxadiazol-2(3H)-one | | 601 | 601 |
| 16.134 | 11.08 | 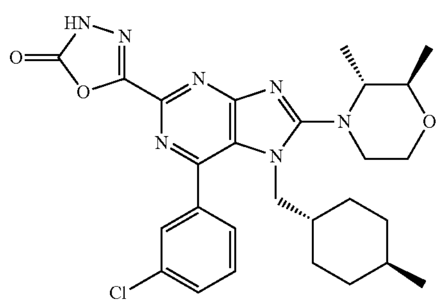 [SMILES: C[C@@H]1[C@@H](C)OCCN1c1nc2nc(-c3n[nH]c(=O)o3)nc(-c3cccc(Cl)c3)c2n1C[C@H]1CC[C@H](C)CC1] | 5-{6-(3-chlorophenyl)-8-[(trans)-2,3-dimethylmorpholin-4-yl]-7-[(trans-4-methylcyclohexyl)methyl]-7H-purin-2-yl}-1,3,4-oxadiazol-2(3H)-one (racemate) | | 538 | 538 |
| 16.135 | 0.504 | 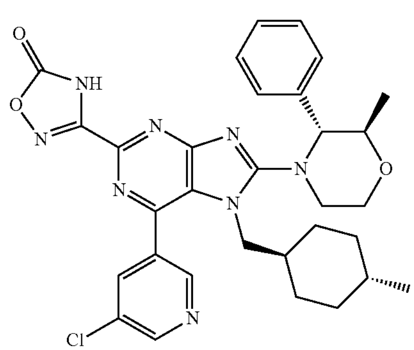 [SMILES: C[C@H]1OCCN(c2nc3nc(-c4noc(=O)[nH]4)nc(-c4cncc(Cl)c4)c3n2C[C@H]2CC[C@H](C)CC2)[C@@H]1c1ccccc1] | 3-{6-(5-chloropyridin-3-yl)-7-[(trans-4-methylcyclohexyl)methyl]-8-[(2R,3R)-2-methyl-3-phenylmorpholin-4-yl]-7H-purin-2-yl}-1,2,4-oxadiazol-5(4H)-one | | 601 | 601 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.136 | 7.194 | 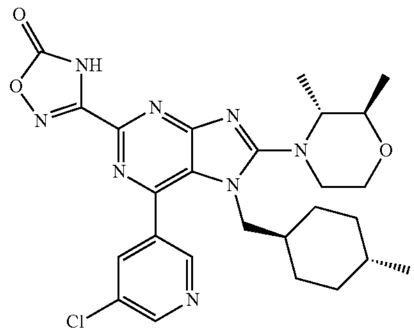 [SMILES: C[C@@H]1[C@@H](C)OCCN1c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[(2R,3R)-2,3-dimethylmorpholin-4-yl]-7-[(trans-4-methylcyclohexyl)methyl]-7H-purin-2-yl}-1,2,4-oxadiazol-5(4H)-one | | 539 | 539 |
| 16.137 | 11.91 | 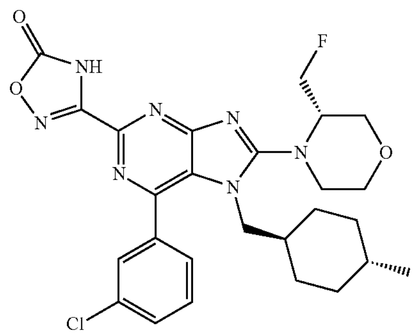 [SMILES: C[C@H]1CC[C@H](Cn2c(N3CCOC[C@H]3CF)nc3nc(-c4noc(=O)[nH]4)nc(-c4cccc(Cl)c4)c32)CC1] | 3-{6-(3-chlorophenyl)-8-[(3S)-3-(fluoromethyl)morpholin-4-yl]-7-[(trans-4-methylcyclohexyl)methyl]-7H-purin-2-yl}-1,2,4-oxadiazol-5(4H)-one | | 542 | 542 |
| 16.138 | 79.14 | 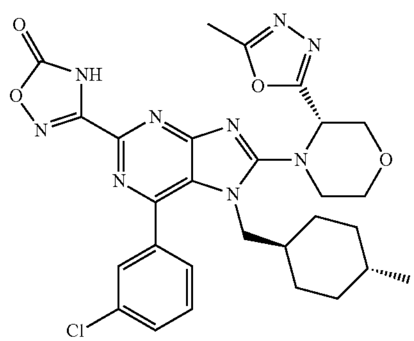 [SMILES: Cc1nnc([C@@H]2COCCN2c2nc3nc(-c4noc(=O)[nH]4)nc(-c4cccc(Cl)c4)c3n2C[C@H]2CC[C@H](C)CC2)o1] | 3-{6-(3-chlorophenyl)-7-[(trans-4-methylcyclohexyl)methyl]-8-[(3S)-3-(5-methyl-1,3,4-oxadiazol-2-yl)morpholin-4-yl]-7H-purin-2-yl}-1,2,4-oxadiazol-5(4H)-one | | 592 | 592 |
| 16.139 | 37.07 | 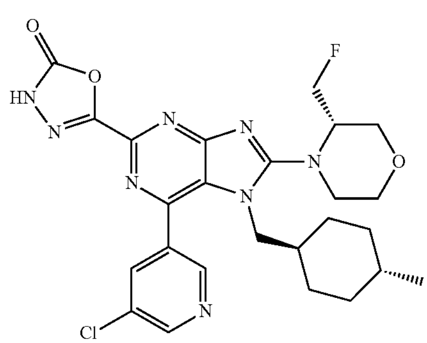 [SMILES: C[C@H]1CC[C@H](Cn2c(N3CCOC[C@H]3CF)nc3nc(-c4n[nH]c(=O)o4)nc(-c4cncc(Cl)c4)c32)CC1] | 5-{6-(5-chloropyridin-3-yl)-8-[(3S)-3-(fluoromethyl)morpholin-4-yl]-7-[(trans-4-methylcyclohexyl)methyl]-7H-purin-2-yl}-1,3,4-oxadiazol-2(3H)-one | | 543 | 543 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.140 | 9.453 | 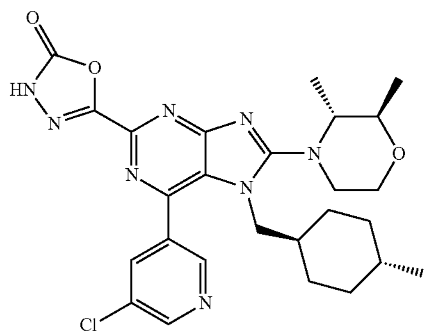 [SMILES: C[C@@H]1[C@@H](C)OCCN1c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[(2R,3R)-2,3-dimethylmorpholin-4-yl]-7-[(trans-4-methylcyclohexyl)methyl]-7H-purin-2-yl}-1,3,4-oxadiazol-2(3H)-one | | 539 | 539 |
| 16.141 | 26.84 | 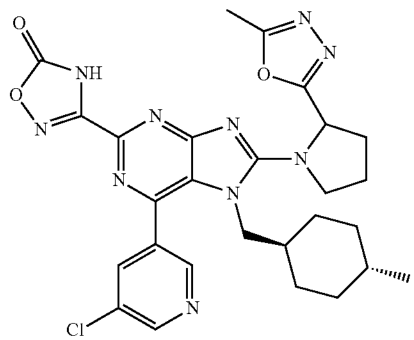 [SMILES: Cc1nnc(C2CCCN2c2nc3nc(-c4noc(=O)[nH]4)nc(-c4cncc(Cl)c4)c3n2C[C@H]2CC[C@H](C)CC2)o1] | 3-{6-(5-chloropyridin-3-yl)-7-[(trans-4-methylcyclohexyl)methyl]-8-[2-(5-methyl-1,3,4-oxadiazol-2-yl)pyrrolidin-1-yl]-7H-purin-2-yl}-1,2,4-oxadiazol-5(4H)-one (racemate) | | 577 | 577 |
| 16.142 | 1.501 | 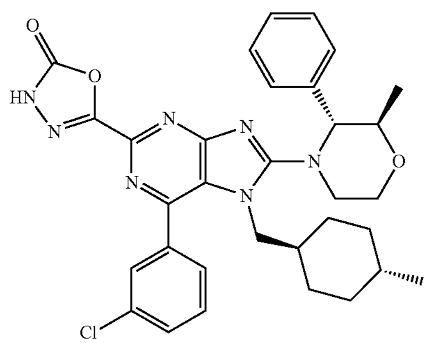 [SMILES: C[C@H]1OCCN(c2nc3nc(-c4n[nH]c(=O)o4)nc(-c4cccc(Cl)c4)c3n2C[C@H]2CC[C@H](C)CC2)[C@@H]1c1ccccc1] | 5-{6-(3-chlorophenyl)-7-[(trans-4-methylcyclohexyl)methyl]-8-[(2R,3R)-2-methyl-3-phenylmorpholin-4-yl]-7H-purin-2-yl}-1,3,4-oxadiazol-2(3H)-one | | 600 | 600 |
| 16.143 | 1.477 | 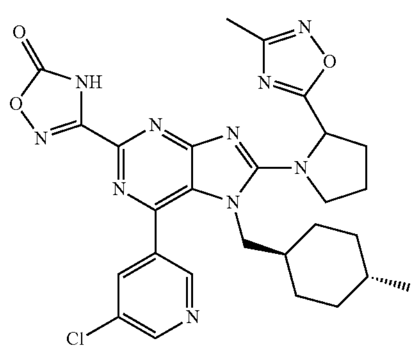 [SMILES: Cc1noc(C2CCCN2c2nc3nc(-c4noc(=O)[nH]4)nc(-c4cncc(Cl)c4)c3n2C[C@H]2CC[C@H](C)CC2)n1] | 3-{6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purin-2-yl}-1,2,4-oxadiazol-5(4H)-one (racemate) | | 577 | 577 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.144 | 19.11 | 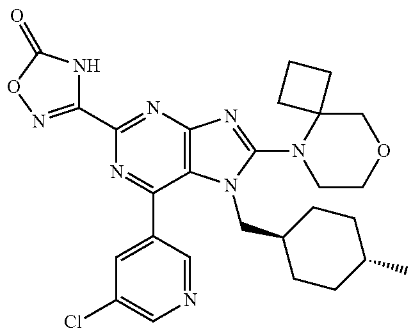 [SMILES: C[C@H]1CC[C@H](Cn2c(N3CCOCC34CCC4)nc3nc(-c4noc(=O)[nH]4)nc(-c4cncc(Cl)c4)c32)CC1] | 3-(6-(5-chloropyridin-3-yl)-7-[(trans-4-methylcyclohexyl)methyl]-8-(8-oxa-5-azaspiro[3.5]non-5-yl)-7H-purin-2-yl]-1,2,4-oxadiazol-5(4H)-one | | 551 | 551 |
| 16.145 | 3.919 | 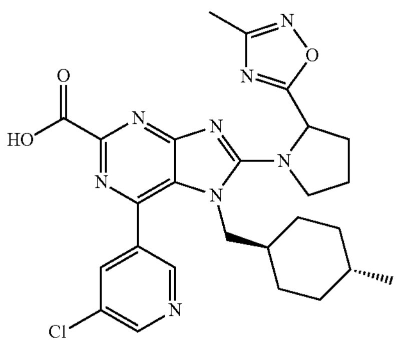 [SMILES: Cc1noc(C2CCCN2c2nc3nc(C(=O)O)nc(-c4cncc(Cl)c4)c3n2C[C@H]2CC[C@H](C)CC2)n1] | 6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purine-2-carboxylic acid (racemate) | | 537 | 537 |
| 16.146 | 3.036 | 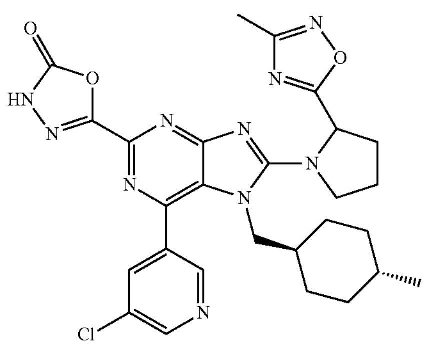 [SMILES: Cc1noc(C2CCCN2c2nc3nc(-c4n[nH]c(=O)o4)nc(-c4cncc(Cl)c4)c3n2C[C@H]2CC[C@H](C)CC2)n1] | 5-{6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purin-2-yl}-1,3,4-oxadiazol-2(3H)-one (racemate) | | 577 | 577 |
| 16.147 | 5.521 | 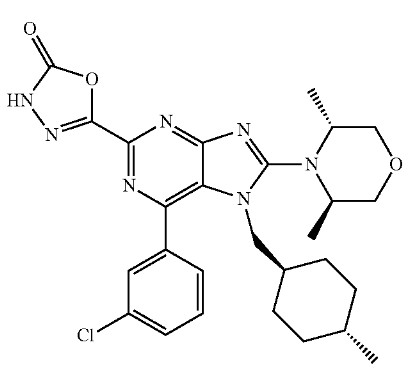 [SMILES: C[C@@H]1COC[C@@H](C)N1c1nc2nc(-c3n[nH]c(=O)o3)nc(-c3cccc(Cl)c3)c2n1C[C@H]1CC[C@H](C)CC1] | 5-{6-(3-chlorophenyl)-8-[(3R,5R)-3,5-dimethylmorpholin-4-yl]-7-[(trans-4-methylcyclohexyl)methyl]-7H-purin-2-yl}-1,3,4-oxadiazol-2(3H)-one | | 538 | 538 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.148 | 15.09 | 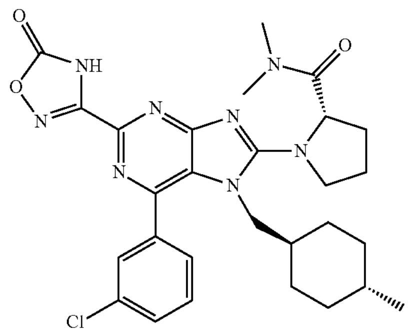 [SMILES: CN(C)C(=O)[C@@H]1CCCN1c1nc2nc(-c3noc(=O)[nH]3)nc(-c3cccc(Cl)c3)c2n1C[C@H]1CC[C@H](C)CC1] | 1-[6-(3-chlorophenyl)-7-[(trans-4-methylcyclohexyl)methyl]-2-(5-oxo-4,5-dihydro-1,2,4-oxadiazol-3-yl)-7H-purin-8-yl]-N,N-dimethyl-L-prolinamide | TFA | 565 | 565 |
| 16.149 | 3.771 | 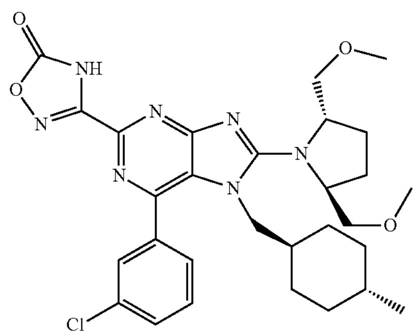 [SMILES: COC[C@@H]1CC[C@@H](COC)N1c1nc2nc(-c3noc(=O)[nH]3)nc(-c3cccc(Cl)c3)c2n1C[C@H]1CC[C@H](C)CC1] | 3-{8-[(2S,5S)-2,5-bis(methoxymethyl)pyrrolidin-1-yl]-6-(3-chlorophenyl)-7-[(trans-4-methylcyclohexyl)methyl]-7H-purin-2-yl}-1,2,4-oxadiazol-5(4H)-one | TFA | 582 | 582 |
| 16.150 | 44.99 | 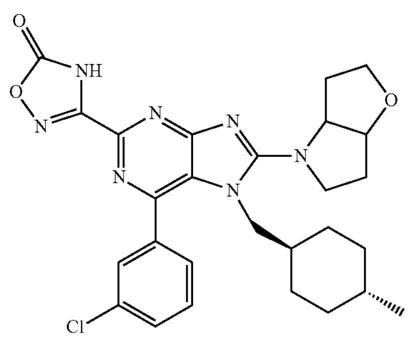 [SMILES: C[C@H]1CC[C@H](Cn2c(N3CCC4OCCC43)nc3nc(-c4noc(=O)[nH]4)nc(-c4cccc(Cl)c4)c32)CC1] | 3-{6-(3-chlorophenyl)-8-(hexahydro-4H-furo[3,2-b]pyrrol-4-yl)-7-[(trans-4-methylcyclohexyl)methyl]-7H-purin-2-yl}-1,2,4-oxadiazol-5(4H)-one | TFA | 536 | 536 |
| 16.151 | 1.697 | 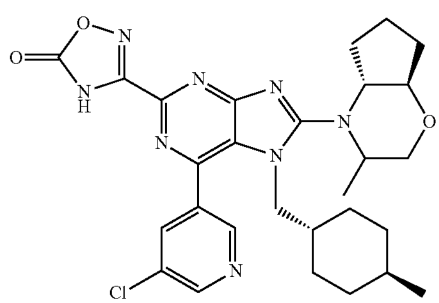 [SMILES: CC1CO[C@@H]2CCC[C@H]2N1c1nc2nc(-c3noc(=O)[nH]3)nc(-c3cncc(Cl)c3)c2n1C[C@H]1CC[C@H](C)CC1] | 3-{6-(5-chloropyridin-3-yl)-7-[(trans-4-methylcyclohexyl)methyl]-8-[(trans)-3-methylhexahydrocyclopenta[b][1,4]oxazin-4(4aH)-yl]-7H-purin-2-yl}-1,2,4-oxadiazol-5(4H)-one (racemic; major diastereomer) | | 565 | 565 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.152 | 5.679 | 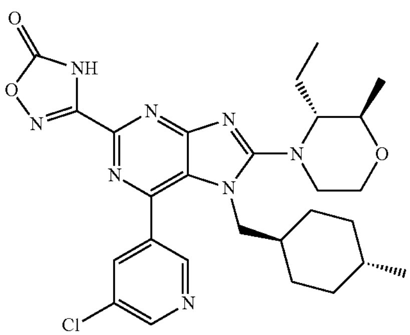 [SMILES: CC[C@@H]1[C@@H](C)OCCN1c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[(2R,3R)-3-ethyl-2-methylmorpholin-4-yl]-7-[(trans-4-methylcyclohexyl)methyl]-7H-purin-2-yl}-1,2,4-oxadiazol-5(4H)-one | | 553 | 553 |
| 16.153 | 9.997 | 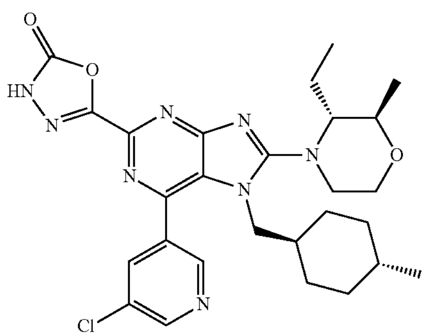 [SMILES: CC[C@@H]1[C@@H](C)OCCN1c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[(2R,3R)-3-ethyl-2-methylmorpholin-4-yl]-7-[(trans-4-methylcyclohexyl)methyl]-7H-purin-2-yl}-1,3,4-oxadiazol-2(3H)-one | | 553 | 553 |
| 16.154 | 67.20 | 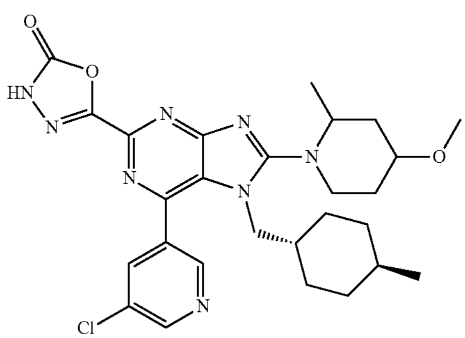 [SMILES: COC1CCN(c2nc3nc(-c4n[nH]c(=O)o4)nc(-c4cncc(Cl)c4)c3n2C[C@H]2CC[C@H](C)CC2)C(C)C1] | 5-{6-(5-chloropyridin-3-yl)-8-[(cis)-4-methoxy-2-methylpiperidin-1-yl]-7-[(trans-4-methylcyclohexyl)methyl]-7H-purin-2-yl}-1,3,4-oxadiazol-2(3H)-one (racemate) | | 553 | 553 |
| 16.155 | 49.10 | 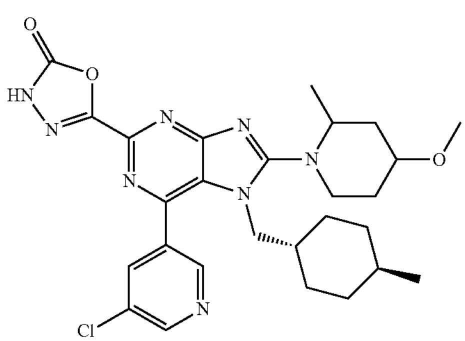 [SMILES: COC1CCN(c2nc3nc(-c4n[nH]c(=O)o4)nc(-c4cncc(Cl)c4)c3n2C[C@H]2CC[C@H](C)CC2)C(C)C1] | 5-{6-(5-chloropyridin-3-yl)-8-[(trans)-4-methoxy-2-methylpiperidin-1-yl]-7-[(trans-4-methylcyclohexyl)methyl]-7H-purin-2-yl}-1,3,4-oxadiazol-2(3H)-one (racemate) | | 553 | 553 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.156 | 0.851 | 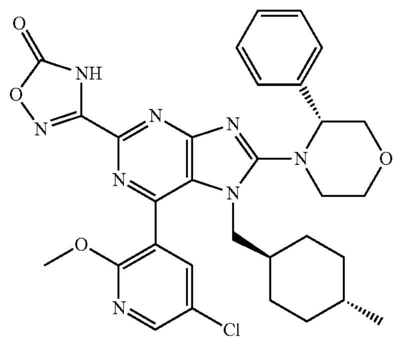 [SMILES: COc1ncc(Cl)cc1-c1nc(-c2noc(=O)[nH]2)nc2nc(N3CCOC[C@H]3c3ccccc3)n(C[C@H]3CC[C@H](C)CC3)c12] | 3-{6-(5-chloro-2-methoxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one | | 617 | 617 |
| 16.157 | 0.882 | 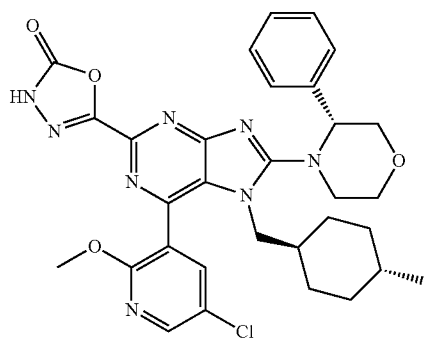 [SMILES: COc1ncc(Cl)cc1-c1nc(-c2n[nH]c(=O)o2)nc2nc(N3CCOC[C@H]3c3ccccc3)n(C[C@H]3CC[C@H](C)CC3)c12] | 5-{6-(5-chloro-2-methoxypyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one | | 617 | 617 |
| 16.158 | 0.601 | 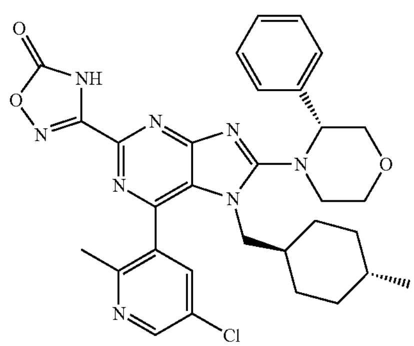 [SMILES: Cc1ncc(Cl)cc1-c1nc(-c2noc(=O)[nH]2)nc2nc(N3CCOC[C@H]3c3ccccc3)n(C[C@H]3CC[C@H](C)CC3)c12] | 3-{6-(5-chloro-2-methylpyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one | | 601 | 601 |
| 16.159 | 0.704 | 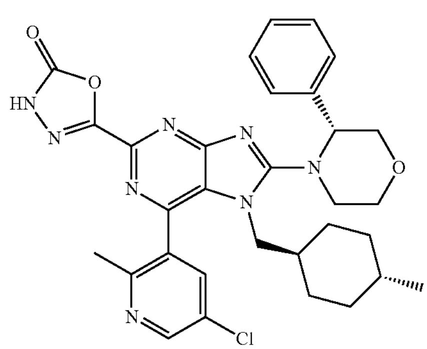 [SMILES: Cc1ncc(Cl)cc1-c1nc(-c2n[nH]c(=O)o2)nc2nc(N3CCOC[C@H]3c3ccccc3)n(C[C@H]3CC[C@H](C)CC3)c12] | 5-{6-(5-chloro-2-methylpyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one | | 601 | 601 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.160 | 21.00 | 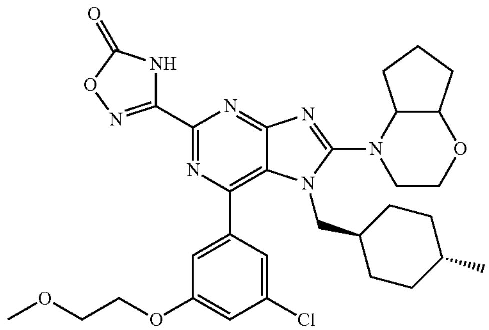 | 3-{6-[3-chloro-5-(2-methoxyethoxy)phenyl]-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one (racemate) | | 624 | 624 |
| 16.161 | 3.650 | 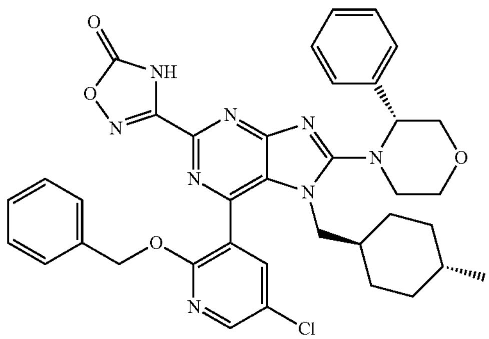 [SMILES: C[C@H]1CC[C@H](Cn2c(N3CCOC[C@H]3c3ccccc3)nc3nc(-c4noc(=O)[nH]4)nc(-c4cc(Cl)cnc4OCc4ccccc4)c32)CC1] | 3-{6-[2-(benzyloxy)-5-chloropyridin-3-yl]-7-[(trans-4-methylcyclohexyl)methyl]-8-[(3R)-3-phenylmorpholin-4-yl]-7H-purin-2-yl}-1,2,4-oxadiazol-5(4H)-one | | 693 | 693 |
| 16.162 | 0.847 | 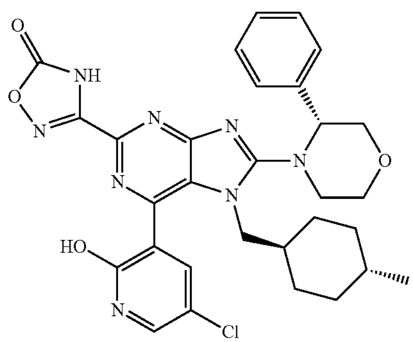 [SMILES: C[C@H]1CC[C@H](Cn2c(N3CCOC[C@H]3c3ccccc3)nc3nc(-c4noc(=O)[nH]4)nc(-c4cc(Cl)cnc4O)c32)CC1] | 3-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one | | 603 | 603 |
| 16.163 | 1.232 | 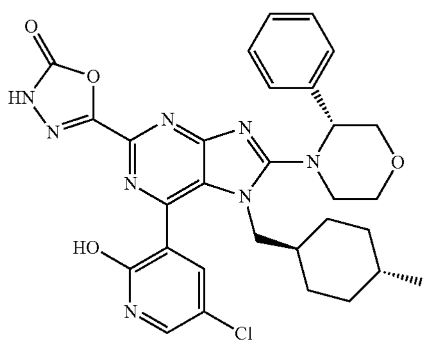 [SMILES: C[C@H]1CC[C@H](Cn2c(N3CCOC[C@H]3c3ccccc3)nc3nc(-c4n[nH]c(=O)o4)nc(-c4cc(Cl)cnc4O)c32)CC1] | 5-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one | | 603 | 603 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.164 | 2.094 | 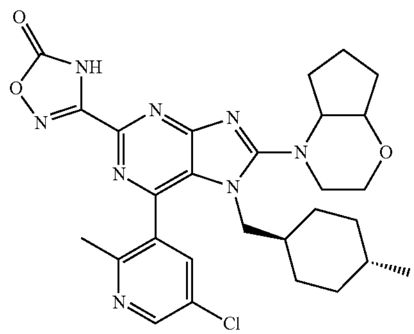 [SMILES: Cc1ncc(Cl)cc1-c1nc(-c2noc(=O)[nH]2)nc2nc(N3CCOC4CCCC43)n(C[C@H]3CC[C@H](C)CC3)c12] | 3-{6-(5-chloro-2-methylpyridin-3-yl)-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one (racemate) | | 565 | 565 |
| 16.165 | 5.079 | 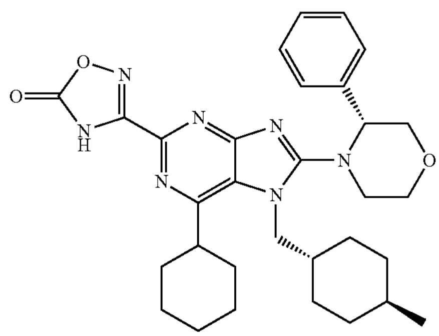 [SMILES: C[C@H]1CC[C@H](Cn2c(N3CCOC[C@H]3c3ccccc3)nc3nc(-c4noc(=O)[nH]4)nc(C4CCCCC4)c32)CC1] | 3-{6-cyclohexyl-7-[(trans-4-methylcyclohexyl)methyl]-8-[(3R)-3-phenylmorpholin-4-yl]-7H-purin-2-yl}-1,2,4-oxadiazol-5(4H)-one | | 558 | 558 |
| 16.166 | 9.216 | 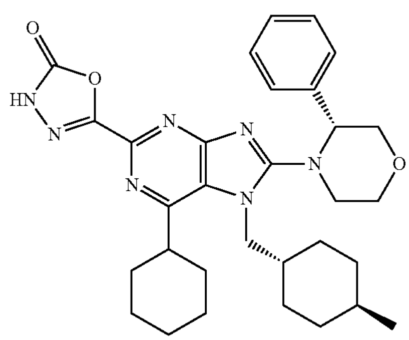 [SMILES: C[C@H]1CC[C@H](Cn2c(N3CCOC[C@H]3c3ccccc3)nc3nc(-c4n[nH]c(=O)o4)nc(C4CCCCC4)c32)CC1] | 5-{6-cyclohexyl-7-[(trans-4-methylcyclohexyl)methyl]-8-[(3R)-3-phenylmorpholin-4-yl]-7H-purin-2-yl}-1,3,4-oxadiazol-2(3H)-one | | 558 | 558 |
| 16.167 | 46.64 | 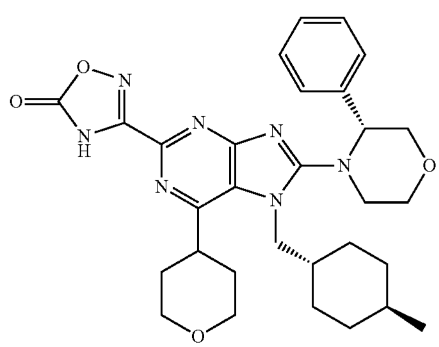 [SMILES: C[C@H]1CC[C@H](Cn2c(N3CCOC[C@H]3c3ccccc3)nc3nc(-c4noc(=O)[nH]4)nc(C4CCOCC4)c32)CC1] | 3-{7-[(trans-4-methylcyclohexyl)methyl]-8-[(3R)-3-phenylmorpholin-4-yl]-6-(tetrahydro-2H-pyran-4-yl)-7H-purin-2-yl}-1,2,4-oxadiazol-5(4H)-one | | 560 | 560 |

TABLE 16-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 16.168 | 67.14 | 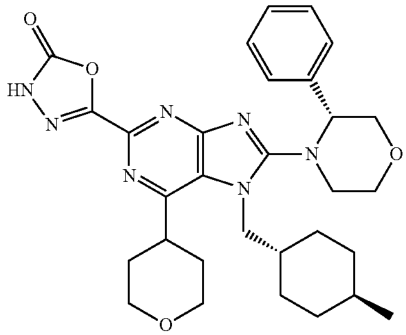 [SMILES: C[C@H]1CC[C@H](Cn2c(N3CCOC[C@H]3c3ccccc3)nc3nc(-c4n[nH]c(=O)o4)nc(C4CCOCC4)c32)CC1] | 5-{7-[(trans-4-methylcyclohexyl)methyl]-8-[(3R)-3-phenylmorpholin-4-yl]-6-(tetrahydro-2H-pyran-4-yl)-7H-purin-2-yl}-1,3,4-oxadiazol-2(3H)-one | | 560 | 560 |
| 16.169 | 2.529 | 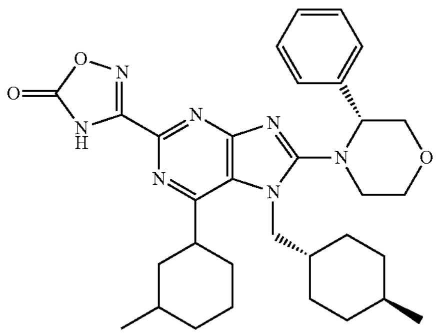 [SMILES: CC1CCCC(c2nc(-c3noc(=O)[nH]3)nc3nc(N4CCOC[C@H]4c4ccccc4)n(C[C@H]4CC[C@H](C)CC4)c23)C1] | 3-{6-(3-methylcyclohexyl)-7-[(trans-4-methylcyclohexyl)methyl]-8-[(3R)-3-phenylmorpholin-4-yl]-7H-purin-2-yl}-1,2,4-oxadiazol-5(4H)-one (mixture of diastereomers) | | 572 | 572 |
| 16.170 | 8.296 | 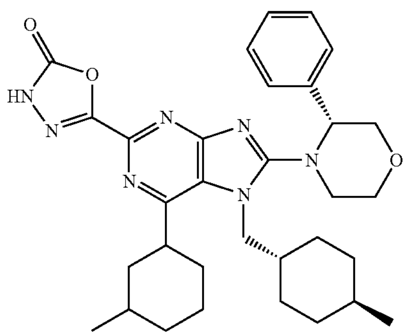 [SMILES: CC1CCCC(c2nc(-c3n[nH]c(=O)o3)nc3nc(N4CCOC[C@H]4c4ccccc4)n(C[C@H]4CC[C@H](C)CC4)c23)C1] | 5-{6-(3-methylcyclohexyl)-7-[(trans-4-methylcyclohexyl)methyl]-8-[(3R)-3-phenylmorpholin-4-yl]-7H-purin-2-yl}-1,3,4-oxadiazol-2(3H)-one (mixture of diastereomers) | | 572 | 572 |

Example 17.1 and Example 17.2

6-ethoxy-8-(3-methylphenyl)-7-[4-(trifluoromethyl)benzyl]-7H-purine-2-carboxylic acid (Example 17.1) and 6-(cyclopropylmethoxy)-8-(3-methylphenyl)-7-[4-(trifluoromethyl)benzyl]-7H-purine-2-carboxylic acid (Example 17.2)

Example 17.1

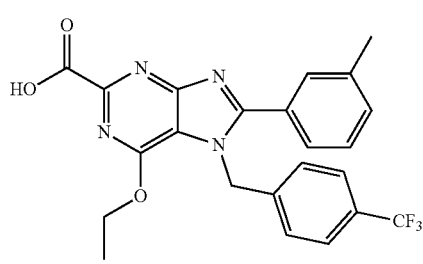

Example 17.2

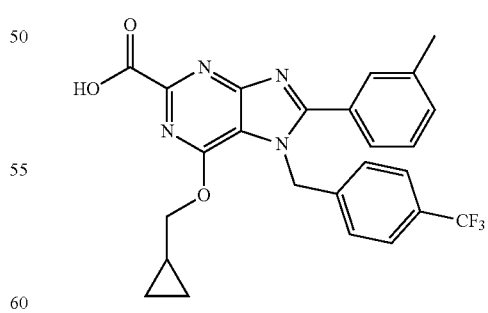

Step 1: Under an atmosphere of N$_2$, a dry vial was charged with 60% NaH (37.4 mg, 0.935 mmol) and THF (2 mL). Cyclpropanemethanol (0.092 mL, 1.17 mmol) was added dropwise by syringe and evolution of gas was observed. The reaction was stirred at room temperature for 15 minutes and then cooled to 0° C. A solution of 6-chloro-8-(3-methylphenyl)-7-[4-(trifluoromethyl)benzyl]-7H-purine-2-carbonitrile (Preparative Example 6.2) (100 mg, 0.234 mmol) in THF (1 mL) was added by syringe. After 30 minutes, the reaction was quenched with 2N HCl (2 mL). The reaction was diluted with EtOAc (50 mL) and washed with brine (2×10 mL). The organic layer was dried over $Na_2SO_4$, filtered, and concentrated. Purification of the residue on a Biotage 25 g silica gel column using 0 to 100% EtOAc/hexanes afforded 6-(cyclopropylmethoxy)-8-(3-methylphenyl)-7-[4-(trifluoromethyl) benzyl]-7H-purine-2-carbonitrile. $^1$H NMR (600 MHz, $CDCl_3$) 7.57 (d, J=7.2 Hz, 2H), 7.52 (s, 1H), 7.36-7.39 (m, 3H), 7.11 (d, J=8.4 Hz, 2H), 5.70 (s, 2H), 4.29 (d, J=7.8 Hz, 2H), 2.38 (s, 3H), 0.80-1.3 (m, 1H), 0.49 (d, J=7.8 Hz, 2H), 0.18 (d, J=4.8 Hz, 2H). MS(ES)=464.1 (M+1)$^+$.

Step 2: To a suspension of 6-(cyclopropylmethoxy)-8-(3-methylphenyl)-7-[4-(trifluoromethyl)benzyl]-7H-purine-2-carbonitrile (20 mg, 0.043 mmol) in EtOH (1 mL) was added 5N NaOH (0.5 mL, 2.5 mmol). The reaction was stirred vigorously at room temperature for 2 hours and then quenched with 1N HCl (5 mL). The mixture was diluted with EtOAc (30 mL) and washed with water (5 mL) and brine (5 mL). The organic layer was dried over $Na_2SO_4$, filtered, and concentrated. Purification of the residue on a Biotage 10 g silica gel column using 0 to 100% EtOAc/ hexanes afforded a~1:1 mixture of ethyl 6-(cyclopropylmethoxy)-8-(3-methylphenyl)-7-[4-(trifluoromethyl)benzyl]-7H-purine-2-carboxylate and ethyl 6-ethoxy-8-(3-methylphenyl)-7-[4-(trifluoromethyl)benzyl]-7H-purine-2-carboxylate. MS(ES)=511.2 and 485.1 (M+1)$^+$.

Step 3: To a mixture of ethyl 6-(cyclopropylmethoxy)-8-(3-methylphenyl)-7-[4-(trifluoromethyl)benzyl]-7H-purine-2-carboxylate and ethyl 6-ethoxy-8-(3-methylphenyl)-7-[4-(trifluoromethyl)benzyl]-7H-purine-2-carboxylate (14.7 mg) in THF (1 mL) was added water (0.2 mL) containing LiOH (6.9 mg, 0.29 mmol). After 30 minutes, the reaction was quenched with 2N HCl (0.5 mL). The reaction was diluted with EtOAc (30 mL) and washed with brine (2×5 mL). The organic layer was dried over $Na_2SO_4$, filtered, and concentrated. Purification of the residue by mass triggered reverse phase HPLC (C-18), eluting with acetonitrile/water containing 0.1% TFA afforded 6-ethoxy-8-(3-methylphenyl)-7-[4-(trifluoromethyl)benzyl]-7H-purine-2-carboxylic acid (TFA salt) and 6-(cyclopropylmethoxy)-8-(3-methylphenyl)-7-[4-(trifluoromethyl)benzyl]-7H-purine-2-carboxylic acid (TFA salt). 6-ethoxy-8-(3-methylphenyl)-7-[4-(trifluoromethyl)benzyl]-7H-purine-2-carboxylic acid (TFA salt): $^1$H NMR (600 MHz, d6-DMSO) δ 7.66 (d, J=10.2 Hz, 2H), 7.51 (s, 1H), 7.40-7.48 (m, 3H), 7.23 (d, J=9.6 Hz, 2H), 5.72 (s, 2H), 4.45 (q, J=8.4 Hz, 2H), 2.34 (s, 3H), 1.09 (t, J=8.4 Hz, 3H). LCMS=457.1 (M+1)$^+$. 6-(cyclopropylmethoxy)-8-(3-methylphenyl)-7-[4-(trifluoromethyl)benzyl]-7H-purine-2-carboxylic acid (TFA salt): $^1$H NMR (600 MHz, d6-DMSO) δ 7.66 (d, J=10.2 Hz, 2H), 7.53 (s, 1H), 7.41-7.48 (m, 3H), 7.24 (d, J=10.2 Hz, 2H), 5.74 (s, 2H), 4.26 (d, J=8.4 Hz, 2H), 2.34 (s, 3H), 1.04 (m, 1H), 0.36 (m, 2H), 0.13 (m, 2H). MS(ES)=483.2 (M+1)$^+$.

Example 17.3

6-(cyclobutylmethoxy)-8-(3-methylphenyl)-7-[4-(trifluoromethyl)benzyl]-7H-purine-2-carboxylic acid

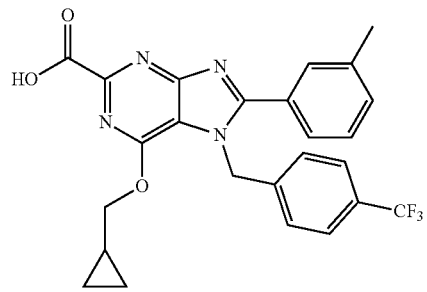 [SMILES: Cc1cccc(-c2nc3nc(C(=O)O)nc(OCC4CC4)c3n2Cc2ccc(C(F)(F)F)cc2)c1]

6-(cyclobutylmethoxy)-8-(3-methylphenyl)-7-[4-(trifluoromethyl)benzyl]-7H-purine-2-carboxylic acid, was prepared using procedures similar to those described for Examples 17.1 and 17.2, starting from 6-chloro-8-(3-methylphenyl)-7-[4-(trifluoromethyl)benzyl]-7H-purine-2-carbonitrile and cyclobutanemethanol. MS(ES)=497.1 (M+1)$^+$.

Example 17.4

6-(1-cyclobutylethoxy)-8-(3-methylphenyl)-7-[4-(trifluoromethyl)benzyl]-7H-purine-2-carboxylic acid

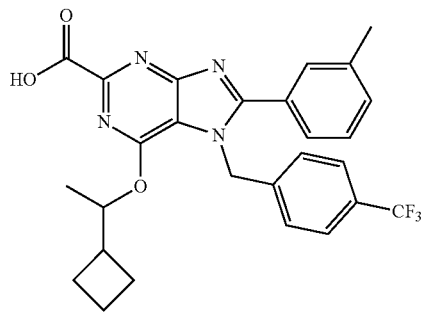 [SMILES: Cc1cccc(-c2nc3nc(C(=O)O)nc(OC(C)C4CCC4)c3n2Cc2ccc(C(F)(F)F)cc2)c1]

Step 1: Using a procedure analogous to that described in Step 1 of Examples 17.1 and 17.2 and starting from 6-chloro-8-(3-methylphenyl)-7-[4-(trifluoromethyl)benzyl]-7H-purine-2-carbonitrile and 1-cyclobutylethanol (purchased from Chinglu Pharmaceutical Research), 6-(1-cyclobutylethoxy)-8-(3-methylphenyl)-7-[4-(trifluoromethyl) benzyl]-7H-purine-2-carbonitrile was prepared. $^1$H NMR (600 MHz, $CDCl_3$) δ 7.60 (d, J=8.4 Hz, 2H), 7.49 (s, 1H), 7.32-7.37 (m, 3H), 7.08 (d, J=7.8 Hz, 2H), 5.71 (d, J=16.8 Hz, 1H), 6.62 (d, J=17.4 Hz, 1H), 5.44 (m, 1H), 2.36 (s, 3H), 2.30 (m, 1H), 1.88 (m, 1H), 1.78 (m, 1H), 1.55-1.68 (m, 4H), 1.06 (d, J=6.0 Hz, 3H). MS(ES)=492.2 (M+1)$^+$.

Step 2: Using a procedure analagous to that described in Step 2 of Examples 17.1 & 17.2, ethyl 6-(1-cyclobutylethoxy)-8-(3-methylphenyl)-7-[4-(trifluoromethyl)benzyl]-7H-purine-2-carboxylate was prepared. $^1$H NMR (600 MHz, $CDCl_3$) δ 7.57 (d, J=8.4 Hz, 2H), 7.49 (s, 1H), 7.36 (m, 1H), 7.32 (d, J=4.2 Hz, 2H), 7.08 (d, J=8.4 Hz, 2H), 5.72 (d, J=16.8 Hz, 1H), 5.64 (d, J=16.8 Hz, 1H), 5.56 (m, 1H), 4.48 (q, J=7.2 Hz, 2H), 2.35 (s, 3H), 2.30 (m, 1H), 1.86 (m, 1H), 1.74 (m, 1H), 1.58-1.66 (m, 4H), 1.45 (t, J=7.2 Hz, 3H), 1.07 (d, J=6.0 Hz, 3H). MS(ES)=539.2 (M+1)⁺. Ethyl 6-(1-cyclobutylethoxy)-8-(3-methylphenyl)-7-[4-(trifluoromethyl)benzyl]-7H-purine-2-carboxylate (racemate) could be separated into its enantiomers using a Chiral Technology Lux4 column and SFC with 30/70 MeOH/CO₂. With a flow rate of 70 mL/min and a run time of 6.5 minutes, peak 1 eluted at 3.5 minutes and peak 2 eluted at 5.5 minutes.

Step 3: Using a procedure analogous to that described in Step 3 of Examples 17.1 and 17.2, 6-(1-cyclobutylethoxy)-8-(3-methylphenyl)-7-[4-(trifluoromethyl)benzyl]-7H-purine-2-carboxylic acid (TFA salt, Example 17.4) was prepared. ¹H NMR (600 MHz, d6-DMSO) δ 7.69 (d, J=9.6 Hz, 2H), 7.50 (s, 1H), 7.38-7.45 (m, 3H), 7.24 (d, J=9.6 Hz, 2H), 5.77 (d, J=21 Hz, 1H), 5.68 (d, J=21 Hz, 1H), 5.41 (m, 1H), 2.33 (s, 3H), 2.28 (m, 1H), 1.42-1.78 (m, 6H), 0.99 (d, J=7.8 Hz, 3H). MS(ES)=511.2 (M+1)⁺.

Example 17.5

(R or S) 6-(1-cyclobutylethoxy)-8-(3-methylphenyl)-7-[4-(trifluoromethyl)benzyl]-7H-purine-2-carboxylic acid Example 17.6

(R or S) 6-(1-cyclobutylethoxy)-8-(3-methylphenyl)-7-[4-(trifluoromethyl)benzyl]-7H-purine-2-carboxylic acid Hydrolysis of enantiomers 1 and 2 from step 2 of Example 17.4, using a procedure analogous to that described in Step 3 of Examples 17.1 and 17.2, gave the following 2 examples: Examples 17.5 and 17.6.

Example 17.7

6-(1-cyclobutylethoxy)-7-[3-fluoro-4-(trifluoromethyl)benzyl]-8-[4-(propan-2-yl)pyridin-2-yl]-7H-purine-2-carboxylic acid

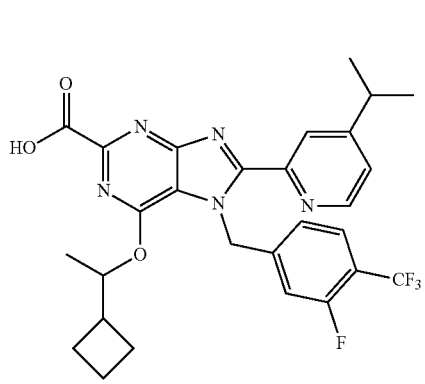 [SMILES: CC(C)c1ccnc(-c2nc3nc(C(=O)O)nc(OC(C)C4CCC4)c3n2Cc2ccc(C(F)(F)F)c(F)c2)c1]

Step 1: Using a procedure analogous to that described in Step 1 of Examples 17.1 and 17.2 and starting from 6-chloro-7-[3-fluoro-4-(trifluoromethyl)benzyl]-8-[4-(propan-2-yl)pyridin-2-yl]-7H-purine-2-carbonitrile and 1-cyclobutylethanol (purchased from Chinglu Pharmaceutical Research), 6-(1-cyclobutylethoxy)-7-[3-fluoro-4-(trifluoromethyl)benzyl]-8-[4-(propan-2-yl)pyridin-2-yl]-7H-purine-2-carbonitrile was prepared. ¹H NMR (600 MHz, CDCl₃) δ 8.47 (d, J=5.4 Hz, 1H), 8.45 (s, 1H), 7.48 (t, J=7.8 Hz, 1H), 7.26 (dd, J=5.4, 1.8 Hz, 1H), 6.93 (d, J=4.2 Hz, 1H), 6.91 (s, 1H), 6.45 (bs, 2H), 5.51 (m, 1H), 2.99 (m, 1H), 2.47 (m, 1H), 1.97 (m, 1H), 1.83 (m, 1H), 1.64-1.86 (m, 4H), 1.30 (d, J=7.2 Hz, 6H), 1.80 (d, J=6.0 Hz, 3H). MS(ES)=539.2 (M+1)⁺.

Step 2: To a suspension of 6-(1-cyclobutylethoxy)-7-[3-fluoro-4-(trifluoromethyl)benzyl]-8-[4-(propan-2-yl)pyridin-2-yl]-7H-purine-2-carbonitrile (45.4 mg, 0.084 mmol) in EtOH (5 mL) was added 5N NaOH (2.5 mL, 12.50 mmol). The reaction was stirred at room temperature for 1 hour, then heated slowly to 50° C., and finally heated at 70° C. for 2 minutes and then quickly cooled to room temperature. The reaction was quenched with 2N HCl (10 mL), diluted with EtOAc (50 mL) and washed with brine (2×10 mL). The organic layer was dried over Na₂SO₄, filtered, and concentrated. Purification of the residue by mass triggered reverse phase HPLC (C-18), eluting with acetonitrile/water containing 0.1% TFA afforded 6-(1-cyclobutylethoxy)-7-[3-fluoro-4-(trifluoromethyl)benzyl]-8-[4-(propan-2-yl)pyridin-2-yl]-7H-purine-2-carboxylic acid (TFA salt). ¹H NMR (600 MHz, d6-DMSO) δ 8.53 (d, J=6.0 Hz, 1H), 6.29 (d, J=1.8 Hz, 1H), 7.68 (t, J=9.6 Hz, 1H), 7.48 (dd, J=6.0, 1.8 Hz, 1H), 7.37 (d, J=14.4 Hz, 1H), 7.04 (d, J=10.2 Hz, 1H), 6.40 (d, J=19.8 Hz, 1H), 6.26 (d, J=21 Hz, 1H), 5.45 (m, 1H), 3.05 (m, 1H), 2.35 (m, 1H), 1.80 (m, 1H), 1.67 (m, 1H), 1.46-1.62 (m, 4H), 1.26 (d, J=9.0 Hz, 6H), 1.07 (d, J=7.2 Hz, 3H). MS(ES)=558.2 (M+1)⁺.

Example 17.8

6-(1-cyclobutylethoxy)-7-[(trans-4-methylcyclohexyl)methyl]-8-[4-(propan-2-yl)pyridin-2-yl]-7H-purine-2-carboxylic acid

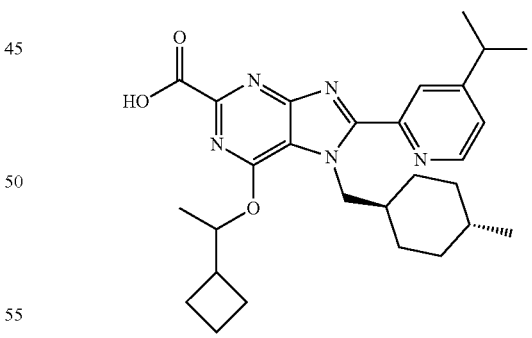

Using procedures analogous to those described in Example 17.7, and starting from 6-chloro-7-[(trans-4-methylcyclohexyl)methyl]-8-[4-(propan-2-yl)pyridin-2-yl]-7H-purine-2-carbonitrile, 6-(1-cyclobutylethoxy)-7-[(trans-4-methylcyclohexyl)methyl]-8-[4-(propan-2-yl)pyridin-2-yl]-7H-purine-2-carboxylic acid (TFA salt) was prepared. MS(ES)=492.3 (M+1)⁺.

TABLE 17.1

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.1 | 5899 | 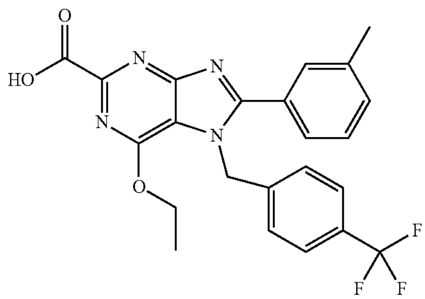 [SMILES: CCOc1nc(C(=O)O)nc2nc(-c3cccc(C)c3)n(Cc3ccc(C(F)(F)F)cc3)c12] | 6-ethoxy-8-(3-methylphenyl)-7-[4-(trifluoromethyl)benzyl]-7H-purine-2-carboxylic acid | TFA | 457 | 457 |
| 17.2 | 813.7 | 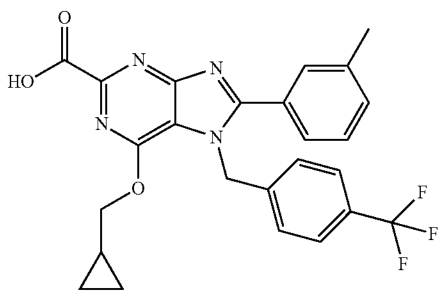 [SMILES: Cc1cccc(-c2nc3nc(C(=O)O)nc(OCC4CC4)c3n2Cc2ccc(C(F)(F)F)cc2)c1] | 6-(cyclopropylmethoxy)-8-(3-methylphenyl)-7-[4-(trifluoromethyl)benzyl]-7H-purine-2-carboxylic acid | TFA | 483 | 483 |
| 17.3 | 192.3 | 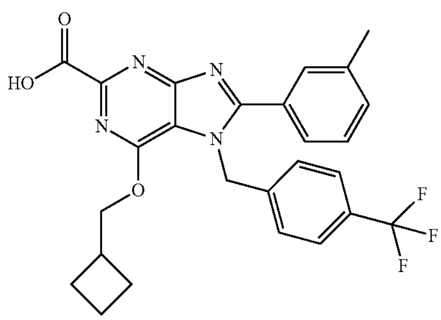 [SMILES: Cc1cccc(-c2nc3nc(C(=O)O)nc(OCC4CCC4)c3n2Cc2ccc(C(F)(F)F)cc2)c1] | 6-(cyclobutylmethoxy)-8-(3-methylphenyl)-7-[4-(trifluoromethyl)benzyl]-7H-purine-2-carboxylic acid | TFA | 497 | 497 |
| 17.4 | 67.12 | 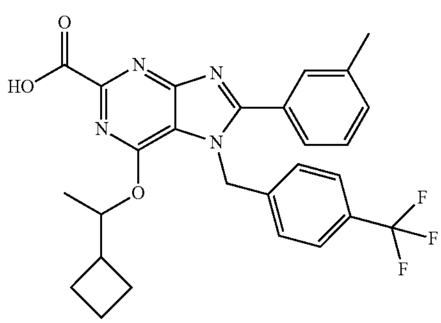 [SMILES: Cc1cccc(-c2nc3nc(C(=O)O)nc(OC(C)C4CCC4)c3n2Cc2ccc(C(F)(F)F)cc2)c1] | 6-(1-cyclobutylethoxy)-8-(3-methylphenyl)-7-[4-(trifluoromethyl)benzyl]-7H-purine-2-carboxylic acid (racemic) | TFA | 511 | 511 |
| 17.5 | 605.2 | 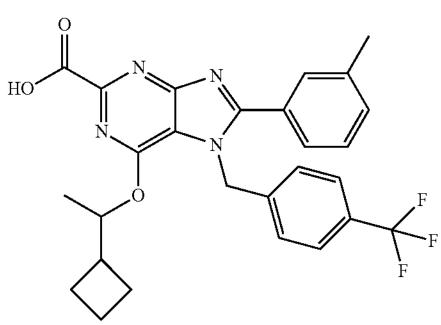 [SMILES: Cc1cccc(-c2nc3nc(C(=O)O)nc(OC(C)C4CCC4)c3n2Cc2ccc(C(F)(F)F)cc2)c1] | 6-(1-cyclobutylethoxy)-8-(3-methylphenyl)-7-[4-(trifluoromethyl)benzyl]-7H-purine-2-carboxylic acid (enantiomer 1) | TFA | 511 | 511 |

TABLE 17.1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.6 | 28.02 | 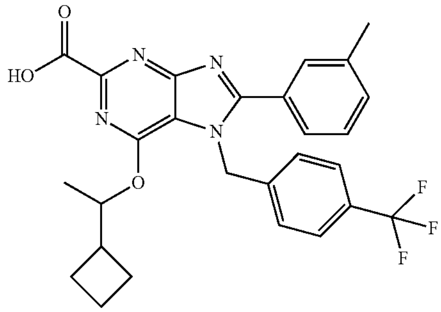 [SMILES: Cc1cccc(-c2nc3nc(C(=O)O)nc(OC(C)C4CCC4)c3n2Cc2ccc(C(F)(F)F)cc2)c1] | 6-(1-cyclobutylethoxy)-8-(3-methylphenyl)-7-[4-(trifluoromethyl)benzyl]-7H-purine-2-carboxylic acid (enantiomer 2) | TFA | 511 | 511 |
| 17.7 | 14.97 | 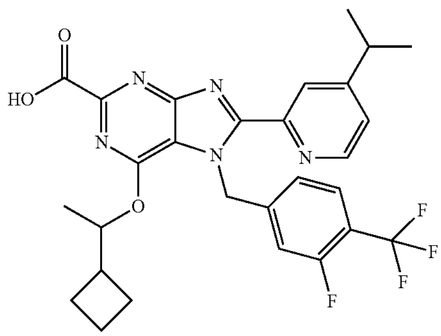 [SMILES: CC(C)c1ccnc(-c2nc3nc(C(=O)O)nc(OC(C)C4CCC4)c3n2Cc2ccc(C(F)(F)F)c(F)c2)c1] | 6-(1-cyclobutylethoxy)-7-[3-fluoro-4-(trifluoromethyl)benzyl]-8-[4-(1-methylethyl)pyridin-2-yl]-7H-purine-2-carboxylic acid (racemate) | TFA | 558 | 558 |
| 17.8 | 10.28 | 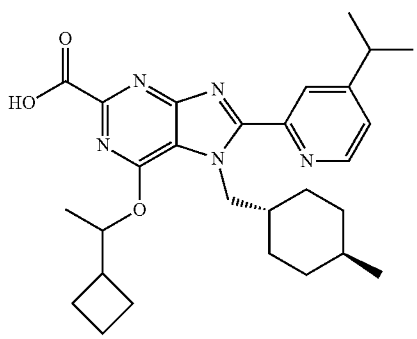 [SMILES: CC(C)c1ccnc(-c2nc3nc(C(=O)O)nc(OC(C)C4CCC4)c3n2C[C@H]2CC[C@H](C)CC2)c1] | 6-(1-cyclobutylethoxy)-7-[(trans-4-methylcyclohexyl)methyl]-8-[4-(1-methylethyl)pyridin-2-yl]-7H-purine-2-carboxylic acid (racemate) | TFA | 492 | 492 |

Example 17.9

3-(8-((R)-4-acetyl-2-methylpiperazin-1-yl)-6-(((R)-1-cyclobutylethyl)amino)-7-((trans-4-methylcyclohexyl)methyl)-7H-purin-2-yl)-1,2,4-oxadiazol-5(4H)-one

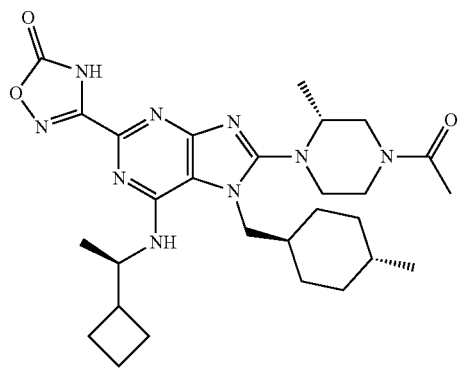 [SMILES: CC(=O)N1CCN(c2nc3nc(-c4noc(=O)[nH]4)nc(N[C@H](C)C4CCC4)c3n2C[C@H]2CC[C@H](C)CC2)[C@H](C)C1]

Step 1: To a reaction vial was added 8-bromo-6-(((R)-1-cyclobutylethyl)amino)-7-((trans-4-methylcyclohexyl)methyl)-7H-purine-2-carbonitrile (Preparative Example 11.7, 400 mg, 0.927 mmol), (R)-tert-butyl 3-methylpiperazine-1-carboxylate (HCl salt, 659 mg, 2.78 mmol), potassium fluoride (431 mg, 7.42 mmol), DMSO (2 ml) and DIEA (0.648 ml, 3.71 mmol). The vial was sealed and heated at 110° C. overnight. The reaction was then cooled to room temperature and diluted with EtOAc. The organic layer was washed with water and brine, dried over sodium sulfate, filtered, and concentrated. The residue was purified by column chromatography on silica gel, eluting with 0:100 to 100:0 EtOAc:DCM to give (R)-tert-butyl 4-(2-cyano-6-(((R)-1-cyclobutylethyl)amino)-7-((trans-4-methylcyclohexyl)methyl)-7H-purin-8-yl)-3-methylpiperazine-1-carboxylate. MS ESI calc'd. for $C_{30}H_{46}N_8O_2$ [M+H]$^+$ 551. found 551.

Step 2: TFA (2 ml, 26.0 mmol) was added into a solution of (R)-tert-butyl 4-(2-cyano-6-(((R)-1-cyclobutylethyl)amino)-7-((trans-4-methylcyclohexyl)methyl)-7H-purin-8-yl)-3-methylpiperazine-1-carboxylate (486 mg, 0.882 mmol) in CH$_2$Cl$_2$ (2 ml) at room temperature, and the reaction mixture was stirred for 16 h. The solvent was then evaporated and the crude 6-(((R)-1-cyclobutylethyl)amino)-7-((trans-4-methylcyclohexyl)methyl)-8-((R)-2-methylpiperazin-1-yl)-7H-purine-2-carbonitrile was used directly in the next step. MS ESI calc'd. for C$_{25}$H$_{38}$N$_8$ [M+H]$^+$ 451. found 451.

Step 3: Acetyl chloride (0.014 ml, 0.200 mmol) was added to a stirred, cooled 0° C. mixture of 6-(((R)-1-cyclobutylethyl)amino)-7-((trans-4-methylcyclohexyl)methyl)-8-((R)-2-methylpiperazin-1-yl)-7H-purine-2-carbonitrile (0.045 g, 0.1 mmol) and N,N-diisopropylethylamine (0.052 g, 0.400 mmol) in 1,4-Dioxane (2 ml). The reaction mixture was stirred at room temperature for 2 h. EtOH (0.5 ml) was added and the reaction mixture was concentrated. The crude 8-((R)-4-acetyl-2-methylpiperazin-1-yl)-6-(((R)-1-cyclobutylethyl)amino)-7-((trans-4-methylcyclohexyl)methyl)-7H-purine-2-carbonitrile was directly used in the next step. MS ESI calc'd. for C$_{27}$H$_{40}$N$_8$O [M+H]$^+$ 493. found 493.

Step 4: Hydroxylamine hydrochloride (0.021 g, 0.300 mmol), sodium bicarbonate (0.034 g, 0.400 mmol) and water (0.250 ml) were combined in a vial and allowed to stir for 15 minutes to allow for gas evolution via a pierced septa (homogeneous solution) before adding half of the solution to a vial containing 8-((R)-4-acetyl-2-methylpiperazin-1-yl)-6-(((R)-1-cyclobutylethyl)amino)-7-((trans-4-methylcyclohexyl)methyl)-7H-purine-2-carbonitrile in ethanol (1 ml). The vial was sealed and the reaction mixture was heated to 100° C. for 2 h. The mixture was then diluted with EtOAc. The organic layer was washed with water and brine, dried over sodium sulfate, filtrated and concentrated in vacuo. The crude 8-((R)-4-acetyl-2-methylpiperazin-1-yl)-6-(((R)-1-cyclobutylethyl)amino)-N'-hydroxy-7-((trans-4-methylcyclohexyl)methyl)-7H-purine-2-carboximidamide was used directly in the next step. MS ESI calc'd. for C$_{27}$H$_{43}$N$_9$O$_2$ [M+H]$^+$ 526. found 526.

Step 5: To a solution of 8-((R)-4-acetyl-2-methylpiperazin-1-yl)-6-(((R)-1-cyclobutylethyl)amino)-N'-hydroxy-7-((trans-4-methylcyclohexyl)methyl)-7H-purine-2-carboximidamide (52.6 mg, 0.1 mmol) and CDI (24.32 mg, 0.150 mmol) in acetonitrile (1.1 ml) was added DBU (60 µl, 0.4 mmol) and the resulting mixture was stirred at room temperature for 1 h. The reaction mixture was diluted with CH$_2$Cl$_2$, washed with water, dried over Na$_2$SO$_4$, filtered, and the solvent evaporated in vacuo. The residue was purified by preparative reverse phase HPLC (C-18), eluting with acetonitrile/water+0.1% TFA, to give 3-(8-((R)-4-acetyl-2-methylpiperazin-1-yl)-6-(((R)-1-cyclobutylethyl)amino)-7-((trans-4-methylcyclohexyl)methyl)-7H-purin-2-yl)-1,2,4-oxadiazol-5(4H)-one as the TFA salt. MS ESI calc'd. for C$_{28}$H$_{41}$N$_9$O$_3$ [M+H]$^+$ 552. found 552. $^1$H NMR δ (ppm) (DMSO-d$_6$): 0.75 (3H, d, J=6.45 Hz), 1.06 (3H, d, J=6.35 Hz), 1.20-0.70 (7H, m), 2.04-1.48 (12H, m), 2.48-2.47 (3H, s), 3.05 (1H, d, J=30.25 Hz), 3.24 (6H, m), 3.78-3.70 (1H, m), 4.37-4.30 (1H, m), 4.54-4.51 (1H, m), 6.42 (1H, dd, J=8.69, 3.96 Hz).

The following compounds in Table 17.2 (other than Example 17.9) were prepared using procedures which were analogous to those described above in Example 17.9.

TABLE 17.2

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.9 | 2.613 | 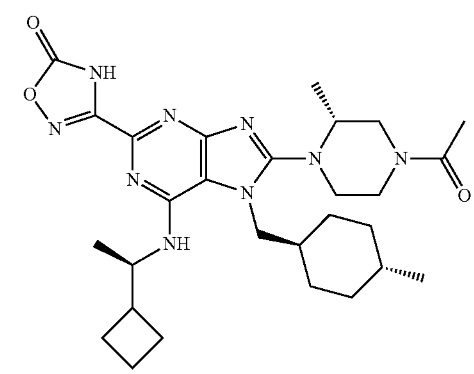 [SMILES: CC(=O)N1CCN(c2nc3nc(-c4noc(=O)[nH]4)nc(N[C@H](C)C4CCC4)c3n2C[C@H]2CC[C@H](C)CC2)[C@H](C)C1] | 3-(8-((R)-4-acetyl-2-methylpiperazin-1-yl)-6-(((R)-1-cyclobutylethyl)amino)-7-((trans-4-methylcyclohexyl)methyl)-7H-purin-2-yl)-1,2,4-oxadiazol-5(4H)-one | TFA | 552 | 552 |
| 17.10 | 0.2149 | 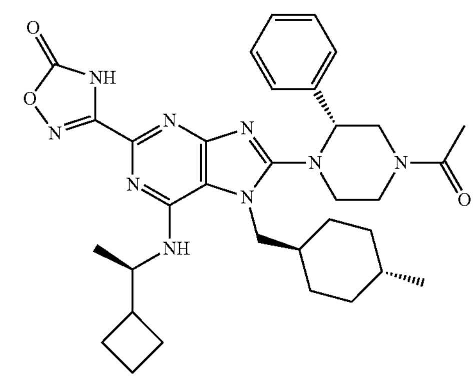 [SMILES: CC(=O)N1CCN(c2nc3nc(-c4noc(=O)[nH]4)nc(N[C@H](C)C4CCC4)c3n2C[C@H]2CC[C@H](C)CC2)[C@H](c2ccccc2)C1] | 3-{8-[(2R)-4-acetyl-2-phenylpiperazin-1-yl]-6-{[(1R)-1-cyclobutylethyl]amino}-7-[(trans-4-methylcyclohexyl)methyl]-7H-purin-2-yl}-1,2,4-oxadiazol-5(4H)-one | TFA | 614 | 614 |

TABLE 17.2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.11 | 6.334 | 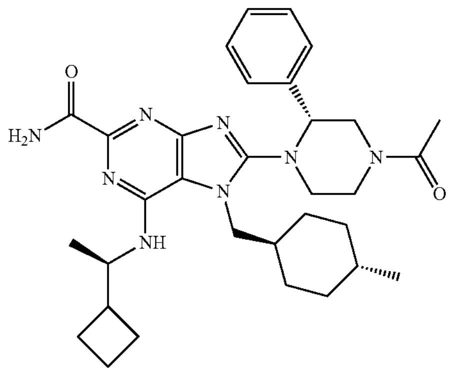 [SMILES: CC(=O)N1CCN(c2nc3nc(C(N)=O)nc(N[C@H](C)C4CCC4)c3n2C[C@H]2CC[C@H](C)CC2)[C@H](c2ccccc2)C1] | 8-[(2R)-4-acetyl-2-phenylpiperazin-1-yl]-6-{[(1R)-1-cyclobutylethyl]amino}-7-[(trans-4-methylcyclohexyl)methyl]-7H-purine-2-carboxamide | TFA | 573 | 573 |
| 17.12 | 4.604 | 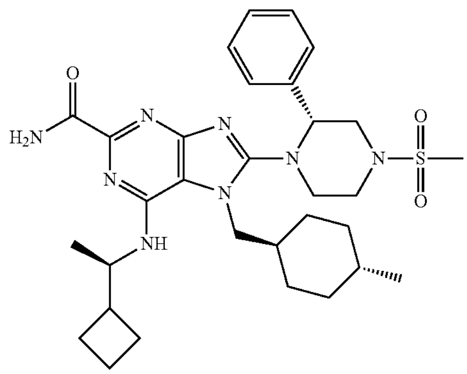 [SMILES: C[C@@H](Nc1nc(C(N)=O)nc2nc(N3CCN(S(C)(=O)=O)C[C@H]3c3ccccc3)n(C[C@H]3CC[C@H](C)CC3)c12)C1CCC1] | 6-{[(1R)-1-cyclobutylethyl]amino}-7-[(trans-4-methylcyclohexyl)methyl]-8-[(2R)-4-(methylsulfonyl)-2-phenylpiperazin-1-yl]-7H-purine-2-carboxamide | TFA | 609 | 609 |
| 17.13 | 1.859 | 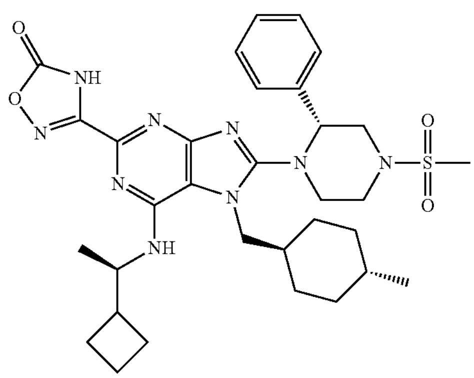 [SMILES: C[C@@H](Nc1nc(-c2noc(=O)[nH]2)nc2nc(N3CCN(S(C)(=O)=O)C[C@H]3c3ccccc3)n(C[C@H]3CC[C@H](C)CC3)c12)C1CCC1] | 3-(6-{[(1R)-1-cyclobutylethyl]amino}-7-[(trans-4-methyl-cyclohexyl)methyl]-8-[(2R)-4-(methylsulfonyl)-2-phenylpiperazin-1-yl]-7H-purin-2-yl)-1,2,4-oxadiazol-5(4H)-one | TFA | 650 | 650 |
| 17.14 | 4.931 | 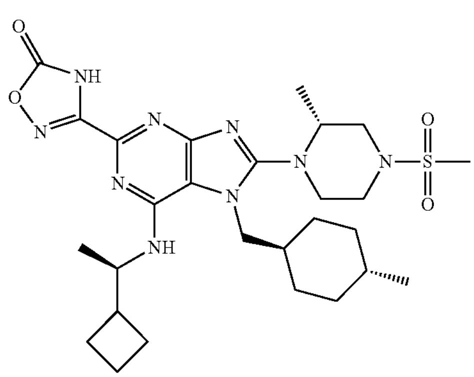 [SMILES: C[C@@H]1CN(S(C)(=O)=O)CCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(2R)-2-methyl-4-(methylsulfonyl)piperazin-1-yl]-7H-purin-2-yl)-1,2,4-oxadiazol-5(4H)-one | TFA | 588 | 588 |

TABLE 17.2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.15 | 4.299 | 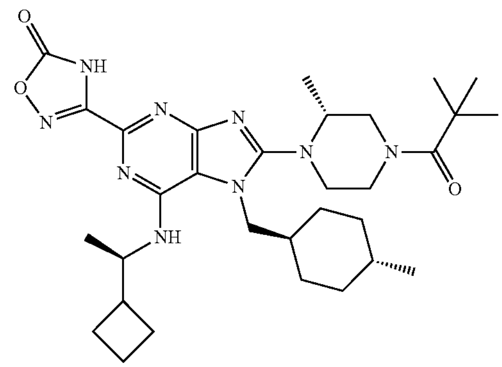 [SMILES: C[C@@H]1CN(C(=O)C(C)(C)C)CCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(2R)-4-(2,2-dimethylpropanoyl)-2-methylpiperazin-1-yl]-7-[(trans-4-methylcyclohexyl)methyl]-7H-purin-2-yl)-1,2,4-oxadiazol-5(4H)-one | TFA | 594 | 594 |
| 17.16 | 1.224 | 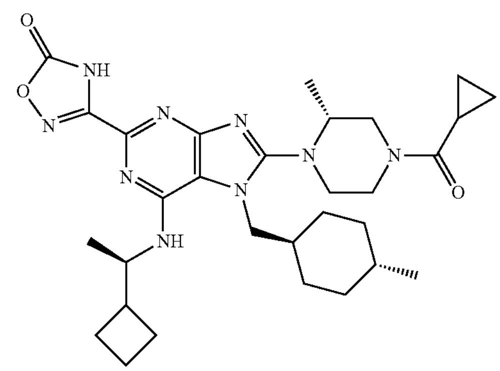 [SMILES: C[C@@H]1CN(C(=O)C2CC2)CCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(2R)-4-(cyclopropylcarbonyl)-2-methylpiperazin-1-yl]-7-[(trans-4-methylcyclohexyl)methyl]-7H-purin-2-yl)-1,2,4-oxadiazol-5(4H)-one | TFA | 578 | 578 |
| 17.17 | 10.08 | 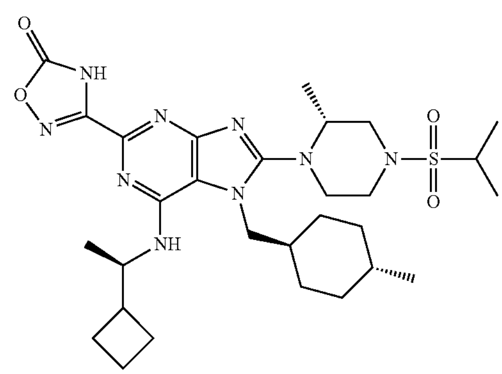 [SMILES: CC(C)S(=O)(=O)N1CCN(c2nc3nc(-c4noc(=O)[nH]4)nc(N[C@H](C)C4CCC4)c3n2C[C@H]2CC[C@H](C)CC2)[C@H](C)C1] | 3-(6-{[(1R)-1-cyclobutylethyl]amino}-7-[(trans-4-methylcyclohexyl)methyl]-8-{(2R)-2-methyl-4-[(1-methylethyl)sulfonyl]piperazin-1-yl}-7H-purin-2-yl)-1,2,4-oxadiazol-5(4H)-one | TFA | 616 | 616 |
| 17.18 | 3.789 | 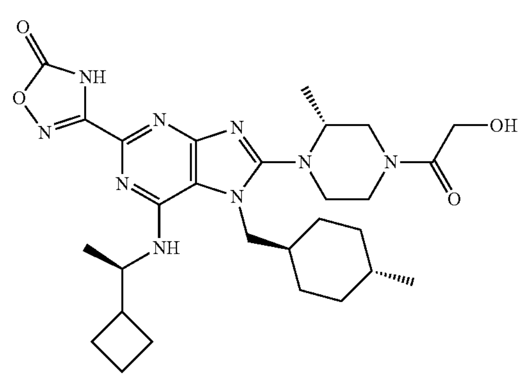 [SMILES: C[C@@H]1CN(C(=O)CO)CCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(2R)-4-(hydroxyacetyl)-2-methylpiperazin-1-yl]-7-[(trans-4-methylcyclohexyl)methyl]-7H-purin-2-yl)-1,2,4-oxadiazol-5(4H)-one | TFA | 568 | 568 |

TABLE 17.2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.19 | 15.48 | 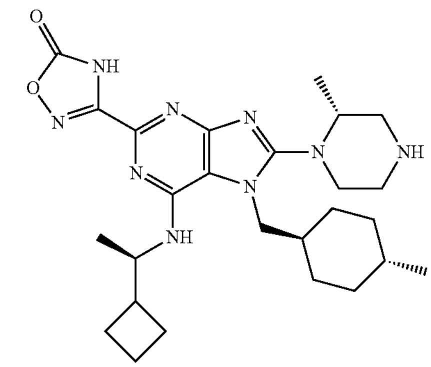 [SMILES: C[C@@H]1CNCCN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-7-[(trans-4-methylcyclohexyl)methyl]-8-[(2R)-2-methylpiperazin-1-yl]-7H-purin-2-yl)-1,2,4-oxadiazol-5(4H)-one | | 510 | 510 |
| 17.20 | 14.75 | 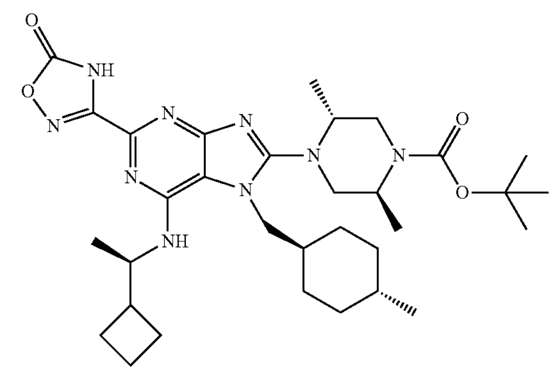 [SMILES: C[C@@H]1CN(C(=O)OC(C)(C)C)[C@@H](C)CN1c1nc2nc(-c3noc(=O)[nH]3)nc(N[C@H](C)C3CCC3)c2n1C[C@H]1CC[C@H](C)CC1] | tert-butyl (2S,5R)-4-[6-{[(1R)-1-cyclobutylethyl]amino}-7-[(trans-4-methylcyclohexyl)methyl]-2-(5-oxo-4,5-dihydro-1,2,4-oxadiazol-3-yl)-7H-purin-8-yl]-2,5-dimethylpiperazine-1-carboxylate | TFA | 624 | 624 |
| 17.21 | 20.14 | 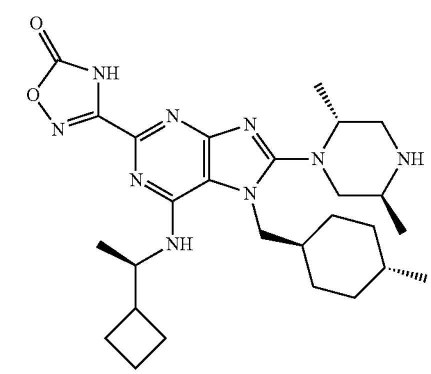 [SMILES: C[C@@H]1CN[C@@H](C)CN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(2R,5S)-2,5-dimethylpiperazin-1-yl]-7-[(trans-4-methylcyclohexyl)methyl]-7H-purin-2-yl)-1,2,4-oxadiazol-5(4H)-one | TFA | 524 | 524 |
| 17.22 | 4.352 | 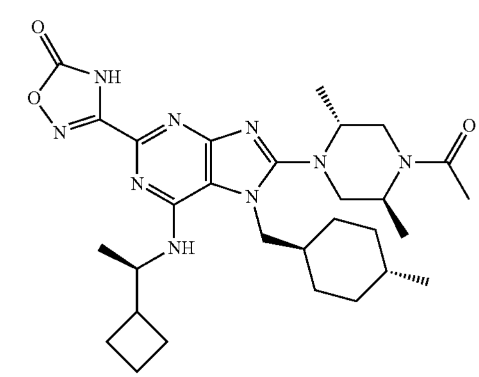 [SMILES: CC(=O)N1C[C@@H](C)N(c2nc3nc(-c4noc(=O)[nH]4)nc(N[C@H](C)C4CCC4)c3n2C[C@H]2CC[C@H](C)CC2)C[C@@H]1C] | 3-{8-[(2R,5S)-4-acetyl-2,5-dimethylpiperazin-1-yl]-6-{[(1R)-1-cyclobutylethyl]amino}-7-[(trans-4-methylcyclohexyl)methyl]-7H-purin-2-yl}-1,2,4-oxadiazol-5(4H)-one | TFA | 566 | 566 |

TABLE 17.2-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 17.23 | 4.877 | 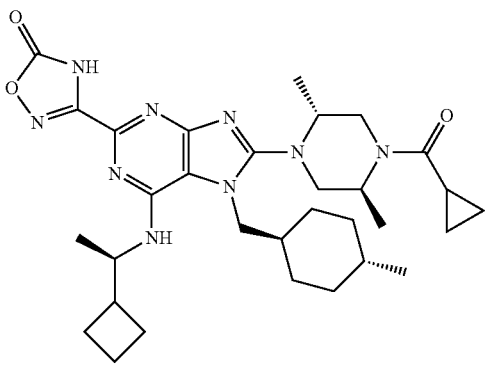 [SMILES: C[C@@H]1CN(C(=O)C2CC2)[C@@H](C)CN1c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(2R,5S)-4-(cyclopropylcarbonyl)-2,5-dimethylpiperazin-1-yl]-7-[(trans-4-methylcyclohexyl)methyl]-7H-purin-2-yl)-1,2,4-oxadiazol-5(4H)-one | TFA | 592 | 592 |

Preparative Example 18.1 trans-1-(bromomethyl)-4-(trifluoromethyl)cyclohexane

Step 1: BH$_3$ (100 mL, 0.1 mol, 1.0 M solution in THF) was added dropwise to a 0° C. solution of trans-4-(trifluoromethyl)cyclohexanecarboxylic acid (19.6 g, 0.1 mol) in dry THF (100 mL). The reaction was stirred at room temperature for 5 h, quenched with water, extracted with EtOAc, washed with brine, dried over Na$_2$SO$_4$, filtered and concentrated to give (trans-4-(trifluoromethyl)cyclohexyl)methanol. $^1$H NMR (300 MHz, CDCl$_3$): δ 3.48-3.47 (d, 2H), 2.00-1.89 (m, 5H), 1.51-1.43 (m, 1H), 1.35-1.26 (m, 2H), 1.05-0.96 (m, 2H).

Step 2: PPh$_3$ (30.75 g, 117.4 mmol) was added slowly to a solution of (trans-4-(trifluoromethyl)cyclohexyl)methanol (17.8 g, 97.8 mmol) and CBr$_4$ (38.85 g, 117.4 mmol) in dry DCM (200 mL) at 0° C. The reaction was stirred at room temperature overnight and then concentrated. Hexane/EtOAc (9/1, 300 ml) was added and the mixture was stirred for 1 hour, filtered, concentrated, and distilled in vacuum to give trans-1-(bromomethyl)-4-(trifluoromethyl)cyclohexane. $^1$H NMR (300 MHz, CDCl$_3$): δ 3.30-3.28 (d, 2H), 2.02-1.92 (m, 5H), 1.70-1.59 (m, 1H), 1.40-1.27 (m, 2H), 1.13-1.00 (m, 2H).

Preparative Example 18.2

2,6-dichloro-7-((trans-4-(trifluoromethyl)cyclohexyl)methyl)-7H-purine

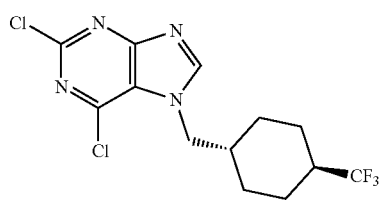 [SMILES: FC(F)(F)[C@H]1CC[C@H](Cn2cnc3nc(Cl)nc(Cl)c32)CC1]

Step 1: To a solution of trans-1-(bromomethyl)-4-(trifluoromethyl)cyclohexane (Preparative Example 18.1, 2.94 g, 12 mmol) and 3-methyl-1H-purine-2,6(3H,7H)-dione (1.66 g, 10 mmol) in dry DMF (30 mL) was added Na$_2$CO$_3$ (12.72 g, 12 mmol). The reaction was stirred at 100° C. overnight and then quenched with 1N HCl (60 ml). The precipitate was collected by filtration and dried under vacuum to give 3-methyl-7-((trans-4-(trifluoromethyl)cyclohexyl)methyl)-1H-purine-2,6(3H,7H)-dione. $^1$H NMR (300 MHz, CDCl$_3$): δ 7.52 (s, 1H), 4.13-4.11 (d, 2H), 3.55 (s, 1H), 2.03-1.86 (m, 4H), 1.81-1.75 (m, 2H), 1.38-1.24 (m, 2H), 1.11-0.98 (m, 2H).

Step 2: DBU (6.63 g, 43.6 mmol) was added to a mixture of 3-methyl-7-((trans-4-(trifluoromethyl)cyclohexyl)methyl)-1H-purine-2,6(3H,7H)-dione (3.1 g, crude) in POCl$_3$ (30 mL) at 60° C. The reaction mixture was stirred at 120° C. for 2 h, cooled to room temperature, concentrated, diluted with EtOAc, washed with saturated aq. NaHCO$_3$ solution and brine, dried over Na$_2$SO$_4$, filtered, concentrated and purified by flash chromatography on silica gel to give 2,6-dichloro-7-((trans-4-(trifluoromethyl)cyclohexyl)methyl)-7H-purine. MS ESI calc'd. for C$_{13}$H$_{13}$Cl$_2$F$_3$N$_4$ [M+H]$^+$ 353. found 353. $^1$H NMR (300 MHz, CDCl$_3$): δ 8.18 (s, 1H), 4.32-4.30 (d, 2H), 2.07-1.77 (m, 6H), 1.38-1.06 (m, 4H).

Example 18.1

6-(((R)-1-cyclobutylethyl)amino)-8-(4-isopropylpyridin-2-yl)-7-((trans-4-(trifluoromethyl)cyclohexyl)methyl)-7H-purine-2-carboxylic acid

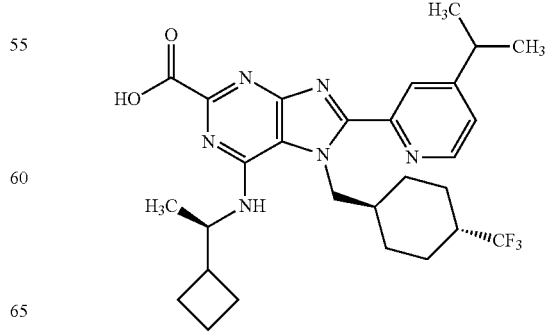

Step 1: A mixture of 2,6-dichloro-7-((trans-4-(trifluoromethyl)cyclohexyl)methyl)-7H-purine (400 mg, 1.13 mmol), (R)-1-cyclobutylethylamine (766.5 mg, 5.66 mmol) and diisopropyl ethylamine (731 mg, 5.66 mmol) in ethanol (5.0 mL) was heated to reflux for 12 hours. Then the reaction mixture was cooled to room temperature and concentrated. The residue was dissolved in EtOAc (30 mL) and the organic layer was washed with water (15 mL) and brine (15 mL), dried over anhydrous $Na_2SO_4$, filtered, and concentrated in vacuo. Purification of the crude material by silica gel column chromatography (60% EtOAc/hexanes) afforded 2-chloro-N—((R)-1-cyclobutylethyl)-7-((trans-4-(trifluoromethyl)cyclohexyl)methyl)-7H-purin-6-amine as white solid. $^1$H NMR (400 MHz, $CDCl_3$) δ7.76 (s, 1H), 4.59 (d, J=8.0 Hz, 2H), 4.45-4.41 (m, 1H), 4.15 (dd, J=16.0, 12.0 Hz, 1H), 4.05 (dd, J=16.0, 16.0 Hz, 1H), 2.37-2.43 (m, 1H), 1.66-2.10 (m, 10H), 1.26-1.30 (m, 2H), 1.25 (d, J=9.6 Hz, 3H), 1.12-1.16 (m, 2H). MS (APCI)=416 $(M+1)^+$.

Step 2: A mixture of 2-chloro-N—((R)-1-cyclobutylethyl)-7-((trans-4-(trifluoromethyl)cyclohexyl)methyl)-7H-purin-6-amine (400 mg, 0.96 mmol) and zinc cyanide (90.3 mg, 0.76 mmol) in DMA (5 ml) in a sealable tube was degassed with Ar for 30 minutes. $Pd(PPh_3)_4$ (221 mg, 0.19 mmol) was then added and the vessel was evacuated and refilled with Ar three times, sealed, and heated at 120° C. for 12 hours. The reaction mixture was cooled to room temperature. Ice-cooled water (40 ml) was added slowly and the reaction mixture was extracted with ethyl acetate (3×50 mL). The combined organic layers were dried over sodium sulfate, filtered, and concentrated under reduced pressure. Purification of the residue on a Redisep 12 g silica gel column with 0 to 100% EtOAc/hexanes afforded 6-(((R)-1-cyclobutylethyl)amino)-7-((trans-4-(trifluoromethyl)cyclohexyl)methyl)-7H-purine-2-carbonitrile as white solid. $^1$H NMR (400 MHz, $CDCl_3$) δ7.85 (s, 1H), 4.59 (d, J=8.0 Hz, 2H), 4.38 (m, 1H), 4.11 (dd, J=16.0, 16.0 Hz, 1H), 4.03 (dd, J=16.0, 16.0 Hz, 1H), 2.05-2.39 (m, 1H), 1.66-2.05 (m, 10H), 1.20-1.24 (m, 2H), 1.18 (d, J=6.4 Hz, 3H), 1.12-1.16 (m, 2H). MS(APCI)=407 $(M+1)^+$.

Step 3: A solution of palladium acetate (22.0 mg, 0.09 mmol) and Catacxium® A (70.5 mg, 0.19 mmol) in 1,4-dioxane (4.0 mL) under Ar was heated at 50° C. for 30 minutes then cooled to room temperature. The above catalyst mixture was added to a mixture of 6-(((R)-1-cyclobutylethyl)amino)-7-((trans-4-(trifluoromethyl)cyclohexyl)methyl)-7H-purine-2-carbonitrile (100 mg, 0.24 mmol), 2-bromo-4-isopropyl pyridine (99 mg 0.49 mmol), CsF (112.1 mg, 0.73 mmol) and pivalic acid (32.6 mg, 0.31 mmol) in 1,4-dioxane (4.0 mL) under Ar. The reaction mixture was heated at 110° C. overnight in a sealed tube. After evaporation of the solvent, the residue was diluted with water (10 mL) and extracted with EtOAc (3×20 mL). The combined organic layers were washed with water and brine, dried over anhydrous $Na_2SO_4$, filtered and concentrated in vacuo. Purification of the residue on a Redisep 4 g silica gel column (0 to 50% EtOAc/hexanes) afforded 6-(((R)-1-cyclobutylethyl)amino)-8-(4-isopropylpyridin-2-yl)-7-((trans-4-(trifluoromethyl)cyclohexyl)methyl)-7H-purine-2-carbonitrile as an off-white solid. $^1$H NMR (400 MHz, $CDCl_3$) δ 8.54 (d, J=4.6 Hz, 1H), 8.40 (s, 1H), 7.47 (d, J=4.6 Hz, 1H), 4.77 (d, J=8.0 Hz, 2H), 4.51 (m, 1H), 2.98-3.02 (m, 1H), 2.43-2.44 (m, 1H), 1.67-2.17 (m, 12H), 1.39 (d, J=8.8 Hz, 6H), 1.28 (d, J=8.0 Hz, 3H), 0.85-1.15 (m, 4H). MS (ES)=526 $(M+1)^+$.

Step 4: 6-(((R)-1-cyclobutylethyl)amino)-8-(4-isopropylpyridin-2-yl)-7-((trans-4-(trifluoromethyl)cyclohexyl)methyl)-7H-purine-2-carbonitrile (42.0 mg, 0.07 mmol) was suspended in HCl in MeOH (3.0 mL, 3.0 M) and heated at 75° C. for 4 hours. The solvent was evaporated under reduced pressure, the crude product was suspended in $CH_2Cl_2$ (40 mL) and washed with aqueous sat. $NaHCO_3$. The organic layer was separated and dried over $Na_2SO_4$, filtered and concentrated in vacuo. The crude residue was purified on a Redisep 12 g silica gel column (0 to 100% EtOAc/hexanes) to afford methyl 6-(((R)-1-cyclobutylethyl)amino)-8-(4-isopropylpyridin-2-yl)-7-((trans-4-(trifluoromethyl)cyclohexyl)methyl)-7H-purine-2-carboxylate as a white solid. $^1$H NMR (400 MHz, $CDCl_3$) δ 8.53 (d, J=4.8 Hz, 1H), 8.42 (s, 1H), 7.23 (d, J=4.8 Hz, 1H), 4.73 (d, J=8.0 Hz, 2H), 4.61 (m, 1H), 4.00 (s, 3H), 3.00 (m, 1H), 2.31-2.46 (m, 1H), 1.42-2.29 (m, 10H), 1.28 (d, J=6.8 Hz, 6H), 1.22 (d, J=6.4 Hz, 3H), 0.89-1.16 (m, 3H). MS (ES)=559 $(M+1)^+$.

Step 5: Aqueous LiOH solution (4.71 mg, 0.03 mmol, in 0.5 mL water) was added to a solution of methyl 6-(((R)-1-cyclobutylethyl)amino)-8-(4-isopropylpyridin-2-yl)-7-((trans-4-(trifluoromethyl)cyclohexyl)methyl)-7H-purine-2-carboxylate (22 mg, 0.03 mmol) in THF (2.0 mL) at room temperature. The reaction mixture was stirred at room temperature for 1.5 hours and was concentrated in vacuo. The residue was dissolved in water (1.5 mL) and neutralized to pH 7 with aqueous HCl solution (1M). The precipitate was collected by filtration, washed with water and dried under vacuum to afford 6-(((R)-1-cyclobutylethyl)amino)-8-(4-isopropylpyridin-2-yl)-7-((trans-4-(trifluoromethyl)cyclohexyl)methyl)-7H-purine-2-carboxylic acid as a white solid. $^1$H NMR (400 MHz, $CD_3OD$) δ8.65 (s, 1H), 8.22 (s, 1H), 7.47 (d, J=4.8 Hz, 1H), 5.31-5.43 (m, 1H), 4.75-4.82 (m, 1H), 3.05-3.08 (m, 1H), 2.59-2.61 (m, 1H), 1.65-2.15 (m, 12H), 1.40-1.43 (m, 1H), 1.34 (d, J=8.8 Hz, 6H), 1.28 (d, J=6.8 Hz, 3H), 0.89-1.17 (m, 4H). MS (ES)=545 $(M+1)^+$.

Preparative Example 18.3 trans-1-(bromomethyl)-4-ethylcyclohexane

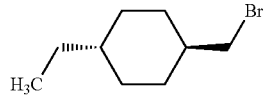

Step 1: Borane in THF (1M, 64.1 mL, 64.1 mmol) was added dropwise to trans-4-ethylcyclohexanecarboxylic acid (10.0 g, 64.1 mmol) in dry THF (100 mL) at −60° C. under nitrogen atmosphere. The mixture was allowed to warm to room temperature and stirred for 12 h. The reaction was quenched with saturated ammonium chloride solution at 0° C., diluted with water (200 mL), and extracted with ethyl acetate (3×100 mL). The organic layer was washed with water (2×200 mL) and brine (100 mL), dried over anhydrous $Na_2SO_4$, filtered, then concentrated in vacuo to obtain (trans-4-ethylcyclohexyl)methanol which was taken forward without further purification: $^1$H NMR (300 MHz, $CDCl_3$): δ3.44 (d, J=6.0 Hz, 2H); 1.85-1.70 (dd, J=1.19, 10.5 Hz, 4H); 1.50-1.35 (m, 1H); 1.30-1.10 (m, 4H); 0.95-0.85 (m, 6H).

Step 2: (Trans-4-ethylcyclohexyl)methanol (8.90 g, 62.6 mmol), carbon tetrabromide (20.8 g, 62.6 mmol), and triphenylphosphine (17.4 g, 62.6 mmol) were dissolved in dichloromethane (100 mL) and stirred at room temperature for 12 hours. The reaction mixture was concentrated, diluted with hexane/EtOAc (90/10, 250 mL) and stirred for 1 h. The solids were removed by filtration and washed with hexane/EtOAc (90/10, 50 mL). The filtrate was concentrated, and the residue was taken up and filtered through a plug of silica gel with 10% EtOAc/hexanes to obtain trans-1-(bromomethyl)-4-ethylcyclohexane. The compound was used without further purification. $^1$H NMR (300 MHz, $CDCl_3$): δ3.29-

3.27 (d, J=6.52 Hz, 2H); 1.81-1.77 (d, J=10.3 Hz, 4H); 1.70-1.50 (m, 1H); 1.40-1.20 (m, 4H); 1.10-0.70 (m, 6H).

Preparative Example 18.4

2,6-dichloro-7-((trans-4-ethylcyclohexyl)methyl)-7H-purine

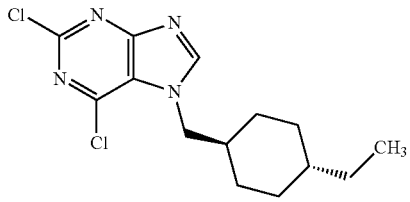 [SMILES: CC[C@H]1CC[C@H](Cn2cnc3nc(Cl)nc(Cl)c32)CC1]

Step 1: 3-Methyl-1H-purine-2,6(3H,7H)-dione (5.0 g, 30.1 mmol), trans-1-(bromomethyl)-4-ethylcyclohexane (8.6 g, 42.1 mmol) and sodium carbonate (3.16 g, 30.1 mmol) were suspended in anhydrous DMF (130 mL). The reaction mixture was heated at 100° C. for 14 h. The reaction was cooled to room temperature and quenched with ~40 mL of 1N aq. HCl solution at 0° C. (final pH=2 to 3). The resulting white solid was collected by filtration and dried under vacuum to obtain 9-((trans-4-ethylcyclohexyl) methyl)-3-methyl-1H-purine-2,6(3H,9H)-dione: $^1$H NMR (300 MHz, $D_6$ DMSO): δ11.07 (s, 1H), 8.00 (s, 1H), 4.07 (d, J=7.3 Hz, 2H); 3.34 (s, 3H); 1.73-1.49 (m, 5H), 1.29-1.12 (m, 2H); 1.02-0.73 (m, 8H).

Step 2: DBU (4.5 mL) was added to a suspension of 9-((trans-4-ethylcyclohexyl)methyl)-3-methyl-1H-purine-2, 6(3H,9H)-dione (2.3 g, 7.93 mmol) in $POCl_3$ (12.0 mL) at 60° C. The reaction mixture was heated at 120° C. for 3 h and then cooled to ambient temperature. The reaction mixture was poured onto crushed ice and the pH of the solution was adjusted to neutral using 29% aqueous $NH_4OH$. The aqueous mixture was extracted with dichloromethane (3×50 mL) and the combined organic layers were dried over $Na_2SO_4$, filtered, and concentrated. The residue was purified by silica gel column chromatography (EtOAc/hexanes 2:3) to afford 2,6-dichloro-7-((trans-4-ethylcyclohexyl)methyl)-7H-purine as white solid: $^1$H NMR (300 MHz, $CDCl_3$): δ8.53 (s, 1H), 4.35 (d, J=7.2 Hz, 2H); 1.82-1.79 (m, 3H); 1.67-1.64 (m, 2H); 1.26-1.08 (m, 6H); 0.86-0.84 (m, 4H).

Example 18.2

6-(((R)-1-cyclobutylethyl)amino)-7-((trans-4-ethylcyclohexyl)methyl)-8-(4-isopropylpyridin-2-yl)-7H-purine-2-carboxylic acid

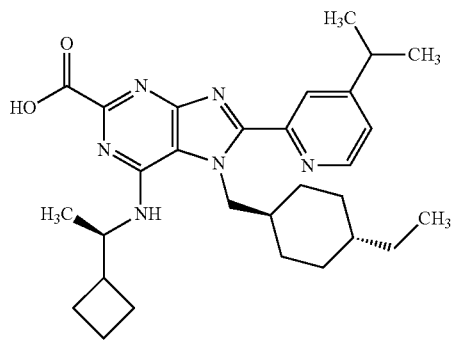 [SMILES: CC[C@H]1CC[C@H](Cn2c(-c3cc(C(C)C)ccn3)nc3nc(C(=O)O)nc(N[C@H](C)C4CCC4)c32)CC1]

Using a procedure analogous to that described in Example 18.1, and starting with 2,6-dichloro-7-((trans-4-ethylcyclohexyl)methyl)-7H-purine (Preparative Example 18.4), 6-(((R)-1-cyclobutylethyl)amino)-7-((trans-4-ethylcyclohexyl)methyl)-8-(4-isopropylpyridin-2-yl)-7H-purine-2-carboxylic acid was prepared. MS ESI calc'd. for $C_{29}H_{40}N_6O_2$ [M+H]+ 505. found 505.

Preparative Example 18.5

4-(bromomethyl)-1,1-difluorocyclohexane

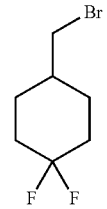

Step 1: To a stirred solution of ethyl 4,4-difluorocyclohexanecarboxylate (5.00 g, 26.0 mmol) in THF (50 mL) was added LAH (28.5 mL, 28.5 mmol, 1 M in THF) at 0° C. and the reaction mixture was stirred at 0° C. for 1 hour under a nitrogen atmosphere. The reaction mixture was then quenched with saturated $Na_2SO_4$, filtered through a pad of celite washing with ethyl acetate, and the filtrate was concentrated to afford crude (4,4-difluorocyclohexyl)methanol. $^1$H NMR (400 MHz, $CDCl_3$) δ 3.52 (d, J=4.8 Hz, 2H), 2.07-2.15 (m, 2H), 1.65-1.86 (m, 3H), 1.45-1.64 (m, 2H), 1.24-1.41 (m, 2H).

Step 2: To a stirred solution of (4,4-difluorocyclohexyl) methanol (6.0 g, 39.9 mmol) in dichloromethane (70 mL) was added triphenylphosphine (12.5 g, 47.9 mmol). The reaction mixture was cooled to 0° C. and $CBr_4$ (15.9 g, 47.9 mmol) was added. After the addition was complete, the reaction mixture was warmed to room temperature and stirred for 12 hours. The reaction mixture was concentrated and the resulting residue was purified on a RediSep 40 g silica gel column (10 to 100% EtOAc/hexanes) to afford 4-(bromomethyl)-1,1-difluorocyclohexane. $^1$H NMR (400 MHz, $CDCl_3$) δ 3.30 (d, J=4.8 Hz, 2H), 2.06-2.16 (m, 2H), 1.93-1.96 (m, 2H), 1.66-1.82 (m, 3H), 1.33-1.44 (m, 2H).

Example 18.3

(R)-6-((1-cyclobutylethyl)amino)-7-((4,4-difluorocyclohexyl)methyl)-8-(4-isopropylpyridin-2-yl)-7H-purine-2-carboxylic acid

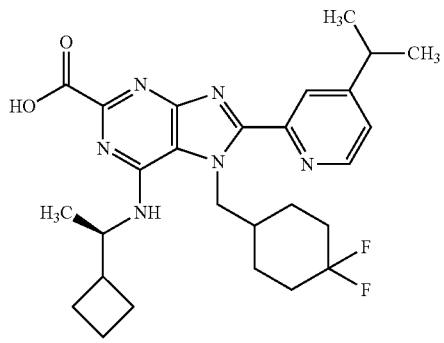 [SMILES: CC(C)c1ccnc(-c2nc3nc(C(=O)O)nc(N[C@H](C)C4CCC4)c3n2CC2CCC(F)(F)CC2)c1]

Following a procedure analogous to that described for the synthesis of Example 18.1, and starting with 4-(bromomethyl)-1,1-difluorocyclohexane (Preparative Example 18.5), (R)-6-((1-cyclobutylethyl)amino)-7-((4,4-difluorocyclohexyl)methyl)-8-(4-isopropylpyridin-2-yl)-7H-purine-2-carboxylic acid was prepared. $^1$H NMR (400 MHz, DMSO-d$_6$) δ 8.65 (d, J=5.0 Hz, 1H), 8.13 (br s, 1H), 7.46 (dd, J=5.0, 1.6 Hz, 1H), 6.38 (br s, 1H), 5.27 (m, 1H), 4.93 (m, 1H), 4.50 (m, 1H), 3.06 (m, 1H), 1.49-2.05 (m, 15H), 1.20-1.28 (m, 6H), 1.13 (d, J=6.8 Hz, 3H), 0.89 (m, 1H). MS (ES)=513 (M+1)$^+$.

Preparative Example 18.6

1-(bromomethyl)-3-ethylcyclopentane

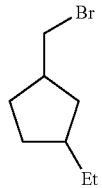

Step 1: To a stirred solution of 3-ethylcyclopentanone (4.00 g, 35.7 mmol) in THF (70 mL) was added LDA (2 M in THF, 22.8 mL, 46.4 mmol) at 78° C. and the reaction was stirred at that temperature for 30 minutes. Next, N-phenyl-bis(trifluoromethanesulfonimide) (14.0 g, 39.2 mmol) in THF (70 mL) was added at −78° C. The mixture was allowed to warm to room temperature and stirred for 17 hours under a nitrogen atmosphere. The reaction mixture was then cooled to 0° C. and slowly quenched with aqueous ammonium chloride and extracted with methyl tertiary-butyl ether (3×30 mL). The combined organic layers were washed with brine (2×30 mL), dried over anhydrous Na$_2$SO$_4$, and concentrated. Purification of the residue on a silica gel column (10 to 100% EtOAc/hexanes) afforded 3-ethylcyclopent-1-en-1-yl trifluoromethanesulfonate. $^1$H NMR (400 MHz, CDCl$_3$) δ 5.57 (m, 1H), 2.67 (m, 1H), 2.50-2.58 (m, 2H), 2.17-2.35 (m, 2H), 1.37-1.50 (m, 2H), 0.91 (t, J=7.6 Hz, 3H). MS (ES)=245 (M+1)$^+$.

Step 2: To a stirred solution of 3-ethylcyclopent-1-en-1-yl trifluoromethanesulfonate (1.0 g, 4.08 mmol) in methanol (15 mL) and DMF (10 mL) was added Pd(OAc)$_2$ (45 mg, 0.20 mmol), 1,1'-bis(diphenylphosphino)ferrocene (226 mg, 0.40 mmol) and Et$_3$N (2.3 mL, 16.3 mmol). The mixture was degassed with CO for 15 minutes and then stirred at room temperature under CO atmosphere (balloon) for 16 hours. Next, water was added to the reaction mixture and it was extracted with methyl tertiary-butyl ether (3×30 mL). The combined organic layers were washed with brine, dried over Na$_2$SO$_4$, and concentrated. Purification of the residue on a silica gel column (0 to 100% EtOAc/hexanes) afforded methyl 3-ethylcyclopent-1-enecarboxylate.

Step 3: To a stirred solution of methyl 3-ethylcyclopent-1-enecarboxylate (1.60 g, 10.3 mmol) in methanol (15 mL) was added 10% Pd on carbon (100 mg) and the mixture was purged with hydrogen for 10 minutes. Then reaction mixture was then stirred at room temperature for 16 hours under a hydrogen atmosphere (balloon). The reaction mixture was then filtered through a pad of celite, washing the pad with methanol, and the filtrate was to afford crude methyl 3-ethylcyclopentanecarboxylate. $^1$H NMR (400 MHz, CDCl$_3$) δ 3.66 (s, 3H), 2.59-2.85 (m, 1H), 2.65 (q, J=7.6 Hz, 2H), 1.70-1.91 (m, 2H), 1.32-1.48 (m, 1H), 1.20-1.30 (m, 4H), 1.24 (t, J=6.4 Hz, 3H).

Step 4: To a stirred solution of methyl 3-ethylcyclopentanecarboxylate (1.50 g, 9.61 mmol) in THF (10 mL) was added LAH (1 M in THF; 9.6 mL, 9.6 mmol) at 0° C., and the reaction mixture was stirred at 0° C. for 1 hour. The reaction mixture was quenched with saturated Na$_2$SO$_4$ and filtered through a pad of celite, washing the pad with ethyl acetate. The filtrate was concentrated to dryness to afford crude (3-ethylcyclopentyl)methanol. $^1$H NMR (300 MHz, CDCl$_3$) δ 3.51 (d, J=6.9 Hz, 1H), 3.49 (d, J=7.2 Hz, 1H), 2.11 (m, 1H), 1.65-1.85 (m, 2H), 1.54 (m, 1H), 1.14-1.34 (m, 6H), 0.85-0.91 (m, 3H).

Step 5: To a stirred solution of (3-ethylcyclopentyl)methanol (1.80 g, 14.1 mmol) in dichloromethane (18 mL) was added triphenylphosphine (4.42 g, 16.9 mmol). The reaction mixture was cooled to 0° C. and CBr$_4$ (5.59 g, 16.9 mmol) was added. After the addition was complete, the reaction mixture was warmed to room temperature and stirred for 12 hours. The reaction mixture was then concentrated and the residue was purified on a silica gel column (10 to 100% EtOAc/hexanes) to afford 1-(bromomethyl)-3-ethylcyclopentane. $^1$H NMR (400 MHz, CDCl$_3$) δ 3.38 (d, J=6.8 Hz, 1H), 3.36 (d, J=6.8 Hz, 1H), 2.31 (m, 1H), 2.05 (m, 1H), 1.77-1.91 (m, 2H), 1.15-1.47 (m, 6H), 0.85-0.90 (m, 3H).

Example 18.4

3-(6-(((R)-1-cyclobutylethyl)amino)-7-((3-ethylcyclopentyl)methyl)-8-(4-isopropylpyridin-2-yl)-7H-purin-2-yl)-1,2,4-oxadiazol-5(4H)-one

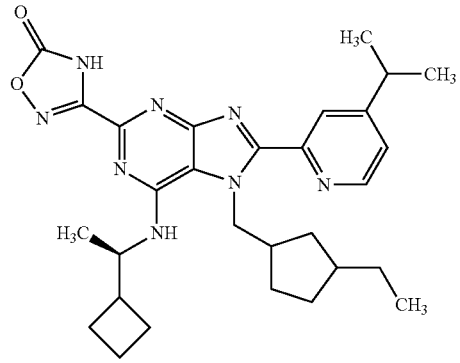 [SMILES: CCC1CCC(Cn2c(-c3cc(C(C)C)ccn3)nc3nc(-c4noc(=O)[nH]4)nc(N[C@H](C)C4CCC4)c32)C1]

Using a procedure analogous to that described in Example 18.1, followed by a procedure analogous to that described in Example 16.1, (Step 3 and Step 4), and starting with 1-(bromomethyl)-3-ethylcyclopentane (Preparative Example 18.6), 3-(6-(((R)-1-cyclobutylethyl)amino)-7-((3-ethylcyclopentyl)methyl)-8-(4-isopropylpyridin-2-yl)-7H-purin-2-yl)-1,2,4-oxadiazol-5(4H)-one was prepared as 1:1 mixture of diastereomers. $^1$H NMR (400 MHz, CD$_3$OD) δ 8.65 (d, J=5.2 Hz, 1H), 8.10 (br s, 1H), 7.48 (d, J=5.2 Hz, 1H), 5.19 (m, 1H), 4.90 (m, 1H), 4.74 (m, 1H), 3.09 (m, 1H), 2.62 (m, 1H), 2.19-2.24 (m, 2H), 1.98-2.13 (m, 3H), 1.86-1.95 (m, 4H), 1.72-1.80 (m, 2H), 1.55-1.72 (m, 3H), 1.34-1.36 (m, 6H), 1.18-1.28 (m, 5H), 0.65-0.80 (m, 3H). MS (ES)=531 (M+1)$^+$.

Example 18.5

6-(((R) 1-cyclobutylethyl)amino)-8-(4-isopropylpyridin-2-yl)-7-((4-methylcyclohex-3-en-1-yl)methyl)-7H-purine-2-carboxylic acid

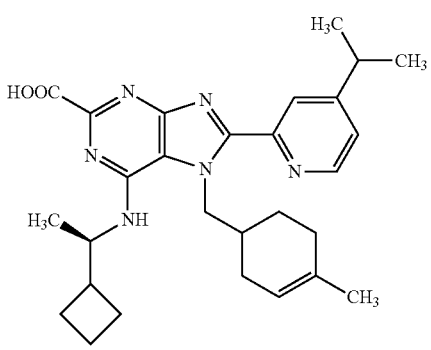 [SMILES: CC1=CCC(Cn2c(-c3cc(C(C)C)ccn3)nc3nc(C(=O)O)nc(N[C@H](C)C4CCC4)c32)CC1]

Step 1: Using a procedure analogous to Preparative Example 18.5 (step 2), and starting with (4-methylcyclohex-3-en-1-yl)methanol, 4-(bromomethyl)-1-methylcyclohex-1-ene, was prepared. $^1$H NMR (400 MHz, CDCl$_3$) δ 5.34 (m, 1H), 3.35 (d, J=6.4 Hz, 2H), 2.19 (m, 1H), 1.95-2.04 (m, 2H), 1.83-1.94 (m, 2H), 1.77 (m, 1H), 1.64 (s, 3H), 1.37 (m, 1H).

Step 2: Using a procedure analogous to that described for the synthesis of Example 18.1, and starting with 4-(bromomethyl)-1-methylcyclohex-1-ene, 6-(((R)-1-cyclobutylethyl)amino)-8-(4-isopropylpyridin-2-yl)-7-((4-methylcyclohex-3-en-1-yl)methyl)-7H-purine-2-carboxylic acid was prepared. $^1$H NMR (400 MHz, CD$_3$OD) δ 8.64 (m, 1H), 8.20 (d, J=6.8 Hz, 1H), 7.47 (m, 1H), 5.34 (m, 1H), 5.12 (m, 1H), 4.85-5.01 (m, 2H), 3.08 (m, 1H), 2.62 (m, 1H), 2.15 (m, 1H), 1.80-2.09 (m, 9H), 1.51 (s, 3H), 1.58-1.78 (m, 3H), 1.30-1.33 (m, 6H), 1.21-1.24 (m, 3H). MS (ES)=489 (M+1)$^+$

Example 18.6

6-(((R)-1-cyclobutylethyl)amino)-7-((4-ethylcyclohex-3-en-1-yl)methyl)-8-(4-isopropylpyridin-2-yl)-7H-purine-2-carboxylic acid (mixture of diastereomers)

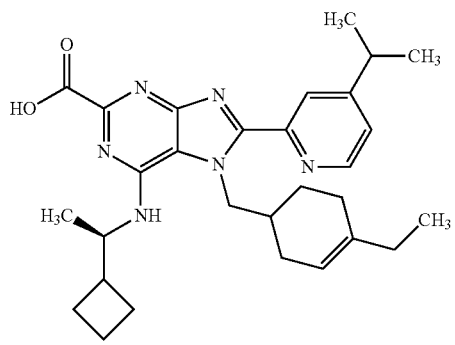 [SMILES: CCC1=CCC(Cn2c(-c3cc(C(C)C)ccn3)nc3nc(C(=O)O)nc(N[C@H](C)C4CCC4)c32)CC1]

Step 1: Using a procedure analogous to that described in Preparative Example 18.5 (Step 2), and starting with spiro[2.5]octan-6-ylmethanol, 6-(bromomethyl)spiro[2.5]octane, was prepared. $^1$H NMR (300 MHz, CDCl$_3$) δ 3.33 (d, J=6.3 Hz, 2H), 1.76-1.89 (m, 2H), 1.61-1.76 (m, 3H), 1.14-1.28 (m, 2H), 0.86-0.95 (m, 2H), 0.26-0.33 (m, 2H), 0.14-0.22 (m, 2H).

Step 2: Using a procedure analogous to that described for the synthesis of Preparative Example 11.3, and starting with 3-methyl-1H-purine-2,6(3H,9H)-dione, 3-methyl-7-(spiro[2.5]octan-6-ylmethyl)-1H-purine-2,6(3H,7H)-dione, was prepared. $^1$H NMR (300 MHz, DMSO-d$_6$) 11.15 (s, 1H), 8.05 (s, 1H), 4.11 (d, J=7.5 Hz, 2H), 3.43 (br s, 3H), 1.72-1.96 (m, 1H), 1.36-1.64 (m, 4H), 1.03-1.19 (m, 2H), 0.82-0.95 (m, 2H), 0.10-0.32 (m, 4H).

Step 3: Using a procedure analogous to that described in Preparative Example 11.4, and starting with 3-methyl-7-(spiro[2.5]octan-6-ylmethyl)-1H-purine-2,6(3H,7H)-dione, 2,6-dichloro-7-((4-chloro-4-ethylcyclohexyl)methyl)-7H-purine was prepared. $^1$H NMR (400 MHz, CDCl$_3$) δ 8.20 (s, 1H), 4.34 (d, J=7.2 Hz, 2H), 2.00-2.09 (m, 2H), 1.82-1.94 (m, 1H), 1.78 (q, J 7.2 Hz, 2H), 1.60-1.73 (m, 2H), 1.49-1.57 (m, 2H), 1.36-1.49 (m, 2H), 1.03 (t, J=7.2 Hz, 3H).

Step 4: Using a procedure analogous to that described in Example 18.1 (Step 1), and starting with 2,6-dichloro-7-((4-chloro-4-ethylcyclohexyl)methyl)-7H-purine, 2-chloro-N—((R)-1-cyclobutylethyl)-7-((4-ethylcyclohex-3-en-1-yl)methyl)-7H-purin-6-amine was prepared. $^1$H NMR (300 MHz, CDCl$_3$) δ 7.72-7.82 (m, 1H), 5.30-5.38 (m, 1H), 4.53-4.63 (m, 1H), 4.37-4.48 (m, 1H), 3.99-4.19 (m, 2H), 2.32-2.47 (m, 1H), 1.90-2.11 (m, 5H), 1.51-1.90 (m, 6H), 1.22-1.50 (m, 1H), 1.15-1.22 (m, 4H), 0.94-1.07 (m, 4H), 0.82-0.91 (m, 1H).

Step 5: Using a procedure analogous to that described in Example 18.1 (Step 2 to Step 5), and starting with 2-chloro-N—((R)-1-cyclobutylethyl)-7-((4-ethylcyclohex-3-en-1-yl)methyl)-7H-purin-6-amine, 6-(((R)-1-cyclobutylethyl)amino)-7-((4-ethylcyclohex-3-en-1-yl)methyl)-8-(4-isopropylpyridin-2-yl)-7H-purine-2-carboxylic acid was prepared. $^1$H NMR (400 MHz, DMSO-d$_6$) δ 8.64 (d, J=4.8 Hz, 1H), 8.12 (s, 0.5H), 8.11 (s, 0.5H), 7.48 (d, J=4.8 Hz, 1H), 6.65 (t, J=7.2 Hz, 1H), 4.82-5.40 (m, 3H), 4.45-4.60 (m, 1H), 2.99-3.11 (m, 1H), 2.54-2.68 (m, 1H), 1.98-2.10 (m, 1H), 1.90-1.98 (m, 1H), 1.70-1.90 (m, 8H), 1.40-1.70 (m, 3H), 1.20-1.35 (m, 2H), 1.28 (d, J=6.8 Hz, 6H), 1.15 (d, J=6.4 Hz, 3H), 0.80 (t, J=7.2 Hz, 3H). MS (ES)=503 (M+1)$^+$.

Example 18.7

3-(6-(((R)-1-cyclobutylethyl)amino)-7-((4-ethylcyclohex-3-en-1-yl)methyl)-8-(4-isopropylpyridin-2-yl)-7H-purin-2-yl)-1,2,4-oxadiazol-5(4H)-one (mixture of diastereomers)

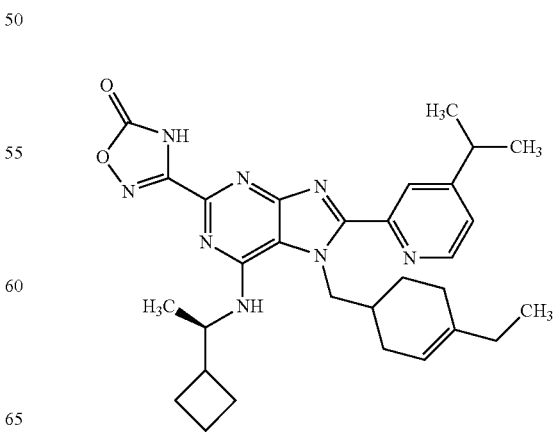

Using a procedure analogous to that described in Example 18.4, and starting with 6-(((R)-1-cyclobutylethyl)amino)-7-((4-ethylcyclohex-3-en-1-yl)methyl)-8-(4-isopropylpyridin-2-yl)-7H-purine-2-carbonitrile (mixture of diastereomers), 3-(6-(((R)-1-cyclobutylethyl)amino)-7-((4-ethylcyclohex-3-en-1-yl)methyl)-8-(4-isopropylpyridin-2-yl)-7H-purin-2-yl)-1,2,4-oxadiazol-5(4H)-one was prepared. $^1$H NMR (400 MHz, DMSO-d$_6$) δ 12.90 (s, 1H), 8.62-8.70 (m, 1H), 8.13 (d, J=4.4 Hz, 1H), 7.45-7.52 (m, 1H), 6.67-6.76 (m, 1H), 4.90-5.40 (m, 3H), 4.60-4.73 (m, 1H), 2.99-3.10 (m, 1H), 2.53-2.66 (m, 1H), 1.96-2.10 (m, 1H), 1.87-1.96 (m, 1H), 1.70-1.87 (m, 9H), 1.39-1.70 (m, 4H), 1.28 (d, J=7.2 Hz, 6H), 1.18 (d, J=6.4 Hz, 3H), 0.80 (t, J=7.6 Hz, 3H). MS (ES)=543 (M+1)$^+$.

Preparative Example 18.7

4-(bromomethyl)-1,1-dimethylcyclohexane

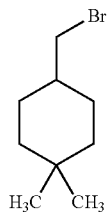

Step 1: To a stirred solution of spiro[2.5]octan-6-ylmethanol (1.0 g, 7.13 mmol) in EtOAc/AcOH (5:1, 72 mL) was added PtO$_2$ (300 mg) at room temperature. The resulting mixture was stirred under hydrogen atmosphere for 24 hours. The reaction mixture was filtered through celite eluting with EtOAc (60 mL). The solvent was removed under reduced pressure and the resulting residue was purified on a RediSep 40 g silica gel column (0 to 20% EtOAc/hexanes) to afford (4,4-dimethylcyclohexyl)methanol. $^1$H NMR (400 MHz, CDCl$_3$) δ 3.47 (d, J=6.4 Hz, 2H), 1.54-1.62 (m, 2H), 1.34-1.45 (m, 3H), 1.05-1.24 (m, 4H), 0.90 (s, 3H), 0.87 (s, 3H).

Step 2: Using a procedure analogous to that described in Preparative Example 18.5 (Step 2), and starting with (4,4-dimethylcyclohexyl)methanol, 4-(bromomethyl)-1,1-dimethylcyclohexane was prepared. $^1$H NMR (300 MHz, CDCl$_3$) δ 3.31 (d, J=6.3 Hz, 2H), 1.60-1.78 (m, 2H), 1.30-1.48 (m, 2H), 1.18-1.20 (m, 5H), 0.91 (s, 3H), 0.87 (s, 3H).

Example 18.8

(R)-6-((1-cyclobutylethyl)amino)-7-((4,4-dimethylcyclohexyl)methyl)-8-(4-isopropylpyridin-2-yl)-7H-purine-2-carboxylic acid

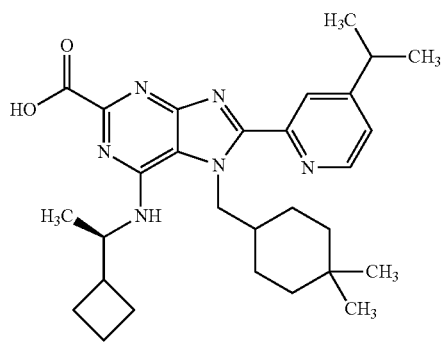 [SMILES: CC(C)c1ccnc(-c2nc3nc(C(=O)O)nc(N[C@H](C)C4CCC4)c3n2CC2CCC(C)(C)CC2)c1]

Step 1: Using a procedure analogous to that described for the synthesis of Preparative Example 11.3, and starting with 3-methyl-1H-purine-2,6(3H,9H)-dione, 7-((4,4-dimethylcyclohexyl)methyl)-3-methyl-1H-purine-2,6(3H,7H)-dione was prepared. $^1$H NMR (400 MHz, DMSO-d$_6$) δ 11.08 (s, 1H), 8.00 (s, 1H), 4.09 (d, J=7.6 Hz, 2H), 3.34 (s, 3H), 1.65-1.80 (m, 1H), 1.20-1.40 (m, 4H), 1.00-1.20 (m, 4H), 0.86 (s, 3H), 0.85 (s, 3H). MS (ES)=291 (M+1)$^+$.

Step 2: Using a procedure analogous to that described in Preparative Example 11.4, and starting with 7-((4,4-dimethylcyclohexyl)methyl)-3-methyl-1H-purine-2,6(3H,7H)-dione, 2,6-dichloro-7-((4,4-dimethylcyclohexyl)methyl)-7H-purine was prepared. $^1$H NMR (400 MHz, DMSO-d$_6$) δ 8.86 (s, 1H), 4.32 (d, J=7.6 Hz, 2H), 1.65-1.80 (m, 1H), 1.30-1.40 (m, 4H), 1.17-1.29 (m, 2H), 1.03-1.13 (m, 2H), 0.88 (s, 3H), 0.86 (s, 3H). MS (ES)=313 (M+1)$^+$.

Step 3: Using a procedure analogous to that described in Example 18.1 (Step 1), and starting with 2,6-dichloro-7-((4,4-dimethylcyclohexyl)methyl)-7H-purine, (R)-2-chloro-N-(1-cyclobutylethyl)-7-((4,4-dimethylcyclohexyl)methyl)-7H-purin-6-amine was prepared. $^1$H NMR (400 MHz, DMSO-d$_6$) δ 8.23 (s, 1H), 6.54 (d, J=8.4 Hz, 1H), 4.55 (dd, J=14.4, 6.0 Hz, 1H), 4.22-4.34 (m, 1H), 4.16 (dd, J=14.4, 8.8 Hz, 1H), 2.52-2.63 (m, 1H), 1.97-2.06 (m, 1H), 1.87-1.97 (m, 1H), 1.68-1.87 (m, 4H), 1.43-1.54 (m, 1H), 1.15-1.43 (m, 4H), 1.11 (d, J=6.8 Hz, 3H), 0.89-1.09 (m, 4H), 0.84 (s, 3H), 0.83 (s, 3H). MS (ES)=376 (M+1)$^+$.

Step 4: Using a procedure analogous to that described in Example 18.1 (Step 2), and starting with (R)-2-chloro-N-(1-cyclobutylethyl)-7-((4,4-dimethylcyclohexyl)methyl)-7H-purin-6-amine, (R)-6-((1-cyclobutylethyl)amino)-7-((4,4-dimethylcyclohexyl)methyl)-7H-purine-2-carbonitrile was prepared. $^1$H NMR (400 MHz, DMSO-d$_6$) δ 8.42 (s, 1H), 6.68 (d, J=8.4 Hz, 1H), 4.61 (dd, J=14.4, 6.0 Hz, 1H), 4.29-4.38 (m, 1H), 4.23 (dd, J=14.4, 8.4 Hz, 1H), 2.54-2.65 (m, 1H), 1.97-2.08 (m, 1H), 1.88-1.97 (m, 1H), 1.72-1.88 (m, 4H), 1.42-1.55 (m, 1H), 1.20-1.41 (m, 4H), 1.13 (d, J=6.4 Hz, 3H), 0.88-1.12 (m, 4H), 0.84 (s, 3H), 0.83 (s, 3H). MS (ES)=367 (M+1)$^+$.

Step 5: Using a procedure analogous to that described in Example 18.1 (Step 3), and starting with (R)-6-((1-cyclobutylethyl)amino)-7-((4,4-dimethylcyclohexyl)methyl)-7H-purine-2-carbonitrile, (R)-6-((1-cyclobutylethyl)amino)-7-((4,4-dimethylcyclohexyl)methyl)-8-(4-isopropylpyridin-2-yl)-7H-purine-2-carbonitrile was prepared. $^1$H NMR (400 MHz, DMSO-d$_6$) δ 8.67 (d, J=5.2 Hz, 1H), 8.13 (s, 1H), 7.49 (br d, J=5.2 Hz, 1H), 6.88 (d, J=8.4 Hz, 1H), 5.19-5.33 (m, 1H), 4.84-4.96 (m, 1H), 4.35-4.46 (m, 1H), 3.02-3.12 (m, 1H), 2.55-2.64 (m, 1H), 1.90-2.10 (m, 3H), 1.65-1.90 (m, 3H), 1.37-1.49 (m, 1H), 1.27 (d, J=6.8 Hz, 6H), 1.13-1.26 (m, 4H), 1.15 (d, J=6.4 Hz, 3H), 0.80-1.04 (m, 4H), 0.75 (s, 3H), 0.70 (s, 3H). MS (APCI)=486 (M+1)$^+$.

Step 6: Using a procedure analogous to that described in Example 18.1 (Step 4 and 5), and starting with (R)-6-((1-cyclobutylethyl)amino)-7-((4,4-dimethylcyclohexyl)methyl)-8-(4-isopropylpyridin-2-yl)-7H-purine-2-carbonitrile, (R)-6-((1-cyclobutylethyl)amino)-7-((4,4-dimethylcyclohexyl)methyl)-8-(4-isopropylpyridin-2-yl)-7H-purine-2-carboxylic acid was prepared. $^1$H NMR (400 MHz, DMSO-d$_6$) δ 8.66 (d, J=5.2 Hz, 1H), 8.13 (s, 1H), 7.47 (d, J=5.2 Hz, 1H), 6.57 (d, J=8.4 Hz, 1H), 5.15-5.35 (m, 1H), 4.80-4.95 (m, 1H), 4.45-4.60 (m, 1H), 3.00-3.12 (m, 1H), 2.54-2.66 (m, 1H), 2.00-2.10 (m, 1H), 1.90-2.00 (m, 1H), 1.70-90 (m, 4H), 1.41-1.53 (m, 1H), 1.28 (d, J=6.8 Hz, 6H), 1.18-1.26 (m, 2H), 1.15 (d, J=6.4 Hz, 3H), 0.79-1.12 (m, 6H), 0.75 (s, 3H), 0.72 (s, 3H). MS (ES)=505 (M+1)⁺.

Example 18.9

(R)-3-(6-((1-cyclobutylethyl)amino)-7-((4,4-dimethylcyclohexyl)methyl)-8-(4-isopropylpyridin-2-yl)-7H-purin-2-yl)-1,2,4-oxadiazol-5(4H)-one

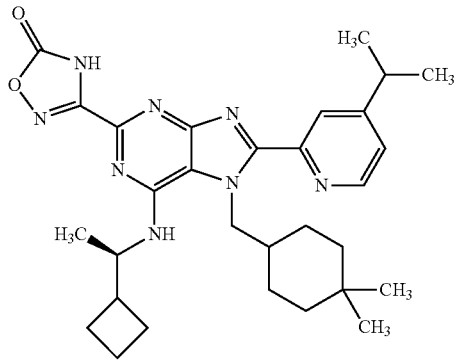 [SMILES: CC(C)c1ccnc(-c2nc3nc(-c4noc(=O)[nH]4)nc(N[C@H](C)C4CCC4)c3n2CC2CCC(C)(C)CC2)c1]

Using a procedure analogous to that described in Example 18.4, and starting (R)-6-((1-cyclobutylethyl)amino)-7-((4,4-dimethylcyclohexyl)methyl)-8-(4-isopropylpyridin-2-yl)-7H-purine-2-carbonitrile, (R)-3-(6-((1-cyclobutylethyl)amino)-7-((4,4-dimethylcyclohexyl)methyl)-8-(4-isopropylpyridin-2-yl)-7H-purin-2-yl)-1,2,4-oxadiazol-5(4H)-one was prepared. ¹H NMR (400 MHz, DMSO-d₆) δ 12.90 (s, 1H), 8.67 (d, J=5.2 Hz, 1H), 8.14 (s, 1H), 7.48 (d, J=5.2 Hz, 1H), 6.69 (d, J=8.4 Hz, 1H), 5.20-5.40 (m, 1H), 4.80-5.00 (m, 1H), 4.60-4.80 (m, 1H), 3.00-3.15 (m, 1H), 2.55-2.65 (m, 1H), 2.00-2.11 (m, 1H), 1.90-2.00 (m, 1H), 1.75-1.90 (m, 4H), 1.42-1.55 (m, 1H), 1.27 (d, J=6.8 Hz, 6H), 1.18-1.26 (m, 2H), 1.14 (d, J=6.0 Hz, 3H), 1.05-1.18 (m, 2H), 0.82-1.05 (m, 4H), 0.76 (s, 3H), 0.72 (s, 3H). MS (ES)=545 (M+1)⁺.

Preparative Example 18.8 trans-1-(bromomethyl)-4-(fluoromethyl)cyclohexane

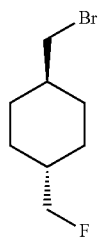

Step 1: To stirred solution of trans-4-(methoxycarbonyl)cyclohexanecarboxylic acid (5.0 g, 26.8 mmol) in anhydrous THF was added Et₃N (2.8 mL, 30 mmol) followed by methyl chloroformate (2.2 mL, 30 mmol) at −5° C. and the reaction mixture was stirred for 1 hour at 0° C. Then the reaction was filtered through celite and the filtrate was added to a mixture of NaBH₄ (2.00 g, 53.7 mmol) in water (100 mL) at 10° C. After 30 minutes, the reaction was quenched by adjusting to pH 1 with aqueous 1 N HCl. The mixture was extracted with EtOAc (3×100 mL). The combined organic layers were dried over anhydrous Na₂SO₄ and concentrated. The residue was purified on RediSep 80 g silica gel column (0 to 40% EtOAc/hexanes) to afford trans-methyl 4-(hydroxymethyl)cyclohexanecarboxylate. ¹H NMR (400 MHz, CDCl₃) δ 4.32 (d, J=6.0 Hz, 1H), 4.16 (d, J=6.0 Hz, 1H), 3.67 (s, 3H), 2.25-2.33 (m, 1H), 2.01-2.23 (m, 2H), 1.82-1.88 (m, 3H), 1.47-1.52 (m, 2H), 1.12-1.38 (m, 2H).

Step 2: To a stirred solution of trans-methyl 4-(hydroxymethyl)cyclohexane carboxylate (6.0 g, 35 mmol) in dichloromethane was added DAST (5.5 mL, 42 mmol) at 10° C. The reaction mixture was stirred for 6 hours at room temperature under a nitrogen atmosphere. Then the reaction mixture was filtered through silica gel using hexanes/CH₂Cl₂ (1:1). The resulting filtrate was concentrated to dryness and the residue was purified on RediSep 40 g silica gel column (0 to 50% EtOAc/hexanes) to afford trans-methyl 4-(fluoromethyl)cyclohexane carboxylate. ¹H NMR (400 MHz, CDCl₃) δ 3.67 (s, 3H), 3.47 (d, J=6.3 Hz, 2H), 2.31-2.53 (m, 1H), 2.20-2.29 (m, 2H), 1.90-2.05 (m, 2H), 1.06-1.51 (m, 3H), 1.04-1.18 (m, 2H).

Step 3: To a stirred solution of trans-methyl 4-(fluoromethyl)cyclohexanecarboxylate (4.50 g, 25.8 mmol) in anhydrous THF was added LAH (1.47 g, 38.7 mmol) at 10° C. The reaction mixture was stirred for 3 hours at room temperature under a nitrogen atmosphere. Then the reaction mixture was quenched with saturated NH₄Cl (50 mL) solution at 10° C. and extracted with EtOAc (2×50 mL). The combined organic layers were dried over anhydrous Na₂SO₄ and concentrated to dryness. The residue was purified on RediSep 40 g silica gel column using (0-100% EtOAc/hexanes) to afford (trans-4-(fluoromethyl)cyclohexyl)methanol. ¹H NMR (400 MHz, CDCl₃) δ 4.32 (d, J=6.0 Hz, 1H), 4.17 (d, J=6.3 Hz, 1H), 3.47 (d, J=6.0 Hz, 2H), 1.83-1.87 (m, 4H), 1.62-1.69 (m, 2H), 1.42-1.49 (m, 1H), 0.96-1.06 (m, 3H).

Step 4: (trans-4-(fluoromethyl)cyclohexyl)methanol (3.50 g, 23.9 mmol), carbon tetrabromide (9.4 g, 35.9 mmol) and triphenylphosphine (11.7 g, 35.9 mmol) were dissolved in dichloromethane (50 mL) and stirred at room temperature for 12 hours under a nitrogen atmosphere. The reaction mixture was then concentrated under reduced pressure, diluted with hexanes/EtOAc (90/10, 100 mL), and stirred for 1 hour. The solids were removed by filtration, washing with hexanes/EtOAc (90/10, 50 mL), and the filtrate was concentrated to dryness in vacuo. The residue was purified by silica gel column chromatography (10% EtOAc/hexanes) to afford trans-1-(bromomethyl)-4-(fluoromethyl)cyclohexane. ¹H NMR (400 MHz, CDCl₃) δ 4.30 (d, J=6.0 Hz, 1H), 4.18 (d, J=6.0 Hz, 1H), 3.29 (dd, J=6.4, 1.6 Hz, 2H), 1.82-1.96 (m, 4H), 1.61-1.65 (m, 3H), 1.04-1.09 (m, 3H).

Example 18.10

6-(((R)-1-cyclobutylethyl)amino)-7-((trans-4-(fluoromethyl)cyclohexyl)methyl)-8-(4-isopropylpyridin-2-yl)-7H-purine-2-carboxylic acid

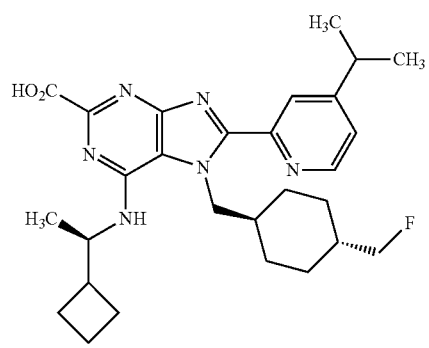 [SMILES: CC(C)c1ccnc(-c2nc3nc(C(=O)O)nc(N[C@H](C)C4CCC4)c3n2C[C@H]2CC[C@H](CF)CC2)c1]

Step 1: Using a procedure analogous to that described for the synthesis of Preparative Example 18.2 Step 1), and starting with trans-1-(bromomethyl)-4-(trifluoromethyl)cyclohexane (1.5 g, 9.0 mmol), trans-trifluoromethyl cyclohexylmethyl bromide, 7-((trans-4-(fluoromethyl)cyclohexyl)methyl)-3-methyl-1H-purine-2,6(3H,7H)-dione was prepared. $^1$H NMR (300 MHz, DMSO-$d_6$) δ 11.07 (s, 1H), 8.01 (s, 1H), 4.30 (d, J=6.0 Hz, 1H), 4.06-4.14 (m, 3H), 3.29 (s, 3H), 1.68-1.76 (m, 2H), 1.53-1.55 (m, 2H), 1.24-1.29 (m, 2H), 0.94-1.06 (m, 2H), 0.74-0.90 (m, 2H). MS (ES)=295 (M+1)$^+$.

Step 2: Using a procedure analogous to that described for the synthesis of Preparative Example 18.2 (Step 2), and starting with 7-((trans-4-(fluoromethyl)cyclohexyl)methyl)-3-methyl-1H-purine-2,6(3H,7H)-dione, 2,6-dichloro-7-((trans-4-(fluoromethyl)cyclohexyl)methyl)-7H-purine was prepared. $^1$H NMR (300 MHz, CDCl$_3$) δ 8.19 (s, 1H), 4.28-4.30 (m, 3H), 4.17 (d, J=4.5 Hz, 1H), 1.84-1.87 (m, 2H), 1.64-1.73 (m, 4H), 0.98-1.18 (m, 4H). MS (ES)=317 (M+1)$^+$.

Step 3: Using a procedure analogous to that described for the synthesis of Example 18.1 (Step 1), and starting with 2,6-dichloro-7-((trans-4-(fluoromethyl)cyclohexyl)methyl)-7H-purine, 2-chloro-N—((R)-1-cyclobutylethyl)-7-((trans-4-(fluoromethyl)cyclohexyl)methyl)-7H-purin-6-amine was prepared. $^1$H NMR (300 MHz, CDCl$_3$) δ 7.75 (s, 1H), 4.58 (d, J=9.0 Hz, 1H), 4.37-4.45 (m, 1H), 4.31 (d, J=6.0 Hz, 1H), 4.15 (d, J=6.0 Hz, 1H), 3.94-4.06 (m, 2H), 2.39-2.42 (m, 1H), 1.98-2.21 (m, 7H), 1.59-1.89 (m, 5H), 1.20 (d, J=6.0 Hz, 3H), 0.96-1.12 (m, 4H). MS (APCI)=380 (M+1)$^+$.

Step 4: Using a procedure analogous to that described for the synthesis of Example 18.1 (Step 2), and starting with 2-chloro-N—((R)-1-cyclobutylethyl)-7-((trans-4-(fluoromethyl)cyclohexyl)methyl)-7H-purin-6-amine, 6-(((R)-1-cyclobutylethyl)amino)-7-((trans-4-(fluoromethyl)cyclohexyl)methyl)-7H-purine-2-carbonitrile was prepared. $^1$H NMR (300 MHz, CDCl$_3$) δ 7.89 (s, 1H), 4.61 (d, J=9.0 Hz, 1H), 4.38-4.47 (m, 1H), 4.32 (d, J=6.0 Hz, 1H), 4.17 (d, J=6.0 Hz, 1H), 3.96-4.08 (m, 2H), 2.40-2.45 (m, 1H), 1.89-2.26 (m, 7H), 1.59-1.79 (m, 5H), 1.25 (d, J=6.0 Hz, 3H), 0.96-1.14 (m, 4H). MS (APCI)=371 (M+1)$^+$.

Step 5: Using a procedure analogous to that described for the synthesis of Example 18.1 (Step 3), and starting with 6-(((R)-1-cyclobutylethyl)amino)-7-((trans-4-(fluoromethyl)cyclohexyl)methyl)-7H-purine-2-carbonitrile, 6-(((R)-1-cyclobutylethyl)amino)-7-((trans-4-(fluoromethyl)cyclohexyl)methyl)-8-(4-isopropylpyridin-2-yl)-7H-purine-2-carbonitrile was prepared. $^1$H NMR (300 MHz, CDCl$_3$) δ 8.55 (d, J=3.0 Hz, 1H), 8.38 (s, 1H), 7.77 (d, J=6.0 Hz, 1H), 4.82 (d, J=9.0 Hz, 1H), 4.46-4.54 (m, 1H), 4.25 (d, J=6.0 Hz, 1H), 4.09 (d, J=6.0 Hz, 1H), 2.95-3.04 (m, 1H), 2.69-2.76 (m, 1H), 1.87-2.35 (m, 7H), 1.59-1.79 (m, 7H), 1.34 (d, J=6.0 Hz, 6H), 1.28 (d, J=6.0 Hz, 3H), 0.96-1.18 (m, 4H). MS (APCI)=490 (M+1)$^+$.

Step 6: Using a procedure analogous to that described for the synthesis of Example 18.1 (Step 4), and starting with 6-(((R)-1-cyclobutylethyl)amino)-7-((trans-4-(fluoromethyl)cyclohexyl)methyl)-8-(4-isopropylpyridin-2-yl)-7H-purine-2-carbonitrile, methyl 6-(((R)-1-cyclobutylethyl)amino)-7-((trans-4-(fluoromethyl)cyclohexyl)methyl)-8-(4-isopropylpyridin-2-yl)-7H-purine-2-carboxylate was prepared. $^1$H NMR (300 MHz, CDCl$_3$) δ 8.54 (d, J=5.1 Hz, 1H), 8.39 (br s, 1H), 7.77 (d, J=5.1 Hz, 1H), 4.74 (d, J=6.0 Hz, 1H), 4.60-4.65 (m, 1H), 4.24 (d, J=6.0 Hz, 1H), 4.08 (d, J=6.0 Hz, 1H), 4.00 (s, 3H), 2.92-3.03 (m, 1H), 2.67-2.75 (m, 1H), 1.85-2.35 (m, 8H), 1.54-1.75 (m, 6H), 1.32 (d, J=6.0 Hz, 6H), 1.28 (d, J=6.0 Hz, 3H), 0.96-1.18 (m, 4H). MS (ES)=523 (M+1)$^+$.

Step 7: Using a procedure analogous to that described for the synthesis of Example 18.1 (Step 5), and starting with methyl 6-(((R)-1-cyclobutylethyl)amino)-7-((trans-4-(fluoromethyl)cyclohexyl)methyl)-8-(4-isopropylpyridin-2-yl)-7H-purine-2-carboxylate, 6-(((R)-1-cyclobutylethyl)amino)-7-((trans-4-(fluoromethyl)cyclohexyl)methyl)-8-(4-isopropylpyridin-2-yl)-7H-purine-2-carboxylic acid was prepared. $^1$H NMR (300 MHz, CDCl$_3$) 8.62 (d, J=5.1 Hz, 1H), 8.10 (br s, 1H), 7.44 (d, J=5.1 Hz, 1H), 5.09-5.12 (m, 1H), 4.60-4.65 (m, 1H), 4.18 (d, J=6.0 Hz, 1H), 4.02 (d, J=6.0 Hz, 1H), 3.03-3.08 (m, 1H), 2.51-2.57 (m, 1H), 1.88-2.11 (m, 8H), 1.67-1.72 (m, 6H), 1.35 (d, J=6.0 Hz, 6H), 1.21 (d, J=6.0 Hz, 3H), 1.01-1.18 (m, 2H), 0.98-1.00 (m, 2H). MS (ES)=523 (M+1)$^+$.

Preparative Example 18.9 trans-5-(bromomethyl)-1,1-difluoro-2-methylcyclohexane

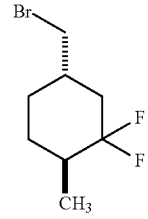

Step 1: A 100 mL round bottom flask was charged with (4-methylcyclohex-3-en-1-yl)methanol (2.50 g, 20 mmol), imidazole (2.72 g, 40 mmol) and DMF (40 mL). Tert-butyl diphenylchlorosilane (6.00 g, 22 mmol) was added dropwise at room temperature and the reaction was stirred for 16 hours. The reaction was then diluted with water and extracted using EtOAc (100 mL). The organic layer was washed with water and brine, dried over anhydrous sodium sulfate, filtered, and concentrated. The residue was purified on a RediSep 40 g silica gel column (0 to 10% EtOAc/hexanes) to afford tert-butyl((4-methylcyclohex-3-en-1-yl)methoxy)diphenylsilane. $^1$H NMR (300 MHz, CD$_3$OD) δ 7.65 7.70 (m, 4H), 7.30-7.55 (m, 6H), 5.35 (br s, 1H), 3.35 (d, J=6.5 Hz, 2H), 1.70-2.30 (m, 5H), 1.62 (s, 3H), 1.22-1.43 (m, 2H), 1.05 (s, 9H).

Step 2: A 250 mL round bottom flask was charged with tert-butyl((4-methylcyclohex-3-en-1-yl)methoxy)diphenylsilane (5.00 g, 13.6 mmol) and THF (60 mL). BH$_3$.THF (20 mL, 20 mmol) was added dropwise at 0° C. and the reaction was stirred for 2 hours. 1 N aqueous NaOH (28 mL) was added to the reaction followed by 30% H$_2$O$_2$ in water (28 mL) at 0° C. The reaction was gradually warmed to room temperature and stirred for 16 hours. The reaction was diluted with water and extracted using EtOAc (200 mL). The organic layer was washed with water and brine, dried over anhydrous sodium sulfate, filtered, and concentrated. The residue was purified on a RediSep 80 g silica gel column (0 to 20% EtOAc/hexanes) to afford 5-(((tert-butyldiphenylsilyl)oxy)methyl)-2-methylcyclohexanol. $^1$H NMR (300 MHz, CD$_3$OD) δ 7.61-7.68 (m, 4H), 7.32-7.46 (m, 6H), 3.173.65 (m, 3H), 2.04 (m, 1H), 1.19-1.80 (m, 6H), 1.05 (d, J=6.4 Hz, 1.5H), 1.22-1.43 (m, 2H), 1.04 (s, 9H), 0.92 (d, J=6.4 Hz, 1.5H), 0.81-1.10 (m, 2H).

Step 3: A 250 mL round bottom flask was charged with 5-(((tert-butyldiphenylsilyl)oxy)methyl)-2-methylcyclohexanol (5.00 g, 13.3 mmol) and CH$_2$Cl$_2$ (170 mL). Dess-Martin periodinane (7.10 g, 17 mmol) was added portionwise at 0° C. The reaction was gradually warmed to room temperature and stirred for 16 hours. The reaction was filtered through celite and the filtrate was washed with saturated aqueous NaHCO$_3$ (50 mL), water, and brine, dried over anhydrous sodium sulfate, filtered, and concentrated. The residue was purified on a RediSep 80 g silica gel column (0 to 20% EtOAc/hexanes) to afford 5-(((tert-butyldiphenylsilyl)oxy)methyl)-2-methylcyclohexanone as a mixture of diastereomers. This material was then dissolved in anhydrous methanol (50 mL) and NaOCH$_3$ (150 mg, 2.7 mmol) was added. The mixture was heated at 50° C. for 16 hours. The solvent was evaporated and the residue was suspended in EtOAc (200 mL), washed with water and brine, and dried over anhydrous sodium sulfate. The solvent was evaporated and the residue was purified on a RediSep 80 g silica gel column (0 to 20% EtOAc/hexanes) to afford trans-5-(((tert-butyldiphenylsilyl)oxy)methyl)-2-methylcyclohexanone. $^1$H NMR (300 MHz, CD$_3$OD) δ 7.62-7.68 (m, 4H), 7.34-7.43 (m, 6H), 3.53-3.59 (m, 2H), 1.83-2.51 (m, 6H), 1.56 (m, 1H), 1.36 (m, 1H), 1.05 (d, J=6.5 Hz, 3H), 1.04 (s, 9H).

Step 4: A 250 mL round bottom flask was charged with trans-5-(((tert-butyldiphenylsilyl)oxy)methyl)-2-methylcyclohexanone (4.20 g, 10.9 mmol) and toluene (100 mL). DAST (8.80 g, 54.8 mmol) was added and the reaction was heated at 50° C. for 4 hours. The reaction was cooled on an ice bath, saturated aqueous NaHCO$_3$ (50 mL) was added carefully, and the mixture was extracted using EtOAc (200 mL). The organic layer was washed with water and brine and dried over anhydrous sodium sulfate. The solvent was evaporated and the residue was purified on a RediSep 80 g silica gel column (0 to 20% EtOAc/hexanes) to afford tert-butyl((3,3-difluoro-4-methylcyclohexyl)methoxy)diphenylsilane. This compound was then dissolved in 3M HCl in methanol (20 mL) and heated in sealed tube at 50° C. for 16 hours. The solvent was evaporated and the residue was suspended in EtOAc (200 mL) and washed with saturated aqueous NaHCO$_3$ (50 mL), water, and brine and dried over anhydrous sodium sulfate. The solvent was evaporated and the residue was purified on a RediSep 40 g silica gel column (0 to 20% EtOAc/hexanes) to afford (trans-3,3-difluoro-4-methylcyclohexyl)methanol. $^1$H NMR (300 MHz, CDCl$_3$) δ 3.48-3.59 (m, 2H), 2.19 (m, 1H), 1.89 (m, 1H), 1.70-1.80 (m, 3H), 1.2-1.40 (m, 2H), 1.05 (d, J=6.6 Hz, 3H), 0.90 (m, 1H).

Step 5: Following a procedure analogous to that described for the synthesis of Preparative Example 18.8 (Step 4), and starting with (trans-3,3-difluoro-4-methylcyclohexyl)methanol, trans-5-(bromomethyl)-1,1-difluoro-2-methylcyclohexane was prepared. $^1$H NMR (300 MHz, CDCl$_3$) δ 3.82 (dd, J=10.2, 3.3 Hz, 2H), 3.42-3.60 (m, 2H), 2.18-2.31 (m, 2H), 2.06-2.17 (m, 1H), 1.90-2.04 (m, 1H), 1.65-1.85 (m, 3H) 0.97 (d, J=6.6 Hz, 3H).

Preparative Example 18.10

2,6-dichloro-7-(((trans)-3,3-difluoro-4-methylcyclohexyl)methyl)-7H-purine

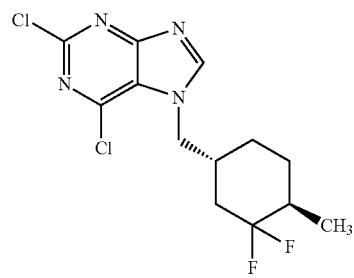 [SMILES: C[C@@H]1CC[C@@H](Cn2cnc3nc(Cl)nc(Cl)c32)CC1(F)F]

Following a procedure analogous to that described for the synthesis of Preparative Example 18.2, and starting with trans-5-(bromomethyl)-1,1-difluoro-2-methylcyclohexane, 2,6-dichloro-7-(((trans)-3,3-difluoro-4-methylcyclohexyl)methyl)-7H-purine, Preparative Example 18.10, was prepared. $^1$H NMR (300 MHz, CDCl$_3$) δ 8.18 (s, 1H), 4.30-3.41 (m, 2H), 2.25 (m, 1H), 1.50-1.88 (m, 3H), 1.10-1.45 (m, 4H), 1.05 (d, J=6.5 Hz, 3H); MS (ES)=335 (M+1)$^+$.

Example 18.11

3-(6-(((R)-1-cyclobutylethyl)amino)-7-((trans-3,3-difluoro-4-methylcyclohexyl)methyl)-8-(4-isopropylpyridin-2-yl)-7H-purin-2-yl)-1,2,4-oxadiazol-5(4H)-one

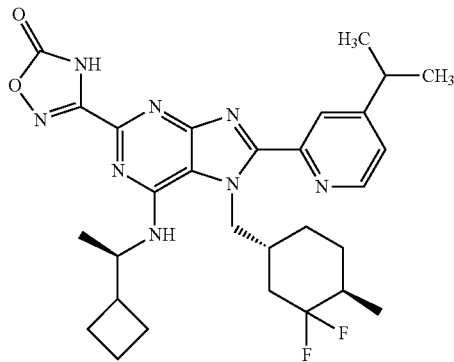 [SMILES: CC(C)c1ccnc(-c2nc3nc(-c4noc(=O)[nH]4)nc(N[C@H](C)C4CCC4)c3n2C[C@@H]2CC[C@@H](C)C(F)(F)C2)c1]

Following a procedure analogous to that described for the synthesis of Example 18.4, and starting with Preparative Example 18.10, 2,6-dichloro-7-(((trans)-3,3-difluoro-4-methylcyclohexyl)methyl)-7H-purine, 3-(6-(((R)-1-cyclobutylethyl)amino)-7-((trans-3,3-difluoro-4-methylcyclohexyl)methyl)-8-(4-isopropylpyridin-2-yl)-7H-purin-2-yl)-1,2,4-oxadiazol-5(4H)-one was prepared. $^1$H NMR (300 MHz, CDCl$_3$) δ 8.57 (br s, 1H), 8.38 (s, 1H), 7.29 (s, 1H), 4.76-4.86 (m, 2H), 4.54-4.66 (m, 2H), 2.94 (m, 1H), 2.47 (m, 1H), 1.60-2.25 (m, 10H), 1.40-1.50 (m, 2H), 1.33 (d, J=7.4 Hz, 3H), 1.24 (d, J=6.6 Hz, 3H), 1.10-1.20 (m, 2H), 0.98 (d, J=6.3 Hz, 6H). MS (ES)=567 (M+1)$^+$.

Preparative Example 18.11

2,6-dichloro-7-(1-(trans-4-methylcyclohexyl)ethyl)-7H-purine (racemic)

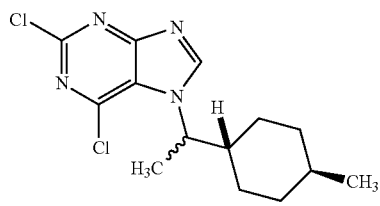 [SMILES: CC([C@H]1CC[C@H](C)CC1)n1cnc2nc(Cl)nc(Cl)c21]

Step 1: Acetic acid (5 mL) was added to a suspension of 6-amino-1-methylpyrimidine-2,4(1H,3H)-dione (5.00 g, 35 mmol) in water (80 mL). The reaction mixture was cooled to −5° C. and NaNO$_2$ (2.70 g, 39 mmol) was added portionwise. After addition, the reaction mixture was warmed to room temperature and stirred at room temperature overnight. The purple solid was collected by filtration, washed with water and dried in vacuo, affording 6-amino-1-methyl-5-nitrosopyrimidine-2,4(1H,3H)-dione. MS (APC)=171 (M+1)$^+$.

Step 2: Na$_2$S$_2$O$_4$ (13.0 g, 74.1 mmol) was added to a suspension of 6-amino-1-methyl-5-nitrosopyrimidine-2,4(1H,3H)-dione (4.20 g, 24.7 mmol) in saturated ammonium hydroxide solution (42 mL) at 30° C. portionwise. After the addition was complete, the reaction mixture was warmed to 50° C. and stirred for 2 hours. The reaction mixture was then cooled to room temperature. The precipitate was collected by filtration, washed with water, and dried in vacuo to afford 5,6-diamino-1-methylpyrimidine-2,4(1H,3H)-dione. MS (APC)=156 (M+1)$^+$.

Step 3: To a mixture of 1-(trans-4-methylcyclohexyl)ethanone (1.20 g, 7.69 mmol) and 5,6-diamino-1-methylpyrimidine-2,4(1H,3H)-dione (1.18 g, 8.46 mmol) in MeOH (30 mL) was added acetic acid (73 µL, 1.28 mmol). NaCNBH$_3$ (1.35 g, 21.5 mmol) was added portion wise. The resulting mixture was heated at 50° C. for 16 hours. The reaction mixture was concentrated in vacuo and the residue was diluted with water. The solid precipitate was collected by filtration, washed with sat. NaHCO$_3$ solution and water, and dried in vacuo to afford crude 6-amino-1-methyl-5-((1-(trans-4-methylcyclohexyl)ethyl)amino)pyrimidine-2,4(1H,3H)-dione, which was used in next step without purification. MS (APC)=281 (M+1)$^+$.

Step 4: 6-Amino-1-methyl-5-((1-(trans-4-methylcyclohexyl)ethyl)amino)pyrimidine-2,4(1H,3H)-dione (900 mg, product from previous step) in triethyl orthoformate was heated at 150° C. for 4 hours. The reaction mixture was cooled to room temperature and concentrated in vacuo to afford (crude) 3-methyl-7-(1-(trans-4-methylcyclohexyl)ethyl)-1H-purine-2,6(3H,7H)-dione, which was used in next step without further purification. MS (APC)=291 (M+1)$^+$.

Step 5: To a suspension of 3-methyl-7-(1-(trans-4-methylcyclohexyl)ethyl)-1H-purine-2,6(3H,7H)-dione (900 mg, crude product from previous step) in POCl$_3$ (5 mL) was added DBU (2.3 mL) drop wise at room temperature. After the addition was complete, the reaction mixture was heated at 120° C. for 2 hours and then cooled to room temperature. Ice water was added to the reaction. The mixture was extracted with EtOAc (3×15 mL). The combined organic layers were washed with brine, dried over Na$_2$SO$_4$ and concentrated in vacuo. Purification of the residue on a Redisep 80 g silica gel column with 0 to 40% EtOAc/hexanes afforded 2,6-dichloro-7-(1-(trans-4-methylcyclohexyl)ethyl)-7H-purine. $^1$H NMR (400 MHz, CDCl$_3$) δ 8.33 (s, 1H), 4.94 (dq, J=6.8, 6.8 Hz, 1H), 1.67-1.79 (m, 4H), 1.64 (d, J=6.8 Hz, 3H), 1.26-1.42 (m, 4H), 0.81-0.96 (m, 2H), 0.87 (d, J=6.6 Hz, 3H). MS (APC)=313 (M+1)$^+$.

Example 18.12 (Diastereomer A) and Example 18.13 (Diastereomer B)

3-(6-{[(1R)-1-cyclobutylethyl]amino}-7-[1-(trans-4-methylcyclohexyl)ethyl]-8-[(3R)-3-methylmorpholin-4-yl]-7H-purin-2-yl)-1,2,4-oxadiazol-5(4H)-one

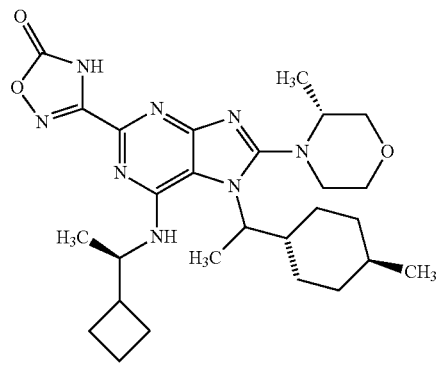 [SMILES: CC([C@H]1CC[C@H](C)CC1)n1c(N2CCOC[C@H]2C)nc2nc(-c3noc(=O)[nH]3)nc(N[C@H](C)C3CCC3)c21]

Step 1: To a solution of 2,6-dichloro-7-(1-((trans)-4-methylcyclohexyl)ethyl)-7H-purine (260 mg, 0.83 mmol) in isopropyl alcohol (10 mL) was added (R)-1-cyclobutylethanamine hydrochloride (253 mg, 2.08 mmol), followed by the addition of DIEA (0.58 ml, 3.53 mmol) at room temperature. The reaction mixture was heated at 85° C. for 15 hours and then cooled to room temperature. The solvent was removed in vacuo. Purification of the residue on a Redisep 24 g silica gel column with 0 to 80% EtOAc/hexanes afforded 2-chloro-N—((R)-1-cyclobutylethyl)-7-(1-((trans)-4-methylcyclohexyl)ethyl)-7H-purin-6-amine Diastereomer A (fast eluting in EA/Hexanes) and Diastereomer B (slow eluting in EA/Hexanes). Diastereomer A: $^1$H NMR (400 MHz, CDCl$_3$) δ 7.92 (s, 1H), 4.60 (d, J=7.6 Hz, 1H), 4.44 (dq, J=12.8, 6.4 Hz, 1H), 4.12 (dq, J=6.8, 6.8 Hz, 1H), 2.41 (m, 1H), 1.72-2.19 (m, 9H), 1.63 (d, J=6.8 Hz, 3H), 1.49 (m, 1H), 1.35 (m, 1H), 1.21 (d, J=6.4 Hz, 3H), 1.03-1.16 (m, 2H), 0.80-0.98 (m, 3H), 0.88 (d, J=6.8 Hz, 3H). MS (APC)=376 (M+1)$^+$. Diastereomer B: $^1$H NMR (400 MHz, CDCl$_3$) δ 7.93 (s, 1H), 4.58 (d, J=8.0 Hz, 1H), 4.44 (dq, J=12.8, 6.4 Hz, 1H), 4.17 (dq, J=6.8, 6.8 Hz, 1H), 2.40 (m, 1H), 1.71-2.13 (m, 9H), 1.64 (d, J=6.8 Hz, 3H), 1.47 (m, 1H), 1.32 (m, 1H), 1.25 (d, J=6.4 Hz, 3H), 1.05-1.18 (m, 2H), 0.80-0.98 (m, 3H), 0.87 (d, J=6.8 Hz, 3H). MS (APC)=376 (M+1)$^+$.

Step 2: Using a procedure analogous to that described in Example 18.1 (Step 2) and starting with 2-chloro-N—((R)-1-cyclobutylethyl)-7-(1-((trans)-4-methylcyclohexyl)ethyl)-7H-purin-6-amine, 6-(((R)-1-cyclobutylethyl)amino)-7-(1-((trans)-4-methylcyclohexyl)ethyl)-7H-purine-2-carbonitrile Diastereomer A and Diastereomer B were prepared. Diastereomer A: MS (APC)=367 (M+1)$^+$. Diastereomer B: MS (APC)=367 (M+1)$^+$.

Step 3: Using a procedure analogous to that described in Preparative Example 16.1 (Step 2) and starting with 6-(((R)-1-cyclobutylethyl)amino)-7-(1-((trans)-4-methylcyclohexyl)ethyl)-7H-purine-2-carbonitrile, 8-bromo-6-(((R)-1-cyclobutylethyl)amino)-7-(1-((trans)-4-methylcyclohexyl)ethyl)-7H-purine-2-carbonitrile Diastereomer A and Diastereomer B were prepared. Diastereomer A: MS (APC)=445 (M+1)$^+$. Diastereomer B: MS (APC)=445 (M+1)$^+$.

Step 4: Using a general procedure for amination analogous to that described in Example 16.2 (Step 1) and starting with 8-bromo-6-(((R)-1-cyclobutylethyl)amino)-7-(1-((trans)-4-methylcyclohexyl)ethyl)-7H-purine-2-carbonitrile and (R)-methyl morpholine, 6-(((R)-1-cyclobutylethyl)amino)-7-(1-((trans)-4-methylcyclohexyl)ethyl)-8-((R)-3-methylmorpholino)-7H-purine-2-carbonitrile Diastereomer A and Diastereomer B were prepared. Diastereomer A: $^1$H NMR (300 MHz, CDCl$_3$) δ 4.65 (d, J=8.1 Hz, 1H), 4.45 (m, 1H), 4.33 (m, 1H), 3.96 (m, 1H), 3.82-3.87 (m, 2H), 3.68 (m, 1H), 3.51 (dd, J=11.4, 6.6 Hz, 1H), 3.25 (m, 1H), 3.01 (m, 1H), 2.44 (m, 1H), 1.95-2.14 (m, 6H), 1.64 (d, J=7.2 Hz, 3H), 1.52-1.61 (m, 2H), 1.35 (m, 1H), 1.18 (d, J=6.3 Hz, 3H), 1.09 (d, J=6.3 Hz, 3H), 0.96-1.08 (m, 2H), 0.81-0.86 (m, 2H), 0.82 (d, J=6.8 Hz, 3H), 0.56-0.79 (m, 3H). MS (APC)=466 (M+1)$^+$. Diastereomer B: $^1$H NMR (300 MHz, CDCl$_3$) δ 4.71 (d, J=8.1 Hz, 1H), 4.36-4.55 (m, 2H), 3.68-4.01 (m, 3H), 3.46-3.54 (m, 2H), 3.35 (m, 1H), 3.13 (m, 1H), 2.42 (m, 1H), 1.76-2.13 (m, 7H), 1.56 (m, 1H), 1.54 (d, J=7.2 Hz, 3H), 1.26-1.33 (m, 2H), 1.06 (m, 1H), 1.20 (d, J=6.3 Hz, 3H), 0.94-1.14 (m, 2H), 1.05 (d, J=6.0 Hz, 3H), 0.88 (d, J=6.3 Hz, 3H), 0.63-0.85 (m, 3H). MS (APC)=466 (M+1)$^+$.

Step 5: Using a procedure analogous to that described in Example 16.1 (Step 3 and Step 4), and starting with 6-(((R)-1-cyclobutylethyl)amino)-7-(1-((trans)-4-methylcyclohexyl)ethyl)-8-((R)-3-methylmorpholino)-7H-purine-2-carbonitrile, 3-(6-{[(1R)-1-cyclobutylethyl]amino}-7-[1-(trans-4-methylcyclohexyl)ethyl]-8-[(3R)-3-methylmorpholin-4-yl]-7H-purin-2-yl)-1,2,4-oxadiazol-5(4H)-one Example 18.12 (Diastereomer A) and Example 18.13 (Diastereomer B) were prepared. Example 18.12 (Diastereomer A): $^1$H NMR (400 MHz, CDCl$_3$) δ 4.71 (d, J=8.0 Hz, 1H), 4.54 (dq, J=14.2, 7.8 Hz, 1H), 4.34 (m, 1H), 3.96 (dd, J=11.3, 2.8 Hz, 1H), 3.80-3.89 (m, 2H), 3.66 (m, 1H), 3.52 (dd, J=11.3, 6.6 Hz, 1H), 3.28 (m, 1H), 3.04 (m, 1H), 2.46 (m, 1H), 1.80-2.11 (m, 7H), 1.68 (d, J=7.2 Hz, 3H), 1.50-1.63 (m, 3H), 1.21 (d, J=6.4 Hz, 3H), 1.11 (d, J=6.4 Hz, 3H), 1.07 (m, 1H), 0.80-0.88 (m, 2H), 0.84 (d, J=6.4 Hz, 3H), 0.57-0.80 (m, 3H). MS (ES)=525 (M+1)$^+$. Example 18.13 (Diastereomer B): $^1$H NMR (400 MHz, CDCl$_3$) δ 4.78 (d, J=6.8 Hz, 1H), 4.45-4.58 (m, 2H), 3.96 (m 1H), 3.86 (m, 1H), 3.78 (m, 1H), 3.47-3.50 (m, 2H), 3.35 (m, 1H), 3.16 (m, 1H), 2.45 (m, 1H), 1.52-2.07 (m, 10H), 1.56 (d, J=7.2 Hz, 3H), 1.23 (d, J=6.0 Hz, 3H), 1.06 (m, 1H), 1.05 (d, J=6.4 Hz, 3H), 0.82-0.91 (m, 2H), 0.88 (d, J=6.4 Hz, 3H), 0.65-0.80 (m, 3H). MS (ES)=525 (M+1)$^+$.

Example 18.14

5-(6-(5-Chloropyridin-3-yl)-7-(1-((trans)-4-methylcyclohexyl)ethyl)-8-((R)-3-phenylmorpholino)-7H-purin-2-yl)-1,3,4-oxadiazol-2(3H)-one

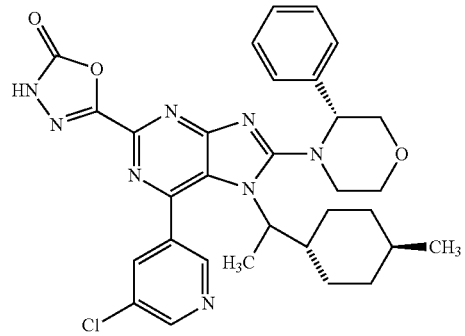 [SMILES: CC([C@H]1CC[C@H](C)CC1)n1c(N2CCOC[C@H]2c2ccccc2)nc2nc(-c3n[nH]c(=O)o3)nc(-c3cncc(Cl)c3)c21]

Step 1: Using procedures analogous to those described in Preparative Example 16.1 (step 1 and step 2), and starting with 2,6-dichloro-7-(1-((trans)-4-methylcyclohexyl)ethyl)-7H-purine, 8-bromo-2-chloro-6-(5-chloropyridin-3-yl)-7-(1-((trans)-4-methylcyclohexyl)ethyl)-7H-purine was prepared. MS (ES)=468 (M+1)$^+$.

Step 2: Using a procedure analogous to that described in Example 16.2 (Step 1), and starting with 8-bromo-2-chloro-6-(5-chloropyridin-3-yl)-7-(1-((trans)-4-methylcyclohexyl)ethyl)-7H-purine, (3R)-4-(2-chloro-6-(5-chloropyridin-3-yl)-7-(1-((trans)-4-methylcyclohexyl)ethyl)-7H-purin-8-yl)-3-phenylmorpholine Diastereomer A (fast eluting in EA/Hexanes) and Diastereomer B (slow eluting in EA/Hexanes) were prepared. MS (APC)=551.

Step 3: Using a procedure analogous to that described in Example 16.2 (Step 2), and starting with (3R)-4-(2-chloro-6-(5-chloropyridin-3-yl)-7-(1-((trans)-4-methylcyclohexyl)ethyl)-7H-purin-8-yl)-3-phenylmorpholine, 6-(5-chloropyridin-3-yl)-7-(1-((trans)-4-methylcyclohexyl)ethyl)-8-((R)-3-phenylmorpholino)-7H-purine-2-carbonitrile (Diastereomer B) was prepared. MS (APC)=542 (M+1)$^+$.

Step 4: Using a procedure analogous to that described in Example 16.7 (Step 1 to 3), and starting with 6-(5-chloropyridin-3-yl)-7-(1-((trans)-4-methylcyclohexyl)ethyl)-8-((R)-3-phenylmorpholino)-7H-purine-2-carbonitrile, 5-(6-(5-chloropyridin-3-yl)-7-(1-((trans)-4-methylcyclohexyl)ethyl)-8-((R)-3-phenylmorpholino)-7H-purin-2-yl)-1,3,4-oxadiazol-2(3H)-one (Diastereomer B) was prepared. $^1$H NMR (400 MHz, CDCl$_3$) δ 8.74 (d, J=2.2 Hz, 1H), 8.58 (d, J=2.2 Hz, 1H), 7.84 (d, J=2.2 Hz, 1H), 7.47 (t, J=7.0 Hz, 2H), 7.23-7.28 (m, 3H), 5.15 (t, J=10.8 Hz, 1H), 4.18 (d, J=4.4 Hz, 2H), 3.83-4.00 (m, 3H), 3.52 (m, 1H), 3.31 (m, 1H), 1.37-1.49 (m, 4H), 1.15-1.25 (m, 2H), 1.12 (d, J=7.2 Hz, 3H), 0.81 (d, J=6.4 Hz, 3H), 0.63-0.74 (m, 2H), 0.42-0.50 (m, 2H). MS (ES)=601 (M+1)$^+$.

The following compounds in Table 18 (other than Example 18.1 to 18.14) were prepared using procedures which were analogous to those described above.

TABLE 18

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.1 | 3.462 | 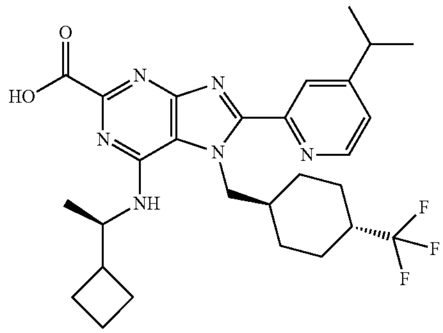 [SMILES: CC(C)c1ccnc(-c2nc3nc(C(=O)O)nc(N[C@H](C)C4CCC4)c3n2C[C@H]2CC[C@H](C(F)(F)F)CC2)c1] | 6-(((R)-1-cyclobutylethyl)amino)-8-(4-isopropylpyridin-2-yl)-7-((trans-4-(trifluoromethyl)cyclohexyl)methyl)-7H-purine-2-carboxylic acid | | 545 | 545 |
| 18.2 | 2.492 | 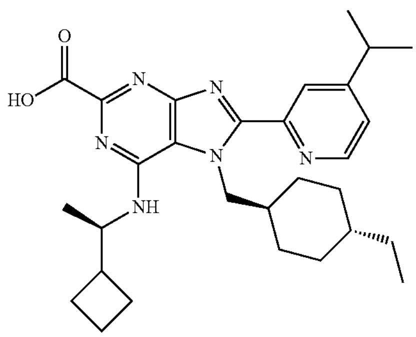 | 6-(((R)-1-cyclobutylethyl)amino)-7-((trans-4-ethylcyclohexyl)methyl)-8-(4-isopropylpyridin-2-yl)-7H-purine-2-carboxylic acid | TFA | 505 | 505 |
| 18.3 | 57.42 | 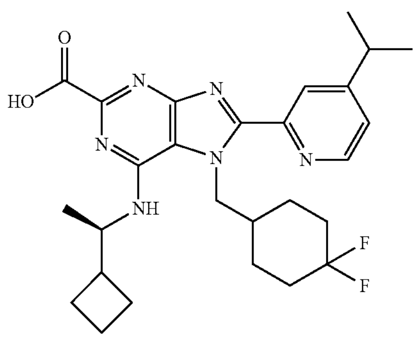 [SMILES: CC(C)c1ccnc(-c2nc3nc(C(=O)O)nc(N[C@H](C)C4CCC4)c3n2CC2CCC(F)(F)CC2)c1] | (R)-6-((1-cyclobutylethyl)amino)-7-((4,4-difluorocyclohexyl)methyl)-8-(4-isopropylpyridin-2-yl)-7H-purine-2-carboxylic acid | | 513 | 513 |
| 18.4 | 131.3 | 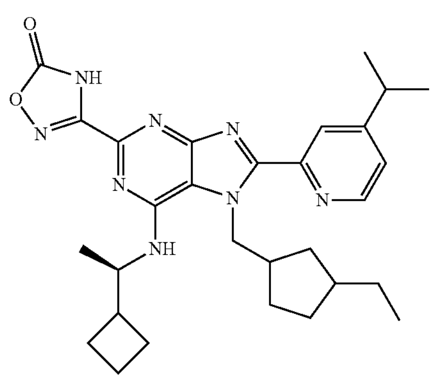 [SMILES: CCC1CCC(Cn2c(-c3cc(C(C)C)ccn3)nc3nc(-c4noc(=O)[nH]4)nc(N[C@H](C)C4CCC4)c32)C1] | 3-(6-(((R)-1-cyclobutylethyl)amino)-7-((3-ethylcyclopentyl)methyl)-8-(4-isopropylpyridin-2-yl)-7H-purin-2-yl)-1,2,4-oxadiazol-5(4H)-one | | 531 | 531 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.5 | 6.481 | 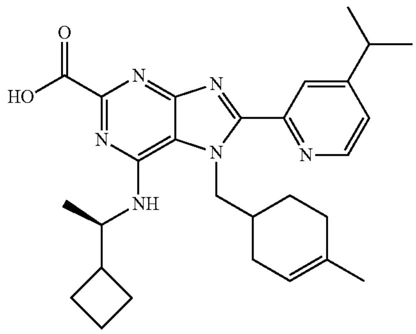 [SMILES: CC1=CCC(Cn2c(-c3cc(C(C)C)ccn3)nc3nc(C(=O)O)nc(N[C@H](C)C4CCC4)c32)CC1] | 6-(((R)-1-cyclobutylethyl)amino)-8-(4-isopropylpyridin-2-yl)-7-((4-methylcyclohex-3-en-1-yl)methyl)-7H-purine-2-carboxylic acid | | 489 | 489 |
| 18.6 | 15.86 | 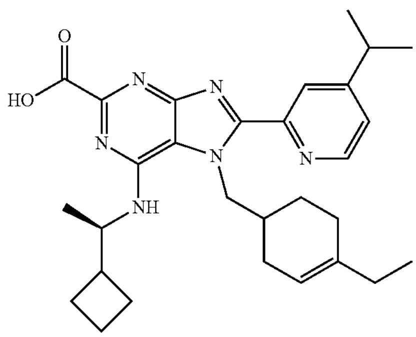 [SMILES: CCC1=CCC(Cn2c(-c3cc(C(C)C)ccn3)nc3nc(C(=O)O)nc(N[C@H](C)C4CCC4)c32)CC1] | 6-(((R)-1-cyclobutylethyl)amino)-7-((4-ethylcyclohex-3-en-1-yl)methyl)-8-(4-isopropylpyridin-2-yl)-7H-purine-2-carboxylic acid | | 503 | 503 |
| 18.7 | 43.97 | 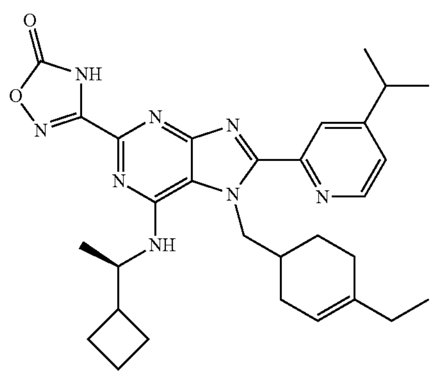 [SMILES: CCC1=CCC(Cn2c(-c3cc(C(C)C)ccn3)nc3nc(-c4noc(=O)[nH]4)nc(N[C@H](C)C4CCC4)c32)CC1] | 3-(6-(((R)-1-cyclobutylethyl)amino)-7-((4-ethylcyclohex-3-en-1-yl)methyl)-8-(4-isopropylpyridin-2-yl)-7H-purin-2-yl)-1,2,4-oxadiazol-5(4H)-one | | 543 | 543 |
| 18.8 | 59.47 | 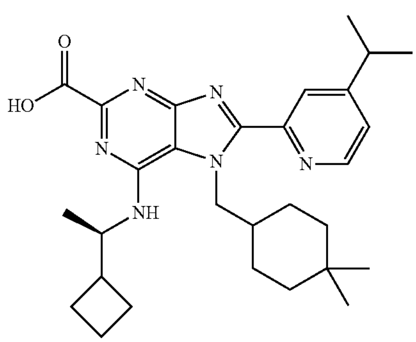 [SMILES: CC(C)c1ccnc(-c2nc3nc(C(=O)O)nc(N[C@H](C)C4CCC4)c3n2CC2CCC(C)(C)CC2)c1] | (R)-6-((1-cyclobutylethyl)amino)-7-((4,4-dimethylcyclohexyl)methyl)-8-(4-isopropylpyridin-2-yl)-7H-purine-2-carboxylic acid | | 505 | 505 |

TABLE 18-continued

| Ex. | FRET IC₅₀ (nM) | Structure | Chemical Name | Salt Form | [M + H]⁺ Calc'd | [M + H]⁺ Obsv'd |
|---|---|---|---|---|---|---|
| 18.9 | 394.1 | 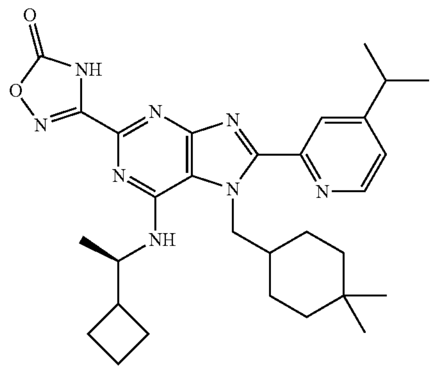 [SMILES: CC(C)c1ccnc(-c2nc3nc(-c4noc(=O)[nH]4)nc(N[C@H](C)C4CCC4)c3n2CC2CCC(C)(C)CC2)c1] | (R)-3-(6-((1-cyclobutylethyl)amino)-7-((4,4-dimethylcyclohexyl)methyl)-8-(4-isopropylpyridin-2-yl)-7H-purin-2-yl)-1,2,4-oxadiazol-5(4H)-one | | 545 | 545 |
| 18.10 | 9.384 | 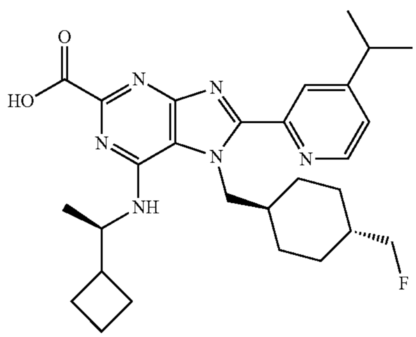 [SMILES: CC(C)c1ccnc(-c2nc3nc(C(=O)O)nc(N[C@H](C)C4CCC4)c3n2C[C@H]2CC[C@H](CF)CC2)c1] | 6-(((R)-1-cyclobutylethyl)amino)-7-((trans-4-(fluoromethyl)cyclohexyl)methyl)-8-(4-isopropylpyridin-2-yl)-7H-purine-2-carboxylic acid | | 509 | 509 |
| 18.11 | 2.79 | 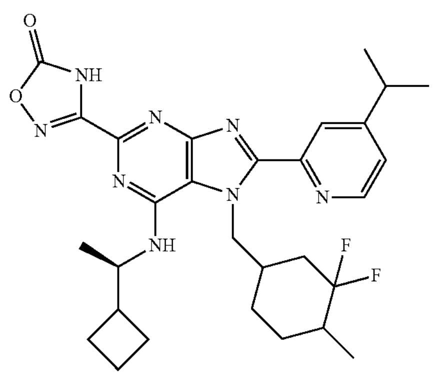 [SMILES: CC(C)c1ccnc(-c2nc3nc(-c4noc(=O)[nH]4)nc(N[C@H](C)C4CCC4)c3n2CC2CCC(C)C(F)(F)C2)c1] | 3-(6-(((R)-1-cyclobutylethyl)amino)-7-((trans-3,3-difluoro-4-methylcyclohexyl)methyl)-8-(4-isopropylpyridin-2-yl)-7H-purin-2-yl)-1,2,4-oxadiazol-5(4H)-one | | 567 | 567 |
| 18.12 | 2.819 | 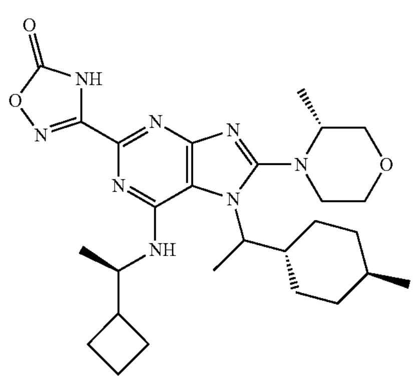 [SMILES: CC([C@H]1CC[C@H](C)CC1)n1c(N2CCOC[C@H]2C)nc2nc(-c3noc(=O)[nH]3)nc(N[C@H](C)C3CCC3)c21] | 3-(6-{[(1R)-1-cyclobutylethyl]amino}-7-[1-(trans-4-methylcyclohexyl)ethyl]-8-[(3R)-3-methylmorpholin-4-yl]-7H-purin-2-yl)-1,2,4-oxadiazol-5(4H)-one (Diastereomer A) | | 525 | 525 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.13 | 2.271 | 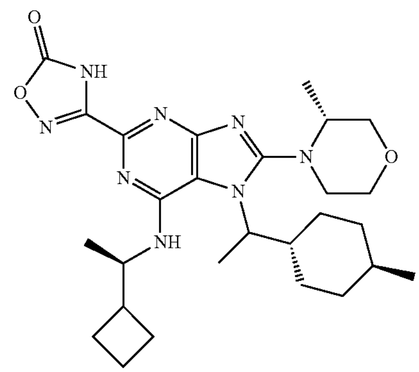 [SMILES: CC([C@H]1CC[C@H](C)CC1)n1c(N2CCOC[C@H]2C)nc2nc(-c3noc(=O)[nH]3)nc(N[C@H](C)C3CCC3)c21] | 3-(6-{[(1R)-1-cyclobutylethyl]amino}-7-[1-(trans-4-methylcyclohexyl)ethyl]-8-[(3R)-3-methylmorpholin-4-yl]-7H-purin-2-yl)-1,2,4-oxadiazol-5(4H)-one (Diastereomer B) | | 525 | 525 |
| 18.14 | 0.62 | 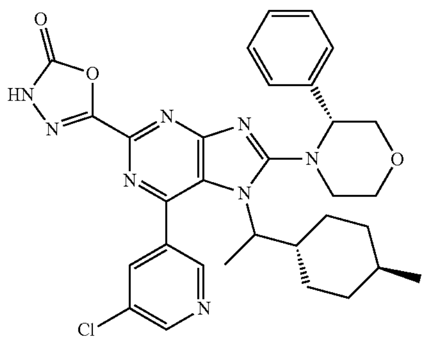 [SMILES: CC([C@H]1CC[C@H](C)CC1)n1c(N2CCOC[C@H]2c2ccccc2)nc2nc(-c3n[nH]c(=O)o3)nc(-c3cncc(Cl)c3)c21] | 5-(6-(5-chloropyridin-3-yl)-7-(1-((trans)-4-methylcyclohexyl)ethyl)-8-((R)-3-phenylmorpholino)-7H-purin-2-yl)-1,3,4-oxadiazol-2(3H)-one | | 601 | 601 |
| 18.15 | 201.1 | 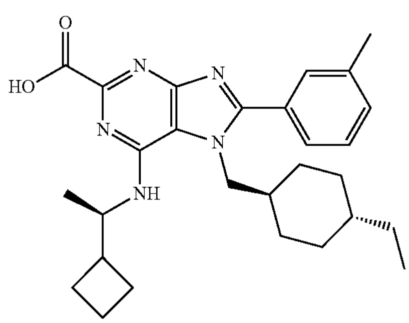 [SMILES: CC[C@H]1CC[C@H](Cn2c(-c3cccc(C)c3)nc3nc(C(=O)O)nc(N[C@H](C)C4CCC4)c32)CC1] | 6-{[(1R)-1-cyclobutylethyl]amino}-7-[(trans-4-ethylcyclohexyl)methyl]-8-(3-methylphenyl)-7H-purine-2-carboxylic acid | | 476 | 476 |
| 18.16 | 31.8 | 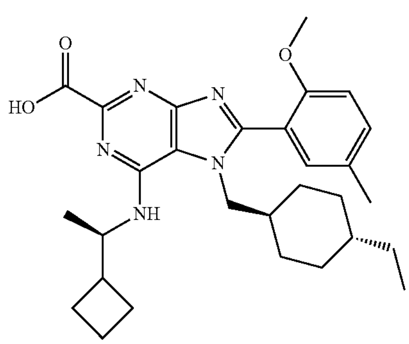 [SMILES: CC[C@H]1CC[C@H](Cn2c(-c3cc(C)ccc3OC)nc3nc(C(=O)O)nc(N[C@H](C)C4CCC4)c32)CC1] | 6-{[(1R)-1-cyclobutylethyl]amino}-7-[(trans-4-ethylcyclohexyl)methyl]-8-(2-methoxy-5-methylphenyl)-7H-purine-2-carboxylic acid | | 506 | 506 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.17 | 8.158 | 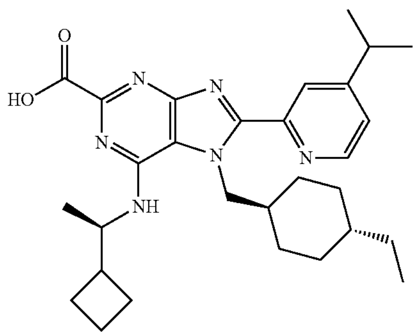 [SMILES: CC[C@H]1CC[C@H](Cn2c(-c3cc(C(C)C)ccn3)nc3nc(C(=O)O)nc(N[C@H](C)C4CCC4)c32)CC1] | 6-{[(1R)-1-cyclobutylethyl]amino}-7-[(trans-4-ethylcyclohexyl)methyl]-8-[4-(1-methylethyl)pyridin-2-yl]-7H-purine-2-carboxylic acid | | 505 | 505 |
| 18.18 | 8.596 | 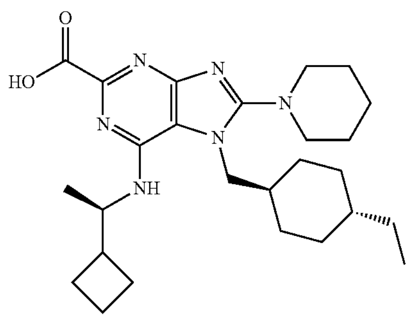 [SMILES: CC[C@H]1CC[C@H](Cn2c(N3CCCCC3)nc3nc(C(=O)O)nc(N[C@H](C)C4CCC4)c32)CC1] | 6-{[(1R)-1-cyclobutylethyl]amino}-7-[(trans-4-ethylcyclohexyl)methyl]-8-piperidin-1-yl-7H-purine-2-carboxylic acid | | 469 | 469 |
| 18.19 | 13.05 | 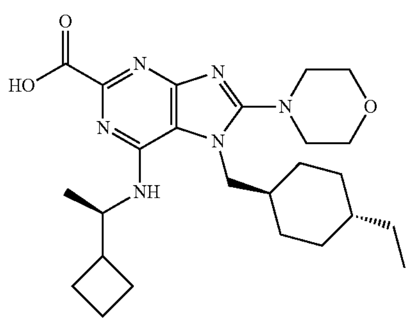 [SMILES: CC[C@H]1CC[C@H](Cn2c(N3CCOCC3)nc3nc(C(=O)O)nc(N[C@H](C)C4CCC4)c32)CC1] | 6-{[(1R)-1-cyclobutylethyl]amino}-7-[(trans-4-ethylcyclohexyl)methyl]-8-morpholin-4-yl-7H-purine-2-carboxylic acid | | 471 | 471 |
| 18.20 | 15.71 | 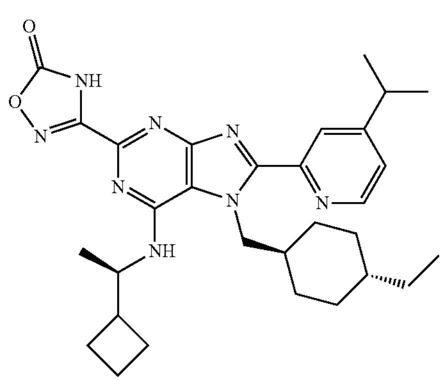 [SMILES: CC[C@H]1CC[C@H](Cn2c(-c3cc(C(C)C)ccn3)nc3nc(-c4noc(=O)[nH]4)nc(N[C@H](C)C4CCC4)c32)CC1] | 3-(6-{[(1R)-1-cyclobutylethyl]amino}-7-[(trans-4-ethylcyclohexyl)methyl]-8-[4-(1-methylethyl)pyridin-2-yl]-7H-purin-2-yl)-1,2,4-oxadiazol-5(4H)-one | TFA | 545 | 545 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.21 | 0.5478 | 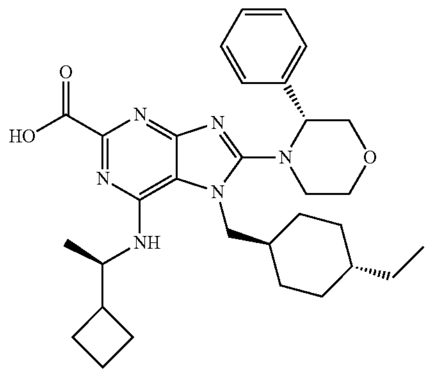 [SMILES: CC[C@H]1CC[C@H](Cn2c(N3CCOC[C@H]3c3ccccc3)nc3nc(C(=O)O)nc(N[C@H](C)C4CCC4)c32)CC1] | 6-{[(1R)-1-cyclobutylethyl]amino}-7-[(trans-4-ethylcyclohexyl)methyl]-8-[(3R)-3-phenylmorpholin-4-yl]-7H-purine-2-carboxylic acid | TFA | 547 | 547 |
| 18.22 | 3.859 | 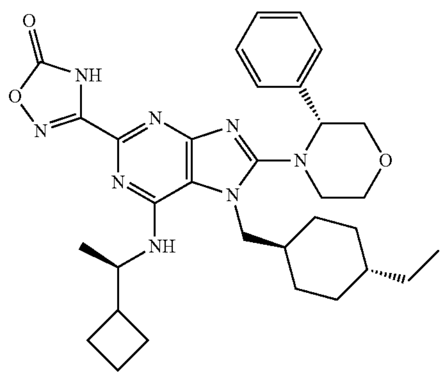 [SMILES: CC[C@H]1CC[C@H](Cn2c(N3CCOC[C@H]3c3ccccc3)nc3nc(-c4noc(=O)[nH]4)nc(N[C@H](C)C4CCC4)c32)CC1] | 3-(6-{[(1R)-1-cyclobutylethyl]amino}-7-[(trans-4-ethylcyclohexyl)methyl]-8-[(3R)-3-phenylmorpholin-4-yl]-7H-purin-2-yl)-1,2,4-oxadiazol-5(4H)-one | TFA | 587 | 587 |
| 18.23 | 26.39 | 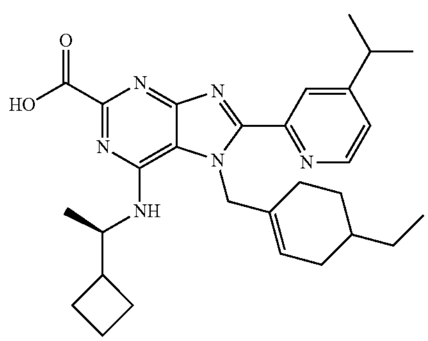 [SMILES: CCC1CC=C(Cn2c(-c3cc(C(C)C)ccn3)nc3nc(C(=O)O)nc(N[C@H](C)C4CCC4)c32)CC1] | 6-{[(1R)-1-cyclobutylethyl]amino}-7-[(4-ethylcyclohex-1-en-1-yl)methyl]-8-[4-(1-methylethyl)pyridin-2-yl]-7H-purine-2-carboxylic acid | TFA | 503 | 503 |
| 18.24 | 15.86 | 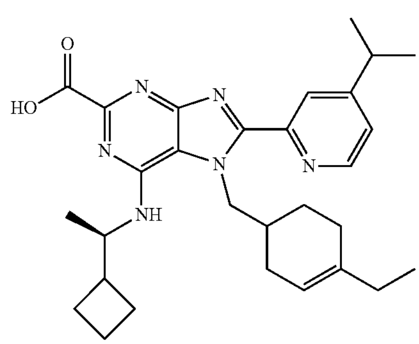 [SMILES: CCC1=CCC(Cn2c(-c3cc(C(C)C)ccn3)nc3nc(C(=O)O)nc(N[C@H](C)C4CCC4)c32)CC1] | 6-{[(1R)-1-cyclobutylethyl]amino}-7-[(4-ethylcyclohex-3-en-1-yl)methyl]-8-[4-(1-methylethyl)pyridin-2-yl]-7H-purine-2-carboxylic acid | | 503 | 503 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.25 | 43.97 | 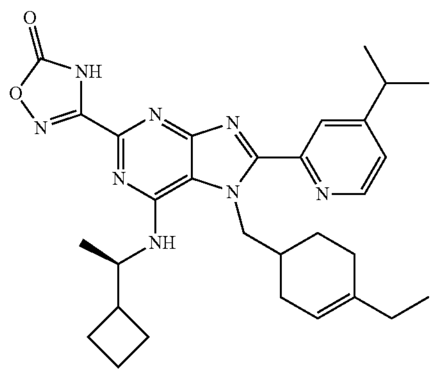 [SMILES: CCC1=CCC(Cn2c(-c3cc(C(C)C)ccn3)nc3nc(-c4noc(=O)[nH]4)nc(N[C@H](C)C4CCC4)c32)CC1] | 3-(6-{[(1R)-1-cyclobutylethyl]amino}-7-[(4-ethylcyclohex-3-en-1-yl)methyl]-8-[4-(1-methylethyl)pyridin-2-yl]-7H-purin-2-yl)-1,2,4-oxadiazol-5(4H)-one | | 543 | 543 |
| 18.26 | 297.1 | 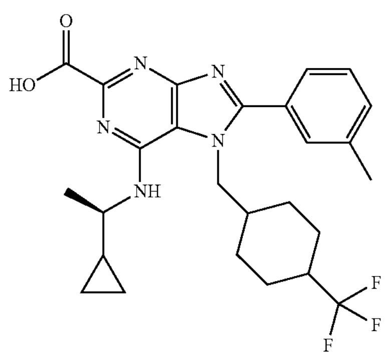 [SMILES: Cc1cccc(-c2nc3nc(C(=O)O)nc(N[C@H](C)C4CC4)c3n2CC2CCC(C(F)(F)F)CC2)c1] | 6-{[(1R)-1-cyclopropylethyl]amino}-8-(3-methylphenyl)-7-{[4-(trifluoromethyl)cyclohexyl]methyl}-7H-purine-2-carboxylic acid | | 502 | 502 |
| 18.27 | 337.7 | 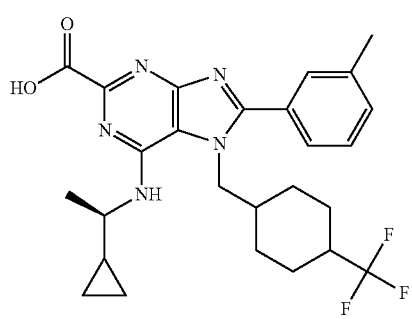 [SMILES: Cc1cccc(-c2nc3nc(C(=O)O)nc(N[C@H](C)C4CC4)c3n2CC2CCC(C(F)(F)F)CC2)c1] | 6-{[(1R)-1-cyclopropylethyl]amino}-8-(3-methylphenyl)-7-{[4-(trifluoromethyl)cyclohexyl]methyl}-7H-purine-2-carboxylic acid (stereoisomer 1) | | 502 | 502 |
| 18.28 | 386.2 | 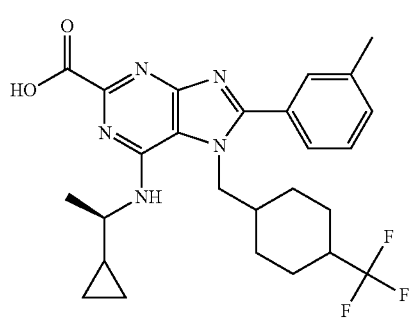 [SMILES: Cc1cccc(-c2nc3nc(C(=O)O)nc(N[C@H](C)C4CC4)c3n2CC2CCC(C(F)(F)F)CC2)c1] | 6-{[(1R)-1-cyclopropylethyl]amino}-8-(3-methylphenyl)-7-{[4-(trifluoromethyl)cyclohexyl]methyl}-7H-purine-2-carboxylic acid (stereoisomer 2) | | 502 | 502 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.29 | 677.1 | 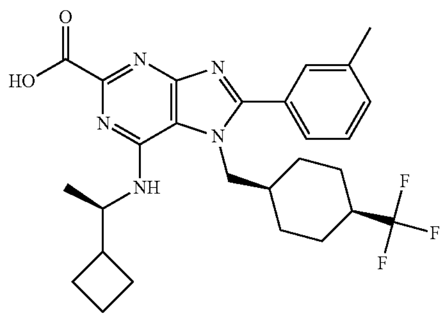 [SMILES: Cc1cccc(-c2nc3nc(C(=O)O)nc(N[C@H](C)C4CCC4)c3n2C[C@H]2CC[C@@H](C(F)(F)F)CC2)c1] | 6-{[(1R)-1-cyclobutylethyl]amino}-8-(3-methylphenyl)-7-{[cis-4-(trifluoromethyl)cyclohexyl]methyl}-7H-purine-2-carboxylic acid | | 516 | 516 |
| 18.30 | 12.98 | 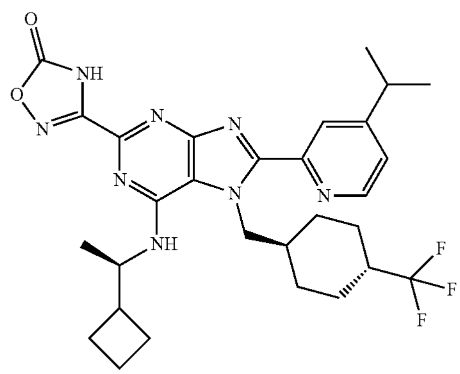 [SMILES: CC(C)c1ccnc(-c2nc3nc(-c4noc(=O)[nH]4)nc(N[C@H](C)C4CCC4)c3n2C[C@H]2CC[C@H](C(F)(F)F)CC2)c1] | 3-(6-{[(1R)-1-cyclobutylethyl]amino}-8-[4-(1-methylethyl)pyridin-2-yl]-7-{[trans-4-(trifluoromethyl)cyclohexyl]methyl}-7H-purin-2-yl)-1,2,4-oxadiazol-5(4H)-one | | 585 | 585 |
| 18.31 | 8.123 | 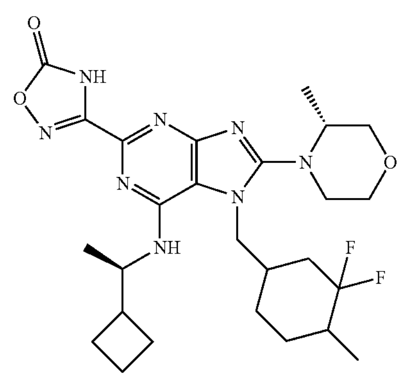 [SMILES: CC1CCC(Cn2c(N3CCOC[C@H]3C)nc3nc(-c4noc(=O)[nH]4)nc(N[C@H](C)C4CCC4)c32)CC1(F)F] | 3-(6-{[(1R)-1-cyclobutylethyl]amino}-7-{[trans-3,3-difluoro-4-methylcyclohexyl]methyl}-8-[(3R)-3-methylmorpholin-4-yl]-7H-purin-2-yl)-1,2,4-oxadiazol-5(4H)-one (diastereoisomer 1) | | 547 | 547 |
| 18.32 | 11.23 | 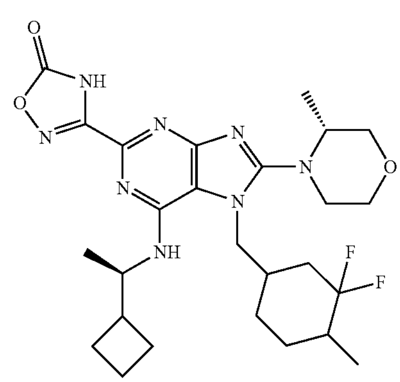 [SMILES: CC1CCC(Cn2c(N3CCOC[C@H]3C)nc3nc(-c4noc(=O)[nH]4)nc(N[C@H](C)C4CCC4)c32)CC1(F)F] | 3-(6-{[(1R)-1-cyclobutylethyl]amino}-7-{[trans-3,3-difluoro-4-methylcyclohexyl]methyl}-8-[(3R)-3-methylmorpholin-4-yl]-7H-purin-2-yl)-1,2,4-oxadiazol-5(4H)-one (diastereoisomer 2) | | 547 | 547 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.33 | 3.142 | 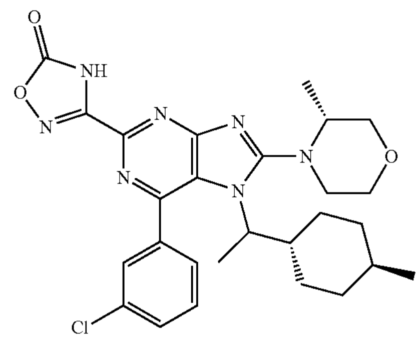 [SMILES: CC([C@H]1CC[C@H](C)CC1)n1c(N2CCOC[C@H]2C)nc2nc(-c3noc(=O)[nH]3)nc(-c3cccc(Cl)c3)c21] | 3-{6-(3-chlorophenyl)-7-[1-(trans-4-methylcyclohexyl)ethyl]-8-[(3R)-3-methylmorpholin-4-yl]-7H-purin-2-yl}-1,2,4-oxadiazol-5(4H)-one (diastereomer 1) | | 538 | 538 |
| 18.34 | 5.625 | 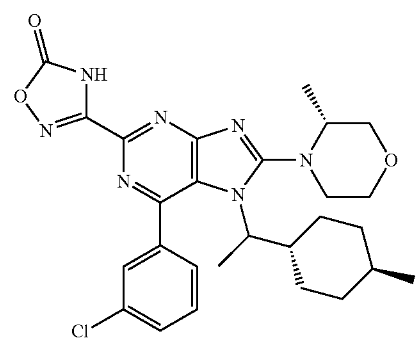 [SMILES: CC([C@H]1CC[C@H](C)CC1)n1c(N2CCOC[C@H]2C)nc2nc(-c3noc(=O)[nH]3)nc(-c3cccc(Cl)c3)c21] | 3-{6-(3-chlorophenyl)-7-[1-(trans-4-methylcyclohexyl)ethyl]-8-[(3R)-3-methylmorpholin-4-yl]-7H-purin-2-yl}-1,2,4-oxadiazol-5(4H)-one (diastereomer 2) | | 538 | 538 |
| 18.35 | 5.045 | 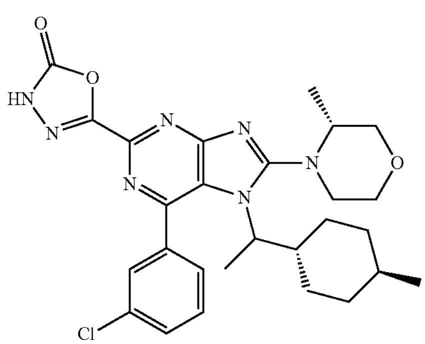 [SMILES: CC([C@H]1CC[C@H](C)CC1)n1c(N2CCOC[C@H]2C)nc2nc(-c3n[nH]c(=O)o3)nc(-c3cccc(Cl)c3)c21] | 5-{6-(3-chlorophenyl)-7-[1-(trans-4-methylcyclohexyl)ethyl]-8-[(3R)-3-methylmorpholin-4-yl]-7H-purin-2-yl}-1,3,4-oxadiazol-2(3H)-one (diastereomer 1) | | 538 | 538 |
| 18.36 | 8.874 | 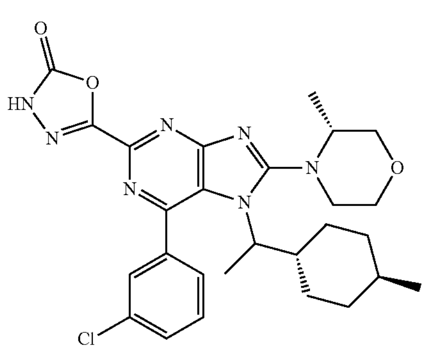 [SMILES: CC([C@H]1CC[C@H](C)CC1)n1c(N2CCOC[C@H]2C)nc2nc(-c3n[nH]c(=O)o3)nc(-c3cccc(Cl)c3)c21] | 5-{6-(3-chlorophenyl)-7-[1-(trans-4-methylcyclohexyl)ethyl]-8-[(3R)-3-methylmorpholin-4-yl]-7H-purin-2-yl}-1,3,4-oxadiazol-2(3H)-one (diastereomer 2) | | 538 | 538 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.37 | 2.214 | 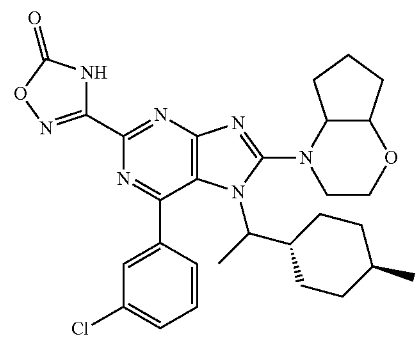 [SMILES: CC([C@H]1CC[C@H](C)CC1)n1c(N2CCOC3CCCC32)nc2nc(-c3noc(=O)[nH]3)nc(-c3cccc(Cl)c3)c21] | 3-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one (stereoisomer 1) | | 564 | 564 |
| 18.38 | 16.55 | 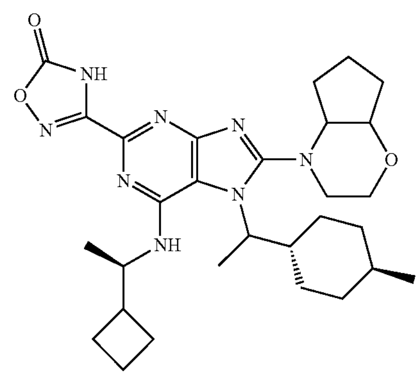 [SMILES: CC([C@H]1CC[C@H](C)CC1)n1c(N2CCOC3CCCC32)nc2nc(-c3noc(=O)[nH]3)nc(N[C@H](C)C3CCC3)c21] | 3-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,2,4-oxadiazol-5(4H)-one (stereoisomer 1) | | 551 | 551 |
| 18.39 | 3.726 | 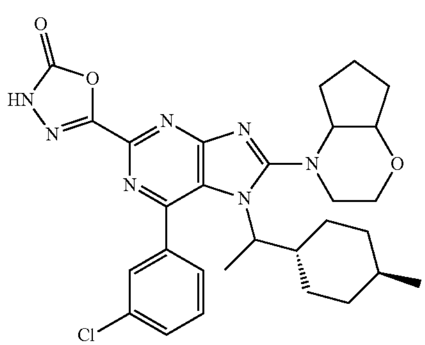 [SMILES: CC([C@H]1CC[C@H](C)CC1)n1c(N2CCOC3CCCC32)nc2nc(-c3n[nH]c(=O)o3)nc(-c3cccc(Cl)c3)c21] | 5-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,3,4-oxadiazol-2(3H)-one (stereoisomer 1) | | 564 | 564 |
| 18.40 | 7.862 | 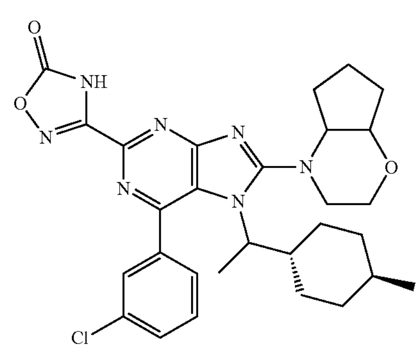 [SMILES: CC([C@H]1CC[C@H](C)CC1)n1c(N2CCOC3CCCC32)nc2nc(-c3noc(=O)[nH]3)nc(-c3cccc(Cl)c3)c21] | 3-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one (stereoisomer 2) | | 564 | 564 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.41 | 2.573 | 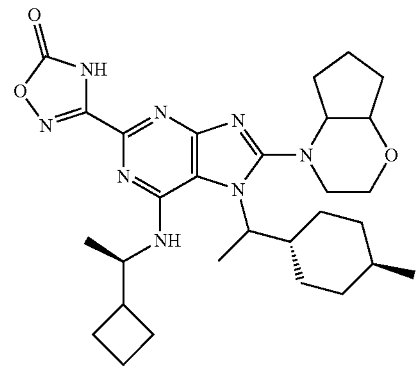 [SMILES: CC([C@H]1CC[C@H](C)CC1)n1c(N2CCOC3CCCC32)nc2nc(-c3noc(=O)[nH]3)nc(N[C@H](C)C3CCC3)c21] | 3-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,2,4-oxadiazol-5(4H)-one (stereoisomer 2) | | 551 | 551 |
| 18.42 | 5.766 | 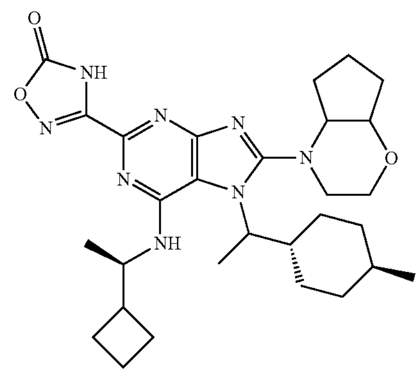 [SMILES: CC([C@H]1CC[C@H](C)CC1)n1c(N2CCOC3CCCC32)nc2nc(-c3noc(=O)[nH]3)nc(N[C@H](C)C3CCC3)c21] | 3-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,2,4-oxadiazol-5(4H)-one (stereoisomer 3) | | 551 | 551 |
| 18.43 | 13.97 | 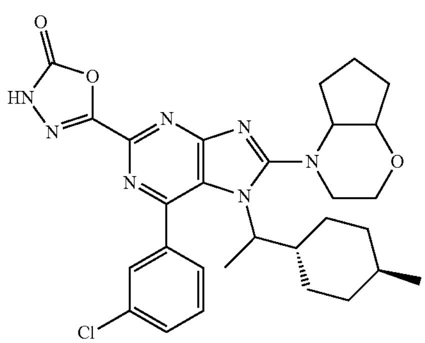 [SMILES: CC([C@H]1CC[C@H](C)CC1)n1c(N2CCOC3CCCC32)nc2nc(-c3n[nH]c(=O)o3)nc(-c3cccc(Cl)c3)c21] | 5-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,3,4-oxadiazol-2(3H)-one (stereoisomer 2) | | 564 | 564 |
| 18.44 | 5.374 | 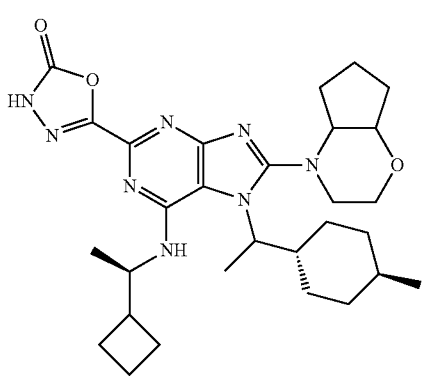 [SMILES: CC([C@H]1CC[C@H](C)CC1)n1c(N2CCOC3CCCC32)nc2nc(-c3n[nH]c(=O)o3)nc(N[C@H](C)C3CCC3)c21] | 5-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,3,4-oxadiazol-2(3H)-one (mixture of diastereomers) | | 551 | 551 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.45 | 2.418 | 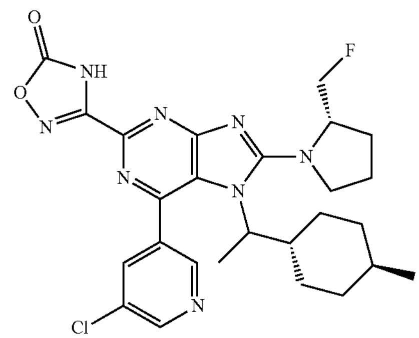 [SMILES: CC([C@H]1CC[C@H](C)CC1)n1c(N2CCC[C@H]2CF)nc2nc(-c3noc(=O)[nH]3)nc(-c3cncc(Cl)c3)c21] | 3-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,2,4-oxadiazol-5(4H)-one (diastereomer 1) | TFA | 541 | 541 |
| 18.46 | 5.493 | 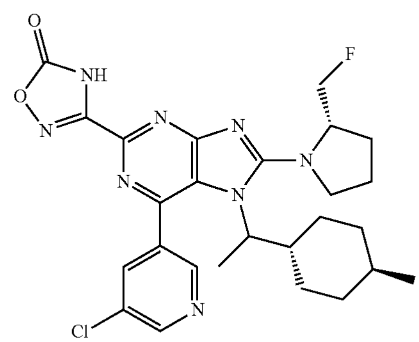 [SMILES: CC([C@H]1CC[C@H](C)CC1)n1c(N2CCC[C@H]2CF)nc2nc(-c3noc(=O)[nH]3)nc(-c3cncc(Cl)c3)c21] | 3-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,2,4-oxadiazol-5(4H)-one (diastereomer 2) | TFA | 541 | 541 |
| 18.47 | 5.141 | 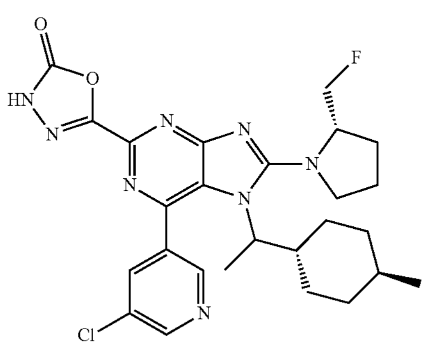 [SMILES: CC([C@H]1CC[C@H](C)CC1)n1c(N2CCC[C@H]2CF)nc2nc(-c3n[nH]c(=O)o3)nc(-c3cncc(Cl)c3)c21] | 5-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,3,4-oxadiazol-2(3H)-one (diastereomer 1) | TFA | 541 | 541 |
| 18.48 | 8.118 | 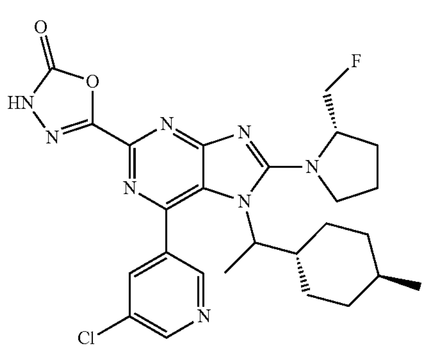 [SMILES: CC([C@H]1CC[C@H](C)CC1)n1c(N2CCC[C@H]2CF)nc2nc(-c3n[nH]c(=O)o3)nc(-c3cncc(Cl)c3)c21] | 5-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,3,4-oxadiazol-2(3H)-one (diastereomer 2) | TFA | 541 | 541 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.49 | 0.670 | 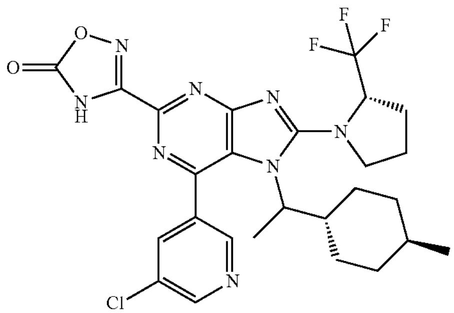 [SMILES: CC([C@H]1CC[C@H](C)CC1)n1c(N2CCC[C@H]2C(F)(F)F)nc2nc(-c3noc(=O)[nH]3)nc(-c3cncc(Cl)c3)c21] | 3-{6-(5-chloropyridin-3-yl)-7-[1-(trans-4-methylcyclohexyl)ethyl]-8-[(2S)-2-(trifluoromethyl)pyrrolidin-1-yl]-7H-purin-2-yl}-1,2,4-oxadiazol-5(4H)-one (mixture of diastereomers) | TFA | 577 | 577 |
| 18.50 | 7.044 | 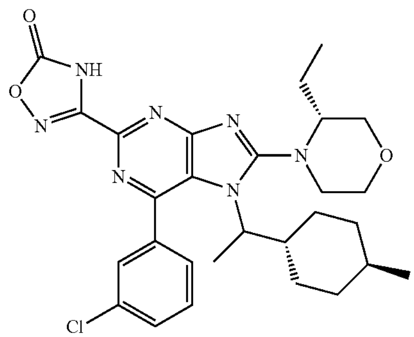 [SMILES: CC[C@@H]1COCCN1c1nc2nc(-c3noc(=O)[nH]3)nc(-c3cccc(Cl)c3)c2n1C(C)[C@H]1CC[C@H](C)CC1] | 3-{6-(3-chlorophenyl)-8-[(3R)-3-ethylmorpholin-4-yl]-7-[1-(trans-4-methylcyclohexyl)ethyl]-7H-purin-2-yl}-1,2,4-oxadiazol-5(4H)-one (diastereomer 1) | | 552 | 552 |
| 18.51 | 10.51 | 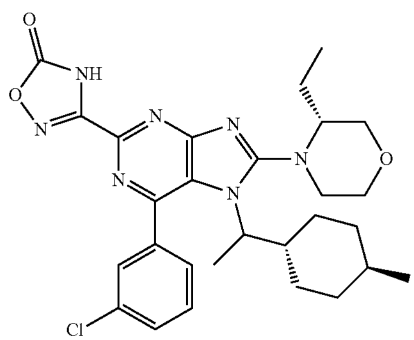 [SMILES: CC[C@@H]1COCCN1c1nc2nc(-c3noc(=O)[nH]3)nc(-c3cccc(Cl)c3)c2n1C(C)[C@H]1CC[C@H](C)CC1] | 3-{6-(3-chlorophenyl)-8-[(3R)-3-ethylmorpholin-4-yl]-7-[1-(trans-4-methylcyclohexyl)ethyl]-7H-purin-2-yl}-1,2,4-oxadiazol-5(4H)-one (diastereomer 2) | | 552 | 552 |
| 18.52 | 5.436 | 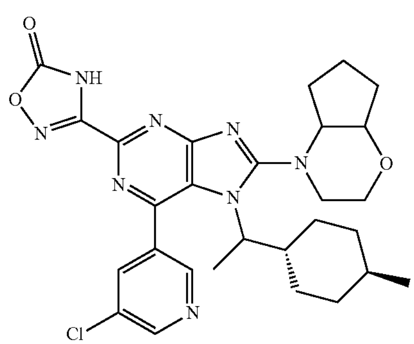 | 3-{6-(5-chloropyridin-3-yl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one (stereoisomer 1) | | 565 | 565 |

TABLE 18-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 18.53 | 7.361 | 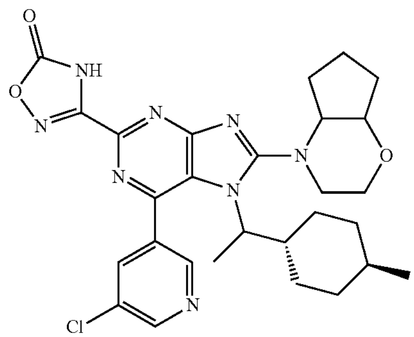 [SMILES: CC([C@H]1CC[C@H](C)CC1)n1c(N2CCOC3CCCC32)nc2nc(-c3noc(=O)[nH]3)nc(-c3cncc(Cl)c3)c21] | 3-{6-(5-chloropyridin-3-yl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one (stereoisomer 2) | | 565 | 565 |

Example 19.1

3-[6-{[(1R)-1-cyclobutylethyl]amino}-7-[(trans-4-methylcyclohexyl)methyl]-8-(phenylsulfanyl)-7H-purin-2-yl]-1,2,4-oxadiazol-5(4H)-one

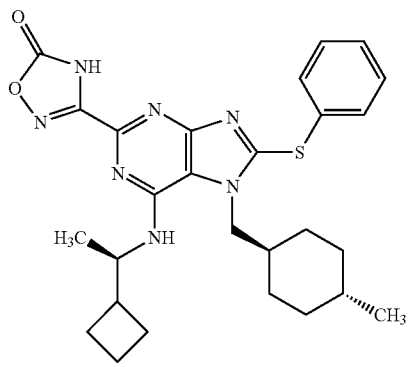 [SMILES: C[C@@H](Nc1nc(-c2noc(=O)[nH]2)nc2nc(Sc3ccccc3)n(C[C@H]3CC[C@H](C)CC3)c12)C1CCC1]

Step 1: To a mixture of K$_2$CO$_3$ (32 mg, 0.23 mmol) in DMF (0.5 mL) was added thiophenol (51 mg, 0.46 mmol) and the reaction mixture was stirred for 5 minutes at room temperature. Then 8-bromo-6-(((R)-1-cyclobutylethyl)amino)-7-(((trans)-4-methylcyclohexyl)methyl)-7H-purine-2-carbonitrile (Preparative Example 11.7, 50 mg, 0.11 mmol) in 0.3 mL of DMF was added and the reaction was continued for 30 minutes at room temperature under nitrogen atmosphere. The reaction was quenched with aqueous 1 N NaOH (5 mL) and extracted with ethyl acetate (2×5 mL). The combined organic extracts were washed with brine (5 mL), dried over anhydrous Na$_2$SO$_4$, filtered, and concentrated. Purification of the residue on a RediSep 4 g silica gel column (0 to 100% EtOAc/hexanes) afforded 6-(((R)-1-cyclobutylethyl)amino)-7-((trans-4-methylcyclohexyl)methyl)-8-(phenylthio)-7H-purine-2-carbonitrile. MS (ES)=461 (M+1)$^+$.

Step 2: Using a procedure analogous to that described in Example 16.1 (step 3 and step 4) and starting with 6-(((R)-1-cyclobutylethyl)amino)-7-((trans-4-methylcyclohexyl)methyl)-8-(phenylthio)-7H-purine-2-carbonitrile, 3-[6-{[(1R)-1-cyclobutylethyl]amino}-7-[(trans-4-methylcyclohexyl)methyl]-8-(phenylsulfanyl)-7H-purin-2-yl]-1,2,4-oxadiazol-5(4H)-one was prepared. $^1$H NMR (400 MHz, CD$_3$OD) δ 7.55-7.58 (m, 2H), 7.43-7.45 (m, 3H), 4.65 (m, 1H), 4.46 (dd, J=15.2, 6.4 Hz, 1H), 4.28 (dd, J=15.2, 8.4 Hz, 1H), 2.57 (m, 1H), 2.02-2.12 (m, 2H), 1.83-1.98 (m, 4H), 1.63-1.75 (m, 4H), 1.47-1.26 (m, 3H), 1.17-1.25 (m, 4H), 0.86-0.92 (m, 4H), 0.80 (m, 1H). MS (ES)=520 (M+1)$^+$.

Example 19.2

3-[6-{[(1R)-1-cyclobutylethyl]amino}-7-[(trans-4-methylcyclohexyl)methyl]-8-(phenylsulfinyl)-7H-purin-2-yl]-1,2,4-oxadiazol-5(4H)-one

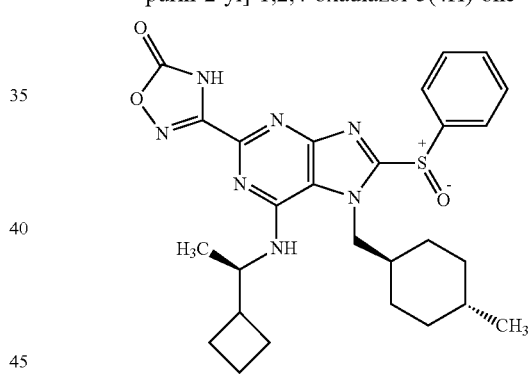

Step 1: To a mixture of 6-(((R)-1-cyclobutylethyl)amino)-7-((trans-4-methylcyclohexyl)methyl)-8-(phenylthio)-7H-purine-2-carbonitrile (Example 19.1, step 1) (50 mg, 0.10 mmol) in dichloromethane (1.5 mL) was added mCPBA (18 mg, 0.10 mmol) at 0° C. and the reaction mixture was stirred for 1 hour at 0° C. under nitrogen atmosphere. The reaction was quenched with aqueous saturated NaHCO$_3$ solution (5 mL) and extracted with ethyl acetate (2×5 mL). The combined organic extracts were washed with brine (5 mL), dried over anhydrous Na$_2$SO$_4$, filtered, and concentrated to dryness. Purification of the residue on a RediSep 4 g silica gel column (0 to 100% EtOAc/hexanes) afforded 6-(((R)-1-cyclobutylethyl)amino)-7-(((trans)-4-methylcyclohexyl)methyl)-8-(phenylsulfinyl)-7H-purine-2-carbonitrile. MS (ES)=477 (M+1)$^+$.

Step 2: Using a procedure analogous to that described in Example 16.1 (step 3 and step 4) and starting with 6-(((R)-1-cyclobutylethyl)amino)-7-(((trans)-4-methylcyclohexyl)methyl)-8-(phenylsulfinyl)-7H-purine-2-carbonitrile, 3-[6-{[(1R)-1-cyclobutylethyl]amino}-7-[(trans-4-methylcyclohexyl)methyl]-8-(phenylsulfinyl)-7H-purin-2-yl]-1,2,4-oxadiazol-5(4H)-one was prepared. ¹H NMR (400 MHz, CD₃OD) δ ¹H NMR (400 MHz, CD₃OD) δ 7.82-7.88 (m, 2H), 7.62 (d, J=6.4 Hz, 3H), 4.50-4.70 (m, 2H), 2.54 (m, 1H), 1.98-2.10 (m, 2H), 1.80-1.91 (m, 4H), 1.48-1.69 (m, 5H), 1.23-1.40 (m, 3H), 0.78-0.94 (m, 5H), 0.79-0.94 (m, 3H), 0.70 (m, 1H). MS (ES)=536 (M+1)⁺.

Example 19.3

3-[6-{[(1R)-1-cyclobutylethyl]amino}-7-[(trans-4-methylcyclohexyl)methyl]-8-(phenylsulfonyl)-7H-purin-2-yl]-1,2,4-oxadiazol-5(4H)-one

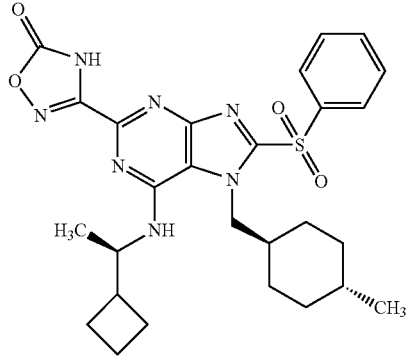 [SMILES: C[C@@H](Nc1nc(-c2noc(=O)[nH]2)nc2nc(S(=O)(=O)c3ccccc3)n(C[C@H]3CC[C@H](C)CC3)c12)C1CCC1]

Step 1: To a mixture of 6-(((R)-1-cyclobutylethyl)amino)-7-((trans-4-methylcyclohexyl)methyl)-8-(phenylthio)-7H-purine-2-carbonitrile (Example 19.1, step 1) (50 mg, 0.10 mmol) in dichloromethane (1.5 mL) was added mCPBA (56 mg, 0.32 mmol) at 0° C. and the reaction mixture was stirred for 1 hour at 0° C. under a nitrogen atmosphere. The reaction was quenched with aqueous saturated NaHCO₃ solution (5 mL) and extracted with ethyl acetate (2×5 mL). The combined organic extracts were washed with brine (5 mL), dried over anhydrous Na₂SO₄, filtered, and concentrated to dryness. Purification of the residue on a RediSep 4 g silica gel column (0 to 100% EtOAc/hexanes) afforded 6-(((R)-1-cyclobutylethyl)amino)-7-(((trans)-4-methylcyclohexyl)methyl)-8-(phenylsulfonyl)-7H-purine-2-carbonitrile. MS (ES)=493 (M+1)⁺.

Step 2: Using a procedure analogous to that described in Example 16.1 (step 3 and step 4) and starting with 6-(((R)-1-cyclobutylethyl)amino)-7-(((trans)-4-methylcyclohexyl)methyl)-8-(phenylsulfonyl)-7H-purine-2-carbonitrile, 3-[6-{[(1R)-1-cyclobutylethyl]amino}-7-[(trans-4-methylcyclohexyl)methyl]-8-(phenylsulfonyl)-7H-purin-2-yl]-1,2,4-oxadiazol-5(4H)-one was prepared. ¹H NMR (400 MHz, CD₃OD) δ 8.09 (d, J=8.0 Hz, 2H), 7.78 (m, 1H), 7.68 (t, J=8.0 Hz, 2H), 4.68-4.75 (m, 2H), 2.55 (m, 1H), 2.01-2.18 (m, 2H), 1.84-1.98 (m, 3H), 1.62-1.80 (m, 3H), 1.55 (m, 1H), 1.24-1.38 (m, 3H), 1.17 (d, J=8.0 Hz, 5H), 0.84-0.89 (m, 5H), 0.73 (m, 1H). MS (ES)=552 (M+1)⁺.

Example 19.4

5-{6-(5-chloropyridin-3-yl)-8-(cyclopentylsulfanyl)-7-[(trans-4-methylcyclohexyl)methyl]-7H-purin-2-yl}-1,3,4-oxadiazol-2(3H)-one

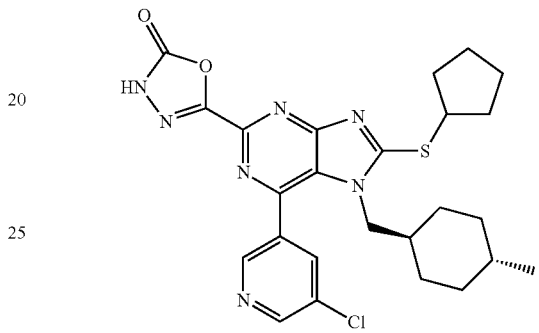

Using procedures similar to those described in Example 19.1 (Steps 1 and 2) and starting with 8-bromo-6-(5-chloropyridin-3-yl)-7-(((trans)-4-methylcyclohexyl)methyl)-7H-purine-2-carbonitrile (Preparative Example 16.8), 6-(5-chloropyridin-3-yl)-8-(cyclopentylthio)-7-(((trans)-4-methylcyclohexyl)methyl)-7H-purine-2-carbonitrile was prepared. This was followed by a three step sequence similar to that described in Example 16.7 (Steps 1-3) to afford 5-{6-(5-chloropyridin-3-yl)-8-(cyclopentylsulfanyl)-7-[(trans-4-methylcyclohexyl)methyl]-7H-purin-2-yl}-1,3,4-oxadiazol-2(3H)-one. ¹H NMR (400 MHz, CDCl₃) δ 9.34 (br s, 1H), 8.77 (d, J=2.0 Hz, 1H), 8.69 (d, J=2.0 Hz, 1H), 8.01 (t, J=2.0 Hz, 1H), 4.40 (m, 1H), 3.76 (d, J=6.8 Hz, 2H), 2.36-2.41 (m, 2H), 1.71-1.82 (m, 5H), 1.52-1.56 (m, 3H), 1.18 (m, 1H), 1.02-1.09 (m, 3H), 0.77 (d, J=6.4 Hz, 3H), 0.74-0.78 (m, 2H), 0.51-0.60 (m, 2H). MS (ES)=526 (M+1)⁺.

TABLE 19

| Ex. | FRET IC₅₀ (nM) | Structure | Chemical Name | Salt Form | [M + H]⁺ Calc'd | [M + H]⁺ Obsv'd |
|---|---|---|---|---|---|---|
| 19.1 | 0.7627 | 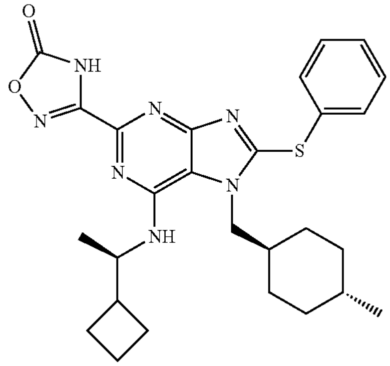 [SMILES: C[C@@H](Nc1nc(-c2noc(=O)[nH]2)nc2nc(Sc3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(phenylsulfanyl)-7H-purin-2-yl]-1,2,4-oxadiazol-5(4H)-one | | 520 | 520 |

TABLE 19-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 19.2 | 1.766 | 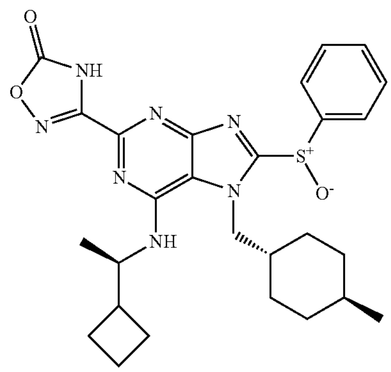 [SMILES: C[C@@H](Nc1nc(-c2noc(=O)[nH]2)nc2nc([S+]([O-])c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(phenylsulfinyl)-7H-purin-2-yl]-1,2,4-oxadiazol-5(4H)-one | | 536 | 536 |
| 19.3 | 0.9433 | 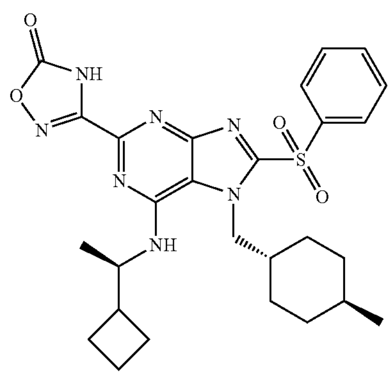 [SMILES: C[C@@H](Nc1nc(-c2noc(=O)[nH]2)nc2nc(S(=O)(=O)c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(phenylsulfonyl)-7H-purin-2-yl]-1,2,4-oxadiazol-5(4H)-one | | 552 | 552 |
| 19.4 | 3.048 | 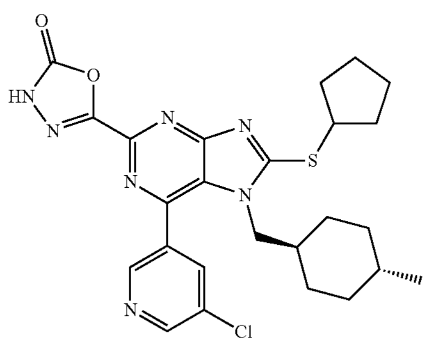 [SMILES: C[C@H]1CC[C@H](Cn2c(SC3CCCC3)nc3nc(-c4n[nH]c(=O)o4)nc(-c4cncc(Cl)c4)c32)CC1] | 5-{6-(5-chloropyridin-3-yl)-8-(cyclopentylsulfanyl)-7-[(trans-4-methylcyclohexyl)methyl]-7H-purin-2-yl}-1,3,4-oxadiazol-2(3H)-one | | 526 | 526 |
| 19.5 | 5.834 | 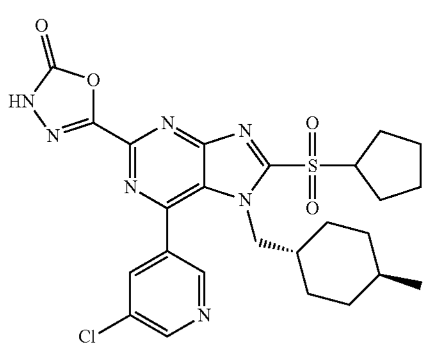 [SMILES: C[C@H]1CC[C@H](Cn2c(S(=O)(=O)C3CCCC3)nc3nc(-c4n[nH]c(=O)o4)nc(-c4cncc(Cl)c4)c32)CC1] | 5-{6-(5-chloropyridin-3-yl)-8-(cyclopentylsulfonyl)-7-[(trans-4-methylcyclohexyl)methyl]-7H-purin-2-yl}-1,3,4-oxadiazol-2(3H)-one | | 558 | 558 |

TABLE 19-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 19.6 | 3.138 | 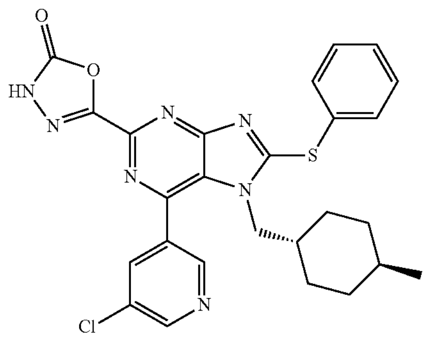 [SMILES: C[C@H]1CC[C@H](Cn2c(Sc3ccccc3)nc3nc(-c4n[nH]c(=O)o4)nc(-c4cncc(Cl)c4)c32)CC1] | 5-[6-(5-chloropyridin-3-yl)-7-[(trans-4-methylcyclohexyl)methyl]-8-(phenylsulfanyl)-7H-purin-2-yl]-1,3,4-oxadiazol-2(3H)-one | | 534 | 534 |

Preparative Example 20.1

6-amino-1-methyl-5-{[(trans-4-methylcyclohexyl)methyl]amino}pyrimidine-2,4(1H,3H)-dione

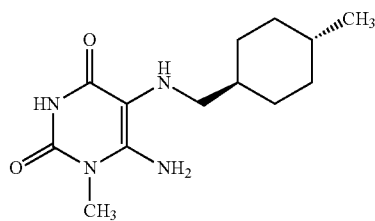 [SMILES: Cn1c(N)c(NC[C@H]2CC[C@H](C)CC2)c(=O)[nH]c1=O]

Step 1: To a suspension of 6-amino-1-methylpyrimidine-2,4(1H,3H)-dione (20.0 g, 142 mmol) in methanol (200 mL) was added sodium bicarbonate (12.0 g, 142 mmol). The suspension was cooled to 0° C. and bromine (7.3 mL) was added over 15 minutes at 0° C. The suspension was stirred at room temperature for 12 hours. The resultant solid was collected by filtration and washed with cold water (500 mL) and methanol (200 mL). The solid was dried in vacuo to afford 6-amino-5-bromo-1-methylpyrimidine-2,4(1H,3H)-dione. $^1$H NMR (300 MHz, DMSO-d$_6$) δ 10.89 (s, 1H), 7.01 (s, 2H), 3.29 (s, 3H).

Step 2: To a suspension of 6-amino-5-bromo-1-methylpyrimidine-2,4(1H,3H)-dione (7.00 g, 31.8 mmol) in NMP (100 mL) was added (trans-4-methylcyclohexyl)methanamine (6.07 g, 47.7 mmol). The resulting mixture was heated at 120° C. for 30 minutes. The reaction mixture was then cooled to room temperature, poured into ice water (500 mL) and stirred for 20 minutes until a precipitate formed. The solid was collected by filtration, washed with acetone (30 mL), and dried in vacuo to afford 6-amino-1-methyl-5-{[(trans-4-methylcyclohexyl)methyl]amino}pyrimidine-2,4(1H,3H)-dione. $^1$H NMR (300 MHz, DMSO-d$_6$) δ 10.43 (s, 1H), 6.24 (s, 2H), 3.23 (s, 3H), 2.71 (s, 1H), 2.45 (d, J=6.0 Hz, 2H), 2.15-2.18 (m, 1H), 1.80-1.93 (m, 3H), 1.65-1.67 (m, 2H), 1.29-1.35 (m, 2H), 0.95-0.90 (m, 2H), 0.87 (d, J=9.0 Hz, 3H). MS (APCI)=267 (M+1)$^+$.

Example 20.1

6-{[(1R)-1-cyclobutylethyl]amino}-7-[(trans-4-methylcyclohexyl)methyl]-8-(1-phenylcyclobutyl)-7H-purine-2-carboxylic acid

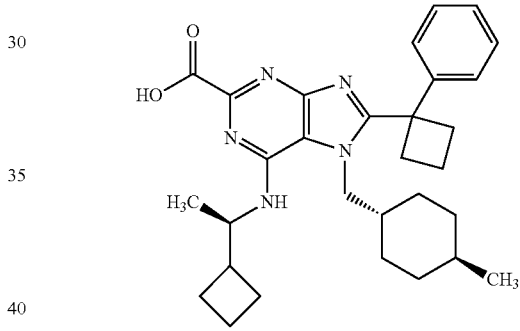

Step 1: To a stirred solution of 6-amino-1-methyl-5-{[(trans-4-methylcyclohexyl)methyl]amino}pyrimidine-2,4(1H,3H)-dione (Preparative Example 20.1, 1.20 g, 4.51 mmol) in DMF (10 mL) was added 1-phenylcyclobutanecarboxylic acid (1.58 g, 9.02 mmol), HATU (3.43 g, 9.02 mmol), and DIPEA (1.60 mL, 9.02 mmol) and the reaction mixture was heated at 60° C. for 12 hours. The reaction mixture was then cooled to room temperature and water (50 mL) was added. The mixture was extracted with EtOAc (2×50 mL). The combined organic layers were dried over Na$_2$SO$_4$, filtered and concentrated in vacuo. Purification of the residue on a Redisep 12 g silica gel column (0 to 50% EtOAc/hexanes) afforded N-(6-amino-1-methyl-2,4-dioxo-1,2,3,4-tetrahydropyrimidin-5-yl)-N-[(trans-4-methylcyclohexyl)methyl]-1-phenylcyclobutanecarboxamide. MS (ES)=425 (M+1)$^+$.

Step 2: To a stirred solution of N-(6-amino-1-methyl-2,4-dioxo-1,2,3,4-tetrahydropyrimidin-5-yl)-N-[(trans-4-methylcyclohexyl)methyl]-1-phenylcyclobutanecarboxamide (750 mg, 1.76 mmol) in hexamethyldisilazane (75 mL) was added ammonium sulphate (70 mg, 0.53 mmol) and the reaction mixture was heated at 120° C. for 12 hours. The reaction mixture was cooled to room temperature and concentrated in vacuo. The residue was cooled to 0° C. and methanol and water (30 mL, 1:1) were added. The precipitate was collected by filtration and washed with a mixture of methanol and water (10 mL), then dried to afford 3-methyl-7-[(trans-4-methylcyclohexyl)methyl]-8-(1-phenylcyclobutyl)-3,7-dihydro-1H-purine-2,6-dione. $^1$H NMR (400 MHz, CDCl$_3$) δ 7.28-7.37 (m, 5H), 3.58-3.61 (m, 4H), 2.98-3.05 (m, 2H), 2.61-2.67 (m, 2H), 1.98-2.15 (m, 2H), 1.46-1.53 (m, 4H), 1.13-1.24 (m, 2H), 0.94-1.09 (m, 2H), 0.74 (d, J=6.4 Hz, 3H), 0.66 (m, 1H), 0.51-0.57 (m, 2H). MS (ES)=407 (M+1)$^+$.

Step 3: 3-methyl-7-[(trans-4-methylcyclohexyl)methyl]-8-(1-phenylcyclobutyl)-3,7-dihydro-1H-purine-2,6-dione (400 mg, 0.98 mmol) was dissolved in POCl$_3$ (15 mL) and the mixture was heated to 60° C., then DBU (4.0 mL) was added and the temperature of the reaction was raised to 120° C. The reaction mixture was heated at 120° C. for 2 hours. Then the reaction mixture was then cooled to room temperature and poured into ice water and the resulting brown precipitate was collected by filtration and air-dried to afford 2,6-dichloro-7-((trans-4-methylcyclohexyl)methyl)-8-(1-phenylcyclobutyl)-7H-purine. MS (ES)=429 (M+1)$^+$.

Step 4: A mixture of 2,6-dichloro-7-((trans-4-methylcyclohexyl)methyl)-8-(1-phenylcyclobutyl)-7H-purine (350 mg, 0.81 mmol) and (R)-1-cyclobutylethylamine (220 mg, 1.63 mmol) in ethanol (6.0 mL) was heated at reflux for 3 hours. Then the reaction mixture was cooled to room temperature and concentrated under reduced pressure. The residue was dissolved in EtOAc (30 mL) and the organic layer was washed with water (15 mL) and brine (15 mL), dried over anhydrous Na$_2$SO$_4$, filtered, and concentrated in vacuo. Purification of the crude residue by column chromatography (30% EtOAc/hexanes) afforded 2-chloro-N—((R)-1-cyclobutylethyl)-7-((trans-4-methylcyclohexyl)methyl)-8-(1-phenylcyclobutyl)-7H-purin-6-amine. MS (ES)=492 (M+1)$^+$.

Step 5: A mixture of 2-chloro-N—((R)-1-cyclobutylethyl)-7-((trans-4-methylcyclohexyl)methyl)-8-(1-phenylcyclobutyl)-7H-purin-6-amine (150 mg, 0.75 mmol) and zinc cyanide (21.0 mg, 0.18 mmol) in DMA (2.0 mL) in a sealed tube was degassed with Ar for 30 minutes. Pd(PPh$_3$)$_4$ (70 mg, 0.06 mmol) was then added to the reaction and the reaction was evacuated and refilled with Ar three times and then heated at 120° C. for 12 hours. The reaction was cooled to room temperature and ice water (40 mL) was added slowly. The reaction mixture was then extracted with EtOAc (3×50 mL). The combined organic layers were dried over sodium sulfate, filtered and concentrated under reduced pressure. Purification of the residue on a Redisep 12 g silica gel column (0 to 100% EtOAc/hexanes) afforded 6-(((R)-1-cyclobutylethyl)amino)-7-((trans-4-methylcyclohexyl)methyl)-8-(1-phenylcyclobutyl)-7H-purine-2-carbonitrile as a white solid. $^1$H NMR (300 MHz, CDCl$_3$) δ7.48-7.62 (m, 5H), 4.56 (d, J=6.0 Hz, 1H), 4.45 (m, 1H), 3.60-3.72 (m, 2H), 3.01-3.17 (m, 2H), 2.63-2.74 (m, 2H), 2.35 (m, 1H), 1.79-2.11 (m, 9H), 1.43-1.52 (m, 2H), 1.20 (m, 1H), 0.98-1.13 (m, 5H), 0.76 (d, J=6.6 Hz, 3H), 0.38-0.62 (m, 3H). MS (ES)=483 (M+1)$^+$.

Step 6: Using a procedure analogous to that described in Example 10.1 (Step 5 and 6), and starting with 6-(((R)-1-cyclobutylethyl)amino)-7-((trans-4-methylcyclohexyl)methyl)-8-(1-phenylcyclobutyl)-7H-purine-2-carbonitrile, 6-{[(1R)-1-cyclobutylethyl]amino}-7-[(trans-4-methylcyclohexyl)methyl]-8-(1-phenylcyclobutyl)-7H-purine-2-carboxylic acid was prepared. $^1$H NMR (400 MHz, CD$_3$OD) δ 7.47 (d, J=8.4 Hz, 2H), 7.37 (t, J=7.6 Hz, 2H), 7.26 (t, J=7.4 Hz, 1H), 3.74 (d, J=23.6 Hz, 1H), 3.97 (d, J=23.6 Hz, 1H), 3.13 (m, 1H), 2.80-3.08 (m, 2H), 2.47-2.80 (m, 2H), 1.78-2.23 (m, 9H), 1.30-1.43 (m, 2H), 1.36 (m, 1H), 1.07-1.26 (m, 5H), 0.95-1.05 (m, 2H), 0.72 (d, J=6.4 Hz, 3H), 0.39-0.62 (m, 3H). MS (ES)=502 (M+1)$^+$.

Example 20.2

6-{[(1R)-1-cyclobutylethyl]amino}-7-[(trans-4-methylcyclohexyl)methyl]-8-(1-methyl-1-phenylethyl)-7H-purine-2-carboxylic acid

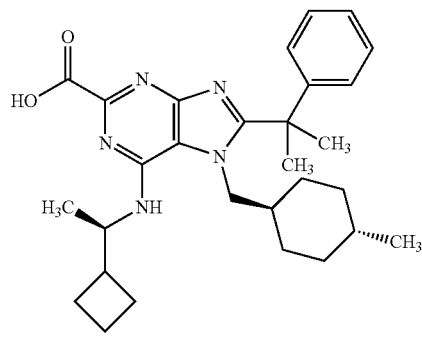 [SMILES: C[C@@H](Nc1nc(C(=O)O)nc2nc(C(C)(C)c3ccccc3)n(C[C@H]3CC[C@H](C)CC3)c12)C1CCC1]

Using a procedure analogous to that described in Example 20.1 and starting with 2-methyl-2-phenylpropanoic acid, 6-{[(1R)-1-cyclobutylethyl]amino}-7-[(trans-4-methylcyclohexyl)methyl]-8-(1-methyl-1-phenylethyl)-7H-purine-2-carboxylic acid was prepared. $^1$H NMR (400 MHz, CD$_3$OD) δ 7.28-7.43 (m, 5H), 3.63-4.26 (m, 2H), 2.53 (br s, 1H), 2.06-2.15 (m, 1H), 1.97-2.30 (m, 1H), 1.80-1.92 (m, 10H), 1.44-1.56 (m, 2H), 1.31 (m, 1H), 1.12-1.21 (m, 5H), 1.01-1.12 (m, 2H), 0.76 (d, J=6.4 Hz, 3H), 0.49-0.68 (m, 3H). MS (ES)=488 (M−1)$^−$.

Example 20.3

6-{[(1R)-1-cyclobutylethyl]amino}-8-(1-phenylcyclopropyl)-7-[4-(trifluoromethyl)benzyl]-7H-purine-2-carboxylic acid

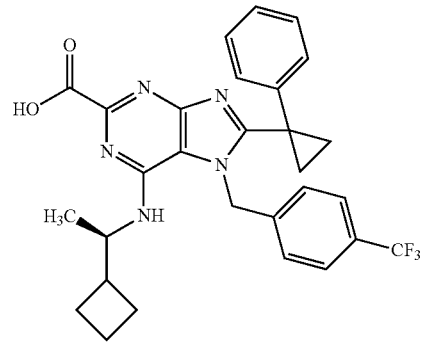 [SMILES: C[C@@H](Nc1nc(C(=O)O)nc2nc(C3(c4ccccc4)CC3)n(Cc3ccc(C(F)(F)F)cc3)c12)C1CCC1]

Using a procedure analogous to that described in Example 20.1 and starting with 1-phenylcyclopropanecarboxylic acid and 6-amino-1-methyl-5-{[4-(trifluoromethyl)benzyl]amino}pyrimidine-2,4(1H,3H)-dione (Preparative Example 6.1, Step 2), 6-{[(1R)-1-cyclobutylethyl]amino}-8-(1-phenylcyclopropyl)-7-[4-(trifluoromethyl)benzyl]-7H-purine-2-carboxylic acid was prepared. $^1$H NMR (400 MHz, CD$_3$OD) δ 7.49 (d, J=8.0 Hz, 2H), 7.07-7.20 (m, 5H), 6.92 (d, J=8.0 Hz, 2H), 5.76 (br s, 2H), 4.52 (m, 1H), 1.96 (m, 1H), 1.88 (m, 1H), 1.46-1.79 (m, 7H), 1.28-1.39 (m, 2H), 0.85 (d, J=6.4 Hz, 3H). MS (ES)=536 (M+1)⁺.

Example 20.4

6-{[(1R)-1-cyclobutylethyl]amino}-7-[(trans-4-methylcyclohexyl)methyl]-8-(1-phenylcyclopropyl)-7H-purine-2-carboxylic acid

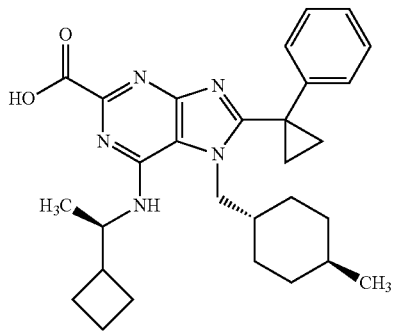 [SMILES: C[C@@H](Nc1nc(C(=O)O)nc2nc(C3(c4ccccc4)CC3)n(C[C@H]3CC[C@H](C)CC3)c12)C1CCC1]

Step 1: A microwave vial (15 mL) was charged with 8-bromo-6-(((R)-1-cyclobutylethyl)amino)-7-((trans-4-methylcyclohexyl)methyl)-7H-purine-2-carbonitrile (Preparative Example 11.7, 100 mg, 0.23 mmol), (1-phenylvinyl)boronic acid (68 mg, 0.46 mmol) and aqueous Na₂CO₃ (0.5 mL, 1M). DME (2.5 mL) was added to the vial and the mixture was degassed using N₂ for 15 minutes before Pd(PPh₃)₄ (80 mg, 0.069 mmol) was added to the reaction. The reaction was heated at 100° C. under microwave irradiation for 15 minutes. The reaction was then cooled and extracted with EtOAc (2×10 mL). The combined organic layers were washed with water and brine, dried over Na₂SO₄, filtered, and concentrated in vacuo. The crude product was purified using a Redisep 12 g silica gel column (0 to 100% EtOAc/hexanes) to afford 6-(((R)-1-cyclobutylethyl)amino)-7-((trans-4-methylcyclohexyl)methyl)-8-(1-phenylvinyl)-7H-purine-2-carbonitrile. ¹H NMR (300 MHz, CDCl₃) δ 7.28-7.38 (m, 5H), 6.09 (s, 1H), 5.93 (s, 1H), 4.39-4.58 (m, 2H), 3.66 (d, J=6.9 Hz, 2H), 2.47 (m, 1H), 2.07 (m, 1H), 1.80-1.90 (m, 5H), 1.71-1.78 (m, 2H), 1.17-1.43 (m, 5H), 0.76-0.90 (m, 9H). MS (ES)=455 (M+1)⁺.

Step 2: A round bottom flask was charged with DMSO (1 mL) and trimethylsulfoxonium iodide (50 mg, 0.23 mmol). Potassium tert-butoxide (26 mg, 0.23 mmol) was added and then the reaction was stirred at room temperature for 5 minutes. A solution of 6-(((R)-1-cyclobutylethyl)amino)-7-((trans-4-methylcyclohexyl)methyl)-8-(1-phenylvinyl)-7H-purine-2-carbonitrile (70 mg, 0.15 mmol) in anhydrous THF (0.5 mL) was then added dropwise to the reaction and the reaction was stirred at room temperature for 1.5 hours. The reaction was then diluted with EtOAc (10 mL), the organic layer was washed with water and brine, dried over Na₂SO₄, filtered, and concentrated in vacuo. Purification of the residue on a RediSep 12 g silica gel column (0 to 50% EtOAc/hexanes) afforded 6-(((R)-1-cyclobutylethyl)amino)-7-((trans-4-methylcyclohexyl)methyl)-8-(1-phenylcyclopropyl)-7H-purine-2-carbonitrile. ¹H NMR (300 MHz, CDCl₃) δ 7.19-7.26 (m, 5H), 4.39-4.50 (m, 2H), 3.68-3.82 (m, 2H), 2.47 (m, 1H), 1.53-1.96 (m, 11H), 1.38-1.48 (m, 3H), 1.13-1.19 (m, 4H), 0.69-0.90 (m, 8H). MS (ES)=469 (M+1)⁺.

Step 3: Using a procedure analogous to that described in Example 10.1 (steps 5 and 6) and starting with 6-(((R)-1-cyclobutylethyl)amino)-7-((trans-4-methylcyclohexyl)methyl)-8-(1-phenylcyclopropyl)-7H-purine-2-carbonitrile, 6-{[(1R)-1-cyclobutylethyl]amino}-7-[(trans-4-methylcyclohexyl)methyl]-8-(1-phenylcyclopropyl)-7H-purine-2-carboxylic acid was prepared. ¹H NMR (400 MHz, CD₃OD) δ 7.24-7.31 (m, 5H), 4.54 (br s, 1H), 3.88-4.12 (m, 2H), 2.47 (m, 1H), 2.07 (m, 1H), 1.85-1.99 (m, 5H), 1.71-1.78 (m, 2H), 1.41-1.63 (m, 6H), 1.28-1.37 (m, 2H), 1.18 (m, 1H), 1.12 (d, J=6.4 Hz, 3H), 0.98 (m, 1H), 0.87-0.92 (m, 2H), 0.78 (d, J=6.4 Hz, 3H). MS (ES)=488 (M+1)⁺.

Example 20.5

3-[6-{[(1R)-1-cyclobutylethyl]amino}-7-[(trans-4-methylcyclohexyl)methyl]-8-(1-phenylcyclopropyl)-7H-purin-2-yl]-1,2,4-oxadiazol-5(4H)-one

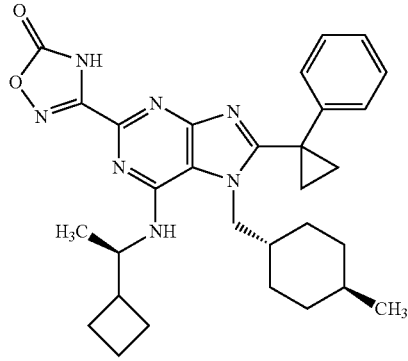 [SMILES: C[C@@H](Nc1nc(-c2noc(=O)[nH]2)nc2nc(C3(c4ccccc4)CC3)n(C[C@H]3CC[C@H](C)CC3)c12)C1CCC1]

Using a procedure analogous to that in Example 16.1 (Step 3 and 4), and starting with 6-(((R)-1-cyclobutylethyl)amino)-7-((trans-4-methylcyclohexyl)methyl)-8-(1-phenylcyclopropyl)-7H-purine-2-carbonitrile (Example 20.4, step 2), 3-[6-{[(1R)-1-cyclobutylethyl]amino}-7-[(trans-4-methylcyclohexyl)methyl]-8-(1-phenylcyclopropyl)-7H-purin-2-yl]-1,2,4-oxadiazol-5(4H)-one was prepared. ¹H NMR (300 MHz, CD₃OD) δ 7.24-7.32 (m, 5H), 4.54 (br s, 1H), 4.07-4.13 (m, 2H), 2.47 (m, 1H), 2.00-2.06 (m, 3H), 1.74-1.90 (m, 3H), 1.52-1.60 (m, 5H), 1.31-1.39 (m, 7H), 1.27 (d, J=7.8 Hz, 3H), 0.88 (d, J=6.4 Hz, 3H), 0.80-0.87 (m, 2H). MS (ES)=528 (M+1)⁺.

Example 20.6

6-{[(1R)-1-cyclobutylethyl]amino}-8-(2,2-dimethylpropyl)-7-[(trans-4-methylcyclohexyl)methyl]-7H-purine-2-carboxylic acid

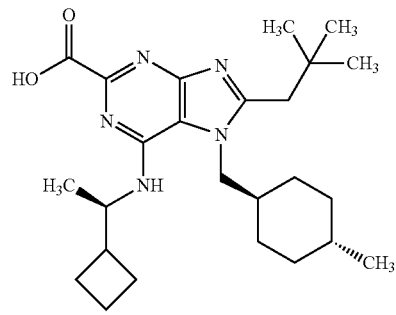 [SMILES: C[C@@H](Nc1nc(C(=O)O)nc2nc(CC(C)(C)C)n(C[C@H]3CC[C@H](C)CC3)c12)C1CCC1]

Using a procedure analogous to that described in Example 20.1 and starting with 3,3-dimethylbutanoic acid, 6-{[(1R)-1-cyclobutylethyl]amino}-8-(2,2-dimethylpropyl)-7-[(trans-4-methylcyclohexyl)methyl]-7H-purine-2-carboxylic acid was prepared. $^1$H NMR (400 MHz, CD$_3$OD) δ 4.79-4.81 (m, 1H), 4.50 (dd, J=12.0, 4.0 Hz, 1H), 4.26 (dd, J=16.0, 8.0 Hz, 1H), 2.81-2.94 (m, 2H), 2.53-2.57 (m, 1H), 1.87-2.12 (m, 7H), 1.59-1.74 (m, 4H), 1.31-1.37 (m, 2H), 1.16 (d, J=8.0 Hz, 3H), 1.12-1.15 (m, 1H), 1.03 (s, 9H), 0.90-0.91 (m, 1H), 0.89 (d, J=8.0 Hz, 3H), 0.73-0.79 (m, 1H). MS (ES)=442 (M+1)$^+$.

Example 20.7

3-(6-{[(1R)-1-cyclobutylethyl]amino}-8-(2,2-dimethylpropyl)-7-[(trans-4-methylcyclohexyl)methyl]-7H-purin-2-yl)-1,2,4-oxadiazol-5(4H)-one

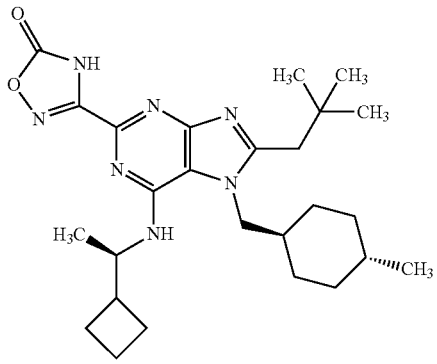 [SMILES: C[C@@H](Nc1nc(-c2noc(=O)[nH]2)nc2nc(CC(C)(C)C)n(C[C@H]3CC[C@H](C)CC3)c12)C1CCC1]

Using a procedure analogous to that described in Example 16.1 (Step 3 and 4), and starting with 6-(((R)-1-cyclobutylethyl)amino)-7-((trans-4-methylcyclohexyl)methyl)-8-neopentyl-7H-purine-2-carbonitrile (an intermediate in the synthesis of Example 20.6), 3-(6-{[(1R)-1-cyclobutylethyl]amino}-8-(2,2-dimethylpropyl)-7-[(trans-4-methylcyclohexyl)methyl]-7H-purin-2-yl)-1,2,4-oxadiazol-5(4H)-one was prepared. $^1$H NMR (400 MHz, CD$_3$OD) δ 4.64-4.71 (m, 1H), 4.45-4.48 (m, 1H), 4.18-4.24 (m, 1H), 2.93 (d, J=16.0 Hz, 1H), 2.83 (d, J=16.0 Hz, 1H), 2.52-2.58 (m, 1H), 1.61-2.12 (m, 10H), 1.32-1.36 (m, 1H), 1.24-1.30 (m, 2H), 1.16 (d, J=8.0 Hz, 3H), 1.12-1.15 (m, 1H), 1.03 (s, 9H), 0.90-0.91 (m, 1H), 0.89 (d, J=8.0 Hz, 3H), 0.73-0.79 (m, 1H). MS (APCI)=482 (M+1)$^+$.

Example 20.8

3-[6-{[(1R)-1-cyclobutylethyl]amino}-7-[(trans-4-methylcyclohexyl)methyl]-8-(1-phenylcyclobutyl)-7H-purin-2-yl]-1,2,4-oxadiazol-5(4H)-one

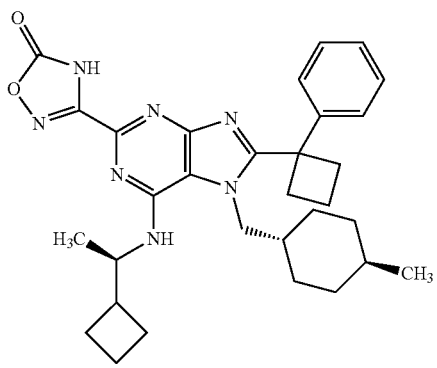 [SMILES: C[C@@H](Nc1nc(-c2noc(=O)[nH]2)nc2nc(C3(c4ccccc4)CCC3)n(C[C@H]3CC[C@H](C)CC3)c12)C1CCC1]

Using a procedure analogous to that in Example 16.1 (Step 3 and 4), and starting with 6-(((R)-1-cyclobutylethyl)amino)-7-((trans-4-methylcyclohexyl)methyl)-8-(1-phenylcyclobutyl)-7H-purine-2-carbonitrile (Example 20.1, Step 5), 3-[6-{[(1R)-1-cyclobutylethyl]amino}-7-[(trans-4-methylcyclohexyl)methyl]-8-(1-phenylcyclobutyl)-7H-purin-2-yl]-1,2,4-oxadiazol-5(4H)-one was prepared. $^1$H NMR (400 MHz, CD$_3$OD) δ 7.46 (d, J=7.6 Hz, 2H), 7.36-7.39 (m, 2H), 7.25 (m, 1H), 4.76 (m, 1H), 4.00 (m, 1H), 3.84 (m, 1H), 3.76 (m, 1H), 3.12 (m, 1H), 2.87-2.97 (m, 2H), 2.67 (m, 1H), 2.48 (m, 1H), 1.70-2.07 (m, 11H), 1.46 (m, 1H), 1.36 (m, 1H), 1.11-1.19 (m, 4H), 0.84-1.19 (m, 3H), 0.69-0.76 (m, 3H). MS (ES)=542 (M+1)$^+$.

Example 20.9

5-[6-{[(1R)-1-cyclobutylethyl]amino}-7-[(trans-4-methylcyclohexyl)methyl]-8-(1-phenylcyclobutyl)-7H-purin-2-yl]-4-methyl-2,4-dihydro-3H-1,2,4-triazol-3-one

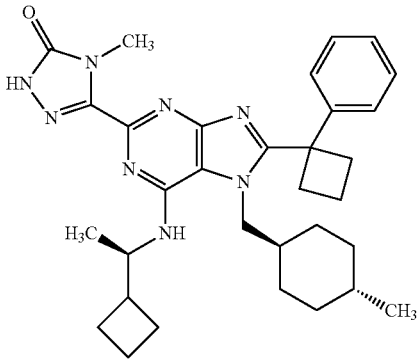 [SMILES: C[C@@H](Nc1nc(-c2n[nH]c(=O)n2C)nc2nc(C3(c4ccccc4)CCC3)n(C[C@H]3CC[C@H](C)CC3)c12)C1CCC1]

Step 1: To a mixture of 6-{[(1R)-1-cyclobutylethyl]amino}-7-[(trans-4-methylcyclohexyl)methyl]-8-(1-phenylcyclobutyl)-7H-purine-2-carboxylic acid (Example 20.1) (170 mg, 0.33 mmol) in dichloromethane (3.0 mL) was added oxalyl chloride (215 mg, 1.69 mmol) dropwise at 0° C. and the reaction mixture was stirred for 1 hour at room temperature under a nitrogen atmosphere. Next, the reaction mixture was concentrated to dryness and the residue was dissolved in THF (8 mL). This solution was added dropwise at 0° C. to a flask containing hydrazine (1M in THF, 6.5 mL, 6.5 mmol) and the reaction was stirred for 1 hour at room temperature under a nitrogen atmosphere. The reaction mixture was concentrated; the residue was dissolved in ethyl acetate (10 mL) and washed with water (5 mL). The combined organic extracts were washed with brine (5 mL), dried over anhydrous Na$_2$SO$_4$, filtered, and concentrated to afford crude 6-(((R)-1-cyclobutylethyl)amino)-7-(((trans)-4-methylcyclohexyl)methyl)-8-(1-phenylcyclobutyl)-7H-purine-2-carbohydrazide. MS (ES)=516 (M+1)$^+$.

Step 2: To a mixture 6-(((R)-1-cyclobutylethyl)amino)-7-(((trans)-4-methylcyclohexyl)methyl)-8-(1-phenylcyclobutyl)-7H-purine-2-carbohydrazide (70 mg, 0.13 mmol) in dichloromethane (3.0 mL) was added p-tolyl methylcarbamate (39 mg, 0.20 mmol) and DIPEA (22 mg, 0.17 mmol) and the reaction mixture was stirred for 16 hours at room temperature under a nitrogen atmosphere. Then reaction mixture was concentrated to dryness under reduced pressure and hexane was added to the resulting residue. The resulting solid was collected by filtration under vacuum to afford crude 2-(6-(((R)-1-cyclobutylethyl)amino)-7-(((trans)-4-methylcyclohexyl)methyl)-8-(1-phenylcyclobutyl)-7H-purine-2-carbonyl)-N-methylhydrazinecarboxamide. MS (ES)=573 (M+1)$^+$.

Step 3: Aqueous NaOH (5 N, 0.124 mL, 0.62 mmol) was added to 2-(6-(((R)-1-cyclobutylethyl)amino)-7-(((trans)-4-methylcyclohexyl)methyl)-8-(1-phenylcyclobutyl)-7H-purine-2-carbonyl)-N-methylhydrazinecarboxamide (60 mg, 0.10 mmol) the reaction mixture was heated at 100° C. for 2 hours under nitrogen atmosphere. Next, the reaction mixture was cooled to 0° C., neutralized with aqueous 1 N HCl and extracted with ethyl acetate (2×5 mL). The combined organic extracts were washed with brine (5 mL), dried over anhydrous Na$_2$SO$_4$, filtered, and concentrated to dryness. Purification of the residue on a RediSep 4 g Biotage C18 column (0 to 100% water/acetonitrile) afforded 5-[6-{[(1R)-1-cyclobutylethyl]amino}-7-[(trans-4-methylcyclohexyl)methyl]-8-(1-phenylcyclobutyl)-7H-purin-2-yl]-4-methyl-2,4-dihydro-3H-1,2,4-triazol-3-one. $^1$H NMR (400 MHz, CD$_3$OD) δ 7.48 (d, J=7.2 Hz, 2H), 7.40 (d, J=7.6 Hz, 2H), 7.31 (t, J=7.6 Hz, 1H), 4.60 (m, 1H), 4.08 (m, 1H), 3.85 (m, 1H), 3.75 (s, 3H), 3.21 (m, 1H), 2.92-3.01 (m, 2H), 2.70 (m, 1H), 2.50 (m, 1H), 2.09-2.19 (m, 2H), 1.98-2.02 (m, 3H), 1.86-1.92 (m, 4H), 1.51 (m, 1H), 1.39 (m, 1H), 1.18 (d, J=6.4 Hz, 3H), 0.97-1.08 (m, 3H), 0.82-0.94 (m, 2H), 0.72 (d, J=6.4 Hz, 3H), 0.41-0.60 (m, 3H). MS (ES)=555 (M+1)$^+$.

Example 20.10 was prepared starting from 6-(((R)-1-cyclobutylethyl)amino)-7-((trans-4-methylcyclohexyl)methyl)-8-(1-phenylcyclobutyl)-7H-purine-2-carbonitrile (Example 20.1, Step 5) using procedures analogous to those described in Example 16.3)

Example 20.11

3-[6-(5-chloropyridin-3-yl)-7-[(trans-4-methylcyclohexyl)methyl]-8-(1-phenylcyclobutyl)-7H-purin-2-yl]-1,2,4-oxadiazol-5(4H)-one

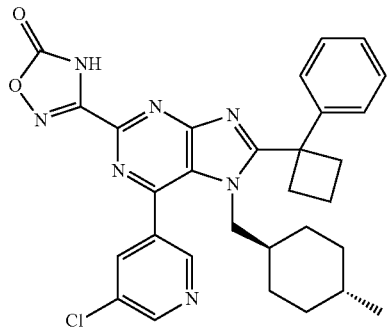 [SMILES: C[C@H]1CC[C@H](Cn2c(C3(c4ccccc4)CCC3)nc3nc(-c4noc(=O)[nH]4)nc(-c4cncc(Cl)c4)c32)CC1]

Step 1: 1,4-dioxane was added to 2,6-dichloro-7-(trans)-4-methylcyclohexyl)methyl)-8-(1-phenylcyclobutyl)-7H-purine (Example 20.1, Step 3; 300 mg, 0.70 mmol), (5-chloropyridin-3-yl)boronic acid (121 mg, 0.77 mmol), and cesium carbonate (1.14 g, 3.50 mmol). The mixture was degassed and then refilled with argon (3 times). PdCl$_2$(dppf) (102 mg, 0.14 mmol) was then added and the mixture was degassed with argon for another 15 minutes. The reaction was sealed and heated at 90° C. for 3 hours. The reaction was then diluted with water, extracted with EtOAc (2×50 mL), and the organics were washed with water (50 mL). The combined organic extracts were dried over anhydrous Na$_2$SO$_4$, filtered, and concentrated. The residue was purified on a silica gel column (0 to 100% EtOAc/hexanes) to afford 2-chloro-6-(5-chloropyridin-3-yl)-7-(((trans)-4-methylcyclohexyl)methyl)-8-(1-phenylcyclobutyl)-7H-purine. MS (ES)=506 (M+1)$^+$.

Step 2: Palladium(II) acetate (70 mg, 0.312 mmol) and (R)-(+)-2,2'-bis(diphenylphosphino)-1,1'-binaphthyl (195 mg, 0.313 mmol) were combined in a sealable tube. N,N-dimethylacetamide (18.7 mL) was added and the mixture was degassed for three minutes with nitrogen. Sulfuric acid (0.015 mL) was added and the mixture was degassed again for three minutes with nitrogen. The tube was sealed and heated to 80° C. for 30 minutes. The catalyst solution was cooled to room temperature and added to a separate nitrogen purged flask containing 2-chloro-6-(5-chloropyridin-3-yl)-7-(((trans)-4-methylcyclohexyl)methyl)-8-(1-phenylcyclobutyl)-7H-purine (0.5 g, 0.9 mmol), zinc cyanide (46 mg, 0.45 mmol), and zinc (6 mg, 0.09 mmol). The flask was purged with nitrogen for five minutes, sealed, and heated to 100° C. for 2 hrs. The reaction was then cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford 6-(5-chloropyridin-3-yl)-7-(((trans)-4-methylcyclohexyl)methyl)-8-(1-phenylcyclobutyl)-7H-purine-2-carbonitrile. MS (ES)=497 (M+1)$^+$.

Steps 3 and 4: Using a procedure similar to that described in Example 16.1 (Steps 3 and 4), 6-(5-chloropyridin-3-yl)-7-(((trans)-4-methylcyclohexyl)methyl)-8-(1-phenylcyclobutyl)-7H-purine-2-carbonitrile was converted to 3-[6-(5-chloropyridin-3-yl)-7-[(trans-4-methylcyclohexyl)methyl]-8-(1-phenylcyclobutyl)-7H-purin-2-yl]-1,2,4-oxadiazol-5(4H)-one. $^1$H NMR (400 MHz, CD$_3$OD) δ 8.85 (dt, J=9.2, 2.0 Hz, 1H), 8.81 (d, J=2.0 Hz, 1H), 8.39 (m, 1H), 7.51 (d, J=7.6 Hz, 2H), 7.38 (d, J=7.2 Hz, 2H), 7.27 (t, J=7.2 Hz, 1H), 3.65 (d, J=7.2 Hz, 2H), 3.18-3.27 (m, 3H), 2.75-2.90 (m, 2H), 2.05 (m, 1H), 1.90 (m, 1H), 1.55 (m, 1H), 1.11-1.36 (m, 3H), 0.70-1.34 (m, 3H), 0.61 (d, J=6.4 Hz, 3H), 0.30-0.53 (m, 2H). MS (ES)=556 (M+1)$^+$.

Example 20.12

5-[6-(5-chloropyridin-3-yl)-7-[(trans-4-methylcyclohexyl)methyl]-8-(1-phenylcyclobutyl)-7H-purin-2-yl]-1,3,4-oxadiazol-2(3H)-one

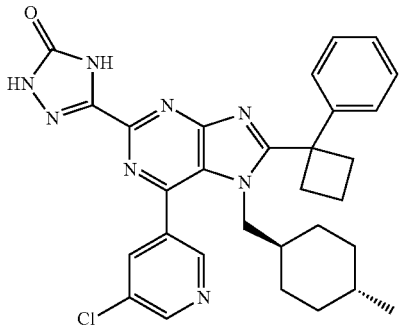 [SMILES: C[C@H]1CC[C@H](Cn2c(C3(c4ccccc4)CCC3)nc3nc(-c4n[nH]c(=O)[nH]4)nc(-c4cncc(Cl)c4)c32)CC1]

Using a procedure similar to that described in Example 16.7 (Steps 1-3), 6-(5-chloropyridin-3-yl)-7-(((trans)-4-methylcyclohexyl)methyl)-8-(1-phenylcyclobutyl)-7H-purine-2-carbonitrile (Example 20.11, Step 2) was converted to 5-[6-(5-chloropyridin-3-yl)-7-[(trans-4-methylcyclohexyl)methyl]-8-(1-phenylcyclobutyl)-7H-purin-2-yl]-1,3,4-oxadiazol-2(3H)-one. $^1$H NMR (400 MHz, CD$_3$OD) δ 8.81 (dd, J=13.2, 2.0 Hz, 2H), 8.34 (d, J=2.0 Hz, 1H), 7.52 (d, J=8.8 Hz, 2H), 7.39 (d, J=7.2 Hz, 2H), 7.27 (d, J=7.2 Hz, 1H), 3.65 (d, J=7.2 Hz, 2H), 3.22 (m, 1H), 2.85 (m, 1H), 2.20 (m, 1H), 2.05 (m, 1H), 1.85 (m, 1H), 1.18-1.39 (m, 4H), 0.84-0.96 (m, 2H), 0.77 (m, 1H), 0.61 (d, J=6.8 Hz, 3H), 0.40-0.56 (m, 2H), 0.09-0.20 (m, 2H). MS (ES)=556 (M+1)$^+$.

Example 20.13

5-[6-(5-chloro-1-oxidopyridin-3-yl)-7-[(trans-4-methylcyclohexyl)methyl]-8-(1-phenylcyclobutyl)-7H-purin-2-yl]-1,3,4-oxadiazol-2(3H)-one

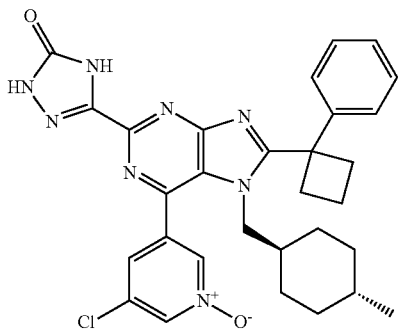 [SMILES: C[C@H]1CC[C@H](Cn2c(C3(c4ccccc4)CCC3)nc3nc(-c4n[nH]c(=O)[nH]4)nc(-c4cc(Cl)c[n+]([O-])c4)c32)CC1]

To a 0° C. solution of 5-[6-(5-chloropyridin-3-yl)-7-[(trans-4-methylcyclohexyl)methyl]-8-(1-phenylcyclobutyl)-7H-purin-2-yl]-1,3,4-oxadiazol-2(3H)-one (Example 20.12, 20 mg, 0.036 mmol) in dichloromethane (2.0 mL) was added mCPBA (31 mg, 0.10 mmol) and the reaction mixture was stirred for 12 hours at room temperature under a nitrogen atmosphere. The reaction was quenched with aqueous saturated NaHCO$_3$ solution (5 mL) and extracted with dichloromethane (2×5 mL). The combined organic extracts were washed with brine (5 mL), dried over anhydrous Na$_2$SO$_4$, filtered, and concentrated. Purification of the residue on a C18 column (0 to 100% water/acetonitrile) afforded 5-[6-(5-chloro-1-oxidopyridin-3-yl)-7-[(trans-4-methylcyclohexyl)methyl]-8-(1-phenylcyclobutyl)-7H-purin-2-yl]-1,3,4-oxadiazol-2(3H)-one. $^1$H NMR (400 MHz, CD$_3$OD) δ 8.75 (s, 1H), 8.66 (s, 1H), 8.11 (s, 1H), 7.52 (d, J=7.6 Hz, 2H), 7.38 (d, J=8.0 Hz, 2H), 7.27 (d, J=7.2 Hz, 1H), 3.67 (d, J=7.2 Hz, 2H), 3.20 (m, 1H), 2.84 (m, 1H), 2.18 (m, 1H), 2.04 (m, 1H), 0.79-0.30 (m, 5H), 0.64 (d, J=7.2 Hz, 3H), 0.49-0.53 (m, 5H), 0.20-0.30 (m, 2H). MS (ES)=572 (M+1)$^+$.

Examples in Table 20 have been described above or were prepared using procedures similar to those described above.

TABLE 20

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 20.1 | 1.455 | 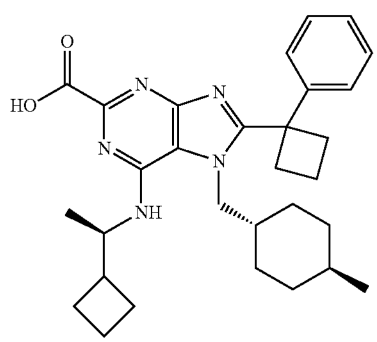 [SMILES: C[C@@H](Nc1nc(C(=O)O)nc2nc(C3(c4ccccc4)CCC3)n(C[C@H]3CC[C@H](C)CC3)c12)C1CCC1] | 6-{[(1R)-1-cyclobutylethyl]amino}-7-[(trans-4-methylcyclohexyl)methyl]-8-(1-phenylcyclobutyl)-7H-purine-2-carboxylic acid | | 502 | 502 |
| 20.2 | 3.451 | 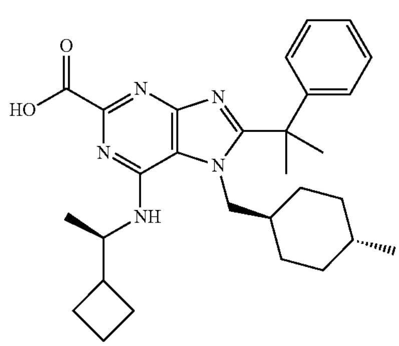 [SMILES: C[C@@H](Nc1nc(C(=O)O)nc2nc(C(C)(C)c3ccccc3)n(C[C@H]3CC[C@H](C)CC3)c12)C1CCC1] | 6-{[(1R)-1-cyclobutylethyl]amino}-7-[(trans-4-methylcyclohexyl)methyl]-8-(1-methyl-1-phenylethyl)-7H-purine-2-carboxylic acid | | 490 | 490 |

TABLE 20-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 20.3 | 8.575 | 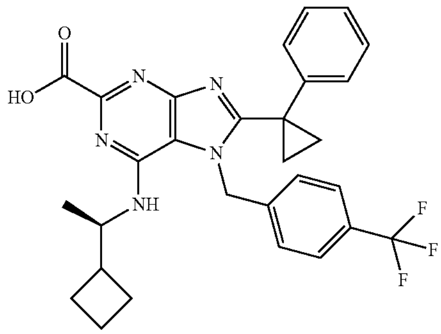 [SMILES: C[C@@H](Nc1nc(C(=O)O)nc2nc(C3(c4ccccc4)CC3)n(Cc3ccc(C(F)(F)F)cc3)c12)C1CCC1] | 6-{[(1R)-1-cyclobutylethyl]amino}-8-(1-phenylcyclopropyl)-7-[4-(trifluoromethyl)benzyl]-7H-purine-2-carboxylic acid | | 536 | 536 |
| 20.4 | 2.585 | 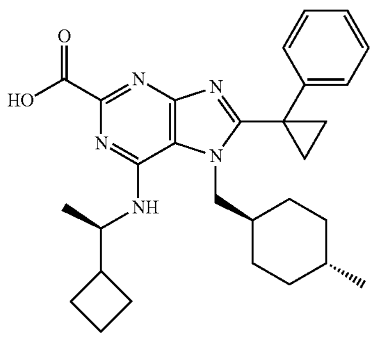 [SMILES: C[C@@H](Nc1nc(C(=O)O)nc2nc(C3(c4ccccc4)CC3)n(C[C@H]3CC[C@H](C)CC3)c12)C1CCC1] | 6-{[(1R)-1-cyclobutylethyl]amino}-7-[(trans-4-methylcyclohexyl)methyl]-8-(1-phenylcyclopropyl)-7H-purine-2-carboxylic acid | | 488 | 488 |
| 20.5 | 4.978 | 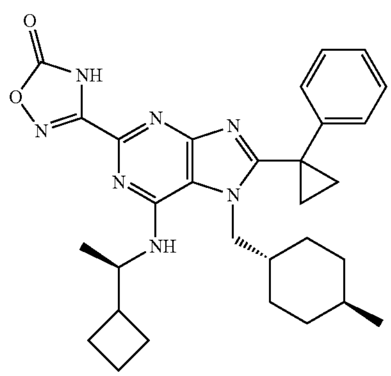 [SMILES: C[C@@H](Nc1nc(-c2noc(=O)[nH]2)nc2nc(C3(c4ccccc4)CC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(1-phenylcyclopropyl)-7H-purin-2-yl]-1,2,4-oxadiazol-5(4H)-one | | 528 | 528 |
| 20.6 | 13.88 | 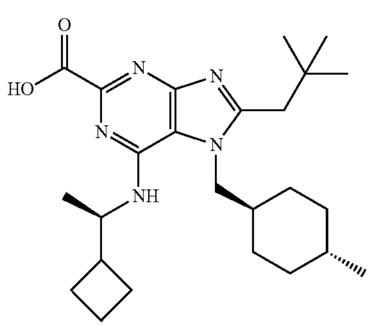 [SMILES: C[C@@H](Nc1nc(C(=O)O)nc2nc(CC(C)(C)C)n(C[C@H]3CC[C@H](C)CC3)c12)C1CCC1] | 6-{[(1R)-1-cyclobutylethyl]amino}-8-(2,2-dimethylpropyl)-7-[(trans-4-methylcyclohexyl)methyl]-7H-purine-2-carboxylic acid | | 442 | 442 |

TABLE 20-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 20.7 | 20.88 | 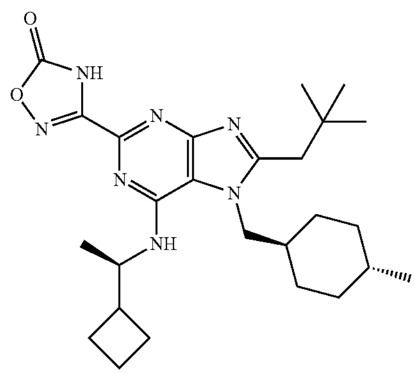 [SMILES: C[C@@H](Nc1nc(-c2noc(=O)[nH]2)nc2nc(CC(C)(C)C)n(C[C@H]3CC[C@H](C)CC3)c12)C1CCC1] | 3-(6-{[(1R)-1-cyclobutylethyl]amino}-8-(2,2-dimethylpropyl)-7-[(trans-4-methylcyclohexyl)methyl]-7H-purin-2-yl)-1,2,4-oxadiazol-5(4H)-one | | 482 | 482 |
| 20.8 | 5.959 | 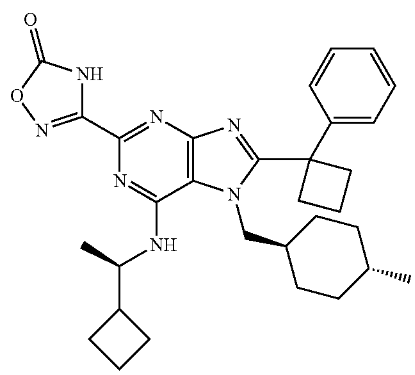 [SMILES: C[C@@H](Nc1nc(-c2noc(=O)[nH]2)nc2nc(C3(c4ccccc4)CCC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(1-phenylcyclobutyl)-7H-purin-2-yl]-1,2,4-oxadiazol-5(4H)-one | | 542 | 542 |
| 20.9 | 84.42 | 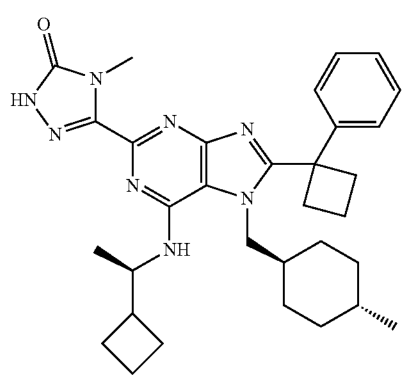 [SMILES: C[C@@H](Nc1nc(-c2n[nH]c(=O)n2C)nc2nc(C3(c4ccccc4)CCC3)n(C[C@H]3CC[C@H](C)CC3)c12)C1CCC1] | 5-[6-{[(1R)-1-cyclobutylethyl]amino}-7-[(trans-4-methylcyclohexyl)methyl]-8-(1-phenylcyclobutyl)-7H-purin-2-yl]-4-methyl-2,4-dihydro-3H-1,2,4-triazol-3-one | | 555 | 555 |
| 20.10 | 28.87 | 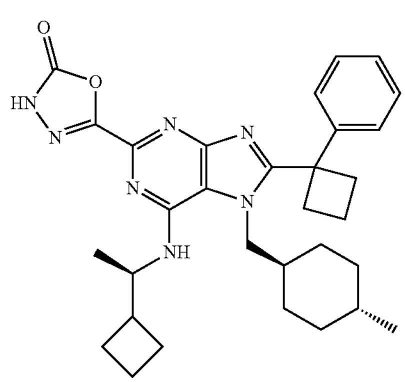 [SMILES: C[C@@H](Nc1nc(-c2n[nH]c(=O)o2)nc2nc(C3(c4ccccc4)CCC3)n(C[C@H]3CC[C@H](C)CC3)c12)C1CCC1] | 5-[6-{[(1R)-1-cyclobutylethyl]amino}-7-[(trans-4-methylcyclohexyl)methyl]-8-(1-phenylcyclobutyl)-7H-purin-2-yl]-1,3,4-oxadiazol-2(3H)-one | | 542 | 542 |

TABLE 20-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 20.11 | 3.390 | 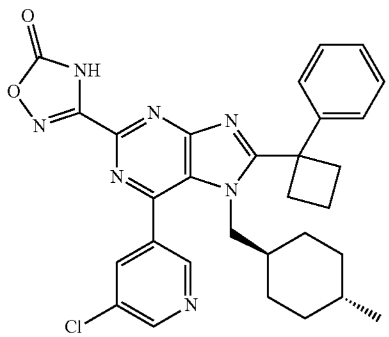 [SMILES: C[C@H]1CC[C@H](Cn2c(C3(c4ccccc4)CCC3)nc3nc(-c4noc(=O)[nH]4)nc(-c4cncc(Cl)c4)c32)CC1] | 3-[6-(5-chloropyridin-3-yl)-7-[(trans-4-methylcyclohexyl)methyl]-8-(1-phenylcyclobutyl)-7H-purin-2-yl]-1,2,4-oxadiazol-5(4H)-one | | 556 | 556 |
| 20.12 | 9.593 | 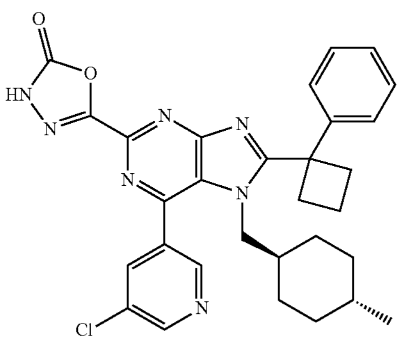 [SMILES: C[C@H]1CC[C@H](Cn2c(C3(c4ccccc4)CCC3)nc3nc(-c4n[nH]c(=O)o4)nc(-c4cncc(Cl)c4)c32)CC1] | 5-[6-(5-chloropyridin-3-yl)-7-[(trans-4-methylcyclohexyl)methyl]-8-(1-phenylcyclobutyl)-7H-purin-2-yl]-1,3,4-oxadiazol-2(3H)-one | | 556 | 556 |
| 20.13 | 22.75 | 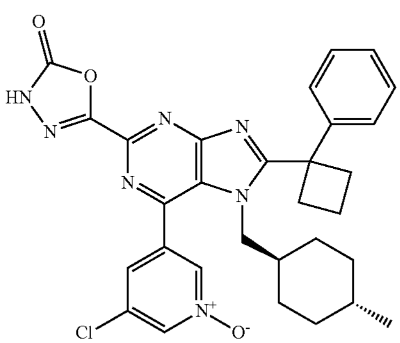 [SMILES: C[C@H]1CC[C@H](Cn2c(C3(c4ccccc4)CCC3)nc3nc(-c4n[nH]c(=O)o4)nc(-c4cc(Cl)c[n+]([O-])c4)c32)CC1] | 5-[6-(5-chloro-1-oxidopyridin-3-yl)-7-[(trans-4-methylcyclohexyl)methyl]-8-(1-phenylcyclobutyl)-7H-purin-2-yl]-1,3,4-oxadiazol-2(3H)-one | | 572 | 572 |
| 20.14 | 6.115 | 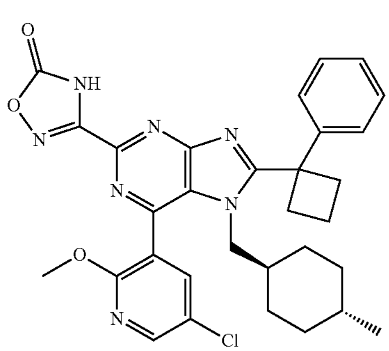 [SMILES: COc1ncc(Cl)cc1-c1nc(-c2noc(=O)[nH]2)nc2nc(C3(c4ccccc4)CCC3)n(C[C@H]3CC[C@H](C)CC3)c12] | 3-[6-(5-chloro-2-methoxypyridin-3-yl)-7-[(trans-4-methylcyclohexyl)methyl]-8-(1-phenylcyclobutyl)-7H-purin-2-yl]-1,2,4-oxadiazol-5(4H)-one | | 586 | 586 |

Example 21.1 and Example 21.2

6-{[(1R)-1-cyclobutylethyl]amino}-8-(2-phenylcyclohexyl)-7-[4-(trifluoromethyl)benzyl]-7H-purine-2-carboxylic acid

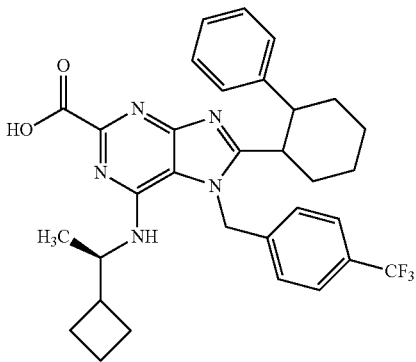 [SMILES: C[C@@H](Nc1nc(C(=O)O)nc2nc(C3CCCCC3c3ccccc3)n(Cc3ccc(C(F)(F)F)cc3)c12)C1CCC1]

Step 1: A solution of 2-phenylcyclohexanone (2.0 g, 11.5 mmol) in DMF (10 mL) was added dropwise to a mixture of NaH (0.87 g, 21.8 mmol, 60%) in DMF (30 mL) at 0° C. The mixture was warmed to room temperature and stirred for 2 hours. 1,1,1-Trifluoro-N-phenyl-N-(trifluoromethylsulfonyl)methanesulfonamide (4.72 g, 13.2 mmol) was then added in one portion and the reaction mixture was stirred at room temperature overnight. The reaction mixture was then treated with water (20 mL) and EtOAc (50 mL). The layers were separated and the organic layer was washed with water and brine, dried over anhydrous $Na_2SO_4$, filtered and concentrated in vacuo. Purification of the residue on a Redisep 24 g silica gel column (0 to 2% EtOAc/hexanes) afforded 3,4,5,6-tetrahydro-[1,1'-biphenyl]-2-yl trifluoromethanesulfonate as a colorless oil. $^1$H NMR (400 MHz, $CDCl_3$) δ 7.24-7.34 (m, 5H), 2.45-2.51 (m, 4H), 1.86-1.89 (m, 2H), 1.76-1.79 (m, 2H).

Step 2: A mixture of 3,4,5,6-tetrahydro-[1,1'-biphenyl]-2-yl trifluoromethanesulfonate (500 mg, 1.63 mmol), bis(pinacolato)diboron (457 mg, 1.80 mmol), potassium carbonate (337 mg, 2.45 mmol), triphenylphosphine (84 mg, 0.33 mmol) and bis(triphenylphosphine) palladium(II) chloride (115 mg, 0.16 mmol) in 1,4-dioxane (10 mL) was degassed under Ar for 10 minutes and then heated at 90° C. in sealed tube for 18 hours. The reaction was then cooled and diluted with EtOAc and water. The layers were separated and the aqueous layer was extracted with EtOAc (3×10 mL). The combined organic layers were washed with water and brine, dried over anhydrous $Na_2SO_4$, filtered and concentrated in vacuo. Purification of the residue on a Redisep 12 g silica gel column (0 to 10% EtOAc/hexanes) afforded 4,4,5,5-tetramethyl-2-(3,4,5,6-tetrahydro-[1,1'-biphenyl]-2-yl)-1,3,2-dioxaborolane as a colorless oil. $^1$H NMR (400 MHz, $CDCl_3$) δ 7.20-7.25 (m, 5H), 2.32-2.36 (m, 2H), 2.22-2.27 (m, 2H), 1.71-1.77 (m, 2H), 1.61-1.66 (m, 2H), 1.08 (s, 12H). MS (ES)=512 (M+1)$^+$.

Step 3: A solution of (R)-8-bromo-6-((1-cyclobutylethyl)amino)-7-(4-(trifluoromethyl)benzyl)-7H-purine-2-carbonitrile (Preparative Example 2.1, 200 mg, 0.42 mmol) and 4,4,5,5-tetramethyl-2-(3,4,5,6-tetrahydro-[1,1'-biphenyl]-2-yl)-1,3,2-dioxaborolane (240 mg, 0.83 mmol) in dimethoxyethane (10 mL) was treated with $Na_2CO_3$ aqueous solution (2.1 mL, 2.1 mmol, 1.0 M) and tetrakis(triphenylphosphine) palladium (0) (120 mg, 0.105 mmol). The reaction mixture was degassed and heated at 150° C. under microwave irradiation for 14 minutes in a sealed tube and then cooled to room temperature. The reaction was diluted with water (5.0 mL) and extracted with EtOAc (3×10 mL). The combined organic layers were washed with water and brine, dried over anhydrous $Na_2SO_4$, filtered and concentrated in vacuo. Purification of the residue on a Redisep 4 g silica gel column (0 to 35% EtOAc/hexanes) afforded (R)-6-((1-cyclobutylethyl)amino)-8-(3,4,5,6-tetrahydro-[1,1'-biphenyl]-2-yl)-7-(4-(trifluoromethyl)benzyl)-7H-purine-2-carbonitrile as a yellow solid. $^1$H NMR (400 MHz, $CDCl_3$) δ 7.48 (d, J=8.2 Hz, 2H), 7.06-7.17 (m, 5H), 6.62 (d, J=8.2 Hz, 2H), 4.97-5.17 (m, 2H), 4.09 (m, 1H), 3.85 (d, J=8.8 Hz, 1H), 1.24-1.87 (m, 14H), 0.86 (m, 1H), 0.67 (d, J=6.0 Hz, 3H). MS (ES)=557 (M+1)$^+$.

Step 4: (R)-6-((1-Cyclobutylethyl)amino)-8-(3,4,5,6-tetrahydro-[1,1'-biphenyl]-2-yl)-7-(4-(trifluoromethyl)benzyl)-7H-purine-2-carbonitrile (110 mg, 0.20 mmol) was dissolved in HCl solution in MeOH (3.0 M, 5.0 mL). The resulting mixture was heated at reflux for 2 hours and concentrated in vacuo. The residue was dissolved in $CH_2Cl_2$ and quenched with sat. aqueous $NaHCO_3$ solution. The aqueous layer was extracted with $CH_2Cl_2$ (3×10 mL). The combined organic layers were washed with brine, dried over anhydrous $Na_2SO_4$, filtered and concentrated in vacuo. Purification of the residue on a Redisep 4 g silica gel column (0 to 70% EtOAc/hexanes) afforded (R)-methyl 6-((1-cyclobutylethyl)amino)-8-(3,4,5,6-tetrahydro-[1,1'-biphenyl]-2-yl)-7-(4-(trifluoromethyl)benzyl)-7H-purine-2-carboxylate as a pale yellow solid. $^1$H NMR (400 MHz, $CDCl_3$) δ 7.45 (d, J=8.0 Hz, 2H), 7.02-7.15 (m, 5H), 6.62 (d, J=8.0 Hz, 2H), 4.94-5.23 (m, 2H), 4.22 (m, 1H), 3.98 (s, 3H), 3.80 (d, J=8.0 Hz, 1H), 1.28-1.85 (m, 14H), 0.87 (m, 1H), 0.70 (d, J=6.4 Hz, 3H). MS (ES)=590 (M+1)$^+$.

Step 5: A round bottom flask was charged with Pd/C (15 mg) under $N_2$. A solution of (R)-methyl 6-((1-cyclobutylethyl)amino)-8-(3,4,5,6-tetrahydro-[1,1'-biphenyl]-2-yl)-7-(4-(trifluoromethyl)benzyl)-7H-purine-2-carboxylate (25 mg, 0.04 mmol) in MeOH (3.0 mL) was added. The reaction mixture was stirred at room temperature under $H_2$ (1 atm) overnight, and then filtered through celite, rinsing with MeOH. The filtrate was concentrated in vacuo and purification of the residue on a Redisep 4 g silica gel column (0 to 70% EtOAc/hexanes) afforded cis-diastereomer A, methyl 6-(((R)-1-cyclobutylethyl)amino)-8-(2-phenylcyclohexyl)-7-(4-(trifluoromethyl)benzyl)-7H-purine-2-carboxylate as a white solid and cis-diastereomer B, methyl 6-(((R)-1-cyclobutylethyl)amino)-8-(2-phenylcyclohexyl)-7-(4-(trifluoromethyl)benzyl)-7H-purine-2-carboxylate as a white solid. cis-diastereomer A, methyl 6-(((R)-1-cyclobutylethyl)amino)-8-(2-phenylcyclohexyl)-7-(4-(trifluoromethyl)benzyl)-7H-purine-2-carboxylate: $^1$H NMR (400 MHz, $CDCl_3$) δ 7.51 (d, J=8.0 Hz, 2H), 7.09-7.18 (m, 3H), 6.99 (d, J=8.0 Hz, 2H), 6.67 (d, J=8.0 Hz, 2H), 4.85 (d, J=18.4 Hz, 1H), 4.78 (d, J=18.4 Hz, 1H), 4.26 (m, 1H), 4.00 (s, 3H), 3.89 (d, J=7.6 Hz, 1H), 3.36 (br s, 1H), 3.03-3.09 (m, 2H), 2.59 (m, 1H), 1.20-2.10 (m, 12H), 0.88 (m, 1H), 0.80 (d, J=6.4 Hz, 3H). MS (ES)=592 (M+1)$^+$. cis-diastereomer B, methyl 6-(((R)-1-cyclobutylethyl)amino)-8-(2-phenylcyclohexyl)-7-(4-(trifluoromethyl)benzyl)-7H-purine-2-carboxylate: $^1$H NMR (400 MHz, $CDCl_3$) δ 7.47 (d, J=8.1 Hz, 2H), 7.06-7.15 (m, 5H), 6.61 (d, J=8.1 Hz, 2H), 4.95 (d, J=18.5 Hz, 1H), 4.81 (d, J=18.5 Hz, 1H), 4.25 (m, 1H), 4.00 (s, 3H), 3.91 (d, J=7.8 Hz, 1H), 3.36 (br s, 1H), 3.07-3.14 (m, 2H), 2.55 (m, 1H), 1.18-2.10 (m, 12H), 0.82 (m, 1H), 0.81 (d, J=6.3 Hz, 3H). MS (ES)=592 (M+1)$^+$.

Step 6: Using a procedure analogous to that described in Example 10.1 (Step 6) and starting with methyl 6-(((R)-1-cyclobutylethyl)amino)-8-(2-phenylcyclohexyl)-7-(4-(trifluoromethyl)benzyl)-7H-purine-2-carboxylate (diastereomer A); 6-{[(1R)-1-cyclobutylethyl]amino}-8-(2-phenylcyclohexyl)-7-[4-(trifluoromethyl)benzyl]-7H-purine-2-carboxylic acid (diastereomer A), Example 21.1, was prepared. $^1$H NMR (400 MHz, CD$_3$OD) δ 7.52 (d, J=8.2 Hz, 2H), 7.01-7.11 (m, 5H), 6.78 (d, J=8.2 Hz, 2H), 5.28 (d, J=18.6 Hz, 1H), 5.12 (d, J=18.6 Hz, 1H), 4.51 (dq, J=9.0, 6.4 Hz, 1H), 3.64 (br s, 1H), 3.14 (m, 1H), 2.91 (m, 1H), 2.45 (m, 1H), 1.95-2.09 (m, 3H), 1.79-1.91 (m, 2H), 1.55-1.68 (m, 6H), 1.30-1.40 (m, 2H), 0.85 (d, J=6.4 Hz, 3H). MS (ES)=578 (M+1)$^+$.

Using a procedure analogous to that described in Example 10.1 (Step 6) and starting with methyl 6-(((R)-1-cyclobutylethyl)amino)-8-(2-phenylcyclohexyl)-7-(4-(trifluoromethyl)benzyl)-7H-purine-2-carboxylate (diastereomer B), 6-{[(1R)-1-cyclobutylethyl]amino}-8-(2-phenylcyclohexyl)-7-[4-(trifluoromethyl)benzyl]-7H-purine-2-carboxylic acid (diastereomer B), Example 21.2, was prepared. $^1$H NMR (400 MHz, CD$_3$OD) δ 7.43 (d, J=8.0 Hz, 2H), 7.03-7.09 (m, 5H), 6.60 (d, J=8.0 Hz, 2H), 5.44 (br s, 2H), 4.55 (dq, J=9.2, 6.4 Hz, 1H), 3.67 (br s, 1H), 3.07-3.13 (m, 2H), 1.79-2.24 (m, 6H), 1.63-1.73 (m, 6H), 1.34-1.52 (m, 2H), 0.92 (d, J=6.4 Hz, 3H). MS (ES)=578 (M+1)$^+$.

Example 21.3

6-{[(1R)-1-cyclobutylethyl]amino}-8-(2-phenylcyclohex-1-en-1-yl)-7-[4-(trifluoromethyl)benzyl]-7H-purine-2-carboxylic acid

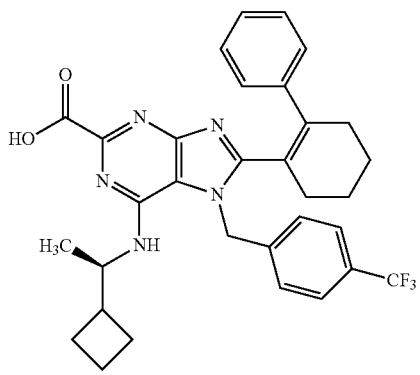 [SMILES: C[C@@H](Nc1nc(C(=O)O)nc2nc(C3=C(c4ccccc4)CCCC3)n(Cc3ccc(C(F)(F)F)cc3)c12)C1CCC1]

Using a procedure analogous to that described in Example 10.1 (Step 6) and starting with (R)-methyl 6-((1-cyclobutylethyl)amino)-8-(3,4,5,6-tetrahydro-[1,1'-biphenyl]-2-yl)-7-(4-(trifluoromethyl)benzyl)-7H-purine-2-carboxylate (Example 21.1, step 4), 6-{[(1R)-1-cyclobutylethyl]amino}-8-(2-phenylcyclohex-1-en-1-yl)-7-[4-(trifluoromethyl)benzyl]-7H-purine-2-carboxylic acid was prepared. $^1$H NMR (400 MHz, CD$_3$OD) δ 7.53-7.64 (m, 2H), 7.05-7.22 (m, 5H), 6.83-6.92 (m, 2H), 5.36 (br s, 2H), 4.46 (dq, J=9.0, 6.4 Hz, 1H), 2.64-2.83 (m, 2H), 1.83-1.98 (m, 6H), 1.51-1.70 (m, 4H), 1.22-1.40 (m, 3H), 0.92 (d, J=6.4 Hz, 3H). MS (ES)=576 (M+1)$^+$.

Example 21.4

6-{[(1R)-1-cyclobutylethyl]amino}-8-(2-phenylcyclopent-1-en-1-yl)-7-[4-(trifluoromethyl)benzyl]-7H-purine-2-carboxylic acid

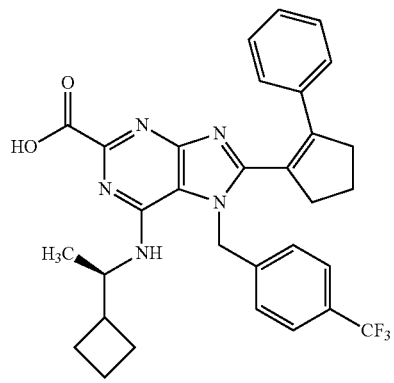 [SMILES: C[C@@H](Nc1nc(C(=O)O)nc2nc(C3=C(c4ccccc4)CCC3)n(Cc3ccc(C(F)(F)F)cc3)c12)C1CCC1]

Using procedures analogous to that described in Example 21.1 and 21.3 and starting with (R)-8-bromo-6-((1-cyclobutylethyl)amino)-7-(4-(trifluoromethyl)benzyl)-7H-purine-2-carbonitrile (Preparative Example 2.1) and 2-phenylcyclopentanone, 6-{[(1R)-1-cyclobutylethyl]amino}-8-(2-phenylcyclopent-1-en-1-yl)-7-[4-(trifluoromethyl)benzyl]-7H-purine-2-carboxylic acid was prepared. $^1$H NMR (300 MHz, CD$_3$OD) δ 7.51 (d, J=8.4 Hz, 2H), 7.10-7.20 (m, 5H), 7.89 (d, J=8.4 Hz, 2H), 5.40 (d, J=18.0 Hz, 1H), 5.27 (d, J=18.0 Hz, 1H), 4.54 (m, 1H), 2.90-3.07 (m, 3H), 2.83 (m, 1H), 2.11-2.18 (m, 2H), 2.00 (m, 1H), 1.66 (m, 1H), 1.16-1.54 (m, 3H), 1.37-1.45 (m, 2H), 0.88 (d, J=6.3 Hz, 3H). MS (ES)=562 (M+1)$^+$.

Example 21.5

6-{[(1R)-1-cyclobutylethyl]amino}-8-(2-phenylcyclopentyl)-7-[4-(trifluoromethyl)benzyl]-7H-purine-2-carboxylic acid

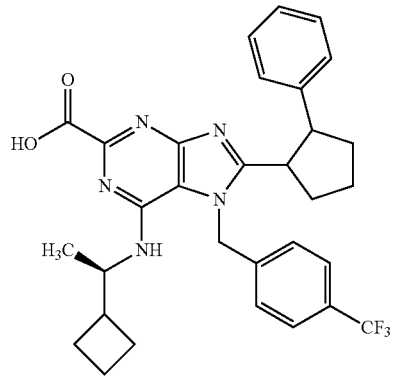 [SMILES: C[C@@H](Nc1nc(C(=O)O)nc2nc(C3CCCC3c3ccccc3)n(Cc3ccc(C(F)(F)F)cc3)c12)C1CCC1]

Using a procedure analogous to that described in Example 21.1 and starting with (R)-8-bromo-6-((1-cyclobutylethyl)amino)-7-(4-(trifluoromethyl)benzyl)-7H-purine-2-carbonitrile (Preparative Example 2.1) and 2-phenylcyclopentanone, 6-{[(1R)-1-cyclobutylethyl]amino}-8-(2-phenylcyclopentyl)-7-[4-(trifluoromethyl)benzyl]-7H-purine-2-carboxylic acid (diastereomer A faster eluting from column) was prepared. $^1$H NMR (400 MHz, CD$_3$OD) δ 7.62

(d, J 8.0 Hz, 2H), 6.96-7.09 (m, 7H), 5.43 (d, J 18.4 Hz, 1H), 5.30 (d, J=18.4 Hz, 1H), 4.54 (m, 1H), 3.89 (m, 1H), 3.68 (m, 1H), 2.49 (m, 1H), 2.36-2.16 (m, 3H), 2.14 (m, 1H), 1.84-1.99 (m, 2H), 1.80 (m, 1H), 1.50-1.62 (m, 3H), 1.16-1.22 (m, 2H), 0.96 (d, J=6.4 Hz, 3H). MS (ES)=564 (M+1)$^+$.

Example 21.6

6-{[(1R)-1-cyclobutylethyl]amino}-8-(2-phenylcyclopentyl)-7-[4-(trifluoromethyl)benzyl]-7H-purine-2-carboxylic acid

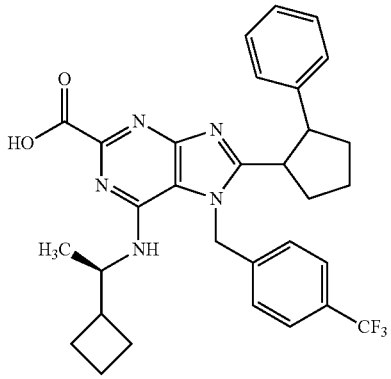 [SMILES: C[C@@H](Nc1nc(C(=O)O)nc2nc(C3CCCC3c3ccccc3)n(Cc3ccc(C(F)(F)F)cc3)c12)C1CCC1]

Using a procedure analogous to that described in Example 21.1 and starting with (R)-8-bromo-6-((1-cyclobutylethyl)amino)-7-(4-(trifluoromethyl)benzyl)-7H-purine-2-carbonitrile (Preparative Example 2.1) and 2-phenylcyclopentanone, 6-{[(1R)-1-cyclobutylethyl]amino}-8-(2-phenylcyclopentyl)-7-[4-(trifluoromethyl)benzyl]-7H-purine-2-carboxylic acid was prepared (diastereomer B—slower eluting from column). $^1$H NMR (400 MHz, CD$_3$OD) δ 7.56 (d, J=8.4 Hz, 2H), 6.97-7.06 (m, 5H), 6.88 (d, J=8.0 Hz, 2H), 5.49 (d, J=18.4 Hz, 1H), 5.21 (d, J=18.4 Hz, 1H), 4.52 (m, 1H), 3.92 (m, 1H), 3.61 (m, 1H), 2.55 (m, 1H), 2.23-2.39 (m, 3H), 2.13-2.06 (m, 2H), 1.83-1.90 (m, 2H), 1.53-1.77 (m, 5H), 0.76 (d, J=6.4 Hz, 3H). MS (ES)=564 (M+1)$^+$.

Example 21.7

6-{[(1R)-1-cyclobutylethyl]amino}-8-(4-phenyltetrahydrofuran-3-yl)-7-[4-(trifluoromethyl)benzyl]-7H-purine-2-carboxylic acid

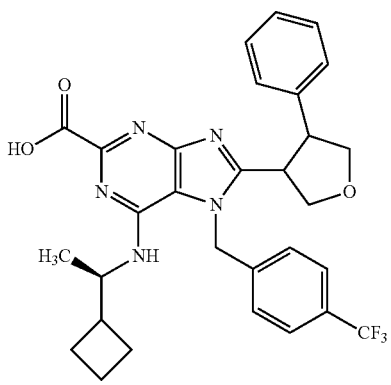 [SMILES: C[C@@H](Nc1nc(C(=O)O)nc2nc(C3COCC3c3ccccc3)n(Cc3ccc(C(F)(F)F)cc3)c12)C1CCC1]

Using a procedure analogous to that described in Example 21.1 and starting with (R)-8-bromo-6-((1-cyclobutylethyl)amino)-7-(4-(trifluoromethyl)benzyl)-7H-purine-2-carbonitrile (Preparative Example 2.1) and 4-phenyldihydrofuran-3(2H)-one, 6-{[(1R)-1-cyclobutylethyl]amino}-8-(4-phenyltetrahydrofuran-3-yl)-7-[4-(trifluoromethyl)benzyl]-7H-purine-2-carboxylic acid was prepared (diastereomer A—faster eluting from column). $^1$H NMR (400 MHz, CD$_3$OD) δ 7.62 (d, J=8.0 Hz, 2H), 7.07-7.11 (m, 5H), 6.99 (d, J=8.0 Hz, 2H), 5.53 (d, J=18.4 Hz, 1H), 5.42 (d, J=18.4 Hz, 1H), 4.77 (m, 1H), 4.52 (m, 1H), 4.38 (m, 1H), 4.20-4.29 (m, 3H), 4.05 (m, 1H), 1.98 (m, 1H), 1.80 (m, 1H), 1.51-1.63 (m, 3H), 1.17-1.29 (m, 2H), 0.95 (d, J=6.4 Hz, 3H). MS (ES)=566 (M+1)$^+$.

Example 21.8

6-{[(1R)-1-cyclobutylethyl]amino}-8-(4-phenyltetrahydrofuran-3-yl)-7-[4-(trifluoromethyl)benzyl]-7H-purine-2-carboxylic acid

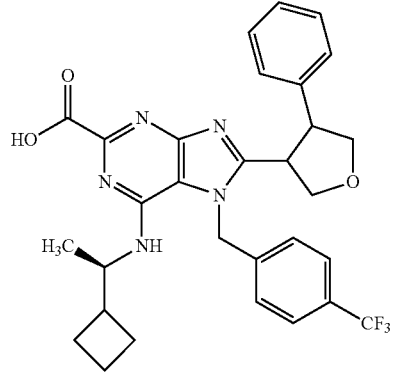

Using a procedure analogous to that described in Example 21.1 and starting with (R)-8-bromo-6-((1-cyclobutylethyl)amino)-7-(4-(trifluoromethyl)benzyl)-7H-purine-2-carbonitrile (Preparative Example 2.1) and 4-phenyldihydrofuran-3(2H)-one, 6-{[(1R)-1-cyclobutylethyl]amino}-8-(4-phenyltetrahydrofuran-3-yl)-7-[4-(trifluoromethyl)benzyl]-7H-purine-2-carboxylic acid was prepared (diastereomer B—slower eluting from column). $^1$H NMR (400 MHz, CD$_3$OD) δ 7.56 (d, J=8.0 Hz, 2H), 6.99-7.11 (m, 5H), 6.90 (d, J=8.0 Hz, 2H), 5.63 (d, J=18.4 Hz, 1H), 5.39 (d, J=18.4 Hz, 1H), 4.74 (m, 1H), 4.50 (m, 1H), 4.40 (m, 1H), 4.20-4.30 (m, 3H), 3.96 (m, 1H), 2.09 (m, 1H), 1.88 (m, 1H), 1.57-1.76 (m, 3H), 1.49-1.56 (m, 2H), 0.77 (d, J=6.4 Hz, 3H). MS (ES)=566 (M+1)$^+$.

Example 21.9

6-{[(1R)-1-cyclobutylethyl]amino}-8-methyl-7-[(trans-4-methylcyclohexyl)methyl]-7H-purine-2-carboxylic acid

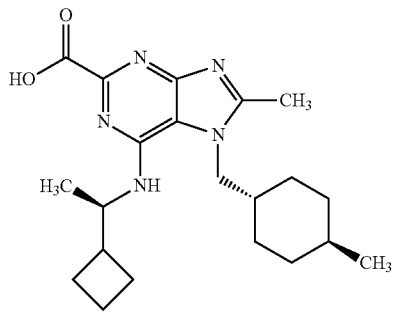 [SMILES: Cc1nc2nc(C(=O)O)nc(N[C@H](C)C3CCC3)c2n1C[C@H]1CC[C@H](C)CC1]

Step 1: A microwave vial equipped with a stir bar was charged with 8-bromo-6-(((R)-1-cyclobutylethyl)amino)-7-((trans-4-methylcyclohexyl)methyl)-7H-purine-2-carbonitrile (Preparative Example 11.7, 100 mg, 0.23 mmol), methylboronic acid (80 mg, 1.85 mmol), $Na_2CO_3$ (122 mg, 1.15 mmol), $Pd(PPh_3)_2Cl_2$ (48 mg, 0.069 mmol), THF (6.0 mL), and water (1.0 mL). The mixture was degassed with nitrogen for 15 minutes and the vial was then sealed and heated at 100° C. for 10 minutes in a microwave. The reaction was then cooled to room temperature, diluted with ethyl acetate (3.0 mL) and the organics were washed with brine (5.0 mL). The organic layer was dried over anhydrous $Na_2SO_4$, filtered, and concentrated to dryness. Purification of the residue on a RediSep 4 g silica gel column with 0 to 100% EtOAc/hexanes afforded 6-(((R)-1-cyclobutylethyl)amino)-8-methyl-7-((trans-4-methylcyclohexyl)methyl)-7H-purine-2-carbonitrile. MS (ES)=367 $(M+1)^+$.

Step 2: Using a procedure analogous to that in Example 10.5 (Step 3), and starting with 6-(((R)-1-cyclobutylethyl)amino)-8-methyl-7-((trans-4-methylcyclohexyl)methyl)-7H-purine-2-carbonitrile, 6-{[(1R)-1-cyclobutylethyl]amino}-8-methyl-7-[(trans-4-methylcyclohexyl)methyl]-7H-purine-2-carboxylic acid was prepared. $^1$H NMR (400 MHz, $CD_3OD$) δ 4.40 (dd, J=15.2, 6.4 Hz, 1H), 4.16 (dd, J=15.2, 8.4 Hz, 1H), 2.61 (s, 3H), 2.55 (m, 1H), 2.01-2.21 (m, 2H), 1.82-1.98 (m, 5H), 1.57-1.82 (m, 4H), 1.28-1.39 (m, 2H), 1.06-1.21 (m, 5H), 0.77-0.97 (m, 5H). MS (ES)=386 $(M+1)^+$.

Example 21.10

3-(6-{[(1R)-1-cyclobutylethyl]amino}-8-methyl-7-[(trans-4-methylcyclohexyl)methyl]-7H-purin-2-yl)-1,2,4-oxadiazol-5(4H)-one

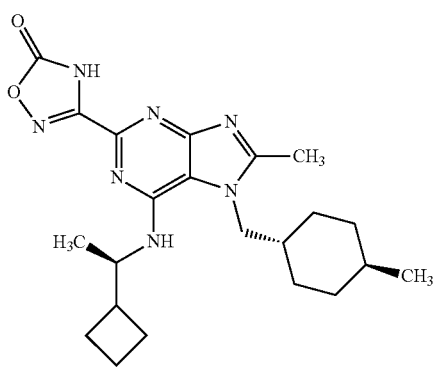 [SMILES: Cc1nc2nc(-c3noc(=O)[nH]3)nc(N[C@H](C)C3CCC3)c2n1C[C@H]1CC[C@H](C)CC1]

Using a procedure analogous to that in Example 16.1 (Step 3 and 4), and starting with 6-(((R)-1-cyclobutylethyl)amino)-8-methyl-7-((trans-4-methylcyclohexyl)methyl)-7H-purine-2-carbonitrile (Example 21.9, Step 1), 3-(6-{[(1R)-1-cyclobutylethyl]amino}-8-methyl-7-[(trans-4-methylcyclohexyl)methyl]-7H-purin-2-yl)-1,2,4-oxadiazol-5(4H)-one was prepared. $^1$H NMR (400 MHz, $CD_3OD$) δ 4.70 (m, 1H), 4.44 (m, 1H), 4.19 (m, 1H), 2.67 (s, 3H), 2.57 (m, 1H), 2.04-2.13 (m, 2H), 1.65-1.94 (m, 9H), 1.28-1.42 (m, 2H), 1.23 (m, 1H), 1.19 (d, J=6.5 Hz, 3H), 1.14 (m, 1H), 0.81-0.97 (m, 4H). MS (ES)=426 $(M+1)^+$.

Example 21.11

6-{[(1R)-1-cyclobutylethyl]amino}-8-(3-oxo-2-phenylcyclohexyl)-7-[4-(trifluoromethyl)benzyl]-7H-purine-2-carboxylic acid (mixture of trans diastereomers)

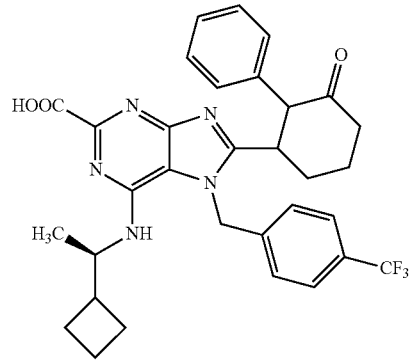 [SMILES: C[C@@H](Nc1nc(C(=O)O)nc2nc(C3CCCC(=O)C3c3ccccc3)n(Cc3ccc(C(F)(F)F)cc3)c12)C1CCC1]

Step 1: To a solution of 2-phenylcyclohexane-1,3-dione (200 mg, 1.06 mmol) and pyridine (171 µL, 2.12 mmol) in dichloromethane (8 mL) was added $Tf_2O$ (215 µL, 1.28 mmol) slowly at −78° C. The reaction mixture was stirred for another 10 minutes at −78° C. and warmed to 0° C. After the consumption of the starting diketone, the mixture was acidified with HCl (0.2 N, aqueous) and extracted with dichloromethane (3×5 mL). The combined organic layers were washed with aqueous $NaHCO_3$ solution and water, dried over anhydrous $Na_2SO_4$, and concentrated to dryness. Purification of the residue on a RediSep 12 g silica gel column (0 to 2% EtOAc/hexanes) afforded 6-oxo-3,4,5,6-tetrahydro-[1,1'-biphenyl]-2-yl trifluoromethane sulfonate as a white solid. $^1$H NMR (300 MHz, $CDCl_3$) δ 7.37-7.42 (m, 3H), 7.15-7.18 (m, 2H), 2.93 (t, J=6.3 Hz, 2H), 2.65 (t, J=6.3 Hz, 2H), 2.18-2.27 (m, 2H).

Step 2: To a solution of methyl 6-(((R)-1-cyclobutylethyl)amino)-8-(3-oxo-2-phenylcyclohex-1-en-yl)-7-(4-(trifluoromethyl)benzyl)-7H-purine-2-carboxylate (70 mg, 0.12 mmol) (prepared according to procedures reported for the synthesis of Example 21.1 and Example 21.2 and starting from 6-oxo-3,4,5,6-tetrahydro-[1,1'-biphenyl]-2-yl trifluoromethane sulfonate prepared in Step 1), in EtOH/$H_2O$ (6 mL:1 mL) was added $NH_4Cl$ (249 mg, 4.63 mmol), followed by the addition of activated Zn (45 mg, 0.70 mmol). The reaction mixture was stirred at room temperature for 2 hours and filtered through a celite bed. The filtrate was concentrated in vacuo and the residue was partitioned into $H_2O$ and $CH_2Cl_2$. The aqueous layer was extracted with $CH_2Cl_2$ (3×5 mL). The combined organic layers were washed with brine, dried over anhydrous $Na_2SO_4$, filtered, and concentrated in vacuo, to afford methyl 6-(((R)-1-cyclobutylethyl)amino)-8-(3-oxo-2-phenylcyclohexyl)-7-(4-(trifluoromethyl)benzyl)-7H-purine-2-carboxylate (mixture of four diastereomers). NaOMe (1.5 mg, 0.027 mmol) was added to a solution of the above mixture of methyl 6-(((R)-1-cyclobutylethyl)amino)-8-(3-oxo-2-phenylcyclohexyl)-7-(4-(trifluoromethyl)benzyl)-7H-purine-2-carboxylate (mixture of four diastereomers) (55 mg, 0.091 mmol) in methanol (2 mL). The reaction mixture was stirred at room temperature overnight and quenched with aqueous 1 M HCl. After concentration of solvent, the residue was dissolved in $CH_2Cl_2$. The organic layer was washed with sat. $NaHCO_3$ aqueous solution and brine, dried over Na₂SO₄ and concentrated in vacuo. Purification of the residue on a RediSep 4 g silica gel column (0 to 5% MeOH/CH₂Cl₂) afforded methyl 6-(((R)-1-cyclobutylethyl)amino)-8-(3-oxo-2-phenylcyclohexyl)-7-(4-(trifluoromethyl)benzyl)-7H-purine-2-carboxylate (mixture of trans diastereomers). ¹H NMR (300 MHz, CDCl₃) δ 7.43 (d, J=8.6 Hz, 1H), 7.49 (d, J=8.6 Hz, 1H), 6.97-7.26 (m, 5H), 6.63 (d, J=7.8 Hz, 1H), 6.57 (d, J=7.8 Hz, 1H), 5.19 (s, 1H), 5.14 (s, 1H), 4.52 (d, J=10.8 Hz, 0.5H), 4.49 (d, J=10.8 Hz, 0.5H), 4.24 (m, 1H), 3.98 (s, 3H), 3.91 (m, 1H), 3.39 (m, 1H), 2.67-2.72 (m, 2H), 2.48 (m, 1H), 2.30 (m, 1H), 2.18 (m, 1H), 1.97-1.22 (m, 8H), 0.85 (d, J=6.3 Hz, 1.5H), 0.69 (d, J=6.3 Hz, 1.5H). MS (APCI)=606 (M+1)⁺.

Step 3: Using a procedure analogous to that in Example 10.1 (Step 6), and starting with methyl 6-(((R)-1-cyclobutylethyl)amino)-8-(3-oxo-2-phenylcyclohexyl)-7-(4-(trifluoromethyl)benzyl)-7H-purine-2-carboxylate, 6-{[(1R)-1-cyclobutylethyl]amino}-8-(3-oxo-2-phenylcyclohexyl)-7-[4-(trifluoromethyl)benzyl]-7H-purine-2-carboxylic acid (mixture of trans diastereomers) was prepared. ¹H NMR (400 MHz, CD₃OD) δ 7.58 (d, J=8.0 Hz, 1H), 7.49 (d, J=8.0 Hz, 1H), 6.98-7.12 (m, 5H), 6.85 (d, J=8.0 Hz, 1H), 6.63 (d, J=8.0 Hz, 1H), 5.70-5.79 (m, 2H), 4.39-4.53 (m, 2H), 3.95 (m, 1H), 2.75 (td, J=14.2, 6.0 Hz, 1H), 2.57 (d, J=14.2 Hz, 1H), 2.21-2.36 (m, 2H), 1.97-2.12 (m, 3H), 1.85 (m, 1H), 1.54-1.71 (m, 3H), 1.43 (m, 1H), 1.26 (m, 1H), 0.98 (d, J=6.4 Hz, 1.5H), 0.85 (d, J=6.4 Hz, 1.5H). MS (ES)=592 (M+1)⁺.

Example 21.12

6-{[(1R)-1-cyclobutylethyl]amino}-8-(2-phenylcyclohexyl)-7-[4-(trifluoromethyl)benzyl]-7H-purine-2-carboxylic acid (mixture of trans diastereomers)

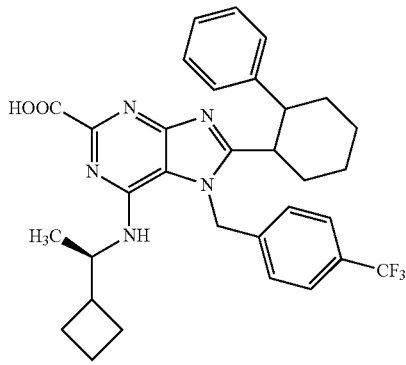 [SMILES: C[C@@H](Nc1nc(C(=O)O)nc2nc(C3CCCCC3c3ccccc3)n(Cc3ccc(C(F)(F)F)cc3)c12)C1CCC1]

Step 1: 4-Methylbenzenesulfonohydrazide (19 mg, 0.099 mmol) was added to a solution of methyl 6-(((R)-1-cyclobutylethyl)amino)-8-(3-oxo-2-phenylcyclohexyl)-7-(4-(trifluoromethyl)benzyl)-7H-purine-2-carboxylate (Example 21.11 step 2, mixture of trans diastereomers) (50 mg, 0.083 mmol) in EtOH (6 mL). The reaction mixture was heated at reflux for 2 hours and concentrated in vacuo, to afford 50 mg (crude) of methyl 6-(((R)-1-cyclobutylethyl)amino)-8-(2-phenyl-3-(2-tosylhydrazono)cyclohexyl)-7-(4-(trifluoromethyl)benzyl)-7H-purine-2-carboxylate. To a solution of crude methyl 6-(((R)-1-cyclobutylethyl)amino)-8-(2-phenyl-3-(2-tosylhydrazono)cyclohexyl)-7-(4-(trifluoromethyl)benzyl)-7H-purine-2-carboxylate (50 mg, 0.065 mmol) in DMF:DMSO:cyclohexane (2 mL: 2 mL: 2 mL) was added NaBH₃CN (42 mg, 0.66 mmol), followed by p-TSA (28 mg, 0.15 mmol). The reaction mixture was stirred at 110° C. for 2 hours and partitioned into water and EtOAc. The aqueous layer was extracted with EtOAc (3×5 mL). The combined organic layers were washed with brine, dried over Na₂SO₄ and concentrated in vacuo. Purification of the residue on a RediSep 4 g silica gel column (0 to 5% MeOH/CH₂Cl₂) afforded methyl 6-(((R)-1-cyclobutylethyl)amino)-8-(2-phenylcyclohexyl)-7-(4-(trifluoromethyl)benzyl)-7H-purine-2-carboxylate (mixture of trans diastereomers). ¹H NMR (400 MHz, CDCl₃) δ 7.53 (d, J=8.8 Hz, 1H), 7.50 (d, J=8.8 Hz, 1H), 7.04-7.11 (m, 5H), 6.67 (d, J=8.0 Hz, 1H), 6.62 (d, J=8.0 Hz, 1H), 5.03-5.18 (m, 2H), 4.22 (dt, J=14.4, 6.4 Hz, 1H), 4.00 (s, 3H), 3.87 (d, J=8.0 Hz, 0.5H), 3.83 (d, J=8.0 Hz, 0.5H), 3.39 (m, 1H), 2.86 (m, 1H), 1.52-2.14 (m, 15H), 0.83 (d, J=6.4 Hz, 1.5H), 0.70 (d, J=6.4 Hz, 1.5H). MS (APCI)=592 (M+1)⁺.

Step 2: Using a procedure analogous to that in Example 10.1 (Step 6), and starting with methyl 6-((R)-1-cyclobutylethylamino)-8-(2-phenylcyclohexyl)-7-(4-(trifluoromethyl)benzyl)-7H-purine-2-carboxylate (mixture of trans diastereomers), 6-{[(1R)-1-cyclobutylethyl]amino}-8-(2-phenylcyclohexyl)-7-[4-(trifluoromethyl)benzyl]-7H-purine-2-carboxylic acid (mixture of trans diastereomers) was prepared. ¹H NMR (400 MHz, CD₃OD) δ 7.57 (d, J=8.2 Hz, 1H), 7.49 (d, J=8.2 Hz, 1H), 6.95-7.48 (m, 5H), 6.80 (d, J=7.9 Hz, 1H), 6.60 (d, J=7.9 Hz, 1H), 5.67 (s, 1H), 5.58 (s, 1H), 4.48 (m, 1H), 1.21-2.06 (m, 17H), 0.92-0.81 (m, 3H). MS (ES)=578 (M+1)⁺.

Example 21.13

3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one

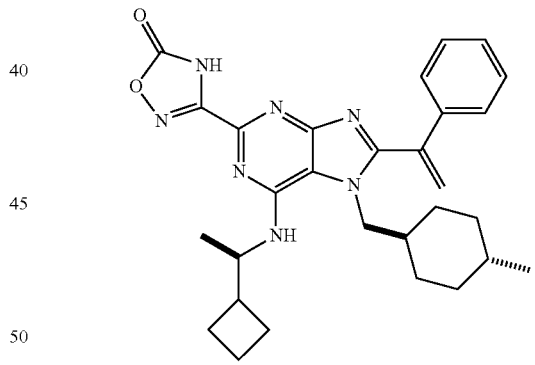

Step 1: A vial was charged with 8-bromo-6-{[(1R)-1-cyclobutylethyl]amino}-7-[(trans-4-methylcyclohexyl)methyl]-7H-purine-2-carbonitrile (Preparative Example 11.7, 2.26 g, 5.24 mmol), 4,4,5,5-tetramethyl-2-(1-phenylethenyl)-1,3,2-dioxaborolane (1.808 g, 7.86 mmol), PdCl₂(dppf)-CH₂Cl₂ (0.428 g, 0.524 mmol), and potassium phosphate (3.34 g, 15.72 mmol). The tube was evacuated and backfilled with argon (3×). Fully degassed dioxane (23.81 ml) and water (2.381 ml) were added. The vial was capped and heated at 50° C. for 11 hours. The mixture was cooled to room temperature, diluted with saturated aqueous sodium bicarbonate and extracted with ethyl acetate (2×). Combined organics were dried over magnesium sulfate, filtered, and concentrated under reduced pressure. The resulting residue was purified via silica gel chromatography (ethyl acetate/ hexanes) to afford 6-{[(1R)-1-cyclobutylethyl]amino}-7-[(trans-4-methylcyclohexyl)methyl]-8-(1-phenylethenyl)-7H-purine-2-carbonitrile as an off-white foam. MS ESI calc'd. for $C_{28}H_{34}N_6$ [M+H]$^+$ 455. found 455.

Step 2: Hydroxylamine hydrochloride (0.654 g, 9.41 mmol), sodium bicarbonate (1.186 g, 14.12 mmol) and water (14.12 ml) were combined and allowed to stir for 15 minutes to allow for gas evolution. The resulting solution was added to a solution of 6-{[(1R)-1-cyclobutylethyl]amino}-7-[(trans-4-methylcyclohexyl)methyl]-8-(1-phenylethenyl)-7H-purine-2-carbonitrile (2.14 g, 4.71 mmol) in ethanol (33.0 ml). A reflux condenser was attached and the resulting mixture was stirred at 100° C. for 1 hour. Upon cooling, precipitate was observed. The mixture was diluted with water and ethyl acetate and extracted with ethyl acetate (2×). Combined organics were dried over magnesium sulfate, filtered, and concentrated in vacuo to afford 6-{[(1R)-1-cyclobutylethyl]amino}-N'-hydroxy-7-[(trans-4-methylcyclohexyl)methyl]-8-(1-phenylethenyl)-7H-purine-2-carboximidamide as a yellow solid. MS ESI calc'd. for $C_{28}H_{37}N_7O$ [M+H]$^+$ 488. found 488.

Step 3: To a solution of 6-{[(1R)-1-cyclobutylethyl]amino}-N'-hydroxy-7-[(trans-4-methylcyclohexyl)methyl]-8-(1-phenylethenyl)-7H-purine-2-carboximidamide (2.17 g, 4.45 mmol) and 1,1'-carbonyldiimidazole (0.794 g, 4.90 mmol) dissolved in acetonitrile (44.5 ml) was added 1,8-diazabicyclo[5.4.0]undec-7-ene (2.66 ml, 17.80 mmol). The resulting mixture was stirred at room temperature for 2 hours and then concentrated under reduced pressure. The residue was taken up in DCM and washed with 2N aqueous HCl. The aqueous layer was back extracted with DCM (2×). Combined organics were dried over magnesium sulfate, filtered, and concentrated under reduced pressure. The resulting residue was purified via silica gel chromatography (methanol/ethyl acetate) to afford 3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one. MS ESI calc'd. for $C_{29}H_{35}N_7O_2$ [M+H]$^+$ 514. found 514. $^1$H NMR (500 MHz, DMSO-d$_6$) δ 12.91 (s, 1H), 7.43-7.46 (m, 5H), 6.54 (d, J=9.0 Hz, 1H), 6.25 (s, 1H), 5.82 (s, 1H), 4.59-4.55 (m, 2H), 4.30-4.26 (m, 1H), 3.72-3.68 (m, 1H), 2.54-2.50 (m, 1H), 2.25-1.99 (m, 1H), 1.91-1.88 (m, 1H), 1.82-1.75 (m, 4H), 1.55-1.34 (m, 4H), 1.09 (d, J=6.5 Hz, 3H), 1.07-0.99 (m, 2H), 0.81-0.75 (m, 1H), 0.72 (d, J=6.0 Hz, 3H), 0.69-0.53 (m, 2H).

Example 21.14 and Example 21.15

3-(6-{[(1R)-1-cyclobutylethyl]amino}-7-[(trans-4-methylcyclohexyl)methyl]-8-[(1R or S)-1-phenylethyl]-7H-purin-2-yl)-1,2,4-oxadiazol-5(4H)-one (diastereoisomer 1) and 3-(6-{[(1R)-1-cyclobutylethyl]amino}-7-[(trans-4-methylcyclohexyl)methyl]-8-[(1S or R)-1-phenylethyl]-7H-purin-2-yl)-1,2,4-oxadiazol-5(4H)-one (diastereoisomer 2)

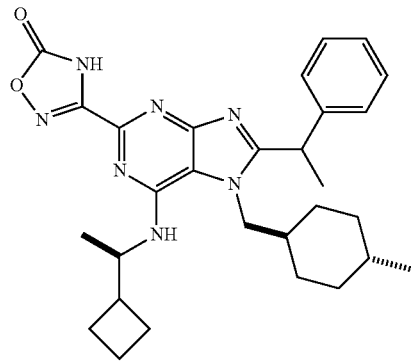

Palladium on carbon (10 wt %, 409 mg, 0.385 mmol) was taken up in a solution of 3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one (Example 21.13) (790 mg, 1.538 mmol) in THF (25.6 ml) under argon. The flask was evacuated and backfilled with hydrogen (6×) via balloon and left to stir at room temperature for 3.5 hours. The mixture was then filtered through celite, washing with ethyl acetate. The filtrate was concentrated and purified via silica gel chromatography (isochratic, 80:30:10 DCM:hexanes:methanol+1% acetic acid) to afford a light yellow solid. This solid was further purified via chiral SFC (Chiral Technologies OZ-H, 21×250 mm, 5 uM, 35%/65% methanol+0.25% dimethylethylamine/CO$_2$, 70 mL/Min, 254 nm to afford 3-(6-{[(1R)-1-cyclobutylethyl]amino}-7-[(trans-4-methylcyclohexyl)methyl]-8-[(1R or S)-1-phenylethyl]-7H-purin-2-yl)-1,2,4-oxadiazol-5(4H)-one (diastereoisomer 1, Example 21.14, faster eluting) and 3-(6-{[(1R)-1-cyclobutylethyl]amino}-7-[(trans-4-methylcyclohexyl)methyl]-8-[(1S or R)-1-phenylethyl]-7H-purin-2-yl)-1,2,4-oxadiazol-5(4H)-one (diastereoisomer 2), Example 21.15, slower eluting). Diastereoisomer 1, faster eluting: t$_R$=2.7 min. MS ESI calc'd. for $C_{29}H_{37}N_7O_2$ [M+H]$^+$ 516. found 516. $^1$H NMR (500 MHz, DMSO-d$_6$) δ 7.32-7.27 (m, 4H), 7.22-7.19 (m, 1H), 6.24 (d, J=8.5 Hz, 1H), 4.55-4.51 (m, 2H), 4.49-4.45 (m, 1H), 4.42-4.39 (m, 1H), 3.93-3.88 (m, 1H), 2.48-1.45 (m, 1H), 1.99-1.95 (m, 1H), 1.92-1.87 (m, 1H), 1.81-1.70 (m, 4H), 1.67 (d, J=6.5 Hz, 3H), 1.62-1.54 (m, 2H), 1.52-1.40 (m, 1H), 1.25-1.21 (m, 1H), 1.07-1.02 (m, 6H), 0.77 (d, J=6.5 Hz, 3H), 0.72-0.58 (m, 2H). Diastereoisomer 2, slower eluting, t$_R$=3.2 min. MS ESI calcd. for $C_{29}H_{37}N_7O_2$ [M+H]$^+$ 516. found 516. $^1$H NMR (500 MHz, DMSO-d6) δ 7.38-7.36 (m, 2H), 7.31-7.28 (m, 2H), 7.22-7.19 (m, 1H), 6.26 (d, J=8.5 Hz, 1H), 4.58-4.52 (m, 2H), 4.30-4.25 (m, 2H), 2.69-2.65 (m, 1H), 1.97-1.94 (m, 1H), 1.85-1.82 (m, 1H), 1.78-1.70 (m, 4H), 1.64 (d, J=6.5 Hz, 3H), 1.50-1.40 (m, 2H), 1.22-0.80 (m 5H), 1.07-1.04 (m, 3H), 1.03-0.97 (m, 1H), 0.71 (d, J=6.5 Hz, 3H), 0.52-0.48 (m, 2H).

Example 21.38

6-{[(1R)-1-cyclobutylethyl]amino}-8-cyclohexyl-7-[(trans-4-methylcyclohexyl)methyl]-7H-purine-2-carboxylic acid

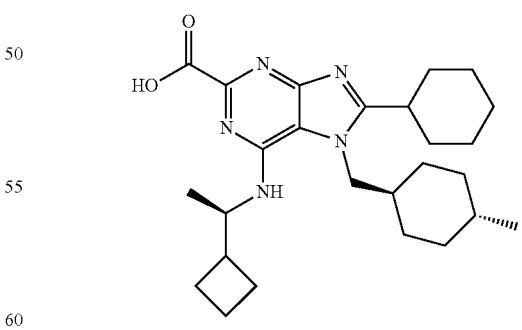

Step 1: A microwave vial equipped with a stir bar was charged with 8-bromo-6-(((R)-1-cyclobutylethyl)amino)-7-((trans-4-methylcyclohexyl)methyl)-7H-purine-2-carbonitrile (Preparative Example 11.7, 350 mg, 0.813 mmol), cyclohex-1-en-1-ylboronic acid (152 mg, 1.22 mmol), Na$_2$CO$_3$ (431 mg, 4.06 mmol), Pd(PPh$_3$)$_4$ (47 mg, 0.040 mmol), 1,4-dioxane (4.0 mL), and water (4.0 mL). The mixture was degassed with nitrogen for 15 minutes and the vial was then sealed and heated at 100° C. for 30 minutes in a microwave. The reaction was then cooled to room temperature and concentrated. The residue was dissolved in ethyl acetate (15 mL) and washed with brine (10 mL). The organic layer was dried over anhydrous $Na_2SO_4$, filtered, and concentrated. Purification of the residue on a silica gel column with 0 to 100% EtOAc/hexanes afforded 6-(((R)-1-cyclobutylethyl)amino)-8-(cyclohex-1-en-1-yl)-7-((trans-4-methylcyclohexyl)methyl)-7H-purine-2-carboxamide. MS (ES)=451 (M+1)$^+$.

Step 2: Using a procedure similar to that described in Example 21.1, Step 5, 6-(((R)-1-cyclobutylethyl)amino)-8-(cyclohex-1-en-1-yl)-7-((trans-4-methylcyclohexyl) methyl)-7H-purine-2-carboxamide was reduced to afford 6-(((R)-1-cyclobutylethyl)amino)-8-cyclohexyl-7-((trans-4-methylcyclohexyl)methyl)-7H-purine-2-carboxamide. MS (ES)=453 (M+1)$^+$.

Step 3: To a solution of 6-(((R)-1-cyclobutylethyl)amino)-8-cyclohexyl-7-((trans-4-methylcyclohexyl)methyl)-7H-purine-2-carboxamide (15.0 mg, 0.033 mmol) in MeOH (2.0 mL) and water (2.0 mL) was added NaOH (3.9 mg, 0.099 mmol) and the reaction mixture was warmed to reflux temperature and stirred for 12 hours. The reaction was then cooled to room temperature, concentrated, and the residue was dissolved in water (4.0 mL). The pH was adjusted to 6.5 using aqueous HCl (2.0 N), and the aqueous layer was extracted with ethyl acetate (3×10 mL). The combined organic layers were concentrated under reduced pressure and the resulting residue was purified by reverse phase column chromatography (C18) (10 to 90% $CH_3CN$/water) to afford 6-{[(1R)-1-cyclobutylethyl]amino}-8-cyclohexyl-7-[(trans-4-methylcyclohexyl)methyl]-7H-purine-2-carboxylic acid. $^1$H NMR (400 MHz, DMSO-d$_6$) δ 6.16 (br d, J=8.4 Hz, 1H), 4.38-4.50 (m, 2H), 4.08-4.20 (m, 1H), 2.89-3.00 (m, 1H), 2.41-2.60 (m, 1H), 1.99-2.09 (m, 1H), 1.89-1.99 (m, 1H), 1.55-1.87 (m, 11H), 1.35-1.55 (m, 6H), 1.20-1.35 (m, 2H), 1.11 (d, J=6.4 Hz, 3H), 0.96-1.20 (m, 3H), 0.80 (d, J=6.8 Hz, 3H), 0.58-0.84 (m, 2H). MS (ES)=454 (M+1)$^+$.

Example 21.39

3-(6-{[(1R)-1-cyclobutylethyl]amino}-8-cyclohexyl-7-[(trans-4-methylcyclohexyl)methyl]-7H-purin-2-yl)-1,2,4-oxadiazol-5(4H)-one

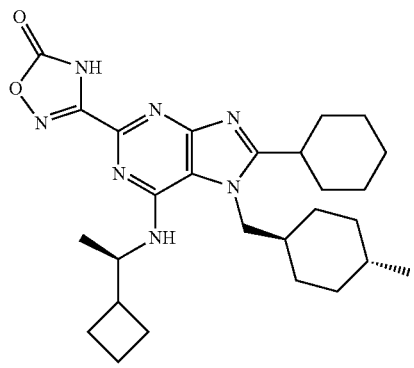 [SMILES: C[C@@H](Nc1nc(-c2noc(=O)[nH]2)nc2nc(C3CCCCC3)n(C[C@H]3CC[C@H](C)CC3)c12)C1CCC1]

Step 1: To a solution of 6-(((R)-1-cyclobutylethyl)amino)-8-cyclohexyl-7-((trans-4-methylcyclohexyl)methyl)-7H-purine-2-carboxamide (Example 21.38, Step 2; 22 mg, 0.048 mmol) in pyridine (1.0 mL) was added POCl$_3$ (22.4 mg, 0.146 mmol) and the reaction was stirred at 120° C. for 2 hours. Next, the reaction was quenched with ice water (10 mL) and extracted with EtOAc (2×10 mL). The combined organic layers were washed with brine (50 mL), dried over anhydrous $Na_2SO_4$, filtered, and concentrated. The residue was purified on a silica gel column (10 to 40% EtOAc/hexanes) to afford 6-(((R)-1-cyclobutylethyl)amino)-8-cyclohexyl-7-((trans-4-methylcyclohexyl)methyl)-7H-purine-2-carbonitrile. MS (ES)=435 (M+1)$^+$.

Steps 2 and 3: Using procedures similar to those described in Example 21.13 (Steps 2 and 3), 6-(((R)-1-cyclobutylethyl)amino)-8-cyclohexyl-7-((trans-4-methylcyclohexyl)methyl)-7H-purine-2-carbonitrile was converted to 3-(6-{[(1R)-1-cyclobutylethyl]amino}-8-cyclohexyl-7-[(trans-4-methylcyclohexyl)methyl]-7H-purin-2-yl)-1,2,4-oxadiazol-5(4H)-one. $^1$H NMR (400 MHz, DMSO-d$_6$) δ 6.29 (d, J=8.4 Hz, 1H), 4.41-4.60 (m, 2H), 4.10-4.21 (m, 1H), 2.91-3.03 (m, 1H), 2.38-2.59 (m, 1H), 1.35-2.10 (m, 18H), 0.92-1.35 (m, 6H), 1.11 (d, J=6.4 Hz, 3H), 0.58-0.85 (m, 2H), 0.80 (d, J=6.4 Hz, 3H). MS (ES)=494 (M+1)$^+$.

Examples 21.41 and 21.42

3-(6-{[(1R)-1-cyclobutylethyl]amino}-8-[(1R or S)-2-methoxy-1-phenylethyl]-7-[(trans-4-methylcyclohexyl)methyl]-7H-purin-2-yl)-1,2,4-oxadiazol-5(4H)-one (Diastereomer 1) and 3-(6-{[(1R)-1-cyclobutylethyl]amino}-8-[(1S or R)-2-methoxy-1-phenylethyl]-7-[(trans-4-methylcyclohexyl)methyl]-7H-purin-2-yl)-1,2,4-oxadiazol-5(4H)-one (Diastereomer 2)

diastereomer 1

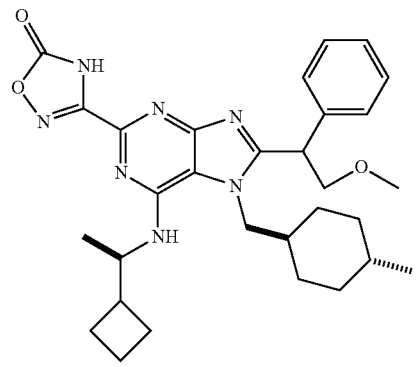

diastereomer 2

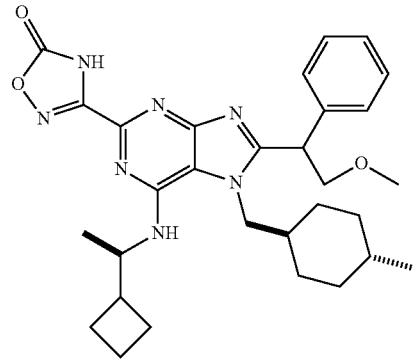

3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one (Example 21.13, 197 mg, 0.384 mmol) was taken up in MeOH (2500 µl) at room temperature and sodium methoxide (25 wt % in methanol, 1800 µl, 7.87 mmol) was added. The reaction vial was sealed and heated at 75° C. for 60 hours. The reaction was then cooled to room temperature, diluted with aqueous saturated ammonium chloride, and extracted with ethyl acetate. The organic layer was dried over magnesium sulfate, filtered, and concentrated under reduced pressure. Purification via silica gel chromatography (80:30:10 DCM: hexanes: methanol+1% acetic acid, isochratic) afforded a mixture of 3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one and 3-(6-{[(1R)-1-cyclobutylethyl]amino}-8-(2-methoxy-1-phenylethyl)-7-[(trans-4-methylcyclohexyl)methyl]-7H-purin-2-yl)-1,2,4-oxadiazol-5(4H)-one. This mixture was further separated by chiral supercirital fluid chromatography (Chiralcel OZ-H, 21×250 (mm), 30% methanol/$CO_2$+0.25% dimethylethylamine modifier, wavelength=220 nm, flow rate=60 mL/min) to afford 3-(6-{[(1R)-1-cyclobutylethyl]amino}-8-[(1R or S)-2-methoxy-1-phenylethyl]-7-[(trans-4-methylcyclohexyl)methyl]-7H-purin-2-yl)-1,2,4-oxadiazol-5(4H)-one (Diastereomer 1) and 3-(6-{[(1R)-1-cyclobutylethyl]amino}-8-[(1S or R)-2-methoxy-1-phenylethyl]-7-[(trans-4-methylcyclohexyl)methyl]-7H-purin-2-yl)-1,2,4-oxadiazol-5(4H)-one (Diastereomer 2).

Diastereomer 1, faster eluting: $\tau_R$=3.69 min. MS ESI calc'd. for $C_{30}H_{39}N_7O_3$ [M+H]$^+$ 546. found 546. $^1$H NMR (500 MHz, DMSO-$d_6$) δ 12.53 (br s, 1H), 7.41-7.39 (m, 2H), 7.31-7.28 (m, 2H), 7.24-7.21 (m, 1H), 6.26 (d, J=8.5 Hz, 1H), 4.67-4.64 (m, 1H), 4.52-4.46 (m, 1H), 4.43-4.38 (m, 1H), 4.17-4.14 (m, 1H), 4.08-4.00 (m, 1H), 3.84-3.81 (m, 1H), 3.25 (s, 3H), 2.66-2.60 (m, 1H), 2.41-2.39 (m, 2H), 2.05-1.96 (m, 2H), 1.81-1.71 (m, 4H), 1.58-1.53 (m, 2H), 1.44-1.37 (m, 2H), 1.24-1.10 (m, 2H), 1.03 (d, J=6.5 Hz, 3H), 0.76 (d, J=6.5 Hz, 3H), 0.68-0.55 (m, 2H).

Diastereomer 2, slower eluting: $\tau_R$=4.38 min. MS ESI calc'd. for $C_{30}H_{39}N_7O_3$ [M+H]$^+$ 546. found 546. $^1$H NMR (500 MHz, DMSO-$d_6$) δ 12.38 (br s, 1H), 7.50-7.48 (m, 2H), 7.32-7.29 (m, 2H), 7.25-7.23 (m, 1H), 6.33 (d, J=8.5 Hz, 1H), 4.75-4.71 (m, 1H), 4.56-4.51 (m, 1H), 4.36-4.28 (m, 2H), 4.09-4.05 (m, 1H), 3.78-3.75 (m, 1H), 3.22 (s, 3H), 2.66-2.60 (m, 1H), 2.42-2.40 (m, 2H), 2.02-1.94 (m, 1H), 1.88-1.82 (m, 1H), 1.79-1.70 (m, 4H), 1.50-1.42 (m, 2H), 1.40-1.30 (m, 1H), 1.28-1.17 (m, 2H), 1.07 (d, J=6.5 Hz, 3H), 1.01-0.94 (m, 1H), 0.69 (d, J=6.5 Hz, 3H), 0.50-0.41 (m, 2H).

The following compounds in Table 21 have been described above or were prepared using procedures which were analogous to those described above.

TABLE 21

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.1 | 10.22 | 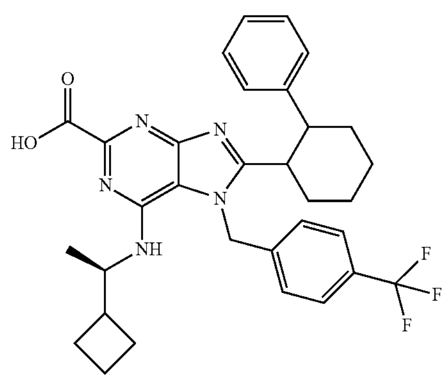 | 6-{[(1R)-1-cyclobutylethyl]amino}-8-(2-phenylcyclohexyl)-7-[4-(trifluoromethyl)benzyl]-7H-purine-2-carboxylic acid (diastereoisomer A) | | 578 | 578 |
| 21.2 | 2.356 | 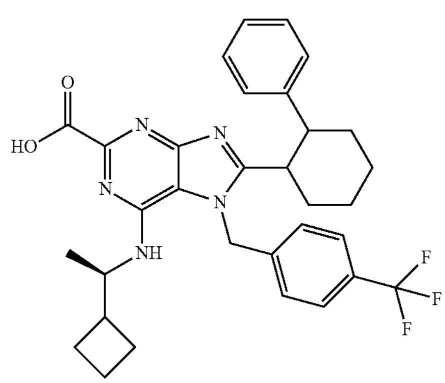 | 6-{[(1R)-1-cyclobutylethyl]amino}-8-(2-phenylcyclohexyl)-7-[4-(trifluoromethyl)benzyl]-7H-purine-2-carboxylic acid (diastereoisomer B) | | 578 | 578 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.3 | 5.817 | 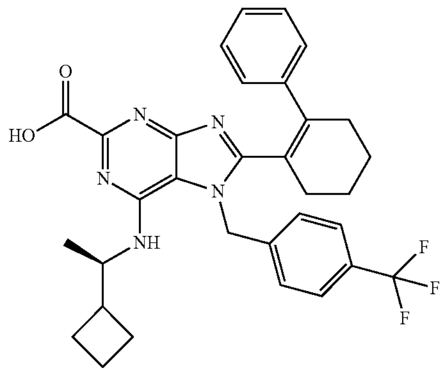 [SMILES: C[C@@H](Nc1nc(C(=O)O)nc2nc(C3=C(c4ccccc4)CCCC3)n(Cc3ccc(C(F)(F)F)cc3)c12)C1CCC1] | 6-{[(1R)-1-cyclobutylethyl]amino}-8-(2-phenylcyclohex-1-en-1-yl)-7-[4-(trifluoromethyl)benzyl]-7H-purine-2-carboxylic acid | | 576 | 576 |
| 21.4 | 6.987 | 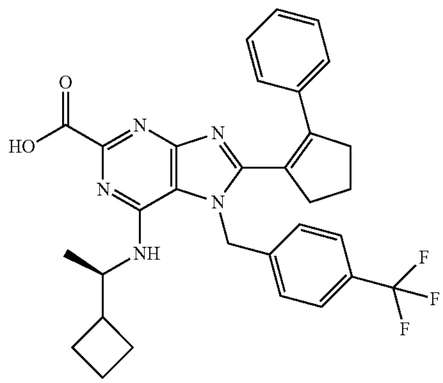 [SMILES: C[C@@H](Nc1nc(C(=O)O)nc2nc(C3=C(c4ccccc4)CCC3)n(Cc3ccc(C(F)(F)F)cc3)c12)C1CCC1] | 6-{[(1R)-1-cyclobutylethyl]amino}-8-(2-phenylcyclopent-1-en-1-yl)-7-[4-(trifluoromethyl)benzyl]-7H-purine-2-carboxylic acid | | 562 | 562 |
| 21.5 | 26.53 | 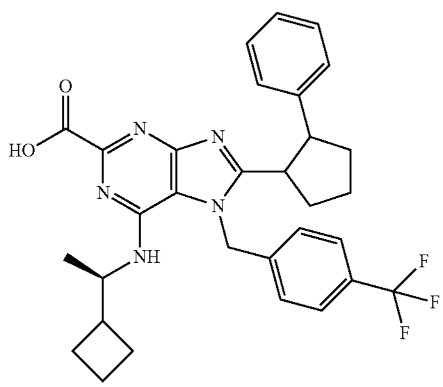 | 6-{[(1R)-1-cyclobutylethyl]amino}-8-(2-phenylcyclopentyl)-7-[4-(trifluoromethyl)benzyl]-7H-purine-2-carboxylic acid | | 564 | 564 |
| 21.6 | 1.357 | 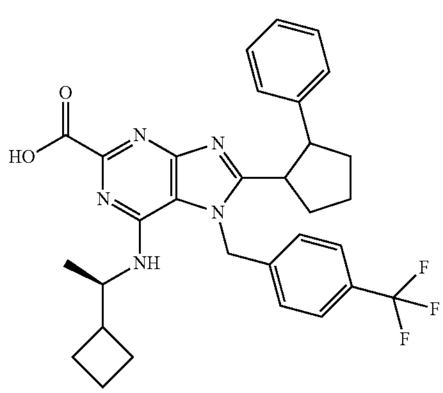 [SMILES: C[C@@H](Nc1nc(C(=O)O)nc2nc(C3CCCC3c3ccccc3)n(Cc3ccc(C(F)(F)F)cc3)c12)C1CCC1] | 6-{[(1R)-1-cyclobutylethyl]amino}-8-(2-phenylcyclopentyl)-7-[4-(trifluoromethyl)benzyl]-7H-purine-2-carboxylic acid | | 564 | 564 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.7 | 28.69 | 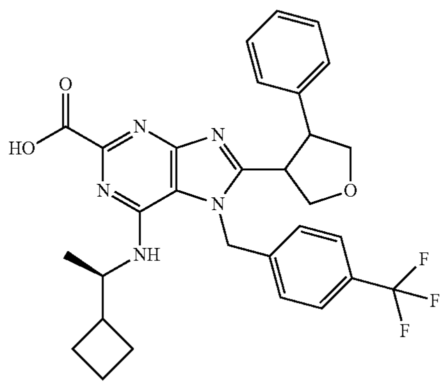 [SMILES: C[C@@H](Nc1nc(C(=O)O)nc2nc(C3COCC3c3ccccc3)n(Cc3ccc(C(F)(F)F)cc3)c12)C1CCC1] | 6-{[(1R)-1-cyclobutylethyl]amino}-8-(4-phenyltetrahydrofuran-3-yl)-7-[4-(trifluoromethyl)benzyl]-7H-purine-2-carboxylic acid | | 566 | 566 |
| 21.8 | 3.8 | 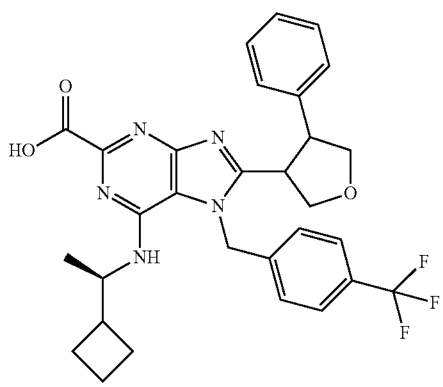 [SMILES: C[C@@H](Nc1nc(C(=O)O)nc2nc(C3COCC3c3ccccc3)n(Cc3ccc(C(F)(F)F)cc3)c12)C1CCC1] | 6-{[(1R)-1-cyclobutylethyl]amino}-8-(4-phenyltetrahydrofuran-3-yl)-7-[4-(trifluoromethyl)benzyl]-7H-purine-2-carboxylic acid | | 566 | 566 |
| 21.9 | 100.8 | 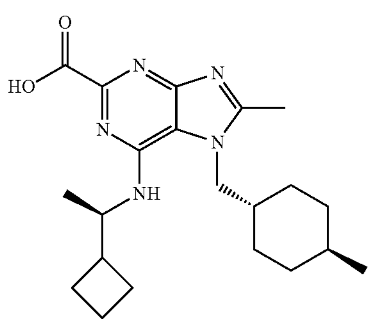 [SMILES: Cc1nc2nc(C(=O)O)nc(N[C@H](C)C3CCC3)c2n1C[C@H]1CC[C@H](C)CC1] | 6-{[(1R)-1-cyclobutylethyl]amino}-8-methyl-7-[(trans-4-methylcyclohexyl)methyl]-7H-purine-2-carboxylic acid | | 386 | 386 |
| 21.10 | 37.74 | 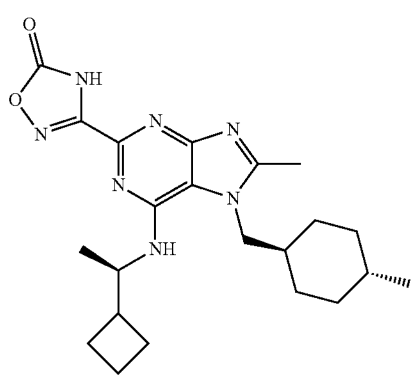 [SMILES: Cc1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-methyl-7-[(trans-4-methylcyclohexyl)methyl]-7H-purin-2-yl)-1,2,4-oxadiazol-5(4H)-one | TFA | 426 | 426 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.11 | 8.724 | 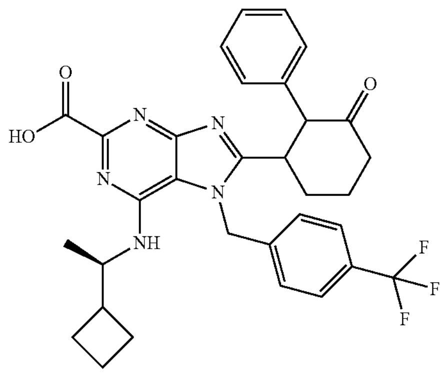 [SMILES: C[C@@H](Nc1nc(C(=O)O)nc2nc(C3CCCC(=O)C3c3ccccc3)n(Cc3ccc(C(F)(F)F)cc3)c12)C1CCC1] | 6-{[(1R)-1-cyclobutylethyl]amino}-8-(3-oxo-2-phenylcyclohexyl)-7-[4-(trifluoromethyl)benzyl]-7H-purine-2-carboxylic acid | | 592 | 592 |
| 21.12 | 4.571 | 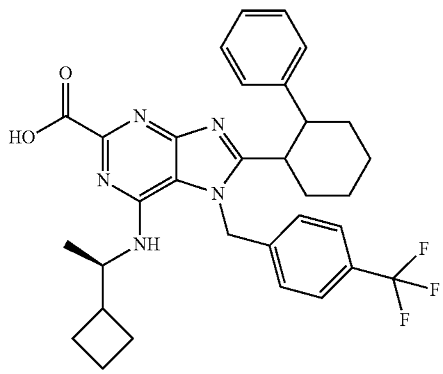 [SMILES: C[C@@H](Nc1nc(C(=O)O)nc2nc(C3CCCCC3c3ccccc3)n(Cc3ccc(C(F)(F)F)cc3)c12)C1CCC1] | 6-{[(1R)-1-cyclobutylethyl]amino}-8-(2-phenylcyclohexyl)-7-[4-(trifluoromethyl)benzyl]-7H-purine-2-carboxylic acid | | 578 | 578 |
| 21.13 | 1.901 | 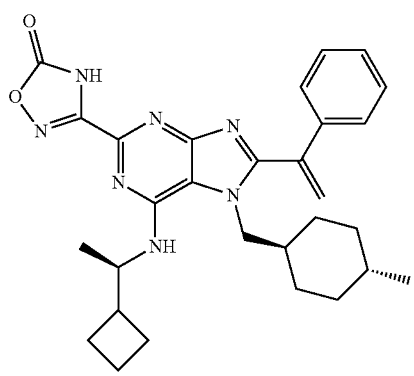 [SMILES: C=C(c1ccccc1)c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5(4H)-one | TFA | 514 | 514 |
| 21.14 | 19.8 | 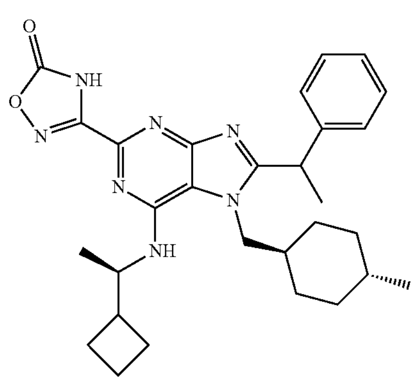 [SMILES: CC(c1ccccc1)c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(1-phenylethyl)-7H-purin-2-yl]-1,2,4-oxadiazol-5(4H)-one (diastereoisomer 1) | | 516 | 516 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.15 | 2.04 | 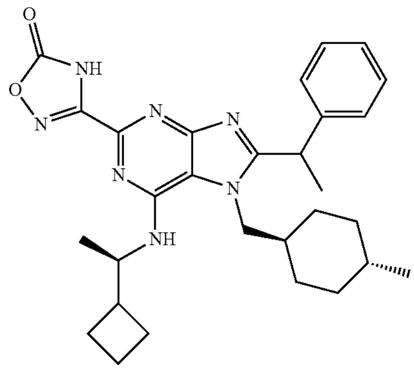 [SMILES: CC(c1ccccc1)c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(1-phenylethyl)-7H-purin-2-yl]-1,2,4-oxadiazol-5(4H)-one (diastereoisomer 2) | | 516 | 516 |
| 21.16 | 12.17 | 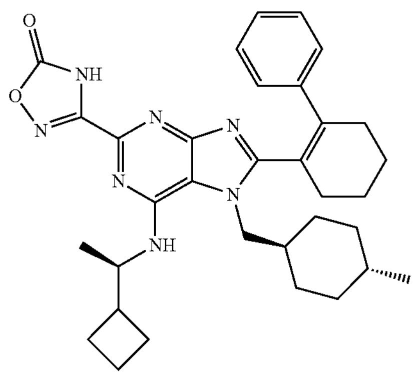 [SMILES: C[C@@H](Nc1nc(-c2noc(=O)[nH]2)nc2nc(C3=C(c4ccccc4)CCCC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenylcyclohex-1-en-1-yl)-7H-purin-2-yl]-1,2,4-oxadiazol-5(4H)-one | TFA | 568 | 568 |
| 21.17 | 4.303 | 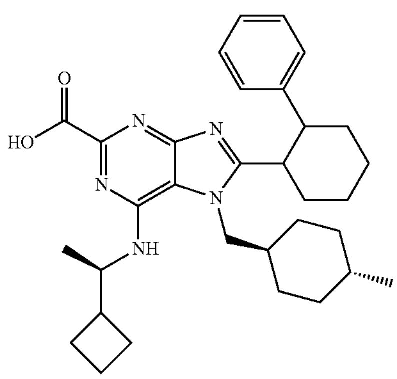 [SMILES: C[C@@H](Nc1nc(C(=O)O)nc2nc(C3CCCCC3c3ccccc3)n(C[C@H]3CC[C@H](C)CC3)c12)C1CCC1] | 6-{[(1R)-1-cyclobutylethyl]amino}-7-[(trans-4-methylcyclohexyl)methyl]-8-(2-phenylcyclohexyl)-7H-purine-2-carboxylic acid | | 530 | 530 |
| 21.18 | 6.495 | 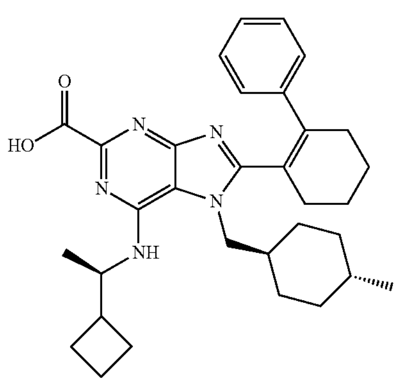 [SMILES: C[C@@H](Nc1nc(C(=O)O)nc2nc(C3=C(c4ccccc4)CCCC3)n(C[C@H]3CC[C@H](C)CC3)c12)C1CCC1] | 6-{[(1R)-1-cyclobutylethyl]amino}-7-[(trans-4-methylcyclohexyl)methyl]-8-(2-phenylcyclohex-1-en-1-yl)-7H-purine-2-carboxylic acid | | 528 | 528 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.19 | 0.9307 | 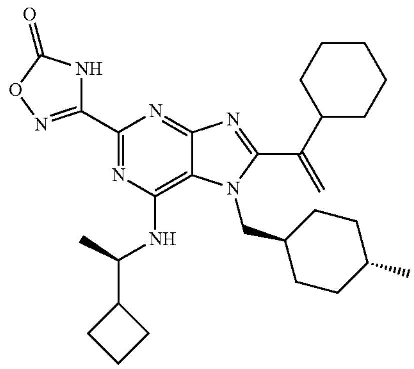 [SMILES: C=C(c1nc2nc(-c3noc(=O)[nH]3)nc(N[C@H](C)C3CCC3)c2n1C[C@H]1CC[C@H](C)CC1)C1CCCCC1] | 3-(6-{[(1R)-1-cyclobutylethyl]amino}-8-(1-cyclohexylethenyl)-7-[(trans-4-methylcyclohexyl)methyl]-7H-purin-2-yl)-1,2,4-oxadiazol-5(4H)-one | TFA | 520 | 520 |
| 21.20 | 1.889 | 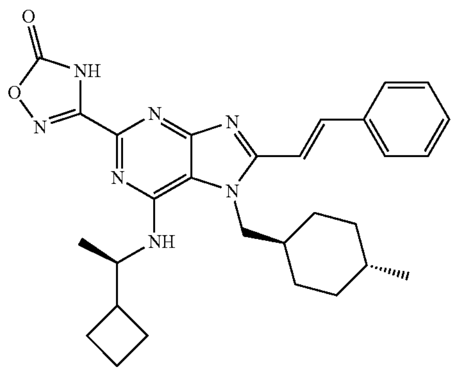 [SMILES: C[C@@H](Nc1nc(-c2noc(=O)[nH]2)nc2nc(/C=C/c3ccccc3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(E)-2-phenylethenyl]-7H-purin-2-yl)-1,2,4-oxadiazol-5(4H)-one | TFA | 514 | 514 |
| 21.21 | 7.166 | 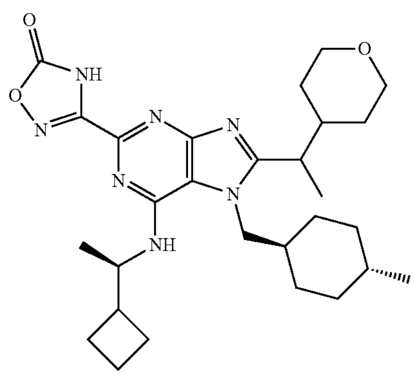 [SMILES: CC(c1nc2nc(-c3noc(=O)[nH]3)nc(N[C@H](C)C3CCC3)c2n1C[C@H]1CC[C@H](C)CC1)C1CCOCC1] | 3-(6-{[(1R)-1-cyclobutylethyl]amino}-7-[(trans-4-methylcyclohexyl)methyl]-8-[1-(tetrahydro-2H-pyran-4-yl)ethyl]-7H-purin-2-yl)-1,2,4-oxadiazol-5(4H)-one | | 524 | 524 |
| 21.22 | 7.805 | 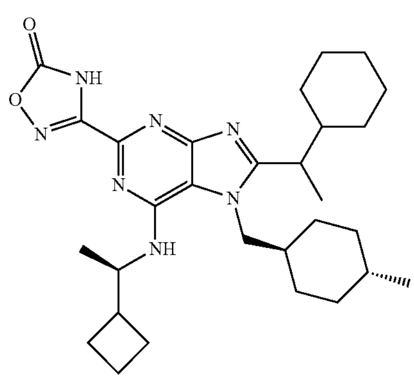 [SMILES: CC(c1nc2nc(-c3noc(=O)[nH]3)nc(N[C@H](C)C3CCC3)c2n1C[C@H]1CC[C@H](C)CC1)C1CCCCC1] | 3-(6-{[(1R)-1-cyclobutylethyl]amino}-8-(1-cyclohexylethyl)-7-[(trans-4-methylcyclohexyl)methyl]-7H-purin-2-yl)-1,2,4-oxadiazol-5(4H)-one (diastereoisomer 1) | TFA | 522 | 522 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.23 | 1.816 | 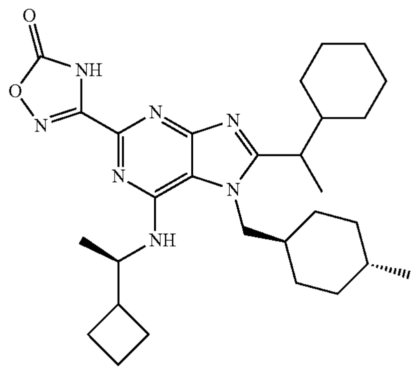 [SMILES: CC(c1nc2nc(-c3noc(=O)[nH]3)nc(N[C@H](C)C3CCC3)c2n1C[C@H]1CC[C@H](C)CC1)C1CCCCC1] | 3-(6-{[(1R)-1-cyclobutylethyl]amino}-8-(1-cyclohexylethyl)-7-[(trans-4-methylcyclohexyl)methyl]-7H-purin-2-yl)-1,2,4-oxadiazol-5(4H)-one (diastereoisomer 2) | TFA | 522 | 522 |
| 21.24 | 8.022 | 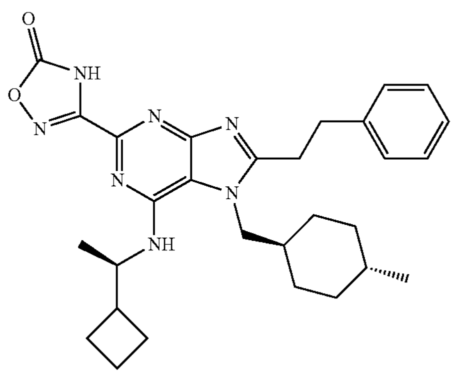 [SMILES: C[C@@H](Nc1nc(-c2noc(=O)[nH]2)nc2nc(CCc3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenylethyl)-7H-purin-2-yl]-1,2,4-oxadiazol-5(4H)-one | TFA | 516 | 516 |
| 21.25 | 28.9 | 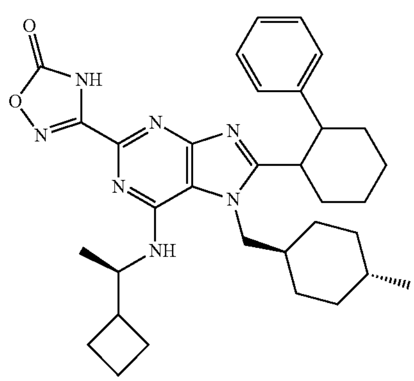 | 3-[6-{[(1R)-1-cyclobutylethyl]amino}-7-[(trans-4-methylcyclohexyl)methyl]-8-(2-phenylcyclohexyl)-7H-purin-2-yl]-1,2,4-oxadiazol-5(4H)-one (diastereoisomer 1) | | 570 | 570 |
| 21.26 | 21.55 | 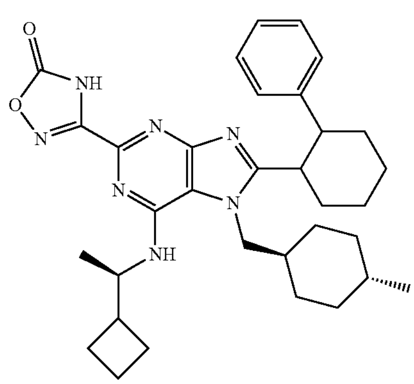 [SMILES: C[C@@H](Nc1nc(-c2noc(=O)[nH]2)nc2nc(C3CCCCC3c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenylcyclohexyl)-7H-purin-2-yl]-1,2,4-oxadiazol-5(4H)-one (diastereoisomer 2) | | 570 | 570 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.27 | 18.02 | 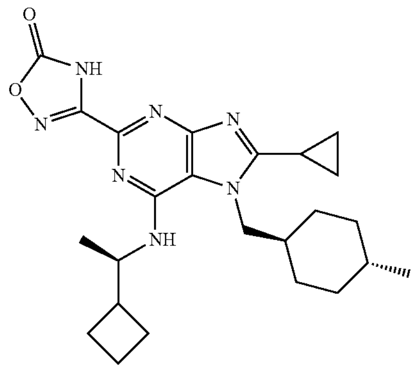 [SMILES: C[C@@H](Nc1nc(-c2noc(=O)[nH]2)nc2nc(C3CC3)n(C[C@H]3CC[C@H](C)CC3)c12)C1CCC1] | 3-(6-{[(1R)-1-cyclobutylethyl]amino}-8-cyclopropyl-7-[(trans-4-methylcyclohexyl)methyl]-7H-purin-2-yl)-1,2,4-oxadiazol-5(4H)-one | | 452 | 452 |
| 21.28 | 3.348 | 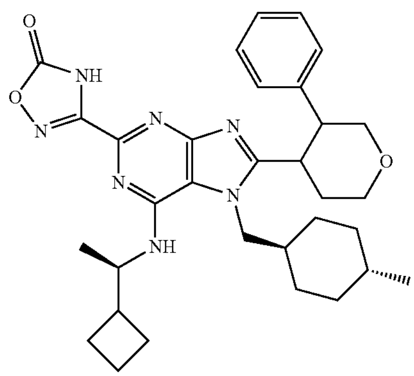 [SMILES: C[C@@H](Nc1nc(-c2noc(=O)[nH]2)nc2nc(C3CCOCC3c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(3-phenyltetrahydro-2H-pyran-4-yl)-7H-purin-2-yl]-1,2,4-oxadiazol-5(4H)-one (diastereoisomer 1) | | 572 | 572 |
| 21.29 | 20.18 | 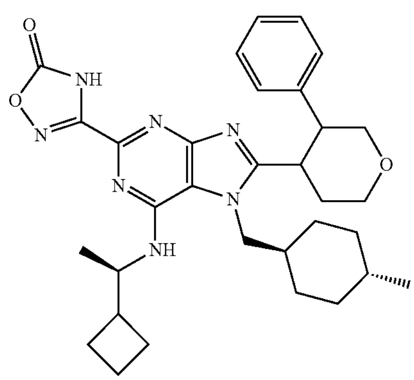 [SMILES: C[C@@H](Nc1nc(-c2noc(=O)[nH]2)nc2nc(C3CCOCC3c3ccccc3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(3-phenyltetrahydro-2H-pyran-4-yl)-7H-purin-2-yl]-1,2,4-oxadiazol-5(4H)-one (diastereoisomer 2) | | 572 | 572 |
| 21.30 | 1.84 | 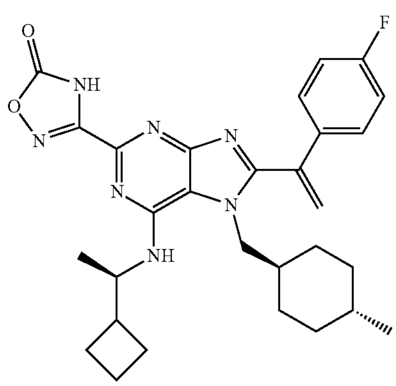 [SMILES: C=C(c1ccc(F)cc1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[1-[4-fluorophenyl)ethenyl]-7-[(trans-4-methylcyclohexyl)methyl]-7H-purin-2-yl)-1,2,4-oxadiazol-5(4H)-one | TFA | 532 | 532 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.31 | 10.47 | 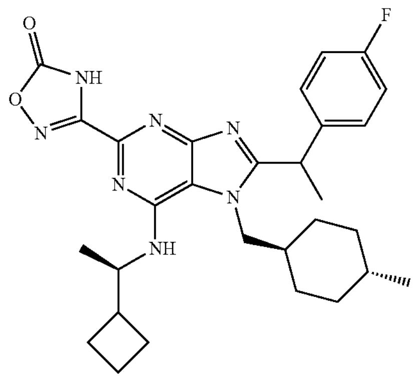 [SMILES: CC(c1ccc(F)cc1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[1-(4-fluorophenyl)ethyl]-7-[(trans-4-methylcyclohexyl)methyl]-7H-purin-2-yl)-1,2,4-oxadiazol-5(4H)-one | TFA | 534 | 534 |
| 21.32 | 4.872 | 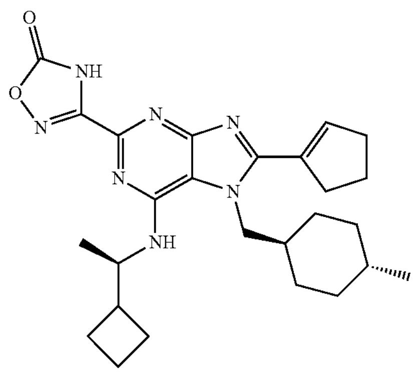 [SMILES: C[C@@H](Nc1nc(-c2noc(=O)[nH]2)nc2nc(C3=CCCC3)n(C[C@H]3CC[C@H](C)CC3)c12)C1CCC1] | 3-(6-{[(1R)-1-cyclobutylethyl]amino}-8-cyclopent-1-en-1-yl-7-[(trans-4-methylcyclohexyl)methyl]-7H-purin-2-yl)-1,2,4-oxadiazol-5(4H)-one | | 478 | 478 |
| 21.33 | 5.671 | 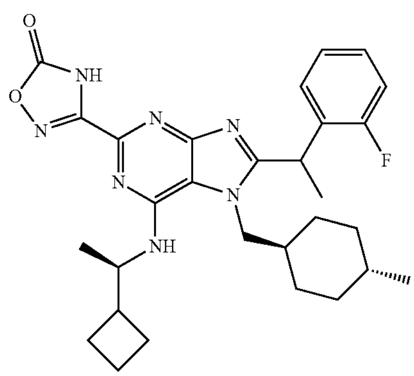 [SMILES: CC(c1ccccc1F)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5(4H)-one (mixture of diastereomers) | | 534 | 534 |
| 21.34 | 7.759 | 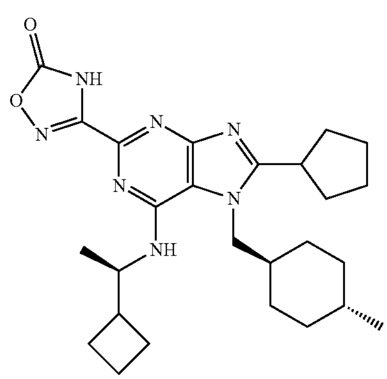 [SMILES: C[C@@H](Nc1nc(-c2noc(=O)[nH]2)nc2nc(C3CCCC3)n(C[C@H]3CC[C@H](C)CC3)c12)C1CCC1] | 3-(6-{[(1R)-1-cyclobutylethyl]amino}-8-cyclopentyl-7-[(trans-4-methylcyclohexyl)methyl]-7H-purin-2-yl)-1,2,4-oxadiazol-5(4H)-one | | 480 | 480 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.35 | 2.032 | 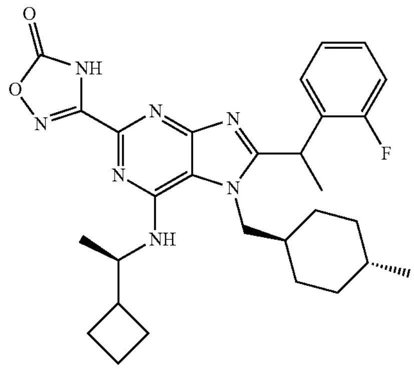 [SMILES: CC(c1ccccc1F)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5(4H)-one (Diastereomer 1) | | 534 | 534 |
| 21.36 | 43.09 | 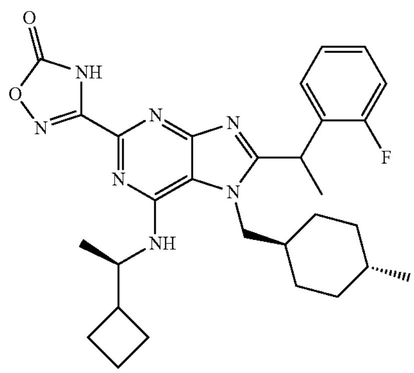 [SMILES: CC(c1ccccc1F)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5(4H)-one (Diastereomer 2) | | 534 | 534 |
| 21.37 | 3.788 | 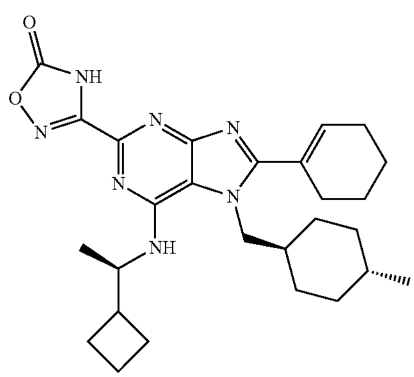 [SMILES: C[C@@H](Nc1nc(-c2noc(=O)[nH]2)nc2nc(C3=CCCCC3)n(C[C@H]3CC[C@H](C)CC3)c12)C1CCC1] | 3-(6-{[(1R)-1-cyclobutylethyl]amino}-8-cyclohex-1-en-1-yl-7-[(trans-4-methylcyclohexyl)methyl]-7H-purin-2-yl)-1,2,4-oxadiazol-5(4H)-one | | 492 | 492 |
| 21.38 | 2.684 | 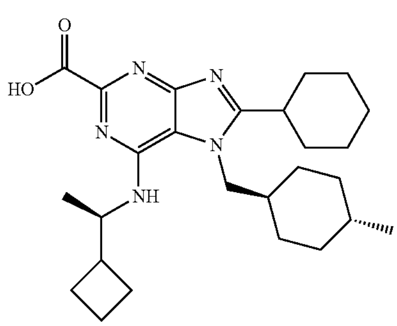 [SMILES: C[C@@H](Nc1nc(C(=O)O)nc2nc(C3CCCCC3)n(C[C@H]3CC[C@H](C)CC3)c12)C1CCC1] | 6-{[(1R)-1-cyclobutylethyl]amino}-8-cyclohexyl-7-[(trans-4-methylcyclohexyl)methyl]-7H-purine-2-carboxylic acid | | 454 | 454 |

TABLE 21-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 21.39 | 7.871 | 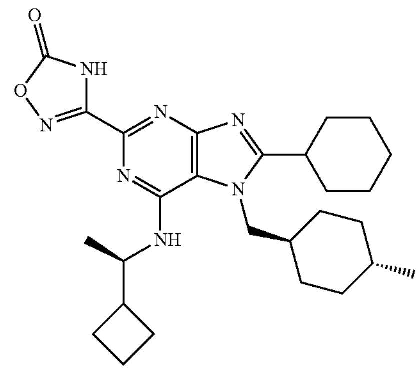 [SMILES: C[C@@H](Nc1nc(-c2noc(=O)[nH]2)nc2nc(C3CCCCC3)n(C[C@H]3CC[C@H](C)CC3)c12)C1CCC1] | 3-(6-{[(1R)-1-cyclobutylethyl]amino}-8-cyclohexyl-7-[(trans-4-methylcyclohexyl)methyl]-7H-purin-2-yl)-1,2,4-oxadiazol-5(4H)-one | | 494 | 494 |
| 21.40 | 4.292 | 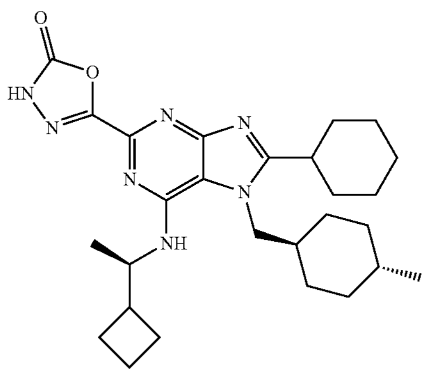 [SMILES: C[C@@H](Nc1nc(-c2n[nH]c(=O)o2)nc2nc(C3CCCCC3)n(C[C@H]3CC[C@H](C)CC3)c12)C1CCC1] | 5-(6-{[(1R)-1-cyclobutylethyl]amino}-8-cyclohexyl-7-[(trans-4-methylcyclohexyl)methyl]-7H-purin-2-yl)-1,3,4-oxadiazol-2(3H)-one | | 494 | 494 |
| 21.41 | 3.245 | 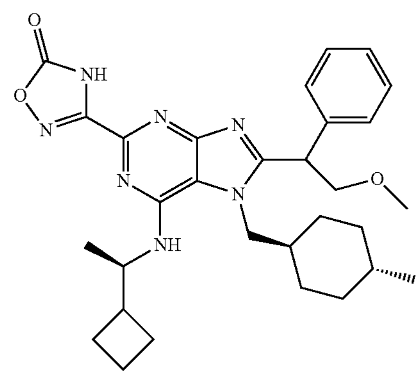 [SMILES: COCC(c1ccccc1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(1R or S)-2-methoxy-1-phenylethyl]-7-[(trans-4-methylcyclohexyl)methyl]-7H-purin-2-yl)-1,2,4-oxadiazol-5(4H)-one (diastereomer 1) | | 546 | 546 |
| 21.42 | 3.414 | 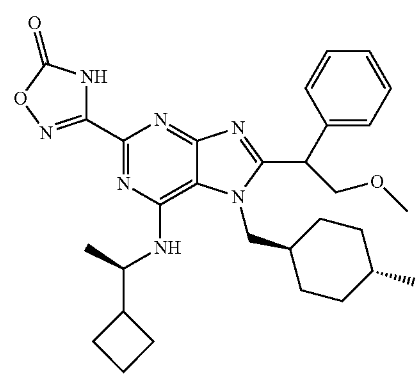 [SMILES: COCC(c1ccccc1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[(1S or R)-2-methoxy-1-phenylethyl]-7-[(trans-4-methylcyclohexyl)methyl]-7H-purin-2-yl)-1,2,4-oxadiazol-5(4H)-one (diastereomer 2) | | 546 | 546 |

Example 22.1

3-(6-{[(1R)-1-cyclobutylethyl]amino}-8-(2,2-dimethylpropanoyl)-7-[(trans-4-methylcyclohexyl)methyl]-7H-purin-2-yl)-1,2,4-oxadiazol-5(4H)-one

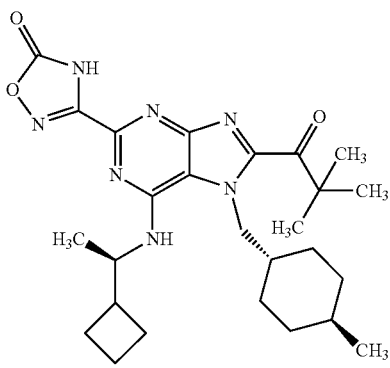 [SMILES: C[C@@H](Nc1nc(-c2noc(=O)[nH]2)nc2nc(C(=O)C(C)(C)C)n(C[C@H]3CC[C@H](C)CC3)c12)C1CCC1]

Step 1: n-BuLi (2.5 mL, 5.0 mmol, 2 M in hexanes) was added dropwise to a solution of 2,2,6,6-tetramethylpiperidine (0.85 mL, 5.0 mmol) in anhydrous THF (15 mL) at −10° C. The reaction mixture was stirred at −10° C. for 15 minutes and then cooled to 78° C. A solution of 6-(((R)-1-cyclobutylethyl)amino)-7-((trans-4-methylcyclohexyl)methyl)-7H-purine-2-carbonitrile (Preparative Example 11.6, 500 mg, 1.42 mmol) in anhydrous THF (5 mL) was added dropwise over 5 minutes. The reaction mixture was stirred at −78° C. for 30 minutes and pivaloyl chloride (0.87 mL, 7.1 mmol) was then added in one portion. The reaction mixture was stirred at −78° C. for 2 hours and then quenched with saturated aqueous NH$_4$Cl solution. The layers were separated and the aqueous layer was extracted with EtOAc (3×10 mL). The combined organic layers were washed with brine, dried over anhydrous Na$_2$SO$_4$, filtered and concentrated in vacuo. Purification of the residue on a RediSep 12 g silica gel column (0 to 50% EtOAc/hexanes) afforded 6-(((R)-1-cyclobutylethyl)amino)-7-((trans-4-methylcyclohexyl)methyl)-8-pivaloyl-7H-purine-2-carbonitrile. MS (ES)=437 (M+1)$^+$.

Step 2: To a solution of NH$_2$OH.HCl (55 mg, 0.79 mmol) and water (0.7 mL) was added NaHCO$_3$ (87 mg, 1.04 mmol) and the mixture was stirred for 10 minutes to get a clear solution. This solution was then added to a solution of 6-(((R)-1-cyclobutylethyl)amino)-7-((trans-4-methylcyclohexyl)methyl)-8-pivaloyl-7H-purine-2-carbonitrile (268 mg, 0.61 mmol) in EtOH (1.0 mL) and the reaction was heated at 100° C. for 1 hour. The reaction mixture was cooled and concentrated to dryness under reduced pressure. Water (10 mL) was then added and the resulting solid was collected by filtration under vacuum. Air drying of the solid afforded 6-(((R)-1-cyclobutylethyl)amino)-N'-hydroxy-7-((trans-4-methylcyclohexyl)methyl)-8-pivaloyl-7H-purine-2-carboximidamide. MS (ES)=470 (M+1)$^+$.

Step 3: CDI (94 mg, 0.58 mmol) was added to a solution of 6-(((R)-1-cyclobutylethyl)amino)-N'-hydroxy-7-((trans-4-methylcyclohexyl)methyl)-8-pivaloyl-7H-purine-2-carboximidamide (250 mg, 0.53 mmol) in acetonitrile (4.0 mL) at room temperature. The reaction mixture was stirred at room temperature for 1 hour. The reaction mixture was concentrated to dryness. The residue was dissolved in CH$_2$Cl$_2$ (10 mL) and the organic layer was washed with brine, dried over anhydrous Na$_2$SO$_4$, filtered and concentrated to dryness. Purification of the residue on a RediSep 12 g silica gel column (0 to 5% MeOH/CH$_2$Cl$_2$) afforded 3-(6-{[(1R)-1-cyclobutylethyl]amino}-8-(2,2-dimethylpropanoyl)-7-[(trans-4-methylcyclohexyl)methyl]-7H-purin-2-yl)-1,2,4-oxadiazol-5(4H)-one. $^1$H NMR (400 MHz, CD$_3$OD) δ 4.75 (m, 1H), 4.53-4.69 (m, 2H), 2.56 (m, 1H), 2.03-2.13 (m, 2H), 1.88-1.97 (m, 3H), 1.57-1.71 (m, 4H), 1.46 (s, 9H), 1.28-1.31 (m, 3H), 1.20 (d, J=6.4 Hz, 3H), 0.98-1.10 (m, 2H), 0.84 (d, J=6.4 Hz, 3H), 0.73-0.80 (m, 3H). MS (ES)=496 (M+1)$^+$.

Example 22.2

3-(6-{[(1R)-1-cyclobutylethyl]amino}-8-(1-hydroxy-1,2,2-trimethylpropyl)-7-[(trans-4-methylcyclohexyl)methyl]-7H-purin-2-yl)-1,2,4-oxadiazol-5(4H)-one

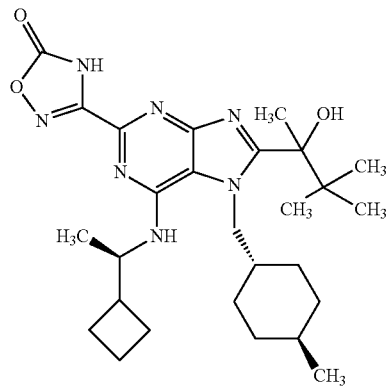 [SMILES: C[C@@H](Nc1nc(-c2noc(=O)[nH]2)nc2nc(C(C)(O)C(C)(C)C)n(C[C@H]3CC[C@H](C)CC3)c12)C1CCC1]

CH$_3$MgBr (3 M in hexanes; 0.30 mL, 0.90 mmol) was added dropwise to a solution of Example 22.1, 3-(6-{[(1R)-1-cyclobutylethyl]amino}-8-(2,2-dimethylpropanoyl)-7-[(trans-4-methylcyclohexyl)methyl]-7H-purin-2-yl)-1,2,4-oxadiazol-5(4H)-one (88 mg, 0.18 mmol) in anhydrous THF (2 mL) at −10° C. The reaction mixture was stirred at −10° C. for 30 minutes and then at room temperature for 2.5 hours. The reaction was quenched with saturated aqueous NH$_4$Cl solution (3 mL). The layers were separated and the aqueous layer was extracted with CH$_2$Cl$_2$ (3×10 mL). The combined organic layers were washed with brine, dried over anhydrous Na$_2$SO$_4$, filtered and concentrated to dryness. Purification of the residue on a RediSep 4 g silica gel column with 0 to 10% MeOH/CH$_2$Cl$_2$ afforded 3-(6-{[(1R)-1-cyclobutylethyl]amino}-8-(1-hydroxy-1,2,2-trimethylpropyl)-7-[(trans-4-methylcyclohexyl)methyl]-7H-purin-2-yl)-1,2,4-oxadiazol-5(4H)-one (mixture of diastereomers). $^1$H NMR (400 MHz, CD$_3$OD) δ 5.39 (m, 1H), 4.73 (m, 1H), 4.28 (m, 1H), 2.56 (m, 1H), 1.83-2.12 (m, 6H), 1.61-1.78 (m, 7H), 1.28-1.32 (m, 2H), 1.12-1.26 (m, 5H), 0.97 (s, 9H), 0.89-0.92 (m, 2H), 0.84 (d, J=6.4 Hz, 1.5H), 0.83 (d, J=6.4 Hz, 1.5H), 0.69 (m, 1H). MS (ES)=512 (M+1)$^+$.

Example 22.3 and Example 22.4

3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5(4H)-one

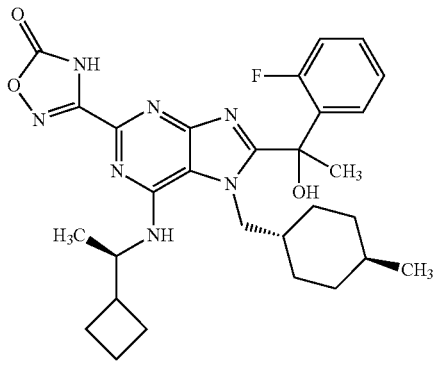 [SMILES: C[C@@H](Nc1nc(-c2noc(=O)[nH]2)nc2nc(C(C)(O)c3ccccc3F)n(C[C@H]3CC[C@H](C)CC3)c12)C1CCC1]

Step 1: n-BuLi (7.1 mL, 14.2 mmol, 2 M in hexanes) was added dropwise to a solution of 2,2,6,6-tetramethylpiperidine (2.4 mL, 14.2 mmol) in anhydrous THF (15 mL) at −10° C. The reaction mixture was stirred at −10° C. for 15 minutes and then cooled to −78° C. A solution of 6-(((R)-1-cyclobutylethyl)amino)-7-((trans-4-methylcyclohexyl)methyl)-7H-purine-2-carbonitrile (Preparative Example 11.6, 1.0 g, 2.84 mmol) in anhydrous THF (10 mL) was added dropwise over 5 minutes. The reaction mixture was stirred at −78° C. for 30 minutes and 1-(2-fluorophenyl)ethanone (706 mg, 5.1 mmol) was then added dropwise. The reaction mixture was stirred at −78° C. for 2 hours and then quenched with saturated aqueous NH₄Cl solution (20 mL). The layers were separated and the aqueous layer was extracted with EtOAc (3×10 mL). The combined organic layers were washed with brine, dried over anhydrous Na₂SO₄, filtered and concentrated in vacuo. Purification of the residue on a Redisep 40 g silica gel column with 0 to 50% EtOAc/hexanes afforded 6-(((R)-1-cyclobutylethyl)amino)-8-(1-(2-fluorophenyl)-1-hydroxyethyl)-7-((trans-4-methylcyclohexyl)methyl)-7H-purine-2-carbonitrile (diastereomer A and diastereomer B). MS (ES)=491 (M+1)⁺.

Step 2: Following a two step procedure reported in Example 16.1 (Step 3 and 4) and starting with of 6-(((R)-1-cyclobutylethyl)amino)-8-(1-(2-fluorophenyl)-1-hydroxyethyl)-7-((trans-4-methylcyclohexyl)methyl)-7H-purine-2-carbonitrile (diastereomer A and diastereomer B), 3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5(4H)-one, Example 22.3 (diastereomer A) and Example 22.4 (diastereomer B) were prepared. Example 22.3 (diastereomer A) ¹H NMR (400 MHz, CD₃OD) δ 7.98 (m, 1H), 7.29-7.39 (m, 2H), 7.01 (m, 1H), 4.68 (m, 1H), 4.12-4.61 (m, 2H), 2.49 (m, 1H), 2.13 (s, 3H), 2.10 (m, 1H), 1.62-2.08 (m, 6H), 1.54 (m, 1H), 1.41 (m, 1H), 1.28-1.39 (m, 3H), 1.35 (d, J=6.4 Hz, 3H), 0.87-1.02 (m, 3H), 0.79 (d, J=6.4 Hz, 3H), 0.61 (m, 1H). MS (ES)=550 (M+1)⁺. Example 22.4 (diastereomer B) ¹H NMR (400 MHz, CD₃OD) δ 7.95 (m, 1H), 7.28-7.36 (m, 2H), 6.97 (m, 1H), 4.66 (m, 1H), 3.98-4.11 (m, 2H), 2.47 (m, 1H), 2.10 (s, 3H), 2.03-2.08 (m, 2H), 1.83-1.89 (m, 4H), 1.43-1.60 (m, 3H), 1.13-1.38 (m, 4H), 1.12 (d, J=6.4 Hz, 3H), 0.80 (d, J=6.4 Hz, 3H), 0.63-0.71 (m, 3H). MS (ES)=550 (M+1)⁺.

Example 22.5

3-(6-{[(1R)-1-cyclobutylethyl]amino}-8-[1-(2-fluorophenyl)cyclopropyl]-7-[(trans-4-methylcyclohexyl)methyl]-7H-purin-2-yl)-1,2,4-oxadiazol-5(4H)-one

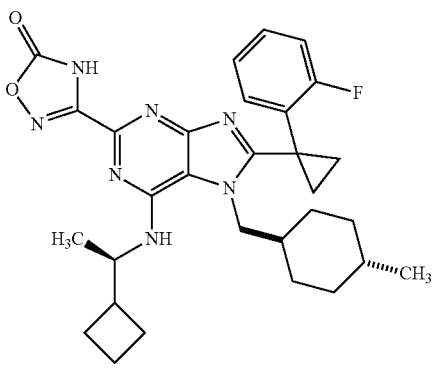

Step 1: To a solution of 3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5(4H)-one (diastereomers A and B) (108 mg, 0.2 mmol) [prepared following the procedure reported for Example 22.3] in CH₂Cl₂ (3 mL) was added SOCl₂ (2 mL) dropwise. The reaction mixture was refluxed at 40° C. for 5 hours. The reaction was cooled to room temperature and then concentrated to dryness in vacuo. The residue was diluted with EtOAc (10 mL) and washed with saturated aqueous NaHCO₃ solution (3×5 mL). The organic layer was washed with brine, dried over anhydrous Na₂SO₄, filtered and concentrated in vacuo. Purification of the residue on a Redisep 4 g silica gel column with 0 to 50% EtOAc/CH₂Cl₂ afforded 3-(6-(((R)-1-cyclobutylethyl)amino)-8-(1-(2-fluorophenyl)vinyl)-7-((trans-4-methylcyclohexyl)methyl)-7H-purin-2-yl)-1,2,4-oxadiazol-5(4H)-one; MS (ES)=532 (M+1)⁺.

Step 2: A round bottom flask was charged with anhydrous DMSO (0.4 mL) and trimethylsulfoxonium iodide (27 mg, 0.12 mmol). KOtBu (14 mg, 0.12 mmol) was added and reaction was stirred at room temperature for 5 minutes. A solution of 3-(6-(((R)-1-cyclobutylethyl)amino)-8-(1-(2-fluorophenyl)vinyl)-7-((trans-4-methylcyclohexyl)methyl)-7H-purin-2-yl)-1,2,4-oxadiazol-5(4H)-one (22 mg, 0.04 mmol) in anhydrous THF (0.1 mL) was then added dropwise and the reaction was stirred at room temperature for 1.5 hours. The reaction was diluted with EtOAc (5 mL), the organic layer was washed with water and brine, dried over anhydrous Na₂SO₄, filtered, and concentrated under vacuum. Purification of the residue on a RediSep 4 g silica gel column with 0 to 20% MeOH/CH₂Cl₂ afforded 3-(6-{[(1R)-1-cyclobutylethyl]amino}-8-[1-(2-fluorophenyl)cyclopropyl]-7-[(trans-4-methylcyclohexyl)methyl]-7H-purin-2-yl)-1,2,4-oxadiazol-5(4H)-one. ¹H NMR (400 MHz, CD₃OD) δ 7.57 (m, 1H), 7.35 (m, 1H), 7.23 (m, 1H), 7.08 (m, 1H), 4.66 (m, 1H), 4.08-4.54 (m, 2H), 2.50 (m, 1H), 2.01-2.07 (m, 3H), 1.86-1.99 (m, 5H), 1.50-1.84 (m, 7H), 1.20-1.28 (m, 2H), 1.13 (d, J=6.4 Hz, 3H), 1.87-1.91 (m, 2H), 0.81 (d, J=6.4 Hz, 3H), 0.67-0.75 (m, 1H). MS (ES)=546 (M+1)⁺.

Example 22.6 and Example 22.7

3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5(4H)-one

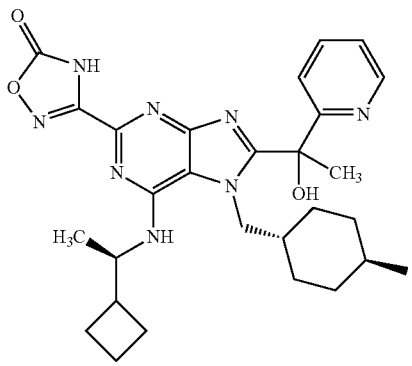 [SMILES: C[C@@H](Nc1nc(-c2noc(=O)[nH]2)nc2nc(C(C)(O)c3ccccn3)n(C[C@H]3CC[C@H](C)CC3)c12)C1CCC1]

Step 1: Using a procedure analogous to that in Example 22.3/22.4, and starting with 6-(((R)-1-cyclobutylethyl)amino)-7-((trans-4-methylcyclohexyl)methyl)-7H-purine-2-carbonitrile (Preparative Example 11.6) and 1-(pyridin-2-yl)ethanone, 6-(((R)-1-cyclobutylethyl)amino)-8-(1-hydroxy-1-(pyridin-2-yl)ethyl)-7-((trans-4-methylcyclohexyl)methyl)-7H-purine-2-carbonitrile was prepared. Separation of diastereomers was done on a chiral column (OD column; 9:1 heptane/IPA). Diastereomer A (slow eluting from chiral column) ¹H NMR (400 MHz, CDCl₃) δ 8.55 (m, 1H), 7.70 (m, 1H), 7.55 (m, 1H), 7.30 (m, 1H), 6.45 (br s, 1H), 4.64 (d, J=8.0 Hz, 1H), 4.44 (m, 1H), 4.03-4.32 (m, 2H), 2.36 (m, 1H), 2.07 (s, 3H), 1.80-1.96 (m, 6H), 1.64 (m, 1H), 1.40-1.48 (m, 2H), 1.15 (d, J=6.4 Hz, 3H), 1.01-1.12 (m, 4H), 0.89 (m, 1H), 0.85 (d, J=6.4 Hz, 3H), 0.59-0.63 (m, 2H). MS (ES)=474 (M+1)⁺. Diastereomer B (fast eluting from chiral column) ¹H NMR (400 MHz, CDCl₃) δ 8.55 (d, J=4.8 Hz, 1H), 7.70 (m, 1H), 7.46 (d, 8.0 Hz, 1H), 7.28 (m, 1H), 6.42 (br s, 1H), 4.68 (d, J=8.4 Hz, 1H), 4.44 (m, 1H), 4.03-4.29 (m, 2H), 2.37 (m, 1H), 2.08 (s, 3H), 1.79-2.05 (m, 6H), 1.67 (m, 1H), 1.39-1.48 (m, 3H), 1.08-1.25 (m, 6H), 0.88 (m, 1H), 0.85 (d, J=6.4 Hz, 3H), 0.63-0.70 (m, 2H). MS (ES)=474 (M+1)⁺.

Step 2: Following a two step procedure reported in Example 16.1 (Step 3 and 4) and starting with 6-(((R)-1-cyclobutylethyl)amino)-8-(1-hydroxy-1-(pyridin-2-yl)ethyl)-7-((trans-4-methylcyclohexyl)methyl)-7H-purine-2-carbonitrile (diastereomer A and diastereomer B, step 1), 3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5(4H)-one, Example 22.6 (diastereomer A) and Example 22.7 (diastereomer B) were prepared.

Example 22.6 (diastereomer A) ¹H NMR (400 MHz, CD₃OD) δ 8.45 (d, J=4.4 Hz, 1H), 7.81-7.90 (m, 2H), 7.34 (m, 1H), 4.67 (m, 1H), 4.49 (m, 1H), 4.12 (m, 1H), 2.50 (m, 1H), 1.79-2.05 (m, 9H), 1.56 (m, 1H), 1.25-1.49 (m, 4H), 1.12 (d, J=6.4 Hz, 3H), 1.06 (m, 1H), 0.89-0.92 (m, 2H), 0.74 (d, J=6.4 Hz, 3H), 0.44-0.58 (m, 3H). MS (ES)=533 (M+1)⁺.

Example 22.7 (diastereomer B) ¹H NMR (400 MHz, DMSO d₆) δ12.86 (br s, 1H), 8.41 (d, J=4.8 Hz, 1H), 7.81-7.92 (m, 2H), 7.31 (m, 1H), 6.67 (s, 1H), 6.25 (d, J=8.0 Hz, 1H), 4.58 (m, 1H), 4.38-4.13 (m, 2H), 1.76-2.00 (m, 9H), 1.49-1.52 (m, 3H), 1.04-1.20 (m, 7H), 0.84 (d, J=6.4 Hz, 3H), 0.49-0.53 (m, 3H). MS (ES)=533 (M+1)⁺.

Example 22.8 and Example 22.9

3-(6-{[(1R)-1-cyclobutylethyl]amino}-8-(1-fluoro-1-pyridin-2-ylethyl)-7-[(trans-4-methylcyclohexyl)methyl]-7H-purin-2-yl)-1,2,4-oxadiazol-5(4H)-one

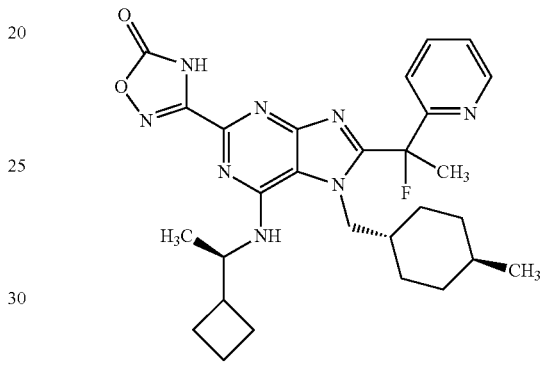

A solution of 3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5(4H)-one (mixture of diastereomers, Example 22.6/22.7) (65 mg, 0.12 mmol) in anhydrous CH₂Cl₂ (2 mL) was cooled to 0° C. and DAST (39 mg, 0.24 mmol) was added dropwise. The reaction was stirred at 0° C. for 30 minutes and then quenched with saturated aqueous NaHCO₃ solution (0.5 mL). The reaction was diluted with CH₂Cl₂ (5 mL), the organic layer was separated, washed with brine, dried over anhydrous Na₂SO₄, filtered and concentrated in vacuo. Purification of the residue on RediSep 4 g silica gel column with 0 to 20% MeOH/CH₂Cl₂ afforded 3-(6-{[(1R)-1-cyclobutylethyl]amino}-8-(1-fluoro-1-pyridin-2-ylethyl)-7-[(trans-4-methylcyclohexyl)methyl]-7H-purin-2-yl)-1,2,4-oxadiazol-5(4H)-one as mixture of diastereomers. Separation of diastereomers using prep HPLC (Luna C18 (2) column, 70% acetonitrile/water isocratic method) afforded diastereomer A (fast eluting on HPLC, Example 22.8) and diastereomer B (slow eluting on HPLC, Example 22.9). (Diastereomer A) Example 22.8: ¹H NMR (400 MHz, CD₃OD) δ 8.48 (d, J=4.4 Hz, 1H), 7.97 (m, 1H), 7.80 (d, J=7.6 Hz, 1H), 7.42 (m, 1H), 4.70 (m, 1H), 4.18-4.21 (m, 2H), 2.51 (m, 1H), 2.23 (d, J=23.6 Hz, 3H), 1.84-2.10 (m, 6H), 1.55-1.59 (m, 2H), 1.25-1.32 (m, 2H), 1.16 (d, J=6.4 Hz, 3H), 1.02-1.23 (m, 2H), 1.93-1.96 (m, 2H), 0.77 (d, J=6.4 Hz, 3H), 0.59-0.66 (m, 2H). MS (ES)=535 (M+1)⁺. (Diastereomer B) Example 22.9: ¹H NMR (400 MHz, CD₃OD) δ 8.44 (br s, 1H), 7.97 (m, 1H), 7.77 (d, J=8.0 Hz, 1H), 7.40 (m, 1H), 4.68 (m, 1H), 4.13-4.18 (m, 1H), 3.82 (m, 1H), 2.50 (m, 1H), 2.25 (d, J=23.2 Hz, 3H), 1.84-2.10 (m, 6H), 1.49-1.68 (m, 5H), 1.23 (m, 1H), 1.13 (d, J=6.3 Hz, 3H), 1.05 (m, 1H), 0.92 (m, 1H), 0.82 (d, J=6.6 Hz, 3H), 0.59-0.66 (m, 2H). MS (ES)=535 (M+1)+.

Example 22.10

3-[6-{[(1R)-1-cyclobutylethyl]amino}-7-[(trans-4-methylcyclohexyl)methyl]-8-(1-pyridin-2-ylcyclopropyl)-7H-purin-2-yl]-1,2,4-oxadiazol-5(4H)-one

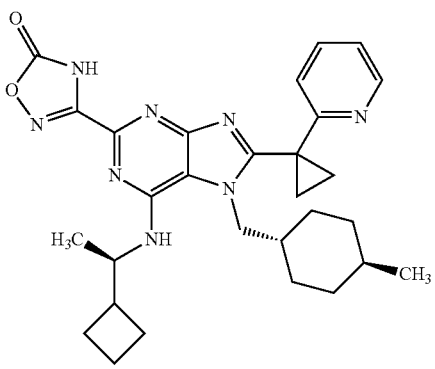 [SMILES: C[C@@H](Nc1nc(-c2noc(=O)[nH]2)nc2nc(C3(c4ccccn4)CC3)n(C[C@H]3CC[C@H](C)CC3)c12)C1CCC1]

Step 1: A round bottom flask equipped with a stir bar was charged with 6-(((R)-1-cyclobutylethyl)amino)-8-(1-hydroxy-1-(pyridin-2-yl)ethyl)-7-((trans-4-methylcyclohexyl)methyl)-7H-purine-2-carbonitrile (mixture of diastereomers, obtained from Step 1, Example 22.6/22.7) (140 mg, 1.89 mmol) and SOCl₂ (5 mL). The reaction mixture was heated at 80° C. for 5 hours. The reaction was then cooled to room temperature, the solvent was evaporated, and the residue was diluted with CH₂Cl₂ (8 mL). The organic layer was washed with saturated aqueous NaHCO₃ (10 mL) and brine (10 mL), dried over anhydrous Na₂SO₄, filtered and concentrated in vacuo. Purification of the residue on a RediSep 12 g silica gel column with 0 to 100% EtOAc/Hexanes afforded 8-(1-chloro-1-(pyridin-2-yl)ethyl)-6-((R)-1-cyclobutylethylamino)-7-((trans-4-methylcyclohexyl)methyl)-7H-purine-2-carbonitrile. MS(ES)=492 (M+1)+.

Step 2: A round bottom flask equipped with a stir bar was charged with 8-(1-chloro-1-(pyridin-2-yl)ethyl)-6-((R)-1-cyclobutylethylamino)-7-((trans-4-methylcyclohexyl)methyl)-7H-purine-2-carbonitrile (72 mg, 0.15 mmol) and toluene (5 mL). DBU (0.023 mL 0.15 mmol) was added and the reaction mixture was stirred at room temperature for 18 hours. The solvent was evaporated and purification of the residue on a RediSep 4 g silica gel column with 0 to 100% EtOAc/Hexanes afforded 6-(((R)-1-cyclobutylethyl)amino)-8-(1-(pyridin-2-yl)vinyl)-7-((trans-4-methylcyclohexyl)methyl)-7H-purine-2-carbonitrile. MS(ES)=456 (M+1)+.

Step 3: Following a procedure analogous to that described for Example 22.5 (Step 2) followed by a two step procedure reported in Example 16.1 (Step 3 and 4) and starting with 6-(((R)-1-cyclobutylethyl)amino)-8-(1-(pyridin-2-yl)vinyl)-7-((trans-4-methylcyclohexyl)methyl)-7H-purine-2-carbonitrile, 3-[6-{[(1R)-1-cyclobutylethyl]amino}-7-[(trans-4-methylcyclohexyl)methyl]-8-(1-pyridin-2-ylcyclopropyl)-7H-purin-2-yl]-1,2,4-oxadiazol-5(4H)-one was prepared.
¹H NMR (400 MHz, CD₃OD) δ 8.47 (d, J=4.0 Hz, 1H), 7.73 (m, 1H), 7.28 (m, 1H), 7.19 (d, J=8.0 Hz, 1H), 4.72 (m, 1H), 4.06-4.22 (m, 2H), 2.53 (m, 1H), 1.80-2.03 (m, 6H), 1.55-1.66 (m, 4H), 1.21-1.43 (m, 5H), 1.19 (d, J=6.4 Hz, 3H), 0.92-0.96 (m, 2H), 0.79 (d, J=6.4 Hz, 3H), 0.65-0.76 (m, 3H). MS (ES)=529 (M+1)+.

Example 22.11

3-(6-{[(1R)-1-cyclobutylethyl]amino}-8-(2,2-dimethyl-1-methylidenepropyl)-7-[(trans-4-methylcyclohexyl)methyl]-7H-purin-2-yl)-1,2,4-oxadiazol-5(4H)-one

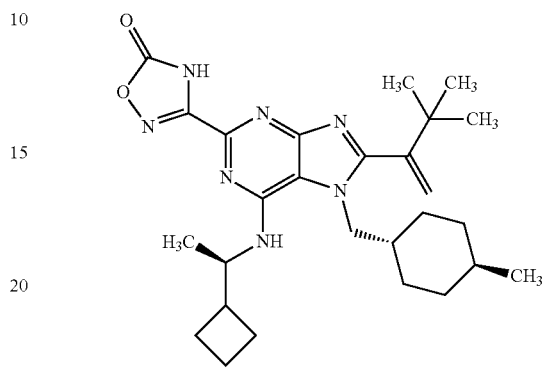

Following a procedure analogous to that described for Example 22.5 (Step 1) and starting with 3-(6-{[(1R)-1-cyclobutylethyl]amino}-8-(1-hydroxy-1,2,2-trimethylpropyl)-7-[(trans-4-methylcyclohexyl)methyl]-7H-purin-2-yl)-1,2,4-oxadiazol-5(4H)-one (Example 22.2), 3-(6-{[(1R)-1-cyclobutylethyl]amino}-8-(2,2-dimethyl-1-methylidenepropyl)-7-[(trans-4-methylcyclohexyl)methyl]-7H-purin-2-yl)-1,2,4-oxadiazol-5(4H)-one was prepared.
¹H NMR (400 MHz, CD₃OD) δ 5.87 (s, 1H), 5.37 (s, 1H), 4.33 (m, 1H), 4.06-4.13 (m, 2H), 2.56 (m, 1H), 2.02-2.15 (m, 3H), 1.81-1.96 (m, 5H), 1.57-1.79 (m, 5H), 1.21 (s, 9H), 0.97-1.10 (m, 4H), 0.86 (d, J=6.8 Hz, 3H), 0.72-0.79 (m, 2H). MS (ES)=494 (M+1)+.

Example 22.12 and Example 22.13

3-[6-{[(1R)-1-cyclobutylethyl]amino}-7-[(trans-4-methylcyclohexyl)methyl]-8-(2,2,2-trifluoro-1-hydroxy-1-methylethyl)-7H-purin-2-yl]-1,2,4-oxadiazol-5(4H)-one

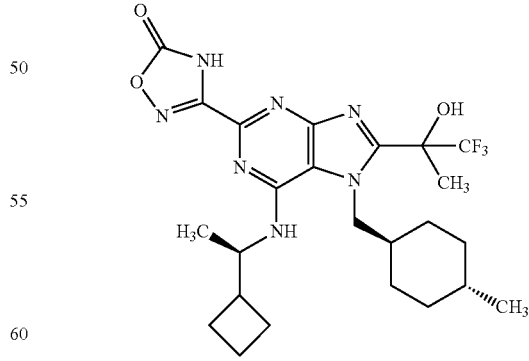

Step 1: n-BuLi (29.7 mL, 56.6 mmol, 2 M in hexanes) was added dropwise to a solution of 2,2,6,6-tetramethylpiperidine (9.5 mL, 56.6 mmol) in anhydrous THF (60 mL) at 10° C. The reaction mixture was stirred at 10° C. for 15 minutes and then cooled to 78° C. A solution of 6-(((R)-1-cyclobutylethyl)amino)-7-((trans-4-methylcyclohexyl)methyl)-7H-purine-2-carbonitrile (Preparative Example 11.6, 4.00 g, 11.3 mmol) in anhydrous THF (40 mL) was added at 78° C. dropwise over 10 minutes. The reaction mixture was stirred at 78° C. for 1 hour and acetaldehyde (598 mg, 13.5 mmol) was then added dropwise over 10 minutes. The reaction mixture was stirred at 78° C. for 2 hours and then quenched with saturated aqueous NH$_4$Cl solution (100 mL). The layers were separated and the aqueous layer was extracted with EtOAc (2×100 mL). The combined organic layers were washed with brine (100 mL), dried over anhydrous Na$_2$SO$_4$, filtered and concentrated. Purification of the residue on a Redisep 40 g silica gel column with 0 to 50% EtOAc/hexanes afforded 6-(((R)-1-cyclobutylethyl)amino)-8-(1-hydroxyethyl)-7-(((trans)-4-methylcyclohexyl)methyl)-7H-purine-2-carbonitrile. MS (ES)=397 (M+1)$^+$.

Step 2: A 250 mL round bottom flask was charged with 6-(((R)-1-cyclobutylethyl)amino)-8-(1-hydroxyethyl)-7-(((trans)-4-methylcyclohexyl)methyl)-7H-purine-2-carbonitrile (3.90 g, 9.83 mmol) and CH$_2$Cl$_2$ (80 mL). Dess-Martin periodinane (5.43 g, 12.8 mmol) was added portionwise at 0° C. The reaction was gradually warmed to room temperature and stirred for 2 hours. The reaction was filtered through celite and the filtrate was washed with saturated aqueous NaHCO$_3$ (100 mL), water (100 mL), brine (100 mL), dried over anhydrous Na$_2$SO$_4$ and filtered. The solvent was evaporated and the residue was purified on a RediSep 40 g silica gel column with 0 to 30% EtOAc/hexanes to afford 8-acetyl-6-(((R)-1-cyclobutylethyl)amino)-7-(((trans)-4-methylcyclohexyl)methyl)-7H-purine-2-carbonitrile. MS (ES)=395 (M+1)$^+$.

Step 3: To a stirred solution of 8-acetyl-6-(((R)-1-cyclobutylethyl)amino)-7-(((trans)-4-methylcyclohexyl)methyl)-7H-purine-2-carbonitrile (100 mg, 0.25 mmol) in THF (5 mL) was added tetrabutylammonium fluoride (331 mg, 1.26 mmol) and trifluoromethyl trimethylsilane (180 mg, 1.26 mmol). Then reaction mixture was heated at 80° C. for 16 hours in a sealed tube. The reaction mixture was diluted with EtOAc (50 mL) and the organic layer was washed with water (2×20 mL) and brine (20 mL), dried over anhydrous Na$_2$SO$_4$, filtered, and concentrated. Purification of the residue on a Redisep R$_f$ 12 g silica gel column with 0 to 40% EtOAc/hexanes afforded diastereomer A (first eluting diastereomer from column) and diastereomer B (second eluting diastereomer from column) of 6-(((R)-1-cyclobutylethyl)amino)-7-(((trans)-4-methylcyclohexyl)methyl)-8-(1,1,1-trifluoro-2-hydroxypropan-2-yl)-7H-purine-2-carbonitrile. Diastereomer A: $^1$H NMR (400 MHz, CD$_3$OD) δ 5.09 (br s, 1H), 4.27-4.62 (m, 2H), 2.57 (m, 1H), 1.95-2.15 (m, 3H), 1.94 (m, 3H), 1.82-1.93 (m, 3H), 1.68-1.81 (m, 2H), 1.62 (m, 1H), 1.22 (m, 5H), 1.17 (d, J=6.4 Hz, 3H), 0.86-0.92 (m, 2H), 0.84 (d, J=6.4 Hz, 3H). MS (ES)=465 (M+1)$^+$.

Diastereomer B: $^1$H NMR (400 MHz, CD$_3$OD) δ 5.09 (br s, 1H), 4.43-4.63 (m, 2H), 2.56 (m, 1H), 2.07-2.21 (m, 2H), 1.81-1.91 (m, 5H), 1.55-1.80 (m, 4H), 1.05-1.47 (m, 8H), 0.75-0.95 (m, 6H). MS (ES)=465 (M+1)$^+$.

Step 4: Using a procedure analogous to that described in Example 16.1 (steps 3 and 4) and starting with 6-(((R)-1-cyclobutylethyl)amino)-7-((trans)-4-methylcyclohexyl)methyl)-8-(1,1,1-trifluoro-2-hydroxypropan-2-yl)-7H-purine-2-carbonitrile (diastereomer A and diastereomer B), 3-[6-{[(1R)-1-cyclobutylethyl]amino}-7-[(trans-4-methylcyclohexyl)methyl]-8-(2,2,2-trifluoro-1-hydroxy-1-methylethyl)-7H-purin-2-yl]-1,2,4-oxadiazol-5(4H)-one, Example 22.12 and (Diastereomer A) and Example 22.13 (Diastereomer B) were prepared. Example 22.12 (Diastereomer A) $^1$H NMR (400 MHz, CD$_3$OD) δ 5.11 (br s, 1H), 4.71 (m, 1H), 4.45 (br s, 1H), 2.55 (m, 1H), 2.12 (m, 2H), 1.99 (s, 3H), 1.85-1.97 (m, 4H), 1.75-1.84 (m, 3H), 1.63 (m, 1H), 1.25-1.38 (m, 2H), 1.22 (m, 1H), 1.17 (d, J=6.4 Hz, 3H), 1.06 (m, 1H), 0.91 (m, 1H), 0.84 (d, J=6.4 Hz, 3H), 0.70 (m, 1H). MS (ES)=524 (M+1)$^+$. Example 22.13 (Diastereomer B). $^1$H NMR (400 MHz, CD$_3$OD) δ 4.64-4.78 (m, 2H), 4.36 (m, 1H), 2.58 (m, 1H), 1.55-2.27 (m, 12H), 0.96-1.44 (m, 8H), 0.85 (d, J=6.4 Hz, 3H), 0.64-0.95 (m, 2H). MS (ES) =524 (M+1)$^+$.

Example 22.14 and Example 22.15

3-(6-{[(1R)-1-cyclobutylethyl]amino}-8-(1-hydroxyethyl)-7-[(trans-4-methylcyclohexyl)methyl]-7H-purin-2-yl)-1,2,4-oxadiazol-5(2H)-one

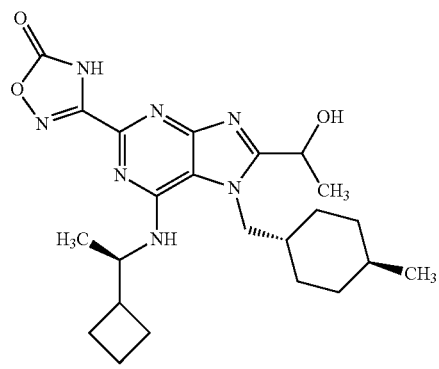 [SMILES: CC(O)c1nc2nc(-c3noc(=O)[nH]3)nc(N[C@H](C)C3CCC3)c2n1C[C@H]1CC[C@H](C)CC1]

Step 1: To a solution of NH$_2$OH.HCl (1.18 g, 17.0 mmol) and water (5.0 mL) was added NaHCO$_3$ (2.14 g, 25.5 mmol) and the mixture was stirred for 10 minutes to get a clear solution. This solution was then added to a solution of 6-(((R)-1-cyclobutylethyl)amino)-7-((trans-4-methylcyclohexyl)methyl)-7H-purine-2-carbonitrile (Preparative Example 11.6, 3.0 g, 8.51 mmol) in EtOH (30 mL) and the reaction was heated at 100° C. for 1 hour. The reaction mixture was concentrated to dryness under reduced pressure. Water (20 mL) was then added and the resulting solid was collected by filtration under vacuum. Air drying of the solid afforded 6-(((R)-1-cyclobutylethyl)amino)-N-hydroxy-7-((trans-4-methylcyclohexyl)methyl)-7H-purine-2-carboximidamide. MS (ES)=386 (M+1)$^+$.

Step 2: CDI (1.48 g, 9.13 mmol) was added to a solution of 6-(((R)-1-cyclobutylethyl)amino)-N-hydroxy-7-((trans-4-methylcyclohexyl)methyl)-7H-purine-2-carboximidamide (3.20 g, 8.30 mmol) in acetonitrile (35 mL) at room temperature. The reaction mixture was stirred at room temperature for 1 hour. The reaction mixture was concentrated to dryness. The residue was dissolved in CH$_2$Cl$_2$ (150 mL) and the organic layer was washed 1M HCl solution (30 mL) and brine (30 mL), dried over anhydrous Na$_2$SO$_4$, filtered and concentrated to dryness. Purification of the residue by reverse phase column chromatography (10 to 90% water/CH$_3$CN) afforded 3-(6-(((R)-1-cyclobutylethyl)amino)-7-((trans-4-methylcyclohexyl)methyl)-7H-purin-2-yl)-1,2,4-oxadiazol-5(4H)-one. $^1$H NMR (400 MHz, DMSO-d$_6$) δ 12.90 (br s, 1H), 8.36 (s, 1H), 6.52 (d, J=8.4 Hz, 1H), 4.52-4.66 (m, 2H), 4.17 (dd, J=14.4, 8.8 Hz, 1H), 2.53-2.64 (m, 1H), 1.99-2.09 (m, 1H), 1.89-1.97 (m, 1H), 1.73-1.87 (m, 4H), 1.47-1.71 (m, 4H), 1.09-1.32 (m, 2H), 1.13 (d, J=6.4 Hz, 3H), 0.89-1.08 (m, 2H), 0.81 (d, J=6.4 Hz, 3H), 0.62-0.80 (m, 2H). MS (ES)=412 (M+1)⁺.

Step 3: Using a procedure analogous to that described in Example 22.3 (Step 1), and starting with, 3-(6-(((R)-1-cyclobutylethyl)amino)-7-((trans-4-methylcyclohexyl)methyl)-7H-purin-2-yl)-1,2,4-oxadiazol-5(4H)-one and acetaldehyde, 3-(6-{[(1R)-1-cyclobutylethyl]amino}-8-(1-hydroxyethyl)-7-[(trans-4-methylcyclohexyl)methyl]-7H-purin-2-yl)-1,2,4-oxadiazol-5(2H)-one (diastereomer A), Example 22.14 and (diastereomer B), Example 22.15 were prepared. Example 22.14 (diastereomer A) ¹H NMR (400 MHz, DMSO-d₆) δ 12.83 (br s, 1H), 6.41 (d, J=8.8 Hz, 1H), 5.03 (q, J=6.4 Hz, 1H), 4.58-4.70 (m, 1H), 4.35-4.51 (m, 3H), 2.53-2.64 (m, 1H), 1.97-2.08 (m, 1H), 1.87-1.96 (m, 1H), 1.74-1.87 (m, 4H), 1.59-1.70 (m, 3H), 1.56 (d, J=6.4 Hz, 3H), 1.33-1.48 (m, 2H), 1.18-1.33 (m, 1H), 1.11 (d, J=6.4 Hz, 3H), 1.00-1.10 (m, 2H), 0.80 (d, J=6.8 Hz, 3H), 0.65-0.79 (m, 2H). MS (ES)=456 (M+1)⁺. Example 22.15 (diastereomer B)¹H NMR (400 MHz, DMSO-d₆) 12.83 (br s, 1H), 6.43 (d, J=8.4 Hz, 1H), 5.00 (q, J=6.4 Hz, 1H), 4.53-4.67 (m, 3H), 4.33 (dd, J=15.2, 9.6 Hz, 1H), 2.52-2.61 (m, 1H), 2.00-2.10 (m, 1H), 1.90-2.00 (m, 1H), 1.73-1.89 (m, 4H), 1.50-1.72 (m, 4H), 1.59 (d, J=6.4 Hz, 3H), 1.20-1.34 (m, 1H), 0.94-1.18 (m, 3H), 1.11 (d, J=6.4 Hz, 3H), 0.58-0.84 (m, 2H), 0.80 (d, J=6.4 Hz, 3H). MS (ES)=456 (M+1)⁺.

Example 22.16

3-(6-{[(1R)-1-cyclobutylethyl]amino}-8-(2-hydroxy-2-methylpropyl)-7-[(trans-4-methylcyclohexyl)methyl]-7H-purin-2-yl)-1,2,4-oxadiazol-5(4H)-one

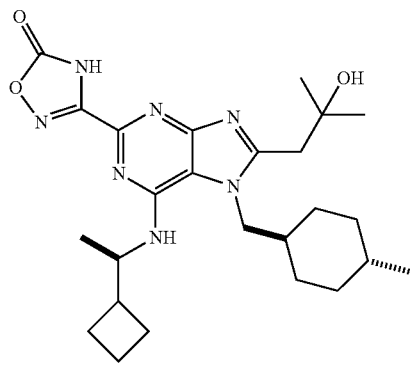

Step 1: To a cooled (−78° C.) solution of 2,2,6,6-tetramethylpiperidine (0.361 mL, 2.128 mmol) in 3000 uL THF under argon was added nBuLi (1.6 M in hexanes, 1.330 mL, 2.128 mmol). The mixture was stirred for 30 minutes at −78° C. A solution of 6-{[(1R)-1-cyclobutylethyl]amino}-7-[(trans-4-methylcyclohexyl)methyl]-7H-purine-2-carbonitrile (Preparative Example 11.6, 250 mg, 0.709 mmol) in 2600 uL THF was added and the resulting solution was stirred for 45 minutes at −78° C. 2,2-Dimethyloxirane (0.095 mL, 1.064 mmol) and (diethyl ether)(trifluoro)boron (0.135 mL, 1.064 mmol) were sequentially added. The mixture was stirred at −78° C. for one hour and then warmed to room temperature and stirred as such overnight. The mixture was then quenched via the addition of saturated aqueous ammonium chloride. The resulting slurry was diluted with water and extracted with ethyl acetate. The organic layer was dried over magnesium sulfate, filtered, and concentrated under reduced pressure. The resulting residue was purified via mass guided reverse phase HPLC (acetonitrile/water+1% TFA modifier). Desired fractions were combined, diluted with ethyl acetate, and washed with saturated aqueous sodium bicarbonate. The organic layer was dried over magnesium sulfate, filtered, and concentrated under reduced pressure to afford 6-{[(1R)-1-cyclobutylethyl]amino}-8-(2-hydroxy-2-methylpropyl)-7-[(trans-4-methylcyclohexyl)methyl]-7H-purine-2-carbonitrile as an off-white foam. MS ESI calc'd. for $C_{24}H_{36}N_6O$ [M+H]⁺ 425. found 425.

Step 2: Hydroxylamine hydrochloride (3.27 mg, 0.047 mmol), sodium bicarbonate (5.94 mg, 0.071 mmol) and water (70.7 μl) were combined in a vial and allowed to stir for 15 minutes to allow for gas evolution via a pierced septa. The resulting solution was added to a vial containing 6-{[(1R)-1-cyclobutylethyl]amino}-8-(2-hydroxy-2-methylpropyl)-7-[(trans-4-methylcyclohexyl)methyl]-7H-purine-2-carbonitrile (10 mg, 0.024 mmol) in ethanol (165 μl). The vial was capped and stirred at 100° C. for 1 hour. The mixture was cooled, diluted with water and extracted with ethyl acetate (2×). The combined organics were dried over sodium sulfate, filtered, and concentrated in vacuo to afford 6-{[(1R)-1-cyclobutylethyl]amino}-N-hydroxy-8-(2-hydroxy-2-methylpropyl)-7-[(trans-4-methylcyclohexyl)methyl]-7H-purine-2-carboximidamide as a yellow solid. MS ESI calcd. for $C_{24}H_{39}N_7O_2$ [M+H]⁺ 458. found 458.

Step 3: To a solution of 6-{[(1R)-1-cyclobutylethyl]amino}-N-hydroxy-8-(2-hydroxy-2-methylpropyl)-7-[(trans-4-methylcyclohexyl)methyl]-7H-purine-2-carboximidamide (10.78 mg, 0.024 mmol) and 1,1'-carbonyldiimidazole (4.20 mg, 0.026 mmol) dissolved in acetonitrile (236 μl) was added 1,8-diazabicyclo[5.4.0]undec-7-ene (14.08 μl, 0.094 mmol). The resulting solution was stirred at room temperature overnight, barrier filtered, and submitted for mass guided reverse phase HPLC (acetonitrile/water+0.1% TFA modifier). Desired fractions were diluted with ethyl acetate and washed with saturated aqueous sodium bicarbonate. The organic layer was dried over magnesium sulfate, filtered, and concentrated under reduced pressure to afford 3-(6-{[(1R)-1-cyclobutylethyl]amino}-8-(2-hydroxy-2-methylpropyl)-7-[(trans-4-methylcyclohexyl)methyl]-7H-purin-2-yl)-1,2,4-oxadiazol-5(4H)-one as a white solid. MS ESI calc'd. for $C_{25}H_{37}N_7O_3$ [M+H]⁺ 484. found 484. ¹H NMR (500 MHz, DMSO-d₆) δ 6.36 (d, J=8.0 Hz, 1H), 4.86 (s, 1H), 4.58-4.48 (m, 2H), 4.32-4.26 (m, 1H), 3.04 (d, J=14.0 Hz, 1H), 2.91 (d, J=14.0 Hz, 1H), 2.53-2.51 (m, 1H), 2.04-1.96 (m, 1H), 1.94-1.87 (m, 1H), 1.83-1.72 (m, 4H), 1.65-1.43 (m, 4H), 1.24-1.21 (m, 5H), 1.15 (s, 3H), 1.09 (d, J=6.0 Hz, 3H), 1.03-0.98 (m, 2H), 0.78 (d, J=6.0 Hz, 3H), 0.75-0.72 (m, 1H), 0.67-0.62 (m, 1H).

Example 22.17 and Example 22.18

3-(6-{[(1R)-1-cyclobutylethyl]amino}-8-[(1R or S)-1,2-dihydroxyethyl]-7-[(trans-4-methylcyclohexyl)methyl]-7H-purin-2-yl)-1,2,4-oxadiazol-5(4H)-one (TFA salt, diastereomer A) and 3-(6-{[(1R)-1-cyclobutylethyl]amino}-8-[(1S or R)-1,2-dihydroxyethyl]-7-[(trans-4-methylcyclohexyl)methyl]-7H-purin-2-yl)-1,2,4-oxadiazol-5(4H)-one (TFA salt, diastereomer B)

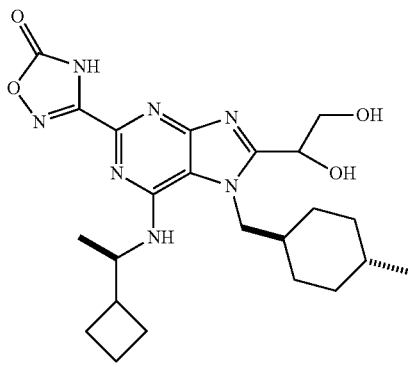

Step 1: To a cooled (−78° C.) solution of 2,2,6,6-tetramethylpiperidine (0.361 mL, 2.128 mmol) in 3000 uL THF under argon was added nBuLi (1.6 M in hexanes, 1.330 mL, 2.128 mmol). The mixture was stirred for 30 minutes at −78° C. A solution of 6-{[(1R)-1-cyclobutylethyl]amino}-7-[(trans-4-methylcyclohexyl)methyl]-7H-purine-2-carbonitrile (Preparative Example 11.6, 250 mg, 0.709 mmol) in 2600 uL THF was then added and the mixture stirred for 45 minutes at −78° C. 2-((tert-Butyldimethylsilyl)oxy)acetaldehyde (0.162 mL, 0.851 mmol) was then added and the reaction stirred at −78° C. for 1 hour. The mixture was quenched via the addition of saturated aqueous ammonium chloride and warmed to room temperature. The resulting slurry was diluted with water and extracted with ethyl acetate (2×). Combined organics were dried over magnesium sulfate, filtered, and concentrated under reduced pressure. The resulting residue was purified via silica gel chromatography to afford 8-(2-{[tert-butyl(dimethyl)silyl]oxy}-1-hydroxyethyl)-6-{[(1R)-1-cyclobutylethyl]amino}-7-[(trans-4-methylcyclohexyl)methyl]-7H-purine-2-carbonitrile (a mixture of diastereomers) as a light yellow solid. MS ESI calc'd. for $C_{28}H_{46}N_6O_2Si$ $[M+H]^+$ 527. found 527.

Step 2: Hydroxylamine hydrochloride (27.4 mg, 0.395 mmol), sodium bicarbonate (49.8 mg, 0.592 mmol) and water (592 μl) were combined and allowed to stir for 15 minutes to allow for gas evolution. The resulting solution was added to a solution of 8-(2-{[tert-butyl(dimethyl)silyl]oxy}-1-hydroxyethyl)-6-{[(1R)-1-cyclobutylethyl]amino}-7-[(trans-4-methylcyclohexyl)methyl]-7H-purine-2-carbonitrile (104 mg, 0.197 mmol) in ethanol (1382 μl). The reaction was stirred at 100° C. for 1 hour. The mixture was then cooled to room temperature, diluted with water and brine, and extracted with ethyl acetate (2×). The combined organics were dried over sodium sulfate, filtered, and concentrated in vacuo to afford 8-(2-{[tert-butyl(dimethyl)silyl]oxy}-1-hydroxyethyl)-6-{[(1R)-1-cyclobutylethyl]amino}-N-hydroxy-7-[(trans-4-methylcyclohexyl)methyl]-7H-purine-2-carboximidamide (a mixture of diastereomers) as a yellow solid. MS ESI calc'd. for $C_{28}H_{49}N_7O_3Si$ $[M+H]^+$ 560. found 560.

Step 3: To a solution of 8-(2-{[tert-butyl(dimethyl)silyl]oxy}-1-hydroxyethyl)-6-{[(1R)-1-cyclobutylethyl]amino}-N-hydroxy-7-[(trans-4-methylcyclohexyl)methyl]-7H-purine-2-carboximidamide (111 mg, 0.198 mmol) and 1,1'-carbonyldiimidazole (35.4 mg, 0.218 mmol) dissolved in acetonitrile (1983 μl) was added 1,8-diazabicyclo[5.4.0]undec-7-ene (118 μl, 0.793 mmol). The resulting solution was stirred at room temperature for 2 hours. The mixture was diluted with DCM and washed with 2N aqueous HCl. The organic layer was dried over magnesium sulfate, filtered, and concentrated under reduced pressure to afford 3-{8-(2-{[tert-butyl(dimethyl)silyl]oxy}-1-hydroxyethyl)-6-{[(1R)-1-cyclobutylethyl]amino}-7-[(trans-4-methylcyclohexyl)methyl]-7H-purin-2-yl}-1,2,4-oxadiazol-5(4H)-one (a mixture of diastereomers) as a white solid. MS ESI calc'd. for $C_{29}H_{47}N_7O_4Si$ $[M+H]^+$ 586. found 586.

Step 4: 3-{8-(2-{[tert-butyl(dimethyl)silyl]oxy}-1-hydroxyethyl)-6-{[(1R)-1-cyclobutylethyl]amino}-7-[(trans-4-methylcyclohexyl)methyl]-7H-purin-2-yl}-1,2,4-oxadiazol-5(4H)-one (90 mg, 0.154 mmol) was taken up in THF (1536 μl) and TBAF (1.0 M in THF, 307 μl, 0.307 mmol) was added. The mixture was stirred at room temperature for one hour. The solvent was removed under reduced pressure and the resulting residue was purified via mass guided reverse phase HPLC (acetonitrile/water+0.1% TFA modifier) to afford 3-(6-{[(1R)-1-cyclobutylethyl]amino}-8-[(1R or S)-1,2-dihydroxyethyl]-7-[(trans-4-methylcyclohexyl)methyl]-7H-purin-2-yl)-1,2,4-oxadiazol-5(4H)-one (TFA salt) (diastereomer A, Example 22.17) and 3-(6-{[(1R)-1-cyclobutylethyl]amino}-8-[(1S or R)-1,2-dihydroxyethyl]-7-[(trans-4-methylcyclohexyl)methyl]-7H-purin-2-yl)-1,2,4-oxadiazol-5(4H)-one (TFA salt) (diastereomer B, Example 22.18). Diastereomer A, faster eluting: MS ESI calc'd. for $C_{23}H_{33}N_7O_4$ $[M+H]^+$ 472. found 472. $^1$H NMR (500 MHz, DMSO-$d_6$) δ 12.85 (s, 1H), 6.46 (d, J=8.5 Hz, 1H), 4.84 (t, J=6.5 Hz, 1H), 4.64-4.58 (m, 2H), 4.52-4.48 (m, 1H), 4.34-4.30 (m, 2H), 6.76 (d, J=6.5 Hz, 2H), 2.55-2.50 (m, 1H), 2.03-1.98 (m, 1H), 1.92-1.88 (m, 1H), 1.84-1.76 (m, 4H), 1.62-1.57 (m, 4H), 1.45-1.42 (m, 1H), 1.35-1.33 (m, 1H), 1.27-1.20 (m, 1H), 1.09 (d, J=6.0 Hz, 3H), 1.06-1.00 (m, 1H), 0.79 (d, J=7.0 Hz, 3H), 0.76-0.67 (m, 2H). Diastereomer B, slower eluting: MS ESI calc'd. for $C_{23}H_{33}N_7O_4$ $[M+H]^+$ 472. found 472. $^1$H NMR (500 MHz, DMSO-$d_6$) δ 12.85 (s, 1H), 6.44 (d, J=8.5 Hz, 1H), 4.78 (d, J=6.5 Hz, 1H), 4.59-4.55 (m, 2H), 4.34-4.30 (m, 1H), 3.93-3.90 (m, 2H), 3.80-3.76 (m, 2H), 2.56-2.50 (m, 1H), 2.03-1.99 (m, 1H), 1.94-1.90 (m, 1H), 1.84-1.76 (m, 4H), 1.65-1.55 (m, 4H), 1.28-1.20 (m, 2H), 1.18-1.12 (m, 1H), 1.09 (d, J=6.5 Hz, 3H), 1.04-0.99 (m, 1H), 0.78 (d, J=6.5 Hz, 3H), 0.74-0.63 (m, 2H).

Example 22.19 and Example 22.20

3-(6-{[(1R)-1-cyclobutylethyl]amino}-8-[(R or S)-methoxy(phenyl)methyl]-7-[(trans-4-methylcyclohexyl)methyl]-7H-purin-2-yl)-1,2,4-oxadiazol-5(4H)-one and 3-(6-{[(1R)-1-cyclobutylethyl]amino}-8-[(S or R)-methoxy(phenyl)methyl]-7-[(trans-4-methylcyclohexyl)methyl]-7H-purin-2-yl)-1,2,4-oxadiazol-5(4H)-one

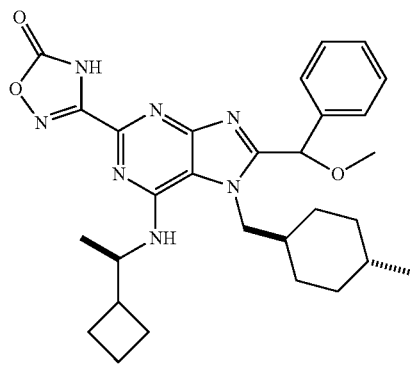

Step 1: Sodium hydride (60%, 17.44 mg, 0.436 mmol) was added in one portion to a solution of 6-{[(1R)-1-cyclobutylethyl]amino}-8-[hydroxy(phenyl)methyl]-7-[(trans-4-methylcyclohexyl)methyl]-7H-purine-2-carbonitrile (100 mg, 0.218 mmol) (prepared following procedures similar to Example 22.17, Step 1) in THF (2181 µl) at 0° C. The resulting bright yellow solution was stirred for 30 minutes, at which time iodomethane (13.63 µl, 0.218 mmol) was added. The reaction was stirred at 0° C. for 2.5 hours. The mixture was then quenched with saturated aqueous ammonium chloride and extracted with ethyl acetate. The organic layer was dried over magnesium sulfate, filtered, and concentrated under reduced pressure. Purification via silica gel chromatography (ethyl acetate/hexanes) afforded 6-{[(1R)-1-cyclobutylethyl]amino}-8-[methoxy(phenyl)methyl]-7-[(trans-4-methylcyclohexyl)methyl]-7H-purine-2-carbonitrile as a white solid. MS ESI calc'd. for $C_{28}H_{36}N_6O$ $[M+H]^+$ 473. found 473.

Step 2: Hydroxylamine hydrochloride (19.41 mg, 0.279 mmol), sodium bicarbonate (35.2 mg, 0.419 mmol) and water (419 µl) were combined and allowed to stir for 15 minutes to allow for gas evolution. The resulting solution was added to a vial containing 6-{[(1R)-1-cyclobutylethyl]amino}-8-[methoxy(phenyl)methyl]-7-[(trans-4-methylcyclohexyl)methyl]-7H-purine-2-carbonitrile (66 mg, 0.140 mmol) in ethanol (978 µl). The vial was capped and stirred at 100° C. for 1 hour. The mixture was cooled to room temperature, diluted with water, and extracted with ethyl acetate (2×). Combined organics were dried over sodium sulfate, filtered, and concentrated in vacuo to afford 6-{[(1R)-1-cyclobutylethyl]amino}-N-hydroxy-8-[methoxy(phenyl)methyl]-7-[(trans-4-methylcyclohexyl)methyl]-7H-purine-2-carboximidamide as a white solid. MS ESI calcd. for $C_{28}H_{39}N_7O_2$ $[M+H]^+$ 506. found 506.

Step 3: To a solution of 6-{[(1R)-1-cyclobutylethyl]amino}-N-hydroxy-8-[methoxy(phenyl)methyl]-7-[(trans-4-methylcyclohexyl)methyl]-7H-purine-2-carboximidamide (70.6 mg, 0.140 mmol) and 1,1'-carbonyldiimidazole (36.2 mg, 0.223 mmol) dissolved in acetonitrile (1396 µl) was added 1,8-diazabicyclo[5.4.0]undec-7-ene (125 µl, 0.838 mmol). The resulting mixture was stirred at room temperature for 2 hours. An additional portion of 1,1'-carbonyldiimidazole (36.2 mg, 0.223 mmol) and 1,8-diazabicyclo[5.4.0]undec-7-ene (125 µl, 0.838 mmol) was added and the mixture was stirred at room temperature for 2 hours. The mixture was then diluted with DMSO and purified by automated mass guided reverse phase HPLC (acetonitrile/water+0.1% TFA modifier). Desired fractions were diluted with ethyl acetate, washed with aqueous sodium bicarbonate, dried over magnesium sulfate, filtered, and concentrated in vacuo. The resulting mixture of diastereomers was separated by chiral SFC (Chiral Technology AD-H 2.1×25 cm, 5 uM, 25%/75% ethanol/$CO_2$, 70 mL/min, 220 nm) to afford 3-(6-{[(1R)-1-cyclobutylethyl]amino}-8-[(R or S)-methoxy(phenyl)methyl]-7-[(trans-4-methylcyclohexyl)methyl]-7H-purin-2-yl)-1,2,4-oxadiazol-5(4H)-one (diastereomer A, Example 22.19, faster eluting) and 3-(6-{[(1R)-1-cyclobutylethyl]amino}-8-[(S or R)-methoxy(phenyl)methyl]-7-[(trans-4-methylcyclohexyl)methyl]-7H-purin-2-yl)-1,2,4-oxadiazol-5(4H)-one (diastereomer B, Example 22.20, slower eluting) both as white solids. Diastereomer A—faster eluting, $t_R$=2.78 min. MS ESI calc'd. for $C_{29}H_{37}N_7O_3$ $[M+H]^+$ 532. found 532. $^1$H NMR (500 MHz, DMSO-d6) δ 12.87 (s, 1H), 7.49-7.48 (m, 2H), 7.39-7.30 (m, 3H), 6.40 (d, J=8.5 Hz, 1H), 5.84 (s, 1H), 4.56-4.52 (m, 1H), 4.47-4.42 (m, 1H), 4.25-4.19 (m, 1H), 3.37 (s, 3H), 2.52-2.50 (m, 1H), 2.04-1.96 (m, 1H), 1.93-1.86 (m, 1H), 1.81-1.73 (m, 4H), 1.59-1.49 (m, 2H), 1.44-1.37 (m, 2H), 1.21-1.52 (m, 2H), 1.05 (d, J=6.0 Hz, 3H), 0.83-0.80 (m, 2H), 0.76 (d, J=6.5 Hz, 3H), 0.68-0.52 (m, 2H). Diastereomer B—slower eluting, $t_R$=4.30 min. MS ESI calc'd. for $C_{29}H_{37}N_7O_3$ $[M+H]^+$ 532. found 532. $^1$H NMR (500 MHz, DMSO-d6) δ 12.86 (s, 1H), 7.47-7.45 (m, 2H), 7.40-7.32 (m, 3H), 6.45 (d, J=8.5 Hz, 1H), 5.80 (s, 1H), 4.58-4.53 (m, 1H), 4.50-4.47 (m, 1H), 4.26-4.18 (m, 1H), 3.35 (s, 3H), 2.55-2.50 (m, 1H), 2.02-1.96 (m, 1H), 1.91-1.88 (m, 1H), 1.81-1.72 (m, 4H), 1.59-1.51 (m, 2H), 1.49-1.38 (m, 2H), 1.24-1.18 (m, 2H), 1.07 (d, J=6.5 Hz, 3H), 1.02-0.95 (m, 2H), 0.76 (d, J=6.5 Hz, 3H), 0.68-0.56 (m, 2H).

Example 22.21

3-[6-{[(1R)-1-cyclobutylethyl]amino}-7-[(trans-4-methylcyclohexyl)methyl]-8-(phenylcarbonyl)-7H-purin-2-yl]-1,2,4-oxadiazol-5(4H)-one

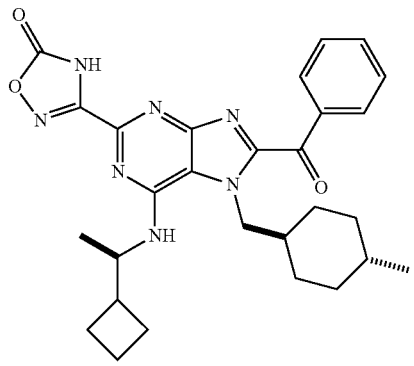

923

Step 1: To a cooled (−78° C.) solution of 2,2,6,6-tetramethylpiperidine (0.289 mL, 1.702 mmol) in 3000 uL THF under argon was added nBuLi (1.6 M in hexanes, 1.064 mL, 1.702 mmol). The reaction was stirred for 30 minutes at −78° C. A solution of 6-{[(1R)-1-cyclobutylethyl]amino}-7-[(trans-4-methylcyclohexyl)methyl]-7H-purine-2-carbonitrile (Preparative Example 11.6, 200 mg, 0.567 mmol) in 2600 uL THF was then added and the mixture stirred for 45 minutes at −78° C. Benzoyl chloride (0.079 mL, 0.681 mmol) was then added and the mixture stirred an additional one hour at −78° C. The reaction was quenched via the addition of saturated aqueous ammonium chloride and warmed to room temperature. The resulting slurry was diluted with water and extracted with ethyl acetate (2×). Combined organics were dried over magnesium sulfate, filtered, and concentrated under reduced pressure. The resulting residue was purified via silica gel chromatography (ethyl acetate/hexanes) to afford 6-{[(1R)-1-cyclobutylethyl]amino}-7-[(trans-4-methylcyclohexyl)methyl]-8-(phenylcarbonyl)-7H-purine-2-carbonitrile as a light yellow solid. MS ESI calc'd. for $C_{27}H_{32}N_6O$ $[M+H]^+$ 457. found 457.

Step 2: Hydroxylamine hydrochloride (13.70 mg, 0.197 mmol), sodium bicarbonate (24.84 mg, 0.296 mmol) and water (296 μl) were combined in a vial and allowed to stir for 15 minutes to allow for gas evolution. The resulting solution was added to a vial containing 6-{[(1R)-1-cyclobutylethyl]amino}-7-[(trans-4-methylcyclohexyl)methyl]-8-(phenylcarbonyl)-7H-purine-2-carbonitrile (45 mg, 0.099 mmol) in ethanol (690 μl). The vial was capped and stirred at 100° C. for 1 hour. The mixture was then cooled, diluted with water, and extracted with ethyl acetate (2×). Combined organics were dried over sodium sulfate, filtered, and concentrated in vacuo to afford 6-{[(1R)-1-cyclobutylethyl]amino}-N-hydroxy-7-[(trans-4-methylcyclohexyl)methyl]-8-(phenylcarbonyl)-7H-purine-2-carboximidamide as a yellow solid. MS ESI calc'd. for $C_{27}H_{35}N_7O_2$ $[M+H]^+$ 490. found 490.

Step 3: To a solution of 6-{[(1R)-1-cyclobutylethyl]amino}-N-hydroxy-7-[(trans-4-methylcyclohexyl)methyl]-8-(phenylcarbonyl)-7H-purine-2-carboximidamide (44 mg, 0.090 mmol) and 1,1'-carbonyldiimidazole (16.03 mg, 0.099 mmol) dissolved in acetonitrile (899 μl) was added 1,8-diazabicyclo[5.4.0]undec-7-ene (53.7 μl, 0.359 mmol). The resulting solution was stirred at room temperature for 1 hour. The mixture was diluted with DMSO and directly purified via automated mass guided reverse phase HPLC purification (acetonitrile/water+0.1% TFA modifier) to afford 3-[6-{[(1R)-1-cyclobutylethyl]amino}-7-[(trans-4-methylcyclohexyl)methyl]-8-(phenylcarbonyl)-7H-purin-2-yl]-1,2,4-oxadiazol-5(4H)-one (TFA salt) as a yellow solid. MS ESI calc'd. for $C_{28}H_{33}N_7O_3$ $[M+H]^+$ 516. found 516. $^1$H NMR (500 MHz, DMSO-$d_6$) δ 12.98 (s, 1H), 8.14-8.12 (m, 2H), 7.77-7.73 (m, 1H), 7.61-7.58 (m, 2H), 6.93 (d, J=8.5 Hz, 1H), 4.80-4.76 (m, 1H), 4.68-4.58 (m, 2H), 2.61-2.57 (m, 1H), 2.06-2.02 (m, 1H), 1.95-1.91 (m, 1H), 1.85-1.76 (m, 4H), 1.59-1.49 (m, 4H), 1.23-1.16 (m, 2H), 1.14 (d, J=6.5 Hz, 3H), 1.00-0.97 (m, 1H), 0.89-0.81 (m, 1H), 0.74 (d, J=6.5 Hz, 3H), 0.70-0.60 (m, 2H).

924

Example 22.22

5-[6-{[(1R)-1-cyclobutylethyl]amino}-7-[(trans-4-methylcyclohexyl)methyl]-8-(phenylcarbonyl)-7H-purin-2-yl]-1,3,4-oxadiazol-2(3H)-one

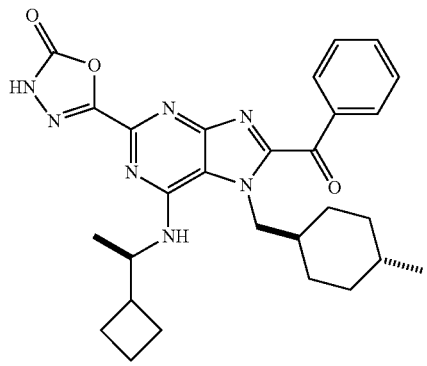

To a cooled (−78° C.) solution of 2,2,6,6-tetramethylpiperidine (0.103 ml, 0.608 mmol) in 500 uL THF under argon was added dropwise nBuLi (1.6 M in hexanes, 0.380 ml, 0.608 mmol). The resulting mixture was stirred for 30 minutes at −78° C. A solution of 5-(6-{[(1R)-1-cyclobutylethyl]amino}-7-[(trans-4-methylcyclohexyl)methyl]-7H-purin-2-yl)-1,3,4-oxadiazol-2(3H)-one (prepared from 6-{[(1R)-1-cyclobutylethyl]amino}-7-[(trans-4-methylcyclohexyl)methyl]-7H-purine-2-carbonitrile (Preparative Example 11.6) using a procedure similar to that described in Example 16.7) (50 mg, 0.122 mmol) in 1000 uL THF was then added and the resulting mixture stirred for 45 minutes at −78° C. Benzoyl chloride (0.017 ml, 0.146 mmol) was then added and the resulting mixture stirred at −78° C. for an additional 2 hours. The mixture was quenched via the addition of saturated aqueous ammonium chloride and warmed to room temperature. The resulting slurry was diluted with water and extracted with ethyl acetate (2×). Combined organics were dried over magnesium sulfate, filtered, and concentrated under reduced pressure. The resulting residue was purified via automated mass guided reverse phase HPLC (acetonitrile/water+1% TFA modifier) to afford 5-[6-{[(1R)-1-cyclobutylethyl]amino}-7-[(trans-4-methylcyclohexyl)methyl]-8-(phenylcarbonyl)-7H-purin-2-yl]-1,3,4-oxadiazol-2(3H)-one (TFA salt) as a light yellow solid. MS ESI calc'd. for $C_{28}H_{33}N_7O_3$ $[M+H]^+$ 516. found 516. $^1$H NMR (500 MHz, DMSO-$d_6$) δ 12.71 (s, 1H), 8.12 (d, J=7.5 Hz, 2H), 7.75 (t, J=7.5 Hz, 1H), 7.60 (t, J=7.5 Hz, 2H), 6.88 (d, J=8.5 Hz, 1H), 4.78-4.74 (m, 1H), 4.61-4.56 (m, 1H), 4.51-4.46 (m, 1H), 2.64-2.58 (m, 1H), 2.07-2.02 (m, 1H), 1.97-1.93 (m, 1H), 1.86-1.76 (m, 4H), 1.58-1.48 (m, 4H), 1.22-1.19 (m, 2H), 1.16 (d, J=6.5 Hz, 3H), 1.01-0.94 (m, 1H), 0.88-0.80 (m, 1H), 0.74 (d, J=7.0 Hz, 3H), 0.70-0.59 (m, 2H).

Example 22.23 and Example 22.24

3-(6-{[(1R)-1-cyclobutylethyl]amino}-8-[(1R or S)-1-hydroxy-1-phenylethyl]-7-[(trans-4-methylcyclohexyl)methyl]-7H-purin-2-yl)-1,2,4-oxadiazol-5(4H)-one (diastereomer A) and 3-(6-{[(1R)-1-cyclobutylethyl]amino}-8-[(1S or R)-1-hydroxy-1-phenylethyl]-7-[(trans-4-methylcyclohexyl)methyl]-7H-purin-2-yl)-1,2,4-oxadiazol-5(4H)-one (diastereomer B)

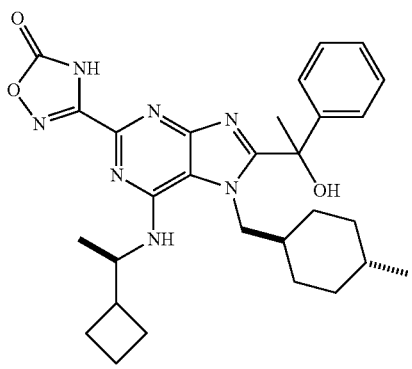

To a solution of 3-[6-{[(1R)-1-cyclobutylethyl]amino}-7-[(trans-4-methylcyclohexyl)methyl]-8-(phenylcarbonyl)-7H-purin-2-yl]-1,2,4-oxadiazol-5(4H)-one (Example 22.21) (130 mg, 0.252 mmol) in THF (2521 µl) at 0° C. was added dropwise methyl magnesium bromide (3.0 M in diethylether, 400 µl, 1.20 mmol). The reaction was stirred and slowly warmed to ambient temperature over 5 hours. The reaction was then quenched via the addition of saturated aqueous ammonium chloride and extracted with EtOAc (2×). The combined organics were dried over magnesium sulfate, filtered, and concentrated under reduced pressure. The resulting residue was purified via silica gel chromatography (methanol/ethyl acetate). The resulting mixture of diastereomers were separated by chiral SFC (Chiralpak AS-H column, 21×250 mm, 80% CO$_2$/20% MeOH+0.25% dimethylethylamine modifier, UV at 220 nm, flow rate 70 ml/min, 100 bar back pressure) to afford 3-(6-{[(1R)-1-cyclobutylethyl]amino}-8-[(1R or S)-1-hydroxy-1-phenylethyl]-7-[(trans-4-methylcyclohexyl)methyl]-7H-purin-2-yl)-1,2,4-oxadiazol-5(4H)-one (diastereomer A) and 3-(6-{[(1R)-1-cyclobutylethyl]amino}-8-[(1S or R)-1-hydroxy-1-phenylethyl]-7-[(trans-4-methylcyclohexyl)methyl]-7H-purin-2-yl)-1,2,4-oxadiazol-5(4H)-one (diastereomer B) as white solids. Diastereomer A (Example 22.23), faster elutung: $t_R$=1.8 min. MS ESI calc'd. for C$_{29}$H$_{37}$N$_7$O$_3$ [M+H]$^+$ 532. found 532. $^1$H NMR (500 MHz, DMSO-d$_6$) δ 7.43-7.39 (m, 2H), 7.33-7.30 (m, 2H), 7.25-7.22 (m, 1H), 6.56 (s, 1H), 6.26 (d, J=7.5 Hz, 1H), 4.58-4.41 (m, 2H), 4.32-4.22 (m, 1H), 2.58-2.51 (m, 1H), 1.99-1.94 (m, 1H), 1.93 (s, 3H), 1.88-1.82 (m, 1H), 1.77-1.67 (m, 4H), 1.45-1.38 (m, 2H), 1.22-1.14 (m, 4H), 1.03 (d, J=6.5 Hz, 3H), 0.85-0.80 (m, 2H), 0.69-0.59 (m, 5H). Diastereomer B (Example 22.24), slower eluting: $t_R$=2.3 min. MS ESI calc'd. for C$_{29}$H$_{37}$N$_7$O$_3$ [M+H]$^+$ 532. found 532. $^1$H NMR (500 MHz, DMSO-d$_6$) δ 7.33-7.30 (m, 3H), 7.24-7.22 (m, 2H), 6.52 (s, 1H), 6.22-6.59 (m, 1H), 4.57-4.50 (m, 1H), 4.16-3.98 (m, 2H), 2.58-2.54 (m, 1H), 1.98-1.94 (m, 1H), 1.93 (s, 3H), 1.88-1.83 (m, 1H), 1.78-1.69 (m, 4H), 1.56-1.42 (m, 4H), 1.15-1.12 (m, 2H), 1.03-1.01 (m, 6H), 0.85-0.80 (m, 2H), 0.78-0.70 (m, 2H).

Example 22.25

3-(6-{[(1R)-1-cyclobutylethyl]amino}-7-[(trans-4-methylcyclohexyl)methyl]-8-[(1R or S)-2,2,2-trifluoro-1-hydroxy-1-phenylethyl]-7H-purin-2-yl)-1,2,4-oxadiazol-5(4H)-one (Isomer 1)

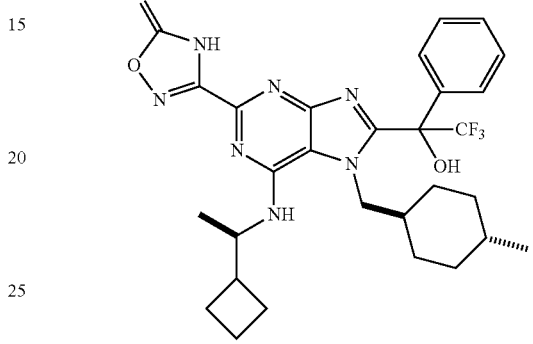

Step 1: 6-{[(1R)-1-cyclobutylethyl]amino}-7-[(trans-4-methylcyclohexyl)methyl]-8-(phenylcarbonyl)-7H-purine-2-carbonitrile (Example 22.21, step 1) (65 mg, 0.142 mmol) was taken up in THF (2 mL) and trimethyl(trifluoromethyl)silane (0.063 mL, 0.427 mmol) was added followed by tetramethylammonium fluoride (39.8 mg, 0.427 mmol). The reaction was stirred at room temperature for 2 hours at which time an additional portion of trimethyl(trifluoromethyl)silane (0.063 mL, 0.427 mmol) and tetramethylammonium fluoride (39.8 mg, 0.427 mmol) was added and the reaction was stirred at room temperature overnight. The mixture was then diluted with DCM and brine. The layers were separated and the aqueous layer was extracted with DCM. The organic layer was dried over magnesium sulfate, filtered, and concentrated under reduced pressure. The resulting residue was purified via silica gel chromatography (ethyl acetate/hexanes) to afford 6-{[(1R)-1-cyclobutylethyl]amino}-7-[(trans-4-methylcyclohexyl)methyl]-8-[(1R or S)-2,2,2-trifluoro-1-hydroxy-1-phenylethyl]-7H-purine-2-carbonitrile (Isomer 1) and 6-{[(1R)-1-cyclobutylethyl]amino}-7-[(trans-4-methylcyclohexyl)methyl]-8-[(1S or R)-2,2,2-trifluoro-1-hydroxy-1-phenylethyl]-7H-purine-2-carbonitrile (Isomer 2). Isomer 1, faster eluting: MS ESI calc'd. for C$_{28}$H$_{33}$F$_3$N$_6$O [M+H]$^+$ 527. found 527. Isomer 2, slower eluting: MS ESI calc'd. for C$_{28}$H$_{33}$F$_3$N$_6$O [M+H]$^+$ 527. found 527.

Step 2: Hydroxylamine hydrochloride (6.60 mg, 0.095 mmol), sodium bicarbonate (11.96 mg, 0.142 mmol) and water (142 µl) were combined in a vial and allowed to stir for 15 minutes to allow for gas evolution. The resulting solution was added to a vial containing 6-{[(1R)-1-cyclobutylethyl]amino}-7-[(trans-4-methylcyclohexyl)methyl]-8-[(1R or S)-2,2,2-trifluoro-1-hydroxy-1-phenylethyl]-7H-purine-2-carbonitrile (Isomer 1) (25 mg, 0.047 mmol) in ethanol (332 µl). The vial was capped and stirred at 100° C. for 1 hour. The mixture was cooled to room temperature, diluted with water, and extracted with ethyl acetate (2×). Combined organics were dried over sodium sulfate, filtered, and concentrated in vacuo to afford 6-{[(1R)-1-cyclobutylethyl]amino}-N'-hydroxy-7-[(trans-4-methylcyclohexyl)methyl]-8-[(1R or S)-2,2,2-trifluoro-1-hydroxy-1-phenylethyl]-7H-purine-2-carboximidamide (Isomer 1) as a white solid. MS ESI calc'd. for $C_{28}H_{36}F_3N_7O_2$ [M+H]560. found 560.

Step 3: To a solution of 6-{[(1R)-1-cyclobutylethyl]amino}-N'-hydroxy-7-[(trans-4-methylcyclohexyl)methyl]-8-[(1R or S)-2,2,2-trifluoro-1-hydroxy-1-phenylethyl]-7H-purine-2-carboximidamide (Isomer 1) (26.6 mg, 0.048 mmol) and 1,1'-carbonyldiimidazole (8.48 mg, 0.052 mmol) dissolved in acetonitrile (475 μl) was added 1,8-diazabicyclo [5.4.0]undec-7-ene (28.4 μl, 0.190 mmol). The resulting mixture was stirred at room temperature for 1 hour. The mixture was diluted with DMSO and purified via automated mass guided reverse phase HPLC purification (acetonitrile/water+0.1% TFA modifier) to afford 3-(6-{[(1R)-1-cyclobutylethyl]amino}-7-[(trans-4-methylcyclohexyl)methyl]-8-[(1R or S)-2,2,2-trifluoro-1-hydroxy-1-phenylethyl]-7H-purin-2-yl)-1,2,4-oxadiazol-5(4H)-one (TFA salt) (Isomer 1) as a white solid. MS ESI calc'd. for $C_{29}H_{34}F_3N_7O_3$ [M+H]$^+$ 586. found 586. $^1$H NMR (500 MHz, DMSO-$d_6$) δ 12.96 (s, 1H), 8.26 (s, 1H), 7.44-7.41 (m, 5H), 6.50 (d, J=7.5 Hz, 1H), 4.64-4.62 (m, 1H), 4.20-4.15 (m, 2H), 2.55-2.51 (m, 1H), 1.99-1.94 (m, 2H), 1.89-1.74 (m, 5H), 1.49-1.35 (m, 3H), 1.17-1.15 (m, 2H), 1.05 (d, J=6.0 Hz, 3H), 0.93-0.88 (m, 2H), 0.73-0.70 (m, 3H), 0.51-0.42 (m, 2H).

Example 22.26 and Example 22.27

3-(6-(((R)-1-cyclobutylethyl)amino)-7-(((trans)-4-methylcyclohexyl)methyl)-8-(1-(thiazol-4-yl)ethyl)-7H-purin-2-yl)-1,2,4-oxadiazol-5(4H)-one (diastereomer A and B)

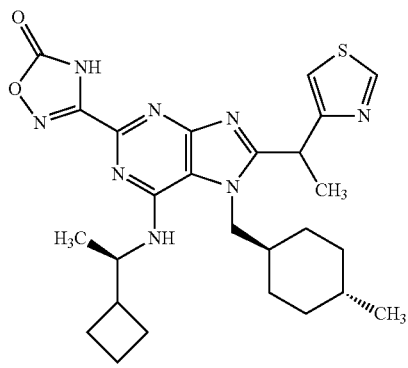 [SMILES: CC(c1cscn1)c1nc2nc(-c3noc(=O)[nH]3)nc(N[C@H](C)C3CCC3)c2n1C[C@H]1CC[C@H](C)CC1]

Step 1: A solution of 6-(((R)-1-cyclobutylethyl)amino)-7-(((trans)-4-methylcyclohexyl)methyl)-8-(1-(thiazol-4-yl)vinyl)-7H-purine-2-carbonitrile (250 mg, 0.54 mmol, prepared following a procedure analogous to that described in Example 22.10, Step 1 and Step 2) in EtOH/EtOAc (2:1, 6 mL) was degassed using $N_2$ for 10 minutes. Pd/C (50 mg, 10% w/w) was added and the suspension was degassed using $H_2$ for 5 minutes. The reaction was then stirred under $H_2$ (1 atm) for 1 hour and filtered through celite. The solvent was evaporated under vacuum to afford 6-(((R)-1-cyclobutylethyl)amino)-7-(((trans)-4-methylcyclohexyl)methyl)-8-(1-(thiazol-4-yl)ethyl)-7H-purine-2-carbonitrile as mixture of diastereomers. Separation of diastereomers was performed using prep HPLC [Luna C18 (2) column, 70% acetonitrile/water isocratic method] to afford Diastereomer A (fast eluting in HPLC) and Diastereomer B (slow eluting in HPLC). MS (ES)=464 (M+1)$^+$.

Step 2: Using a procedure analogous to that in Example 16.1 (Step 3 and 4) and starting with 6-(((R)-1-cyclobutylethyl)amino)-7-(((trans)-4-methylcyclohexyl)methyl)-8-(1-(thiazol-4-yl)ethyl)-7H-purine-2-carbonitrile (diastereomer A and diastereomer B), 3-(6-(((R)-1-cyclobutylethyl)amino)-7-(((trans)-4-methylcyclohexyl)methyl)-8-(1-(thiazol-4-yl)ethyl)-7H-purin-2-yl)-1,2,4-oxadiazol-5(4H)-one (diastereomer A and diastereomer B) were prepared. Example 22.26 (Diastereomer A) $^1$H NMR (400 MHz, CD$_3$OD) δ 8.95 (s, 1H), 7.43 (s, 1H), 4.68 (m, 1H), 4.33 (q, J=8.0 Hz, 2H), 2.54 (m, 1H), 2.01-2.11 (m, 2H), 1.80-1.86 (m, 3H), 1.59-1.72 (m, 3H), 1.54 (m, 1H), 1.40-1.46 (m, 2H), 1.24-1.36 (m, 5H), 1.19 (d, J=6.4 Hz, 3H), 0.86-0.98 (m, 2H), 0.83 (d, J=6.8 Hz, 3H), 0.66-0.80 (m, 2H). MS (ES)=523 (M+1)$^+$. Example 22.27 (Diastereomer B)$^1$H NMR (300 MHz, CD$_3$OD) δ 8.92 (s, 1H), 7.37 (s, 1H), 4.65 (m, 1H), 4.42 (dd, J=15.3, 5.4 Hz, 1H), 4.21 (dd, J=15.6, 9.3 Hz, 1H), 2.54 (m, 1H), 2.02-2.11 (m, 2H), 1.58-2.00 (m, 7H), 1.52-1.80 (m, 3H), 1.46-1.49 (m, 3H), 1.17 (d, J=6.3 Hz, 6H), 0.80-0.98 (m, 5H). MS (ES)=523 (M+1)$^+$.

Example 22.70

3-(8-cyclobutyl-6-{[(1R)-1-cyclobutylethyl]amino}-7-[(trans-4-methylcyclohexyl)methyl]-7H-purin-2-yl)-1,2,4-oxadiazol-5(4H)-one

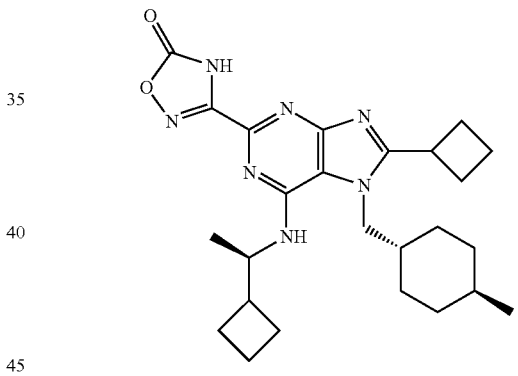

Step 1: A round bottom flask was charged with Pd/C (15 mg) under $N_2$. A solution of 8-(cyclobut-1-en-1-yl)-6-(((R)-1-cyclobutylethyl)amino)-7-(((trans)-4-methylcyclohexyl)methyl)-7H-purine-2-carbonitrile (prepared following procedures analogous to those described for Example 22.3, Step 1 and Example 22.5, Step 1; 35 mg, 0.04 mmol) in EtOH/EtOAc (3.0 mL, 1:1) was added and reaction mixture was stirred at room temperature under $H_2$ (1 atm) overnight, and then filtered through celite, washing the celite with MeOH. The filtrate was concentrated in vacuo and purification of the residue on a silica gel column (0 to 70% EtOAc/hexanes) afforded 8-cyclobutyl-6-(((R)-1-cyclobutylethyl)amino)-7-(((trans)-4-methylcyclohexyl)methyl)-7H-purine-2-carbonitrile. MS (ES)=407 (M+1)$^+$.

Steps 2 and 3: Using procedures analogous to those described in Example 16.1 (Steps 3 and 4), 8-cyclobutyl-6-(((R)-1-cyclobutylethyl)amino)-7-(((trans)-4-methylcyclohexyl)methyl)-7H-purine-2-carbonitrile was converted to 3-(8-cyclobutyl-6-{[(1R)-1-cyclobutylethyl]amino}-7-[(trans-4-methylcyclohexyl)methyl]-7H-purin-2-yl)-1,2,4-oxadiazol-5(4H)-one $^1$H NMR (300 MHz, CD$_3$OD) δ 4.66

(m, 1H), 4.31 (m, 1H), 4.08 (m, 1H), 3.90 (m, 1H), 2.42-2.65 (m, 5H), 2.01-2.29 (m, 4H), 1.54-1.74 (m, 5H), 1.25-1.42 (m, 3H), 1.02-1.25 (m, 6H), 0.74-0.95 (m, 6H). MS (ES)=466 (M+1)$^+$.

Example 22.79

3-(6-{[(1R)-1-cyclobutylethyl]amino}-8-[difluoro (phenyl)methyl]-7-[(trans-4-methylcyclohexyl) methyl]-7H-purin-2-yl)-1,2,4-oxadiazol-5(4H)-one

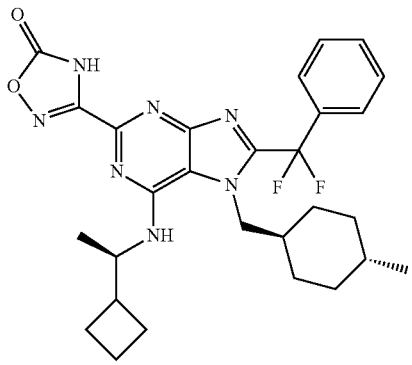 [SMILES: C[C@@H](Nc1nc(-c2noc(=O)[nH]2)nc2nc(C(F)(F)c3ccccc3)n(C[C@H]3CC[C@H](C)CC3)c12)C1CCC1]

Step 1: A sealable tube was charged with 6-{[(1R)-1-cyclobutylethyl]amino}-7-[(trans-4-methylcyclohexyl) methyl]-8-(phenylcarbonyl)-7H-purine-2-carbonitrile (Example 22.21, Step 1; 160 mg, 0.350 mmol). Deoxofluor (200 μl, 1.085 mmol) was added via syringe. The tube was capped and heated to 90° C. for 24 hours. The reaction mixture was then cooled to room temperature, diluted with dichloromethane, washed with water, saturated aqueous sodium bicarbonate, and brine. The organic layer was dried over magnesium sulfate, filtered, and concentrated under reduced pressure. The resulting residue was purified via silica gel chromatography (0-50% ethyl acetate/hexanes) to afford 6-{[(1R)-1-cyclobutylethyl]amino}-8-[difluoro(phenyl) methyl]-7-[(trans-4-methylcyclohexyl)methyl]-7H-purine-2-carbonitrile (semi-pure). MS ESI calc'd. for $C_{27}H_{32}F_2N_6$ [M+H]$^+$ 479. found 479.

Step 2: Hydroxylamine hydrochloride (11.04 mg, 0.159 mmol), sodium bicarbonate (20.01 mg, 0.238 mmol) and water (238 μl) were combined in a vial and stirred for 15 minutes to allow for gas evolution via a pierced septa. The resulting solution was added to a second vial containing 6-{[(1R)-1-cyclobutylethyl]amino}-8-[difluoro(phenyl) methyl]-7-[(trans-4-methylcyclohexyl)methyl]-7H-purine-2-carbonitrile (38 mg, 0.079 mmol) in ethanol (556 μl). The vial was capped and stirred at 100° C. for 1 hour and then cooled to room temperature. Water and brine were added and the mixture was extracted with ethyl acetate (2×). The combined organics were dried over sodium sulfate, filtered, and concentrated in vacuo to afford crude 6-{[(1R)-1-cyclobutylethyl]amino}-8-[difluoro(phenyl)methyl]-N'-hydroxy-7-[(trans-4-methylcyclohexyl)methyl]-7H-purine-2-carboximidamide, which was used without further purification. MS ESI calc'd. for $C_{27}H_{35}F_2N_7O$ [M+H]$^+$ 512. found 512.

Step 3: To a solution of 6-{[(1R)-1-cyclobutylethyl] amino}-8-[difluoro(phenyl)methyl]-N'-hydroxy-7-[(trans-4-methylcyclohexyl)methyl]-7H-purine-2-carboximidamide (40.6 mg, 0.079 mmol) and 1,1'-carbonyldiimidazole (25.7 mg, 0.159 mmol) dissolved in acetonitrile (794 μl) was added 1,8-diazabicyclo[5.4.0]undec-7-ene (83 μl, 0.556 mmol). The reaction was stirred at room temperature for 2 hours and then diluted with DMSO. Purification by automated mass guided reverse phase HPLC (acetonitrile/water+ 0.1% TFA modifier) afforded 3-(6-{[(1R)-1-cyclobutylethyl]amino}-8-[difluoro(phenyl)methyl]-7-[(trans-4-methylcyclohexyl)methyl]-7H-purin-2-yl)-1,2,4-oxadiazol-5(4H)-one (TFA salt). MS ESI calc'd. for $C_{28}H_{33}F_2N_7O_2$ [M+H]$^+$ 538. found 538. $^1$H NMR (500 MHz, DMSO-d6) δ 12.91 (s, 1H), 7.62-7.58 (m, 3H), 7.56-7.53 (m, 2H), 6.76 (d, J=8.5 Hz, 1H), 4.66-4.58 (m, 2H), 4.26-4.15 (m, 1H), 2.56-2.51 (m, 2H), 2.20-1.99 (m, 1H), 1.97-1.89 (m, 1H), 1.83-1.76 (m, 4H), 1.61-1.53 (m, 4H), 1.21-1.13 (m, 1H), 1.09 (d, J=6.5 Hz, 3H), 1.03-0.98 (m, 1H), 0.93-0.89 (m, 1H), 0.77 (d, J=6.5 Hz, 3H), 0.73-0.60 (m, 2H).

Example 22.80

3-(6-{[(1R)-1-cyclobutylethyl]amino}-8-(1,3-dihydro-2-benzofuran-1-yl)-7-[(trans-4-methylcyclohexyl)methyl]-7H-purin-2-yl)-1,2,4-oxadiazol-5 (4H)-one

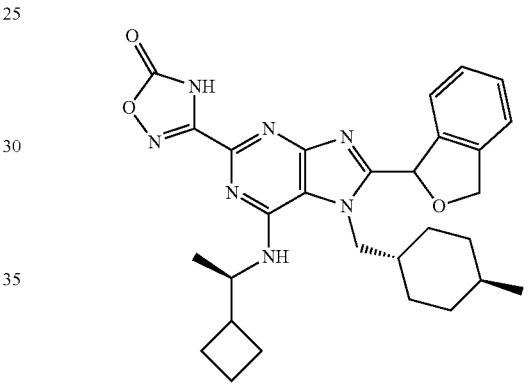

Step 1: n-BuLi (0.71 mL, 1.42 mmol, 2M in hexanes) was added dropwise to a solution of 2,2,6,6-tetramethylpiperidine (201 mg, 1.42 mmol) in anhydrous THF (5 mL) at 20° C. The reaction was stirred at 20° C. for 15 minutes and then cooled to 78° C. A solution of 6-[[(1R)-1-cyclobutylethyl] amino]-7-[(trans-4-methylcyclohexyl)methyl]-7H-purine-2-carbonitrile (Preparative Example 11.6, 100 mg, 0.28 mmol) in anhydrous THF (1 mL) was added. The reaction was stirred at 78° C. for 30 minutes and then a solution of 2-(bromomethyl)benzaldehyde (282 mg, 1.42 mmol) in THF (0.5 mL) was added dropwise. The reaction mixture was stirred at −78° C. for 2 hours and then slowly warmed to room temperature and quenched with saturated aqueous NH$_4$Cl solution. The layers were separated and the aqueous layer was extracted with EtOAc (3 times). The combined organic layers were washed with brine, dried over anhydrous Na$_2$SO$_4$, filtered, and concentrated in vacuo. Purification of the residue on a silica gel column (0 to 30% EtOAc/hexanes) afforded 6-(((R)-1-cyclobutylethyl)amino)-8-(1,3-dihydroisobenzofuran-1-yl)-7-(((trans)-4-methylcyclohexyl) methyl)-7H-purine-2-carbonitrile as a mixture of diastereomers. MS (APCI)=471 (M+1)$^+$.

Steps 2 and 3: Using procedures similar to those described in Example 16.1 (Steps 3 and 4), 6-(((R)-1-cyclobutylethyl) amino)-8-(1,3-dihydroisobenzofuran-1-yl)-7-(((trans)-4-methylcyclohexyl)methyl)-7H-purine-2-carbonitrile was converted to 3-(6-{[(1R)-1-cyclobutylethyl]amino}-8-(1,3- dihydro-2-benzofuran-1-yl)-7-[(trans-4-methylcyclohexyl)methyl]-7H-purin-2-yl)-1,2,4-oxadiazol-5(4H)-one. ¹H NMR (300 MHz, CDCl₃) δ 7.29-7.44 (m, 4H), 6.55 (s, 1H), 5.24 (br s, 2H), 4.68 (m, 1H), 4.56 (m, 1H), 4.08-4.30 (m, 2H), 2.42 (m, 1H), 1.51-2.13 (m, 10H), 1.14-1.23 (m, 7H), 0.87 (d, J=6.2 Hz, 1.5H), 0.86 (d, J=6.2 Hz, 1.5H), 0.69-0.99 (m, 2H). MS (ES)=530 (M+1)⁺.

Example 22.81

3-[6-{[(1R)-1-cyclobutylethyl]amino}-7-[(trans-4-methylcyclohexyl)methyl]-8-(2-phenyloxetan-2-yl)-7H-purin-2-yl]-1,2,4-oxadiazol-5(4H)-one

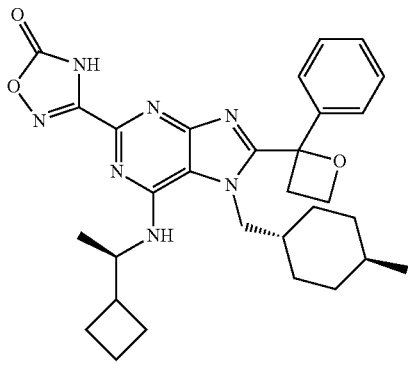 [SMILES: C[C@@H](Nc1nc(-c2noc(=O)[nH]2)nc2nc(C3(c4ccccc4)CCO3)n(C[C@H]3CC[C@H](C)CC3)c12)C1CCC1]

Step 1: A solution of 6-[[(1R)-1-cyclobutylethyl]amino]-7-[(trans-4-methylcyclohexyl)methyl]-7H-purine-2-carbonitrile (Preparative Example 11.6, 100 mg, 0.28 mmol) in THF (1 mL) was added to a −78° C. solution of LiTMP (prepared as described in Step 1 of Example 22.80; 3.5 mL, 0.4 M in THF, 1.4 mmol) and the reaction was stirred at −78° C. for one hour. Next, a solution of 3-chloro-1-phenylpropan-1-one (95 mg, 0.56 mmol) in THF (0.5 mL) was added and stirring was continued for 2 hours at −78° C. The reaction was quenched with saturated aqueous NH₄Cl and the mixture was extracted with EtOAc. The organic layer was washed with brine, dried over MgSO₄, filtered, and concentrated. Purification of the residue on a silica gel column (0-50% EtOAc/hexanes) afforded 6-(((R)-1-cyclobutylethyl)amino)-7-(((trans)-4-methylcyclohexyl)methyl)-8-(2-phenyloxetan-2-yl)-7H-purine-2-carbonitrile. MS (ES)=485 (M+1)⁺.

Steps 2 and 3: Using procedures similar to those described in Example 16.1 (Steps 3 and 4), 6-(((R)-1-cyclobutylethyl)amino)-7-(((trans)-4-methylcyclohexyl)methyl)-8-(2-phenyloxetan-2-yl)-7H-purine-2-carbonitrile was converted to 3-[6-{[(1R)-1-cyclobutylethyl]amino}-7-[(trans-4-methylcyclohexyl)methyl]-8-(2-phenyloxetan-2-yl)-7H-purin-2-yl]-1,2,4-oxadiazol-5(4H)-one. ¹H NMR (300 MHz, CD₃OD) δ8.04 (d, J=7.6 Hz, 2H), 7.48-7.64 (m, 3H), 4.68 (m, 1H), 4.45 (m, 2H), 4.30 (m, 1H), 3.72-374 (m, 2H), 2.56 (m, 1H), 2.04-2.11 (m, 2H), 1.89-1.95 (m, 4H), 1.67-1.74 (m, 5H), 1.51 (m, 1H), 1.12-1.28 (m, 6H), 0.75-0.97 (m, 5H). MS (ES)=544 (M+1)⁺.

Example 22.82

3-(6-{[(1R)-1-cyclobutylethyl]amino}-8-[1-(hydroxymethyl)propyl]-7-[(trans-4-methylcyclohexyl)methyl]-7H-purin-2-yl)-1,2,4-oxadiazol-5(4H)-one

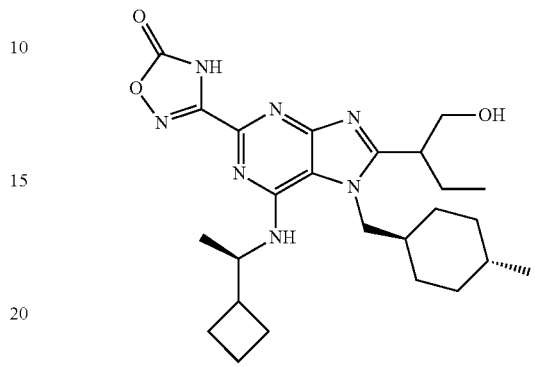

Step 1: To a 0° C. solution of ethyl 2-hydroxybutanoate (500 mg, 3.80 mmol) in CH₂Cl₂ (30 mL) was added 2,6-lutidine (813 mg, 7.6 mmol) followed by triflic anhydride (1.83 g, 6.5 mmol) and the reaction was stirred for 30 minutes. The reaction was then diluted with MTBE (250 mL) and washed with a mixture of brine (75 mL) and 1N HCl (45 mL). The organic layer was separated, dried over MgSO₄, filtered, and concentrated to afford crude ethyl 2-(((trifluoromethyl)sulfonyl)oxy)butanoate.

Step 2: To a −78° C. solution of 6-[[(1R)-1-cyclobutylethyl]amino]-7-[(trans-4-methylcyclohexyl)methyl]-7H-purine-2-carbonitrile (Preparative Example 11.6, 704 mg, 2.0 mmol) in THF (15 mL) was added LiTMP (prepared as described in Step 1 of Example 22.80; 25 mL, 0.4M in THF, 10 mmol) and the reaction was stirred at 78° C. for one hour. A solution of ethyl 2-(((trifluoromethyl)sulfonyl)oxy)butanoate (1.53 g, 6.0 mmol) in THF (1.0 mL) was added and stirring was continued for 2 hours at 78° C. The reaction was quenched by adding saturated aqueous ammonium chloride and extracted using EtOAc (250 mL). The organic layer was washed with brine (75 mL), dried over MgSO₄, filtered, and concentrated. Purification of the residue on a silica gel column (0-50% EtOAc/CH₂Cl₂) afforded ethyl 2-(2-cyano-6-(((R)-1-cyclobutylethyl)amino)-7-(((trans)-4-methylcyclohexyl)methyl)-7H-purin-8-yl)butanoate. MS (ES)=467 (M+1)⁺.

Step 3: LiBH₄ (21.7 mg, 1.0 mmol) was added to a 0° C. solution of ethyl 2-(2-cyano-6-(((R)-1-cyclobutylethyl)amino)-7-(((trans)-4-methylcyclohexyl)methyl)-7H-purin-8-yl)butanoate (120 mg, 0.25 mmol) in THF (4.0 mL). The reaction was slowly warmed to room temperature and stirred for 2 hours. The reaction was quenched by adding crushed ice and extracted using EtOAc (20 mL). The organic layer was separated, dried over MgSO₄, filtered, and concentrated. Purification of the residue on a silica gel column (0-50% EtOAc/CH₂Cl₂) afforded 6-(((R)-1-cyclobutylethyl)amino)-8-(1-hydroxybutan-2-yl)-7-(((trans)-4-methylcyclohexyl)methyl)-8,9-dihydro-7H-purine-2-carbonitrile. This product underwent air oxidation over two days when stored neat at room temperature and was purified on a silica gel column (0-50% EtOAc/Hexanes) to afford 6-(((R)-1-cyclobutylethyl)amino)-8-(1-hydroxybutan-2-yl)-7-(((trans)-4-methylcyclohexyl)methyl)-7H-purine-2-carbonitrile. MS (ES)=425 (M+1)⁺.

Steps 4 and 5: Using procedures similar to those described in Example 16.1 (Steps 3 and 4), 6-(((R)-1-cyclobutylethyl)amino)-8-(1-hydroxybutan-2-yl)-7-(((trans)-4-methylcyclohexyl)methyl)-7H-purine-2-carbonitrile was converted to 3-(6-{[(1R)-1-cyclobutylethyl]amino}-8-[1-(hydroxymethyl)propyl]-7-[(trans-4-methylcyclohexyl)methyl]-7H-purin-2-yl)-1,2,4-oxadiazol-5(4H)-one (mixture of diastereomers. $^1$H NMR (400 MHz, CD$_3$OD) δ 4.90 (m, 1H), 4.70 (m, 1H), 4.40-4.60 (m, 2H), 4.30 (m, 1H), 2.56 (m, 1H), 1.82-2.12 (m, 7H), 1.60-1.75 (m, 3H), 1.25-1.60 (m, 5H), 1.16 (d, J=6.2 Hz, 3H), 1.85-1.15 (m, 2H), 1.08 (t, J=7.5 Hz, 3H) 0.85 (d, J=5.8 Hz, 3H), 0.70-0.95 (m, 2H). MS (ES)=484 (M+1)$^+$.

The following compounds in Table 22 were described above or were prepared using procedures which were analogous to those described above.

TABLE 22

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.1 | 4.653 | 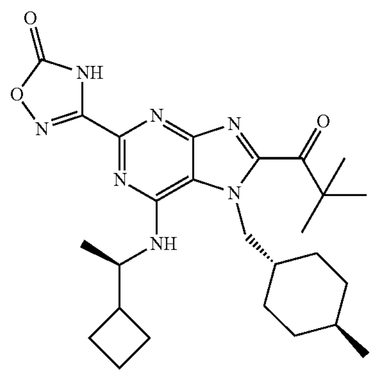 [SMILES: C[C@@H](Nc1nc(-c2noc(=O)[nH]2)nc2nc(C(=O)C(C)(C)C)n(C[C@H]3CC[C@H](C)CC3)c12)C1CCC1] | 3-(6-{[(1R)-1-cyclobutylethyl]amino}-8-(2,2-dimethylpropanoyl)-7-[(trans-4-methylcyclohexyl)methyl]-7H-purin-2-yl)-1,2,4-oxadiazol-5(4H)-one | | 496 | 496 |
| 22.2 | 10.57 | 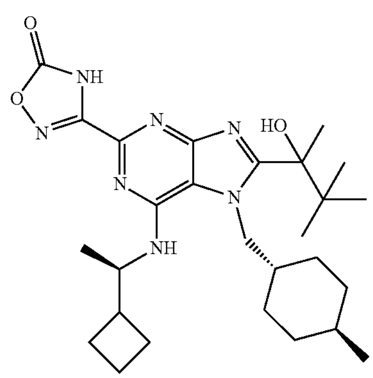 [SMILES: C[C@@H](Nc1nc(-c2noc(=O)[nH]2)nc2nc(C(C)(O)C(C)(C)C)n(C[C@H]3CC[C@H](C)CC3)c12)C1CCC1] | 3-(6-{[(1R)-1-cyclobutylethyl]amino}-8-(1-hydroxy-1,2,2-trimethylpropyl)-7-[(trans-4-methylcyclohexyl)methyl]-7H-purin-2-yl)-1,2,4-oxadiazol-5(4H)-one | | 512 | 512 |
| 22.3 | 7.214 | 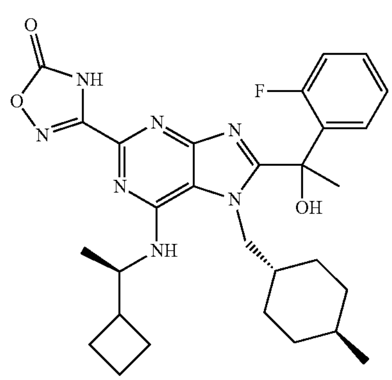 [SMILES: C[C@@H](Nc1nc(-c2noc(=O)[nH]2)nc2nc(C(C)(O)c3ccccc3F)n(C[C@H]3CC[C@H](C)CC3)c12)C1CCC1] | 3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5(4H)-one (diastereoisomer A) | | 550 | 550 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.4 | 41.2 | 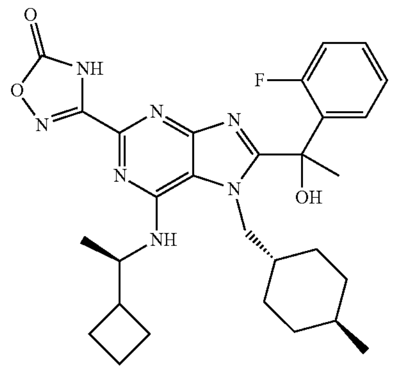 [SMILES: C[C@@H](Nc1nc(-c2noc(=O)[nH]2)nc2nc(C(C)(O)c3ccccc3F)n(C[C@H]3CC[C@H](C)CC3)c12)C1CCC1] | 3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5(4H)-one (diastereoisomer B) | | 550 | 550 |
| 22.5 | 3.573 | 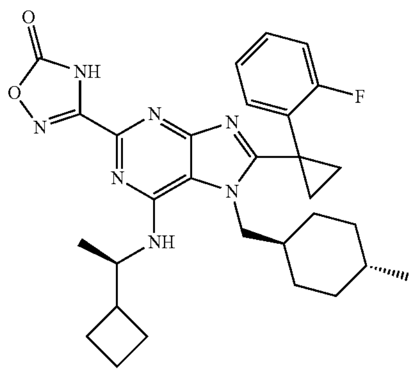 [SMILES: C[C@@H](Nc1nc(-c2noc(=O)[nH]2)nc2nc(C3(c4ccccc4F)CC3)n(C[C@H]3CC[C@H](C)CC3)c12)C1CCC1] | 3-(6-{[(1R)-1-cyclobutylethyl]amino}-8-[1-(2-fluorophenyl)cyclopropyl]-7-[(trans-4-methylcyclohexyl)methyl]-7H-purin-2-yl)-1,2,4-oxadiazol-5(4H)-one | | 546 | 546 |
| 22.6 | 10.45 | 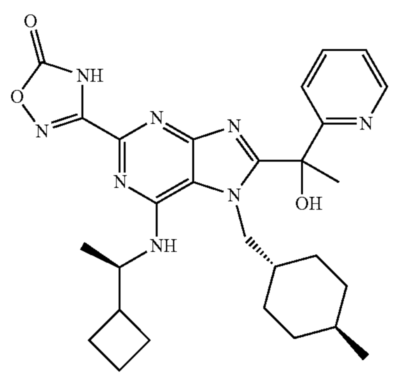 [SMILES: C[C@@H](Nc1nc(-c2noc(=O)[nH]2)nc2nc(C(C)(O)c3ccccn3)n(C[C@H]3CC[C@H](C)CC3)c12)C1CCC1] | 3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5(4H)-one (diastereomer A) | | 533 | 533 |
| 22.7 | 19.94 | 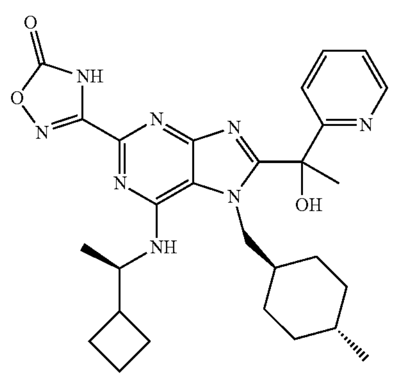 [SMILES: C[C@@H](Nc1nc(-c2noc(=O)[nH]2)nc2nc(C(C)(O)c3ccccn3)n(C[C@H]3CC[C@H](C)CC3)c12)C1CCC1] | 3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5(4H)-one (diastereomer B) | | 533 | 533 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.8 | 1.305 | 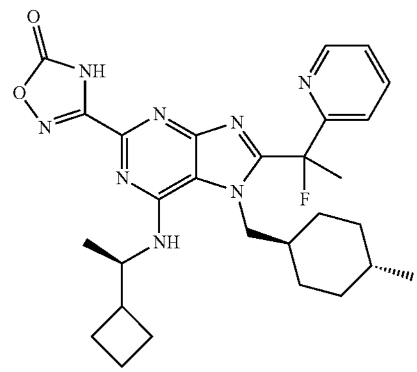 [SMILES: C[C@@H](Nc1nc(-c2noc(=O)[nH]2)nc2nc(C(C)(F)c3ccccn3)n(C[C@H]3CC[C@H](C)CC3)c12)C1CCC1] | 3-(6-{[(1R)-1-cyclobutylethyl]amino}-8-(1-fluoro-1-pyridin-2-ylethyl)-7-[(trans-4-methylcyclohexyl)methyl]-7H-purin-2-yl)-1,2,4-oxadiazol-5(4H)-one (diastereomer A) | | 535 | 535 |
| 22.9 | 2.835 | 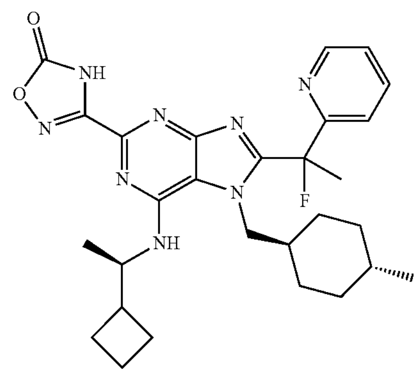 [SMILES: C[C@@H](Nc1nc(-c2noc(=O)[nH]2)nc2nc(C(C)(F)c3ccccn3)n(C[C@H]3CC[C@H](C)CC3)c12)C1CCC1] | 3-(6-{[(1R)-1-cyclobutylethyl]amino}-8-(1-fluoro-1-pyridin-2-ylethyl)-7-[(trans-4-methylcyclohexyl)methyl]-7H-purin-2-yl)-1,2,4-oxadiazol-5(4H)-one (diastereomer B) | | 535 | 535 |
| 22.10 | 6.294 | 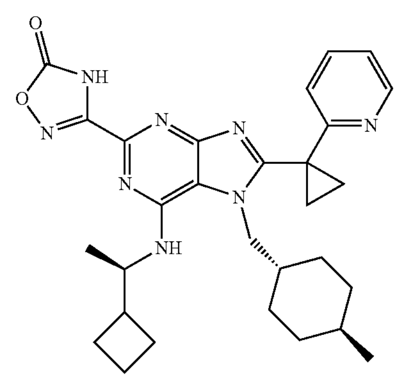 [SMILES: C[C@@H](Nc1nc(-c2noc(=O)[nH]2)nc2nc(C3(c4ccccn4)CC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(1-pyridin-2-ylcyclopropyl)-7H-purin-2-yl]-1,2,4-oxadiazol-5(4H)-one | | 529 | 529 |
| 22.11 | 5.725 | 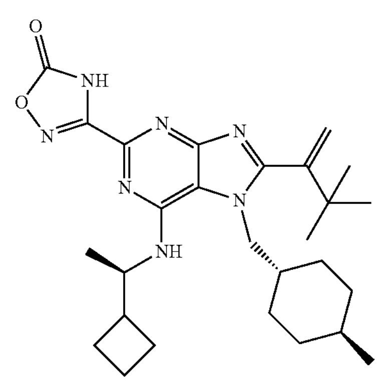 [SMILES: C=C(c1nc2nc(-c3noc(=O)[nH]3)nc(N[C@H](C)C3CCC3)c2n1C[C@H]1CC[C@H](C)CC1)C(C)(C)C] | 3-(6-{[(1R)-1-cyclobutylethyl]amino}-8-(2,2-dimethyl-1-methylidenepropyl)-7-[(trans-4-methylcyclohexyl)methyl]-7H-purin-2-yl)-1,2,4-oxadiazol-5(4H)-one | | 494 | 494 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.12 | 26.69 | 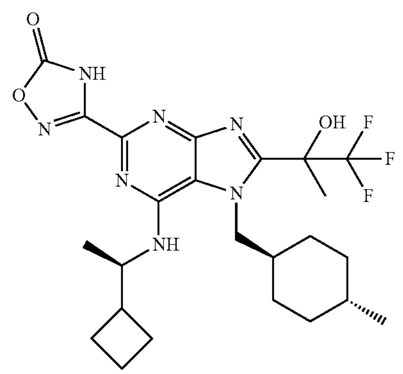 [SMILES: C[C@@H](Nc1nc(-c2noc(=O)[nH]2)nc2nc(C(C)(O)C(F)(F)F)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2,2,2-trifluoro-1-hydroxy-1-methylethyl)-7H-purin-2-yl]-1,2,4-oxadiazol-5(4H)-one (diastereomer A) | | 524 | 524 |
| 22.13 | 5.838 | 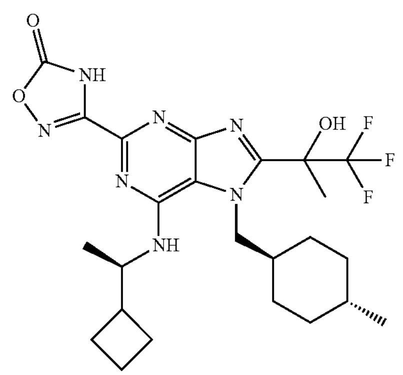 [SMILES: C[C@@H](Nc1nc(-c2noc(=O)[nH]2)nc2nc(C(C)(O)C(F)(F)F)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2,2,2-trifluoro-1-hydroxy-1-methylethyl)-7H-purin-2-yl]-1,2,4-oxadiazol-5(4H)-one (diastereomer B) | | 524 | 524 |
| 22.14 | 81.1 | 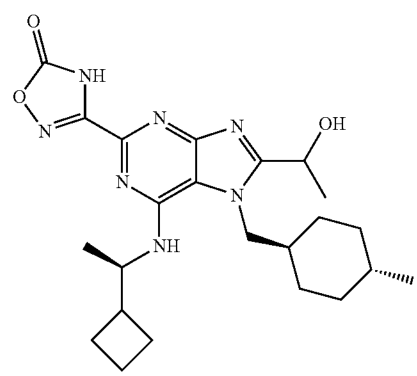 [SMILES: CC(O)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-(1-hydroxyethyl)-7-[(trans-4-methylcyclohexyl)methyl]-7H-purin-2-yl)-1,2,4-oxadiazol-5(4H)-one (diastereomer A) | TFA | 456 | 456 |
| 22.15 | 45.08 | 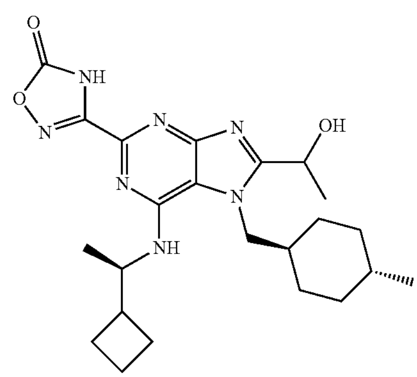 [SMILES: CC(O)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-(1-hydroxyethyl)-7-[(trans-4-methylcyclohexyl)methyl]-7H-purin-2-yl)-1,2,4-oxadiazol-5(2H)-one (diastereomer B) | TFA | 456 | 456 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.16 | 55.6 | 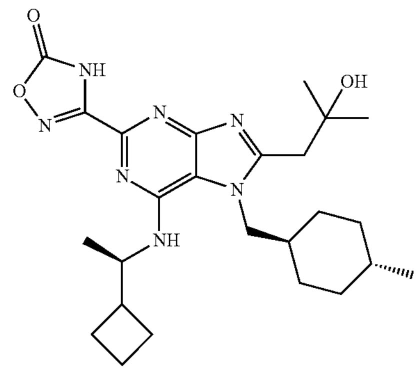 [SMILES: C[C@@H](Nc1nc(-c2noc(=O)[nH]2)nc2nc(CC(C)(C)O)n(C[C@H]3CC[C@H](C)CC3)c12)C1CCC1] | 3-(6-{[(1R)-1-cyclobutylethyl]amino}-8-(2-hydroxy-2-methylpropyl)-7-[(trans-4-methylcyclohexyl)methyl]-7H-purin-2-yl)-1,2,4-oxadiazol-5(4H)-one | | 484 | 484 |
| 22.17 | 147.8 | 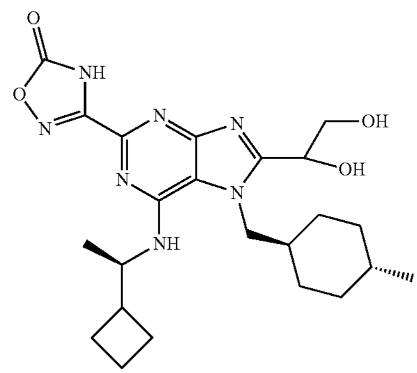 [SMILES: C[C@@H](Nc1nc(-c2noc(=O)[nH]2)nc2nc(C(O)CO)n(C[C@H]3CC[C@H](C)CC3)c12)C1CCC1] | 3-(6-{[(1R)-1-cyclobutylethyl]amino}-8-(1,2-dihydroxyethyl)-7-[(trans-4-methylcyclohexyl)methyl]-7H-purin-2-yl)-1,2,4-oxadiazol-5(4H)-one (diastereomer A) | TFA | 472 | 472 |
| 22.18 | 91.81 | 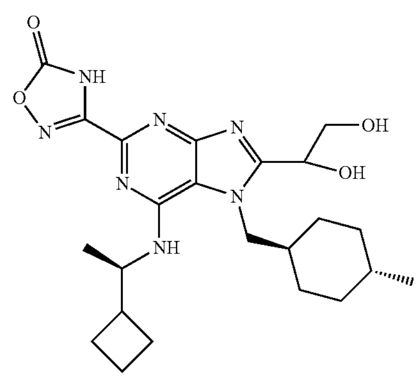 [SMILES: C[C@@H](Nc1nc(-c2noc(=O)[nH]2)nc2nc(C(O)CO)n(C[C@H]3CC[C@H](C)CC3)c12)C1CCC1] | 3-(6-{[(1R)-1-cyclobutylethyl]amino}-8-(1,2-dihydroxyethyl)-7-[(trans-4-methylcyclohexyl)methyl]-7H-purin-2-yl)-1,2,4-oxadiazol-5(4H)-one (diastereomer B) | TFA | 472 | 472 |
| 22.19 | 7.7 | 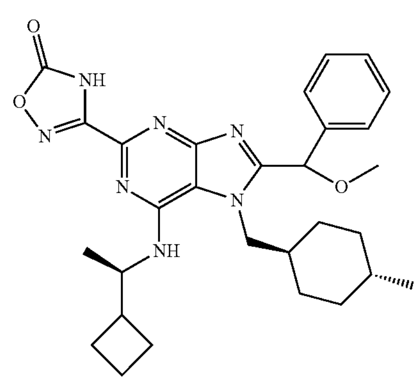 [SMILES: COC(c1ccccc1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[methoxy(phenyl)methyl]-7-[(trans-4-methylcyclohexyl)methyl]-7H-purin-2-yl)-1,2,4-oxadiazol-5(4H)-one (diastereomer A) | | 532 | 532 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.20 | 1.5 | 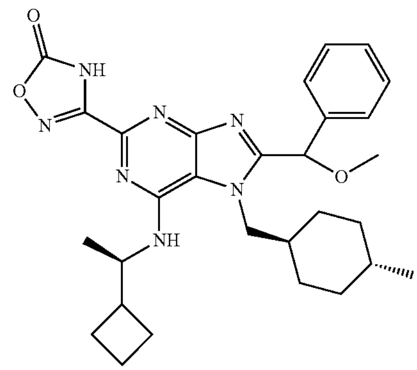 [SMILES: COC(c1ccccc1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[methoxy(phenyl)methyl]-7-[(trans-4-methylcyclohexyl)methyl]-7H-purin-2-yl)-1,2,4-oxadiazol-5(4H)-one (diastereomer B) | | 532 | 532 |
| 22.21 | 1 | 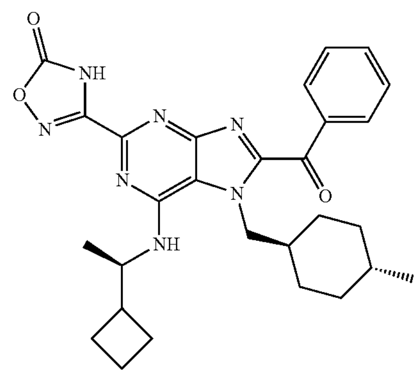 | 3-[6-{[(1R)-1-cyclobutylethyl]amino}-7-[(trans-4-methylcyclohexyl)methyl]-8-(phenylcarbonyl)-7H-purin-2-yl]-1,2,4-oxadiazol-5(4H)-one | TFA | 516 | 516 |
| 22.22 | 3.927 | 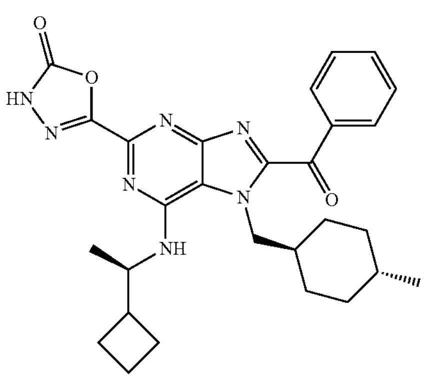 [SMILES: C[C@@H](Nc1nc(-c2n[nH]c(=O)o2)nc2nc(C(=O)c3ccccc3)n(C[C@H]3CC[C@H](C)CC3)c12)C1CCC1] | 5-[6-{[(1R)-1-cyclobutylethyl]amino}-7-[(trans-4-methylcyclohexyl)methyl]-8-(phenylcarbonyl)-7H-purin-2-yl]-1,3,4-oxadiazol-2(3H)-one | TFA | 516 | 516 |
| 22.23 | 6.376 | 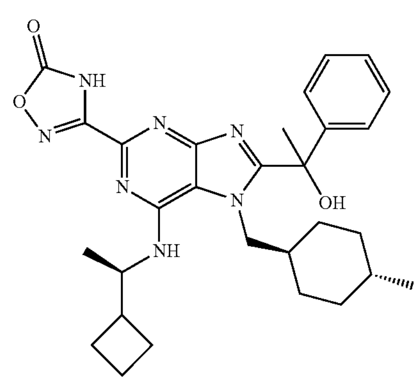 [SMILES: C[C@@H](Nc1nc(-c2noc(=O)[nH]2)nc2nc(C(C)(O)c3ccccc3)n(C[C@H]3CC[C@H](C)CC3)c12)C1CCC1] | 3-(6-{[(1R)-1-cyclobutylethyl]amino}-8-(1-hydroxy-1-phenylethyl)-7-[(trans-4-methylcyclohexyl)methyl]-7H-purin-2-yl)-1,2,4-oxadiazol-5(4H)-one (diastereomer A) | | 532 | 532 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.24 | 33.82 | 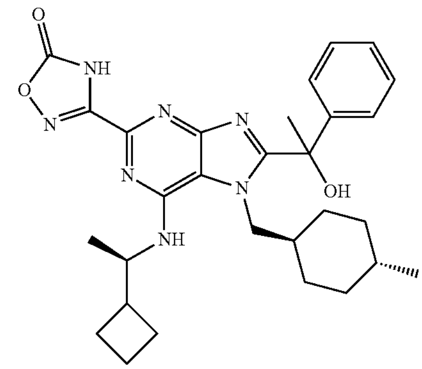 [SMILES: C[C@@H](Nc1nc(-c2noc(=O)[nH]2)nc2nc(C(C)(O)c3ccccc3)n(C[C@H]3CC[C@H](C)CC3)c12)C1CCC1] | 3-(6-{[(1R)-1-cyclobutylethyl]amino}-8-(1-hydroxy-1-phenylethyl)-7-[(trans-4-methylcyclohexyl)methyl]-7H-purin-2-yl)-1,2,4-oxadiazol-5(4H)-one (diastereomer B) | | 532 | 532 |
| 22.25 | 501 | 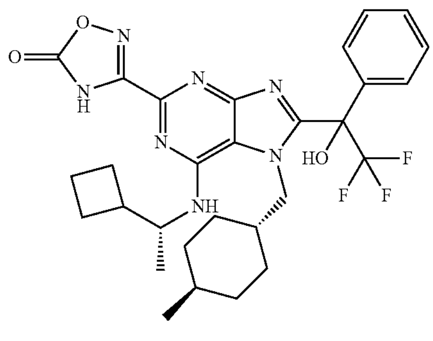 [SMILES: C[C@@H](Nc1nc(-c2noc(=O)[nH]2)nc2nc(C(O)(c3ccccc3)C(F)(F)F)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(1R or S)-2,2,2-trifluoro-1-hydroxy-1-phenylethyl]-7H-purin-2-yl)-1,2,4-oxadiazol-5(4H)-one (Isomer 1) | TFA | 586 | 586 |
| 22.26 | 1.43 | 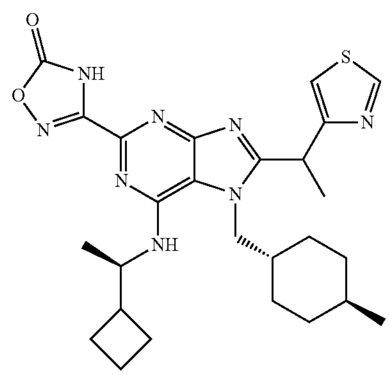 [SMILES: CC(c1cscn1)c1nc2nc(-c3noc(=O)[nH]3)nc(N[C@H](C)C3CCC3)c2n1C[C@H]1CC[C@H](C)CC1] | 3-(6-(((R)-1-cyclobutylethyl)amino)-7-(((trans)-4-methylcyclohexyl)methyl)-8-(1-(thiazol-4-yl)ethyl)-7H-purin-2-yl)-1,2,4-oxadiazol-5(4H)-one (diastereomer A) | | 523 | 523 |
| 22.27 | 14.3 | 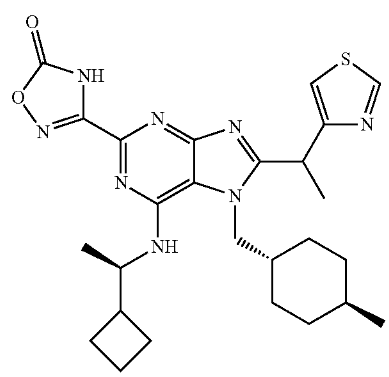 [SMILES: CC(c1cscn1)c1nc2nc(-c3noc(=O)[nH]3)nc(N[C@H](C)C3CCC3)c2n1C[C@H]1CC[C@H](C)CC1] | 3-(6-(((R)-1-cyclobutylethyl)amino)-7-(((trans)-4-methylcyclohexyl)methyl)-8-(1-(thiazol-4-yl)ethyl)-7H-purin-2-yl)-1,2,4-oxadiazol-5(4H)-one (diastereomer B) | | 523 | 523 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.28 | 27.3 | 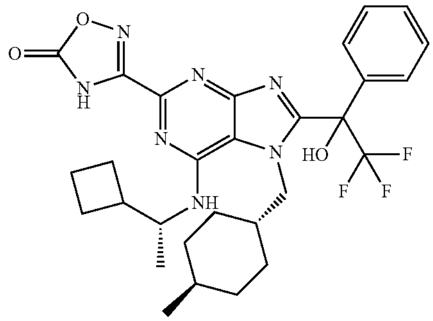 [SMILES: C[C@@H](Nc1nc(-c2noc(=O)[nH]2)nc2nc(C(O)(c3ccccc3)C(F)(F)F)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[(1S or R)-2,2,2-trifluoro-1-hydroxy-1-phenylethyl]-7H-purin-2-yl)-1,2,4-oxadiazol-5(4H)-one (Isomer 2) | TFA | 586 | 586 |
| 22.29 | 1.66 | 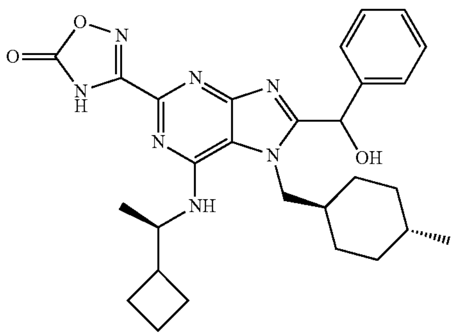 [SMILES: C[C@@H](Nc1nc(-c2noc(=O)[nH]2)nc2nc(C(O)c3ccccc3)n(C[C@H]3CC[C@H](C)CC3)c12)C1CCC1] | 3-(6-{[(1R)-1-cyclobutylethyl]amino}-8-[hydroxy(phenyl)methyl]-7-[(trans-4-methylcyclohexyl)methyl]-7H-purin-2-yl)-1,2,4-oxadiazol-5(4H)-one | TFA | 518 | 518 |
| 22.30 | 10.05 | 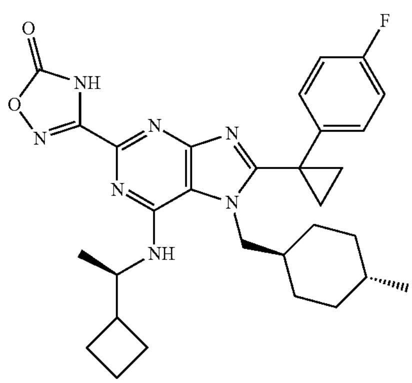 [SMILES: C[C@@H](Nc1nc(-c2noc(=O)[nH]2)nc2nc(C3(c4ccc(F)cc4)CC3)n(C[C@H]3CC[C@H](C)CC3)c12)C1CCC1] | 3-(6-{[(1R)-1-cyclobutylethyl]amino}-8-[1-(4-fluorophenyl)cyclopropyl]-7-[(trans-4-methylcyclohexyl)methyl]-7H-purin-2-yl)-1,2,4-oxadiazol-5(4H)-one | | 546 | 546 |
| 22.31 | 6.448 | 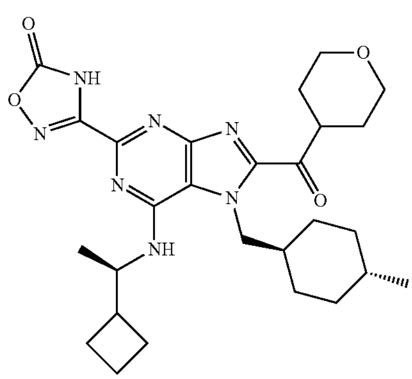 [SMILES: C[C@@H](Nc1nc(-c2noc(=O)[nH]2)nc2nc(C(=O)C3CCOCC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(tetrahydro-2H-pyran-4-ylcarbonyl)-7H-purin-2-yl]-1,2,4-oxadiazol-5(4H)-one | | 524 | 524 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.32 | 25.27 | 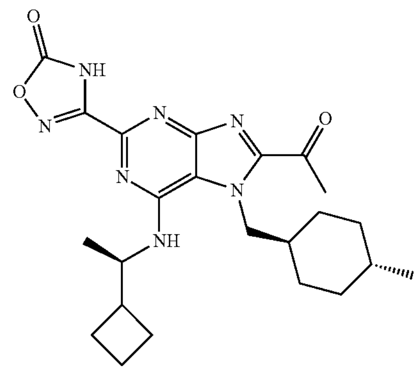 [SMILES: CC(=O)c1nc2nc(-c3noc(=O)[nH]3)nc(N[C@H](C)C3CCC3)c2n1C[C@H]1CC[C@H](C)CC1] | 3-(8-acetyl-6-{[(1R)-1-cyclobutylethyl]amino}-7-[(trans-4-methylcyclohexyl)methyl]-7H-purin-2-yl)-1,2,4-oxadiazol-5(2H)-one | | 454 | 454 |
| 22.33 | 290.9 | 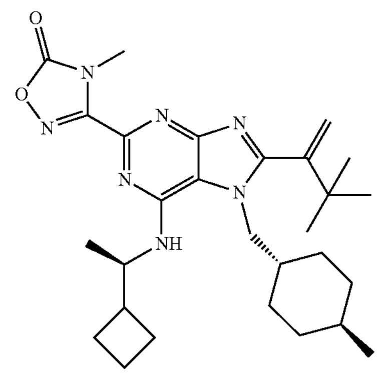 [SMILES: C=C(c1nc2nc(-c3noc(=O)n3C)nc(N[C@H](C)C3CCC3)c2n1C[C@H]1CC[C@H](C)CC1)C(C)(C)C] | 3-(6-{[(1R)-1-cyclobutylethyl]amino}-8-(2,2-dimethyl-1-methylidenepropyl)-7-[(trans-4-methylcyclohexyl)methyl]-7H-purin-2-yl)-4-methyl-1,2,4-oxadiazol-5(4H)-one | | 508 | 508 |
| 22.34 | 24.65 | 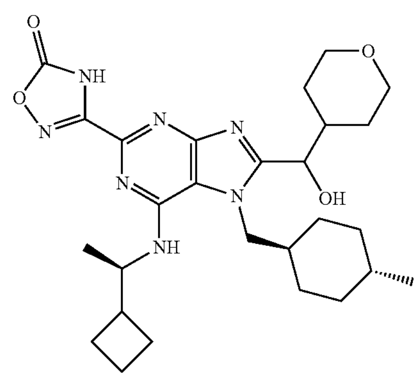 [SMILES: C[C@@H](Nc1nc(-c2noc(=O)[nH]2)nc2nc(C(O)C3CCOCC3)n(C[C@H]3CC[C@H](C)CC3)c12)C1CCC1] | 3-(6-{[(1R)-1-cyclobutylethyl]amino}-8-[hydroxy(tetrahydro-2H-pyran-4-yl)methyl]-7-[(trans-4-methylcyclohexyl)methyl]-7H-purin-2-yl)-1,2,4-oxadiazol-5(4H)-one | | 526 | 526 |
| 22.35 | 47.01 | 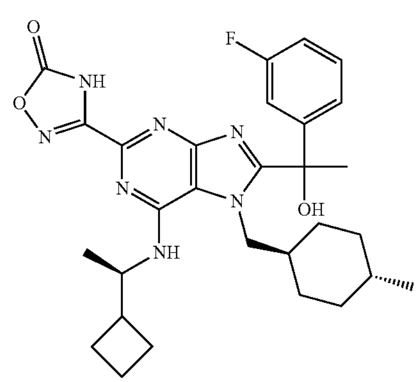 [SMILES: C[C@@H](Nc1nc(-c2noc(=O)[nH]2)nc2nc(C(C)(O)c3cccc(F)c3)n(C[C@H]3CC[C@H](C)CC3)c12)C1CCC1] | 3-(6-{[(1R)-1-cyclobutylethyl]amino}-8-[1-(3-fluorophenyl)-1-hydroxyethyl]-7-[(trans-4-methylcyclohexyl)methyl]-7H-purin-2-yl)-1,2,4-oxadiazol-5(4H)-one (diastereomer 1) | | 550 | 550 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.36 | 13.65 | 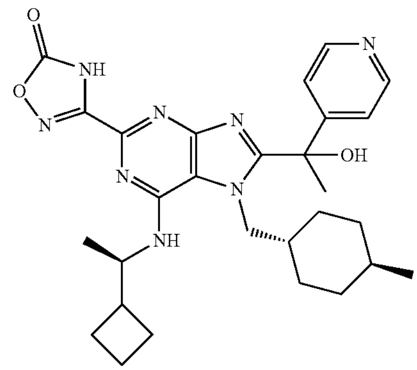 [SMILES: C[C@@H](Nc1nc(-c2noc(=O)[nH]2)nc2nc(C(C)(O)c3ccncc3)n(C[C@H]3CC[C@H](C)CC3)c12)C1CCC1] | 3-(6-{[(1R)-1-cyclobutylethyl]amino}-8-(1-hydroxy-1-pyridin-4-ylethyl)-7-[(trans-4-methylcyclohexyl)methyl]-7H-purin-2-yl)-1,2,4-oxadiazol-5(4H)-one | | 533 | 533 |
| 22.37 | 277.3 | 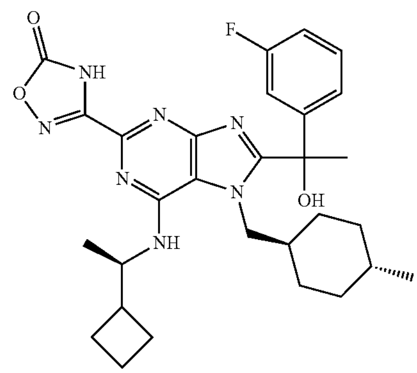 [SMILES: C[C@@H](Nc1nc(-c2noc(=O)[nH]2)nc2nc(C(C)(O)c3cccc(F)c3)n(C[C@H]3CC[C@H](C)CC3)c12)C1CCC1] | 3-(6-{[(1R)-1-cyclobutylethyl]amino}-8-[1-(3-fluorophenyl)-1-hydroxyethyl]-7-[(trans-4-methylcyclohexyl)methyl]-7H-purin-2-yl)-1,2,4-oxadiazol-5(4H)-one (diastereomer 2) | | 550 | 550 |
| 22.38 | 4.755 | 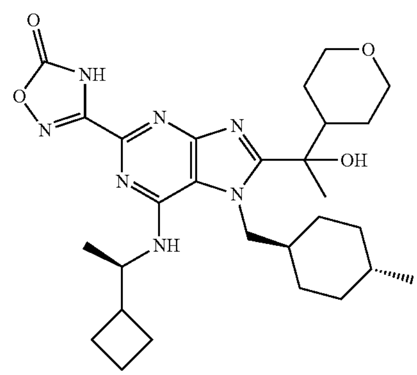 [SMILES: C[C@@H](Nc1nc(-c2noc(=O)[nH]2)nc2nc(C(C)(O)C3CCOCC3)n(C[C@H]3CC[C@H](C)CC3)c12)C1CCC1] | 3-(6-{[(1R)-1-cyclobutylethyl]amino}-8-[1-hydroxy-1-(tetrahydro-2H-pyran-4-yl)ethyl]-7-[(trans-4-methylcyclohexyl)methyl]-7H-purin-2-yl)-1,2,4-oxadiazol-5(4H)-one | | 540 | 540 |
| 22.39 | 13.92 | 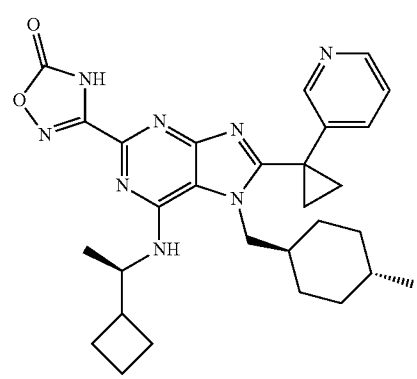 [SMILES: C[C@@H](Nc1nc(-c2noc(=O)[nH]2)nc2nc(C3(c4cccnc4)CC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(1-pyridin-3-ylcyclopropyl)-7H-purin-2-yl]-1,2,4-oxadiazol-5(2H)-one | | 529 | 529 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.40 | 41.6 | 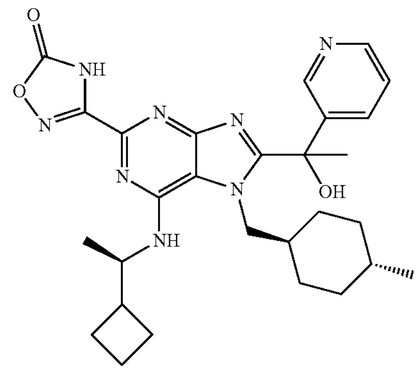 [SMILES: C[C@@H](Nc1nc(-c2noc(=O)[nH]2)nc2nc(C(C)(O)c3cccnc3)n(C[C@H]3CC[C@H](C)CC3)c12)C1CCC1] | 3-(6-{[(1R)-1-cyclobutylethyl]amino}-8-(1-hydroxy-1-pyridin-3-ylethyl)-7-[(trans-4-methylcyclohexyl)methyl]-7H-purin-2-yl)-1,2,4-oxadiazol-5(2H)-one | | 533 | 533 |
| 22.41 | 1.211 | 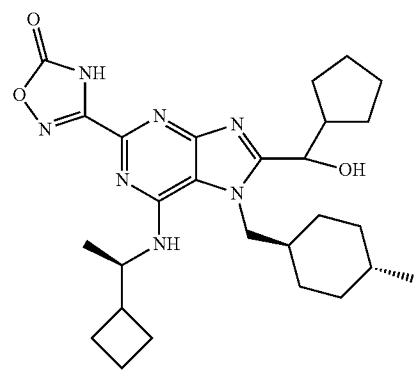 [SMILES: C[C@@H](Nc1nc(-c2noc(=O)[nH]2)nc2nc(C(O)C3CCCC3)n(C[C@H]3CC[C@H](C)CC3)c12)C1CCC1] | 3-(6-{[(1R)-1-cyclobutylethyl]amino}-8-[cyclopentyl(hydroxy)methyl]-7-[(trans-4-methylcyclohexyl)methyl]-7H-purin-2-yl)-1,2,4-oxadiazol-5(2H)-one | TFA | 510 | 510 |
| 22.42 | 5.069 | 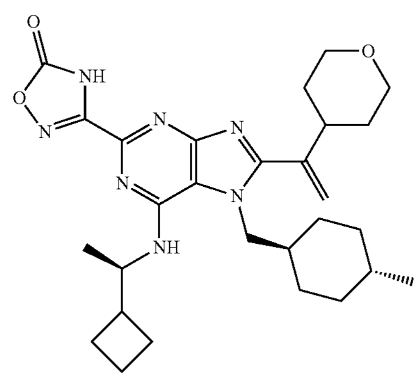 [SMILES: C=C(c1nc2nc(-c3noc(=O)[nH]3)nc(N[C@H](C)C3CCC3)c2n1C[C@H]1CC[C@H](C)CC1)C1CCOCC1] | 3-(6-{[(1R)-1-cyclobutylethyl]amino}-7-[(trans-4-methylcyclohexyl)methyl]-8-[1-(tetrahydro-2H-pyran-4-yl)ethenyl]-7H-purin-2-yl)-1,2,4-oxadiazol-5(4H)-one | | 522 | 522 |
| 22.43 | 13.09 | 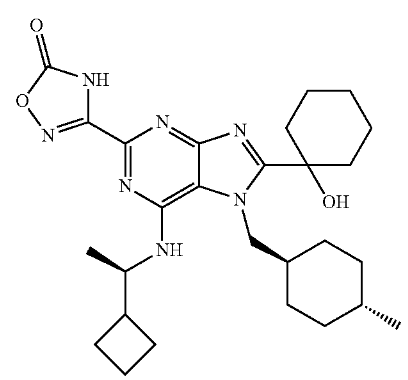 [SMILES: C[C@@H](Nc1nc(-c2noc(=O)[nH]2)nc2nc(C3(O)CCCCC3)n(C[C@H]3CC[C@H](C)CC3)c12)C1CCC1] | 3-(6-{[(1R)-1-cyclobutylethyl]amino}-8-(1-hydroxycyclohexyl)-7-[(trans-4-methylcyclohexyl)methyl]-7H-purin-2-yl)-1,2,4-oxadiazol-5(4H)-one | TFA | 510 | 510 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.44 | 20.52 | 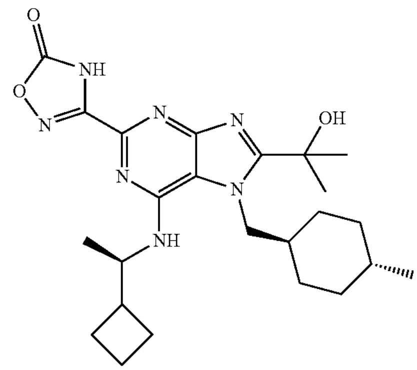 [SMILES: C[C@@H](Nc1nc(-c2noc(=O)[nH]2)nc2nc(C(C)(C)O)n(C[C@H]3CC[C@H](C)CC3)c12)C1CCC1] | 3-(6-{[(1R)-1-cyclobutylethyl]amino}-8-(1-hydroxy-1-methylethyl)-7-[(trans-4-methylcyclohexyl)methyl]-7H-purin-2-yl)-1,2,4-oxadiazol-5(4H)-one | TFA | 470 | 470 |
| 22.45 | 3.662 | 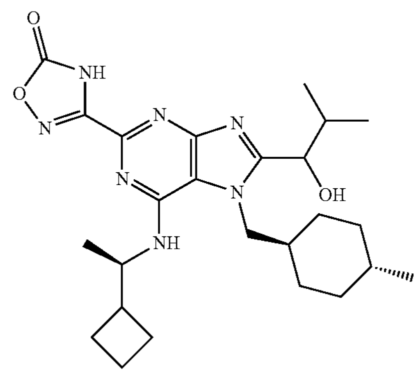 [SMILES: CC(C)C(O)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-(1-hydroxy-2-methylpropyl)-7-[(trans-4-methylcyclohexyl)methyl]-7H-purin-2-yl)-1,2,4-oxadiazol-5(4H)-one | TFA | 484 | 484 |
| 22.46 | 444.8 | 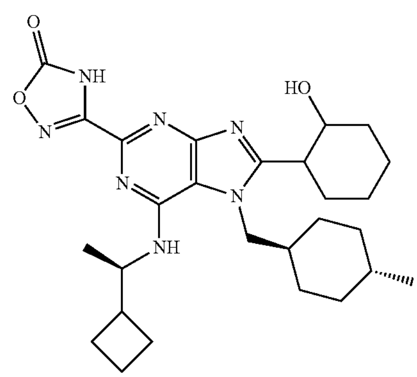 [SMILES: C[C@@H](Nc1nc(-c2noc(=O)[nH]2)nc2nc(C3CCCCC3O)n(C[C@H]3CC[C@H](C)CC3)c12)C1CCC1] | 3-(6-{[(1R)-1-cyclobutylethyl]amino}-8-(2-hydroxycyclohexyl)-7-[(trans-4-methylcyclohexyl)methyl]-7H-purin-2-yl)-1,2,4-oxadiazol-5(4H)-one | TFA | 510 | 510 |
| 22.47 | 5.044 | 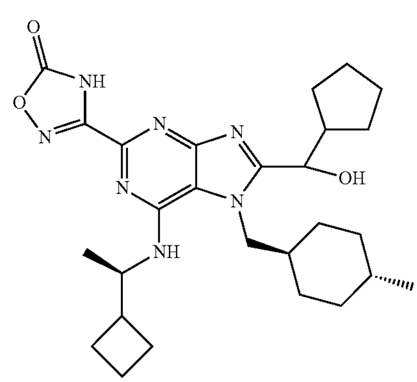 [SMILES: C[C@@H](Nc1nc(-c2noc(=O)[nH]2)nc2nc(C(O)C3CCCC3)n(C[C@H]3CC[C@H](C)CC3)c12)C1CCC1] | 3-(6-{[(1R)-1-cyclobutylethyl]amino}-8-[cyclopentyl(hydroxy)methyl]-7-[(trans-4-methylcyclohexyl)methyl]-7H-purin-2-yl)-1,2,4-oxadiazol-5(4H)-one | TFA | 510 | 510 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.48 | 30.23 | 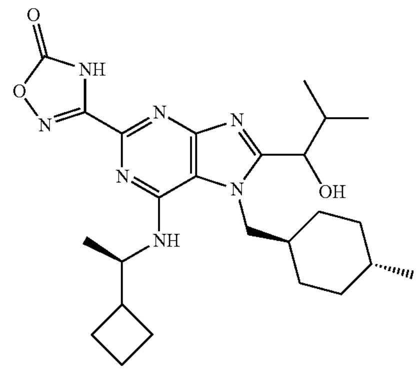 [SMILES: CC(C)C(O)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-(1-hydroxy-2-methylpropyl)-7-[(trans-4-methylcyclohexyl)methyl]-7H-purin-2-yl)-1,2,4-oxadiazol-5(4H)-one | TFA | 484 | 484 |
| 22.49 | 16.92 | 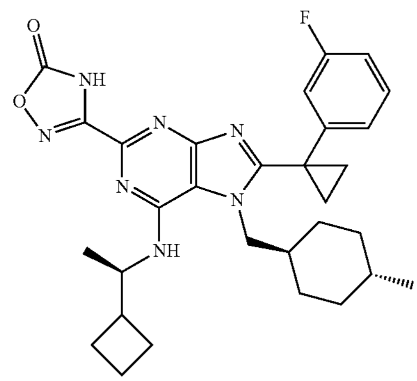 [SMILES: C[C@@H](Nc1nc(-c2noc(=O)[nH]2)nc2nc(C3(c4cccc(F)c4)CC3)n(C[C@H]3CC[C@H](C)CC3)c12)C1CCC1] | 3-(6-{[(1R)-1-cyclobutylethyl]amino}-8-[1-(3-fluorophenyl)cyclopropyl]-7-[(trans-4-methylcyclohexyl)methyl]-7H-purin-2-yl)-1,2,4-oxadiazol-5(4H)-one | | 546 | 546 |
| 22.50 | 10.26 | 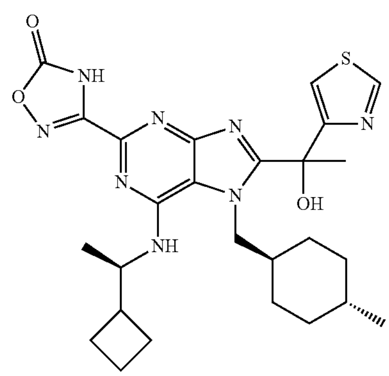 [SMILES: C[C@@H](Nc1nc(-c2noc(=O)[nH]2)nc2nc(C(C)(O)c3cscn3)n(C[C@H]3CC[C@H](C)CC3)c12)C1CCC1] | 3-(6-{[(1R)-1-cyclobutylethyl]amino}-8-[1-hydroxy-1-(1,3-thiazol-4-yl)ethyl]-7-[(trans-4-methylcyclohexyl)methyl]-7H-purin-2-yl)-1,2,4-oxadiazol-5(4H)-one | | 539 | 539 |
| 22.51 | 21.22 | 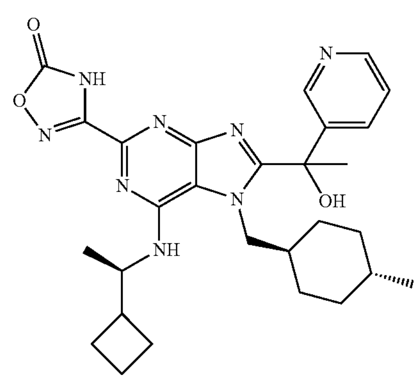 [SMILES: C[C@@H](Nc1nc(-c2noc(=O)[nH]2)nc2nc(C(C)(O)c3cccnc3)n(C[C@H]3CC[C@H](C)CC3)c12)C1CCC1] | 3-(6-{[(1R)-1-cyclobutylethyl]amino}-8-(1-hydroxy-1-pyridin-3-ylethyl)-7-[(trans-4-methylcyclohexyl)methyl]-7H-purin-2-yl)-1,2,4-oxadiazol-5(2H)-one | | 533 | 533 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.52 | 1.846 | 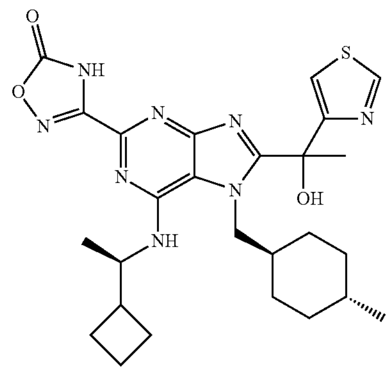 [SMILES: C[C@@H](Nc1nc(-c2noc(=O)[nH]2)nc2nc(C(C)(O)c3cscn3)n(C[C@H]3CC[C@H](C)CC3)c12)C1CCC1] | 3-(6-{[(1R)-1-cyclobutylethyl]amino}-8-[1-hydroxy-1-(1,3-thiazol-4-yl)ethyl]-7-[(trans-4-methylcyclohexyl)methyl]-7H-purin-2-yl)-1,2,4-oxadiazol-5(4H)-one | | 539 | 539 |
| 22.53 | 4.596 | 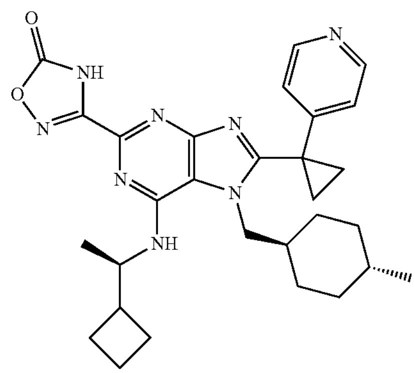 [SMILES: C[C@@H](Nc1nc(-c2noc(=O)[nH]2)nc2nc(C3(c4ccncc4)CC3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(1-pyridin-4-ylcyclopropyl)-7H-purin-2-yl]-1,2,4-oxadiazol-5(4H)-one | | 529 | 529 |
| 22.54 | 2.263 | 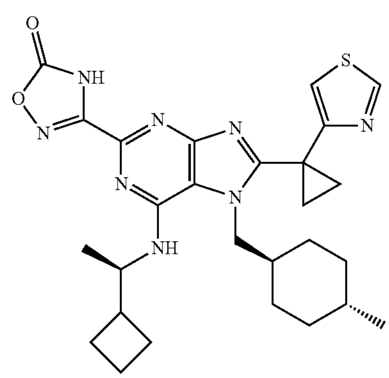 [SMILES: C[C@@H](Nc1nc(-c2noc(=O)[nH]2)nc2nc(C3(c4cscn4)CC3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[1-(1,3-thiazol-4-yl)cyclopropyl]-7H-purin-2-yl)-1,2,4-oxadiazol-5(4H)-one | | 535 | 535 |
| 22.55 | 22.72 | 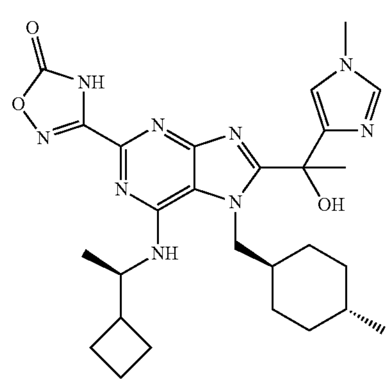 [SMILES: C[C@@H](Nc1nc(-c2noc(=O)[nH]2)nc2nc(C(C)(O)c3cn(C)cn3)n(C[C@H]3CC[C@H](C)CC3)c12)C1CCC1] | 3-(6-{[(1R)-1-cyclobutylethyl]amino}-8-[1-hydroxy-1-(1-methyl-1H-pyrazol-3-yl)ethyl]-7-[(trans-4-methylcyclohexyl)methyl]-7H-purin-2-yl)-1,2,4-oxadiazol-5(2H)-one | | 536 | 536 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.56 | 2.451 | 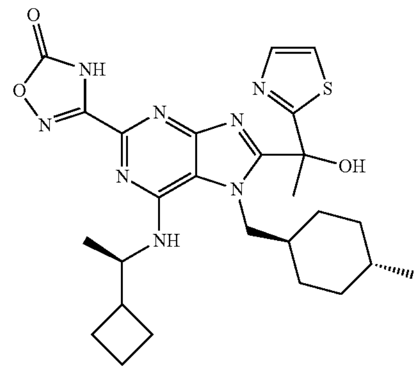 [SMILES: C[C@@H](Nc1nc(-c2noc(=O)[nH]2)nc2nc(C(C)(O)c3nccs3)n(C[C@H]3CC[C@H](C)CC3)c12)C1CCC1] | 3-(6-{[(1R)-1-cyclobutylethyl]amino}-8-[1-hydroxy-1-(1,3-thiazol-2-yl)ethyl]-7-[(trans-4-methylcyclohexyl)methyl]-7H-purin-2-yl)-1,2,4-oxadiazol-5(4H)-one | | 539 | 539 |
| 22.57 | 9.754 | 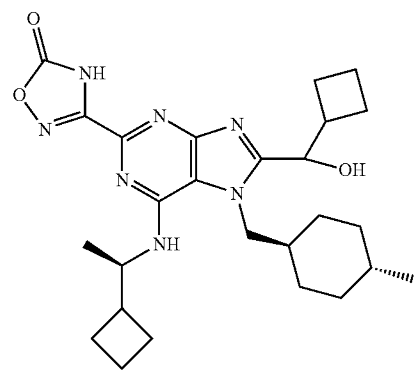 [SMILES: C[C@@H](Nc1nc(-c2noc(=O)[nH]2)nc2nc(C(O)C3CCC3)n(C[C@H]3CC[C@H](C)CC3)c12)C1CCC1] | 3-(6-{[(1R)-1-cyclobutylethyl]amino}-8-[cyclobutyl(hydroxy)methyl]-7-[(trans-4-methylcyclohexyl)methyl]-7H-purin-2-yl)-1,2,4-oxadiazol-5(4H)-one | TFA | 496 | 496 |
| 22.58 | 7.209 | 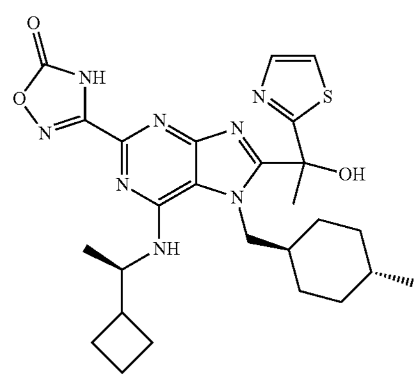 [SMILES: C[C@@H](Nc1nc(-c2noc(=O)[nH]2)nc2nc(C(C)(O)c3nccs3)n(C[C@H]3CC[C@H](C)CC3)c12)C1CCC1] | 3-(6-{[(1R)-1-cyclobutylethyl]amino}-8-[1-hydroxy-1-(1,3-thiazol-2-yl)ethyl]-7-[(trans-4-methylcyclohexyl)methyl]-7H-purin-2-yl)-1,2,4-oxadiazol-5(4H)-one | | 539 | 539 |
| 22.59 | 2.301 | 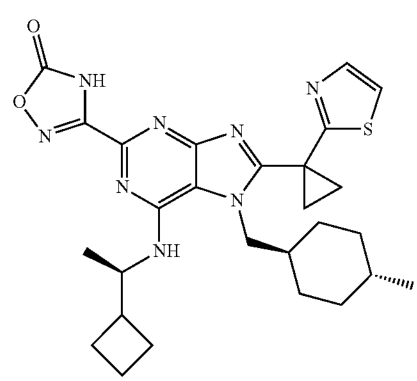 [SMILES: C[C@@H](Nc1nc(-c2noc(=O)[nH]2)nc2nc(C3(c4nccs4)CC3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[1-(1,3-thiazol-2-yl)cyclopropyl]-7H-purin-2-yl)-1,2,4-oxadiazol-5(4H)-one | | 535 | 535 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.60 | 113 | 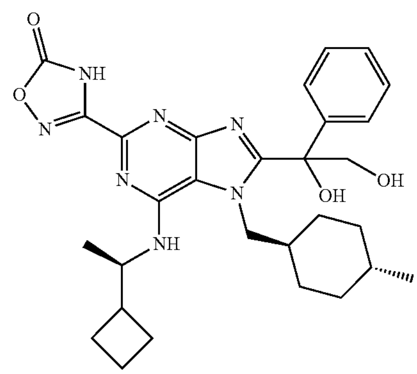 [SMILES: C[C@@H](Nc1nc(-c2noc(=O)[nH]2)nc2nc(C(O)(CO)c3ccccc3)n(C[C@H]3CC[C@H](C)CC3)c12)C1CCC1] | 3-(6-{[(1R)-1-cyclobutylethyl]amino}-8-(1,2-dihydroxy-1-phenylethyl)-7-[(trans-4-methylcyclohexyl)methyl]-7H-purin-2-yl)-1,2,4-oxadiazol-5(4H)-one (diastereomer A) | TFA | 548 | 548 |
| 22.61 | 2.798 | 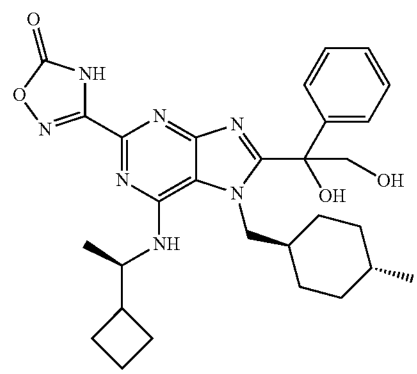 [SMILES: C[C@@H](Nc1nc(-c2noc(=O)[nH]2)nc2nc(C(O)(CO)c3ccccc3)n(C[C@H]3CC[C@H](C)CC3)c12)C1CCC1] | 3-(6-{[(1R)-1-cyclobutylethyl]amino}-8-(1,2-dihydroxy-1-phenylethyl)-7-[(trans-4-methylcyclohexyl)methyl]-7H-purin-2-yl)-1,2,4-oxadiazol-5(4H)-one (diastereomer B) | TFA | 548 | 548 |
| 22.62 | 0.563 | 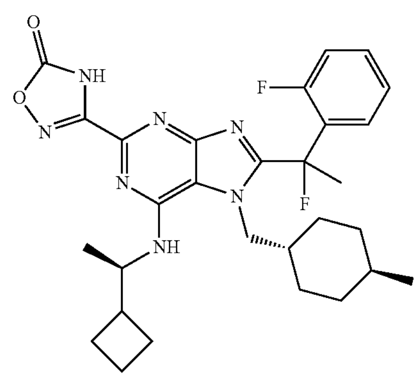 [SMILES: C[C@@H](Nc1nc(-c2noc(=O)[nH]2)nc2nc(C(C)(F)c3ccccc3F)n(C[C@H]3CC[C@H](C)CC3)c12)C1CCC1] | 3-(6-{[(1R)-1-cyclobutylethyl]amino}-8-[1-fluoro-1-(2-fluorophenyl)ethyl]-7-[(trans-4-methylcyclohexyl)methyl]-7H-purin-2-yl)-1,2,4-oxadiazol-5(4H)-one (diastereomer 1) | | 552 | 552 |
| 22.63 | 7.93 | 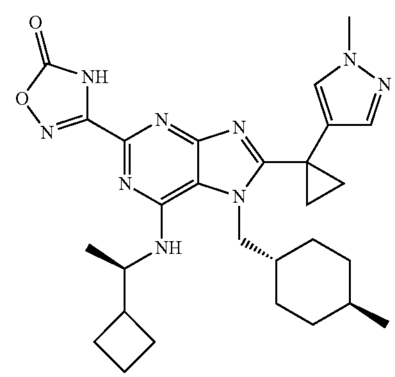 [SMILES: C[C@@H](Nc1nc(-c2noc(=O)[nH]2)nc2nc(C3(c4cnn(C)c4)CC3)n(C[C@H]3CC[C@H](C)CC3)c12)C1CCC1] | 3-(6-{[(1R)-1-cyclobutylethyl]amino}-7-[(trans-4-methylcyclohexyl)methyl]-8-[1-(1-methyl-1H-pyrazol-4-yl)cyclopropyl]-7H-purin-2-yl)-1,2,4-oxadiazol-5(2H)-one | | 532 | 532 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.64 | 48.96 | 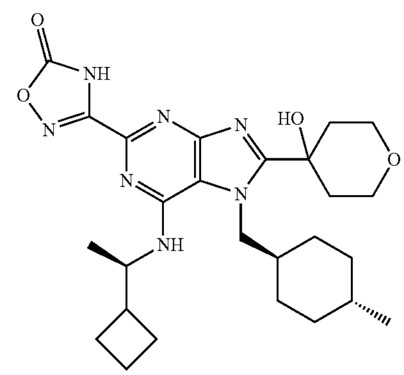 [SMILES: C[C@@H](Nc1nc(-c2noc(=O)[nH]2)nc2nc(C3(O)CCOCC3)n(C[C@H]3CC[C@H](C)CC3)c12)C1CCC1] | 3-(6-{[(1R)-1-cyclobutylethyl]amino}-8-(4-hydroxytetrahydro-2H-pyran-4-yl)-7-[(trans-4-methylcyclohexyl)methyl]-7H-purin-2-yl)-1,2,4-oxadiazol-5(4H)-one | | 512 | 512 |
| 22.65 | 22.65 | 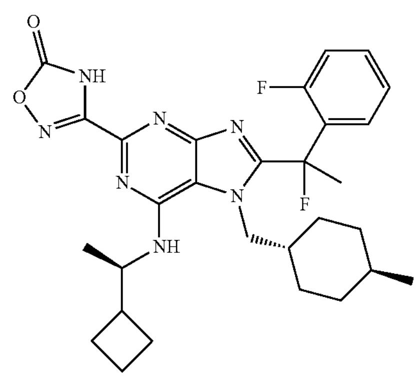 [SMILES: C[C@@H](Nc1nc(-c2noc(=O)[nH]2)nc2nc(C(C)(F)c3ccccc3F)n(C[C@H]3CC[C@H](C)CC3)c12)C1CCC1] | 3-(6-{[(1R)-1-cyclobutylethyl]amino}-8-[1-fluoro-1-(2-fluorophenyl)ethyl]-7-[(trans-4-methylcyclohexyl)methyl]-7H-purin-2-yl)-1,2,4-oxadiazol-5(4H)-one (diastereomer 2) | | 552 | 552 |
| 22.66 | 7.119 | 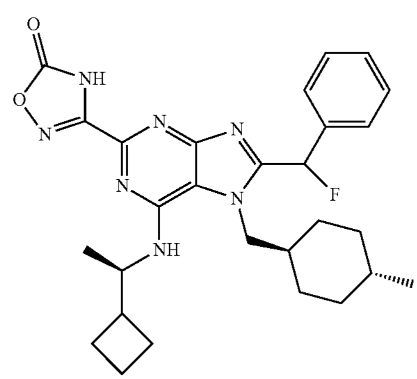 [SMILES: C[C@@H](Nc1nc(-c2noc(=O)[nH]2)nc2nc(C(F)c3ccccc3)n(C[C@H]3CC[C@H](C)CC3)c12)C1CCC1] | 3-(6-{[(1R)-1-cyclobutylethyl]amino}-8-[fluoro(phenyl)methyl]-7-[(trans-4-methylcyclohexyl)methyl]-7H-purin-2-yl)-1,2,4-oxadiazol-5(4H)-one | | 520 | 520 |
| 22.67 | 19.31 | 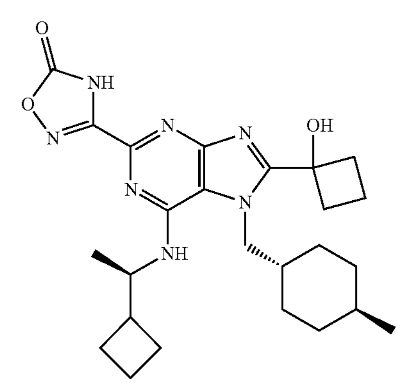 [SMILES: C[C@@H](Nc1nc(-c2noc(=O)[nH]2)nc2nc(C3(O)CCC3)n(C[C@H]3CC[C@H](C)CC3)c12)C1CCC1] | 3-(6-{[(1R)-1-cyclobutylethyl]amino}-8-(1-hydroxycyclobutyl)-7-[(trans-4-methylcyclohexyl)methyl]-7H-purin-2-yl)-1,2,4-oxadiazol-5(2H)-one | | 482 | 482 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.68 | 16.86 | 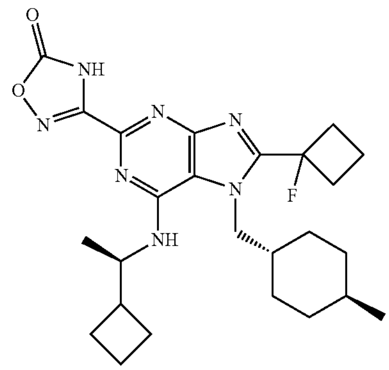 [SMILES: C[C@@H](Nc1nc(-c2noc(=O)[nH]2)nc2nc(C3(F)CCC3)n(C[C@H]3CC[C@H](C)CC3)c12)C1CCC1] | 3-(6-{[(1R)-1-cyclobutylethyl]amino}-8-(1-fluorocyclobutyl)-7-[(trans-4-methylcyclohexyl)methyl]-7H-purin-2-yl)-1,2,4-oxadiazol-5(4H)-one | | 484 | 484 |
| 22.69 | 4.536 | 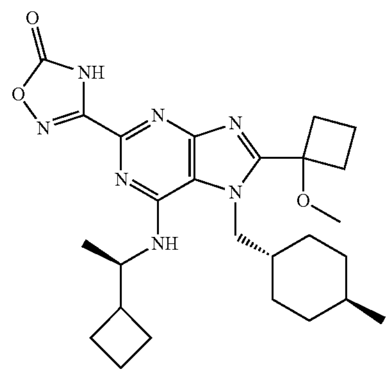 [SMILES: COC1(c2nc3nc(-c4noc(=O)[nH]4)nc(N[C@H](C)C4CCC4)c3n2C[C@H]2CC[C@H](C)CC2)CCC1] | 3-(6-{[(1R)-1-cyclobutylethyl]amino}-8-(1-methoxycyclobutyl)-7-[(trans-4-methylcyclohexyl)methyl]-7H-purin-2-yl)-1,2,4-oxadiazol-5(4H)-one | | 496 | 496 |
| 22.70 | 15.05 | 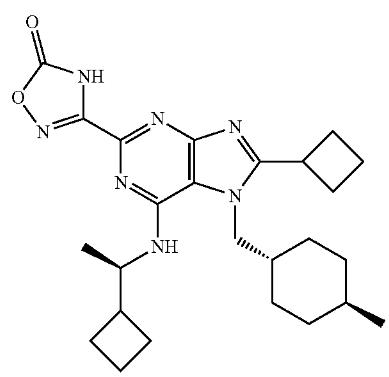 [SMILES: C[C@@H](Nc1nc(-c2noc(=O)[nH]2)nc2nc(C3CCC3)n(C[C@H]3CC[C@H](C)CC3)c12)C1CCC1] | 3-(8-cyclobutyl-6-{[(1R)-1-cyclobutylethyl]amino}-7-[(trans-4-methylcyclohexyl)methyl]-7H-purin-2-yl)-1,2,4-oxadiazol-5(4H)-one | | 466 | 466 |
| 22.71 | 6.486 | 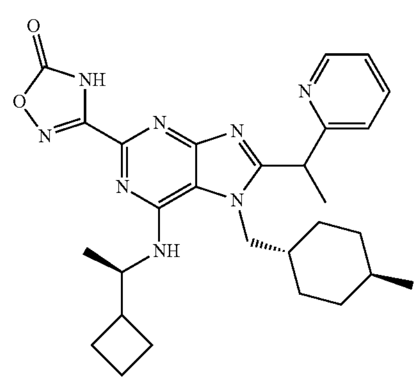 [SMILES: CC(c1ccccn1)c1nc2nc(-c3noc(=O)[nH]3)nc(N[C@H](C)C3CCC3)c2n1C[C@H]1CC[C@H](C)CC1] | 3-[6-{[(1R)-1-cyclobutylethyl]amino}-7-[(trans-4-methylcyclohexyl)methyl]-8-(1-pyridin-2-ylethyl)-7H-purin-2-yl]-1,2,4-oxadiazol-5(4H)-one | | 517 | 517 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.72 | 3.040 | 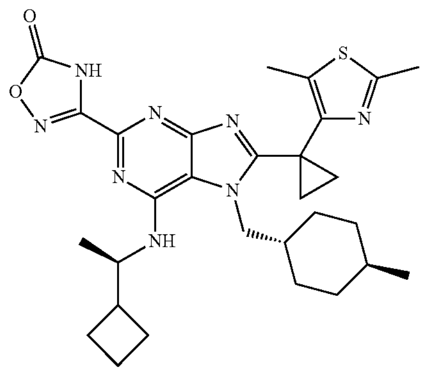 [SMILES: Cc1nc(C2(c3nc4nc(-c5noc(=O)[nH]5)nc(N[C@H](C)C5CCC5)c4n3C[C@H]3CC[C@H](C)CC3)CC2)c(C)s1] | 3-(6-{[(1R)-1-cyclobutylethyl]amino}-8-[1-(2,5-dimethyl-1,3-thiazol-4-yl)cyclopropyl]-7-[(trans-4-methylcyclohexyl)methyl]-7H-purin-2-yl)-1,2,4-oxadiazol-5(4H)-one | | 563 | 563 |
| 22.73 | 4.058 | 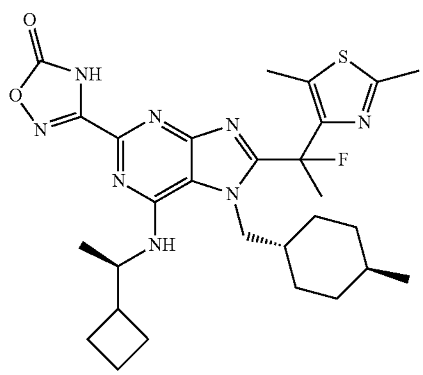 [SMILES: Cc1nc(C(C)(F)c2nc3nc(-c4noc(=O)[nH]4)nc(N[C@H](C)C4CCC4)c3n2C[C@H]2CC[C@H](C)CC2)c(C)s1] | 3-(6-{[(1R)-1-cyclobutylethyl]amino}-8-[1-(2,5-dimethyl-1,3-thiazol-4-yl)-1-fluoroethyl]-7-[(trans-4-methylcyclohexyl)methyl]-7H-purin-2-yl)-1,2,4-oxadiazol-5(4H)-one (diastereomer 1) | | 569 | 569 |
| 22.74 | 2.628 | 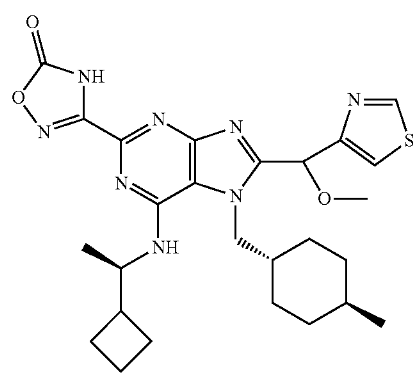 [SMILES: COC(c1cscn1)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[methoxy(1,3-thiazol-4-yl)methyl]-7-[(trans-4-methylcyclohexyl)methyl]-7H-purin-2-yl)-1,2,4-oxadiazol-5(4H)-one | | 539 | 539 |
| 22.75 | 5.482 | 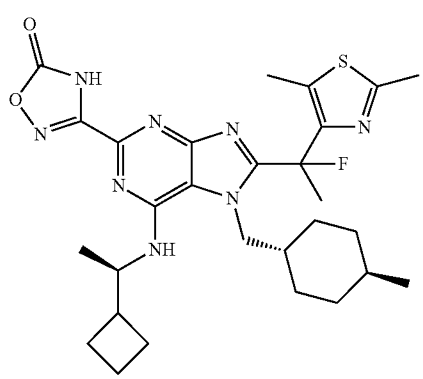 [SMILES: Cc1nc(C(C)(F)c2nc3nc(-c4noc(=O)[nH]4)nc(N[C@H](C)C4CCC4)c3n2C[C@H]2CC[C@H](C)CC2)c(C)s1] | 3-(6-{[(1R)-1-cyclobutylethyl]amino}-8-[1-(2,5-dimethyl-1,3-thiazol-4-yl)-1-fluoroethyl]-7-[(trans-4-methylcyclohexyl)methyl]-7H-purin-2-yl)-1,2,4-oxadiazol-5(4H)-one (diastereomer 2) | | 569 | 569 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.76 | 4.218 | 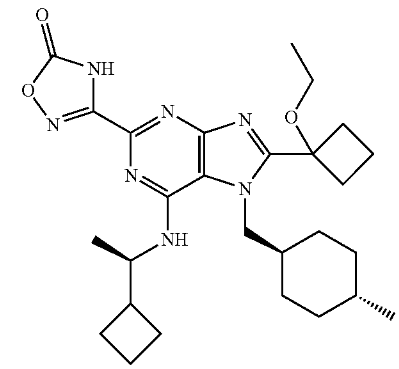 [SMILES: CCOC1(c2nc3nc(-c4noc(=O)[nH]4)nc(N[C@H](C)C4CCC4)c3n2C[C@H]2CC[C@H](C)CC2)CCC1] | 3-(6-{[(1R)-1-cyclobutylethyl]amino}-8-(1-ethoxycyclobutyl)-7-[(trans-4-methylcyclohexyl)methyl]-7H-purin-2-yl)-1,2,4-oxadiazol-5(4H)-one | | 510 | 510 |
| 22.77 | 2.949 | 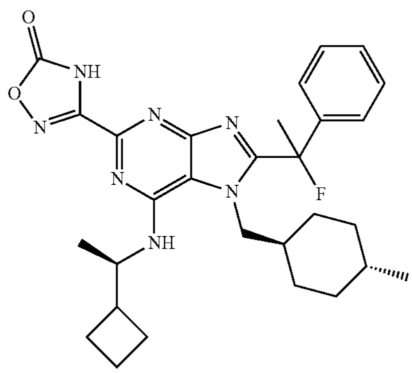 [SMILES: C[C@@H](Nc1nc(-c2noc(=O)[nH]2)nc2nc(C(C)(F)c3ccccc3)n(C[C@H]3CC[C@H](C)CC3)c12)C1CCC1] | 3-(6-{[(1R)-1-cyclobutylethyl]amino}-8-(1-fluoro-1-phenylethyl)-7-[(trans-4-methylcyclohexyl)methyl]-7H-purin-2-yl)-1,2,4-oxadiazol-5(4H)-one (diastereomer 1) | | 534 | 534 |
| 22.78 | 12.35 | 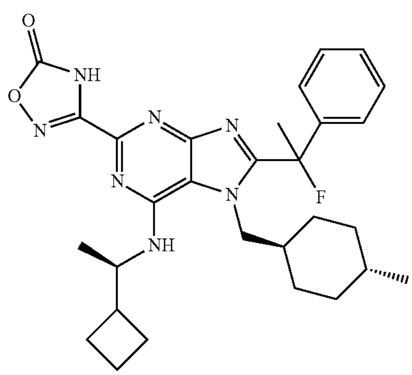 [SMILES: C[C@@H](Nc1nc(-c2noc(=O)[nH]2)nc2nc(C(C)(F)c3ccccc3)n(C[C@H]3CC[C@H](C)CC3)c12)C1CCC1] | 3-(6-{[(1R)-1-cyclobutylethyl]amino}-8-(1-fluoro-1-phenylethyl)-7-[(trans-4-methylcyclohexyl)methyl]-7H-purin-2-yl)-1,2,4-oxadiazol-5(4H)-one (diastereomer 2) | | 534 | 534 |
| 22.79 | 3.363 | 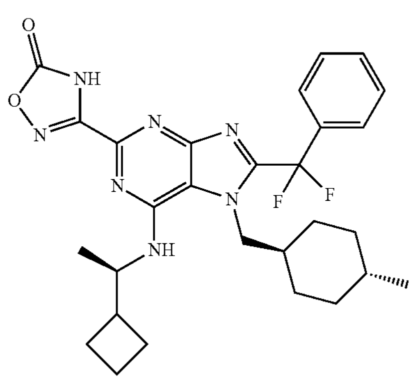 [SMILES: C[C@@H](Nc1nc(-c2noc(=O)[nH]2)nc2nc(C(F)(F)c3ccccc3)n(C[C@H]3CC[C@H](C)CC3)c12)C1CCC1] | 3-(6-{[(1R)-1-cyclobutylethyl]amino}-8-[difluoro(phenyl)methyl]-7-[(trans-4-methylcyclohexyl)methyl]-7H-purin-2-yl)-1,2,4-oxadiazol-5(4H)-one | TFA | 538 | 538 |

TABLE 22-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 22.80 | 2.466 | 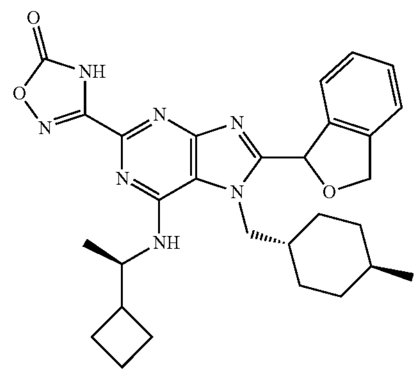 [SMILES: C[C@@H](Nc1nc(-c2noc(=O)[nH]2)nc2nc(C3OCc4ccccc43)n(C[C@H]3CC[C@H](C)CC3)c12)C1CCC1] | 3-(6-{[(1R)-1-cyclobutylethyl]amino}-8-(1,3-dihydro-2-benzofuran-1-yl)-7-[(trans-4-methylcyclohexyl)methyl]-7H-purin-2-yl)-1,2,4-oxadiazol-5(4H)-one (mixture of diastereomers) | | 530 | 530 |
| 22.81 | 11.04 | 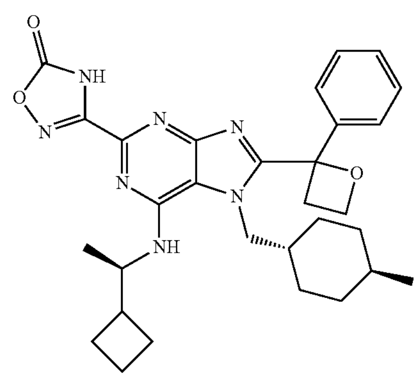 [SMILES: C[C@@H](Nc1nc(-c2noc(=O)[nH]2)nc2nc(C3(c4ccccc4)CCO3)n(C[C@H]3CC[C@H](C)CC3)c12)C1CCC1] | 3-[6-{[(1R)-1-cyclobutylethyl]amino}-7-[(trans-4-methylcyclohexyl)methyl]-8-(2-phenyloxetan-2-yl)-7H-purin-2-yl]-1,2,4-oxadiazol-5(4H)-one (mixture of diastereomers) | | 544 | 544 |
| 22.82 | 10.10 | 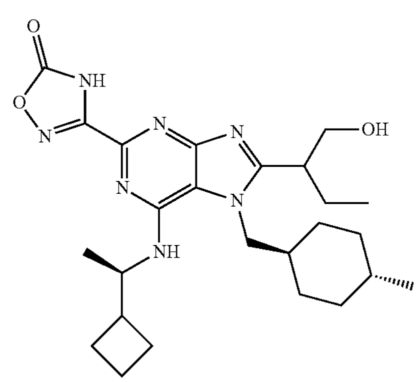 [SMILES: CCC(CO)c1nc2nc(-c3noc(=O)[nH]3)nc(N[C@H](C)C3CCC3)c2n1C[C@H]1CC[C@H](C)CC1] | 3-(6-{[(1R)-1-cyclobutylethyl]amino}-8-[1-(hydroxymethyl)propyl]-7-[(trans-4-methylcyclohexyl)methyl]-7H-purin-2-yl)-1,2,4-oxadiazol-5(4H)-one (mixture of diastereomers) | | 484 | 484 |

Example 23.1

5-{6-(3-chlorophenyl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one

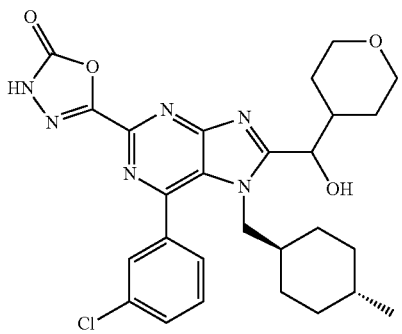 [SMILES: C[C@H]1CC[C@H](Cn2c(C(O)C3CCOCC3)nc3nc(-c4n[nH]c(=O)o4)nc(-c4cccc(Cl)c4)c32)CC1]

Step 1: 6-(3-Chlorophenyl)-7-(((trans)-4-methylcyclohexyl)methyl)-7H-purine-2-carbonitrile (Preparative Example 16.3, Step 1; 100 mg, 0.27 mmol) was dissolved in THF (10 mL) and cooled to 78° C. 2,2,6,6-Tetramethylpiperidinylmagnesium chloride, lithium chloride complex (1 M in THF/toluene, 1.4 mL, 1.36 mmol) was added slowly to the solution at 78° C. This reaction mixture was stirred at 78° C. for 2 hours. Next, tetrahydro-2H-pyran-4-carbaldehyde (0.14 mL, 1.36 mmol) was added into the reaction mixture at 78° C. The reaction was warmed to room temperature and stirred for 8 hours. The reaction was quenched with saturated NH$_4$Cl solution at 78° C. (5 mL) and extracted with EtOAc (2×10 mL). The combined organic extracts were dried over anhydrous Na$_2$SO$_4$ and concentrated under reduced pressure. The residue was purified on a silica gel column (0 to 100% EtOAc/hexanes) to afford 6-(3-chlorophenyl)-8-(hydroxy(tetrahydro-2H-pyran-4-yl)methyl)-7-(((trans)-4-methylcyclohexyl)methyl)-7H-purine-2-carbonitrile. MS (ES)=480 (M+1)$^+$.

Step 2: 6-(3-Chlorophenyl)-8-(hydroxy(tetrahydro-2H-pyran-4-yl)methyl)-7-(((trans)-4-methylcyclohexyl)methyl)-7H-purine-2-carbonitrile (100 mg, 0.28 mmol) was dissolved in 3N HCl in MeOH (10 mL) and stirred at reflux for 4 hours. The reaction was cooled to room temperature and concentrated. Water (15 mL) was added, and the mixture was extracted with EtOAc (2×10 mL). The combined organic extracts were dried over anhydrous Na$_2$SO$_4$, filtered, and concentrated under reduced pressure to afford methyl 6-(3-chlorophenyl)-8-(hydroxy(tetrahydro-2H-pyran-4-yl)methyl)-7-(((trans)-4-methylcyclohexyl)methyl)-7H-purine-2-carboxylate. MS (ES)=513 (M+1)$^+$.

Step 3: Methyl 6-(3-chlorophenyl)-8-(hydroxy(tetrahydro-2H-pyran-4-yl)methyl)-7-(((trans)-4-methylcyclohexyl)methyl)-7H-purine-2-carboxylate (95 mg, 0.18 mmol) was dissolved in MeOH (0.5 mL) and then a solution of 1.0 M hydrazine in THF (7 mL, 7 mmol) was added at room temperature and stirred for 2 hours. The reaction was quenched with water (13 mL) and extracted with EtOAc (2×10 mL). The combined organic layers were dried over anhydrous Na$_2$SO$_4$, filtered, and concentrated under reduced pressure to afford 6-(3-chlorophenyl)-8-(hydroxy(tetrahydro-2H-pyran-4-yl)methyl)-7-(((trans)-4-methylcyclohexyl)methyl)-7H-purine-2-carbohydrazide. MS (ES)=513 (M+1)$^+$.

Step 4: To a solution of 6-(3-chlorophenyl)-8-(hydroxy(tetrahydro-2H-pyran-4-yl)methyl)-7-(((trans)-4-methylcyclohexyl)methyl)-7H-purine-2-carbohydrazide (53.0 mg, 0.10 mmol) and 1,1'-carbonyldiimidazole (85.0 mg, 0.52 mmol) in acetonitrile (5 mL) was added 1,8-diazabicyclo[5.4.0]undec-7-ene (0.047 mL, 0.31 mmol) dropwise. The reaction mixture was stirred at room temperature for 2 hours. The reaction was concentrated and the residue was dissolved in CH$_2$Cl$_2$ (50 mL) and washed with water (20 mL). The organic layer was dried over anhydrous Na$_2$SO$_4$ and concentrated under reduced pressure. The residue was purified on a silica gel column (0 to 10% MeOH/CH$_2$Cl$_2$) to afford 5-{6-(3-chlorophenyl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one. $^1$H NMR (400 MHz, DMSO-d$_6$) δ 12.89 (br s, 1H), 7.84 (br s, 1H), 7.63-7.76 (m, 3H), 5.90 (d, J=7.6 Hz, 1H), 4.65 (d, J=8.0 Hz, 1H), 3.87-4.08 (m, 3H), 3.77-3.85 (m, 1H), 2.33-2.42 (m, 1H), 1.91-2.01 (m, 1H), 1.21-1.53 (m, 6H), 1.03-1.18 (m, 1H), 0.89-1.01 (m, 2H), 0.67-0.88 (m, 4H), 0.72 (d, J=6.4 Hz, 3H), 0.41-0.53 (m, 2H). MS (ES)=539 (M+1)$^+$.

Example 23.2

3-{6-(3-chlorophenyl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one

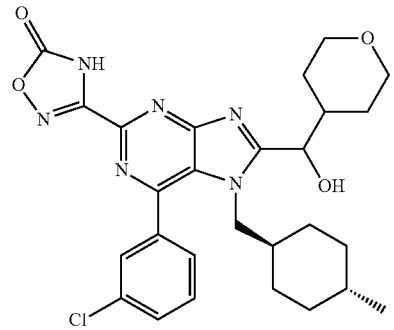 [SMILES: C[C@H]1CC[C@H](Cn2c(C(O)C3CCOCC3)nc3nc(-c4noc(=O)[nH]4)nc(-c4cccc(Cl)c4)c32)CC1]

Step 1: Hydroxylamine hydrochloride (14.0 mg, 0.20 mmol) and sodium bicarbonate (25.1 mg, 0.31 mmol) were dissolved in water (2 mL) and stirred at room temperature for 15 minutes. This solution was then added to 6-(3-chlorophenyl)-8-(hydroxyl(tetrahydro-2H-pyran-4-yl)methyl)-7-(((trans)-4-methylcyclohexyl)methyl)-7H-purine-2-carbonitrile (Example 23.1, Step 1; 50.0 mg, 0.10 mmol) dissolved in ethanol (5 mL). The reaction was stirred at 100° C. for 2 hours. Next, the reaction was diluted with EtOAc (15 mL) and washed with water (10 mL). The organic layer was dried over anhydrous Na$_2$SO$_4$ and concentrated under reduced pressure to afford 6-(3-chlorophenyl)-N-hydroxy-8-(hydroxy(tetrahydro-2H-pyran-4-yl)methyl)-7-(((trans)-4-methylcyclohexyl)methyl)-7H-purine-2-carboximidamide. MS (ES)=513 (M+1)$^+$.

Step 2: To a solution of 6-(3-chlorophenyl)-N-hydroxy-8-(hydroxy(tetrahydro-2H-pyran-4-yl)methyl)-7-(((trans)-4-methylcyclohexyl)methyl)-7H-purine-2-carboximidamide (40.0 mg, 0.07 mmol) and 1,1'-carbonyldiimidazole (63.0 mg, 0.41 mmol) in acetonitrile (5 mL) was added 1,8-diazabicyclo[5.4.0]undec-7-ene (0.034 mL, 0.23 mmol). The reaction was stirred at room temperature for 2 hours and then concentrated. The residue was dissolved in CH$_2$Cl$_2$ (15 mL) and washed with water (8 mL). The organic layer was dried over anhydrous $Na_2SO_4$ and concentrated under reduced pressure. The residue was purified on a silica gel column (0 to 10% MeOH/$CH_2Cl_2$) to afford 3-{6-(3-chlorophenyl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one. $^1$H NMR (400 MHz, DMSO-$d_6$) δ 13.91 (br s, 1H), 7.88 (br s, 1H), 7.63-7.74 (m, 3H), 5.92 (d, J=7.2 Hz, 1H), 4.65 (d, J=8.0 Hz, 1H), 4.05-4.13 (m, 1H), 3.92-4.01 (m, 2H), 3.80-3.86 (m, 1H), 2.32-2.46 (m, 2H), 1.93-1.57 (m, 5H), 1.03-1.16 (m, 1H), 0.88-0.97 (m, 2H), 0.67-0.86 (m, 5H), 0.72 (d, J=6.4 Hz, 3H), 0.41-0.53 (m, 2H). MS (APCI)=539 (M+1)$^+$.

Example 23.3

3-[6-(3-chlorophenyl)-7-[(trans-4-methylcyclohexyl)methyl]-8-(tetrahydro-2H-pyran-4-ylcarbonyl)-7H-purin-2-yl]-1,2,4-oxadiazol-5(4H)-one

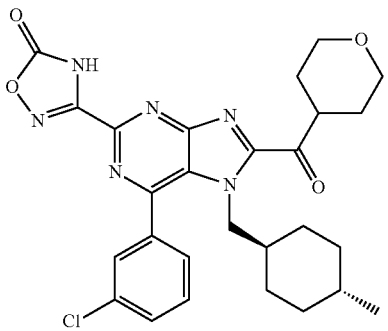 [SMILES: C[C@H]1CC[C@H](Cn2c(C(=O)C3CCOCC3)nc3nc(-c4noc(=O)[nH]4)nc(-c4cccc(Cl)c4)c32)CC1]

DMSO (0.034 mL, 0.44 mmol) was added dropwise to a solution of oxalyl chloride (0.028 mL, 0.33 mmol) in $CH_2Cl_2$ (3 mL) at –78° C. and the reaction was stirred for 30 minutes. Next, a solution of 3-{6-(3-chlorophenyl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one (Example 23.2, 60.0 mg, 0.11 mmol) in $CH_2Cl_2$ (3 mL) was added dropwise at –78° C. and the reaction was stirred for 30 minutes. Triethylamine (0.056 mL, 0.44 mmol) was added dropwise at –78° C. and the reaction was warmed to room temperature and stirred for 30 minutes. The reaction was quenched by the addition of water (8 mL) and extracted with $CH_2Cl_2$ (2×10 mL). The combined organic extracts were dried over anhydrous $Na_2SO_4$ and concentrated under reduced pressure. The residue was purified on a silica gel column (0 to 10% MeOH/$CH_2Cl_2$) to afford 3-[6-(3-chlorophenyl)-7-[(trans-4-methylcyclohexyl)methyl]-8-(tetrahydro-2H-pyran-4-ylcarbonyl)-7H-purin-2-yl]-1,2,4-oxadiazol-5(4H)-one. $^1$H NMR (400 MHz, DMSO-$d_6$) δ 13.34 (br s, 1H), 7.89 (s, 1H), 7.64-7.78 (m, 3H), 4.23-4.39 (m, 1H), 3.90-4.08 (m, 3H), 3.45-3.63 (m, 2H), 1.89 (dd, J=12.8, 2.0 Hz, 2H), 1.57-1.72 (m, 2H), 1.36-1.48 (m, 2H), 1.19-1.28 (m, 1H), 0.93-1.14 (m, 2H), 0.76-0.90 (m, 2H), 0.72 (d, J=6.4 Hz, 3H), 0.58-0.71 (m, 2H), 0.41-0.57 (m, 2H). MS (ES)=537 (M+1)$^+$.

Example 23.4

3-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,2,4-oxadiazol-5(4H)-one

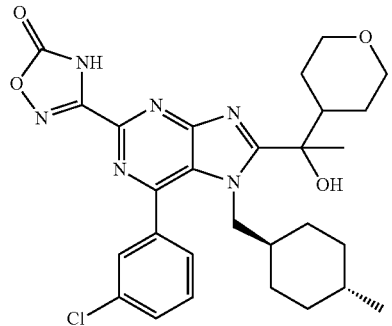 [SMILES: CC(O)(c1nc2nc(-c3noc(=O)[nH]3)nc(-c3cccc(Cl)c3)c2n1C[C@H]1CC[C@H](C)CC1)C1CCOCC1]

To a solution of 3-[6-(3-chlorophenyl)-7-[(trans-4-methylcyclohexyl)methyl]-8-(tetrahydro-2H-pyran-4-ylcarbonyl)-7H-purin-2-yl]-1,2,4-oxadiazol-5(4H)-one (Example 23.3, 20.0 mg, 0.03 mmol) in THF (3 mL) was added methyl magnesium bromide (3M in THF, 0.11 mL, 0.037 mmol) at –78° C. The reaction was warmed to room temperature and stirred for 30 minutes. The reaction was then quenched with saturated aqueous $NH_4Cl$ (5 mL) and extracted with $CH_2Cl_2$ (15 mL). The organic layer was dried over anhydrous $Na_2SO_4$ and concentrated under reduced pressure. The residue was purified on a silica gel column (0 to 10% MeOH/$CH_2Cl_2$) to afford 3-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,2,4-oxadiazol-5(4H)-one. $^1$H NMR (400 MHz, $CD_3OD$) δ 7.82 (br s, 1H), 7.58-7.67 (m, 3H), 3.95-4.01 (m, 3H), 3.34-3.43 (m, 2H), 1.73-1.85 (m, 3H), 1.58-1.68 (m, 2H), 1.42-1.55 (m, 4H), 1.26-1.35 (m, 1H), 1.06-1.20 (m, 3H), 0.87-0.94 (m, 2H), 0.63-0.81 (m, 2H), 0.75 (d, J=6.8 Hz, 3H), 0.51-0.58 (m, 2H). MS (ES)=553 (M+1)$^+$.

Example 23.12

3-{6-(3-chlorophenyl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one

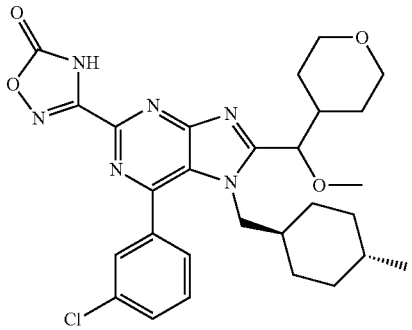 [SMILES: COC(c1nc2nc(-c3noc(=O)[nH]3)nc(-c3cccc(Cl)c3)c2n1C[C@H]1CC[C@H](C)CC1)C1CCOCC1]

Step 1: 6-(3-chlorophenyl)-8-(hydroxy(tetrahydro-2H-pyran-4-yl)methyl)-7-(((trans)-4-methylcyclohexyl)methyl)-7H-purine-2-carbonitrile (Example 23.1, Step 1; 50.0 mg, 0.10 mmol) was dissolved in THF (3 mL). Sodium hydride (4.0 mg, 0.20 mmol) was added to the reaction at 0° C., and the reaction stirred for 15 minutes. Next, methyl iodide (0.022 mL, 0.15 mmol) was added at 0° C. The reaction was warmed to room temperature and stirred for 30 minutes. The reaction was then quenched with saturated NH$_4$Cl solution (12 mL) and extracted with EtOAC (2×10 mL). The combined organic extracts were dried over anhydrous Na$_2$SO$_4$, filtered and concentrated under reduced pressure to afford 6-(3-chlorophenyl)-8-(methoxy(tetrahydro-2H-pyran-4-yl)methyl)-7-(((trans)-4-methylcyclohexyl)methyl)-7H-purine-2-carbonitrile. MS (ES)=494 (M+1)$^+$.

Steps 2 and 3: Using procedures similar to those described in Example 23.2 (Steps 1 and 2), 6-(3-chlorophenyl)-8-(methoxy(tetrahydro-2H-pyran-4-yl)methyl)-7-(((trans)-4-methylcyclohexyl)methyl)-7H-purine-2-carbonitrile was converted to 3-{6-(3-chlorophenyl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one. $^1$H NMR (400 MHz, CD$_3$OD) δ 7.87 (br s, 1H), 7.63-7.69 (m, 3H), 4.64 (d, J=7.6 Hz, 1H), 4.07-4.15 (m, 2H), 3.11-3.31 (m, 1H), 3.89-3.93 (m, 1H), 3.41-3.46 (m, 1H), 3.34-3.37 (m, 4H), 2.26-2.38 (m, 1H), 1.83-1.91 (m, 1H), 1.48-1.67 (m, 3H), 1.27-1.41 (m, 1H), 1.11-1.21 (m, 1H), 0.99-1.01 (m, 2H), 0.86-0.89 (m, 3H), 0.77-0.78 (m, 1H), 0.76 (d, J=6.8 Hz, 3H), 0.42-0.58 (m, 2H). MS (ESI)=553 (M+1)$^+$.

Example 23.17

3-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one

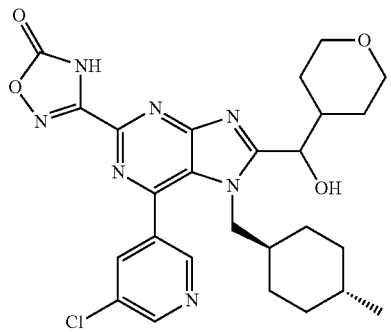 [SMILES: C[C@H]1CC[C@H](Cn2c(C(O)C3CCOCC3)nc3nc(-c4noc(=O)[nH]4)nc(-c4cncc(Cl)c4)c32)CC1]

Step 1: 6-(5-chloropyridin-3-yl)-7-(((trans)-4-methylcyclohexyl)methyl)-7H-purine-2-carbonitrile (Preparative Example 16.8, Step 1; 200 mg, 0.54 mmol) was dissolved in THF (6 mL) and cooled to −78° C. 2,2,6,6-tetramethylpiperidinylmagnesium chloride, lithium chloride complex (1.0M in THF/toluene, 2.7 mL, 2.7 mmol) was added slowly at −78° C. The reaction was stirred at −78° C. for 2 hours. Next, tetrahydro-2H-pyran-4-carbaldehyde (0.34 ml, 2.73 mmol) was added to the reaction mixture at −78° C. The reaction was allowed to warm to room temperature and stirred for 8 hours. The reaction was then quenched with saturated NH$_4$Cl solution (12 mL) at −78° C. and extracted with EtOAc (2×20 mL). The combined organic extracts were dried over anhydrous Na$_2$SO$_4$ and concentrated under reduced pressure. The residue was purified on a silica gel column (0 to 100% EtOAc/hexanes) to afford 6-(5-chloropyridin-3-yl)-8-(hydroxy(tetrahydro-2H-pyran-4-yl)methyl)-7-(((trans)-4-methylcyclohexyl)methyl)-7H-purine-2-carbonitrile. MS (ES)=481 (M+1)$^+$.

Steps 2 and 3: Using procedures similar to those described in Example 23.2 (Steps 1 and 2), 6-(5-chloropyridin-3-yl)-8-(hydroxy(tetrahydro-2H-pyran-4-yl)methyl)-7-(((trans)-4-methylcyclohexyl)methyl)-7H-purine-2-carbonitrile was converted to 3-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one. $^1$H NMR (400 MHz, CD$_3$OD) δ 8.86 (dd, J=12.0, J=12.0 Hz, 3.2 Hz, 2H), 8.40 (m, 1H), 4.26-4.41 (m, 1H), 4.12-4.13 (m, 1H), 3.87-3.98 (m, 1H), 3.41-3.56 (m, 2H), 2.38-2.53 (m, 1H), 2.01-2.10 (m, 2H), 1.51-1.62 (m, 3H), 1.38-1.48 (m, 2H), 1.12-1.23 (m, 2H), 0.78-1.05 (m, 5H), 0.77 (d, J=6.4 Hz, 3H), 0.48-0.61 (m, 2H). MS (ES)=540 (M+1)$^+$.

Example 23.24

5-{6-(5-chloropyridin-3-yl)-8-[1-fluoro-1-(2-methoxyphenyl)ethyl]-7-[(trans-4-methylcyclohexyl)methyl]-7H-purin-2-yl}-1,3,4-oxadiazol-2(3H)-one

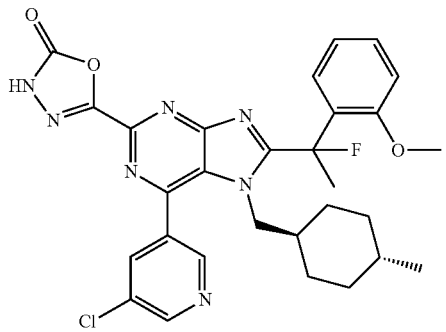 [SMILES: COc1ccccc1C(C)(F)c1nc2nc(-c3n[nH]c(=O)o3)nc(-c3cncc(Cl)c3)c2n1C[C@H]1CC[C@H](C)CC1]

Step 1: To a stirred solution of 2-chloro-6-(5-chloropyridin-3-yl)-7-(((trans)-4-methylcyclohexyl)methyl)-7H-purine (Preparative Example 16.5, Step 1; 1.0 g, 2.65 mmol) in THF (50 ml) was added 2,2,6,6-tetramethylpiperidinylmagnesium chloride, lithium chloride complex (1M in THF/toluene, 7.97 mL, 7.97 mmol) at −78° C. and the reaction was stirred at −78° C. for 2 hours under a nitrogen atmosphere. 2-methoxybenzaldehyde (1.28 mL, 10.6 mmol) was added slowly at −78° C. and the reaction was stirred for 2 hours at −78° C. and then slowly warmed to −40° C. and stirred for 1 hour. The reaction was quenched with aqueous saturated NH$_4$Cl solution (40 mL) and extracted with ethyl acetate (2×30 mL). The combined organic extracts were washed with brine (5 mL), dried over anhydrous Na$_2$SO$_4$, filtered, and concentrated. Purification of the residue on a silica gel column (0 to 100% EtOAc/hexanes) afforded (2-chloro-6-(5-chloropyridin-3-yl)-7-(((trans)-4-methylcyclohexyl)methyl)-7H-purin-8-yl)(2-methoxyphenyl)methanol. MS (ES)=512 (M+1)$^+$.

Step 2: To a 0° C. solution of (2-chloro-6-(5-chloropyridin-3-yl)-7-(((trans)-4-methylcyclohexyl)methyl)-7H-purin-8-yl)(2-methoxyphenyl)methanol (700 mg, 1.36 mmol) in DCM (20 mL) was added Dess Martin periodinane (1.15 g, 2.73 mmol). The reaction was stirred at 0° C. for 2 hours and then quenched with aqueous saturated NH$_4$Cl solution (40 mL) and extracted with DCM (2×30 mL). The combined organic extracts were washed with brine (15 mL), dried over anhydrous Na$_2$SO$_4$, filtered, and concentrated. Purification of the residue on a silica gel column (0 to 100% EtOAc/hexanes) afforded (2-chloro-6-(5-chloropyridin-3-yl)-7-(((trans)-4-methylcyclohexyl)methyl)-7H-purin-8-yl)(2-methoxyphenyl)methanone. MS (ES)=510 (M+1)$^+$.

Step 3: To a −78° C. solution of (2-chloro-6-(5-chloropyridin-3-yl)-7-(((trans)-4-methylcyclohexyl)methyl)-7H-purin-8-yl)(2-methoxyphenyl)methanone (900 mg, 1.76 mmol) in THF (30 mL) was added methylmagnesium bromide (1.74 mL of a 3M solution in Et$_2$O, 5.22 mmol) and the reaction was stirred for 1.5 hours. The reaction was then quenched with aqueous saturated NH$_4$Cl solution (40 mL) and extracted with ethyl acetate (2×35 mL). The combined organic extracts were washed with brine (10 mL), dried over anhydrous Na$_2$SO$_4$, filtered, and concentrated. Purification of the residue on a silica gel column (0 to 100% EtOAc/hexanes) afforded 1-(2-chloro-6-(5-chloropyridin-3-yl)-7-(((trans)-4-methylcyclohexyl)methyl)-7H-purin-8-yl)-1-(2-methoxyphenyl)ethanol. MS (ES)=526 (M+1)$^+$.

Step 4: Using a procedure similar to that described in Example 20.11 (Step 2), 1-(2-chloro-6-(5-chloropyridin-3-yl)-7-(((trans)-4-methylcyclohexyl)methyl)-7H-purin-8-yl)-1-(2-methoxyphenyl)ethanol was converted to 6-(5-chloropyridin-3-yl)-8-(1-hydroxy-1-(2-methoxyphenyl)ethyl)-7-(((trans)-4-methylcyclohexyl)methyl)-7H-purine-2-carbonitrile. MS (ES)=517 (M+1)$^+$.

Step 5: To a −10° C. solution of 6-(5-chloropyridin-3-yl)-8-(1-hydroxy-1-(2-methoxyphenyl)ethyl)-7-(((trans)-4-methylcyclohexyl)methyl)-7H-purine-2-carbonitrile (300 mg, 0.58 mmol) in DCM (20 mL) was added DAST (0.23 mL, 1.74 mmol). The reaction was stirred for 1 hour at −10° C. and then quenched with aqueous saturated NaHCO$_3$ solution (40 mL) and extracted with DCM (2×20 mL). The combined organic extracts were washed with brine (10 mL), dried over anhydrous Na$_2$SO$_4$, filtered, and concentrated. Purification of the residue on a silica gel column (0 to 100% EtOAc/hexanes) afforded 6-(5-chloropyridin-3-yl)-8-(1-fluoro-1-(2-methoxyphenyl)ethyl)-7-(((trans)-4-methylcyclohexyl)methyl)-7H-purine-2-carbonitrile. MS (ES)=519 (M+1)$^+$. The two enantiomers of 6-(5-chloropyridin-3-yl)-8-(1-fluoro-1-(2-methoxyphenyl)ethyl)-7-(((trans)-4-methylcyclohexyl)methyl)-7H-purine-2-carbonitrile were separated on an AD chiral column using 10% IPA/heptanes as eluent.

Steps 6-8: Using a procedure similar to that described in Example 16.7 (Steps 1-3), the faster eluting enantiomer of 6-(5-chloropyridin-3-yl)-8-(1-fluoro-1-(2-methoxyphenyl)ethyl)-7-(((trans)-4-methylcyclohexyl)methyl)-7H-purine-2-carbonitrile was converted to 5-{6-(5-chloropyridin-3-yl)-8-[1-fluoro-1-(2-methoxyphenyl)ethyl]-7-[(trans-4-methylcyclohexyl)methyl]-7H-purin-2-yl}-1,3,4-oxadiazol-2(3H)-one. $^1$H NMR (400 MHz, CD$_3$OD) δ 8.79 (d, J=2.4 Hz, 2H), 8.32 (s, 1H), 7.70 (d, J=8.0 Hz, 1H), 7.43 (t, J=8.0 Hz, 1H), 7.14 (t, J=7.6 Hz, 1H), 7.00 (d, J=6.0 Hz, 1H), 3.75-3.85 (m, 2H), 3.51 (s, 3H), 2.29 (d, J=24.0 Hz, 3H), 1.26-1.41 (m, 3H), 0.85-0.91 (m, 2H), 0.73 (d, J=6.4 Hz, 3H), 0.52-0.55 (m, 2H), 0.29-0.32 (m, 3H). MS (ES)=578 (M+1)$^+$.

Example 23.28

3-{6-(5-chloropyridin-3-yl)-8-(3-fluorooxetan-3-yl)-7-[(trans-4-methylcyclohexyl)methyl]-7H-purin-2-yl}-1,2,4-oxadiazol-5(4H)-one

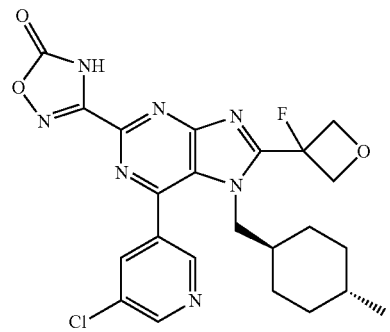 [SMILES: C[C@H]1CC[C@H](Cn2c(C3(F)COC3)nc3nc(-c4noc(=O)[nH]4)nc(-c4cncc(Cl)c4)c32)CC1]

Step 1: To a −78° C. solution of 6-(5-chloropyridin-3-yl)-7-(((trans)-4-methylcyclohexyl)methyl)-7H-purine-2-carbonitrile (Preparative Example 16.8, Step 1; 0.18 g, 0.491 mmol) in THF (50 ml) was added 2,2,6,6-tetramethylpiperidinylmagnesium chloride, lithium chloride complex (1M in THF/toluene, 1.47 mL, 1.47 mmol) and the reaction was stirred at −78° C. for 2 hours under a nitrogen atmosphere. Oxetan-3-one (0.106 g, 1.47 mmol) was added dropwise at −78° C. The reaction was stirred for 2 hours at −78° C. and then slowly warmed to −40° C. and stirred for 1 hour. The reaction was quenched with aqueous saturated NH$_4$Cl solution (40 mL) and extracted with ethyl acetate (2×30 mL). The combined organic extracts were washed with brine (15 mL), dried over anhydrous Na$_2$SO$_4$, filtered, and concentrated. Purification of the residue on a silica gel column (0 to 100% EtOAc/hexanes) afforded 6-(5-chloropyridin-3-yl)-8-(3-hydroxyoxetan-3-yl)-7-(((trans)-4-methylcyclohexyl)methyl)-7H-purine-2-carbonitrile. MS (ES)=439 (M+1)$^+$.

Step 2: DAST (0.09 mL, 0.57 mmoL) was added to a −10° C. solution of 6-(5-chloropyridin-3-yl)-8-(3-hydroxyoxetan-3-yl)-7-(((trans)-4-methylcyclohexyl)methyl)-7H-purine-2-carbonitrile (100 mg, 0.22 mmol) in DCM (2 mL) and the reaction was stirred for 1 hour. The reaction was then quenched with aqueous saturated NaHCO$_3$ solution (40 mL) and extracted with DCM (2×20 mL). The combined organic extracts were washed with brine (10 mL), dried over anhydrous Na$_2$SO$_4$, filtered, and concentrated. Purification of the residue on a silica gel column (0 to 100% EtOAc/CH$_2$Cl$_2$) afforded 6-(5-chloropyridin-3-yl)-8-(3-fluorooxetan-3-yl)-7-(((trans)-4-methylcyclohexyl)methyl)-7H-purine-2-carbonitrile. MS (ES)=441 (M+1)$^+$.

Steps 3 and 4: Using a procedure similar to that described in Example 16.1 (Steps 3 and 4) 6-(5-chloropyridin-3-yl)-8-(3-fluorooxetan-3-yl)-7-(((trans)-4-methylcyclohexyl)methyl)-7H-purine-2-carbonitrile was converted to 3-{6-(5-chloropyridin-3-yl)-8-(3-fluorooxetan-3-yl)-7-[(trans-4-methylcyclohexyl)methyl]-7H-purin-2-yl}-1,2,4-oxadiazol-5(4H)-one. $^1$H NMR (300 MHz, DMSO-d$_6$) δ 8.99 (d, J=1.8 Hz, 1H), 8.95 (d, J=2.4 Hz, 1H), 8.511 (t, J=2.1 Hz, 1H), 5.14-5.417 (m, 4H), 3.81 (d, J=5.7 Hz, 2H), 1.40-1.64 (m, 4H), 1.07 (m, 1H), 0.79-0.95 (m, 3H), 8.95 (d, J=6.3 Hz, 3H), 0.38-0.50 (m, 2H). MS (ES)=500 (M+1)$^+$.

Example 23.41

3-{6-(3-chlorophenyl)-8-[hydroxy(phenyl)methyl]-7-[(trans-4-methylcyclohexyl)methyl]-7H-purin-2-yl}-1,2,4-oxadiazol-5(4H)-one (enantiomer 1)

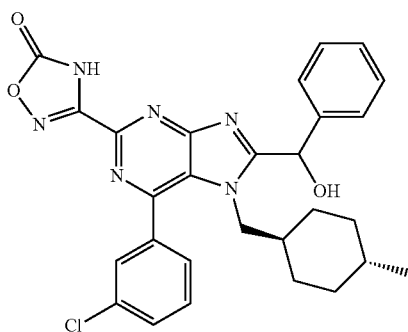 [SMILES: C[C@H]1CC[C@H](Cn2c(C(O)c3ccccc3)nc3nc(-c4noc(=O)[nH]4)nc(-c4cccc(Cl)c4)c32)CC1]

Step 1: To an oven-dried, nitrogen cooled flask was added 2,2,6,6-tetramethylpiperidinylmagnesium chloride, lithium chloride complex (1M in THF/toluene, 3.0 mL, 3.0 mmol). The solution was cooled to −78° C., and then 6-(3-chlorophenyl)-7-(((trans)-4-methylcyclohexyl)methyl)-7H-purine-2-carbonitrile (Preparative Example 16.3, Step 1; 500 mg, 1.37 mmol) dissolved in THF (6.8 mL) was added dropwise. The reaction was stirred at −78° C. for 45 minutes, and then benzaldehyde (166 μL, 1.64 mmol) was added. The reaction was stirred at −78° C. for 1 hour and then quenched with saturated aqueous ammonium chloride and extracted with ethyl acetate (2×). The combined organic layers were dried over sodium sulfate, filtered, and concentrated under reduced pressure. The residue was purified by silica gel chromatography (0-100% ethyl acetate/hexanes, linear gradient) to afford racemic 6-(3-chlorophenyl)-8-[hydroxy(phenyl)methyl]-7-[(trans-4-methylcyclohexyl)methyl]-7H-purine-2-carbonitrile. MS ESI calc'd. for $C_{27}H_{26}ClN_5O$ [M+H]$^+$ 472. found 472. Enantiomers were separated by chiral supercritical fluid chromatography (Chiralpak AS-H, 21×250 mm, 15% methanol in $CO_2$+0.25% dimethylethylamine modifier).

Step 2: Hydroxylamine hydrochloride (8.83 mg, 0.127 mmol), sodium bicarbonate (16 mg, 0.191 mmol), and water (0.191 mL) were combined in a vial and stirred for 15 minutes. This solution was added to a vial containing the faster eluting enantiomer of 6-(3-chlorophenyl)-8-[hydroxy(phenyl)methyl]-7-[(trans-4-methylcyclohexyl)methyl]-7H-purine-2-carbonitrile (30 mg, 0.064 mmol) dissolved in ethanol (0.445 mL). The reaction was sealed and heated at 100° C. for 1 hour. The reaction was then cooled to room temperature, quenched with water, and extracted with ethyl acetate (2×). The combined organic layers were dried over sodium sulfate, filtered, and concentrated under reduced pressure to afford 6-(3-chlorophenyl)-N'-hydroxy-8-[(R or S)-hydroxy(phenyl)methyl]-7-[(trans-4-methylcyclohexyl)methyl]-7H-purine-2-carboximidamide. MS ESI calc'd. for $C_{27}H_{29}ClN_6O_2$ [M+H]$^+$ 505. found 505.

Step 3: To a solution of 6-(3-chlorophenyl)-N'-hydroxy-8-[(R or S)-hydroxy(phenyl)methyl]-7-[(trans-4-methylcyclohexyl)methyl]-7H-purine-2-carboximidamide (26.7 mg, 0.053 mmol) and 1,1'-carbonyldiimidazole (9.43 mg, 0.058 mmol) dissolved in acetonitrile (1 mL) was added 1,8-diazabicyclo[5.4.0]undec-7-ene (31.6 L, 0.211 mmol). The reaction was stirred at room temperature for 1 hour. The reaction was then diluted with water and extracted with dichloromethane. The organic layer was dried over sodium sulfate, filtered, and concentrated under reduced pressure. The residue was purified by mass triggered, reverse phase (C-18) preparative HPLC (acetonitrile:water:0.1% v/v trifluoroacetic acid modifier) to afford 3-{6-(3-chlorophenyl)-8-[(R or S)-hydroxy(phenyl)methyl]-7-[(trans-4-methylcyclohexyl)methyl]-7H-purin-2-yl}-1,2,4-oxadiazol-5(4H)-one (TFA salt) (Enantiomer 1). MS ESI calc'd. for $C_{28}H_{27}ClN_6O_3$ [M+H]$^+$ 531. found 531. $^1$H NMR (600 MHz, DMSO-$d_6$) δ 13.20 (s, 1H), 7.86 (s, 1H), 7.72-7.60 (m, 3H), 7.52 (d, J=7.6, 2H), 7.37 (t, J=7.6, 2H), 7.31 (d, J=7.1, 1H), 6.76 (s, 1H), 6.20 (s, 1H), 4.02 (s, 1H), 1.41-1.30 (m, 2H), 0.98 (s, 1H), 0.84-0.59 (m, 7H), 0.51-0.41 (m, 1H), 0.39-0.28 (m, 2H).

Example 23.43

3-[6-(3-chlorophenyl)-7-[(trans-4-methylcyclohexyl)methyl]-8-(phenylcarbonyl)-7H-purin-2-yl]-1,2,4-oxadiazol-5(4H)-one

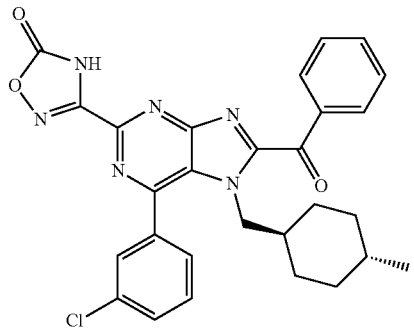 [SMILES: C[C@H]1CC[C@H](Cn2c(C(=O)c3ccccc3)nc3nc(-c4noc(=O)[nH]4)nc(-c4cccc(Cl)c4)c32)CC1]

Step 1: To a room temperature solution of 6-(3-chlorophenyl)-8-[hydroxy(phenyl)methyl]-7-[(trans-4-methylcyclohexyl)methyl]-7H-purine-2-carbonitrile (Example 23.41, Step 1; 33.2 mg, 0.07 mmol) in DCM (0.7 mL) was added Dess-Martin periodinane (32.8 mg, 0.08 mmol). The reaction was stirred for 1 hour and then quenched with saturated aqueous sodium thiosulfate. The mixture was diluted with water and extracted with ethyl acetate (2×). The combined organic layers were dried over sodium sulfate, filtered, and concentrated under reduced pressure to afford 6-(3-chlorophenyl)-7-[(trans-4-methylcyclohexyl)methyl]-8-(phenylcarbonyl)-7H-purine-2-carbonitrile. MS ESI calc'd for $C_{27}H_{24}ClN_5O$ [M+H]$^+$ 470. found 470.

Steps 2 and 3: Using procedures similar to those described in Example 23.41 (Steps 2 and 3), 6-(3-chlorophenyl)-7-[(trans-4-methylcyclohexyl)methyl]-8-(phenylcarbonyl)-7H-purine-2-carbonitrile was converted to 3-[6-(3-chlorophenyl)-7-[(trans-4-methylcyclohexyl)methyl]-8-(phenylcarbonyl)-7H-purin-2-yl]-1,2,4-oxadiazol-5(4H)-one (TFA salt). MS ESI calc'd. for $C_{28}H_{25}ClN_6O_3$ [M+H]$^+$ 529. found 529. $^1$H NMR (600 MHz, DMSO-$d_6$) δ 13.35 (s, 1H), 8.15 (d, J=1.1, 1H), 8.13 (d, J=1.4, 1H), 7.94 (t, J=1.7, 1H), 7.83-7.73 (m, 3H), 7.69-7.63 (m, 3H), 4.15-4.08 (m, 2H), 1.38-1.32 (m, 2H), 1.05-0.90 (m, 2H), 0.86-0.79 (m, 2H), 0.66 (d, J=6.4, 3H), 0.62-0.54 (m, 2H), 0.48-0.38 (m, 2H).

Example 23.44

3-{6-(3-chlorophenyl)-8-[methoxy(phenyl)methyl]-7-[(trans-4-methylcyclohexyl)methyl]-7H-purin-2-yl}-1,2,4-oxadiazol-5(4H)-one

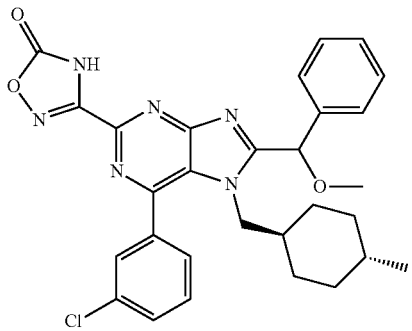 [SMILES: COC(c1ccccc1)c1nc2nc(-c3noc(=O)[nH]3)nc(-c3cccc(Cl)c3)c2n1C[C@H]1CC[C@H](C)CC1]

Step 1: Sodium hydride (14.8 mg, 0.37 mmol) was added in one portion to a solution of the slower eluting enantiomer of 6-(3-chlorophenyl)-8-[hydroxy(phenyl)methyl]-7-[(trans-4-methylcyclohexyl)methyl]-7H-purine-2-carbonitrile (Example 23.41, Step 1; 145.5 mg, 0.308 mmol) in THF (3.1 mL) at 0° C. The resulting solution was stirred for 30 minutes at 0° C. and then methyl iodide (21.2 µL, 0.339 mmol) was added. The reaction mixture was stirred for 2.5 hours at 0° C., and then quenched with saturated aqueous ammonium chloride. The mixture was extracted with ethyl acetate (2×), and the combined organic layers were dried over sodium sulfate, filtered, and concentrated under reduced pressure. The residue was purified by silica gel chromatography (0-100% ethyl acetate/hexanes, linear gradient) to afford 6-(3-chlorophenyl)-8-[(S or R)-methoxy(phenyl)methyl]-7-[(trans-4-methylcyclohexyl)methyl]-7H-purine-2-carbonitrile. MS ESI calc'd for $C_{28}H_{28}ClN_5O$ $[M+H]^+$ 486. found 486.

Steps 2 and 3: Using procedures similar to those described in Example 23.41 (Steps 2 and 3), 6-(3-chlorophenyl)-8-[(S or R)-methoxy(phenyl)methyl]-7-[(trans-4-methylcyclohexyl)methyl]-7H-purine-2-carbonitrile was converted to 3-{6-(3-chlorophenyl)-8-[(S or R)-methoxy(phenyl)methyl]-7-[(trans-4-methylcyclohexyl)methyl]-7H-purin-2-yl}-1,2,4-oxadiazol-5(4H)-one (TFA salt) (Enantiomer 2). MS ESI calc'd. for $C_{29}H_{29}ClN_6O_3$ $[M+H]^+$ 545. found 545. $^1$H NMR (600 MHz, DMSO-$d_6$) δ 13.23 (s, 1H), 7.89 (s, 1H), 7.70 (d, J=8.3, 2H), 7.65-7.60 (m, 1H), 7.56 (d, J=7.4, 2H), 7.40 (t, J=7.4, 2H), 7.36 (t, J=7.0, 1H), 5.93 (s, 1H), 4.05-3.95 (m, 1H), 3.37 (s, 3H), 1.40-1.30 (m, 2H), 1.09-0.95 (m, 1H), 0.85-0.72 (m, 2H), 0.67 (d, J=6.4, 5H), 0.64-0.52 (m, 2H), 0.40-0.28 (m, 2H).

Example 23.49

3-{6-(5-chloropyridin-3-yl)-8-[1-(2-fluorophenyl)-1-methoxyethyl]-7-[(trans-4-methylcyclohexyl)methyl]-7H-purin-2-yl}-1,2,4-oxadiazol-5(4H)-one

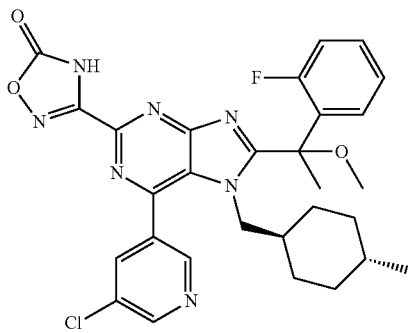 [SMILES: COC(C)(c1ccccc1F)c1nc2nc(-c3noc(=O)[nH]3)nc(-c3cncc(Cl)c3)c2n1C[C@H]1CC[C@H](C)CC1]

Step 1: To a solution of 6-(5-chloropyridin-3-yl)-8-(1-(2-fluorophenyl)-1-hydroxyethyl)-7-(((trans)-4-methylcyclohexyl)methyl)-7H-purine-2-carbonitrile (prepared in a manner similar to Example 23.24, steps 1-4; 105 mg, 0.2 mmol) in anhydrous THF (5 mL), CH$_3$I (591 mg, 4.16 mmol) and sodium bis(trimethylsilyl)amide (1M THF solution, 0.62 mL, 0.62 mmol) were added dropwise at 0° C. The reaction was stirred at 0° C. for 2 hours and then quenched with ice water (10 mL). The reaction was extracted with CH$_2$Cl$_2$ (15 mL), and the organic layer was washed with brine, dried over anhydrous Na$_2$SO$_4$, filtered, and concentrated in vacuo. Purification of the residue on a silica gel column with 0 to 50% EtOAc/hexanes afforded 6-(5-chloropyridin-3-yl)-8-(1-(2-fluorophenyl)-1-methoxyethyl)-7-(((trans)-4-methylcyclohexyl)methyl)-7H-purine-2-carbonitrile MS (ES)=519 $(M+1)^+$. The two enantiomers of 6-(5-chloropyridin-3-yl)-8-(1-(2-fluorophenyl)-1-methoxyethyl)-7-(((trans)-4-methylcyclohexyl)methyl)-7H-purine-2-carbonitrile were separated on an Chiralpak-AD column using 3% IPA/heptanes as eluent.

Steps 2 and 3: Using procedures similar to those described in Example 23.2 (Steps 1 and 2), the faster eluting enantiomer of 6-(5-chloropyridin-3-yl)-8-(1-(2-fluorophenyl)-1-methoxyethyl)-7-(((trans)-4-methylcyclohexyl)methyl)-7H-purine-2-carbonitrile was converted to 3-{6-(5-chloropyridin-3-yl)-8-[(1R or S)-1-(2-fluorophenyl)-1-methoxyethyl]-7-[(trans-4-methylcyclohexyl)methyl]-7H-purin-2-yl}-1,2,4-oxadiazol-5(4H)-one (Enantiomer 1). $^1$H NMR (400 MHz, CD$_3$OD) δ 8.79 (d, J=2.4 Hz, 1H), 8.77 (s, 1H), 8.35 (t, J=2.0 Hz, 1H), 7.93 (dt, J=9.6, 2.0 Hz, 1H), 7.41 (m, 1H), 7.32 (dt, J=8.8, 1.2 Hz, 1H), 7.05 (m, 1H), 3.81 (brs, 2H), 3.34 (s, 3H), 2.16 (s, 3H), 1.15-1.43 (m, 3H), 0.72-0.92 (m, 2H), 0.66 (d, J=6.4 Hz, 3H), 0.47-0.59 (m, 2H), 0.15-0.42 (m, 3H). MS (ES)=578 $(M+1)^+$.

Example 23.100

3-{6-(5-chloropyridin-3-yl)-8-[1-(2-fluorophenyl)cyclopropyl]-7-[(trans-4-methylcyclohexyl)methyl]-7H-purin-2-yl}-1,2,4-oxadiazol-5(4H)-one

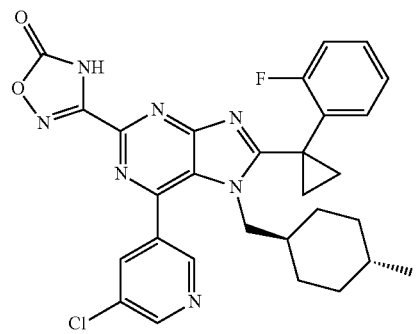 [SMILES: C[C@H]1CC[C@H](Cn2c(C3(c4ccccc4F)CC3)nc3nc(-c4noc(=O)[nH]4)nc(-c4cncc(Cl)c4)c32)CC1]

Step 1: DAST (0.19 mL, 1.22 mmol) was added drop wise to a −10° C. solution of 6-(5-chloropyridin-3-yl)-8-(1-(2-fluorophenyl)-1-hydroxyethyl)-7-(((trans)-4-methylcyclohexyl)methyl)-7H-purine-2-carbonitrile (prepared in a manner similar to Example 23.24, steps 1-4; 245 mg, 0.48 mmol) in CH$_2$Cl$_2$ (10 mL). The reaction mixture was stirred at −10° C. for 1 hour and quenched by adding saturated aqueous NaHCO$_3$ solution (10 mL). The layers were separated and the aqueous layer was extracted with CH$_2$Cl$_2$ (10 mL×2). The combined organic layers were washed with brine, dried over anhydrous Na$_2$SO$_4$, filtered, and concentrated in vacuo to afford a crude mixture of 6-(5-chloropyridin-3-yl)-8-(1-fluoro-1-(2-fluorophenyl)ethyl)-7-(((trans)-4-methylcyclohexyl)methyl)-7H-purine-2-carbonitrile and 6-(5-chloropyridin-3-yl)-8-(1-(2-fluorophenyl)vinyl)-7-(((trans)-4-methylcyclohexyl)methyl)-7H-purine-2-carbonitrile. Purification of the crude material on a silica gel column with 0 to 20% EtOAc/hexanes afforded pure 6-(5-chloropyridin-3-yl)-8-(1-(2-fluorophenyl)vinyl)-7-(((trans)-4-methylcyclohexyl)methyl)-7H-purine-2-carbonitrile. MS (ES)=487 (M+1)$^+$.

Step 2: Using a procedure similar to that described in Example 22.5 (Step 2), 6-(5-chloropyridin-3-yl)-8-(1-(2-fluorophenyl)vinyl)-7-(((trans)-4-methylcyclohexyl)methyl)-7H-purine-2-carbonitrile was converted to 6-(5-chloropyridin-3-yl)-8-(1-(2-fluorophenyl)cyclopropyl)-7-(((trans)-4-methylcyclohexyl)methyl)-7H-purine-2-carbonitrile. MS (ES)=501 (M+1)$^+$.

Steps 3 and 4: Using procedures similar to those described in Example 23.2 (Steps 1 and 2), 6-(5-chloropyridin-3-yl)-8-(1-(2-fluorophenyl)cyclopropyl)-7-(((trans)-4-methylcyclohexyl)methyl)-7H-purine-2-carbonitrile was converted to 3-{6-(5-chloropyridin-3-yl)-8-[1-(2-fluorophenyl)cyclopropyl]-7-[(trans-4-methylcyclohexyl)methyl]-7H-purin-2-yl}-1,2,4-oxadiazol-5(4H)-one. $^1$H NMR (400 MHz, CD$_3$OD) δ 8.77-8.83 (m, 2H), 8.34 (m, 1H), 7.58 (m, 1H), 7.38 (m, 1H), 7.26 (m, 1H), 7.11 (m, 1H), 3.86 (d, J=6.0 Hz, 2H), 1.85-1.98 (m, 2H), 1.62-1.74 (m, 2H), 1.26-1.44 (m, 5H), 0.76 (m, 1H), 0.70 (d, J=6.4 Hz, 3H), 0.26-0.48 (m, 4H). MS (ES)=560 (M+1)$^+$.

Example 23.101

3-{6-(3-chlorophenyl)-7-[(trans-4-methylcyclohexyl)methyl]-8-[1-(5-methyl-1,3-oxazol-4-yl)cyclopropyl]-7H-purin-2-yl}-1,2,4-oxadiazol-5(4H)-one

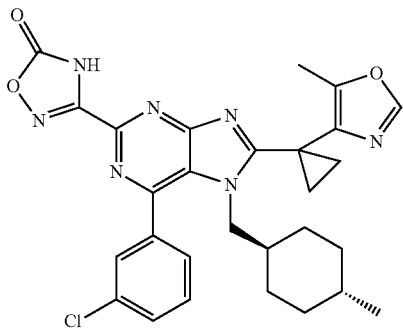 [SMILES: Cc1ocnc1C1(c2nc3nc(-c4noc(=O)[nH]4)nc(-c4cccc(Cl)c4)c3n2C[C@H]2CC[C@H](C)CC2)CC1]

Step 1: CDI (478 mg, 2.95 mmol) was added to a solution of 5-methyloxazole-4-carboxylic acid (250 mg, 1.96 mmol) in DMF (1.5 mL), and the reaction was stirred for 4 hours. In a second flask, triethylamine (1.64 mL, 11.8 mmol) was added to a stirring solution of N-methoxy methaneamine hydrochloride (959 mg, 9.83 mmol) in DMF (8 mL) at 0° C. The contents of the first reaction flask were added to the second at 0° C. and the reaction was gradually warmed to room temperature and stirred for 16 hours. The reaction was quenched with saturated aqueous NaHCO$_3$ solution (25 mL) and extracted using EtOAc (30 mL). The organic layer was washed with brine solution (50 mL), dried over anhydrous Na$_2$SO$_4$, filtered, and concentrated in vacuo. Purification of the residue on a silica gel column with 0 to 60% EtOAc/Hexanes afforded N-methoxy-N,5-dimethyloxazole-4-carboxamide. MS (ES)=171 (M+1)$^+$.

Step 2: 2,2,6,6-tetramethylpiperidinylmagnesium chloride, lithium chloride complex (1M in THF/toluene, 6.16 mL, 6.16 mmol) was added to a −78° C. solution of 6-(3-chlorophenyl)-7-(((trans)-4-methylcyclohexyl)methyl)-7H-purine-2-carbonitrile (Preparative Example 16.3, Step 1; 750 mg, 2.05 mmol) in THF (25 mL). The reaction was stirred for 2 hours at −78° C. and then N-methoxy-N,5-dimethyloxazole-4-carboxamide (698 mg, 4.10 mmol) in THF (5 mL) was added at −78° C. The reaction was gradually warmed to 0° C. and stirred for 2 hours. The reaction was then quenched with saturated aqueous NH$_4$Cl solution (40 mL) and extracted with EtOAc (3×25 mL). The combined organic layers were washed with brine (30 mL), dried over anhydrous Na$_2$SO$_4$, filtered, and concentrated in vacuo. Purification of the residue on a silica gel column with 0 to 40% ethyl acetate/hexanes afforded 6-(3-chlorophenyl)-7-(((trans)-4-methylcyclohexyl)methyl)-8-(5-methyloxazole-4-carbonyl)-7H-purine-2-carbonitrile. MS (ES)=475 (M+1)$^+$.

Step 3: Using a procedure similar to that described for Example 23.24 (Step 3) 6-(3-chlorophenyl)-7-(((trans)-4-methylcyclohexyl)methyl)-8-(5-methyloxazloe-4-carbonyl)-7H-purine-2-carbonitrile was converted to 6-(3-chlorophenyl)-8-(1-hydroxy-1-(5-methyloxazol-4-yl)ethyl)-7-(((trans)-4-methylcyclohexyl)methyl)-7H-purine-2-carbonitrile. MS (ES)=491 (M+1)$^+$.

Step 4: 6-(3-chlorophenyl)-8-(1-hydroxy-1-(5-methyloxazol-4-yl)ethyl)-7-(((trans)-4-methylcyclohexyl)methyl)-7H-purine-2-carbonitrile (50 mg, 0.10 mmol) was dissolved in SOCl$_2$ (0.6 mL). The reaction was heated at 50° C. for 2 hours. The reaction mixture was quenched with saturated aqueous NaHCO$_3$ solution (10 mL) and extracted with EtOAc (3×15 mL). The combined organic layers were washed with brine, dried over anhydrous Na$_2$SO$_4$, filtered, and concentrated in vacuo. Toluene (1 mL) and DBU (0.07 mL, 0.50 mmol) were added to the crude residue. The reaction mixture was stirred for 3 hours and then quenched with water (15 mL) and extracted with EtOAc (30 mL). The organic layer was washed with aqueous 1N HCl solution (10 mL) and brine (10 mL), dried over anhydrous Na$_2$SO$_4$, filtered, and concentrated in vacuo. Purification of the residue on a silica gel column with 0 to 40% EtOAc/hexanes afforded 6-(3-chlorophenyl)-7-(((trans)-4-methylcyclohexyl)methyl)-8-(1-(5-methyloxazol-4-yl)vinyl)-7H-purine-2-carbonitrile. MS (ES)=473 (M+1)$^+$.

Step 5: Using a procedures similar to that described for Example 22.5 (Step 2), 6-(3-chlorophenyl)-7-(((trans)-4-methylcyclohexyl)methyl)-8-(1-(5-methyloxazol-4-yl)vinyl)-7H-purine-2-carbonitrile was converted to 6-(3-chlorophenyl)-7-(((trans)-4-methylcyclohexyl)methyl)-8-(1-(5-methyloxazol-4-yl)cyclopropyl)-7H-purine-2-carbonitrile. MS (ES)=487 (M+1)$^+$.

Steps 6 and 7: Using procedures similar to those described in Example 23.2 (Steps 1 and 2), 6-(3-chlorophenyl)-7-(((trans)-4-methylcyclohexyl)methyl)-8-(1-(5-methyloxazol-4-yl)cyclopropyl)-7H-purine-2-carbonitrile was converted to 3-{6-(3-chlorophenyl)-7-[(trans-4-methylcyclohexyl)methyl]-8-[1-(5-methyl-1,3-oxazol-4-yl)cyclopropyl]-7H-purin-2-yl}-1,2,4-oxadiazol-5(4H)-one. $^1$H NMR (300 MHz, CD$_3$OD) δ 7.99 (s, 1H), 7.82 (s, 1H), 7.46-7.68 (m, 3H), 3.83-4.09 (m, 2H), 3.49-3.66 (m, 2H), 3.05 (m, 1H), 2.66 (m, 1H), 2.13-2.27 (m, 3H), 1.96-2.12

(m, 2H), 1.57-1.86 (m, 6H), 0.85-0.94 (m, 2H), 0.72 (d, J=6.6 Hz, 3H). MS (ES)=546 (M+1)+.

Example 23.103

5-{6-(5-chloropyridin-3-yl)-8-[(2-fluorophenyl)(methoxy)methyl]-7-[(trans-4-methylcyclohexyl)methyl]-7H-purin-2-yl}-1,3,4-oxadiazol-2(3H)-one

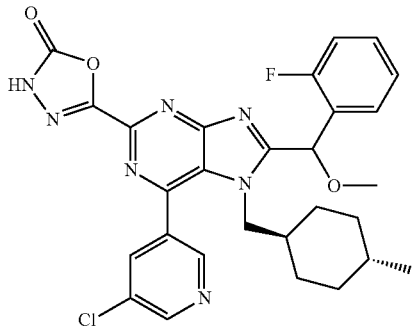 [SMILES: COC(c1ccccc1F)c1nc2nc(-c3n[nH]c(=O)o3)nc(-c3cncc(Cl)c3)c2n1C[C@H]1CC[C@H](C)CC1]

Step 1: SOCl$_2$ (356 mg, 3.00 mmol) was added in several portions to a 0° C. solution of (2-chloro-6-(5-chloropyridin-3-yl)-7-(((trans)-4-methylcyclohexyl)methyl)-7H-purin-8-yl)(2-fluorophenyl)methanol (prepared in a manner similar to Example 23.24, Step 1; 150 mg, 0.30 mmol) in CH$_2$Cl$_2$ (10 mL). The reaction was stirred for 1 hour at 0° C. and then quenched with saturated aqueous NaHCO$_3$ solution (50 mL). The layers were separated and the aqueous layer was extracted with CH$_2$Cl$_2$ (2×30 mL). The combined organic layers were washed with brine (50 mL), dried over anhydrous Na$_2$SO$_4$, filtered, and concentrated. Purification of the residue on a silica gel column with 0 to 50% EtOAc/hexanes afforded 2-chloro-8-(chloro(2-fluorophenyl)methyl)-6-(5-chloropyridin-3-yl)-7-(((trans)-4-methylcyclohexyl)methyl)-7H-purine. MS (ES)=518 (M+1)+.

Step 2: Cs$_2$CO$_3$ (75.6 mg, 0.23 mmol) was added at room temperature to a solution of 2-chloro-8-(chloro(2-fluorophenyl)methyl)-6-(5-chloropyridin-3-yl)-7-(((trans)-4-methylcyclohexyl)methyl)-7H-purine (120 mg, 0.23 mmol) in MeOH (8 mL). The reaction was stirred for 2 hours at room temperature and then concentrated. The residue was diluted with CH$_2$Cl$_2$ (40 mL) and water (25 mL). The layers were separated and the aqueous layer was extracted with CH$_2$Cl$_2$ (2×15 mL). The combined organic layers were washed with brine (40 mL), dried over anhydrous Na$_2$SO$_4$, filtered, and concentrated. Purification of the residue on a silica gel column with 0 to 50% EtOAc/hexanes afforded 2-chloro-6-(5-chloropyridin-3-yl)-8-((2-fluorophenyl)(methoxy)methyl)-7-(((trans)-4-methylcyclohexyl)methyl)-7H-purine.

Steps 3-6: Using procedures similar to those described in Example 20.11 (Step 2) and Example 16.7 (Steps 1-3), 2-chloro-6-(5-chloropyridin-3-yl)-8-((2-fluorophenyl)(methoxy)methyl)-7-(((trans)-4-methylcyclohexyl)methyl)-7H-purine was converted to 5-{6-(5-chloropyridin-3-yl)-8-[(2-fluorophenyl)(methoxy)methyl]-7-[(trans-4-methylcyclohexyl)methyl]-7H-purin-2-yl}-1,3,4-oxadiazol-2(3H)-one (racemate). $^1$H NMR (400 MHz, CD$_3$OD) δ 8.84 (dd, J=6.8, 1.6 Hz, 2H), 8.37 (t, J=2.0 Hz, 1H), 8.38 (m, 1H), 7.68 (dt, J=9.2, 1.6 Hz, 1H), 7.44 (m, 1H), 7.28 (dt, J=8.8, 1.2 Hz, 1H), 7.17 (m, 1H), 6.13 (s, 1H), 4.01-4.05 (m, 2H), 3.51 (s, 3H), 1.41-1.57 (m, 2H), 1.32 (m, 1H), 1.12 (m, 1H), 0.85-0.95 (m, 2H), 0.75 (d, J=6.4 Hz, 3H), 0.68 (m, 1H), 0.42-0.56 (m, 2H). MS (ES)=564 (M+1)+.

Example 23.104

3-{6-(5-chloropyridin-3-yl)-8-(3,4-dihydro-1H-isochromen-1-yl)-7-[(trans-4-methylcyclohexyl)methyl]-7H-purin-2-yl}-1,2,4-oxadiazol-5(4H)-one (enantiomer 1)

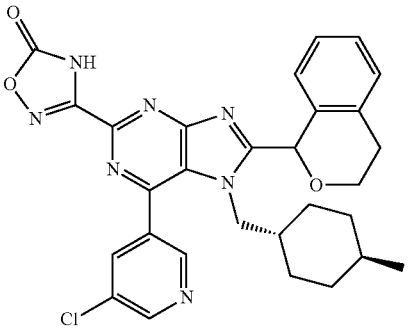 [SMILES: C[C@H]1CC[C@H](Cn2c(C3OCCc4ccccc43)nc3nc(-c4noc(=O)[nH]4)nc(-c4cncc(Cl)c4)c32)CC1]

Step 1: 2,2,6,6-Tetramethylpiperidinylmagnesium chloride, lithium chloride complex (1 M in THF/toluene, 2.4 mL, 2.4 mmol) was added slowly to a −78° C. solution of 2-chloro-6-(5-chloropyridin-3-yl)-7-(((trans)-4-methylcyclohexyl)methyl)-7H-purine (Preparative Example 16.5, Step 1; 300 mg, 0.80 mmol) in THF (15 mL). The reaction was stirred at −78° C. for 2 hours. Next, 2-(2-bromoethyl)benzaldehyde (255 mg, 1.20 mmol) was added to the reaction at −78° C. The reaction mixture was allowed to warm slowly to room temperature and stirred for 16 hours. The reaction was quenched with saturated NH$_4$Cl solution and extracted with EtOAc (2×10 mL). The combined organic layers were dried over anhydrous Na$_2$SO$_4$, filtered, and concentrated. The residue was purified on a silica gel column (0 to 50% EtOAc/hexanes) to afford (2-(2-bromoethyl)phenyl)(2-chloro-6-(5-chloropyridin-3-yl)-7-(((trans)-4-methylcyclohexyl)methyl)-7H-purin-8-yl)methanol. MS (APCI)=588 (M+1)+.

Step 2: Cs$_2$CO$_3$ (239 mg, 0.73 mmol) was added to a 0° C. solution of (2-(2-bromoethyl)phenyl)(2-chloro-6-(5-chloropyridin-3-yl)-7-(((trans)-4-methylcyclohexyl)methyl)-7H-purin-8-yl)methanol (216 mg, 0.37 mmol) in acetonitrile (10 mL) Next, NaI (23 mg, 0.15 mmol) was added and the reaction was warmed to room temperature and stirred for 2 hours. The reaction was then partitioned between water and EtOAc and the aqueous layer was extracted 3× with EtOAc. The combined organic layers were dried over anhydrous Na$_2$SO$_4$, filtered, and concentrated in vacuo. The residue was purified on a silica gel column (0 to 50% EtOAc/hexanes) to afford 2-chloro-6-(5-chloropyridin-3-yl)-8-(isochroman-1-yl)-7-(((trans)-4-methylcyclohexyl)methyl)-7H-purine (racemate). MS (APCI)=508 (M+1)+.

Step 3: Using a procedure similar to that described in Example 20.11 (Step 2), 2-chloro-6-(5-chloropyridin-3-yl)-8-(isochroman-1-yl)-7-(((trans)-4-methylcyclohexyl)methyl)-7H-purine (racemate) was converted to 6-(5-chloropyridin-3-yl)-8-(isochroman-1-yl)-7-(((trans)-4-methylcyclohexyl)methyl)-7H-purine-2-carbonitrile (racemate). MS (APCI)=499 (M+1)+. The two enantiomers of 6-(5-chloropyridin-3-yl)-8-(isochroman-1-yl)-7-(((trans)-

4-methylcyclohexyl)methyl)-7H-purine-2-carbonitrile were separated using an AD chiral column and IPA/heptanes as eluent.

Steps 4-5: Using procedures similar to those described in Example 23.2 (Steps 1-2), the faster eluting enantiomer of 6-(5-chloropyridin-3-yl)-8-(isochroman-1-yl)-7-(((trans)-4-methylcyclohexyl)methyl)-7H-purine-2-carbonitrile was converted to 3-{6-(5-chloropyridin-3-yl)-8-(3,4-dihydro-1H-isochromen-1-yl)-7-[(trans-4-methylcyclohexyl)methyl]-7H-purin-2-yl}-1,2,4-oxadiazol-5(4H)-one (enantiomer 1). ¹H NMR (400 MHz, CDCl₃) δ 8.79 (br s, 1H), 8.71 (br s, 1H), 8.07 (br s, 1H), 6.97-7.16 (m, 4H), 6.39 (br s, 1H), 3.87-4.33 (m, 4H), 2.86-3.18 (m, 2H), 1.33-1.49 (m, 2H), 0.54-1.15 (m, 5H), 0.73 (d, J=6.4 Hz, 3H), 0.26-0.42 (m, 3H). MS (ES)=558 (M+1)⁺.

Example 23.109

2-{[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl](methoxy)methyl}benzonitrile

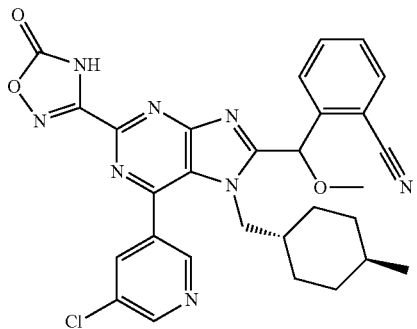 [SMILES: COC(c1ccccc1C#N)c1nc2nc(-c3noc(=O)[nH]3)nc(-c3cncc(Cl)c3)c2n1C[C@H]1CC[C@H](C)CC1]

Steps 1-3: Starting with 2-chloro-6-(5-chloropyridin-3-yl)-7-(((trans)-4-methylcyclohexyl)methyl)-7H-purine (Preparative Example 16.5) and 2-bromobenzaldehyde, and following a three step sequence of procedures similar to those described in Example 23.24 (Step 1) and Example 23.103 (Steps 1 and 2), 8-((2-bromophenyl)(methoxy)methyl)-2-chloro-6-(5-chloropyridin-3-yl)-7-(((trans)-4-methylcyclohexyl)methyl)-7H-purine was prepared. MS (APCI)=574 (M+1)⁺.

Step 4: DMA (5 mL) was added to a mixture of 8-((2-bromophenyl)(methoxy)methyl)-2-chloro-6-(5-chloropyridin-3-yl)-7-(((trans)-4-methylcyclohexyl)methyl)-7H-purine (100 mg, 0.17 mmol) and Zn(CN)₂ (21 mg, 0.18 mmol) under argon. Tetrakis(triphenylphosphine)palladium(0) (69 mg, 0.06 mmol) was added and the mixture was degassed for 5 minutes. The reaction vial was sealed and heated at 80° C. for 5 hours. The reaction was then diluted with water (10 mL) and extracted with EtOAc (2×8 mL). The combined organic extracts were dried over anhydrous Na₂SO₄, filtered, and concentrated in vacuo. The residue was purified on a silica gel column (0 to 50% EtOAc/hexanes) to afford 6-(5-chloropyridin-3-yl)-8-((2-cyanophenyl)(methoxy)methyl)-7-(((trans)-4-methylcyclohexyl)methyl)-7H-purine-2-carbonitrile. MS (APCI)=512 (M+1)⁺.

Steps 5-6: Using procedures similar to those described in Example 23.2 (Steps 1-2), 6-(5-chloropyridin-3-yl)-8-((2-cyanophenyl)(methoxy)methyl)-7-(((trans)-4-methylcyclohexyl)methyl)-7H-purine-2-carbonitrile was converted to 2-{[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl](methoxy)methyl}benzonitrile. ¹H NMR (400 MHz, CDCl₃) δ 8.83 (br s, 1H), 8.73 (br s, 1H), 8.06 (br s, 1H), 7.89 (d, J=7.6 Hz, 1H), 7.73-7.82 (m, 2H), 7.57 (m, 1H), 6.01 (s, 1H), 4.04-4.21 (m, 2H), 3.53 (s, 3H), 1.41-1.52 (m, 2H), 0.99-1.34 (m, 4H), 0.79 (d, J=6.0 Hz, 3H), 0.70-0.91 (m, 2H), 0.48-0.64 (m, 2H). MS (ES)=571 (M+1)⁺.

Example 23.113

3-{6-(5-chloropyridin-3-yl)-8-[1-(2-fluorophenyl)ethyl]-7-[(trans-4-methylcyclohexyl)methyl]-7H-purin-2-yl}-1,2,4-oxadiazol-5(4H)-one (racemate)

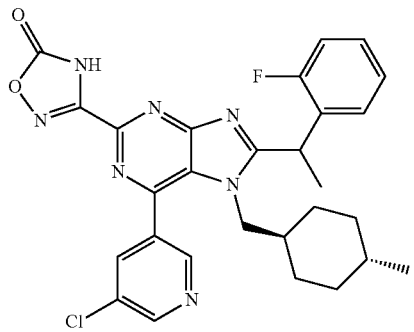 [SMILES: CC(c1ccccc1F)c1nc2nc(-c3noc(=O)[nH]3)nc(-c3cncc(Cl)c3)c2n1C[C@H]1CC[C@H](C)CC1]

Step 1: Pd/C (10% by wt, 30 mg) was added to a solution of 6-(5-chloropyridin-3-yl)-8-(1-(2-fluorophenyl)vinyl)-7-(((trans)-4-methylcyclohexyl)methyl)-7H-purine-2-carbonitrile (Example 23.100, Step 1; 300 mg, 0.61 mmol) in ethanol: ethyl acetate (2:1; 18 mL). Hydrogen was purged through the reaction for 10 minutes and then the reaction was stirred at room temperature under an atmosphere of hydrogen (balloon) for 1 hour. The reaction mixture was then filtered through celite, washing the filter cake with ethyl acetate, and the filtrate was concentrated in vacuo. Purification of the residue on a silica gel column with 0 to 50% EtOAc/hexanes afforded 6-(5-chloropyridin-3-yl)-8-(1-(2-fluorophenyl)ethyl)-7-(((trans)-4-methylcyclohexyl)methyl)-7H-purine-2-carbonitrile. MS (ES)=489 (M+1)⁺.

Steps 2 and 3: Using procedures similar to those described in Example 23.2 (Steps 1-2), 6-(5-chloropyridin-3-yl)-8-(1-(2-fluorophenyl)ethyl)-7-(((trans)-4-methylcyclohexyl)methyl)-7H-purine-2-carbonitrile was converted to 3-{6-(5-chloropyridin-3-yl)-8-[1-(2-fluorophenyl)ethyl]-7-[(trans-4-methylcyclohexyl)methyl]-7H-purin-2-yl}-1,2,4-oxadiazol-5(4H)-one. ¹H NMR (400 MHz, CD₃OD) δ 8.81 (m, 2H), 8.34 (t, J=2.0 Hz, 1H), 7.29-7.42 (m, 2H), 7.13-7.20 (m, 2H), 4.95 (q, J=6.8 Hz, 1H), 3.86-3.92 (m, 2H), 1.85 (d, J=6.8 Hz, 3H), 1.36-1.55 (m, 3H), 0.99-1.14 (m, 2H), 0.81-0.95 (m, 2H), 0.73 (d, J=6.4 Hz, 3H), 0.37-0.51 (m, 3H). MS (ES)=548 (M+1)⁺.

The compounds in Table 23 were prepared as described above or using procedures similar to those described above.

TABLE 23

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.1 | 67.31 | 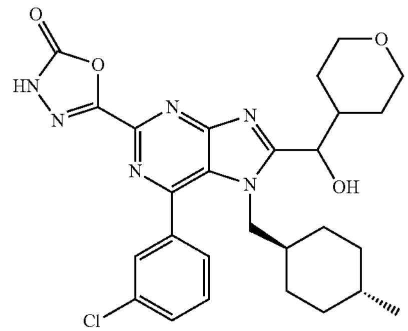 [SMILES: C[C@H]1CC[C@H](Cn2c(C(O)C3CCOCC3)nc3nc(-c4n[nH]c(=O)o4)nc(-c4cccc(Cl)c4)c32)CC1] | 5-{6-(3-chlorophenyl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one (racemate) | | 539 | 539 |
| 23.2 | 51.48 | 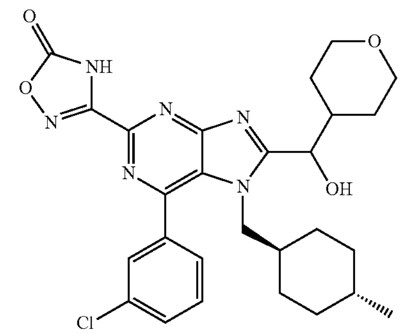 [SMILES: C[C@H]1CC[C@H](Cn2c(C(O)C3CCOCC3)nc3nc(-c4noc(=O)[nH]4)nc(-c4cccc(Cl)c4)c32)CC1] | 3-{6-(3-chlorophenyl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one (racemate) | | 539 | 539 |
| 23.3 | 21.40 | 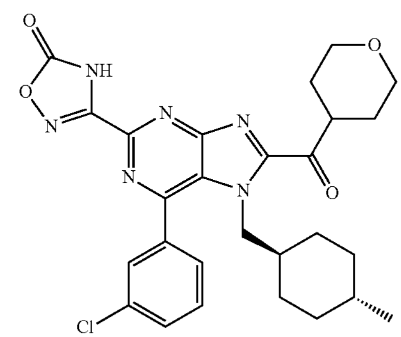 [SMILES: C[C@H]1CC[C@H](Cn2c(C(=O)C3CCOCC3)nc3nc(-c4noc(=O)[nH]4)nc(-c4cccc(Cl)c4)c32)CC1] | 3-[6-(3-chlorophenyl)-7-[(trans-4-methylcyclohexyl)methyl]-8-(tetrahydro-2H-pyran-4-ylcarbonyl)-7H-purin-2-yl]-1,2,4-oxadiazol-5(4H)-one | | 537 | 537 |
| 23.4 | 19.23 | 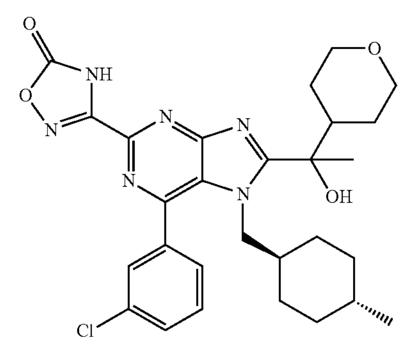 [SMILES: CC(O)(c1nc2nc(-c3noc(=O)[nH]3)nc(-c3cccc(Cl)c3)c2n1C[C@H]1CC[C@H](C)CC1)C1CCOCC1] | 3-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,2,4-oxadiazol-5(4H)-one (racemate) | | 553 | 553 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.5 | 7.166 | 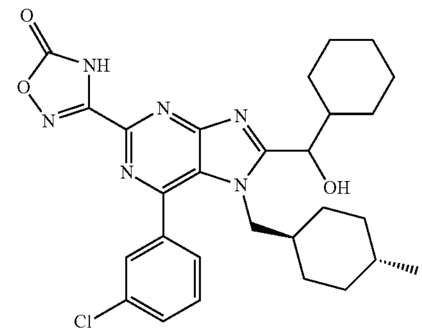 [SMILES: C[C@H]1CC[C@H](Cn2c(C(O)C3CCCCC3)nc3nc(-c4noc(=O)[nH]4)nc(-c4cccc(Cl)c4)c32)CC1] | 3-{6-(3-chlorophenyl)-8-[cyclohexyl(hydroxy)methyl]-7-[(trans-4-methylcyclohexyl)methyl]-7H-purin-2-yl}-1,2,4-oxadiazol-5(4H)-one (racemate) | | 537 | 537 |
| 23.6 | 13.86 | 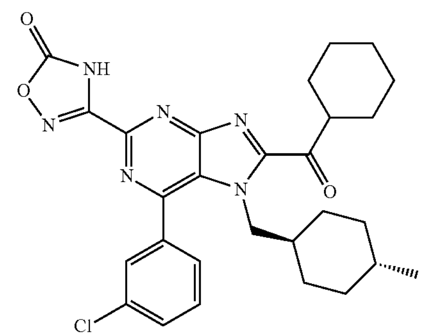 | 3-{6-(3-chlorophenyl)-8-(cyclohexylcarbonyl)-7-[(trans-4-methylcyclohexyl)methyl]-7H-purin-2-yl}-1,2,4-oxadiazol-5(4H)-one | | 535 | 535 |
| 23.7 | 20.17 | 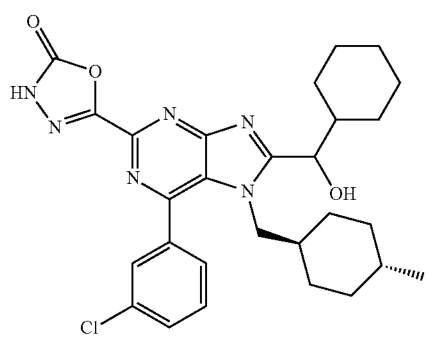 [SMILES: C[C@H]1CC[C@H](Cn2c(C(O)C3CCCCC3)nc3nc(-c4n[nH]c(=O)o4)nc(-c4cccc(Cl)c4)c32)CC1] | 5-{6-(3-chlorophenyl)-8-[cyclohexyl(hydroxy)methyl]-7-[(trans-4-methylcyclohexyl)methyl]-7H-purin-2-yl}-1,3,4-oxadiazol-2(3H)-one (racemate) | | 537 | 537 |
| 23.8 | 65.77 | 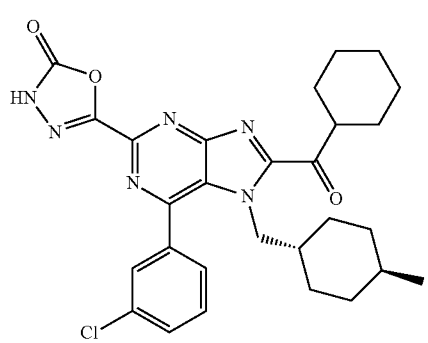 [SMILES: C[C@H]1CC[C@H](Cn2c(C(=O)C3CCCCC3)nc3nc(-c4n[nH]c(=O)o4)nc(-c4cccc(Cl)c4)c32)CC1] | 5-{6-(3-chlorophenyl)-8-(cyclohexylcarbonyl)-7-[(trans-4-methylcyclohexyl)methyl]-7H-purin-2-yl}-1,3,4-oxadiazol-2(3H)-one | | 535 | 535 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.9 | 24.61 | 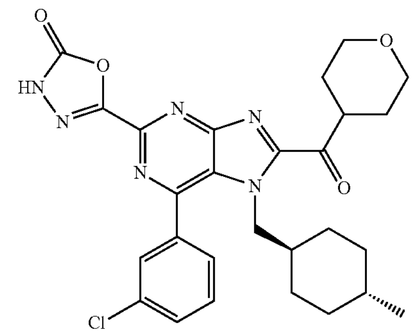 [SMILES: C[C@H]1CC[C@H](Cn2c(C(=O)C3CCOCC3)nc3nc(-c4n[nH]c(=O)o4)nc(-c4cccc(Cl)c4)c32)CC1] | 5-[6-(3-chlorophenyl)-7-[(trans-4-methylcyclohexyl)methyl]-8-(tetrahydro-2H-pyran-4-ylcarbonyl)-7H-purin-2-yl]-1,3,4-oxadiazol-2(3H)-one | | 537 | 537 |
| 23.10 | 15.63 | 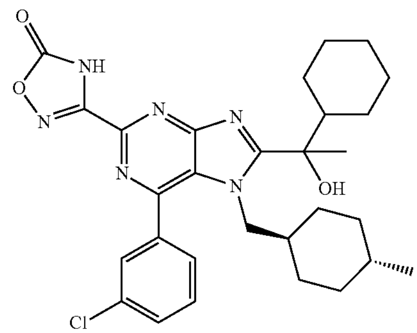 [SMILES: CC(O)(c1nc2nc(-c3noc(=O)[nH]3)nc(-c3cccc(Cl)c3)c2n1C[C@H]1CC[C@H](C)CC1)C1CCCCC1] | 3-{6-(3-chlorophenyl)-8-(1-cyclohexyl-1-hydroxyethyl)-7-[(trans-4-methylcyclohexyl)methyl]-7H-purin-2-yl}-1,2,4-oxadiazol-5(4H)-one (racemate) | | 551 | 551 |
| 23.11 | 213.9 | 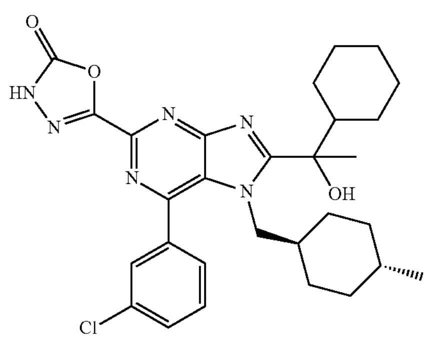 [SMILES: CC(O)(c1nc2nc(-c3n[nH]c(=O)o3)nc(-c3cccc(Cl)c3)c2n1C[C@H]1CC[C@H](C)CC1)C1CCCCC1] | 5-{6-(3-chlorophenyl)-8-(1-cyclohexyl-1-hydroxyethyl)-7-[(trans-4-methylcyclohexyl)methyl]-7H-purin-2-yl}-1,3,4-oxadiazol-2(3H)-one (racemate) | | 551 | 551 |
| 23.12 | 13.31 | 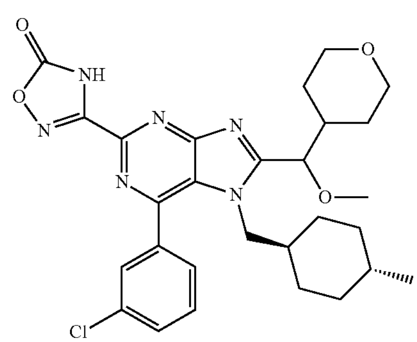 | 3-{6-(3-chlorophenyl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one (racemate) | | 553 | 553 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.13 | 22.66 | 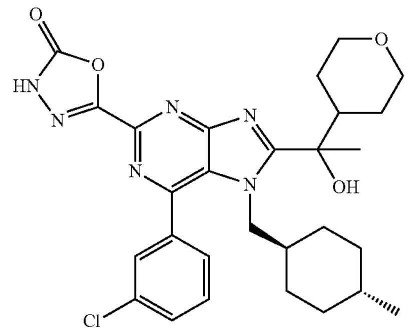 [SMILES: CC(O)(c1nc2nc(-c3n[nH]c(=O)o3)nc(-c3cccc(Cl)c3)c2n1C[C@H]1CC[C@H](C)CC1)C1CCOCC1] | 5-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,3,4-oxadiazol-2(3H)-one (racemate) | | 553 | 553 |
| 23.14 | 9.033 | 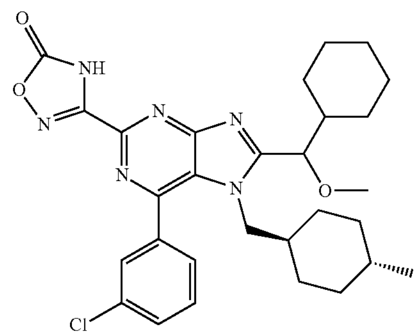 [SMILES: COC(c1nc2nc(-c3noc(=O)[nH]3)nc(-c3cccc(Cl)c3)c2n1C[C@H]1CC[C@H](C)CC1)C1CCCCC1] | 3-{6-(3-chlorophenyl)-8-[cyclohexyl(methoxy)methyl]-7-[(trans-4-methylcyclohexyl)methyl]-7H-purin-2-yl}-1,2,4-oxadiazol-5(4H)-one (racemate) | | 551 | 551 |
| 23.15 | 22.96 | 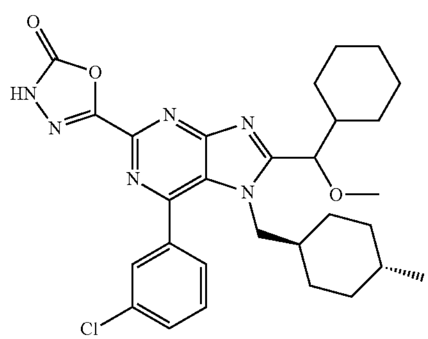 [SMILES: COC(c1nc2nc(-c3n[nH]c(=O)o3)nc(-c3cccc(Cl)c3)c2n1C[C@H]1CC[C@H](C)CC1)C1CCCCC1] | 5-{6-(3-chlorophenyl)-8-[cyclohexyl(methoxy)methyl]-7-[(trans-4-methylcyclohexyl)methyl]-7H-purin-2-yl}-1,3,4-oxadiazol-2(3H)-one (racemate) | | 551 | 551 |
| 23.16 | 12.35 | 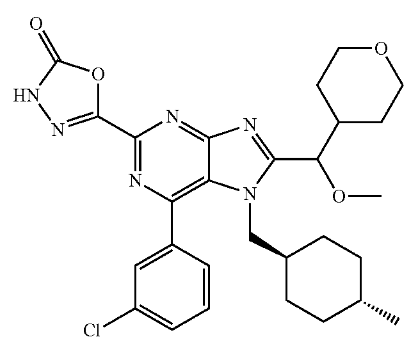 [SMILES: COC(c1nc2nc(-c3n[nH]c(=O)o3)nc(-c3cccc(Cl)c3)c2n1C[C@H]1CC[C@H](C)CC1)C1CCOCC1] | 5-{6-(3-chlorophenyl)-8-[methoxy(tetrahydro-2H-pyran-4-yl)methyl]-7-[(trans-4-methylcyclohexyl)methyl]-7H-purin-2-yl}-1,3,4-oxadiazol-2(3H)-one (racemate) | | 553 | 553 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.17 | 67.32 | 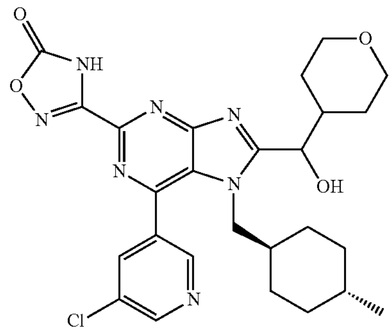 [SMILES: C[C@H]1CC[C@H](Cn2c(C(O)C3CCOCC3)nc3nc(-c4noc(=O)[nH]4)nc(-c4cncc(Cl)c4)c32)CC1] | 3-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one (racemate) | | 540 | 540 |
| 23.18 | 24.07 | 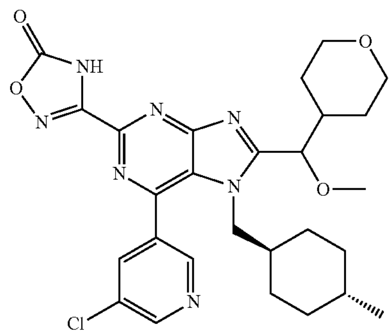 [SMILES: COC(c1nc2nc(-c3noc(=O)[nH]3)nc(-c3cncc(Cl)c3)c2n1C[C@H]1CC[C@H](C)CC1)C1CCOCC1] | 3-{6-(5-chloropyridin-3-yl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one (racemate) | | 554 | 554 |
| 23.19 | 104.4 | 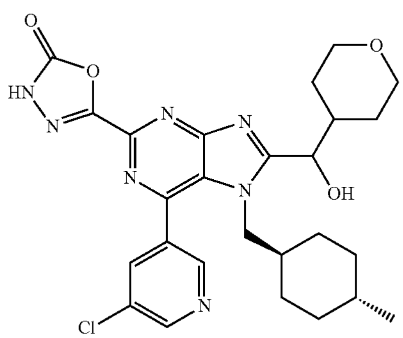 | 5-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one (racemate) | | 540 | 540 |
| 23.20 | 27.62 | 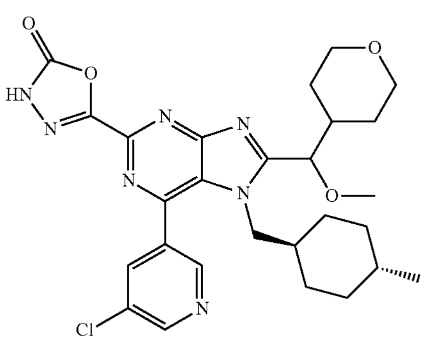 [SMILES: COC(c1nc2nc(-c3n[nH]c(=O)o3)nc(-c3cncc(Cl)c3)c2n1C[C@H]1CC[C@H](C)CC1)C1CCOCC1] | 5-{6-(5-chloropyridin-3-yl)-8-[methoxy(tetrahydro-2H-pyran-4-yl)methyl]-7-[(trans-4-methylcyclohexyl)methyl]-7H-purin-2-yl}-1,3,4-oxadiazol-2(3H)-one (racemate) | | 554 | 554 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.21 | 10.43 | 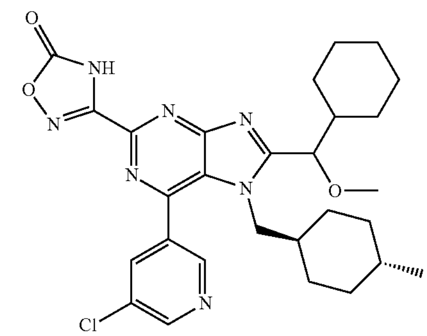 [SMILES: COC(c1nc2nc(-c3noc(=O)[nH]3)nc(-c3cncc(Cl)c3)c2n1C[C@H]1CC[C@H](C)CC1)C1CCCCC1] | 3-{6-(5-chloropyridin-3-yl)-8-[cyclohexyl(methoxy)methyl]-7-[(trans-4-methylcyclohexyl)methyl]-7H-purin-2-yl}-1,2,4-oxadiazol-5(4H)-one (racemate) | | 552 | 552 |
| 23.22 | 12.00 | 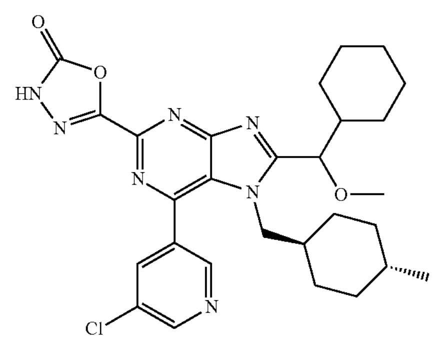 | 5-{6-(5-chloropyridin-3-yl)-8-[cyclohexyl(methoxy)methyl]-7-[(trans-4-methylcyclohexyl)methyl]-7H-purin-2-yl}-1,3,4-oxadiazol-2(3H)-one (racemate) | | 552 | 552 |
| 23.23 | 8.783 | 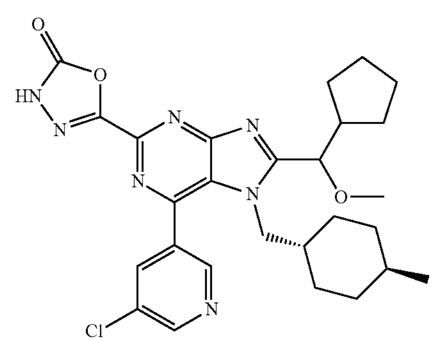 [SMILES: COC(c1nc2nc(-c3n[nH]c(=O)o3)nc(-c3cncc(Cl)c3)c2n1C[C@H]1CC[C@H](C)CC1)C1CCCC1] | 5-{6-(5-chloropyridin-3-yl)-8-[cyclopentyl(methoxy)methyl]-7-[(trans-4-methylcyclohexyl)methyl]-7H-purin-2-yl}-1,3,4-oxadiazol-2(3H)-one (racemate) | | 538 | 538 |
| 23.24 | 7.805 | 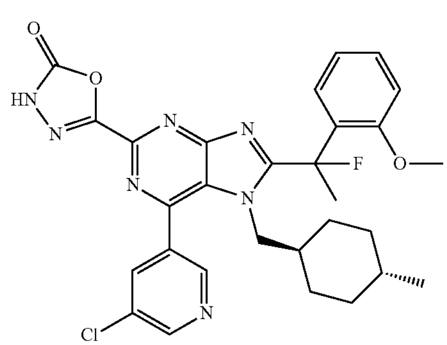 [SMILES: COc1ccccc1C(C)(F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-fluoro-1-(2-methoxyphenyl)ethyl]-7-[(trans-4-methylcyclohexyl)methyl]-7H-purin-2-yl}-1,3,4-oxadiazol-2(3H)-one (enantiomer 1) | | 578 | 578 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.25 | 3.220 | 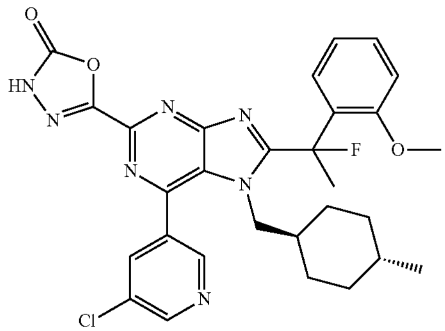 [SMILES: COc1ccccc1C(C)(F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-fluoro-1-(2-methoxyphenyl)ethyl]-7-[(trans-4-methylcyclohexyl)methyl]-7H-purin-2-yl}-1,3,4-oxadiazol-2(3H)-one (enantiomer 2) | | 578 | 578 |
| 23.26 | 5.371 | 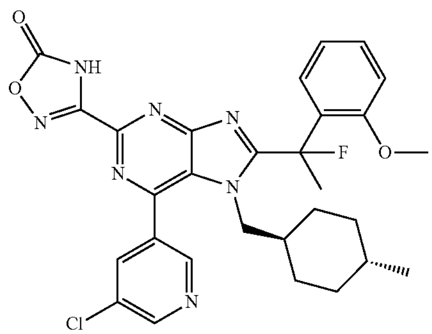 [SMILES: COc1ccccc1C(C)(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-fluoro-1-(2-methoxyphenyl)ethyl]-7-[(trans-4-methylcyclohexyl)methyl]-7H-purin-2-yl}-1,2,4-oxadiazol-5(4H)-one (enantiomer 1) | | 578 | 578 |
| 23.27 | 1.620 | 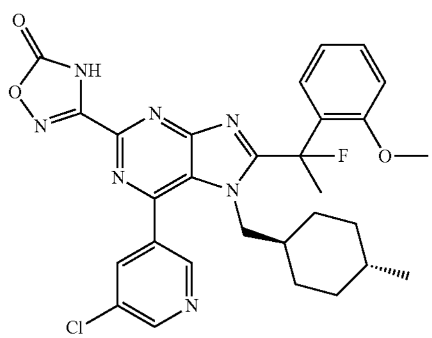 [SMILES: COc1ccccc1C(C)(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-fluoro-1-(2-methoxyphenyl)ethyl]-7-[(trans-4-methylcyclohexyl)methyl]-7H-purin-2-yl}-1,2,4-oxadiazol-5(4H)-one (enantiomer 2) | | 578 | 578 |
| 23.28 | 62.80 | 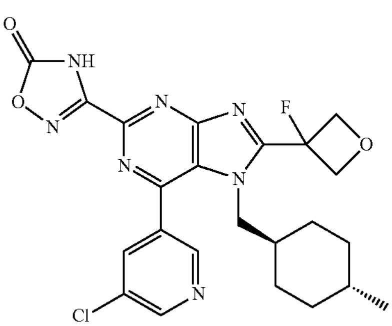 [SMILES: C[C@H]1CC[C@H](Cn2c(C3(F)COC3)nc3nc(-c4noc(=O)[nH]4)nc(-c4cncc(Cl)c4)c32)CC1] | 3-{6-(5-chloropyridin-3-yl)-8-(3-fluorooxetan-3-yl)-7-[(trans-4-methylcyclohexyl)methyl]-7H-purin-2-yl}-1,2,4-oxadiazol-5(4H)-one | | 500 | 500 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.29 | 34.76 | 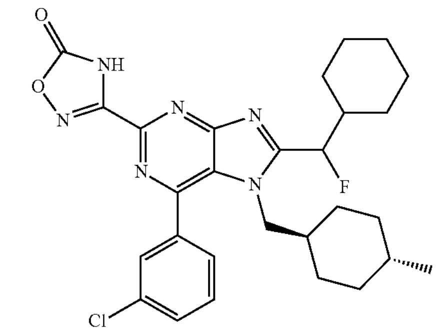 | 3-{6-(3-chlorophenyl)-8-[cyclohexyl(fluoro)methyl]-7-[(trans-4-methylcyclohexyl)methyl]-7H-purin-2-yl}-1,2,4-oxadiazol-5(4H)-one (racemate) | | 539 | 539 |
| 23.30 | 6.699 | 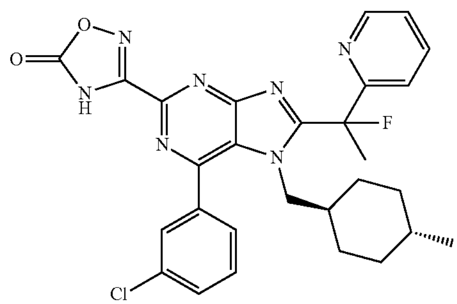 [SMILES: CC(F)(c1ccccn1)c1nc2nc(-c3noc(=O)[nH]3)nc(-c3cccc(Cl)c3)c2n1C[C@H]1CC[C@H](C)CC1] | 3-{6-(3-chlorophenyl)-8-(1-fluoro-1-pyridin-2-ylethyl)-7-[(trans-4-methylcyclohexyl)methyl]-7H-purin-2-yl}-1,2,4-oxadiazol-5(4H)-one (enantiomer 1) | | 548 | 548 |
| 23.31 | 3.730 | 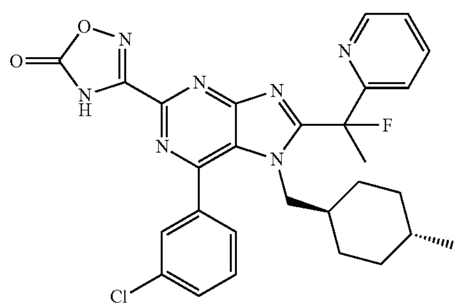 [SMILES: CC(F)(c1ccccn1)c1nc2nc(-c3noc(=O)[nH]3)nc(-c3cccc(Cl)c3)c2n1C[C@H]1CC[C@H](C)CC1] | 3-{6-(3-chlorophenyl)-8-(1-fluoro-1-pyridin-2-ylethyl)-7-[(trans-4-methylcyclohexyl)methyl]-7H-purin-2-yl}-1,2,4-oxadiazol-5(4H)-one (enantiomer 2) | | 548 | 548 |
| 23.32 | 16.04 | 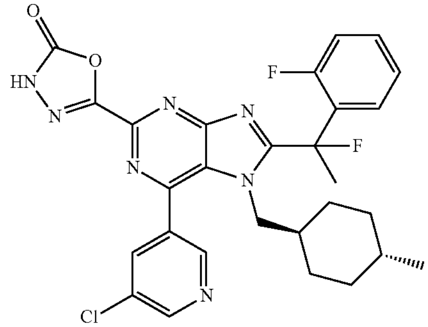 [SMILES: CC(F)(c1ccccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-fluoro-1-(2-fluorophenyl)ethyl]-7-[(trans-4-methylcyclohexyl)methyl]-7H-purin-2-yl}-1,3,4-oxadiazol-2(3H)-one (enantiomer 1) | | 566 | 566 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.33 | 0.453 | 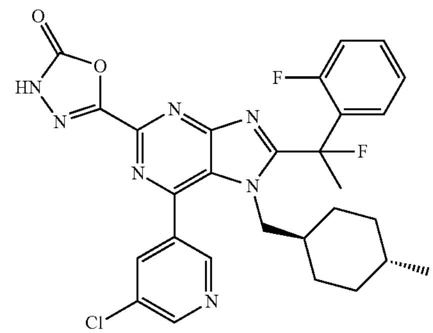 [SMILES: CC(F)(c1ccccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-fluoro-1-(2-fluorophenyl)ethyl]-7-[{trans-4-methylcyclohexyl)methyl]-7H-purin-2-yl}-1,3,4-oxadiazol-2(3H)-one (enantiomer 2) | | 566 | 566 |
| 23.34 | 9.298 | 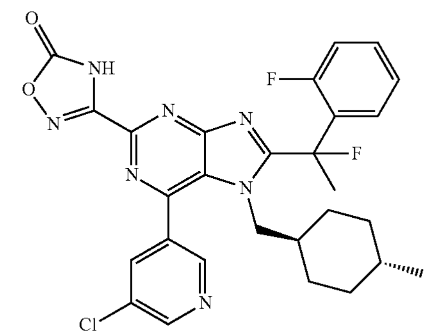 [SMILES: CC(F)(c1ccccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-fluoro-1-(2-fluorophenyl)ethyl]-7-[(trans-4-methylcyclohexyl)methyl]-7H-purin-2-yl}-1,2,4-oxadiazol-5(4H)-one (enantiomer 1) | | 566 | 566 |
| 23.35 | 0.424 | 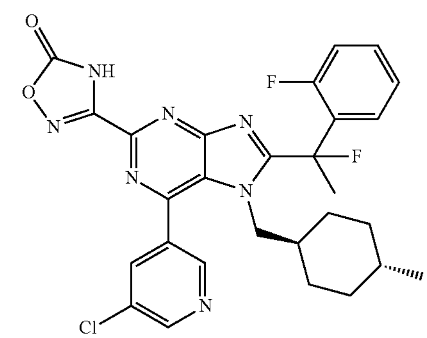 [SMILES: CC(F)(c1ccccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-fluoro-1-(2-fluorophenyl)ethyl]-7-[(trans-4-methylcyclohexyl)methyl] 7H-purin-2-yl}-1,2,4-oxadiazol-5(4H)-one (enantiomer 2) | | 566 | 566 |
| 23.36 | 9.679 | 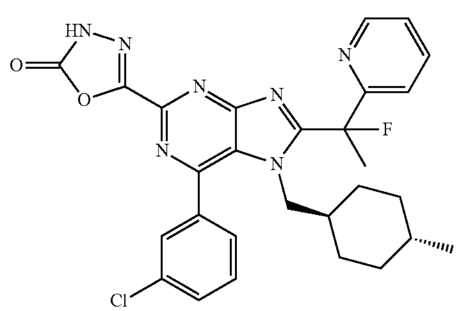 [SMILES: CC(F)(c1ccccn1)c1nc2nc(-c3n[nH]c(=O)o3)nc(-c3cccc(Cl)c3)c2n1C[C@H]1CC[C@H](C)CC1] | 5-{6-(3-chlorophenyl)-8-[1-fluoro-1-(pyridin-2-yl)ethyl]-7-[(trans-4-methylcyclohexyl)methyl]-7H-purin-2-yl}-1,3,4-oxadiazol-2(3H)-one (enantiomer 1) | | 548 | 548 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.37 | 9.655 | 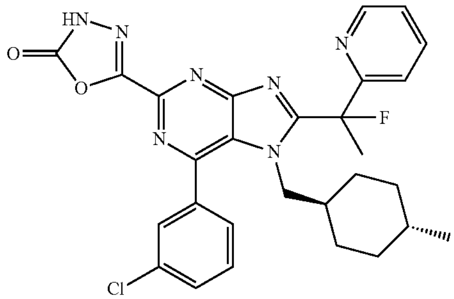 [SMILES: CC(F)(c1ccccn1)c1nc2nc(-c3n[nH]c(=O)o3)nc(-c3cccc(Cl)c3)c2n1C[C@H]1CC[C@H](C)CC1] | 5-{6-(3-chlorophenyl)-8-[1-fluoro-1-(pyridin-2-yl)ethyl]-7-[{trans-4-methylcyclohexyl)methyl]-7H-purin-2-yl}-1,3,4-oxadiazol-2(3H)-one (enantiomer 2) | | 548 | 548 |
| 23.38 | 31.11 | 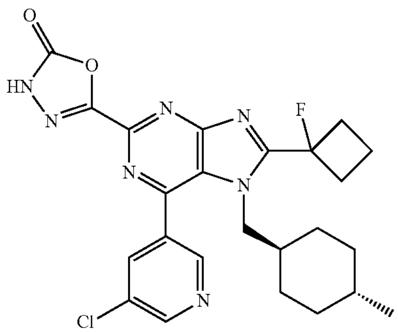 [SMILES: C[C@H]1CC[C@H](Cn2c(C3(F)CCC3)nc3nc(-c4n[nH]c(=O)o4)nc(-c4cncc(Cl)c4)c32)CC1] | 5-{6-(5-chloropyridin-3-yl)-8-(1-fluorocyclobutyl)-7-[(trans-4-methylcyclohexyl)methyl]-7H-purin-2-yl}-1,3,4-oxadiazol-2(3H)-one | | 498 | 498 |
| 23.39 | 18.06 | 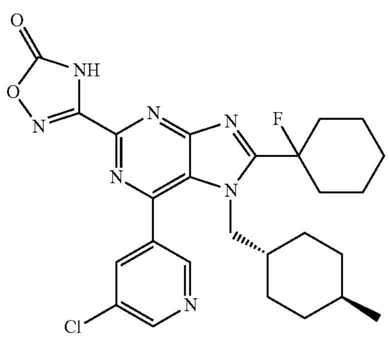 [SMILES: C[C@H]1CC[C@H](Cn2c(C3(F)CCCCC3)nc3nc(-c4noc(=O)[nH]4)nc(-c4cncc(Cl)c4)c32)CC1] | 3-{6-(5-chloropyridin-3-yl)-8-(1-fluorocyclohexyl)-7-[(trans-4-methylcyclohexyl)methyl]-7H-purin-2-yl}-1,2,4-oxadiazol-5(4H)-one | | 526 | 526 |
| 23.40 | 15.02 | 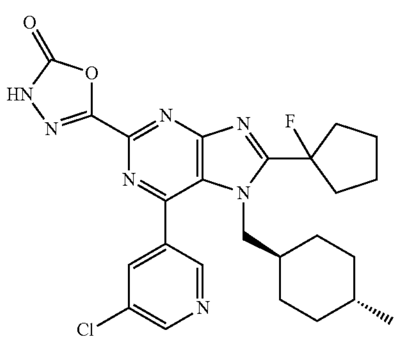 [SMILES: C[C@H]1CC[C@H](Cn2c(C3(F)CCCC3)nc3nc(-c4n[nH]c(=O)o4)nc(-c4cncc(Cl)c4)c32)CC1] | 5-{6-(5-chloropyridin-3-yl)-8-(1-fluorocyclopentyl)-7-[(trans-4-methylcyclohexyl)methyl]-7H-purin-2-yl}-1,3,4-oxadiazol-2(3H)-one | | 512 | 512 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.41 | 18.54 | 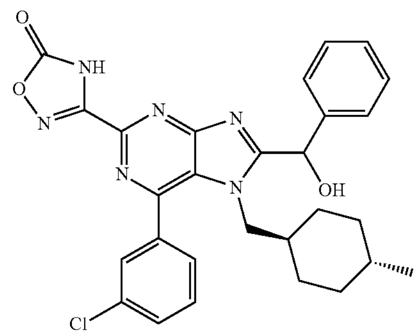 [SMILES: C[C@H]1CC[C@H](Cn2c(C(O)c3ccccc3)nc3nc(-c4noc(=O)[nH]4)nc(-c4cccc(Cl)c4)c32)CC1] | 3-{6-(3-chlorophenyl)-8-[hydroxy(phenyl)methyl]-7-[(trans-4-methylcyclohexyl)methyl]-7H-purin-2-yl}-1,2,4-oxadiazol-5(4H)-one (enantiomer 1) | TFA | 531 | 531 |
| 23.42 | 6.891 | 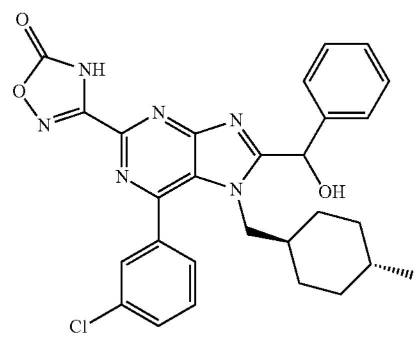 [SMILES: C[C@H]1CC[C@H](Cn2c(C(O)c3ccccc3)nc3nc(-c4noc(=O)[nH]4)nc(-c4cccc(Cl)c4)c32)CC1] | 3-{6-(3-chlorophenyl)-8-[hydroxy(phenyl)methyl]-7-[(trans-4-methylcyclohexyl)methyl]-7H-purin-2-yl}-1,2,4-oxadiazol-5(4H)-one (enantiomer 2) | TFA | 531 | 531 |
| 23.43 | 72.68 | 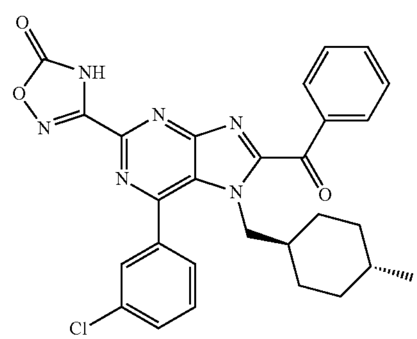 [SMILES: C[C@H]1CC[C@H](Cn2c(C(=O)c3ccccc3)nc3nc(-c4noc(=O)[nH]4)nc(-c4cccc(Cl)c4)c32)CC1] | 3-[6-(3-chlorophenyl)-7-[(trans-4-methylcyclohexyl)methyl]-8-(phenylcarbonyl)-7H-purin-2-yl]-1,2,4-oxadiazol-5(4H)-one | TFA | 529 | 529 |
| 23.44 | 4.533 | 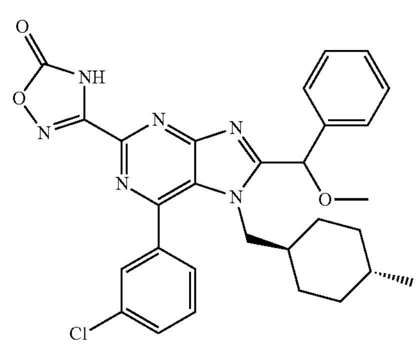 [SMILES: COC(c1ccccc1)c1nc2nc(-c3noc(=O)[nH]3)nc(-c3cccc(Cl)c3)c2n1C[C@H]1CC[C@H](C)CC1] | 3-{6-(3-chlorophenyl)-8-[methoxy(phenyl)methyl]-7-[(trans-4-methylcyclohexyl)methyl]-7H-purin-2-yl}-1,2,4-oxadiazol-5(4H)-one (enantiomer 2) | TFA | 545 | 545 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.45 | 5.151 | 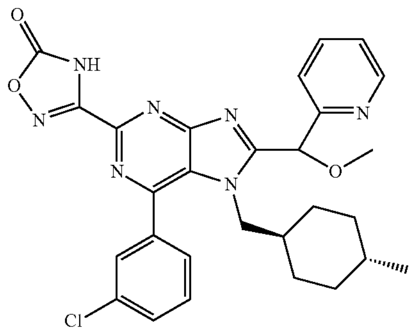 [SMILES: COC(c1ccccn1)c1nc2nc(-c3noc(=O)[nH]3)nc(-c3cccc(Cl)c3)c2n1C[C@H]1CC[C@H](C)CC1] | 3-{6-(3-chlorophenyl)-8-[methoxy(pyridin-2-yl)methyl]-7-[(trans-4-methylcyclohexyl)methyl]-7H-purin-2-yl}-1,2,4-oxadiazol-5(4H)-one (enantiomer 1) | TFA | 546 | 546 |
| 23.46 | 8.272 | 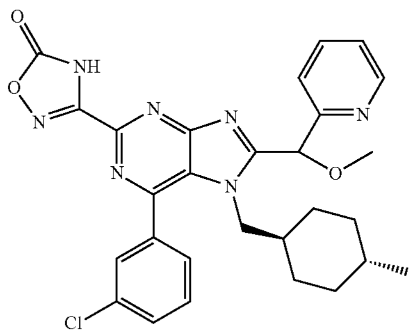 [SMILES: COC(c1ccccn1)c1nc2nc(-c3noc(=O)[nH]3)nc(-c3cccc(Cl)c3)c2n1C[C@H]1CC[C@H](C)CC1] | 3-{6-(3-chlorophenyl)-8-[methoxy(pyridin-2-yl)methyl]-7-[(trans-4-methylcyclohexyl)methyl]-7H-purin-2-yl}-1,2,4-oxadiazol-5(4H)-one (enantiomer 2) | TFA | 546 | 546 |
| 23.47 | 9.768 | 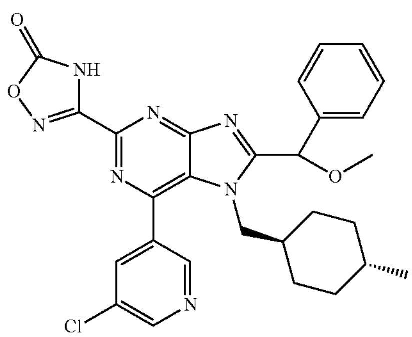 [SMILES: COC(c1ccccc1)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[methoxy(phenyl)methyl]-7-[(trans-4-methylcyclohexyl)methyl]-7H-purin-2-yl}-1,2,4-oxadiazol-5(4H)-one (enantiomer 1) | | 546 | 546 |
| 23.48 | 4.216 | 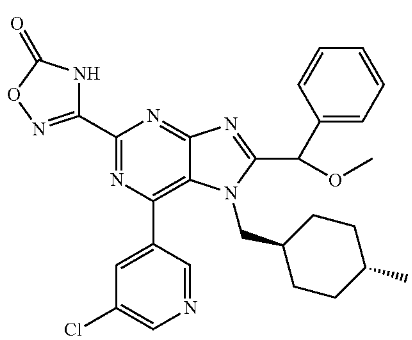 [SMILES: COC(c1ccccc1)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[methoxy(phenyl)methyl]-7-[(trans-4-methylcyclohexyl)methyl]-7H-purin-2-yl}-1,2,4-oxadiazol-5(4H)-one (enantiomer 2) | | 546 | 546 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.49 | 0.888 | 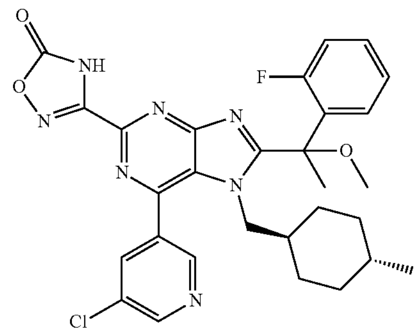 [SMILES: COC(C)(c1ccccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2-fluorophenyl)-1-methoxyethyl]-7-[(trans-4-methylcyclohexyl)methyl]-7H-purin-2-yl}-1,2,4-oxadiazol-5(4H)-one (enantiomer 1) | | 578 | 578 |
| 23.50 | 6.546 | 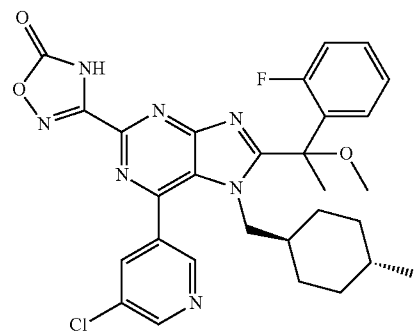 [SMILES: COC(C)(c1ccccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2-fluorophenyl)-1-methoxyethyl]-7-[(trans-4-methylcyclohexyl)methyl]-7H-purin-2-yl}-1,2,4-oxadiazol-5(4H)-one (enantiomer 2) | | 578 | 578 |
| 23.51 | 5.190 | 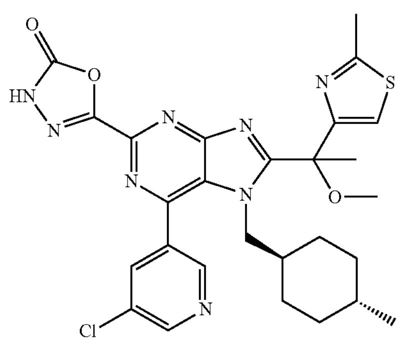 [SMILES: COC(C)(c1csc(C)n1)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-methoxy-1-(2-methyl-1,3-thiazol-4-yl)ethyl]-7-[(trans-4-methylcyclohexyl)methyl]-7H-purin-2-yl}-1,3,4-oxadiazol-2(3H)-one (racemate) | | 581 | 581 |
| 23.52 | 6.221 | 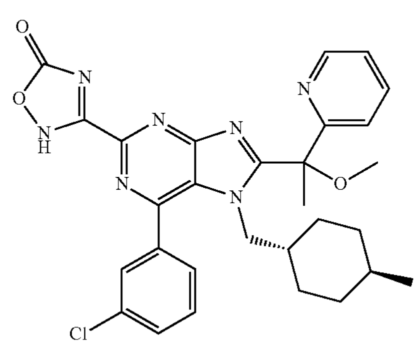 [SMILES: COC(C)(c1ccccn1)c1nc2nc(-c3nc(=O)o[nH]3)nc(-c3cccc(Cl)c3)c2n1C[C@H]1CC[C@H](C)CC1] | 3-{6-(3-chlorophenyl)-8-[1-methoxy-1-(pyridin-2-yl)ethyl]-7-[(trans-4-methylcyclohexyl)methyl]-7H-purin-2-yl}-1,2,4-oxadiazol-5(2H)-one (enantiomer 1) | | 560 | 560 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.53 | 3.337 | 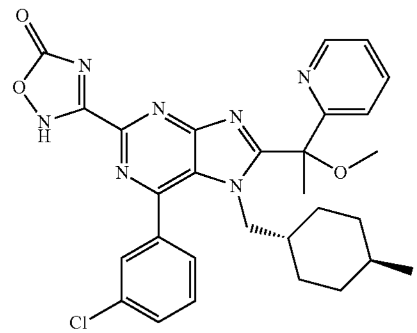 [SMILES: COC(C)(c1ccccn1)c1nc2nc(-c3nc(=O)o[nH]3)nc(-c3cccc(Cl)c3)c2n1C[C@H]1CC[C@H](C)CC1] | 3-{6-(3-chlorophenyl)-8-[1-methoxy-1-(pyridin-2-yl)ethyl]-7-[(trans-4-methylcyclohexyl)methyl]-7H-purin-2-yl}-1,2,4-oxadiazol-5(2H)-one (enantiomer 2) | | 560 | 560 |
| 23.54 | 13.64 | 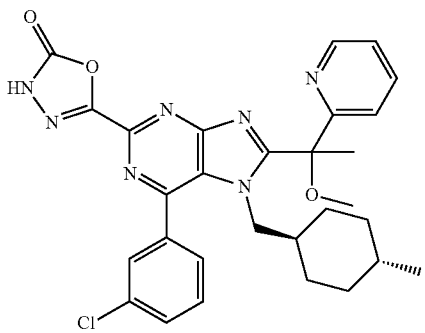 [SMILES: COC(C)(c1ccccn1)c1nc2nc(-c3n[nH]c(=O)o3)nc(-c3cccc(Cl)c3)c2n1C[C@H]1CC[C@H](C)CC1] | 5-{6-(3-chlorophenyl)-8-(1-methoxy-1-pyridin-2-ylethyl)-7-[(trans-4-methylcyclohexyl)methyl]-7H-purin-2-yl}-1,3,4-oxadiazol-2(3H)-one (enantiomer 1) | | 560 | 560 |
| 23.55 | 4.265 | 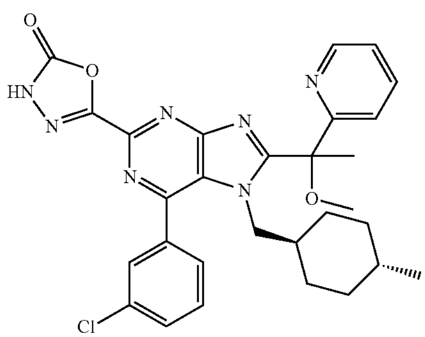 [SMILES: COC(C)(c1ccccn1)c1nc2nc(-c3n[nH]c(=O)o3)nc(-c3cccc(Cl)c3)c2n1C[C@H]1CC[C@H](C)CC1] | 5-{6-(3-chlorophenyl)-8-(1-methoxy-1-pyridin-2-ylethyl)-7-[(trans-4-methylcyclohexyl)methyl]-7H-purin-2-yl}-1,3,4-oxadiazol-2(3H)-one (enantiomer 2) | | 560 | 560 |
| 23.56 | 10.65 | 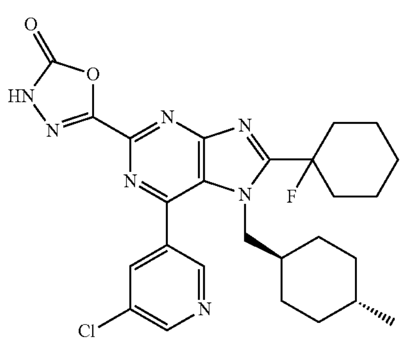 [SMILES: C[C@H]1CC[C@H](Cn2c(C3(F)CCCCC3)nc3nc(-c4n[nH]c(=O)o4)nc(-c4cncc(Cl)c4)c32)CC1] | 5-{6-(5-chloropyridin-3-yl)-8-(1-fluorocyclohexyl)-7-[(trans-4-methylcyclohexyl)methyl]-7H-purin-2-yl}-1,3,4-oxadiazol-2(3H)-one | | 526 | 526 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.57 | 2.067 | 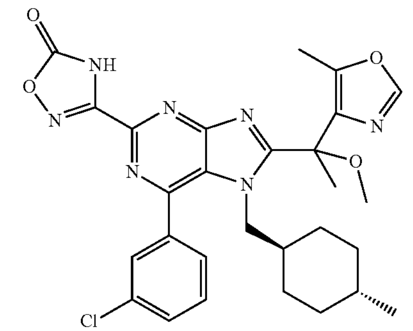 [SMILES: COC(C)(c1ncoc1C)c1nc2nc(-c3noc(=O)[nH]3)nc(-c3cccc(Cl)c3)c2n1C[C@H]1CC[C@H](C)CC1] | 3-{6-(3-chlorophenyl)-8-[1-methoxy-1-(5-methyl-1,3-oxazol-4-yl)ethyl]-7-[(trans-4-methylcyclohexyl)methyl]-7H-purin-2-yl}-1,2,4-oxadiazol-5(4H)-one (racemate) | | 564 | 564 |
| 23.58 | 1.949 | 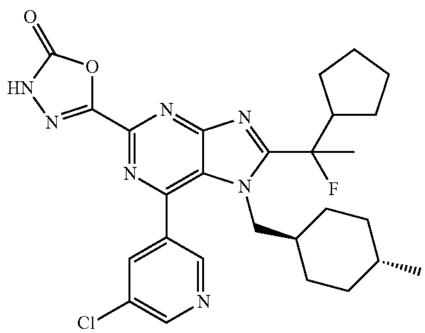 [SMILES: CC(F)(c1nc2nc(-c3n[nH]c(=O)o3)nc(-c3cncc(Cl)c3)c2n1C[C@H]1CC[C@H](C)CC1)C1CCCC1] | 5-{6-(5-chloropyridin-3-yl)-8-(1-cyclopentyl-1-fluoroethyl)-7-[(trans-4-methylcyclohexyl)methyl]-7H-purin-2-yl}-1,3,4-oxadiazol-2(3H)-one (racemate) | | 540 | 540 |
| 23.59 | 0.896 | 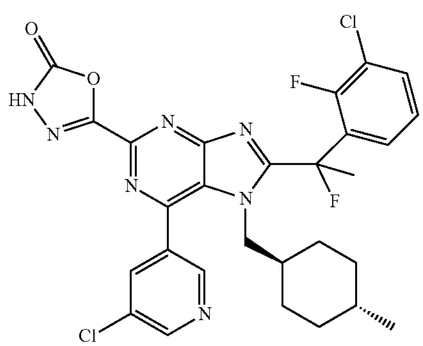 [SMILES: CC(F)(c1cccc(Cl)c1F)c1nc2nc(-c3n[nH]c(=O)o3)nc(-c3cncc(Cl)c3)c2n1C[C@H]1CC[C@H](C)CC1] | 5-{8-[1-(3-chloro-2-fluorophenyl)-1-fluoroethyl]-6-(5-chloropyridin-3-yl)-7-[(trans-4-methylcyclohexyl)methyl]-7H-purin-2-yl}-1,3,4-oxadiazol-2(3H)-one (enantiomer 1) | | 600 | 600 |
| 23.60 | 29.00 | 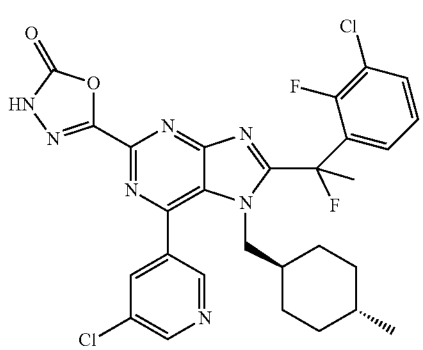 [SMILES: CC(F)(c1cccc(Cl)c1F)c1nc2nc(-c3n[nH]c(=O)o3)nc(-c3cncc(Cl)c3)c2n1C[C@H]1CC[C@H](C)CC1] | 5-{8-[1-(3-chloro-2-fluorophenyl)-1-fluoroethyl]-6-(5-chloropyridin-3-yl)-7-[(trans-4-methylcyclohexyl)methyl]-7H-purin-2-yl}-1,3,4-oxadiazol-2(3H)-one (enantiomer 2) | | 600 | 600 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.61 | 4.637 | 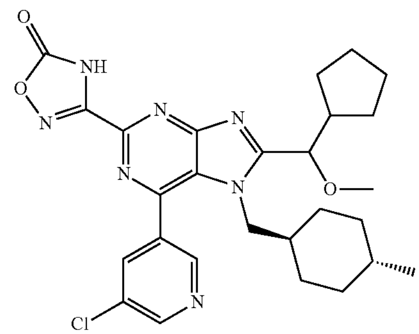 [SMILES: COC(c1nc2nc(-c3noc(=O)[nH]3)nc(-c3cncc(Cl)c3)c2n1C[C@H]1CC[C@H](C)CC1)C1CCCC1] | 3-{6-(5-chloropyridin-3-yl)-8-[cyclopentyl(methoxy)methyl]-7-[(trans-4-methylcyclohexyl)methyl]-7H-purin-2-yl}-1,2,4-oxadiazol-5(4H)-one (racemate) | | 538 | 538 |
| 23.62 | 13.09 | 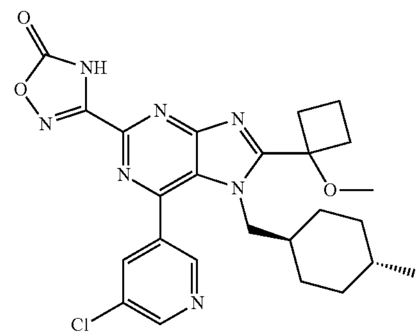 [SMILES: COC1(c2nc3nc(-c4noc(=O)[nH]4)nc(-c4cncc(Cl)c4)c3n2C[C@H]2CC[C@H](C)CC2)CCC1] | 3-{6-(5-chloropyridin-3-yl)-8-(1-methoxycyclobutyl)-7-[(trans-4-methylcyclohexyl)methyl]-7H-purin-2-yl}-1,2,4-oxadiazol-5(4H)-one | | 510 | 510 |
| 23.63 | 7.637 | 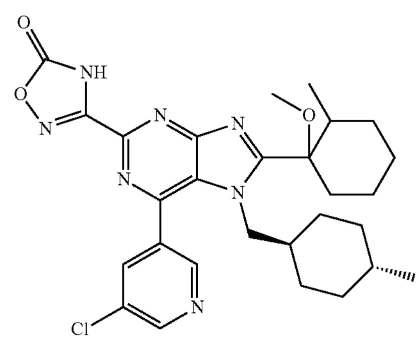 [SMILES: COC1(c2nc3nc(-c4noc(=O)[nH]4)nc(-c4cncc(Cl)c4)c3n2C[C@H]2CC[C@H](C)CC2)CCCCC1C] | 3-{6-(5-chloropyridin-3-yl)-8-(1-methoxy-2-methylcyclohexyl)-7-[(trans-4-methylcyclohexyl)methyl]-7H-purin-2-yl}-1,2,4-oxadiazol-5(4H)-one (mixture of stereoisomers) | | 552 | 552 |
| 23.64 | 8.805 | 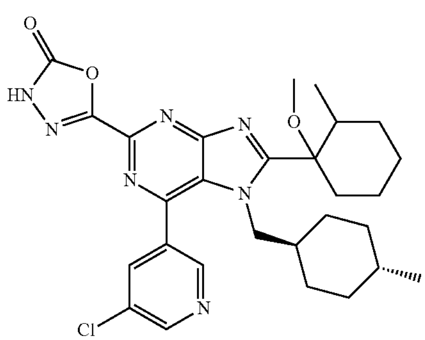 [SMILES: COC1(c2nc3nc(-c4n[nH]c(=O)o4)nc(-c4cncc(Cl)c4)c3n2C[C@H]2CC[C@H](C)CC2)CCCCC1C] | 5-{6-(5-chloropyridin-3-yl)-8-(1-methoxy-2-methylcyclohexyl)-7-[(trans-4-methylcyclohexyl)methyl]-7H-purin-2-yl}-1,3,4-oxadiazol-2(3H)-one | | 552 | 552 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.65 | 6.634 | 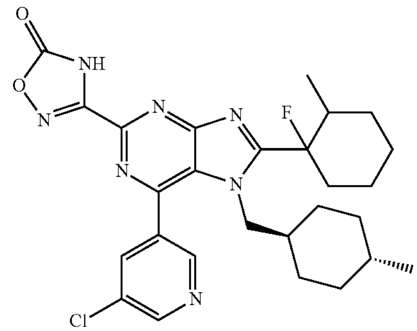 [SMILES: CC1CCCCC1(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-(1-fluoro-2-methylcyclohexyl)-7-[(trans-4-methylcyclohexyl)methyl]-7H-purin-2-yl}-1,2,4-oxadiazol-5(4H)-one | | 540 | 540 |
| 23.66 | 5.821 | 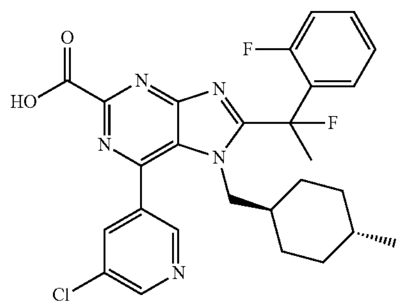 [SMILES: CC(F)(c1ccccc1F)c1nc2nc(C(=O)O)nc(-c3cncc(Cl)c3)c2n1C[C@H]1CC[C@H](C)CC1] | 6-(5-chloropyridin-3-yl)-8-[1-fluoro-1-(2-fluorophenyl)ethyl]-7-[(trans-4-methylcyclohexyl)methyl]-7H-purine-2-carboxylic acid (enantiomer 1) | | 526 | 526 |
| 23.67 | 0.176 | 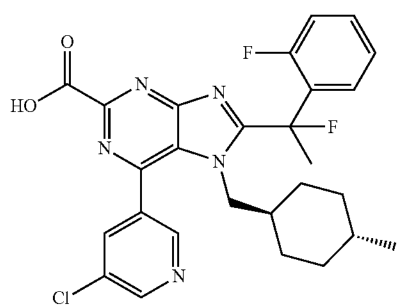 [SMILES: CC(F)(c1ccccc1F)c1nc2nc(C(=O)O)nc(-c3cncc(Cl)c3)c2n1C[C@H]1CC[C@H](C)CC1] | 6-(5-chloropyridin-3-yl)-8-[1-fluoro-1-(2-fluorophenyl)ethyl]-7-[(trans-4-methylcyclohexyl)methyl]-7H-purine-2-carboxylic acid (enantiomer 2) | | 526 | 526 |
| 23.68 | 4.261 | 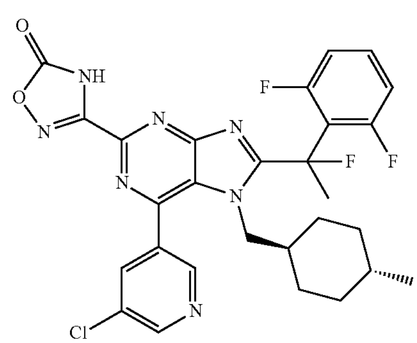 [SMILES: CC(F)(c1c(F)cccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2,6-difluorophenyl)-1-fluoroethyl]-7-[(trans-4-methylcyclohexyl)methyl]-7H-purin-2-yl}-1,2,4-oxadiazol-5(4H)-one (enantiomer 1) | | 584 | 584 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.69 | 0.156 | 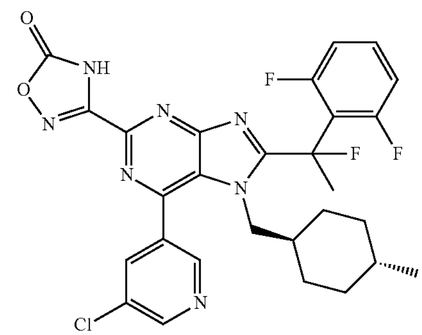 [SMILES: CC(F)(c1c(F)cccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2,6-difluorophenyl)-1-fluoroethyl]-7-[(trans-4-methylcyclohexyl)methyl]-7H-purin-2-yl}-1,2,4-oxadiazol-5(4H)-one (enantiomer 2) | | 584 | 584 |
| 23.70 | 9.437 | 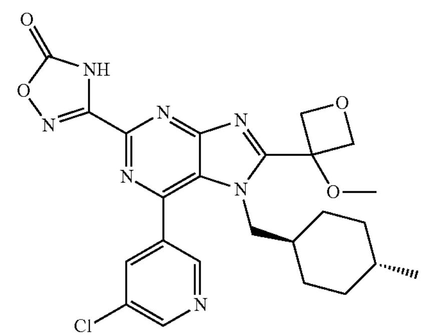 | 3-{6-(5-chloropyridin-3-yl)-8-(3-methoxyoxetan-3-yl)-7-[(trans-4-methylcyclohexyl)methyl]-7H-purin-2-yl}-1,2,4-oxadiazol-5(4H)-one | | 512 | 512 |
| 23.71 | 1.293 | 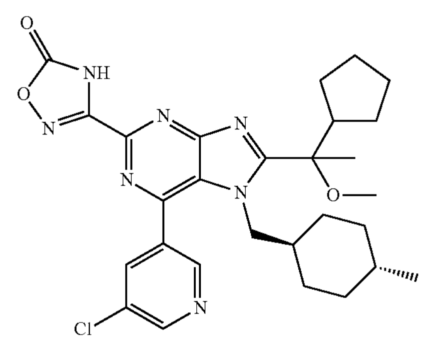 [SMILES: COC(C)(c1nc2nc(-c3noc(=O)[nH]3)nc(-c3cncc(Cl)c3)c2n1C[C@H]1CC[C@H](C)CC1)C1CCCC1] | 3-{6-(5-chloropyridin-3-yl)-8-(1-cyclopentyl-1-methoxyethyl)-7-[(trans-4-methylcyclohexyl)methyl]-7H-purin-2-yl}-1,2,4-oxadiazol-5(4H)-one (racemate) | | 552 | 552 |
| 23.72 | 2.598 | 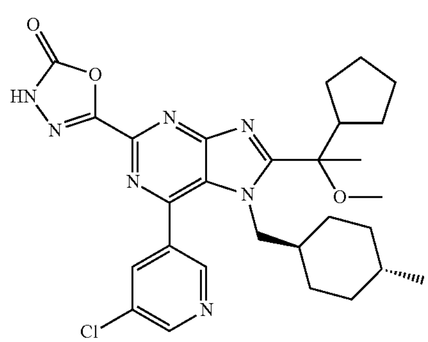 [SMILES: COC(C)(c1nc2nc(-c3n[nH]c(=O)o3)nc(-c3cncc(Cl)c3)c2n1C[C@H]1CC[C@H](C)CC1)C1CCCC1] | 5-{6-(5-chloropyridin-3-yl)-8-(1-cyclopentyl-1-methoxyethyl)-7-[(trans-4-methylcyclohexyl)methyl]-7H-purin-2-yl}-1,3,4-oxadiazol-2(3H)-one (racemate) | | 552 | 552 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.73 | 0.623 | 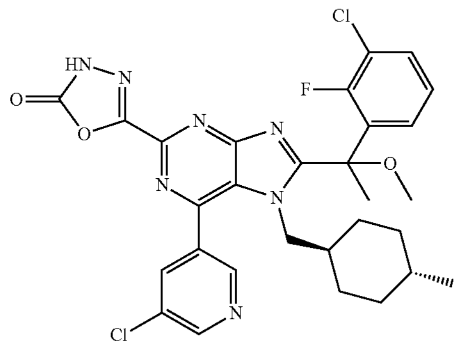 [SMILES: COC(C)(c1cccc(Cl)c1F)c1nc2nc(-c3n[nH]c(=O)o3)nc(-c3cncc(Cl)c3)c2n1C[C@H]1CC[C@H](C)CC1] | 5-{8-[1-(3-chloro-2-fluorophenyl)-1-methoxyethyl]-6-(5-chloropyridin-3-yl)-7-[(trans-4-methylcyclohexyl)methyl]-7H-purin-2-yl}-1,3,4-oxadiazol-2(3H)-one (enantiomer 1) | | 612 | 612 |
| 23.74 | 17.82 | 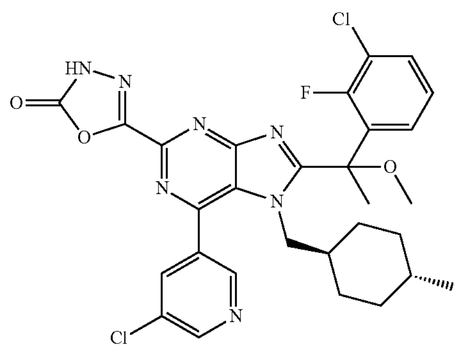 [SMILES: COC(C)(c1cccc(Cl)c1F)c1nc2nc(-c3n[nH]c(=O)o3)nc(-c3cncc(Cl)c3)c2n1C[C@H]1CC[C@H](C)CC1] | 5-{8-[1-(3-chloro-2-fluorophenyl)-1-methoxyethyl]-6-(5-chloropyridin-3-yl)-7-[(trans-4-methylcyclohexyl)methyl]-7H-purin-2-yl}-1,3,4-oxadiazol-2(3H)-one (enantiomer 2) | | 612 | 612 |
| 23.75 | 30.68 | 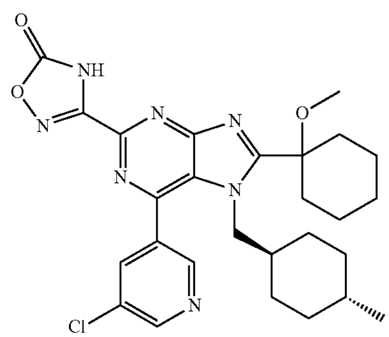 [SMILES: COC1(c2nc3nc(-c4noc(=O)[nH]4)nc(-c4cncc(Cl)c4)c3n2C[C@H]2CC[C@H](C)CC2)CCCCC1] | 3-{6-(5-chloropyridin-3-yl)-8-(1-methoxycyclohexyl)-7-[(trans-4-methylcyclohexyl)methyl]-7H-purin-2-yl}-1,2,4-oxadiazol-5(4H)-one | | 538 | 538 |
| 23.76 | 14.15 | 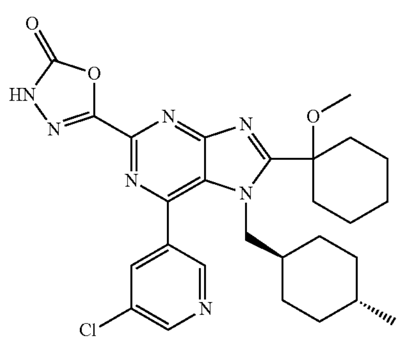 [SMILES: COC1(c2nc3nc(-c4n[nH]c(=O)o4)nc(-c4cncc(Cl)c4)c3n2C[C@H]2CC[C@H](C)CC2)CCCCC1] | 5-{6-(5-chloropyridin-3-yl)-8-(1-methoxycyclohexyl)-7-[(trans-4-methylcyclohexyl)methyl]-7H-purin-2-yl}-1,3,4-oxadiazol-2(3H)-one | | 538 | 538 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.77 | 8.060 | 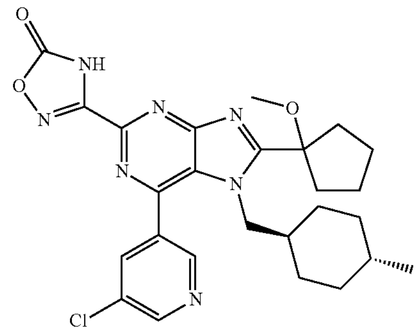 [SMILES: COC1(c2nc3nc(-c4noc(=O)[nH]4)nc(-c4cncc(Cl)c4)c3n2C[C@H]2CC[C@H](C)CC2)CCCC1] | 3-{6-(5-chloropyridin-3-yl)-8-(1-methoxycyclopentyl)-7-[(trans-4-methylcyclohexyl)methyl]-7H-purin-2-yl}-1,2,4-oxadiazol-5(4H)-one | | 524 | 524 |
| 23.78 | 8.222 | 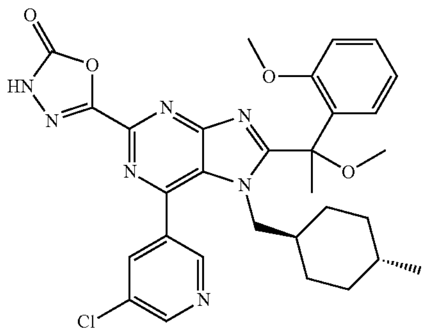 [SMILES: COc1ccccc1C(C)(OC)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-methoxy-1-(2-methoxyphenyl)ethyl]-7-[(trans-4-methylcyclohexyl)methyl]-7H-purin-2-yl}-1,3,4-oxadiazol-2(3H)-one (racemic) | | 590 | 590 |
| 23.79 | 3.799 | 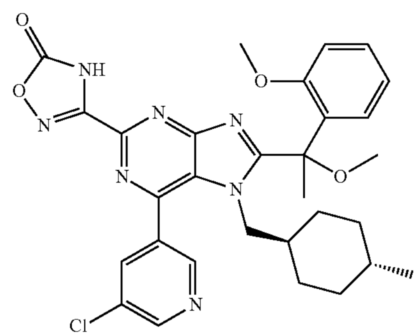 [SMILES: COc1ccccc1C(C)(OC)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-methoxy-1-(2-methoxyphenyl)ethyl]-7-[(trans-4-methylcyclohexyl)methyl]-7H-purin-2-yl}-1,2,4-oxadiazol-5(4H)-one (racemic) | | 590 | 590 |
| 23.80 | 10.74 | 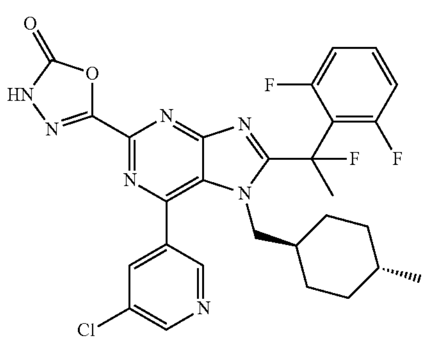 [SMILES: CC(F)(c1c(F)cccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(2,6-difluorophenyl)-1-fluoroethyl]-7-[(trans-4-methylcyclohexyl)methyl]-7H-purin-2-yl}-1,3,4-oxadiazol-2(3H)-one (enantiomer 1) | | 584 | 584 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.81 | 0.289 | 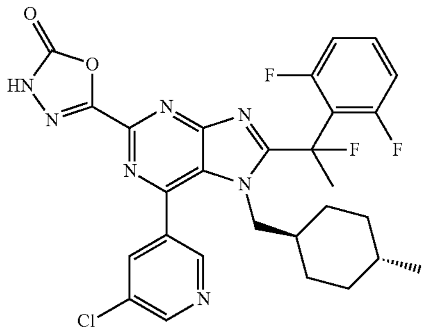 [SMILES: CC(F)(c1c(F)cccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(2,6-difluorophenyl)-1-fluoroethyl]-7-[(trans-4-methylcyclohexyl)methyl]-7H-purin-2-yl}-1,3,4-oxadiazol-2(3H)-one (enantiomer 2) | | 584 | 584 |
| 23.82 | 7.630 | 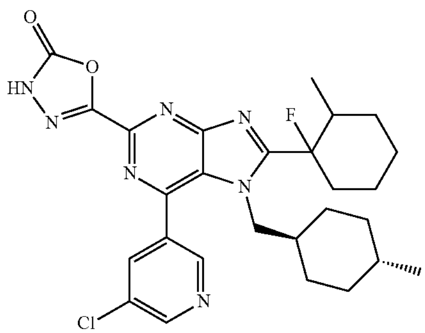 [SMILES: CC1CCCCC1(F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-(1-fluoro-2-methylcyclohexyl)-7-[(trans-4-methylcyclohexyl)methyl]-7H-purin-2-yl}-1,3,4-oxadiazol-2(3H)-one (racemic diastereomer 1) | | 540 | 540 |
| 23.83 | 6.305 | 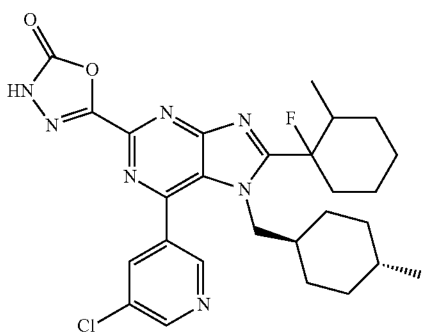 [SMILES: CC1CCCCC1(F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-(1-fluoro-2-methylcyclohexyl)-7-[(trans-4-methylcyclohexyl)methyl]-7H-purin-2-yl}-1,3,4-oxadiazol-2(3H)-one (racemic diastereomer 2) | | 540 | 540 |
| 23.84 | 16.48 | 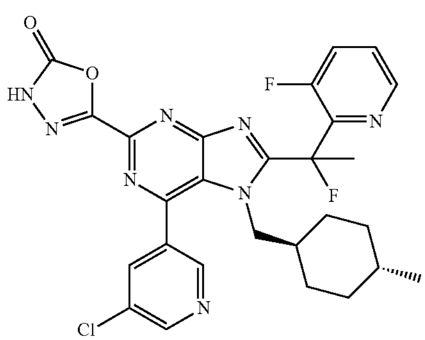 [SMILES: CC(F)(c1ncccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,3,4-oxadiazol-2(3H)-one (enantiomer 1) | | 567 | 567 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.85 | 0.359 | 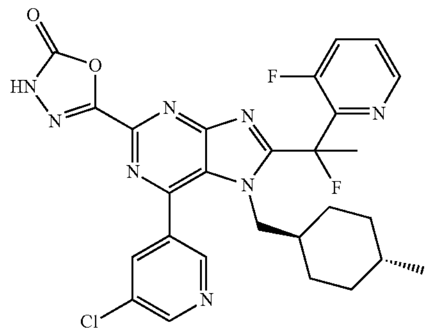 [SMILES: CC(F)(c1ncccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,3,4-oxadiazol-2(3H)-one (enantiomer 2) | | 567 | 567 |
| 23.86 | 0.675 | 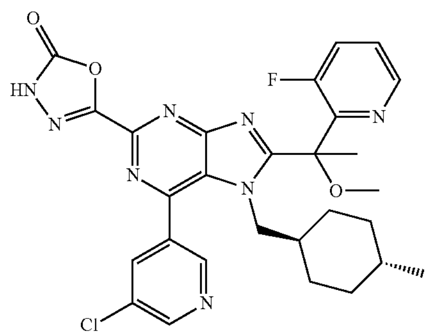 [SMILES: COC(C)(c1ncccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(3-fluoropyridin-2-yl)-1-methoxyethyl]-7-[(trans-4-methylcyclohexyl)methyl]-7H-purin-2-yl}-1,3,4-oxadiazol-2(3H)-one (enantiomer 1) | | 579 | 579 |
| 23.87 | 19.63 | 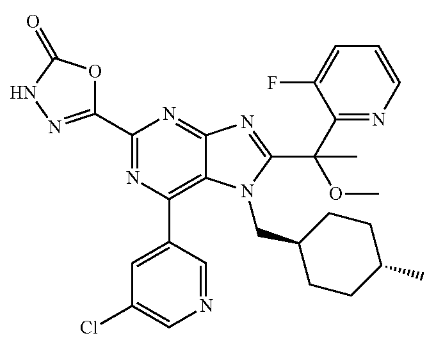 [SMILES: COC(C)(c1ncccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(3-fluoropyridin-2-yl)-1-methoxyethyl]-7-[(trans-4-methylcyclohexyl)methyl]-7H-purin-2-yl}-1,3,4-oxadiazol-2(3H)-one (enantiomer 2) | | 579 | 579 |
| 23.88 | 0.598 | 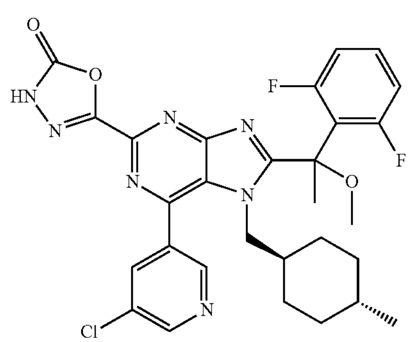 [SMILES: COC(C)(c1c(F)cccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(2,6-difluorophenyl)-1-methoxyethyl]-7-[(trans-4-methylcyclohexyl)methyl]-7H-purin-2-yl}-1,3,4-oxadiazol-2(3H)-one (enantiomer 1) | | 596 | 596 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.89 | 5.124 | 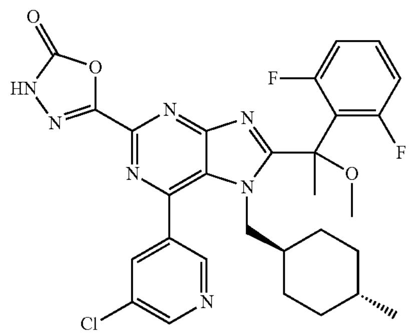 [SMILES: COC(C)(c1c(F)cccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(2,6-difluorophenyl)-1-methoxyethyl]-7-[(trans-4-methylcyclohexyl)methyl]-7H-purin-2-yl}-1,3,4-oxadiazol-2(3H)-one (enantiomer 2) | | 596 | 596 |
| 23.90 | 7.413 | 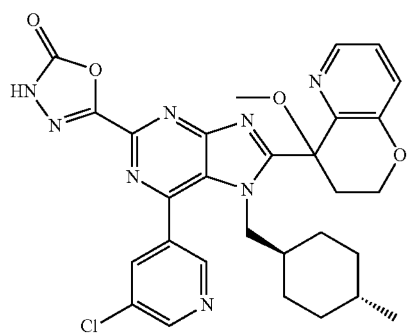 [SMILES: COC1(c2nc3nc(-c4n[nH]c(=O)o4)nc(-c4cncc(Cl)c4)c3n2C[C@H]2CC[C@H](C)CC2)CCOc2cccnc21] | 5-{6-(5-chloropyridin-3-yl)-8-(4-methoxy-3,4-dihydro-2H-pyrano[3,2-b]pyridin-4-yl)-7-[(trans-4-methylcyclohexyl)methyl]-7H-purin-2-yl}-1,3,4-oxadiazol-2(3H)-one (racemate) | | 589 | 589 |
| 23.91 | 12.96 | 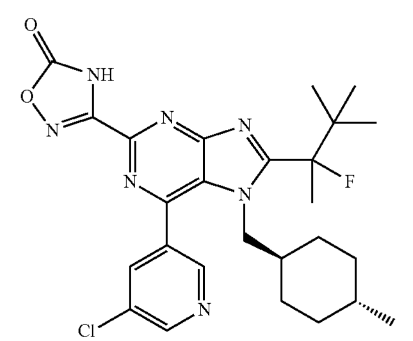 [SMILES: CC(C)(C)C(C)(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-(1-fluoro-1,2,2-trimethylpropyl)-7-[(trans-4-methylcyclohexyl)methyl]-7H-purin-2-yl}-1,2,4-oxadiazol-5(4H)-one (racemate) | | 528 | 528 |
| 23.92 | 2.447 | 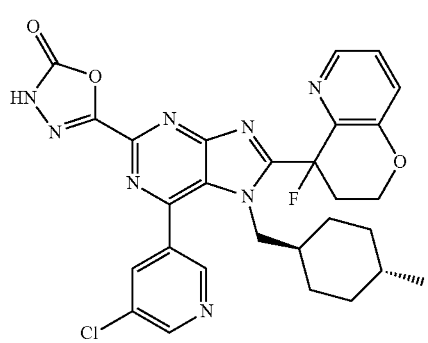 [SMILES: C[C@H]1CC[C@H](Cn2c(C3(F)CCOc4cccnc43)nc3nc(-c4n[nH]c(=O)o4)nc(-c4cncc(Cl)c4)c32)CC1] | 5-{6-(5-chloropyridin-3-yl)-8-(4-fluoro-3,4-dihydro-2H-pyrano[3,2-b]pyridin-4-yl)-7-[(trans-4-methylcyclohexyl)methyl]-7H-purin-2-yl}-1,3,4-oxadiazol-2(3H)-one (racemate) | | 577 | 577 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.93 | 0.452 | 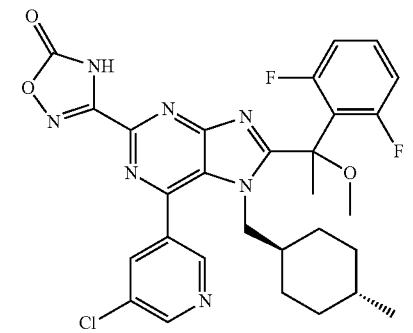 [SMILES: COC(C)(c1c(F)cccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2,6-difluorophenyl)-1-methoxyethyl]-7-[(trans-4-methylcyclohexyl)methyl]-7H-purin-2-yl}-1,2,4-oxadiazol-5(4H)-one (enantiomer 2) | | 596 | 596 |
| 23.94 | 23.41 | 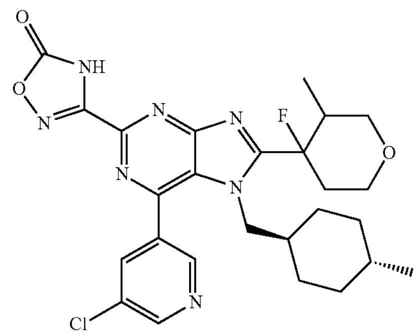 [SMILES: CC1COCCC1(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-(4-fluoro-3-methyltetrahydro-2H-pyran-4-yl)-7-[(trans-4-methylcyclohexyl)methyl]-7H-purin-2-yl}-1,2,4-oxadiazol-5(4H)-one (racemic diastereomer 1) | | 542 | 542 |
| 23.95 | 4.331 | 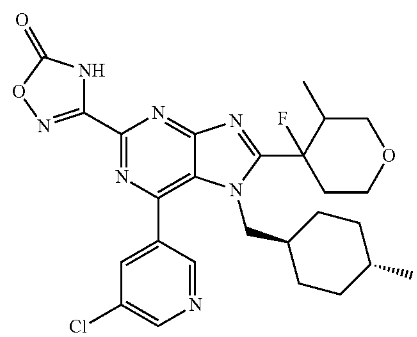 [SMILES: CC1COCCC1(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-(4-fluoro-3-methyltetrahydro-2H-pyran-4-yl)-7-[(trans-4-methylcyclohexyl)methyl]-7H-purin-2-yl}-1,2,4-oxadiazol-5(4H)-one (racemic diastereomer 2) | | 542 | 542 |
| 23.96 | 12.11 | 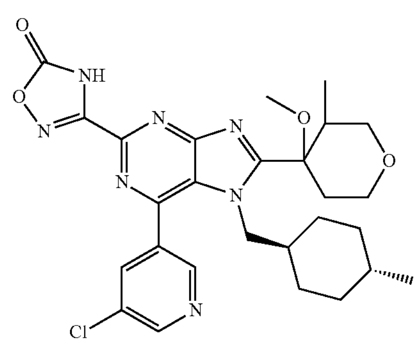 [SMILES: COC1(c2nc3nc(-c4noc(=O)[nH]4)nc(-c4cncc(Cl)c4)c3n2C[C@H]2CC[C@H](C)CC2)CCOCC1C] | 1,5-anhydro-3-C-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-2,4-dideoxy-2-methyl-3-O-methylpentitol (racemic diastereomer 1) | | 554 | 554 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.97 | 11.29 | 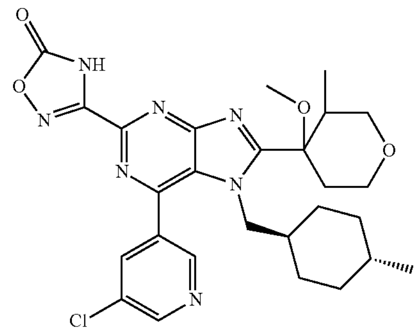 [SMILES: COC1(c2nc3nc(-c4noc(=O)[nH]4)nc(-c4cncc(Cl)c4)c3n2C[C@H]2CC[C@H](C)CC2)CCOCC1C] | 1,5-anhydro-3-C-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-2,4-dideoxy-2-methyl-3-O-methylpentitol (racemic diastereomer 2) | | 554 | 554 |
| 23.98 | 9.739 | 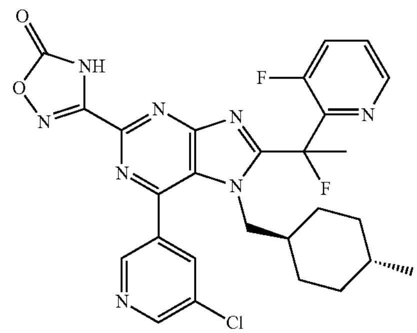 [SMILES: CC(F)(c1ncccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,2,4-oxadiazol-5(4H)-one (enantiomer 1) | | 567 | 567 |
| 23.99 | 0.315 | 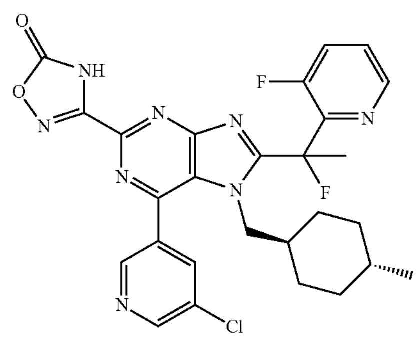 [SMILES: CC(F)(c1ncccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,2,4-oxadiazol-5(4H)-one (enantiomer 2) | | 567 | 567 |
| 23.100 | 5.940 | 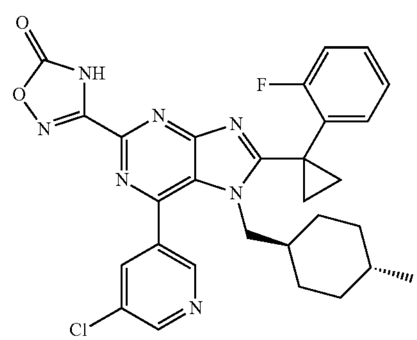 [SMILES: C[C@H]1CC[C@H](Cn2c(C3(c4ccccc4F)CC3)nc3nc(-c4noc(=O)[nH]4)nc(-c4cncc(Cl)c4)c32)CC1] | 3-{6-(5-chloropyridin-3-yl)-8-[1-(2-fluorophenyl)cyclopropyl]-7-[(trans-4-methylcyclohexyl)methyl]-7H-purin-2-yl}-1,2,4-oxadiazol-5(4H)-one | | 560 | 560 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.101 | 30.06 | 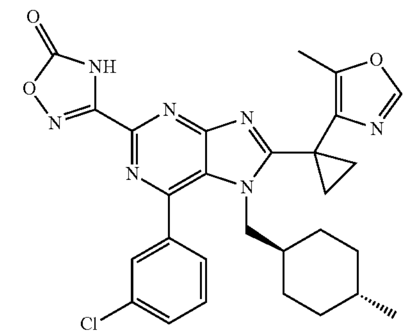 [SMILES: Cc1ocnc1C1(c2nc3nc(-c4noc(=O)[nH]4)nc(-c4cccc(Cl)c4)c3n2C[C@H]2CC[C@H](C)CC2)CC1] | 3-{6-(3-chlorophenyl)-7-[(trans-4-methylcyclohexyl)methyl]-8-[1-(5-methyl-1,3-oxazol-4-yl)cyclopropyl]-7H-purin-2-yl}-1,2,4-oxadiazol-5(4H)-one | | 546 | 546 |
| 23.102 | 16.96 | 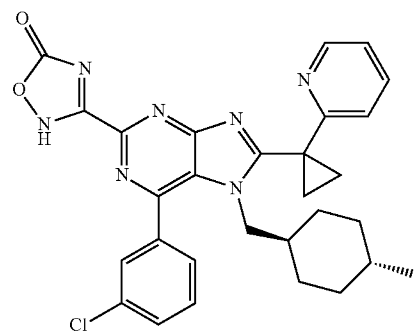 [SMILES: C[C@H]1CC[C@H](Cn2c(C3(c4ccccn4)CC3)nc3nc(-c4nc(=O)o[nH]4)nc(-c4cccc(Cl)c4)c32)CC1] | 3-[6-(3-chlorophenyl)-7-[(trans-4-methylcyclohexyl)methyl]-8-(1-pyridin-2-ylcyclopropyl)-7H-purin-2-yl]-1,2,4-oxadiazol-5(2H)-one | | 542 | 542 |
| 23.103 | 1.700 | 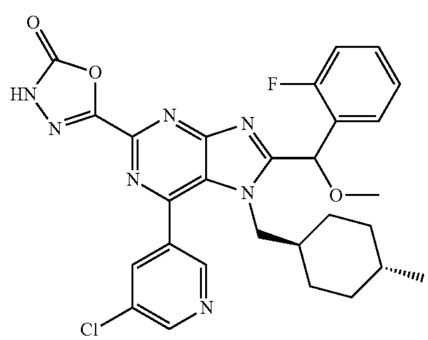 [SMILES: COC(c1ccccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[(2-fluorophenyl)(methoxy)methyl]-7-[(trans-4-methylcyclohexyl)methyl]-7H-purin-2-yl}-1,3,4-oxadiazol-2(3H)-one (racemate) | | 564 | 564 |
| 23.104 | 1.033 | 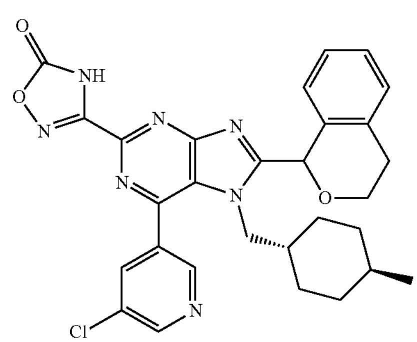 [SMILES: C[C@H]1CC[C@H](Cn2c(C3OCCc4ccccc43)nc3nc(-c4noc(=O)[nH]4)nc(-c4cncc(Cl)c4)c32)CC1] | 3-{6-(5-chloropyridin-3-yl)-8-(3,4-dihydro-1H-isochromen-1-yl)-7-[(trans-4-methylcyclohexyl)methyl]-7H-purin-2-yl}-1,2,4-oxadiazol-5(4H)-one (enantiomer 1) | | 558 | 558 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.105 | 2.163 | 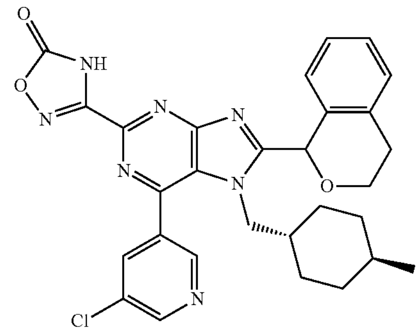 [SMILES: C[C@H]1CC[C@H](Cn2c(C3OCCc4ccccc43)nc3nc(-c4noc(=O)[nH]4)nc(-c4cncc(Cl)c4)c32)CC1] | 3-{6-(5-chloropyridin-3-yl)-8-(3,4-dihydro-1H-isochromen-1-yl)-7-[(trans-4-methylcyclohexyl)methyl]-7H-purin-2-yl}-1,2,4-oxadiazol-5(4H)-one (enantiomer 2) | | 558 | 558 |
| 23.106 | 3.933 | 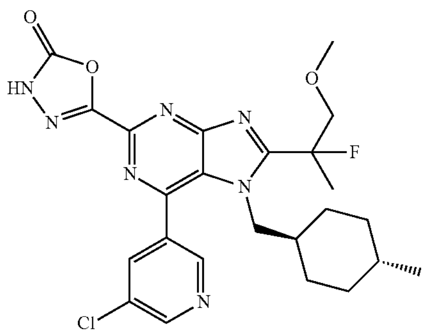 [SMILES: COCC(C)(F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-(1-fluoro-2-methoxy-1-methylethyl)-7-[(trans-4-methylcyclohexyl)methyl]-7H-purin-2-yl}-1,3,4-oxadiazol-2(3H)-one (racemate) | | 516 | 516 |
| 23.107 | 5.366 | 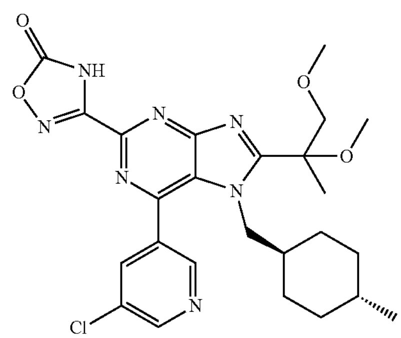 [SMILES: COCC(C)(OC)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-(1,2-dimethoxy-1-methylethyl)-7-[(trans-4-methylcyclohexyl)methyl]-7H-purin-2-yl}-1,2,4-oxadiazol-5(4H)-one (racemate) | | 528 | 528 |
| 23.108 | 3.769 | 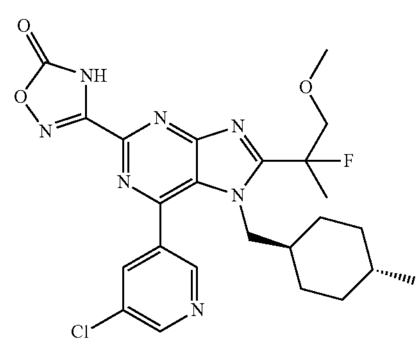 [SMILES: COCC(C)(F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-(1-fluoro-2-methoxy-1-methylethyl)-7-[(trans-4-methylcyclohexyl)methyl]-7H-purin-2-yl}-1,2,4-oxadiazol-5(4H)-one (racemate) | | 516 | 516 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.109 | 0.707 | 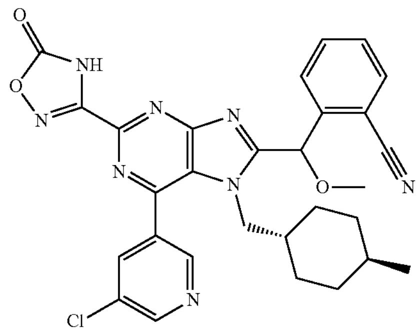 [SMILES: COC(c1ccccc1C#N)c1nc2nc(-c3noc(=O)[nH]3)nc(-c3cncc(Cl)c3)c2n1C[C@H]1CC[C@H](C)CC1] | 2-{[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl](methoxy)methyl}benzonitrile (racemate) | | 571 | 571 |
| 23.110 | 0.515 | 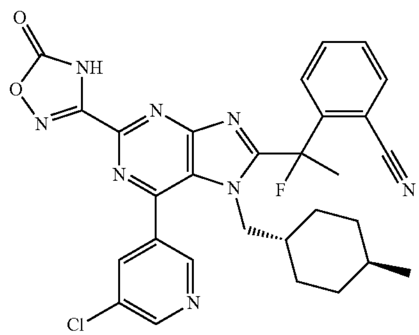 [SMILES: CC(F)(c1ccccc1C#N)c1nc2nc(-c3noc(=O)[nH]3)nc(-c3cncc(Cl)c3)c2n1C[C@H]1CC[C@H](C)CC1] | 2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-fluoroethyl}benzonitrile (racemate) | | 573 | 573 |
| 23.111 | 0.4350 | 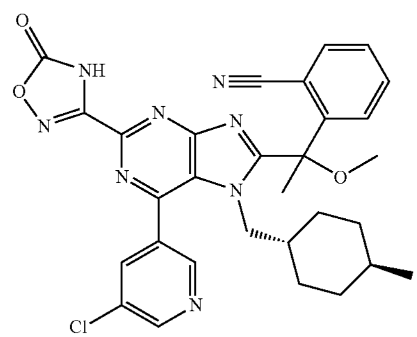 [SMILES: COC(C)(c1ccccc1C#N)c1nc2nc(-c3noc(=O)[nH]3)nc(-c3cncc(Cl)c3)c2n1C[C@H]1CC[C@H](C)CC1] | 2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-methoxyethyl}benzonitrile (enantiomer 1) | | 585 | 585 |
| 23.112 | 2.775 | 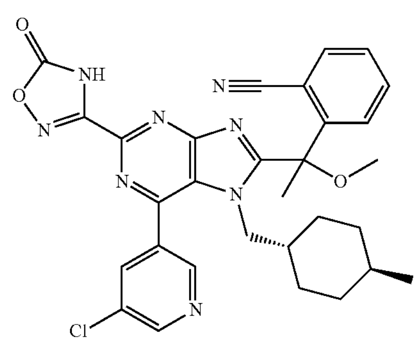 [SMILES: COC(C)(c1ccccc1C#N)c1nc2nc(-c3noc(=O)[nH]3)nc(-c3cncc(Cl)c3)c2n1C[C@H]1CC[C@H](C)CC1] | 2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-methoxyethyl}benzonitrile (enantiomer 2) | | 585 | 585 |

TABLE 23-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 23.113 | 1.388 | 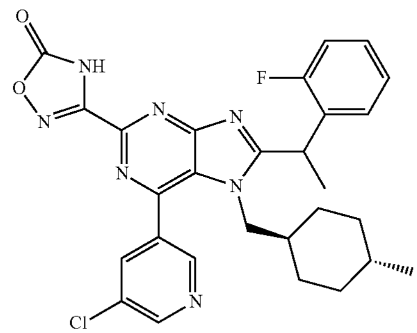 [SMILES: CC(c1ccccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2-fluorophenyl)ethyl]-7-[(trans-4-methylcyclohexyl)methyl]-7H-purin-2-yl}-1,2,4-oxadiazol-5(4H)-one (racemate) | | 548 | 548 |
| 23.114 | 2.126 | 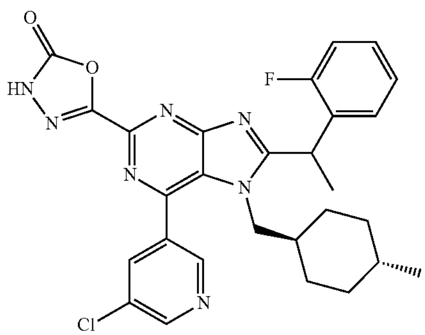 [SMILES: CC(c1ccccc1F)c1nc2nc(-c3n[nH]c(=O)o3)nc(-c3cncc(Cl)c3)c2n1C[C@H]1CC[C@H](C)CC1] | 5-{6-(5-chloropyridin-3-yl)-8-[1-(2-fluorophenyl)ethyl]-7-[(trans-4-methylcyclohexyl)methyl]-7H-purin-2-yl}-1,3,4-oxadiazol-2(3H)-one (racemate) | | 548 | 548 |
| 23.115 | 2.229 | 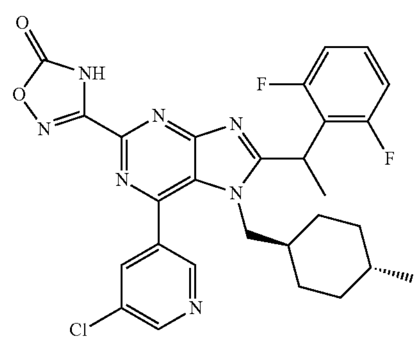 [SMILES: CC(c1c(F)cccc1F)c1nc2nc(-c3noc(=O)[nH]3)nc(-c3cncc(Cl)c3)c2n1C[C@H]1CC[C@H](C)CC1] | 3-{6-(5-chloropyridin-3-yl)-8-[1-(2,6-difluorophenyl)ethyl]-7-[(trans-4-methylcyclohexyl)methyl]-7H-purin-2-yl}-1,2,4-oxadiazol-5(4H)-one (racemate) | | 566 | 566 |
| 23.116 | 2.378 | 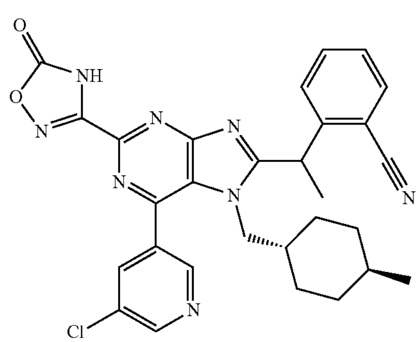 [SMILES: CC(c1ccccc1C#N)c1nc2nc(-c3noc(=O)[nH]3)nc(-c3cncc(Cl)c3)c2n1C[C@H]1CC[C@H](C)CC1] | 2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]ethyl}benzonitrile (racemate) | | 555 | 555 |

Example 24.1

5-{6-(3-chlorophenyl)-8-cyclopropyl-7-[(trans-4-methylcyclohexyl)methyl]-7H-purin-2-yl}-1,3,4-oxadiazol-2(3H)-one

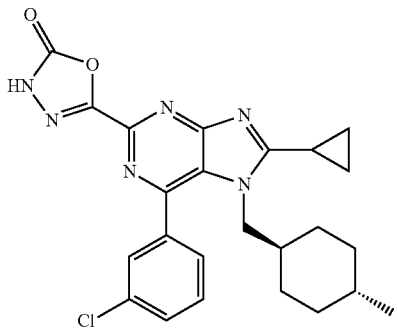 [SMILES: C[C@H]1CC[C@H](Cn2c(C3CC3)nc3nc(-c4n[nH]c(=O)o4)nc(-c4cccc(Cl)c4)c32)CC1]

Step 1: 8-bromo-6-(3-chlorophenyl)-7-(((trans)-4-methylcyclohexyl)methyl)-7H-purine-2-carbonitrile (Preparative Example 16.3, 150 mg, 0.34 mmol), cyclopropylboronic acid (57.5 mg, 0.67 mmol), and potassium phosphate (142 mg, 0.67 mmol) were added to degassed toluene (5 mL) and water (0.5 mL). The resulting mixture was then degassed for another 5 minutes before adding PdCl$_2$(dppf) (50.0 mg, 0.07 mmol). The reaction was sealed and heated at 120° C. in a microwave for 1 hour. The reaction mixture was diluted with water (30 mL) and extracted with EtOAc (2×30 mL). The combined organic extracts were dried over anhydrous Na$_2$SO$_4$, filtered, and concentrated. The residue was purified on a silica gel column (0 to 100% EtOAc/hexanes) to afford 6-(3-chlorophenyl)-8-cyclopropyl-7-(((trans)-4-methylcyclohexyl)methyl)-7H-purine-2-carbonitrile.

Steps 2-4: Following a procedure similar to that described in Example 23.1 (Steps 2-4), 6-(3-chlorophenyl)-8-cyclopropyl-7-(((trans)-4-methylcyclohexyl)methyl)-7H-purine-2-carbonitrile was converted to 5-{6-(3-chlorophenyl)-8-cyclopropyl-7-[(trans-4-methylcyclohexyl)methyl]-7H-purin-2-yl}-1,3,4-oxadiazol-2(3H)-one. $^1$H NMR (400 MHz, CD$_3$OD): δ 7.79-7.75 (m, 1H), 7.69-7.58 (m, 3H), 4.07 (d, J=7.1 Hz, 2H), 2.38-2.29 (m, 1H), 1.58-1.48 (m, 2H), 1.41-1.25 (m, 4H), 1.23-1.05 (m, 2H), 1.04-0.96 (m, 2H), 0.89-0.80 (m, 2H), 0.78 (d, J=6.5 Hz, 3H), 0.66-0.51 (m, 2H). MS (ES)=465 (M+1)$^+$.

Example 24.2

3-{6-(3-chlorophenyl)-8-cyclopropyl-7-[(trans-4-methylcyclohexyl)methyl]-7H-purin-2-yl}-1,2,4-oxadiazol-5(4H)-one

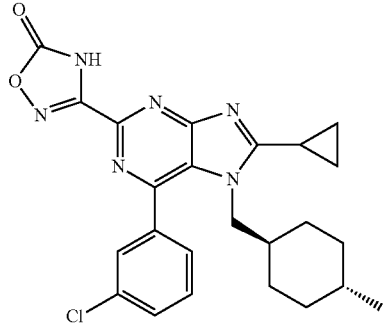 [SMILES: C[C@H]1CC[C@H](Cn2c(C3CC3)nc3nc(-c4noc(=O)[nH]4)nc(-c4cccc(Cl)c4)c32)CC1]

Using a procedure similar to that described in Example 23.2 (Steps 1 and 2), 6-(3-chlorophenyl)-8-cyclopropyl-7-(((trans)-4-methylcyclohexyl)methyl)-7H-purine-2-carbonitrile (Example 24.1, Step 1) was converted to 3-{6-(3-chlorophenyl)-8-cyclopropyl-7-[(trans-4-methylcyclohexyl)methyl]-7H-purin-2-yl}-1,2,4-oxadiazol-5(4H)-one. $^1$H NMR (400 MHz, CD$_3$OD) δ 7.85-7.86 (m, 1H), 7.64-7.69 (m, 3H), 4.00 (d, J=6.8 Hz, 2H), 1.45-1.54 (m, 2H), 1.23-1.35 (m, 5H), 0.96-1.12 (m, 2H), 0.77-0.89 (m, 4H), 0.72 (d, J=6.2 Hz, 3H), 0.50-0.53 (m, 2H). MS (APCI)=465 (M+1)$^+$.

Example 24.3

3-{6-(3-chlorophenyl)-7-[(trans-4-methylcyclohexyl)methyl]-8-[1-(tetrahydro-2H-pyran-4-yl)ethyl]-7H-purin-2-yl}-1,2,4-oxadiazol-5(4H)-one

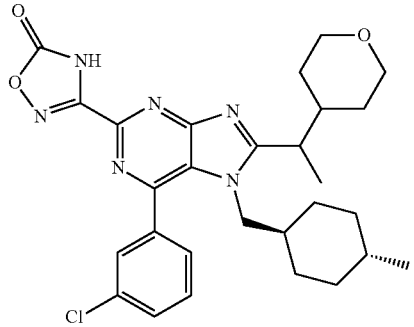 [SMILES: CC(c1nc2nc(-c3noc(=O)[nH]3)nc(-c3cccc(Cl)c3)c2n1C[C@H]1CC[C@H](C)CC1)C1CCOCC1]

Step 1: A microwave via was charged with 8-bromo-6-(3-chlorophenyl)-7-(((trans)-4-methylcyclohexyl)methyl)-7H-purine-2-carbonitrile (Preparative Example 16.3, 330 mg, 0.75 mmol) and 4,4,5,5-tetramethyl-2-(1-(tetrahydro-2H-pyran-4-yl)vinyl)-1,3,2-dioxaborolane (190 mg, 0.79 mmol). Dimethoxyethane (6.0 mL) was added to the vial and the mixture was degassed with N$_2$ for 15 minutes. Next, Pd(PPh$_3$)$_4$ (200 mg, 0.17 mmol) and 3.3 N Na$_2$CO$_3$ solution (0.75 mL, 2.5 mmol) were added sequentially and the reaction was heated at 75° C. under microwave irradiation for 1 hour. The reaction was cooled, diluted with water (10 mL) and extracted with ethyl acetate (2×10 mL). The combined organic extracts were washed with water (10 mL) and brine (10 mL), dried over sodium sulfate, filtered, and concentrated. Purification of the residue on a silica gel column (0 to 60% EtOAc/hexanes) afforded 6-(3-chlorophenyl)-7-(((trans)-4-methylcyclohexyl)methyl)-8-(1-(tetrahydro-2H-pyran-4-yl)vinyl)-7H-purine-2-carbonitrile. MS (ES)=476 (M+1)$^+$.

Step 2: A round bottom flask was charged with Pd/C (30 mg) under N$_2$. A solution of 6-(3-chlorophenyl)-7-(((trans)-4-methylcyclohexyl)methyl)-8-(1-(tetrahydro-2H-pyran-4-yl)vinyl)-7H-purine-2-carbonitrile (24 mg, 0.05 mmol) in MeOH (3.0 mL) was added. The reaction mixture was stirred at room temperature under H$_2$ (1 atm) for 2 hours, and then filtered through celite washing the filter cake with MeOH. The filtrate was concentrated in vacuo and purification of the residue on a silica gel column (0 to 70% EtOAc/hexanes) afforded 6-(3-chlorophenyl)-7-(((trans)-4-methylcyclohexyl)methyl)-8-(1-(tetrahydro-2H-pyran-4-yl)ethyl)-7H-purine-2-carbonitrile. MS (ES)=478 (M+1)$^+$.

Step 3: Using a procedure analogous to that described in Example 23.2 (Steps 1 and 2), 6-(3-chlorophenyl)-7-(((trans)-4-methylcyclohexyl)methyl)-8-(1-(tetrahydro-2H-pyran-4-yl)ethyl)-7H-purine-2-carbonitrile was converted to 3-{6-(3-chlorophenyl)-7-[(trans-4-methylcyclohexyl)methyl]-8-[1-(tetrahydro-2H-pyran-4-yl)ethyl]-7H-purin-2-yl}-1,2,4-oxadiazol-5(4H)-one. $^1$H NMR (400 MHz, CD$_3$OD) δ7.82 (s, 1H), 7.61-7.68 (m, 3H), 3.94-4.09 (m, 3H), 3.88 (d, J=11.6 Hz, 1H), 3.40-3.48 (m, 2H), 3.15 (dd, J=8.4, 7.2 Hz, 1H), 2.13-2.15 (m, 1H), 1.91 (d, J=11.6 Hz, 1H), 1.51-1.54 (m, 3H), 1.43 (d, J=6.8 Hz, 3H), 1.38-1.44 (m, 2H), 1.19-1.11 (m, 1H), 1.00-1.11 (m, 2H), 0.79-1.91 (m, 3H), 0.76 (d, J=6.4 Hz, 3H), 0.51-0.65 (m, 2H). MS (ES)=537 (M+1)$^+$.

TABLE 24

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 24.1 | 62.79 | 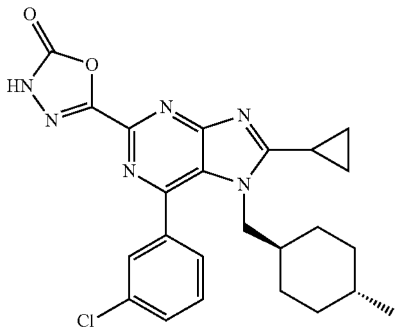 [SMILES: C[C@H]1CC[C@H](Cn2c(C3CC3)nc3nc(-c4n[nH]c(=O)o4)nc(-c4cccc(Cl)c4)c32)CC1] | 5-{6-(3-chlorophenyl)-8-cyclopropyl-7-[(trans-4-methylcyclohexyl)methyl]-7H-purin-2-yl}-1,3,4-oxadiazol-2(3H)-one | | 465 | 465 |
| 24.2 | 41.69 | 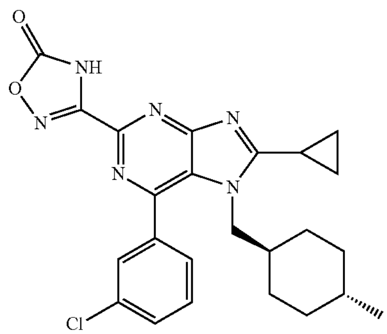 [SMILES: C[C@H]1CC[C@H](Cn2c(C3CC3)nc3nc(-c4noc(=O)[nH]4)nc(-c4cccc(Cl)c4)c32)CC1] | 3-{6-(3-chlorophenyl)-8-cyclopropyl-7-[(trans-4-methylcyclohexyl)methyl]-7H-purin-2-yl}-1,2,4-oxadiazol-5(4H)-one | | 465 | 465 |
| 24.3 | 14.24 | 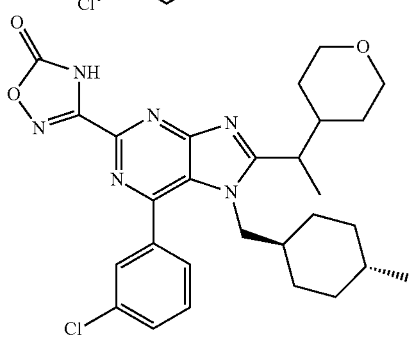 | 3-{6-(3-chlorophenyl)-7-[(trans-4-methylcyclohexyl)methyl]-8-[1-(tetrahydro-2H-pyran-4-yl)ethyl]-7H-purin-2-yl}-1,2,4-oxadiazol-5(4H)-one | | 537 | 537 |

Example 25.1

5-chloro-1-{7-[(trans-4-methylcyclohexyl)methyl]-2-(5-oxo-4,5-dihydro-1,2,4-oxadiazol-3-yl)-8-[(3R)-3-phenylmorpholin-4-yl]-7H-purin-6-yl}pyridin-2(1H)-one

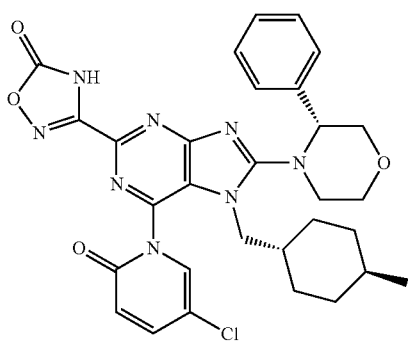 [SMILES: C[C@H]1CC[C@H](Cn2c(N3CCOC[C@H]3c3ccccc3)nc3nc(-c4noc(=O)[nH]4)nc(-n4cc(Cl)ccc4=O)c32)CC1]

Step 1: A mixture of (R)-4-(2,6-dichloro-7-((trans-4-methylcyclohexyl)methyl)-7H-purin-8-yl)-3-phenylmorpholine (Preparative Example 12.5; 500 mg, 1.09 mmol), 5-chloropyridin-2(1H)-one (160 mg, 1.20 mmol) and Cs$_2$CO$_3$ (430 mg, 1.30 mmol) in DMF (15 mL) was heated at 75° C. for 16 hours. The reaction was then cooled to room temperature and partitioned between EtOAc and water. The two layers were separated and the aqueous layer was extracted three times with EtOAc. The combined organic layers were washed with brine, dried over anhydrous Na$_2$SO$_4$, filtered, and concentrated in vacuo. Purification of the residue on a silica gel column (0 to 50% EtOAc/hexanes) afforded both 5-chloro-1-(2-chloro-7-(((trans)-4-methylcyclohexyl)methyl)-8-((R)-3-phenylmorpholino)-7H-purin-6-yl)pyridin-2(1H)-one; MS (APCI)=553 (M+1)$^+$ and (R)-4-(2-chloro-6-((5-chloropyridin-2-yl)oxy)-7-(((trans)-4-methylcyclohexyl)methyl)-7H-purin-8-yl)-3-phenylmorpholine; MS (APCI)=553 (M+1)$^+$ Step 2: A mixture of 5-chloro-1-(2-chloro-7-(((trans)-4-methylcyclohexyl)methyl)-8-((R)-3-phenylmorpholino)-7H-purin-6-yl)pyridin-2(1H)-one (150 mg, 0.27 mmol) and zinc cyanide (16 mg, 0.16 mmol) in DMA (5 mL) was degassed with argon for 20 minutes. Tetrakis(triphenylphosphine)palladium(0) (31 mg, 0.027 mmol) was then added and the mixture was degassed for an additional 5 minutes. The reaction vial was sealed and heated at 120° C. for 5 hours. The reaction was then cooled to room temperature and diluted with water (10 mL). The mixture was extracted with EtOAc (2×8 mL) and the combined organic extracts were dried over anhydrous $Na_2SO_4$, filtered, and concentrated in vacuo. The residue was purified on a silica gel column (0 to 50% EtOAc/hexanes) to afford 6-(5-chloro-2-oxopyridin-1(2H)-yl)-7-(((trans)-4-methylcyclohexyl)methyl)-8-((R)-3-phenylmorpholino)-7H-purine-2-carbonitrile. MS (APCI)=544 (M+1)$^+$.

Steps 3-4: Using procedures similar to those described in Example 23.41 (Steps 2 and 3), 6-(5-chloro-2-oxopyridin-1(2H)-yl)-7-(((trans)-4-methylcyclohexyl)methyl)-8-((R)-3-phenylmorpholino)-7H-purine-2-carbonitrile was converted to 5-chloro-1-{7-[(trans-4-methylcyclohexyl)methyl]-2-(5-oxo-4,5-dihydro-1,2,4-oxadiazol-3-yl)-8-[(3R)-3-phenylmorpholin-4-yl]-7H-purin-6-yl}pyridin-2(1H)-one. $^1$H NMR (400 MHz, CDCl$_3$) δ7.79 (s, 1H), 7.42-7.57 (m, 3H), 7.28-7.38 (m, 3H), 6.63 (d, J=9.6 Hz, 1H), 5.24 (br s, 1H), 3.43-4.34 (m, 8H), 1.56-1.64 (m, 2H), 0.96-1.11 (m, 4H), 0.80 (d, J=6.8 Hz, 3H), 0.48-0.73 (m, 4H). MS (ES)=603 (M+1)$^+$.

Example 25.2

3-{6-[(5-chloropyridin-2-yl)oxy]-7-[(trans-4-methylcyclohexyl)methyl]-8-[(3R)-3-phenylmorpholin-4-yl]-7H-purin-2-yl}-1,2,4-oxadiazol-5(4H)-one

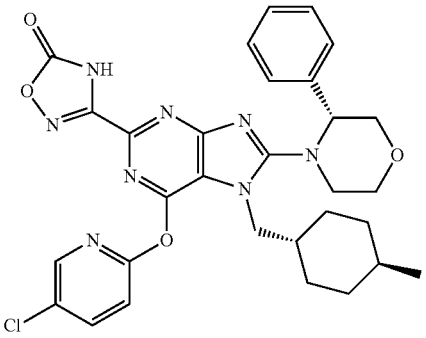 [SMILES: C[C@H]1CC[C@H](Cn2c(N3CCOC[C@H]3c3ccccc3)nc3nc(-c4noc(=O)[nH]4)nc(Oc4ccc(Cl)cn4)c32)CC1]

Step 1: Using a procedure similar to that described in Example 25.1 (Step 2), (R)-4-(2-chloro-6-((5-chloropyridin-2-yl)oxy)-7-(((trans)-4-methylcyclohexyl)methyl)-7H-purin-8-yl)-3-phenylmorpholine (isolated in Example 25.1, Step 1) was converted to 6-((5-chloropyridin-2-yl)oxy)-7-(((trans)-4-methylcyclohexyl)methyl)-8-((R)-3-phenylmorpholino)-7H-purine-2-carbonitrile. MS (APCI)=544 (M+1)$^+$.

Steps 2-3: Using procedures similar to those described in Example 23.41 (Steps 2 and 3), 6-((5-chloropyridin-2-yl)oxy)-7-(((trans)-4-methylcyclohexyl)methyl)-8-((R)-3-phenylmorpholino)-7H-purine-2-carbonitrile was converted to 3-{6-[(5-chloropyridin-2-yl)oxy]-7-[(trans-4-methylcyclohexyl)methyl]-8-[(3R)-3-phenylmorpholin-4-yl]-7H-purin-2-yl}-1,2,4-oxadiazol-5(4H)-one. $^1$H NMR (400 MHz, CDCl$_3$) δ 8.28 (d, J=2.4 Hz, 1H), 7.83 (dd, J=8.8, 2.4 Hz, 1H), 7.45 (d, J=6.8 Hz, 2H), 7.16-7.36 (m, 4H), 4.91 (br s, 1H), 3.40-4.22 (m, 6H), 3.40-3.55 (m, 2H), 1.86 (m, 1H), 1.61-1.64 (m, 2H), 1.20-1.45 (m, 3H), 0.98 (q, J=12.0 Hz, 2H), 0.86 (d, J=6.4 Hz, 3H), 0.69-0.82 (m, 2H). MS (ES)=603 (M+1)$^+$.

Example 25.3

5-{6-[(5-chloropyridin-2-yl)oxy]-7-[(trans-4-methylcyclohexyl)methyl]-8-[(3R)-3-phenylmorpholin-4-yl]-7H-purin-2-yl}-1,3,4-oxadiazol-2(3H)-one

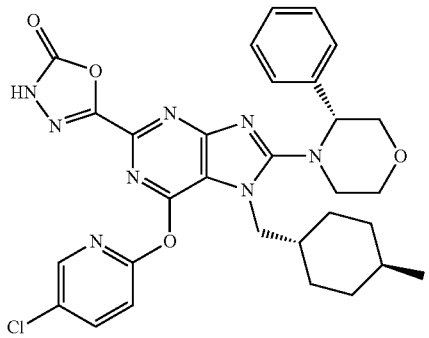

Using procedures similar to those described in Example 16.7 (Steps 1-3), 6-((5-chloropyridin-2-yl)oxy)-7-(((trans)-4-methylcyclohexyl)methyl)-8-((R)-3-phenylmorpholino)-7H-purine-2-carbonitrile (Example 25.2, Step 1) was converted to 5-{6-[(5-chloropyridin-2-yl)oxy]-7-[(trans-4-methylcyclohexyl)methyl]-8-[(3R)-3-phenylmorpholin-4-yl]-7H-purin-2-yl}-1,3,4-oxadiazol-2(3H)-one. $^1$H NMR (400 MHz, CDCl$_3$) δ 8.27 (d, J=2.4 Hz, 1H), 7.81 (dd, J=8.4, 2.4 Hz, 1H), 7.44 (d, J=7.2 Hz, 2H), 7.19-7.29 (m, 4H), 4.90 (br s, 1H), 3.88-4.17 (m, 6H), 3.46 (br s, 2H), 1.84 (m, 1H), 1.61-1.64 (m, 2H), 1.20-1.41 (m, 3H), 0.96 (q, J=12.0 Hz, 2H), 0.85 (d, J=6.4 Hz, 3H), 0.67-0.81 (m, 2H). MS (ES)=603 (M+1)$^+$.

Preparation of the compounds in Table 25 was described above.

TABLE 25

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 25.1 | 1.011 | 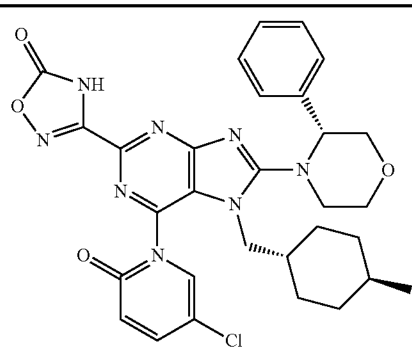 | 5-chloro-1-{7-[(trans-4-methylcyclohexyl)methyl]-2-(5-oxo-4,5-dihydro-1,2,4-oxadiazol-3-yl)-8-[(3R)-3-phenylmorpholin-4-yl]-7H-purin-6-yl}pyridin-2(1H)-one | | 603 | 603 |

TABLE 25-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 25.2 | 15.45 | 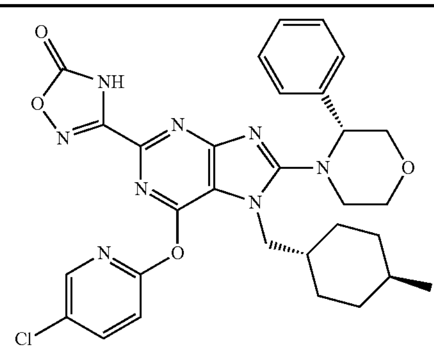 | 3-{6-[(5-chloropyridin-2-yl)oxy]-7-[(trans-4-methylcyclohexyl)methyl]-8-[(3R)-3-phenylmorpholin-4-yl]-7H-purin-2-yl}-1,2,4-oxadiazol-5(4H)-one | | 603 | 603 |
| 25.3 | 20.12 | 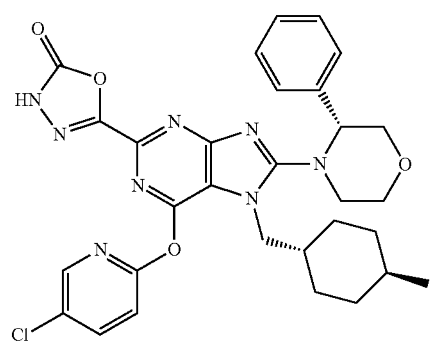 [SMILES: C[C@H]1CC[C@H](Cn2c(N3CCOC[C@H]3c3ccccc3)nc3nc(-c4n[nH]c(=O)o4)nc(Oc4ccc(Cl)cn4)c32)CC1] | 5-{6-[(5-chloropyridin-2-yl)oxy]-7-[(trans-4-methylcyclohexyl)methyl]-8-[(3R)-3-phenylmorpholin-4-yl]-7H-purin-2-yl}-1,3,4-oxadiazol-2(3H)-one | | 603 | 603 |

Example 26.2

{6-(3-chlorophenyl)-7-[(trans-4-methylcyclohexyl)methyl]-8-[(3R)-3-methylmorpholin-4-yl]-7H-purin-2-yl}acetic acid

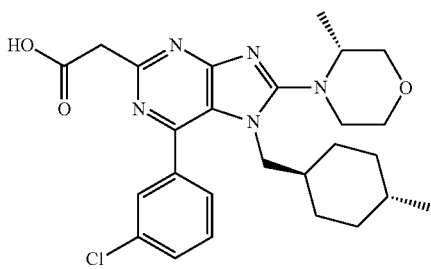 [SMILES: C[C@@H]1COCCN1c1nc2nc(CC(=O)O)nc(-c3cccc(Cl)c3)c2n1C[C@H]1CC[C@H](C)CC1]

Step 1: A microwave vial was flushed with nitrogen and charged with (R)-4-(2-chloro-6-(3-chlorophenyl)-7-(((trans)-4-methylcyclohexyl)methyl)-7H-purin-8-yl)-3-methylmorpholine (Example 16.6, Step 1; 160 mg, 0.34 mmol), 2-(2-ethoxyvinyl)-4,4,5,5-tetramethyl-1,3,2-dioxaborolane (0.08 mL, 0.37 mmol), Pd(PPh$_3$)$_4$ (39.0 mg, 0.034 mmol) and Na$_2$CO$_3$ (72.0 mg, 0.68 mmol). 1,4-dioxane (2.7 mL) and water (0.7 mL) were added, the mixture was degassed, and the reaction was sealed and irradiated in a microwave reactor at 100° C. for 15 minutes. The reaction was cooled to room temperature, diluted with water (10 mL) and extracted with ethyl acetate (3×20 mL). The combined organic extracts were washed with brine (10 mL), dried over anhydrous Na$_2$SO$_4$, filtered, and concentrated. Purification of the residue on a silica gel column (0 to 100% EtOAc/hexanes) afforded (R)-4-(6-(3-chlorophenyl)-2-(2-ethoxyvinyl)-7-((trans-4-methylcyclohexyl)methyl)-7H-purin-8-yl)-3-methylmorpholine. MS (ES)=510 (M+1)$^+$.

Step 2: To a solution of (R)-4-(6-(3-chlorophenyl)-2-(2-ethoxyvinyl)-7-((trans-4-methylcyclohexyl)methyl)-7H-purin-8-yl)-3-methylmorpholine (35.0 mg, 0.069 mmol) in THF (0.4 mL) at room temperature was added HCl (3 M in H$_2$O, 0.05 mL, 0.15 mmol) and the resulting solution was stirred at room temperature for 48 hours under a nitrogen atmosphere. The reaction was then concentrated, diluted with water (2.0 mL), and extracted with ethyl acetate (3×10 mL). The combined organic extracts were washed with brine (10 mL), dried over anhydrous Na$_2$SO$_4$, filtered, and concentrated to afford 2-(6-(3-chlorophenyl)-7-((trans-4-methylcyclohexyl)methyl)-8-((R)-3-methylmorpholino)-7H-purin-2-yl)acetaldehyde, which was carried forward to the next step without further purification. MS (ES)=482 (M+1)$^+$.

Step 3: To a stirred solution of 2-(6-(3-chlorophenyl)-7-((trans-4-methylcyclohexyl)methyl)-8-((R)-3-methylmorpholino)-7H-purin-2-yl)acetaldehyde (33.0 mg, 0.068 mmol) in 2:5:1 THF/$^t$BuOH/H$_2$O (3.5 mL) was added KH$_2$PO$_4$ (28.0 mg, 0.14 mmol), 2-methyl-2-butene (1 M in THF, 0.4 mL, 0.4 mmol), and NaClO$_2$ (34.0 mg, 0.37 mmol) sequentially at room temperature under a nitrogen atmosphere. The resulting solution was stirred for 1.5 hours. The reaction was then concentrated, diluted with water (2.0 mL), and extracted with dichloromethane (3×20 mL). The combined organic extracts were washed with brine (10 mL), dried over anhydrous Na$_2$SO$_4$, filtered, and concentrated. Purification of the residue on a C18 column (0 to 100% acetonitrile/water), followed by preparative TLC (5% MeOH/DCM, 2 elutions), and finally by semi-preparative reverse phase HPLC (20 to 90% acetonitrile/water) afforded {6-(3-chlorophenyl)-7-[(trans-4-methylcyclohexyl)methyl]-

8-[(3R)-3-methylmorpholin-4-yl]-7H-purin-2-yl}acetic acid. $^1$H NMR (400 MHz, CDCl$_3$) δ 7.63-7.66 (m, 1H), 7.46-7.57 (m, 3H), 4.84 (s, 2H), 3.76-4.01 (m, 4H), 3.51-3.69 (m, 4H), 3.40-3.49 (m, 1H), 1.42-1.51 (m, 2H), 1.39 (d, J=6.8 Hz, 3H), 0.90-1.17 (m, 2H), 0.75 (d, J=6.4 Hz, 3H), 0.71-0.83 (m, 2H), 0.42-0.69 (m, 4H). MS (ES)=498 (M+1)$^+$.

Example 26.3

3-{7-[(trans-4-methylcyclohexyl)methyl]-6-(2-methylmorpholin-4-yl)-8-[(3R)-3-phenylmorpholin-4-yl]-7H-purin-2-yl}-1,2,4-oxadiazol-5(4H)-one

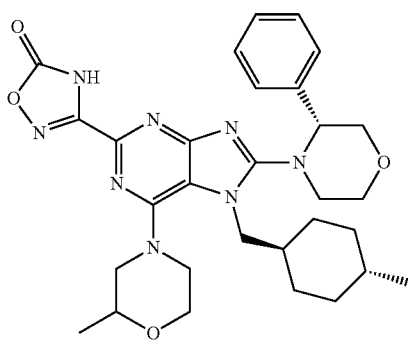 [SMILES: CC1CN(c2nc(-c3noc(=O)[nH]3)nc3nc(N4CCOC[C@H]4c4ccccc4)n(C[C@H]4CC[C@H](C)CC4)c23)CCO1]

Step 1: Lithium aluminum hydride (100 mg, 2.63 mmol) was added to a 0° C. solution of 4-benzyl-2-methylmorpholin-3-one (500 mg, 2.44 mmol) in THF (10 mL), and the reaction was stirred at 0° C. for 2 hours. After quenching the excess lithium aluminum hydride with ethyl acetate (1.0 mL), saturated Na$_2$SO$_4$ (5.0 mL) solution was added. The reaction mixture was then extracted with EtOAc (2×20 mL) and the combined organic layers were washed with water (10 mL). Evaporation of solvent in vacuo gave the crude product, which was purified on a silica gel column (0 to 50% EtOAc/Hexanes) to afford 4-benzyl-2-methylmorpholine. MS (APCI)=192 (M+1)$^+$.

Step 2: Palladium hydroxide (30 mg of 10% w/w on carbon) was added to a solution of 4-benzyl-2-methylmorpholine (280 mg, 1.46 mmol) in methanol (10.0 mL). The reaction mixture was flushed with hydrogen and then stirred under a hydrogen atmosphere for two hours at room temperature. Next, aqueous HCl (2.0 mL of 2.0 M solution) was added to the reaction and the reaction mixture filtered through a pad of celite. The pad was rinsed with methanol and the filtrate was concentrated in vacuo to afford crude 2-methylmorpholine hydrochloride, which was used without further purification for the next reaction.

Step 3: Crude 2-methylmorpholine hydrochloride (100 mg, 0.73 mmol) and NaHCO$_3$ (170 mg, 2.0 mmol) were added to a solution of (R)-4-(2,6-dichloro-7-((trans-4-methylcyclohexyl)methyl)-7H-purin-8-yl)-3-phenylmorpholine (Preparative Example 12.5; 335 mg, 0.73 mmol) in isopropanol (10 mL). The reaction was refluxed for 6 hours and then cooled to room temperature. The reaction was then diluted with ethyl acetate (2×20 mL) and the combined organic layers were washed with water (10 mL). Evaporation of the solvent in vacuo gave the crude product, which was purified on a silica gel column (0 to 50% EtOAc/hexanes) to afford 4-(2-chloro-7-(((trans)-4-methylcyclohexyl)methyl)-8-((R)-3-phenylmorpholino)-7H-purin-6-yl)-2-methylmorpholine (mixture of diastereomers). MS (APCI)=525 (M+1)$^+$.

Steps 4-6: Using procedures similar to those described in Example 25.1 (Step 2) and Example 23.41 (Steps 2 and 3), 4-(2-chloro-7-(((trans)-4-methylcyclohexyl)methyl)-8-((R)-3-phenylmorpholino)-7H-purin-6-yl)-2-methylmorpholine was converted to 3-{7-[(trans-4-methylcyclohexyl)methyl]-6-(2-methylmorpholin-4-yl)-8-[(3R)-3-phenylmorpholin-4-yl]-7H-purin-2-yl}-1,2,4-oxadiazol-5(4H)-one (mixture of diastereomers). $^1$H NMR (400 MHz, CDCl$_3$) δ 9.12 (br s, 1H), 7.44-7.49 (m, 2H), 7.27-7.35 (m, 3H), 4.98-5.06 (m, 1H), 4.10-4.30 (m, 2H), 3.90-4.05 (m, 3H), 3.48-3.85 (m, 8H), 3.18-3.28 (m, 0.5H), 3.03-3.13 (m, 0.5; H), 2.85-2.95 (m, 0.5H), 2.74-2.82 (m, 0.5; H), 1.45-1.60 (m, 3H), 1.25 (d, J=6.2 Hz, 1.5H), 1.24 (d, J=6.2 Hz, 1.5H), 1.05-1.22 (m, 2H), 0.88-0.96 (m, 1H), 0.80 (d, J=6.5 Hz, 3H), 0.55-0.80 (m, 4H); MS (ESI)=575 (M+1)$^+$.

Preparation of the compounds in Table 26 was described above.

TABLE 26

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 26.2 | 782.9 | 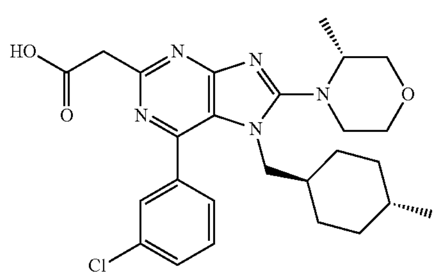 [SMILES: C[C@@H]1COCCN1c1nc2nc(CC(=O)O)nc(-c3cccc(Cl)c3)c2n1C[C@H]1CC[C@H](C)CC1] | {6-(3-chlorophenyl)-7-[(trans-4-methylcyclohexyl)methyl]-8-[(3R)-3-methylmorpholin-4-yl]-7H-purin-2-yl}acetic acid | | 498 | 498 |

TABLE 26-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 26.3 | 14.49 | 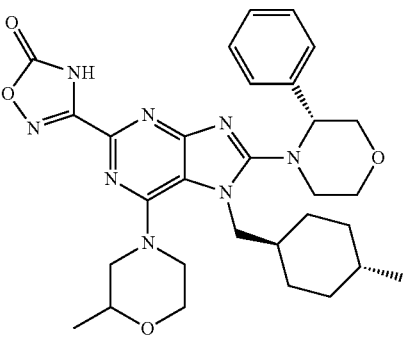 [SMILES: CC1CN(c2nc(-c3noc(=O)[nH]3)nc3nc(N4CCOC[C@H]4c4ccccc4)n(C[C@H]4CC[C@H](C)CC4)c23)CCO1] | 3-{7-[(trans-4-methylcyclohexyl)methyl]-6-(2-methylmorpholin-4-yl)-8-[(3R)-3-phenylmorpholin-4-yl]-7H-purin-2-yl}-1,2,4-oxadiazol-5(4H)-one (mixture of diastereomers) | | 575 | 575 |

Example 2

FRET Assay

Methods: An HDM2 FRET assay was developed to assess the compounds' inhibitory activity towards binding of p53 protein. A truncated version of HDM2 with residues 17 to 125 (containing p53 binding surface, Science (1994) 265, 346-355), with N-terminal His and Thioredoxin tag was generated in pET32a expression vector and expressed in *E. coli* strain BL21(DE3)Rosetta. Protein was purified using Ni-affinity chromatography, followed by size exclusion chromatography using Superdex 75 26/60 column. To assess inhibition of p53 binding to HDM2, a FITC labeled 8-mer peptide (sequence: Ac-Phe-Arg-Dpr-Ac6c-(6-Br)Trp-Glu-Glu-Leu-NH$_2$; Anal Biochem. 2004 Aug. 1; 331(1):138-46) with strong affinity towards p53 binding pocket of HDM2 was used. The HDM2 assay buffer contained 1× Phosphate Buffered Saline (Invitrogen, Cat#14190), 0.01% BSA (Jackson ImmunoResearch, Cat#001-000-162), 0.01% Tween-20. In the 1× assay buffer recombinant HDM2 protein, peptide and Lumi4-Tb Cryptate-conjugate mouse anti-6×His antibody (cisbio, Cat# Tb61HISTLB) were added and transferred to ProxiPlate PLUS (PerkinElmer, Cat#6008269), containing compounds so that final DMSO concentration is 0.1%. Final concentrations of reagents in the assay wells are 0.5 nM HDM2, 0.25 nM anti HIS (Tb label) antibody and 3 nM peptide. After two hour incubation at room temperature in a humidified chamber plates were read on EnVision plate reader with the following settings: excitation: UV, 340 nM, two emission filters: 520 nm and 495 nm respectively. Ratio of em520/em495 was used to calculate % inhibition and to obtain IC$_{50}$ with 4-parameter logistic equation.

IC$_{50}$ DETERMINATIONS: Dose-response curves were plotted from the inhibition data, from 10 point serial dilutions of inhibitory compounds. Concentration of compound was plotted against em520/Cem495 ratio signal. To generate IC$_{50}$ values, the dose-response curves were fitted to a standard sigmoidal curve and IC$_{50}$ values were derived by nonlinear regression analysis.

Example 3

Cell Viability Assay

Additionally, compounds can be tested for activity at the HDM2 protein using the Cell Viability Assay, which measures the number of viable cells in culture after treatment with the inventive compound for a certain period of time e.g. 72 hours based on quantitation of the ATP present (Cell Viability. IC$_{50}$). [CellTiter-Glo® Luminescent Cell Viability Assay from Promega].

What is claimed is:
1. A compound represented by Formula I:

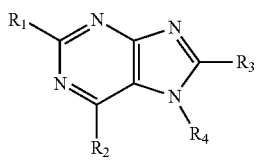

Wherein $R^1$ is selected from the group consisting of $C_1$-$C_6$alkyl, —$(CR^a{}_2)_n COOR^{11}$, —$(CR^a{}_2)_n NR^5 SO_2 R^6$, —$(CR^a{}_2)_n SO_2 NR^5 R^6$, —$(CR^a{}_2)_n C(O)NR^5 SO_2 N(R^c)_2$, —$(CR^a{}_2)_n C(O)R^5$, —$(CR^a{}_2)_n CONR^5 R^6$, —$(CR^a{}_2)_n CONR^5 SO_2 R^6$, —$(CR^a{}_2)_n CONR^5 OR^6$, —$(CR^a{}_2)_n OR^5$, —$(CR^a{}_2)_n S(O)R^c$, —$(CR^a{}_2)_n S(O)_2 R^c$, and nitrogen containing 5 or 6-membered heteroaryl, heterocyclic and heterocyclenyl ring, wherein the alkyl and 5 or 6-membered ring can be optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, $C_3$-$C_8$cycloalkyl, —W—$(CR^a R^9)_r R^7$, and heterocyclic, wherein W is $NR^c$ or O, wherein the aryl, heteroaryl, cycloalkyl or heterocyclic is optionally substituted with $R^{12}$ selected from the group consisting of halo, CN, halo$C_1$-$C_6$alkyl, $C_1$-$C_6$alkyl, —$(CR^a{}_2)_z OR^8$, —$(CR^a{}_2)_z NHR^8$, —$(CR^a{}_2)_z C(O)NR^c R^c$, —$(CR^a{}_2)_z COOR^{10}$, —$(CR^a{}_2)_z S(O)_2 R^c$, —$(CR^a{}_2)_z$aryl, —$(CR^a{}_2)_z$heteroaryl, —$(CR^a{}_2)_z$heterocyclic, —$(CR^a{}_2)_z C_3$-$C_8$cycloalkyl, —$(CR^a{}_2)_z$cyclenyl, and —$(CR^a{}_2)_z$heterocyclenyl, wherein the alkyl, aryl, heteroaryl, heterocyclic, cycloalkyl, cyclenyl and heterocyclenyl of $R^{12}$ can be optionally substituted with OH, $NH_2$, nitro, CN, $CON(R^c)_2$, —$(CR^a{}_2)_z COOR^{10}$, $C_1$-$C_6$alkoxy, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^3$ is selected from the group consisting of —$(CR^a{}_2)_q NR^c R^8$, —$(CR^a{}_2)_q OR^8$, —$(CR^a{}_2)_q SR^8$, —$(CR^a{}_2)_q C(O)R^8$, —$(CR^a{}_2)_q S(O)R^8$, —$(CR^a{}_2)_q S(O)_2 R^8$, —$(CR^a{}_2)_q CONR^c R^8$, —$(CR^a{}_2)_q NR^c C(O)R^8$, -T-$C_1$-$C_6$alkyl, $C_2$-$C_6$alkenyl, -T-aryl, -T-heteroaryl, -T-heterocyclic, -T-$C_3$-$C_8$cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, $SR^c$, $OR^c$, halo$C_1$-$C_6$alkyl, halo$C_1$-$C_6$alkoxy, —$(CR^a{}_2)_z CN$, $C_1$-$C_6$alkyl, $C_2$-$C_6$alkenyl, $C_2$-$C_6$alkynyl, —$(CR^a{}_2)_z C(O)OR^{10}$, —$(CR^a{}_2)_z C(O)R^8$, —$(CR^a{}_2)_z OR^8$, —$(CR^a{}_2)_z NR^c R^8$, —$(CR^a{}_2)_z S(O)_2 R^8$, —$(CR^a{}_2)_z C(O)NR^c R^8$, —$(CR^a{}_2)_z$aryl, —$(CR^a{}_2)_z$heteroaryl, —$(CR^a{}_2)_z C_3$-$C_8$cycloalkyl, —$(CR^a{}_2)_z$heterocyclic, —$(CR^a{}_2)_z$heterocyclenyl, —$(CR^a{}_2)_z$cyclenyl, —$(CR^a{}_2)_z SO_2 NR^c R^8$, or —$(CR^a{}_2)_z O(CR^a{}_2)_z D(CR^a{}_2)_v Q$, said alkyl, alkenyl, alkynyl, aryl, heteroaryl, cycloalkyl, heterocyclic, heterocyclenyl and cyclenyl can further be optionally substituted with SH, OH, $NH_2$, nitro, CN, $CON(R)_2$, $COOR^{10} C_1$-$C_6$alkoxy, $C_1$-$C_6$alkyl, $C_2$-$C_6$alkenyl, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^4$ is selected from the group consisting of $C_1$-$C_6$alkyl, —$(CR^a{}_2)_m$aryl, —$(CR^a{}_2)_m$heteroaryl, —$(CR^a{}_2)_m$heterocyclic, —$(CR^a{}_2)_m C_3$-$C_8$cycloalkyl, —$(CR^a{}_2)_m$cyclenyl, and —$(CR^a{}_2)_m$heterocyclenyl, wherein the alkyl, aryl, heteroaryl, heterocyclic, cycloalkyl, cyclenyl, and heterocyclenyl can be optionally substituted with OH, SH, $NH_2$, nitro, CN, $CON(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^5$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, and heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkyloxy, $C_2$-$C_6$alkenyl, $C_2$-$C_6$alkynyl, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, —$C_0$-$C_6$alkylheterocyclic, —$C_0$-$C_6$alkylheterocyclenyl, —$C_0$-$C_6$alkylcyclenyl, —$(CR^a{}_2)_z NR^5 R^6$, —$(CR^a{}_2)_z NR^5 SO_2 R^6$, —$(CR^a{}_2)_z SO_2 NR^5 R^6$, —$(CR^a{}_2)_z C(O)R^5$, —(CR$^a{}_2$)$_z$C(O)OR$^{10}$, —(CR$^a{}_2$)$_z$CONR$^5$R$^6$, —(CR$^a{}_2$)$_z$CONR$^5$OR$^6$, —(CR$^a{}_2$)$_z$NR$^5$C(O)OR$^6$, —(CR$^a{}_2$)$_z$NR$^5$C(O)R$^6$, —(CR$^a{}_2$)$_z$OR$^5$, —(CR$^a{}_2$)$_z$S(O)R$^c$, and —(CR$^a{}_2$)$_z$S(O)$_2$R$^c$;

R$^8$ is independently selected from the group consisting of H, —(CR$^a{}_2$)$_s$-heteroaryl, —(CR$^a{}_2$)$_s$-aryl, —(CR$^a{}_2$)$_s$-heterocyclic, —(CR$^a{}_2$)$_s$-heterocyclenyl, —(CR$^a{}_2$)$_s$-cyclenyl, —(CR$^a{}_2$)$_s$C$_3$-C$_8$cycloalkyl, and C$_1$-C$_6$alkyl, wherein the heteroaryl, aryl, heterocyclic, heterocyclenyl, cyclenyl, cycloalkyl, and alkyl can be optionally substituted with OH, —N(R$^c$)$_2$, NH$_2$, nitro, CN, CON (R$^c$)$_2$, COOR$^{10}$, C$_1$-C$_6$alkoxy, C$_1$-C$_6$alkyl, C$_2$-C$_6$alkenyl, C$_3$-C$_6$cycloalkyl, C$_1$-C$_6$haloalkyl, C$_1$-C$_6$haloalkyloxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R, C$_1$-C$_6$alkylsulfonyl, C$_1$-C$_6$alkylamino, di(C$_1$-C$_6$)alkylamino, heteroaryl, aryl, heterocyclic, heterocyclenyl, or cyclenyl;

R$^9$ is independently selected from the group consisting of H, C$_1$-C$_6$alkyl, C$_1$-C$_6$haloalkyl, C$_3$-C$_8$cycloalkyl, aryl, heteroaryl, and heterocyclic, wherein the alkyl, cycloalkyl, aryl, heteroaryl, and heterocyclic can be optionally substituted with —C$_0$-C$_6$alkylOR$^c$, C$_0$-C$_6$alkylN(R)$_2$, COOR$^{10}$, nitro, CN, C$_1$-C$_6$alkyl, C$_1$-C$_6$haloalkyl, C$_1$-C$_6$haloalkyloxy, C$_1$-C$_6$hydroxyalkyl, C$_2$-C$_6$alkenyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, heterocylic, or C(O)NHR$^c$;

R$^{10}$ is independently selected from the group consisting of C$_1$-C$_6$alkyl, —(CR$^c{}_2$)$_z$C$_3$-C$_8$cycloalkyl, —(CR$^c{}_2$)$_z$-heteroaryl, —(CR$^c{}_2$)$_z$-aryl, and —(CR$^c{}_2$)$_z$-heterocyclic, wherein the heteroaryl, aryl, heterocyclic, cycloalkyl and alkyl can be optionally substituted with C$_1$-C$_6$alkyl, OH, halo, or haloC$_1$-C$_6$alkyl;

R$^{11}$ is independently selected from the group consisting of H, C$_1$-C$_6$alkyl, —(CR$^c{}_2$)$_z$C$_3$-C$_8$cycloalkyl, —(CR$^c{}_2$)$_z$heteroaryl, —(CR$^c{}_2$)$_z$aryl, and —(CR$^c{}_2$)$_z$heterocyclic wherein the heteroaryl, aryl, heterocyclic, cycloalkyl and alkyl can be optionally substituted with C$_1$-C$_6$alkyl, OH, halo, or haloC$_1$-C$_6$alkyl;

R$^a$ is independently H, OR$^c$, NH$_2$, halo, C$_1$-C$_3$alkyl, or C$_2$-C$_4$alkenyl, said alkyl or alkenyl is optionally substituted with OH, C$_1$-C$_4$alkoxy, NH$_2$, halo, haloC$_1$-C$_4$alkyl, C$_3$-C$_6$cycloalkyl, or C$_2$-C$_4$alkenyl;

R$^c$ is independently H or C$_1$-C$_3$alkyl optionally substituted with C$_2$-C$_3$alkenyl, C$_3$-C$_6$cycloalkyl, C$_1$-C$_3$alkoxy, OH, halo, NH$_2$, C$_1$-C$_3$alkylamino, or C$_1$-C$_3$dialkylamino;

T is independently C$_2$-C$_3$alkenyl, —(CR$^a{}_2$)$_q$—, —C(=CH$_2$)—, —(CR$^a{}_2$)$_q$—C(=CH$_2$)—, —C(=CH$_2$)—(CR$^a{}_2$)$_q$—, —C(=NH)—, —(CR$^a{}_2$)$_q$—C(=NH)—, or —C(=NH)—(CR$^a{}_2$)$_q$—;

D is a bond, —C(O)NR$^c$—, —NR$^c$C(O)—, or —NR$^c$—;

Q is H, COOR$^{10}$, OH, heteroaryl or heterocyclic;

n is independently 0, 1, 2 or 3;

m is independently 0, 1 or 2;

q is independently 0, 1, 2, or 3;

s is independently 0, 1 or 2;

t is independently 0, 1, or 2;

v is independently 1, 2, 3 or 4;

z is independently 0, 1, 2 or 3;

or a pharmaceutically acceptable salt thereof.

2. The compound of claim 1, wherein R$^1$ is selected from the group consisting of C$_1$-C$_6$alkyl, —(CR$^a{}_2$)$_n$COOR$^{11}$, —(CR$^a{}_2$)$_n$NR$^5$SO$_2$R$^6$, —(CR$^a{}_2$)$_n$SO$_2$NR$^5$R$^6$, —(CR$^a{}_2$)$_n$C(O)NR$^c$SO$_2$N(R$^c$)$_2$, —(CR$^a{}_2$)$_n$C(O)R$^5$, —(CR$^a{}_2$)$_n$CONR$^5$R$^6$, —(CR$^a{}_2$)$_n$CONR$^5$SO$_2$R$^6$, —(CR$^a{}_2$)$_n$CONR$^5$OR$^6$, —(CR$^a{}_2$)$_n$OR$^5$, —(CR$^a{}_2$)$_n$S(O)R$^c$, —(CR$^a{}_2$)$_n$S(O)$_2$R$^c$, and nitrogen containing 5 or 6-membered heteroaryl, heterocyclic and heterocyclenyl ring, wherein the alkyl and 5 or 6-membered ring can be optionally substituted with OR$^c$, SR$^c$, NH$_2$, nitro, CN, amide, COOR$^{11}$, C$_1$-C$_6$alkyl, C$_1$-C$_6$haloalkyl, C$_1$-C$_6$haloalkyloxy, C$_1$-C$_6$hydroxyalkyl, C$_2$-C$_6$alkenyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$) alkylamino;

R$^2$ is selected from the group consisting of aryl, heteroaryl, —W—(CR$^a$R$^9$)$_t$R$^7$, and heterocyclic, wherein W is NR$^c$ or O, wherein the aryl, heteroaryl, or heterocyclic is optionally substituted with R$^{12}$ selected from the group consisting of halo, CN, haloC$_1$-C$_6$alkyl, C$_1$-C$_6$alkyl, —(CR$^a{}_2$)$_z$OR$^c$, —(CR$^a{}_2$)$_z$NHR$^8$, —(CR$^a{}_2$)$_z$C(O)NR$^c$R$^c$, —(CR$^a{}_2$)$_z$COOR$^{10}$, —(CR$^a{}_2$)$_z$aryl, —(CR$^a{}_2$)$_z$heteroaryl, —(CR$^a{}_2$)$_z$heterocyclic, —(CR$^a{}_2$)$_z$C$_3$-C$_8$cycloalkyl, —(CR$^a{}_2$)$_z$cyclenyl, and —(CR$^a{}_2$)$_z$heterocyclenyl, wherein the alkyl, aryl, heteroaryl, heterocyclic, cycloalkyl, cyclenyl and heterocyclenyl of R$^{12}$ can be optionally substituted with OH, NH$_2$, nitro, CN, CON(R$^c$)$_2$, —(CR$^a{}_2$)$_z$COOR$^{10}$, C$_1$-C$_6$alkoxy, C$_1$-C$_6$alkyl, C$_1$-C$_6$haloalkyl, C$_1$-C$_6$haloalkyloxy, C$_1$-C$_6$hydroxyalkyl, C$_2$-C$_6$alkenyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^3$ is selected from the group consisting of —(CR$^a{}_2$)$_q$NR$^c$R$^8$, —(CR$^a{}_2$)$_q$OR, —(CR$^a{}_2$)$_q$SR$^8$, —(CR$^a{}_2$)$_q$C(O)R$^8$, —(CR$^a{}_2$)$_q$S(O)R, —(CR$^a{}_2$)$_q$S(O)$_2$R, —(CR$^a{}_2$)$_q$CONR$^c$R$^8$, —(CR$^a{}_2$)$_q$NR$^c$C(O)R$^8$, -T-C$_1$-C$_6$alkyl, C$_2$-C$_6$alkenyl, -T-aryl, -T-heteroaryl, -T-heterocyclic, -T-C$_3$-C$_8$cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, OR$^c$, SH, haloC$_1$-C$_6$alkyl, haloC$_1$-C$_6$alkoxy, —(CR$^a{}_2$)$_z$CN, C$_1$-C$_6$alkyl, C$_2$-C$_6$alkenyl, C$_2$-C$_6$alkynyl, —(CR$^a{}_2$)$_z$C(O)OR$^{10}$, —(CR$^a{}_2$)$_z$C(O)R, —(CR$^a{}_2$)$_z$OR, —(CR$^a{}_2$)$_z$NR$^c$R$^8$, —(CR$^a{}_2$)$_z$S(O)$_2$R$^8$, —(CR$^a{}_2$)$_z$C(O)NR$^c$R$^8$, —(CR$^a{}_2$)$_z$aryl, —(CR$^a{}_2$)$_z$heteroaryl, —(CR$^a{}_2$)$_z$C$_3$-C$_8$cycloalkyl, —(CR$^a{}_2$)$_z$heterocyclic, —(CR$^a{}_2$)$_z$heterocyclenyl, —(CR$^a{}_2$)$_z$cyclenyl, —(CR$^a{}_2$)$_z$SO$_2$NR$^c$R$^8$, or —(CR$^a{}_2$)$_z$O(CR$^a{}_2$)$_z$D(CR$^a{}_2$)$_v$Q, said alkyl, alkenyl, alkynyl, aryl, heteroaryl, cycloalkyl, heterocyclic, heterocyclenyl and cyclenyl can further be optionally substituted with OH, SH, NH$_2$, nitro, CN, CON(R$^c$)$_2$, COOR$^{10}$C$_1$-C$_6$alkoxy, C$_1$-C$_6$alkyl, C$_2$-C$_6$alkenyl, C$_1$-C$_6$haloalkyl, C$_1$-C$_6$haloalkyloxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$) alkylamino;

R$^4$ is selected from the group consisting of C$_1$-C$_6$alkyl, —(CR$^a{}_2$)$_m$aryl, —(CR$^a{}_2$)$_m$heteroaryl, —(CR$^a{}_2$)$_m$heterocyclic, —(CR$^a{}_2$)$_m$C$_3$-C$_8$cycloalkyl, —(CR$^a{}_2$)$_m$cyclenyl, and —(CR$^a{}_2$)$_m$heterocyclenyl, wherein the alkyl, aryl, heteroaryl, heterocyclic, cycloalkyl, cyclenyl, and heterocyclenyl can be optionally substituted with OH, SH, NH$_2$, nitro, CN, CON(R$^c$)$_2$, COOR$^{10}$, C$_1$-C$_6$alkoxy, C$_1$-C$_6$alkyl, C$_3$-C$_6$cycloalkyl, haloC$_2$-C$_6$alkenyl, C$_2$-C$_6$alkenyl, C$_2$-C$_6$alkenoxy, C$_1$-C$_6$haloalkyl, C$_1$-C$_6$haloalkyloxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$) alkylamino;

$R^5$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, and heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkyloxy, $C_2$-$C_6$alkenyl, $C_2$-$C_6$alkynyl, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, —$C_0$-$C_6$alkylheterocyclic, —$C_0$-$C_6$alkylheterocyclenyl, —$C_0$-$C_6$alkylcyclenyl, —$(CR^a_2)_z NR^5 R^6$, —$(CR^a_2)_z NR^5$$SO_2 R^6$, —$(CR^a_2)_z SO_2 NR^5 R^6$, —$(CR^a_2)_z C(O)R^5$, —$(CR^a_2)_z C(O)OR^{10}$, —$(CR^a_2)_z CONR^5 R^6$, —$(CR^a_2)_z CONR^5 OR^6$, —$(CR^a_2)_z NR^5 C(O)OR^6$, —$(CR^a_2)_z NR^5 C(O)R^6$, —$(CR^a_2)_z OR^5$, —$(CR^a_2)_z S(O)R^c$, and —$(CR^a_2)_z S(O)_2 R^c$;

$R^8$ is independently selected from the group consisting of H, —$(CR^a_2)_s$-heteroaryl, —$(CR^a_2)_s$-aryl, —$(CR^a_2)_s$-heterocyclic, —$(CR^a_2)_s$-heterocyclenyl, —$(CR^a_2)_s$-cyclenyl, —$(CR^a_2)_s C_3$-$C_8$cycloalkyl, and $C_1$-$C_6$alkyl, wherein the heteroaryl, aryl, heterocyclic, heterocyclenyl, cyclenyl, cycloalkyl, and alkyl can be optionally substituted with OH, —$N(R^c)_2$, $NH_2$, nitro, CN, CON$(R^c)_2$, $COOR^{10}$, $C_1$-$C_6$alkoxy, $C_1$-$C_6$alkyl, $C_2$-$C_6$alkenyl, $C_3$-$C_6$cycloalkyl, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R$, $C_1$-$C_6$alkylsulfonyl, $C_1$-$C_6$alkylamino, di($C_1$-$C_6$)alkylamino, heteroaryl, aryl, heterocyclic, heterocyclenyl, or cyclenyl;

$R^9$ is independently selected from the group consisting of H, $C_1$-$C_6$alkyl, $C_1$-$C_6$haloalkyl, $C_3$-$C_8$cycloalkyl, aryl, heteroaryl, and heterocyclic, wherein the alkyl, cycloalkyl, aryl, heteroaryl, and heterocyclic can be optionally substituted with —$C_0$-$C_6$alkylOR^c$, $C_0$-$C_6$alkylN(R^c)_2$, $COOR^{10}$, nitro, CN, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, heterocyclic, or $C(O)NHR^c$;

$R^{10}$ is independently selected from the group consisting of $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic, wherein the heteroaryl, aryl, heterocyclic, cycloalkyl and alkyl can be optionally substituted with $C_1$-$C_6$alkyl, OH, halo, or halo$C_1$-$C_6$alkyl;

$R^{11}$ is independently selected from the group consisting of H, $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic wherein the heteroaryl, aryl, heterocyclic, cycloalkyl and alkyl can be optionally substituted with $C_1$-$C_6$alkyl, OH, halo, or halo$C_1$-$C_6$alkyl;

$R^a$ is independently H, $OR^c$, $NH_2$, halo, $C_1$-$C_3$alkyl, or $C_2$-$C_4$alkenyl, said alkyl or alkenyl is optionally substituted with OH, $C_1$-$C_4$alkoxy, $NH_2$, halo, halo$C_1$-$C_4$alkyl, $C_3$-$C_6$cycloalkyl, or $C_2$-$C_4$alkenyl;

$R^c$ is independently H or $C_1$-$C_3$alkyl optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, or $C_1$-$C_3$dialkylamino;

T is independently $C_2$-$C_3$alkenyl, —$(CR^a_2)_q$—, —C(=CH_2)—, —$(CR^a_2)_q$—C(=CH_2)—, —C(=CH_2)—$(CR^a_2)_q$—, —C(=NH)—, —$(CR^a_2)_q$—C(=NH)—, or —C(=NH)—$(CR^a_2)_q$—;

D is a bond, —C(O)NR^c—, —NR^c C(O)—, or —NR^c—;

Q is H, $COOR^{10}$, OH, heteroaryl or heterocyclic;

n is independently 0, 1, 2 or 3;

m is independently 0, 1 or 2;

q is independently 0, 1, 2, or 3;

s is independently 0, 1 or 2;

t is independently 0, 1, or 2;

v is independently 1, 2, 3 or 4;

z is independently 0, 1, 2 or 3;

or a pharmaceutically acceptable salt thereof.

3. The compound of claim 2, wherein $R^1$ is selected from the group consisting of $C_1$-$C_6$alkyl, $COOR^{11}$, —$NR^c SO_2 R^c$, —$SO_2 NR^c R^c$, —C(O)$NR^c SO_2 N(R^c)_2$, —C(O)$R^c$, —$CONR^c R^c$, —$CONR^c OR^c$, —$CONR^c SO_2 R^c$, —OR, —S(O)$R^c$, —$S(O)_2 R^c$, and nitrogen containing 5-membered heteroaryl, heterocyclic and heterocyclenyl ring, wherein the alkyl and 5-membered ring can be optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkyloxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2 NR^c R^c$, —$NR^c SO_2 R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, W—$(CR^a R^9)R^7$, and heterocyclic, wherein W is $NR^c$ or O, wherein the aryl, heteroaryl, and heterocyclic is optionally substituted with $R^{12}$ selected from the group consisting of halo, CN, halo$C_1$-$C_6$alkyl, $C_1$-$C_6$alkyl, —$(CR^a_2)OR^c$, and —$(CR^a_2)C(O)NR^c R^c$, wherein the alkyl of $R^{12}$ can be optionally substituted with OH, CN, halo, halo$C_1$-$C_6$alkyl, or $CON(R^c)_2$;

$R^3$ is selected from the group consisting of —$NR^c R^8$, —$OR^8$, —$SR^8$, —C(O)$R^8$, —S(O)$R^8$, —$S(O)_2 R^8$, —$CONR^c R^8$, —$NR^c C(O)R^8$, -T-$C_1$-$C_6$alkyl, $C_2$-$C_6$alkenyl, -T-aryl, -T-heteroaryl, -T-heterocyclic, -T-cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, $OR^c$, SH, halo$C_1$-$C_6$alkyl, halo$C_1$-$C_6$alkoxy, —$(CR^a_2)_z CN$, $C_1$-$C_6$alkyl, $C_2$-$C_6$alkenyl, $C_2$-$C_6$alkynyl, —$(CR^a_2)_z C(O)OR^{10}$, —$(CR^a_2)_z C(O)R^8$, —$(CR^a_2)_z OR^8$, —$(CR^a_2)_z NR^c R^8$, —$(CR^a_2)_z S(O)_2 R^8$, —$(CR^a_2)_z C(O)NR^c R^8$, —$(CR^a_2)_z$aryl, —$(CR^a_2)_z$heteroaryl, —$(CR^a_2)_z C_3$-$C_8$cycloalkyl, —$(CR^a_2)_z$heterocyclic, —$(CR^a_2)_z SO_2 NR^c R^8$, or —$(CR^a_2)_z O(CR^a_2)_z D(CR^a_2)_v Q$, said alkyl, alkenyl, alkynyl, aryl, heteroaryl, cycloalkyl, and heterocyclic can further be optionally substituted with OH, SH, halo, or $C_2$-$C_6$alkenyl;

$R^4$ is selected from the group consisting of —$(CR^a_2)$aryl, —$(CR^a_2)$heteroaryl, —$(CR^a_2)$heterocyclic, —$(CR^a_2)C_3$-$C_8$cycloalkyl, —$(CR^a_2)$cyclenyl, and —$(CR^a_2)$heterocyclenyl, wherein the aryl, heteroaryl, heterocyclic, cycloalkyl, cyclenyl, and heterocyclenyl can be optionally substituted with OH, SH, $NH_2$, nitro, CN, CON$(R^c)_2$, $COOR^{10}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkyloxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^7$ is selected from the group consisting of C$_1$-C$_6$alkyl, C$_3$-C$_8$cycloalkyl, heteroaryl, aryl, and heterocyclic, wherein the alkyl, cycloalkyl, heteroaryl, aryl or heterocyclic can be optionally substituted with halo, nitro, CN, C$_1$-C$_6$haloalkyl, C$_1$-C$_6$haloalkyloxy, C$_1$-C$_6$alkyl, or —(CR$^a{}_2$)$_z$OR$^c$;

R$^8$ is independently selected from the group consisting of —(CR$^a{}_2$)-heteroaryl, —(CR$^a{}_2$)-aryl, —(CR$^a{}_2$)-heterocyclic, —(CR$^a{}_2$)-heterocyclenyl, —(CR$^a{}_2$)cyclenyl, —(CR$^a{}_2$)cycloalkyl, and C$_1$-C$_6$alkyl, wherein the heteroaryl, aryl, heterocyclic, heterocyclenyl, cyclenyl, cycloalkyl, and alkyl can be optionally substituted with OH, N(R$^c$)$_2$, C$_1$-C$_6$alkoxy, C$_1$-C$_6$alkyl, C$_3$-C$_6$cycloalkyl, C$_1$-C$_6$haloalkyl, C$_1$-C$_6$haloalkyloxy, C$_1$-C$_6$hydroxyalkyl, or halo group;

R$^9$ is H, C$_1$-C$_3$alkyl, C$_1$-C$_3$haloalkyl, C$_3$-C$_4$cycloalkyl, wherein the alkyl or cycloalkyl can be optionally substituted with OR$^c$, N(R$^c$)$_2$, heterocyclic, C(O)NHCH$_2$CH$_2$OH, C(O)NH$_2$, or C(O)NHC$_1$-C$_3$alkyl;

R$^{10}$ is independently C$_1$-C$_6$alkyl optionally substituted with OH, halo, or haloC$_1$-C$_6$alkyl;

R$^{11}$ is independently selected from the group consisting of H and C$_1$-C$_6$alkyl, wherein alkyl can be optionally substituted with OH or halo;

R$^a$ is independently H, OR$^c$, NH$_2$, halo, C$_1$-C$_3$alkyl, or C$_2$-C$_4$alkenyl, said alkyl or alkenyl is optionally substituted with OH, C$_1$-C$_4$alkoxy, NH$_2$, F, CF$_3$, C$_3$-C$_6$cycloalkyl, or C$_2$-C$_4$alkenyl;

R$^c$ is independently H or C$_1$-C$_3$alkyl optionally substituted with C$_2$-C$_3$alkenyl, C$_3$-C$_6$cycloalkyl, C$_1$-C$_3$alkoxy, OH, halo, NH$_2$, C$_1$-C$_3$alkylamino, or C$_1$-C$_3$dialkylamino;

T is independently C$_2$-C$_3$alkenyl, —(CR$^a{}_2$)$_q$—, or —C(=CH$_2$)—;

D is a bond, —C(O)NR$^c$—, —NR$^c$C(O)—, or —NR$^c$—;

Q is H, COOR$^{10}$, OH, heteroaryl or heterocyclic;

q is independently 0 or 1;

v is independently 1 or 2; and z is independently 0, 1 or 2.

4. The compound of claim 2, wherein

R$^1$ is selected from the group consisting of COOR$^{11}$, —NR$^c$SO$_2$R$^c$, —SO$_2$NR$^c$R$^c$, —C(O)NR$^c$SO$_2$N(R$^c$)$_2$, C(O)NR$^c$SO$_2$R$^c$, —C(O)R$^c$, —CONR$^c$R$^c$, —CONR$^c$OR$^c$, —OR$^c$, —S(O)R$^c$, —S(O)$_2$R$^c$, and nitrogen containing 5-membered heterocyclic, heteroaryl and heterocyclenyl ring, wherein the 5-membered ring can be optionally substituted with OR$^c$, SR$^c$, NH$_2$, nitro, CN, amide, COOR$^{11}$, C$_1$-C$_6$alkyl, C$_1$-C$_6$haloalkyl, C$_1$-C$_6$haloalkyloxy, C$_1$-C$_6$hydroxyalkyl, C$_2$-C$_6$alkenyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^2$ is selected from the group consisting of aryl, heteroaryl, and —NR$^c$—(CR$^a$R$^9$)R$^7$, wherein the aryl, or heteroaryl is optionally substituted with R$^{12}$ selected from the group consisting of halo, CN, haloC$_1$-C$_6$alkyl, C$_1$-C$_6$alkyl, —(CR$^a{}_2$)OR$^c$, wherein the alkyl of R$^{12}$ can be optionally substituted with OH, CN, halo, haloC$_1$-C$_6$alkyl, or CON(R$^c$)$_2$;

R$^3$ is selected from the group consisting of —NR$^c$R$^8$, -T-heteroaryl, and -T-heterocyclic, wherein the heteroaryl, and heterocyclic can be optionally substituted with halo, OR$^c$, SH, haloC$_1$-C$_6$alkyl, haloC$_1$-C$_6$alkoxy, —(CR$^a{}_2$)$_z$CN, C$_1$-C$_6$alkyl, C$_2$-C$_6$alkenyl, C$_2$-C$_6$alkynyl, —(CR$^a{}_2$)$_z$C(O)OR$^{10}$, —(CR$^a{}_2$)$_z$C(O)R$^8$, —(CR$^a{}_2$)$_z$OR$^8$, —(CR$^a{}_2$)$_z$NR$^c$R$^8$, —(CR$^a{}_2$)$_z$S(O)$_2$R$^8$, —(CR$^a{}_2$)$_z$C(O)NR$^c$R$^8$, —(CR$^a{}_2$)$_z$aryl, —(CR$^a{}_2$)$_z$heteroaryl, —(CR$^a{}_2$)$_z$C$_3$-C$_8$cycloalkyl, —(CR$^a{}_2$)$_z$heterocyclic, —(CR$^a{}_2$)$_z$SO$_2$NR$^c$R$^8$, or —(CR$^a{}_2$)$_z$O(CR$^a{}_2$)$_z$D(CR$^a{}_2$)$_v$Q;

said alkyl, alkenyl, alkynyl, aryl, heteroaryl, cycloalkyl, and heterocyclic can further be substituted with OH, SH, halo, or C$_2$-C$_6$alkenyl;

R$^4$ is selected from the group consisting of —(CR$^a{}_2$)aryl, —(CR$^a{}_2$)C$_3$-C$_6$cycloalkyl, and —(CR$^a{}_2$)C$_3$-C$_6$cyclenyl, wherein the aryl, cycloalkyl, and cyclenyl can be optionally substituted with OH, SH, NH$_2$, nitro, CN, CON(R$^c$)$_2$, COOR$^{10}$, C$_1$-C$_6$alkoxy, C$_1$-C$_6$alkyl, C$_3$-C$_6$cycloalkyl, haloC$_2$-C$_6$alkenyl, C$_2$-C$_6$alkenyl, C$_2$-C$_6$alkenoxy, C$_1$-C$_6$haloalkyl, C$_1$-C$_6$haloalkyloxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^7$ is C$_3$-C$_6$cycloalkyl optionally substituted with halo, nitro, CN, C$_1$-C$_6$haloalkyl, C$_1$-C$_6$haloalkyloxy, C$_1$-C$_6$alkyl, or —(CR$^a{}_2$)$_z$OR$^c$;

R$^9$ is C$_1$-C$_3$alkyl;

and all other substituents are as defined in claim 2.

5. The compound of claim 2, wherein R$^1$ is COOH or a nitrogen containing 5-membered heteroaryl, heterocyclic or heterocyclenyl ring selected from the group consisting of tetrazolyl, oxadiazolyl, oxadiazolone, dihydro-oxadiazolyl, triazolyl, dihydro-triazolyl, dihydro-triazolone, pyrrolidinyl, and imidazolyl, wherein the nitrogen containing 5-membered ring can be optionally substituted with halo, C$_1$-C$_6$alkyl, haloC$_1$-C$_6$alkyl, NH$_2$, OR$^c$, SR$^c$, COOH, or —NR$^c$SO$_2$R$^c$.

6. The compound of claim 2, wherein

R$^1$ is COOH,

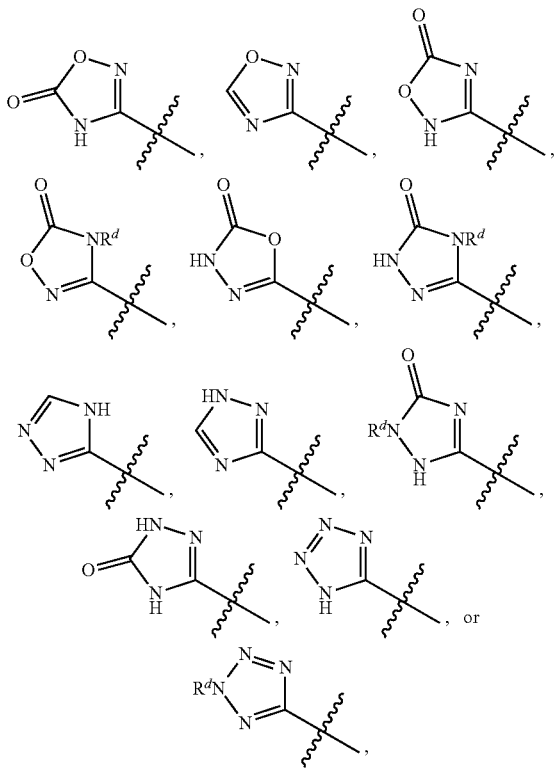

wherein R$^d$ is CH$_3$ or H.

7. The compound of claim 2, wherein $R^2$ is

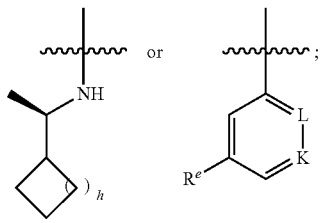

$R^e$ is H, $-(CR^a{}_2)_zC(O)OR^{10}$, halo, haloC$_1$-C$_3$alkyl or C$_1$-C$_3$alkyl;
K and L are independently CR$^{14}$ or N;
$R^{14}$ is independently H, halo, CN, haloC$_1$-C$_6$alkyl, C$_1$-C$_6$alkyl, $-(CR^a{}_2)_zC(O)NR^cR^c$, $-(CR^a{}_2)_zOR^c$, $-(CR^a{}_2)_z$aryl, $-(CR^a{}_2)_z$heteroaryl, $-(CR^a{}_2)_z$heterocyclic, $-(CR^a{}_2)_zC_3$-C$_8$cycloalkyl, $-(CR^a{}_2)_z$cyclenyl, $-(CR^a{}_2)_z$heterocyclenyl, wherein the alkyl, aryl, heteroaryl, heterocyclic, cycloalkyl, cyclenyl or heterocyclenyl can be optionally substituted with OH, CN, halo, haloC$_1$-C$_3$alkyl, or CON(R)$_2$; and
h is 0 or 1.

8. The compound of claim 2, wherein $R^3$ is -T-heterocyclic or -T-heteroaryl, wherein the heterocyclic or heteroaryl can be optionally substituted with halo, OR$^c$, SH, haloC$_1$-C$_6$alkyl, haloC$_1$-C$_6$alkoxy, CN, C$_1$-C$_6$alkyl, C$_2$-C$_6$alkenyl, C$_2$-C$_6$alkynyl, $-(CR^a{}_2)_zC(O)OR^{10}$, $-(CR^a{}_2)_zC(O)R^8$, $-(CR^a{}_2)_zOR^8$, $-(CR^a{}_2)_zNR^cR^8$, $-(CR^a{}_2)_zS(O)_2R^8$, $-(CR^a{}_2)_zC(O)NR^cR^8$, $-(CR^a{}_2)_z$aryl, $-(CR^a{}_2)_z$heteroaryl, $-(CR^a{}_2)_zC_3$-C$_8$cycloalkyl, $-(CR^a{}_2)_z$heterocyclic, $-(CR^a{}_2)_zSO_2NR^cR^8$, or $-(CR^a{}_2)_zO(CR^a{}_2)_vD(CR^a{}_2)_yQ$;
said alkyl, alkenyl, alkynyl, aryl, heteroaryl, cycloalkyl, and heterocyclic can further be optionally substituted with OH, SH, halo, or C$_2$-C$_6$alkenyl.

9. The compound of claim 2, wherein $R^3$ is

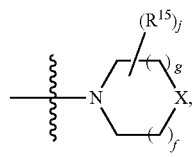

X is NR$^{19}$, CR$^{16}{}_2$, S, S(O)$_2$ or O;
$R^{15}$ is independently selected from the group consisting of phenyl, 5 or 6-membered heterocyclic or heteroaryl, haloC$_1$-C$_6$alkyl, haloC$_2$-C$_6$alkenyl, halo, C(O)R$^c$, S(O)$_2$R$^c$, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, C$_3$-C$_6$cycloalkyl, amino, CN, OH, and SH; two adjacent R$^{15}$ form a fused C$_3$-C$_7$cycloalkyl or heterocyclic ring; two non-adjacent R$^{15}$ form a C$_1$-C$_3$alkylene; or two R$^{15}$ attached to the same carbon form a C$_3$-C$_7$cycloalkyl or heterocyclic ring, wherein the phenyl, heteroaryl, cycloalkyl or heterocyclic can be optionally substituted with R$^{13}$ selected from the group consisting of haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, or SH;
$R^{16}$ is independently selected from the group consisting of H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, and SH;
$R^{19}$ is independently selected from the group consisting of H, haloC$_1$-C$_6$alkyl, haloC$_2$-C$_6$alkenyl, C$_1$-C$_6$alkoxyC$_1$-C$_6$alkyl, C$_1$-C$_6$alkyl, and C$_2$-C$_6$alkenyl;

f is 0, 1 or 2;
g is 0, 1 or 2;
j is independently 0, 1, 2, 3, 4, 5, 6, 7, or 8.

10. The compound of claim 2, wherein $R^3$ is

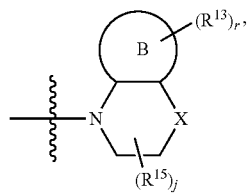

Ring B is a fused C$_3$-C$_7$cycloalkyl;
X is CR$^{16}{}_2$, S, or O;
$R^{13}$, $R^{15}$ and $R^{16}$ are independently haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_3$-C$_6$cycloalkyl, C$_2$-C$_6$alkenyl, amino, CN, OH, or SH;
r is independently 0, 1, 2, 3, 4, 5, 6, 7 or 8; and
j is independently 0, 1, 2, 3, or 4.

11. The compound of claim 2, wherein $R^3$ is

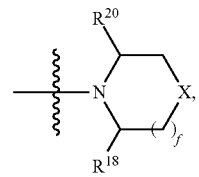

X is CH$_2$ or O;
$R^{18}$ and $R^{20}$ are independently H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_3$-C$_6$cycloalkyl, C$_2$-C$_6$alkenyl, C$_3$-C$_6$alkyl, amino, CN, OH, or SH; and
f is 0, 1 or 2.

12. The compound of claim 2, wherein $R^4$ is —CH$_2$-E or —CH$_2$(CH$_3$)-E, wherein E is phenyl, cyclopentyl, cyclopentenyl, cyclohexyl or cyclohexenyl optionally substituted with haloC$_1$-C$_3$alkyl, haloC$_2$-C$_3$alkenyl, halo, C$_3$-C$_4$cycloalkyl, haloC$_1$-C$_3$alkoxy, C$_1$-C$_3$alkoxy, C$_2$-C$_3$alkenoxy, C$_1$-C$_3$alkyl, C$_2$-C$_3$alkenyl, amino, CN, OH, or SH.

13. The compound of claim 1 selected from the group consisting of:
- (R)-6-((1-cyclobutylethyl)amino)-8-(5-(dimethylamino)-2-(trifluoromethoxy)phenyl)-7-(4-(trifluoromethyl)benzyl)-7H-purine-2-carboxylic acid;
- (R)-8-(2-chloro-5-ethylphenyl)-6-((1-cyclobutylethyl)amino)-7-(4-(trifluoromethyl)benzyl)-7H-purine-2-carboxylic acid;
- (R)-6-((1-cyclobutylethyl)amino)-7-(3-fluoro-4-(trifluoromethyl)benzyl)-8-(5-isopropyl-2-(trifluoromethoxy)phenyl)-7H-purine-2-carb oxylic acid;
- (R)-6-((1-cyclobutylethyl)amino)-8-(2-isopropylpyridin-4-yl)-7-(4-(trifluoromethyl)benzyl)-7H-purine-2-carboxylic acid;
- (R)-6-((1-cyclobutylethyl)amino)-8-(6-methyl-4-(prop-1-en-2-yl)pyridin-2-yl)-7-(4-(trifluoromethyl)benzyl)-7H-purine-2-carboxylic acid;
- 7-(4-chloro-3-fluorobenzyl)-6-{[(1R)-1-cyclobutylethyl]amino}-8-[4-(propan-2-yl)pyridin-2-yl]-7H-purine-2-carboxylic acid;

6-{[(1R)-1-cyclobutylethyl]amino}-8-[4-(propan-2-yl) pyridin-2-yl]-7-{[5-(trifluoromethyl)thiophen-2-yl] methyl}-7H-purine-2-carboxylic acid;

6-(((R)-1-cyclobutylethyl)amino)-8-(4-(hydroxy(phenyl) methyl)pyridin-2-yl)-7-(4-(trifluoromethyl)benzyl)-7H-purine-2-carboxylic acid;

(R)-8-(4-benzylpyridin-2-yl)-6-((1-cyclobutylethyl) amino)-7-(4-(trifluoromethyl)benzyl)-7H-purine-2-carboxylic acid;

(R)-6-((1-cyclobutylethyl)amino)-8-(5-fluoro-4-isopropylpyridin-2-yl)-7-(4-(trifluoromethyl)benzyl)-7H-purine-2-carboxylic acid;

(R)-6-((1-cyclobutylethyl)amino)-8-(2-hydroxy-5-isopropylphenyl)-7-(4-(trifluoromethyl)benzyl)-7H-purine-2-carboxylic acid;

(R)-6-((1-cyclobutylethyl)amino)-8-(2-ethoxy-5-isopropylphenyl)-7-(4-(trifluoromethyl)benzyl)-7H-purine-2-carboxylic acid;

(R)-6-((1-cyclobutylethyl)(methyl)amino)-7-(3-fluoro-4-(trifluoromethyl)benzyl)-8-(4-isopropylpyridin-2-yl)-7H-purine-2-carboxylic acid;

8-(4-(sec-butyl)pyridin-2-yl)-6-(((R)-1-cyclobutylethyl) amino)-7-(4-(trifluoromethyl)benzyl)-7H-purine-2-carboxylic acid;

6-{[(1R)-1-cyclobutylethyl]amino}-8-pyridin-2-yl-7-[4-(trifluoromethyl)benzyl]-7H-purine-2-carboxylic acid;

6-{[(1R)-1-cyclobutylethyl]amino}-8-(4-methylpyridin-2-yl)-7-[4-(trifluoromethyl)benzyl]-7H-purine-2-carboxylic acid;

6-{[(1R)-1-cyclobutylethyl]amino}-8-(3-methylpyridin-2-yl)-7-[4-(trifluoromethyl)benzyl]-7H-purine-2-carboxylic acid;

6-{[(1R)-1-cyclobutylethyl]amino}-8-(6-methylpyridin-2-yl)-7-[4-(trifluoromethyl)benzyl]-7H-purine-2-carboxylic acid;

6-{[(1R)-1-cyclobutylethyl]amino}-8-(5-methoxypyridin-2-yl)-7-[4-(trifluoromethyl)benzyl]-7H-purine-2-carboxylic acid;

6-{[(1R)-1-cyclobutylethyl]amino}-8-(3,6-dimethylpyridin-2-yl)-7-[4-(trifluoromethyl)benzyl]-7H-purine-2-carboxylic acid;

6-{[(1R)-1-cyclobutylethyl]amino}-8-[4-(1-methylethyl) pyridin-2-yl]-7-[4-(trifluoromethyl)benzyl]-7H-purine-2-carboxylic acid;

6-{[(1R)-1-cyclobutylethyl]amino}-8-(3-methoxy-6-methylpyridin-2-yl)-7-[4-(trifluoromethyl)benzyl]-7H-purine-2-carboxylic acid;

6-{[(1R)-1-cyclobutylethyl]amino}-8-[4-(methylsulfonyl)phenyl]-7-[4-(trifluoromethyl)benzyl]-7H-purine-2-carboxylic acid;

6-{[(1R)-1-cyclopropylethyl]amino}-8-(7-methylquinolin-6-yl)-7-[4-(trifluoromethyl)benzyl]-7H-purine-2-carboxylic acid;

6-{[(1R)-1-cyclobutylethyl]amino}-8-(4-phenylpyridin-2-yl)-7-[4-(trifluoromethyl)benzyl]-7H-purine-2-carboxylic acid;

6-{[(1R)-1-cyclobutylethyl]amino}-8-[4-(1-hydroxy-1-methylethyl)pyridin-2-yl]-7-[4-(trifluoromethyl)benzyl]-7H-purine-2-carboxylic acid;

6-{[(1R)-1-cyclobutylethyl]amino}-8-[4-(1-hydroxyethyl)pyridin-2-yl]-7-[4-(trifluoromethyl)benzyl]-7H-purine-2-carboxylic acid;

6-{[(1R)-1-cyclobutylethyl]amino}-8-(5-ethyl-2-hydroxyphenyl)-7-[4-(trifluoromethyl)benzyl]-7H-purine-2-carboxylic acid;

6-{[(1R)-1-cyclobutylethyl]amino}-8-[2-(methoxymethoxy)-5-(1-methylethyl)phenyl]-7-[4-(trifluoromethyl)benzyl]-7H-purine-2-carboxylic acid;

6-{[(1R)-1-cyclobutylethyl]amino}-8-(5-ethyl-2-methoxyphenyl)-7-[4-(trifluoromethyl)benzyl]-7H-purine-2-carboxylic acid;

6-{[(1R)-1-cyclobutylethyl]amino}-8-(2-ethoxy-5-ethylphenyl)-7-[4-(trifluoromethyl)benzyl]-7H-purine-2-carboxylic acid;

6-{[(1R)-1-cyclobutylethyl]amino}-8-[2-ethoxy-5-(trifluoromethyl)phenyl]-7-[4-(trifluoromethyl)benzyl]-7H-purine-2-carboxylic acid;

6-{[(1R)-1-cyclobutylethyl]amino}-8-[2-methoxy-5-(trifluoromethyl)phenyl]-7-[4-(trifluoromethyl)benzyl]-7H-purine-2-carboxylic acid;

6-{[(1R)-1-cyclobutylethyl]amino}-8-[5-ethyl-2-(methoxymethoxy)phenyl]-7-[4-(trifluoromethyl)benzyl]-7H-purine-2-carboxylic acid;

8-(3-carbamoylphenyl)-6-{[(1R)-1-cyclobutylethyl] amino}-7-[4-(trifluoromethyl)benzyl]-7H-purine-2-carboxylic acid;

6-{[(1R)-1-cyclobutylethyl]amino}-8-[2-fluoro-5-(trifluoromethyl)phenyl]-7-[4-(trifluoromethyl)benzyl]-7H-purine-2-carboxylic acid;

6-{[(1R)-1-cyclobutylethyl]amino}-8-[5-(dimethylamino)-2-methylphenyl]-7-[4-(trifluoromethyl)benzyl]-7H-purine-2-carboxylic acid;

6-{[(1R)-1-cyclobutylethyl]amino}-8-(5-ethyl-2-fluorophenyl)-7-[4-(trifluoromethyl)benzyl]-7H-purine-2-carboxylic acid;

6-{[(1R)-1-cyclobutylethyl]amino}-8-[2-methoxy-5-(1-methylethyl)phenyl]-7-[4-(trifluoromethyl)benzyl]-7H-purine-2-carboxylic acid;

6-{[(1R)-1-cyclobutylethyl]amino}-8-[5-(dimethylamino)-2-hydroxyphenyl]-7-[4-(trifluoromethyl)benzyl]-7H-purine-2-carboxylic acid;

6-{[(1R)-1-cyclobutylethyl]amino}-8-(4-ethoxypyridin-2-yl)-7-[4-(trifluoromethyl)benzyl]-7H-purine-2-carboxylic acid;

8-(4-chloropyridin-2-yl)-6-{[(1R)-1-cyclobutylethyl] amino}-7-[4-(trifluoromethyl)benzyl]-7H-purine-2-carboxylic acid;

6-{[(1R)-1-cyclobutylethyl]amino}-8-[4-(cyclobutyloxy) pyridin-2-yl]-7-[4-(trifluoromethyl)benzyl]-7H-purine-2-carboxylic acid;

6-{[(1R)-1-cyclobutylethyl]amino}-8-[4-(difluoromethyl)pyridin-2-yl]-7-[4-(trifluoromethyl)benzyl]-7H-purine-2-carboxylic acid;

6-{[(1R)-1-cyclobutylethyl]amino}-8-[4-(dimethylamino)pyridin-2-yl]-7-[4-(trifluoromethyl)benzyl]-7H-purine-2-carboxylic acid;

6-{[(1R)-1-cyclobutylethyl]amino}-8-[4-(3-methyl-1H-pyrazol-1-yl)pyridin-2-yl]-7-[4-(trifluoromethyl)benzyl]-7H-purine-2-carboxylic acid;

6-{[(1R)-1-cyclobutylethyl]amino}-7-[3-fluoro-4-(trifluoromethyl)benzyl]-8-[4-(1-methylethyl)pyridin-2-yl]-7H-purine-2-carboxylic acid;

6-{[(1 S)-1-cyclobutylethyl]amino}-8-[4-(1-methylethyl) pyridin-2-yl]-7-[4-(trifluoromethyl)benzyl]-7H-purine-2-carboxylic acid;

6-{[(1R)-1-cyclobutylethyl]amino}-8-(4-cyclopropylpyridin-2-yl)-7-[4-(trifluoromethyl)benzyl]-7H-purine-2-carboxylic acid;

6-{[(1R)-1-cyclobutylethyl]amino}-8-[5-(1-methylethyl)-2-(trifluoromethoxy)phenyl]-7-[4-(trifluoromethyl)benzyl]-7H-purine-2-carboxylic acid;

8-(4-tert-butylpyridin-2-yl)-6-{[(1R)-1-cyclobutylethyl] amino}-7-[4-(trifluoromethyl)benzyl]-7H-purine-2-carboxylic acid;

6-{[(1R)-1-cyclobutylethyl]amino}-8-(4-cyclobutylpyridin-2-yl)-7-[4-(trifluoromethyl)benzyl]-7H-purine-2-carboxylic acid;

6-{[(1R)-1-cyclobutylethyl]amino}-8-(4-cyclopentylpyridin-2-yl)-7-[4-(trifluoromethyl)benzyl]-7H-purine-2-carboxylic acid;

6-{[(1R)-1-cyclobutylethyl]amino}-8-(4-cyclohexylpyridin-2-yl)-7-[4-(trifluoromethyl)benzyl]-7H-purine-2-carboxylic acid;

6-{[(1R)-1-cyclobutylethyl]amino}-8-(4-thiophen-2-ylpyridin-2-yl)-7-[4-(trifluoromethyl)benzyl]-7H-purine-2-carboxylic acid;
6-{[(1R)-1-cyclobutylethyl]amino}-8-[4-(cyclohexyloxy)pyridin-2-yl]-7-[4-(trifluoromethyl)benzyl]-7H-purine-2-carboxylic acid;
6-{[(1R)-1-cyclobutylethyl]amino}-8-[4-(1-methylethoxy)pyridin-2-yl]-7-[4-(trifluoromethyl)benzyl]-7H-purine-2-carboxylic acid;
6-{[(1R)-1-cyclobutylethyl]amino}-7-[4-(trifluoromethyl)benzyl]-8-[4-(trifluoromethyl)pyridin-2-yl]-7H-purine-2-carboxylic acid;
6-{[(1R)-1-cyclobutylethyl]amino}-8-(2,3-dihydro-1H-isoindol-4-yl)-7-[4-(trifluoromethyl)benzyl]-7H-purine-2-carboxylic acid;
6-{[(1R)-1-cyclobutylethyl]amino}-8-isoquinolin-3-yl-7-[4-(trifluoromethyl)benzyl]-7H-purine-2-carboxylic acid;
6-{[(1R)-1-cyclobutylethyl]amino}-8-(6-phenylpyridin-2-yl)-7-[4-(trifluoromethyl)benzyl]-7H-purine-2-carboxylic acid;
8-[4,6-bis(difluoromethyl)pyridin-2-yl]-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-[5-(1,3-dioxolan-2-yl)pyridin-2-yl]-7-[4-(trifluoromethyl)benzyl]-7H-purine-2-carboxylic acid;
6-{[(1R)-1-cyclobutylethyl]amino}-8-[5-(difluoromethoxy)pyridin-2-yl]-7-[4-(trifluoromethyl)benzyl]-7H-purine-2-carboxylic acid;
6-{[(1R)-1-cyclobutylethyl]amino}-8-(4-methoxypyridin-2-yl)-7-[4-(trifluoromethyl)benzyl]-7H-purine-2-carboxylic acid;
6-{[(1R)-1-cyclobutylethyl]amino}-8-(4-propylpyridin-2-yl)-7-[4-(trifluoromethyl)benzyl]-7H-purine-2-carboxylic acid;
6-{[(1R)-1-cyclobutylethyl]amino}-8-(4-ethylpyridin-2-yl)-7-[4-(trifluoromethyl)benzyl]-7H-purine-2-carboxylic acid;
6-{[(1R)-1-cyclobutylethyl]amino}-8-[6-(1-methylethyl)pyridin-2-yl]-7-[4-(trifluoromethyl)benzyl]-7H-purine-2-carboxylic acid;
6-{[(1R)-1-cyclobutylethyl]amino}-7-[3-fluoro-4-(trifluoromethoxy)benzyl]-8-[4-(1-methylethyl)pyridin-2-yl]-7H-purine-2-carboxylic acid;
6-{[(1R)-1-cyclobutylethyl]amino}-8-[4-(1-methylethyl)pyridin-2-yl]-7-[4-(trifluoromethoxy)benzyl]-7H-purine-2-carboxylic acid;
6-{[(1R)-1-cyclobutylethyl]amino}-8-isoquinolin-1-yl-7-[4-(trifluoromethyl)benzyl]-7H-purine-2-carboxylic acid;
6-{[(1R)-1-cyclobutylethyl]amino}-8-(4-methoxy-3-methylpyridin-2-yl)-7-[4-(trifluoromethyl)benzyl]-7H-purine-2-carboxylic acid;
6-{[(1R)-1-cyclobutylethyl]amino}-8-(3-phenylpyridin-2-yl)-7-[4-(trifluoromethyl)benzyl]-7H-purine-2-carboxylic acid;
8-(4-tert-butylpyridin-2-yl)-6-{[(1R)-1-cyclobutylethyl]amino}-7-[3-fluoro-4-(trifluoromethyl)benzyl]-7H-purine-2-carboxylic acid;
6-{[(1R)-1-cyclobutylethyl]amino}-8-(4-cyclopropylpyridin-2-yl)-7-[3-fluoro-4-(trifluoromethyl)benzyl]-7H-purine-2-carboxylic acid;
6-{[(1R)-1-cyclobutylethyl]amino}-8-(4-cyclobutylpyridin-2-yl)-7-[3-fluoro-4-(trifluoromethyl)benzyl]-7H-purine-2-carboxylic acid;
6-{[(1R)-1-cyclobutylethyl]amino}-8-(4-ethylpyridin-2-yl)-7-[3-fluoro-4-(trifluoromethyl)benzyl]-7H-purine-2-carboxylic acid;
6-{[(1R)-1-cyclobutylethyl]amino}-7-[3-fluoro-4-(trifluoromethyl)benzyl]-8-(4-propylpyridin-2-yl)-7H-purine-2-carboxylic acid;
6-{[(1R)-1-cyclobutylethyl]amino}-8-[5-(1-methylethyl)pyridin-3-yl]-7-[4-(trifluoromethyl)benzyl]-7H-purine-2-carboxylic acid;
6-{[(1R)-1-cyclobutylethyl]amino}-8-(3-fluoro-4-methylpyridin-2-yl)-7-[4-(trifluoromethyl)benzyl]-7H-purine-2-carboxylic acid;
6-{[(1R)-1-cyclobutylethyl]amino}-7-[3-fluoro-4-(trifluoromethoxy)benzyl]-8-[5-(1-methylethyl)-2-(trifluoromethoxy)phenyl]-7H-purine-2-carboxylic acid;
6-{[(1R)-1-cyclobutylethyl]amino}-8-[5-methyl-2-(trifluoromethoxy)phenyl]-7-[4-(trifluoromethyl)benzyl]-7H-purine-2-carboxylic acid;
6-{[(1R)-1-cyclobutylethyl]amino}-8-[4-(2-methylpropyl)pyridin-2-yl]-7-[4-(trifluoromethyl)benzyl]-7H-purine-2-carboxylic acid;
6-{[(1R)-1-cyclobutylethyl]amino}-8-[5-methyl-4-(1-methylethyl)pyridin-2-yl]-7-[4-(trifluoromethyl)benzyl]-7H-purine-2-carboxylic acid;
6-{[(1R)-1-cyclobutylethyl]amino}-8-[3-methyl-4-(1-methylethyl)pyridin-2-yl]-7-[4-(trifluoromethyl)benzyl]-7H-purine-2-carboxylic acid;
6-{[(1R)-1-cyclobutylethyl]amino}-8-[4-(3,3-dimethylbutyl)pyridin-2-yl]-7-[4-(trifluoromethyl)benzyl]-7H-purine-2-carboxylic acid;
6-{[(1R)-1-cyclobutylethyl]amino}-8-[4-(2-cyclopropylethyl)pyridin-2-yl]-7-[4-(trifluoromethyl)benzyl]-7H-purine-2-carboxylic acid;
6-{[(1R)-1-cyclobutylethyl]amino}-7-[3-fluoro-4-(trifluoromethoxy)benzyl]-8-[5-methyl-4-(1-methylethyl)pyridin-2-yl]-7H-purine-2-carboxylic acid;
6-{[(1R)-1-cyclobutylethyl]amino}-7-[3-fluoro-4-(trifluoromethoxy)benzyl]-8-[3-methyl-4-(1-methylethyl)pyridin-2-yl]-7H-purine-2-carboxylic acid;
6-{[(1R)-1-cyclobutylethyl]amino}-7-[3-fluoro-4-(trifluoromethyl)benzyl]-8-[5-methyl-4-(1-methylethyl)pyridin-2-yl]-7H-purine-2-carboxylic acid;
6-{[(1R)-1-cyclobutylethyl]amino}-8-[6-methyl-4-(1-methylethyl)pyridin-2-yl]-7-[4-(trifluoromethyl)benzyl]-7H-purine-2-carboxylic acid;
6-{[(1R)-1-cyclobutylethyl]amino}-8-(1,3-dimethyl-1H-pyrazol-5-yl)-7-[4-(trifluoromethyl)benzyl]-7H-purine-2-carboxylic acid;
6-{[(1R)-1-cyclobutylethyl]amino}-8-(1,5-dimethyl-1H-pyrazol-4-yl)-7-[4-(trifluoromethyl)benzyl]-7H-purine-2-carboxylic acid;
6-{[(1R)-1-cyclopropylethyl]amino}-8-phenyl-7-[4-(trifluoromethyl)benzyl]-7H-purine-2-carboxylic acid;
6-{[(1R)-1-cyclopropylethyl]amino}-8-(4-morpholin-4-ylphenyl)-7-[4-(trifluoromethyl)benzyl]-7H-purine-2-carboxylic acid;
6-{[(1R)-1-cyclopropylethyl]amino}-8-[3-(1-methylethoxy)phenyl]-7-[4-(trifluoromethyl)benzyl]-7H-purine-2-carboxylic acid;
6-{[(1R)-1-cyclobutylethyl]amino}-8-(2,5-dimethylphenyl)-7-[4-(trifluoromethyl)benzyl]-7H-purine-2-carboxylic acid;
6-{[(1R)-1-cyclobutylethyl]amino}-8-[4-(difluoromethoxy)phenyl]-7-[4-(trifluoromethyl)benzyl]-7H-purine-2-carboxylic acid;
6-{[(1R)-1-cyclobutylethyl]amino}-8-[4-(1-hydroxyethyl)phenyl]-7-[4-(trifluoromethyl)benzyl]-7H-purine-2-carboxylic acid;
6-{[(1R)-1-cyclobutylethyl]amino}-8-(3-fluoro-4-methylphenyl)-7-[4-(trifluoromethyl)benzyl]-7H-purine-2-carboxylic acid;
6-{[(1R)-1-cyclobutylethyl]amino}-8-(5-fluoro-2-methylphenyl)-7-[4-(trifluoromethyl)benzyl]-7H-purine-2-carboxylic acid;
6-{[(1R)-1-cyclobutylethyl]amino}-8-(3-fluoro-4-methoxyphenyl)-7-[4-(trifluoromethyl)benzyl]-7H-purine-2-carboxylic acid;

6-{[(1R)-1-cyclobutylethyl]amino}-8-(4-methoxy-3-methylphenyl)-7-[4-(trifluoromethyl)benzyl]-7H-purine-2-carboxylic acid;
6-{[(1R)-1-cyclobutylethyl]amino}-8-quinoxalin-6-yl-7-[4-(trifluoromethyl)benzyl]-7H-purine-2-carboxylic acid;
6-{[(1R)-1-cyclobutylethyl]amino}-8-[3-(1H-pyrrol-1-yl)phenyl]-7-[4-(trifluoromethyl)benzyl]-7H-purine-2-carboxylic acid;
6-{[(1R)-1-cyclobutylethyl]amino}-8-(1-methyl-1H-indol-5-yl)-7-[4-(trifluoromethyl)benzyl]-7H-purine-2-carboxylic acid;
8-biphenyl-4-yl-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-(4-cyclohexylphenyl)-7-[4-(trifluoromethyl)benzyl]-7H-purine-2-carboxylic acid;
6-{[(1R)-1-cyclobutylethyl]amino}-8-(2-methylquinolin-6-yl)-7-[4-(trifluoromethyl)benzyl]-7H-purine-2-carboxylic acid;
6-{[(1R)-1-cyclobutylethyl]amino}-8-(2-fluorobiphenyl-4-yl)-7-[4-(trifluoromethyl)benzyl]-7H-purine-2-carboxylic acid;
6-{[(1R)-1-cyclobutylethyl]amino}-8-[4-(dimethylamino)phenyl]-7-[4-(trifluoromethyl)benzyl]-7H-purine-2-carboxylic acid;
8-(4-tert-butylphenyl)-6-{[(1R)-1-cyclobutylethyl]amino}-7-[4-(trifluoromethyl)benzyl]-7H-purine-2-carboxylic acid;
8-[4-chloro-3-(trifluoromethyl)phenyl]-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-[4-(cyclopropylcarbonyl)phenyl]-7-[4-(trifluoromethyl)benzyl]-7H-purine-2-carboxylic acid;
8-(1-benzofuran-5-yl)-6-{[(1R)-1-cyclobutylethyl]amino}-7-[4-(trifluoromethyl)benzyl]-7H-purine-2-carboxylic acid;
6-{[(1R)-1-cyclopropylethyl]amino}-8-(2-methylpyridin-4-yl)-7-[4-(trifluoromethyl)benzyl]-7H-purine-2-carboxylic acid;
6-{[(1R)-1-cyclobutylethyl]amino}-8-(2-methoxy-5-methylphenyl)-7-[4-(trifluoromethyl)benzyl]-7H-purine-2-carboxylic acid;
8-(2-chloro-5-methylphenyl)-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-(2,3-dihydro-1-benzofuran-5-yl)-7-[4-(trifluoromethyl)benzyl]-7H-purine-2-carboxylic acid;
6-{[(1R)-1-cyclobutylethyl]amino}-7-[4-(trifluoromethyl)benzyl]-8-[6-(trifluoromethyl)pyridin-2-yl]-7H-purine-2-carboxylic acid;
6-{[(1R)-1-cyclobutylethyl]amino}-8-(3-methoxy-5-methylphenyl)-7-[4-(trifluoromethyl)benzyl]-7H-purine-2-carboxylic acid;
8-(4-chloro-3-methoxyphenyl)-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-(4-methyl-3,4-dihydro-2H-1,4-benzoxazin-7-yl)-7-[4-(trifluoromethyl)benzyl]-7H-purine-2-carboxylic acid;
6-{[(1R)-1-cyclobutylethyl]amino}-8-(2,3-dimethylphenyl)-7-[4-(trifluoromethyl)benzyl]-7H-purine-2-carboxylic acid;
6-{[(1R)-1-cyclobutylethyl]amino}-8-[3-(1-methylethoxy)phenyl]-7-[4-(trifluoromethyl)benzyl]-7H-purine-2-carboxylic acid;
6-{[(1R)-1-cyclobutylethyl]amino}-8-(3,5-di-tert-butylphenyl)-7-[4-(trifluoromethyl)benzyl]-7H-purine-2-carboxylic acid;
6-{[(1R)-1-cyclobutylethyl]amino}-8-[2-methyl-4-(trifluoromethoxy)phenyl]-7-[4-(trifluoromethyl)benzyl]-7H-purine-2-carboxylic acid;
6-{[(1R)-1-cyclobutylethyl]amino}-8-[3-(phenylamino)phenyl]-7-[4-(trifluoromethyl)benzyl]-7H-purine-2-carboxylic acid;
6-{[(1R)-1-cyclobutylethyl]amino}-8-(3,5-dimethylphenyl)-7-[4-(trifluoromethyl)benzyl]-7H-purine-2-carboxylic acid;
8-(5-chloro-2-methylphenyl)-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-(6-methoxynaphthalen-2-yl)-7-[4-(trifluoromethyl)benzyl]-7H-purine-2-carboxylic acid;
6-{[(1R)-1-cyclobutylethyl]amino}-8-(4-methoxy-3,5-dimethylphenyl)-7-[4-(trifluoromethyl)benzyl]-7H-purine-2-carboxylic acid;
6-{[(1R)-1-cyclobutylethyl]amino}-7-[4-(trifluoromethyl)benzyl]-8-[3-(trifluoromethyl)pyridin-2-yl]-7H-purine-2-carboxylic acid;
6-{[(1R)-1-cyclobutylethyl]amino}-8-(2-fluoro-4-methoxyphenyl)-7-[4-(trifluoromethyl)benzyl]-7H-purine-2-carboxylic acid;
6-{[(1R)-1-cyclobutylethyl]amino}-8-(4-fluoro-3-methylphenyl)-7-[4-(trifluoromethyl)benzyl]-7H-purine-2-carboxylic acid;
6-{[(1R)-1-cyclobutylethyl]amino}-8-(2-ethoxy-5-methylphenyl)-7-[4-(trifluoromethyl)benzyl]-7H-purine-2-carboxylic acid;
(R)-6-((1-cyclobutylethyl)amino)-8-(3-methoxyphenyl)-7-(4-(trifluoromethyl)benzyl)-7H-purine-2-carboxylic acid;
(R)-6-((1-cyclobutylethyl)amino)-8-(4-cyclopropyl-2-methylphenyl)-7-(4-(trifluoromethyl)benzyl)-7H-purine-2-carboxylic acid;
(R)-8-benzyl-6-((1-cyclobutylethyl)amino)-7-(4-(trifluoromethyl)benzyl)-7H-purine-2-carboxylic acid;
(R)-6-((1-cyclobutylethyl)amino)-8-cyclohexyl-7-(4-(trifluoromethyl)benzyl)-7H-purine-2-carboxylic acid;
7-(4-chlorobenzyl)-8-(3-chlorophenyl)-6-{[(1R)-1-cyclopropylethyl]amino}-7H-purine-2-carboxylic acid;
7-(4-chlorobenzyl)-6-{[(1R)-1-cyclopropylethyl]amino}-8-(3-methylphenyl)-7H-purine-2-carboxylic acid;
8-(1-benzothiophen-5-yl)-7-(4-chlorobenzyl)-6-{[(1R)-1-cyclopropylethyl]amino}-7H-purine-2-carboxylic acid;
6-{[(1R)-1-cyclopropylethyl]amino}-8-(3-methylphenyl)-7-[4-(trifluoromethyl)benzyl]-7H-purine-2-carboxylic acid;
7-(4-chlorobenzyl)-8-(4-chlorophenyl)-6-{[(1R)-1-cyclopropylethyl]amino}-7H-purine-2-carboxylic acid;
8-(1-benzothiophen-5-yl)-7-(4-chlorobenzyl)-6-{[(1R)-1-cyclobutylethyl]amino}-7H-purine-2-carboxylic acid;
6-{[(1R)-1-cyclobutylethyl]amino}-8-(3-methylphenyl)-7-[4-(trifluoromethyl)benzyl]-7H-purine-2-carboxylic acid;
7-(4-chlorobenzyl)-6-{[(1R)-1-cyclopropylethyl]amino}-8-(2,5-dimethylphenyl)-7H-purine-2-carboxylic acid;
7-(4-chlorobenzyl)-6-{[(1R)-1-cyclopropylethyl]amino}-8-(4-fluoro-3-methylphenyl)-7H-purine-2-carboxylic acid;
6-{[(1R)-1-cyclopropylethyl]amino}-8-(3-methoxyphenyl)-7-[4-(trifluoromethyl)benzyl]-7H-purine-2-carboxylic acid;
6-{[(1R)-1-cyclopropylethyl]amino}-8-(3-ethoxyphenyl)-7-[4-(trifluoromethyl)benzyl]-7H-purine-2-carboxylic acid;
6-{[(1R)-1-cyclopropylethyl]amino}-8-(3-ethylphenyl)-7-[4-(trifluoromethyl)benzyl]-7H-purine-2-carboxylic acid;

6-{[(1R)-1-cyclobutylethyl]amino}-8-(3-ethoxyphenyl)-7-[4-(trifluoromethyl)benzyl]-7H-purine-2-carboxylic acid;

6-{[(1R)-1-cyclopropylethyl]amino}-8-[3-(1-methylethyl)phenyl]-7-[4-(trifluoromethyl)benzyl]-7H-purine-2-carboxylic acid;

8-(3-tert-butylphenyl)-6-{[(1R)-1-cyclopropylethyl]amino}-7-[4-(trifluoromethyl)benzyl]-7H-purine-2-carboxylic acid;

6-{[(1R)-1-cyclopropylethyl]amino)}-7-[4-(trifluoromethyl)benzyl]-8-[4-(trifluoromethyl)phenyl]-7H-purine-2-carboxylic acid;

6-{[(1R)-1-cyclopropylethyl]amino}-8-(4-methoxyphenyl)-7-[4-(trifluoromethyl)benzyl]-7H-purine-2-carboxylic acid;

8-(3-chlorophenyl)-6-{[(1R)-1-cyclopropylethyl]amino}-7-[4-(trifluoromethyl)benzyl]-7H-purine-2-carboxylic acid;

6-{[(1R)-1-cyclobutylethyl]amino}-8-(3-ethylphenyl)-7-[4-(trifluoromethyl)benzyl]-7H-purine-2-carboxylic acid;

6-{[(1R)-1-cyclobutylethyl]amino}-8-[3-(1-methylethyl)phenyl]-7-[4-(trifluoromethyl)benzyl]-7H-purine-2-carboxylic acid;

8-(3-tert-butylphenyl)-6-{[(1R)-1-cyclobutylethyl]amino}-7-[4-(trifluoromethyl)benzyl]-7H-purine-2-carboxylic acid;

6-{[(1R)-1-cyclopropylethyl]amino}-8-[3-(trifluoromethoxy)phenyl]-7-[4-(trifluoromethyl)benzyl]-7H-purine-2-carboxylic acid;

6-{[(1R)-1-cyclopropylethyl]amino}-8-[4-(trifluoromethoxy)phenyl]-7-[4-(trifluoromethyl)benzyl]-7H-purine-2-carboxylic acid;

6-{[(1R)-1-cyclopropylethyl]amino}-8-(3,5-dimethoxyphenyl)-7-[4-(trifluoromethyl)benzyl]-7H-purine-2-carboxylic acid;

6-{[(1R)-1-cyclopropylethyl]amino}-8-[3-(dimethylamino)phenyl]-7-[4-(trifluoromethyl)benzyl]-7H-purine-2-carboxylic acid;

6-{[(1R)-1-cyclopropylethyl]amino}-8-(2-methylphenyl)-7-[4-(trifluoromethyl)benzyl]-7H-purine-2-carboxylic acid;

6-{[(1R)-1-cyclopropylethyl]amino}-8-(3,4-dichlorophenyl)-7-[4-(trifluorometethyl)benzyl]-7H-purine-2-carboxylic acid;

8-(4-tert-butylphenyl)-6-{[(1R)-1-cyclopropylethyl]amino}-7-[4-(trifluoromethyl)benzyl]-7H-purine-2-carboxylic acid;

6-{[(1R)-1-cyclopropylethyl]amino}-8-(4-methylphenyl)-7-[4-(trifluoromethyl)benzyl]-7H-purine-2-carboxylic acid;

6-{[(1R)-1-cyclopropylethyl]amino}-8-[2-(trifluoromethoxy)phenyl]-7-[4-(trifluoromethyl)benzyl]-7H-purine-2-carboxylic acid;

6-{[(1R)-1-cyclopropylethyl]amino}-8-(1-methyl-1H-pyrazol-4-yl)-7-[4-(trifluoromethyl)benzyl]-7H-purine-2-carboxylic acid;

6-{[(1R)-1-cyclopropylethyl]amino}-8-(6-methylpyridin-3-yl)-7-[4-(trifluoromethyl)benzyl]-7H-purine-2-carboxylic acid;

6-{[(1R)-1-cyclobutylethyl]amino}-8-[3-(dimethylamino)phenyl]-7-[4-(trifluoromethyl)benzyl]-7H-purine-2-carboxylic acid;

6-{[(1R)-1-cyclobutylethyl]amino}-7-[4-(trifluoromethyl)benzyl]-8-[3-(trifluoromethyl)phenyl]-7H-purine-2-carboxylic acid;

6-{[(1R)-1-cyclobutylethyl]amino}-8-[3-(trifluoromethoxy)phenyl]-7-[4-(trifluoromethyl)benzyl]-7H-purine-2-carboxylic acid;

8-(3-chlorophenyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[4-(methylsulfamoyl)phenyl]-7-[4-(trifluoromethyl)benzyl]-7H-purine-2-carboxylic acid;

7-(4-chlorobenzyl)-8-cyclopropyl-6-{[(1R)-1-cyclopropylethyl]amino}-7H-purine-2-carboxylic acid;

8-benzyl-7-(4-chlorobenzyl)-6-{[(1R)-1-cyclopropylethyl]amino}-7H-purine-2-carboxylic acid;

6-{[(1R)-1-cyclopropylethyl]amino}-8-pyridin-3-yl-7-[4-(trifluoromethyl)benzyl]-7H-purine-2-carboxylic acid;

8-(3-cyanophenyl)-6-{[(1R)-1-cyclobutylethyl]amino}-7-[4-(trifluoromethyl)benzyl]-7H-purine-2-carboxylic acid;

8-(5-chloro-6-methoxypyridin-3-yl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(2-fluorophenyl)-7-[4-(trifluoromethyl)benzyl]-7H-purine-2-carboxylic acid;

6-{[(1R)-1-cyclopropylethyl]amino}-8-(6-methoxypyridin-3-yl)-7-[4-(trifluoromethyl)benzyl]-7H-purine-2-carboxylic acid;

6-{[(1R)-1-cyclopropylethyl]amino}-8-(5-fluoro-6-methoxypyridin-3-yl)-7-[4-(trifluoromethyl)benzyl]-7H-purine-2-carboxylic acid;

6-{[(1R)-1-cyclopropylethyl]amino}-8-(3,5-dimethylphenyl)-7-[4-(trifluoromethyl)benzyl]-7H-purine-2-carboxylic acid;

6-{[(1R)-1-cyclopropylethyl]amino}-8-(5-fluoro-6-hydroxypyridin-3-yl)-7-[4-(trifluoromethyl)benzyl]-7H-purine-2-carboxylic acid;

6-{[(1R)-1-cyclopropylethyl]amino}-8-(2,4-dimethylphenyl)-7-[4-(trifluoromethyl)benzyl]-7H-purine-2-carboxylic acid;

8-(4-chloro-3-fluorophenyl)-6-{[(1R)-1-cyclopropylethyl]amino}-7-[4-(trifluoromethyl)benzyl]-7H-purine-2-carboxylic acid;

6-{[(1R)-1-cyclopropylethyl]amino}-8-[2-methyl-4-(trifluoromethoxy)phenyl]-7-[4-(trifluoromethyl)benzyl]-7H-purine-2-carboxylic acid;

8-(2-chlorophenyl)-6-{[(1R)-1-cyclopropylethyl]amino}-7-[4-(trifluoromethyl)benzyl]-7H-purine-2-carboxylic acid;

6-{[(1R)-1-cyclopropylethyl]amino}-8-(3-fluorophenyl)-7-[4-(trifluoromethyl)benzyl]-7H-purine-2-carboxylic acid;

8-(4-cyanophenyl)-6-{[(1R)-1-cyclopropylethyl]amino}-7-[4-(trifluoromethyl)benzyl]-7H-purine-2-carboxylic acid;

6-{[(1R)-1-cyclopropylethyl]amino}-8-(2,4-dichlorophenyl)-7-[4-(trifluorometethyl)benzyl]-7H-purine-2-carboxylic acid;

6-{[(1R)-1-cyclopropylethyl]amino}-8-(2,3-dimethylphenyl)-7-[4-(trifluoromethyl)benzyl]-7H-purine-2-carboxylic acid;

6-{[(1R)-1-cyclopropylethyl]amino}-8-naphthalen-2-yl-7-[4-(trifluoromethyl)benzyl]-7H-purine-2-carboxylic acid;

8-(3-chloro-4-fluorophenyl)-6-{[(1R)-1-cyclobutylethyl]amino}-7-[4-(trifluoromethyl)benzyl]-7H-purine-2-carboxylic acid;

6-{[(1R)-1-cyclopropylethyl]amino}-8-(2,6-dimethylphenyl)-7-[4-(trifluoromethyl)benzyl]-7H-purine-2-carboxylic acid;

6-{[(1R)-1-cyclobutylethyl]amino}-8-(2,5-dichlorophenyl)-7-[4-(trifluoromethyl)benzyl]-7H-purine-2-carboxylic acid;

8-(3-cyano-5-methoxyphenyl)-6-{[(1R)-1-cyclobutylethyl]amino}-7-[4-(trifluoromethyl)benzyl]-7H-purine-2-carboxylic acid;

6-{[(1R)-1-cyclopropylethyl]amino}-8-(2-fluoro-3-methylphenyl)-7-[4-(trifluoromethyl)benzyl]-7H-purine-2-carboxylic acid;
8-(3-chloro-4-methoxyphenyl)-6-{[(1R)-1-cyclopropylethyl]amino}-7-[4-(trifluoromethyl)benzyl]-7H-purine-2-carboxylic acid;
6-{[(1R)-1-cyclobutylethyl]amino}-8-[3-(difluoromethoxy)phenyl]-7-[4-(trifluoromethyl)benzyl]-7H-purine-2-carboxylic acid;
6-{[(1R)-1-cyclobutylethyl]amino}-8-(2,4-difluorophenyl)-7-[4-(trifluoromethyl)benzyl]-7H-purine-2-carboxylic acid;
6-{[(1R)-1-cyclopropylethyl]amino}-8-quinolin-6-yl-7-[4-(trifluoromethyl)benzyl]-7H-purine-2-carboxylic acid;
6-{[(1R)-1-cyclopropylethyl]amino}-8-[2-(dimethylamino)pyrimidin-5-yl]-7-[4-(trifluoromethyl)benzyl]-7H-purine-2-carboxylic acid;
6-{[(1R)-1-cyclopropylethyl]amino}-8-(2-methoxypyridin-4-yl)-7-[4-(trifluoromethyl)benzyl]-7H-purine-2-carboxylic acid;
6-{[(1R)-1-cyclopropylethyl]amino}-8-(6-ethoxypyridin-3-yl)-7-[4-(trifluoromethyl)benzyl]-7H-purine-2-carboxylic acid;
6-{[(1R)-1-cyclopropylethyl]amino}-8-(2,3-difluorophenyl)-7-[4-(trifluoromethyl)benzyl]-7H-purine-2-carboxylic acid;
6-{[(1R)-1-cyclopropylethyl]amino}-8-(2,3-dihydro-1H-inden-5-yl)-7-[4-(trifluoromethyl)benzyl]-7H-purine-2-carboxylic acid;
8-(4-bromo-2-fluorophenyl)-6-{[(1R)-1-cyclopropylethyl]amino}-7-[4-(trifluoromethyl)benzyl]-7H-purine-2-carboxylic acid;
6-{[(1R)-1-cyclobutylethyl]amino}-8-(3,4-dichlorophenyl)-7-[4-(trifluoromethyl)benzyl]-7H-purine-2-carboxylic acid;
6-{[(1R)-1-cyclobutylethyl]amino}-8-pyridin-4-yl-7-[4-(trifluoromethyl)benzyl]-7H-purine-2-carboxylic acid;
8-(2-carbamoylphenyl)-6-{[(1R)-1-cyclopropylethyl]amino}-7-[4-(trifluoromethyl)benzyl]-7H-purine-2-carboxylic acid;
6-{[(1R)-1-cyclobutylethyl]amino}-7-[4-(trifluoromethyl)benzyl]-8-[2-(trifluoromethyl)phenyl]-7H-purine-2-carboxylic acid;
6-{[(1R)-1-cyclobutylethyl]amino}-8-(2-ethyl-5-methoxyphenyl)-7-[4-(trifluoromethyl)benzyl]-7H-purine-2-carboxylic acid;
6-{[(1R)-1-cyclobutylethyl]amino}-8-(2-ethylphenyl)-7-[4-(trifluoromethyl)benzyl]-7H-purine-2-carboxylic acid;
6-{[(1R)-1-cyclobutylethyl]amino}-8-(2-ethyl-5-methylphenyl)-7-[4-(trifluoromethyl)benzyl]-7H-purine-2-carboxylic acid;
6-{[(1R)-1-cyclobutylethyl]amino}-8-(1-methyl-1H-pyrazol-4-yl)-7-[4-(trifluoromethyl)benzyl]-7H-purine-2-carboxylic acid;
6-{[(1R)-1-cyclobutylethyl]amino}-8-(3,5-dimethylisoxazol-4-yl)-7-[4-(trifluoromethyl)benzyl]-7H-purine-2-carboxylic acid;
(R)-6-((1-cyclobutylethyl)amino)-8-(1-methyl-1H-imidazol-2-yl)-7-(4-(trifluoromethyl) benzyl)-7H-purine-2-carboxylic acid;
(R)-6-((1-cyclobutylethyl)amino)-8-(4-isopropylpyrimidin-2-yl)-7-(4-(trifluoromethyl)benzyl)-7H-purine-2-carboxylic acid;
(R)-6-((1-cyclobutylethyl)amino)-8-(5-isopropylthiazol-2-yl)-7-(4-(trifluoromethyl)benzyl)-7H-purine-2-carboxylic acid;
6-{[(1R)-1-cyclobutylethyl]amino}-8-pyrimidin-2-yl-7-[4-(trifluoromethyl)benzyl]-7H-purine-2-carboxylic acid;
6-{[(1R)-1-cyclobutylethyl]amino}-8-(1,3-oxazol-2-yl)-7-[4-(trifluoromethyl)benzyl]-7H-purine-2-carboxylic acid;
6-{[(1R)-1-cyclobutylethyl]amino}-8-[4-(1-methylethyl)-1,3-thiazol-2-yl]-7-[4-(trifluoromethyl)benzyl]-7H-purine-2-carboxylic acid;
6-{[(1R)-1-cyclobutylethyl]amino}-8-(5-methyl-1,3-thiazol-2-yl)-7-[4-(trifluoromethyl)benzyl]-7H-purine-2-carboxylic acid;
7-(4-chlorobenzyl)-6-{[(1R)-1-cyclopropylethyl]amino}-8-(1,3-thiazol-2-yl)-7H-purine-2-carboxylic acid;
6-{[(1R)-1-cyclobutylethyl]amino}-8-(1,3-thiazol-2-yl)-7-[4-(trifluoromethyl)benzyl]-7H-purine-2-carboxylic acid;
(R)-7-(4-chlorobenzyl)-6-((1-cyclobutylethyl)amino)-8-(2-ethoxy-5-methylphenyl)-7H-purine-2-carboxylic acid;
(R)-7-(4-chlorobenzyl)-6-((1-cyclobutylethyl)amino)-8-(2, 5-dimethylphenyl)-7H-purine-2-carboxylic acid;
(R)-8-(2-(but-3-en-1-yloxy)-5-methylphenyl)-7-(4-chlorobenzyl)-6-((1-cyclopropylethyl)amino)-7H-purine-2-carboxylic acid;
(R)-7-(4-chlorobenzyl)-6-((1-cyclobutylethyl)amino)-8-(2-(3-methoxypropoxy)-5-methylphenyl)-7H-purine-2-carboxylic acid;
(R)-7-(4-chlorobenzyl)-6-((1-cyclopropylethyl)amino)-8-(2-(3-methoxypropoxy)-5-methylphenyl)-7H-purine-2-carboxylic acid;
(R)-7-(4-chlorobenzyl)-6-((1-cyclobutylethyl)amino)-8-(2-(3-hydroxypropoxy)-5-methylphenyl)-7H-purine-2-carboxylic acid;
(R)-7-(4-chlorobenzyl)-6-((1-cyclopropylethyl)amino)-8-(2-ethoxy-5-methylphenyl)-7H-purine-2-carboxylic acid;
(R)-7-(4-chlorobenzyl)-6-((1-cyclobutylethyl)amino)-8-(2-(2-methoxyethoxy)-5-methylphenyl)-7H-purine-2-carboxylic acid;
(R)-7-(4-chlorobenzyl)-6-((1-cyclopropylethyl)amino)-8-(2-(2-methoxyethoxy)-5-methylphenyl)-7H-purine-2-carboxylic acid;
(R)-7-(4-chlorobenzyl)-6-((1-cyclopropylethyl)amino)-8-(2-(2-hydroxyethoxy)-5-methylphenyl)-7H-purine-2-carboxylic acid;
(R)-8-(2-(2-carboxyethoxy)-5-methylphenyl)-7-(4-chlorobenzyl)-6-((1-cyclopropylethyl)amino)-7H-purine-2-carboxylic acid;
(R)-7-(4-chlorobenzyl)-6-((1-cyclopropylethyl)amino)-8-(2-(3-((2-hydroxyethyl)amino)-3-oxopropoxy)-5-methylphenyl)-7H-purine-2-carboxylic acid;
(R)-7-(4-chlorobenzyl)-6-((1-cyclopropylethyl)amino)-8-(5-methyl-2-(3-(methylamino)-3-oxopropoxy)phenyl)-7H-purine-2-carboxylic acid;
(R)-7-(4-chlorobenzyl)-6-((1-cyclopropylethyl)amino)-8-(5-methyl-2-(3-morpholinopropoxy)phenyl)-7H-purine-2-carboxylic acid;
(R)-8-(2-(3-(bis(2-methoxyethyl)amino)propoxy)-5-methylphenyl)-7-(4-chlorobenzyl)-6-((1-cyclopropylethyl)amino)-7H-purine-2-carboxylic acid;
(R)-7-(4-cyanobenzyl)-6-((1-cyclopropylethyl)amino)-8-(2-(3-hydroxypropoxy)-5-methylphenyl)-7H-purine-2-carboxylic acid;
(R)-7-(4-chlorobenzyl)-6-(1-cyclopropylethylamino)-8-(5-methyl-2-(3-(4-methylpiperazin-1-yl)propoxy)phenyl)-7H-purine-2-carboxylic acid;
(R)-7-(4-chlorobenzyl)-6-((1-cyclopropylethyl)amino)-8-(2-hydroxy-5-methylphenyl)-7H-purine-2-carboxylic acid;
7-(4-chlorobenzyl)-6-(((R)-1-cyclopropylethyl)amino)-8-(2-(2,3-dihydroxypropoxy)-5-methylphenyl)-7H-purine-2-carboxylic acid;

(R)-7-(4-chlorobenzyl)-6-((1-cyclopropylethyl)amino)-8-(2-(3-hydroxypropoxy)-5-methylphenyl)-7H-purine-2-carboxylic acid;

7-[1-(4-chlorophenyl)ethyl]-6-{[(1R)-1-cyclopropylethyl]amino}-8-(3-methylphenyl)-7H-purine-2-carboxylic acid;

7-[1-(4-chlorophenyl)ethyl]-6-[(cyclopropylmethyl)amino]-8-(3-methylphenyl)-7H-purine-2-carboxylic acid;

7-[1-(4-chlorophenyl)ethyl]-6-{[(1S)-1-cyclopropylethyl]amino}-8-(3-methylphenyl)-7H-purine-2-carboxylic acid;

6-{[(1R)-1-cyclopropylethyl]amino}-7-[4-fluoro-3-(trifluoromethyl)benzyl]-8-(3-methylphenyl)-7H-purine-2-carboxylic acid;

6-{[(1R)-1-cyclopropylethyl]amino}-7-(2-ethoxy-5-(trifluoromethyl)benzyl)-8-(3-methylphenyl)-7H-purine-2-carboxylic acid;

6-{[(1R)-1-cyclobutylethyl]amino}-7-(2-ethoxybenzyl)-8-(3-methylphenyl)-7H-purine-2-carboxylic acid;

6-{[(1R)-1-cyclopropylethyl]amino}-7-[4-(1-methylethyl)benzyl]-8-(3-methylphenyl)-7H-purine-2-carboxylic acid;

6-{[(1R)-1-cyclopropylethyl]amino}-8-(3-methylphenyl)-7-[4-(trifluoromethoxy)benzyl]-7H-purine-2-carboxylic acid;

6-{[(1R)-1-cyclopropylethyl]amino}-7-[3-fluoro-4-(trifluoromethyl)benzyl]-8-(3-methylphenyl)-7H-purine-2-carboxylic acid;

6-{[(1R)-1-cyclobutylethyl]amino}-7-(4-cyclopropylbenzyl)-8-(3-methylphenyl)-7H-purine-2-carboxylic acid;

6-{[(1R)-1-cyclobutylethyl]amino}-7-(2,4-dichlorobenzyl)-8-(3-methylphenyl)-7H-purine-2-carboxylic acid;

7-[2-chloro-4-(trifluoromethyl)benzyl]-6-{[(1R)-1-cyclobutylethyl]amino}-8-(3-methylphenyl)-7H-purine-2-carboxylic acid;

6-{[(1R)-1-cyclobutylethyl]amino}-7-[4-(difluoromethoxy)benzyl]-8-(3-methylphenyl)-7H-purine-2-carboxylic acid;

6-{[(1R)-1-cyclobutylethyl]amino}-7-[3-fluoro-4-(trifluoromethoxy)benzyl]-8-(3-methylphenyl)-7H-purine-2-carboxylic acid;

7-[3-chloro-4-(trifluoromethyl)benzyl]-6-{[(1R)-1-cyclopropylethyl]amino}-8-(3-methylphenyl)-7H-purine-2-carboxylic acid;

6-{[(1R)-1-cyclopropylethyl]amino}-8-(3-methylphenyl)-7-[2-(trifluoromethyl)benzyl]-7H-purine-2-carboxylic acid;

6-{[(1R)-1-cyclobutylethyl]amino}-7-[2-fluoro-4-(trifluoromethyl)benzyl]-8-(3-methylphenyl)-7H-purine-2-carb oxylic acid;

6-{[(1R)-1-cyclobutylethyl]amino}-7-[2-ethoxy-4-(trifluoromethyl)benzyl]-8-(3-methylphenyl)-7H-purine-2-carb oxylic acid;

6-{[(1R)-1-cyclobutylethyl]amino}-7-(4-methoxybenzyl)-8-(3-methylphenyl)-7H-purine-2-carboxylic acid;

6-{[(1R)-1-cyclopropylethyl]amino}-7-(4-ethylbenzyl)-8-(3-methylphenyl)-7H-purine-2-carboxylic acid;

6-{[(1R)-1-cyclopropylethyl]amino}-7-(4-methylbenzyl)-8-(3-methylphenyl)-7H-purine-2-carboxylic acid;

6-(3-ethylpyrrolidin-1-yl)-8-(3-methylphenyl)-7-[4-(trifluoromethyl)benzyl]-7H-purine-2-carboxylic acid;

7-(4-chlorobenzyl)-6-{[(1R)-1-cyclobutylethyl]amino}-8-(3-methylphenyl)-7H-purine-2-carboxylic acid;

7-(4-chlorobenzyl)-6-{[(1R)-1-cyclopentylethyl]amino}-8-(3-methylphenyl)-7H-purine-2-carboxylic acid;

7-(4-chlorobenzyl)-6-{[(1R)-1-cyclohexylethyl]amino}-8-(3-methylphenyl)-7H-purine-2-carboxylic acid;

7-(4-bromobenzyl)-6-{[(1R)-1-cyclopropylethyl]amino}-8-(3-methylphenyl)-7H-purine-2-carboxylic acid;

7-(4-chlorobenzyl)-6-[(1-cyclopropyl-1-methylethyl)amino]-8-(3-methylphenyl)-7H-purine-2-carboxylic acid;

7-(4-bromobenzyl)-6-{[(1R)-1-cyclobutylethyl]amino}-8-(3-methylphenyl)-7H-purine-2-carboxylic acid;

6-[(2-methylcyclohexyl)amino]-8-(3-methylphenyl)-7-[4-(trifluoromethyl)benzyl]-7H-purine-2-carboxylic acid;

7-(4-bromobenzyl)-6-[(2-methylcyclohexyl)amino]-8-(3-methylphenyl)-7H-purine-2-carboxylic acid;

7-(4-bromobenzyl)-6-[(2-methylcyclohexyl)amino]-8-(3-methylphenyl)-7H-purine-2-carboxylic acid;

7-(4-chlorobenzyl)-6-[(1-cyclopropylethyl)(methyl)
amino]-8-(3-methylphenyl)-7H-purine-2-carboxylic
acid;
7-(4-chlorobenzyl)-8-(3-chlorophenyl)-6-[(cyclopropyl-
methyl)amino]-7H-purine-2-carboxylic acid;
8-(1-benzothiophen-5-yl)-6-{[(1R)-1-cyclopropylethyl]
amino}-7-[4-(trifluoromethyl)benzyl]-7H-purine-2-
carboxylic acid;
8-(1-benzothiophen-5-yl)-6-{[(1R)-1-cyclobutylethyl]
amino}-7-[4-(trifluoromethyl)benzyl]-7H-purine-2-
carboxylic acid;
7-(3-chloro-4-fluorobenzyl)-6-{[(1R)-1-cyclopropyl-
ethyl]amino}-8-(3-methylphenyl)-7H-purine-2-car-
boxylic acid;
6-{[(1R)-1-cyclopropylethyl]amino}-7-(3,4-dichloroben-
zyl)-8-(3-methylphenyl)-7H-purine-2-carboxylic acid;
7-(4-chloro-3-fluorobenzyl)-6-{[(1R)-1-cyclopropyl-
ethyl]amino}-8-(3-methylphenyl)-7H-purine-2-car-
boxylic acid;
3-cyclopropyl-3-({8-(3-methylphenyl)-7-[4-(trifluorom-
ethyl)benzyl]-7H-purin-6-yl}amino)propanoic acid;
6-[(4-methylcyclohexyl)amino]-8-(3-methylphenyl)-7-
[4-(trifluoromethyl)benzyl]-7H-purine-2-carboxylic
acid;
6-[(3-methylcyclohexyl)amino]-8-(3-methylphenyl)-7-
[4-(trifluoromethyl)benzyl]-7H-purine-2-carboxylic
acid;
6-[(2-methylcyclopentyl)amino]-8-(3-methylphenyl)-7-
[4-(trifluoromethyl)benzyl]-7H-purine-2-carboxylic
acid;
6-(cyclopentylamino)-8-(3-methylphenyl)-7-[4-(trifluo-
romethyl)benzyl]-7H-purine-2-carboxylic acid;
8-(3-methylphenyl)-6-pyrrolidin-1-yl-7-[4-(trifluorom-
ethyl)benzyl]-7H-purine-2-carboxylic acid;
6-[(dicyclopropylmethyl)amino]-8-(3-methylphenyl)-7-
[4-(trifluoromethyl)benzyl]-7H-purine-2-carboxylic
acid;
8-(3-methylphenyl)-6-[(2-phenylethyl)amino]-7-[4-(trif-
luoromethyl)benzyl]-7H-purine-2-carboxylic acid;
6-{[(1S)-1-(3-chlorophenyl)ethyl]amino}-8-(3-methyl-
phenyl)-7-[4-(trifluoromethyl)benzyl]-7H-purine-2-
carboxylic acid;
6-{[(1R)-1-(3-chlorophenyl)ethyl]amino}-8-(3-methyl-
phenyl)-7-[4-(trifluoromethyl)benzyl]-7H-purine-2-
carboxylic acid;
6-(cyclohexylamino)-8-(3-methylphenyl)-7-[4-(trifluo-
romethyl)benzyl]-7H-purine-2-carboxylic acid;
6-(benzylamino)-8-(3-methylphenyl)-7-[4-(trifluorom-
ethyl)benzyl]-7H-purine-2-carboxylic acid;
8-(3-methylphenyl)-6-{[(1R)-1-phenylethyl]amino}-7-
[4-(trifluoromethyl)benzyl]-7H-purine-2-carboxylic
acid;
8-(3-methylphenyl)-6-{[(1S)-1-phenylethyl]amino}-7-
[4-(trifluoromethyl)benzyl]-7H-purine-2-carboxylic
acid;
6-[(1-cyclopentylethyl)amino]-8-(3-methylphenyl)-7-[4-
(trifluoromethyl)benzyl]-7H-purine-2-carboxylic acid;
6-[(2,4-dimethylcyclohexyl)amino]-8-(3-methylphenyl)-
7-[4-(trifluoromethyl)benzyl]-7H-purine-2-carboxylic
acid;
6-[(2,4-dimethylcyclohexyl)amino]-8-(3-methylphenyl)-
7-[4-(trifluoromethyl)benzyl]-7H-purine-2-carboxylic
acid;
6-[(4-{[(tert-butoxycarbonyl)amino]methyl}cyclohexyl)
amino]-8-(3-methylphenyl)-7-[4-(trifluoromethyl)ben-
zyl]-7H-purine-2-carboxylic acid;
6-[(cyclopropylmethyl)amino]-8-(3-methylphenyl)-7-[4-
(trifluoromethyl)benzyl]-7H-purine-2-carboxylic acid;
6-{[1-(2-methylcyclopropyl)ethyl]amino}-8-(3-methyl-
phenyl)-7-[4-(trifluoromethyl)benzyl]-7H-purine-2-
carboxylic acid;
6-{[1-(2-methylcyclopropyl)ethyl]amino}-8-(3-methyl-
phenyl)-7-[4-(trifluoromethyl)benzyl]-7H-purine-2-
carboxylic acid;
6-[(2-hydroxy-1,2-dimethylpropyl)amino]-8-(3-methyl-
phenyl)-7-[4-(trifluoromethyl)benzyl]-7H-purine-2-
carboxylic acid;
6-{[4-(hydroxymethyl)cyclohexyl]amino}-8-(3-methyl-
phenyl)-7-[4-(trifluoromethyl)benzyl]-7H-purine-2-
carb oxylic acid;
8-(3-methylphenyl)-7-[4-(trifluoromethyl)benzyl]-6-
{[(1S)-1,2,2-trimethylpropyl]amino}-7H-purine-2-car-
boxylic acid;
6-{[(1R)-1-cyclohexylethyl]amino}-8-(3-methylphenyl)-
7-[4-(trifluoromethyl)benzyl]-7H-purine-2-carboxylic
acid;
8-(3-methylphenyl)-6-(tetrahydro-2H-pyran-4-ylamino)-
7-[4-(trifluoromethyl)benzyl]-7H-purine-2-carboxylic
acid;
6-{[(1R)-1-(4-chlorophenyl)ethyl]amino}-8-(3-methyl-
phenyl)-7-[4-(trifluoromethyl)benzyl]-7H-purine-2-
carboxylic acid;
6-{[(1 S)-1-cyclohexylethyl]amino}-8-(3-methylphenyl)-
7-[4-(trifluoromethyl)benzyl]-7H-purine-2-carboxylic
acid;
6-{[(1S)-1-(4-chlorophenyl)ethyl]amino}-8-(3-methyl-
phenyl)-7-[4-(trifluoromethyl)benzyl]-7H-purine-2-
carboxylic acid;
8-(3-methylphenyl)-7-[4-(trifluoromethyl)benzyl]-6-
{[(1R)-1,2,2-trimethylpropyl]amino}-7H-purine-2-
carboxylic acid;
6-{[(1R)-1,2-dimethylpropyl]amino}-8-(3-methylphe-
nyl)-7-[4-(trifluoromethyl)benzyl]-7H-purine-2-car-
boxylic acid;
6-{[(1S)-1,2-dimethylpropyl]amino}-8-(3-methylphe-
nyl)-7-[4-(trifluoromethyl)benzyl]-7H-purine-2-car-
boxylic acid;
6-[(cyclohexylmethyl)amino]-8-(3-methylphenyl)-7-[4-
(trifluoromethyl)benzyl]-7H-purine-2-carboxylic acid;
6-(diethylamino)-8-(3-methylphenyl)-7-[4-(trifluorom-
ethyl)benzyl]-7H-purine-2-carboxylic acid;
6-{[(1R)-1-cyclopropyl-2,2,2-trifluoroethyl]amino}-8-
(3-methylphenyl)-7-[4-(trifluoromethyl)benzyl]-7H-
purine-2-carboxylic acid;
6-{[(1 S)-1-cyclopropyl-2,2,2-trifluoroethyl]amino}-8-
(3-methylphenyl)-7-[4-(trifluoromethyl)benzyl]-7H-
purine-2-carboxylic acid;
6-{[(1 S)-1-cyclobutylpropyl]amino}-8-[4-(1-methyl-
ethyl)pyridin-2-yl]-7-[4-(trifluoromethyl)benzyl]-7H-
purine-2-carboxylic acid;
6-{[(1R)-1-cyclobutylpropyl]amino}-8-[4-(1-methyl-
ethyl)pyridin-2-yl]-7-[4-(trifluoromethyl)benzyl]-7H-
purine-2-carboxylic acid;
6-{[(1R)-1-(2,2-dimethylcyclopropyl)ethyl]amino}-8-(2-
methoxy-5-methylphenyl)-7-[4-(trifluoromethyl)ben-
zyl]-7H-purine-2-carboxylic acid;
6-{[(R)-cyclobutyl(phenyl)methyl]amino}-8-[4-(1-
methylethyl)pyridin-2-yl]-7-[4-(trifluoromethyl)ben-
zyl]-7H-purine-2-carboxylic acid;
6-{[(S)-cyclobutyl(phenyl)methyl]amino}-8-[4-(1-
methylethyl)pyridin-2-yl]-7-[4-(trifluoromethyl)ben-
zyl]-7H-purine-2-carboxylic acid;
6-[ethyl(methyl)amino]-8-(3-methylphenyl)-7-[4-(trif-
luoromethyl)benzyl]-7H-purine-2-carboxylic acid;
8-(3-methylphenyl)-6-{[(1R)-1-methylpropyl]amino}-7-
[4-(trifluoromethyl)benzyl]-7H-purine-2-carboxylic
acid;
8-(3-methylphenyl)-6-{[(1 S)-1-methylpropyl]amino}-7-
[4-(trifluoromethyl)benzyl]-7H-purine-2-carboxylic
acid;
6-[(1,3-dimethylbutyl)amino]-8-(3-methylphenyl)-7-[4-
(trifluoromethyl)benzyl]-7H-purine-2-carboxylic acid;

6-[(2-methylbutyl)amino]-8-(3-methylphenyl)-7-[4-(trifluoromethyl)benzyl]-7H-purine-2-carboxylic acid;
8-(3-methylphenyl)-6-[(1-propylbutyl)amino]-7-[4-(trifluoromethyl)benzyl]-7H-purine-2-carboxylic acid;
6-[cyclopentyl(methyl)amino]-8-(3-methylphenyl)-7-[4-(trifluoromethyl)benzyl]-7H-purine-2-carboxylic acid;
6-(1,3-dihydro-2H-isoindol-2-yl)-8-(3-methylphenyl)-7-[4-(trifluoromethyl)benzyl]-7H-purine-2-carboxylic acid;
6-[benzyl(methyl)amino]-8-(3-methylphenyl)-7-[4-(trifluoromethyl)benzyl]-7H-purine-2-carboxylic acid;
6-[butyl(propyl)amino]-8-(3-methylphenyl)-7-[4-(trifluoromethyl)benzyl]-7H-purine-2-carboxylic acid;
6-[butyl(ethyl)amino]-8-(3-methylphenyl)-7-[4-(trifluoromethyl)benzyl]-7H-purine-2-carboxylic acid;
6-[ethyl(propyl)amino]-8-(3-methylphenyl)-7-[4-(trifluoromethyl)benzyl]-7H-purine-2-carboxylic acid;
6-[methyl(2-methylpropyl)amino]-8-(3-methylphenyl)-7-[4-(trifluoromethyl)benzyl]-7H-purine-2-carboxylic acid;
6-[methyl(2-methylpropyl)amino]-8-(3-methylphenyl)-7-[4-(trifluoromethyl)benzyl]-7H-purine-2-carboxylic acid;
6-[(1,2-dimethylpropyl)amino]-8-(3-methylphenyl)-7-[4-(trifluoromethyl)benzyl]-7H-purine-2-carboxylic acid;
8-(3-methylphenyl)-7-[4-(trifluoromethyl)benzyl]-6-[(1,2,2-trimethylpropyl)amino]-7H-purine-2-carboxylic acid;
6-[(cyclobutylmethyl)amino]-8-(3-methylphenyl)-7-[4-(trifluoromethyl)benzyl]-7H-purine-2-carboxylic acid;
8-(3-methylphenyl)-6-[2-(2-methylpropyl)pyrrolidin-1-yl]-7-[4-(trifluoromethyl)benzyl]-7H-purine-2-carboxylic acid;
6-[methyl(3-methylbutyl)amino]-8-(3-methylphenyl)-7-[4-(trifluoromethyl)benzyl]-7H-purine-2-carboxylic acid;
6-(2-ethylpyrrolidin-1-yl)-8-(3-methylphenyl)-7-[4-(trifluoromethyl)benzyl]-7H-purine-2-carboxylic acid;
6-[methyl(1-methylbutyl)amino]-8-(3-methylphenyl)-7-[4-(trifluoromethyl)benzyl]-7H-purine-2-carboxylic acid;
6-(2-cyclohexylpyrrolidin-1-yl)-8-(3-methylphenyl)-7-[4-(trifluoromethyl)benzyl]-7H-purine-2-carboxylic acid;
6-[(1,2-dimethylpropyl)(methyl)amino]-8-(3-methylphenyl)-7-[4-(trifluoromethyl)benzyl]-7H-purine-2-carboxylic acid;
6-[(2,2-dimethylpropyl)(methyl)amino]-8-(3-methylphenyl)-7-[4-(trifluoromethyl)benzyl]-7H-purine-2-carboxylic acid;
6-[butyl(methyl)amino]-8-(3-methylphenyl)-7-[4-(trifluoromethyl)benzyl]-7H-purine-2-carboxylic acid;
6-[(dicyclopropylmethyl)(methyl)amino]-8-(3-methylphenyl)-7-[4-(trifluoromethyl)benzyl]-7H-purine-2-carboxylic acid;
6-[2-(1-methylethyl)pyrrolidin-1-yl]-8-(3-methylphenyl)-7-[4-(trifluoromethyl)benzyl]-7H-purine-2-carboxylic acid;
8-(3-methylphenyl)-6-(2-propylpyrrolidin-1-yl)-7-[4-(trifluoromethyl)benzyl]-7H-purine-2-carboxylic acid;
6-(2-tert-butylpyrrolidin-1-yl)-8-(3-methylphenyl)-7-[4-(trifluoromethyl)benzyl]-7H-purine-2-carboxylic acid;
6-[(1-cyclopropylethyl)(methyl)amino]-8-(3-methylphenyl)-7-[4-(trifluoromethyl)benzyl]-7H-purine-2-carboxylic acid;
6-[methyl(2-methylbutyl)amino]-8-(3-methylphenyl)-7-[4-(trifluoromethyl)benzyl]-7H-purine-2-carboxylic acid;
6-{[(2,2-dimethylcyclopropyl)methyl](methyl)amino}-8-(3-methylphenyl)-7-[4-(trifluoromethyl)benzyl]-7H-purine-2-carboxylic acid;
6-[methyl(pentyl)amino]-8-(3-methylphenyl)-7-[4-(trifluoromethyl)benzyl]-7H-purine-2-carboxylic acid;
6-(2-cyclobutylpyrrolidin-1-yl)-8-(3-methylphenyl)-7-[4-(trifluoromethyl)benzyl]-7H-purine-2-carboxylic acid;
6-(2-cyclobutylazetidin-1-yl)-8-(3-methylphenyl)-7-[4-(trifluoromethyl)benzyl]-7H-purine-2-carboxylic acid;
8-(3-methylphenyl)-6-[(3-methylphenyl)amino]-7-[4-(trifluoromethyl)benzyl]-7H-purine-2-carboxylic acid;
6-(2-cyclobutylpiperidin-1-yl)-8-(3-methylphenyl)-7-[4-(trifluoromethyl)benzyl]-7H-purine-2-carboxylic acid;
(R)-Methyl-7-(4-chlorobenzyl)-6-{[(1R)-1-cyclobutyl-4-hydroxybutyl]amino}-8-(3-methylphenyl)-7H-purine-2-carboxylic acid;
6-{[(1R)-1-cyclobutyl-4-hydroxybutyl]amino}-8-(3-methylphenyl)-7-[4-(trifluoromethyl)benzyl]-7H-purine-2-carboxylic acid;
(4R)-4-cyclobutyl-4-({8-(3-methylphenyl)-7-[4-(trifluoromethyl)benzyl]-7H-purin-6-yl}amino)butan-1-ol;
6-{[(1R)-1-cyclobutylbutyl]amino}-8-(3-methylphenyl)-7-[4-(trifluoromethyl)benzyl]-7H-purine-2-carboxylic acid;
6-({(1R)-1-cyclobutyl-4-[(2-hydroxyethyl)amino]-4-oxobutyl}amino)-8-(3-methylphenyl)-7-[4-(trifluoromethyl)benzyl]-7H-purine-2-carboxylic acid;
6-[(2R)-2-cyclobutylpyrrolidin-1-yl]-8-(3-methylphenyl)-7-[4-(trifluoromethyl)benzyl]-7H-purine-2-carboxylic acid;
6-[(2R)-2-cyclobutylpyrrolidin-1-yl]-8-(3-methylphenyl)-7-[4-(trifluoromethyl)benzyl]-7H-purine;
6-{[(1R)-1-cyclobutyl-4-(4-methylpiperazin-1-yl)butyl]amino}-8-(3-methylphenyl)-7-[4-(trifluoromethyl)benzyl]-7H-purine-2-carboxylic acid;
6-{[(1R)-1-cyclobutyl-4-(dimethylamino)butyl]amino}-8-(3-methylphenyl)-7-[4-(trifluoromethyl)benzyl]-7H-purine-2-carboxylic acid;
6-{[(1R)-4-amino-1-cyclobutyl-4-oxobutyl]amino}-8-(3-methylphenyl)-7-[4-(trifluoromethyl)benzyl]-7H-purine-2-carboxylic acid;
6-{[(1R)-1-cyclobutyl-4-(methylamino)-4-oxobutyl]amino}-8-(3-methylphenyl)-7-[4-(trifluoromethyl)benzyl]-7H-purine-2-carboxylic acid;
6-{[(1R)-1-cyclobutyl-3,4-dihydroxybutyl]amino}-8-(3-methylphenyl)-7-[4-(trifluoromethyl)benzyl]-7H-purine-2-carboxylic acid;
6-{[(S)-cyclobutyl(phenyl)methyl]amino}-8-[4-(1-methylethyl)pyridin-2-yl]-7-[4-(trifluoromethyl)benzyl]-7H-purine-2-carboxylic acid;
6-{[(1R)-1-(3,3-difluorocyclobutyl)ethyl]amino}-8-(2-methoxy-5-methylphenyl)-7-[4-(trifluoromethyl)benzyl]-7H-purine-2-carboxylic acid;
8-(2-methoxy-5-methylphenyl)-6-{[1-(3-methylcyclobutyl)ethyl]amino}-7-[4-(trifluoromethyl)benzyl]-7H-purine-2-carboxylic acid;
6-{[(1R)-1-(2,2-difluorocyclopropyl)ethyl]amino}-8-(2-methoxy-5-methylphenyl)-7-[4-(trifluoromethyl)benzyl]-7H-purine-2-carboxylic acid;
7-[2-amino-4-(trifluoromethyl)benzyl]-6-{[(1R)-1-cyclobutylethyl]amino}-8-[4-(1-methylethyl)pyridin-2-yl]-7H-purine-2-carboxylic acid;
6-{[(1R)-1-cyclobutylethyl]amino}-8-{[(1S)-1-(4-fluorophenyl)ethyl]amino}-7-[4-(trifluoromethyl)benzyl]-7H-purine-2-carboxylic acid;
6-{[(1R)-1-cyclobutylethyl]amino}-8-[methyl(phenyl)amino]-7-[4-(trifluoromethyl)benzyl]-7H-purine-2-carboxylic acid;
8-(2-benzylpiperidin-1-yl)-6-{[(1R)-1-cyclobutylethyl]amino}-7-[4-(trifluoromethyl)benzyl]-7H-purine-2-carboxylic acid;
3-{7-(4-chloro-3-fluorobenzyl)-6-{[(1R)-1-cyclobutylethyl]amino}-8-[(3R)-3-phenylmorpholin-4-yl]-7H-purin-2-yl}-1,2,4-oxadiazol-5(4H)-one;

6-{[(1R)-1-cyclopropylethyl]amino}-8-(4-methylpiper-azin-1-yl)-7-[4-(trifluoromethyl)benzyl]-7H-purine-2-carboxylic acid;

6-{[(1R)-1-cyclobutylethyl]amino}-8-{[(1R)-2-hydroxy-1-phenylethyl]amino}-7-[4-(trifluoromethyl)benzyl]-7H-purine-2-carboxylic acid;

6-{[(1R)-1-cyclobutylethyl]amino}-8-{[(1R)-2-hydroxy-1-methylethyl]amino}-7-[4-(trifluoromethyl)benzyl]-7H-purine-2-carboxylic acid;

6-{[(1R)-1-cyclobutylethyl]amino}-8-{[(1 S)-2-hydroxy-1-phenylethyl]amino}-7-[4-(trifluoromethyl)benzyl]-7H-purine-2-carboxylic acid;

7-(4-chlorobenzyl)-6-{[(1R)-1-cyclopropylethyl]amino}-8-morpholin-4-yl-7H-purine-2-carboxylic acid;

6-{[(1R)-1-cyclobutylethyl]amino}-8-{[(1 S)-2-hydroxy-1-methylethyl]amino}-7-[4-(trifluoromethyl)benzyl]-7H-purine-2-carboxylic acid;

6-{[(1R)-1-cyclobutylethyl]amino}-8-piperidin-1-yl-7-[4-(trifluoromethyl)benzyl]-7H-purine-2-carboxylic acid;

6-{[(1R)-1-cyclobutylethyl]amino}-8-(cyclohexylamino)-7-[4-(trifluoromethyl)benzyl]-7H-purine-2-carboxylic acid;

8-(benzylamino)-6-{[(1R)-1-cyclobutylethyl]amino}-7-[4-(trifluoromethyl)benzyl]-7H-purine-2-carboxylic acid;

8-[benzyl(methyl)amino]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[cyclohexyl(methyl)amino]-7-[4-(trifluoromethyl)benzyl]-7H-purine-2-carboxylic acid;

6-{[(1R)-1-cyclobutylethyl]amino}-8-{[(1S)-1-phenylethyl]amino}-7-[4-(trifluoromethyl)benzyl]-7H-purine-2-carboxylic acid;

6-{[(1R)-1-cyclobutylethyl]amino}-8-{[(1R)-1-phenylethyl]amino}-7-[4-(trifluoromethyl)benzyl]-7H-purine-2-carboxylic acid;

6-{[(1R)-1-cyclobutylethyl]amino}-8-(2,2-dimethylmorpholin-4-yl)-7-[4-(trifluoromethyl)benzyl]-7H-purine-2-carboxylic acid;

6-{[(1R)-1-cyclobutylethyl]amino}-8-(2,2,6,6-tetramethylmorpholin-4-yl)-7-[4-(trifluoromethyl)benzyl]-7H-purine-2-carboxylic acid;

6-{[(1R)-1-cyclobutylethyl]amino}-8-(2-methylmorpholin-4-yl)-7-[4-(trifluoromethyl)benzyl]-7H-purine-2-carboxylic acid;

6-{[(1R)-1-cyclobutylethyl]amino}-8-(phenylamino)-7-[4-(trifluoromethyl)benzyl]-7H-purine-2-carboxylic acid;

6-{[(1R)-1-cyclobutylethyl]amino}-8-(2-phenylmorpholin-4-yl)-7-[4-(trifluoromethyl)benzyl]-7H-purine-2-carboxylic acid;

6-{[(1R)-1-cyclobutylethyl]amino}-7-[4-(trifluoromethyl)benzyl]-8-[2-(trifluoromethyl)morpholin-4-yl]-7H-purine-2-carboxylic acid;

6-{[(1R)-1-cyclobutylethyl]amino}-8-[2-(methoxymethyl)morpholin-4-yl]-7-[4-(trifluoromethyl)benzyl]-7H-purine-2-carboxylic acid;

6-{[(1R)-1-cyclobutylethyl]amino}-8-(6-oxa-9-azaspiro[4.5]dec-9-yl)-7-[4-(trifluoromethyl)benzyl]-7H-purine-2-carboxylic acid;

6-{[(1R)-1-cyclobutylethyl]amino}-8-(2-prop-2-yn-1-ylmorpholin-4-yl)-7-[4-(trifluoromethyl)benzyl]-7H-purine-2-carboxylic acid;

6-{[(1R)-1-cyclobutylethyl]amino}-8-[(1R,4R)-2-oxa-5-azabicyclo[2.2.1]hept-5-yl]-7-[4-(trifluoromethyl)benzyl]-7H-purine-2-carboxylic acid;

7-(4-chlorobenzyl)-6-{[(1R)-1-cyclopropylethyl]amino}-8-[(3 S)-3-methylmorpholin-4-yl]-7H-purine-2-carboxylic acid;

(2R)-2-[(6-{[(1R)-1-cyclobutylethyl]amino}-7-[4-(trifluoromethyl)benzyl]-7H-purin-8-yl)amino]-2-phenylethanol;

6-{[(1R)-1-cyclobutylethyl]amino}-8-[(1-pyridin-3-ylethyl)amino]-7-[4-(trifluoromethyl)benzyl]-7H-purine-2-carboxylic acid;

6-{[(1R)-1-cyclobutylethyl]amino}-8-[(1-pyridin-2-ylethyl)amino]-7-[4-(trifluoromethyl)benzyl]-7H-purine-2-carboxylic acid;

6-{[(1R)-1-cyclobutylethyl]amino}-8-[(3 S)-3-methylmorpholin-4-yl]-7-[4-(trifluoromethyl)benzyl]-7H-purine-2-carboxylic acid;

6-{[(1R)-1-cyclobutylethyl]amino}-8-[(3R)-3-methylmorpholin-4-yl]-7-[4-(trifluoromethyl)benzyl]-7H-purine-2-carboxylic acid;

6-{[(1R)-1-cyclobutylethyl]amino}-8-{[(1S)-1-phenylpropyl]amino}-7-[4-(trifluoromethyl)benzyl]-7H-purine-2-carboxylic acid;

6-{[(1R)-1-cyclobutylethyl]amino}-8-{methyl[(1 S)-1-phenylethyl]amino}-7-[4-(trifluoromethyl)benzyl]-7H-purine-2-carboxylic acid;

6-{[(1R)-1-cyclobutylethyl]amino}-8-[(phenylcarbonyl)amino]-7-[4-(trifluoromethyl)benzyl]-7H-purine-2-carboxylic acid;

6-{[(1R)-1-cyclobutylethyl]amino}-8-{[(1S)-1-(3-fluorophenyl)ethyl]amino}-7-[4-(trifluoromethyl)benzyl]-7H-purine-2-carboxylic acid;

6-{[(1R)-1-cyclobutylethyl]amino}-8-(3-methylpiperidin-1-yl)-7-[4-(trifluoromethyl)benzyl]-7H-purine-2-carboxylic acid;

6-{[(1R)-1-cyclobutylethyl]amino}-8-(3-phenylpiperidin-1-yl)-7-[4-(trifluoromethyl)benzyl]-7H-purine-2-carboxylic acid;

6-{[(1R)-1-cyclobutylethyl]amino}-8-[(3-methylbutanoyl)amino]-7-[4-(trifluoromethyl)benzyl]-7H-purine-2-carboxylic acid;

6-{[(1R)-1-cyclobutylethyl]amino}-8-[(cyclohexylcarbonyl)amino]-7-[4-(trifluoromethyl)benzyl]-7H-purine-2-carboxylic acid;

6-{[(1R)-1-cyclobutylethyl]amino}-8-(2-phenylpiperidin-1-yl)-7-[4-(trifluoromethyl)benzyl]-7H-purine-2-carboxylic acid;

6-{[(1R)-1-cyclobutylethyl]amino}-8-(3,3-dimethylpiperidin-1-yl)-7-[4-(trifluoromethyl)benzyl]-7H-purine-2-carboxylic acid;

6-{[(1R)-1-cyclobutylethyl]amino}-8-[3-(1-methylethyl)piperidin-1-yl]-7-[4-(trifluoromethyl)benzyl]-7H-purine-2-carboxylic acid;

6-{[(1R)-1-cyclobutylethyl]amino}-7-[3-fluoro-4-(trifluoromethyl)benzyl]-8-(2-phenylpiperidin-1-yl)-7H-purine-2-carboxylic acid;

6-{[(1R)-1-cyclobutylethyl]amino}-7-[3-fluoro-4-(trifluoromethyl)benzyl]-8-(2-phenylpiperidin-1-yl)-7H-purine-2-carboxylic acid;

6-{[(R)-1-cyclobutylethyl]amino}-8-{[(1S)-1-phenylethyl](propyl)amino}-7-[4-(trifluoromethyl)benzyl]-7H-purine-2-carboxylic acid;

6-{[(1R)-1-cyclobutylethyl]amino}-8-[(3R)-3-phenylmorpholin-4-yl]-7-[4-(trifluoromethyl)benzyl]-7H-purine-2-carboxylic acid;

6-{[(1R)-1-cyclobutylethyl]amino}-8-[(3 S)-3-phenylmorpholin-4-yl]-7-[4-(trifluoromethyl)benzyl]-7H-purine-2-carboxylic acid;

6-{[(1R)-1-cyclobutylethyl]amino}-8-(2-phenylpyrrolidin-1-yl)-7-[4-(trifluoromethyl)benzyl]-7H-purine-2-carboxylic acid;

6-{[(1R)-1-cyclobutylethyl]amino}-8-(2-pyridin-2-ylpiperidin-1-yl)-7-[4-(trifluoromethyl)benzyl]-7H-purine-2-carboxylic acid;

6-{[(1R)-1-cyclobutylethyl]amino}-8-(2-phenylazetidin-1-yl)-7-[4-(trifluoromethyl)benzyl]-7H-purine-2-carboxylic acid;

3-[6-{[(1R)-1-cyclobutylethyl]amino}-7-[3-fluoro-4-(trifluoromethyl)benzyl]-8-(3-phenylmorpholin-4-yl)-7H-purin-2-yl]-1,2,4-oxadiazol-5 (4H)-one;
3-[6-{[(1R)-1-cyclobutylethyl]amino}-7-[3-fluoro-4-(trifluoromethyl)benzyl]-8-(3-phenylmorpholin-4-yl)-7H-purin-2-yl]-1,2,4-oxadiazol-5 (4H)-one;
3-(6-{[(1R)-1-cyclobutylethyl]amino}-8-[(3R)-3-phenylmorpholin-4-yl]-7-[4-(trifluoromethyl)benzyl]-7H-purin-2-yl)-1,2,4-oxadiazol-5(4H)-one;
6-{[(1R)-1-cyclobutylethyl]amino}-8-{methyl[(1 S)-1-phenylpropyl]amino}-7-[4-(trifluoromethyl)benzyl]-7H-purine-2-carboxylic acid;
6-{[(1R)-1-cyclobutylethyl]amino}-8-(3,5-dimethyl-1H-pyrazol-1-yl)-7-[4-(trifluoromethyl)benzyl]-7H-purine-2-carboxylic acid;
6-{[(1R)-1-cyclobutylethyl]amino}-8-[2-(3-fluorophenyl)pyrrolidin-1-yl]-7-[4-(trifluoromethyl)benzyl]-7H-purine-2-carboxylic acid;
6-{[(1R)-1-cyclobutylethyl]amino}-8-(5-methyl-3-phenyl-1H-pyrazol-1-yl)-7-[4-(trifluoromethyl)benzyl]-7H-purine-2-carboxylic acid;
6-{[(1R)-1-cyclobutylethyl]amino}-8-[(2R)-2-phenylpiperidin-1-yl]-7-[4-(trifluoromethyl)benzyl]-7H-purine-2-carboxylic acid;
6-{[(1R)-1-cyclobutylethyl]amino}-8-[(2S)-2-phenylpiperidin-1-yl]-7-[4-(trifluoromethyl)benzyl]-7H-purine-2-carboxylic acid;
6-{[(1R)-1-cyclobutylethyl]amino}-8-(2-phenylpyrrolidin-1-yl)-7-[4-(trifluoromethyl)benzyl]-7H-purine-2-carboxylic acid;
6-{[(1R)-1-cyclobutylethyl]amino}-8-[3-(2-methylpropyl)morpholin-4-yl]-7-[4-(trifluoromethyl)benzyl]-7H-purine-2-carboxylic acid;
3-(6-{[(1R)-1-cyclobutylethyl]amino}-8-(2-phenylpiperidin-1-yl)-7-[4-(trifluoromethyl)benzyl]-7H-purin-2-yl)-1,2,4-oxadiazol-5(4H)-one;
6-{[(1R)-1-cyclobutylethyl]amino}-7-[4-(trifluoromethyl)benzyl]-8-{2-[3-(trifluoromethyl)benzyl]piperidin-1-yl}-7H-purine-2-carboxylic acid;
6-{[(1R)-1-cyclobutylethyl]amino}-8-[2-(4-fluorobenzyl)piperidin-1-yl]-7-[4-(trifluoromethyl)benzyl]-7H-purine-2-carboxylic acid;
6-{[(1R)-1-cyclobutylethyl]amino}-8-[2-(4-methoxyphenyl)piperidin-1-yl]-7-[4-(trifluoromethyl)benzyl]-7H-purine-2-carboxylic acid;
3-(6-{[(1R)-1-cyclobutylethyl]amino}-7-[3-fluoro-4-(trifluoromethyl)benzyl]-8-[methyl(1-phenylpropyl)amino]-7H-purin-2-yl)-1,2,4-oxadiazol-5(4H)-one;
3-(6-{[(1R)-1-cyclobutylethyl]amino}-7-[3-fluoro-4-(trifluoromethyl)benzyl]-8-[methyl(1-pyridin-2-ylethyl)amino]-7H-purin-2-yl)-1,2,4-oxadiazol-5(4H)-one;
3-(6-{[(1R)-1-cyclobutylethyl]amino}-8-{[1-(3-fluorophenyl)ethyl](methyl)amino}-7-[3-fluoro-4-(trifluoromethyl)benzyl]-7H-purin-2-yl)-1,2,4-oxadiazol-5 (4H)-one;
6-{[(1R)-1-cyclobutylethyl]amino}-8-(2,3-dihydro-1'H-spiro[indene-1,2'-pyrrolidin]-1'-yl)-7-[4-(trifluoromethyl)benzyl]-7H-purine-2-carboxylic acid;
3-(6-{[(1R)-1-cyclobutylethyl]amino}-8-[(1-pyridin-2-ylethyl)amino]-7-[4-(trifluoromethyl)benzyl]-7H-purin-2-yl)-1,2,4-oxadiazol-5(4H)-one;
6-{[(1R)-1-cyclobutylethyl]amino}-8-(3-oxa-8-azabicyclo[3.2.1]oct-8-yl)-7-[4-(trifluoromethyl)benzyl]-7H-purine-2-carboxylic acid;
6-{[(1R)-1-cyclobutylethyl]amino}-8-(8-oxa-3-azabicyclo[3.2.1]oct-3-yl)-7-[4-(trifluoromethyl)benzyl]-7H-purine-2-carboxylic acid;
8-(8-azabicyclo[3.2.1]oct-8-yl)-6-{[(1R)-1-cyclobutylethyl]amino}-7-[4-(trifluoromethyl)benzyl]-7H-purine-2-carboxylic acid;
6-{[(1R)-1-cyclobutylethyl]amino}-8-[(3-exo)-3-phenyl-8-azabicyclo[3.2.1]oct-8-yl]-7-[4-(trifluoromethyl)benzyl]-7H-purine-2-carboxylic acid;
8-[(3-exo)-3-(4-chloro-3-fluorophenoxy)-8-azabicyclo[3.2.1]oct-8-yl]-6-{[(1R)-1-cyclobutylethyl]amino}-7-[4-(trifluoromethyl)benzyl]-7H-purine-2-carboxylic acid;
3-(6-{[(1R)-1-cyclobutylethyl]amino}-8-[methyl(2-methylpropyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-[cyclopentyl(methyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-(2,2-dimethylpyrrolidin-1-yl)-7-[4-(trifluoromethyl)benzyl]-7H-purin-2-yl)-1,2,4-oxadiazol-5(4H)-one;
3-(6-{[(1R)-1-cyclobutylethyl]amino}-8-[(2,2-dimethylpropyl)(methyl)amino]-7-[4-(trifluoromethyl)benzyl]-7H-purin-2-yl)-1,2,4-oxadiazol-5(4H)-one;
3-{8-(4-azaspiro[2.5]oct-4-yl)-6-{[(1R)-1-cyclobutylethyl]amino}-7-[4-(trifluoromethyl)benzyl]-7H-purin-2-yl}-1,2,4-oxadiazol-5(4H)-one;
3-(6-{[(1R)-1-cyclobutylethyl]amino}-8-[2-(1-methylethyl)pyrrolidin-1-yl]-7-[4-(trifluoromethyl)benzyl]-7H-purin-2-yl)-1,2,4-oxadiazol-5(4H)-one;
3-(6-{[(1R)-1-cyclobutylethyl]amino}-8-[cyclohexyl(methyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-(3,3-dimethylmorpholin-4-yl)-7-[4-(trifluoromethyl)benzyl]-7H-purin-2-yl)-1,2,4-oxadiazol-5(4H)-one;
3-(6-{[(1R)-1-cyclobutylethyl]amino}-8-{[1-(methoxymethyl)cyclopropyl](methyl)amino}-7-[4-(trifluoromethyl)benzyl]-7H-purin-2-yl)-1,2,4-oxadiazol-5(4H)-one;
3-(6-{[(1R)-1-cyclobutylethyl]amino}-8-[2-(fluoromethyl)piperidin-1-yl]-7-[4-(trifluoromethyl)benzyl]-7H-purin-2-yl)-1,2,4-oxadiazol-5(4H)-one;
3-(6-{[(1R)-1-cyclobutylethyl]amino}-8-[2-(2-methylpropyl)pyrrolidin-1-yl]-7-[4-(trifluoromethyl)benzyl]-7H-purin-2-yl)-1,2,4-oxadiazol-5(4H)-one;
3-(6-{[(1R)-1-cyclobutylethyl]amino}-8-[3-(2-methylpropyl)pyrrolidin-1-yl]-7-[4-(trifluoromethyl)benzyl]-7H-purin-2-yl)-1,2,4-oxadiazol-5(4H)-one;
3-(6-{[(1R)-1-cyclobutylethyl]amino}-8-[methyl(tetrahydro-2H-pyran-4-ylmethyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-[methyl(2-phenylethyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-[(cyclohexylmethyl)(ethyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-[cyclohexyl(propyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-[ethyl(2-pyrrolidin-1-ylethyl)amino]-7-[4-(trifluoromethyl)benzyl]-7H-purin-2-yl)-1,2,4-oxadiazol-5(4H)-one;
3-(6-{[(1R)-1-cyclobutylethyl]amino}-8-{[(1,3-dimethylpyrrolidin-3-yl)methyl](methyl)amino}-7-[4-(trifluoromethyl)benzyl]-7H-purin-2-yl)-1,2,4-oxadiazol-5 (4H)-one;
3-(6-{[(1R)-1-cyclobutylethyl]amino}-8-{methyl[(1-methylpiperidin-3-yl)methyl]amino}-7-[4-(trifluoromethyl)benzyl]-7H-purin-2-yl)-1,2,4-oxadiazol-5(4H)-one;
3-(6-{[(1R)-1-cyclobutylethyl]amino}-8-[methyl(3-pyrrolidin-1-ylpropyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[3-(2-methylpropyl)morpholin-4-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2,3-dihydro-1H-inden-1-yl(methyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-(2-cyclohexylpyrrolidin-1-yl)-7-[4-(trifluoromethyl)benzyl]-7H-purin-2-yl)-1,2,4-oxadiazol-5(4H)-one;

3-(6-{[(1R)-1-cyclobutylethyl]amino}-8-[methyl(2-methyl-3-pyrrolidin-1-ylpropyl)amino]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(pyridin-3-ylmethyl)pyrrolidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(1-methyl-1H-imidazol-2-yl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(3-methyl-1,2,4-oxadiazol-5-yl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-(methyl {[1-(2-methylpropyl)pyrrolidin-3-yl]methyl}amino)-7-[4-(trifluoromethyl)benzyl]-7H-purin-2-yl)-1,2,4-oxadiazol-5 (4H)-one;

3-{8-(2-benzylpiperidin-1-yl)-6-{[(1R)-1-cyclobutylethyl]amino}-7-[4-(trifluoromethyl)benzyl]-7H-purin-2-yl}-1,2,4-oxadiazol-5 (4H)-one;

3-(6-{[(1R)-1-cyclobutylethyl]amino}-8-(2-methylpiperidin-1-yl)-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(methoxymethyl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(4-fluorophenyl)piperidin-1-yl]-7-[4-(trifluoromethyl)benzyl]-7H-purin-2-yl)-1,2,4-oxadiazol-5(4H)-one;

3-(6-{[(1R)-1-cyclobutylethyl]amino}-8-[2-(3-fluorophenyl)piperidin-1-yl]-7-[4-(trifluoromethyl)benzyl]-7H-purin-2-yl)-1,2,4-oxadiazol-5(4H)-one;

6-{[(1R)-1-cyclobutylethyl]amino}-8-(2-pyridin-3-ylpiperidin-1-yl)-7-[4-(trifluoromethyl)benzyl]-7H-purine-2-carboxylic acid;

6-{[(1R)-1-cyclobutylethyl]amino}-8-(2-pyridin-4-ylpiperidin-1-yl)-7-[4-(trifluoromethyl)benzyl]-7H-purine-2-carboxylic acid;

6-{[(1R)-1-cyclobutylethyl]amino}-8-[2-(3-fluorophenyl)piperidin-1-yl]-7-[4-(trifluoromethyl)benzyl]-7H-purine-2-carboxylic acid;

6-{[(1R)-1-cyclobutylethyl]amino}-8-[2-(4-fluorophenyl)piperidin-1-yl]-7-[4-(trifluoromethyl)benzyl]-7H-purine-2-carboxylic acid;

6-{[(1R)-1-cyclobutylethyl]amino}-8-morpholin-4-yl-7-[4-(trifluoromethyl)benzyl]-7H-purine-2-carboxylic acid;

6-{[(1R)-1-cyclobutylethyl]amino}-8-[2-(1-methylethyl)piperidin-1-yl]-7-[4-(trifluoromethyl)benzyl]-7H-purine-2-carboxylic acid;

6-{[(1R)-1-cyclobutylethyl]amino}-8-[2-(2-methylpropyl)piperidin-1-yl]-7-[4-(trifluoromethyl)benzyl]-7H-purine-2-carboxylic acid;

6-{[(1R)-1-cyclobutylethyl]amino}-8-(3,4-dihydroisoquinolin-2(1H)-yl)-7-[4-(trifluoromethyl)benzyl]-7H-purine-2-carboxylic acid;

6-{[(1R)-1-cyclobutylethyl]amino}-8-(2-cyclohexylpiperidin-1-yl)-7-[4-(trifluoromethyl)benzyl]-7H-purine-2-carboxylic acid;

6-{[(1R)-1-cyclobutylethyl]amino}-8-[(1-methyl-1-phenylethyl)amino]-7-[4-(trifluoromethyl)benzyl]-7H-purine-2-carboxylic acid;

6-{[(1R)-1-cyclobutylethyl]amino}-8-(3,4-dihydroquinolin-1(2H)-yl)-7-[4-(trifluoromethyl)benzyl]-7H-purine-2-carboxylic acid;

3-(6-{[(1R)-1-cyclobutylethyl]amino}-8-[(3R)-3-methylmorpholin-4-yl]-7-[4-(trifluoromethyl)benzyl]-7H-purin-2-yl)-1,2,4-oxadiazol-5(4H)-one;

6-{[(1R)-1-cyclobutylethyl]amino}-8-(phenoxymethyl)-7-[4-(trifluoromethyl)benzyl]-7H-purine-2-carboxylic acid;

8-[(benzyloxy)methyl]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-[methyl(3-methylbutanoyl)amino]-7-[4-(trifluoromethyl)benzyl]-7H-purine-2-carboxylic acid;

6-{[(1R)-1-cyclobutylethyl]amino}-8-[(cyclohexylcarbonyl)(methyl)amino]-7-[4-(trifluoromethyl)benzyl]-7H-purine-2-carboxylic acid;

6-{[(1R)-1-cyclobutylethyl]amino}-8-[1-(2-methylpropoxy)ethyl]-7-[4-(trifluoromethyl)benzyl]-7H-purine-2-carboxylic acid;

8-[1-(benzyloxy)ethyl]-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(1-hydroxyethyl)-7-[4-(trifluoromethyl)benzyl]-7H-purine-2-carboxylic acid;

6-{[(1R)-1-cyclobutylethyl]amino}-8-(1-phenoxyethyl)-7-[4-(trifluoromethyl)benzyl]-7H-purine-2-carboxylic acid;

6-{[(1R)-1-cyclobutylethyl]amino}-8-{1-[methyl(2-methylpropyl)amino]ethyl}-7-[4-(trifluoromethyl)benzyl]-7H-purine-2-carboxylic acid;

6-{[(1R)-1-cyclobutylethyl]amino}-8-{1-[methyl(phenyl)amino]ethyl}-7-[4-(trifluoromethyl)benzyl]-7H-purine-2-carboxylic acid;

6-{[(1R)-1-cyclobutylethyl]amino}-8-{1-[cyclohexyl(methyl)amino]ethyl}-7-[4-(trifluoromethyl)benzyl]-7H-purine-2-carboxylic acid;

8-{1-[benzyl(methyl)amino]ethyl}-6-{[(1R)-1-cyclobutylethyl]amino}-7-[4-(trifluoromethyl)benzyl]-7H-purine-2-carboxylic acid;

8-{[benzyl(methyl)amino]methyl}-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-{[cyclohexyl(methyl)amino]methyl}-7-[4-(trifluoromethyl)benzyl]-7H-purine-2-carboxylic acid;

6-{[(1R)-1-cyclobutylethyl]amino}-8-{[(1R)-2-hydroxy-1-phenylethyl]carbamoyl}-7-[4-(trifluoromethyl)benzyl]-7H-purine-2-carboxylic acid;

6-{[(1R)-1-cyclobutylethyl]amino}-8-[(2-methylpropyl)carbamoyl]-7-[4-(trifluoromethyl)benzyl]-7H-purine-2-carboxylic acid;

6-{[(1R)-1-cyclobutylethyl]amino}-8-[(cyclopropylmethyl)carbamoyl]-7-[4-(trifluoromethyl)benzyl]-7H-purine-2-carboxylic acid;

8-(benzylcarbamoyl)-6-{[(1R)-1-cyclobutylethyl]amino}-7-[4-(trifluoromethyl)benzyl]-7H-purine-2-carboxylic acid;

6-{[(1R)-1-cyclobutylethyl]amino}-8-(cyclohexylcarbamoyl)-7-[4-(trifluoromethyl)benzyl]-7H-purine-2-carboxylic acid;

6-{[(1R)-1-cyclobutylethyl]amino}-8-(phenylcarbamoyl)-7-[4-(trifluoromethyl)benzyl]-7H-purine-2-carboxylic acid;

6-{[(1R)-1-cyclobutylethyl]amino}-8-[(3,3-dimethylpiperidin-1-yl)carbonyl]-7-[4-(trifluoromethyl)benzyl]-7H-purine-2-carboxylic acid;

6-{[(1R)-1-cyclobutylethyl]amino}-8-[(4R)-4-phenyl-4,5-dihydro-1,3-oxazol-2-yl]-7-[4-(trifluoromethyl)benzyl]-7H-purine-2-carboxylic acid;
6-{[(1R)-1-cyclobutylethyl]amino}-8-(1-methylpiperidin-2-yl)-7-[4-(trifluoromethyl)benzyl]-7H-purine-2-carboxylic acid;
6-{[(1R)-1-cyclobutylethyl]amino}-8-piperidin-2-yl-7-[4-(trifluoromethyl)benzyl]-7H-purine-2-carboxylic acid;
6-{[(1R)-1-cyclobutylethyl]amino}-8-(1-ethylpiperidin-2-yl)-7-[4-(trifluoromethyl)benzyl]-7H-purine-2-carboxylic acid;
6-{[(1R)-1-cyclobutylethyl]amino}-8-{[(1S)-1-(3-fluorophenyl)ethyl](propyl)amino}-7-[4-(trifluoromethyl)benzyl]-7H-purine-2-carboxylic acid;
6-{[(1R)-1-cyclobutylethyl]amino}-8-{[(1S)-1-(3-fluorophenyl)ethyl](prop-2-en-1-yl)amino}-7-[4-(trifluoromethyl)benzyl]-7H-purine-2-carboxylic acid;
6-{[(1R)-1-cyclobutylethyl](prop-2-en-1-yl)amino}-8-{[(1 S)-1-(3-fluorophenyl)ethyl]amino}-7-[4-(trifluoromethyl)benzyl]-7H-purine-2-carboxylic acid;
6-{[(1R)-1-cyclobutylethyl]amino}-8-{(cyclopropylmethyl)[(1 S)-1-phenylethyl]amino}-7-[4-(trifluoromethyl)benzyl]-7H-purine-2-carboxylic acid;
6-{[(1R)-1-cyclobutylethyl]amino}-8-[prop-2-en-1-yl(1-pyridin-2-ylethyl)amino]-7-[4-(trifluoromethyl)benzyl]-7H-purine-2-carboxylic acid;
6-{[(1R)-1-cyclobutylethyl](prop-2-en-1-yl)amino}-8-[(1-pyridin-2-ylethyl)amino]-7-[4-(trifluoromethyl)benzyl]-7H-purine-2-carboxylic acid;
6-{[(1R)-1-cyclobutylethyl]amino}-8-[propyl(1-pyridin-2-ylethyl)amino]-7-[4-(trifluoromethyl)benzyl]-7H-purine-2-carboxylic acid;
6-{[(1R)-1-cyclobutylethyl]amino}-8-(1,4-dimethylpiperidin-2-yl)-7-[(trans-4-methylcyclohexyl)methyl]-7H-purine-2-carboxylic acid;
6-{[(1R)-1-cyclobutylethyl]amino}-8-(1-ethyl-4-methylpiperidin-2-yl)-7-[(trans-4-methylcyclohexyl)methyl]-7H-purine-2-carboxylic acid;
6-{[(1R)-1-cyclobutylethyl]amino}-8-(2,3-dimethylpiperidin-1-yl)-7-[(trans-4-methylcyclohexyl)methyl]-7H-purine-2-carboxylic acid;
6-{[(1R)-1-cyclobutylethyl]amino}-7-[(trans-4-methylcyclohexyl)methyl]-8-[2-(2-methylpropyl)piperidin-1-yl]-7H-purine-2-carboxylic acid;
3-(6-{[(1R)-1-cyclobutylethyl]amino}-7-[(trans-4-methylcyclohexyl)methyl]-8-[2-(2-methylpropyl)piperidin-1-yl]-7H-purin-2-yl)-1,2,4-oxadiazol-5 (4H)-one;
6-{[(1R)-1-cyclobutylethyl]amino}-8-(2-cyclohexylpiperidin-1-yl)-7-[(trans-4-methylcyclohexyl)methyl]-7H-purine-2-carboxylic acid;
3-(6-{[(1R)-1-cyclobutylethyl]amino}-8-(2-cyclohexylpiperidin-1-yl)-7-[(trans-4-methylcyclohexyl)methyl]-7H-purin-2-yl)-1,2,4-oxadiazol-5 (4H)-one;
6-{[(1R)-1-cyclobutylethyl]amino}-7-[(trans-4-methylcyclohexyl)methyl]-8-(3-methyl-2-phenylpiperidin-1-yl)-7H-purine-2-carboxylic acid;
3-[6-{[(1R)-1-cyclobutylethyl]amino}-7-[(trans-4-methylcyclohexyl)methyl]-8-(3-methyl-2-phenylpiperidin-1-yl)-7H-purin-2-yl]-1,2,4-oxadiazol-5 (4H)-one;
3-(6-{[(1R)-1-cyclobutylethyl]amino}-8-[(2S)-2-(fluoromethyl)pyrrolidin-1-yl]-7-[(trans-4-methylcyclohexyl)methyl]-7H-purin-2-yl)-1,2,4-oxadiazol-5 (4H)-one;
3-{6-[(2R)-2-cyclobutylazetidin-1-yl]-7-[(trans-4-methylcyclohexyl)methyl]-8-[(3R)-3-phenylmorpholin-4-yl]-7H-purin-2-yl}-1,2,4-oxadiazol-5(4H)-one;
6-{[(1R)-1-cyclobutylethyl]amino}-7-[(trans-4-methylcyclohexyl)methyl]-8-[(3R)-3-phenylmorpholin-4-yl]-7H-purine-2-carboxylic acid;

3-(6-{[(1R)-1-cyclobutylethyl]amino}-7-[(trans-4-methylcyclohexyl)methyl]-8-[(3R)-3-phenylmorpholin-4-yl]-7H-purin-2-yl)-1,2,4-oxadiazol-5 (4H)-one;
6-{[(1R)-1-cyclobutylethyl]amino}-7-[(trans-4-methylcyclohexyl)methyl]-8-[(2R)-2-phenylpiperidin-1-yl]-7H-purine-2-carboxylic acid;
3-(6-{[(1R)-1-cyclobutylethyl]amino}-7-[(trans-4-methylcyclohexyl)methyl]-8-[(2R)-2-phenylpiperidin-1-yl]-7H-purin-2-yl)-1,2,4-oxadiazol-5 (4H)-one;
6-{[(1R)-1-cyclobutylethyl]amino}-7-[(trans-4-methylcyclohexyl)methyl]-8-[(2S)-2-phenylpiperidin-1-yl]-7H-purine-2-carboxylic acid;
3-(6-{[(1R)-1-cyclobutylethyl]amino}-7-[(trans-4-methylcyclohexyl)methyl]-8-[(2S)-2-phenylpiperidin-1-yl]-7H-purin-2-yl)-1,2,4-oxadiazol-5 (4H)-one;
6-{[(1R)-1-cyclobutylethyl]amino}-8-[2-(3-fluorophenyl)piperidin-1-yl]-7-[(trans-4-methylcyclohexyl)methyl]-7H-purine-2-carboxylic acid;
6-{[(1R)-1-cyclobutylethyl]amino}-8-(3,4-dihydroisoquinolin-2(1H)-yl)-7-[(trans-4-methylcyclohexyl)methyl]-7H-purine-2-carboxylic acid;
6-{[(1R)-1-cyclobutylethyl]amino}-8-[2-(4-fluorophenyl)piperidin-1-yl]-7-[(trans-4-methylcyclohexyl)methyl]-7H-purine-2-carboxylic acid;
6-{[(1R)-1-cyclobutylethyl]amino}-7-[(trans-4-methylcyclohexyl)methyl]-8-(2-pyridin-3-ylpiperidin-1-yl)-7H-purine-2-carboxylic acid;
6-{[(1R)-1-cyclobutylethyl]amino}-7-[(trans-4-methylcyclohexyl)methyl]-8-(octahydroquinolin-1(2H)-yl)-7H-purine-2-carboxylic acid;
6-{[(1R)-1-cyclobutylethyl]amino}-7-[(trans-4-methylcyclohexyl)methyl]-8-(2-pyridin-2-ylpiperidin-1-yl)-7H-purine-2-carboxylic acid;
6-{[(1R)-1-cyclobutylethyl]amino}-7-[(trans-4-methylcyclohexyl)methyl]-8-(octahydroisoquinolin-2(1H)-yl)-7H-purine-2-carboxylic acid;
6-{[(1R)-1-cyclobutylethyl]amino}-7-[(trans-4-methylcyclohexyl)methyl]-8-(octahydroquinolin-1(2H)-yl)-7H-purine-2-carboxylic acid;
3-(6-{[(1R)-1-cyclobutylethyl]amino}-7-[(trans-4-methylcyclohexyl)methyl]-8-[methyl(1-pyridin-2-ylethyl)amino]-7H-purin-2-yl)-1,2,4-oxadiazol-5 (4H)-one;
3-(6-{[(1R)-1-cyclobutylethyl]amino}-7-[(trans-4-methylcyclohexyl)methyl]-8-[methyl(1-pyridin-2-ylethyl)amino]-7H-purin-2-yl)-1,2,4-oxadiazol-5 (4H)-one;
8-(8-azabicyclo[3.2.1]oct-8-yl)-6-{[(1R)-1-cyclobutylethyl]amino}-7-[(trans-4-methylcyclohexyl)methyl]-7H-purine-2-carboxylic acid;
3-{8-(8-azabicyclo[3.2.1]oct-8-yl)-6-{[(1R)-1-cyclobutylethyl]amino}-7-[(trans-4-methylcyclohexyl)methyl]-7H-purin-2-yl}-1,2,4-oxadiazol-5(4H)-one;
6-{[(1R)-1-cyclobutylethyl]amino}-8-[2-(3-fluorophenyl)pyrrolidin-1-yl]-7-[(trans-4-methylcyclohexyl)methyl]-7H-purine-2-carboxylic acid;
6-{[(1R)-1-cyclobutylethyl]amino}-7-[(trans-4-methylcyclohexyl)methyl]-8-(2-methylpiperidin-1-yl)-7H-purine-2-carboxylic acid;
6-{[(1R)-1-cyclobutylethyl]amino}-7-[(trans-4-methylcyclohexyl)methyl]-8-[methyl(2-methylpropyl)amino]-7H-purine-2-carboxylic acid;
6-{[(1R)-1-cyclobutylethyl]amino}-8-[2-(3-methoxyphenyl)piperidin-1-yl]-7-[(trans-4-methylcyclohexyl)methyl]-7H-purine-2-carboxylic acid;
3-(6-{[(1R)-1-cyclobutylethyl]amino}-8-[2-(ethoxymethyl)pyrrolidin-1-yl]-7-[(trans-4-methylcyclohexyl)methyl]-7H-purin-2-yl)-1,2,4-oxadiazol-5 (2H)-one;
3-(6-{[(1R)-1-cyclobutylethyl]amino}-8-(2-ethylpyrrolidin-1-yl)-7-[(trans-4-methylcyclohexyl)methyl]-7H-purin-2-yl)-1,2,4-oxadiazol-5 (2H)-one;
3-[6-{[(1R)-1-cyclobutylethyl]amino}-7-[(trans-4-methylcyclohexyl)methyl]-8-(2-methylpyrrolidin-1-yl)-7H-purin-2-yl]-1,2,4-oxadiazol-5 (2H)-one;

3-[6-{[(1R)-1-cyclobutylethyl]amino}-7-[(trans-4-methylcyclohexyl)methyl]-8-(2-propylpyrrolidin-1-yl)-7H-purin-2-yl]-1,2,4-oxadiazol-5(2H)-one;

3-{8-(2-tert-butylpyrrolidin-1-yl)-6-{[(1R)-1-cyclobutylethyl]amino}-7-[(trans-4-methylcyclohexyl)methyl]-7H-purin-2-yl}-1,2,4-oxadiazol-5(2H)-one;

3-(6-{[(1R)-1-cyclobutylethyl]amino}-8-[2-(2,2-dimethylpropyl)pyrrolidin-1-yl]-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-(2-cyclobutylpyrrolidin-1-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[2-(methoxymethyl)piperidin-1-yl]-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[2-(fluoromethyl)piperidin-1-yl]-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[3-(2-methylpropyl)morpholin-4-yl]-7H-purin-2-yl)-1,2,4-oxadiazol-5 (2H)-one;

3-(6-{[(1R)-1-cyclobutylethyl]amino}-8-[(cyclopropylmethyl)(methyl)amino]-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[(2,2-dimethylpropyl)(methyl)amino]-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[methyl(propyl)amino]-7H-purin-2-yl)-1,2,4-oxadiazol-5 (2H)-one;

3-{8-(2-benzylpiperidin-1-yl)-6-{[(1R)-1-cyclobutylethyl]amino}-7-[(trans-4-methylcyclohexyl)methyl]-7H-purin-2-yl}-1,2,4-oxadiazol-5(2H)-one;

3-(6-{[(1R)-1-cyclobutylethyl]amino}-7-[(trans-4-methylcyclohexyl)methyl]-8-[2-(1-methylethyl)pyrrolidin-1-yl]-7H-purin-2-yl)-1, 2,4-oxadiazol-5 (2H)-one;

3-[6-{[(1R)-1-cyclobutylethyl]amino}-7-[(trans-4-methylcyclohexyl)methyl]-8-(2-methylpiperidin-1-yl)-7H-purin-2-yl]-1,2,4-oxadiazol-5(4H)-one;

3-(6-{[(1R)-1-cyclobutylethyl]amino}-7-[(trans-4-methylcyclohexyl)methyl]-8-[methyl(2-methylpropyl)amino]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(2-pyridin-3-ylpiperidin-1-yl)-7H-purin-2-yl]-1,2,4-oxadiazol-5(4H)-one;

3-(6-{[(1R)-1-cyclobutylethyl]amino}-7-[(trans-4-methylcyclohexyl)methyl]-8-(2-pyridin-3-ylpiperidin-1-yl)-7H-purin-2-yl]-1,2,4-oxadiazol-5(4H)-one;

7-[(trans-4-methylcyclohexyl)methyl]-8-[(3R)-3-phenylmorpholin-4-yl]-6-{[(1R)-2,2,2-trifluoro-1-methylethyl]amino}-7H-purine-2-carboxylic acid;

6-{[(1R)-1-cyclobutylethyl]amino}-8-(2-ethylpiperidin-1-yl)-7-[(trans-4-methylcyclohexyl)methyl]-7H-purine-2-carboxylic acid;

3-(7-[(trans-4-methylcyclohexyl)methyl]-8-[(3R)-3-phenylmorpholin-4-yl]-6-{[(1R)-2,2,2-trifluoro-1-methylethyl]amino}-7H-purin-2-yl)-1,2,4-oxadiazol-5 (4H)-one;

6-{[(1R)-1-cyclobutylethyl]amino}-7-[(trans-4-methylcyclohexyl)methyl]-8-[2-(1-methylethyl)piperidin-1-yl]-7H-purine-2-carboxylic acid;

5-(6-{[(1R)-1-cyclobutylethyl]amino}-7-[(trans-4-methylcyclohexyl)methyl]-8-[(3R)-3-phenylmorpholin-4-yl]-7H-purin-2-yl)-1,3,4-oxadiazol-2(3H)-one;

6-{[(1R)-1-cyclobutylethyl]amino}-8-[2-(4-fluorobenzyl)piperidin-1-yl]-7-[(trans-4-methylcyclohexyl)methyl]-7H-purine-2-carboxylic acid;

3-(6-{[(1R)-1-cyclobutylethyl]amino}-8-(1H-imidazol-1-yl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(2R)-2-methylpiperidin-1-yl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[(2S)-2-methylpiperidin-1-yl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[(4aR,8aS)-octahydroquinolin-1 (2H)-yl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(4aS,8aR)-octahydroquinolin-1 (2H)-yl]-7H-purin-2-yl)-1,2,4-oxadiazol-5 (4H)-one;

3-{6-(2-cyclobutylpyrrolidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-(6-{[(1R)-1-cyclobutylethyl]amino}-7-[(trans-4-methylcyclohexyl)methyl]-8-{methyl[(4-methyl-1,2, 5-oxadiazol-3-yl)methyl]amino}-7H-purin-2-yl)-1,2,4-oxadiazol-5(4H)-one;

3-(6-{[(1R)-1-cyclobutylethyl]amino}-8-[(isoxazol-3-ylmethyl)(methyl)amino]-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(3R)-3-methylmorpholin-4-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(3 S)-3-methylmorpholin-4-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(3 S)-3-phenylmorpholin-4-yl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(4-methyl-2-phenylpiperidin-1-yl)-7H-purin-2-yl]-1,2,4-oxadiazol-5 (4H)-one;

3-[6-{[(1R)-1-cyclobutylethyl]amino}-7-[(trans-4-methylcyclohexyl)methyl]-8-(4-methyl-2-phenylpiperidin-1-yl)-7H-purin-2-yl]-1,2,4-oxadiazol-5 (4H)-one;

3-(6-{[(1R)-1-cyclobutylethyl]amino}-7-[(trans-4-methylcyclohexyl)methyl]-8-[methyl(pyrimidin-4-ylmethyl)amino]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-{methyl[(1-methyl-1H-pyrazol-4-yl)methyl]amino}-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[methyl(pyrazin-2-ylmethyl)amino]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[methyl(1,3-thiazol-5-ylmethyl)amino]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[methyl(1,3-thiazol-4-ylmethyl)amino]-7H-purin-2-yl)-1,2,4-oxadiazol-5 (2H)-one;

3-(6-{[(1R)-1-cyclobutylethyl]amino}-8-{[(5-cyclopropyl-1,2,4-oxadiazol-3-yl)methyl](methyl)amino}-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-{methyl[(4-methyl-1,3-thiazol-2-yl)methyl]amino}-7H-purin-2-yl)-1,2,4-oxadiazol-5(2H)-one;

3-(6-{[(1R)-1-cyclobutylethyl]amino}-7-[(trans-4-methylcyclohexyl)methyl]-8-{methyl[(3-methylisoxazol-5-yl)methyl]amino}-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[2-(5-methylfuran-2-yl)piperidin-1-yl]-7H-purin-2-yl)-1,2,4-oxadiazol-5 (4H)-one;

3-(6-{[(1R)-1-cyclobutylethyl]amino}-8-(1,1-dioxidothiomorpholin-4-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-(4,4-difluoropiperidin-1-yl)-7-[(trans-4-methylcyclohexyl)methyl]-7H-purin-2-yl)-1,2,4-oxadiazol-5 (2H)-one;

3-{6-(2-cyclobutylpiperidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(2-cyclobutylpiperidin-1-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-(6-{[(1R)-1-cyclobutylethyl]amino}-7-[(trans-4-methylcyclohexyl)methyl]-8-[(2R)-2-(2-methylpropyl)piperidin-1-yl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(2S)-2-(2-methylpropyl)piperidin-1-yl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(1-pyrimidin-5-ylethyl)amino]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-{[1-(2-methyl-1,3-thiazol-4-yl)ethyl]amino}-7H-purin-2-yl)-1,2,4-oxadiazol-5 (2H)-one;

3-(6-{[(1R)-1-cyclobutylethyl]amino}-8-[(1-isoxazol-5-ylethyl)amino]-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-{[1-(1,3-thiazol-4-yl)ethyl]amino}-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[(1-pyrimidin-4-ylethyl)amino]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-{[1-(3-methyl-1,2,4-oxadiazol-5-yl)ethyl]amino}-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[(1-pyrazin-2-ylethyl)amino]-7H-purin-2-yl)-1,2,4-oxadiazol-5(2H)-one;

3-(6-{[(1R)-1-cyclobutylethyl]amino}-7-[(trans-4-methylcyclohexyl)methyl]-8-[(1-pyrimidin-5-ylethyl)amino]-7H-purin-2-yl)-1,2,4-oxadiazol-5(2H)-one;

3-[6-{[(1R)-1-cyclobutylethyl]amino}-7-[(trans-4-methylcyclohexyl)methyl]-8-(3-oxa-8-azabicyclo[3.2.1]oct-8-yl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,2,4-oxadiazol-5 (4H)-one;

5-(6-{[(1R)-1-cyclobutylethyl]amino}-7-[(trans-4-methylcyclohexyl)methyl]-8-[(3R)-3-methylmorpholin-4-yl]-7H-purin-2-yl)-1,3,4-oxadiazol-2(3H)-one;

3-(6-{[(1R)-1-cyclobutylethyl]amino}-8-(3,3-dimethylmorpholin-4-yl)-7-[(trans-4-methylcyclohexyl)methyl]-7H-purin-2-yl)-1,2,4-oxadiazol-5 (4H)-one;

3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;

3-{8-[(3R)-3-benzylmorpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;

3-(6-{[(1R)-1-cyclobutylethyl]amino}-8-(3-methoxy-3-methylazetidin-1-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-(3-hydroxy-3-methylazetidin-1-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-(6,6-difluoro-1,4-oxazepan-4-yl)-7-[(trans-4-methylcyclohexyl)methyl]-7H-purin-2-yl)-1,2,4-oxadiazol-5 (2H)-one;

3-[6-{[(1R)-1-cyclobutylethyl]amino}-7-[(trans-4-methylcyclohexyl)methyl]-8-(1,4-oxazepan-4-yl)-7H-purin-2-yl]-1,2,4-oxadiazol-5(2H)-one;

3-(6-{[(1R)-1-cyclobutylethyl]amino}-8-{[(1S)-1-(3-fluorophenyl)ethyl]amino}-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[2-(1-methoxy-1-methylethyl)pyrrolidin-1-yl]-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[2-(4-methyl-1,2,5-oxadiazol-3-yl)pyrrolidin-1-yl]-7H-purin-2-yl)-1,2,4-oxadiazol-5 (2H)-one;

3-(6-{[(1R)-1-cyclobutylethyl]amino}-8-{[(1,3-dimethyl-1H-pyrazol-4-yl)methyl]amino}-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[(2S)-2-(1-methyl-1H-tetrazol-5-yl)pyrrolidin-1-yl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-{[(4-methyl-1,2,5-oxadiazol-3-yl)methyl]amino}-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-{[(3-phenyl-1H-pyrazol-4-yl)methyl]amino}-7H-purin-2-yl)-1,2,4-oxadiazol-5 (2H)-one;

3-(6-{[(1R)-1-cyclobutylethyl]amino}-8-(3-hydroxy-3-methylpyrrolidin-1-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-(3-methoxypyrrolidin-1-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[ethyl(methyl)amino]-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[(2-methoxyethyl)(methyl)amino]-7-[(trans-4-methylcyclohexyl)methyl]-7H-purin-2-yl)-1,2,4-oxadiazol-5 (2H)-one;

3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;

3-{8-[3-(2-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;

3-{8-[3-(4-chlorophenyl)morpholin-4-yl]-6-{[(1R)-1-cyclobutylethyl]amino}-7-[(trans-4-methylcyclohexyl)methyl]-7H-purin-2-yl}-1,2,4-oxadiazol-5(4H)-one;

(5R)-4-[6-{[(1R)-1-cyclobutylethyl]amino}-7-[(trans-4-methylcyclohexyl)methyl]-2-(5-oxo-4,5-dihydro-1,2,4-oxadiazol-3-yl)-7H-purin-8-yl]-1,5-dimethylpiperazin-2-one;

3-(6-{[(1R)-1-cyclobutylethyl]amino}-8-[(2-hydroxy-1-phenylethyl)amino]-7-[(trans-4-methylcyclohexyl)methyl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(3-methylthiomorpholin-4-yl)-7H-purin-2-yl]-1,2,4-oxadiazol-5 (2H)-one;

3-[6-{[(1R)-1-cyclobutylethyl]amino}-7-[(trans-4-methylcyclohexyl)methyl]-8-(3-methyl-1,1-dioxidothiomorpholin-4-yl)-7H-purin-2-yl]-1,2,4-oxadiazol-5 (2H)-one;

5-[6-{[(1R)-1-cyclobutylethyl]amino}-7-[(trans-4-methylcyclohexyl)methyl]-8-(octahydro-4H-1,4-benzoxazin-4-yl)-7H-purin-2-yl]-1,3,4-oxadiazol-2(3H)-one;

3-[6-{[(1R)-1-cyclobutylethyl]amino}-7-[(trans-4-methylcyclohexyl)methyl]-8-(2-oxa-5-azabicyclo[4.1.0]hept-5-yl)-7H-purin-2-yl]-1,2,4-oxadiazol-5(4H)-one;

3-(6-{[(1R)-1-cyclobutylethyl]amino}-7-[(trans-4-methylcyclohexyl)methyl]-8-[(2S)-2-(trifluoromethyl)pyrrolidin-1-yl]-7H-purin-2-yl)-1,2,4-oxadiazol-5(4H)-one;

3-(6-{[(1R)-1-cyclobutylethyl]amino}-8-[(3R,5R)-3,5-dimethylmorpholin-4-yl]-7-[(trans-4-methylcyclohexyl)methyl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(2-phenylpyrrolidin-1-yl)-7H-purin-2-yl]-1,2,4-oxadiazol-5(4H)-one;

3-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-{[(1R,2S)-2-hydroxycyclohexyl](methyl)amino}-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-{[(1R,2S)-2-hydroxycyclohexyl](methyl)amino}-7-[(trans-4-methylcyclohexyl)methyl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(2-phenylpyrrolidin-1-yl)-7H-purin-2-yl]-1,2,4-oxadiazol-5(4H)-one;

5-(6-{[(1R)-1-cyclobutylethyl]amino}-7-[(trans-4-methylcyclohexyl)methyl]-8-[(2S)-2-(trifluoromethyl)pyrrolidin-1-yl]-7H-purin-2-yl)-1,3,4-oxadiazol-2(3H)-one;

N-[(1R)-1-cyclobutylethyl]-8-[4-(propan-2-yl)pyridin-2-yl]-2-(1H-tetrazol-5-yl)-7-[4-(trifluoromethyl)benzyl]-7H-purin-6-amine;

(6-{[(1R)-1-cyclobutylethyl]amino}-8-[4-(propan-2-yl)pyridin-2-yl]-7-[4-(trifluoromethyl)benzyl]-7H-purin-2-yl)methanol;

N-[(1R)-1-cyclobutylethyl]-8-[4-(propan-2-yl)pyridin-2-yl]-2-(1H-1,2,3-triazol-5-yl)-7-[4-(trifluoromethyl)benzyl]-7H-purin-6-amine;

2-(aminomethyl)-N-[(1R)-1-cyclobutylethyl]-7-[(trans-4-methylcyclohexyl)methyl]-8-[4-(propan-2-yl)pyridin-2-yl]-7H-purin-6-amine;

1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanone;

1-(6-{[(1R)-1-cyclobutylethyl]amino}-7-[(trans-4-methylcyclohexyl)methyl]-8-[4-(propan-2-yl)pyridin-2-yl]-7H-purin-2-yl)ethanol;

2-(6-{[(1R)-1-cyclobutylethyl]amino}-7-[(trans-4-methylcyclohexyl)methyl]-8-[4-(propan-2-yl)pyridin-2-yl]-7H-purin-2-yl)propan-2-ol;

N-[(1R)-1-cyclobutylethyl]-7-[(trans-4-methylcyclohexyl)methyl]-8-[4-(propan-2-yl)pyridin-2-yl]-2-(1H-tetrazol-5-yl)-7H-purin-6-amine;

N-[(6-{[(1R)-1-cyclobutylethyl]amino}-7-[(trans-4-methylcyclohexyl)methyl]-8-[4-(propan-2-yl)pyridin-2-yl]-7H-purin-2-yl)methyl]methanesulfonamide;

N-[(6-{[(1R)-1-cyclobutylethyl]amino}-7-[(trans-4-methylcyclohexyl)methyl]-8-[4-(propan-2-yl)pyridin-2-yl]-7H-purin-2-yl)methyl]-2,2,2-trifluoroacetamide;

N-[(1R)-1-cyclobutylethyl]-7-[(trans-4-methylcyclohexyl)methyl]-2-(2-methyl-2H-tetrazol-5-yl)-8-[(3R)-3-phenylmorpholin-4-yl]-7H-purin-6-amine;

N-[(1R)-1-cyclobutylethyl]-7-[(trans-4-methylcyclohexyl)methyl]-2-(1-methyl-1H-tetrazol-5-yl)-8-[(3R)-3-phenylmorpholin-4-yl]-7H-purin-6-amine;

methyl 6-{[(1R)-1-cyclobutylethyl]amino}-7-[(trans-4-methylcyclohexyl)methyl]-8-[(3R)-3-phenylmorpholin-4-yl]-7H-purine-2-carboxylate;

2-(6-{[(1R)-1-cyclobutylethyl]amino}-7-[(trans-4-methylcyclohexyl)methyl]-8-[(3R)-3-phenylmorpholin-4-yl]-7H-purin-2-yl)propan-2-ol;

5-(6-{[(1R)-1-cyclobutylethyl]amino}-7-[(trans-4-methylcyclohexyl)methyl]-8-[(3R)-3-phenylmorpholin-4-yl]-7H-purin-2-yl)-4-methyl-2,4-dihydro-3H-1,2,4-triazol-3-one;

N-[(1R)-1-cyclobutylethyl]-7-[(trans-4-methylcyclohexyl)methyl]-8-[(3R)-3-phenylmorpholin-4-yl]-2-(4H-1,2,4-triazol-3-yl)-7H-purin-6-amine;

6-{[(1R)-1-cyclobutylethyl]amino}-N-ethyl-7-[(trans-4-methylcyclohexyl)methyl]-8-[(3R)-3-phenylmorpholin-4-yl]-7H-purine-2-carboxamide;

6-{[(1R)-1-cyclobutylethyl]amino}-7-[(trans-4-methylcyclohexyl)methyl]-N-(methylsulfonyl)-8-[(3R)-3-phenylmorpholin-4-yl]-7H-purine-2-carboxamide;

5-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methyl-1,2-dihydro-3H-1,2,4-triazol-3-one;

1-(6-(((R)-1-cyclobutylethyl)amino)-7-((trans-4-methylcyclohexyl)methyl)-8-((R)-3-phenylmorpholino)-7H-purin-2-yl)ethane-1,2-diol;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)ethanone;

(6-{[(1R)-1-cyclobutylethyl]amino}-7-[(trans-4-methylcyclohexyl)methyl]-8-[(3R)-3-phenylmorpholin-4-yl]-7H-purin-2-yl)methanol;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)ethanone;

6-{[(1R)-1-cyclobutylethyl]amino}-N-(dimethylsulfamoyl)-7-[(trans-4-methylcyclohexyl)methyl]-8-[(3R)-3-phenylmorpholin-4-yl]-7H-purine-2-carboxamide;

6-{[(1R)-1-cyclopropylethyl]amino}-8-(3-methylphenyl)-N-(methyl sulfonyl)-7-[4-(trifluoromethyl)benzyl]-7H-purine-2-carboxamide;

N-[(1R)-1-cyclopropylethyl]-8-(3-methylphenyl)-2-(1H-tetrazol-5-yl)-7-[4-(trifluoromethyl)benzyl]-7H-purin-6-amine;

6-{[(1R)-1-cyclopropylethyl]amino}-8-(3-methylphenyl)-7-[4-(trifluoromethyl)benzyl]-7H-purine-2-carboxamide;

N-[(1R)-1-cyclopropylethyl]-8-(3-methylphenyl)-2-(1H-1,2,4-triazol-3-yl)-7-[4-(trifluoromethyl)benzyl]-7H-purin-6-amine;

6-{[(1R)-1-cyclobutylethyl]amino}-8-(3-methylphenyl)-7-[4-(trifluoromethyl)benzyl]-7H-purine-2-carboxamide;

6-{[(1R)-1-cyclobutylethyl]amino}-N-methyl-8-(3-methylphenyl)-7-[4-(trifluoromethyl)benzyl]-7H-purine-2-carb oxamide;

6-{[(1R)-1-cyclobutylethyl]amino}-8-(2,5-dimethylphenyl)-7-[4-(trifluoromethyl)benzyl]-7H-purine-2-carboxamide;

6-{[(1R)-1-cyclobutylethyl]amino}-N-methoxy-8-[4-(1-methylethyl)pyridin-2-yl]-7-[4-(trifluoromethyl)benzyl]-7H-purine-2-carboxamide;

(6-{[(1R)-1-cyclobutylethyl]amino}-8-[(3R)-3-phenylmorpholin-4-yl]-7-[4-(trifluoromethyl)benzyl]-7H-purin-2-yl)methanol;

(6-{[(1R)-1-cyclobutylethyl]amino}-7-[(trans-4-methylcyclohexyl)methyl]-8-[4-(1-methylethyl)pyridin-2-yl]-7H-purin-2-yl)methanol;

2-((6-(((R)-1-cyclobutylethyl)amino)-7-((trans-4-methylcyclohexyl)methyl)-8-((R)-3-phenylmorpholino)-7H-purin-2-yl)amino)ethanol;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-L-proline;

N$^6$-[(1R)-1-cyclobutylethyl]-N$^2$-methyl-7-[(trans-4-methylcyclohexyl)methyl]-8-[(3R)-3-phenylmorpholin-4-yl]-7H-purine-2,6-diamine;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-D-proline;

N-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methylalanine;

N-(6-{[(1R)-1-cyclobutylethyl]amino}-7-[(trans-4-methylcyclohexyl)methyl]-8-[(3R)-3-phenylmorpholin-4-yl]-7H-purin-2-yl)glycine;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-2-methyl-D-proline;

N-(6-{[(1R)-1-cyclobutylethyl]amino}-7-[(trans-4-methylcyclohexyl)methyl]-8-[(3R)-3-phenylmorpholin-4-yl]-7H-purin-2-yl)-N-methylglycine;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)pyrrolidine-3-carboxylic acid;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-3-(methylsulfanyl)pyrrolidine-3-carboxylic acid;

1-(6-{[(1R)-1-cyclobutylethyl]amino}-7-[(trans-4-methylcyclohexyl)methyl]-8-[(3R)-3-phenylmorpholin-4-yl]-7H-purin-2-yl)-4,4-dimethylpyrrolidine-3-carboxylic acid;

N—((R)-1-cyclobutylethyl)-7-((trans-4-methylcyclohexyl)methyl)-2-(methylsulfonyl)-8-((R)-3-phenylmorpholino)-7H-purin-6-amine;

N—((R)-1-cyclobutylethyl)-7-((trans-4-methylcyclohexyl)methyl)-2-(methylsulfinyl)-8-((R)-3-phenylmorpholino)-7H-purin-6-amine;

N-[(1R)-1-cyclobutylethyl]-7-[(trans-4-methylcyclohexyl)methyl]-8-[4-(1-methylethyl)pyridin-2-yl]-2-(methyl sulfonyl)-7H-purin-6-amine;

N-[(1R)-1-cyclobutylethyl]-2-(ethylsulfonyl)-7-[(trans-4-methylcyclohexyl)methyl]-8-[(3R)-3-phenylmorpholin-4-yl]-7H-purin-6-amine;

N-[(1R)-1-cyclobutylethyl]-7-[(trans-4-methylcyclohexyl)methyl]-2-[(1-methylethyl)sulfonyl]-8-[(3R)-3-phenylmorpholin-4-yl]-7H-purin-6-amine;

N-[(1R)-1-cyclobutylethyl]-2-(ethylsulfinyl)-7-[(trans-4-methylcyclohexyl)methyl]-8-[(3R)-3-phenylmorpholin-4-yl]-7H-purin-6-amine;

N-[(1R)-1-cyclobutylethyl]-7-[(trans-4-methylcyclohexyl)methyl]-2-[(1-methylethyl)sulfinyl]-8-[(3R)-3-phenylmorpholin-4-yl]-7H-purin-6-amine;

N-[(1R)-1-cyclobutylethyl]-7-[(trans-4-methylcyclohexyl)methyl]-2-(methylsulfonyl)-8-(2-phenylpiperidin-1-yl)-7H-purin-6-amine;

N-[(1R)-1-cyclobutylethyl]-7-[(trans-4-methylcyclohexyl)methyl]-2-(methylsulfinyl)-8-(2-phenylpiperidin-1-yl)-7H-purin-6-amine;

N-[(1R)-1-cyclobutylethyl]-7-[(trans-4-methylcyclohexyl)methyl]-8-[(3R)-3-phenylmorpholin-4-yl]-2-[(2,2,2-trifluoroethyl)sulfonyl]-7H-purin-6-amine;

(6-{[(1R)-1-cyclobutylethyl]amino}-7-[(trans-4-methylcyclohexyl)methyl]-8-[(3R)-3-phenylmorpholin-4-yl]-7H-purin-2-yl)(2,2,2-trifluoroethyl)sulfoniumolate;

2-[(6-{[(1R)-1-cyclobutylethyl]amino}-7-[(trans-4-methylcyclohexyl)methyl]-8-[(3R)-3-phenylmorpholin-4-yl]-7H-purin-2-yl)sulfonyl]ethanol;

6-(((R)-1-cyclobutylethyl)amino)-8-(4-isopropylpyridin-2-yl)-7-((trans-4-methylcyclohexyl)methyl)-7H-purine-2-carboxylic acid;

6-(((R)-1-cyclobutylethyl)(methyl)amino)-8-(4-isopropylpyridin-2-yl)-7-((trans-4-methylcyclohexyl)methyl)-7H-purine-2-carboxylic acid;

6-(((R)-1-cyclobutylethyl)amino)-8-(4-isopropyl-6-oxo-1,6-dihydropyridin-2-yl)-7-((trans-4-methylcyclohexyl)methyl)-7H-purine-2-carboxylic acid;

6-(((R)-1-cyclobutylethyl)amino)-8-(6-ethoxy-4-isopropylpyridin-2-yl)-7-((trans-4-methyl cyclohexyl)methyl)-7H-purine-2-carb oxylic acid;

3-(6-(((R)-1-cyclobutylethyl)amino)-8-(6-fluoro-4-isopropylpyridin-2-yl)-7-((trans-4-methylcyclohexyl)methyl)-7H-purin-2-yl)-1,2,4-oxadiazol-5 (2H)-one;

6-(((R)-1-Cyclobutylethyl)amino)-8-(3-fluoro-4-isopropylpyridin-2-yl)-7-((trans-4-methylcyclohexyl)methyl)-7H-purine-2-carboxylic acid;

3-(6-((R)-1-cyclobutylethylamino)-8-(3-fluoro-4-isopropylpyridin-2-yl)-7-((trans-4-methylcyclohexyl)methyl)-7H-purin-2-yl)-1,2,4-oxadiazol-5 (4H)-one;

6-(((R)-1-cyclobutylethyl)amino)-8-(5-fluoro-4-isopropylpyridin-2-yl)-7-((trans-4-methylcyclohexyl)methyl)-7H-purine-2-carboxylic acid;

3-(6-(((R)-1-cyclobutylethyl)amino)-8-(5-fluoro-4-(2-hydroxypropan-2-yl)pyridin-2-yl)-7-((trans-4-methylcyclohexyl)methyl)-7H-purin-2-yl)-1,2,4-oxadiazol-5 (4H)-one;

3-(6-(((R)-1-cyclobutylethyl)amino)-8-(5-fluoro-4-isopropylpyridin-2-yl)-7-((trans-4-methylcyclohexyl)methyl)-7H-purin-2-yl)-1,2,4-oxadiazol-5 (4H)-one;

6-(((R)-1-cyclobutylethyl)amino)-7-((trans-4-methylcyclohexyl)methyl)-8-(thiazol-2-yl)-7H-purine-2-carboxylic acid;

3-(6-(((R)-1-cyclobutylethyl)amino)-7-((trans-4-methylcyclohexyl)methyl)-8-(thiazol-2-yl)-7H-purin-2-yl)-1,2,4-oxadiazol-5(4H)-one;

6-{[(1R)-1-cyclobutylethyl]amino}-8-(2-methoxy-5-methylphenyl)-7-[(trans-4-methylcyclohexyl)methyl]-7H-purine-2-carboxylic acid;

6-{[(1R)-1-cyclobutylethyl]amino}-7-[(trans-4-methylcyclohexyl)methyl]-8-(3-methylphenyl)-7H-purine-2-carboxylic acid;

6-{[(1R)-1-cyclobutylethyl]amino}-7-[(trans-4-methylcyclohexyl)methyl]-8-[4-(1-methylethyl)pyridin-2-yl]-7H-purine-2-carboxylic acid;

8-(4-tert-butylpyridin-2-yl)-6-{[(1R)-1-cyclobutylethyl]amino}-7-[(trans-4-methylcyclohexyl)methyl]-7H-purine-2-carboxylic acid;

6-{[(1R)-1-cyclobutylethyl]amino}-8-(4-cyclopropylpyridin-2-yl)-7-[(trans-4-methylcyclohexyl)methyl]-7H-purine-2-carboxylic acid;

6-{[(1R)-1-cyclobutylethyl]amino}-8-(4-cyclobutylpyridin-2-yl)-7-[(trans-4-methylcyclohexyl)methyl]-7H-purine-2-carboxylic acid;

6-{[(1R)-1-cyclobutylethyl]amino}-8-(4-ethylpyridin-2-yl)-7-[(trans-4-methylcyclohexyl)methyl]-7H-purine-2-carboxylic acid;

8-(4-tert-butylpyridin-2-yl)-6-{[(1R)-1-cyclobutylethyl](methyl)amino}-7-[(trans-4-methylcyclohexyl)methyl]-7H-purine-2-carboxylic acid;

6-{[(1R)-1-cyclobutylethyl]amino}-8-(4,5-dimethylpyridin-2-yl)-7-[(trans-4-methylcyclohexyl)methyl]-7H-purine-2-carboxylic acid;

7-[(trans-4-methylcyclohexyl)methyl]-8-[4-(1-methylethyl)pyridin-2-yl]-6-{[(1R)-2,2,2-trifluoro-1-methylethyl]amino}-7H-purine-2-carboxylic acid;

3-(6-{[(1R)-1-cyclobutylethyl]amino}-8-[4-(1-hydroxy-1-methylethyl)pyridin-2-yl]-7-[(trans-4-methylcyclohexyl)methyl]-7H-purin-2-yl)-1,2,4-oxadiazol-5 (4H)-one;

3-(6-{[(1R)-1-cyclobutylethyl](ethyl)amino}-7-[(trans-4-methylcyclohexyl)methyl]-8-[4-(1-methylethyl)pyridin-2-yl]-7H-purin-2-yl)-1,2,4-oxadiazol-5 (4H)-one;

6-[6-{[(1R)-1-cyclobutylethyl]amino}-7-[(trans-4-methylcyclohexyl)methyl]-2-(5-oxo-2,5-dihydro-1,2,4-oxadiazol-3-yl)-7H-purin-8-yl]-4-(1-methylethyl)pyridin-2(1H)-one;

3-(6-(3-chlorophenyl)-7-(((trans)-4-methylcyclohexyl)methyl)-8-morpholino-7H-purin-2-yl)-1,2,4-oxadiazol-5(4H)-one;

3-(6-(3-chlorophenyl)-7-(((trans)-4-methylcyclohexyl)methyl)-8-((S)-3-methylmorpholino)-7H-purin-2-yl)-1,2,4-oxadiazol-5(4H)-one;

5-(7-(((trans)-4-methylcyclohexyl)methyl)-8-morpholino-6-(m-tolyl)-7H-purin-2-yl)-1,3,4-oxadiazol-2(3H)-one;

3-(6-(3-chlorophenyl)-8-(((R)-1-hydroxypropan-2-yl)amino)-7-(((trans)-4-methylcyclohexyl)methyl)-7H-purin-2-yl)-1,2,4-oxadiazol-5 (4H)-one;

3-(6-(3-chlorophenyl)-8-(((S)-1-hydroxy-2-phenylpropan-2-yl)amino)-7-(((trans)-4-methylcyclohexyl)methyl)-7H-purin-2-yl)-1,2,4-oxadiazol-5 (4H)-one;

3-(6-(3-chlorophenyl)-7-(((trans)-4-methylcyclohexyl)methyl)-8-((R)-3-methylmorpholino)-7H-purin-2-yl)-1,2,4-oxadiazol-5(4H)-one;

5-(6-(3-chlorophenyl)-7-(((trans)-4-methylcyclohexyl)methyl)-8-((R)-3-methylmorpholino)-7H-purin-2-yl)-1,3,4-oxadiazol-2(3H)-one;

3-(6-(3-chlorophenyl)-8-(((1R,2 S)-2-hydroxy-1-phenylpropyl)amino)-7-(((trans)-4-methylcyclohexyl)methyl)-7H-purin-2-yl)-1,2,4-oxadiazol-5 (4H)-one;

3-(6-(3-chlorophenyl)-8-((4R,5 S)-5-methyl-2-oxo-4-phenyloxazolidin-3-yl)-7-(((trans)-4-methylcyclohexyl)methyl)-7H-purin-2-yl)-1,2,4-oxadiazol-5 (4H)-one;

3-(6-(5-chloropyridin-3-yl)-7-(((trans)-4-methylcyclohexyl)methyl)-8-((R)-3-methylmorpholino)-7H-purin-2-yl)-1,2,4-oxadiazol-5(4H)-one;

5-(6-(5-chloropyridin-3-yl)-7-(((trans)-4-methylcyclohexyl)methyl)-8-((R)-3-methylmorpholino)-7H-purin-2-yl)-1,3,4-oxadiazol-2(3H)-one;

3-(7-(((trans)-4-methylcyclohexyl)methyl)-6-phenyl-8-((R)-3-phenylmorpholino)-7H-purin-2-yl)-1,2,4-oxadiazol-5(4H)-one;

6-(4-fluorophenyl)-7-{(trans-4-methylcyclohexyl)methyl]-8-[4-(1-methylethyl)pyridin-2-yl]-7H-purine-2-carboxylic acid;

7-[(trans-4-methylcyclohexyl)methyl]-8-[4-(1-methylethyl)pyridin-2-yl]-6-(3-methylphenyl)-7H-purine-2-carboxylic acid;

3-{7-[(trans-4-methylcyclohexyl)methyl]-8-[4-(1-methylethyl)pyridin-2-yl]-6-(3-methylphenyl)-7H-purin-2-yl}-1,2,4-oxadiazol-5 (4H)-one;

3-{6-(3-chlorophenyl)-7-[(trans-4-methylcyclohexyl)methyl]-8-[4-(1-methylethyl)pyridin-2-yl]-7H-purin-2-yl}-1,2,4-oxadiazol-5 (4H)-one;

3-{7-[(trans-4-methylcyclohexyl)methyl]-6-(3-methylphenyl)-8-[(3R)-3-phenylmorpholin-4-yl]-7H-purin-2-yl}-1,2,4-oxadiazol-5 (4H)-one;

3-{6-(3-chlorophenyl)-7-[(trans-4-methylcyclohexyl)methyl]-8-[(3R)-3-phenylmorpholin-4-yl]-7H-purin-2-yl}-1,2,4-oxadiazol-5 (4H)-one;

3-{6-(3,5-dichlorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3-chloro-5-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(3-chlorophenyl)-7-[(trans-4-methylcyclohexyl)methyl]-8-[(3R)-3-phenylmorpholin-4-yl]-7H-purin-2-yl}-1,3,4-oxadiazol-2(3H)-one;

6-(3-chlorophenyl)-7-[(trans-4-methylcyclohexyl)methyl]-8-[(3R)-3-phenylmorpholin-4-yl]-7H-purine-2-carboxylic acid;

3-{6-(3-chloro-2-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3-chloro-4-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloro-2-fluorophenyl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloropyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{7-[(trans-4-methylcyclohexyl)methyl]-6-(3-methylphenyl)-8-morpholin-4-yl-7H-purin-2-yl}-1,2,4-oxadiazol-5(4H)-one;

3-{7-[(trans-4-methylcyclohexyl)methyl]-8-[(3R)-3-methylmorpholin-4-yl]-6-(3-methylphenyl)-7H-purin-2-yl}-1,2,4-oxadiazol-5 (4H)-one;

3-{6-(3-chlorophenyl)-8-(3,3-dimethylmorpholin-4-yl)-7-[(trans-4-methylcyclohexyl)methyl]-7H-purin-2-yl}-1,2,4-oxadiazol-5 (4H)-one;

3-{6-(3-ethylphenyl)-7-[(trans-4-methylcyclohexyl)methyl]-8-[(3R)-3-phenylmorpholin-4-yl]-7H-purin-2-yl}-1,2,4-oxadiazol-5 (4H)-one;

3-{6-[3-(difluoromethyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one;

5-{7-[(trans-4-methylcyclohexyl)methyl]-8-[(3R)-3-methylmorpholin-4-yl]-6-(3-methylphenyl)-7H-purin-2-yl}-1,3,4-oxadiazol-2(3H)-one;

5-{6-(3-chlorophenyl)-7-[(trans-4-methylcyclohexyl)methyl]-8-morpholin-4-yl-7H-purin-2-yl}-1,3,4-oxadiazol-2(3H)-one;

3-{7-[(trans-4-methylcyclohexyl)methyl]-8-[(3 S)-3-methylmorpholin-4-yl]-6-(3-methylphenyl)-7H-purin-2-yl}-1,2,4-oxadiazol-5 (4H)-one;

5-{6-(5-chloropyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(3-chlorophenyl)-8-[4-(1-hydroxy-1-methylethyl)pyridin-2-yl]-7-[(trans-4-methylcyclohexyl)methyl]-7H-purin-2-yl}-1,2,4-oxadiazol-5(4H)-one;

5-{7-[(trans-4-methylcyclohexyl)methyl]-8-[(3 S)-3-methylmorpholin-4-yl]-6-(3-methylphenyl)-7H-purin-2-yl}-1,3,4-oxadiazol-2(3H)-one;

3-{6-(3-chlorophenyl)-8-{[(1R)-2-hydroxy-1-phenylethyl]amino}-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[(3 S)-3-(2-methylpropyl)morpholin-4-yl]-7H-purin-2-yl}-1,2,4-oxadiazol-5(4H)-one;

3-{6-(3-chlorophenyl)-7-[(trans-4-methylcyclohexyl)methyl]-8-[(3R)-3-(2-methylpropyl)morpholin-4-yl]-7H-purin-2-yl}-1,2,4-oxadiazol-5(4H)-one;

3-{6-(3-chlorophenyl)-8-[(2-hydroxy-1,1-dimethylethyl)amino]-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[(3R)-3-(1-methylethyl)morpholin-4-yl]-7H-purin-2-yl}-1,2,4-oxadiazol-5(4H)-one;

3-{6-(5-chloropyridin-3-yl)-7-[(trans-4-methylcyclohexyl)methyl]-8-[(3 S)-3-methylmorpholin-4-yl]-7H-purin-2-yl}-1,2,4-oxadiazol-5(2H)-one;

3-{6-[3-chloro-5-(hydroxymethyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(3-chlorophenyl)-8-[(3R)-3-(hydroxymethyl)morpholin-4-yl]-7-[(trans-4-methylcyclohexyl)methyl]-7H-purin-2-yl}-1,2,4-oxadiazol-5(4H)-one;

5-{6-(3-chlorophenyl)-8-{[(1R)-2-hydroxy-1-methylethyl]amino}-7-[(trans-4-methylcyclohexyl)methyl]-7H-purin-2-yl}-1,3,4-oxadiazol-2(3H)-one;

3-{6-(3-chlorophenyl)-8-[(3R)-3-ethylmorpholin-4-yl]-7-[(trans-4-methylcyclohexyl)methyl]-7H-purin-2-yl}-1,2,4-oxadiazol-5 (4H)-one;

methyl (3 S)-4-[6-(3-chlorophenyl)-7-[(trans-4-methylcyclohexyl)methyl]-2-(5-oxo-4,5-dihydro-1,2,4-oxadiazol-3-yl)-7H-purin-8-yl]morpholine-3-carboxylate;

3-{6-(3-chlorophenyl)-8-{[(1S)-1-(3-fluorophenyl)ethyl]amino}-7-[(trans-4-methylcyclohexyl)methyl]-7H-purin-2-yl}-1,2,4-oxadiazol-5(4H)-one;

3-[6-(3-chlorophenyl)-7-[(trans-4-methylcyclohexyl)methyl]-8-{[(1S)-1-phenylpropyl]amino}-7H-purin-2-yl]-1,2,4-oxadiazol-5(4H)-one;

3-[6-(5-chloropyridin-3-yl)-7-[(trans-4-methylcyclohexyl)methyl]-8-(octahydro-4H-1,4-benzoxazin-4-yl)-7H-purin-2-yl]-1,2,4-oxadiazol-5(4H)-one;

3-{6-(3-chlorophenyl)-8-(2,4-dimethylpiperazin-1-yl)-7-[(trans-4-methylcyclohexyl)methyl]-7H-purin-2-yl}-1,2,4-oxadiazol-5 (4H)-one;

3-{6-(3-chlorophenyl)-7-[(trans-4-methylcyclohexyl)methyl]-8-[(2R)-2-methylpiperazin-1-yl]-7H-purin-2-yl}-1,2,4-oxadiazol-5 (4H)-one;

5-{6-(3-chlorophenyl)-8-{[(1S)-1-(3-fluorophenyl)ethyl]amino}-7-[(trans-4-methylcyclohexyl)methyl]-7H-purin-2-yl}-1,3,4-oxadiazol-2(3H)-one;

3-{8-[benzyl(methyl)amino]-6-(3-chlorophenyl)-7-[(trans-4-methylcyclohexyl)methyl]-7H-purin-2-yl}-1,2,4-oxadiazol-5(4H)-one;

5-{6-(3-chlorophenyl)-8-{[(1R,2S)-2-hydroxy-1-phenylpropyl]amino}-7-[(trans-4-methylcyclohexyl)methyl]-7H-purin-2-yl}-1,3,4-oxadiazol-2(3H)-one;

5-{6-(3-chlorophenyl)-8-[(3R)-3-ethylmorpholin-4-yl]-7-[(trans-4-methylcyclohexyl)methyl]-7H-purin-2-yl}-1,3,4-oxadiazol-2(3H)-one;

3-{6-(3-chlorophenyl)-8-[(3R)-3-(methoxymethyl)morpholin-4-yl]-7-[(trans-4-methylcyclohexyl)methyl]-7H-purin-2-yl}-1,2,4-oxadiazol-5(4H)-one;

3-{6-(3-chlorophenyl)-8-[(3R,5R)-3,5-dimethylmorpholin-4-yl]-7-[(trans-4-methylcyclohexyl)methyl]-7H-purin-2-yl}-1,2,4-oxadiazol-5(4H)-one;

5-[6-(3-chlorophenyl)-7-[(trans-4-methylcyclohexyl)methyl]-8-{[(1S)-1-phenylpropyl]amino}-7H-purin-2-yl]-1,3,4-oxadiazol-2(3H)-one;

5-{8-[benzyl(methyl)amino]-6-(3-chlorophenyl)-7-[(trans-4-methylcyclohexyl)methyl]-7H-purin-2-yl}-1,3,4-oxadiazol-2(3H)-one;

3-{6-(3-chlorophenyl)-8-[(3 S)-3-(1-methoxy-1-methylethyl)morpholin-4-yl]-7-[(trans-4-methylcyclohexyl)methyl]-7H-purin-2-yl}-1,2,4-oxadiazol-5(4H)-one;

3-{6-(3-chlorophenyl)-8-{[(1S)-1-(3-fluorophenyl)propyl]amino}-7-[(trans-4-methylcyclohexyl)methyl]-7H-purin-2-yl}-1,2,4-oxadiazol-5(4H)-one;

3-{6-(3-chlorophenyl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one;

3-{6-(3-chlorophenyl)-8-[(3R,5 S)-3,5-dimethylmorpholin-4-yl]-7-[(trans-4-methylcyclohexyl)methyl]-7H-purin-2-yl}-1,2,4-oxadiazol-5(4H)-one;

(5R)-4-[6-(3-chlorophenyl)-7-[(trans-4-methylcyclohexyl)methyl]-2-(5-oxo-4,5-dihydro-1,2,4-oxadiazol-3-yl)-7H-purin-8-yl]-1,5-dimethylpiperazin-2-one;

3-{6-(3-chlorophenyl)-7-[(trans-4-methylcyclohexyl)methyl]-8-[(2S)-2-(trifluoromethyl)pyrrolidin-1-yl]-7H-purin-2-yl}-1,2,4-oxadiazol-5(4H)-one;

5-{6-(3-chlorophenyl)-8-[2-(1-methoxy-1-methylethyl)pyrrolidin-1-yl]-7-[(trans-4-methylcyclohexyl)methyl]-7H-purin-2-yl}-1,3,4-oxadiazol-2(3H)-one;

3-{6-(5-chloropyridin-3-yl)-8-[2-(1-methoxy-1-methylethyl)pyrrolidin-1-yl]-7-[(trans-4-methylcyclohexyl)methyl]-7H-purin-2-yl}-1,2,4-oxadiazol-5(4H)-one;

3-{6-(5-chloropyridin-3-yl)-7-[(trans-4-methylcyclohexyl)methyl]-8-[(2S)-2-(trifluoromethyl)pyrrolidin-1-yl]-7H-purin-2-yl}-1,2,4-oxadiazol-5(4H)-one;

6-ethoxy-8-(3-methylphenyl)-7-[4-(trifluoromethyl)benzyl]-7H-purine-2-carboxylic acid;

6-(cyclopropylmethoxy)-8-(3-methylphenyl)-7-[4-(trifluoromethyl)benzyl]-7H-purine-2-carboxylic acid;

6-(cyclobutylmethoxy)-8-(3-methylphenyl)-7-[4-(trifluoromethyl)benzyl]-7H-purine-2-carboxylic acid;

6-(1-cyclobutylethoxy)-8-(3-methylphenyl)-7-[4-(trifluoromethyl)benzyl]-7H-purine-2-carboxylic acid;

6-(1-cyclobutylethoxy)-7-[3-fluoro-4-(trifluoromethyl)benzyl]-8-[4-(1-methylethyl)pyridin-2-yl]-7H-purine-2-carboxylic acid;

6-(1-cyclobutylethoxy)-7-[(trans-4-methylcyclohexyl)methyl]-8-[4-(1-methylethyl)pyridin-2-yl]-7H-purine-2-carboxylic acid;

3-(8-((R)-4-acetyl-2-methylpiperazin-1-yl)-6-(((R)-1-cyclobutylethyl)amino)-7-((trans-4-methylcyclohexyl)methyl)-7H-purin-2-yl)-1,2,4-oxadiazol-5 (4H)-one;

3-{8-[(2R)-4-acetyl-2-phenylpiperazin-1-yl]-6-{[(1R)-1-cyclobutylethyl]amino}-7-[(trans-4-methylcyclohexyl)methyl]-7H-purin-2-yl}-1,2,4-oxadiazol-5(4H)-one;

8-[(2R)-4-acetyl-2-phenylpiperazin-1-yl]-6-{[(1R)-1-cyclobutylethyl]amino}-7-[(trans-4-methylcyclohexyl)methyl]-7H-purine-2-carboxamide;

6-{[(1R)-1-cyclobutylethyl]amino}-7-[(trans-4-methylcyclohexyl)methyl]-8-[(2R)-4-(methyl sulfonyl)-2-phenylpiperazin-1-yl]-7H-purine-2-carboxamide;

3-(6-{[(1R)-1-cyclobutylethyl]amino}-7-[(trans-4-methylcyclohexyl)methyl]-8-[(2R)-4-(methyl sulfonyl)-2-phenylpiperazin-1-yl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(2R)-2-methyl-4-(methyl sulfonyl)piperazin-1-yl]-7H-purin-2-yl)-1,2,4-oxadiazol-5 (4H)-one;

3-(6-{[(1R)-1-cyclobutylethyl]amino}-8-[(2R)-4-(2,2-dimethylpropanoyl)-2-methylpiperazin-1-yl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[(2R)-4-(cyclopropylcarbonyl)-2-methylpiperazin-1-yl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-{(2R)-2-methyl-4-[(1-methylethyl)sulfonyl]piperazin-1-yl}-7H-purin-2-yl)-1,2,4-oxadiazol-5(4H)-one;

3-(6-{[(1R)-1-cyclobutylethyl]amino}-8-[(2R)-4-(hydroxyacetyl)-2-methylpiperazin-1-yl]-7-[(trans-4-methylcyclohexyl)methyl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-[(2R)-2-methylpiperazin-1-yl]-7H-purin-2-yl)-1,2,4-oxadiazol-5 (4H)-one;

tert-butyl (2S,5R)-4-[6-{[(1R)-1-cyclobutylethyl]amino}-7-[(trans-4-methylcyclohexyl)methyl]-2-(5-oxo-4,5-dihydro-1,2,4-oxadiazol-3-yl)-7H-purin-8-yl]-2,5-dimethylpiperazine-1-carboxylate;

3-(6-{[(1R)-1-cyclobutylethyl]amino}-8-[(2R,5 S)-2,5-dimethylpiperazin-1-yl]-7-[(trans-4-methylcyclohexyl)methyl]-7H-purin-2-yl)-1,2,4-oxadiazol-5 (4H)-one;

3-{8-[(2R,5 S)-4-acetyl-2,5-dimethylpiperazin-1-yl]-6-{[(1R)-1-cyclobutylethyl]amino}-7-[(trans-4-methylcyclohexyl)methyl]-7H-purin-2-yl}-1,2,4-oxadiazol-5(4H)-one;

3-(6-{[(1R)-1-cyclobutylethyl]amino}-8-[(2R,5 S)-4-(cyclopropylcarbonyl)-2,5-dimethylpiperazin-1-yl]-7-[(trans-4-methylcyclohexyl)methyl]-7H-purin-2-yl)-1,2,4-oxadiazol-5(4H)-one;

6-(((R)-1-cyclobutylethyl)amino)-8-(4-isopropylpyridin-2-yl)-7-((trans-4-(trifluoromethyl)cyclohexyl)methyl)-7H-purine-2-carboxylic acid;

6-(((R)-1-cyclobutylethyl)amino)-7-((trans-4-ethylcyclohexyl)methyl)-8-(4-isopropylpyridin-2-yl)-7H-purine-2-carboxylic acid;

(R)-6-((1-cyclobutylethyl)amino)-7-((4,4-difluorocyclohexyl)methyl)-8-(4-isopropylpyridin-2-yl)-7H-purine-2-carboxylic acid;

3-(6-(((R)-1-cyclobutylethyl)amino)-7-((3-ethylcyclopentyl)methyl)-8-(4-isopropylpyridin-2-yl)-7H-purin-2-yl)-1,2,4-oxadiazol-5(4H)-one;

6-(((R)-1-cyclobutylethyl)amino)-8-(4-isopropylpyridin-2-yl)-7-((4-methylcyclohex-3-en-1-yl)methyl)-7H-purine-2-carboxylic acid;

6-(((R)-1-cyclobutylethyl)amino)-7-((4-ethylcyclohex-3-en-1-yl)methyl)-8-(4-isopropylpyridin-2-yl)-7H-purine-2-carboxylic acid;

3-(6-(((R)-1-cyclobutylethyl)amino)-7-((4-ethylcyclohex-3-en-1-yl)methyl)-8-(4-isopropylpyridin-2-yl)-7H-purin-2-yl)-1,2,4-oxadiazol-5(4H)-one;

(R)-6-((1-cyclobutylethyl)amino)-7-((4,4-dimethylcyclohexyl)methyl)-8-(4-isopropylpyridin-2-yl)-7H-purine-2-carboxylic acid;

(R)-3-(6-((1-cyclobutylethyl)amino)-7-((4,4-dimethylcyclohexyl)methyl)-8-(4-isopropylpyridin-2-yl)-7H-purin-2-yl)-1,2,4-oxadiazol-5 (4H)-one;

6-(((R)-1-cyclobutylethyl)amino)-7-((trans-4-(fluoromethyl)cyclohexyl)methyl)-8-(4-isopropylpyridin-2-yl)-7H-purine-2-carboxylic acid;

3-(6-(((R)-1-cyclobutylethyl)amino)-7-((trans-3,3-difluoro-4-methylcyclohexyl)methyl)-8-(4-isopropylpyridin-2-yl)-7H-purin-2-yl)-1,2,4-oxadiazol-5(4H)-one;

3-(6-{[(1R)-1-cyclobutylethyl]amino}-7-[1-(trans-4-methylcyclohexyl)ethyl]-8-[(3R)-3-methylmorpholin-4-yl]-7H-purin-2-yl)-1,2,4-oxadiazol-5(4H)-one;

5-(6-(5-chloropyridin-3-yl)-7-(1-((trans)-4-methylcyclohexyl)ethyl)-8-((R)-3-phenylmorpholino)-7H-purin-2-yl)-1,3,4-oxadiazol-2(3H)-one;

6-{[(1R)-1-cyclobutylethyl]amino}-7-[(trans-4-ethylcyclohexyl)methyl]-8-(3-methylphenyl)-7H-purine-2-carboxylic acid;

6-{[(1R)-1-cyclobutylethyl]amino}-7-[(trans-4-ethylcyclohexyl)methyl]-8-(2-methoxy-5-methylphenyl)-7H-purine-2-carboxylic acid;

6-{[(1R)-1-cyclobutylethyl]amino}-7-[(trans-4-ethylcyclohexyl)methyl]-8-[4-(1-methylethyl)pyridin-2-yl]-7H-purine-2-carboxylic acid;

6-{[(1R)-1-cyclobutylethyl]amino}-7-[(trans-4-ethylcyclohexyl)methyl]-8-piperidin-1-yl-7H-purine-2-carboxylic acid;

6-{[(1R)-1-cyclobutylethyl]amino}-7-[(trans-4-ethylcyclohexyl)methyl]-8-morpholin-4-yl-7H-purine-2-carboxylic acid;

3-(6-{[(1R)-1-cyclobutylethyl]amino}-7-[(trans-4-ethylcyclohexyl)methyl]-8-[4-(1-methylethyl)pyridin-2-yl]-7H-purin-2-yl)-1,2,4-oxadiazol-5 (4H)-one;

6-{[(1R)-1-cyclobutylethyl]amino}-7-[(trans-4-ethylcyclohexyl)methyl]-8-[(3R)-3-phenylmorpholin-4-yl]-7H-purine-2-carboxylic acid;

3-(6-{[(1R)-1-cyclobutylethyl]amino}-7-[(trans-4-ethylcyclohexyl)methyl]-8-[(3R)-3-phenylmorpholin-4-yl]-7H-purin-2-yl)-1,2,4-oxadiazol-5 (4H)-one;

6-{[(1R)-1-cyclobutylethyl]amino}-7-[(4-ethylcyclohex-1-en-1-yl)methyl]-8-[4-(1-methylethyl)pyridin-2-yl]-7H-purine-2-carboxylic acid;

6-{[(1R)-1-cyclobutylethyl]amino}-7-[(4-ethylcyclohex-3-en-1-yl)methyl]-8-[4-(1-methylethyl)pyridin-2-yl]-7H-purine-2-carboxylic acid;

3-(6-{[(1R)-1-cyclobutylethyl]amino}-7-[(4-ethylcyclohex-3-en-1-yl)methyl]-8-[4-(1-methylethyl)pyridin-2-yl]-7H-purin-2-yl)-1,2,4-oxadiazol-5 (4H)-one;

6-{[(1R)-1-cyclopropylethyl]amino}-8-(3-methylphenyl)-7-{[4-(trifluoromethyl)cyclohexyl]methyl}-7H-purine-2-carboxylic acid;

6-{[(1R)-1-cyclopropylethyl]amino}-8-(3-methylphenyl)-7-{[4-(trifluoromethyl)cyclohexyl]methyl}-7H-purine-2-carboxylic acid;

6-{[(1R)-1-cyclobutylethyl]amino}-8-(3-methylphenyl)-7-{[cis-4-(trifluoromethyl)cyclohexyl]methyl}-7H-purine-2-carboxylic acid;

3-(6-{[(1R)-1-cyclobutylethyl]amino}-8-[4-(1-methylethyl)pyridin-2-yl]-7-{[trans-4-(trifluoromethyl)cyclohexyl]methyl}-7H-purin-2-yl)-1,2,4-oxadiazol-5(4H)-one;

3-(6-{[(1R)-1-cyclobutylethyl]amino}-7-{[trans-3,3-difluoro-4-methylcyclohexyl]methyl}-8-[(3R)-3-methylmorpholin-4-yl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(phenyl sulfanyl)-7H-purin-2-yl]-1,2,4-oxadiazol-5 (4H)-one;

3-[6-{[(1R)-1-cyclobutylethyl]amino}-7-[(trans-4-methylcyclohexyl)methyl]-8-(phenylsulfinyl)-7H-purin-2-yl]-1,2,4-oxadiazol-5(4H)-one;

3-[6-{[(1R)-1-cyclobutylethyl]amino}-7-[(trans-4-methylcyclohexyl)methyl]-8-(phenyl sulfonyl)-7H-purin-2-yl]-1,2,4-oxadiazol-5 (4H)-one;

6-{[(1R)-1-cyclobutylethyl]amino}-7-[(trans-4-methylcyclohexyl)methyl]-8-(1-phenylcyclobutyl)-7H-purine-2-carboxylic acid;

6-{[(1R)-1-cyclobutylethyl]amino}-7-[(trans-4-methylcyclohexyl)methyl]-8-(1-methyl-1-phenylethyl)-7H-purine-2-carboxylic acid;

6-{[(1R)-1-cyclobutylethyl]amino}-8-(1-phenylcyclopropyl)-7-[4-(trifluoromethyl)benzyl]-7H-purine-2-carboxylic acid;

6-{[(1R)-1-cyclobutylethyl]amino}-7-[(trans-4-methylcyclohexyl)methyl]-8-(1-phenylcyclopropyl)-7H-purine-2-carboxylic acid;

3-[6-{[(1R)-1-cyclobutylethyl]amino}-7-[(trans-4-methylcyclohexyl)methyl]-8-(1-phenylcyclopropyl)-7H-purin-2-yl]-1,2,4-oxadiazol-5(4H)-one;

6-{[(1R)-1-cyclobutylethyl]amino}-8-(2,2-dimethylpropyl)-7-[(trans-4-methylcyclohexyl)methyl]-7H-purine-2-carboxylic acid;

3-(6-{[(1R)-1-cyclobutylethyl]amino}-8-(2,2-dimethylpropyl)-7-[(trans-4-methylcyclohexyl)methyl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(1-phenylcyclobutyl)-7H-purin-2-yl]-1,2,4-oxadiazol-5 (4H)-one;

5-[6-{[(1R)-1-cyclobutylethyl]amino}-7-[(trans-4-methylcyclohexyl)methyl]-8-(1-phenylcyclobutyl)-7H-purin-2-yl]-4-methyl-2,4-dihydro-3H-1,2,4-triazol-3-one;

5-[6-{[(1R)-1-cyclobutylethyl]amino}-7-[(trans-4-methylcyclohexyl)methyl]-8-(1-phenylcyclobutyl)-7H-purin-2-yl]-1,3,4-oxadiazol-2(3H)-one;

6-{[(1R)-1-cyclobutylethyl]amino}-8-(2-phenylcyclohexyl)-7-[4-(trifluoromethyl)benzyl]-7H-purine-2-carboxylic acid;

6-{[(1R)-1-cyclobutylethyl]amino}-8-(2-phenylcyclohex-1-en-1-yl)-7-[4-(trifluoromethyl)benzyl]-7H-purine-2-carboxylic acid;

6-{[(1R)-1-cyclobutylethyl]amino}-8-(2-phenylcyclopent-1-en-1-yl)-7-[4-(trifluoromethyl)benzyl]-7H-purine-2-carboxylic acid;

6-{[(1R)-1-cyclobutylethyl]amino}-8-(2-phenylcyclopentyl)-7-[4-(trifluoromethyl)benzyl]-7H-purine-2-carboxylic acid;

6-{[(1R)-1-cyclobutylethyl]amino}-8-(2-phenylcyclopentyl)-7-[4-(trifluoromethyl)benzyl]-7H-purine-2-carboxylic acid;

6-{[(1R)-1-cyclobutylethyl]amino}-8-(4-phenyltetrahydrofuran-3-yl)-7-[4-(trifluoromethyl)benzyl]-7H-purine-2-carboxylic acid;

6-{[(1R)-1-cyclobutylethyl]amino}-8-(4-phenyltetrahydrofuran-3-yl)-7-[4-(trifluoromethyl)benzyl]-7H-purine-2-carboxylic acid;
6-{[(1R)-1-cyclobutylethyl]amino}-8-methyl-7-[(trans-4-methylcyclohexyl)methyl]-7H-purine-2-carboxylic acid;
3-(6-{[(1R)-1-cyclobutylethyl]amino}-8-methyl-7-[(trans-4-methylcyclohexyl)methyl]-7H-purin-2-yl)-1,2,4-oxadiazol-5(4H)-one;
6-{[(1R)-1-cyclobutylethyl]amino}-8-(3-oxo-2-phenylcyclohexyl)-7-[4-(trifluoromethyl)benzyl]-7H-purine-2-carboxylic acid;
6-{[(1R)-1-cyclobutylethyl]amino}-8-(2-phenylcyclohexyl)-7-[4-(trifluoromethyl)benzyl]-7H-purine-2-carboxylic acid;
3-[6-{[(1R)-1-cyclobutylethyl]amino}-7-[(trans-4-methylcyclohexyl)methyl]-8-(1-phenylethenyl)-7H-purin-2-yl]-1,2,4-oxadiazol-5 (4H)-one;
3-[6-{[(1R)-1-cyclobutylethyl]amino}-7-[(trans-4-methylcyclohexyl)methyl]-8-(1-phenylethyl)-7H-purin-2-yl]-1,2,4-oxadiazol-5(4H)-one;
3-[6-{[(1R)-1-cyclobutylethyl]amino}-7-[(trans-4-methylcyclohexyl)methyl]-8-(2-phenylcyclohex-1-en-1-yl)-7H-purin-2-yl]-1,2,4-oxadiazol-5(4H)-one;
6-{[(1R)-1-cyclobutylethyl]amino}-7-[(trans-4-methylcyclohexyl)methyl]-8-(2-phenylcyclohexyl)-7H-purine-2-carboxylic acid;
6-{[(1R)-1-cyclobutylethyl]amino}-7-[(trans-4-methylcyclohexyl)methyl]-8-(2-phenylcyclohex-1-en-1-yl)-7H-purine-2-carboxylic acid;
3-(6-{[(1R)-1-cyclobutylethyl]amino}-8-(1-cyclohexylethenyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-7-[(trans-4-methylcyclohexyl)methyl]-8-[(E)-2-phenylethenyl]-7H-purin-2-yl)-1,2,4-oxadiazol-5 (4H)-one;
3-(6-{[(1R)-1-cyclobutylethyl]amino}-7-[(trans-4-methylcyclohexyl)methyl]-8-[1-(tetrahydro-2H-pyran-4-yl)ethyl]-7H-purin-2-yl)-1,2,4-oxadiazol-5 (4H)-one;
3-(6-{[(1R)-1-cyclobutylethyl]amino}-8-(1-cyclohexylethyl)-7-[(trans-4-methylcyclohexyl)methyl]-7H-purin-2-yl)-1,2,4-oxadiazol-5 (4H)-one;
3-[6-{[(1R)-1-cyclobutylethyl]amino}-7-[(trans-4-methylcyclohexyl)methyl]-8-(2-phenylethyl)-7H-purin-2-yl]-1,2,4-oxadiazol-5(4H)-one;
3-[6-{[(1R)-1-cyclobutylethyl]amino}-7-[(trans-4-methylcyclohexyl)methyl]-8-(2-phenylcyclohexyl)-7H-purin-2-yl]-1,2,4-oxadiazol-5 (4H)-one;
3-(6-{[(1R)-1-cyclobutylethyl]amino}-8-cyclopropyl-7-[(trans-4-methylcyclohexyl)methyl]-7H-purin-2-yl)-1,2,4-oxadiazol-5(4H)-one;
3-[6-{[(1R)-1-cyclobutylethyl]amino}-7-[(trans-4-methylcyclohexyl)methyl]-8-(3-phenyltetrahydro-2H-pyran-4-yl)-7H-purin-2-yl]-1,2,4-oxadiazol-5 (4H)-one;
3-(6-{[(1R)-1-cyclobutylethyl]amino}-8-[1-(4-fluorophenyl)ethenyl]-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-[1-(4-fluorophenyl)ethyl]-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-cyclopent-1-en-1-yl-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-cyclopentyl-7-[(trans-4-methylcyclohexyl)methyl]-7H-purin-2-yl)-1,2,4-oxadiazol-5(4H)-one;
3-(6-{[(1R)-1-cyclobutylethyl]amino}-8-(2,2-dimethylpropanoyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-(1-hydroxy-1,2,2-trimethylpropyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-[1-(2-fluorophenyl)-1-hydroxyethyl]-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-[1-(2-fluorophenyl)cyclopropyl]-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-(1-hydroxy-1-pyridin-2-ylethyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-(1-fluoro-1-pyridin-2-ylethyl)-7-[(trans-4-methylcyclohexyl)methyl]-7H-purin-2-yl)-1,2,4-oxadiazol-5 (4H)-one;
3-[6-{[(1R)-1-cyclobutylethyl]amino}-7-[(trans-4-methylcyclohexyl)methyl]-8-(1-pyridin-2-ylcyclopropyl)-7H-purin-2-yl]-1,2,4-oxadiazol-5 (4H)-one;
3-(6-{[(1R)-1-cyclobutylethyl]amino}-8-(2,2-dimethyl-1-methylidenepropyl)-7-[(trans-4-methylcyclohexyl)methyl]-7H-purin-2-yl)-1,2,4-oxadiazol-5 (4H)-one;
3-[6-{[(1R)-1-cyclobutylethyl]amino}-7-[(trans-4-methylcyclohexyl)methyl]-8-(2,2,2-trifluoro-1-hydroxy-1-methylethyl)-7H-purin-2-yl]-1,2,4-oxadiazol-5 (4H)-one;
3-(6-{[(1R)-1-cyclobutylethyl]amino}-8-(1-hydroxyethyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-(2-hydroxy-2-methylpropyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-(1,2-dihydroxyethyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-[methoxy(phenyl)methyl]-7-[(trans-4-methylcyclohexyl)methyl]-7H-purin-2-yl)-1,2,4-oxadiazol-5 (4H)-one;
3-[6-{[(1R)-1-cyclobutylethyl]amino}-7-[(trans-4-methylcyclohexyl)methyl]-8-(phenylcarbonyl)-7H-purin-2-yl]-1,2,4-oxadiazol-5 (4H)-one;
5-[6-{[(1R)-1-cyclobutylethyl]amino}-7-[(trans-4-methylcyclohexyl)methyl]-8-(phenylcarbonyl)-7H-purin-2-yl]-1,3,4-oxadiazol-2(3H)-one;
3-(6-{[(1R)-1-cyclobutylethyl]amino}-8-(1-hydroxy-1-phenylethyl)-7-[(trans-4-methylcyclohexyl)methyl]-7H-purin-2-yl)-1,2,4-oxadiazol-5 (4H)-one;
3-(6-{[(1R)-1-cyclobutylethyl]amino}-7-[(trans-4-methylcyclohexyl)methyl]-8-[(1RorS)-2,2,2-trifluoro-1-hydroxy-1-phenylethyl]-7H-purin-2-yl)-1,2,4-oxadiazol-5 (4H)-one;
3-(6-(((R)-1-cyclobutylethyl)amino)-7-(((trans)-4-methylcyclohexyl)methyl)-8-(1-(thiazol-4-yl)ethyl)-7H-purin-2-yl)-1,2,4-oxadiazol-5(4H)-one;
3-(6-{[(1R)-1-cyclobutylethyl]amino}-8-[hydroxy(phenyl)methyl]-7-[(trans-4-methylcyclohexyl)methyl]-7H-purin-2-yl)-1,2,4-oxadiazol-5 (4H)-one;
3-(6-{[(1R)-1-cyclobutylethyl]amino}-8-[1-(4-fluorophenyl)cyclopropyl]-7-[(trans-4-methylcyclohexyl)methyl]-7H-purin-2-yl)-1,2,4-oxadiazol-5 (4H)-one;
3-[6-{[(1R)-1-cyclobutylethyl]amino}-7-[(trans-4-methylcyclohexyl)methyl]-8-(tetrahydro-2H-pyran-4-ylcarbonyl)-7H-purin-2-yl]-1,2,4-oxadiazol-5(4H)-one;
3-(8-acetyl-6-{[(1R)-1-cyclobutylethyl]amino}-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-(2,2-dimethyl-1-methylidenepropyl)-7-[(trans-4-methylcyclohexyl)methyl]-7H-purin-2-yl)-4-methyl-1,2,4-oxadiazol-5 (4H)-one;

3-(6-{[(1R)-1-cyclobutylethyl]amino}-8-[hydroxy(tetrahydro-2H-pyran-4-yl)methyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-(3-fluorophenyl)-1-hydroxyethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-hydroxy-1-pyridin-4-ylethyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-hydroxy-1-(tetrahydro-2H-pyran-4-yl)ethyl]-7-[(trans-4-methylcyclohexyl)methyl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(1-pyridin-3-ylcyclopropyl)-7H-purin-2-yl]-1,2,4-oxadiazol-5 (2H)-one;

3-(6-{[(1R)-1-cyclobutylethyl]amino}-8-(1-hydroxy-1-pyridin-3-ylethyl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[cyclopentyl(hydroxy)methyl]-7-[(trans-4-methylcyclohexyl)methyl]-7H-purin-2-yl)-1,2,4-oxadiazol-5 (2H)-one;

3-(6-{[(1R)-1-cyclobutylethyl]amino}-7-[(trans-4-methylcyclohexyl)methyl]-8-[1-(tetrahydro-2H-pyran-4-yl)ethenyl]-7H-purin-2-yl)-1,2,4-oxadiazol-5(4H)-one;

3-(6-{[(1R)-1-cyclobutylethyl]amino}-8-(1-hydroxycyclohexyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-hydroxy-1-methylethyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-hydroxy-2-methylpropyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(2-hydroxycyclohexyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[cyclopentyl(hydroxy)methyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-hydroxy-2-methylpropyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-(3-fluorophenyl)cyclopropyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-hydroxy-1-(1,3-thiazol-4-yl)ethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-hydroxy-1-pyridin-3-ylethyl)-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[1-hydroxy-1-(1,3-thiazol-4-yl)ethyl]-7-[(trans-4-methylcyclohexyl)methyl]-7H-purin-2-yl)-1,2,4-oxadiazol-5 (4H)-one;

3-[6-{[(1R)-1-cyclobutylethyl]amino}-7-[(trans-4-methylcyclohexyl)methyl]-8-(1-pyridin-4-ylcyclopropyl)-7H-purin-2-yl]-1,2,4-oxadiazol-5 (4H)-one;

3-(6-{[(1R)-1-cyclobutylethyl]amino}-7-[(trans-4-methylcyclohexyl)methyl]-8-[1-(1,3-thiazol-4-yl)cyclopropyl]-7H-purin-2-yl)-1,2,4-oxadiazol-5(4H)-one;

3-(6-{[(1R)-1-cyclobutylethyl]amino}-8-[1-hydroxy-1-(1-methyl-1H-pyrazol-3-yl)ethyl]-7-[(trans-4-methylcyclohexyl)methyl]-7H-purin-2-yl)-1,2,4-oxadiazol-5 (2H)-one;

3-(6-{[(1R)-1-cyclobutylethyl]amino}-8-[1-hydroxy-1-(1,3-thiazol-2-yl)ethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[cyclobutyl(hydroxy)methyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-hydroxy-1-(1,3-thiazol-2-yl)ethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[1-(1,3-thiazol-2-yl)cyclopropyl]-7H-purin-2-yl)-1,2,4-oxadiazol-5(4H)-one;

3-(6-{[(1R)-1-cyclobutylethyl]amino}-8-(1,2-dihydroxy-1-phenylethyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-fluoro-1-(2-fluorophenyl)ethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[1-(1-methyl-1H-pyrazol-4-yl)cyclopropyl]-7H-purin-2-yl)-1,2,4-oxadiazol-5 (2H)-one;

3-(6-{[(1R)-1-cyclobutylethyl]amino}-8-(4-hydroxytetrahydro-2H-pyran-4-yl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-fluoro-1-(2-fluorophenyl)ethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[fluoro(phenyl)methyl]-7-[(trans-4-methylcyclohexyl)methyl]-7H-purin-2-yl)-1,2,4-oxadiazol-5 (4H)-one; and 3-(6-{[(1R)-1-cyclobutylethyl]amino}-8-(1-hydroxycyclobutyl)-7-[(trans-4-methylcyclohexyl)methyl]-7H-purin-2-yl)-1,2,4-oxadiazol-5 (2H)-one;

or a stereoisomer thereof;
or a pharmaceutically acceptable salt thereof;
or a pharmaceutically acceptable salt of the stereoisomer thereof.

14. The compound of claim 1 selected from the group consisting of:

5-(6-{[(1R)-1-cyclobutylethyl]amino}-8-(hexahydrocyclopenta[b][1,4]oxazin-4(4aH)-yl)-7-[(trans-4-methylcyclohexyl)methyl]-7H-purin-2-yl)-1,3,4-oxadiazol-2 (3H)-one;

3-(6-{[(1R)-1-cyclobutylethyl]amino}-7-[(trans-4-methylcyclohexyl)methyl]-8-[(3R)-3-pyridin-2-ylmorpholin-4-yl]-7H-purin-2-yl)-1,2,4-oxadiazol-5(4H)-one;

3-(6-{[(1R)-1-cyclobutylethyl]amino}-8-(hexahydro-2H-pyrano[4,3-b]pyridin-1(5H)-yl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[(3R)-3-pyridin-4-ylmorpholin-4-yl]-7H-purin-2-yl)-1,2,4-oxadiazol-5(4H)-one;

3-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[3-(methoxymethyl)morpholin-4-yl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-[2-(trifluoromethyl)-3-azabicyclo[3.1.0]hex-3-yl]-7H-purin-2-yl)-1,2,4-oxadiazol-5(4H)-one;

3-(6-{[(1R)-1-cyclobutylethyl]amino}-7-[(trans-4-methylcyclohexyl)methyl]-8-{2-[(methyl sulfonyl)methyl]pyrrolidin-1-yl}-7H-purin-2-yl)-1,2,4-oxadiazol-5 (4H)-one;

3-(6-{[(1R)-1-cyclobutylethyl]amino}-7-[(trans-4-methylcyclohexyl)methyl]-8-{2-[(methyl sulfinyl)methyl]pyrrolidin-1-yl}-7H-purin-2-yl)-1,2,4-oxadiazol-5 (4H)-one;

5-(6-{[(1R)-1-cyclobutylethyl]amino}-8-[(cis)-2,3-dimethylmorpholin-4-yl]-7-[(trans-4-methylcyclohexyl)methyl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,2,4-oxadiazol-5(4H)-one;

5-(6-{[(1R)-1-cyclobutylethyl]amino}-7-[(trans-4-methylcyclohexyl)methyl]-8-[(cis)-octahydro-4H-1,4-benzoxazin-4-yl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(2S,3R)-2-methyl-3-phenylmorpholin-4-yl]-7H-purin-2-yl)-1,2,4-oxadiazol-5(4H)-one;

5-(6-{[(1R)-1-cyclobutylethyl]amino}-7-[(trans-4-methylcyclohexyl)methyl]-8-[(2S,3R)-2-methyl-3-phenylmorpholin-4-yl]-7H-purin-2-yl)-1,3,4-oxadiazol-2(3H)-one;

3-(6-{[(1R)-1-cyclobutylethyl]amino}-7-[(trans-4-methylcyclohexyl)methyl]-8-[(2R,3R)-2-methyl-3-phenylmorpholin-4-yl]-7H-purin-2-yl)-1,2,4-oxadiazol-5(4H)-one;

5-(6-{[(1R)-1-cyclobutylethyl]amino}-7-[(trans-4-methylcyclohexyl)methyl]-8-[(2R,3R)-2-methyl-3-phenylmorpholin-4-yl]-7H-purin-2-yl)-1,3,4-oxadiazol-2(3H)-one;

5-(6-{[(1R)-1-cyclobutylethyl]amino}-8-[(trans)-2,3-dimethylmorpholin-4-yl]-7-[(trans-4-methylcyclohexyl)methyl]-7H-purin-2-yl)-1,3,4-oxadiazol-2(3H)-one;

5-{6-(3-chlorophenyl)-7-[(trans-4-methylcyclohexyl)methyl]-8-[(3R)-3-(1-methylethyl)morpholin-4-yl]-7H-purin-2-yl}-1,3,4-oxadiazol-2(3H)-one;

5-{6-(3-chlorophenyl)-8-{[(1S)-1-(3-fluorophenyl)propyl]amino}-7-[(trans-4-methylcyclohexyl)methyl]-7H-purin-2-yl}-1,3,4-oxadiazol-2(3H)-one;

3-[6-(3-chlorophenyl)-7-[(trans-4-methylcyclohexyl)methyl]-8-(octahydro-4H-1,4-benzoxazin-4-yl)-7H-purin-2-yl]-1,2,4-oxadiazol-5(4H)-one;

3-[6-(3-chlorophenyl)-7-[(trans-4-methylcyclohexyl)methyl]-8-(7-oxa-4-azaspiro[2.5]oct-4-yl)-7H-purin-2-yl]-1,2,4-oxadiazol-5(4H)-one;

3-[6-(3-chlorophenyl)-7-[(trans-4-methylcyclohexyl)methyl]-8-(8-oxa-5-azaspiro[3.5]non-5-yl)-7H-purin-2-yl]-1,2,4-oxadiazol-5(4H)-one;

3-{6-(3-chlorophenyl)-8-[(4aS,7aS)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

3-{6-(3-chlorophenyl)-8-[(4aR,7aR)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

5-{6-(3-chlorophenyl)-8-[(4aS,7aS)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

5-{6-(3-chlorophenyl)-8-[(4aR,7aR)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

3-{6-(3-chlorophenyl)-8-{[(1R)-2-methoxy-1-phenylethyl]amino}-7-[(trans-4-methylcyclohexyl)methyl]-7H-purin-2-yl}-1,2,4-oxadiazol-5(4H)-one;

3-{6-(5-chloropyridin-3-yl)-8-[(4aS,7aS)-hexahydrocyclopentat[b][1,4]oxazin-4(4aH)-yl]-7-[(trans-4-methylcyclohexyl)methyl]-7H-purin-2-yl}-1,2,4-oxadiazol-5(4H)-one;

3-{6-(5-chloropyridin-3-yl)-8-[(4aR,7aR)-hexahydrocyclopenta[b][1,4]oxazin-4(4aH)-yl]-7-[(trans-4-methylcyclohexyl)methyl]-7H-purin-2-yl}-1,2,4-oxadiazol-5(4H)-one;

5-[6-(3-chlorophenyl)-7-[(trans-4-methylcyclohexyl)methyl]-8-(7-oxa-4-azaspiro[2.5]oct-4-yl)-7H-purin-2-yl]-1,3,4-oxadiazol-2(3H)-one;

5-[6-(3-chlorophenyl)-7-[(trans-4-methylcyclohexyl)methyl]-8-(8-oxa-5-azaspiro[3.5]non-5-yl)-7H-purin-2-yl]-1,3,4-oxadiazol-2(3H)-one;

5-{6-(5-chloropyridin-3-yl)-8-[(4aR,7aR)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

5-{6-(5-chloropyridin-3-yl)-8-[(4aS,7aS)-hexahydrocyclopenta[b][1,4]oxazin-4(4aH)-yl]-7-[(trans-4-methylcyclohexyl)methyl]-7H-purin-2-yl}-1,3,4-oxadiazol-2(3H)-one;

3-{6-(5-chloropyridin-3-yl)-8-[(3R)-3-(2-fluorophenyl)morpholin-4-yl]-7-[(trans-4-methylcyclohexyl)methyl]-7H-purin-2-yl}-1,2,4-oxadiazol-5(4H)-one;

3-{6-(5-chloropyridin-3-yl)-8-[(3R)-3-(4-fluorophenyl)morpholin-4-yl]-7-[(trans-4-methylcyclohexyl)methyl]-7H-purin-2-yl}-1,2,4-oxadiazol-5(4H)-one;

5-{6-(5-chloropyridin-3-yl)-8-[(3R)-3-(4-fluorophenyl)morpholin-4-yl]-7-[(trans-4-methylcyclohexyl)methyl]-7H-purin-2-yl}-1,3,4-oxadiazol-2(3H)-one;

5-{6-(5-chloropyridin-3-yl)-8-[(3R)-3-(2-fluorophenyl)morpholin-4-yl]-7-[(trans-4-methylcyclohexyl)methyl]-7H-purin-2-yl}-1,3,4-oxadiazol-2(3H)-one;

3-{6-(3-chlorophenyl)-7-[(trans-4-methylcyclohexyl)methyl]-8-[(3R)-3-pyridin-4-ylmorpholin-4-yl]-7H-purin-2-yl}-1,2,4-oxadiazol-5(4H)-one;

5-{6-(3-chlorophenyl)-7-[(trans-4-methylcyclohexyl)methyl]-8-[(3R)-3-pyridin-4-ylmorpholin-4-yl]-7H-purin-2-yl}-1,3,4-oxadiazol-2(3H)-one;

3-{6-(3-chlorophenyl)-7-[(trans-4-methylcyclohexyl)methyl]-8-[(3R)-3-pyridin-2-ylmorpholin-4-yl]-7H-purin-2-yl}-1,2,4-oxadiazol-5(4H)-one;

5-{6-(3-chlorophenyl)-7-[(trans-4-methylcyclohexyl)methyl]-8-[(3R)-3-pyridin-2-ylmorpholin-4-yl]-7H-purin-2-yl}-1,3,4-oxadiazol-2(3H)-one;

3-{6-(3-chlorophenyl)-8-[(cis)-2,3-dimethylmorpholin-4-yl]-7-[(trans-4-methylcyclohexyl)methyl]-7H-purin-2-yl}-1,2,4-oxadiazol-5(4H)-one;

5-{6-(3-chlorophenyl)-8-[(cis)-2,3-dimethylmorpholin-4-yl]-7-[(trans-4-methylcyclohexyl)methyl]-7H-purin-2-yl}-1,3,4-oxadiazol-2(3H)-one;

3-{6-(3-chlorophenyl)-8-[(trans)-2,3-dimethylmorpholin-4-yl]-7-[(trans-4-methylcyclohexyl)methyl]-7H-purin-2-yl}-1,2,4-oxadiazol-5(4H)-one;

5-{6-(5-chloropyridin-3-yl)-8-[(2S,3R)-2,3-dimethylmorpholin-4-yl]-7-[(trans-4-methylcyclohexyl)methyl]-7H-purin-2-yl}-1,3,4-oxadiazol-2(3H)-one;

5-{6-(5-chloropyridin-3-yl)-8-[(2S)-2-(fluoromethyl)pyrrolidin-1-yl]-7-[(trans-4-methylcyclohexyl)methyl]-7H-purin-2-yl}-1,3,4-oxadiazol-2(3H)-one;

5-{6-(5-chloropyridin-3-yl)-8-[(3R,5R)-3,5-dimethylmorpholin-4-yl]-7-[(trans-4-methylcyclohexyl)methyl]-7H-purin-2-yl}-1,3,4-oxadiazol-2(3H)-one;

5-{6-(5-chloropyridin-3-yl)-7-[(trans-4-methylcyclohexyl)methyl]-8-[(2S)-2-(trifluoromethyl)pyrrolidin-1-yl]-7H-purin-2-yl}-1,3,4-oxadiazol-2(3H)-one;

3-{6-(2,6-dichloropyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloro-2-fluoropyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(2-chloro-6-methoxypyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(2-chloropyridin-4-yl)-7-[(trans-4-methylcyclohexyl)methyl]-8-[(3R)-3-phenylmorpholin-4-yl]-7H-purin-2-yl}-1,2,4-oxadiazol-5(4H)-one;

3-{6-[3-chloro-5-(methylsulfonyl)phenyl]-7-[(trans-4-methylcyclohexyl)methyl]-8-[(3R)-3-phenylmorpholin-4-yl]-7H-purin-2-yl}-1,2,4-oxadiazol-5(4H)-one;
3-{7-[(trans-4-methylcyclohexyl)methyl]-6-[3-(5-methyl-1,2,4-oxadiazol-3-yl)phenyl]-8-[(3R)-3-phenylmorpholin-4-yl]-7H-purin-2-yl}-1,2,4-oxadiazol-5(4H)-one;
3-{6-(3-chloro-5-pyrrolidin-1-ylphenyl)-7-[(trans-4-methylcyclohexyl)methyl]-8-[(3R)-3-phenylmorpholin-4-yl]-7H-purin-2-yl}-1,2,4-oxadiazol-5(4H)-one;
3-{6-(3-chloro-5-methylphenyl)-7-[(trans-4-methylcyclohexyl)methyl]-8-[(3R)-3-phenylmorpholin-4-yl]-7H-purin-2-yl}-1,2,4-oxadiazol-5(4H)-one;
3-{7-[(trans-4-methylcyclohexyl)methyl]-6-(5-methylpyridin-3-yl)-8-[(3R)-3-phenylmorpholin-4-yl]-7H-purin-2-yl}-1,2,4-oxadiazol-5(4H)-one;
3-{6-(3-chlorophenyl)-7-[(trans-4-methylcyclohexyl)methyl]-8-[(3 S)-3-(3-methyl-1,2,4-oxadiazol-5-yl)morpholin-4-yl]-7H-purin-2-yl}-1,2,4-oxadiazol-5(4H)-one;
(3 S)-4-[6-(3-chlorophenyl)-7-[(trans-4-methylcyclohexyl)methyl]-2-(5-oxo-4, 5-dihydro-1,2,4-oxadiazol-3-yl)-7H-purin-8-yl]morpholine-3-carboxamide;
3-{6-(3-chlorophenyl)-8-(hexahydro-2H-pyrano[4,3-b]pyridin-1(5H)-yl)-7-[(trans-4-methylcyclohexyl)methyl]-7H-purin-2-yl}-1,2,4-oxadiazol-5(4H)-one;
3-{6-(3-chlorophenyl)-7-[(trans-4-methylcyclohexyl)methyl]-8-[(3 S)-3-(4-methyl-1,3-thiazol-2-yl)morpholin-4-yl]-7H-purin-2-yl}-1,2,4-oxadiazol-5(4H)-one;
5-{6-(3-chlorophenyl)-7-[(trans-4-methylcyclohexyl)methyl]-8-[(3 S)-3-(3-methyl-1,2,4-oxadiazol-5-yl)morpholin-4-yl]-7H-purin-2-yl}-1,3,4-oxadiazol-2(3H)-one;
5-{6-(5-chloropyridin-3-yl)-8-(hexahydro-2H-pyrano[4,3-b]pyridin-1(5H)-yl)-7-[(trans-4-methylcyclohexyl)methyl]-7H-purin-2-yl}-1,3,4-oxadiazol-2(3H)-one;
5-{6-(3-chlorophenyl)-8-(hexahydro-2H-pyrano[4,3-b]pyridin-1 (5H)-yl)-7-[(trans-4-methylcyclohexyl)methyl]-7H-purin-2-yl}-1,3,4-oxadiazol-2(3H)-one;
3-{6-(3-chlorophenyl)-7-[(trans-4-methylcyclohexyl)methyl]-8-[(2S,3R)-2-methyl-3-phenylmorpholin-4-yl]-7H-purin-2-yl}-1,2,4-oxadiazol-5(4H)-one;
3-{6-(3-chlorophenyl)-7-[(trans-4-methylcyclohexyl)methyl]-8-[(2R,3R)-2-methyl-3-phenylmorpholin-4-yl]-7H-purin-2-yl}-1,2,4-oxadiazol-5(4H)-one;
5-{6-(5-chloropyridin-3-yl)-7-[(trans-4-methylcyclohexyl)methyl]-8-[(cis)-octahydro-4H-1,4-benzoxazin-4-yl]-7H-purin-2-yl}-1,3,4-oxadiazol-2(3H)-one;
3-{6-(5-chloropyridin-3-yl)-7-[(trans-4-methylcyclohexyl)methyl]-8-[(2S,3R)-2-methyl-3-phenylmorpholin-4-yl]-7H-purin-2-yl}-1,2,4-oxadiazol-5(4H)-one;
5-{6-(5-chloropyridin-3-yl)-7-[(trans-4-methylcyclohexyl)methyl]-8-[(2S,3R)-2-methyl-3-phenylmorpholin-4-yl]-7H-purin-2-yl}-1,3,4-oxadiazol-2(3H)-one;
3-{6-(5-chloropyridin-3-yl)-7-[(trans-4-methylcyclohexyl)methyl]-8-[(cis)-octahydro-4H-1,4-benzoxazin-4-yl]-7H-purin-2-yl}-1,2,4-oxadiazol-5 (4H)-one;
5-{6-(3-chlorophenyl)-7-[(trans-4-methylcyclohexyl)methyl]-8-[(2S,3R)-2-methyl-3-phenylmorpholin-4-yl]-7H-purin-2-yl}-1,3,4-oxadiazol-2(3H)-one;
5-{6-(5-chloropyridin-3-yl)-7-[(trans-4-methylcyclohexyl)methyl]-8-[(2R,3R)-2-methyl-3-phenylmorpholin-4-yl]-7H-purin-2-yl}-1,3,4-oxadiazol-2(3H)-one;
5-{6-(3-chlorophenyl)-8-[(trans)-2,3-dimethylmorpholin-4-yl]-7-[(trans-4-methylcyclohexyl)methyl]-7H-purin-2-yl}-1,3,4-oxadiazol-2(3H)-one;
3-{6-(5-chloropyridin-3-yl)-7-[(trans-4-methylcyclohexyl)methyl]-8-[(2R,3R)-2-methyl-3-phenylmorpholin-4-yl]-7H-purin-2-yl}-1,2,4-oxadiazol-5(4H)-one;
3-{6-(5-chloropyridin-3-yl)-8-[(2R,3R)-2,3-dimethylmorpholin-4-yl]-7-[(trans-4-methylcyclohexyl)methyl]-7H-purin-2-yl}-1,2,4-oxadiazol-5(4H)-one;
3-{6-(3-chlorophenyl)-8-[(3 S)-3-(fluoromethyl)morpholin-4-yl]-7-[(trans-4-methylcyclohexyl)methyl]-7H-purin-2-yl}-1,2,4-oxadiazol-5(4H)-one;
3-{6-(3-chlorophenyl)-7-[(trans-4-methylcyclohexyl)methyl]-8-[(3 S)-3-(5-methyl-1,3,4-oxadiazol-2-yl)morpholin-4-yl]-7H-purin-2-yl}-1,2,4-oxadiazol-5(4H)-one;
5-{6-(5-chloropyridin-3-yl)-8-[(3 S)-3-(fluoromethyl)morpholin-4-yl]-7-[(trans-4-methylcyclohexyl)methyl]-7H-purin-2-yl}-1,3,4-oxadiazol-2(3H)-one;
5-{6-(5-chloropyridin-3-yl)-8-[(2R,3R)-2,3-dimethylmorpholin-4-yl]-7-[(trans-4-methylcyclohexyl)methyl]-7H-purin-2-yl}-1,3,4-oxadiazol-2(3H)-one;
3-{6-(5-chloropyridin-3-yl)-7-[(trans-4-methylcyclohexyl)methyl]-8-[2-(5-methyl-1,3,4-oxadiazol-2-yl)pyrrolidin-1-yl]-7H-purin-2-yl}-1,2,4-oxadiazol-5(4H)-one;
5-{6-(3-chlorophenyl)-7-[(trans-4-methylcyclohexyl)methyl]-8-[(2R,3R)-2-methyl-3-phenylmorpholin-4-yl]-7H-purin-2-yl}-1,3,4-oxadiazol-2(3H)-one;
3-{6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purin-2-yl}-1,2,4-oxadiazol-5(4H)-one;
3-[6-(5-chloropyridin-3-yl)-7-[(trans-4-methylcyclohexyl)methyl]-8-(8-oxa-5-azaspiro[3.5]non-5-yl)-7H-purin-2-yl]-1,2,4-oxadiazol-5(4H)-one;
6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purine-2-carboxylic acid;
5-{6-(5-chloropyridin-3-yl)-7-[(trans-4-methylcyclohexyl)methyl]-8-[2-(3-methyl-1,2,4-oxadiazol-5-yl)pyrrolidin-1-yl]-7H-purin-2-yl}-1,3,4-oxadiazol-2(3H)-one;
5-{6-(3-chlorophenyl)-8-[(3R,5R)-3,5-dimethylmorpholin-4-yl]-7-[(trans-4-methylcyclohexyl)methyl]-7H-purin-2-yl}-1,3,4-oxadiazol-2(3H)-one;
1-[6-(3-chlorophenyl)-7-[(trans-4-methylcyclohexyl)methyl]-2-(5-oxo-4, 5-dihydro-1,2,4-oxadiazol-3-yl)-7H-purin-8-yl]-N,N-dimethyl-L-prolinamide;
3-{8-[(2S,5 S)-2,5-bis(methoxymethyl)pyrrolidin-1-yl]-6-(3-chlorophenyl)-7-[(trans-4-methylcyclohexyl)methyl]-7H-purin-2-yl}-1,2,4-oxadiazol-5(4H)-one;
3-{6-(3-chlorophenyl)-8-(hexahydro-4H-furo[3,2-b]pyrrol-4-yl)-7-[(trans-4-methylcyclohexyl)methyl]-7H-purin-2-yl}-1,2,4-oxadiazol-5(4H)-one;
3-{6-(5-chloropyridin-3-yl)-7-[(trans-4-methylcyclohexyl)methyl]-8-[(trans)-3-methylhexahydrocyclopenta[b][1,4]oxazin-4(4aH)-yl]-7H-purin-2-yl}-1,2,4-oxadiazol-5(4H)-one;
3-{6-(5-chloropyridin-3-yl)-8-[(2R,3R)-3-ethyl-2-methylmorpholin-4-yl]-7-[(trans-4-methylcyclohexyl)methyl]-7H-purin-2-yl}-1,2,4-oxadiazol-5(4H)-one;
5-{6-(5-chloropyridin-3-yl)-8-[(2R,3R)-3-ethyl-2-methylmorpholin-4-yl]-7-[(trans-4-methylcyclohexyl)methyl]-7H-purin-2-yl}-1,3,4-oxadiazol-2(3H)-one;
5-{6-(5-chloropyridin-3-yl)-8-[(cis)-4-methoxy-2-methylpiperidin-1-yl]-7-[(trans-4-methylcyclohexyl)methyl]-7H-purin-2-yl}-1,3,4-oxadiazol-2(3H)-one;
5-{6-(5-chloropyridin-3-yl)-8-[(trans)-4-methoxy-2-methylpiperidin-1-yl]-7-[(trans-4-methylcyclohexyl)methyl]-7H-purin-2-yl}-1,3,4-oxadiazol-2(3H)-one;
3-{6-(5-chloro-2-methoxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;
5-{6-(5-chloro-2-methoxypyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;
3-{6-(5-chloro-2-methylpyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(5-chloro-2-methylpyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-[3-chloro-5-(2-methoxyethoxy)phenyl]-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5 (4H)-one;

3-{6-[2-(benzyloxy)-5-chloropyridin-3-yl]-7-[(trans-4-methylcyclohexyl)methyl]-8-[(3R)-3-phenylmorpholin-4-yl]-7H-purin-2-yl}-1,2,4-oxadiazol-5(4H)-one;

3-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(5-chloro-2-hydroxypyridin-3-yl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(5-chloro-2-methylpyridin-3-yl)-8-[(trans)-hexahydrocyclopenta[b][1,4]oxazin-4(4aH)-yl]-7-[(trans-4-methylcyclohexyl)methyl]-7H-purin-2-yl}-1,2,4-oxadiazol-5 (4H)-one;

3-{6-cyclohexyl-7-[(trans-4-methylcyclohexyl)methyl]-8-[(3R)-3-phenylmorpholin-4-yl]-7H-purin-2-yl}-1,2,4-oxadiazol-5(4H)-one;

5-{6-cyclohexyl-7-[(trans-4-methylcyclohexyl)methyl]-8-[(3R)-3-phenylmorpholin-4-yl]-7H-purin-2-yl}-1,3,4-oxadiazol-2(3H)-one;

3-{7-[(trans-4-methylcyclohexyl)methyl]-8-[(3R)-3-phenylmorpholin-4-yl]-6-(tetrahydro-2H-pyran-4-yl)-7H-purin-2-yl}-1,2,4-oxadiazol-5 (4H)-one;

5-{7-[(trans-4-methylcyclohexyl)methyl]-8-[(3R)-3-phenylmorpholin-4-yl]-6-(tetrahydro-2H-pyran-4-yl)-7H-purin-2-yl}-1,3,4-oxadiazol-2(3H)-one;

3-{6-(3-methylcyclohexyl)-7-[(trans-4-methylcyclohexyl)methyl]-8-[(3R)-3-phenylmorpholin-4-yl]-7H-purin-2-yl}-1,2,4-oxadiazol-5(4H)-one;

5-{6-(3-methylcyclohexyl)-7-[(trans-4-methylcyclohexyl)methyl]-8-[(3R)-3-phenylmorpholin-4-yl]-7H-purin-2-yl}-1,3,4-oxadiazol-2(3H)-one;

3-{6-(3-chlorophenyl)-7-[1-(trans-4-methylcyclohexyl)ethyl]-8-[(3R)-3-methylmorpholin-4-yl]-7H-purin-2-yl}-1,2,4-oxadiazol-5 (4H)-one;

5-{6-(3-chlorophenyl)-7-[1-(trans-4-methylcyclohexyl)ethyl]-8-[(3R)-3-methylmorpholin-4-yl]-7H-purin-2-yl}-1,3,4-oxadiazol-2(3H)-one;

3-{6-(3-chlorophenyl)-8-(hexahydrocyclopentaa[b][1,4]oxazin-4(4aH)-yl)-7-[1-(trans-4-methylcyclohexyl)ethyl]-7H-purin-2-yl}-1,2,4-oxadiazol-5(4H)-one;

3-(6-{[(1R)-1-cyclobutylethyl]amino}-8-(hexahydrocyclopenta[b][1,4]oxazin-4(4aH)-yl)-7-[1-(trans-4-methylcyclohexyl)ethyl]-7H-purin-2-yl)-1,2,4-oxadiazol-5 (4H)-one;

5-{6-(3-chlorophenyl)-8-(hexahydrocyclopenta[b][1,4]oxazin-4(4aH)-yl)-7-[1-(trans-4-methylcyclohexyl)ethyl]-7H-purin-2-yl}-1,3,4-oxadiazol-2(3H)-one;

5-(6-{[(1R)-1-cyclobutylethyl]amino}-8-(hexahydrocyclopentta[b][1,4]oxazin-4(4aH)-yl)-7-[1-(trans-4-methylcyclohexyl)ethyl]-7H-purin-2-yl)-1,3,4-oxadiazol-2(3H)-one;

3-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,2,4-oxadiazol-5(4H)-one;

5-{6-(5-chloropyridin-3-yl)-8-[(2S)-2-(fluoromethyl)pyrrolidin-1-yl]-7-[1-(trans-4-methylcyclohexyl)ethyl]-7H-purin-2-yl}-1,3,4-oxadiazol-2(3H)-one;

3-{6-(5-chloropyridin-3-yl)-7-[1-(trans-4-methylcyclohexyl)ethyl]-8-[(2S)-2-(trifluoromethyl)pyrrolidin-1-yl]-7H-purin-2-yl}-1,2,4-oxadiazol-5(4H)-one;

3-{6-(3-chlorophenyl)-8-[(3R)-3-ethylmorpholin-4-yl]-7-[1-(trans-4-methylcyclohexyl)ethyl]-7H-purin-2-yl}-1,2,4-oxadiazol-5 (4H)-one;

3-{6-(5-chloropyridin-3-yl)-8-(hexahydrocyclopenta[b][1,4]oxazin-4(4aH)-yl)-7-[1-(trans-4-methylcyclohexyl)ethyl]-7H-purin-2-yl}-1,2,4-oxadiazol-5(4H)-one;

5-{6-(5-chloropyridin-3-yl)-8-(cyclopentylsulfanyl)-7-[(trans-4-methylcyclohexyl)methyl]-7H-purin-2-yl}-1,3,4-oxadiazol-2(3H)-one;

5-{6-(5-chloropyridin-3-yl)-8-(cyclopentylsulfonyl)-7-[(trans-4-methylcyclohexyl)methyl]-7H-purin-2-yl}-1,3,4-oxadiazol-2(3H)-one;

5-[6-(5-chloropyridin-3-yl)-7-[(trans-4-methylcyclohexyl)methyl]-8-(phenylsulfanyl)-7H-purin-2-yl]-1,3,4-oxadiazol-2(3H)-one;

3-[6-(5-chloropyridin-3-yl)-7-[(trans-4-methylcyclohexyl)methyl]-8-(1-phenylcyclobutyl)-7H-purin-2-yl]-1,2,4-oxadiazol-5 (4H)-one;

5-[6-(5-chloropyridin-3-yl)-7-[(trans-4-methylcyclohexyl)methyl]-8-(1-phenylcyclobutyl)-7H-purin-2-yl]-1,3,4-oxadiazol-2(3H)-one;

5-[6-(5-chloro-1-oxidopyridin-3-yl)-7-[(trans-4-methylcyclohexyl)methyl]-8-(1-phenylcyclobutyl)-7H-purin-2-yl]-1,3,4-oxadiazol-2(3H)-one;

3-[6-(5-chloro-2-methoxypyridin-3-yl)-7-[(trans-4-methylcyclohexyl)methyl]-8-(1-phenylcyclobutyl)-7H-purin-2-yl]-1,2,4-oxadiazol-5 (4H)-one;

3-(6-{[(1R)-1-cyclobutylethyl]amino}-8-[1-(2-fluorophenyl)ethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-cyclohex-1-en-1-yl-7-[(trans-4-methylcyclohexyl)methyl]-7H-purin-2-yl)-1,2,4-oxadiazol-5 (4H)-one;

6-{[(1R)-1-cyclobutylethyl]amino}-8-cyclohexyl-7-[(trans-4-methylcyclohexyl)methyl]-7H-purine-2-carboxylic acid;

3-(6-{[(1R)-1-cyclobutylethyl]amino}-8-cyclohexyl-7-[(trans-4-methylcyclohexyl)methyl]-7H-purin-2-yl)-1,2,4-oxadiazol-5(4H)-one;

5-(6-{[(1R)-1-cyclobutylethyl]amino}-8-cyclohexyl-7-[(trans-4-methylcyclohexyl)methyl]-7H-purin-2-yl)-1,3,4-oxadiazol-2(3H)-one;

3-(6-{[(1R)-1-cyclobutylethyl]amino}-8-[(1R or S)-2-methoxy-1-phenylethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-fluorocyclobutyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-methoxycyclobutyl)-7-[(trans-4-methylcyclohexyl)methyl]-7H-purin-2-yl)-1,2,4-oxadiazol-5 (4H)-one;

3-(8-cyclobutyl-6-{[(1R)-1-cyclobutylethyl]amino}-7-[(trans-4-methylcyclohexyl)methyl]-7H-purin-2-yl)-1,2,4-oxadiazol-5(4H)-one;

3-[6-{[(1R)-1-cyclobutylethyl]amino}-7-[(trans-4-methylcyclohexyl)methyl]-8-(1-pyridin-2-ylethyl)-7H-purin-2-yl]-1,2,4-oxadiazol-5 (4H)-one;

3-(6-{[(1R)-1-cyclobutylethyl]amino}-8-[1-(2,5-dimethyl-1,3-thiazol-4-yl)cyclopropyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[1-(2,5-dimethyl-1,3-thiazol-4-yl)-1-fluoroethyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-[methoxy(1,3-thiazol-4-yl)methyl]-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-ethoxycyclobutyl)-7-[(trans-4-methylcyclohexyl)methyl]-7H-purin-2-yl)-1,2,4-oxadiazol-5 (4H)-one;

3-(6-{[(1R)-1-cyclobutylethyl]amino}-8-(1-fluoro-1-phenylethyl)-7-[(trans-4-methylcyclohexyl)methyl]-7H-purin-2-yl]-1,2,4-oxadiazol-5 (4H)-one;
3-(6-{[(1R)-1-cyclobutylethyl]amino}-8-[difluoro(phenyl)methyl]-7-[(trans-4-methylcyclohexyl)methyl]-7H-purin-2-yl]-1,2,4-oxadiazol-5 (4H)-one;
3-(6-{[(1R)-1-cyclobutylethyl]amino}-8-(1,3-dihydro-2-benzofuran-1-yl)-7-[(trans-4-methylcyclohexyl)methyl]-7H-purin-2-yl]-1,2,4-oxadiazol-5 (4H)-one;
3-[6-{[(1R)-1-cyclobutylethyl]amino}-7-[(trans-4-methylcyclohexyl)methyl]-8-(2-phenyloxetan-2-yl)-7H-purin-2-yl]-1,2,4-oxadiazol-5(4H)-one;
3-(6-{[(1R)-1-cyclobutylethyl]amino}-8-[1-(hydroxymethyl)propyl]-7-[(trans-4-methylcyclohexyl)methyl]-7H-purin-2-yl]-1,2,4-oxadiazol-5 (4H)-one;
5-{6-(3-chlorophenyl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one;
3-{6-(3-chlorophenyl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one;
3-[6-(3-chlorophenyl)-7-[(trans-4-methylcyclohexyl)methyl]-8-(tetrahydro-2H-pyran-4-ylcarbonyl)-7H-purin-2-yl]-1,2,4-oxadiazol-5 (4H)-one;
3-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,2,4-oxadiazol-5(4H)-one;
3-{6-(3-chlorophenyl)-8-[cyclohexyl(hydroxy)methyl]-7-[(trans-4-methylcyclohexyl)methyl]-7H-purin-2-yl}-1,2,4-oxadiazol-5 (4H)-one;
3-{6-(3-chlorophenyl)-8-(cyclohexylcarbonyl)-7-[(trans-4-methylcyclohexyl)methyl]-7H-purin-2-yl}-1,2,4-oxadiazol-5(4H)-one;
5-{6-(3-chlorophenyl)-8-[cyclohexyl(hydroxy)methyl]-7-[(trans-4-methylcyclohexyl)methyl]-7H-purin-2-yl}-1,3,4-oxadiazol-2(3H)-one;
5-{6-(3-chlorophenyl)-8-(cyclohexylcarbonyl)-7-[(trans-4-methylcyclohexyl)methyl]-7H-purin-2-yl}-1,3,4-oxadiazol-2(3H)-one;
5-[6-(3-chlorophenyl)-7-[(trans-4-methylcyclohexyl)methyl]-8-(tetrahydro-2H-pyran-4-ylcarbonyl)-7H-purin-2-yl]-1,3,4-oxadiazol-2(3H)-one;
3-{6-(3-chlorophenyl)-8-(1-cyclohexyl-1-hydroxyethyl)-7-[(trans-4-methylcyclohexyl)methyl]-7H-purin-2-yl}-1,2,4-oxadiazol-5 (4H)-one;
5-{6-(3-chlorophenyl)-8-(1-cyclohexyl-1-hydroxyethyl)-7-[(trans-4-methylcyclohexyl)methyl]-7H-purin-2-yl}-1,3,4-oxadiazol-2(3H)-one;
3-{6-(3-chlorophenyl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one;
5-{6-(3-chlorophenyl)-8-[1-hydroxy-1-(tetrahydro-2H-pyran-4-yl)ethyl]-7-[(trans-4-methylcyclohexyl)methyl]-7H-purin-2-yl}-1,3,4-oxadiazol-2(3H)-one;
3-{6-(3-chlorophenyl)-8-[cyclohexyl(methoxy)methyl]-7-[(trans-4-methylcyclohexyl)methyl]-7H-purin-2-yl}-1,2,4-oxadiazol-5 (4H)-one;
5-{6-(3-chlorophenyl)-8-[cyclohexyl(methoxy)methyl]-7-[(trans-4-methylcyclohexyl)methyl]-7H-purin-2-yl}-1,3,4-oxadiazol-2(3H)-one;
5-{6-(3-chlorophenyl)-8-[methoxy(tetrahydro-2H-pyran-4-yl)methyl]-7-[(trans-4-methylcyclohexyl)methyl]-7H-purin-2-yl}-1,3,4-oxadiazol-2(3H)-one;
3-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,2,4-oxadiazol-5(4H)-one;
3-{6-(5-chloropyridin-3-yl)-8-[methoxy(tetrahydro-2H-pyran-4-yl)methyl]-7-[(trans-4-methylcyclohexyl)methyl]-7H-purin-2-yl}-1,2,4-oxadiazol-5(4H)-one;
5-{6-(5-chloropyridin-3-yl)-8-[hydroxy(tetrahydro-2H-pyran-4-yl)methyl]-7-[(trans-4-methylcyclohexyl)methyl]-7H-purin-2-yl}-1,3,4-oxadiazol-2(3H)-one;
5-{6-(5-chloropyridin-3-yl)-8-[methoxy(tetrahydro-2H-pyran-4-yl)methyl]-7-[(trans-4-methylcyclohexyl)methyl]-7H-purin-2-yl}-1,3,4-oxadiazol-2(3H)-one;
3-{6-(5-chloropyridin-3-yl)-8-[cyclohexyl(methoxy)methyl]-7-[(trans-4-methylcyclohexyl)methyl]-7H-purin-2-yl}-1,2,4-oxadiazol-5(4H)-one;
5-{6-(5-chloropyridin-3-yl)-8-[cyclohexyl(methoxy)methyl]-7-[(trans-4-methylcyclohexyl)methyl]-7H-purin-2-yl}-1,3,4-oxadiazol-2(3H)-one;
5-{6-(5-chloropyridin-3-yl)-8-[cyclopentyl(methoxy)methyl]-7-[(trans-4-methylcyclohexyl)methyl]-7H-purin-2-yl}-1,3,4-oxadiazol-2(3H)-one;
5-{6-(5-chloropyridin-3-yl)-8-[1-fluoro-1-(2-methoxyphenyl)ethyl]-7-[(trans-4-methylcyclohexyl)methyl]-7H-purin-2-yl}-1,3,4-oxadiazol-2(3H)-one;
3-{6-(5-chloropyridin-3-yl)-8-[1-fluoro-1-(2-methoxyphenyl)ethyl]-7-[(trans-4-methylcyclohexyl)methyl]-7H-purin-2-yl}-1,2,4-oxadiazol-5(4H)-one;
3-{6-(5-chloropyridin-3-yl)-8-(3-fluorooxetan-3-yl)-7-[(trans-4-methylcyclohexyl)methyl]-7H-purin-2-yl}-1,2,4-oxadiazol-5(4H)-one;
3-{6-(3-chlorophenyl)-8-[cyclohexyl(fluoro)methyl]-7-[(trans-4-methylcyclohexyl)methyl]-7H-purin-2-yl}-1,2,4-oxadiazol-5(4H)-one;
3-{6-(3-chlorophenyl)-8-(1-fluoro-1-pyridin-2-ylethyl)-7-[(trans-4-methylcyclohexyl)methyl]-7H-purin-2-yl}-1,2,4-oxadiazol-5 (4H)-one;
5-{6-(5-chloropyridin-3-yl)-8-[1-fluoro-1-(2-fluorophenyl)ethyl]-7-[(trans-4-methylcyclohexyl)methyl]-7H-purin-2-yl}-1,3,4-oxadiazol-2(3H)-one;
3-{6-(5-chloropyridin-3-yl)-8-[1-fluoro-1-(2-fluorophenyl)ethyl]-7-[(trans-4-methylcyclohexyl)methyl]-7H-purin-2-yl}-1,2,4-oxadiazol-5(4H)-one;
5-{6-(3-chlorophenyl)-8-[1-fluoro-1-(pyridin-2-yl)ethyl]-7-[(trans-4-methylcyclohexyl)methyl]-7H-purin-2-yl}-1,3,4-oxadiazol-2(3H)-one;
5-{6-(5-chloropyridin-3-yl)-8-(1-fluorocyclobutyl)-7-[(trans-4-methylcyclohexyl)methyl]-7H-purin-2-yl}-1,3,4-oxadiazol-2(3H)-one;
3-{6-(5-chloropyridin-3-yl)-8-(1-fluorocyclohexyl)-7-[(trans-4-methylcyclohexyl)methyl]-7H-purin-2-yl}-1,2,4-oxadiazol-5(4H)-one;
5-{6-(5-chloropyridin-3-yl)-8-(1-fluorocyclopentyl)-7-[(trans-4-methylcyclohexyl)methyl]-7H-purin-2-yl}-1,3,4-oxadiazol-2(3H)-one;
3-{6-(3-chlorophenyl)-8-[hydroxy(phenyl)methyl]-7-[(trans-4-methylcyclohexyl)methyl]-7H-purin-2-yl}-1,2,4-oxadiazol-5(4H)-one;
3-[6-(3-chlorophenyl)-7-[(trans-4-methylcyclohexyl)methyl]-8-(phenylcarbonyl)-7H-purin-2-yl]-1,2,4-oxadiazol-5(4H)-one;
3-{6-(3-chlorophenyl)-8-[methoxy(phenyl)methyl]-7-[(trans-4-methylcyclohexyl)methyl]-7H-purin-2-yl}-1,2,4-oxadiazol-5(4H)-one;
3-{6-(3-chlorophenyl)-8-[methoxy(pyridin-2-yl)methyl]-7-[(trans-4-methylcyclohexyl)methyl]-7H-purin-2-yl}-1,2,4-oxadiazol-5(4H)-one;
3-{6-(5-chloropyridin-3-yl)-8-[methoxy(phenyl)methyl]-7-[(trans-4-methylcyclohexyl)methyl]-7H-purin-2-yl}-1,2,4-oxadiazol-5(4H)-one;
3-{6-(5-chloropyridin-3-yl)-8-[1-(2-fluorophenyl)-1-methoxyethyl]-7-[(trans-4-methylcyclohexyl)methyl]-7H-purin-2-yl}-1,2,4-oxadiazol-5(4H)-one;
5-{6-(5-chloropyridin-3-yl)-8-[1-methoxy-1-(2-methyl-1,3-thiazol-4-yl)ethyl]-7-[(trans-4-methylcyclohexyl)methyl]-7H-purin-2-yl}-1,3,4-oxadiazol-2(3H)-one;
3-{6-(3-chlorophenyl)-8-[1-methoxy-1-(pyridin-2-yl)ethyl]-7-[(trans-4-methylcyclohexyl)methyl]-7H-purin-2-yl}-1,2,4-oxadiazol-5(2H)-one;
5-{6-(3-chlorophenyl)-8-(1-methoxy-1-pyridin-2-ylethyl)-7-[(trans-4-methylcyclohexyl)methyl]-7H-purin-2-yl}-1,3,4-oxadiazol-2(3H)-one;

5-{6-(5-chloropyridin-3-yl)-8-(1-fluorocyclohexyl)-7-[(trans-4-methylcyclohexyl)methyl]-7H-purin-2-yl}-1,3,4-oxadiazol-2(3H)-one;

3-{6-(3-chlorophenyl)-8-[1-methoxy-1-(5-methyl-1,3-oxazol-4-yl)ethyl]-7-[(trans-4-methylcyclohexyl)methyl]-7H-purin-2-yl}-1,2,4-oxadiazol-5(4H)-one;

5-{6-(5-chloropyridin-3-yl)-8-(1-cyclopentyl-1-fluoroethyl)-7-[(trans-4-methylcyclohexyl)methyl]-7H-purin-2-yl}-1,3,4-oxadiazol-2(3H)-one;

5-{8-[1-(3-chloro-2-fluorophenyl)-1-fluoroethyl]-6-(5-chloropyridin-3-yl)-7-[(trans-4-methylcyclohexyl)methyl]-7H-purin-2-yl}-1,3,4-oxadiazol-2(3H)-one;

3-{6-(5-chloropyridin-3-yl)-8-[cyclopentyl(methoxy)methyl]-7-[(trans-4-methylcyclohexyl)methyl]-7H-purin-2-yl}-1,2,4-oxadiazol-5(4H)-one;

3-{6-(5-chloropyridin-3-yl)-8-(1-methoxycyclobutyl)-7-[(trans-4-methylcyclohexyl)methyl]-7H-purin-2-yl}-1,2,4-oxadiazol-5(4H)-one;

3-{6-(5-chloropyridin-3-yl)-8-(1-methoxy-2-methylcyclohexyl)-7-[(trans-4-methylcyclohexyl)methyl]-7H-purin-2-yl}-1,2,4-oxadiazol-5(4H)-one;

5-{6-(5-chloropyridin-3-yl)-8-(1-methoxy-2-methylcyclohexyl)-7-[(trans-4-methylcyclohexyl)methyl]-7H-purin-2-yl}-1,3,4-oxadiazol-2(3H)-one;

3-{6-(5-chloropyridin-3-yl)-8-(1-fluoro-2-methylcyclohexyl)-7-[(trans-4-methylcyclohexyl)methyl]-7H-purin-2-yl}-1,2,4-oxadiazol-5(4H)-one;

6-(5-chloropyridin-3-yl)-8-[1-fluoro-1-(2-fluorophenyl)ethyl]-7-[(trans-4-methylcyclohexyl)methyl]-7H-purine-2-carboxylic acid;

3-{6-(5-chloropyridin-3-yl)-8-[1-(2,6-difluorophenyl)-1-fluoroethyl]-7-[(trans-4-methylcyclohexyl)methyl]-7H-purin-2-yl}-1,2,4-oxadiazol-5(4H)-one;

3-{6-(5-chloropyridin-3-yl)-8-(3-methoxyoxetan-3-yl)-7-[(trans-4-methylcyclohexyl)methyl]-7H-purin-2-yl}-1,2,4-oxadiazol-5 (4H)-one;

3-{6-(5-chloropyridin-3-yl)-8-(1-cyclopentyl-1-methoxyethyl)-7-[(trans-4-methylcyclohexyl)methyl]-7H-purin-2-yl}-1,2,4-oxadiazol-5(4H)-one;

5-{6-(5-chloropyridin-3-yl)-8-(1-cyclopentyl-1-methoxyethyl)-7-[(trans-4-methylcyclohexyl)methyl]-7H-purin-2-yl}-1,3,4-oxadiazol-2(3H)-one;

5-{8-[1-(3-chloro-2-fluorophenyl)-1-methoxyethyl]-6-(5-chloropyridin-3-yl)-7-[(trans-4-methylcyclohexyl)methyl]-7H-purin-2-yl}-1,3,4-oxadiazol-2(3H)-one;

3-{6-(5-chloropyridin-3-yl)-8-(1-methoxycyclohexyl)-7-[(trans-4-methylcyclohexyl)methyl]-7H-purin-2-yl}-1,2,4-oxadiazol-5 (4H)-one;

5-{6-(5-chloropyridin-3-yl)-8-(1-methoxycyclohexyl)-7-[(trans-4-methylcyclohexyl)methyl]-7H-purin-2-yl}-1,3,4-oxadiazol-2(3H)-one;

3-{6-(5-chloropyridin-3-yl)-8-(1-methoxycyclopentyl)-7-[(trans-4-methylcyclohexyl)methyl]-7H-purin-2-yl}-1,2,4-oxadiazol-5 (4H)-one;

5-{6-(5-chloropyridin-3-yl)-8-[1-methoxy-1-(2-methoxyphenyl)ethyl]-7-[(trans-4-methylcyclohexyl)methyl]-7H-purin-2-yl}-1,3,4-oxadiazol-2(3H)-one;

3-{6-(5-chloropyridin-3-yl)-8-[1-methoxy-1-(2-methoxyphenyl)ethyl]-7-[(trans-4-methylcyclohexyl)methyl]-7H-purin-2-yl}-1,2,4-oxadiazol-5(4H)-one;

5-{6-(5-chloropyridin-3-yl)-8-[1-(2,6-difluorophenyl)-1-fluoroethyl]-7-[(trans-4-methylcyclohexyl)methyl]-7H-purin-2-yl}-1,3,4-oxadiazol-2(3H)-one;

5-{6-(5-chloropyridin-3-yl)-8-(1-fluoro-2-methylcyclohexyl)-7-[(trans-4-methylcyclohexyl)methyl]-7H-purin-2-yl}-1,3,4-oxadiazol-2(3H)-one;

5-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,3,4-oxadiazol-2(3H)-one;

5-{6-(5-chloropyridin-3-yl)-8-[1-(3-fluoropyridin-2-yl)-1-methoxyethyl]-7-[(trans-4-methylcyclohexyl)methyl]-7H-purin-2-yl}-1,3,4-oxadiazol-2(3H)-one;

5-{6-(5-chloropyridin-3-yl)-8-[1-(2,6-difluorophenyl)-1-methoxyethyl]-7-[(trans-4-methylcyclohexyl)methyl]-7H-purin-2-yl}-1,3,4-oxadiazol-2(3H)-one;

5-{6-(5-chloropyridin-3-yl)-8-(4-methoxy-3,4-dihydro-2H-pyrano[3,2-b]pyridin-4-yl)-7-[(trans-4-methylcyclohexyl)methyl]-7H-purin-2-yl}-1,3,4-oxadiazol-2(3H)-one;

3-{6-(5-chloropyridin-3-yl)-8-(1-fluoro-1,2,2-trimethylpropyl)-7-[(trans-4-methylcyclohexyl)methyl]-7H-purin-2-yl}-1,2,4-oxadiazol-5(4H)-one;

5-{6-(5-chloropyridin-3-yl)-8-(4-fluoro-3,4-dihydro-2H-pyrano[3,2-b]pyridin-4-yl)-7-[(trans-4-methylcyclohexyl)methyl]-7H-purin-2-yl}-1,3,4-oxadiazol-2(3H)-one;

3-{6-(5-chloropyridin-3-yl)-8-[1-(2,6-difluorophenyl)-1-methoxyethyl]-7-[(trans-4-methylcyclohexyl)methyl]-7H-purin-2-yl}-1,2,4-oxadiazol-5(4H)-one;

3-{6-(5-chloropyridin-3-yl)-8-(4-fluoro-3-methyltetrahydro-2H-pyran-4-yl)-7-[(trans-4-methylcyclohexyl)methyl]-7H-purin-2-yl}-1,2,4-oxadiazol-5(4H)-one;

1,5-anhydro-3-C-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-2,4-dideoxy-2-methyl-3-O-methylpentitol;

3-{6-(5-chloropyridin-3-yl)-8-[1-fluoro-1-(3-fluoropyridin-2-yl)ethyl]-7-[(trans-4-methylcyclohexyl)methyl]-7H-purin-2-yl}-1,2,4-oxadiazol-5(4H)-one;

3-{6-(5-chloropyridin-3-yl)-8-[1-(2-fluorophenyl)cyclopropyl]-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[1-(5-methyl-1,3-oxazol-4-yl)cyclopropyl]-7H-purin-2-yl}-1,2,4-oxadiazol-5(4H)-one;

3-[6-(3-chlorophenyl)-7-[(trans-4-methylcyclohexyl)methyl]-8-(1-pyridin-2-ylcyclopropyl)-7H-purin-2-yl]-1,2,4-oxadiazol-5 (2H)-one;

5-{6-(5-chloropyridin-3-yl)-8-[(2-fluorophenyl)(methoxy)methyl]-7-[(trans-4-methylcyclohexyl)methyl]-7H-purin-2-yl}-1,3,4-oxadiazol-2(3H)-one;

3-{6-(5-chloropyridin-3-yl)-8-(3,4-dihydro-1H-isochromen-1-yl)-7-[(trans-4-methylcyclohexyl)methyl]-7H-purin-2-yl}-1,2,4-oxadiazol-5(4H)-one;

5-{6-(5-chloropyridin-3-yl)-8-(1-fluoro-2-methoxy-1-methylethyl)-7-[(trans-4-methylcyclohexyl)methyl]-7H-purin-2-yl}-1,3,4-oxadiazol-2(3H)-one;

3-{6-(5-chloropyridin-3-yl)-8-(1,2-dimethoxy-1-methylethyl)-7-[(trans-4-methylcyclohexyl)methyl]-7H-purin-2-yl}-1,2,4-oxadiazol-5(4H)-one;

3-{6-(5-chloropyridin-3-yl)-8-(1-fluoro-2-methoxy-1-methylethyl)-7-[(trans-4-methylcyclohexyl)methyl]-7H-purin-2-yl}-1,2,4-oxadiazol-5(4H)-one;

2-{[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl](methoxy)methyl}benzonitrile;

2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-fluoroethyl}benzonitrile;

2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]-1-methoxyethyl}benzonitrile;

3-{6-(5-chloropyridin-3-yl)-8-[1-(2-fluorophenyl)ethyl]-7-[(trans-4-methylcyclohexyl)methyl]-7H-purin-2-yl}-1,2,4-oxadiazol-5 (4H)-one;

5-{6-(5-chloropyridin-3-yl)-8-[1-(2-fluorophenyl)ethyl]-7-[(trans-4-methylcyclohexyl)methyl]-7H-purin-2-yl}-1,3,4-oxadiazol-2(3H)-one;

3-{6-(5-chloropyridin-3-yl)-8-[1-(2,6-difluorophenyl)ethyl]-7-[(trans-4-methylcyclohexyl)methyl]-7H-purin-2-yl}-1,2,4-oxadiazol-5(4H)-one;

2-{1-[6-(5-chloropyridin-3-yl)-7-[(trans-4-methylcyclohexyl)methyl]-2-(5-oxo-4,5-dihydro-1,2,4-oxadiazol-3-yl)-7H-purin-8-yl]ethyl}benzonitrile;

5-{6-(3-chlorophenyl)-8-cyclopropyl-7-[(trans-4-methylcyclohexyl)methyl]-7H-purin-2-yl}-1,3,4-oxadiazol-2(3H)-one;

3-{6-(3-chlorophenyl)-8-cyclopropyl-7-[(trans-4-methylcyclohexyl)methyl]-7H-purin-2-yl}-1,2,4-oxadiazol-5(4H)-one;

3-{6-(3-chlorophenyl)-7-[(trans-4-methylcyclohexyl)methyl]-8-[1-(tetrahydro-2H-pyran-4-yl)ethyl]-7H-purin-2-yl}-1,2,4-oxadiazol-5(4H)-one;

5-chloro-1-{7-[(trans-4-methylcyclohexyl)methyl]-2-(5-oxo-4,5-dihydro-1,2,4-oxadiazol-3-yl)-8-[(3R)-3-phenylmorpholin-4-yl]-7H-purin-6-yl}pyridin-2(1H)-one;

3-{6-[(5-chloropyridin-2-yl)oxy]-7-[(trans-4-methylcyclohexyl)methyl]-8-[(3R)-3-phenylmorpholin-4-yl]-7H-purin-2-yl}-1,2,4-oxadiazol-5 (4H)-one;

5-{6-[(5-chloropyridin-2-yl)oxy]-7-[(trans-4-methylcyclohexyl)methyl]-8-[(3R)-3-phenylmorpholin-4-yl]-7H-purin-2-yl}-1,3,4-oxadiazol-2(3H)-one;

{6-(3-chlorophenyl)-7-[(trans-4-methylcyclohexyl)methyl]-8-[(3R)-3-methylmorpholin-4-yl]-7H-purin-2-yl}acetic acid; and 3-{7-[(trans-4-methylcyclohexyl)methyl]-6-(2-methylmorpholin-4-yl)-8-[(3R)-3-phenylmorpholin-4-yl]-7H-purin-2-yl}-1,2,4-oxadiazol-5(4H)-one;

or a stereoisomer thereof;
or a pharmaceutically acceptable salt thereof;
or a pharmaceutically acceptable salt of the stereoisomer thereof.

15. A pharmaceutical composition comprising a therapeutically effective amount of at least one compound of claim 1 or a pharmaceutically acceptable salt thereof, in combination with at least one pharmaceutically acceptable carrier.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: labeled peptide
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES
<222> LOCATION: (4)..(4)
<223> OTHER INFORMATION: 1-AMINO-CYCLOHEXANE CARBOXYLIC ACID
<220> FEATURE:
```

```
<221> NAME/KEY: MOD_RES
<222> LOCATION: (5)..(5)
<223> OTHER INFORMATION: 6-BR

<400> SEQUENCE: 1

Phe Arg Xaa Xaa Trp Glu Glu Leu
1               5
```